US012534499B2

(12) United States Patent
Qi et al.

(10) Patent No.: US 12,534,499 B2
(45) Date of Patent: Jan. 27, 2026

(54) MESOPHILIC ARGONAUTE SYSTEMS AND USES THEREOF

(71) Applicants: The Board of Trustees of the Leland Stanford Junior University, Stanford, CA (US); Intima Bioscience, Inc., New York, NY (US)

(72) Inventors: Lei S. Qi, Stanford, CA (US); Modassir Choudhry, New York, NY (US); Xueqiu Lin, San Bruno, CA (US); Trevor N. Collingwood, Novato, CA (US); Thomas Henley, Soham (GB); Benjamin Klapholz, Cambridge (GB); Tilmann Buerckstuemmer, Vienna (AT); Sejla Salic, Vienna (AT)

(73) Assignees: The Board of Trustees of the Leland Stanford Junior University, Stanford, CA (US); Intima Bioscience, Inc., New York, NY (US)

( * ) Notice: Subject to any disclaimer, the term of this patent is extended or adjusted under 35 U.S.C. 154(b) by 963 days.

(21) Appl. No.: 17/464,635

(22) Filed: Sep. 1, 2021

(65) Prior Publication Data

US 2022/0089659 A1 Mar. 24, 2022

Related U.S. Application Data

(63) Continuation of application No. PCT/US2020/021163, filed on Mar. 5, 2020.

(60) Provisional application No. 62/814,787, filed on Mar. 6, 2019.

(51) Int. Cl.

| | |
|---|---|
| ***C07K 14/33*** | (2006.01) |
| ***A61K 31/7088*** | (2006.01) |
| ***A61K 38/16*** | (2006.01) |
| ***A61K 38/46*** | (2006.01) |
| ***C12N 9/14*** | (2006.01) |
| ***C12N 9/22*** | (2006.01) |
| ***C12N 15/11*** | (2006.01) |

(52) U.S. Cl.

CPC .......... *C07K 14/33* (2013.01); *A61K 31/7088* (2013.01); *A61K 38/164* (2013.01); *A61K 38/46* (2013.01); *A61K 38/465* (2013.01); *C12N 9/14* (2013.01); *C12N 9/22* (2013.01); *C12N 15/11* (2013.01); *C12Y 306/04012* (2013.01); *C07K 2319/80* (2013.01); *C12N 2310/20* (2017.05)

(58) Field of Classification Search

None

See application file for complete search history.

(56) References Cited

U.S. PATENT DOCUMENTS

| | | | |
|---|---|---|---|
| 2015/0089681 | A1 | 3/2015 | Van Der Oost et al. |
| 2018/0073012 | A1 | 3/2018 | Liu et al. |
| 2018/0201913 | A1 | 7/2018 | Donohoue et al. |

FOREIGN PATENT DOCUMENTS

| | | | |
|---|---|---|---|
| WO | 2018/011236 | A1 | 1/2018 |
| WO | 2018/172798 | A1 | 9/2018 |
| WO | 2019/051278 | A1 | 3/2019 |

OTHER PUBLICATIONS

Bowie et al. (Science, 1990, 247:1306-1310).*

Burgess et al. (J. Cell Biol. 111:2129-2138, 1990).*

Lazar et al. (Mol. Cell. Biol., 8:1247-1252, 1988).*

European Patent Application No. EP 20766813.8, Extended European Search Report, Oct. 31, 2022, 10 pages.

Hegge, J. et al., "DNA-guided DNA cleavage at moderate temperatures by Clostridium butyricum argonaute," bioRxiv, Jan. 29, 2019, 39 pages.

Hunt, E. et al., "Single-stranded binding proteins and helicase enhance the activity of prokaryotic argonautes in vitro," PLOS One, vol. 13 No. 8, Aug. 29, 2018, 20 pages.

International Patent Application No. PCT/US2020/021163, International Preliminary Report on Patentability, Sep. 16, 2021, 9 pages.

International Patent Application No. PCT/US2020/021163, International Search Report and Written Opinion of the International Searching Authority, Jun. 12, 2020, 11 pages.

Kuzmenko, A. et al., "Programmable DNA cleavage by Ago nucleases from mesophilic bacteria Clostridium butyricum and Limnothrix rosea," bioRxiv, Feb. 22, 2019, 34 pages.

* cited by examiner

*Primary Examiner* — Brian Gangle

(74) *Attorney, Agent, or Firm* — Kilpatrick Townsend & Stockton LLP

(57) ABSTRACT

Constructs comprising Argonautes and neighboring genes are disclosed for use in gene editing. Disclosed are also compositions and methods utilizing these Argonautes and neighboring genes. Also disclosed are the methods of making and using the Argonautes and neighboring genes in treating various diseases, conditions, and cancer.

9 Claims, 123 Drawing Sheets

Specification includes a Sequence Listing.

| | Selected Agos | Positive In-Vitro |
|---|---|---|
| Branch representatives | 80 | 8/80 (10%) |
| refined selection | 7 | 2/7 (28.5%) |

| Id(NCBI) | Organism | Taxonomy |
|---|---|---|
| 498541161 | Thermobrachium celere DSM 8682 | Bacteria Firmicutes Clostridia Clostridiales Clostridiaceae Thermobrachium |
| 653057194 | Caloramator sp. ALD01 | Bacteria Firmicutes Clostridia Clostridiales Clostridiaceae Caloramator |
| 1120387159 | Caloramator proteoclasticus DSM 10124 | Bacteria Firmicutes Clostridia Clostridiales Clostridiaceae Caloramator |
| 942023251 | Fusicatenibacter saccharivorans | Bacteria Firmicutes Clostridia Clostridiales Lachnospiraceae Fusicatenibacter |
| 941884733 | Fusicatenibacter saccharivorans | Bacteria Firmicutes Clostridia Clostridiales Lachnospiraceae Fusicatenibacter |
| 941823761 | Dorea longicatena | Bacteria Firmicutes Clostridia Clostridiales Lachnospiraceae Dorea |
| 961526009 | Clostridium butyricum | Bacteria Firmicutes Clostridia Clostridiales Clostridiaceae Clostridium |
| 959868240 | Clostridium butyricum | Bacteria Firmicutes Clostridia Clostridiales Clostridiaceae Clostridium |
| 1029991103 | Clostridium butyricum | Bacteria Firmicutes Clostridia Clostridiales Clostridiaceae Clostridium |
| 770938333 | Clostridium butyricum CWBI1009 | Bacteria Firmicutes Clostridia Clostridiales Clostridiaceae Clostridium |
| **422345013(Ago69)** | Clostridium perfringens WAL-14572 | Bacteria Firmicutes Clostridia Clostridiales Clostridiaceae Clostridium |
| **755046694(Ago70)** | Clostridium saudiense | Bacteria Firmicutes Clostridia Clostridiales Clostridiaceae Clostridium |
| **942050038(Ago41)** | Clostridium disparicum | Bacteria Firmicutes Clostridia Clostridiales Clostridiaceae Clostridium |

FIG. 3

| Id(NCBI) | Temperature_Range | Sample_Collection_Site | Sample_Isolation_Comments | Ecosystem_Subtype | Specific_Ecosystem |
|---|---|---|---|---|---|
| 498541161 | | | | | |
| 653057194 | | | Etoliko lagoon in Western Greece | Unclassified | Unclassified |
| 1120387159 | 55 C | Thermophile | Mesophilic granular sludge from a lab-scale UASB reactor that was treating whey | Unclassified | Unclassified |
| 942023251 | | | | | |
| 941884733 | | | | | |
| 941823761 | | | | | |
| 961526009 | | | the pit mud of a Chinese liquor factory | | |
| 959868240 | | | Fecal sample of pig | Digestive system | Fecal |
| 1029991103 | | | probiotics | | |
| 770938333 | | | | | |
| **422345013(Ago69)** | | Mesophile | Human fecas | Digestive system | Large intestine |
| **755046694(Ago70)** | | 25-37 C | Human fecal sample | Digestive system | Large intestine |
| **942050039(Ago41)** | | | rat caecum | Digestive system | Large intestine |

FIG. 4

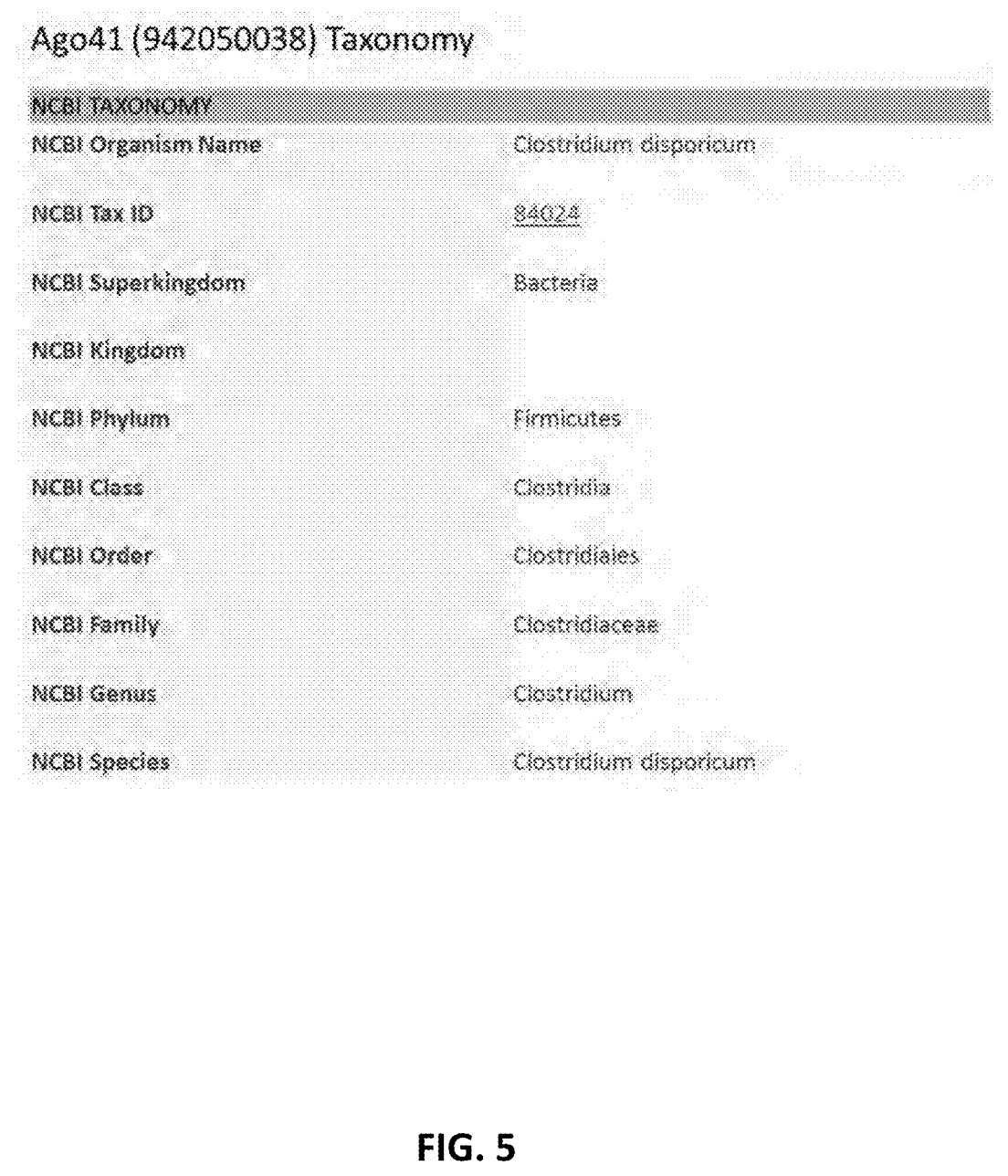

Ago41 (942050038) Taxonomy

| NCBI TAXONOMY | |
|---|---|
| NCBI Organism Name | Clostridium disporicum |
| NCBI Tax ID | 84024 |
| NCBI Superkingdom | Bacteria |
| NCBI Kingdom | |
| NCBI Phylum | Firmicutes |
| NCBI Class | Clostridia |
| NCBI Order | Clostridiales |
| NCBI Family | Clostridiaceae |
| NCBI Genus | Clostridium |
| NCBI Species | Clostridium disporicum |

FIG. 5

NCBI Order: Clostridiales
NCBI Family: Clostridiaceae
NCBI Genus: Clostridium

| | All Species | Ago41 Branch Species |
|---|---|---|
| All | 503 | 13 |
| **Order** Clostridiales | 36 | 13 |
| **Family** Clostridiaceae | 12 | 10 |
| **Genus** Clostridium | 9 | 7 |

Reaction Buffer: 20 mM Tris/HCl pH7.5, 125 mM NaCl, 5 mM $MnCl_2$, 1.6 mM b-MeOH, 0.3% BSA Template: T1 - 90 nt ssDNA; expected cleavage product: 66 + 24nt AGO : gDNA : Template = 1 : 1 : 1 (250 nM : 250 nM : 250 nM)

Preloading: gDNA + AGO at 37°C for 15 min

Reaction Buffer: 20 mM Tris/HCl pH7.5, 125 mM NaCl, 5 mM $MnCl_2$, 1.6 mM b-MeOH, 0.3% BSA Template: T1 - 90 nt ssDNA; expected cleavage product: 66 + 24nt AGO : gDNA : Template = 1 : 1 : 1 (250 nM : 250 nM : 250 nM)

Preloading: gDNA + AGO at 37°C for 15 min

*...pipetting mistake
**...it takes a couple of seconds to stop the reaction

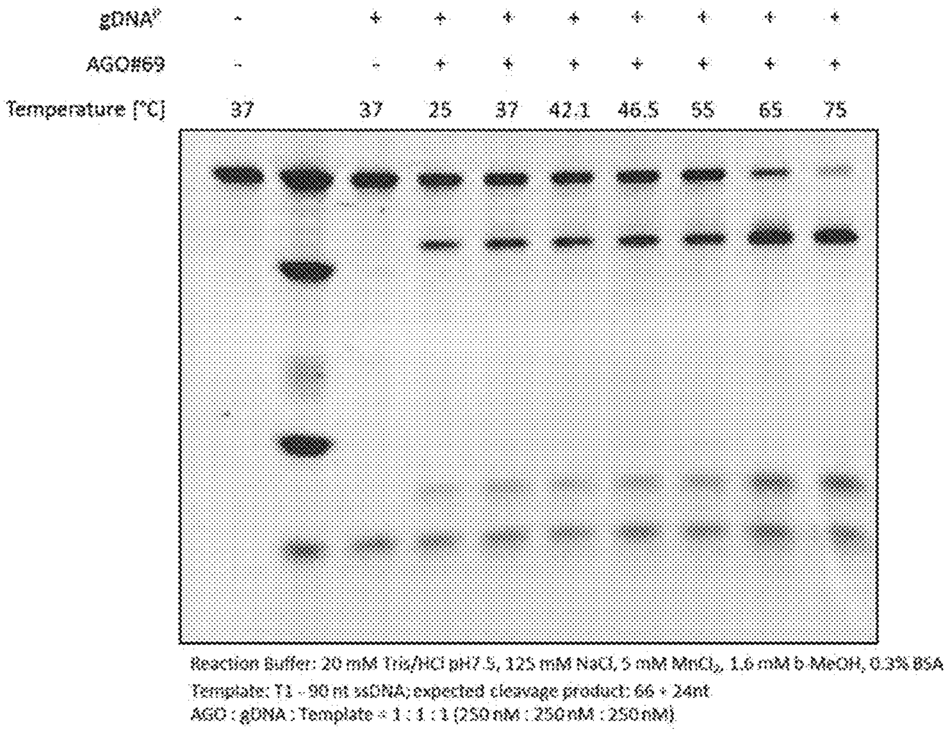
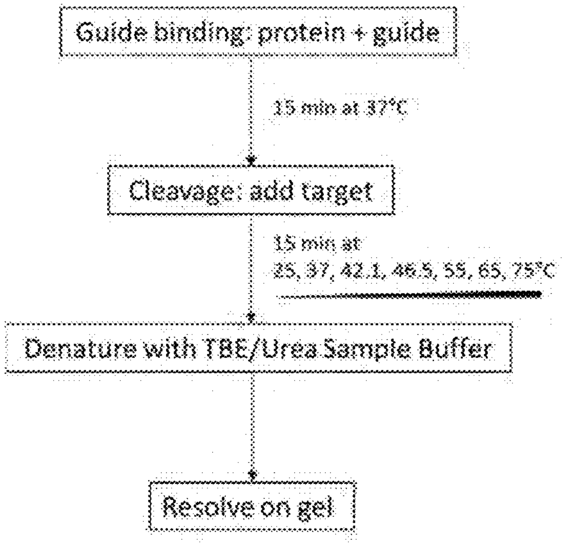
FIG. 13

Reaction Buffer: 20 mM Tris/HCl pH7.5, 125 mM NaCl, 5 mM $MnCl_2$, 1.6 mM b-MeOH, 0.3% BSA
Template: T1 - 90 nt ssDNA; expected cleavage product: 66 + 24nt
AGO : gDNA : Template = 1 : 1 : 1 (250 nM : 250 nM : 250 nM)

Location of guides relative to ssDNA target sequence and secondary structure

[illegible]

FIG. 18

Reaction Buffer: 20 mM Tris/HCl pH7.5, 125 mM NaCl, 5 mM $MnCl_2$, 1.6 mM b-MeOH, 0.3% BSA, RNase inhibitor

Template: T1 - 90 nt ssDNA; expected cleavage product: 66 + 24nt gRNA: Phosphorothioate bonds on 5' and 3' end AGO : gDNA : Template = 1 : 1 : 1 (250 nM : 250 nM : 250 nM)

Preloading: gDNA + AGO at 37°C for 15 min

*** experimental error: D1(p) instead of no gDNA*

AGO29*: protein amounts used = ½ volume of protein (125ng)

AGO29*: 125ng/reaction

>> * Expected cutting pattern at 500mM NaCl

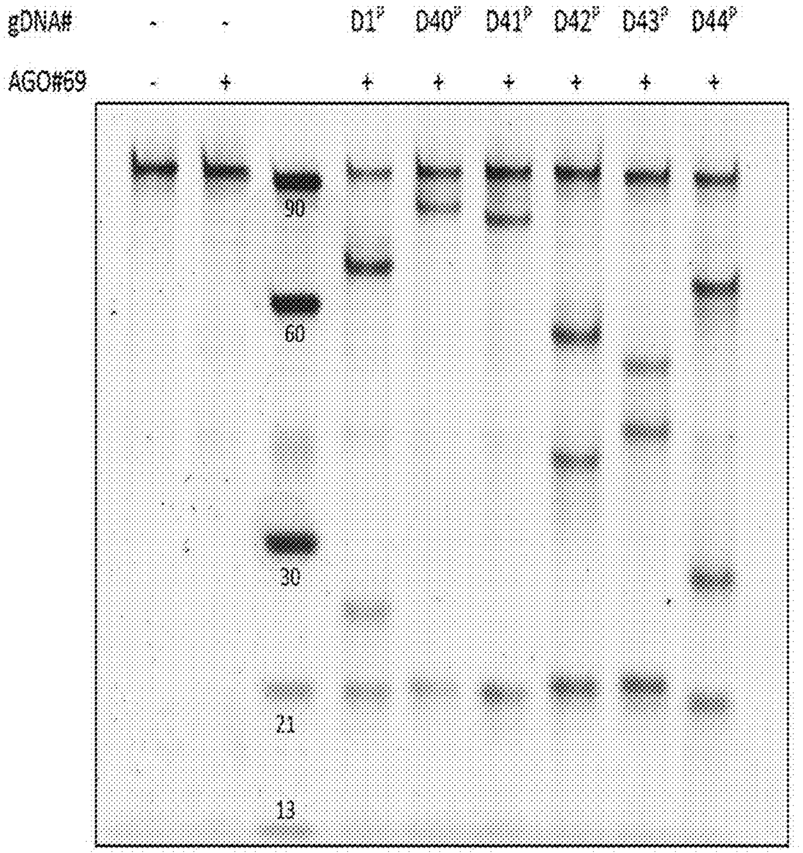
| gDNA# | Sequence | GC content | Expected cleavage products |
|---|---|---|---|
| D1P | 5'-GCTGCCATCCAGATCGTTATC-3' | 52% | 66 + 24 |
| D40P | 5'-CGTTATCGCCCATGGGGTGCA-3' | 62% | 79 + 11 |
| D41P | 5'-GATCGTTATCGCCCATGGGGT-3' | 57% | 76 + 14 |
| D42P | 5'-GGTGCGGGTGAAGCTGCCATC-3' | 67% | 53 + 37 |
| D43P | 5'-ACTTAGACTGAAGGTGCGGGT-3' | 52% | 49 + 41 |
| D44P | 5'-AGTAATCGTCATCACTTAGAC-3' | 38% | 62 + 28 |
Data for AGO#02, AGO#41 and AGO#70 - Slides 13, 14 & 15
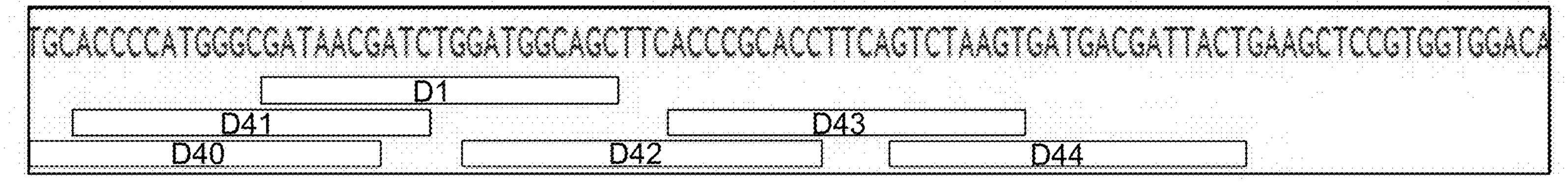
*FIG. 40*

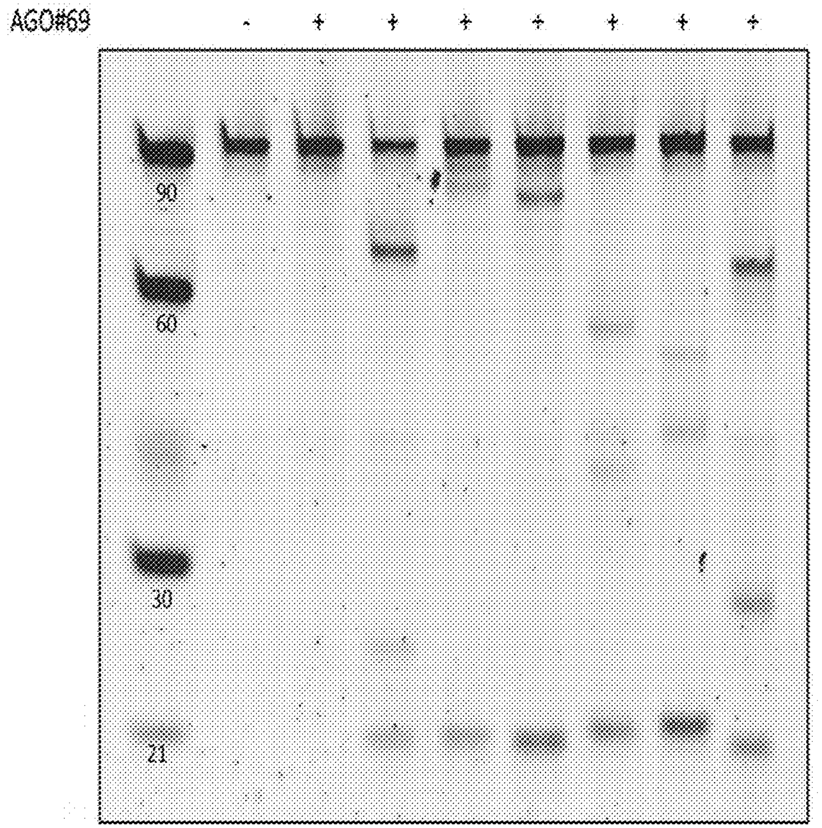
| gDNA# | Sequence | GC content | Expected cleavage products |
|---|---|---|---|
| D1$^P$ | 5'-GCTGCCATCCAGATCGTTATC-3' | 52% | 66 + 24 |
| D40$^P$ | 5'-CGTTATCGCCCATGGGGTGCA-3' | 62% | 79 + 11 |
| D41$^P$ | 5'-GATCGTTATCGCCCATGGGGT-3' | 57% | 76 + 14 |
| D42$^P$ | 5'-GGTGCGGGTGAAGCTGCCATC-3' | 67% | 53 + 37 |
| D43$^P$ | 5'-ACTTAGACTGAAGGTGCGGGT-3' | 52% | 49 + 41 |
| D44$^P$ | 5'-AGTAATCGTCATCACTTAGAC-3' | 38% | 62 + 28 |
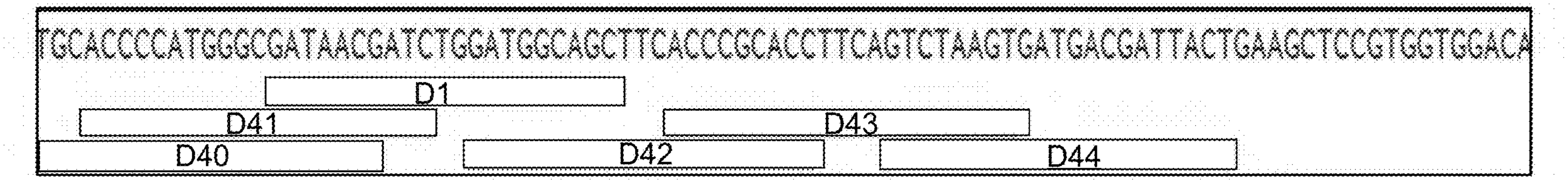
FIG. 41

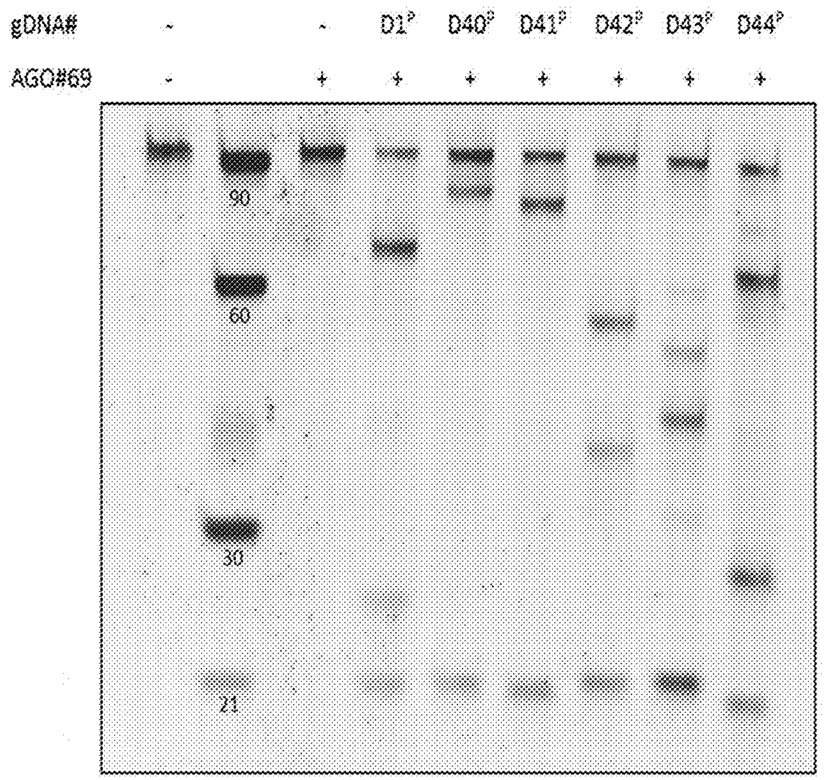
| gDNA# | Sequence | GC content | Expected cleavage products |
|---|---|---|---|
| D1[P] | 5'-GCTGCCATCCAGATCGTTATC-3' | 52% | 66 + 24 |
| D40[P] | 5'-CGTTATCGCCCATGGGGTGCA-3' | 62% | 79 + 11 |
| D41[P] | 5'-GATCGTTATCGCCCATGGGGT-3' | 57% | 76 + 14 |
| D42[P] | 5'-GGTGCGGGTGAAGCTGCCATC-3' | 67% | 53 + 37 |
| D43[P] | 5'-ACTTAGACTGAAGGTGCGGGT-3' | 52% | 49 + 41 |
| D44[P] | 5'-AGTAATCGTCATCACTTAGAC-3' | 38% | 62 + 28 |
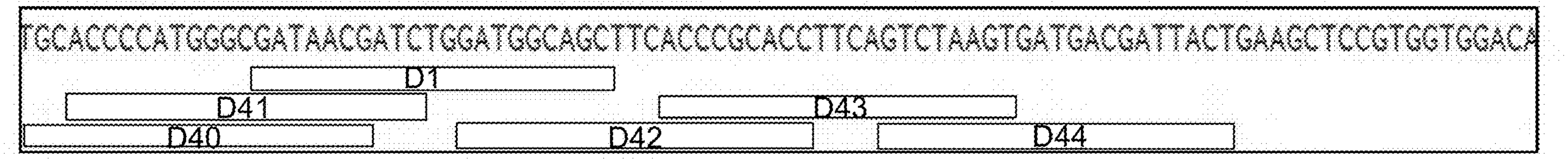
*FIG. 42*

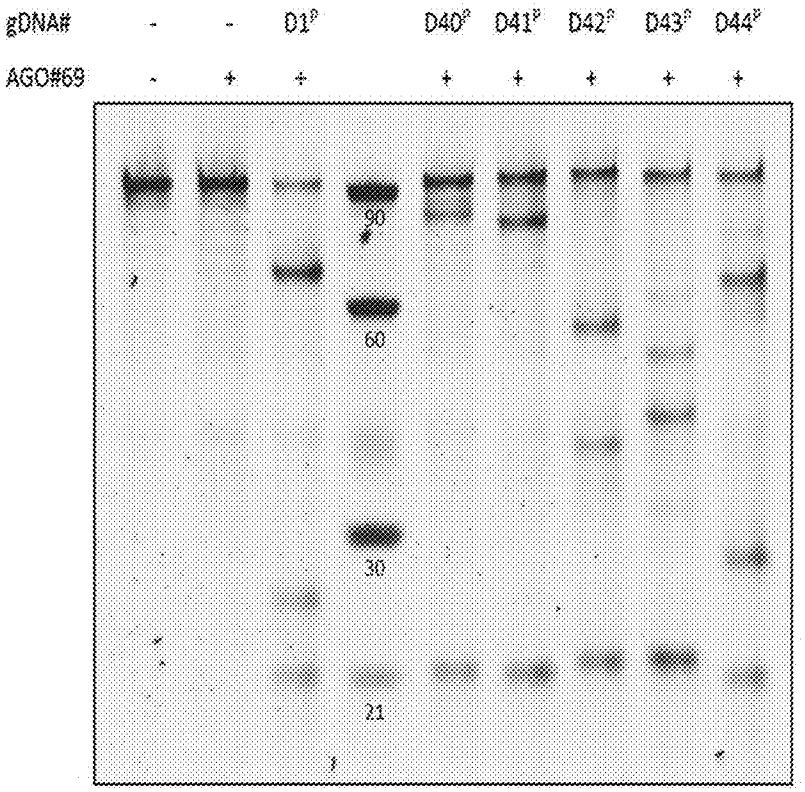
| gDNA# | Sequence | GC content | Expected cleavage products |
|---|---|---|---|
| D1$^P$ | 5'-GCTGCCATCCAGATCGTTATC-3' | 52% | 66 + 24 |
| D40$^P$ | 5'-CGTTATCGCCCATGGGGTGCA-3' | 62% | 79 + 11 |
| D41$^P$ | 5'-GATCGTTATCGCCCATGGGGT-3' | 57% | 76 + 14 |
| D42$^P$ | 5'-GGTGCGGGTGAAGCTGCCATC-3' | 67% | 53 + 37 |
| D43$^P$ | 5'-ACTTAGACTGAAGGTGCGGGT-3' | 52% | 49 + 41 |
| D44$^P$ | 5'-AGTAATCGTCATCACTTAGAC-3' | 38% | 62 + 28 |
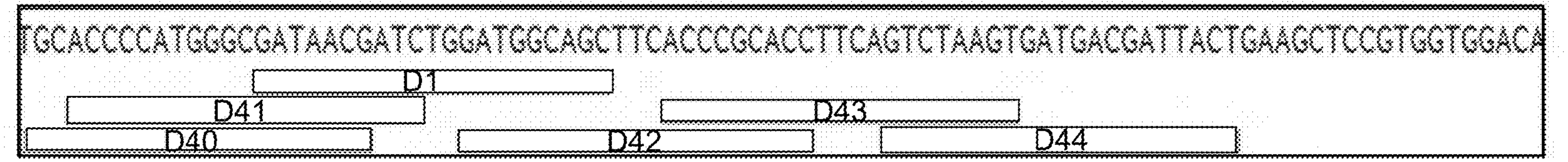
*FIG. 43* dsDNA nicking/cleavage

| Time (min) | without ET-SSB | | | | | |
|---|---|---|---|---|---|---|
| | +ATP | | | -ATP | | |
| 0 | 602 | 510 | 486 | 376 | 379 | 380 |
| 5 | 1105 | 1015 | 1056 | 376 | 371 | 373 |
| 10 | 1281 | 1190 | 1352 | 374 | 370 | 377 |
| 15 | 1375 | 1283 | 1366 | 382 | 381 | 386 |

| Time (min) | with ET-SSB (250 ng/reaction) | | | | | |
|---|---|---|---|---|---|---|
| | +ATP | | | -ATP | | |
| 0 | 708 | 677 | 604 | 404 | 399 | 398 |
| 5 | 1741 | 2184 | 2096 | 406 | 399 | 396 |
| 10 | 1961 | 2587 | 2536 | 411 | 406 | 412 |
| 15 | 2054 | 2761 | 2734 | 426 | 422 | 426 |

| | | ET-SSB + RecQ | | | | | ET-SSB + RecQ | | | |
|---|---|---|---|---|---|---|---|---|---|---|
| Time [min] | no Helicase | 0 | 500 ng | 250 ng | 50 ng | no Helicase | 0 | 500 ng | 250 ng | 50 ng |
| 0 | 241 | 2418 | 2059 | 2141 | 1432 | 224 | 2058 | 2414 | 1983 | 1784 |
| 1 | 231 | 3130 | 3174 | 3465 | 2491 | 217 | 2839 | 3794 | 3255 | 3205 |
| 2 | 230 | 3793 | 4202 | 4563 | 3369 | 217 | 3535 | 5000 | 4238 | 4198 |
| 3 | 228 | 4449 | 5136 | 5481 | 4122 | 211 | 4186 | 6026 | 5112 | 5003 |
| 4 | 228 | 4955 | 5918 | 6269 | 4743 | 214 | 4713 | 6822 | 5813 | 5662 |
| 5 | 228 | 5479 | 6655 | 6966 | 5370 | 217 | 5270 | 7568 | 6500 | 6302 |
| 6 | 227 | 5926 | 7263 | 7527 | 5879 | 215 | 5714 | 8187 | 7056 | 6823 |
| 7 | 228 | 6342 | 7805 | 8041 | 6362 | 217 | 6170 | 8654 | 7582 | 7305 |
| 8 | 227 | 6725 | 8243 | 8516 | 6784 | 215 | 6544 | 9037 | 7987 | 7700 |
| 9 | 228 | 7043 | 8625 | 8870 | 7155 | 216 | 6905 | 9378 | 8403 | 8067 |
| 10 | 230 | 7397 | 8934 | 9234 | 7491 | 217 | 7259 | 9620 | 8743 | 8400 |
| 11 | 229 | 7677 | 9206 | 9513 | 7756 | 220 | 7560 | 9815 | 9022 | 8688 |
| 12 | 233 | 7927 | 9418 | 9747 | 8060 | 220 | 7827 | 10000 | 9300 | 8960 |
| 13 | 229 | 8205 | 9597 | 9973 | 8264 | 220 | 8067 | 10080 | 9506 | 9139 |
| 14 | 230 | 8437 | 9798 | 10180 | 8525 | 223 | 8353 | 10222 | 9738 | 9414 |
| 15 | 230 | 8573 | 9874 | 10214 | 8636 | 220 | 8517 | 10240 | 9770 | 9498 |

| Eco-SSB | 1500 ng | 750 ng | 375 ng | 0 ng | 1500 ng | 750 ng | 375 ng | 0 ng | 1500 ng | 750 ng | 375 ng | 0 ng |
|---|---|---|---|---|---|---|---|---|---|---|---|---|
| Time [min] | +RecQ | | | | +RecQ | | | | +RecQ | | | |
| 0 | 1613 | 1646 | 1639 | 1129 | 1576 | 1780 | 1668 | 1219 | 1586 | 1290 | 1627 | 979 |
| 1 | 3053 | 2852 | 2802 | 1372 | 2866 | 3044 | 2860 | 1472 | 2788 | 2078 | 2491 | 1118 |
| 2 | 4489 | 4095 | 3989 | 1647 | 4098 | 4309 | 4041 | 1716 | 3954 | 2842 | 3307 | 1258 |
| 3 | 5712 | 5129 | 4998 | 1850 | 5116 | 5361 | 5059 | 1907 | 4873 | 3490 | 3965 | 1367 |
| 4 | 6944 | 6139 | 6047 | 2079 | 6215 | 6468 | 6149 | 2137 | 5879 | 4168 | 4673 | 1505 |
| 5 | 7983 | 6960 | 6893 | 2256 | 7078 | 7365 | 7054 | 2330 | 6724 | 4717 | 5295 | 1624 |
| 6 | 8984 | 7693 | 7717 | 2478 | 7958 | 8213 | 7891 | 2539 | 7535 | 5234 | 5907 | 1750 |
| 7 | 9850 | 8336 | 8423 | 2688 | 8784 | 9087 | 8858 | 2746 | 8299 | 5724 | 6489 | 1887 |
| 8 | 10647 | 8960 | 9033 | 2901 | 9536 | 9715 | 9400 | 2962 | 9003 | 6137 | 7061 | 2027 |
| 9 | 11280 | 9362 | 9344 | 3106 | 10143 | 10355 | 10014 | 3161 | 9621 | 6535 | 7586 | 2157 |
| 10 | 11745 | 9762 | 9979 | 3300 | 10680 | 10873 | 10490 | 3358 | 10126 | 6875 | 8020 | 2296 |
| 11 | #Sat | 10108 | 10398 | 3500 | 11210 | 11324 | 10977 | 3568 | 10617 | 7193 | 8444 | 2439 |
| 12 | #Sat | 10365 | 10652 | 3691 | 11558 | 11610 | 11322 | 3731 | 10977 | 7398 | 8722 | 2543 |
| 13 | #Sat | 10594 | 10817 | 3866 | 11995 | 11925 | 11597 | 3916 | 11365 | 7677 | 9081 | 2678 |
| 14 | #Sat | 10858 | 11176 | 4076 | 12271 | 12237 | 11808 | 4124 | 11568 | 7906 | 9363 | 2837 |
| 15 | #Sat | 11043 | 11423 | 4275 | #Sat | #Sat | #Sat | 4324 | 11928 | 8193 | 9706 | 2981 |

| Lane | 1 | 2 | 3 | 4 | 5 | 6 | 7 | 8 | 9 | 10 | 11 | 12 |
|---|---|---|---|---|---|---|---|---|---|---|---|---|
| AGO41 | WT | WT | WT | WT | MUT | MUT | MUT | MUT | - | - | - | - |
| Guide | - | D1 | D1(p) | DNT(p) | - | D1 | D1(p) | DNT(p) | - | D1 | D1(p) | DNT(p) |
| Temp 1 | + | + | + | + | + | + | + | + | + | + | + | + |

AGO#69

MPKKKRKVEDPKKKRKVGSGSMVGGYKVSNLTVEAFEGIGSVNPMLFYQYKVTGKGKYDN
VYKIIKSARYKMHSKNRFKPVFIKDDKLYTLEKLPDIEDLDFANINFVKSEVLSIEDNMS
IYGEVVEYYINLKLKKVKVLGKYPKYRINYSKEILSNTLLTRELKDEFKKSNKGFNLKRK
FRISPVVNKMGKVILYLSCSADFSTNKNIYEMLKEGLEVEGLAVKSEWSNISGNLVIESV
LETKISEPTSLGQSLIDYYKNNNQGYRVKDFTDEDLNANIVNVRGNKKIYMYIPHALKPI
ITREYLAKNDPEFSKEIEQLIKMNMNYRYETLKSFVNDIGVIEELNNLSFKNKYYEDVKL
LGYSSGKIDEPVLMGAKGIIKNKMQIFSNGFYKLPEGKVRFGVLYPKEFDGVSRKAIRAI
YDFSKEGKYHGESNKYIAEHLINVEFNPKECIFEGYELGDITEYKKAALKLNNYNNVDFV
IAIVPNMSDEEIENSYNPFKKIWAELNLPSQMISVKTAEIFANSRDNTALYYLHNIVLGI
LGKIGGIPWVVKDMKGDVDCFVGL[redacted]VGTREKGIHYPACSVVFDKYGKLINYYKPNIPQNG
[redacted]KINTEILQEIFDKVLISYEEENGAYPKNIVIHRDGFSREDLDWYENYFGKKNIKFNIIE
VKKSTPLKIASINEGNITNPEKGSYILRGNKAYMVTTDIKENLGSPKPLKIEKSYGDIDM
LTALSQIYALTQIHVGATKSLRLPITTGYA[redacted]KICKAIEFIPQGRVDNRLFFL

FIG. 49

AGO#69

MPKKKRKVEDPKKKRKVGSGSMVGGYKVSNLTVEAFEGIGSVNPMLFYQYKVTGKGKYDN
VYKIIKSARYKMHSKNRFKPVFIKDDKLYTLEKLPDIEDLDFANINFVKSEVLSIEDNMS
IYGEVVEYYINLKLKKVKVLGKYPKYRINYSKEILSNTLLTRELKDEFKKSNKGFNLKRK
FRISPVVNKMGKVILYLSCSADFSTNKNIYEMLKEGLEVEGLAVKSEWSNISGNLVIESV
LETKISEPTSLGQSLIDYYKNNNQGYRVKDFTDEDLNANIVNVRGNKKIYMYIPHALKPI
ITREYLAKNDPEFSKEIEQLIKMNMNYRYETLKSFVNDIGVIEELNNLSFKNKYYEDVKL
LGYSSGKIDEPVLMGAKGIIKNKMQIFSNGFYKLPEGKVRFGVLYPKEFDGVSRKAIRAI
YDFSKEGKYHGESNKYIAEHLINVEFNPKECIFEGYELGDITEYKKAALKLNNYNNVDFV
IAIVPNMSDEEIENSYNPFKKIWAELNLPSQMISVKTAEIFANSRDNTALYYLHNIVLGI
LGKIGGIPWVVKDMKGDVDCFVGLDVGTREKGIHYPACSVVFDKYGKLINYYKPNIPQNG
EKINTEILQEIFDKVLISYEEENGAYPKNIVIHRDGFSREDLDWYENYFGKKNIKFNIIE
VKKSTPLKIASINEGNITNPEKGSYILRGNKAYMVTTDIKENLGSPKPLKIEKSYGDIDM
LTALSQIYALTQIHVGATKSLRLPITTGYADKICKAIEFIPQGRVDNRLFFL

FIG. 50

Guide DNA location and Tm

Expected cleavage product: 4487 + 1827

Expected cleavage product: 4596 + 1089 + 552 + 77

Expected Cleavage Product:4604 + 1388 + 35 bp

Expected Cleavage Product:4604 + 1388 + 35 bp

AE1 (D54/55)- AP056- RE KpnI-HF: 4723 + 1591

| Plasmid # 70 | | | |
|---|---|---|---|
| Guides | RE | % GC | Expected cleavage product |
| D54/D55 | BamHII | 23.8 | 375 + 4741 |
| D1/D30 | BamHII | 52.38 | 1857 + 3259 |
| D2/D31 | BamHII | 66.67 | 1902 + 3214 |
| D3/D32 | BamHII | 76.19 | 1892 + 3224 |
| D106/D107 | BamHII | 9.52 | 460 + 4656 |

| Plasmid # 56 | | | |
|---|---|---|---|
| Guides | RE | % GC | Expected cleavage product |
| D54/D55 | KpnI | 23.8 | 1591 + 4723 |
| D94/D95 | KpnI | 28.57 | 1040 + 5274 |
| D82/D83 | KpnI | 38.10 | 1022 + 5292 |
| D104/D105 | KpnI | 47.62 | 1553 + 4761 |
| D102/D103 | KpnI | 52.38 | 1452 + 4862 |
| D86/D87 | KpnI | 57.14 | 1320 + 4994 |
| D92/D/93 | KpnI | 61.90 | 1098 + 5216 |
| D88/D89 | KpnI | 66.67 | 1200 + 5114 |
| D90/D91 | KpnI | 71.43 | 1299 + 5015 |

Swapped guide binding sites

P…HAT guide forward + reverse (pair)
F…HAT guide forward (single)
R…Hat guide reverse (single)

| % Amino Acid Identity Between: | Ago69, HG2, HG4 | Ago69, HG2 | Ago69, HG4 |
|---|---|---|---|
| PIWI Domains | 27.7% | 72.8% | 34.1% |
| Whole Protein Sequence | 19.1% | 61.3% | 25.2% |

| Accession # | Internal ID | Species | MW with Tags | |
|---|---|---|---|---|
| WP_002566035.1 | HG1 | Clostridium bolteae | 152.2 kDa | |
| WP_045143632.1 | HG2 | Clostridium butyricum | 117.3 kDa | |
| WP_061307001.1 | HG3 | Clostridium botulinum | 85.2 kDa | |
| WP_016205751.1 | HG4 | Clostridium sartagoforme | 113.98 kDa | |
| WP_048925809.1 | HG5 | Clostridium sp. 1_1_41A1FAA | 117.5 kDa | |
| WP_119866036.1 | HG6 | | 117.8 kDa | |
| WP_118721317.1 | HG7 | | 120.3 kDa | |
| CpAgo | HG8 | Clostridium perfringens | 117.0 kDa | |
| IbAgo | HG9 | Intestinibacter bartlettii | 117.4 kDa | |

FIG. 97

SEQUENCE LISTING

```
<160> NUMBER OF SEQ ID NOS: 170

<210> SEQ ID NO 1
<211> LENGTH: 751
<212> TYPE: PRT
<213> ORGANISM: Clostridium perfringens

<400> SEQUENCE: 1

Met Val Gly Gly Tyr Lys Val Ser Asn Leu Thr Val Glu Ala Phe Glu
1               5                   10                  15

Gly Ile Gly Ser Val Asn Pro Met Leu Phe Tyr Gln Tyr Lys Val Thr
            20                  25                  30

Gly Lys Gly Lys Tyr Asp Asn Val Tyr Lys Ile Ile Lys Ser Ala Arg
        35                  40                  45

Tyr Lys Met His Ser Lys Asn Arg Phe Lys Pro Val Phe Ile Lys Asp
    50                  55                  60

Asp Lys Leu Tyr Thr Leu Glu Lys Leu Pro Asp Ile Glu Asp Leu Asp
65                  70                  75                  80
```

```
Phe Ala Asn Ile Asn Phe Val Lys Ser Glu Val Leu Ser Ile Glu Asp
                85                  90                  95

Asn Met Ser Ile Tyr Gly Glu Val Val Glu Tyr Tyr Ile Asn Leu Lys
            100                 105                 110

Leu Lys Lys Val Lys Val Leu Gly Lys Tyr Pro Lys Tyr Arg Ile Asn
        115                 120                 125

Tyr Ser Lys Glu Ile Leu Ser Asn Thr Leu Leu Thr Arg Glu Leu Lys
    130                 135                 140

Asp Glu Phe Lys Lys Ser Asn Lys Gly Phe Asn Leu Lys Arg Lys Phe
145                 150                 155                 160

Arg Ile Ser Pro Val Val Asn Lys Met Gly Lys Val Ile Leu Tyr Leu
                165                 170                 175

Ser Cys Ser Ala Asp Phe Ser Thr Asn Lys Asn Ile Tyr Glu Met Leu
            180                 185                 190

Lys Glu Gly Leu Glu Val Glu Gly Leu Ala Val Lys Ser Glu Trp Ser
        195                 200                 205

Asn Ile Ser Gly Asn Leu Val Ile Glu Ser Val Leu Glu Thr Lys Ile
    210                 215                 220

Ser Glu Pro Thr Ser Leu Gly Gln Ser Leu Ile Asp Tyr Tyr Lys Asn
225                 230                 235                 240

Asn Asn Gln Gly Tyr Arg Val Lys Asp Phe Thr Asp Glu Asp Leu Asn
                245                 250                 255

Ala Asn Ile Val Asn Val Arg Gly Asn Lys Lys Ile Tyr Met Tyr Ile
            260                 265                 270

Pro His Ala Leu Lys Pro Ile Ile Thr Arg Glu Tyr Leu Ala Lys Asn
        275                 280                 285

Asp Pro Glu Phe Ser Lys Glu Ile Glu Gln Leu Ile Lys Met Asn Met
    290                 295                 300

Asn Tyr Arg Tyr Glu Thr Leu Lys Ser Phe Val Asn Asp Ile Gly Val
305                 310                 315                 320

Ile Glu Glu Leu Asn Asn Leu Ser Phe Lys Asn Lys Tyr Tyr Glu Asp
                325                 330                 335

Val Lys Leu Leu Gly Tyr Ser Ser Gly Lys Ile Asp Glu Pro Val Leu
            340                 345                 350

Met Gly Ala Lys Gly Ile Ile Lys Asn Lys Met Gln Ile Phe Ser Asn
        355                 360                 365

Gly Phe Tyr Lys Leu Pro Glu Gly Lys Val Arg Phe Gly Val Leu Tyr
    370                 375                 380

Pro Lys Glu Phe Asp Gly Val Ser Arg Lys Ala Ile Arg Ala Ile Tyr
385                 390                 395                 400

Asp Phe Ser Lys Glu Gly Lys Tyr His Gly Glu Ser Asn Lys Tyr Ile
                405                 410                 415

Ala Glu His Leu Ile Asn Val Glu Phe Asn Pro Lys Glu Cys Ile Phe
            420                 425                 430

Glu Gly Tyr Glu Leu Gly Asp Ile Thr Glu Tyr Lys Lys Ala Ala Leu
        435                 440                 445

Lys Leu Asn Asn Tyr Asn Asn Val Asp Phe Val Ile Ala Ile Val Pro
    450                 455                 460

Asn Met Ser Asp Glu Glu Ile Glu Asn Ser Tyr Asn Pro Phe Lys Lys
465                 470                 475                 480

Ile Trp Ala Glu Leu Asn Leu Pro Ser Gln Met Ile Ser Val Lys Thr
                485                 490                 495
```

```
Ala Glu Ile Phe Ala Asn Ser Arg Asp Asn Thr Ala Leu Tyr Tyr Leu
            500                 505                 510

His Asn Ile Val Leu Gly Ile Leu Gly Lys Ile Gly Gly Ile Pro Trp
        515                 520                 525

Val Val Lys Asp Met Lys Gly Asp Val Asp Cys Phe Val Gly Leu Asp
    530                 535                 540

Val Gly Thr Arg Glu Lys Gly Ile His Tyr Pro Ala Cys Ser Val Val
545                 550                 555                 560

Phe Asp Lys Tyr Gly Lys Leu Ile Asn Tyr Tyr Lys Pro Asn Ile Pro
                565                 570                 575

Gln Asn Gly Glu Lys Ile Asn Thr Glu Ile Leu Gln Glu Ile Phe Asp
            580                 585                 590

Lys Val Leu Ile Ser Tyr Glu Glu Glu Asn Gly Ala Tyr Pro Lys Asn
        595                 600                 605

Ile Val Ile His Arg Asp Gly Phe Ser Arg Glu Asp Leu Asp Trp Tyr
    610                 615                 620

Glu Asn Tyr Phe Gly Lys Lys Asn Ile Lys Phe Asn Ile Ile Glu Val
625                 630                 635                 640

Lys Lys Ser Thr Pro Leu Lys Ile Ala Ser Ile Asn Glu Gly Asn Ile
                645                 650                 655

Thr Asn Pro Glu Lys Gly Ser Tyr Ile Leu Arg Gly Asn Lys Ala Tyr
            660                 665                 670

Met Val Thr Thr Asp Ile Lys Glu Asn Leu Gly Ser Pro Lys Pro Leu
        675                 680                 685

Lys Ile Glu Lys Ser Tyr Gly Asp Ile Asp Met Leu Thr Ala Leu Ser
    690                 695                 700

Gln Ile Tyr Ala Leu Thr Gln Ile His Val Gly Ala Thr Lys Ser Leu
705                 710                 715                 720

Arg Leu Pro Ile Thr Thr Gly Tyr Ala Asp Lys Ile Cys Lys Ala Ile
                725                 730                 735

Glu Phe Ile Pro Gln Gly Arg Val Asp Asn Arg Leu Phe Phe Leu
            740                 745                 750


<210> SEQ ID NO 2
<211> LENGTH: 745
<212> TYPE: PRT
<213> ORGANISM: Clostridium disporicum

<400> SEQUENCE: 2

Met Asn Asn Leu Thr Leu Glu Ala Phe Arg Gly Ile Gly Thr Ile Lys
1               5                   10                  15

Pro Leu Leu Phe Tyr Arg Tyr Lys Leu Ile Gly Lys Gly Lys Ile Glu
            20                  25                  30

Asn Thr Tyr Lys Thr Ile Arg Asn Ala Gln Asn Arg Met Ser Phe Asn
        35                  40                  45

Asn Lys Phe Lys Ala Thr Phe Ser Lys Asp Glu Ile Ile Tyr Thr Leu
    50                  55                  60

Glu Lys Phe Glu Ile Ile Pro Thr Leu Asp Asp Val Thr Ile Ile Phe
65                  70                  75                  80

Asp Gly Glu Glu Val Leu Pro Ile Lys Asp Asn Asn Lys Ile Tyr Ser
                85                  90                  95

Glu Val Ile Glu Phe Tyr Ile Asn Asn Asn Leu Arg Asn Val Lys Phe
            100                 105                 110

Asn Tyr Lys Tyr Pro Lys Tyr Arg Ala Ala Asn Thr Arg Glu Ile Thr
        115                 120                 125
```

```
Gly Asn Val Ile Leu Asp Lys Asp Met Asn Glu Lys Tyr Lys Lys Ser
    130                 135                 140

Asn Lys Gly Phe Glu Leu Lys Arg Lys Phe Ile Ile Ser Pro Lys Val
145                 150                 155                 160

Asp Asp Glu Gly Lys Val Thr Leu Phe Leu Asp Leu Asn Ala Ser Phe
                165                 170                 175

Asp Tyr Asp Lys Asn Ile Tyr Gln Met Ile Lys Ala Gly Ile Asp Val
            180                 185                 190

Val Gly Glu Glu Val Ile Asn Ile Trp Ser Asn Lys Lys Gln Arg Gly
        195                 200                 205

Lys Ile Lys Glu Ile Ser Asp Ile Lys Ile Asn Glu Pro Cys Asn Phe
    210                 215                 220

Gly Gln Ser Leu Ile Asp Tyr Tyr Ile Ser Ser Asn Gln Ala Ser Arg
225                 230                 235                 240

Val Asn Gly Phe Thr Glu Glu Glu Lys Asn Thr Asn Val Ile Ile Val
                245                 250                 255

Glu Ser Gly Lys Ser Arg Leu Ser Tyr Ile Pro His Ala Leu Lys Pro
            260                 265                 270

Ile Ile Thr Arg Glu Tyr Ile Ala Lys Asn Asp Glu Val Phe Ser Lys
        275                 280                 285

Glu Ile Glu Gly Leu Ile Lys Ile Asn Met Asn Tyr Arg Tyr Glu Ile
    290                 295                 300

Leu Lys Arg Phe Val Ser Asp Ile Gly Thr Ile Lys Glu Leu Asn Asn
305                 310                 315                 320

Leu Arg Phe Glu Lys Ile Tyr Met Asp Asn Ile Glu Ser Leu Gly Tyr
                325                 330                 335

Glu Gln Gly Gln Leu Lys Asp Pro Val Leu Ile Gly Gly Lys Gly Ile
            340                 345                 350

Leu Lys Asp Lys Ile His Val Phe Lys Ser Gly Phe Tyr Lys Ser Pro
        355                 360                 365

Asn Asp Glu Ile Lys Phe Gly Val Ile Tyr Pro Arg Gly Tyr Ile Lys
    370                 375                 380

Asp Thr Gln Ser Val Ile Arg Ala Ile Tyr Asp Phe Cys Thr Glu Gly
385                 390                 395                 400

Lys Tyr Gln Gly Lys Asp Asn Ile Phe Ile Asn Asn Lys Leu Met Asn
                405                 410                 415

Ile Lys Phe Ser Asn Lys Glu Cys Val Phe Glu Glu Tyr Glu Leu Asn
            420                 425                 430

Asp Ile Thr Glu Tyr Lys Arg Ala Ala Asn Lys Leu Lys Lys Asn Glu
        435                 440                 445

Asn Ile Lys Phe Val Ile Ala Ile Ile Pro Thr Ile Asn Glu Ser Asp
    450                 455                 460

Ile Glu Asn Pro Tyr Asn Pro Phe Lys Arg Val Cys Ala Glu Ile Asn
465                 470                 475                 480

Leu Pro Ser Gln Met Ile Ser Leu Lys Thr Ala Lys Arg Phe Ser Thr
                485                 490                 495

Ser Arg Gly Gln Ser Glu Leu Tyr Phe Leu His Asn Ile Ser Leu Gly
            500                 505                 510

Ile Leu Gly Lys Ile Gly Gly Val Pro Trp Val Ile Lys Asp Met Pro
        515                 520                 525

Gly Glu Val Asp Cys Phe Val Gly Leu Asp Val Gly Thr Lys Glu Lys
    530                 535                 540
```

```
Gly Ile His Tyr Pro Ala Cys Ser Val Leu Phe Asp Lys Tyr Gly Lys
545                 550                 555                 560

Leu Ile Asn Tyr Tyr Lys Pro Thr Ile Pro Gln Ser Gly Glu Ile Ile
                565                 570                 575

Lys Thr Asp Val Leu Gln Glu Ile Phe Asp Lys Val Leu Leu Ser Tyr
            580                 585                 590

Glu Glu Glu Asn Gly Gln Tyr Pro Arg Asn Ile Val Ile His Arg Asp
        595                 600                 605

Gly Phe Ser Arg Glu Asp Leu Glu Trp Tyr Lys Asn Tyr Phe Leu Lys
    610                 615                 620

Lys Asn Ile Glu Phe Ser Ile Val Glu Val Arg Lys Asn Phe Ala Thr
625                 630                 635                 640

Arg Leu Val Asn Asn Phe Asn Asp Glu Val Ser Asn Pro Ser Lys Gly
                645                 650                 655

Ser Phe Ile Leu Arg Asp Asn Glu Ala Ile Val Val Thr Thr Asp Ile
            660                 665                 670

Asn Asp Asn Met Gly Ala Pro Lys Pro Ile Lys Val Glu Lys Thr Tyr
        675                 680                 685

Gly Asp Ile Asp Met Leu Thr Ile Ile Asn Gln Ile Tyr Ala Leu Thr
    690                 695                 700

Gln Ile His Val Gly Ser Ala Lys Ser Leu Arg Leu Pro Ile Thr Thr
705                 710                 715                 720

Gly Tyr Ala Asp Lys Ile Cys Lys Ala Ile Asp Tyr Ile Pro Ser Gly
                725                 730                 735

Gln Val Asp Asn Arg Leu Phe Phe Leu
            740                 745


<210> SEQ ID NO 3
<211> LENGTH: 745
<212> TYPE: PRT
<213> ORGANISM: Clostridium saudiense

<400> SEQUENCE: 3

Met Asn Asn Leu Met Leu Glu Ala Phe Lys Gly Ile Gly Thr Ile Lys
1               5                   10                  15

Pro Leu Val Phe Tyr Arg Tyr Lys Leu Ile Gly Lys Gly Lys Ile Glu
            20                  25                  30

Asn Thr Tyr Lys Thr Ile Ser Asn Ala Lys Asn Lys Met Ser Phe Asn
        35                  40                  45

Asn Lys Phe Lys Ala Thr Phe Ser Lys Gly Glu Thr Ile Tyr Thr Leu
    50                  55                  60

Glu Lys Phe Glu Val Met Pro Asn Leu Asn Asp Val Thr Ile Glu Phe
65                  70                  75                  80

Asp Gly Glu Glu Val Leu Pro Ile Lys Asp Asn Asn Glu Ile Tyr Ser
                85                  90                  95

Glu Val Val Gln Phe Tyr Ile Asn Asn Asn Leu Arg Lys Ile Lys Leu
            100                 105                 110

Asp Asn Lys Tyr Gln Lys Tyr Arg Ala Thr Asn Thr Arg Glu Ile Thr
        115                 120                 125

Gly Asn Val Ile Leu Asp Lys Asp Phe Lys Glu Lys Tyr Lys Lys Ser
    130                 135                 140

Lys Ser Gly Phe Gln Leu Lys Arg Lys Phe Ile Ile Ser Pro Lys Val
145                 150                 155                 160

Asn Asp Glu Gly Lys Val Thr Leu Phe Leu Asp Leu Asn Ser Ser Phe
                165                 170                 175
```

```
Asp Tyr Asp Lys Asn Ile Tyr Gln Met Ile Lys Ala Gly Met Asp Val
            180                 185                 190

Val Gly Gln Glu Val Ile Asn Thr Trp Asn Asn Lys Lys Gln Lys Gly
        195                 200                 205

Lys Ile Lys Lys Ile Ser Glu Leu Thr Ile Ser Glu Pro Cys Asn Phe
    210                 215                 220

Gly Gln Ser Leu Ile Asp Tyr Tyr Val Ser Leu Asn Gln Ala Val Arg
225                 230                 235                 240

Val Lys Asn Phe Thr Glu Glu Glu Lys Asn Thr Asn Val Ile Val Val
                245                 250                 255

Gln Val Gly Lys Gly Glu Val Glu Tyr Ile Pro His Ala Leu Lys Pro
            260                 265                 270

Ile Ile Thr Arg Glu Tyr Ile Lys Lys Tyr Asp Glu Ala Phe Ser Lys
        275                 280                 285

Glu Val Glu Asn Leu Ile Lys Ile Asn Met Ser Tyr Arg Tyr Glu Ile
    290                 295                 300

Leu Lys Lys Phe Ile Asp Asp Ile Gly Ser Ile Thr Glu Leu Asn Asn
305                 310                 315                 320

Leu Lys Phe Glu Asn Thr Tyr Ile Asp Asn Ile Glu Ser Leu Gly Tyr
                325                 330                 335

Gln Gln Gly Lys Leu Asn Asp Pro Val Leu Ile Gly Gly Lys Gly Ile
            340                 345                 350

Leu Lys Asp Lys Ile His Val Phe Lys Ser Gly Phe Tyr Lys Ser Pro
        355                 360                 365

Ile Asp Glu Val Lys Phe Gly Val Ile Tyr Pro Lys Gly His Thr Asn
    370                 375                 380

Asp Ser Lys Ser Thr Ile Arg Ala Ile Tyr Asp Phe Cys Thr Asp Gly
385                 390                 395                 400

Lys Tyr Gln Gly Lys Asp Asn Ile Phe Ile Asn Asn Lys Leu Met Asn
                405                 410                 415

Ile Lys Phe Ser Asn Gln Asp Cys Val Phe Glu Glu Tyr Glu Leu Asn
            420                 425                 430

Asp Ile Thr Glu Tyr Lys Arg Ala Ala Asn Lys Leu Lys Asn Asn Glu
        435                 440                 445

Asn Ile Lys Phe Val Ile Ala Ile Ile Pro Ala Ile Asp Glu Ser Asp
    450                 455                 460

Ile Glu Asn Pro Tyr Asn Pro Phe Lys Arg Val Cys Ala Glu Leu Asn
465                 470                 475                 480

Leu Pro Ser Gln Met Val Ser Leu Lys Thr Ala Lys Arg Phe Gly Thr
                485                 490                 495

Ser Lys Gly Asn Asn Glu Leu Tyr Phe Leu His Asn Ile Ser Leu Gly
            500                 505                 510

Ile Leu Gly Lys Ile Gly Gly Val Pro Trp Val Ile Lys Asp Met Pro
        515                 520                 525

Gly Glu Val Asp Cys Phe Val Gly Leu Asp Val Gly Thr Lys Glu Lys
    530                 535                 540

Gly Ile His Tyr Pro Ala Cys Ser Val Leu Phe Asp Lys Tyr Gly Lys
545                 550                 555                 560

Leu Ile Asn Tyr Tyr Lys Pro Thr Ile Pro Gln Ser Gly Glu Ile Ile
                565                 570                 575

Lys Thr Asp Val Leu Gln Glu Ile Phe Asp Lys Val Leu Leu Ser Tyr
            580                 585                 590
```

```
Glu Glu Glu Asn Gly Gln Tyr Pro Arg Asn Ile Val Ile His Arg Asp
        595                 600                 605

Gly Phe Ser Arg Glu Asp Leu Glu Trp Tyr Lys Asn Tyr Phe Ile Lys
    610                 615                 620

Lys Asn Ile Asn Phe Thr Ile Val Glu Ile Lys Lys Asn Phe Ala Thr
625                 630                 635                 640

Arg Val Ala Asn Asn Ile Asn Asn Glu Val Ser Asn Pro Phe Lys Gly
                645                 650                 655

Ser Phe Ile Leu Arg Glu Asn Glu Ala Ile Val Val Thr Thr Asp Ile
            660                 665                 670

Lys Asp Asn Ile Gly Ala Pro Lys Pro Ile Lys Val Glu Lys Thr Tyr
        675                 680                 685

Gly Asp Ile Asp Met Met Thr Ile Ile Asn Gln Ile Tyr Ala Leu Thr
    690                 695                 700

Gln Ile His Val Gly Ser Ala Lys Ser Met Arg Leu Pro Ile Thr Thr
705                 710                 715                 720

Gly Tyr Ala Asp Lys Ile Cys Lys Ser Ile Glu Tyr Ile Pro Ser Gly
                725                 730                 735

Arg Val Asp Asn Arg Leu Phe Phe Leu
            740                 745


<210> SEQ ID NO 4
<211> LENGTH: 758
<212> TYPE: PRT
<213> ORGANISM: Rhodopirellula maiorica

<400> SEQUENCE: 4

Met Leu Gln Leu Asn Gly Phe Ser Ile Glu Ile Ala Gly Gly Ser Leu
1               5                   10                  15

Thr Val Leu Lys Ser Lys Ile Ala Pro Thr Asp Val Lys Glu Thr Arg
            20                  25                  30

Arg Ser Leu Glu Asp Asp Trp Phe Thr Met Tyr His Glu Gly His Leu
        35                  40                  45

Tyr Ser Leu Ala Lys Asn Ser Asn Ala Ser Gly Gly Leu Gly Glu Thr
    50                  55                  60

Glu Leu Leu Val Leu Ser Asp His Leu Gly Leu Arg Phe Val Lys Ala
65                  70                  75                  80

Met Leu Asp Gln Ala Met Arg Gly Val Phe Glu Ala Tyr Asp Pro Val
                85                  90                  95

Arg Asp Arg Pro Phe Thr Phe Leu Ala Arg Asn Val Asp Leu Val Ala
            100                 105                 110

Leu Ala Ala Glu Asn Leu Glu Ser Lys Pro Ser Leu Leu Ser Lys Phe
        115                 120                 125

Glu Ile Arg Pro Lys Tyr Glu Leu Glu Ala Lys Val Val Glu Phe Arg
    130                 135                 140

Pro Gly Glu Leu Glu Leu Met Leu Ala Leu Asn Leu Thr Thr Arg Trp
145                 150                 155                 160

Ile Cys Asn Ala Ser Val Asp Glu Leu Ile Glu Lys Asn Ile Pro Val
                165                 170                 175

Arg Gly Met His Leu Ile Arg Arg Asn Arg Glu Pro Gly Gln Arg Ser
            180                 185                 190

Leu Val Gly Thr Phe Asp Arg Met Glu Gly Asp Asn Ala Leu Leu Gln
        195                 200                 205

Asp Ala Tyr Asp Gly Gln Asp Lys Ile Ala Ala Ser Gln Val Arg Ile
    210                 215                 220
```

```
Glu Gly Ser Lys Glu Val Phe Ala Thr Ser Leu Arg Arg Leu Leu Gly
225                 230                 235                 240

Asn Arg Tyr Thr Ser Phe Met His Ser Val Asp Asn Glu Tyr Gly Lys
                245                 250                 255

Leu Cys Gly Gly Leu Gly Phe Asp Gly Glu Leu Arg Lys Met Gln Gly
            260                 265                 270

Phe Leu Ala Lys Lys Ser Pro Ile Gln Leu His Gly Gly Val Glu Val
        275                 280                 285

Ser Val Gly Gln Arg Val Gln Leu Thr Asn Gln Pro Gly Tyr Lys Thr
    290                 295                 300

Thr Val Glu Leu Leu Gln Ser Lys Tyr Cys Phe Asp Arg Ser Arg Thr
305                 310                 315                 320

Lys Leu His Pro Tyr Ala Trp Asp Gly Leu Ala Arg Phe Gly Pro Phe
                325                 330                 335

Asp Arg Gly Ser Phe Pro Thr Arg Ser Pro Arg Ile Leu Leu Val Thr
            340                 345                 350

Pro Asp Ser Ala Ser Gly Lys Val Ser Gln Ala Leu Lys Lys Phe Arg
        355                 360                 365

Asp Gly Phe Gly Ser Ser Gln Ser Ser Met Tyr Asp Gly Phe Leu Asp
    370                 375                 380

Thr Phe His Leu Ser Asn Ala Pro Phe Phe Pro Leu Pro Val Lys Leu
385                 390                 395                 400

Asp Gly Val Gln Arg Ser Asp Val Gly Lys Ala Tyr Arg Lys Ala Ile
                405                 410                 415

Glu Asp Lys Leu Ala Arg Asp Asp Asp Phe Asp Ala Ala Phe Asn Ile
            420                 425                 430

Leu Leu Asp Glu His Ala Asn Leu Pro Asp Ser His Asn Pro Tyr Leu
        435                 440                 445

Val Ala Lys Ser Ile Leu Leu Ser His Gly Ile Pro Val Gln Glu Ala
    450                 455                 460

Arg Val Ser Thr Leu Thr Ala Asn Glu Tyr Ser Leu Gln His Thr Phe
465                 470                 475                 480

Arg Asn Val Ala Thr Ala Leu Tyr Ala Lys Met Gly Gly Val Pro Trp
                485                 490                 495

Thr Val Asp His Gly Glu Thr Val Asp Asp Glu Leu Val Val Gly Ile
            500                 505                 510

Gly Asn Ala Glu Leu Ser Gly Ser Arg Phe Glu Lys Arg Gln Arg His
        515                 520                 525

Ile Gly Ile Thr Thr Val Phe Arg Gly Asp Gly Asn Tyr Leu Leu Ser
    530                 535                 540

Asn Leu Ser Lys Glu Cys Arg Tyr Glu Asp Tyr Pro Asp Val Leu Arg
545                 550                 555                 560

Glu Ser Thr Ile Ala Val Leu Arg Glu Val Lys Gln Arg Asn Asn Trp
                565                 570                 575

Leu Pro Gly Gln Thr Val Arg Ile Val Phe His Ala Phe Lys Pro Leu
            580                 585                 590

Lys Asn Val Glu Ile Ala Asp Ile Ile Ala Ser Ser Val Lys Glu Val
        595                 600                 605

Gly Ser Glu Gln Thr Ile Glu Phe Ala Phe Leu Asn Val Ser Leu Asp
    610                 615                 620

His Ser Phe Thr Leu Leu Asp Met Ala Gln Arg Gly Ile Thr Lys Lys
625                 630                 635                 640
```

```
Asn Gln Thr Lys Gly Ile Tyr Val Pro Arg Arg Gly Met Thr Val Gln
                645                 650                 655

Val Gly Arg Tyr Thr Arg Leu Val Thr Ser Ile Gly Pro His Met Val
            660                 665                 670

Lys Arg Ala Asn Leu Ala Leu Pro Arg Pro Leu Leu Ile His Leu His
        675                 680                 685

Lys Gln Ser Thr Tyr Arg Asp Leu Ser Tyr Leu Ser Glu Gln Val Leu
    690                 695                 700

Asn Phe Thr Thr Leu Ser Trp Arg Ser Thr Leu Pro Ser Glu Lys Pro
705                 710                 715                 720

Val Thr Ile Leu Tyr Ser Ser Leu Ile Ala Asp Leu Leu Gly Arg Leu
                725                 730                 735

Lys Ser Val Asp Asp Trp Ser Pro Ala Val Leu Asn Thr Lys Leu Arg
            740                 745                 750

Asn Ser Lys Trp Phe Leu
        755


<210> SEQ ID NO 5
<211> LENGTH: 705
<212> TYPE: PRT
<213> ORGANISM: Paenibacillus odorifer

<400> SEQUENCE: 5

Met Asn Thr Pro Leu Thr His Tyr Val Leu Thr Glu Trp Glu Ser Asp
1               5                   10                  15

Thr Asn Thr Asn Val Leu His Ile His Leu Tyr Thr Leu Pro Val Arg
            20                  25                  30

Asn Val Phe Glu Gln His Lys Glu Asn Gly Asn Ala Cys Phe Asp Leu
        35                  40                  45

Arg Lys Leu Asn Arg Ser Leu Ile Ile Asp Phe Tyr Asp Gln Tyr Ile
    50                  55                  60

Val Ser Trp Gln Pro Ile Glu Asn Trp Gly Glu Tyr Thr Phe Thr Gln
65                  70                  75                  80

His Glu Tyr Arg Ser Ile Asn Pro Thr Ile Leu Ala Glu Arg Ala Ile
                85                  90                  95

Leu Glu Arg Leu Leu Leu Arg Thr Ile Glu Ser Val Gln Pro Lys Lys
            100                 105                 110

Glu Ile Ala Ala Gly Ser Arg Lys Phe Thr Trp Leu Lys Ala Glu Lys
        115                 120                 125

Val Val Glu Asn Ile Ser Ile His Arg Val Ile Gln Cys Asp Val Thr
    130                 135                 140

Val Asp Tyr Ala Gly Lys Ile Ser Val Gly Phe Asp Leu Asn His Ser
145                 150                 155                 160

Tyr Arg Thr Asn Glu Ser Val Tyr Asp Leu Met Lys Ser Asn Ala Ile
                165                 170                 175

Phe Lys Gly Asp Arg Val Ile Asp Ile Tyr Asn Asn Leu His Tyr Glu
            180                 185                 190

Phe Val Glu Ile Ser Asn Ser Thr Ile Asn Asp Ser Ile Pro Glu Leu
        195                 200                 205

Asn Gln Ser Val Val Asn Tyr Phe Thr Lys Glu Arg Lys Gln Ala Trp
    210                 215                 220

Lys Val Asp Lys Leu Glu Gln Ser Met Pro Val Val Tyr Leu Lys Ala
225                 230                 235                 240

Phe Asn Gly Ser Arg Ile Ala Tyr Ala Pro Ala Met Leu Gln Lys Glu
                245                 250                 255
```

```
Leu Thr Phe Glu Ser Leu Pro Thr Asn Val Val Arg Gln Thr Ser Glu
            260                 265                 270

Ile Phe Lys Gln Asn Ala Asn Gln Lys Ile Lys Thr Leu Leu Asp Glu
        275                 280                 285

Ile Gln Lys Ile Leu Ala Arg Thr Asp Lys Ile Lys Phe Asn Lys Gln
    290                 295                 300

Lys Leu Leu Val Gln Gln Ala Gly Tyr Glu Ile Leu Glu Leu Ser Asn
305                 310                 315                 320

Pro Asn Leu Gln Phe Gly Lys Asn Val Thr Gln Thr Gln Leu Lys Tyr
                325                 330                 335

Gly Leu Asp Lys Gly Gly Val Val Ala Ser Lys Pro Leu Ser Ile Asn
            340                 345                 350

Leu Leu Val Tyr Pro Glu Leu Ile Asp Thr Lys Leu Asp Val Ile Asn
        355                 360                 365

Asp Phe Asn Asp Lys Leu Asn Ala Leu Ser His Lys Trp Gly Val Pro
    370                 375                 380

Leu Ser Ile Leu Lys Lys Ser Gly Ala Tyr Arg Asn Arg Pro Ile Asp
385                 390                 395                 400

Phe Thr Asn Pro His Gln Leu Ala Ile Leu Leu Lys Glu Leu Thr Lys
                405                 410                 415

Asn Leu Phe Gln Glu Leu Thr Leu Val Ile Ile Pro Glu Lys Ile Ser
            420                 425                 430

Gly Met Trp Tyr Asp Leu Val Lys Lys Glu Phe Gly Gly Asn Ser Ser
        435                 440                 445

Val Pro Thr Gln Phe Ile Thr Ile Glu Thr Leu Gln Lys Ala Asn Asp
    450                 455                 460

Tyr Ile Leu Gly Asn Leu Leu Leu Gly Leu Tyr Ser Lys Ser Gly Ile
465                 470                 475                 480

Gln Pro Trp Ile Leu Asn Ser Pro Leu Ser Ser Asp Cys Phe Ile Gly
                485                 490                 495

Leu Asp Val Ser His Glu Ala Gly Arg His Ser Thr Gly Ile Val Gln
            500                 505                 510

Val Val Gly Lys Asp Gly Arg Val Leu Ser Ser Lys Ala Asn Thr Ser
        515                 520                 525

Asn Glu Ala Gly Glu Lys Ile Arg His Glu Thr Met Cys Gln Ile Val
    530                 535                 540

Tyr Ser Ala Ile Asp Gln Tyr Gln Gln His Tyr Asn Glu Arg Pro Lys
545                 550                 555                 560

His Val Thr Phe His Arg Asp Gly Phe Cys Arg Glu Asp Leu Leu Ser
                565                 570                 575

Leu Asp Glu Val Met Asn Ser Leu Asp Val Gln Tyr Asp Met Val Glu
            580                 585                 590

Ile Ile Lys Lys Thr Asn Arg Arg Met Ala Leu Thr Val Gly Lys Gln
        595                 600                 605

Gly Trp Glu Thr Lys Pro Gly Leu Cys Tyr Leu Lys Asp Glu Ser Ala
    610                 615                 620

Tyr Leu Ile Ala Thr Asn Pro His Pro Arg Val Gly Thr Ala Gln Pro
625                 630                 635                 640

Ile Lys Ile Ile Lys Lys Lys Gly Ser Leu Pro Ile Glu Ala Ile Ile
                645                 650                 655

Gln Asp Ile Tyr His Leu Ser Phe Met His Ile Gly Ser Leu Leu Lys
            660                 665                 670
```

Cys Arg Leu Pro Ile Thr Thr Tyr Tyr Ala Asp Leu Ser Ser Thr Phe
675 680 685

Phe Asn Arg Gln Trp Leu Pro Ile Asp Ser Gly Glu Ala Leu His Phe
690 695 700

Val
705

<210> SEQ ID NO 6
<211> LENGTH: 766
<212> TYPE: PRT
<213> ORGANISM: Hyphomonas sp.

<400> SEQUENCE: 6

Met Pro His Thr Ser Leu Leu Leu Asn Phe Leu Pro Val Ser Leu Ser
1 5 10 15

Gly Asp Thr Arg Ile His Val Gly Tyr Arg Pro Tyr Asn Glu Asp Val
20 25 30

Leu Arg Glu Leu Arg Glu Glu Phe Gly Glu Ser His Val Phe Lys Arg
35 40 45

Asp Tyr Gln Glu Asp Thr Ile Ser Glu Ile Pro Val Ile Pro Gly Ala
50 55 60

Glu Pro Leu Ser Asp Lys Ser Thr Gly Val Asp Leu Ala Glu Ala Arg
65 70 75 80

Trp Leu Trp Lys Pro Leu Leu Asn Ala Ala Leu Leu Arg Leu Phe Ser
85 90 95

Gly Ser Arg Glu Ile Thr Ser Asp Tyr Pro Val Ser Val Leu Gly Asn
100 105 110

Pro Lys Asn Asn Phe Ile Ser His Ala Asn Leu Pro Asp Trp Val Arg
115 120 125

Ile Leu Pro Leu Leu Glu Phe Glu Ser Arg Thr Leu Phe Gly Gly Lys
130 135 140

Ser Gly Pro Gln Phe Gly Leu Val Cys Asn Ala Arg Thr Arg His Gln
145 150 155 160

Val Leu Ala Gly Cys Asp His Leu Ile Glu Arg Gly Ile Ser Pro Ile
165 170 175

Gly Arg Tyr Val Gln Ile Asp Gln Pro Gln Arg Asp Ser Arg Leu Ala
180 185 190

Pro Arg Gly Leu Thr Val Gly Lys Val Ser Ser Ile Asp Gly Asp Thr
195 200 205

Leu Ile Leu Glu Asp His Arg Lys Gly Tyr Glu Arg Val Lys Ala Ser
210 215 220

Asp Ala Arg Leu Thr Gly Asn Arg Ala Asp Phe Asp Trp Cys Val Asn
225 230 235 240

Ala Leu Leu Pro Gly Gln Gly Gln Ala Thr Leu Ser Arg Ala Trp Asp
245 250 255

Ala Met Ser Ala Leu Asn Gln Gly Pro Gly Arg Leu Gln Met Ile Asn
260 265 270

Gln Thr Ala Glu Tyr Leu Arg Thr Val Asn Leu Glu Ala Val Pro Gly
275 280 285

Val Ala Phe Glu Ile Gly Glu Trp Leu Ser Ser Thr Asp Ala Gln Phe
290 295 300

Pro Val Thr Glu Thr Ile Asp Arg Pro Thr Leu Val Phe His Pro Ser
305 310 315 320

Gly Arg Pro Asn Asp Thr Trp Asn Glu Arg Gly Ile Lys Asp Asn Gly
325 330 335

-continued

```
Pro His Asp Gln Arg Thr Phe Thr Pro Lys Gln Leu Asn Ile Ala Val
            340                 345                 350

Ile Cys Gln Gly Arg Phe Glu Gly Gln Val Asp Arg Phe Val Gly Lys
        355                 360                 365

Leu Leu Asp Gly Ile Pro Asp Phe Gln Leu Arg Asn Gly Arg Lys Pro
    370                 375                 380

Tyr Asp Asp Gly Phe Leu Ser Arg Phe Arg Leu Glu Arg Ala Asn Val
385                 390                 395                 400

Gln Thr Phe Gln Ala Asn Ser Ala Ser Arg Glu Ala Tyr Glu Ala Ala
                405                 410                 415

Cys Glu Asp Ala Leu Lys His Ala Ala Asp Asn Gly Phe Gly Trp Asp
            420                 425                 430

Leu Ala Ile Val Gln Ile Glu Glu Asp Phe Lys Ala Leu Pro Gly Pro
        435                 440                 445

Gln Asn Pro Tyr Tyr Ala Thr Lys Ala Met Leu Leu Arg Asn Asn Val
    450                 455                 460

Ala Val Gln Asn Ile Arg Ile Glu Thr Met Ser Glu Pro Asp Lys Ser
465                 470                 475                 480

Leu Val Tyr Thr Met Asn Gln Val Ser Leu Ala Cys Tyr Ala Lys Leu
                485                 490                 495

Gly Gly Arg Pro Trp Leu Leu Gly Ala Gln Gln Ser Val Ala His Glu
            500                 505                 510

Leu Val Ile Gly Leu Gly Ser His Thr Glu Gln Gln Ser Arg Phe Asp
        515                 520                 525

Gln Ser Val Arg Tyr Val Gly Ile Thr Thr Val Phe Ser Ser Asp Gly
    530                 535                 540

Gly Tyr His Leu Ser Glu Arg Thr Gly Val Val Pro Phe Glu Asp Tyr
545                 550                 555                 560

Ala Lys Glu Leu Thr Asp Thr Leu Thr Arg Thr Ile Glu Arg Val Arg
                565                 570                 575

Arg Glu Asp Asn Trp Lys Asn Thr Asp Arg Val Arg Leu Val Phe His
            580                 585                 590

Ala Phe Lys Gln Ile Lys Asp Ile Glu Ala Glu Ala Ile Lys Gln Ala
        595                 600                 605

Val Glu Ser Leu Asp Leu Glu Asn Val Val Phe Ala Phe Val His Val
    610                 615                 620

Ala Glu His His Pro Tyr Leu Ile Phe Asp Gln Asn Gln Glu Gly Leu
625                 630                 635                 640

Pro His Trp Glu Lys Asn Arg Ser Lys Arg Lys Gly Val Leu Gly Pro
                645                 650                 655

Ser Arg Gly Val His Ile Lys Leu Ala Asp Ser Glu Ser Leu Val Val
            660                 665                 670

Phe Ala Gly Ala Ser Glu Leu Lys Gln Ala Ala His Gly Met Pro Arg
        675                 680                 685

Ala Cys Leu Leu Lys Leu His Arg Asn Ser Thr Phe Arg Asp Met Thr
    690                 695                 700

Tyr Leu Ala Arg Gln Ala Phe Asp Phe Thr Ala His Ser Trp Arg Val
705                 710                 715                 720

Met Thr Pro Glu Pro Phe Pro Ile Thr Ile Lys Tyr Ser Asp Leu Ile
                725                 730                 735

Ala Glu Arg Leu Ala Gly Leu Lys Gln Ile Glu Thr Trp Asp Asp Asp
            740                 745                 750
```

```
Ala Val Arg Phe Arg Asn Ile Gly Lys Ala Pro Trp Phe Leu
        755                 760                 765


<210> SEQ ID NO 7
<211> LENGTH: 808
<212> TYPE: PRT
<213> ORGANISM: Calothrix sp.

<400> SEQUENCE: 7

Met Ile Met Ser Leu Glu Ser Asn Ile Phe Thr Phe Ser Asn Leu Gly
1               5                   10                  15

Thr Leu Thr Thr Gln Tyr Arg Leu Tyr Glu Ile Arg Gly Leu Gln Lys
            20                  25                  30

Arg His Gln Glu Tyr Tyr Gln Asn Arg Gln Ile Leu Ile His Arg Leu
        35                  40                  45

Ser Tyr Leu Leu Lys Asn Ala Val Thr Ile Ile Glu Arg Asp Glu Lys
    50                  55                  60

Leu Tyr Leu Val Val Ala Ala Asp Ala Pro Glu Pro Pro Asn Ser Tyr
65                  70                  75                  80

Pro Ile Val Arg Gly Val Ile Tyr Phe Lys Pro Thr Gly Gln Ile Leu
                85                  90                  95

Thr Leu Asp Tyr Ser Leu Arg Thr Pro Gln Asn Glu Glu Ile Cys Gln
            100                 105                 110

Arg Phe Leu His Phe Met Val Gln Ser Ala Leu Phe Gln Asn Ala Asn
        115                 120                 125

Leu Trp Gln Pro Ser Ala Gly Lys Ala Phe Phe Glu Lys Lys Pro Ser
    130                 135                 140

Phe Glu Phe Gly Ser Ile Leu Leu Phe Gln Gly Phe Ser Val Arg Pro
145                 150                 155                 160

Ile Phe Thr Lys Asp Lys Ile Gly Leu Cys Val Asp Ile His His Lys
                165                 170                 175

Phe Val Ser Lys Glu Pro Leu Pro Ser Tyr Leu Asn Phe Asn Glu Phe
            180                 185                 190

Gln Lys Tyr Arg Gly Val Ser Cys Ile Tyr His Phe Gly His Gln Trp
        195                 200                 205

Tyr Glu Ile Gln Leu Ser Glu Leu Ser Glu Leu Asn Ala Thr Glu Ala
    210                 215                 220

Met Val Pro Ile Glu Asn Lys Phe Val Thr Leu Ile Asn Tyr Ile Thr
225                 230                 235                 240

Gln Gln Ala Arg Lys Pro Ile Pro Glu Glu Leu Ala Asn Val Ser Gln
                245                 250                 255

Asp Ala Ala Val Val His Tyr Phe Asn Asn Gln Asn Gln Asp Arg Met
            260                 265                 270

Ala Val Thr Ser Leu Cys Tyr Gln Val Tyr Asp Asn Ser Tyr Pro Glu
        275                 280                 285

Ile Arg Lys Tyr His Gln His Thr Ile Leu Lys Pro His Ile Arg Arg
    290                 295                 300

Ser Ala Ile His Gly Ile Val Gln Lys Tyr Leu Ala Glu Leu Arg Phe
305                 310                 315                 320

Gly Asp Ile Thr Leu Lys Val Ser Thr Ile Pro Glu Leu Val Pro Gln
                325                 330                 335

Glu Met Phe Asn Leu Pro Asp Tyr Cys Phe Gly Asn Asp Tyr Lys Leu
            340                 345                 350

Ser Val Lys Gly Ser Glu Gly Thr Ala Gln Ile Ser Leu Asp Gln Val
        355                 360                 365
```

```
Gly Lys Gln Arg Leu Glu Leu Leu Ser Lys Ala Glu Ala Gly Ile Tyr
    370                 375                 380

Val Gln Glu Lys Phe Asp Arg Gln Tyr Ile Leu Leu Pro Gln Thr Val
385                 390                 395                 400

Gly Asp Ser Phe Gly Ser Arg Phe Ile Asp Asp Leu Lys Lys Thr Val
                405                 410                 415

Asp Lys Leu Tyr Pro Ala Gly Gly Gly Tyr Asp Pro Lys Ile Ile Tyr
            420                 425                 430

Tyr Pro Asp Arg Gly Leu Arg Thr Tyr Ile Glu Gln Gly Arg Ala Ile
        435                 440                 445

Leu Lys Thr Val Glu Glu Asn Glu Leu Gln Pro Gly Tyr Gly Ile Val
    450                 455                 460

Met Leu His Asp Ser Pro Asp Arg Leu Leu Arg Gln His Asp Lys Leu
465                 470                 475                 480

Ala Ala Leu Val Ile Arg Glu Leu Lys Asp Tyr Asp Leu Tyr Val Ala
                485                 490                 495

Val Ile His Ser Lys Thr Gly Arg Glu Cys Tyr Glu Leu Arg Tyr Asn
            500                 505                 510

Asn Gln Gly Glu Pro Phe Tyr Ala Val Ile His Glu Lys Arg Gly Lys
        515                 520                 525

Leu Tyr Gly Tyr Met Arg Gly Val Ala Leu Asn Lys Val Leu Leu Thr
    530                 535                 540

Asn Glu Arg Trp Pro Phe Val Leu Ser Thr Pro Leu Asn Ala Asp Val
545                 550                 555                 560

Val Ile Gly Ile Asp Val Lys His His Thr Ala Gly Tyr Ile Val Val
                565                 570                 575

Asn Lys Asn Gly Ser Arg Ile Trp Thr Leu Pro Thr Ile Thr Ser Lys
            580                 585                 590

Gln Lys Glu Arg Leu Pro Ser Ile Gln Ile Lys Ala Ser Leu Ile Glu
        595                 600                 605

Ile Ile Thr Lys Glu Ala Glu Gln Thr Val Asp Gln Leu His Asn Ile
    610                 615                 620

Val Ile His Arg Asp Gly Arg Ile His Glu Ser Glu Ile Glu Gly Ala
625                 630                 635                 640

Lys Gln Ala Met Ala Glu Leu Ile Ser Arg Cys Thr Leu Pro Val Asn
                645                 650                 655

Ala Thr Leu Thr Ile Leu Glu Val Ala Lys Ser Ser Pro Val Ser Phe
            660                 665                 670

Arg Leu Phe Asp Val Ser Asn Thr Asn Ser Lys Asp Pro Phe Val Gln
        675                 680                 685

Asn Pro Gln Val Gly Cys Tyr Tyr Ile Ala Asn Ser Thr Asp Ala Tyr
    690                 695                 700

Leu Cys Ser Thr Gly Arg Ala Phe Leu Lys Phe Gly Thr Val Asn Pro
705                 710                 715                 720

Leu His Ile Arg Tyr Val Glu Gly Thr Leu Pro Leu Lys Leu Cys Leu
                725                 730                 735

Glu Asp Val Tyr Tyr Leu Thr Ala Leu Pro Trp Thr Lys Pro Asp Gly
            740                 745                 750

Cys Ile Arg Tyr Pro Ile Thr Val Lys Ile Asn Asp Arg Arg Leu Gly
        755                 760                 765

Glu Asp Ala Ser Glu Tyr Asp Glu Asp Ala Leu Arg Phe Glu Leu Phe
    770                 775                 780
```

Glu Ser Leu Glu Ser Glu Asp Asp Phe Asp Glu Met Thr Asp Ser Asp
785 790 795 800

Phe Asn Gln Glu Glu Thr Met Val
805

<210> SEQ ID NO 8
<211> LENGTH: 674
<212> TYPE: PRT
<213> ORGANISM: Deinococcus sp.

<400> SEQUENCE: 8

Leu Lys Leu Asn His Phe Pro Leu Asn Pro Asp Leu Pro Leu Tyr Ile
1 5 10 15

Thr Glu Tyr Ala His Arg Asn Pro Arg Ala Leu Leu Gly Phe Val Arg
20 25 30

Gly Gln Gly Phe Trp Ala Gln Gln Val Gly Glu Gln Val Gln Val Tyr
35 40 45

His Gly Arg Pro Gln Pro Thr Phe Arg Gly Val Gln Val Ile Ser His
50 55 60

Thr Arg Leu Asp Pro Asp His Pro Ala Phe Asp Gln Gly Val Leu Ser
65 70 75 80

Leu Ile Arg Gln Ala Leu Val Arg Ala Gly Tyr Val Leu Thr Tyr Arg
85 90 95

Glu Arg Met Ala Ile His Pro Arg Leu Glu Arg Val Val Leu Arg Pro
100 105 110

Pro Asp Arg His Pro Ala Glu Leu Thr Val His Ala His Leu Arg Trp
115 120 125

Glu Trp Glu Leu Glu Arg His Ser Gly Gln Arg Trp Leu Val Leu Arg
130 135 140

Pro Gly Arg Arg His Leu Ser Ala Leu Pro Trp Pro Ala Glu Ala Val
145 150 155 160

Gln Met Trp Ser Ala Ala Leu Pro Ala Thr Cys Gln Lys Leu His Ala
165 170 175

Leu Cys Leu Asp Arg Gly Gln Gln Met Ala Leu Leu Arg Gln Glu Asp
180 185 190

Gly Trp His Phe Ala Asn Pro Gly Ala Ala Thr Gln Gly Arg Trp His
195 200 205

Leu Ser Phe Ser Pro Gln Ala Leu His Glu Leu Gly Leu Ala Gln Ala
210 215 220

Ala His His Ala Ala Ala Phe Arg Trp Asp Glu Val Gln Arg Leu Val
225 230 235 240

Gln Leu Thr Asp Leu Trp Lys Pro Phe Val Thr Ser Leu Glu Pro Leu
245 250 255

Glu Val Ala Ala Pro Ile Ile Ala Gly Lys Arg Leu Arg Phe Gly Arg
260 265 270

Gly Leu Gly Arg Asp Val Thr Glu Val His Lys Arg Gly Ile Leu Glu
275 280 285

Pro Pro Pro Leu Pro Val Arg Leu Ala Val Val Ser Pro His Leu Pro
290 295 300

Asp Glu His Ala Asn Ala Gln Leu Arg Arg Glu Leu Leu Ala His Leu
305 310 315 320

Leu Pro Arg His Gln Val Leu Arg Ser Ala Glu Ser Arg Gln Gly Leu
325 330 335

His Glu His Leu Arg Arg Gln Asp Gln Asp Asp Thr Leu Tyr Thr Phe
340 345 350

```
Trp Ser Gly Gly Glu Tyr Arg Lys Leu Gly Leu Pro Pro Phe Asp Leu
        355                 360                 365

Ala Arg Gly Leu His Thr Tyr Asp Pro Ala Ser Gly Gln Leu Gln Gln
    370                 375                 380

Pro Ala Ala Leu Ala Pro Ala Pro Ala Gln Ala Thr Gln Ala Gly Arg
385                 390                 395                 400

Gln Leu Ile Ala Leu Val Val Leu Pro Asp Asp Leu Thr Arg Ser Val
                405                 410                 415

Arg Asp Thr Leu Phe Gln Gln Leu Gln Gln Leu Gly Leu Arg Cys Leu
            420                 425                 430

Phe Ser Val Ser Arg Thr Leu Leu His Arg Pro Arg Thr Glu Tyr Met
        435                 440                 445

Ala Trp Val Asn Met Ala Val Lys Leu Ala Arg Thr Ala Gly Ala Val
    450                 455                 460

Pro Trp Asp Leu Ala Asp Leu Pro Gly Val Thr Glu Gln Thr Phe Phe
465                 470                 475                 480

Val Gly Val Asp Leu Gly His Asp His Thr His Gln Gln Ser Leu Pro
                485                 490                 495

Ala Phe Thr Leu His Asp His Arg Gly Arg Pro Leu Gln Ser Trp Thr
            500                 505                 510

Pro Pro Arg Arg Thr Asn Asn Glu Arg Leu Ser Leu Ala Glu Leu Lys
        515                 520                 525

Lys Gly Leu His Arg Leu Leu Ala Arg Arg Ser Val Asp Gln Val Ile
    530                 535                 540

Val His Arg Asp Gly Arg Phe Leu Ala Gly Glu Val Asp Asp Phe Thr
545                 550                 555                 560

Leu Ala Leu His Asp Leu Gly Ile Pro Gln Phe Ser Leu Leu Ala Ile
                565                 570                 575

Lys Lys Ser Asn His Ser Val Ala Val Gln Ala Glu Glu Gly Ser Val
            580                 585                 590

Leu Ser Leu Asp Glu Arg Arg Cys Leu Leu Val Thr Asn Thr Gln Ala
        595                 600                 605

Ala Leu Pro Arg Pro Thr Glu Leu Glu Leu Val His Ser Asp Arg Leu
    610                 615                 620

Ser Leu Ala Thr Leu Thr Glu Gln Val Phe Trp Leu Thr Arg Val Phe
625                 630                 635                 640

Met Asn Asn Ala Gln His Ala Gly Ser Asp Pro Ala Thr Ile Glu Trp
                645                 650                 655

Ala Asn Gly Ile Ala Arg Thr Gly Gln Arg Val Pro Leu Ala Gly Trp
            660                 665                 670

Arg Leu


<210> SEQ ID NO 9
<211> LENGTH: 744
<212> TYPE: PRT
<213> ORGANISM: Chroococcidiopsis thermalis

<400> SEQUENCE: 9

Met Asn Asn Val Met Gln Glu Phe Pro Val Ala Ser Phe Pro Thr Phe
1               5                   10                  15

Leu Ser Glu Ile Ser Leu Leu Asp Ile Thr Pro Lys Asn Phe Ile Cys
            20                  25                  30

Phe Arg Leu Thr Pro Glu Ile Glu Arg Lys Thr Gly Asn Ser Phe Ser
        35                  40                  45
```

```
Trp Arg Phe Ser Gln Lys Phe Pro Asp Ala Val Val Ile Trp His Asn
    50                  55                  60

Lys Phe Phe Trp Val Leu Ala Lys Pro Asn Arg Pro Met Pro Ser Gln
65                  70                  75                  80

Glu Gln Trp Arg Glu Lys Leu Leu Glu Ile Cys Glu Glu Leu Lys Lys
                85                  90                  95

Asp Ile Gly Asp Arg Thr Tyr Ala Ile Gln Trp Val Ser Gln Pro Gln
            100                 105                 110

Ile Thr Pro Glu Ile Leu Ser Gln Leu Ala Val Arg Val Leu Lys Ile
        115                 120                 125

Asn Cys Arg Phe Ser Ser Pro Ser Val Ile Ser Val Asn Gln Val Glu
    130                 135                 140

Val Lys Arg Glu Ile Asp Phe Trp Ala Glu Thr Ile Glu Ile Gln Thr
145                 150                 155                 160

Gln Ile Gln Pro Ala Leu Thr Ile Thr Val His Ser Ser Phe Phe Tyr
                165                 170                 175

Gln Arg His Leu Glu Glu Phe Tyr Asn Asn His Pro Tyr Arg Gln Asn
            180                 185                 190

Pro Glu Gln Leu Leu Ile Gly Leu Lys Val Arg Asp Ile Glu Arg Asn
        195                 200                 205

Ser Phe Ala Thr Ile Thr Asp Ile Val Gly Thr Ile Ala Asp His Arg
    210                 215                 220

Gln Lys Leu Leu Glu Asp Ala Thr Gly Ala Ile Ser Lys Gln Ala Leu
225                 230                 235                 240

Ile Glu Ala Pro Glu Glu Gln Pro Val Val Ala Val Gln Phe Gly Lys
                245                 250                 255

Asn Gln Gln Pro Phe Tyr Tyr Ala Met Ala Ala Leu Arg Pro Cys Ile
            260                 265                 270

Thr Ala Glu Thr Ala Arg Lys Phe Asp Val Asp Tyr Gly Lys Leu Leu
        275                 280                 285

Ser Ala Thr Lys Ile Pro Tyr Leu Glu Arg Lys Glu Leu Leu Ala Leu
    290                 295                 300

Tyr Lys Lys Glu Ala Gly Gln Ser Leu Ala Thr Tyr Gly Phe Gln Leu
305                 310                 315                 320

Lys Ile Ser Ile Asn Ser Arg Arg His Pro Glu Leu Phe Phe Ser Pro
                325                 330                 335

Ser Val Lys Leu Ser Glu Thr Lys Leu Val Phe Gly Lys Asn Gln Ile
            340                 345                 350

Gly Val Gln Gly Gln Ile Leu Ser Gly Leu Ser Lys Gly Gly Val Tyr
        355                 360                 365

Arg Arg His Glu Asp Phe Ser Asp Leu Ser Arg Pro Ile Arg Ile Ala
    370                 375                 380

Ala Leu Lys Leu Cys Asp Tyr Pro Ala Asn Ser Phe Leu Gln Glu Thr
385                 390                 395                 400

Arg Gln Arg Leu Lys Arg Tyr Gly Phe Glu Thr Leu Leu Pro Val Glu
                405                 410                 415

Asn Lys Lys Thr Leu Leu Val Asp Asp Leu Ser Gly Val Glu Ala Arg
            420                 425                 430

Ala Lys Ala Glu Glu Ala Val Asp Glu Leu Met Val Asn His Pro Asp
        435                 440                 445

Ile Val Leu Thr Phe Leu Pro Thr Ser Asp Arg His Ser Asp Asn Thr
    450                 455                 460
```

```
Glu Gly Gly Ser Leu Tyr Ser Trp Ile Tyr Ser Arg Leu Leu Arg Arg
465                 470                 475                 480

Gly Ile Ala Ser Gln Val Ile Tyr Glu Asp Thr Leu Lys Ser Val Glu
                485                 490                 495

Ala Lys Tyr Leu Leu Asn Gln Val Ile Pro Gly Ile Leu Ala Lys Leu
            500                 505                 510

Gly Asn Leu Pro Phe Val Leu Ala Glu Pro Leu Gly Ile Ala Asp Tyr
        515                 520                 525

Phe Ile Gly Leu Asp Ile Ser Arg Ser Ala Lys Lys Arg Gly Ser Gly
    530                 535                 540

Thr Met Asn Ala Cys Ala Ser Val Arg Leu Tyr Gly Arg Lys Gly Glu
545                 550                 555                 560

Phe Ile Arg Tyr Arg Leu Glu Asp Ala Leu Ile Glu Gly Glu Glu Ile
                565                 570                 575

Pro Gln Arg Ile Leu Glu Ser Phe Leu Pro Ala Ala Gln Leu Lys Gly
            580                 585                 590

Lys Val Val Leu Ile Tyr Arg Asp Gly Arg Phe Cys Gly Asp Glu Val
        595                 600                 605

Gln His Leu Lys Glu Arg Ala Lys Ala Ile Gly Ser Glu Phe Ile Leu
    610                 615                 620

Val Glu Cys Tyr Lys Ser Gly Ile Pro Arg Leu Tyr Asn Trp Glu Glu
625                 630                 635                 640

Glu Val Ile Lys Ala Pro Thr Leu Gly Leu Ala Leu Arg Leu Ser Ala
                645                 650                 655

Arg Glu Val Ile Leu Val Thr Thr Glu Leu Asn Ser Ala Lys Ile Gly
            660                 665                 670

Leu Pro Leu Pro Leu Arg Leu Arg Ile His Glu Ala Gly His Gln Val
        675                 680                 685

Ser Leu Glu Ser Leu Val Glu Ala Thr Leu Lys Leu Thr Leu Leu His
    690                 695                 700

His Gly Ser Leu Asn Glu Pro Arg Leu Pro Ile Pro Leu Phe Gly Ser
705                 710                 715                 720

Asp Arg Met Ala Tyr Arg Arg Leu Gln Gly Ile Tyr Pro Gly Leu Leu
                725                 730                 735

Glu Gly Asp Arg Gln Phe Trp Leu
            740


<210> SEQ ID NO 10
<211> LENGTH: 730
<212> TYPE: PRT
<213> ORGANISM: Thermosynechococcus elongates

<400> SEQUENCE: 10

Met Pro Thr Gln Phe Gln Glu Val Glu Val Ile Leu Asn Arg Phe Phe
1               5                   10                  15

Val Lys Lys Leu Ser Arg Pro Asp Leu Thr Phe His Glu Tyr Gln Cys
            20                  25                  30

Gln Phe Thr Gln Val Pro Glu Gln Gly Ser Glu Gln Lys Ala Ile Ser
        35                  40                  45

Ser Val Cys Tyr Lys Leu Gly Val Thr Ala Val Arg Leu Gly Ser Cys
    50                  55                  60

Ile Ile Thr Arg Glu Pro Ile Asp Pro Glu Arg Met Arg Thr Lys Asp
65                  70                  75                  80

Trp Gln Leu Gln Leu Ile Gly Cys Arg Glu Leu Ser Cys Gln Asn Tyr
                85                  90                  95
```

```
Arg Glu Arg Gln Ala Leu Glu Thr Phe Glu Arg Lys Ile Leu Glu Glu
            100                 105                 110

Lys Leu Lys Glu Thr Phe Lys Lys Thr Ile Ile Glu Lys Asp Tyr Glu
        115                 120                 125

Leu Gly Leu Ile Trp Trp Ile Ser Gly Glu Glu Gly Leu Glu Lys Thr
    130                 135                 140

Gly His Gly Trp Glu Val His Arg Gly Arg Gln Ile Asp Leu Lys Ile
145                 150                 155                 160

Glu Thr Asp Glu Lys Leu Tyr Leu Glu Ile Asp Ile His His Arg Phe
                165                 170                 175

Tyr Thr Pro Phe Lys Leu Glu Trp Trp Leu Ser Glu Tyr Pro Asn Ile
            180                 185                 190

Gln Ile Lys Tyr Val Arg Asn Thr Tyr Lys Asp Lys Lys Lys Trp Ile
        195                 200                 205

Leu Glu Asn Phe Ala Asp Lys Ser Pro Asn Glu Ile Gln Ile Glu Ala
    210                 215                 220

Leu Gly Ile Ser Leu Ala Glu Tyr His Arg Gln Glu Gly Ala Thr Gln
225                 230                 235                 240

Gln Glu Ile Asp Glu Ser Arg Val Val Ile Val Lys Lys Ile Ser Asp
                245                 250                 255

Tyr Lys Ala Lys Pro Val Tyr His Leu Ser Gln Arg Leu Ser Pro Ile
            260                 265                 270

Leu Thr Met Glu Thr Leu Ala Gln Ile Ala Glu Gln Gly Arg Glu Lys
        275                 280                 285

Lys Glu Ile Gln Gly Val Phe Asp Tyr Ile Arg Lys Asn Ile Gly Thr
    290                 295                 300

Arg Leu Gln Glu Ser Gln Lys Ile Ala Gln Val Ile Phe Lys Asn Val
305                 310                 315                 320

Tyr Asn Leu Ser Ser Gln Pro Glu Ile Met Lys Val Asn Gly Phe Val
                325                 330                 335

Met Pro Arg Ala Lys Leu Leu Ala Arg Asn Asn Lys Glu Val Asn Gln
            340                 345                 350

Thr Ala Arg Ile Lys Ser Phe Gly Cys Ala Lys Ile Gly Glu Thr Lys
        355                 360                 365

Phe Gly Cys Leu Asn Leu Phe Asp Asn Lys Pro Glu Tyr Pro Glu Glu
    370                 375                 380

Val His Lys Cys Leu Leu Ala Ile Ala Arg Ser Ser Gly Val Gln Ile
385                 390                 395                 400

Lys Ile Asp Ser Tyr Phe Thr Gly Ser Asp Tyr Pro Lys Asp Asp Leu
                405                 410                 415

Ala Gln Gln Arg Phe Trp Gln Gln Trp Ala Ala Gln Gly Ile Lys Thr
            420                 425                 430

Val Leu Val Val Met Pro Trp Ser Pro His Glu Glu Lys Thr Arg Leu
        435                 440                 445

Arg Ile Gln Ala Leu Lys Ala Gly Ile Ala Thr Gln Phe Met Ile Pro
    450                 455                 460

Thr Pro Gln Asp Asn Pro Tyr Lys Ala Leu Asn Val Ala Leu Gly Leu
465                 470                 475                 480

Leu Cys Lys Ala Lys Trp Gln Pro Val Tyr Leu Lys Pro Leu Asp Asp
                485                 490                 495

Pro Gln Ala Ala Asp Leu Ile Ile Gly Phe Asp Thr Ser Thr Asn Arg
            500                 505                 510
```

```
Arg Leu Tyr Tyr Gly Thr Ser Ala Phe Ala Ile Leu Ala Asn Gly Gln
        515                 520                 525

Ser Leu Gly Trp Glu Leu Pro Asp Ile Gln Arg Gly Glu Thr Phe Ser
    530                 535                 540

Gly Gln Ser Ile Trp Gln Val Val Ser Lys Leu Val Leu Lys Phe Gln
545                 550                 555                 560

Asp Asn Tyr Asp Ser Tyr Pro Lys Lys Ile Leu Leu Met Arg Asp Gly
                565                 570                 575

Leu Val Gln Asp Gly Glu Phe Glu Gln Thr Ile Arg Glu Leu Thr His
            580                 585                 590

Gln Gly Ile Asp Val Asp Ile Leu Ser Val Arg Lys Ser Gly Ser Gly
        595                 600                 605

Arg Met Gly Arg Glu Leu Thr Ser Gly Asn Thr Ala Ile Thr Tyr Asp
    610                 615                 620

Asp Ala Glu Val Gly Thr Val Ile Phe Tyr Ser Ala Thr Asp Ser Phe
625                 630                 635                 640

Ile Leu Gln Thr Thr Glu Val Ile Lys Thr Lys Thr Gly Pro Leu Gly
                645                 650                 655

Ser Ala Arg Pro Leu Arg Val Val Arg His Tyr Gly Asn Thr Pro Leu
            660                 665                 670

Glu Leu Leu Ala Leu Gln Thr Tyr His Leu Thr Gln Leu His Pro Ala
        675                 680                 685

Ser Gly Phe Arg Ser Cys Arg Leu Pro Trp Val Leu His Leu Ala Asp
    690                 695                 700

Arg Ser Ser Lys Glu Phe Gln Arg Ile Gly Gln Ile Ser Leu Leu Gln
705                 710                 715                 720

Asn Val Asp Arg Glu Lys Leu Ile Ala Val
                725                 730


<210> SEQ ID NO 11
<211> LENGTH: 2256
<212> TYPE: DNA
<213> ORGANISM: Clostridium perfringens

<400> SEQUENCE: 11

atggtaggag gctataaagt gtcaaattta acagttgaag catttgaagg aattggaagt      60

gtaaacccta tgttgtttta tcaatataag gtaactggaa aaggcaaata tgataatgtg     120

tataaaatca ttaagagtgc aaggtataaa atgcattcaa aaaatagatt taagcctgta     180

tttataaaag atgataagct ttatacatta gaaaaacttc cagatataga agatttagat     240

tttgcaaata taaactttgt taaaagcgag gttttgagta tagaggacaa tatgagtata     300

tatggggagg ttgttgagta ttatataaat ttaaagctta agaaagttaa agttttaggt     360

aagtatccta aatatagaat taattattct aaggagatac ttagcaatac tttgttaaca     420

agagagttaa aggatgaatt taagaaaagt aataaaggat ttaatttaaa gcgtaaattt     480

cgaatttcac cagtagttaa taaaatgggt aaagtgattt tatatttaag ctgttcagct     540

gatttttcaa ctaataagaa tatttatgaa atgcttaaag aaggattaga agtagaaggg     600

ttagctgtaa aaagtgaatg gtcaaatata agtggaaact tagttataga aagtgtatta     660

gaaacaaaaa taagtgagcc aacaagttta gggcaatctt tgatagatta ctataaaaat     720

aataatcaag ggtatagagt taaagatttt actgatgagg atttaaatgc aaacatagta     780

aatgtaaggg gcaataagaa aatatatatg tacataccac atgcattaaa acctattata     840

actagggagt atttagctaa aaatgatcca gaattttcta aagagataga acaattaata     900
```

```
aaaatgaata tgaattatag atatgagacc ttaaagtcat ttgtgaatga tattggagtt    960
attgaagaac ttaataactt aagttttaaa aataaatatt atgaagatgt taaattatta   1020
ggttatagca gtgggaaaat agatgaacca gtacttatgg gagcaaaagg gattataaaa   1080
aataagatgc aaatcttttc taatggattt tataagttac cagaggggaa agttaggttt   1140
ggagttttat atcctaaaga gtttgatgga gtaagtagaa aagctataag agctatatat   1200
gatttttcta aagagggaaa atatcatggc gaaagtaata aatacatagc agagcattta   1260
ataaatgtag aatttaatcc taaagaatgt atctttgaag gatatgaact aggagatatt   1320
actgaatata aaaaggctgc attaaagtta aataattata ataatgtaga ttttgtaata   1380
gctattgtac ctaatatgag tgatgaagag atagaaaatt catataatcc ttttaagaag   1440
atatgggctg aattgaattt accatctcaa atgatatctg taaagacagc agaaatcttt   1500
gcaaatagta gagataatac agcattatat tatttacata atatagtctt aggcattttg   1560
ggaaaaatag gaggaatacc atgggttgtt aaggatatga agggggatgt agattgtttt   1620
gttggattag atgttggaac tagggagaag ggaatacact atccagcgtg ttcagttgtt   1680
tttgataaat atgggaagct tataaattac tataaaccta atatacctca aaatggtgaa   1740
aagattaata ctgaaatact tcaagagatt tttgataaag tattaatttc atatgaagag   1800
gaaaatggag cttatcctaa aaatattgtt atacataggg atggcttttc aagagaagat   1860
ttagattggt atgaaaatta ttttggaaaa aagaatataa agtttaatat aatagaagtt   1920
aaaaaaagta caccattaaa aattgcatct attaatgagg gcaatataac aaacccagaa   1980
aagggaagtt atatattaag aggaaataag gcatatatgg ttactactga tattaaagaa   2040
aatttaggat caccaaaacc attaaagata gaaaaatctt atggggatat agatatgtta   2100
actgcattga gtcagatata tgcactaact caaatacatg ttggagcaac aaagagttta   2160
agacttccaa taactacagg atatgcagat aagatttgta aagcaataga gtttattcct   2220
caaggaagag ttgataatag attgttcttt ttatga                             2256
```

<210> SEQ ID NO 12
<211> LENGTH: 2253
<212> TYPE: DNA
<213> ORGANISM: Clostridium perfringens

<400> SEQUENCE: 12

```
atggtcggcg gctataaagt cagcaatttg acagtggaag cgttcgaagg tatcgggagt     60
gtcaacccga tgctgtttta ccaatacaaa gtcaccggaa agggaaagta cgataatgtg    120
tataagatta tcaaaagcgc acggtacaag atgcattcta agaaccgatt caagcccgtg    180
ttcatcaagg acgacaaact gtacaccctc gagaagctcc cggatataga agacctggat    240
ttcgcaaaca ttaacttcgt gaaaagcgag gttctcagca tagaggataa tatgtcaatt    300
tatggcgagg tggtggaata ctatatcaat ctcaagctga aaaaagtgaa ggtgttggga    360
aaataccccca agtacaggat caattacagc aaagagattc tcagtaatac gctgctgaca    420
cgagagctca aagacgagtt taagaaatca aataagggtt ttaacctgaa acggaagttt    480
agaatttccc ccgtggtgaa taagatgggc aaagtgatac tctatttgtc ctgcagtgct    540
gatttcagca ccaacaagaa catttacgaa atgttgaaag agggcttgga ggttgagggg    600
ctggccgtta agagcgagtg gagcaatatc agtggcaacc tggtgatcga gagcgtactg    660
gaaaccaaga tatccgagcc cactagcctg ggccaatccc tgatagacta ctataagaat    720
```

aacaaccagg gctatagggt gaaggatttc accgatgagg atctgaatgc caacattgtc 780
aacgtgagag gaaataagaa gatctatatg tatattccgc acgcgttgaa gccgataatc 840
acccgggagt acctggccaa gaacgatcca gagttttcta aggagatcga gcagcttatc 900
aagatgaata tgaactaccg atatgaaacc ctcaagtcat ttgtgaatga catcggggtc 960
attgaagagc tgaacaacct gagcttcaaa aacaaatact acgaagatgt gaaactgctg 1020
ggttactcca gcggcaaaat agacgaaccc gtcctgatgg gggcaaaagg gatcataaag 1080
aacaaaatgc agatttttc caatggattc tacaaactcc ccgaaggcaa ggtacgattt 1140
ggcgttctgt acccaaaaga atttgatggc gtgtcaagga aagctatccg cgccatttat 1200
gacttcagta aggagggcaa ataccacggc gaaagcaaca agtatatcgc ggaacacctg 1260
ataaacgtgg agttcaatcc aaaggagtgc atatttgagg gatacgaact gggcgatatc 1320
accgaataca agaaggcggc tctgaaactt aataactaca acaatgtcga cttcgtaatc 1380
gcaatagtcc cgaacatgtc cgacgaagag atagagaaca gctacaatcc gttcaagaaa 1440
atatgggccg aactgaatct gcccagccag atgattagcg tcaagacggc cgaaatcttt 1500
gccaatagca gggataacac ggcgctttac tacctgcata acatcgtcct cggtatcctg 1560
ggtaagatag gagggattcc ctgggtggtt aaagacatga agggcgacgt ggattgcttc 1620
gttggactcg atgtcggcac cagggagaag ggcatacatt accccgcctg cagcgttgtg 1680
tttgacaagt acggcaagct tattaactat tacaagccta acatcccgca gaacggagag 1740
aagattaaca cagaaatact tcaggaaatt ttcgacaagg tgctcataag ctatgaggag 1800
gagaatggag cctacccgaa gaatatcgtg atccacaggg acggctttag ccgagaggac 1860
cttgactggt atgagaacta cttcggtaag aaaaacataa agtttaacat catcgaagtc 1920
aaaaagtcaa ctccgttgaa aatcgccagt ataaacgagg gaaatatcac gaatcctgaa 1980
aagggttcct acatcctgcg cggcaacaaa gcctacatgg tgaccacaga tattaaggaa 2040
aacctgggaa gcccaaagcc cctgaagata gaaaagagct acggcgacat agacatgctc 2100
acagctctca gccaaatata cgcactcacg caaatccatg tgggggcgac caaaagcctg 2160
cgcctcccaa tcaccaccgg ctacgccgac aagatttgca aggcgatcga gttcatcccc 2220
caagggcgcg tggacaaccg ccttttcttt ctg 2253

<210> SEQ ID NO 13
<211> LENGTH: 2238
<212> TYPE: DNA
<213> ORGANISM: Clostridium saudiense

<400> SEQUENCE: 13
atgaataatt taatgttaga agcttttaaa ggaataggaa caataaaacc attggttttt 60
tatagataca aattaatagg aaaaggtaaa atagaaaata catataaaac cataagcaat 120
gctaaaaata agatgagttt taataataaa tttaaagcaa catttagtaa aggagaaaca 180
atatatacat tagaaaagtt tgaagtaatg ccaaatttaa atgatgtaac aattgaattt 240
gatggtgagg aagtattacc tataaaagat aataatgaaa tttattctga agttgttcaa 300
ttttatatta ataataattt acgtaagatt aagttagata ataaatatca aaagtataga 360
gctacaaata caagggaaat aacaggtaat gttatattag ataaagattt taaggaaaaa 420
tataaaaaga gtaaaagtgg atttcaatta aaaagaaaat ttataatttc tcctaaggta 480
aatgatgagg gaaaagtaac tttattttta gatttaaatt ctagttttga ttatgataaa 540
aatatttacc aaatgataaa ggctggaatg gatgtagtag gtcaagaggt aattaataca 600

```
tggaacaata aaaaacaaaa agggaagatc aagaaaatat cagaattaac aataagtgag    660
ccatgtaact ttggacaatc cttaattgat tactatgtta gtttaaatca agctgtcagg    720
gttaagaact tcacagaaga agagaagaat acaaatgtta tagtagttca agttggaaaa    780
ggtgaagtag aatatattcc acatgcatta aaaccaatta taactaggga gtatattaaa    840
aaatatgatg aagctttttc aaaagaagta gaaaatctaa tcaaaataaa tatgagttat    900
aggtatgaaa tacttaagaa atttattgat gatataggaa gtataactga gttaaataat    960
ttaaagtttg aaaatacata tatagataat attgaaagtt tggggtacca gcaaggtaaa   1020
ttgaatgatc cagtattaat tgggggtaaa gggatactaa aagataagat tcatgtattt   1080
aaaagtggat tttataaatc tccaattgat gaggtgaagt ttggagttat ttatccaaaa   1140
ggacatacta atgatagcaa aagtacaatt agagctatat atgatttttg tactgatgga   1200
aaatatcagg gaaaagataa tatatttata aataataaat taatgaatat aaaatttagt   1260
aatcaagatt gtgtttttga agagtatgaa ttaaatgata ttacagagta taaaagggct   1320
gctaataagc ttaaaaataa tgaaaatatt aaatttgtca ttgctattat accagcaata   1380
gatgaaagtg atattgaaaa tccatataat ccttttaaga gagtttgtgc agaattaaat   1440
ttaccatcac aaatggtttc tttaaaaact gcaaaaagat ttgggacaag taaaggtaat   1500
aatgaacttt attttttaca taatatttct ttaggtatat taggtaagat aggaggagtt   1560
ccatgggtaa ttaaagatat gcctggagaa gtagattgtt ttgttggatt agatgtggga   1620
acaaaggaga aaggaataca ttatcccgct tgttcagtgc tttttgataa gtatggtaag   1680
ttaataaatt attataagcc tacaatacct caaagtggag aaataattaa aacggatgtt   1740
ttacaagaga tatttgataa ggtactactt tcttatgaag aggaaaatgg gcagtatcca   1800
agaaatattg ttattcatag ggatggtttt tctagggaag atttagagtg gtataagaat   1860
tattttatta aaaagaatat taattttaca atagtagaaa ttaaaaagaa ctttgcaact   1920
agggtagcaa ataatattaa taatgaagtt agtaatcctt ttaagggaag ttttatttta   1980
agggaaaatg aagcaatagt agttacaacg gatattaagg ataatattgg agcacctaag   2040
ccaattaagg tggaaaagac atatggagat attgatatga tgactataat aaatcaaata   2100
tatgcattaa ctcaaattca tgttggatct gcaaagagta tgagattgcc aataacaaca   2160
ggttatgcag ataagatttg taaatctata gagtatatac cttcagggcg agttgataat   2220
agattgttct ttttatag                                                 2238
```

<210> SEQ ID NO 14
<211> LENGTH: 2238
<212> TYPE: DNA
<213> ORGANISM: Clostridium disporicum

<400> SEQUENCE: 14

```
atgaataact tgacactaga agcatttaga gggataggaa caataaagcc actacttttt     60
tatagatata aattgatagg aaaaggtaaa atagaaaata catataaaac aataagaaat    120
gctcaaaata gaatgagttt taataataaa tttaaagcaa catttagtaa agatgaaata    180
atatatacat tagaaaaatt tgaaataata ccaactttag atgatgtaac aatcattttt    240
gatggagaag aggttttacc tataaaagat aataataaaa tttattctga agtaattgag    300
ttttatatta ataataattt acgtaatgtc aaatttaatt ataaatatcc aaagtatagg    360
gcagcaaata caagagaaat aacagggaat gttatattag ataaagatat gaatgagaaa    420
```

-continued

```
tacaaaaaga gtaataaggg gtttgagtta aaaagaaaat ttataatttc tcctaaggta    480

gatgatgagg gaaaagtaac tttatttta gatttaaatg caagttttga ttatgataaa    540

aatatttatc aaatgataaa agctggaata gatgtagtag gagaagaggt tattaatatc    600

tggagtaata aaaaacaaag aggaaaaatt aaagagatat cagatataaa aataaacgaa    660

ccgtgtaatt ttggacaatc attaattgat tattatatta gttctaatca agcttctaga    720

gttaatggat ttactgaaga agaaaaaaat acaaatgtaa taatagttga atcaggaaaa    780

agtcgcttaa gttatattcc acatgcatta aaaccaatta taacgagaga atatattgcg    840

aaaaatgatg aagttttttc aaaagaaatt gaaggtttaa ttaaaattaa tatgaactat    900

agatatgaaa tacttaagag atttgttagt gatataggaa ctataaaaga attaaataat    960

ttgaggtttg aaaaaatata tatggataat atcgaaagtt tagggtatga gcaaggtcaa   1020

ttaaaggatc cagtattgat tgggggtaaa ggaatactaa aagataaaat tcatgttttt   1080

aaaagtggat tttataaatc accaaacgat gaaataaagt ttggagttat ttatcctagg   1140

ggatatatta aggatactca aagtgtgatc agagctatat atgacttttg tactgaagga   1200

aaatatcagg gaaaagataa tatatttata aataataaat taatgaatat aaagtttagt   1260

aataaagagt gtgtttttga agagtatgaa ttaaatgata ttactgagta taaaagagct   1320

gcaaataaac ttaaaaagaa tgaaaatatt aaatttgtta ttgctattat accaacaata   1380

aatgaaagtg atattgaaaa tccatataat ccttttaaga gagtttgtgc tgaaataaat   1440

ttaccatcac aaatgatttc tttgaaaaca gcaaaaagat ttagtacaag caggggacag   1500

agtgaacttt atttttaca taatatttcc ttaggtatat taggaaagat aggaggagtt   1560

ccatgggtaa ttaaagatat gcctggagaa gtagattgtt ttgttggatt agatgtggga   1620

acaaaggaga aaggaataca ttatccagct tgttcagtac tttttgataa gtatggtaag   1680

ttaataaatt attataaacc tacaatacct caaagtggag aaataattaa aacggatgtt   1740

ttacaagaga tatttgataa ggtattactt tcttatgaag aggaaaatgg tcagtatcca   1800

agaaatattg ttattcatag ggatggtttt tctagggaag atttagaatg gtataagaac   1860

tattttctta aaaagaacat tgaattctct attgtagaag taagaaagaa tttcgcaact   1920

aggttagtga ataattttaa tgatgaagtt agcaatccta gtaaaggaag ttttatttta   1980

agagataatg aagcaatagt agttacaact gatattaatg ataatatggg ggcacctaag   2040

ccaattaagg tggaaaagac atatggagat attgatatgt taactataat aaatcaaata   2100

tacgcattaa ctcaaattca tgttggttct gctaagagtt taaggttgcc tataacaact   2160

ggatatgcag ataagatttg taaggctata gattatatac cttctggaca agttgataat   2220

aggttattct ttttatag                                                 2238
```

<210> SEQ ID NO 15
<211> LENGTH: 2277
<212> TYPE: DNA
<213> ORGANISM: Rhodopirellula maiorica

<400> SEQUENCE: 15

```
atgctgcaac tgaacggatt ttcaatcgag attgccggcg ggtcgttgac ggtactgaag     60

tcgaagatcg caccgacgga cgtcaaggaa acgcgacgtt cgctcgagga cgattggttt    120

acgatgtatc acgaagggca cctctattcc cttgcaaaga actcgaacgc atcgggcggg    180

cttggtgaga cggaactctt ggtgctctcc gaccacctcg ggctgcgttt tgtaaaagcc    240

atgctcgatc aggcgatgcg aggcgtcttt gaagcgtacg atcctgtacg cgatcgcccg    300
```

```
tttacctttc tggctcgcaa tgtcgatctt gtcgcgttag ctgccgagaa tttggaatca    360
aagcccagtt tgctttctaa gtttgagatt cgacctaagt atgaactaga agcaaaagtg    420
gttgagttcc ggccgggcga gctggaattg atgctcgcac tcaatctgac cactcgttgg    480
atctgcaacg ccagcgtgga tgaattgatc gaaaagaaca ttccagtccg gggaatgcat    540
ctgattcgca ggaatcgtga gccaggacaa cgaagcttgg tcgggacttt cgaccgaatg    600
gaaggagaca acgctctact ccaggatgcg tacgacggcc aggacaagat cgctgcatcg    660
caagtccgaa tcgagggatc gaaggaggtc ttcgcgacaa gtctccggcg tctgcttggc    720
aatcggtaca ccagctttat gcactcagtg gacaatgagt atgggaagtt gtgtggcggt    780
cttgggtttg acggtgagct tcgcaaaatg caaggatttc ttgcgaagaa gagcccgatt    840
caattgcatg gcggtgtgga ggtgtcggtc ggacagcgag ttcagctaac caatcagccg    900
gggtacaaaa cgactgtcga actgctgcaa agcaaatact gcttcgaccg atctcgaacg    960
aaactacatc catacgcttg ggacggttta gctagattcg ggccgtttga ccgcggaagc   1020
tttcccacac gatctccgcg cattttgctt gtcacacccg attcggcatc cggcaaggtc   1080
agccaagctt tgaagaaatt tcgcgacggt ttcgggtcaa gccaatcgag catgtacgac   1140
ggatttctcg atactttcca tctttcgaac gcaccctttt tcccgctccc tgtcaaattg   1200
gatggcgtcc agcgatcgga tgttggcaag gcatatcgaa aagcaatcga agacaagttg   1260
gcccgtgatg atgatttcga tgctgcgttt aacattctgc tggatgaaca cgccaatctc   1320
cccgactcgc acaacccgta tctggttgcc aaatcaatcc tgctctcgca tggaatcccc   1380
gtgcaagaag ccagggtgtc gacgcttact gcgaacgagt attcgctaca gcacacattc   1440
agaaatgttg ccaccgcact gtacgcaaaa atgggcggag tcccttggac ggtcgatcac   1500
ggcgaaacgg ttgacgatga actggtggtg ggaattggga acgctgaact gtccggcagc   1560
cgcttcgaga aacgacagcg tcacatcgga atcaccacgg tattccgtgg cgatggcaac   1620
tatcttctct caaatctgtc caaagagtgc agatacgaag actaccccga cgtgcttcgc   1680
gaatcgacga tcgcagtcct tcgcgaagtc aaacaacgaa acaactggct gcccggacaa   1740
acagtgagaa ttgttttcca tgcgttcaaa ccgctgaaga atgtcgagat cgcggacatc   1800
atcgcgtcaa gcgtcaaaga agtcggcagc gaacagacga ttgaattcgc tttcttgaat   1860
gtctcgctgg accattcgtt cacgttgctg gatatggccc agcgaggaat aacgaagaag   1920
aaccagacga aaggaattta cgttcctcgc cgaggaatga ccgttcaggt tggacggtac   1980
acacggctcg tcacgtcaat cggtcctcac atggtcaagc gtgcaaacct tgcgttgccc   2040
aggcccctgt tgatccacct gcacaagcaa tcgacttacc gcgacctttc ctacctttct   2100
gagcaggtgc tgaacttcac gacgctgtcg tggcgatcaa cgctgccgtc ggagaagccg   2160
gtcacgattc tttactcatc acttatcgct gacttgctgg gccgtctcaa gtccgtggac   2220
gattggtcgc cagcggtcct caataccaaa cttcgcaaca gcaagtggtt tctgtga      2277
```

<210> SEQ ID NO 16
<211> LENGTH: 2118
<212> TYPE: DNA
<213> ORGANISM: Paenibacillus odorifer

<400> SEQUENCE: 16

```
atgaatacac cactaacaca ctacgtactt acagaatggg aatcagacac gaacacaaat     60
gttctacata ttcatttata tacgctacca gtgcgtaatg tatttgaaca gcataaagaa    120
```

aacggaaatg cttgttttga ccttagaaaa ttaaacagat cgctcattat cgatttttat 180
gatcaatata ttgtaagttg gcaacctatt gaaaattggg gtgaatacac attcactcag 240
catgaatatc gctcaattaa tcccaccatc ttagcagaaa gagctatctt ggaacgatta 300
cttttaagaa ctatagaaag cgttcagcca aaaaaagaaa ttgctgctgg aagtcgaaaa 360
ttcacgtggt taaaagctga aaaagtcgta gaaaatattt caatacacag ggttatacaa 420
tgtgatgtta ctgtagatta tgcgggcaaa atttccgttg gctttgattt aaatcatagt 480
tatcgtacaa atgaatcggt atatgatctc atgaaatcaa atgctatttt taaaggcgat 540
cgagtaattg atatatataa caatcttcat tatgagtttg tggaaatctc caattccaca 600
atcaatgatt caattccaga acttaatcaa tctgttgtta attattttac taaagaacga 660
aagcaagctt ggaaagttga taaacttgaa cagagtatgc ctgttgtcta tctaaaagcg 720
tttaatggat ctcgtattgc ttatgcacct gctatgctac aaaaagaact tacttttgag 780
tcgcttccta ctaatgtagt acgtcaaaca tcagaaattt ttaaacaaaa cgcaaatcaa 840
aaaattaaga cattgctgga tgaaatacaa aaaatattag cacgcactga taaaattaaa 900
tttaataaac aaaagctcct agtccagcaa gctgggtatg aaatattgga gttgtcaaat 960
cctaatcttc aattcggaaa aaatgttact caaacacagc ttaaatatgg acttgataag 1020
ggcggtgttg tagcctcaaa acctttatca attaatttgc ttgtataccc agaactgata 1080
gatacaaaac tcgatgtcat aaatgacttt aatgataaat taaatgcgct atcccataaa 1140
tggggtgtac cattatcaat cttaaaaaaa tcaggagcat atcggaacag accgatagat 1200
ttcacaaatc cacaccaact tgccatccta ctgaaagaac ttacaaaaaa tttatttcaa 1260
gagttgacgc tcgtgataat tccggagaaa atttcaggaa tgtggtatga cttggtaaag 1320
aaggaattcg gaggaaattc ctcagtacca actcagttca taactataga aactcttcaa 1380
aaagctaatg actacattct aggcaatcta ttattaggac tctattctaa atctggcatt 1440
caaccgtgga tcttaaattc tcctctgtca tctgattgtt ttattgggtt ggatgtatct 1500
catgaagctg gtagacactc tacaggaatt gtacaggtcg taggaaaaga cggcagagta 1560
ttgtctagca aggcaaacac ctctaatgag gccggtgaaa aaatccgtca tgaaactatg 1620
tgtcaaattg tatactcagc tatagaccaa tatcagcaac attacaatga aagaccaaag 1680
catgttactt ttcatcggga tggtttttgt agagaagatt tacttagtct agacgaagta 1740
atgaatagtt tggatgtaca atatgacatg gttgaaatca tcaagaaaac gaatcgtcgc 1800
atggctctaa ccgttggtaa gcaaggttgg gagaccaagc caggattgtg ttatctaaaa 1860
gatgagtcgg catatcttat cgccacaaat cctcatccac gtgtcggcac agcacaaccg 1920
attaaaatta tcaagaaaaa gggatcacta ccgattgaag caataattca agatatttat 1980
catctttcgt tcatgcacat tggttcatta ttaaaatgtc gcctacctat tactacgtat 2040
tatgctgatt taagctctac attcttcaac cggcaatggc tcccgatcga ttctggcgaa 2100
gccctacatt ttgtataa 2118

<210> SEQ ID NO 17
<211> LENGTH: 2301
<212> TYPE: DNA
<213> ORGANISM: Hyphomonas sp.

<400> SEQUENCE: 17
atgccgcaca catctcttct cttgaacttt ttgcccgtat cgctctccgg cgatacgcga 60
attcacgttg gctatcggcc ctacaacgaa gacgttttgc gggaactacg agaggagttc 120

```
ggtgaaagcc acgttttcaa acgcgactat caagaagaca caatatcgga gattccagta    180
atccccggtg ccgaaccact ctccgacaaa tcgaccggag tagacctcgc cgaagcacgg    240
tggctttgga agccgcttct gaacgcggct ctcctgcggc tgttttcagg gtccagagag    300
attacaagcg attatcctgt cagcgttttg ggcaatccga agaacaattt catttcgcat    360
gctaacttac ctgattgggt aaggatcttg ccgttactgg aatttgagtc tcgcacgttg    420
ttcggtggca agtcgggtcc gcagttcgga ctggtgtgta atgcgcggac ccgtcaccag    480
gtattggcag gttgcgatca tctcattgag cggggcattt ctccgattgg gcgttatgtt    540
caaatcgatc aaccgcaacg agactcccga ttggcgccgc gcggccttac agtgggaaag    600
gtatcatcga tcgacggtga cacactcatt ttggaagacc atcgcaaagg ctatgaacgg    660
gtcaaagcat ctgatgcgag gttgaccggc aatcgcgctg atttcgactg gtgcgtcaat    720
gcgcttttgc cgggacaagg gcaggctacc ctgtcgaggg cgtgggacgc catgagcgca    780
ttgaaccagg gcccaggtcg cctgcaaatg atcaaccaaa cagccgagta tttgaggaca    840
gtcaatctgg aagctgttcc aggcgttgct tttgaaatcg gcgaatggct gtcgagcacg    900
gacgctcagt ttccggtgac ggaaacgatc gatcgcccca cgcttgtatt tcacccttcg    960
ggaaggccga acgatacgtg gaacgaacgc ggcatcaaag acaatggacc gcacgaccaa   1020
cgcacgttca cgccaaagca actcaacatc gctgtcattt gccaaggccg gttcgaagga   1080
caagtcgatc gtttcgtggg aaaacttctc gatggcatcc ccgactttca actccgaaat   1140
gggcgcaagc cttatgatga cggcttcctt agtcgatttc gtctggaacg agccaatgtg   1200
cagacatttc aggcaaactc agcctcgcgc gaagcatacg aagcagcttg cgaagacgca   1260
ctgaaacatg ctgctgacaa tggctttggc tgggacttgg cgattgtcca gattgaagaa   1320
gacttcaagg cgttgcctgg gcctcagaac ccttactacg ccacgaaggc catgctgctc   1380
cgcaacaatg tagcggtaca gaatattcgt atcgagacga tgagcgagcc ggacaaaagt   1440
ctcgtgtata caatgaatca ggtgagtctt gcctgctatg cgaagctggg cggtcgtccg   1500
tggcttttag ggcgcagca atcggttgcc catgaactcg tcattggcct cgggtcgcac   1560
acagaacaac aatctcgatt tgatcagagc gttcggtatg tcggcattac cactgtgttt   1620
tcgagcgatg gcgggtatca cctcagtgaa cgcaccggcg tcgtgccatt tgaggattac   1680
gccaaggaat taaccgacac gctcacgcgc accatcgaac gggtccgccg ggaagataac   1740
tggaaaaaca cagaccgggt gcggctggtc ttccatgcgt tcaagcaaat caaggacatt   1800
gaggctgagg ccatcaagca ggcggtcgaa tctctcgacc tcgaaaacgt ggttttcgct   1860
ttcgttcatg ttgctgaaca tcatccgtat ttgatcttcg accagaacca agagggattg   1920
ccgcattggg agaaaaatcg gtctaaacga aaaggcgtat tgggcccatc ccgaggcgtg   1980
cacatcaaac tggctgattc tgagtcgctg gttgtgtttg cgggcgcaag tgaacttaag   2040
caagcggccc acgggatgcc gagggcctgc cttctaaaac tgcatcgcaa ttcgaccttc   2100
cgcgatatga cttatctcgc acgccaggcg ttcgacttca ccgcccattc ttggcgagtt   2160
atgacgccgg aaccgtttcc gatcacaatt aagtattccg acctaatcgc tgaacgtctt   2220
gccggcctga agcagatcga gacgtgggat gatgacgccg tccggtttcg caacatcggc   2280
aaggcgccct ggttcctgtg a                                             2301
```

<210> SEQ ID NO 18
<211> LENGTH: 2427
<212> TYPE: DNA

<213> ORGANISM: Calothrix sp.

<400> SEQUENCE: 18

```
atgattatga gtttagaaag taatattttc accttttcca atctcggaac gcttacaact      60
caatatcgtt tgtatgaaat acgaggactt caaaagcgtc atcaagaata ctatcaaaat     120
cgacaaattt tgatacatcg gttgagctat cttctgaaaa acgctgtcac aattatagaa     180
cgtgatgaaa aactgtatct tgttgttgca gcagatgcac cagaacctcc taattcttat     240
ccaattgttc gaggagtaat ttattttaag ccaactgggc aaattttgac tttagactat     300
tcgttacgta caccacagaa tgaagaaatt tgccagcgat tcttacattt tatggtacag     360
tctgcattat tccaaaatgc aaatttatgg caaccatctg caggaaaagc tttctttgag     420
aaaaaaccgt cttttgaatt tggctctatt ctattgtttc aaggttttc tgttcgccct     480
atatttacaa aagataaaat tggattatgt gtagatatcc atcataaatt tgtaagcaaa     540
gaacctctcc caagttattt aaattttaac gagttccaga aatatcgcgg tgttagctgt     600
atttatcact ttggtcatca atggtatgag attcaactta gtgaactttc tgagttaaat     660
gctacagaag caatggttcc tatagaaaac aaatttgtta cattgatcaa ctatattact     720
caacaagctc gtaagccaat tccagaggag ttagcaaacg tttctcaaga tgcagcagta     780
gttcattact ttaataacca aaaccaagac cgtatggctg tcacctcgtt atgttatcaa     840
gtttatgata attcttatcc tgagataaga aaataccatc aacatacgat tcttaagcca     900
catattcggc gttcggcaat ccacggtatt gtccaaaaat atttagctga gttgagattt     960
ggagatatta cgttaaaagt ttcaactata cctgaactag taccacagga aatgtttaac    1020
ttacccgatt attgttttgg taatgattat aaattgtcag tcaagggtag tgaaggaact    1080
gctcaaataa gtttggatca ggttggaaaa caacgactag aattactcag caaggcagaa    1140
gcaggtatat atgtacaaga gaaatttgat agacaatata ttctactacc tcaaacagtt    1200
ggagatagct ttggaagtag atttatagat gatctcaaaa aaactgttga taaactttac    1260
ccagcaggtg gggatacga ccctaagatt atttactatc cggaccgtgg tttacgaact    1320
tatattgaac aaggcagagc gatactcaaa actgttgagg aaaacgagct tcagcctgga    1380
tacggtatag tgatgttgca tgattcacca gatagactac tacgtcagca tgataagctt    1440
gcagctttag taattcgtga attgaaagat tatgacttat atgttgctgt aattcattct    1500
aaaacaggta gagaatgcta tgaacttcgg tataacaatc aaggagaacc attctatgca    1560
gttatacatg aaaaacgtgg gaagctttac gggtacatgc gcggtgttgc tttaaataag    1620
gtgttgttaa caaacgaacg ttggcctttt gtcttaagta cacctctcaa tgcggatgtt    1680
gttattggca ttgatgttaa gcatcatacg gcaggatata tagttgttaa taaaaatgga    1740
agtcgaattt ggactcttcc aacaattact tctaaacaaa aagagcgctt gcctagtatc    1800
caaataaaag ctagtttaat agagattatc acaaaggaag cagaacaaac agtagaccag    1860
cttcataata tagttattca tcgtgatggt cgaattcatg aatcagaaat tgaaggagca    1920
aaacaagcaa tggctgaatt aatatcaaga tgtactttgc cagtaaatgc tacgcttact    1980
attctagaag ttgctaaatc ttcaccagta tcatttaggc tatttgacgt ttcaaatact    2040
aatagtaaag acccatttgt tcaaaatcct caagtaggtt gctattatat agcaaattct    2100
acggatgcat atctctgctc tacaggtcgg gcatttctca aatttggaac tgttaatcca    2160
cttcatatta gatatgtgga aggtacactt cctttaaaat tatgcttaga agatgtttat    2220
tatctcacgg cattaccttg gacaaaacca gatggctgca ttcgttatcc aattacagta    2280
```

aaaattaacg ataggcgcct aggggaagac gcaagcgagt acgatgaaga cgcacttcgt 2340
tttgaattat ttgaaagttt agaatctgaa gatgattttg acgaaatgac ggatagtgat 2400
ttcaaccaag aggaaacaat ggtatga 2427

<210> SEQ ID NO 19
<211> LENGTH: 2025
<212> TYPE: DNA
<213> ORGANISM: Deinococcus sp.

<400> SEQUENCE: 19
ttgaagctca accattttcc cctgaaccct gatctgccgc tctacatcac ggaatatgct 60
caccgcaacc cccgcgccct gctgggcttt gtgcgcgggc agggcttttg ggctcagcag 120
gtgggcgaac aggttcaggt gtatcacggc cgacctcagc ccacgtttcg cggcgtccaa 180
gtcatttcgc acacgcggct tgaccccgac cacccggctt tcgaccaagg ggtgttgtcg 240
ctgattcggc aggcgcttgt gcgagcggga tatgtgctga cgtaccggga acgaatggcc 300
atccatccaa ggctagaacg ggtggtcctg cgcccgcccg accgccaccc ggcagaactc 360
actgtccacg cccatctccg ttgggaatgg gagctggaac ggcattccgg acaacgctgg 420
ctggtgctgc ggccggggcg ccgtcatctg tctgcgctgc cctggccagc cgaggcggtc 480
cagatgtgga gcgcagcctt gcccgccacc tgccaaaagc ttcatgctct gtgtctcgac 540
cgaggccagc agatggcgct tttgcgccaa gaggacggct ggcactttgc caaccccgga 600
gcggcgaccc agggccgctg gcatcttagc ttttctccac aagcgctgca tgagctgggc 660
ctggcccagg ccgcccacca cgccgccgcg ttccgctggg acgaggtgca gcggctcgtg 720
cagctcacag acctctggaa accctttgtg acctcactgg aaccgctgga ggtggctgcg 780
cccatcattg cggggaagag gctgcgcttt gggcgtggcc tggggcgtga cgtgaccgag 840
gttcacaagc ggggaattct ggaaccgccg ccccttcccg tccgactggc ggtggtttca 900
ccccaccttc ccgatgagca cgccaacgcc caactgcggc gcgagctgct ggcccacctg 960
ctgccacgtc accaggtgct gcgttctgct gaatcgcggc aggggctcca cgaacacctg 1020
cggcgtcagg accaggacga caccctgtat accttttgga gtggcggcga gtaccgtaaa 1080
ctgggcctcc cgccttttga tctggcgcgg ggccttcaca cctacgatcc cgccagcggt 1140
cagctgcagc agcccgccgc actggcaccc gcacccgcgc aggccaccca agctggccgc 1200
caactgatcg cgctggtggt cctgcccgac gacctcaccc gcagcgtgcg cgacaccctg 1260
tttcagcagc tccagcagct tggtctccgg tgcctttttt ccgtaagccg cacactcctc 1320
caccggccgc gcaccgagta catggcctgg gtcaatatgg cggtcaagct ggcgcgcacc 1380
gccggcgcgg tgccctggga tctggccgac ctcccgggcg tcaccgagca gactttcttt 1440
gtgggggtgg atttggggca cgatcacacc caccaacaga gcctgcccgc ctttaccctc 1500
cacgaccacc ggggccgacc cctgcagagc tggactccgc ctcgccgcac caacaacgaa 1560
cggctcagcc tggcggagct gaaaaaaggg ttgcaccgcc tgttggcccg ccgctcagtg 1620
gatcaggtga tcgtgcaccg cgacggccgc tttttggcgg gtgaggtgga tgatttcacc 1680
cttgcgctgc acgacctggg cattccccag ttttcgctgc tggccatcaa gaaaagcaac 1740
cacagtgtgg ccgtgcaggc agaagagggc agcgtattgt ctctggatga gcggcgctgc 1800
ctgctggtca ccaacaccca ggcggccctg ccccgaccca cggagcttga gcttgttcac 1860
agtgaccgcc tcagcctagc gacactcacc gagcaggtgt tttggctcac ccgcgtgttt 1920
atgaataacg cccagcacgc cggaagtgac ccggccacca tcgagtgggc caatggaatc 1980
gcgcgcacag ggcagcgcgt gcccctcgcc ggttggaggc tctga 2025

<210> SEQ ID NO 20
<211> LENGTH: 2235
<212> TYPE: DNA
<213> ORGANISM: Chroococcidiopsis thermalis

<400> SEQUENCE: 20
atgaataatg ttatgcaaga atttccagtt gcttcatttc caactttttt aagtgaaatt 60
tcacttctag atattactcc gaaaaatttc atttgttttc gattaactcc agaaatcgaa 120
cgcaaaactg gtaatagctt tagttggcga ttcagtcaaa aatttcctga tgcagttgtt 180
atttggcaca ataaattttt ctgggtttta gccaaaccca atcgaccaat gccaagccaa 240
gaacagtggc gcgagaaact gctagaaatt tgcgaagaat taaaaaaaga tattggcgat 300
cgcacttatg caatacaatg ggtaagccag ccacagatta cacctgagat tctttcacag 360
ttagcagtga gagtattaaa aataaattgc cgtttttcat ctccatctgt aatatcagta 420
aatcaagtag aagtcaaacg agagattgat ttttgggcag aaacgattga aattcaaact 480
cagattcagc cagctttgac aattaccgtc catagtagtt tcttctatca aaggcatcta 540
gaagaatttt acaataatca tccctatcgg cagaatccag agcaactgtt aattggctta 600
aaagtacgag atatcgaacg taatagcttt gcaacaataa ctgatattgt aggtactatt 660
gccgaccaca gacaaaaact acttgaggat gcaactggcg caattagtaa acaagcattg 720
atagaagcac cggaagaaca gccagtcgtt gccgtacagt ttggtaaaaa tcaacaacct 780
ttttattatg caatggcagc tttacgtcct tgcataacag cggaaactgc tagaaaattc 840
gatgtagatt atggaaaatt actgtctgca actaaaattc cttatttaga gcgaaaagaa 900
cttttagcat tgtacaaaaa agaagctgga caaagtttag ctacttatgg atttcaactg 960
aagattagta taaatagccg cagacatcct gaattattct tctctccgtc agttaaatta 1020
tcagaaacaa aactggtgtt tggaaaaaat caaattggcg ttcaaggtca aattttatct 1080
ggtttatcta aaggtggcgt gtatcgccgt catgaagatt ttagcgattt gtcaagacca 1140
attcggattg ctgcattgaa actttgcgat tatccagcaa attcttttct gcaagaaacg 1200
cgacagagac tcaaacgcta tggttttgaa actcttcttc ctgttgaaaa taaaaagaca 1260
ttattggtag atgatttatc tggagttgaa gcgagagcca aagctgaaga agctgtcgat 1320
gaattgatgg taaatcatcc cgatatagtt ttgacatttt taccaactag cgatcgccac 1380
agcgataata cagaaggagg cagcttatat tcttggattt actcacgctt gctcagacgt 1440
ggaattgcca gccaagttat ttacgaagat actttgaaaa gcgttgaagc taaatattta 1500
ttaaatcagg tgattccagg tattctagcc aagctaggca acttgccttt tgtgttagct 1560
gaaccattag gaattgccga ctatttcatc ggcttagata tttccagaag cgccaagaag 1620
agaggttctg gaactatgaa tgcttgcgct agcgtgcgtc tatacggtcg caaaggagaa 1680
tttattcgct atcgattaga agatgcttta attgaagggg aagaaattcc ccaaagaatt 1740
ttagaaagct ttcttcccgc agctcaactg aaaggtaaag tcgtactaat ttaccgcgat 1800
ggacgctttt gtggtgatga agtgcagcat ttaaaagaaa gagcgaaagc aattggttcg 1860
gagtttattt tagtcgagtg ctataaatct gggattcctc ggctctacaa ctgggaagaa 1920
gaagttatta aagcaccaac gctaggatta gcactgcgct tatcggcgcg ggaagttatt 1980
ttagtcacga cagaactaaa ttcggcgaaa atcggtttgc ctctgcctct acgcttgaga 2040

```
attcatgaag caggacatca ggtatcgtta gaaagtttag tagaggcgac tttgaaactt   2100

accttactac atcatggttc gctgaacgag ccgcgcttac caataccgct ttttggttct   2160

gaccgtatgg cttatcgacg gttgcaaggc atttatccag gtttgctaga aggcgatcgc   2220

caattttggt tataa                                                    2235
```

```
<210> SEQ ID NO 21
<211> LENGTH: 2193
<212> TYPE: DNA
<213> ORGANISM: Thermosynechococcus elongates

<400> SEQUENCE: 21

atgcccaccc aattccaaga agttgaagtt atactcaatc gtttttttgt aaaaaaattg     60

agtcgacctg atcttacatt tcatgaatac caatgccaat ttactcaagt gccagaacaa    120

ggtagcgagc aaaaagctat ttccagtgtt tgctacaaac taggagtcac tgctgttcga    180

ctagggagct gcattattac aagggagcct attgaccctg agagaatgcg aactaaggat    240

tggcagttac agctaatagg atgtagagaa ctgagctgtc aaaattatcg tgaaaggcag    300

gctctggaaa cctttgaaag aaaaattcta gaggaaaagt taaaagaaac atttaagaaa    360

actataattg aaaaagacta tgaattaggg ttgatttggt ggatttctgg cgaagaaggg    420

ttagaaaaaa caggtcatgg ctgggaagta catagaggca gacaaattga tctcaaaata    480

gaaacagatg aaaaattata cttagaaatt gatattcatc atcgatttta tactccattc    540

aaacttgagt ggtggctcag tgaatatcct aatatccaaa tcaagtacgt gaggaatacc    600

tacaaagata agaaaaagtg gatccttgaa aattttgcgg acaaaagtcc aaatgaaata    660

caaatagaag ccctaggaat aagcctagca gagtatcacc gtcaagaggg agcaactcaa    720

caagaaatag atgagtcccg agttgtaatt gttaagaaaa tcagcgacta caaggctaag    780

ccagtatatc atttgtctca aagactatca ccaattctca caatggaaac gttagcgcaa    840

attgctgaac aaggaagaga aaaaaaggaa attcaaggtg tttttgacta catcaggaaa    900

aacattggta cacgtttgca agaatcacaa aaaatagctc aggtcatttt caaaaacgtt    960

tataatctca gtagtcagcc agagataatg aaagttaatg gttttgtcat gcctcgtgca   1020

aaactattag ctcgaaacaa taaagaagtc aatcaaacag ctagaattaa atcctttggc   1080

tgtgccaaga ttggcgaaac aaaattcggc tgcctaaatt tatttgataa taaacccgag   1140

tatccagagg aagtacacaa atgtttactg gcaatagcaa gaagtagtgg ggtacagata   1200

aaaatagact cctactttac aggaagtgac tatccaaaag atgatttagc tcaacaacga   1260

ttttggcaac aatgggctgc tcaaggaatt aaaactgttt tagtagtgat gccttggtcc   1320

ccccatgagg agaaaacaag gctacgaatt caggcattaa aggcgggaat cgctactcag   1380

ttcatgatac ccacacccca ggataatccc tacaaagctc tcaatgttgc cttgggactg   1440

ttgtgtaaag ctaagtggca gcctgtctat ctaaaaccat tagatgatcc tcaggctgct   1500

gacttaatta tcggttttga caccagtaca aaccgaaggc tgtactatgg tacgtctgct   1560

tttgcaattt tagccaatgg tcaaagcttg ggttgggagt tgccagatat acaacggggc   1620

gaaactttct ctggtcaatc catttggcaa gttgtgtcta agctagtgct gaaattccaa   1680

gacaactatg attcttaccc taagaagatc ctactgatgc gggacgggct tgttcaagac   1740

ggggagtttg aacaaacaat cagagaacta actcaccagg gtatcgatgt cgatatctta   1800

agtgtccgta agagtggctc ggggaggatg ggacgtgaat tgacttcagg caataccgca   1860
```

```
ataacctatg atgatgctga agtgggcact gtaatttttt attctgcaac tgactcattt   1920

atattacaaa ccactgaggt catcaagacg aaaactggcc cccttggtag tgctagacct   1980

ctgcgggttg tgcgtcacta cggcaataca cctttagagc tactggcttt gcagacctat   2040

cacttgactc aattgcatcc tgccagcgga tttcgctcct gccggctgcc ttgggtactg   2100

cacttggctg atcggagtag taaggagttt cagcggatag gtcagatcag ccttttgcag   2160

aatgttgatc gagaaaagtt aattgctgtt tga                                2193
```

<210> SEQ ID NO 22
<211> LENGTH: 148
<212> TYPE: PRT
<213> ORGANISM: Saccharolobus solfataricus

<400> SEQUENCE: 22

```
Met Glu Glu Lys Val Gly Asn Leu Lys Pro Asn Met Glu Ser Val Asn
1               5                   10                  15

Val Thr Val Arg Val Leu Glu Ala Ser Glu Ala Arg Gln Ile Gln Thr
            20                  25                  30

Lys Asn Gly Val Arg Thr Ile Ser Glu Ala Ile Val Gly Asp Glu Thr
        35                  40                  45

Gly Arg Val Lys Leu Thr Leu Trp Gly Lys His Ala Gly Ser Ile Lys
    50                  55                  60

Glu Gly Gln Val Val Lys Ile Glu Asn Ala Trp Thr Thr Ala Phe Lys
65                  70                  75                  80

Gly Gln Val Gln Leu Asn Ala Gly Ser Lys Thr Lys Ile Ala Glu Ala
                85                  90                  95

Ser Glu Asp Gly Phe Pro Glu Ser Ser Gln Ile Pro Glu Asn Thr Pro
            100                 105                 110

Thr Ala Pro Gln Gln Met Arg Gly Gly Gly Arg Gly Phe Arg Gly Gly
        115                 120                 125

Gly Arg Arg Tyr Gly Arg Arg Gly Gly Arg Arg Gln Glu Asn Glu Glu
    130                 135                 140

Gly Glu Glu Glu
145
```

<210> SEQ ID NO 23
<211> LENGTH: 399
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95
```

```
Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Glu Glu Lys Val
                245                 250                 255

Gly Asn Leu Lys Pro Asn Met Glu Ser Val Asn Val Thr Val Arg Val
            260                 265                 270

Leu Glu Ala Ser Glu Ala Arg Gln Ile Gln Thr Lys Asn Gly Val Arg
        275                 280                 285

Thr Ile Ser Glu Ala Ile Val Gly Asp Glu Thr Gly Arg Val Lys Leu
    290                 295                 300

Thr Leu Trp Gly Lys His Ala Gly Ser Ile Lys Glu Gly Gln Val Val
305                 310                 315                 320

Lys Ile Glu Asn Ala Trp Thr Thr Ala Phe Lys Gly Gln Val Gln Leu
                325                 330                 335

Asn Ala Gly Ser Lys Thr Lys Ile Ala Glu Ala Ser Glu Asp Gly Phe
            340                 345                 350

Pro Glu Ser Ser Gln Ile Pro Glu Asn Thr Pro Thr Ala Pro Gln Gln
        355                 360                 365

Met Arg Gly Gly Gly Arg Gly Phe Arg Gly Gly Gly Arg Arg Tyr Gly
    370                 375                 380

Arg Arg Gly Gly Arg Arg Gln Glu Asn Glu Glu Gly Glu Glu Glu
385                 390                 395
```

<210> SEQ ID NO 24
<211> LENGTH: 243
<212> TYPE: PRT
<213> ORGANISM: Nanoarchaeum equitans

<400> SEQUENCE: 24

```
Met Asp Glu Glu Glu Leu Ile Gln Leu Ile Ile Glu Lys Thr Gly Lys
1               5                   10                  15

Ser Arg Glu Glu Ile Glu Lys Met Val Glu Glu Lys Ile Lys Ala Phe
            20                  25                  30

Asn Asn Leu Ile Ser Arg Arg Gly Ala Leu Leu Leu Val Ala Lys Lys
        35                  40                  45

Leu Gly Val Leu Tyr Lys Asn Thr Pro Lys Glu Lys Lys Ile Gly Glu
    50                  55                  60

Leu Glu Ser Trp Glu Tyr Val Lys Val Lys Gly Lys Ile Leu Lys Ser
65                  70                  75                  80
```

```
Phe Gly Leu Ile Ser Tyr Ser Lys Gly Lys Phe Gln Pro Ile Ile Leu
                85                  90                  95

Gly Asp Glu Thr Gly Thr Ile Lys Ala Ile Ile Trp Asn Thr Asp Lys
            100                 105                 110

Glu Leu Pro Glu Asn Thr Val Ile Glu Ala Ile Gly Lys Thr Lys Ile
        115                 120                 125

Asn Lys Lys Thr Gly Asn Leu Glu Leu His Ile Asp Ser Tyr Lys Ile
    130                 135                 140

Leu Glu Ser Asp Leu Glu Ile Lys Pro Gln Lys Gln Glu Phe Val Gly
145                 150                 155                 160

Ile Cys Ile Val Lys Tyr Pro Lys Lys Gln Thr Gln Lys Gly Thr Ile
                165                 170                 175

Val Ser Lys Ala Ile Leu Thr Ser Leu Asp Arg Glu Leu Pro Val Val
            180                 185                 190

Tyr Phe Asn Asp Phe Asp Trp Glu Ile Gly His Ile Tyr Lys Val Tyr
        195                 200                 205

Gly Lys Leu Lys Lys Asn Ile Lys Thr Gly Lys Ile Glu Phe Phe Ala
    210                 215                 220

Asp Lys Val Glu Glu Ala Thr Leu Lys Asp Leu Lys Ala Phe Lys Gly
225                 230                 235                 240

Glu Ala Asp


<210> SEQ ID NO 25
<211> LENGTH: 496
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190
```

Phe Lys Lys Arg Ile Glu Ala Ile Pro Gln Ile Asp Lys Tyr Leu Lys
195 200 205

Ser Ser Lys Tyr Ile Ala Trp Pro Leu Gln Gly Trp Gln Ala Thr Phe
210 215 220

Gly Gly Gly Asp His Pro Pro Thr Ser Gly Ser Gly Gly Gly Gly Gly
225 230 235 240

Trp Met Ser Glu Asn Leu Tyr Phe Gln Gly Ala Leu Ala Met Asp Glu
245 250 255

Glu Glu Leu Ile Gln Leu Ile Ile Glu Lys Thr Gly Lys Ser Arg Glu
260 265 270

Glu Ile Glu Lys Met Val Glu Glu Lys Ile Lys Ala Phe Asn Asn Leu
275 280 285

Ile Ser Arg Arg Gly Ala Leu Leu Leu Val Ala Lys Lys Leu Gly Val
290 295 300

Leu Tyr Lys Asn Thr Pro Lys Glu Lys Lys Ile Gly Glu Leu Glu Ser
305 310 315 320

Trp Glu Tyr Val Lys Val Lys Gly Lys Ile Leu Lys Ser Phe Gly Leu
325 330 335

Ile Ser Tyr Ser Lys Gly Lys Phe Gln Pro Ile Ile Leu Gly Asp Glu
340 345 350

Thr Gly Thr Ile Lys Ala Ile Ile Trp Asn Thr Asp Lys Glu Leu Pro
355 360 365

Glu Asn Thr Val Ile Glu Ala Ile Gly Lys Thr Lys Ile Asn Lys Lys
370 375 380

Thr Gly Asn Leu Glu Leu His Ile Asp Ser Tyr Lys Ile Leu Glu Ser
385 390 395 400

Asp Leu Glu Ile Lys Pro Gln Lys Gln Glu Phe Val Gly Ile Cys Ile
405 410 415

Val Lys Tyr Pro Lys Lys Gln Thr Gln Lys Gly Thr Ile Val Ser Lys
420 425 430

Ala Ile Leu Thr Ser Leu Asp Arg Glu Leu Pro Val Val Tyr Phe Asn
435 440 445

Asp Phe Asp Trp Glu Ile Gly His Ile Tyr Lys Val Tyr Gly Lys Leu
450 455 460

Lys Lys Asn Ile Lys Thr Gly Lys Ile Glu Phe Phe Ala Asp Lys Val
465 470 475 480

Glu Glu Ala Thr Leu Lys Asp Leu Lys Ala Phe Lys Gly Glu Ala Asp
485 490 495

<210> SEQ ID NO 26
<211> LENGTH: 264
<212> TYPE: PRT
<213> ORGANISM: Thermus aquaticus

<400> SEQUENCE: 26

Met Ala Arg Gly Leu Asn Gln Val Phe Leu Ile Gly Thr Leu Thr Ala
1 5 10 15

Arg Pro Asp Met Arg Tyr Thr Pro Gly Gly Leu Ala Ile Leu Asp Leu
20 25 30

Asn Leu Ala Gly Gln Asp Ala Phe Thr Asp Glu Ser Gly Gln Glu Arg
35 40 45

Glu Val Pro Trp Tyr His Arg Val Arg Leu Leu Gly Arg Gln Ala Glu
50 55 60

Met Trp Gly Asp Leu Leu Glu Lys Gly Gln Leu Ile Phe Val Glu Gly 65 70 75 80

Arg Leu Glu Tyr Arg Gln Trp Glu Lys Asp Gly Glu Lys Lys Ser Glu
85 90 95

Val Gln Val Arg Ala Glu Phe Ile Asp Pro Leu Glu Gly Arg Gly Arg
100 105 110

Glu Thr Leu Glu Asp Ala Arg Gly Gln Pro Arg Leu Arg Arg Ala Leu
115 120 125

Asn Gln Val Ile Leu Met Gly Asn Leu Thr Arg Asp Pro Asp Leu Arg
130 135 140

Tyr Thr Pro Gln Gly Thr Ala Val Val Arg Leu Gly Leu Ala Val Asn
145 150 155 160

Glu Arg Arg Arg Gly Gln Glu Glu Glu Arg Thr His Phe Leu Glu Val
165 170 175

Gln Ala Trp Arg Glu Leu Ala Glu Trp Ala Ser Glu Leu Arg Lys Gly
180 185 190

Asp Gly Leu Leu Val Ile Gly Arg Leu Val Asn Asp Ser Trp Thr Ser
195 200 205

Ser Ser Gly Glu Arg Arg Phe Gln Thr Arg Val Glu Ala Leu Arg Leu
210 215 220

Glu Arg Pro Thr Arg Gly Pro Ala Gln Ala Gly Gly Ser Arg Pro Pro
225 230 235 240

Thr Val Gln Thr Gly Gly Val Asp Ile Asp Glu Gly Leu Glu Asp Phe
245 250 255

Pro Pro Glu Glu Asp Leu Pro Phe
260

<210> SEQ ID NO 27
<211> LENGTH: 515
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 27

Met Lys His His His His His His Asn Thr Ser Ser Asn Ser Met Ser
1 5 10 15

Pro Ile Leu Gly Tyr Trp Lys Ile Lys Gly Leu Val Gln Pro Thr Arg
20 25 30

Leu Leu Leu Glu Tyr Leu Glu Glu Lys Tyr Glu Glu His Leu Tyr Glu
35 40 45

Arg Asp Glu Gly Asp Lys Trp Arg Asn Lys Lys Phe Glu Leu Gly Leu
50 55 60

Glu Phe Pro Asn Leu Pro Tyr Tyr Ile Asp Gly Asp Val Lys Leu Thr
65 70 75 80

Gln Ser Met Ala Ile Ile Arg Tyr Ile Ala Asp Lys His Asn Met Leu
85 90 95

Gly Gly Cys Pro Lys Glu Arg Ala Glu Ile Ser Met Leu Glu Gly Ala
100 105 110

Val Leu Asp Ile Arg Tyr Gly Val Ser Arg Ile Ala Tyr Ser Lys Asp
115 120 125

Phe Glu Thr Leu Lys Val Asp Phe Leu Ser Lys Leu Pro Glu Met Leu
130 135 140

Lys Met Phe Glu Asp Arg Leu Cys His Lys Thr Tyr Leu Asn Gly Asp
145 150 155 160

```
His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Ala Arg Gly Leu
                245                 250                 255

Asn Gln Val Phe Leu Ile Gly Thr Leu Thr Ala Arg Pro Asp Met Arg
            260                 265                 270

Tyr Thr Pro Gly Gly Leu Ala Ile Leu Asp Leu Asn Leu Ala Gly Gln
        275                 280                 285

Asp Ala Phe Thr Asp Glu Ser Gly Gln Glu Arg Glu Val Pro Trp Tyr
    290                 295                 300

His Arg Val Arg Leu Leu Gly Arg Gln Ala Glu Met Trp Gly Asp Leu
305                 310                 315                 320

Leu Glu Lys Gly Gln Leu Ile Phe Val Glu Gly Arg Leu Glu Tyr Arg
                325                 330                 335

Gln Trp Glu Lys Asp Gly Glu Lys Lys Ser Glu Val Gln Val Arg Ala
            340                 345                 350

Glu Phe Ile Asp Pro Leu Glu Gly Arg Gly Arg Glu Thr Leu Glu Asp
        355                 360                 365

Ala Arg Gly Gln Pro Arg Leu Arg Arg Ala Leu Asn Gln Val Ile Leu
    370                 375                 380

Met Gly Asn Leu Thr Arg Asp Pro Asp Leu Arg Tyr Thr Pro Gln Gly
385                 390                 395                 400

Thr Ala Val Val Arg Leu Gly Leu Ala Val Asn Glu Arg Arg Arg Gly
                405                 410                 415

Gln Glu Glu Glu Arg Thr His Phe Leu Glu Val Gln Ala Trp Arg Glu
            420                 425                 430

Leu Ala Glu Trp Ala Ser Glu Leu Arg Lys Gly Asp Gly Leu Leu Val
        435                 440                 445

Ile Gly Arg Leu Val Asn Asp Ser Trp Thr Ser Ser Ser Gly Glu Arg
    450                 455                 460

Arg Phe Gln Thr Arg Val Glu Ala Leu Arg Leu Glu Arg Pro Thr Arg
465                 470                 475                 480

Gly Pro Ala Gln Ala Gly Gly Ser Arg Pro Pro Thr Val Gln Thr Gly
                485                 490                 495

Gly Val Asp Ile Asp Glu Gly Leu Glu Asp Phe Pro Pro Glu Glu Asp
            500                 505                 510

Leu Pro Phe
        515
```

<210> SEQ ID NO 28
<211> LENGTH: 142
<212> TYPE: PRT
<213> ORGANISM: Thermotoga maritima

<400> SEQUENCE: 28

```
Met Gly Ser Phe Phe Asn Lys Ile Ile Leu Ile Gly Arg Leu Val Arg
1               5                   10                  15
```

```
Asp Pro Glu Glu Arg Tyr Thr Leu Ser Gly Thr Pro Val Thr Thr Phe
            20                  25                  30

Thr Ile Ala Val Asp Arg Val Pro Arg Lys Asn Ala Pro Asp Asp Ala
        35                  40                  45

Gln Thr Thr Asp Phe Phe Arg Ile Val Thr Phe Gly Arg Leu Ala Glu
    50                  55                  60

Phe Ala Arg Thr Tyr Leu Thr Lys Gly Arg Leu Val Leu Val Glu Gly
65                  70                  75                  80

Glu Met Arg Met Arg Arg Trp Glu Thr Pro Thr Gly Glu Lys Arg Val
                85                  90                  95

Ser Pro Glu Val Val Ala Asn Val Val Arg Phe Met Asp Arg Lys Pro
            100                 105                 110

Ala Glu Thr Val Ser Glu Thr Glu Glu Glu Leu Glu Ile Pro Glu Glu
        115                 120                 125

Asp Phe Ser Ser Asp Thr Phe Ser Glu Asp Glu Pro Pro Phe
    130                 135                 140


<210> SEQ ID NO 29
<211> LENGTH: 393
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
```

225 230 235 240

Trp Met Ser Glu Asn Leu Tyr Phe Gln Gly Ala Met Gly Ser Phe Phe
245 250 255

Asn Lys Ile Ile Leu Ile Gly Arg Leu Val Arg Asp Pro Glu Glu Arg
260 265 270

Tyr Thr Leu Ser Gly Thr Pro Val Thr Thr Phe Thr Ile Ala Val Asp
275 280 285

Arg Val Pro Arg Lys Asn Ala Pro Asp Asp Ala Gln Thr Thr Asp Phe
290 295 300

Phe Arg Ile Val Thr Phe Gly Arg Leu Ala Glu Phe Ala Arg Thr Tyr
305 310 315 320

Leu Thr Lys Gly Arg Leu Val Leu Val Glu Gly Glu Met Arg Met Arg
325 330 335

Arg Trp Glu Thr Pro Thr Gly Glu Lys Arg Val Ser Pro Glu Val Val
340 345 350

Ala Asn Val Val Arg Phe Met Asp Arg Lys Pro Ala Glu Thr Val Ser
355 360 365

Glu Thr Glu Glu Glu Leu Glu Ile Pro Glu Glu Asp Phe Ser Ser Asp
370 375 380

Thr Phe Ser Glu Asp Glu Pro Pro Phe
385 390

<210> SEQ ID NO 30
<211> LENGTH: 178
<212> TYPE: PRT
<213> ORGANISM: Escherichia coli

<400> SEQUENCE: 30

Met Ala Ser Arg Gly Val Asn Lys Val Ile Leu Val Gly Asn Leu Gly
1 5 10 15

Gln Asp Pro Glu Val Arg Tyr Met Pro Asn Gly Gly Ala Val Ala Asn
20 25 30

Ile Thr Leu Ala Thr Ser Glu Ser Trp Arg Asp Lys Ala Thr Gly Glu
35 40 45

Met Lys Glu Gln Thr Glu Trp His Arg Val Val Leu Phe Gly Lys Leu
50 55 60

Ala Glu Val Ala Ser Glu Tyr Leu Arg Lys Gly Ser Gln Val Tyr Ile
65 70 75 80

Glu Gly Gln Leu Arg Thr Arg Lys Trp Thr Asp Gln Ser Gly Gln Asp
85 90 95

Arg Tyr Thr Thr Glu Val Val Val Asn Val Gly Gly Thr Met Gln Met
100 105 110

Leu Gly Gly Arg Gln Gly Gly Gly Ala Pro Ala Gly Gly Asn Ile Gly
115 120 125

Gly Gly Gln Pro Gln Gly Gly Trp Gly Gln Pro Gln Gln Pro Gln Gly
130 135 140

Gly Asn Gln Phe Ser Gly Gly Ala Gln Ser Arg Pro Gln Gln Ser Ala
145 150 155 160

Pro Ala Ala Pro Ser Asn Glu Pro Pro Met Asp Phe Asp Asp Asp Ile
165 170 175

Pro Phe

<210> SEQ ID NO 31
<211> LENGTH: 431
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 31

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Leu Ala Met Ala Ser
                245                 250                 255

Arg Gly Val Asn Lys Val Ile Leu Val Gly Asn Leu Gly Gln Asp Pro
            260                 265                 270

Glu Val Arg Tyr Met Pro Asn Gly Gly Ala Val Ala Asn Ile Thr Leu
        275                 280                 285

Ala Thr Ser Glu Ser Trp Arg Asp Lys Ala Thr Gly Glu Met Lys Glu
    290                 295                 300

Gln Thr Glu Trp His Arg Val Val Leu Phe Gly Lys Leu Ala Glu Val
305                 310                 315                 320

Ala Ser Glu Tyr Leu Arg Lys Gly Ser Gln Val Tyr Ile Glu Gly Gln
                325                 330                 335

Leu Arg Thr Arg Lys Trp Thr Asp Gln Ser Gly Gln Asp Arg Tyr Thr
            340                 345                 350

Thr Glu Val Val Val Asn Val Gly Gly Thr Met Gln Met Leu Gly Gly
        355                 360                 365

Arg Gln Gly Gly Gly Ala Pro Ala Gly Gly Asn Ile Gly Gly Gly Gln
    370                 375                 380
```

```
Pro Gln Gly Gly Trp Gly Gln Pro Gln Gln Pro Gln Gly Gly Asn Gln
385                 390                 395                 400

Phe Ser Gly Gly Ala Gln Ser Arg Pro Gln Gln Ser Ala Pro Ala Ala
                405                 410                 415

Pro Ser Asn Glu Pro Pro Met Asp Phe Asp Asp Asp Ile Pro Phe
            420                 425                 430


<210> SEQ ID NO 32
<211> LENGTH: 263
<212> TYPE: PRT
<213> ORGANISM: Thermus thermophilus

<400> SEQUENCE: 32

Met Ala Arg Gly Leu Asn Arg Val Phe Leu Ile Gly Ala Leu Ala Thr
1               5                   10                  15

Arg Pro Asp Met Arg Tyr Thr Pro Ala Gly Leu Ala Ile Leu Asp Leu
            20                  25                  30

Thr Leu Ala Gly Gln Asp Leu Leu Leu Ser Asp Asn Gly Gly Glu Arg
        35                  40                  45

Glu Val Ser Trp Tyr His Arg Val Arg Leu Leu Gly Arg Gln Ala Glu
    50                  55                  60

Met Trp Gly Asp Leu Leu Asp Gln Gly Gln Leu Val Phe Val Glu Gly
65                  70                  75                  80

Arg Leu Glu Tyr Arg Gln Trp Glu Arg Glu Gly Glu Lys Arg Ser Glu
                85                  90                  95

Leu Gln Ile Arg Ala Asp Phe Leu Asp Pro Leu Asp Asp Arg Gly Lys
            100                 105                 110

Glu Arg Ala Glu Asp Ser Arg Gly Gln Pro Arg Leu Arg Ala Ala Leu
        115                 120                 125

Asn Gln Val Phe Leu Met Gly Asn Leu Thr Arg Asp Pro Glu Leu Arg
    130                 135                 140

Tyr Thr Pro Gln Gly Thr Ala Val Ala Arg Leu Gly Leu Ala Val Asn
145                 150                 155                 160

Glu Arg Arg Gln Gly Ala Glu Glu Arg Thr His Phe Val Glu Val Gln
                165                 170                 175

Ala Trp Arg Asp Leu Ala Glu Trp Ala Ala Glu Leu Arg Lys Gly Asp
            180                 185                 190

Gly Leu Phe Val Ile Gly Arg Leu Val Asn Asp Ser Trp Thr Ser Ser
        195                 200                 205

Ser Gly Glu Arg Arg Phe Gln Thr Arg Val Glu Ala Leu Arg Leu Glu
    210                 215                 220

Arg Pro Thr Arg Gly Pro Ala Gln Ala Gly Gly Ser Arg Ser Arg Glu
225                 230                 235                 240

Ala Gln Thr Gly Gly Val Asp Ile Asp Glu Gly Leu Glu Asp Phe Pro
                245                 250                 255

Pro Glu Glu Glu Leu Pro Phe
            260


<210> SEQ ID NO 33
<211> LENGTH: 514
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33
```

-continued

```
Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Ala Arg Gly Leu
                245                 250                 255

Asn Arg Val Phe Leu Ile Gly Ala Leu Ala Thr Arg Pro Asp Met Arg
            260                 265                 270

Tyr Thr Pro Ala Gly Leu Ala Ile Leu Asp Leu Thr Leu Ala Gly Gln
        275                 280                 285

Asp Leu Leu Leu Ser Asp Asn Gly Gly Glu Arg Glu Val Ser Trp Tyr
    290                 295                 300

His Arg Val Arg Leu Leu Gly Arg Gln Ala Glu Met Trp Gly Asp Leu
305                 310                 315                 320

Leu Asp Gln Gly Gln Leu Val Phe Val Glu Gly Arg Leu Glu Tyr Arg
                325                 330                 335

Gln Trp Glu Arg Glu Gly Glu Lys Arg Ser Glu Leu Gln Ile Arg Ala
            340                 345                 350

Asp Phe Leu Asp Pro Leu Asp Asp Arg Gly Lys Glu Arg Ala Glu Asp
        355                 360                 365

Ser Arg Gly Gln Pro Arg Leu Arg Ala Ala Leu Asn Gln Val Phe Leu
    370                 375                 380

Met Gly Asn Leu Thr Arg Asp Pro Glu Leu Arg Tyr Thr Pro Gln Gly
385                 390                 395                 400

Thr Ala Val Ala Arg Leu Gly Leu Ala Val Asn Glu Arg Arg Gln Gly
                405                 410                 415

Ala Glu Glu Arg Thr His Phe Val Glu Val Gln Ala Trp Arg Asp Leu
```

```
            420                 425                 430

Ala Glu Trp Ala Ala Glu Leu Arg Lys Gly Asp Gly Leu Phe Val Ile
        435                 440                 445

Gly Arg Leu Val Asn Asp Ser Trp Thr Ser Ser Ser Gly Glu Arg Arg
    450                 455                 460

Phe Gln Thr Arg Val Glu Ala Leu Arg Leu Glu Arg Pro Thr Arg Gly
465                 470                 475                 480

Pro Ala Gln Ala Gly Gly Ser Arg Ser Arg Glu Ala Gln Thr Gly Gly
                485                 490                 495

Val Asp Ile Asp Glu Gly Leu Glu Asp Phe Pro Pro Glu Glu Glu Leu
            500                 505                 510

Pro Phe


<210> SEQ ID NO 34
<211> LENGTH: 143
<212> TYPE: PRT
<213> ORGANISM: Thermotoga neapolitana

<400> SEQUENCE: 34

Met Gly Ser Phe Phe Asn Arg Ile Ile Leu Ile Gly Arg Leu Val Arg
1               5                   10                  15

Asp Pro Glu Glu Arg Tyr Thr Leu Ser Gly Thr Pro Val Thr Thr Phe
            20                  25                  30

Thr Ile Ala Val Asp Arg Val Pro Arg Lys Asn Ala Pro Asp Asp Ala
        35                  40                  45

Gln Thr Thr Asp Phe Phe Arg Val Val Thr Phe Gly Arg Leu Ala Glu
    50                  55                  60

Phe Ala Arg Thr Tyr Leu Thr Lys Gly Arg Leu Ile Leu Val Glu Gly
65                  70                  75                  80

Glu Met Arg Met Arg Arg Trp Glu Thr Gln Thr Gly Glu Lys Arg Val
                85                  90                  95

Ser Pro Glu Val Val Ala Asn Val Val Arg Phe Met Asp Arg Lys Pro
            100                 105                 110

Val Glu Met Pro Ser Glu Asp Ile Glu Glu Lys Leu Glu Ile Pro Glu
        115                 120                 125

Glu Asp Phe Thr Asp Asp Thr Phe Ser Glu Asp Glu Pro Pro Phe
    130                 135                 140


<210> SEQ ID NO 35
<211> LENGTH: 394
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80
```

```
Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Gly Ser Phe Phe
                245                 250                 255

Asn Arg Ile Ile Leu Ile Gly Arg Leu Val Arg Asp Pro Glu Glu Arg
            260                 265                 270

Tyr Thr Leu Ser Gly Thr Pro Val Thr Thr Phe Thr Ile Ala Val Asp
        275                 280                 285

Arg Val Pro Arg Lys Asn Ala Pro Asp Asp Ala Gln Thr Thr Asp Phe
    290                 295                 300

Phe Arg Val Val Thr Phe Gly Arg Leu Ala Glu Phe Ala Arg Thr Tyr
305                 310                 315                 320

Leu Thr Lys Gly Arg Leu Ile Leu Val Glu Gly Glu Met Arg Met Arg
                325                 330                 335

Arg Trp Glu Thr Gln Thr Gly Glu Lys Arg Val Ser Pro Glu Val Val
            340                 345                 350

Ala Asn Val Val Arg Phe Met Asp Arg Lys Pro Val Glu Met Pro Ser
        355                 360                 365

Glu Asp Ile Glu Glu Lys Leu Glu Ile Pro Glu Glu Asp Phe Thr Asp
    370                 375                 380

Asp Thr Phe Ser Glu Asp Glu Pro Pro Phe
385                 390
```

<210> SEQ ID NO 36
<211> LENGTH: 447
<212> TYPE: DNA
<213> ORGANISM: Saccharolobus solfataricus

<400> SEQUENCE: 36

```
atggaagaaa aagtaggcaa cctgaagcct aatatggaat ccgtaaatgt aaccgttcgc      60

gttttagaag cctctgaagc acggcagatc cagaccaaaa atggtgttcg caccatttca     120

gaggcgattg taggggatga aaccgggcgc gtgaaactga ctctgtgggg caaacatgcg     180

ggcagcatca aagaaggcca ggtcgttaaa attgagaacg cctggacaac cgcgttcaaa     240

ggccaggtac agctgaatgc cggtagcaag accaaaattg ccgaggcatc tgaagacggt     300
```

ttccctgaaa gcagccagat cccagaaaat actcctacgg caccgcagca gatgcgtggc 360
ggtgggcggg gctttcgtgg cggaggccgc cgttatggcc gtcgcggtgg gcgccggcaa 420
gaaaacgaag aaggcgaaga agaatag 447

<210> SEQ ID NO 37
<211> LENGTH: 1200
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 37
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360
tcgagaattg catatagtaa agactttgaa actctcaaag ttgattttct tagcaagcta 420
cctgaaatgc tgaaaatgtt cgaagatcgt ttatgtcata aaacatattt aaatggtgat 480
catgtaaccc atcctgactt catgttgtat gacgctcttg atgttgtttt atacatggac 540
ccaatgtgcc tggatgcgtt cccaaaatta gtttgtttta aaaaacgtat tgaagctatc 600
ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gccatggaag aaaaagtagg caacctgaag 780
cctaatatgg aatccgtaaa tgtaaccgtt cgcgttttag aagcctctga agcacggcag 840
atccagacca aaaatggtgt tcgcaccatt tcagaggcga ttgtagggga tgaaaccggg 900
cgcgtgaaac tgactctgtg gggcaaacat gcgggcagca tcaaagaagg ccaggtcgtt 960
aaaattgaga acgcctggac aaccgcgttc aaaggccagg tacagctgaa tgccggtagc 1020
aagaccaaaa ttgccgaggc atctgaagac ggtttccctg aaagcagcca gatcccagaa 1080
aatactccta cggcaccgca gcagatgcgt ggcggtgggc ggggctttcg tggcggaggc 1140
cgccgttatg gccgtcgcgg tgggcgccgg caagaaaacg aagaaggcga agaagaatag 1200

<210> SEQ ID NO 38
<211> LENGTH: 735
<212> TYPE: DNA
<213> ORGANISM: Nanoarchaeum equitans

<400> SEQUENCE: 38
atggatgaag aagagcttat tcagcttatt attgaaaaaa ctgggaagtc gcgcgaggaa 60
attgagaaga tggtagaaga aaaaatcaag gctttcaaca acctgatctc gcgccgtggc 120
gctttgctgt tagtggcgaa gaaacttggt gtactttata aaaacacgcc aaaagaaaaa 180
aagatcgggg aactggagtc ctgggaatac gttaaggtga aaggtaaaat cctgaagtcc 240
ttcggcctga ttagttattc aaagggcaag tttcaaccga tcattcttgg ggacgaaact 300
ggcactatca aagctattat ctggaatact gataaggagt tacctgagaa tacggtcatt 360
gaagctattg gaaagactaa gattaacaaa aaaacaggga atcttgagtt acatattgat 420

```
agttacaaaa ttttagagtc cgacttagag attaagcctc agaaacagga atttgtcggt    480

atttgcatcg ttaaataccc caagaagcag acccaaaagg gtacgattgt aagcaaagct    540

atcctgacat cattagaccg tgagttaccc gtcgtttact ttaatgattt tgactgggag    600

atcgggcata tctataaggt ctacgggaaa ctgaaaaaaa atatcaaaac tggcaaaatc    660

gagtttttg cagacaaggt agaggaagcc accctgaaag atcttaaggc gttcaagggg    720

gaagcagact agtga                                                     735
```

<210> SEQ ID NO 39
<211> LENGTH: 1494
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gcgctagcaa tggatgaaga agagcttatt    780

cagcttatta ttgaaaaaac tgggaagtcg cgcgaggaaa ttgagaagat ggtagaagaa    840

aaaatcaagg ctttcaacaa cctgatctcg cgccgtggcg ctttgctgtt agtggcgaag    900

aaacttggtg tactttataa aaacacgcca aaagaaaaaa agatcgggga actggagtcc    960

tgggaatacg ttaaggtgaa aggtaaaatc ctgaagtcct tcggcctgat tagttattca   1020

aagggcaagt ttcaaccgat cattcttggg gacgaaactg gcactatcaa agctattatc   1080

tggaatactg ataaggagtt acctgagaat acggtcattg aagctattgg aaagactaag   1140

attaacaaaa aaacagggaa tcttgagtta catattgata gttacaaaat tttagagtcc   1200

gacttagaga ttaagcctca gaaacaggaa tttgtcggta tttgcatcgt taaatacccc   1260

aagaagcaga cccaaaaggg tacgattgta agcaaagcta tcctgacatc attagaccgt   1320

gagttacccg tcgtttactt taatgatttt gactgggaga tcgggcatat ctataaggtc   1380

tacgggaaac tgaaaaaaaa tatcaaaact ggcaaaatcg agtttttgc agacaaggta    1440

gaggaagcca ccctgaaaga tcttaaggcg ttcaaggggg aagcagacta gtga         1494
```

<210> SEQ ID NO 40
<211> LENGTH: 795
<212> TYPE: DNA
<213> ORGANISM: Thermus aquaticus

<400> SEQUENCE: 40
atggcgcgcg gtctgaacca ggtatttctg atcggcaccc tcactgcccg tccagatatg 60
cgctataccc cgggcgggct ggcaattctg gatctcaatc ttgctgggca ggatgcgttt 120
accgatgaaa gtgggcaaga gcgtgaagtc ccgtggtatc atcgtgtgcg tctgctcggc 180
cgtcaagcgg aaatgtgggg tgacctgctg gaaaaaggtc agctgatctt tgtggaaggt 240
cgcctggaat accgccaatg ggaaaaagac ggcgaaaaaa agagcgaagt ccaagtccgt 300
gctgagttta ttgatccgct ggaaggtcgc ggccgtgaga cgctcgaaga tgctcgtggt 360
cagccccgct tacgtcgtgc actgaaccag gttattctca tgggtaacct cacccgcgat 420
cccgatttac gctatacccc ccagggtacg gcggtggtac gcctgggcct tgctgtgaac 480
gagcggcgtc gtggccaaga agaagaacgt acccattttc tggaagtgca ggcgtggcgc 540
gagctggccg aatgggctag cgaattacgc aaaggcgacg gtcttctggt catcggtcgc 600
ttggtcaacg attcctggac aagctcctcg ggtgaacgtc gcttccaaac gcgtgtggag 660
gcactgcggt tagaacgtcc gacccgcggc ccggcacagg cgggggggatc ccggccgccc 720 accgtgcaga cggggggtgt ggatatcgat gaggggctgg aagactttcc gcctgaagaa 780
gatctgcctt tctag 795

<210> SEQ ID NO 41
<211> LENGTH: 1548
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 41
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360
tcgagaattg catatagtaa agactttgaa actctcaaag ttgattttct tagcaagcta 420
cctgaaatgc tgaaaatgtt cgaagatcgt ttatgtcata aaacatattt aaatggtgat 480
catgtaaccc atcctgactt catgttgtat gacgctcttg atgttgtttt atacatggac 540
ccaatgtgcc tggatgcgtt cccaaaatta gtttgtttta aaaaacgtat tgaagctatc 600
ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gccatggcgc gcggtctgaa ccaggtattt 780
ctgatcggca ccctcactgc ccgtccagat atgcgctata ccccgggcgg gctggcaatt 840
ctggatctca atcttgctgg gcaggatgcg tttaccgatg aaagtgggca agagcgtgaa 900
gtcccgtggt atcatcgtgt gcgtctgctc ggccgtcaag cggaaatgtg gggtgacctg 960
ctggaaaaag gtcagctgat ctttgtggaa ggtcgcctgg aataccgcca atgggaaaaa 1020
gacggcgaaa aaaagagcga agtccaagtc cgtgctgagt ttattgatcc gctggaaggt 1080
cgcggccgtg agacgctcga agatgctcgt ggtcagcccc gcttacgtcg tgcactgaac 1140

```
caggttattc tcatgggtaa cctcacccgc gatcccgatt tacgctatac cccccagggt   1200

acggcggtgg tacgcctggg ccttgctgtg aacgagcggc gtcgtggcca agaagaagaa   1260

cgtacccatt ttctggaagt gcaggcgtgg cgcgagctgg ccgaatgggc tagcgaatta   1320

cgcaaaggcg acggtcttct ggtcatcggt cgcttggtca acgattcctg gacaagctcc   1380

tcgggtgaac gtcgcttcca aacgcgtgtg gaggcactgc ggttagaacg tccgacccgc   1440

ggcccggcac aggcgggggg atcccggccg cccaccgtgc agacgggggg tgtggatatc   1500

gatgaggggc tggaagactt tccgcctgaa gaagatctgc ctttctag                 1548
```

<210> SEQ ID NO 42
<211> LENGTH: 429
<212> TYPE: DNA
<213> ORGANISM: Thermotoga maritima

<400> SEQUENCE: 42

```
atgggatctt tcttcaacaa aattatcctt atcggccgtc tggtccgcga cccggaagaa     60

cgttatacac tgtctggcac accggtcacc acctttacta ttgccgtcga tcgtgttccg    120

cgcaaaaacg caccggatga tgcccagacc accgattttt ttcgcattgt gactttcggc    180

cgcctggcgg agtttgcccg tacttattta acgaaaggtc gtctcgtgct cgtagagggc    240

gagatgcgca tgcgccgttg ggaaacacca acgggcgaaa aacgtgtgag cccggaagtg    300

gtggccaatg tggttcgttt tatggaccgc aaacctgccg aaaccgtcag cgaaacggaa    360

gaggaactcg aaatcccaga ggaggacttc agctcagaca ccttttcgga agatgaaccc    420

ccgttttag                                                            429
```

<210> SEQ ID NO 43
<211> LENGTH: 1182
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gccatgggat ctttcttcaa caaaattatc    780

cttatcggcc gtctggtccg cgacccggaa gaacgttata cactgtctgg cacaccggtc    840

accaccttta ctattgccgt cgatcgtgtt ccgcgcaaaa acgcaccgga tgatgcccag    900
```

```
accaccgatt tttttcgcat tgtgactttc ggccgcctgg cggagtttgc ccgtacttat    960

ttaacgaaag gtcgtctcgt gctcgtagag ggcgagatgc gcatgcgccg ttgggaaaca   1020

ccaacgggcg aaaaacgtgt gagcccggaa gtggtggcca atgtggttcg ttttatggac   1080

cgcaaacctg ccgaaaccgt cagcgaaacg gaagaggaac tcgaaatccc agaggaggac   1140

ttcagctcag acacctttc ggaagatgaa cccccgtttt ag                       1182
```

<210> SEQ ID NO 44
<211> LENGTH: 540
<212> TYPE: DNA
<213> ORGANISM: Escherichia coli

<400> SEQUENCE: 44

```
atggcatcac gtggcgtcaa caaggtcatt ttagtcggaa accttgggca ggatcctgaa     60

gtccgctaca tgcccaatgg aggcgctgtt gcgaatatca cattggcaac tagtgaaagc    120

tggcgcgata aggctacggg agagatgaag gagcaaacgg agtggcaccg tgtggtattg    180

ttcggcaaat tagctgaagt ggctagtgaa tatttgcgta aaggttcgca agtgtatatt    240

gagggccagc ttcgtacccg taagtggacc gaccaaagtg gacaggaccg ctacactacg    300

gaagtagtgg tcaatgtagg cgggacgatg caaatgcttg gtggacgtca aggtggtgga    360

gctccagcag gaggtaatat cggtggtgga cagccccaag gggggttgggg ccaaccgcaa    420

cagccacagg ggggtaacca attttccggt ggggctcaga gccgtccaca gcagtcggct    480

cccgcagcac caagcaatga acccccgatg gactttgatg acgatattcc tttctagtga    540
```

<210> SEQ ID NO 45
<211> LENGTH: 1299
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 45

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gcgctagcaa tggcatcacg tggcgtcaac    780

aaggtcattt tagtcggaaa ccttgggcag gatcctgaag tccgctacat gcccaatgga    840

ggcgctgttg cgaatatcac attggcaact agtgaaagct ggcgcgataa ggctacggga    900

gagatgaagg agcaaacgga gtggcaccgt gtggtattgt tcggcaaatt agctgaagtg    960
```

```
gctagtgaat atttgcgtaa aggttcgcaa gtgtatattg agggccagct tcgtacccgt   1020

aagtggaccg accaaagtgg acaggaccgc tacactacgg aagtagtggt caatgtaggc   1080

gggacgatgc aaatgcttgg tggacgtcaa ggtggtggag ctccagcagg aggtaatatc   1140

ggtggtggac agccccaagg gggttggggc caaccgcaac agccacaggg gggtaaccaa   1200

ttttccggtg gggctcagag ccgtccacag cagtcggctc ccgcagcacc aagcaatgaa   1260

cccccgatgg actttgatga cgatattcct ttctagtga                          1299
```

<210> SEQ ID NO 46
<211> LENGTH: 792
<212> TYPE: DNA
<213> ORGANISM: Thermus thermophilus

<400> SEQUENCE: 46

```
atggcacgcg gcctgaaccg cgtttttctg attggtgcac tggccacccg cccggatatg     60

cgctataccc cggcaggcct tgcaatttta gacctgaccc ttgcgggcca agatttactg    120

ctttcagaca atggcggtga acgtgaggtg agttggtacc atcgtgtacg cctgttagga    180

cgtcaggccg agatgtgggg cgatctgctt gaccagggcc agctggtgtt tgtggagggc    240

cgccttgagt atcgtcaatg ggaacgtgaa ggtgaaaaac gctccgaact gcagattcgc    300

gctgatttcc tcgatccgtt ggatgatcgc ggtaaggaac gcgcagaaga tagccggggt    360

cagccacggc tccgtgccgc gctgaaccag gtatttttaa tgggcaatct gacccgcgat    420

cccgaactgc gctacactcc acagggcacc gcagtcgctc gtttaggcct ggctgtgaac    480

gaacgccgtc agggcgcgga agaacgtacc cacttcgttg aagtccaggc ctggcgcgac    540

ttagcagagt gggccgcaga gctgcgtaag ggtgacggcc tgttcgttat cgggcgtctc    600

gttaacgact cttggactag ctcgtcaggt gagcgtcgct ttcaaacccg tgtcgaagcc    660

ctgcggctgg aacgcccaac gcggggtccg gcacaggccg gcgggtcgcg ctctcgcgag    720

gcacagacag gcggggttga tattgacgaa gggttagagg atttcccgcc agaggaggag    780

ctgccttttt ag                                                        792
```

<210> SEQ ID NO 47
<211> LENGTH: 1545
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 47

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600
```

ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gccatggcac gcggcctgaa ccgcgttttt 780
ctgattggtg cactggccac ccgccccggat atgcgctata ccccggcagg ccttgcaatt 840
ttagacctga cccttgcggg ccaagattta ctgctttcag acaatggcgg tgaacgtgag 900
gtgagttggt accatcgtgt acgcctgtta ggacgtcagg ccgagatgtg ggcgatctg 960 cttgaccagg gccagctggt gtttgtggag ggccgccttg agtatcgtca atgggaacgt 1020
gaaggtgaaa aacgctccga actgcagatt cgcgctgatt tcctcgatcc gttggatgat 1080
cgcggtaagg aacgcgcaga agatagccgg ggtcagccac ggctccgtgc cgcgctgaac 1140
caggtatttt taatgggcaa tctgacccgc gatcccgaac tgcgctacac tccacagggc 1200
accgcagtcg ctcgtttagg cctggctgtg aacgaacgcc gtcagggcgc ggaagaacgt 1260
acccacttcg ttgaagtcca ggcctggcgc gacttagcag agtgggccgc agagctgcgt 1320
aagggtgacg gcctgttcgt tatcgggcgt ctcgttaacg actcttggac tagctcgtca 1380
ggtgagcgtc gctttcaaac ccgtgtcgaa gccctgcggc tggaacgccc aacgcggggt 1440
ccggcacagg ccggcgggtc gcgctctcgc gaggcacaga caggcggggt tgatattgac 1500
gaagggttag aggatttccc gccagaggag gagctgcctt tttag 1545

<210> SEQ ID NO 48
<211> LENGTH: 432
<212> TYPE: DNA
<213> ORGANISM: Thermotoga neapolitana

<400> SEQUENCE: 48
atgggatcct tctttaaccg tattatttta attggccgcc tggttcggga tcctgaagaa 60
cgctataccc tgtcagggac tccggtgacg acttttacta tcgcggtcga tcgcgttcct 120
cgtaagaatg cccctgatga tgcccagaca actgactttt ttcgtgttgt aacctttggt 180
cgcttggcgg aattcgcacg gacgtatctg accaaaggcc gccttatcct ggtcgagggt 240
gaaatgcgca tgcgtcgctg ggaaacccag actggcgaaa aacgcgtgag cccggaagta 300
gttgcaaatg tcgtgcgttt tatggaccgc aaacccgtgg aaatgccgag cgaagacatt 360
gaagaaaaac tggaaattcc cgaagaagac tttacggacg atacgttttc ggaggatgaa 420
cccccgtttt ag 432

<210> SEQ ID NO 49
<211> LENGTH: 1185
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 49
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360

```
tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gccatgggat ccttctttaa ccgtattatt    780

ttaattggcc gcctggttcg ggatcctgaa gaacgctata ccctgtcagg gactccggtg    840

acgactttta ctatcgcggt cgatcgcgtt cctcgtaaga atgcccctga tgatgcccag    900

acaactgact tttttcgtgt tgtaaccttt ggtcgcttgg cggaattcgc acggacgtat    960

ctgaccaaag gccgccttat cctggtcgag ggtgaaatgc gcatgcgtcg ctgggaaacc   1020

cagactggcg aaaaacgcgt gagcccggaa gtagttgcaa atgtcgtgcg ttttatggac   1080

cgcaaacccg tggaaatgcc gagcgaagac attgaagaaa aactggaaat tcccgaagaa   1140

gactttacgg acgatacgtt ttcggaggat gaaccccccgt tttag                  1185
```

<210> SEQ ID NO 50
<211> LENGTH: 609
<212> TYPE: PRT
<213> ORGANISM: Escherichia coli

<400> SEQUENCE: 50

```
Met Ala Gln Ala Glu Val Leu Asn Leu Glu Ser Gly Ala Lys Gln Val
1               5                   10                  15

Leu Gln Glu Thr Phe Gly Tyr Gln Gln Phe Arg Pro Gly Gln Glu Glu
            20                  25                  30

Ile Ile Asp Thr Val Leu Ser Gly Arg Asp Cys Leu Val Val Met Pro
        35                  40                  45

Thr Gly Gly Gly Lys Ser Leu Cys Tyr Gln Ile Pro Ala Leu Leu Leu
    50                  55                  60

Asn Gly Leu Thr Val Val Val Ser Pro Leu Ile Ser Leu Met Lys Asp
65                  70                  75                  80

Gln Val Asp Gln Leu Gln Ala Asn Gly Val Ala Ala Ala Cys Leu Asn
                85                  90                  95

Ser Thr Gln Thr Arg Glu Gln Gln Leu Glu Val Met Thr Gly Cys Arg
            100                 105                 110

Thr Gly Gln Ile Arg Leu Leu Tyr Ile Ala Pro Glu Arg Leu Met Leu
        115                 120                 125

Asp Asn Phe Leu Glu His Leu Ala His Trp Asn Pro Val Leu Leu Ala
    130                 135                 140

Val Asp Glu Ala His Cys Ile Ser Gln Trp Gly His Asp Phe Arg Pro
145                 150                 155                 160

Glu Tyr Ala Ala Leu Gly Gln Leu Arg Gln Arg Phe Pro Thr Leu Pro
                165                 170                 175

Phe Met Ala Leu Thr Ala Thr Ala Asp Asp Thr Thr Arg Gln Asp Ile
            180                 185                 190

Val Arg Leu Leu Gly Leu Asn Asp Pro Leu Ile Gln Ile Ser Ser Phe
        195                 200                 205

Asp Arg Pro Asn Ile Arg Tyr Met Leu Met Glu Lys Phe Lys Pro Leu
    210                 215                 220

Asp Gln Leu Met Arg Tyr Val Gln Glu Gln Arg Gly Lys Ser Gly Ile
```

```
225                 230                 235                 240

Ile Tyr Cys Asn Ser Arg Ala Lys Val Glu Asp Thr Ala Ala Arg Leu
                245                 250                 255

Gln Ser Lys Gly Ile Ser Ala Ala Ala Tyr His Ala Gly Leu Glu Asn
            260                 265                 270

Asn Val Arg Ala Asp Val Gln Glu Lys Phe Gln Arg Asp Asp Leu Gln
        275                 280                 285

Ile Val Val Ala Thr Val Ala Phe Gly Met Gly Ile Asn Lys Pro Asn
    290                 295                 300

Val Arg Phe Val Val His Phe Asp Ile Pro Arg Asn Ile Glu Ser Tyr
305                 310                 315                 320

Tyr Gln Glu Thr Gly Arg Ala Gly Arg Asp Gly Leu Pro Ala Glu Ala
                325                 330                 335

Met Leu Phe Tyr Asp Pro Ala Asp Met Ala Trp Leu Arg Arg Cys Leu
            340                 345                 350

Glu Glu Lys Pro Gln Gly Gln Leu Gln Asp Ile Glu Arg His Lys Leu
        355                 360                 365

Asn Ala Met Gly Ala Phe Ala Glu Ala Gln Thr Cys Arg Arg Leu Val
    370                 375                 380

Leu Leu Asn Tyr Phe Gly Glu Gly Arg Gln Glu Pro Cys Gly Asn Cys
385                 390                 395                 400

Asp Ile Cys Leu Asp Pro Pro Lys Gln Tyr Asp Gly Ser Thr Asp Ala
                405                 410                 415

Gln Ile Ala Leu Ser Thr Ile Gly Arg Val Asn Gln Arg Phe Gly Met
            420                 425                 430

Gly Tyr Val Val Glu Val Ile Arg Gly Ala Asn Asn Gln Arg Ile Arg
        435                 440                 445

Asp Tyr Gly His Asp Lys Leu Lys Val Tyr Gly Met Gly Arg Asp Lys
    450                 455                 460

Ser His Glu His Trp Val Ser Val Ile Arg Gln Leu Ile His Leu Gly
465                 470                 475                 480

Leu Val Thr Gln Asn Ile Ala Gln His Ser Ala Leu Gln Leu Thr Glu
                485                 490                 495

Ala Ala Arg Pro Val Leu Arg Gly Glu Ser Ser Leu Gln Leu Ala Val
            500                 505                 510

Pro Arg Ile Val Ala Leu Lys Pro Lys Ala Met Gln Lys Ser Phe Gly
        515                 520                 525

Gly Asn Tyr Asp Arg Lys Leu Phe Ala Lys Leu Arg Lys Leu Arg Lys
    530                 535                 540

Ser Ile Ala Asp Glu Ser Asn Val Pro Pro Tyr Val Val Phe Asn Asp
545                 550                 555                 560

Ala Thr Leu Ile Glu Met Ala Glu Gln Met Pro Ile Thr Ala Ser Glu
                565                 570                 575

Met Leu Ser Val Asn Gly Val Gly Met Arg Lys Leu Glu Arg Phe Gly
            580                 585                 590

Lys Pro Phe Met Ala Leu Ile Arg Ala His Val Asp Gly Asp Asp Glu
        595                 600                 605

Glu


<210> SEQ ID NO 51
<211> LENGTH: 862
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 51

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Leu Ala Met Ala Gln
                245                 250                 255

Ala Glu Val Leu Asn Leu Glu Ser Gly Ala Lys Gln Val Leu Gln Glu
            260                 265                 270

Thr Phe Gly Tyr Gln Gln Phe Arg Pro Gly Gln Glu Glu Ile Ile Asp
        275                 280                 285

Thr Val Leu Ser Gly Arg Asp Cys Leu Val Val Met Pro Thr Gly Gly
    290                 295                 300

Gly Lys Ser Leu Cys Tyr Gln Ile Pro Ala Leu Leu Leu Asn Gly Leu
305                 310                 315                 320

Thr Val Val Val Ser Pro Leu Ile Ser Leu Met Lys Asp Gln Val Asp
                325                 330                 335

Gln Leu Gln Ala Asn Gly Val Ala Ala Ala Cys Leu Asn Ser Thr Gln
            340                 345                 350

Thr Arg Glu Gln Gln Leu Glu Val Met Thr Gly Cys Arg Thr Gly Gln
        355                 360                 365

Ile Arg Leu Leu Tyr Ile Ala Pro Glu Arg Leu Met Leu Asp Asn Phe
    370                 375                 380

Leu Glu His Leu Ala His Trp Asn Pro Val Leu Leu Ala Val Asp Glu
385                 390                 395                 400

```
Ala His Cys Ile Ser Gln Trp Gly His Asp Phe Arg Pro Glu Tyr Ala
                405                 410                 415

Ala Leu Gly Gln Leu Arg Gln Arg Phe Pro Thr Leu Pro Phe Met Ala
            420                 425                 430

Leu Thr Ala Thr Ala Asp Asp Thr Thr Arg Gln Asp Ile Val Arg Leu
        435                 440                 445

Leu Gly Leu Asn Asp Pro Leu Ile Gln Ile Ser Ser Phe Asp Arg Pro
    450                 455                 460

Asn Ile Arg Tyr Met Leu Met Glu Lys Phe Lys Pro Leu Asp Gln Leu
465                 470                 475                 480

Met Arg Tyr Val Gln Glu Gln Arg Gly Lys Ser Gly Ile Ile Tyr Cys
                485                 490                 495

Asn Ser Arg Ala Lys Val Glu Asp Thr Ala Ala Arg Leu Gln Ser Lys
            500                 505                 510

Gly Ile Ser Ala Ala Ala Tyr His Ala Gly Leu Glu Asn Asn Val Arg
        515                 520                 525

Ala Asp Val Gln Glu Lys Phe Gln Arg Asp Asp Leu Gln Ile Val Val
    530                 535                 540

Ala Thr Val Ala Phe Gly Met Gly Ile Asn Lys Pro Asn Val Arg Phe
545                 550                 555                 560

Val Val His Phe Asp Ile Pro Arg Asn Ile Glu Ser Tyr Tyr Gln Glu
                565                 570                 575

Thr Gly Arg Ala Gly Arg Asp Gly Leu Pro Ala Glu Ala Met Leu Phe
            580                 585                 590

Tyr Asp Pro Ala Asp Met Ala Trp Leu Arg Arg Cys Leu Glu Glu Lys
        595                 600                 605

Pro Gln Gly Gln Leu Gln Asp Ile Glu Arg His Lys Leu Asn Ala Met
    610                 615                 620

Gly Ala Phe Ala Glu Ala Gln Thr Cys Arg Arg Leu Val Leu Leu Asn
625                 630                 635                 640

Tyr Phe Gly Glu Gly Arg Gln Glu Pro Cys Gly Asn Cys Asp Ile Cys
                645                 650                 655

Leu Asp Pro Pro Lys Gln Tyr Asp Gly Ser Thr Asp Ala Gln Ile Ala
            660                 665                 670

Leu Ser Thr Ile Gly Arg Val Asn Gln Arg Phe Gly Met Gly Tyr Val
        675                 680                 685

Val Glu Val Ile Arg Gly Ala Asn Asn Gln Arg Ile Arg Asp Tyr Gly
    690                 695                 700

His Asp Lys Leu Lys Val Tyr Gly Met Gly Arg Asp Lys Ser His Glu
705                 710                 715                 720

His Trp Val Ser Val Ile Arg Gln Leu Ile His Leu Gly Leu Val Thr
                725                 730                 735

Gln Asn Ile Ala Gln His Ser Ala Leu Gln Leu Thr Glu Ala Ala Arg
            740                 745                 750

Pro Val Leu Arg Gly Glu Ser Ser Leu Gln Leu Ala Val Pro Arg Ile
        755                 760                 765

Val Ala Leu Lys Pro Lys Ala Met Gln Lys Ser Phe Gly Gly Asn Tyr
    770                 775                 780

Asp Arg Lys Leu Phe Ala Lys Leu Arg Lys Leu Arg Lys Ser Ile Ala
785                 790                 795                 800

Asp Glu Ser Asn Val Pro Pro Tyr Val Val Phe Asn Asp Ala Thr Leu
                805                 810                 815
```

```
Ile Glu Met Ala Glu Gln Met Pro Ile Thr Ala Ser Glu Met Leu Ser
            820                 825                 830

Val Asn Gly Val Gly Met Arg Lys Leu Glu Arg Phe Gly Lys Pro Phe
        835                 840                 845

Met Ala Leu Ile Arg Ala His Val Asp Gly Asp Asp Glu Glu
    850                 855                 860


<210> SEQ ID NO 52
<211> LENGTH: 692
<212> TYPE: PRT
<213> ORGANISM: Thermus thermophilus

<400> SEQUENCE: 52

Met Ser Asp Ala Leu Leu Ala Pro Leu Asn Glu Ala Gln Arg Gln Ala
1               5                   10                  15

Val Leu His Phe Glu Gly Pro Ala Leu Val Val Ala Gly Ala Gly Ser
            20                  25                  30

Gly Lys Thr Arg Thr Val Val His Arg Val Ala Tyr Leu Val Ala Arg
        35                  40                  45

Arg Gly Val Phe Pro Ser Glu Ile Leu Ala Val Thr Phe Thr Asn Lys
    50                  55                  60

Ala Ala Glu Glu Met Arg Glu Arg Leu Arg Gly Leu Val Pro Gly Ala
65                  70                  75                  80

Gly Glu Val Trp Val Ser Thr Phe His Ala Ala Ala Leu Arg Ile Leu
                85                  90                  95

Arg Val Tyr Gly Glu Arg Val Gly Leu Arg Pro Gly Phe Val Val Tyr
            100                 105                 110

Asp Glu Asp Asp Gln Thr Ala Leu Leu Lys Glu Val Leu Lys Glu Leu
        115                 120                 125

Ala Leu Ser Ala Arg Pro Gly Pro Ile Lys Ala Leu Leu Asp Arg Ala
    130                 135                 140

Lys Asn Arg Gly Val Gly Leu Lys Ala Leu Leu Gly Glu Leu Pro Glu
145                 150                 155                 160

Tyr Tyr Ala Gly Leu Ser Arg Gly Arg Leu Gly Asp Val Leu Val Arg
                165                 170                 175

Tyr Gln Glu Ala Leu Lys Ala Gln Gly Ala Leu Asp Phe Gly Asp Ile
            180                 185                 190

Leu Leu Tyr Ala Leu Glu Ala Phe Arg Gly Gly Arg Gly Gly Pro Gln
        195                 200                 205

Ala Arg Ala Gln Arg Ala Arg Phe Ile His Val Asp Glu Tyr Gln Asp
    210                 215                 220

Thr Ser Pro Val Gln Tyr Arg Phe Thr Arg Leu Leu Ala Gly Glu Glu
225                 230                 235                 240

Ala Asn Leu Met Ala Val Gly Asp Pro Asp Gln Gly Ile Tyr Ser Phe
                245                 250                 255

Arg Ala Ala Asp Ile Lys Asn Ile Leu Asp Phe Thr Arg Asp Tyr Pro
            260                 265                 270

Glu Ala Arg Val Tyr Arg Leu Glu Glu Asn Tyr Arg Ser Thr Glu Ala
        275                 280                 285

Ile Leu Arg Phe Ala Asn Ala Val Ile Val Lys Asn Ala Leu Arg Leu
    290                 295                 300

Glu Lys Ala Leu Arg Pro Val Lys Arg Gly Gly Glu Pro Val Arg Leu
305                 310                 315                 320

Tyr Arg Ala Glu Asp Ala Arg Glu Glu Ala Arg Phe Val Ala Glu Glu
                325                 330                 335
```

```
Ile Ala Arg Leu Gly Pro Pro Trp Asp Arg Tyr Ala Val Leu Tyr Arg
            340                 345                 350

Thr Asn Ala Gln Ser Arg Leu Leu Glu Gln Ala Leu Ala Gly Arg Gly
        355                 360                 365

Ile Pro Ala Arg Val Val Gly Gly Val Gly Phe Phe Glu Arg Ala Glu
    370                 375                 380

Val Lys Asp Leu Leu Ala Tyr Ala Arg Leu Ala Leu Asn Pro Leu Asp
385                 390                 395                 400

Ala Val Ser Leu Lys Arg Val Leu Asn Thr Pro Pro Arg Gly Ile Gly
                405                 410                 415

Pro Ala Thr Trp Ala Arg Val Gln Leu Leu Ala Gln Glu Lys Gly Leu
            420                 425                 430

Pro Pro Trp Glu Ala Leu Lys Glu Ala Ala Arg Thr Phe Ser Arg Pro
        435                 440                 445

Glu Pro Leu Arg His Phe Val Ala Leu Val Glu Glu Leu Gln Asp Leu
    450                 455                 460

Val Phe Gly Pro Ala Glu Ala Phe Phe Arg His Leu Leu Glu Ala Thr
465                 470                 475                 480

Asp Tyr Pro Ala Tyr Leu Arg Glu Ala Tyr Pro Glu Asp Ala Glu Asp
                485                 490                 495

Arg Leu Glu Asn Val Glu Glu Leu Leu Arg Ala Ala Lys Glu Ala Glu
            500                 505                 510

Asp Leu Gln Asp Phe Leu Asp Arg Val Ala Leu Thr Ala Lys Ala Glu
        515                 520                 525

Glu Pro Ala Glu Ala Glu Gly Arg Val Ala Leu Met Thr Leu His Asn
    530                 535                 540

Ala Lys Gly Leu Glu Phe Pro Val Val Phe Leu Val Gly Val Glu Glu
545                 550                 555                 560

Gly Leu Leu Pro His Arg Asn Ser Val Ser Thr Leu Glu Gly Leu Glu
                565                 570                 575

Glu Glu Arg Arg Leu Phe Tyr Val Gly Ile Thr Arg Ala Gln Glu Arg
            580                 585                 590

Leu Tyr Leu Ser His Ala Glu Glu Arg Glu Val Tyr Gly Arg Arg Glu
        595                 600                 605

Pro Ala Arg Pro Ser Arg Phe Leu Glu Glu Val Glu Glu Gly Leu Tyr
    610                 615                 620

Glu Val Tyr Asp Pro Tyr Arg Arg Pro Pro Ser Pro Pro Pro His Arg
625                 630                 635                 640

Pro Arg Pro Gly Ala Phe Arg Gly Gly Glu Arg Val Val His Pro Arg
                645                 650                 655

Phe Gly Pro Gly Thr Val Val Ala Ala Gln Gly Asp Glu Val Thr Val
            660                 665                 670

His Phe Glu Gly Phe Gly Leu Lys Arg Leu Ser Leu Lys Tyr Ala Glu
        675                 680                 685

Leu Lys Pro Ala
    690
```

<210> SEQ ID NO 53
<211> LENGTH: 945
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Met Lys His His His His His His Asn Thr Ser Ser Asn Ser Met Ser
1 5 10 15

Pro Ile Leu Gly Tyr Trp Lys Ile Lys Gly Leu Val Gln Pro Thr Arg
20 25 30

Leu Leu Leu Glu Tyr Leu Glu Glu Lys Tyr Glu Glu His Leu Tyr Glu
35 40 45

Arg Asp Glu Gly Asp Lys Trp Arg Asn Lys Lys Phe Glu Leu Gly Leu
50 55 60

Glu Phe Pro Asn Leu Pro Tyr Tyr Ile Asp Gly Asp Val Lys Leu Thr
65 70 75 80

Gln Ser Met Ala Ile Ile Arg Tyr Ile Ala Asp Lys His Asn Met Leu
85 90 95

Gly Gly Cys Pro Lys Glu Arg Ala Glu Ile Ser Met Leu Glu Gly Ala
100 105 110

Val Leu Asp Ile Arg Tyr Gly Val Ser Arg Ile Ala Tyr Ser Lys Asp
115 120 125

Phe Glu Thr Leu Lys Val Asp Phe Leu Ser Lys Leu Pro Glu Met Leu
130 135 140

Lys Met Phe Glu Asp Arg Leu Cys His Lys Thr Tyr Leu Asn Gly Asp
145 150 155 160

His Val Thr His Pro Asp Phe Met Leu Tyr Asp Ala Leu Asp Val Val
165 170 175

Leu Tyr Met Asp Pro Met Cys Leu Asp Ala Phe Pro Lys Leu Val Cys
180 185 190

Phe Lys Lys Arg Ile Glu Ala Ile Pro Gln Ile Asp Lys Tyr Leu Lys
195 200 205

Ser Ser Lys Tyr Ile Ala Trp Pro Leu Gln Gly Trp Gln Ala Thr Phe
210 215 220

Gly Gly Gly Asp His Pro Pro Thr Ser Gly Ser Gly Gly Gly Gly Gly
225 230 235 240

Trp Met Ser Glu Asn Leu Tyr Phe Gln Gly Ala Leu Ala Met Ser Asp
245 250 255

Ala Leu Leu Ala Pro Leu Asn Glu Ala Gln Arg Gln Ala Val Leu His
260 265 270

Phe Glu Gly Pro Ala Leu Val Val Ala Gly Ala Gly Ser Gly Lys Thr
275 280 285

Arg Thr Val Val His Arg Val Ala Tyr Leu Val Ala Arg Arg Gly Val
290 295 300

Phe Pro Ser Glu Ile Leu Ala Val Thr Phe Thr Asn Lys Ala Ala Glu
305 310 315 320

Glu Met Arg Glu Arg Leu Arg Gly Leu Val Pro Gly Ala Gly Glu Val
325 330 335

Trp Val Ser Thr Phe His Ala Ala Ala Leu Arg Ile Leu Arg Val Tyr
340 345 350

Gly Glu Arg Val Gly Leu Arg Pro Gly Phe Val Val Tyr Asp Glu Asp
355 360 365

Asp Gln Thr Ala Leu Leu Lys Glu Val Leu Lys Glu Leu Ala Leu Ser
370 375 380

Ala Arg Pro Gly Pro Ile Lys Ala Leu Leu Asp Arg Ala Lys Asn Arg
385 390 395 400

Gly Val Gly Leu Lys Ala Leu Leu Gly Glu Leu Pro Glu Tyr Tyr Ala
405 410 415

```
Gly Leu Ser Arg Gly Arg Leu Gly Asp Val Leu Val Arg Tyr Gln Glu
            420                 425                 430

Ala Leu Lys Ala Gln Gly Ala Leu Asp Phe Gly Asp Ile Leu Leu Tyr
        435                 440                 445

Ala Leu Glu Ala Phe Arg Gly Gly Arg Gly Gly Pro Gln Ala Arg Ala
    450                 455                 460

Gln Arg Ala Arg Phe Ile His Val Asp Glu Tyr Gln Asp Thr Ser Pro
465                 470                 475                 480

Val Gln Tyr Arg Phe Thr Arg Leu Leu Ala Gly Glu Glu Ala Asn Leu
                485                 490                 495

Met Ala Val Gly Asp Pro Asp Gln Gly Ile Tyr Ser Phe Arg Ala Ala
            500                 505                 510

Asp Ile Lys Asn Ile Leu Asp Phe Thr Arg Asp Tyr Pro Glu Ala Arg
        515                 520                 525

Val Tyr Arg Leu Glu Glu Asn Tyr Arg Ser Thr Glu Ala Ile Leu Arg
    530                 535                 540

Phe Ala Asn Ala Val Ile Val Lys Asn Ala Leu Arg Leu Glu Lys Ala
545                 550                 555                 560

Leu Arg Pro Val Lys Arg Gly Gly Glu Pro Val Arg Leu Tyr Arg Ala
                565                 570                 575

Glu Asp Ala Arg Glu Glu Ala Arg Phe Val Ala Glu Glu Ile Ala Arg
            580                 585                 590

Leu Gly Pro Pro Trp Asp Arg Tyr Ala Val Leu Tyr Arg Thr Asn Ala
        595                 600                 605

Gln Ser Arg Leu Leu Glu Gln Ala Leu Ala Gly Arg Gly Ile Pro Ala
    610                 615                 620

Arg Val Val Gly Gly Val Gly Phe Phe Glu Arg Ala Glu Val Lys Asp
625                 630                 635                 640

Leu Leu Ala Tyr Ala Arg Leu Ala Leu Asn Pro Leu Asp Ala Val Ser
                645                 650                 655

Leu Lys Arg Val Leu Asn Thr Pro Pro Arg Gly Ile Gly Pro Ala Thr
            660                 665                 670

Trp Ala Arg Val Gln Leu Leu Ala Gln Glu Lys Gly Leu Pro Pro Trp
        675                 680                 685

Glu Ala Leu Lys Glu Ala Ala Arg Thr Phe Ser Arg Pro Glu Pro Leu
    690                 695                 700

Arg His Phe Val Ala Leu Val Glu Glu Leu Gln Asp Leu Val Phe Gly
705                 710                 715                 720

Pro Ala Glu Ala Phe Phe Arg His Leu Leu Glu Ala Thr Asp Tyr Pro
                725                 730                 735

Ala Tyr Leu Arg Glu Ala Tyr Pro Glu Asp Ala Glu Asp Arg Leu Glu
            740                 745                 750

Asn Val Glu Glu Leu Leu Arg Ala Ala Lys Glu Ala Glu Asp Leu Gln
        755                 760                 765

Asp Phe Leu Asp Arg Val Ala Leu Thr Ala Lys Ala Glu Glu Pro Ala
    770                 775                 780

Glu Ala Glu Gly Arg Val Ala Leu Met Thr Leu His Asn Ala Lys Gly
785                 790                 795                 800

Leu Glu Phe Pro Val Val Phe Leu Val Gly Val Glu Glu Gly Leu Leu
                805                 810                 815

Pro His Arg Asn Ser Val Ser Thr Leu Glu Gly Leu Glu Glu Glu Arg
            820                 825                 830
```

```
Arg Leu Phe Tyr Val Gly Ile Thr Arg Ala Gln Glu Arg Leu Tyr Leu
        835                 840                 845

Ser His Ala Glu Glu Arg Glu Val Tyr Gly Arg Arg Glu Pro Ala Arg
    850                 855                 860

Pro Ser Arg Phe Leu Glu Glu Val Glu Glu Gly Leu Tyr Glu Val Tyr
865                 870                 875                 880

Asp Pro Tyr Arg Arg Pro Pro Ser Pro Pro Pro His Arg Pro Arg Pro
                885                 890                 895

Gly Ala Phe Arg Gly Gly Glu Arg Val Val His Pro Arg Phe Gly Pro
            900                 905                 910

Gly Thr Val Val Ala Ala Gln Gly Asp Glu Val Thr Val His Phe Glu
        915                 920                 925

Gly Phe Gly Leu Lys Arg Leu Ser Leu Lys Tyr Ala Glu Leu Lys Pro
    930                 935                 940

Ala
945


<210> SEQ ID NO 54
<211> LENGTH: 720
<212> TYPE: PRT
<213> ORGANISM: Escherichia coli

<400> SEQUENCE: 54

Met Asp Val Ser Tyr Leu Leu Asp Ser Leu Asn Asp Lys Gln Arg Glu
1               5                   10                  15

Ala Val Ala Ala Pro Arg Ser Asn Leu Leu Val Leu Ala Gly Ala Gly
            20                  25                  30

Ser Gly Lys Thr Arg Val Leu Val His Arg Ile Ala Trp Leu Met Ser
        35                  40                  45

Val Glu Asn Cys Ser Pro Tyr Ser Ile Met Ala Val Thr Phe Thr Asn
    50                  55                  60

Lys Ala Ala Ala Glu Met Arg His Arg Ile Gly Gln Leu Met Gly Thr
65                  70                  75                  80

Ser Gln Gly Gly Met Trp Val Gly Thr Phe His Gly Leu Ala His Arg
                85                  90                  95

Leu Leu Arg Ala His His Met Asp Ala Asn Leu Pro Gln Asp Phe Gln
            100                 105                 110

Ile Leu Asp Ser Glu Asp Gln Leu Arg Leu Leu Lys Arg Leu Ile Lys
        115                 120                 125

Ala Met Asn Leu Asp Glu Lys Gln Trp Pro Pro Arg Gln Ala Met Trp
    130                 135                 140

Tyr Ile Asn Ser Gln Lys Asp Glu Gly Leu Arg Pro His His Ile Gln
145                 150                 155                 160

Ser Tyr Gly Asn Pro Val Glu Gln Thr Trp Gln Lys Val Tyr Gln Ala
                165                 170                 175

Tyr Gln Glu Ala Cys Asp Arg Ala Gly Leu Val Asp Phe Ala Glu Leu
            180                 185                 190

Leu Leu Arg Ala His Glu Leu Trp Leu Asn Lys Pro His Ile Leu Gln
        195                 200                 205

His Tyr Arg Glu Arg Phe Thr Asn Ile Leu Val Asp Glu Phe Gln Asp
    210                 215                 220

Thr Asn Asn Ile Gln Tyr Ala Trp Ile Arg Leu Leu Ala Gly Asp Thr
225                 230                 235                 240

Gly Lys Val Met Ile Val Gly Asp Asp Asp Gln Ser Ile Tyr Gly Trp
                245                 250                 255
```

```
Arg Gly Ala Gln Val Glu Asn Ile Gln Arg Phe Leu Asn Asp Phe Pro
            260                 265                 270

Gly Ala Glu Thr Ile Arg Leu Glu Gln Asn Tyr Arg Ser Thr Ser Asn
        275                 280                 285

Ile Leu Ser Ala Ala Asn Ala Leu Ile Glu Asn Asn Asn Gly Arg Leu
    290                 295                 300

Gly Lys Lys Leu Trp Thr Asp Gly Ala Asp Gly Glu Pro Ile Ser Leu
305                 310                 315                 320

Tyr Cys Ala Phe Asn Glu Leu Asp Glu Ala Arg Phe Val Val Asn Arg
                325                 330                 335

Ile Lys Thr Trp Gln Asp Asn Gly Gly Ala Leu Ala Glu Cys Ala Ile
            340                 345                 350

Leu Tyr Arg Ser Asn Ala Gln Ser Arg Val Leu Glu Glu Ala Leu Leu
        355                 360                 365

Gln Ala Ser Met Pro Tyr Arg Ile Tyr Gly Gly Met Arg Phe Phe Glu
    370                 375                 380

Arg Gln Glu Ile Lys Asp Ala Leu Ser Tyr Leu Arg Leu Ile Ala Asn
385                 390                 395                 400

Arg Asn Asp Asp Ala Ala Phe Glu Arg Val Val Asn Thr Pro Thr Arg
                405                 410                 415

Gly Ile Gly Asp Arg Thr Leu Asp Val Val Arg Gln Thr Ser Arg Asp
            420                 425                 430

Arg Gln Leu Thr Leu Trp Gln Ala Cys Arg Glu Leu Leu Gln Glu Lys
        435                 440                 445

Ala Leu Ala Gly Arg Ala Ala Ser Ala Leu Gln Arg Phe Met Glu Leu
    450                 455                 460

Ile Asp Ala Leu Ala Gln Glu Thr Ala Asp Met Pro Leu His Val Gln
465                 470                 475                 480

Thr Asp Arg Val Ile Lys Asp Ser Gly Leu Arg Thr Met Tyr Glu Gln
                485                 490                 495

Glu Lys Gly Glu Lys Gly Gln Thr Arg Ile Glu Asn Leu Glu Glu Leu
            500                 505                 510

Val Thr Ala Thr Arg Gln Phe Ser Tyr Asn Glu Glu Asp Glu Asp Leu
        515                 520                 525

Met Pro Leu Gln Ala Phe Leu Ser His Ala Ala Leu Glu Ala Gly Glu
    530                 535                 540

Gly Gln Ala Asp Thr Trp Gln Asp Ala Val Gln Leu Met Thr Leu His
545                 550                 555                 560

Ser Ala Lys Gly Leu Glu Phe Pro Gln Val Phe Ile Val Gly Met Glu
                565                 570                 575

Glu Gly Met Phe Pro Ser Gln Met Ser Leu Asp Glu Gly Gly Arg Leu
            580                 585                 590

Glu Glu Glu Arg Arg Leu Ala Tyr Val Gly Val Thr Arg Ala Met Gln
        595                 600                 605

Lys Leu Thr Leu Thr Tyr Ala Glu Thr Arg Arg Leu Tyr Gly Lys Glu
    610                 615                 620

Val Tyr His Arg Pro Ser Arg Phe Ile Gly Glu Leu Pro Glu Glu Cys
625                 630                 635                 640

Val Glu Glu Val Arg Leu Arg Ala Thr Val Ser Arg Pro Val Ser His
                645                 650                 655

Gln Arg Met Gly Thr Pro Met Val Glu Asn Asp Ser Gly Tyr Lys Leu
            660                 665                 670
```

Gly Gln Arg Val Arg His Ala Lys Phe Gly Glu Gly Thr Ile Val Asn
        675                 680                 685

Met Glu Gly Ser Gly Glu His Ser Arg Leu Gln Val Ala Phe Gln Gly
    690                 695                 700

Gln Gly Ile Lys Trp Leu Val Ala Ala Tyr Ala Arg Leu Glu Ser Val
705                 710                 715                 720

<210> SEQ ID NO 55
<211> LENGTH: 973
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Leu Ala Met Asp Val
                245                 250                 255

Ser Tyr Leu Leu Asp Ser Leu Asn Asp Lys Gln Arg Glu Ala Val Ala
            260                 265                 270

Ala Pro Arg Ser Asn Leu Leu Val Leu Ala Gly Ala Gly Ser Gly Lys
        275                 280                 285

Thr Arg Val Leu Val His Arg Ile Ala Trp Leu Met Ser Val Glu Asn
    290                 295                 300

Cys Ser Pro Tyr Ser Ile Met Ala Val Thr Phe Thr Asn Lys Ala Ala
305                 310                 315                 320

```
Ala Glu Met Arg His Arg Ile Gly Gln Leu Met Gly Thr Ser Gln Gly
                325                 330                 335

Gly Met Trp Val Gly Thr Phe His Gly Leu Ala His Arg Leu Leu Arg
            340                 345                 350

Ala His His Met Asp Ala Asn Leu Pro Gln Asp Phe Gln Ile Leu Asp
        355                 360                 365

Ser Glu Asp Gln Leu Arg Leu Leu Lys Arg Leu Ile Lys Ala Met Asn
    370                 375                 380

Leu Asp Glu Lys Gln Trp Pro Pro Arg Gln Ala Met Trp Tyr Ile Asn
385                 390                 395                 400

Ser Gln Lys Asp Glu Gly Leu Arg Pro His His Ile Gln Ser Tyr Gly
                405                 410                 415

Asn Pro Val Glu Gln Thr Trp Gln Lys Val Tyr Gln Ala Tyr Gln Glu
            420                 425                 430

Ala Cys Asp Arg Ala Gly Leu Val Asp Phe Ala Glu Leu Leu Leu Arg
        435                 440                 445

Ala His Glu Leu Trp Leu Asn Lys Pro His Ile Leu Gln His Tyr Arg
    450                 455                 460

Glu Arg Phe Thr Asn Ile Leu Val Asp Glu Phe Gln Asp Thr Asn Asn
465                 470                 475                 480

Ile Gln Tyr Ala Trp Ile Arg Leu Leu Ala Gly Asp Thr Gly Lys Val
                485                 490                 495

Met Ile Val Gly Asp Asp Asp Gln Ser Ile Tyr Gly Trp Arg Gly Ala
            500                 505                 510

Gln Val Glu Asn Ile Gln Arg Phe Leu Asn Asp Phe Pro Gly Ala Glu
        515                 520                 525

Thr Ile Arg Leu Glu Gln Asn Tyr Arg Ser Thr Ser Asn Ile Leu Ser
    530                 535                 540

Ala Ala Asn Ala Leu Ile Glu Asn Asn Asn Gly Arg Leu Gly Lys Lys
545                 550                 555                 560

Leu Trp Thr Asp Gly Ala Asp Gly Glu Pro Ile Ser Leu Tyr Cys Ala
                565                 570                 575

Phe Asn Glu Leu Asp Glu Ala Arg Phe Val Val Asn Arg Ile Lys Thr
            580                 585                 590

Trp Gln Asp Asn Gly Gly Ala Leu Ala Glu Cys Ala Ile Leu Tyr Arg
        595                 600                 605

Ser Asn Ala Gln Ser Arg Val Leu Glu Glu Ala Leu Leu Gln Ala Ser
    610                 615                 620

Met Pro Tyr Arg Ile Tyr Gly Gly Met Arg Phe Phe Glu Arg Gln Glu
625                 630                 635                 640

Ile Lys Asp Ala Leu Ser Tyr Leu Arg Leu Ile Ala Asn Arg Asn Asp
                645                 650                 655

Asp Ala Ala Phe Glu Arg Val Val Asn Thr Pro Thr Arg Gly Ile Gly
            660                 665                 670

Asp Arg Thr Leu Asp Val Val Arg Gln Thr Ser Arg Asp Arg Gln Leu
        675                 680                 685

Thr Leu Trp Gln Ala Cys Arg Glu Leu Leu Gln Glu Lys Ala Leu Ala
    690                 695                 700

Gly Arg Ala Ala Ser Ala Leu Gln Arg Phe Met Glu Leu Ile Asp Ala
705                 710                 715                 720

Leu Ala Gln Glu Thr Ala Asp Met Pro Leu His Val Gln Thr Asp Arg
                725                 730                 735
```

```
Val Ile Lys Asp Ser Gly Leu Arg Thr Met Tyr Glu Gln Glu Lys Gly
            740                 745                 750

Glu Lys Gly Gln Thr Arg Ile Glu Asn Leu Glu Glu Leu Val Thr Ala
        755                 760                 765

Thr Arg Gln Phe Ser Tyr Asn Glu Glu Asp Glu Asp Leu Met Pro Leu
    770                 775                 780

Gln Ala Phe Leu Ser His Ala Ala Leu Glu Ala Gly Glu Gly Gln Ala
785                 790                 795                 800

Asp Thr Trp Gln Asp Ala Val Gln Leu Met Thr Leu His Ser Ala Lys
                805                 810                 815

Gly Leu Glu Phe Pro Gln Val Phe Ile Val Gly Met Glu Glu Gly Met
            820                 825                 830

Phe Pro Ser Gln Met Ser Leu Asp Glu Gly Gly Arg Leu Glu Glu Glu
        835                 840                 845

Arg Arg Leu Ala Tyr Val Gly Val Thr Arg Ala Met Gln Lys Leu Thr
    850                 855                 860

Leu Thr Tyr Ala Glu Thr Arg Arg Leu Tyr Gly Lys Glu Val Tyr His
865                 870                 875                 880

Arg Pro Ser Arg Phe Ile Gly Glu Leu Pro Glu Glu Cys Val Glu Glu
                885                 890                 895

Val Arg Leu Arg Ala Thr Val Ser Arg Pro Val Ser His Gln Arg Met
            900                 905                 910

Gly Thr Pro Met Val Glu Asn Asp Ser Gly Tyr Lys Leu Gly Gln Arg
        915                 920                 925

Val Arg His Ala Lys Phe Gly Glu Gly Thr Ile Val Asn Met Glu Gly
    930                 935                 940

Ser Gly Glu His Ser Arg Leu Gln Val Ala Phe Gln Gly Gln Gly Ile
945                 950                 955                 960

Lys Trp Leu Val Ala Ala Tyr Ala Arg Leu Glu Ser Val
                965                 970
```

<210> SEQ ID NO 56
<211> LENGTH: 808
<212> TYPE: PRT
<213> ORGANISM: Clostridium perfringens

<400> SEQUENCE: 56

```
Met Val Leu Asn Pro Lys Tyr Ser Ile Gly Val Tyr Tyr Asp Glu Leu
1               5                   10                  15

Val Glu Glu Asp Ile Glu Lys Val Tyr Ser Tyr Leu Ser Arg Gly Ile
            20                  25                  30

Val Val His Leu Phe Leu Arg Gly Ile Leu Lys Glu Glu Leu Glu Leu
        35                  40                  45

Asn Glu Tyr Asp Leu Asn Thr Phe Lys Leu Pro Lys Asp Asn Asn Leu
    50                  55                  60

Leu Phe Val Tyr Glu Glu Glu Thr Ser Leu Ser Ser Glu Asn Ile Ile
65                  70                  75                  80

Ile Phe Val Asp Asn Asn Ile Leu Asn Lys Glu Ala Tyr Lys Asn Ile
                85                  90                  95

Thr Glu Asn Arg Glu Cys Glu Phe Asn Lys Asp Gln Tyr Glu Ile Ile
            100                 105                 110

Thr Ala Pro Val Asp Asp Asn Ile Ile Val Thr Ser Gly Ala Gly Thr
        115                 120                 125

Gly Lys Thr Thr Thr Met Ile Asn Arg Leu Ile Tyr Leu Arg Ser Val
    130                 135                 140
```

```
Met Ser Asp Phe Thr Phe Asp Gln Ala Val Leu Ile Thr Phe Thr Asn
145                 150                 155                 160

Lys Ala Ser Ile Glu Met Lys Glu Arg Leu Leu Glu Val Leu Asp Lys
                165                 170                 175

Tyr Phe Arg Val Thr Asn Asp Ile Lys Tyr Leu Asp Tyr Met Glu Glu
            180                 185                 190

Ala Ala Lys Gly Ser Ile Ser Thr Ile His Lys Phe Ala Lys Lys Ile
        195                 200                 205

Leu Asn Lys Ser Gly Arg His Ile Gly Ile Asn Lys Asp Ile Asn Val
    210                 215                 220

Arg Ser Phe Lys Tyr Lys Arg Gln Glu Ala Val Asn Asn Ala Leu Asn
225                 230                 235                 240

Lys Ile Tyr Lys Glu Glu Ser Glu Leu Phe Ser Leu Ile Lys Tyr Tyr
                245                 250                 255

Pro Ile Tyr Glu Val Glu Arg Val Ile Leu Lys Met Trp Glu Ile Leu
            260                 265                 270

Asp Asn Tyr Ser Ile Asp Leu Leu Ser Asn Lys Val Arg Val Asp Phe
        275                 280                 285

Asn Phe Glu Glu Asp Lys Phe Thr Glu Leu Ile Ser Lys Thr Leu Lys
    290                 295                 300

Tyr Ala Gln Glu Ile Leu Asp Tyr Asp Lys Glu Asn Glu Leu Glu Ile
305                 310                 315                 320

Ser Asp Leu Met Lys Lys Leu Ala Tyr Glu Asp Ile Phe Lys Gly Ile
                325                 330                 335

Asp Ser Thr Tyr Lys Val Ile Met Ile Asp Glu Phe Gln Asp Ser Asp
            340                 345                 350

Asn Thr Gln Ile Glu Phe Ile Ser Glu Leu Glu Lys Lys Thr Gly Ala
        355                 360                 365

Arg Ile Leu Val Val Gly Asp Glu Lys Gln Ser Ile Tyr Arg Phe Arg
    370                 375                 380

Gly Ala Glu Tyr Thr Ala Phe Asp Lys Leu Lys Lys Leu Leu Ser Asn
385                 390                 395                 400

Ser Lys Arg Glu Val Lys Glu Tyr Glu Met Thr Arg Asn Tyr Arg Thr
                405                 410                 415

Asn Tyr Asn Ile Leu Asn Glu Ile Asn Arg Ile Phe Ile Glu Val Asp
            420                 425                 430

Lys Lys Leu Glu Cys Phe Asn Tyr Lys Glu Lys Asp Tyr Ile Tyr Ser
        435                 440                 445

Asn Lys Asp Lys Asp Asn Pro Lys Glu Ile Thr Cys Phe Asn Val Ser
    450                 455                 460

Asp Asn Leu Lys Arg Lys Glu Phe Phe Asp Asp Leu Leu Glu Asn Lys
465                 470                 475                 480

Lys Glu Asp Glu Ser Ile Ala Val Leu Phe Arg Ser Asn Ser Asp Ile
                485                 490                 495

Lys Glu Phe Lys Glu Phe Cys Asp Arg Asn Asn Ile Leu Cys Met Val
            500                 505                 510

Asp Ser Thr Gly Gly Phe Tyr Arg His Glu Ala Val Arg Asp Phe Tyr
        515                 520                 525

Ile Met Ile Lys Ser Ile Ile Asp Glu Arg Asn Ser Arg Thr Met Tyr
    530                 535                 540

Ser Phe Ile Asn Thr Pro Tyr Ile Leu Glu Asp Ile Asp Lys Asn Ile
545                 550                 555                 560
```

```
Ile Leu Asn Gly Asn Ser Lys Asp Lys Asn Glu Phe Leu Tyr Tyr Ile
                565                 570                 575

Leu Glu Lys Asn Asn Trp Asn Tyr Phe Arg Glu Ser Ser Asn Phe Lys
            580                 585                 590

Asn Pro Ile Ile Leu Ile Asp Glu Ile Ile Glu Lys Leu Lys Pro Val
        595                 600                 605

Lys Asn Tyr Tyr Val Lys Val Leu Leu Glu Ala Lys Lys Asn Gln His
    610                 615                 620

Asn Tyr Val Asn Ile Ala Lys Met Lys Ala Leu Glu Tyr Lys Leu Asn
625                 630                 635                 640

Leu Glu His Leu Val Phe Ile Leu Lys Lys Glu Phe Ser Glu Asn Ile
                645                 650                 655

Thr Ser Ile Glu Gln Ile Glu Gln Phe Leu Lys Val Lys Ile Ser Thr
            660                 665                 670

Asp Asn Leu Val Asp Val Arg Lys Pro Lys Asp Tyr Glu Asn Asp Tyr
        675                 680                 685

Ile Gln Cys Ser Thr Val His Lys Ala Lys Gly Leu Glu Tyr Asp Tyr
    690                 695                 700

Val Val Leu Asp Lys Leu Thr Asn Arg Phe Leu Ser Asn Ser Arg Lys
705                 710                 715                 720

Val Asn Leu Ile Leu Lys Pro Asp Gly Asp Lys Leu Leu Ile Gly Tyr
                725                 730                 735

Lys Ile Arg Leu Gly Glu Asp Glu Phe Lys Asn Lys Ile Tyr Ser Asp
            740                 745                 750

Asn Leu Lys Tyr Glu Lys Lys Glu Ile Lys Gly Glu Glu Ala Arg Leu
        755                 760                 765

Leu Tyr Val Ala Leu Thr Arg Cys Lys Lys Gly Ile Tyr Leu Asn Met
    770                 775                 780

Ser Gly Glu Leu Ala Ala Thr Glu Ser Leu Asn Thr Trp Lys Ser Leu
785                 790                 795                 800

Ile Gly Gly Thr Ile Asn Tyr Val
                805


<210> SEQ ID NO 57
<211> LENGTH: 1061
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110
```

```
Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Leu Ala Met Val Leu
                245                 250                 255

Asn Pro Lys Tyr Ser Ile Gly Val Tyr Tyr Asp Glu Leu Val Glu Glu
            260                 265                 270

Asp Ile Glu Lys Val Tyr Ser Tyr Leu Ser Arg Gly Ile Val Val His
        275                 280                 285

Leu Phe Leu Arg Gly Ile Leu Lys Glu Glu Leu Glu Leu Asn Glu Tyr
    290                 295                 300

Asp Leu Asn Thr Phe Lys Leu Pro Lys Asp Asn Asn Leu Leu Phe Val
305                 310                 315                 320

Tyr Glu Glu Glu Thr Ser Leu Ser Ser Glu Asn Ile Ile Ile Phe Val
                325                 330                 335

Asp Asn Asn Ile Leu Asn Lys Glu Ala Tyr Lys Asn Ile Thr Glu Asn
            340                 345                 350

Arg Glu Cys Glu Phe Asn Lys Asp Gln Tyr Glu Ile Ile Thr Ala Pro
        355                 360                 365

Val Asp Asp Asn Ile Ile Val Thr Ser Gly Ala Gly Thr Gly Lys Thr
    370                 375                 380

Thr Thr Met Ile Asn Arg Leu Ile Tyr Leu Arg Ser Val Met Ser Asp
385                 390                 395                 400

Phe Thr Phe Asp Gln Ala Val Leu Ile Thr Phe Thr Asn Lys Ala Ser
                405                 410                 415

Ile Glu Met Lys Glu Arg Leu Leu Glu Val Leu Asp Lys Tyr Phe Arg
            420                 425                 430

Val Thr Asn Asp Ile Lys Tyr Leu Asp Tyr Met Glu Glu Ala Ala Lys
        435                 440                 445

Gly Ser Ile Ser Thr Ile His Lys Phe Ala Lys Lys Ile Leu Asn Lys
    450                 455                 460

Ser Gly Arg His Ile Gly Ile Asn Lys Asp Ile Asn Val Arg Ser Phe
465                 470                 475                 480

Lys Tyr Lys Arg Gln Glu Ala Val Asn Asn Ala Leu Asn Lys Ile Tyr
                485                 490                 495

Lys Glu Glu Ser Glu Leu Phe Ser Leu Ile Lys Tyr Tyr Pro Ile Tyr
            500                 505                 510

Glu Val Glu Arg Val Ile Leu Lys Met Trp Glu Ile Leu Asp Asn Tyr
        515                 520                 525
```

```
Ser Ile Asp Leu Leu Ser Asn Lys Val Arg Val Asp Phe Asn Phe Glu
    530                 535                 540

Glu Asp Lys Phe Thr Glu Leu Ile Ser Lys Thr Leu Lys Tyr Ala Gln
545                 550                 555                 560

Glu Ile Leu Asp Tyr Asp Lys Glu Asn Glu Leu Glu Ile Ser Asp Leu
                565                 570                 575

Met Lys Lys Leu Ala Tyr Glu Asp Ile Phe Lys Gly Ile Asp Ser Thr
            580                 585                 590

Tyr Lys Val Ile Met Ile Asp Glu Phe Gln Asp Ser Asp Asn Thr Gln
        595                 600                 605

Ile Glu Phe Ile Ser Glu Leu Glu Lys Lys Thr Gly Ala Arg Ile Leu
    610                 615                 620

Val Val Gly Asp Glu Lys Gln Ser Ile Tyr Arg Phe Arg Gly Ala Glu
625                 630                 635                 640

Tyr Thr Ala Phe Asp Lys Leu Lys Lys Leu Leu Ser Asn Ser Lys Arg
                645                 650                 655

Glu Val Lys Glu Tyr Glu Met Thr Arg Asn Tyr Arg Thr Asn Tyr Asn
            660                 665                 670

Ile Leu Asn Glu Ile Asn Arg Ile Phe Ile Glu Val Asp Lys Lys Leu
        675                 680                 685

Glu Cys Phe Asn Tyr Lys Glu Lys Asp Tyr Ile Tyr Ser Asn Lys Asp
    690                 695                 700

Lys Asp Asn Pro Lys Glu Ile Thr Cys Phe Asn Val Ser Asp Asn Leu
705                 710                 715                 720

Lys Arg Lys Glu Phe Phe Asp Asp Leu Leu Glu Asn Lys Lys Glu Asp
                725                 730                 735

Glu Ser Ile Ala Val Leu Phe Arg Ser Asn Ser Asp Ile Lys Glu Phe
            740                 745                 750

Lys Glu Phe Cys Asp Arg Asn Asn Ile Leu Cys Met Val Asp Ser Thr
        755                 760                 765

Gly Gly Phe Tyr Arg His Glu Ala Val Arg Asp Phe Tyr Ile Met Ile
    770                 775                 780

Lys Ser Ile Ile Asp Glu Arg Asn Ser Arg Thr Met Tyr Ser Phe Ile
785                 790                 795                 800

Asn Thr Pro Tyr Ile Leu Glu Asp Ile Asp Lys Asn Ile Ile Leu Asn
                805                 810                 815

Gly Asn Ser Lys Asp Lys Asn Glu Phe Leu Tyr Tyr Ile Leu Glu Lys
            820                 825                 830

Asn Asn Trp Asn Tyr Phe Arg Glu Ser Ser Asn Phe Lys Asn Pro Ile
        835                 840                 845

Ile Leu Ile Asp Glu Ile Ile Glu Lys Leu Lys Pro Val Lys Asn Tyr
    850                 855                 860

Tyr Val Lys Val Leu Leu Glu Ala Lys Lys Asn Gln His Asn Tyr Val
865                 870                 875                 880

Asn Ile Ala Lys Met Lys Ala Leu Glu Tyr Lys Leu Asn Leu Glu His
                885                 890                 895

Leu Val Phe Ile Leu Lys Lys Glu Phe Ser Glu Asn Ile Thr Ser Ile
            900                 905                 910

Glu Gln Ile Glu Gln Phe Leu Lys Val Lys Ile Ser Thr Asp Asn Leu
        915                 920                 925

Val Asp Val Arg Lys Pro Lys Asp Tyr Glu Asn Asp Tyr Ile Gln Cys
    930                 935                 940

Ser Thr Val His Lys Ala Lys Gly Leu Glu Tyr Asp Tyr Val Val Leu
```

945 950 955 960

Asp Lys Leu Thr Asn Arg Phe Leu Ser Asn Ser Arg Lys Val Asn Leu
965 970 975

Ile Leu Lys Pro Asp Gly Asp Lys Leu Leu Ile Gly Tyr Lys Ile Arg
980 985 990

Leu Gly Glu Asp Glu Phe Lys Asn Lys Ile Tyr Ser Asp Asn Leu Lys
995 1000 1005

Tyr Glu Lys Lys Glu Ile Lys Gly Glu Glu Ala Arg Leu Leu Tyr
1010 1015 1020

Val Ala Leu Thr Arg Cys Lys Lys Gly Ile Tyr Leu Asn Met Ser
1025 1030 1035

Gly Glu Leu Ala Ala Thr Glu Ser Leu Asn Thr Trp Lys Ser Leu
1040 1045 1050

Ile Gly Gly Thr Ile Asn Tyr Val
1055 1060

<210> SEQ ID NO 58
<211> LENGTH: 667
<212> TYPE: PRT
<213> ORGANISM: Clostridium perfringens

<400> SEQUENCE: 58

Met Leu Gly Leu Asn Asn Glu Ser Lys Glu Phe Phe Lys Gly Ile Ser
1 5 10 15

Arg Ile Trp Arg Asn Tyr Lys Asp Tyr Thr Tyr Leu Asp Gly Ile Lys
20 25 30

Leu Ser Gln Ala Gln Ile Asp Ile Ile Glu Lys Glu Glu Asp Gln Leu
35 40 45

Leu Ile Glu Gly Tyr Ala Gly Thr Gly Lys Ser Leu Thr Leu Ile Tyr
50 55 60

Lys Phe Ile Asn Val Leu Val Arg Glu Asp Gly Lys Arg Val Leu Tyr
65 70 75 80

Val Thr Phe Asn Asp Thr Leu Ile Glu Asp Thr Lys Lys Arg Leu Ser
85 90 95

Tyr Cys Asn Glu Tyr Asn Glu Asn Lys Glu Arg His His Val Glu Ile
100 105 110

Cys Thr Phe His Glu Ile Ala Ser Asn Ile Leu Lys Lys Lys Lys Ile
115 120 125

Ile Asp Arg Gly Ile Glu Lys Leu Thr Ala Lys Lys Ile Glu Asp Tyr
130 135 140

Lys Gly Ala Ala Leu Arg Arg Ile Ala Gly Ile Leu Ala Arg Tyr Ile
145 150 155 160

Glu Gly Gly Lys Tyr Tyr Ser Glu Leu Pro Lys Glu Glu Arg Leu Tyr
165 170 175

Lys Thr His Asp Glu Asn Phe Ile Arg Glu Glu Val Ala Trp Ile Lys
180 185 190

Ala Met Gly Phe Ile Glu Lys Glu Lys Tyr Phe Glu Lys Asp Arg Ile
195 200 205

Gly Arg Ser Lys Ser Ile Arg Leu Thr Arg Ser Gln Arg Lys Thr Ile
210 215 220

Phe Lys Ile Phe Glu Lys Tyr Cys Glu Glu Gln Glu Asn Lys Phe Phe
225 230 235 240

Lys Ser Leu Asp Leu Glu Asp Tyr Ala Leu Lys Leu Ile Gln Asn Ile
245 250 255

```
Asp Asn Phe Asp Asp Leu Lys Phe Asp Tyr Ile Phe Val Asp Glu Val
            260                 265                 270

Gln Asp Leu Asp Pro Met Gln Ile Lys Ala Leu Cys Leu Leu Thr Asn
        275                 280                 285

Thr Ser Ile Val Leu Ser Gly Asp Ala Asn Gln Arg Ile Tyr Lys Lys
    290                 295                 300

Ser Pro Val Lys Tyr Glu Glu Leu Gly Leu Arg Ile Lys Glu Lys Gly
305                 310                 315                 320

Lys Arg Lys Ile Leu Asn Lys Asn Tyr Arg Ser Thr Gly Glu Ile Val
                325                 330                 335

Lys Leu Ala Asn Ser Ile Lys Phe Phe Asp Glu Ser Ile Asn Lys Tyr
            340                 345                 350

Asn Glu Lys Gln Phe Val Lys Ser Gly Asp Arg Pro Ile Ile Arg Lys
        355                 360                 365

Val Asn Asp Lys Lys Gly Ala Val Lys Phe Leu Ile Gly Glu Ile Lys
    370                 375                 380

Lys Ile His Glu Glu Asp Pro Tyr Lys Thr Ile Ala Ile Ile His Arg
385                 390                 395                 400

Glu Lys Asn Glu Leu Ile Gly Phe Gln Lys Ser Glu Phe Arg Lys Tyr
                405                 410                 415

Leu Glu Gly Gln Leu Tyr Met Glu Lys Phe Ser Asp Ile Lys Ser Phe
            420                 425                 430

Glu Ser Lys Phe Asp Leu Arg Glu Lys Asn Gln Val Phe Tyr Thr Asn
        435                 440                 445

Gly Tyr Asp Val Lys Gly Leu Glu Phe Asp Val Val Phe Ile Ile Asn
    450                 455                 460

Phe Asn Thr Ala Asn Tyr Pro Leu Ser Lys Glu Leu Lys Lys Ile Lys
465                 470                 475                 480

Asp Glu Asn Asp Gly Lys Glu Met Thr Leu Ile Lys Asp Asp Val Leu
                485                 490                 495

Glu Phe Ile Asn Arg Glu Lys Arg Leu Leu Tyr Val Ala Met Thr Arg
            500                 505                 510

Ala Lys Glu Lys Leu Tyr Leu Val Ala Asp Cys Lys Asn Ser Asn Ile
        515                 520                 525

Ser Ser Phe Ile Tyr Asp Phe Asn Thr Lys Tyr Tyr Glu Ala Gln Asn
    530                 535                 540

Phe Lys Lys Lys Glu Ile Glu Glu Asn Tyr Asn Arg Tyr Lys Ile Asn
545                 550                 555                 560

Met Glu Arg Glu Tyr Gly Ile Ile Ile Glu Asp Asp Asp Ser Asn Asn
                565                 570                 575

Val Lys Asn Asn Asp Thr Lys Gln Glu Asn Lys Phe Asn Thr Glu Ser
            580                 585                 590

Lys Glu Lys Gly Lys Asp Asp Ile Asp Lys Ile Lys Val Phe Phe Ile
        595                 600                 605

Asn Lys Gly Ile Glu Val Val Asp Asn Arg Asp Lys Ser Gly Cys Leu
    610                 615                 620

Trp Ile Val Ala Gly Lys Glu Ala Ile Pro Leu Met Lys Lys Phe Gly
625                 630                 635                 640

Val Leu Gly Tyr Asn Phe Ile Phe Ile Ala Asn Gly Gly Arg Ala Ser
                645                 650                 655

Lys Asn Arg Pro Ala Trp Tyr Leu Lys Asn Ser
            660                 665
```

<210> SEQ ID NO 59
<211> LENGTH: 938
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 59

```
Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Pro Lys Lys Lys
                245                 250                 255

Arg Lys Val Glu Asp Pro Lys Lys Lys Arg Lys Val Gly Ser Gly Ser
            260                 265                 270

Leu Gly Leu Asn Asn Glu Ser Lys Glu Phe Phe Lys Gly Ile Ser Arg
        275                 280                 285

Ile Trp Arg Asn Tyr Lys Asp Tyr Thr Tyr Leu Asp Gly Ile Lys Leu
    290                 295                 300

Ser Gln Ala Gln Ile Asp Ile Ile Glu Lys Glu Glu Asp Gln Leu Leu
305                 310                 315                 320

Ile Glu Gly Tyr Ala Gly Thr Gly Lys Ser Leu Thr Leu Ile Tyr Lys
                325                 330                 335

Phe Ile Asn Val Leu Val Arg Glu Asp Gly Lys Arg Val Leu Tyr Val
            340                 345                 350

Thr Phe Asn Asp Thr Leu Ile Glu Asp Thr Lys Lys Arg Leu Ser Tyr
        355                 360                 365
```

```
Cys Asn Glu Tyr Asn Glu Asn Lys Glu Arg His His Val Glu Ile Cys
    370                 375                 380

Thr Phe His Glu Ile Ala Ser Asn Ile Leu Lys Lys Lys Lys Ile Ile
385                 390                 395                 400

Asp Arg Gly Ile Glu Lys Leu Thr Ala Lys Lys Ile Glu Asp Tyr Lys
                405                 410                 415

Gly Ala Ala Leu Arg Arg Ile Ala Gly Ile Leu Ala Arg Tyr Ile Glu
            420                 425                 430

Gly Gly Lys Tyr Tyr Ser Glu Leu Pro Lys Glu Glu Arg Leu Tyr Lys
        435                 440                 445

Thr His Asp Glu Asn Phe Ile Arg Glu Glu Val Ala Trp Ile Lys Ala
    450                 455                 460

Met Gly Phe Ile Glu Lys Glu Lys Tyr Phe Glu Lys Asp Arg Ile Gly
465                 470                 475                 480

Arg Ser Lys Ser Ile Arg Leu Thr Arg Ser Gln Arg Lys Thr Ile Phe
                485                 490                 495

Lys Ile Phe Glu Lys Tyr Cys Glu Glu Gln Glu Asn Lys Phe Phe Lys
            500                 505                 510

Ser Leu Asp Leu Glu Asp Tyr Ala Leu Lys Leu Ile Gln Asn Ile Asp
        515                 520                 525

Asn Phe Asp Asp Leu Lys Phe Asp Tyr Ile Phe Val Asp Glu Val Gln
    530                 535                 540

Asp Leu Asp Pro Met Gln Ile Lys Ala Leu Cys Leu Leu Thr Asn Thr
545                 550                 555                 560

Ser Ile Val Leu Ser Gly Asp Ala Asn Gln Arg Ile Tyr Lys Lys Ser
                565                 570                 575

Pro Val Lys Tyr Glu Glu Leu Gly Leu Arg Ile Lys Glu Lys Gly Lys
            580                 585                 590

Arg Lys Ile Leu Asn Lys Asn Tyr Arg Ser Thr Gly Glu Ile Val Lys
        595                 600                 605

Leu Ala Asn Ser Ile Lys Phe Phe Asp Glu Ser Ile Asn Lys Tyr Asn
    610                 615                 620

Glu Lys Gln Phe Val Lys Ser Gly Asp Arg Pro Ile Ile Arg Lys Val
625                 630                 635                 640

Asn Asp Lys Lys Gly Ala Val Lys Phe Leu Ile Gly Glu Ile Lys Lys
                645                 650                 655

Ile His Glu Glu Asp Pro Tyr Lys Thr Ile Ala Ile Ile His Arg Glu
            660                 665                 670

Lys Asn Glu Leu Ile Gly Phe Gln Lys Ser Glu Phe Arg Lys Tyr Leu
        675                 680                 685

Glu Gly Gln Leu Tyr Met Glu Lys Phe Ser Asp Ile Lys Ser Phe Glu
    690                 695                 700

Ser Lys Phe Asp Leu Arg Glu Lys Asn Gln Val Phe Tyr Thr Asn Gly
705                 710                 715                 720

Tyr Asp Val Lys Gly Leu Glu Phe Asp Val Val Phe Ile Ile Asn Phe
                725                 730                 735

Asn Thr Ala Asn Tyr Pro Leu Ser Lys Glu Leu Lys Lys Ile Lys Asp
            740                 745                 750

Glu Asn Asp Gly Lys Glu Met Thr Leu Ile Lys Asp Asp Val Leu Glu
        755                 760                 765

Phe Ile Asn Arg Glu Lys Arg Leu Leu Tyr Val Ala Met Thr Arg Ala
    770                 775                 780

Lys Glu Lys Leu Tyr Leu Val Ala Asp Cys Lys Asn Ser Asn Ile Ser
```

785 790 795 800

Ser Phe Ile Tyr Asp Phe Asn Thr Lys Tyr Tyr Glu Ala Gln Asn Phe
805 810 815

Lys Lys Lys Glu Ile Glu Glu Asn Tyr Asn Arg Tyr Lys Ile Asn Met
820 825 830

Glu Arg Glu Tyr Gly Ile Ile Ile Glu Asp Asp Asp Ser Asn Asn Val
835 840 845

Lys Asn Asn Asp Thr Lys Gln Glu Asn Lys Phe Asn Thr Glu Ser Lys
850 855 860

Glu Lys Gly Lys Asp Asp Ile Asp Lys Ile Lys Val Phe Phe Ile Asn
865 870 875 880

Lys Gly Ile Glu Val Val Asp Asn Arg Asp Lys Ser Gly Cys Leu Trp
885 890 895

Ile Val Ala Gly Lys Glu Ala Ile Pro Leu Met Lys Lys Phe Gly Val
900 905 910

Leu Gly Tyr Asn Phe Ile Phe Ile Ala Asn Gly Gly Arg Ala Ser Lys
915 920 925

Asn Arg Pro Ala Trp Tyr Leu Lys Asn Ser
930 935

<210> SEQ ID NO 60
<211> LENGTH: 1833
<212> TYPE: DNA
<213> ORGANISM: Escherichia coli

<400> SEQUENCE: 60
atggcacagg cagaagttct gaacctggaa tccggtgcta aacaagtatt acaggagacc 60
ttcggttatc agcagttccg tcccggacaa gaagaaatta ttgataccgt actgtccggt 120
cgtgattgtt tggtagtcat gccaactggt ggaggaaaga gcctgtgcta tcaaatccct 180
gccttattat tgaatgggtt aacggtagtc gtatcaccat taatttcttt gatgaaggat 240
caagttgatc agcttcaggc gaatggtgta gcagctgcat gccttaatag tacccaaaca 300
cgcgagcaac agttagaagt gatgacaggt tgtcgtacgg gccaaattcg cctgttgtac 360
atcgcccccg aacgtctgat gctggacaat tttttagagc acctggctca ctggaatcca 420
gttttgctgg cggtggacga ggcacactgt atcagtcagt gggggcacga cttccgccct 480
gagtatgctg ccctgggtca gttgcgtcag cgttttccta ccctgccttt tatggctctg 540
acggcgactg ctgacgacac aactcgtcag gatatcgtac gcctgttagg attgaatgac 600
ccactgatcc agatcagttc gtttgaccgc ccaaatatcc gctatatgtt aatggaaaaa 660
tttaaaccct tggatcaatt aatgcgctac gtacaagagc agcgtggtaa gagcggcatt 720
atttactgta acagtcgcgc gaaggttgag gacacagcgg cacgcctgca gagcaaaggc 780
atttcagcgg cggcatacca tgcaggtttg gagaacaatg tacgcgcaga cgttcaggag 840
aagttccagc gcgatgattt gcagatcgtt gtggccactg tagcgttcgg tatggggatc 900
aacaaaccta atgtacgttt cgttgtccac tttgacatcc cacgcaatat tgagagctac 960
tatcaagaga ccggacgcgc agggcgtgat ggtttaccag ccgaggccat gttgttctac 1020
gatccggctg atatggcctg gctgcgtcgc tgtttggagg aaaaacctca aggtcagttg 1080
caagacatcg aacgccacaa attaaatgct atgggtgcgt ttgccgaagc tcaaacatgc 1140
cgtcgcttag ttttacttaa ttattttggt gaggggcgtc aggagccgtg tggtaattgc 1200
gatatttgct tggaccctcc taaacaatat gacgggtcaa cagacgccca gattgcgtta 1260

```
tcgactattg gacgcgtcaa tcagcgtttt ggtatggggt acgtggtcga agtaattcgt   1320

ggagcaaata accaacgtat ccgtgattat gggcacgata aactgaaagt atacggtatg   1380

ggtcgcgata agagtcatga gcactgggtg tcagtcatcc gccaattaat tcaccttggt   1440

ctggttacac aaaacatcgc gcaacactct gcactgcagc ttactgaagc cgctcgtcct   1500

gtattgcgtg gtgagagcag tctgcagttg gccgtgcccc gcattgtggc cttgaaacca   1560

aaagccatgc agaaaagctt tgggggaaat tatgatcgca aattgtttgc caagcttcgc   1620

aaactgcgca aatcaatcgc ggatgagtca aacgtaccac cgtatgttgt cttcaatgac   1680

gcaactttaa tcgagatggc ggagcaaatg ccaatcacag cttcagagat gctgagtgta   1740

aatggcgttg gcatgcgcaa gcttgagcgc ttcggaaagc cgttcatggc attaattcgc   1800

gcccacgtcg atggggatga cgaggagtag tga                                1833
```

<210> SEQ ID NO 61
<211> LENGTH: 2592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gcgctagcaa tggcacaggc agaagttctg    780

aacctggaat ccggtgctaa acaagtatta caggagacct tcggttatca gcagttccgt    840

cccggacaag aagaaattat tgataccgta ctgtccggtc gtgattgttt ggtagtcatg    900

ccaactggtg gaggaaagag cctgtgctat caaatccctg ccttattatt gaatgggtta    960

acggtagtcg tatcaccatt aatttctttg atgaaggatc aagttgatca gcttcaggcg   1020

aatggtgtag cagctgcatg ccttaatagt acccaaacac gcgagcaaca gttagaagtg   1080

atgacaggtt gtcgtacggg ccaaattcgc ctgttgtaca tcgcccccga acgtctgatg   1140

ctggacaatt ttttagagca cctggctcac tggaatccag ttttgctggc ggtggacgag   1200

gcacactgta tcagtcagtg gggcacgac ttccgccctg agtatgctgc cctgggtcag   1260

ttgcgtcagc gttttcctac cctgcctttt atggctctga cggcgactgc tgacgacaca   1320

actcgtcagg atatcgtacg cctgttagga ttgaatgacc cactgatcca gatcagttcg   1380

tttgaccgcc caaatatccg ctatatgtta atggaaaaat ttaaaccctt ggatcaatta   1440
```

atgcgctacg tacaagagca gcgtggtaag agcggcatta tttactgtaa cagtcgcgcg 1500
aaggttgagg acacagcggc acgcctgcag agcaaaggca tttcagcggc ggcataccat 1560
gcaggtttgg agaacaatgt acgcgcagac gttcaggaga agttccagcg cgatgatttg 1620
cagatcgttg tggccactgt agcgttcggt atggggatca acaaacctaa tgtacgtttc 1680
gttgtccact ttgacatccc acgcaatatt gagagctact atcaagagac cggacgcgca 1740
gggcgtgatg gtttaccagc cgaggccatg ttgttctacg atccggctga tatggcctgg 1800
ctgcgtcgct gtttggagga aaaacctcaa ggtcagttgc aagacatcga acgccacaaa 1860
ttaaatgcta tgggtgcgtt tgccgaagct caaacatgcc gtcgcttagt tttacttaat 1920
tattttggtg aggggcgtca ggagccgtgt ggtaattgcg atatttgctt ggaccctcct 1980
aaacaatatg acgggtcaac agacgcccag attgcgttat cgactattgg acgcgtcaat 2040
cagcgttttg gtatggggta cgtggtcgaa gtaattcgtg gagcaaataa ccaacgtatc 2100
cgtgattatg ggcacgataa actgaaagta tacggtatgg gtcgcgataa gagtcatgag 2160
cactgggtgt cagtcatccg ccaattaatt caccttggtc tggttacaca aaacatcgcg 2220
caacactctg cactgcagct tactgaagcc gctcgtcctg tattgcgtgg tgagagcagt 2280
ctgcagttgg ccgtgccccg cattgtggcc ttgaaaccaa aagccatgca gaaaagcttt 2340
gggggaaatt atgatcgcaa attgtttgcc aagcttcgca aactgcgcaa atcaatcgcg 2400
gatgagtcaa acgtaccacc gtatgttgtc ttcaatgacg caactttaat cgagatggcg 2460
gagcaaatgc caatcacagc ttcagagatg ctgagtgtaa atggcgttgg catgcgcaag 2520
cttgagcgct tcggaaagcc gttcatggca ttaattcgcg cccacgtcga tggggatgac 2580
gaggagtagt ga 2592

<210> SEQ ID NO 62
<211> LENGTH: 2841
<212> TYPE: DNA
<213> ORGANISM: Thermus thermophilus

<400> SEQUENCE: 62
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360
tcgagaattg catatagtaa agactttgaa actctcaaag ttgattttct tagcaagcta 420
cctgaaatgc tgaaaatgtt cgaagatcgt ttatgtcata aaacatattt aaatggtgat 480
catgtaaccc atcctgactt catgttgtat gacgctcttg atgttgtttt atacatggac 540
ccaatgtgcc tggatgcgtt cccaaaatta gtttgtttta aaaaacgtat tgaagctatc 600
ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gcgctagcaa tgtctgacgc cttgctggca 780
ccattaaacg aggcacaacg ccaagccgtc ctgcattttg agggtccagc attagtagtg 840
gcaggggccg gatcggggaa gacgcgtacc gtggttcacc gcgtcgcata tctggtggcc 900
cgccgtggcg tgttcccatc cgagattctg gcggtgacat tcacaaataa ggcagccgag 960
gagatgcgtg aacgcttgcg tggcttagtc cctggagccg gagaagtctg ggtttcgact 1020
ttccatgctg cagcgctgcg tatcttacgc gtatacggag aacgcgtggg cctgcgtccc 1080
gggttcgtcg tatacgatga ggatgaccag acagcattat tgaaggaggt gctgaaagaa 1140
ctggctcttt cggcacgtcc cgggccgatt aaggcattgt tagaccgcgc caagaatcgt 1200
ggtgttggcc tgaaagcctt actgggggaa cttcccgagt actacgctgg gttatcgcgc 1260
ggtcgtctgg gagacgtgct ggtacgttac caggaagccc tgaaggctca aggggcttta 1320
gatttcggcg acattttgtt gtatgctctt gaagcgttcc gtggaggacg cggtggtccg 1380
caggcccgcg cgcaacgtgc acgtttcatc catgtggatg agtaccagga cacctcgccg 1440
gttcagtatc gttttacccg tcttttggcc ggtgaagaag caaaccttat ggctgtagga 1500
gaccccgatc aagggattta ctctttccgc gcagcggata ttaagaacat tttagacttc 1560
acacgtgatt atcctgaggc acgtgtatat cgtcttgaag agaactatcg ttcgaccgaa 1620
gccattctgc gtttcgccaa cgccgtaatc gtcaaaaacg cgcttcgctt ggagaaagcc 1680
ttacgccccg tcaaacgtgg gggagagcct gtccgcttat atcgcgcaga ggacgcacgc 1740
gaagaagcac gctttgtcgc agaagagatt gctcgtttgg gaccccccgtg ggatcgctat 1800 gcagtcttat accgcactaa tgctcaaagc cgccttctgg aacaggcgtt agcaggtcgt 1860
gggatccccg cacgcgtcgt tggaggtgtg ggttttttcg agcgtgcaga ggtgaaggac 1920
ttgttggcgt acgctcgttt ggccttgaat cccttggatg ccgtgtccct taagcgcgtc 1980
ctgaacactc cccacgcgg tatcggacca gccacgtggg cccgcgtgca gttacttgcc 2040
caagagaaag gattacccc ctgggaggct cttaaagaag cggcacgcac cttttctcgc 2100
ccagaaccac tgcgccattt cgtagccctt gttgaagagt tgcaagattt agtattcggg 2160
cctgccgagg ctttctttcg ccacttgctg gaggcgactg attaccccgc ctacctgcgt 2220
gaagcgtacc cagaagatgc ggaagaccgc ttggaaaatg tagaagaact gttgcgcgcc 2280
gcgaaagaag cggaggatct tcaggacttc cttgatcgtg tcgcactgac tgccaaggcc 2340
gaggagccgg ccgaagcaga aggacgcgtt gcattgatga cattgcataa cgcaaagggg 2400
ttggagtttc cagtcgtttt cctggttggc gtagaggaag ggttactgcc ccaccgtaac 2460
tcggtgtcga cgttagaagg acttgaagag gaacgtcgtt tgttctatgt cggtatcacc 2520
cgtgctcagg aacgtttgta cctgtcacat gcggaagagc gcgaggttta tggccgccgc 2580
gagcccgcgc gtccgtcccg ctttcttgaa gaggttgaag agggtttata cgaagtatac 2640
gacccatatc gtcgcccacc gtcacccct ccacatcgcc ctcgcccggg ggcatttcgt 2700
ggaggtgaac gcgtcgtaca tccgcgcttt ggacctggca cagtcgtggc cgcgcagggt 2760
gacgaggtta cggtccattt tgagggtttt ggtctgaaac gcctttcatt aaaatatgca 2820
gagctgaaac cagcttagtg a 2841

<210> SEQ ID NO 63
<211> LENGTH: 3600
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 63
atgaaacatc accatcacca tcacaacact agtagcaatt ccatgtcccc tatactaggt 60
tattggaaaa ttaagggcct tgtgcaaccc actcgacttc ttttggaata tcttgaagaa 120

```
aaatatgaag agcatttgta tgagcgcgat gaaggtgata aatggcgaaa caaaaagttt    180
gaattgggtt tggagtttcc caatcttcct tattatattg atggtgatgt taaattaaca    240
cagtctatgg ccatcatacg ttatatagct gacaagcaca acatgttggg tggttgtcca    300
aaagagcgtg cagagatttc aatgcttgaa ggagcggttt tggatattag atacggtgtt    360
tcgagaattg catatagtaa agactttgaa actctcaaag ttgattttct tagcaagcta    420
cctgaaatgc tgaaaatgtt cgaagatcgt ttatgtcata aaacatattt aaatggtgat    480
catgtaaccc atcctgactt catgttgtat gacgctcttg atgttgtttt atacatggac    540
ccaatgtgcc tggatgcgtt cccaaaatta gtttgtttta aaaaacgtat tgaagctatc    600
ccacaaattg ataagtactt gaaatccagc aagtatatag catggccttt gcagggctgg    660
caagccacgt ttggtggtgg cgaccatcct ccaactagtg gatctggtgg tggtggcgga    720
tggatgagcg agaatcttta ttttcagggc gcgctagcaa tgaaacatca ccatcaccat    780
cacaacacta gtagcaattc catgtcccct atactaggtt attggaaaat taagggcctt    840
gtgcaaccca ctcgacttct tttggaatat cttgaagaaa aatatgaaga gcatttgtat    900
gagcgcgatg aaggtgataa atggcgaaac aaaaagtttg aattgggttt ggagtttccc    960
aatcttcctt attatattga tggtgatgtt aaattaacac agtctatggc catcatacgt   1020
tatatagctg acaagcacaa catgttgggt ggttgtccaa aagagcgtgc agagatttca   1080
atgcttgaag gagcggtttt ggatattaga tacggtgttt cgagaattgc atatagtaaa   1140
gactttgaaa ctctcaaagt tgattttctt agcaagctac ctgaaatgct gaaaatgttc   1200
gaagatcgtt tatgtcataa aacatattta aatggtgatc atgtaaccca tcctgacttc   1260
atgttgtatg acgctcttga tgttgtttta tacatggacc caatgtgcct ggatgcgttc   1320
ccaaaattag tttgttttaa aaaacgtatt gaagctatcc cacaaattga taagtacttg   1380
aaatccagca agtatatagc atggcctttg cagggctggc aagccacgtt tggtggtggc   1440
gaccatcctc caactagtgg atctggtggt ggtggcggat ggatgagcga gaatctttat   1500
tttcagggcg cgctagcaat gtctgacgcc ttgctggcac cattaaacga ggcacaacgc   1560
caagccgtcc tgcattttga gggtccagca ttagtagtgg caggggccgg atcggggaag   1620
acgcgtaccg tggttcaccg cgtcgcatat ctggtggccc gccgtggcgt gttcccatcc   1680
gagattctgg cggtgacatt cacaaataag gcagccgagg agatgcgtga acgcttgcgt   1740
ggcttagtcc ctggagccgg agaagtctgg gtttcgactt tccatgctgc agcgctgcgt   1800
atcttacgcg tatacggaga acgcgtgggc ctgcgtcccg ggttcgtcgt atacgatgag   1860
gatgaccaga cagcattatt gaaggaggtg ctgaaagaac tggctctttc ggcacgtccc   1920
gggccgatta aggcattgtt agaccgcgcc aagaatcgtg gtgttggcct gaaagcctta   1980
ctgggggaac ttcccgagta ctacgctggg ttatcgcgcg gtcgtctggg agacgtgctg   2040
gtacgttacc aggaagccct gaaggctcaa ggggctttag atttcggcga cattttgttg   2100
tatgctcttg aagcgttccg tggaggacgc ggtggtccgc aggcccgcgc gcaacgtgca   2160
cgtttcatcc atgtggatga gtaccaggac acctcgccgg ttcagtatcg ttttacccgt   2220
cttttggccg gtgaagaagc aaaccttatg gctgtaggag accccgatca agggatttac   2280
tctttccgcg cagcggatat taagaacatt ttagacttca cacgtgatta tcctgaggca   2340
cgtgtatatc gtcttgaaga gaactatcgt tcgaccgaag ccattctgcg tttcgccaac   2400
gccgtaatcg tcaaaaacgc gcttcgcttg gagaaagcct tacgccccgt caaacgtggg   2460
```

ggagagcctg tccgcttata tcgcgcagag gacgcacgcg aagaagcacg ctttgtcgca 2520
gaagagattg ctcgtttggg acccccgtgg gatcgctatg cagtcttata ccgcactaat 2580
gctcaaagcc gccttctgga acaggcgtta gcaggtcgtg ggatccccgc acgcgtcgtt 2640
ggaggtgtgg gttttttcga gcgtgcagag gtgaaggact tgttggcgta cgctcgtttg 2700
gccttgaatc ccttggatgc cgtgtccctt aagcgcgtcc tgaacactcc cccacgcggt 2760
atcggaccag ccacgtgggc ccgcgtgcag ttacttgccc aagagaaagg attaccccc 2820 tgggaggctc ttaaagaagc ggcacgcacc ttttctcgcc cagaaccact gcgccatttc 2880
gtagcccttg ttgaagagtt gcaagattta gtattcgggc ctgccgaggc tttctttcgc 2940
cacttgctgg aggcgactga ttaccccgcc tacctgcgtg aagcgtaccc agaagatgcg 3000
gaagaccgct tggaaaatgt agaagaactg ttgcgcgccg cgaaagaagc ggaggatctt 3060
caggacttcc ttgatcgtgt cgcactgact gccaaggccg aggagccggc cgaagcagaa 3120
ggacgcgttg cattgatgac attgcataac gcaaaggggt tggagtttcc agtcgttttc 3180
ctggttggcg tagaggaagg gttactgccc caccgtaact cggtgtcgac gttagaagga 3240
cttgaagagg aacgtcgttt gttctatgtc ggtatcaccc gtgctcagga acgtttgtac 3300
ctgtcacatg cggaagagcg cgaggtttat ggccgccgcg agcccgcgcg tccgtcccgc 3360
tttcttgaag aggttgaaga gggtttatac gaagtatacg acccatatcg tcgcccaccg 3420 tcacccccctc cacatcgccc tcgcccgggg gcatttcgtg gaggtgaacg cgtcgtacat 3480
ccgcgctttg gacctggcac agtcgtggcc gcgcagggtg acgaggttac ggtccatttt 3540
gagggttttg gtctgaaacg cctttcatta aaatatgcag agctgaaacc agcttagtga 3600

<210> SEQ ID NO 64
<211> LENGTH: 2166
<212> TYPE: DNA
<213> ORGANISM: Escherichia coli

<400> SEQUENCE: 64
atggacgttt cctacttgct ggactcgttg aacgataagc aacgtgaggc cgttgccgcg 60
cctcgttcca acttattggt gcttgccggc gcaggttccg gcaagacacg cgtcttagtt 120
catcgcatcg cgtggttaat gagcgtggag aattgctcac cgtatagcat catggcagtt 180
acgtttacta acaaggcggc cgcagaaatg cgtcaccgca ttggacaact gatgggaaca 240
agccagggag gtatgtgggt agggactttc cacggccttg cgcaccgtct tcttcgcgca 300
caccacatgg atgccaatct gccgcaggac tttcagatcc ttgattcgga ggatcagttg 360
cgcttgctga agcgcttaat caaagcgatg aatttagatg agaagcagtg gccacccccgt 420 caggcaatgt ggtacatcaa ttcgcaaaag gatgagggtt tgcgccctca ccatatccag 480
tcgtatggca atccagtcga gcaaacatgg cagaaagttt accaggcata tcaggaggcc 540
tgtgatcgcg caggattagt agacttcgca gagcttcttc ttcgcgccca cgagttatgg 600
ctgaataaac ctcacatttt acaacattac cgtgagcgtt ttacgaatat tttagtggat 660
gagttccagg atactaacaa cattcagtac gcttggatcc gcttacttgc cggagatacg 720
gggaaagtta tgatcgttgg tgatgacgac cagtcgatct acggctggcg tggggcacag 780
gtagagaaca tccaacgctt cttaaacgac ttccctggtg ctgagacgat ccgccttgaa 840
cagaattacc gttctacaag caatatcctg tccgcagcga atgcccttat tgagaacaac 900
aacgggcgcc ttggcaagaa gttgtggact gacggagctg atggcgaacc gatctctctg 960
tattgcgcat tcaatgaact ggacgaggca cgcttcgttg tcaatcgcat taagacttgg 1020

```
caggataacg gcggtgcctt ggctgagtgc gctattctgt accgttcaaa cgcccagagc   1080

cgtgtgctgg aggaagcgtt actgcaggct tctatgccgt atcgcattta cggtggtatg   1140

cgcttttttg aacgtcaaga gattaaggac gcgctgtctt atctgcgtct gatcgctaac   1200

cgcaatgacg acgccgcatt tgagcgtgtc gtcaataccc ccactcgcgg gatcggggat   1260

cgcacactgg acgtagtccg ccaaacaagc cgcgaccgtc aattaacact ttggcaggcg   1320

tgccgtgaat tacttcagga aaaggcattg gctggtcgtg ccgcgagcgc ccttcaacgt   1380

tttatggagc ttatcgacgc cctggcacaa gagactgcag acatgccatt gcacgtacag   1440

actgaccgtg tgattaagga cagcgggctg cgtacaatgt atgagcaaga gaaaggagag   1500

aaagggcaga cacgcattga gaacttagaa gaattggtaa cggcgactcg tcaattctcc   1560

tacaacgaag aagatgagga tttaatgcct cttcaggcgt tcttaagtca tgctgcgttg   1620

gaagcaggag aaggacaagc tgatacctgg caagacgcag tccagcttat gactttgcat   1680

tcagcgaagg gcttggaatt tccgcaagtt tttatcgtcg gcatggaaga agggatgttt   1740

ccctcccaga tgagtcttga cgaaggggga cgtttggaag aggaacgtcg tttggcttat   1800

gtcggggtga cacgcgcaat gcaaaagctt actctgacct atgcagaaac ccgtcgcttg   1860

tacgggaaag aagtctatca tcgtcccagc cgtttcattg gcgagctgcc cgaagaatgt   1920

gtcgaagagg tacgccttcg tgccaccgta tctcgcccgg tgtctcacca acgtatgggg   1980

acgcctatgg tagaaaatga ctccggttac aagttgggtc aacgtgtccg ccatgccaag   2040

ttcggcgagg ggaccattgt caatatggaa ggaagcggcg aacactcgcg cttgcaagtg   2100

gctttccaag gacagggcat caaatggctg gttgccgcct atgctcgctt ggagagtgtg   2160

tagtga                                                              2166
```

<210> SEQ ID NO 65
<211> LENGTH: 2925
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gcgctagcaa tggacgtttc ctacttgctg    780

gactcgttga acgataagca acgtgaggcc gttgccgcgc ctcgttccaa cttattggtg    840
```

```
cttgccggcg caggttccgg caagacacgc gtcttagttc atcgcatcgc gtggttaatg    900
agcgtggaga attgctcacc gtatagcatc atggcagtta cgtttactaa caaggcggcc    960
gcagaaatgc gtcaccgcat tggacaactg atgggaacaa gccagggagg tatgtgggta   1020
gggactttcc acggccttgc gcaccgtctt cttcgcgcac accacatgga tgccaatctg   1080
ccgcaggact ttcagatcct tgattcggag gatcagttgc gcttgctgaa gcgcttaatc   1140
aaagcgatga atttagatga gaagcagtgg ccacccccgtc aggcaatgtg gtacatcaat   1200
tcgcaaaagg atgagggttt gcgccctcac catatccagt cgtatggcaa tccagtcgag   1260
caaacatggc agaaagttta ccaggcatat caggaggcct gtgatcgcgc aggattagta   1320
gacttcgcag agcttcttct tcgcgcccac gagttatggc tgaataaacc tcacatttta   1380
caacattacc gtgagcgttt tacgaatatt ttagtggatg agttccagga tactaacaac   1440
attcagtacg cttggatccg cttacttgcc ggagatacgg ggaaagttat gatcgttggt   1500
gatgacgacc agtcgatcta cggctggcgt ggggcacagg tagagaacat ccaacgcttc   1560
ttaaacgact tccctggtgc tgagacgatc cgccttgaac agaattaccg ttctacaagc   1620
aatatcctgt ccgcagcgaa tgcccttatt gagaacaaca acgggcgcct tggcaagaag   1680
ttgtggactg acggagctga tggcgaaccg atctctctgt attgcgcatt caatgaactg   1740
gacgaggcac gcttcgttgt caatcgcatt aagacttggc aggataacgg cggtgccttg   1800
gctgagtgcg ctattctgta ccgttcaaac gcccagagcc gtgtgctgga ggaagcgtta   1860
ctgcaggctt ctatgccgta tcgcatttac ggtggtatgc gcttttttga acgtcaagag   1920
attaaggacg cgctgtctta tctgcgtctg atcgctaacc gcaatgacga cgccgcattt   1980
gagcgtgtcg tcaatacccc cactcgcggg atcggggatc gcacactgga cgtagtccgc   2040
caaacaagcc gcgaccgtca attaacactt tggcaggcgt gccgtgaatt acttcaggaa   2100
aaggcattgg ctggtcgtgc cgcgagcgcc cttcaacgtt ttatggagct tatcgacgcc   2160
ctggcacaag agactgcaga catgccattg cacgtacaga ctgaccgtgt gattaaggac   2220
agcgggctgc gtacaatgta tgagcaagag aaaggagaga aagggcagac acgcattgag   2280
aacttagaag aattggtaac ggcgactcgt caattctcct acaacgaaga agatgaggat   2340
ttaatgcctc ttcaggcgtt cttaagtcat gctgcgttgg aagcaggaga aggacaagct   2400
gatacctggc aagacgcagt ccagcttatg actttgcatt cagcgaaggg cttggaattt   2460
ccgcaagttt ttatcgtcgg catggaagaa gggatgtttc cctcccagat gagtcttgac   2520
gaagggggac gtttggaaga ggaacgtcgt ttggcttatg tcggggtgac acgcgcaatg   2580
caaaagctta ctctgaccta tgcagaaacc cgtcgcttgt acgggaaaga agtctatcat   2640
cgtcccagcc gtttcattgg cgagctgccc gaagaatgtg tcgaagaggt acgccttcgt   2700
gccaccgtat ctcgcccggt gtctcaccaa cgtatgggga cgcctatggt agaaaatgac   2760
tccggttaca agttgggtca acgtgtccgc catgccaagt tcggcgaggg gaccattgtc   2820
aatatggaag gaagcggcga acactcgcgc ttgcaagtgg ctttccaagg acagggcatc   2880
aaatggctgg ttgccgccta tgctcgcttg gagagtgtgt agtga                   2925
```

<210> SEQ ID NO 66
<211> LENGTH: 2430
<212> TYPE: DNA
<213> ORGANISM: Clostridium perfringens

<400> SEQUENCE: 66

```
atggtgctta accctaagta ctcaatcgga gtgtattacg atgaattagt cgaagaggat     60
attgagaaag tctattcgta cctgagccgt ggaatcgtgg tacatttatt tttgcgtggc    120
attttaaagg aagagctgga attgaatgag tatgatttga atacattcaa gctgccgaaa    180
gacaataact tactgtttgt gtacgaggaa gagaccagtt tgtcttccga aaacatcatc    240
atctttgtcg ataacaacat tctgaacaag gaggcgtata agaacatcac cgaaaatcgc    300
gagtgcgagt tcaacaaaga ccaatatgag attattacgg cgcctgtaga tgataacatc    360
attgtgacaa gcggcgcagg aaccggaaag acaacaacca tgatcaaccg ccttatttat    420
ttacgctccg tgatgtcaga ctttacgttt gaccaagcgg tgttaatcac tttcactaac    480
aaagcatcga ttgaaatgaa agaacgcctt ttggaagtgc tggataagta tttccgcgtc    540
acaaacgaca ttaaatactt ggactatatg gaggaagccg caaaggggtc catcagcact    600
attcacaaat ttgccaagaa gattcttaac aagtccggac gtcatattgg gatcaacaaa    660
gacattaacg tgcgctcgtt caagtacaag cgtcaggagg ccgtcaacaa cgccctgaat    720
aaaatctata aggaagagtc tgagctgttt tccctgatca aatactaccc aatctatgaa    780
gtcgaacgtg ttatcttaaa aatgtgggaa atcttagaca attactcgat tgatctttta    840
tcaaacaaag tgcgtgtcga cttcaatttt gaggaggata agttcacaga gcttattagc    900
aaaactttaa agtacgcaca ggagattttg gattatgata aagagaacga gttagagatc    960
tcagacttga tgaagaaatt agcttacgaa gatattttta aggggatcga cagtacgtac   1020
aaagtgatta tgatcgacga atttcaggat agcgacaaca cccaaattga gtttatttct   1080
gaattggaaa aaaaaacagg agcccgcatc ttggttgtgg gagacgaaaa gcaatcaatt   1140
taccgcttcc gcggggcaga atatacagca ttcgacaaat tgaagaagct tttatcaaat   1200
tctaagcgtg aagtcaagga atatgagatg acacgcaatt atcgcacaaa ctacaacatc   1260
ttgaatgaga ttaatcgtat ttttattgag gtcgataaaa agttagagtg ctttaattat   1320
aaagagaagg actacatcta tagcaataag gacaaagata atcctaaaga aatcacgtgt   1380
ttcaacgttt ctgacaatct taaacgtaaa gagttctttg acgaccttct ggagaacaaa   1440
aaggaagacg aatcaattgc tgtcttattt cgctctaatt ctgacattaa agagttcaaa   1500
gagttctgcg atcgcaataa tattctttgt atggttgatt cgacaggagg tttttatcgc   1560
cacgaagctg tacgcgactt ctatattatg attaaatcga ttattgatga gcgcaacagt   1620
cgcacgatgt actctttcat caatacaccg tacattttag aagacatcga caaaaacatt   1680
attttgaacg gtaactccaa agacaaaaat gagttccttt actacatttt agaaaaaaat   1740
aactggaact atttccgcga gtccagtaac tttaagaacc ccattatcct gattgacgag   1800
attatcgaaa agttaaagcc ggtcaaaaac tattacgtta aggtgcttct ggaggcaaag   1860
aaaaaccagc ataattatgt taacattgcg aaaatgaagg cgctggaata caagcttaat   1920
ctggaacact tagtatttat tcttaagaaa gagtttagtg agaatattac ttcaatcgaa   1980
cagattgaac agtttctgaa agtgaagatc agcactgata atcttgtaga cgtacgcaag   2040
ccaaaggatt acgagaatga ctacatccaa tgttcaacag ttcataaggc gaaaggtttg   2100
gagtatgatt acgttgtgct ggacaagttg acgaatcgct tttgtctaa ttcgcgtaaa   2160
gttaacttga tcttaaagcc cgacggagac aagttgttaa ttggatacaa aatccgtttg   2220
ggagaagacg agttcaagaa caagatctac agcgacaatc tgaaatacga gaagaaagag   2280
attaaggggg aggaggcacg cttgttatat gttgcgttga cccgttgcaa aaaggggatc   2340
tatctgaata tgtctggcga actggcggcg accgagtcgc ttaacacctg gaaaagcctg   2400
```

attggaggca ctattaatta tgtttaatag 2430

<210> SEQ ID NO 67
<211> LENGTH: 3189
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 67
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360
tcgagaattg catatagtaa agactttgaa actctcaaag ttgattttct tagcaagcta 420
cctgaaatgc tgaaaatgtt cgaagatcgt ttatgtcata aaacatattt aaatggtgat 480
catgtaaccc atcctgactt catgttgtat gacgctcttg atgttgtttt atacatggac 540
ccaatgtgcc tggatgcgtt cccaaaatta gtttgtttta aaaaacgtat tgaagctatc 600
ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gcgctagcaa tggtgcttaa ccctaagtac 780
tcaatcggag tgtattacga tgaattagtc gaagaggata ttgagaaagt ctattcgtac 840
ctgagccgtg gaatcgtggt acatttattt ttgcgtggca ttttaaagga agagctggaa 900
ttgaatgagt atgatttgaa tacattcaag ctgccgaaag acaataactt actgtttgtg 960
tacgaggaag agaccagttt gtcttccgaa aacatcatca tctttgtcga taacaacatt 1020
ctgaacaagg aggcgtataa gaacatcacc gaaaatcgcg agtgcgagtt caacaaagac 1080
caatatgaga ttattacggc gcctgtagat gataacatca ttgtgacaag cggcgcagga 1140
accggaaaga caacaaccat gatcaaccgc cttatttatt tacgctccgt gatgtcagac 1200
tttacgtttg accaagcggt gttaatcact ttcactaaca aagcatcgat tgaaatgaaa 1260
gaacgccttt tggaagtgct ggataagtat ttccgcgtca caaacgacat taaatacttg 1320
gactatatgg aggaagccgc aaaggggtcc atcagcacta ttcacaaatt tgccaagaag 1380
attcttaaca agtccggacg tcatattggg atcaacaaag acattaacgt gcgctcgttc 1440
aagtacaagc gtcaggaggc cgtcaacaac gccctgaata aaatctataa ggaagagtct 1500
gagctgtttt ccctgatcaa atactaccca atctatgaag tcgaacgtgt tatcttaaaa 1560
atgtgggaaa tcttagacaa ttactcgatt gatcttttat caaacaaagt gcgtgtcgac 1620
ttcaattttg aggaggataa gttcacagag cttattagca aaactttaaa gtacgcacag 1680
gagattttgg attatgataa agagaacgag ttagagatct cagacttgat gaagaaatta 1740
gcttacgaag atatttttaa ggggatcgac agtacgtaca aagtgattat gatcgacgaa 1800
tttcaggata gcgacaacac ccaaattgag tttatttctg aattggaaaa aaaaacagga 1860
gcccgcatct tggttgtggg agacgaaaag caatcaattt accgcttccg cggggcagaa 1920
tatacagcat tcgacaaatt gaagaagctt ttatcaaatt ctaagcgtga agtcaaggaa 1980
tatgagatga cacgcaatta tcgcacaaac tacaacatct tgaatgagat taatcgtatt 2040
tttattgagg tcgataaaaa gttagagtgc tttaattata aagagaagga ctacatctat 2100
agcaataagg acaaagataa tcctaaagaa atcacgtgtt tcaacgtttc tgacaatctt 2160
aaacgtaaag agttctttga cgaccttctg gagaacaaaa aggaagacga atcaattgct 2220
gtcttatttc gctctaattc tgacattaaa gagttcaaag agttctgcga tcgcaataat 2280
attctttgta tggttgattc gacaggaggt ttttatcgcc acgaagctgt acgcgacttc 2340
tatattatga ttaaatcgat tattgatgag cgcaacagtc gcacgatgta ctctttcatc 2400
aatacaccgt acattttaga agacatcgac aaaaacatta ttttgaacgg taactccaaa 2460
gacaaaaatg agttccttta ctacatttta gaaaaaaata actggaacta tttccgcgag 2520
tccagtaact ttaagaaccc cattatcctg attgacgaga ttatcgaaaa gttaaagccg 2580
gtcaaaaact attacgttaa ggtgcttctg gaggcaaaga aaaaccagca taattatgtt 2640
aacattgcga aaatgaaggc gctggaatac aagcttaatc tggaacactt agtatttatt 2700
cttaagaaag agtttagtga gaatattact tcaatcgaac agattgaaca gtttctgaaa 2760
gtgaagatca gcactgataa tcttgtagac gtacgcaagc caaaggatta cgagaatgac 2820
tacatccaat gttcaacagt tcataaggcg aaaggtttgg agtatgatta cgttgtgctg 2880
gacaagttga cgaatcgctt tttgtctaat tcgcgtaaag ttaacttgat cttaaagccc 2940
gacggagaca agttgttaat tggatacaaa atccgtttgg gagaagacga gttcaagaac 3000
aagatctaca gcgacaatct gaaatacgag aagaaagaga ttaaggggga ggaggcacgc 3060
ttgttatatg ttgcgttgac ccgttgcaaa aaggggatct atctgaatat gtctggcgaa 3120
ctggcggcga ccgagtcgct taacacctgg aaaagcctga ttggaggcac tattaattat 3180
gtttaatag 3189

<210> SEQ ID NO 68
<211> LENGTH: 2001
<212> TYPE: DNA
<213> ORGANISM: Clostridium perfringens

<400> SEQUENCE: 68
atgctggggc tgaataatga gtccaaagag ttctttaagg gcattagccg catttggaga 60
aattacaagg actacaccta ccttgacggg attaagctga gccaggcgca gatcgatatc 120
atcgagaagg aggaggacca attgcttata gagggctacg ccggcaccgg taagtccctg 180
acccttatat acaagttcat taacgtgctg gttcgggaag atgggaagag ggtgctgtat 240
gtgactttta acgatacgct gatcgaggat acgaagaaac gccttagtta ttgcaacgag 300
tacaacgaga ataaagagag gcaccacgta gagatttgca cattccatga gatcgccagt 360
aatatcctga agaaaaagaa gatcatagac aggggtattg agaaactgac ggctaaaaag 420
atagaagatt acaaaggtgc cgctctccgc agaattgcgg gaatcctggc taggtacatc 480 gagggggggaa agtattatag cgagttgcct aaagaggaac gcctctacaa gacacatgac 540
gagaacttta tcagggagga ggtggcctgg atcaaggcca tgggctttat agaaaaggag 600
aagtatttcg agaaagatcg cattgggagg tccaagagta tcaggctgac gcgctcacaa 660
cgcaaaacta tattcaagat atttgaaaag tactgcgagg agcaagaaaa caaattcttc 720
aaaagcctcg acttggagga ttacgccctg aagctcatcc agaacataga taatttcgat 780
gaccttaagt tcgactacat ttttgtggac gaggtacagg atctcgatcc catgcaaatt 840

```
aaggcgctgt gtctgctgac caatacgagc atcgtgctgt caggcgacgc gaatcagcgg    900

atttacaaga aatctcccgt gaagtacgag gagctcggcc tcagaatcaa agagaagggg    960

aaacggaaaa ttctgaacaa gaactatcgg tccacgggtg agattgtcaa gctcgcgaac   1020

tcaatcaagt tcttcgacga gtccatcaat aagtataatg aaaagcagtt cgtaaaatcc   1080

ggtgatcgcc cgatcatccg gaaggtgaac gacaaaaagg gtgcggtgaa gttcctgatc   1140

ggcgagatca agaaaatcca cgaagaggac ccctacaaaa caatcgccat catccaccga   1200

gagaaaaacg agcttatcgg cttccaaaag tccgagttcc gaaagtacct ggaaggccag   1260

ctgtacatgg aaaaattcag tgacatcaag tcctttgagt caaagtttga tttgagggaa   1320

aagaaccagg tgttctacac caacggctac gatgtaaagg ggctggaatt tgatgtggtg   1380

ttcatcataa acttcaacac ggccaactac ccactgagta aagagctgaa gaaaatcaag   1440

gacgaaaacg acggcaagga aatgacgctc attaaagacg atgtgctcga gtttatcaat   1500

cgcgagaaga ggctgctgta cgtagctatg accagggcca aagaaaagct gtatctcgtg   1560

gccgactgca aaaacagcaa catcagcagc ttcatctacg actttaacac caagtactat   1620

gaggcacaaa atttcaagaa gaaagagata gaggagaact acaaccggta caagattaac   1680

atggagcgcg aatacggcat catcattgag gacgacgact ccaacaacgt taagaacaat   1740

gacacgaaac aagagaacaa gtttaatacc gaatctaagg aaaagggcaa agatgacatc   1800

gacaagataa aggtgttttt catcaacaag ggaatcgagg tggtggacaa ccgagataag   1860

agcgggtgct tgtggatcgt cgccgggaag gaagcgatcc ctcttatgaa gaagttcggt   1920

gtcctgggct ataacttcat atttatcgca aacggcggtc gggcatctaa gaaccggcca   1980

gcctggtacc tcaagaatag c                                             2001
```

<210> SEQ ID NO 69
<211> LENGTH: 2814
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gccatgccta agaaaaagcg gaaagttgag    780

gaccccaaaa agaaacgaaa agtcggaagc ggctcactgg ggctgaataa tgagtccaaa    840
```

```
gagttcttta agggcattag ccgcatttgg agaaattaca aggactacac ctaccttgac    900
gggattaagc tgagccaggc gcagatcgat atcatcgaga aggaggagga ccaattgctt    960
atagagggct acgccggcac cggtaagtcc ctgaccctta tatacaagtt cattaacgtg   1020
ctggttcggg aagatgggaa gagggtgctg tatgtgactt ttaacgatac gctgatcgag   1080
gatacgaaga aacgccttag ttattgcaac gagtacaacg agaataaaga gaggcaccac   1140
gtagagattt gcacattcca tgagatcgcc agtaatatcc tgaagaaaaa gaagatcata   1200
gacaggggta ttgagaaact gacggctaaa aagatagaag attacaaagg tgccgctctc   1260
cgcagaattg cgggaatcct ggctaggtac atcgaggggg gaaagtatta tagcgagttg   1320
cctaaagagg aacgcctcta caagacacat gacgagaact ttatcaggga ggaggtggcc   1380
tggatcaagg ccatgggctt tatagaaaag gagaagtatt tcgagaaaga tcgcattggg   1440
aggtccaaga gtatcaggct gacgcgctca caacgcaaaa ctatattcaa gatatttgaa   1500
aagtactgcg aggagcaaga aaacaaattc ttcaaaagcc tcgacttgga ggattacgcc   1560
ctgaagctca tccagaacat agataatttc gatgacctta agttcgacta catttttgtg   1620
gacgaggtac aggatctcga tcccatgcaa attaaggcgc tgtgtctgct gaccaatacg   1680
agcatcgtgc tgtcaggcga cgcgaatcag cggatttaca agaaatctcc cgtgaagtac   1740
gaggagctcg gcctcagaat caaagagaag gggaaacgga aaattctgaa caagaactat   1800
cggtccacgg gtgagattgt caagctcgcg aactcaatca agttcttcga cgagtccatc   1860
aataagtata atgaaaagca gttcgtaaaa tccggtgatc gcccgatcat ccggaaggtg   1920
aacgacaaaa agggtgcggt gaagttcctg atcggcgaga tcaagaaaat ccacgaagag   1980
gacccctaca aaacaatcgc catcatccac cgagagaaaa acgagcttat cggcttccaa   2040
aagtccgagt tccgaaagta cctggaaggc cagctgtaca tggaaaaatt cagtgacatc   2100
aagtcctttg agtcaaagtt tgatttgagg gaaaagaacc aggtgttcta caccaacggc   2160
tacgatgtaa aggggctgga atttgatgtg gtgttcatca taaacttcaa cacggccaac   2220
tacccactga gtaaagagct gaagaaaatc aaggacgaaa acgacggcaa ggaaatgacg   2280
ctcattaaag acgatgtgct cgagtttatc aatcgcgaga agaggctgct gtacgtagct   2340
atgaccaggg ccaaagaaaa gctgtatctc gtggccgact gcaaaaacag caacatcagc   2400
agcttcatct acgactttaa caccaagtac tatgaggcac aaaatttcaa gaagaaagag   2460
atagaggaga actacaaccg gtacaagatt aacatggagc gcgaatacgg catcatcatt   2520
gaggacgacg actccaacaa cgttaagaac aatgacacga aacaagagaa caagtttaat   2580
accgaatcta aggaaaaggg caaagatgac atcgacaaga taaaggtgtt tttcatcaac   2640
aagggaatcg aggtggtgga caaccgagat aagagcgggt gcttgtggat cgtcgccggg   2700
aaggaagcga tccctcttat gaagaagttc ggtgtcctgg gctataactt catatttatc   2760
gcaaacggcg gtcgggcatc taagaaccgg ccagcctggt acctcaagaa tagc         2814
```

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Gly Gly Gly Gly Ser
1               5

<210> SEQ ID NO 71
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 71

Ser Gly Ser Gly Gly Gly Gly Ser
1 5

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 72

Ser Gly Ser Glu Thr Pro Gly Thr Ser Glu Ser Ala Thr Pro Glu Ser
1 5 10 15

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 73

Pro Lys Lys Lys Arg Lys Val
1 5

<210> SEQ ID NO 74
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Pro Lys Lys Lys Arg Lys Val Glu Asp Pro Lys Lys Lys Arg Lys Val
1 5 10 15

<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 75

Lys Arg Pro Ala Ala Thr Lys Lys Ala Gly Gln Ala Lys Lys Lys Lys
1 5 10 15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 76

Pro Ala Ala Lys Arg Val Lys Leu Asp
1 5

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic peptide

<400> SEQUENCE: 77

Met Ser Arg Arg Arg Lys Ala Asn Pro Thr Lys Leu Ser Glu Asn Ala
1 5 10 15

Lys Lys Leu Ala Lys Glu Val Glu Asn
20 25

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 78

Lys Leu Lys Ile Lys Arg Pro Val Lys
1 5

<210> SEQ ID NO 79
<211> LENGTH: 1179
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 79

Met Lys His His His His His His Asn Thr Ser Ser Asn Ser Met Ser
1 5 10 15

Pro Ile Leu Gly Tyr Trp Lys Ile Lys Gly Leu Val Gln Pro Thr Arg
20 25 30

Leu Leu Leu Glu Tyr Leu Glu Glu Lys Tyr Glu Glu His Leu Tyr Glu
35 40 45

Arg Asp Glu Gly Asp Lys Trp Arg Asn Lys Lys Phe Glu Leu Gly Leu
50 55 60

Glu Phe Pro Asn Leu Pro Tyr Tyr Ile Asp Gly Asp Val Lys Leu Thr
65 70 75 80

Gln Ser Met Ala Ile Ile Arg Tyr Ile Ala Asp Lys His Asn Met Leu
85 90 95

Gly Gly Cys Pro Lys Glu Arg Ala Glu Ile Ser Met Leu Glu Gly Ala
100 105 110

Val Leu Asp Ile Arg Tyr Gly Val Ser Arg Ile Ala Tyr Ser Lys Asp
115 120 125

Phe Glu Thr Leu Lys Val Asp Phe Leu Ser Lys Leu Pro Glu Met Leu
130 135 140

Lys Met Phe Glu Asp Arg Leu Cys His Lys Thr Tyr Leu Asn Gly Asp
145 150 155 160

His Val Thr His Pro Asp Phe Met Leu Tyr Asp Ala Leu Asp Val Val

```
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Pro Lys Lys Lys
                245                 250                 255

Arg Lys Val Glu Asp Pro Lys Lys Lys Arg Lys Val Gly Ser Gly Ser
            260                 265                 270

Arg Leu Glu Met Glu Glu Lys Val Gly Asn Leu Lys Pro Asn Met Glu
        275                 280                 285

Ser Val Asn Val Thr Val Arg Val Leu Glu Ala Ser Glu Ala Arg Gln
    290                 295                 300

Ile Gln Thr Lys Asn Gly Val Arg Thr Ile Ser Glu Ala Ile Val Gly
305                 310                 315                 320

Asp Glu Thr Gly Arg Val Lys Leu Thr Leu Trp Gly Lys His Ala Gly
                325                 330                 335

Ser Ile Lys Glu Gly Gln Val Val Lys Ile Glu Asn Ala Trp Thr Thr
            340                 345                 350

Ala Phe Lys Gly Gln Val Gln Leu Asn Ala Gly Ser Lys Thr Lys Ile
        355                 360                 365

Ala Glu Ala Ser Glu Asp Gly Phe Pro Glu Ser Ser Gln Ile Pro Glu
    370                 375                 380

Asn Thr Pro Thr Ala Pro Gln Gln Met Arg Gly Gly Gly Arg Gly Phe
385                 390                 395                 400

Arg Gly Gly Gly Arg Arg Tyr Gly Arg Arg Gly Gly Arg Arg Gln Glu
                405                 410                 415

Asn Glu Glu Gly Glu Glu Glu Gly Gly Gly Gly Ser Met Val Gly Gly
            420                 425                 430

Tyr Lys Val Ser Asn Leu Thr Val Glu Ala Phe Glu Gly Ile Gly Ser
        435                 440                 445

Val Asn Pro Met Leu Phe Tyr Gln Tyr Lys Val Thr Gly Lys Gly Lys
    450                 455                 460

Tyr Asp Asn Val Tyr Lys Ile Ile Lys Ser Ala Arg Tyr Lys Met His
465                 470                 475                 480

Ser Lys Asn Arg Phe Lys Pro Val Phe Ile Lys Asp Asp Lys Leu Tyr
                485                 490                 495

Thr Leu Glu Lys Leu Pro Asp Ile Glu Asp Leu Asp Phe Ala Asn Ile
            500                 505                 510

Asn Phe Val Lys Ser Glu Val Leu Ser Ile Glu Asp Asn Met Ser Ile
        515                 520                 525

Tyr Gly Glu Val Val Glu Tyr Tyr Ile Asn Leu Lys Leu Lys Lys Val
    530                 535                 540

Lys Val Leu Gly Lys Tyr Pro Lys Tyr Arg Ile Asn Tyr Ser Lys Glu
545                 550                 555                 560

Ile Leu Ser Asn Thr Leu Leu Thr Arg Glu Leu Lys Asp Glu Phe Lys
                565                 570                 575

Lys Ser Asn Lys Gly Phe Asn Leu Lys Arg Lys Phe Arg Ile Ser Pro
            580                 585                 590
```

```
Val Val Asn Lys Met Gly Lys Val Ile Leu Tyr Leu Ser Cys Ser Ala
        595                 600                 605

Asp Phe Ser Thr Asn Lys Asn Ile Tyr Glu Met Leu Lys Glu Gly Leu
    610                 615                 620

Glu Val Glu Gly Leu Ala Val Lys Ser Glu Trp Ser Asn Ile Ser Gly
625                 630                 635                 640

Asn Leu Val Ile Glu Ser Val Leu Glu Thr Lys Ile Ser Glu Pro Thr
                645                 650                 655

Ser Leu Gly Gln Ser Leu Ile Asp Tyr Tyr Lys Asn Asn Asn Gln Gly
            660                 665                 670

Tyr Arg Val Lys Asp Phe Thr Asp Glu Asp Leu Asn Ala Asn Ile Val
        675                 680                 685

Asn Val Arg Gly Asn Lys Lys Ile Tyr Met Tyr Ile Pro His Ala Leu
    690                 695                 700

Lys Pro Ile Ile Thr Arg Glu Tyr Leu Ala Lys Asn Asp Pro Glu Phe
705                 710                 715                 720

Ser Lys Glu Ile Glu Gln Leu Ile Lys Met Asn Met Asn Tyr Arg Tyr
                725                 730                 735

Glu Thr Leu Lys Ser Phe Val Asn Asp Ile Gly Val Ile Glu Glu Leu
            740                 745                 750

Asn Asn Leu Ser Phe Lys Asn Lys Tyr Tyr Glu Asp Val Lys Leu Leu
        755                 760                 765

Gly Tyr Ser Ser Gly Lys Ile Asp Glu Pro Val Leu Met Gly Ala Lys
    770                 775                 780

Gly Ile Ile Lys Asn Lys Met Gln Ile Phe Ser Asn Gly Phe Tyr Lys
785                 790                 795                 800

Leu Pro Glu Gly Lys Val Arg Phe Gly Val Leu Tyr Pro Lys Glu Phe
                805                 810                 815

Asp Gly Val Ser Arg Lys Ala Ile Arg Ala Ile Tyr Asp Phe Ser Lys
            820                 825                 830

Glu Gly Lys Tyr His Gly Glu Ser Asn Lys Tyr Ile Ala Glu His Leu
        835                 840                 845

Ile Asn Val Glu Phe Asn Pro Lys Glu Cys Ile Phe Glu Gly Tyr Glu
    850                 855                 860

Leu Gly Asp Ile Thr Glu Tyr Lys Lys Ala Ala Leu Lys Leu Asn Asn
865                 870                 875                 880

Tyr Asn Asn Val Asp Phe Val Ile Ala Ile Val Pro Asn Met Ser Asp
                885                 890                 895

Glu Glu Ile Glu Asn Ser Tyr Asn Pro Phe Lys Lys Ile Trp Ala Glu
            900                 905                 910

Leu Asn Leu Pro Ser Gln Met Ile Ser Val Lys Thr Ala Glu Ile Phe
        915                 920                 925

Ala Asn Ser Arg Asp Asn Thr Ala Leu Tyr Tyr Leu His Asn Ile Val
    930                 935                 940

Leu Gly Ile Leu Gly Lys Ile Gly Gly Ile Pro Trp Val Val Lys Asp
945                 950                 955                 960

Met Lys Gly Asp Val Asp Cys Phe Val Gly Leu Asp Val Gly Thr Arg
                965                 970                 975

Glu Lys Gly Ile His Tyr Pro Ala Cys Ser Val Val Phe Asp Lys Tyr
            980                 985                 990

Gly Lys Leu Ile Asn Tyr Tyr Lys  Pro Asn Ile Pro Gln  Asn Gly Glu
        995                 1000                1005
```

```
Lys Ile  Asn Thr Glu Ile Leu  Gln Glu Ile Phe Asp  Lys Val Leu
    1010                 1015                 1020

Ile Ser  Tyr Glu Glu Glu Asn  Gly Ala Tyr Pro Lys  Asn Ile Val
    1025                 1030                 1035

Ile His  Arg Asp Gly Phe Ser  Arg Glu Asp Leu Asp  Trp Tyr Glu
    1040                 1045                 1050

Asn Tyr  Phe Gly Lys Lys Asn  Ile Lys Phe Asn Ile  Ile Glu Val
    1055                 1060                 1065

Lys Lys  Ser Thr Pro Leu Lys  Ile Ala Ser Ile Asn  Glu Gly Asn
    1070                 1075                 1080

Ile Thr  Asn Pro Glu Lys Gly  Ser Tyr Ile Leu Arg  Gly Asn Lys
    1085                 1090                 1095

Ala Tyr  Met Val Thr Thr Asp  Ile Lys Glu Asn Leu  Gly Ser Pro
    1100                 1105                 1110

Lys Pro  Leu Lys Ile Glu Lys  Ser Tyr Gly Asp Ile  Asp Met Leu
    1115                 1120                 1125

Thr Ala  Leu Ser Gln Ile Tyr  Ala Leu Thr Gln Ile  His Val Gly
    1130                 1135                 1140

Ala Thr  Lys Ser Leu Arg Leu  Pro Ile Thr Thr Gly  Tyr Ala Asp
    1145                 1150                 1155

Lys Ile  Cys Lys Ala Ile Glu  Phe Ile Pro Gln Gly  Arg Val Asp
    1160                 1165                 1170

Asn Arg  Leu Phe Phe Leu
    1175


<210> SEQ ID NO 80
<211> LENGTH: 1082
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175
```

```
Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Pro Lys Lys Lys
                245                 250                 255

Arg Lys Val Glu Asp Pro Lys Lys Lys Arg Lys Val Gly Ser Gly Ser
            260                 265                 270

Arg Leu Glu Met Asp Ala Leu Asp Asp Phe Asp Leu Asp Met Leu Gly
        275                 280                 285

Ser Asp Ala Leu Asp Asp Phe Asp Leu Asp Met Leu Gly Ser Asp Ala
    290                 295                 300

Leu Asp Asp Phe Asp Leu Asp Met Leu Gly Ser Asp Ala Leu Asp Asp
305                 310                 315                 320

Phe Asp Leu Asp Met Leu Gly Gly Gly Gly Ser Met Val Gly Gly Tyr
                325                 330                 335

Lys Val Ser Asn Leu Thr Val Glu Ala Phe Glu Gly Ile Gly Ser Val
            340                 345                 350

Asn Pro Met Leu Phe Tyr Gln Tyr Lys Val Thr Gly Lys Gly Lys Tyr
        355                 360                 365

Asp Asn Val Tyr Lys Ile Ile Lys Ser Ala Arg Tyr Lys Met His Ser
    370                 375                 380

Lys Asn Arg Phe Lys Pro Val Phe Ile Lys Asp Asp Lys Leu Tyr Thr
385                 390                 395                 400

Leu Glu Lys Leu Pro Asp Ile Glu Asp Leu Asp Phe Ala Asn Ile Asn
                405                 410                 415

Phe Val Lys Ser Glu Val Leu Ser Ile Glu Asp Asn Met Ser Ile Tyr
            420                 425                 430

Gly Glu Val Val Glu Tyr Tyr Ile Asn Leu Lys Leu Lys Lys Val Lys
        435                 440                 445

Val Leu Gly Lys Tyr Pro Lys Tyr Arg Ile Asn Tyr Ser Lys Glu Ile
    450                 455                 460

Leu Ser Asn Thr Leu Leu Thr Arg Glu Leu Lys Asp Glu Phe Lys Lys
465                 470                 475                 480

Ser Asn Lys Gly Phe Asn Leu Lys Arg Lys Phe Arg Ile Ser Pro Val
                485                 490                 495

Val Asn Lys Met Gly Lys Val Ile Leu Tyr Leu Ser Cys Ser Ala Asp
            500                 505                 510

Phe Ser Thr Asn Lys Asn Ile Tyr Glu Met Leu Lys Glu Gly Leu Glu
        515                 520                 525

Val Glu Gly Leu Ala Val Lys Ser Glu Trp Ser Asn Ile Ser Gly Asn
    530                 535                 540

Leu Val Ile Glu Ser Val Leu Glu Thr Lys Ile Ser Glu Pro Thr Ser
545                 550                 555                 560

Leu Gly Gln Ser Leu Ile Asp Tyr Tyr Lys Asn Asn Asn Gln Gly Tyr
                565                 570                 575

Arg Val Lys Asp Phe Thr Asp Glu Asp Leu Asn Ala Asn Ile Val Asn
            580                 585                 590
```

```
Val Arg Gly Asn Lys Lys Ile Tyr Met Tyr Ile Pro His Ala Leu Lys
        595                 600                 605

Pro Ile Ile Thr Arg Glu Tyr Leu Ala Lys Asn Asp Pro Glu Phe Ser
    610                 615                 620

Lys Glu Ile Glu Gln Leu Ile Lys Met Asn Met Asn Tyr Arg Tyr Glu
625                 630                 635                 640

Thr Leu Lys Ser Phe Val Asn Asp Ile Gly Val Ile Glu Glu Leu Asn
                645                 650                 655

Asn Leu Ser Phe Lys Asn Lys Tyr Tyr Glu Asp Val Lys Leu Leu Gly
            660                 665                 670

Tyr Ser Ser Gly Lys Ile Asp Glu Pro Val Leu Met Gly Ala Lys Gly
        675                 680                 685

Ile Ile Lys Asn Lys Met Gln Ile Phe Ser Asn Gly Phe Tyr Lys Leu
    690                 695                 700

Pro Glu Gly Lys Val Arg Phe Gly Val Leu Tyr Pro Lys Glu Phe Asp
705                 710                 715                 720

Gly Val Ser Arg Lys Ala Ile Arg Ala Ile Tyr Asp Phe Ser Lys Glu
                725                 730                 735

Gly Lys Tyr His Gly Glu Ser Asn Lys Tyr Ile Ala Glu His Leu Ile
            740                 745                 750

Asn Val Glu Phe Asn Pro Lys Glu Cys Ile Phe Glu Gly Tyr Glu Leu
        755                 760                 765

Gly Asp Ile Thr Glu Tyr Lys Lys Ala Ala Leu Lys Leu Asn Asn Tyr
    770                 775                 780

Asn Asn Val Asp Phe Val Ile Ala Ile Val Pro Asn Met Ser Asp Glu
785                 790                 795                 800

Glu Ile Glu Asn Ser Tyr Asn Pro Phe Lys Lys Ile Trp Ala Glu Leu
                805                 810                 815

Asn Leu Pro Ser Gln Met Ile Ser Val Lys Thr Ala Glu Ile Phe Ala
            820                 825                 830

Asn Ser Arg Asp Asn Thr Ala Leu Tyr Tyr Leu His Asn Ile Val Leu
        835                 840                 845

Gly Ile Leu Gly Lys Ile Gly Gly Ile Pro Trp Val Val Lys Asp Met
    850                 855                 860

Lys Gly Asp Val Asp Cys Phe Val Gly Leu Asp Val Gly Thr Arg Glu
865                 870                 875                 880

Lys Gly Ile His Tyr Pro Ala Cys Ser Val Val Phe Asp Lys Tyr Gly
                885                 890                 895

Lys Leu Ile Asn Tyr Tyr Lys Pro Asn Ile Pro Gln Asn Gly Glu Lys
            900                 905                 910

Ile Asn Thr Glu Ile Leu Gln Glu Ile Phe Asp Lys Val Leu Ile Ser
        915                 920                 925

Tyr Glu Glu Glu Asn Gly Ala Tyr Pro Lys Asn Ile Val Ile His Arg
    930                 935                 940

Asp Gly Phe Ser Arg Glu Asp Leu Asp Trp Tyr Glu Asn Tyr Phe Gly
945                 950                 955                 960

Lys Lys Asn Ile Lys Phe Asn Ile Ile Glu Val Lys Lys Ser Thr Pro
                965                 970                 975

Leu Lys Ile Ala Ser Ile Asn Glu Gly Asn Ile Thr Asn Pro Glu Lys
            980                 985                 990

Gly Ser Tyr Ile Leu Arg Gly Asn  Lys Ala Tyr Met Val  Thr Thr Asp
        995                 1000                 1005

Ile Lys  Glu Asn Leu Gly Ser  Pro Lys Pro Leu Lys  Ile Glu Lys
```

```
    1010                1015                1020

Ser Tyr  Gly Asp Ile Asp Met  Leu Thr Ala Leu Ser  Gln Ile Tyr
    1025                1030                1035

Ala Leu  Thr Gln Ile His Val  Gly Ala Thr Lys Ser  Leu Arg Leu
    1040                1045                1050

Pro Ile  Thr Thr Gly Tyr Ala  Asp Lys Ile Cys Lys  Ala Ile Glu
    1055                1060                1065

Phe Ile  Pro Gln Gly Arg Val  Asp Asn Arg Leu Phe  Phe Leu
    1070                1075                1080
```

<210> SEQ ID NO 81
<211> LENGTH: 1033
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

```
Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Val Ser Ser Pro Gln
                245                 250                 255

Gly Tyr Pro Ser Leu Met Pro Lys Lys Lys Arg Lys Val Glu Asp Pro
            260                 265                 270

Lys Lys Lys Arg Lys Val Gly Ser Gly Ser Met Val Gly Gly Tyr Lys
        275                 280                 285
```

```
Val Ser Asn Leu Thr Val Glu Ala Phe Glu Gly Ile Gly Ser Val Asn
    290                 295                 300

Pro Met Leu Phe Tyr Gln Tyr Lys Val Thr Gly Lys Gly Lys Tyr Asp
305                 310                 315                 320

Asn Val Tyr Lys Ile Ile Lys Ser Ala Arg Tyr Lys Met His Ser Lys
                325                 330                 335

Asn Arg Phe Lys Pro Val Phe Ile Lys Asp Asp Lys Leu Tyr Thr Leu
            340                 345                 350

Glu Lys Leu Pro Asp Ile Glu Asp Leu Asp Phe Ala Asn Ile Asn Phe
        355                 360                 365

Val Lys Ser Glu Val Leu Ser Ile Glu Asp Asn Met Ser Ile Tyr Gly
    370                 375                 380

Glu Val Val Glu Tyr Tyr Ile Asn Leu Lys Leu Lys Lys Val Lys Val
385                 390                 395                 400

Leu Gly Lys Tyr Pro Lys Tyr Arg Ile Asn Tyr Ser Lys Glu Ile Leu
                405                 410                 415

Ser Asn Thr Leu Leu Thr Arg Glu Leu Lys Asp Glu Phe Lys Lys Ser
            420                 425                 430

Asn Lys Gly Phe Asn Leu Lys Arg Lys Phe Arg Ile Ser Pro Val Val
        435                 440                 445

Asn Lys Met Gly Lys Val Ile Leu Tyr Leu Ser Cys Ser Ala Asp Phe
    450                 455                 460

Ser Thr Asn Lys Asn Ile Tyr Glu Met Leu Lys Glu Gly Leu Glu Val
465                 470                 475                 480

Glu Gly Leu Ala Val Lys Ser Glu Trp Ser Asn Ile Ser Gly Asn Leu
                485                 490                 495

Val Ile Glu Ser Val Leu Glu Thr Lys Ile Ser Glu Pro Thr Ser Leu
            500                 505                 510

Gly Gln Ser Leu Ile Asp Tyr Tyr Lys Asn Asn Asn Gln Gly Tyr Arg
        515                 520                 525

Val Lys Asp Phe Thr Asp Glu Asp Leu Asn Ala Asn Ile Val Asn Val
    530                 535                 540

Arg Gly Asn Lys Lys Ile Tyr Met Tyr Ile Pro His Ala Leu Lys Pro
545                 550                 555                 560

Ile Ile Thr Arg Glu Tyr Leu Ala Lys Asn Asp Pro Glu Phe Ser Lys
                565                 570                 575

Glu Ile Glu Gln Leu Ile Lys Met Asn Met Asn Tyr Arg Tyr Glu Thr
            580                 585                 590

Leu Lys Ser Phe Val Asn Asp Ile Gly Val Ile Glu Glu Leu Asn Asn
        595                 600                 605

Leu Ser Phe Lys Asn Lys Tyr Tyr Glu Asp Val Lys Leu Leu Gly Tyr
    610                 615                 620

Ser Ser Gly Lys Ile Asp Glu Pro Val Leu Met Gly Ala Lys Gly Ile
625                 630                 635                 640

Ile Lys Asn Lys Met Gln Ile Phe Ser Asn Gly Phe Tyr Lys Leu Pro
                645                 650                 655

Glu Gly Lys Val Arg Phe Gly Val Leu Tyr Pro Lys Glu Phe Asp Gly
            660                 665                 670

Val Ser Arg Lys Ala Ile Arg Ala Ile Tyr Asp Phe Ser Lys Glu Gly
        675                 680                 685

Lys Tyr His Gly Glu Ser Asn Lys Tyr Ile Ala Glu His Leu Ile Asn
    690                 695                 700

Val Glu Phe Asn Pro Lys Glu Cys Ile Phe Glu Gly Tyr Glu Leu Gly
```

```
705                 710                 715                 720

Asp Ile Thr Glu Tyr Lys Lys Ala Ala Leu Lys Leu Asn Asn Tyr Asn
                725                 730                 735

Asn Val Asp Phe Val Ile Ala Ile Val Pro Asn Met Ser Asp Glu Glu
            740                 745                 750

Ile Glu Asn Ser Tyr Asn Pro Phe Lys Lys Ile Trp Ala Glu Leu Asn
        755                 760                 765

Leu Pro Ser Gln Met Ile Ser Val Lys Thr Ala Glu Ile Phe Ala Asn
    770                 775                 780

Ser Arg Asp Asn Thr Ala Leu Tyr Tyr Leu His Asn Ile Val Leu Gly
785                 790                 795                 800

Ile Leu Gly Lys Ile Gly Gly Ile Pro Trp Val Val Lys Asp Met Lys
                805                 810                 815

Gly Asp Val Asp Cys Phe Val Gly Leu Asp Val Gly Thr Arg Glu Lys
            820                 825                 830

Gly Ile His Tyr Pro Ala Cys Ser Val Val Phe Asp Lys Tyr Gly Lys
        835                 840                 845

Leu Ile Asn Tyr Tyr Lys Pro Asn Ile Pro Gln Asn Gly Glu Lys Ile
    850                 855                 860

Asn Thr Glu Ile Leu Gln Glu Ile Phe Asp Lys Val Leu Ile Ser Tyr
865                 870                 875                 880

Glu Glu Glu Asn Gly Ala Tyr Pro Lys Asn Ile Val Ile His Arg Asp
                885                 890                 895

Gly Phe Ser Arg Glu Asp Leu Asp Trp Tyr Glu Asn Tyr Phe Gly Lys
            900                 905                 910

Lys Asn Ile Lys Phe Asn Ile Ile Glu Val Lys Lys Ser Thr Pro Leu
        915                 920                 925

Lys Ile Ala Ser Ile Asn Glu Gly Asn Ile Thr Asn Pro Glu Lys Gly
    930                 935                 940

Ser Tyr Ile Leu Arg Gly Asn Lys Ala Tyr Met Val Thr Thr Asp Ile
945                 950                 955                 960

Lys Glu Asn Leu Gly Ser Pro Lys Pro Leu Lys Ile Glu Lys Ser Tyr
                965                 970                 975

Gly Asp Ile Asp Met Leu Thr Ala Leu Ser Gln Ile Tyr Ala Leu Thr
            980                 985                 990

Gln Ile His Val Gly Ala Thr Lys  Ser Leu Arg Leu Pro  Ile Thr Thr
        995                 1000                 1005

Gly Tyr  Ala Asp Lys Ile Cys  Lys Ala Ile Glu Phe  Ile Pro Gln
    1010                 1015                 1020

Gly Arg  Val Asp Asn Arg Leu  Phe Phe Leu
    1025                 1030


<210> SEQ ID NO 82
<211> LENGTH: 1063
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30
```

```
Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80

Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Pro Lys Lys Lys
                245                 250                 255

Arg Lys Val Glu Asp Pro Lys Lys Lys Arg Lys Val Gly Ser Gly Ser
            260                 265                 270

Arg Leu Glu Met Val Gly Gly Tyr Lys Val Ser Asn Leu Thr Val Glu
        275                 280                 285

Ala Phe Glu Gly Ile Gly Ser Val Asn Pro Met Leu Phe Tyr Gln Tyr
    290                 295                 300

Lys Val Thr Gly Lys Gly Lys Tyr Asp Asn Val Tyr Lys Ile Ile Lys
305                 310                 315                 320

Ser Ala Arg Tyr Lys Met His Ser Lys Asn Arg Phe Lys Pro Val Phe
                325                 330                 335

Ile Lys Asp Asp Lys Leu Tyr Thr Leu Glu Lys Leu Pro Asp Ile Glu
            340                 345                 350

Asp Leu Asp Phe Ala Asn Ile Asn Phe Val Lys Ser Glu Val Leu Ser
        355                 360                 365

Ile Glu Asp Asn Met Ser Ile Tyr Gly Glu Val Val Glu Tyr Tyr Ile
    370                 375                 380

Asn Leu Lys Leu Lys Lys Val Lys Val Leu Gly Lys Tyr Pro Lys Tyr
385                 390                 395                 400

Arg Ile Asn Tyr Ser Lys Glu Ile Leu Ser Asn Thr Leu Leu Thr Arg
                405                 410                 415

Glu Leu Lys Asp Glu Phe Lys Lys Ser Asn Lys Gly Phe Asn Leu Lys
            420                 425                 430

Arg Lys Phe Arg Ile Ser Pro Val Val Asn Lys Met Gly Lys Val Ile
        435                 440                 445

Leu Tyr Leu Ser Cys Ser Ala Asp Phe Ser Thr Asn Lys Asn Ile Tyr
```

```
    450                 455                 460

Glu Met Leu Lys Glu Gly Leu Glu Val Glu Gly Leu Ala Val Lys Ser
465                 470                 475                 480

Glu Trp Ser Asn Ile Ser Gly Asn Leu Val Ile Glu Ser Val Leu Glu
                485                 490                 495

Thr Lys Ile Ser Glu Pro Thr Ser Leu Gly Gln Ser Leu Ile Asp Tyr
            500                 505                 510

Tyr Lys Asn Asn Asn Gln Gly Tyr Arg Val Lys Asp Phe Thr Asp Glu
        515                 520                 525

Asp Leu Asn Ala Asn Ile Val Asn Val Arg Gly Asn Lys Lys Ile Tyr
    530                 535                 540

Met Tyr Ile Pro His Ala Leu Lys Pro Ile Ile Thr Arg Glu Tyr Leu
545                 550                 555                 560

Ala Lys Asn Asp Pro Glu Phe Ser Lys Glu Ile Glu Gln Leu Ile Lys
                565                 570                 575

Met Asn Met Asn Tyr Arg Tyr Glu Thr Leu Lys Ser Phe Val Asn Asp
            580                 585                 590

Ile Gly Val Ile Glu Glu Leu Asn Asn Leu Ser Phe Lys Asn Lys Tyr
        595                 600                 605

Tyr Glu Asp Val Lys Leu Leu Gly Tyr Ser Ser Gly Lys Ile Asp Glu
    610                 615                 620

Pro Val Leu Met Gly Ala Lys Gly Ile Ile Lys Asn Lys Met Gln Ile
625                 630                 635                 640

Phe Ser Asn Gly Phe Tyr Lys Leu Pro Glu Gly Lys Val Arg Phe Gly
                645                 650                 655

Val Leu Tyr Pro Lys Glu Phe Asp Gly Val Ser Arg Lys Ala Ile Arg
            660                 665                 670

Ala Ile Tyr Asp Phe Ser Lys Glu Gly Lys Tyr His Gly Glu Ser Asn
        675                 680                 685

Lys Tyr Ile Ala Glu His Leu Ile Asn Val Glu Phe Asn Pro Lys Glu
    690                 695                 700

Cys Ile Phe Glu Gly Tyr Glu Leu Gly Asp Ile Thr Glu Tyr Lys Lys
705                 710                 715                 720

Ala Ala Leu Lys Leu Asn Asn Tyr Asn Asn Val Asp Phe Val Ile Ala
                725                 730                 735

Ile Val Pro Asn Met Ser Asp Glu Glu Ile Glu Asn Ser Tyr Asn Pro
            740                 745                 750

Phe Lys Lys Ile Trp Ala Glu Leu Asn Leu Pro Ser Gln Met Ile Ser
        755                 760                 765

Val Lys Thr Ala Glu Ile Phe Ala Asn Ser Arg Asp Asn Thr Ala Leu
    770                 775                 780

Tyr Tyr Leu His Asn Ile Val Leu Gly Ile Leu Gly Lys Ile Gly Gly
785                 790                 795                 800

Ile Pro Trp Val Val Lys Asp Met Lys Gly Asp Val Asp Cys Phe Val
                805                 810                 815

Gly Leu Asp Val Gly Thr Arg Glu Lys Gly Ile His Tyr Pro Ala Cys
            820                 825                 830

Ser Val Val Phe Asp Lys Tyr Gly Lys Leu Ile Asn Tyr Tyr Lys Pro
        835                 840                 845

Asn Ile Pro Gln Asn Gly Glu Lys Ile Asn Thr Glu Ile Leu Gln Glu
    850                 855                 860

Ile Phe Asp Lys Val Leu Ile Ser Tyr Glu Glu Glu Asn Gly Ala Tyr
865                 870                 875                 880
```

Pro Lys Asn Ile Val Ile His Arg Asp Gly Phe Ser Arg Glu Asp Leu
885 890 895

Asp Trp Tyr Glu Asn Tyr Phe Gly Lys Lys Asn Ile Lys Phe Asn Ile
900 905 910

Ile Glu Val Lys Lys Ser Thr Pro Leu Lys Ile Ala Ser Ile Asn Glu
915 920 925

Gly Asn Ile Thr Asn Pro Glu Lys Gly Ser Tyr Ile Leu Arg Gly Asn
930 935 940

Lys Ala Tyr Met Val Thr Thr Asp Ile Lys Glu Asn Leu Gly Ser Pro
945 950 955 960

Lys Pro Leu Lys Ile Glu Lys Ser Tyr Gly Asp Ile Asp Met Leu Thr
965 970 975

Ala Leu Ser Gln Ile Tyr Ala Leu Thr Gln Ile His Val Gly Ala Thr
980 985 990

Lys Ser Leu Arg Leu Pro Ile Thr Thr Gly Tyr Ala Asp Lys Ile Cys
995 1000 1005

Lys Ala Ile Glu Phe Ile Pro Gln Gly Arg Val Asp Asn Arg Leu
1010 1015 1020

Phe Phe Leu Thr Ser Gly Gly Gly Gly Ser Gly Lys Pro Ile Pro
1025 1030 1035

Asn Pro Leu Leu Gly Leu Asp Ser Thr Lys Arg Pro Ala Ala Thr
1040 1045 1050

Lys Lys Ala Gly Gln Ala Lys Lys Lys Lys
1055 1060

<210> SEQ ID NO 83
<211> LENGTH: 1026
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

Met Lys His His His His His His Asn Thr Ser Ser Asn Ser Met Ser
1 5 10 15

Pro Ile Leu Gly Tyr Trp Lys Ile Lys Gly Leu Val Gln Pro Thr Arg
20 25 30

Leu Leu Leu Glu Tyr Leu Glu Glu Lys Tyr Glu Glu His Leu Tyr Glu
35 40 45

Arg Asp Glu Gly Asp Lys Trp Arg Asn Lys Lys Phe Glu Leu Gly Leu
50 55 60

Glu Phe Pro Asn Leu Pro Tyr Tyr Ile Asp Gly Asp Val Lys Leu Thr
65 70 75 80

Gln Ser Met Ala Ile Ile Arg Tyr Ile Ala Asp Lys His Asn Met Leu
85 90 95

Gly Gly Cys Pro Lys Glu Arg Ala Glu Ile Ser Met Leu Glu Gly Ala
100 105 110

Val Leu Asp Ile Arg Tyr Gly Val Ser Arg Ile Ala Tyr Ser Lys Asp
115 120 125

Phe Glu Thr Leu Lys Val Asp Phe Leu Ser Lys Leu Pro Glu Met Leu
130 135 140

Lys Met Phe Glu Asp Arg Leu Cys His Lys Thr Tyr Leu Asn Gly Asp
145 150 155 160

His Val Thr His Pro Asp Phe Met Leu Tyr Asp Ala Leu Asp Val Val

```
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Pro Lys Lys Lys
                245                 250                 255

Arg Lys Val Glu Asp Pro Lys Lys Lys Arg Lys Val Gly Ser Gly Ser
            260                 265                 270

Arg Leu Glu Met Val Gly Gly Tyr Lys Val Ser Asn Leu Thr Val Glu
        275                 280                 285

Ala Phe Glu Gly Ile Gly Ser Val Asn Pro Met Leu Phe Tyr Gln Tyr
    290                 295                 300

Lys Val Thr Gly Lys Gly Lys Tyr Asp Asn Val Tyr Lys Ile Ile Lys
305                 310                 315                 320

Ser Ala Arg Tyr Lys Met His Ser Lys Asn Arg Phe Lys Pro Val Phe
                325                 330                 335

Ile Lys Asp Asp Lys Leu Tyr Thr Leu Glu Lys Leu Pro Asp Ile Glu
            340                 345                 350

Asp Leu Asp Phe Ala Asn Ile Asn Phe Val Lys Ser Glu Val Leu Ser
        355                 360                 365

Ile Glu Asp Asn Met Ser Ile Tyr Gly Glu Val Val Glu Tyr Tyr Ile
    370                 375                 380

Asn Leu Lys Leu Lys Lys Val Lys Val Leu Gly Lys Tyr Pro Lys Tyr
385                 390                 395                 400

Arg Ile Asn Tyr Ser Lys Glu Ile Leu Ser Asn Thr Leu Leu Thr Arg
                405                 410                 415

Glu Leu Lys Asp Glu Phe Lys Lys Ser Asn Lys Gly Phe Asn Leu Lys
            420                 425                 430

Arg Lys Phe Arg Ile Ser Pro Val Val Asn Lys Met Gly Lys Val Ile
        435                 440                 445

Leu Tyr Leu Ser Cys Ser Ala Asp Phe Ser Thr Asn Lys Asn Ile Tyr
    450                 455                 460

Glu Met Leu Lys Glu Gly Leu Glu Val Glu Gly Leu Ala Val Lys Ser
465                 470                 475                 480

Glu Trp Ser Asn Ile Ser Gly Asn Leu Val Ile Glu Ser Val Leu Glu
                485                 490                 495

Thr Lys Ile Ser Glu Pro Thr Ser Leu Gly Gln Ser Leu Ile Asp Tyr
            500                 505                 510

Tyr Lys Asn Asn Asn Gln Gly Tyr Arg Val Lys Asp Phe Thr Asp Glu
        515                 520                 525

Asp Leu Asn Ala Asn Ile Val Asn Val Arg Gly Asn Lys Lys Ile Tyr
    530                 535                 540

Met Tyr Ile Pro His Ala Leu Lys Pro Ile Ile Thr Arg Glu Tyr Leu
545                 550                 555                 560

Ala Lys Asn Asp Pro Glu Phe Ser Lys Glu Ile Glu Gln Leu Ile Lys
                565                 570                 575

Met Asn Met Asn Tyr Arg Tyr Glu Thr Leu Lys Ser Phe Val Asn Asp
            580                 585                 590
```

```
Ile Gly Val Ile Glu Glu Leu Asn Asn Leu Ser Phe Lys Asn Lys Tyr
        595                 600                 605

Tyr Glu Asp Val Lys Leu Leu Gly Tyr Ser Ser Gly Lys Ile Asp Glu
    610                 615                 620

Pro Val Leu Met Gly Ala Lys Gly Ile Ile Lys Asn Lys Met Gln Ile
625                 630                 635                 640

Phe Ser Asn Gly Phe Tyr Lys Leu Pro Glu Gly Lys Val Arg Phe Gly
                645                 650                 655

Val Leu Tyr Pro Lys Glu Phe Asp Gly Val Ser Arg Lys Ala Ile Arg
            660                 665                 670

Ala Ile Tyr Asp Phe Ser Lys Glu Gly Lys Tyr His Gly Glu Ser Asn
        675                 680                 685

Lys Tyr Ile Ala Glu His Leu Ile Asn Val Glu Phe Asn Pro Lys Glu
    690                 695                 700

Cys Ile Phe Glu Gly Tyr Glu Leu Gly Asp Ile Thr Glu Tyr Lys Lys
705                 710                 715                 720

Ala Ala Leu Lys Leu Asn Asn Tyr Asn Asn Val Asp Phe Val Ile Ala
                725                 730                 735

Ile Val Pro Asn Met Ser Asp Glu Glu Ile Glu Asn Ser Tyr Asn Pro
            740                 745                 750

Phe Lys Lys Ile Trp Ala Glu Leu Asn Leu Pro Ser Gln Met Ile Ser
        755                 760                 765

Val Lys Thr Ala Glu Ile Phe Ala Asn Ser Arg Asp Asn Thr Ala Leu
    770                 775                 780

Tyr Tyr Leu His Asn Ile Val Leu Gly Ile Leu Gly Lys Ile Gly Gly
785                 790                 795                 800

Ile Pro Trp Val Val Lys Asp Met Lys Gly Asp Val Asp Cys Phe Val
                805                 810                 815

Gly Leu Asp Val Gly Thr Arg Glu Lys Gly Ile His Tyr Pro Ala Cys
            820                 825                 830

Ser Val Val Phe Asp Lys Tyr Gly Lys Leu Ile Asn Tyr Tyr Lys Pro
        835                 840                 845

Asn Ile Pro Gln Asn Gly Glu Lys Ile Asn Thr Glu Ile Leu Gln Glu
    850                 855                 860

Ile Phe Asp Lys Val Leu Ile Ser Tyr Glu Glu Glu Asn Gly Ala Tyr
865                 870                 875                 880

Pro Lys Asn Ile Val Ile His Arg Asp Gly Phe Ser Arg Glu Asp Leu
                885                 890                 895

Asp Trp Tyr Glu Asn Tyr Phe Gly Lys Lys Asn Ile Lys Phe Asn Ile
            900                 905                 910

Ile Glu Val Lys Lys Ser Thr Pro Leu Lys Ile Ala Ser Ile Asn Glu
        915                 920                 925

Gly Asn Ile Thr Asn Pro Glu Lys Gly Ser Tyr Ile Leu Arg Gly Asn
    930                 935                 940

Lys Ala Tyr Met Val Thr Thr Asp Ile Lys Glu Asn Leu Gly Ser Pro
945                 950                 955                 960

Lys Pro Leu Lys Ile Glu Lys Ser Tyr Gly Asp Ile Asp Met Leu Thr
                965                 970                 975

Ala Leu Ser Gln Ile Tyr Ala Leu Thr Gln Ile His Val Gly Ala Thr
            980                 985                 990

Lys Ser Leu Arg Leu Pro Ile Thr  Thr Gly Tyr Ala Asp  Lys Ile Cys
        995                 1000                1005
```

Lys Ala Ile Glu Phe Ile Pro Gln Gly Arg Val Asp Asn Arg Leu
1010 1015 1020

Phe Phe Leu
1025

<210> SEQ ID NO 84
<211> LENGTH: 1165
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 84

Met Lys His His His His His His Asn Thr Ser Ser Asn Ser Met Ser
1 5 10 15

Pro Ile Leu Gly Tyr Trp Lys Ile Lys Gly Leu Val Gln Pro Thr Arg
20 25 30

Leu Leu Leu Glu Tyr Leu Glu Glu Lys Tyr Glu Glu His Leu Tyr Glu
35 40 45

Arg Asp Glu Gly Asp Lys Trp Arg Asn Lys Lys Phe Glu Leu Gly Leu
50 55 60

Glu Phe Pro Asn Leu Pro Tyr Tyr Ile Asp Gly Asp Val Lys Leu Thr
65 70 75 80

Gln Ser Met Ala Ile Ile Arg Tyr Ile Ala Asp Lys His Asn Met Leu
85 90 95

Gly Gly Cys Pro Lys Glu Arg Ala Glu Ile Ser Met Leu Glu Gly Ala
100 105 110

Val Leu Asp Ile Arg Tyr Gly Val Ser Arg Ile Ala Tyr Ser Lys Asp
115 120 125

Phe Glu Thr Leu Lys Val Asp Phe Leu Ser Lys Leu Pro Glu Met Leu
130 135 140

Lys Met Phe Glu Asp Arg Leu Cys His Lys Thr Tyr Leu Asn Gly Asp
145 150 155 160

His Val Thr His Pro Asp Phe Met Leu Tyr Asp Ala Leu Asp Val Val
165 170 175

Leu Tyr Met Asp Pro Met Cys Leu Asp Ala Phe Pro Lys Leu Val Cys
180 185 190

Phe Lys Lys Arg Ile Glu Ala Ile Pro Gln Ile Asp Lys Tyr Leu Lys
195 200 205

Ser Ser Lys Tyr Ile Ala Trp Pro Leu Gln Gly Trp Gln Ala Thr Phe
210 215 220

Gly Gly Gly Asp His Pro Pro Thr Ser Gly Ser Gly Gly Gly Gly Gly
225 230 235 240

Trp Met Ser Glu Asn Leu Tyr Phe Gln Gly Ala Met Glu Glu Lys Val
245 250 255

Gly Asn Leu Lys Pro Asn Met Glu Ser Val Asn Val Thr Val Arg Val
260 265 270

Leu Glu Ala Ser Glu Ala Arg Gln Ile Gln Thr Lys Asn Gly Val Arg
275 280 285

Thr Ile Ser Glu Ala Ile Val Gly Asp Glu Thr Gly Arg Val Lys Leu
290 295 300

Thr Leu Trp Gly Lys His Ala Gly Ser Ile Lys Glu Gly Gln Val Val
305 310 315 320

Lys Ile Glu Asn Ala Trp Thr Thr Ala Phe Lys Gly Gln Val Gln Leu
325 330 335

```
Asn Ala Gly Ser Lys Thr Lys Ile Ala Glu Ala Ser Glu Asp Gly Phe
            340                 345                 350

Pro Glu Ser Ser Gln Ile Pro Glu Asn Thr Pro Thr Ala Pro Gln Gln
        355                 360                 365

Met Arg Gly Gly Gly Arg Gly Phe Arg Gly Gly Gly Arg Arg Tyr Gly
    370                 375                 380

Arg Arg Gly Gly Arg Arg Gln Glu Asn Glu Glu Gly Glu Glu Glu Ser
385                 390                 395                 400

Gly Ser Glu Thr Pro Gly Thr Ser Glu Ser Ala Thr Pro Glu Ser Val
                405                 410                 415

Gly Gly Tyr Lys Val Ser Asn Leu Thr Val Glu Ala Phe Glu Gly Ile
            420                 425                 430

Gly Ser Val Asn Pro Met Leu Phe Tyr Gln Tyr Lys Val Thr Gly Lys
        435                 440                 445

Gly Lys Tyr Asp Asn Val Tyr Lys Ile Ile Lys Ser Ala Arg Tyr Lys
    450                 455                 460

Met His Ser Lys Asn Arg Phe Lys Pro Val Phe Ile Lys Asp Asp Lys
465                 470                 475                 480

Leu Tyr Thr Leu Glu Lys Leu Pro Asp Ile Glu Asp Leu Asp Phe Ala
                485                 490                 495

Asn Ile Asn Phe Val Lys Ser Glu Val Leu Ser Ile Glu Asp Asn Met
            500                 505                 510

Ser Ile Tyr Gly Glu Val Val Glu Tyr Tyr Ile Asn Leu Lys Leu Lys
        515                 520                 525

Lys Val Lys Val Leu Gly Lys Tyr Pro Lys Tyr Arg Ile Asn Tyr Ser
    530                 535                 540

Lys Glu Ile Leu Ser Asn Thr Leu Leu Thr Arg Glu Leu Lys Asp Glu
545                 550                 555                 560

Phe Lys Lys Ser Asn Lys Gly Phe Asn Leu Lys Arg Lys Phe Arg Ile
                565                 570                 575

Ser Pro Val Val Asn Lys Met Gly Lys Val Ile Leu Tyr Leu Ser Cys
            580                 585                 590

Ser Ala Asp Phe Ser Thr Asn Lys Asn Ile Tyr Glu Met Leu Lys Glu
        595                 600                 605

Gly Leu Glu Val Glu Gly Leu Ala Val Lys Ser Glu Trp Ser Asn Ile
    610                 615                 620

Ser Gly Asn Leu Val Ile Glu Ser Val Leu Glu Thr Lys Ile Ser Glu
625                 630                 635                 640

Pro Thr Ser Leu Gly Gln Ser Leu Ile Asp Tyr Tyr Lys Asn Asn Asn
                645                 650                 655

Gln Gly Tyr Arg Val Lys Asp Phe Thr Asp Glu Asp Leu Asn Ala Asn
            660                 665                 670

Ile Val Asn Val Arg Gly Asn Lys Lys Ile Tyr Met Tyr Ile Pro His
        675                 680                 685

Ala Leu Lys Pro Ile Ile Thr Arg Glu Tyr Leu Ala Lys Asn Asp Pro
    690                 695                 700

Glu Phe Ser Lys Glu Ile Glu Gln Leu Ile Lys Met Asn Met Asn Tyr
705                 710                 715                 720

Arg Tyr Glu Thr Leu Lys Ser Phe Val Asn Asp Ile Gly Val Ile Glu
                725                 730                 735

Glu Leu Asn Asn Leu Ser Phe Lys Asn Lys Tyr Tyr Glu Asp Val Lys
            740                 745                 750
```

```
Leu Leu Gly Tyr Ser Ser Gly Lys Ile Asp Glu Pro Val Leu Met Gly
        755                 760                 765

Ala Lys Gly Ile Ile Lys Asn Lys Met Gln Ile Phe Ser Asn Gly Phe
    770                 775                 780

Tyr Lys Leu Pro Glu Gly Lys Val Arg Phe Gly Val Leu Tyr Pro Lys
785                 790                 795                 800

Glu Phe Asp Gly Val Ser Arg Lys Ala Ile Arg Ala Ile Tyr Asp Phe
                805                 810                 815

Ser Lys Glu Gly Lys Tyr His Gly Glu Ser Asn Lys Tyr Ile Ala Glu
            820                 825                 830

His Leu Ile Asn Val Glu Phe Asn Pro Lys Glu Cys Ile Phe Glu Gly
        835                 840                 845

Tyr Glu Leu Gly Asp Ile Thr Glu Tyr Lys Lys Ala Ala Leu Lys Leu
    850                 855                 860

Asn Asn Tyr Asn Asn Val Asp Phe Val Ile Ala Ile Val Pro Asn Met
865                 870                 875                 880

Ser Asp Glu Glu Ile Glu Asn Ser Tyr Asn Pro Phe Lys Lys Ile Trp
                885                 890                 895

Ala Glu Leu Asn Leu Pro Ser Gln Met Ile Ser Val Lys Thr Ala Glu
            900                 905                 910

Ile Phe Ala Asn Ser Arg Asp Asn Thr Ala Leu Tyr Tyr Leu His Asn
        915                 920                 925

Ile Val Leu Gly Ile Leu Gly Lys Ile Gly Gly Ile Pro Trp Val Val
    930                 935                 940

Lys Asp Met Lys Gly Asp Val Asp Cys Phe Val Gly Leu Asp Val Gly
945                 950                 955                 960

Thr Arg Glu Lys Gly Ile His Tyr Pro Ala Cys Ser Val Val Phe Asp
                965                 970                 975

Lys Tyr Gly Lys Leu Ile Asn Tyr Tyr Lys Pro Asn Ile Pro Gln Asn
            980                 985                 990

Gly Glu Lys Ile Asn Thr Glu Ile  Leu Gln Glu Ile Phe  Asp Lys Val
        995                 1000                1005

Leu Ile  Ser Tyr Glu Glu Glu  Asn Gly Ala Tyr Pro  Lys Asn Ile
    1010                1015                1020

Val Ile  His Arg Asp Gly Phe  Ser Arg Glu Asp Leu  Asp Trp Tyr
    1025                1030                1035

Glu Asn  Tyr Phe Gly Lys Lys  Asn Ile Lys Phe Asn  Ile Ile Glu
    1040                1045                1050

Val Lys  Lys Ser Thr Pro Leu  Lys Ile Ala Ser Ile  Asn Glu Gly
    1055                1060                1065

Asn Ile  Thr Asn Pro Glu Lys  Gly Ser Tyr Ile Leu  Arg Gly Asn
    1070                1075                1080

Lys Ala  Tyr Met Val Thr Thr  Asp Ile Lys Glu Asn  Leu Gly Ser
    1085                1090                1095

Pro Lys  Pro Leu Lys Ile Glu  Lys Ser Tyr Gly Asp  Ile Asp Met
    1100                1105                1110

Leu Thr  Ala Leu Ser Gln Ile  Tyr Ala Leu Thr Gln  Ile His Val
    1115                1120                1125

Gly Ala  Thr Lys Ser Leu Arg  Leu Pro Ile Thr Thr  Gly Tyr Ala
    1130                1135                1140

Asp Lys  Ile Cys Lys Ala Ile  Glu Phe Ile Pro Gln  Gly Arg Val
    1145                1150                1155

Asp Asn  Arg Leu Phe Phe Leu
```

1160 1165

<210> SEQ ID NO 85
<211> LENGTH: 1317
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

Met Lys His His His His His His Asn Thr Ser Ser Asn Ser Met Ser
1 5 10 15

Pro Ile Leu Gly Tyr Trp Lys Ile Lys Gly Leu Val Gln Pro Thr Arg
20 25 30

Leu Leu Leu Glu Tyr Leu Glu Glu Lys Tyr Glu Glu His Leu Tyr Glu
35 40 45

Arg Asp Glu Gly Asp Lys Trp Arg Asn Lys Lys Phe Glu Leu Gly Leu
50 55 60

Glu Phe Pro Asn Leu Pro Tyr Tyr Ile Asp Gly Asp Val Lys Leu Thr
65 70 75 80

Gln Ser Met Ala Ile Ile Arg Tyr Ile Ala Asp Lys His Asn Met Leu
85 90 95

Gly Gly Cys Pro Lys Glu Arg Ala Glu Ile Ser Met Leu Glu Gly Ala
100 105 110

Val Leu Asp Ile Arg Tyr Gly Val Ser Arg Ile Ala Tyr Ser Lys Asp
115 120 125

Phe Glu Thr Leu Lys Val Asp Phe Leu Ser Lys Leu Pro Glu Met Leu
130 135 140

Lys Met Phe Glu Asp Arg Leu Cys His Lys Thr Tyr Leu Asn Gly Asp
145 150 155 160

His Val Thr His Pro Asp Phe Met Leu Tyr Asp Ala Leu Asp Val Val
165 170 175

Leu Tyr Met Asp Pro Met Cys Leu Asp Ala Phe Pro Lys Leu Val Cys
180 185 190

Phe Lys Lys Arg Ile Glu Ala Ile Pro Gln Ile Asp Lys Tyr Leu Lys
195 200 205

Ser Ser Lys Tyr Ile Ala Trp Pro Leu Gln Gly Trp Gln Ala Thr Phe
210 215 220

Gly Gly Gly Asp His Pro Pro Thr Ser Gly Ser Gly Gly Gly Gly Gly
225 230 235 240

Trp Met Ser Glu Asn Leu Tyr Phe Gln Gly Ala Met Glu Glu Lys Val
245 250 255

Gly Asn Leu Lys Pro Asn Met Glu Ser Val Asn Val Thr Val Arg Val
260 265 270

Leu Glu Ala Ser Glu Ala Arg Gln Ile Gln Thr Lys Asn Gly Val Arg
275 280 285

Thr Ile Ser Glu Ala Ile Val Gly Asp Glu Thr Gly Arg Val Lys Leu
290 295 300

Thr Leu Trp Gly Lys His Ala Gly Ser Ile Lys Glu Gly Gln Val Val
305 310 315 320

Lys Ile Glu Asn Ala Trp Thr Thr Ala Phe Lys Gly Gln Val Gln Leu
325 330 335

Asn Ala Gly Ser Lys Thr Lys Ile Ala Glu Ala Ser Glu Asp Gly Phe
340 345 350

```
Pro Glu Ser Ser Gln Ile Pro Glu Asn Thr Pro Thr Ala Pro Gln Gln
        355                 360                 365

Met Arg Gly Gly Gly Arg Gly Phe Arg Gly Gly Gly Arg Arg Tyr Gly
    370                 375                 380

Arg Arg Gly Gly Arg Arg Gln Glu Asn Glu Glu Gly Glu Glu Glu Gly
385                 390                 395                 400

Gly Gly Gly Ser Glu Glu Lys Val Gly Asn Leu Lys Pro Asn Met Glu
                405                 410                 415

Ser Val Asn Val Thr Val Arg Val Leu Glu Ala Ser Glu Ala Arg Gln
            420                 425                 430

Ile Gln Thr Lys Asn Gly Val Arg Thr Ile Ser Glu Ala Ile Val Gly
        435                 440                 445

Asp Glu Thr Gly Arg Val Lys Leu Thr Leu Trp Gly Lys His Ala Gly
    450                 455                 460

Ser Ile Lys Glu Gly Gln Val Val Lys Ile Glu Asn Ala Trp Thr Thr
465                 470                 475                 480

Ala Phe Lys Gly Gln Val Gln Leu Asn Ala Gly Ser Lys Thr Lys Ile
                485                 490                 495

Ala Glu Ala Ser Glu Asp Gly Phe Pro Glu Ser Ser Gln Ile Pro Glu
            500                 505                 510

Asn Thr Pro Thr Ala Pro Gln Gln Met Arg Gly Gly Gly Arg Gly Phe
        515                 520                 525

Arg Gly Gly Gly Arg Arg Tyr Gly Arg Arg Gly Gly Arg Arg Gln Glu
    530                 535                 540

Asn Glu Glu Gly Glu Glu Glu Ser Gly Ser Glu Thr Pro Gly Thr Ser
545                 550                 555                 560

Glu Ser Ala Thr Pro Glu Ser Val Gly Gly Tyr Lys Val Ser Asn Leu
                565                 570                 575

Thr Val Glu Ala Phe Glu Gly Ile Gly Ser Val Asn Pro Met Leu Phe
            580                 585                 590

Tyr Gln Tyr Lys Val Thr Gly Lys Gly Lys Tyr Asp Asn Val Tyr Lys
        595                 600                 605

Ile Ile Lys Ser Ala Arg Tyr Lys Met His Ser Lys Asn Arg Phe Lys
    610                 615                 620

Pro Val Phe Ile Lys Asp Asp Lys Leu Tyr Thr Leu Glu Lys Leu Pro
625                 630                 635                 640

Asp Ile Glu Asp Leu Asp Phe Ala Asn Ile Asn Phe Val Lys Ser Glu
                645                 650                 655

Val Leu Ser Ile Glu Asp Asn Met Ser Ile Tyr Gly Glu Val Val Glu
            660                 665                 670

Tyr Tyr Ile Asn Leu Lys Leu Lys Lys Val Lys Val Leu Gly Lys Tyr
        675                 680                 685

Pro Lys Tyr Arg Ile Asn Tyr Ser Lys Glu Ile Leu Ser Asn Thr Leu
    690                 695                 700

Leu Thr Arg Glu Leu Lys Asp Glu Phe Lys Lys Ser Asn Lys Gly Phe
705                 710                 715                 720

Asn Leu Lys Arg Lys Phe Arg Ile Ser Pro Val Val Asn Lys Met Gly
                725                 730                 735

Lys Val Ile Leu Tyr Leu Ser Cys Ser Ala Asp Phe Ser Thr Asn Lys
            740                 745                 750

Asn Ile Tyr Glu Met Leu Lys Glu Gly Leu Glu Val Glu Gly Leu Ala
        755                 760                 765

Val Lys Ser Glu Trp Ser Asn Ile Ser Gly Asn Leu Val Ile Glu Ser
```

```
    770                 775                 780

Val Leu Glu Thr Lys Ile Ser Glu Pro Thr Ser Leu Gly Gln Ser Leu
785                 790                 795                 800

Ile Asp Tyr Tyr Lys Asn Asn Asn Gln Gly Tyr Arg Val Lys Asp Phe
                805                 810                 815

Thr Asp Glu Asp Leu Asn Ala Asn Ile Val Asn Val Arg Gly Asn Lys
            820                 825                 830

Lys Ile Tyr Met Tyr Ile Pro His Ala Leu Lys Pro Ile Ile Thr Arg
        835                 840                 845

Glu Tyr Leu Ala Lys Asn Asp Pro Glu Phe Ser Lys Glu Ile Glu Gln
    850                 855                 860

Leu Ile Lys Met Asn Met Asn Tyr Arg Tyr Glu Thr Leu Lys Ser Phe
865                 870                 875                 880

Val Asn Asp Ile Gly Val Ile Glu Glu Leu Asn Asn Leu Ser Phe Lys
                885                 890                 895

Asn Lys Tyr Tyr Glu Asp Val Lys Leu Leu Gly Tyr Ser Ser Gly Lys
            900                 905                 910

Ile Asp Glu Pro Val Leu Met Gly Ala Lys Gly Ile Ile Lys Asn Lys
        915                 920                 925

Met Gln Ile Phe Ser Asn Gly Phe Tyr Lys Leu Pro Glu Gly Lys Val
    930                 935                 940

Arg Phe Gly Val Leu Tyr Pro Lys Glu Phe Asp Gly Val Ser Arg Lys
945                 950                 955                 960

Ala Ile Arg Ala Ile Tyr Asp Phe Ser Lys Glu Gly Lys Tyr His Gly
                965                 970                 975

Glu Ser Asn Lys Tyr Ile Ala Glu His Leu Ile Asn Val Glu Phe Asn
            980                 985                 990

Pro Lys Glu Cys Ile Phe Glu Gly  Tyr Glu Leu Gly Asp  Ile Thr Glu
        995                 1000                1005

Tyr Lys  Lys Ala Ala Leu Lys  Leu Asn Asn Tyr Asn  Asn Val Asp
    1010                 1015                1020

Phe Val  Ile Ala Ile Val Pro  Asn Met Ser Asp Glu  Glu Ile Glu
    1025                 1030                1035

Asn Ser  Tyr Asn Pro Phe Lys  Lys Ile Trp Ala Glu  Leu Asn Leu
    1040                 1045                1050

Pro Ser  Gln Met Ile Ser Val  Lys Thr Ala Glu Ile  Phe Ala Asn
    1055                 1060                1065

Ser Arg  Asp Asn Thr Ala Leu  Tyr Tyr Leu His Asn  Ile Val Leu
    1070                 1075                1080

Gly Ile  Leu Gly Lys Ile Gly  Gly Ile Pro Trp Val  Val Lys Asp
    1085                 1090                1095

Met Lys  Gly Asp Val Asp Cys  Phe Val Gly Leu Asp  Val Gly Thr
    1100                 1105                1110

Arg Glu  Lys Gly Ile His Tyr  Pro Ala Cys Ser Val  Val Phe Asp
    1115                 1120                1125

Lys Tyr  Gly Lys Leu Ile Asn  Tyr Tyr Lys Pro Asn  Ile Pro Gln
    1130                 1135                1140

Asn Gly  Glu Lys Ile Asn Thr  Glu Ile Leu Gln Glu  Ile Phe Asp
    1145                 1150                1155

Lys Val  Leu Ile Ser Tyr Glu  Glu Glu Asn Gly Ala  Tyr Pro Lys
    1160                 1165                1170

Asn Ile  Val Ile His Arg Asp  Gly Phe Ser Arg Glu  Asp Leu Asp
    1175                 1180                1185
```

Trp Tyr Glu Asn Tyr Phe Gly Lys Lys Asn Ile Lys Phe Asn Ile
1190 1195 1200

Ile Glu Val Lys Lys Ser Thr Pro Leu Lys Ile Ala Ser Ile Asn
1205 1210 1215

Glu Gly Asn Ile Thr Asn Pro Glu Lys Gly Ser Tyr Ile Leu Arg
1220 1225 1230

Gly Asn Lys Ala Tyr Met Val Thr Thr Asp Ile Lys Glu Asn Leu
1235 1240 1245

Gly Ser Pro Lys Pro Leu Lys Ile Glu Lys Ser Tyr Gly Asp Ile
1250 1255 1260

Asp Met Leu Thr Ala Leu Ser Gln Ile Tyr Ala Leu Thr Gln Ile
1265 1270 1275

His Val Gly Ala Thr Lys Ser Leu Arg Leu Pro Ile Thr Thr Gly
1280 1285 1290

Tyr Ala Asp Lys Ile Cys Lys Ala Ile Glu Phe Ile Pro Gln Gly
1295 1300 1305

Arg Val Asp Asn Arg Leu Phe Phe Leu
1310 1315

<210> SEQ ID NO 86
<211> LENGTH: 1320
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 86

Met Lys His His His His His His Asn Thr Ser Ser Asn Ser Met Ser
1 5 10 15

Pro Ile Leu Gly Tyr Trp Lys Ile Lys Gly Leu Val Gln Pro Thr Arg
20 25 30

Leu Leu Leu Glu Tyr Leu Glu Glu Lys Tyr Glu Glu His Leu Tyr Glu
35 40 45

Arg Asp Glu Gly Asp Lys Trp Arg Asn Lys Lys Phe Glu Leu Gly Leu
50 55 60

Glu Phe Pro Asn Leu Pro Tyr Tyr Ile Asp Gly Asp Val Lys Leu Thr
65 70 75 80

Gln Ser Met Ala Ile Ile Arg Tyr Ile Ala Asp Lys His Asn Met Leu
85 90 95

Gly Gly Cys Pro Lys Glu Arg Ala Glu Ile Ser Met Leu Glu Gly Ala
100 105 110

Val Leu Asp Ile Arg Tyr Gly Val Ser Arg Ile Ala Tyr Ser Lys Asp
115 120 125

Phe Glu Thr Leu Lys Val Asp Phe Leu Ser Lys Leu Pro Glu Met Leu
130 135 140

Lys Met Phe Glu Asp Arg Leu Cys His Lys Thr Tyr Leu Asn Gly Asp
145 150 155 160

His Val Thr His Pro Asp Phe Met Leu Tyr Asp Ala Leu Asp Val Val
165 170 175

Leu Tyr Met Asp Pro Met Cys Leu Asp Ala Phe Pro Lys Leu Val Cys
180 185 190

Phe Lys Lys Arg Ile Glu Ala Ile Pro Gln Ile Asp Lys Tyr Leu Lys
195 200 205

Ser Ser Lys Tyr Ile Ala Trp Pro Leu Gln Gly Trp Gln Ala Thr Phe

```
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Glu Glu Lys Val
                245                 250                 255

Gly Asn Leu Lys Pro Asn Met Glu Ser Val Asn Val Thr Val Arg Val
            260                 265                 270

Leu Glu Ala Ser Glu Ala Arg Gln Ile Gln Thr Lys Asn Gly Val Arg
        275                 280                 285

Thr Ile Ser Glu Ala Ile Val Gly Asp Glu Thr Gly Arg Val Lys Leu
    290                 295                 300

Thr Leu Trp Gly Lys His Ala Gly Ser Ile Lys Glu Gly Gln Val Val
305                 310                 315                 320

Lys Ile Glu Asn Ala Trp Thr Thr Ala Phe Lys Gly Gln Val Gln Leu
                325                 330                 335

Asn Ala Gly Ser Lys Thr Lys Ile Ala Glu Ala Ser Glu Asp Gly Phe
            340                 345                 350

Pro Glu Ser Ser Gln Ile Pro Glu Asn Thr Pro Thr Ala Pro Gln Gln
        355                 360                 365

Met Arg Gly Gly Gly Arg Gly Phe Arg Gly Gly Gly Arg Arg Tyr Gly
    370                 375                 380

Arg Arg Gly Gly Arg Arg Gln Glu Asn Glu Glu Gly Glu Glu Glu Ser
385                 390                 395                 400

Gly Ser Gly Gly Gly Gly Ser Glu Glu Lys Val Gly Asn Leu Lys Pro
                405                 410                 415

Asn Met Glu Ser Val Asn Val Thr Val Arg Val Leu Glu Ala Ser Glu
            420                 425                 430

Ala Arg Gln Ile Gln Thr Lys Asn Gly Val Arg Thr Ile Ser Glu Ala
        435                 440                 445

Ile Val Gly Asp Glu Thr Gly Arg Val Lys Leu Thr Leu Trp Gly Lys
    450                 455                 460

His Ala Gly Ser Ile Lys Glu Gly Gln Val Val Lys Ile Glu Asn Ala
465                 470                 475                 480

Trp Thr Thr Ala Phe Lys Gly Gln Val Gln Leu Asn Ala Gly Ser Lys
                485                 490                 495

Thr Lys Ile Ala Glu Ala Ser Glu Asp Gly Phe Pro Glu Ser Ser Gln
            500                 505                 510

Ile Pro Glu Asn Thr Pro Thr Ala Pro Gln Gln Met Arg Gly Gly Gly
        515                 520                 525

Arg Gly Phe Arg Gly Gly Gly Arg Arg Tyr Gly Arg Arg Gly Gly Arg
    530                 535                 540

Arg Gln Glu Asn Glu Glu Gly Glu Glu Glu Ser Gly Ser Glu Thr Pro
545                 550                 555                 560

Gly Thr Ser Glu Ser Ala Thr Pro Glu Ser Val Gly Gly Tyr Lys Val
                565                 570                 575

Ser Asn Leu Thr Val Glu Ala Phe Glu Gly Ile Gly Ser Val Asn Pro
            580                 585                 590

Met Leu Phe Tyr Gln Tyr Lys Val Thr Gly Lys Gly Lys Tyr Asp Asn
        595                 600                 605

Val Tyr Lys Ile Ile Lys Ser Ala Arg Tyr Lys Met His Ser Lys Asn
    610                 615                 620

Arg Phe Lys Pro Val Phe Ile Lys Asp Asp Lys Leu Tyr Thr Leu Glu
625                 630                 635                 640
```

```
Lys Leu Pro Asp Ile Glu Asp Leu Asp Phe Ala Asn Ile Asn Phe Val
                645                 650                 655

Lys Ser Glu Val Leu Ser Ile Glu Asp Asn Met Ser Ile Tyr Gly Glu
            660                 665                 670

Val Val Glu Tyr Tyr Ile Asn Leu Lys Leu Lys Lys Val Lys Val Leu
        675                 680                 685

Gly Lys Tyr Pro Lys Tyr Arg Ile Asn Tyr Ser Lys Glu Ile Leu Ser
    690                 695                 700

Asn Thr Leu Leu Thr Arg Glu Leu Lys Asp Glu Phe Lys Lys Ser Asn
705                 710                 715                 720

Lys Gly Phe Asn Leu Lys Arg Lys Phe Arg Ile Ser Pro Val Val Asn
                725                 730                 735

Lys Met Gly Lys Val Ile Leu Tyr Leu Ser Cys Ser Ala Asp Phe Ser
            740                 745                 750

Thr Asn Lys Asn Ile Tyr Glu Met Leu Lys Glu Gly Leu Glu Val Glu
        755                 760                 765

Gly Leu Ala Val Lys Ser Glu Trp Ser Asn Ile Ser Gly Asn Leu Val
    770                 775                 780

Ile Glu Ser Val Leu Glu Thr Lys Ile Ser Glu Pro Thr Ser Leu Gly
785                 790                 795                 800

Gln Ser Leu Ile Asp Tyr Tyr Lys Asn Asn Asn Gln Gly Tyr Arg Val
                805                 810                 815

Lys Asp Phe Thr Asp Glu Asp Leu Asn Ala Asn Ile Val Asn Val Arg
            820                 825                 830

Gly Asn Lys Lys Ile Tyr Met Tyr Ile Pro His Ala Leu Lys Pro Ile
        835                 840                 845

Ile Thr Arg Glu Tyr Leu Ala Lys Asn Asp Pro Glu Phe Ser Lys Glu
    850                 855                 860

Ile Glu Gln Leu Ile Lys Met Asn Met Asn Tyr Arg Tyr Glu Thr Leu
865                 870                 875                 880

Lys Ser Phe Val Asn Asp Ile Gly Val Ile Glu Glu Leu Asn Asn Leu
                885                 890                 895

Ser Phe Lys Asn Lys Tyr Tyr Glu Asp Val Lys Leu Leu Gly Tyr Ser
            900                 905                 910

Ser Gly Lys Ile Asp Glu Pro Val Leu Met Gly Ala Lys Gly Ile Ile
        915                 920                 925

Lys Asn Lys Met Gln Ile Phe Ser Asn Gly Phe Tyr Lys Leu Pro Glu
    930                 935                 940

Gly Lys Val Arg Phe Gly Val Leu Tyr Pro Lys Glu Phe Asp Gly Val
945                 950                 955                 960

Ser Arg Lys Ala Ile Arg Ala Ile Tyr Asp Phe Ser Lys Glu Gly Lys
                965                 970                 975

Tyr His Gly Glu Ser Asn Lys Tyr Ile Ala Glu His Leu Ile Asn Val
            980                 985                 990

Glu Phe Asn Pro Lys Glu Cys Ile  Phe Glu Gly Tyr Glu  Leu Gly Asp
        995                 1000                1005

Ile Thr  Glu Tyr Lys Lys Ala  Ala Leu Lys Leu Asn  Asn Tyr Asn
    1010                1015                1020

Asn Val  Asp Phe Val Ile Ala  Ile Val Pro Asn Met  Ser Asp Glu
    1025                1030                1035

Glu Ile  Glu Asn Ser Tyr Asn  Pro Phe Lys Lys Ile  Trp Ala Glu
    1040                1045                1050
```

```
Leu Asn  Leu Pro Ser Gln Met  Ile Ser Val Lys Thr  Ala Glu Ile
    1055                 1060                 1065

Phe Ala  Asn Ser Arg Asp Asn  Thr Ala Leu Tyr Tyr  Leu His Asn
    1070                 1075                 1080

Ile Val  Leu Gly Ile Leu Gly  Lys Ile Gly Gly Ile  Pro Trp Val
    1085                 1090                 1095

Val Lys  Asp Met Lys Gly Asp  Val Asp Cys Phe Val  Gly Leu Asp
    1100                 1105                 1110

Val Gly  Thr Arg Glu Lys Gly  Ile His Tyr Pro Ala  Cys Ser Val
    1115                 1120                 1125

Val Phe  Asp Lys Tyr Gly Lys  Leu Ile Asn Tyr Tyr  Lys Pro Asn
    1130                 1135                 1140

Ile Pro  Gln Asn Gly Glu Lys  Ile Asn Thr Glu Ile  Leu Gln Glu
    1145                 1150                 1155

Ile Phe  Asp Lys Val Leu Ile  Ser Tyr Glu Glu Glu  Asn Gly Ala
    1160                 1165                 1170

Tyr Pro  Lys Asn Ile Val Ile  His Arg Asp Gly Phe  Ser Arg Glu
    1175                 1180                 1185

Asp Leu  Asp Trp Tyr Glu Asn  Tyr Phe Gly Lys Lys  Asn Ile Lys
    1190                 1195                 1200

Phe Asn  Ile Ile Glu Val Lys  Lys Ser Thr Pro Leu  Lys Ile Ala
    1205                 1210                 1215

Ser Ile  Asn Glu Gly Asn Ile  Thr Asn Pro Glu Lys  Gly Ser Tyr
    1220                 1225                 1230

Ile Leu  Arg Gly Asn Lys Ala  Tyr Met Val Thr Thr  Asp Ile Lys
    1235                 1240                 1245

Glu Asn  Leu Gly Ser Pro Lys  Pro Leu Lys Ile Glu  Lys Ser Tyr
    1250                 1255                 1260

Gly Asp  Ile Asp Met Leu Thr  Ala Leu Ser Gln Ile  Tyr Ala Leu
    1265                 1270                 1275

Thr Gln  Ile His Val Gly Ala  Thr Lys Ser Leu Arg  Leu Pro Ile
    1280                 1285                 1290

Thr Thr  Gly Tyr Ala Asp Lys  Ile Cys Lys Ala Ile  Glu Phe Ile
    1295                 1300                 1305

Pro Gln  Gly Arg Val Asp Asn  Arg Leu Phe Phe Leu
    1310                 1315                 1320


<210> SEQ ID NO 87
<211> LENGTH: 1329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Met Lys His His His His His His Asn Thr Ser Ser Asn Ser Met Ser
1               5                   10                  15

Pro Ile Leu Gly Tyr Trp Lys Ile Lys Gly Leu Val Gln Pro Thr Arg
            20                  25                  30

Leu Leu Leu Glu Tyr Leu Glu Glu Lys Tyr Glu Glu His Leu Tyr Glu
        35                  40                  45

Arg Asp Glu Gly Asp Lys Trp Arg Asn Lys Lys Phe Glu Leu Gly Leu
    50                  55                  60

Glu Phe Pro Asn Leu Pro Tyr Tyr Ile Asp Gly Asp Val Lys Leu Thr
65                  70                  75                  80
```

```
Gln Ser Met Ala Ile Ile Arg Tyr Ile Ala Asp Lys His Asn Met Leu
                85                  90                  95

Gly Gly Cys Pro Lys Glu Arg Ala Glu Ile Ser Met Leu Glu Gly Ala
            100                 105                 110

Val Leu Asp Ile Arg Tyr Gly Val Ser Arg Ile Ala Tyr Ser Lys Asp
        115                 120                 125

Phe Glu Thr Leu Lys Val Asp Phe Leu Ser Lys Leu Pro Glu Met Leu
    130                 135                 140

Lys Met Phe Glu Asp Arg Leu Cys His Lys Thr Tyr Leu Asn Gly Asp
145                 150                 155                 160

His Val Thr His Pro Asp Phe Met Leu Tyr Asp Ala Leu Asp Val Val
                165                 170                 175

Leu Tyr Met Asp Pro Met Cys Leu Asp Ala Phe Pro Lys Leu Val Cys
            180                 185                 190

Phe Lys Lys Arg Ile Glu Ala Ile Pro Gln Ile Asp Lys Tyr Leu Lys
        195                 200                 205

Ser Ser Lys Tyr Ile Ala Trp Pro Leu Gln Gly Trp Gln Ala Thr Phe
    210                 215                 220

Gly Gly Gly Asp His Pro Pro Thr Ser Gly Ser Gly Gly Gly Gly Gly
225                 230                 235                 240

Trp Met Ser Glu Asn Leu Tyr Phe Gln Gly Ala Met Glu Glu Lys Val
                245                 250                 255

Gly Asn Leu Lys Pro Asn Met Glu Ser Val Asn Val Thr Val Arg Val
            260                 265                 270

Leu Glu Ala Ser Glu Ala Arg Gln Ile Gln Thr Lys Asn Gly Val Arg
        275                 280                 285

Thr Ile Ser Glu Ala Ile Val Gly Asp Glu Thr Gly Arg Val Lys Leu
    290                 295                 300

Thr Leu Trp Gly Lys His Ala Gly Ser Ile Lys Glu Gly Gln Val Val
305                 310                 315                 320

Lys Ile Glu Asn Ala Trp Thr Thr Ala Phe Lys Gly Gln Val Gln Leu
                325                 330                 335

Asn Ala Gly Ser Lys Thr Lys Ile Ala Glu Ala Ser Glu Asp Gly Phe
            340                 345                 350

Pro Glu Ser Ser Gln Ile Pro Glu Asn Thr Pro Thr Ala Pro Gln Gln
        355                 360                 365

Met Arg Gly Gly Gly Arg Gly Phe Arg Gly Gly Gly Arg Arg Tyr Gly
    370                 375                 380

Arg Arg Gly Gly Arg Arg Gln Glu Asn Glu Glu Gly Glu Glu Glu Ser
385                 390                 395                 400

Gly Ser Glu Thr Pro Gly Thr Ser Glu Ser Ala Thr Pro Glu Ser Met
                405                 410                 415

Glu Glu Lys Val Gly Asn Leu Lys Pro Asn Met Glu Ser Val Asn Val
            420                 425                 430

Thr Val Arg Val Leu Glu Ala Ser Glu Ala Arg Gln Ile Gln Thr Lys
        435                 440                 445

Asn Gly Val Arg Thr Ile Ser Glu Ala Ile Val Gly Asp Glu Thr Gly
    450                 455                 460

Arg Val Lys Leu Thr Leu Trp Gly Lys His Ala Gly Ser Ile Lys Glu
465                 470                 475                 480

Gly Gln Val Val Lys Ile Glu Asn Ala Trp Thr Thr Ala Phe Lys Gly
                485                 490                 495
```

```
Gln Val Gln Leu Asn Ala Gly Ser Lys Thr Lys Ile Ala Glu Ala Ser
            500                 505                 510

Glu Asp Gly Phe Pro Glu Ser Ser Gln Ile Pro Glu Asn Thr Pro Thr
        515                 520                 525

Ala Pro Gln Gln Met Arg Gly Gly Gly Arg Gly Phe Arg Gly Gly Gly
    530                 535                 540

Arg Arg Tyr Gly Arg Arg Gly Gly Arg Arg Gln Glu Asn Glu Glu Gly
545                 550                 555                 560

Glu Glu Glu Ser Gly Ser Glu Thr Pro Gly Thr Ser Glu Ser Ala Thr
                565                 570                 575

Pro Glu Ser Val Gly Gly Tyr Lys Val Ser Asn Leu Thr Val Glu Ala
            580                 585                 590

Phe Glu Gly Ile Gly Ser Val Asn Pro Met Leu Phe Tyr Gln Tyr Lys
        595                 600                 605

Val Thr Gly Lys Gly Lys Tyr Asp Asn Val Tyr Lys Ile Ile Lys Ser
    610                 615                 620

Ala Arg Tyr Lys Met His Ser Lys Asn Arg Phe Lys Pro Val Phe Ile
625                 630                 635                 640

Lys Asp Asp Lys Leu Tyr Thr Leu Glu Lys Leu Pro Asp Ile Glu Asp
                645                 650                 655

Leu Asp Phe Ala Asn Ile Asn Phe Val Lys Ser Glu Val Leu Ser Ile
            660                 665                 670

Glu Asp Asn Met Ser Ile Tyr Gly Glu Val Val Glu Tyr Tyr Ile Asn
        675                 680                 685

Leu Lys Leu Lys Lys Val Lys Val Leu Gly Lys Tyr Pro Lys Tyr Arg
    690                 695                 700

Ile Asn Tyr Ser Lys Glu Ile Leu Ser Asn Thr Leu Leu Thr Arg Glu
705                 710                 715                 720

Leu Lys Asp Glu Phe Lys Lys Ser Asn Lys Gly Phe Asn Leu Lys Arg
                725                 730                 735

Lys Phe Arg Ile Ser Pro Val Val Asn Lys Met Gly Lys Val Ile Leu
            740                 745                 750

Tyr Leu Ser Cys Ser Ala Asp Phe Ser Thr Asn Lys Asn Ile Tyr Glu
        755                 760                 765

Met Leu Lys Glu Gly Leu Glu Val Glu Gly Leu Ala Val Lys Ser Glu
    770                 775                 780

Trp Ser Asn Ile Ser Gly Asn Leu Val Ile Glu Ser Val Leu Glu Thr
785                 790                 795                 800

Lys Ile Ser Glu Pro Thr Ser Leu Gly Gln Ser Leu Ile Asp Tyr Tyr
                805                 810                 815

Lys Asn Asn Asn Gln Gly Tyr Arg Val Lys Asp Phe Thr Asp Glu Asp
            820                 825                 830

Leu Asn Ala Asn Ile Val Asn Val Arg Gly Asn Lys Lys Ile Tyr Met
        835                 840                 845

Tyr Ile Pro His Ala Leu Lys Pro Ile Ile Thr Arg Glu Tyr Leu Ala
    850                 855                 860

Lys Asn Asp Pro Glu Phe Ser Lys Glu Ile Glu Gln Leu Ile Lys Met
865                 870                 875                 880

Asn Met Asn Tyr Arg Tyr Glu Thr Leu Lys Ser Phe Val Asn Asp Ile
                885                 890                 895

Gly Val Ile Glu Glu Leu Asn Asn Leu Ser Phe Lys Asn Lys Tyr Tyr
            900                 905                 910

Glu Asp Val Lys Leu Leu Gly Tyr Ser Ser Gly Lys Ile Asp Glu Pro
```

```
        915                 920                 925

Val Leu Met Gly Ala Lys Gly Ile Ile Lys Asn Lys Met Gln Ile Phe
    930                 935                 940

Ser Asn Gly Phe Tyr Lys Leu Pro Glu Gly Lys Val Arg Phe Gly Val
945                 950                 955                 960

Leu Tyr Pro Lys Glu Phe Asp Gly Val Ser Arg Lys Ala Ile Arg Ala
                965                 970                 975

Ile Tyr Asp Phe Ser Lys Glu Gly Lys Tyr His Gly Glu Ser Asn Lys
            980                 985                 990

Tyr Ile Ala Glu His Leu Ile Asn  Val Glu Phe Asn Pro  Lys Glu Cys
        995                 1000                1005

Ile Phe  Glu Gly Tyr Glu Leu  Gly Asp Ile Thr Glu  Tyr Lys Lys
    1010                1015                1020

Ala Ala  Leu Lys Leu Asn Asn  Tyr Asn Asn Val Asp  Phe Val Ile
    1025                1030                1035

Ala Ile  Val Pro Asn Met Ser  Asp Glu Glu Ile Glu  Asn Ser Tyr
    1040                1045                1050

Asn Pro  Phe Lys Lys Ile Trp  Ala Glu Leu Asn Leu  Pro Ser Gln
    1055                1060                1065

Met Ile  Ser Val Lys Thr Ala  Glu Ile Phe Ala Asn  Ser Arg Asp
    1070                1075                1080

Asn Thr  Ala Leu Tyr Tyr Leu  His Asn Ile Val Leu  Gly Ile Leu
    1085                1090                1095

Gly Lys  Ile Gly Gly Ile Pro  Trp Val Val Lys Asp  Met Lys Gly
    1100                1105                1110

Asp Val  Asp Cys Phe Val Gly  Leu Asp Val Gly Thr  Arg Glu Lys
    1115                1120                1125

Gly Ile  His Tyr Pro Ala Cys  Ser Val Val Phe Asp  Lys Tyr Gly
    1130                1135                1140

Lys Leu  Ile Asn Tyr Tyr Lys  Pro Asn Ile Pro Gln  Asn Gly Glu
    1145                1150                1155

Lys Ile  Asn Thr Glu Ile Leu  Gln Glu Ile Phe Asp  Lys Val Leu
    1160                1165                1170

Ile Ser  Tyr Glu Glu Glu Asn  Gly Ala Tyr Pro Lys  Asn Ile Val
    1175                1180                1185

Ile His  Arg Asp Gly Phe Ser  Arg Glu Asp Leu Asp  Trp Tyr Glu
    1190                1195                1200

Asn Tyr  Phe Gly Lys Lys Asn  Ile Lys Phe Asn Ile  Ile Glu Val
    1205                1210                1215

Lys Lys  Ser Thr Pro Leu Lys  Ile Ala Ser Ile Asn  Glu Gly Asn
    1220                1225                1230

Ile Thr  Asn Pro Glu Lys Gly  Ser Tyr Ile Leu Arg  Gly Asn Lys
    1235                1240                1245

Ala Tyr  Met Val Thr Thr Asp  Ile Lys Glu Asn Leu  Gly Ser Pro
    1250                1255                1260

Lys Pro  Leu Lys Ile Glu Lys  Ser Tyr Gly Asp Ile  Asp Met Leu
    1265                1270                1275

Thr Ala  Leu Ser Gln Ile Tyr  Ala Leu Thr Gln Ile  His Val Gly
    1280                1285                1290

Ala Thr  Lys Ser Leu Arg Leu  Pro Ile Thr Thr Gly  Tyr Ala Asp
    1295                1300                1305

Lys Ile  Cys Lys Ala Ile Glu  Phe Ile Pro Gln Gly  Arg Val Asp
    1310                1315                1320
```

Asn Arg Leu Phe Phe Leu
1325

<210> SEQ ID NO 88
<211> LENGTH: 3537
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360
tcgagaattg catatagtaa agactttgaa actctcaaag ttgattttct tagcaagcta 420
cctgaaatgc tgaaaatgtt cgaagatcgt ttatgtcata aaacatattt aaatggtgat 480
catgtaaccc atcctgactt catgttgtat gacgctcttg atgttgtttt atacatggac 540
ccaatgtgcc tggatgcgtt cccaaaatta gtttgtttta aaaaacgtat tgaagctatc 600
ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gcaatgccca agaaaaagcg aaaggtagag 780
gaccccaaaa agaaacgcaa agtgggctcc ggaagccgtc tcgaaatgga agaaaaagta 840
ggcaacctga agcctaatat ggaatccgta aatgtaaccg ttcgcgtttt agaagcctct 900
gaagcacggc agatccagac caaaaatggt gttcgcacca tttcagaggc gattgtaggg 960
gatgaaaccg ggcgcgtgaa actgactctg tggggcaaac atgcgggcag catcaaagaa 1020
ggccaggtcg ttaaaattga gaacgcctgg acaaccgcgt tcaaaggcca ggtacagctg 1080
aatgccggta gcaagaccaa aattgccgag gcatctgaag acggtttccc tgaaagcagc 1140
cagatcccag aaaatactcc tacggcaccg cagcagatgc gtggcggtgg gcggggcttt 1200
cgtggcggag gccgccgtta tggccgtcgc ggtgggcgcc ggcaagaaaa cgaagaaggc 1260
gaagaagaag gcggtggtgg ctcaatggtc ggcggctata aagtcagcaa tttgacagtg 1320
gaagcgttcg aaggtatcgg gagtgtcaac ccgatgctgt tttaccaata caaagtcacc 1380
ggaaagggaa agtacgataa tgtgtataag attatcaaaa gcgcacggta caagatgcat 1440
tctaagaacc gattcaagcc cgtgttcatc aaggacgaca aactgtacac cctcgagaag 1500
ctcccggata tagaggacct ggatttcgca aacattaact tcgtgaaaag cgaggttctc 1560
agcatagagg ataatatgtc aatttatggc gaggtggtgg aatactatat caatctcaag 1620
ctgaaaaaag tgaaggtgtt gggaaaatac cccaagtaca ggatcaatta cagcaaagag 1680
attctcagta atacgctgct gacacgagag ctcaaagacg agtttaagaa atcaaataag 1740
ggttttaacc tgaaacggaa gtttagaatt tcccccgtgg tgaataagat gggcaaagtg 1800
atactctatt tgtcctgcag tgctgatttc agcaccaaca agaacattta cgaaatgttg 1860
aaagagggct tggaggttga ggggctggcc gttaagagcg agtggagcaa tatcagtggc 1920

```
aacctggtga tcgagagcgt actggaaacc aagatatccg agcccactag cctgggccaa   1980
tccctgatag actactataa gaataacaac cagggctata gggtgaagga tttcaccgat   2040
gaggatctga atgccaacat tgtcaacgtg agaggaaata agaagatcta tatgtatatt   2100
ccgcacgcgt tgaagccgat aatcacccgg gagtacctgg ccaagaacga tccagagttt   2160
tctaaggaga tcgagcagct tatcaagatg aatatgaact accgatatga aaccctcaag   2220
tcatttgtga atgacatcgg ggtcattgag gagctgaaca acctgagctt caaaaacaaa   2280
tactacgaag atgtgaaact gctgggttac tccagcggca aaatagacga acccgtcctg   2340
atgggggcaa aagggatcat aaagaacaaa atgcagattt tttccaatgg attctacaaa   2400
ctccccgaag gcaaggtacg atttggcgtt ctgtacccaa aagaatttga tggcgtgtca   2460
aggaaagcta tccgcgccat ttatgacttc agtaaggagg gcaaatacca cggcgaaagc   2520
aacaagtata tcgcggaaca cctgataaac gtggagttca atccaaagga gtgcatattt   2580
gagggatacg aactgggcga tatcaccgaa tacaagaagg cggctctgaa acttaataac   2640
tacaacaatg tcgacttcgt aatcgcaata gtcccgaaca tgtccgacga agagatagag   2700
aacagctaca atccgttcaa gaaaatatgg gccgaactga atctgcccag ccagatgatt   2760
agcgtcaaga cggccgaaat ctttgccaat agcagggata acacggcgct ttactatctg   2820
cataacatcg tcctcggtat cctgggtaag ataggaggga ttccctgggt ggttaaagac   2880
atgaagggcg acgtggattg cttcgttgga ctcgatgtcg gcaccaggga gaagggcata   2940
cattaccccg cctgcagcgt tgtgtttgac aagtacggca agcttattaa ctattacaag   3000
cctaacatcc cgcagaacgg agagaagatt aacacagaaa tacttcagga aattttcgac   3060
aaggtgctca taagctatga ggaggagaat ggagcctacc cgaagaatat cgtgatccac   3120
agggacggct ttagccgaga ggaccttgac tggtatgaga actacttcgg taagaaaaac   3180
ataaagttta acatcatcga agtcaaaaag tcaactccgt tgaaaatcgc cagtataaac   3240
gagggaaata tcacgaatcc tgaaaagggt tcctacatcc tgcgcggcaa caaagcctac   3300
atggtgacca cagatattaa ggaaaacctg ggaagcccaa agcccctgaa gatagaaaag   3360
agctacggcg acatagacat gctcacagct ctcagccaaa tatacgcact cacgcaaatc   3420
catgtggggg cgaccaaaag cctgcgcctc ccaatcacca ccggctacgc cgacaagatt   3480
tgcaaggcga tcgagttcat cccccaaggg cgcgtggaca accgcctttt ctttctg      3537
```

<210> SEQ ID NO 89
<211> LENGTH: 3246
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

```
atgaaacatc accatcacca tcacaacact agtagcaatt ccatgtcccc tatactaggt     60
tattggaaaa ttaagggcct tgtgcaaccc actcgacttc ttttggaata tcttgaagaa    120
aaatatgaag agcatttgta tgagcgcgat gaaggtgata aatggcgaaa caaaaagttt    180
gaattgggtt tggagtttcc caatcttcct tattatattg atggtgatgt taaattaaca    240
cagtctatgg ccatcatacg ttatatagct gacaagcaca acatgttggg tggttgtcca    300
aaagagcgtg cagagatttc aatgcttgaa ggagcggttt tggatattag atacggtgtt    360
tcgagaattg catatagtaa agactttgaa actctcaaag ttgattttct tagcaagcta    420
```

```
cctgaaatgc tgaaaatgtt cgaagatcgt ttatgtcata aaacatattt aaatggtgat    480
catgtaaccc atcctgactt catgttgtat gacgctcttg atgttgtttt atacatggac    540
ccaatgtgcc tggatgcgtt cccaaaatta gtttgtttta aaaaacgtat tgaagctatc    600
ccacaaattg ataagtactt gaaatccagc aagtatatag catggccttt gcagggctgg    660
caagccacgt ttggtggtgg cgaccatcct ccaactagtg gatctggtgg tggtggcgga    720
tggatgagcg agaatcttta ttttcagggc gcaatgccca agaaaaagcg aaaggtagag    780
gaccccaaaa agaaacgcaa agtgggctcc ggaagccgtc tcgaaatgga cgcattggac    840
gattttgatc tggatatgct gggaagtgac gccctcgatg attttgacct tgacatgctt    900
ggttcggatg cccttgatga ctttgacctc gacatgctcg gcagtgacgc ccttgatgat    960
ttcgacctgg acatgctggg cggtggtggc tcaatggtcg gcggctataa agtcagcaat   1020
ttgacagtgg aagcgttcga aggtatcggg agtgtcaacc cgatgctgtt ttaccaatac   1080
aaagtcaccg gaaagggaaa gtacgataat gtgtataaga ttatcaaaag cgcacggtac   1140
aagatgcatt ctaagaaccg attcaagccc gtgttcatca aggacgacaa actgtacacc   1200
ctcgagaagc tcccggatat agaggacctg gatttcgcaa acattaactt cgtgaaaagc   1260
gaggttctca gcatagagga taatatgtca atttatggcg aggtggtgga atactatatc   1320
aatctcaagc tgaaaaaagt gaaggtgttg ggaaaatacc ccaagtacag gatcaattac   1380
agcaaagaga ttctcagtaa tacgctgctg acacgagagc tcaaagacga gtttaagaaa   1440
tcaaataagg gttttaacct gaaacggaag tttagaattt cccccgtggt gaataagatg   1500
ggcaaagtga tactctattt gtcctgcagt gctgatttca gcaccaacaa gaacatttac   1560
gaaatgttga aagagggctt ggaggttgag ggctggccg ttaagagcga gtggagcaat   1620
atcagtggca acctggtgat cgagagcgta ctggaaacca agatatccga gcccactagc   1680
ctgggccaat ccctgataga ctactataag aataacaacc agggctatag ggtgaaggat   1740
ttcaccgatg aggatctgaa tgccaacatt gtcaacgtga gaggaaataa gaagatctat   1800
atgtatattc cgcacgcgtt gaagccgata atcacccggg agtacctggc caagaacgat   1860
ccagagtttt ctaaggagat cgagcagctt atcaagatga atatgaacta ccgatatgaa   1920
accctcaagt catttgtgaa tgacatcggg gtcattgagg agctgaacaa cctgagcttc   1980
aaaaacaaat actacgaaga tgtgaaactg ctgggttact ccagcggcaa aatagacgaa   2040
cccgtcctga tgggggcaaa agggatcata aagaacaaaa tgcagatttt ttccaatgga   2100
ttctacaaac tccccgaagg caaggtacga tttggcgttc tgtacccaaa agaatttgat   2160
ggcgtgtcaa ggaaagctat ccgcgccatt tatgacttca gtaaggaggg caaataccac   2220
ggcgaaagca acaagtatat cgcggaacac ctgataaacg tggagttcaa tccaaaggag   2280
tgcatatttg agggatacga actgggcgat atcaccgaat acaagaaggc ggctctgaaa   2340
cttaataact acaacaatgt cgacttcgta atcgcaatag tcccgaacat gtccgacgaa   2400
gagatagaga acagctacaa tccgttcaag aaaatatggg ccgaactgaa tctgcccagc   2460
cagatgatta gcgtcaagac ggccgaaatc tttgccaata gcagggataa cacggcgctt   2520
tactatctgc ataacatcgt cctcggtatc ctgggtaaga taggagggat tccctgggtg   2580
gttaaagaca tgaagggcga cgtggattgc ttcgttggac tcgatgtcgg caccagggag   2640
aagggcatac attaccccgc ctgcagcgtt gtgtttgaca agtacggcaa gcttattaac   2700
tattacaagc ctaacatccc gcagaacgga gagaagatta acacagaaat acttcaggaa   2760
attttcgaca aggtgctcat aagctatgag gaggagaatg gagcctaccc gaagaatatc   2820
```

```
gtgatccaca gggacggctt tagccgagag gaccttgact ggtatgagaa ctacttcggt   2880

aagaaaaaca taaagtttaa catcatcgaa gtcaaaaagt caactccgtt gaaaatcgcc   2940

agtataaacg agggaaatat cacgaatcct gaaaagggtt cctacatcct gcgcggcaac   3000

aaagcctaca tggtgaccac agatattaag gaaaacctgg gaagcccaaa gcccctgaag   3060

atagaaaaga gctacggcga catagacatg ctcacagctc tcagccaaat atacgcactc   3120

acgcaaatcc atgtgggggc gaccaaaagc ctgcgcctcc caatcaccac cggctacgcc   3180

gacaagattt gcaaggcgat cgagttcatc ccccaagggc gcgtggacaa ccgccttttc   3240

tttctg                                                               3246
```

<210> SEQ ID NO 90
<211> LENGTH: 3105
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 90

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gcggtctcat ctccacaggg gtacccgtct    780

ctaatgccca agaagaagag aaaggtcgag gacccgaaaa agaagcgaaa ggtaggtagt    840

ggttccatgg tcggcggcta taaagtcagc aatttgacag tggaagcgtt cgaaggtatc    900

gggagtgtca acccgatgct gttttaccaa tacaaagtca ccggaaaggg aaagtacgat    960

aatgtgtata agattatcaa aagcgcacgg tacaagatgc attctaagaa ccgattcaag   1020

cccgtgttca tcaaggacga caaactgtac accctcgaga agctcccgga tatagaggac   1080

ctggatttcg caaacattaa cttcgtgaaa agcgaggttc tcagcataga ggataatatg   1140

tcaatttatg gcgaggtggt ggaatactat atcaatctca agctgaaaaa agtgaaggtg   1200

ttgggaaaat accccaagta caggatcaat tacagcaaag agattctcag taatacgctg   1260

ctgacacgag agctcaaaga cgagtttaag aaatcaaata agggttttaa cctgaaacgg   1320

aagtttagaa tttcccccgt ggtgaataag atgggcaaag tgatactcta tttgtcctgc   1380

agtgctgatt tcagcaccaa caagaacatt tacgaaatgt tgaaagaggg cttggaggtt   1440

gaggggctgg ccgttaagag cgagtggagc aatatcagtg gcaacctggt gatcgagagc   1500

gtactggaaa ccaagatatc cgagcccact agcctgggcc aatccctgat agactactat   1560
```

```
aagaataaca accagggcta tagggtgaag gatttcaccg atgaggatct gaatgccaac   1620
attgtcaacg tgagaggaaa taagaagatc tatatgtata ttccgcacgc gttgaagccg   1680
ataatcaccc gggagtacct ggccaagaac gatccagagt tttctaagga gatcgagcag   1740
cttatcaaga tgaatatgaa ctaccgatat gaaaccctca agtcatttgt gaatgacatc   1800
ggggtcattg aggagctgaa caacctgagc ttcaaaaaca aatactacga agatgtgaaa   1860
ctgctgggtt actccagcgg caaaatagac gaacccgtcc tgatgggggc aaaagggatc   1920
ataaagaaca aaatgcagat tttttccaat ggattctaca aactccccga aggcaaggta   1980
cgatttggcg ttctgtaccc aaaagaattt gatggcgtgt caaggaaagc tatccgcgcc   2040
atttatgact tcagtaagga gggcaaatac cacggcgaaa gcaacaagta tatcgcggaa   2100
cacctgataa acgtggagtt caatccaaag gagtgcatat ttgagggata cgaactgggc   2160
gatatcaccg aatacaagaa ggcggctctg aaacttaata actacaacaa tgtcgacttc   2220
gtaatcgcaa tagtcccgaa catgtccgac gaagagatag agaacagcta caatccgttc   2280
aagaaaatat gggccgaact gaatctgccc agccagatga ttagcgtcaa gacggccgaa   2340
atctttgcca atagcaggga taacacggcg ctttactatc tgcataacat cgtcctcggt   2400
atcctgggta agataggagg gattccctgg gtggttaaag acatgaaggg cgacgtggat   2460
tgcttcgttg gactcgatgt cggcaccagg gagaagggca tacattaccc cgcctgcagc   2520
gttgtgtttg acaagtacgg caagcttatt aactattaca agcctaacat cccgcagaac   2580
ggagagaaga ttaacacaga aatacttcag gaaattttcg acaaggtgct cataagctat   2640
gaggaggaga atggagccta cccgaagaat atcgtgatcc acagggacgg ctttagccga   2700
gaggaccttg actggtatga gaactacttc ggtaagaaaa acataaagtt taacatcatc   2760
gaagtcaaaa agtcaactcc gttgaaaatc gccagtataa acgagggaaa tatcacgaat   2820
cctgaaaagg gttcctacat cctgcgcggc aacaaagcct acatggtgac cacagatatt   2880
aaggaaaacc tgggaagccc aaagcccctg aagatagaaa agagctacgg cgacatagac   2940
atgctcacag ctctcagcca aatatacgca ctcacgcaaa tccatgtggg ggcgaccaaa   3000
agcctgcgcc tcccaatcac caccggctac gccgacaaga tttgcaaggc gatcgagttc   3060
atcccccaag ggcgcgtgga caaccgcctt ttctttctgt agtga                   3105
```

<210> SEQ ID NO 91
<211> LENGTH: 3189
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

```
atgaaacatc accatcacca tcacaacact agtagcaatt ccatgtcccc tatactaggt     60
tattggaaaa ttaagggcct tgtgcaaccc actcgacttc ttttggaata tcttgaagaa    120
aaatatgaag agcatttgta tgagcgcgat gaaggtgata aatggcgaaa caaaaagttt    180
gaattgggtt tggagtttcc caatcttcct tattatattg atggtgatgt taaattaaca    240
cagtctatgg ccatcatacg ttatatagct gacaagcaca acatgttggg tggttgtcca    300
aaagagcgtg cagagatttc aatgcttgaa ggagcggttt tggatattag atacggtgtt    360
tcgagaattg catatagtaa agactttgaa actctcaaag ttgattttct tagcaagcta    420
cctgaaatgc tgaaaatgtt cgaagatcgt ttatgtcata aaacatattt aaatggtgat    480
```

```
catgtaaccc atcctgactt catgttgtat gacgctcttg atgttgtttt atacatggac    540
ccaatgtgcc tggatgcgtt cccaaaatta gtttgtttta aaaaacgtat tgaagctatc    600
ccacaaattg ataagtactt gaaatccagc aagtatatag catggccttt gcagggctgg    660
caagccacgt ttggtggtgg cgaccatcct ccaactagtg gatctggtgg tggtggcgga    720
tggatgagcg agaatcttta ttttcagggc gcaatgccca agaaaaagcg aaaggtagag    780
gaccccaaaa agaaacgcaa agtgggctcc ggaagccgtc tcgaaatggt cggcggctat    840
aaagtcagca atttgacagt ggaagcgttc gaaggtatcg ggagtgtcaa cccgatgctg    900
ttttaccaat acaaagtcac cggaaaggga aagtacgata atgtgtataa gattatcaaa    960
agcgcacggt acaagatgca ttctaagaac cgattcaagc ccgtgttcat caaggacgac   1020
aaactgtaca ccctcgagaa gctcccggat atagaggacc tggatttcgc aaacattaac   1080
ttcgtgaaaa gcgaggttct cagcatagag gataatatgt caatttatgg cgaggtggtg   1140
gaatactata tcaatctcaa gctgaaaaaa gtgaaggtgt tgggaaaata ccccaagtac   1200
aggatcaatt acagcaaaga gattctcagt aatacgctgc tgacacgaga gctcaaagac   1260
gagtttaaga aatcaaataa gggttttaac ctgaaacgga agtttagaat ttcccccgtg   1320
gtgaataaga tgggcaaagt gatactctat ttgtcctgca gtgctgattt cagcaccaac   1380
aagaacattt acgaaatgtt gaaagagggc ttggaggttg aggggctggc cgttaagagc   1440
gagtggagca atatcagtgg caacctggtg atcgagagcg tactggaaac caagatatcc   1500
gagcccacta gcctgggcca atccctgata gactactata agaataacaa ccagggctat   1560
agggtgaagg atttcaccga tgaggatctg aatgccaaca ttgtcaacgt gagaggaaat   1620
aagaagatct atatgtatat tccgcacgcg ttgaagccga taatcacccg ggagtacctg   1680
gccaagaacg atccagagtt ttctaaggag atcgagcagc ttatcaagat gaatatgaac   1740
taccgatatg aaaccctcaa gtcatttgtg aatgacatcg ggtcattgga ggagctgaac   1800
aacctgagct tcaaaaacaa atactacgaa gatgtgaaac tgctgggtta ctccagcggc   1860
aaaatagacg aacccgtcct gatgggggca aaagggatca taaagaacaa aatgcagatt   1920
ttttccaatg gattctacaa actccccgaa ggcaaggtac gatttggcgt tctgtaccca   1980
aaagaatttg atggcgtgtc aaggaaagct atccgcgcca tttatgactt cagtaaggag   2040
ggcaaatacc acggcgaaag caacaagtat atcgcggaac acctgataaa cgtggagttc   2100
aatccaaagg agtgcatatt tgagggatac gaactgggcg atatcaccga atacaagaag   2160
gcggctctga aacttaataa ctacaacaat gtcgacttcg taatcgcaat agtcccgaac   2220
atgtccgacg aagagataga gaacagctac aatccgttca agaaaatatg ggccgaactg   2280
aatctgccca gccagatgat tagcgtcaag acggccgaaa tctttgccaa tagcagggat   2340
aacacggcgc tttactatct gcataacatc gtcctcggta tcctgggtaa gataggaggg   2400
attccctggg tggttaaaga catgaagggc gacgtggatt gcttcgttgg actcgatgtc   2460
ggcaccaggg agaagggcat acattacccc gcctgcagcg ttgtgtttga caagtacggc   2520
aagcttatta actattacaa gcctaacatc ccgcagaacg gagagaagat taacacagaa   2580
atacttcagg aaattttcga caaggtgctc ataagctatg aggaggagaa tggagcctac   2640
ccgaagaata tcgtgatcca cagggacggc tttagccgag aggaccttga ctggtatgag   2700
aactacttcg gtaagaaaaa cataaagttt aacatcatcg aagtcaaaaa gtcaactccg   2760
ttgaaaatcg ccagtataaa cgagggaaat atcacgaatc ctgaaaaggg ttcctacatc   2820
```

```
ctgcgcggca acaaagccta catggtgacc acagatatta aggaaaacct gggaagccca   2880
aagcccctga agatagaaaa gagctacggc gacatagaca tgctcacagc tctcagccaa   2940
atatacgcac tcacgcaaat ccatgtgggg gcgaccaaaa gcctgcgcct cccaatcacc   3000
accggctacg ccgacaagat ttgcaaggcg atcgagttca tcccccaagg gcgcgtggac   3060
aaccgccttt tctttctgac tagtggggga ggtggatctg ggaagcccat cccaaacccg   3120
ctgttgggct tggattccac gaagcgaccc gcagcgacta agaaagccgg ccaggccaaa   3180
aagaagaaa                                                           3189
```

<210> SEQ ID NO 92
<211> LENGTH: 3081
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

```
atgaaacatc accatcacca tcacaacact agtagcaatt ccatgtcccc tatactaggt     60
tattggaaaa ttaagggcct tgtgcaaccc actcgacttc ttttggaata tcttgaagaa    120
aaatatgaag agcatttgta tgagcgcgat gaaggtgata aatggcgaaa caaaaagttt    180
gaattgggtt tggagtttcc caatcttcct tattatattg atggtgatgt taaattaaca    240
cagtctatgg ccatcatacg ttatatagct gacaagcaca acatgttggg tggttgtcca    300
aaagagcgtg cagagatttc aatgcttgaa ggagcggttt tggatattag atacggtgtt    360
tcgagaattg catatagtaa agactttgaa actctcaaag ttgattttct tagcaagcta    420
cctgaaatgc tgaaaatgtt cgaagatcgt ttatgtcata aaacatattt aaatggtgat    480
catgtaaccc atcctgactt catgttgtat gacgctcttg atgttgtttt atacatggac    540
ccaatgtgcc tggatgcgtt cccaaaatta gtttgtttta aaaaacgtat tgaagctatc    600
ccacaaattg ataagtactt gaaatccagc aagtatatag catggccttt gcagggctgg    660
caagccacgt ttggtggtgg cgaccatcct ccaactagtg gatctggtgg tggtggcgga    720
tggatgagcg agaatcttta ttttcagggc gcaatgccca agaaaaagcg aaaggtagag    780
gaccccaaaa agaaacgcaa agtgggctcc ggaagccgtc tcgaaatggt cggcggctat    840
aaagtcagca atttgacagt ggaagcgttc gaaggtatcg ggagtgtcaa cccgatgctg    900
ttttaccaat acaaagtcac cggaaaggga aagtacgata atgtgtataa gattatcaaa    960
agcgcacggt acaagatgca ttctaagaac cgattcaagc ccgtgttcat caaggacgac   1020
aaactgtaca ccctcgagaa gctcccggat atagaggacc tggatttcgc aaacattaac   1080
ttcgtgaaaa gcgaggttct cagcatagag gataatatgt caatttatgg cgaggtggtg   1140
gaatactata tcaatctcaa gctgaaaaaa gtgaaggtgt tgggaaaata ccccaagtac   1200
aggatcaatt acagcaaaga gattctcagt aatacgctgc tgacacgaga gctcaaagac   1260
gagtttaaga aatcaaataa gggttttaac ctgaaacgga agtttagaat ttcccccgtg   1320
gtgaataaga tgggcaaagt gatactctat ttgtcctgca gtgctgattt cagcaccaac   1380
aagaacattt acgaaatgtt gaaagagggc ttggaggttg aggggctggc cgttaagagc   1440
gagtggagca atatcagtgg caacctggtg atcgagagcg tactggaaac caagatatcc   1500
gagcccacta gcctgggcca atccctgata gactactata agaataacaa ccagggctat   1560
agggtgaagg atttcaccga tgaggatctg aatgccaaca ttgtcaacgt gagaggaaat   1620
```

```
aagaagatct atatgtatat tccgcacgcg ttgaagccga taatcacccg ggagtacctg   1680
gccaagaacg atccagagtt ttctaaggag atcgagcagc ttatcaagat gaatatgaac   1740
taccgatatg aaaccctcaa gtcatttgtg aatgacatcg ggtcattgga ggagctgaac   1800
aacctgagct tcaaaaacaa atactacgaa gatgtgaaac tgctgggtta ctccagcggc   1860
aaaatagacg aacccgtcct gatgggggca aaagggatca taaagaacaa aatgcagatt   1920
ttttccaatg gattctacaa actccccgaa ggcaaggtac gatttggcgt tctgtaccca   1980
aaagaatttg atggcgtgtc aaggaaagct atccgcgcca tttatgactt cagtaaggag   2040
ggcaaatacc acggcgaaag caacaagtat atcgcggaac acctgataaa cgtggagttc   2100
aatccaaagg agtgcatatt tgagggatac gaactgggcg atatcaccga atacaagaag   2160
gcggctctga aacttaataa ctacaacaat gtcgacttcg taatcgcaat agtcccgaac   2220
atgtccgacg aagagataga gaacagctac aatccgttca agaaaatatg ggccgaactg   2280
aatctgccca gccagatgat tagcgtcaag acggccgaaa tctttgccaa tagcagggat   2340
aacacggcgc tttactatct gcataacatc gtcctcggta tcctgggtaa gataggaggg   2400
attccctggg tggttaaaga catgaagggc gacgtggatt gcttcgttgg actcgatgtc   2460
ggcaccaggg agaagggcat acattacccc gcctgcagcg ttgtgtttga caagtacggc   2520
aagcttatta actattacaa gcctaacatc ccgcagaacg gagagaagat taacacagaa   2580
atacttcagg aaattttcga caaggtgctc ataagctatg aggaggagaa tggagcctac   2640
ccgaagaata tcgtgatcca cagggacggc tttagccgag aggaccttga ctggtatgag   2700
aactacttcg gtaagaaaaa cataaagttt aacatcatcg aagtcaaaaa gtcaactccg   2760
ttgaaaatcg ccagtataaa cgagggaaat atcacgaatc ctgaaaaggg ttcctacatc   2820
ctgcgcggca acaaagccta catggtgacc acagatatta aggaaaacct gggaagccca   2880
aagcccctga agatagaaaa gagctacggc gacatagaca tgctcacagc tctcagccaa   2940
atatacgcac tcacgcaaat ccatgtgggg gcgaccaaaa gcctgcgcct cccaatcacc   3000
accggctacg ccgacaagat ttgcaaggcg atcgagttca tcccccaagg gcgcgtggac   3060
aaccgccttt tctttctgta g                                              3081
```

<210> SEQ ID NO 93
<211> LENGTH: 3501
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 93

```
atgaaacatc accatcacca tcacaacact agtagcaatt ccatgtcccc tatactaggt     60
tattggaaaa ttaagggcct tgtgcaaccc actcgacttc ttttggaata tcttgaagaa    120
aaatatgaag agcatttgta tgagcgcgat gaaggtgata aatggcgaaa caaaaagttt    180
gaattgggtt tggagtttcc caatcttcct tattatattg atggtgatgt taaattaaca    240
cagtctatgg ccatcatacg ttatatagct gacaagcaca acatgttggg tggttgtcca    300
aaagagcgtg cagagatttc aatgcttgaa ggagcggttt tggatattag atacggtgtt    360
tcgagaattg catatagtaa agactttgaa actctcaaag ttgattttct tagcaagcta    420
cctgaaatgc tgaaaatgtt cgaagatcgt ttatgtcata aaacatattt aaatggtgat    480
catgtaaccc atcctgactt catgttgtat gacgctcttg atgttgtttt atacatggac    540
```

```
ccaatgtgcc tggatgcgtt cccaaaatta gtttgtttta aaaaacgtat tgaagctatc    600
ccacaaattg ataagtactt gaaatccagc aagtatatag catggccttt gcagggctgg    660
caagccacgt ttggtggtgg cgaccatcct ccaactagtg gatctggtgg tggtggcgga    720
tggatgagcg agaatcttta ttttcagggc gcaatggagg agaaggtcgg taaccttaag    780
cccaatatgg aatctgtcaa cgttactgtt agagtcctgg aagccagcga ggcgcgccaa    840
atacagacga agaacggggt aaggaccata agcgaggcaa tcgtcggcga cgagactggc    900
agagttaaat tgaccctttg ggaaaacac gctggttcta taaaggaagg tcaagtcgta    960
aagatcgaaa atgcttggac gaccgcattc aagggccagg ttcaactcaa cgccggatct   1020
aaaactaaga tagctgaggc gtcagaagac ggcttcccag aatcaagcca gatacctgag   1080
aacactccaa cggctcctca acaaatgaga ggaggtggac gaggatttcg cgggggggga   1140
cgaagatatg gccgacgcgg aggacgacgc caggaaaatg aagagggtga agaggaaagc   1200
ggctctgaga ctcccggcac atccgaaagc gcaacccctg agtctgtcgg cggctataaa   1260
gtcagcaatt tgacagtgga agcgttcgaa ggtatcggga gtgtcaaccc gatgctgttt   1320
taccaataca aagtcaccgg aaagggaaag tacgataatg tgtataagat tatcaaaagc   1380
gcacggtaca agatgcattc taagaaccga ttcaagcccg tgttcatcaa ggacgacaaa   1440
ctgtacaccc tcgagaagct cccggatata gaggacctgg atttcgcaaa cattaacttc   1500
gtgaaaagcg aggttctcag catagaggat aatatgtcaa tttatggcga ggtggtggaa   1560
tactatatca atctcaagct gaaaaaagtg aaggtgttgg gaaaataccc caagtacagg   1620
atcaattaca gcaaagagat tctcagtaat acgctgctga cacgagagct caaagacgag   1680
tttaagaaat caaataaggg ttttaacctg aaacggaagt ttagaatttc ccccgtggtg   1740
aataagatgg gcaaagtgat actctatttg tcctgcagtg ctgatttcag caccaacaag   1800
aacatttacg aaatgttgaa agagggcttg gaggttgagg ggctggccgt taagagcgag   1860
tggagcaata tcagtggcaa cctggtgatc gagagcgtac tggaaaccaa gatatccgag   1920
cccactagcc tgggccaatc cctgatagac tactataaga ataacaacca gggctatagg   1980
gtgaaggatt tcaccgatga ggatctgaat gccaacattg tcaacgtgag aggaaataag   2040
aagatctata tgtatattcc gcacgcgttg aagccgataa tcacccggga gtacctggcc   2100
aagaacgatc cagagttttc taaggagatc gagcagctta tcaagatgaa tatgaactac   2160
cgatatgaaa ccctcaagtc atttgtgaat gacatcgggg tcattgagga gctgaacaac   2220
ctgagcttca aaaacaaata ctacgaagat gtgaaactgc tgggttactc cagcggcaaa   2280
atagacgaac ccgtcctgat gggggcaaaa gggatcataa agaacaaaat gcagattttt   2340
tccaatggat tctacaaact ccccgaaggc aaggtacgat ttggcgttct gtacccaaaa   2400
gaatttgatg gcgtgtcaag gaaagctatc cgcgccattt atgacttcag taaggagggc   2460
aaataccacg gcgaaagcaa caagtatatc gcggaacacc tgataaacgt ggagttcaat   2520
ccaaaggagt gcatatttga gggatacgaa ctgggcgata tcaccgaata caagaaggcg   2580
gctctgaaac ttaataacta caacaatgtc gacttcgtaa tcgcaatagt cccgaacatg   2640
tccgacgaag agatagagaa cagctacaat ccgttcaaga aaatatgggc cgaactgaat   2700
ctgcccagcc agatgattag cgtcaagacg gccgaaatct ttgccaatag cagggataac   2760
acggcgcttt actatctgca taacatcgtc ctcggtatcc tgggtaagat aggagggatt   2820
ccctgggtgg ttaaagacat gaagggcgac gtggattgct tcgttggact cgatgtcggc   2880
accagggaga agggcataca ttaccccgcc tgcagcgttg tgtttgacaa gtacggcaag   2940
```

cttattaact attacaagcc taacatcccg cagaacggag agaagattaa cacagaaata 3000
cttcaggaaa ttttcgacaa ggtgctcata agctatgagg aggagaatgg agcctacccg 3060
aagaatatcg tgatccacag ggacggcttt agccgagagg accttgactg gtatgagaac 3120
tacttcggta agaaaaacat aaagtttaac atcatcgaag tcaaaaagtc aactccgttg 3180
aaaatcgcca gtataaacga gggaaatatc acgaatcctg aaaagggttc ctacatcctg 3240
cgcggcaaca aagcctacat ggtgaccaca gatattaagg aaaacctggg aagcccaaag 3300
cccctgaaga tagaaaagag ctacggcgac atagacatgc tcacagctct cagccaaata 3360
tacgcactca cgcaaatcca tgtgggggcg accaaaagcc tgcgcctccc aatcaccacc 3420
ggctacgccg acaagatttg caaggcgatc gagttcatcc cccaagggcg cgtggacaac 3480 cgcctttttct ttctgtagtg a 3501

<210> SEQ ID NO 94
<211> LENGTH: 3957
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 94
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360
tcgagaattg catatagtaa agactttgaa actctcaaag ttgattttct tagcaagcta 420
cctgaaatgc tgaaaatgtt cgaagatcgt ttatgtcata aaacatattt aaatggtgat 480
catgtaaccc atcctgactt catgttgtat gacgctcttg atgttgtttt atacatggac 540
ccaatgtgcc tggatgcgtt cccaaaatta gtttgtttta aaaaacgtat tgaagctatc 600
ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gcaatggagg agaaggtcgg taaccttaag 780
cccaatatgg aatctgtcaa cgttactgtt agagtcctgg aagccagcga ggcgcgccaa 840
atacagacga agaacggggt aaggaccata agcgaggcaa tcgtcggcga cgagactggc 900
agagttaaat tgaccctttg ggaaaaacac gctggttcta taaaggaagg tcaagtcgta 960
aagatcgaaa atgcttggac gaccgcattc aagggccagg ttcaactcaa cgccggatct 1020
aaaactaaga tagctgaggc gtcagaagac ggcttcccag aatcaagcca gatacctgag 1080
aacactccaa cggctcctca acaaatgaga ggaggtggac gaggatttcg cgggggggga 1140
cgaagatatg gccgacgcgg aggacgacgc caggaaaatg aagagggtga agaggaaggc 1200
ggtggtggct cagaagaaaa agtgggtaac cttaaaccca acatggagag cgttaacgtc 1260
acggtcagag tactcgaggc gagcgaggcg cggcagatac aaacaaaaaa tggtgtgcgc 1320
accatttccg aagctatagt cggtgacgaa acgggccgcg ttaaattgac gctctgggga 1380
aaacatgcag gttctattaa agagggtcag gtcgtgaaaa tagagaacgc ctggactacg 1440

```
gcgttcaagg gtcaggtcca actgaatgca gggtctaaaa ctaaaattgc ggaggctagt   1500
gaagatggtt ttcccgaatc aagccagatt ccagaaaata cacctacggc accgcaacag   1560
atgcgaggag gcgggcgagg atttcgaggt ggaggtcgac gctacggtag gaggggtggg   1620
cggcgccaag agaacgaaga aggagaggaa gaaagcggct ctgagactcc cggcacatcc   1680
gaaagcgcaa cccctgagtc tgtcggcggc tataaagtca gcaatttgac agtggaagcg   1740
ttcgaaggta tcgggagtgt caacccgatg ctgttttacc aatacaaagt caccggaaag   1800
ggaaagtacg ataatgtgta taagattatc aaaagcgcac ggtacaagat gcattctaag   1860
aaccgattca agcccgtgtt catcaaggac gacaaactgt acaccctcga gaagctcccg   1920
gatatagagg acctggattt cgcaaacatt aacttcgtga aaagcgaggt tctcagcata   1980
gaggataata tgtcaattta tggcgaggtg gtggaatact atatcaatct caagctgaaa   2040
aaagtgaagg tgttgggaaa ataccccaag tacaggatca attacagcaa agagattctc   2100
agtaatacgc tgctgacacg agagctcaaa gacgagttta agaaatcaaa taagggtttt   2160
aacctgaaac ggaagtttag aatttccccc gtggtgaata agatgggcaa agtgatactc   2220
tatttgtcct gcagtgctga tttcagcacc aacaagaaca tttacgaaat gttgaaagag   2280
ggcttggagg ttgaggggct ggccgttaag agcgagtgga gcaatatcag tggcaacctg   2340
gtgatcgaga gcgtactgga aaccaagata tccgagccca ctagcctggg ccaatccctg   2400
atagactact ataagaataa caaccagggc tatagggtga aggatttcac cgatgaggat   2460
ctgaatgcca acattgtcaa cgtgagagga aataagaaga tctatatgta tattccgcac   2520
gcgttgaagc cgataatcac ccgggagtac ctggccaaga acgatccaga gttttctaag   2580
gagatcgagc agcttatcaa gatgaatatg aactaccgat atgaaaccct caagtcattt   2640
gtgaatgaca tcggggtcat tgaggagctg aacaacctga gcttcaaaaa caaatactac   2700
gaagatgtga aactgctggg ttactccagc ggcaaaatag acgaacccgt cctgatgggg   2760
gcaaaaggga tcataaagaa caaaatgcag attttttcca atggattcta caaactcccc   2820
gaaggcaagg tacgatttgg cgttctgtac cccaaaagaat ttgatggcgt gtcaaggaaa   2880
gctatccgcg ccatttatga cttcagtaag gagggcaaat accacggcga aagcaacaag   2940
tatatcgcgg aacacctgat aaacgtggag ttcaatccaa aggagtgcat atttgaggga   3000
tacgaactgg gcgatatcac cgaatacaag aaggcggctc tgaaacttaa taactacaac   3060
aatgtcgact tcgtaatcgc aatagtcccg aacatgtccg acgaagagat agagaacagc   3120
tacaatccgt tcaagaaaat atgggccgaa ctgaatctgc ccagccagat gattagcgtc   3180
aagacggccg aaatctttgc caatagcagg gataacacgg cgctttacta tctgcataac   3240
atcgtcctcg gtatcctggg taagatagga gggattccct gggtggttaa agacatgaag   3300
ggcgacgtgg attgcttcgt tggactcgat gtcggcacca gggagaaggg catacattac   3360
cccgcctgca gcgttgtgtt tgacaagtac ggcaagctta ttaactatta caagcctaac   3420
atcccgcaga acggagagaa gattaacaca gaaatacttc aggaaatttt cgacaaggtg   3480
ctcataagct atgaggagga gaatggagcc tacccgaaga atatcgtgat ccacagggac   3540
ggctttagcc gagaggacct tgactggtat gagaactact tcggtaagaa aaacataaag   3600
tttaacatca tcgaagtcaa aaagtcaact ccgttgaaaa tcgccagtat aaacgaggga   3660
aatatcacga atcctgaaaa gggttcctac atcctgcgcg gcaacaaagc ctacatggtg   3720
accacagata ttaaggaaaa cctgggaagc ccaaagcccc tgaagataga aaagagctac   3780
```

```
ggcgacatag acatgctcac agctctcagc caaatatacg cactcacgca aatccatgtg   3840

ggggcgacca aaagcctgcg cctcccaatc accaccggct acgccgacaa gatttgcaag   3900

gcgatcgagt tcatccccca agggcgcgtg gacaaccgcc ttttctttct gtagtga      3957
```

<210> SEQ ID NO 95
<211> LENGTH: 3966
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 95

```
atgaaacatc accatcacca tcacaacact agtagcaatt ccatgtcccc tatactaggt     60

tattggaaaa ttaagggcct tgtgcaaccc actcgacttc ttttggaata tcttgaagaa    120

aaatatgaag agcatttgta tgagcgcgat gaaggtgata aatggcgaaa caaaaagttt    180

gaattgggtt tggagtttcc caatcttcct tattatattg atggtgatgt taaattaaca    240

cagtctatgg ccatcatacg ttatatagct gacaagcaca acatgttggg tggttgtcca    300

aaagagcgtg cagagatttc aatgcttgaa ggagcggttt tggatattag atacggtgtt    360

tcgagaattg catatagtaa agactttgaa actctcaaag ttgattttct tagcaagcta    420

cctgaaatgc tgaaaatgtt cgaagatcgt ttatgtcata aaacatattt aaatggtgat    480

catgtaaccc atcctgactt catgttgtat gacgctcttg atgttgtttt atacatggac    540

ccaatgtgcc tggatgcgtt cccaaaatta gtttgtttta aaaaacgtat tgaagctatc    600

ccacaaattg ataagtactt gaaatccagc aagtatatag catggccttt gcagggctgg    660

caagccacgt ttggtggtgg cgaccatcct ccaactagtg gatctggtgg tggtggcgga    720

tggatgagcg agaatcttta ttttcagggc gcaatggagg agaaggtcgg taaccttaag    780

cccaatatgg aatctgtcaa cgttactgtt agagtcctgg aagccagcga ggcgcgccaa    840

atacagacga agaacggggt aaggaccata agcgaggcaa tcgtcggcga cgagactggc    900

agagttaaat tgaccctttg ggaaaaacac gctggttcta taaaggaagg tcaagtcgta    960

aagatcgaaa atgcttggac gaccgcattc aagggccagg ttcaactcaa cgccggatct   1020

aaaactaaga tagctgaggc gtcagaagac ggcttcccag aatcaagcca gatacctgag   1080

aacactccaa cggctcctca acaaatgaga ggaggtggac gaggatttcg cggggggggga   1140

cgaagatatg gccgacgcgg aggacgacgc caggaaaatg aagagggtga agaggaatct   1200

ggttccggtg gcggtggtag cgaagaaaaa gtgggtaacc ttaaacccaa catggagagc   1260

gttaacgtca cggtcagagt actcgaggcg agcgaggcgc ggcagataca aacaaaaaat   1320

ggtgtgcgca ccatttccga agctatagtc ggtgacgaaa cgggccgcgt taaattgacg   1380

ctctggggaa aacatgcagg ttctattaaa gagggtcagg tcgtgaaaat agagaacgcc   1440

tggactacgg cgttcaaggg tcaggtccaa ctgaatgcag ggtctaaaac taaaattgcg   1500

gaggctagtg aagatggttt tcccgaatca agccagattc cagaaaatac acctacggca   1560

ccgcaacaga tgcgaggagg cgggcgagga tttcgaggtg gaggtcgacg ctacggtagg   1620

aggggtgggc ggcgccaaga gaacgaagaa ggagaggaag aaagcggctc tgagactccc   1680

ggcacatccg aaagcgcaac ccctgagtct gtcggcggct ataaagtcag caatttgaca   1740

gtggaagcgt tcgaaggtat cgggagtgtc aacccgatgc tgttttacca atacaaagtc   1800

accggaaagg gaaagtacga taatgtgtat aagattatca aaagcgcacg gtacaagatg   1860
```

```
cattctaaga accgattcaa gcccgtgttc atcaaggacg acaaactgta caccctcgag   1920
aagctcccgg atatagagga cctggatttc gcaaacatta acttcgtgaa aagcgaggtt   1980
ctcagcatag aggataatat gtcaatttat ggcgaggtgg tggaatacta tatcaatctc   2040
aagctgaaaa aagtgaaggt gttgggaaaa taccccaagt acaggatcaa ttacagcaaa   2100
gagattctca gtaatacgct gctgacacga gagctcaaag acgagtttaa gaaatcaaat   2160
aagggtttta acctgaaacg gaagtttaga atttcccccg tggtgaataa gatgggcaaa   2220
gtgatactct atttgtcctg cagtgctgat ttcagcacca acaagaacat ttacgaaatg   2280
ttgaaagagg gcttggaggt tgaggggctg gccgttaaga gcgagtggag caatatcagt   2340
ggcaacctgg tgatcgagag cgtactggaa accaagatat ccgagcccac tagcctgggc   2400
caatccctga tagactacta taagaataac aaccagggct atagggtgaa ggatttcacc   2460
gatgaggatc tgaatgccaa cattgtcaac gtgagaggaa ataagaagat ctatatgtat   2520
attccgcacg cgttgaagcc gataatcacc cgggagtacc tggccaagaa cgatccagag   2580
ttttctaagg agatcgagca gcttatcaag atgaatatga actaccgata tgaaaccctc   2640
aagtcatttg tgaatgacat cggggtcatt gaggagctga acaacctgag cttcaaaaac   2700
aaatactacg aagatgtgaa actgctgggt tactccagcg gcaaaataga cgaacccgtc   2760
ctgatggggg caaaagggat cataaagaac aaaatgcaga tttttccaa tggattctac   2820
aaactccccg aaggcaaggt acgatttggc gttctgtacc caaaagaatt tgatggcgtg   2880
tcaaggaaag ctatccgcgc catttatgac ttcagtaagg agggcaaata ccacggcgaa   2940
agcaacaagt atatcgcgga acacctgata aacgtggagt tcaatccaaa ggagtgcata   3000
tttgagggat acgaactggg cgatatcacc gaatacaaga aggcggctct gaaacttaat   3060
aactacaaca atgtcgactt cgtaatcgca atagtcccga acatgtccga cgaagagata   3120
gagaacagct acaatccgtt caagaaaata tgggccgaac tgaatctgcc cagccagatg   3180
attagcgtca agacggccga aatctttgcc aatagcaggg ataacacggc gctttactat   3240
ctgcataaca tcgtcctcgg tatcctgggt aagataggag ggattccctg ggtggttaaa   3300
gacatgaagg gcgacgtgga ttgcttcgtt ggactcgatg tcggcaccag ggagaagggc   3360
atacattacc ccgcctgcag cgttgtgttt gacaagtacg gcaagcttat taactattac   3420
aagcctaaca tcccgcagaa cggagagaag attaacacag aaatacttca ggaaattttc   3480
gacaaggtgc tcataagcta tgaggaggag aatggagcct acccgaagaa tatcgtgatc   3540
cacagggacg gctttagccg agaggacctt gactggtatg agaactactt cggtaagaaa   3600
aacataaagt ttaacatcat cgaagtcaaa aagtcaactc cgttgaaaat cgccagtata   3660
aacgagggaa atatcacgaa tcctgaaaag ggttcctaca tcctgcgcgg caacaaagcc   3720
tacatggtga ccacagatat taaggaaaac ctgggaagcc caaagcccct gaagatagaa   3780
aagagctacg gcgacataga catgctcaca gctctcagcc aaatatacgc actcacgcaa   3840
atccatgtgg gggcgaccaa aagcctgcgc ctcccaatca ccaccggcta cgccgacaag   3900
atttgcaagg cgatcgagtt catcccccaa gggcgcgtgg acaaccgcct tttctttctg   3960
tagtga                                                              3966
```

<210> SEQ ID NO 96
<211> LENGTH: 3977
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 96
atgaaacatc accatcacca tcacaacact agtagcaatt ccatgtcccc tatactaggt 60
tattggaaaa ttaagggcct tgtgcaaccc actcgacttc ttttggaata tcttgaagaa 120
aaatatgaag agcatttgta tgagcgcgat gaaggtgata aatggcgaaa caaaaagttt 180
gaattgggtt tggagtttcc caatcttcct tattatattg atggtgatgt taaattaaca 240
cagtctatgg ccatcatacg ttatatagct gacaagcaca acatgttggg tggttgtcca 300
aaagagcgtg cagagatttc aatgcttgaa ggagcggttt tggatattag atacggtgtt 360
tcgagaattg catatagtaa agactttgaa actctcaaag ttgattttct tagcaagcta 420
cctgaaatgc tgaaaatgtt cgaagatcgt ttatgtcata aaacatattt aaatggtgat 480
catgtaaccc atcctgactt catgttgtat gacgctcttg atgttgtttt atacatggac 540
ccaatgtgcc tggatgcgtt cccaaaatta gtttgtttta aaaaacgtat tgaagctatc 600
ccacaaattg ataagtactt gaaatccagc aagtatatag catggccttt gcagggctgg 660
caagccacgt ttggtggtgg cgaccatcct ccaactagtg gatctggtgg tggtggcgga 720
tggatgagcg agaatcttta ttttcagggc gcaatggagg agaaggtcgg taaccttaag 780
cccaatatgg aatctgtcaa cgttactgtt agagtcctgg aagccagcga ggcgcgccaa 840
atacagacga agaacggggt aaggaccata agcgaggcaa tcgtcggcga cgagactggc 900
agagttaaat tgaccctttg gggaaaacac gctggttcta taaaggaagg tcaagtcgta 960
aagatcgaaa atgcttggac gaccgcattc aagggccagg ttcaactcaa cgccggatct 1020
aaaactaaga tagctgaggc gtcagaagac ggcttcccag aatcaagcca gatacctgag 1080
aacactccaa cggctcctca acaaatgaga ggaggtggac gaggatttcg cggggggga 1140
cgaagatatg gccgacgcgg aggacgacgc caggaaaatg aagagggtga agaggaaagc 1200
ggctctgaga ctcccggcac atccgaaagc gcgaagaaaa agtgggtaac cttaaaccca 1260
acatggagag cgttaacgtc acggtcagag tactcgaggc gagcgaggcg cggcagatac 1320
aaacaaaaaa tggtgtgcgc accatttccg aagctatagt cggtgacgaa acgggccgcg 1380
ttaaattgac gctctgggga aaacatgcag gttctattaa agagggtcag gtcgtgaaaa 1440
tagagaacgc ctggactacg gcgttcaagg gtcaggtcca actgaatgca gggtctaaaa 1500
ctaaaattgc ggaggctagt gaagatggtt ttcccgaatc aagccagatt ccagaaaata 1560
cacctacggc accgcaacag atgcgaggag gcgggcgagg atttcgaggt ggaggtcgac 1620
gctacggtag gaggggtggg cggcgccaag agaacgaaga aggagaggaa gaaagcggct 1680
ctgagactcc cggcacatcc gaaagcgcaa cccctgagtc tgtcggcggc tataaagtca 1740
gcaatttgac agtggaagcg ttcgaaggta tcgggagtgt caacccgatg ctgttttacc 1800
aatacaaagt caccggaaag ggaaagtacg ataatgtgta taagattatc aaaagcgcac 1860
ggtacaagat gcattctaag aaccgattca agcccgtgtt catcaaggac gacaaactgt 1920
acaccctcga gaagctcccg gatatagagg acctggattt cgcaaacatt aacttcgtga 1980
aaagcgaggt tctcagcata gaggataata tgtcaattta tggcgaggtg gtggaatact 2040
atatcaatct caagctgaaa aaagtgaagg tgttgggaaa ataccccaag tacaggatca 2100
attacagcaa agagattctc agtaatacgc tgctgacacg agagctcaaa gacgagttta 2160
agaaatcaaa taagggtttt aacctgaaac ggaagtttag aatttccccc gtggtgaata 2220
agatgggcaa agtgatactc tatttgtcct gcagtgctga tttcagcacc aacaagaaca 2280

```
tttacgaaat gttgaaagag ggcttggagg ttgaggggct ggccgttaag agcgagtgga   2340

gcaatatcag tggcaacctg gtgatcgaga gcgtactgga aaccaagata tccgagccca   2400

ctagcctggg ccaatccctg atagactact ataagaataa caaccagggc tatagggtga   2460

aggatttcac cgatgaggat ctgaatgcca acattgtcaa cgtgagagga aataagaaga   2520

tctatatgta tattccgcac gcgttgaagc cgataatcac ccgggagtac ctggccaaga   2580

acgatccaga gttttctaag gagatcgagc agcttatcaa gatgaatatg aactaccgat   2640

atgaaaccct caagtcattt gtgaatgaca tcggggtcat tgaggagctg aacaacctga   2700

gcttcaaaaa caaatactac gaagatgtga aactgctggg ttactccagc ggcaaaatag   2760

acgaacccgt cctgatgggg gcaaaaggga tcataaagaa caaaatgcag atttttcca   2820

atggattcta caaactcccc gaaggcaagg tacgatttgg cgttctgtac ccaaaagaat   2880

ttgatggcgt gtcaaggaaa gctatccgcg ccatttatga cttcagtaag gagggcaaat   2940

accacggcga aagcaacaag tatatcgcgg aacacctgat aaacgtggag ttcaatccaa   3000

aggagtgcat atttgaggga tacgaactgg gcgatatcac cgaatacaag aaggcggctc   3060

tgaaacttaa taactacaac aatgtcgact tcgtaatcgc aatagtcccg aacatgtccg   3120

acgaagagat agagaacagc tacaatccgt tcaagaaaat atgggccgaa ctgaatctgc   3180

ccagccagat gattagcgtc aagacggccg aaatctttgc caatagcagg gataacacgg   3240

cgctttacta tctgcataac atcgtcctcg gtatcctggg taagatagga gggattccct   3300

gggtggttaa agacatgaag ggcgacgtgg attgcttcgt tggactcgat gtcggcacca   3360

gggagaaggg catacattac cccgcctgca gcgttgtgtt tgacaagtac ggcaagctta   3420

ttaactatta caagcctaac atcccgcaga acggagagaa gattaacaca gaaatacttc   3480

aggaaatttt cgacaaggtg ctcataagct atgaggagga gaatggagcc tacccgaaga   3540

atatcgtgat ccacagggac ggctttagcc gagaggacct tgactggtat gagaactact   3600

tcggtaagaa aaacataaag tttaacatca tcgaagtcaa aaagtcaact ccgttgaaaa   3660

tcgccagtat aaacgaggga aatatcacga atcctgaaaa gggttcctac atcctgcgcg   3720

gcaacaaagc ctacatggtg accacagata ttaaggaaaa cctgggaagc ccaaagcccc   3780

tgaagataga aaagagctac ggcgacatag acatgctcac agctctcagc caaatatacg   3840

cactcacgca aatccatgtg ggggcgacca aaagcctgcg cctcccaatc accaccggct   3900

acgccgacaa gatttgcaag gcgatcgagt tcatccccca agggcgcgtg gacaaccgcc   3960

ttttcttct gtagtga                                                   3977
```

<210> SEQ ID NO 97
<211> LENGTH: 791
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 97

```
Met Pro Lys Lys Lys Arg Lys Val Glu Asp Pro Lys Lys Lys Arg Lys
1               5                   10                  15

Val Gly Ser Gly Ser Gly Lys Pro Ile Pro Asn Pro Leu Leu Gly Leu
            20                  25                  30

Asp Ser Thr Gly Ser Gly Ser Ser Met Val Gly Gly Tyr Lys Val Ser
        35                  40                  45
```

```
Asn Leu Thr Val Glu Ala Phe Glu Gly Ile Gly Ser Val Asn Pro Met
    50                  55                  60

Leu Phe Tyr Gln Tyr Lys Val Thr Gly Lys Gly Lys Tyr Asp Asn Val
65                  70                  75                  80

Tyr Lys Ile Ile Lys Ser Ala Arg Tyr Lys Met His Ser Lys Asn Arg
                85                  90                  95

Phe Lys Pro Val Phe Ile Lys Asp Asp Lys Leu Tyr Thr Leu Glu Lys
            100                 105                 110

Leu Pro Asp Ile Glu Asp Leu Asp Phe Ala Asn Ile Asn Phe Val Lys
        115                 120                 125

Ser Glu Val Leu Ser Ile Glu Asp Asn Met Ser Ile Tyr Gly Glu Val
    130                 135                 140

Val Glu Tyr Tyr Ile Asn Leu Lys Leu Lys Lys Val Lys Val Leu Gly
145                 150                 155                 160

Lys Tyr Pro Lys Tyr Arg Ile Asn Tyr Ser Lys Glu Ile Leu Ser Asn
                165                 170                 175

Thr Leu Leu Thr Arg Glu Leu Lys Asp Glu Phe Lys Lys Ser Asn Lys
            180                 185                 190

Gly Phe Asn Leu Lys Arg Lys Phe Arg Ile Ser Pro Val Val Asn Lys
        195                 200                 205

Met Gly Lys Val Ile Leu Tyr Leu Ser Cys Ser Ala Asp Phe Ser Thr
    210                 215                 220

Asn Lys Asn Ile Tyr Glu Met Leu Lys Glu Gly Leu Glu Val Glu Gly
225                 230                 235                 240

Leu Ala Val Lys Ser Glu Trp Ser Asn Ile Ser Gly Asn Leu Val Ile
                245                 250                 255

Glu Ser Val Leu Glu Thr Lys Ile Ser Glu Pro Thr Ser Leu Gly Gln
            260                 265                 270

Ser Leu Ile Asp Tyr Tyr Lys Asn Asn Asn Gln Gly Tyr Arg Val Lys
        275                 280                 285

Asp Phe Thr Asp Glu Asp Leu Asn Ala Asn Ile Val Asn Val Arg Gly
    290                 295                 300

Asn Lys Lys Ile Tyr Met Tyr Ile Pro His Ala Leu Lys Pro Ile Ile
305                 310                 315                 320

Thr Arg Glu Tyr Leu Ala Lys Asn Asp Pro Glu Phe Ser Lys Glu Ile
                325                 330                 335

Glu Gln Leu Ile Lys Met Asn Met Asn Tyr Arg Tyr Glu Thr Leu Lys
            340                 345                 350

Ser Phe Val Asn Asp Ile Gly Val Ile Glu Glu Leu Asn Asn Leu Ser
        355                 360                 365

Phe Lys Asn Lys Tyr Tyr Glu Asp Val Lys Leu Leu Gly Tyr Ser Ser
    370                 375                 380

Gly Lys Ile Asp Glu Pro Val Leu Met Gly Ala Lys Gly Ile Ile Lys
385                 390                 395                 400

Asn Lys Met Gln Ile Phe Ser Asn Gly Phe Tyr Lys Leu Pro Glu Gly
                405                 410                 415

Lys Val Arg Phe Gly Val Leu Tyr Pro Lys Glu Phe Asp Gly Val Ser
            420                 425                 430

Arg Lys Ala Ile Arg Ala Ile Tyr Asp Phe Ser Lys Glu Gly Lys Tyr
        435                 440                 445

His Gly Glu Ser Asn Lys Tyr Ile Ala Glu His Leu Ile Asn Val Glu
    450                 455                 460

Phe Asn Pro Lys Glu Cys Ile Phe Glu Gly Tyr Glu Leu Gly Asp Ile
```

465 470 475 480

Thr Glu Tyr Lys Lys Ala Ala Leu Lys Leu Asn Asn Tyr Asn Asn Val
485 490 495

Asp Phe Val Ile Ala Ile Val Pro Asn Met Ser Asp Glu Glu Ile Glu
500 505 510

Asn Ser Tyr Asn Pro Phe Lys Lys Ile Trp Ala Glu Leu Asn Leu Pro
515 520 525

Ser Gln Met Ile Ser Val Lys Thr Ala Glu Ile Phe Ala Asn Ser Arg
530 535 540

Asp Asn Thr Ala Leu Tyr Tyr Leu His Asn Ile Val Leu Gly Ile Leu
545 550 555 560

Gly Lys Ile Gly Gly Ile Pro Trp Val Val Lys Asp Met Lys Gly Asp
565 570 575

Val Asp Cys Phe Val Gly Leu Asp Val Gly Thr Arg Glu Lys Gly Ile
580 585 590

His Tyr Pro Ala Cys Ser Val Val Phe Asp Lys Tyr Gly Lys Leu Ile
595 600 605

Asn Tyr Tyr Lys Pro Asn Ile Pro Gln Asn Gly Glu Lys Ile Asn Thr
610 615 620

Glu Ile Leu Gln Glu Ile Phe Asp Lys Val Leu Ile Ser Tyr Glu Glu
625 630 635 640

Glu Asn Gly Ala Tyr Pro Lys Asn Ile Val Ile His Arg Asp Gly Phe
645 650 655

Ser Arg Glu Asp Leu Asp Trp Tyr Glu Asn Tyr Phe Gly Lys Lys Asn
660 665 670

Ile Lys Phe Asn Ile Ile Glu Val Lys Lys Ser Thr Pro Leu Lys Ile
675 680 685

Ala Ser Ile Asn Glu Gly Asn Ile Thr Asn Pro Glu Lys Gly Ser Tyr
690 695 700

Ile Leu Arg Gly Asn Lys Ala Tyr Met Val Thr Thr Asp Ile Lys Glu
705 710 715 720

Asn Leu Gly Ser Pro Lys Pro Leu Lys Ile Glu Lys Ser Tyr Gly Asp
725 730 735

Ile Asp Met Leu Thr Ala Leu Ser Gln Ile Tyr Ala Leu Thr Gln Ile
740 745 750

His Val Gly Ala Thr Lys Ser Leu Arg Leu Pro Ile Thr Thr Gly Tyr
755 760 765

Ala Asp Lys Ile Cys Lys Ala Ile Glu Phe Ile Pro Gln Gly Arg Val
770 775 780

Asp Asn Arg Leu Phe Phe Leu
785 790

<210> SEQ ID NO 98
<211> LENGTH: 944
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 98

Met Pro Lys Lys Lys Arg Lys Val Glu Asp Pro Lys Lys Lys Arg Lys
1 5 10 15

Val Gly Ser Gly Ser Gly Lys Pro Ile Pro Asn Pro Leu Leu Gly Leu
20 25 30

```
Asp Ser Thr Gly Ser Gly Ser Ser Met Glu Glu Lys Val Gly Asn Leu
        35                  40                  45

Lys Pro Asn Met Glu Ser Val Asn Val Thr Val Arg Val Leu Glu Ala
    50                  55                  60

Ser Glu Ala Arg Gln Ile Gln Thr Lys Asn Gly Val Arg Thr Ile Ser
65                  70                  75                  80

Glu Ala Ile Val Gly Asp Glu Thr Gly Arg Val Lys Leu Thr Leu Trp
                85                  90                  95

Gly Lys His Ala Gly Ser Ile Lys Glu Gly Gln Val Val Lys Ile Glu
            100                 105                 110

Asn Ala Trp Thr Thr Ala Phe Lys Gly Gln Val Gln Leu Asn Ala Gly
        115                 120                 125

Ser Lys Thr Lys Ile Ala Glu Ala Ser Glu Asp Gly Phe Pro Glu Ser
    130                 135                 140

Ser Gln Ile Pro Glu Asn Thr Pro Thr Ala Pro Gln Gln Met Arg Gly
145                 150                 155                 160

Gly Gly Arg Gly Phe Arg Gly Gly Gly Arg Arg Tyr Gly Arg Arg Gly
                165                 170                 175

Gly Arg Arg Gln Glu Asn Glu Glu Gly Glu Glu Glu Gly Gly Gly Gly
            180                 185                 190

Ser Met Val Gly Gly Tyr Lys Val Ser Asn Leu Thr Val Glu Ala Phe
        195                 200                 205

Glu Gly Ile Gly Ser Val Asn Pro Met Leu Phe Tyr Gln Tyr Lys Val
    210                 215                 220

Thr Gly Lys Gly Lys Tyr Asp Asn Val Tyr Lys Ile Ile Lys Ser Ala
225                 230                 235                 240

Arg Tyr Lys Met His Ser Lys Asn Arg Phe Lys Pro Val Phe Ile Lys
                245                 250                 255

Asp Asp Lys Leu Tyr Thr Leu Glu Lys Leu Pro Asp Ile Glu Asp Leu
            260                 265                 270

Asp Phe Ala Asn Ile Asn Phe Val Lys Ser Glu Val Leu Ser Ile Glu
        275                 280                 285

Asp Asn Met Ser Ile Tyr Gly Glu Val Val Glu Tyr Tyr Ile Asn Leu
    290                 295                 300

Lys Leu Lys Lys Val Lys Val Leu Gly Lys Tyr Pro Lys Tyr Arg Ile
305                 310                 315                 320

Asn Tyr Ser Lys Glu Ile Leu Ser Asn Thr Leu Leu Thr Arg Glu Leu
                325                 330                 335

Lys Asp Glu Phe Lys Lys Ser Asn Lys Gly Phe Asn Leu Lys Arg Lys
            340                 345                 350

Phe Arg Ile Ser Pro Val Val Asn Lys Met Gly Lys Val Ile Leu Tyr
        355                 360                 365

Leu Ser Cys Ser Ala Asp Phe Ser Thr Asn Lys Asn Ile Tyr Glu Met
    370                 375                 380

Leu Lys Glu Gly Leu Glu Val Glu Gly Leu Ala Val Lys Ser Glu Trp
385                 390                 395                 400

Ser Asn Ile Ser Gly Asn Leu Val Ile Glu Ser Val Leu Glu Thr Lys
                405                 410                 415

Ile Ser Glu Pro Thr Ser Leu Gly Gln Ser Leu Ile Asp Tyr Tyr Lys
            420                 425                 430

Asn Asn Asn Gln Gly Tyr Arg Val Lys Asp Phe Thr Asp Glu Asp Leu
        435                 440                 445

Asn Ala Asn Ile Val Asn Val Arg Gly Asn Lys Lys Ile Tyr Met Tyr
```

```
    450                 455                 460

Ile Pro His Ala Leu Lys Pro Ile Ile Thr Arg Glu Tyr Leu Ala Lys
465                 470                 475                 480

Asn Asp Pro Glu Phe Ser Lys Glu Ile Glu Gln Leu Ile Lys Met Asn
                485                 490                 495

Met Asn Tyr Arg Tyr Glu Thr Leu Lys Ser Phe Val Asn Asp Ile Gly
            500                 505                 510

Val Ile Glu Glu Leu Asn Asn Leu Ser Phe Lys Asn Lys Tyr Tyr Glu
        515                 520                 525

Asp Val Lys Leu Leu Gly Tyr Ser Ser Gly Lys Ile Asp Glu Pro Val
    530                 535                 540

Leu Met Gly Ala Lys Gly Ile Ile Lys Asn Lys Met Gln Ile Phe Ser
545                 550                 555                 560

Asn Gly Phe Tyr Lys Leu Pro Glu Gly Lys Val Arg Phe Gly Val Leu
                565                 570                 575

Tyr Pro Lys Glu Phe Asp Gly Val Ser Arg Lys Ala Ile Arg Ala Ile
            580                 585                 590

Tyr Asp Phe Ser Lys Glu Gly Lys Tyr His Gly Glu Ser Asn Lys Tyr
        595                 600                 605

Ile Ala Glu His Leu Ile Asn Val Glu Phe Asn Pro Lys Glu Cys Ile
    610                 615                 620

Phe Glu Gly Tyr Glu Leu Gly Asp Ile Thr Glu Tyr Lys Lys Ala Ala
625                 630                 635                 640

Leu Lys Leu Asn Asn Tyr Asn Asn Val Asp Phe Val Ile Ala Ile Val
                645                 650                 655

Pro Asn Met Ser Asp Glu Glu Ile Glu Asn Ser Tyr Asn Pro Phe Lys
            660                 665                 670

Lys Ile Trp Ala Glu Leu Asn Leu Pro Ser Gln Met Ile Ser Val Lys
        675                 680                 685

Thr Ala Glu Ile Phe Ala Asn Ser Arg Asp Asn Thr Ala Leu Tyr Tyr
    690                 695                 700

Leu His Asn Ile Val Leu Gly Ile Leu Gly Lys Ile Gly Gly Ile Pro
705                 710                 715                 720

Trp Val Val Lys Asp Met Lys Gly Asp Val Asp Cys Phe Val Gly Leu
                725                 730                 735

Asp Val Gly Thr Arg Glu Lys Gly Ile His Tyr Pro Ala Cys Ser Val
            740                 745                 750

Val Phe Asp Lys Tyr Gly Lys Leu Ile Asn Tyr Tyr Lys Pro Asn Ile
        755                 760                 765

Pro Gln Asn Gly Glu Lys Ile Asn Thr Glu Ile Leu Gln Glu Ile Phe
    770                 775                 780

Asp Lys Val Leu Ile Ser Tyr Glu Glu Glu Asn Gly Ala Tyr Pro Lys
785                 790                 795                 800

Asn Ile Val Ile His Arg Asp Gly Phe Ser Arg Glu Asp Leu Asp Trp
                805                 810                 815

Tyr Glu Asn Tyr Phe Gly Lys Lys Asn Ile Lys Phe Asn Ile Ile Glu
            820                 825                 830

Val Lys Lys Ser Thr Pro Leu Lys Ile Ala Ser Ile Asn Glu Gly Asn
        835                 840                 845

Ile Thr Asn Pro Glu Lys Gly Ser Tyr Ile Leu Arg Gly Asn Lys Ala
    850                 855                 860

Tyr Met Val Thr Thr Asp Ile Lys Glu Asn Leu Gly Ser Pro Lys Pro
865                 870                 875                 880
```

Leu Lys Ile Glu Lys Ser Tyr Gly Asp Ile Asp Met Leu Thr Ala Leu
885 890 895

Ser Gln Ile Tyr Ala Leu Thr Gln Ile His Val Gly Ala Thr Lys Ser
900 905 910

Leu Arg Leu Pro Ile Thr Thr Gly Tyr Ala Asp Lys Ile Cys Lys Ala
915 920 925

Ile Glu Phe Ile Pro Gln Gly Arg Val Asp Asn Arg Leu Phe Phe Leu
930 935 940

<210> SEQ ID NO 99
<211> LENGTH: 788
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 99

Met Pro Lys Lys Lys Arg Lys Val Glu Asp Pro Lys Lys Lys Arg Lys
1 5 10 15

Val Gly Ser Gly Ser Gly Lys Pro Ile Pro Asn Pro Leu Leu Gly Leu
20 25 30

Asp Ser Thr Gly Ser Gly Ser Ser Met Asn Asn Leu Thr Phe Glu Ala
35 40 45

Phe Glu Gly Ile Gly Gln Leu Asn Glu Leu Asn Phe Tyr Lys Tyr Arg
50 55 60

Leu Ile Gly Lys Gly Gln Ile Asp Asn Val His Gln Ala Ile Trp Ser
65 70 75 80

Val Lys Tyr Lys Leu Gln Ala Asn Asn Phe Phe Lys Pro Val Phe Val
85 90 95

Lys Gly Glu Ile Leu Tyr Ser Leu Asp Glu Leu Lys Val Ile Pro Glu
100 105 110

Phe Glu Asn Val Glu Val Ile Leu Asp Gly Asn Ile Ile Leu Ser Ile
115 120 125

Ser Glu Asn Thr Asp Ile Tyr Lys Asp Val Ile Val Phe Tyr Ile Asn
130 135 140

Asn Ala Leu Lys Asn Ile Lys Asp Ile Thr Asn Tyr Arg Lys Tyr Ile
145 150 155 160

Thr Lys Asn Thr Asp Glu Ile Ile Cys Lys Ser Ile Leu Thr Thr Asn
165 170 175

Leu Lys Tyr Gln Tyr Met Lys Ser Glu Lys Gly Phe Lys Leu Gln Arg
180 185 190

Lys Phe Lys Ile Ser Pro Val Val Phe Arg Asn Gly Lys Val Ile Leu
195 200 205

Tyr Leu Asn Cys Ser Ser Asp Phe Ser Thr Asp Lys Ser Ile Tyr Glu
210 215 220

Met Leu Asn Asp Gly Leu Gly Val Val Gly Leu Gln Val Lys Asn Lys
225 230 235 240

Trp Thr Asn Ala Asn Gly Asn Ile Phe Ile Glu Lys Val Leu Asp Asn
245 250 255

Thr Ile Ser Asp Pro Gly Thr Ser Gly Lys Leu Gly Gln Ser Leu Ile
260 265 270

Asp Tyr Tyr Ile Asn Gly Asn Gln Lys Tyr Arg Val Glu Lys Phe Thr
275 280 285

Asp Glu Asp Lys Asn Ala Lys Val Ile Gln Ala Lys Ile Lys Asn Lys

```
    290                 295                 300

Thr Tyr Asn Tyr Ile Pro Gln Ala Leu Thr Pro Val Ile Thr Arg Glu
305                 310                 315                 320

Tyr Leu Ser His Thr Asp Lys Lys Phe Ser Lys Gln Ile Glu Asn Val
                325                 330                 335

Ile Lys Met Asp Met Asn Tyr Arg Tyr Gln Thr Leu Lys Ser Phe Val
            340                 345                 350

Glu Asp Ile Gly Val Ile Lys Glu Leu Asn Asn Leu His Phe Lys Asn
        355                 360                 365

Gln Tyr Tyr Thr Asn Phe Asp Phe Met Gly Phe Glu Ser Gly Val Leu
    370                 375                 380

Glu Glu Pro Val Leu Met Gly Ala Asn Gly Lys Ile Lys Asp Lys Lys
385                 390                 395                 400

Gln Ile Phe Ile Asn Gly Phe Phe Lys Asn Pro Lys Glu Asn Val Lys
                405                 410                 415

Phe Gly Val Leu Tyr Pro Glu Gly Cys Met Glu Asn Ala Gln Ser Ile
            420                 425                 430

Ala Arg Ser Ile Leu Asp Phe Ala Thr Ala Gly Lys Tyr Asn Lys Gln
        435                 440                 445

Glu Asn Lys Tyr Ile Ser Lys Asn Leu Met Asn Ile Gly Phe Lys Pro
    450                 455                 460

Ser Glu Cys Ile Phe Glu Ser Tyr Lys Leu Gly Asp Ile Thr Glu Tyr
465                 470                 475                 480

Lys Ala Thr Ala Arg Lys Leu Lys Glu His Glu Lys Val Gly Phe Val
                485                 490                 495

Ile Ala Val Ile Pro Asp Met Asn Glu Leu Glu Val Glu Asn Pro Tyr
            500                 505                 510

Asn Pro Phe Lys Lys Val Trp Ala Lys Leu Asn Ile Pro Ser Gln Met
        515                 520                 525

Ile Thr Leu Lys Thr Thr Glu Lys Phe Lys Asn Ile Val Asp Lys Ser
    530                 535                 540

Gly Leu Tyr Tyr Leu His Asn Ile Ala Leu Asn Ile Leu Gly Lys Ile
545                 550                 555                 560

Gly Gly Ile Pro Trp Ile Ile Lys Asp Met Pro Gly Asn Ile Asp Cys
                565                 570                 575

Phe Ile Gly Leu Asp Val Gly Thr Arg Glu Lys Gly Ile His Phe Pro
            580                 585                 590

Ala Cys Ser Val Leu Phe Asp Lys Tyr Gly Lys Leu Ile Asn Tyr Tyr
        595                 600                 605

Lys Pro Thr Ile Pro Gln Ser Gly Glu Lys Ile Ala Glu Thr Ile Leu
    610                 615                 620

Gln Glu Ile Phe Asp Asn Val Leu Ile Ser Tyr Lys Glu Glu Asn Gly
625                 630                 635                 640

Glu Tyr Pro Lys Asn Ile Val Ile His Arg Asp Gly Phe Ser Arg Glu
                645                 650                 655

Asn Ile Asp Trp Tyr Lys Glu Tyr Phe Asp Lys Lys Gly Ile Lys Phe
            660                 665                 670

Asn Ile Ile Glu Val Lys Lys Asn Ile Pro Val Lys Ile Ala Lys Val
        675                 680                 685

Val Gly Ser Asn Ile Cys Asn Pro Ile Lys Gly Ser Tyr Val Leu Lys
    690                 695                 700

Asn Asp Lys Ala Phe Ile Val Thr Thr Asp Ile Lys Asp Gly Val Ala
705                 710                 715                 720
```

Ser Pro Asn Pro Leu Lys Ile Glu Lys Thr Tyr Gly Asp Val Glu Met
725 730 735

Lys Ser Ile Leu Glu Gln Ile Tyr Ser Leu Ser Gln Ile His Val Gly
740 745 750

Ser Thr Lys Ser Leu Arg Leu Pro Ile Thr Thr Gly Tyr Ala Asp Lys
755 760 765

Ile Cys Lys Ala Ile Glu Tyr Ile Pro Gln Gly Val Val Asp Asn Arg
770 775 780

Leu Phe Phe Leu
785

<210> SEQ ID NO 100
<211> LENGTH: 745
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 100

Met Pro Lys Lys Lys Arg Lys Val Glu Asp Pro Lys Lys Lys Arg Lys
1 5 10 15

Val Gly Ser Gly Ser Gly Lys Pro Ile Pro Asn Pro Leu Leu Gly Leu
20 25 30

Asp Ser Thr Gly Ser Gly Ser Ser Met Lys Glu Phe Asn Val Ile Thr
35 40 45

Glu Phe Lys Asn Gly Ile Asn Ser Lys Ser Ile Glu Ile Tyr Ile Tyr
50 55 60

Lys Met Met Val Arg Asp Phe Glu Lys Arg His Asn Glu Asn Tyr Asp
65 70 75 80

Val Val Lys Glu Leu Ile Asn Leu Asn Asn Asn Ser Thr Ile Val Phe
85 90 95

Tyr Glu Gln Tyr Ile Ala Ser Phe Lys Glu Ile Glu Lys Trp Gly Asn
100 105 110

Glu Gln Tyr Ile Asn Val Glu Lys Arg Ala Ile Asn Leu Glu Ser Asn
115 120 125

Glu Lys Lys Ile Leu Glu Arg Leu Leu Leu Lys Glu Ile Lys Asn Asn
130 135 140

Ile Asp Asn Asn Lys Tyr Lys Val Val Lys Asp Ser Ile Tyr Ile Asn
145 150 155 160

Lys Pro Val Tyr Asn Glu Lys Gly Ile Lys Ile Asp Arg Tyr Phe Asn
165 170 175

Leu Asp Ile Asn Val Glu Ser Asn Gly Asp Ile Ile Ile Gly Phe Asp
180 185 190

Ile Ser His Asn Phe Glu Tyr Ile Asn Thr Leu Glu Tyr Glu Ile Lys
195 200 205

Asn Asn Asn Ile Lys Ile Gly Asp Arg Val Lys Asp Tyr Phe Tyr Asn
210 215 220

Leu Thr Tyr Glu Tyr Val Gly Ile Ala Pro Phe Thr Ile Ser Glu Glu
225 230 235 240

Asn Glu Tyr Met Gly Cys Ser Ile Val Asp Tyr Tyr Glu Asn Lys Asn
245 250 255

Gln Ser Tyr Ile Val Asn Lys Leu Pro Lys Asp Met Lys Ala Ile Leu
260 265 270

Val Lys Asn Asn Lys Asn Ser Ile Phe Pro Tyr Ile Pro Ser Arg Leu

```
        275                 280                 285

Lys Lys Val Cys Arg Phe Glu Asn Leu Pro Gln Asn Val Leu Arg Asp
    290                 295                 300

Phe Asn Thr Arg Val Lys Gln Lys Thr Asn Glu Lys Met Gln Phe Met
305                 310                 315                 320

Val Asp Glu Val Ile Asn Ile Val Lys Asn Ser Glu His Ile Asp Val
                325                 330                 335

Lys Lys Lys Asn Met Met Cys Asp Asn Ile Gly Tyr Lys Ile Glu Asp
            340                 345                 350

Leu Gln Gln Pro Asp Leu Leu Phe Gly Asn Ala Arg Ala Gln Arg Tyr
        355                 360                 365

Pro Leu Tyr Gly Leu Lys Asn Phe Gly Val Tyr Glu Asn Lys Arg Ile
    370                 375                 380

Glu Ile Lys Tyr Phe Ile Asp Pro Ile Leu Ala Lys Ser Lys Met Asn
385                 390                 395                 400

Leu Glu Lys Ile Ser Lys Phe Cys Asp Glu Leu Glu Gln Phe Ser Ser
                405                 410                 415

Lys Leu Gly Val Gly Leu Asn Arg Val Lys Leu Asn Asn Ile Val Asn
            420                 425                 430

Phe Lys Glu Ile Arg Met Asp Asn Glu Asp Ile Phe Ser Tyr Glu Ile
        435                 440                 445

Arg Lys Ile Val Ser Asn Tyr Asn Glu Thr Thr Ile Val Ile Leu Ser
    450                 455                 460

Glu Glu Asn Leu Asn Lys Tyr Tyr Asn Ile Ile Lys Lys Thr Phe Ser
465                 470                 475                 480

Gly Gly Asn Glu Val Pro Thr Gln Cys Ile Gly Phe Asn Thr Leu Ser
                485                 490                 495

Tyr Thr Glu Lys Asn Lys Asp Ser Ile Phe Leu Asn Ile Leu Leu Gly
            500                 505                 510

Val Tyr Ala Lys Ser Gly Ile Gln Pro Trp Ile Leu Asn Glu Lys Leu
        515                 520                 525

Asn Ser Asp Cys Phe Ile Gly Leu Asp Val Ser Arg Glu Asn Lys Val
    530                 535                 540

Asn Lys Ala Gly Val Ile Gln Val Val Gly Lys Asp Gly Arg Val Leu
545                 550                 555                 560

Lys Thr Lys Val Ile Ser Ser Ser Gln Ser Gly Glu Lys Ile Lys Leu
                565                 570                 575

Glu Thr Leu Arg Glu Ile Val Phe Glu Ala Ile Asn Ser Tyr Glu Asn
            580                 585                 590

Thr Tyr Arg Cys Lys Pro Lys His Ile Thr Phe His Arg Asp Gly Ile
        595                 600                 605

Asn Arg Glu Glu Leu Glu Asn Leu Lys Asn Thr Met Thr Asn Leu Gly
    610                 615                 620

Val Glu Phe Asp Tyr Ile Glu Ile Thr Lys Gly Ile Asn Arg Arg Ile
625                 630                 635                 640

Ala Thr Ile Ser Glu Gly Glu Glu Trp Lys Thr Ile Met Gly Arg Cys
                645                 650                 655

Tyr Tyr Lys Asp Asn Ser Ala Tyr Val Cys Thr Thr Lys Pro Tyr Glu
            660                 665                 670

Gly Ile Gly Met Ala Lys Pro Ile Arg Ile Arg Arg Val Phe Gly Thr
        675                 680                 685

Leu Asp Ile Glu Lys Ile Val Glu Asp Ala Tyr Lys Leu Thr Phe Met
    690                 695                 700
```

```
His Val Gly Ala Ile Asn Lys Ile Arg Leu Pro Ile Thr Thr Tyr Tyr
705                 710                 715                 720

Ala Asp Leu Ser Ser Thr Tyr Gly Asn Arg Asp Leu Ile Pro Thr Asn
                725                 730                 735

Ile Asp Thr Asn Cys Leu Tyr Phe Ile
            740                 745


<210> SEQ ID NO 101
<211> LENGTH: 959
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Met Gly Lys Pro Ile Pro Asn Pro Leu Leu Gly Leu Asp Ser Thr Gly
1               5                   10                  15

Ser Gly Ser Met Pro Lys Lys Lys Arg Lys Val Glu Asp Pro Lys Lys
            20                  25                  30

Lys Arg Lys Val Gly Ser Gly Ser Ser Met Glu Glu Lys Val Gly Asn
        35                  40                  45

Leu Lys Pro Asn Met Glu Ser Val Asn Val Thr Val Arg Val Leu Glu
    50                  55                  60

Ala Ser Glu Ala Arg Gln Ile Gln Thr Lys Asn Gly Val Arg Thr Ile
65                  70                  75                  80

Ser Glu Ala Ile Val Gly Asp Glu Thr Gly Arg Val Lys Leu Thr Leu
                85                  90                  95

Trp Gly Lys His Ala Gly Ser Ile Lys Glu Gly Gln Val Val Lys Ile
            100                 105                 110

Glu Asn Ala Trp Thr Thr Ala Phe Lys Gly Gln Val Gln Leu Asn Ala
        115                 120                 125

Gly Ser Lys Thr Lys Ile Ala Glu Ala Ser Glu Asp Gly Phe Pro Glu
    130                 135                 140

Ser Ser Gln Ile Pro Glu Asn Thr Pro Thr Ala Pro Gln Gln Met Arg
145                 150                 155                 160

Gly Gly Gly Arg Gly Phe Arg Gly Gly Gly Arg Arg Tyr Gly Arg Arg
                165                 170                 175

Gly Gly Arg Arg Gln Glu Asn Glu Glu Gly Glu Glu Glu Gly Gly Gly
            180                 185                 190

Gly Ser Pro Ala Ala Lys Arg Val Lys Leu Asp Gly Gly Gly Gly Ser
        195                 200                 205

Met Val Gly Gly Tyr Lys Val Ser Asn Leu Thr Val Glu Ala Phe Glu
    210                 215                 220

Gly Ile Gly Ser Val Asn Pro Met Leu Phe Tyr Gln Tyr Lys Val Thr
225                 230                 235                 240

Gly Lys Gly Lys Tyr Asp Asn Val Tyr Lys Ile Ile Lys Ser Ala Arg
                245                 250                 255

Tyr Lys Met His Ser Lys Asn Arg Phe Lys Pro Val Phe Ile Lys Asp
            260                 265                 270

Asp Lys Leu Tyr Thr Leu Glu Lys Leu Pro Asp Ile Glu Asp Leu Asp
        275                 280                 285

Phe Ala Asn Ile Asn Phe Val Lys Ser Glu Val Leu Ser Ile Glu Asp
    290                 295                 300

Asn Met Ser Ile Tyr Gly Glu Val Val Glu Tyr Tyr Ile Asn Leu Lys
```

```
305                 310                 315                 320

Leu Lys Lys Val Lys Val Leu Gly Lys Tyr Pro Lys Tyr Arg Ile Asn
                325                 330                 335

Tyr Ser Lys Glu Ile Leu Ser Asn Thr Leu Leu Thr Arg Glu Leu Lys
            340                 345                 350

Asp Glu Phe Lys Lys Ser Asn Lys Gly Phe Asn Leu Lys Arg Lys Phe
        355                 360                 365

Arg Ile Ser Pro Val Val Asn Lys Met Gly Lys Val Ile Leu Tyr Leu
    370                 375                 380

Ser Cys Ser Ala Asp Phe Ser Thr Asn Lys Asn Ile Tyr Glu Met Leu
385                 390                 395                 400

Lys Glu Gly Leu Glu Val Glu Gly Leu Ala Val Lys Ser Glu Trp Ser
                405                 410                 415

Asn Ile Ser Gly Asn Leu Val Ile Glu Ser Val Leu Glu Thr Lys Ile
            420                 425                 430

Ser Glu Pro Thr Ser Leu Gly Gln Ser Leu Ile Asp Tyr Tyr Lys Asn
        435                 440                 445

Asn Asn Gln Gly Tyr Arg Val Lys Asp Phe Thr Asp Glu Asp Leu Asn
    450                 455                 460

Ala Asn Ile Val Asn Val Arg Gly Asn Lys Lys Ile Tyr Met Tyr Ile
465                 470                 475                 480

Pro His Ala Leu Lys Pro Ile Ile Thr Arg Glu Tyr Leu Ala Lys Asn
                485                 490                 495

Asp Pro Glu Phe Ser Lys Glu Ile Glu Gln Leu Ile Lys Met Asn Met
            500                 505                 510

Asn Tyr Arg Tyr Glu Thr Leu Lys Ser Phe Val Asn Asp Ile Gly Val
        515                 520                 525

Ile Glu Glu Leu Asn Asn Leu Ser Phe Lys Asn Lys Tyr Tyr Glu Asp
    530                 535                 540

Val Lys Leu Leu Gly Tyr Ser Ser Gly Lys Ile Asp Glu Pro Val Leu
545                 550                 555                 560

Met Gly Ala Lys Gly Ile Ile Lys Asn Lys Met Gln Ile Phe Ser Asn
                565                 570                 575

Gly Phe Tyr Lys Leu Pro Glu Gly Lys Val Arg Phe Gly Val Leu Tyr
            580                 585                 590

Pro Lys Glu Phe Asp Gly Val Ser Arg Lys Ala Ile Arg Ala Ile Tyr
        595                 600                 605

Asp Phe Ser Lys Glu Gly Lys Tyr His Gly Glu Ser Asn Lys Tyr Ile
    610                 615                 620

Ala Glu His Leu Ile Asn Val Glu Phe Asn Pro Lys Glu Cys Ile Phe
625                 630                 635                 640

Glu Gly Tyr Glu Leu Gly Asp Ile Thr Glu Tyr Lys Lys Ala Ala Leu
                645                 650                 655

Lys Leu Asn Asn Tyr Asn Asn Val Asp Phe Val Ile Ala Ile Val Pro
            660                 665                 670

Asn Met Ser Asp Glu Glu Ile Glu Asn Ser Tyr Asn Pro Phe Lys Lys
        675                 680                 685

Ile Trp Ala Glu Leu Asn Leu Pro Ser Gln Met Ile Ser Val Lys Thr
    690                 695                 700

Ala Glu Ile Phe Ala Asn Ser Arg Asp Asn Thr Ala Leu Tyr Tyr Leu
705                 710                 715                 720

His Asn Ile Val Leu Gly Ile Leu Gly Lys Ile Gly Gly Ile Pro Trp
                725                 730                 735
```

Val Val Lys Asp Met Lys Gly Asp Val Asp Cys Phe Val Gly Leu Asp
740 745 750

Val Gly Thr Arg Glu Lys Gly Ile His Tyr Pro Ala Cys Ser Val Val
755 760 765

Phe Asp Lys Tyr Gly Lys Leu Ile Asn Tyr Tyr Lys Pro Asn Ile Pro
770 775 780

Gln Asn Gly Glu Lys Ile Asn Thr Glu Ile Leu Gln Glu Ile Phe Asp
785 790 795 800

Lys Val Leu Ile Ser Tyr Glu Glu Glu Asn Gly Ala Tyr Pro Lys Asn
805 810 815

Ile Val Ile His Arg Asp Gly Phe Ser Arg Glu Asp Leu Asp Trp Tyr
820 825 830

Glu Asn Tyr Phe Gly Lys Lys Asn Ile Lys Phe Asn Ile Ile Glu Val
835 840 845

Lys Lys Ser Thr Pro Leu Lys Ile Ala Ser Ile Asn Glu Gly Asn Ile
850 855 860

Thr Asn Pro Glu Lys Gly Ser Tyr Ile Leu Arg Gly Asn Lys Ala Tyr
865 870 875 880

Met Val Thr Thr Asp Ile Lys Glu Asn Leu Gly Ser Pro Lys Pro Leu
885 890 895

Lys Ile Glu Lys Ser Tyr Gly Asp Ile Asp Met Leu Thr Ala Leu Ser
900 905 910

Gln Ile Tyr Ala Leu Thr Gln Ile His Val Gly Ala Thr Lys Ser Leu
915 920 925

Arg Leu Pro Ile Thr Thr Gly Tyr Ala Asp Lys Ile Cys Lys Ala Ile
930 935 940

Glu Phe Ile Pro Gln Gly Arg Val Asp Asn Arg Leu Phe Phe Leu
945 950 955

<210> SEQ ID NO 102
<211> LENGTH: 2373
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 102
atgcccaaga aaaagcgaaa ggtagaggac cccaaaaaga aacgcaaagt gggctccgga 60
agcgggaagc ccatcccaaa cccgctgttg ggcttggatt ccacgggcag cggaagctct 120
atggtcggcg gctataaagt cagcaatttg acagtggaag cgttcgaagg tatcgggagt 180
gtcaacccga tgctgtttta ccaatacaaa gtcaccggaa agggaaagta cgataatgtg 240
tataagatta tcaaaagcgc acggtacaag atgcattcta agaaccgatt caagcccgtg 300
ttcatcaagg acgacaaact gtacaccctc gagaagctcc cggatataga ggacctggat 360
ttcgcaaaca ttaacttcgt gaaaagcgag gttctcagca tagaggataa tatgtcaatt 420
tatggcgagg tggtggaata ctatatcaat ctcaagctga aaaaagtgaa ggtgttggga 480
aaatacccca agtacaggat caattacagc aaagagattc tcagtaatac gctgctgaca 540
cgagagctca aagacgagtt taagaaatca aataagggtt ttaacctgaa acggaagttt 600
agaatttccc ccgtggtgaa taagatgggc aaagtgatac tctatttgtc ctgcagtgct 660
gatttcagca ccaacaagaa catttacgaa atgttgaaag agggcttgga ggttgagggg 720
ctggccgtta agagcgagtg gagcaatatc agtggcaacc tggtgatcga gagcgtactg 780
gaaaccaaga tatccgagcc cactagcctg ggccaatccc tgatagacta ctataagaat 840
aacaaccagg gctatagggt gaaggatttc accgatgagg atctgaatgc caacattgtc 900
aacgtgagag gaaataagaa gatctatatg tatattccgc acgcgttgaa gccgataatc 960
acccgggagt acctggccaa gaacgatcca gagttttcta aggagatcga gcagcttatc 1020
aagatgaata tgaactaccg atatgaaacc ctcaagtcat ttgtgaatga catcggggtc 1080
attgaggagc tgaacaacct gagcttcaaa aacaaatact acgaagatgt gaaactgctg 1140
ggttactcca gcggcaaaat agacgaaccc gtcctgatgg gggcaaaagg gatcataaag 1200
aacaaaatgc agatttttc caatggattc tacaaactcc ccgaaggcaa ggtacgattt 1260
ggcgttctgt acccaaaaga atttgatggc gtgtcaagga aagctatccg cgccatttat 1320
gacttcagta aggagggcaa ataccacggc gaaagcaaca agtatatcgc ggaacacctg 1380
ataaacgtgg agttcaatcc aaaggagtgc atatttgagg gatacgaact gggcgatatc 1440
accgaataca agaaggcggc tctgaaactt aataactaca acaatgtcga cttcgtaatc 1500
gcaatagtcc cgaacatgtc cgacgaagag atagagaaca gctacaatcc gttcaagaaa 1560
atatgggccg aactgaatct gcccagccag atgattagcg tcaagacggc cgaaatcttt 1620
gccaatagca gggataacac ggcgctttac tatctgcata acatcgtcct cggtatcctg 1680
ggtaagatag gagggattcc ctgggtggtt aaagacatga agggcgacgt ggattgcttc 1740
gttggactcg atgtcggcac cagggagaag ggcatacatt accccgcctg cagcgttgtg 1800
tttgacaagt acggcaagct tattaactat tacaagccta acatcccgca gaacggagag 1860
aagattaaca cagaaatact tcaggaaatt ttcgacaagg tgctcataag ctatgaggag 1920
gagaatggag cctacccgaa gaatatcgtg atccacaggg acggctttag ccgagaggac 1980
cttgactggt atgagaacta cttcggtaag aaaaacataa agtttaacat catcgaagtc 2040
aaaaagtcaa ctccgttgaa aatcgccagt ataaacgagg gaaatatcac gaatcctgaa 2100
aagggttcct acatcctgcg cggcaacaaa gcctacatgg tgaccacaga tattaaggaa 2160
aacctgggaa gcccaaagcc cctgaagata gaaaagagct acggcgacat agacatgctc 2220
acagctctca gccaaatata cgcactcacg caaatccatg tgggggcgac caaaagcctg 2280
cgcctcccaa tcaccaccgg ctacgccgac aagatttgca aggcgatcga gttcatcccc 2340
caagggcgcg tggacaaccg ccttttcttt ctg 2373

<210> SEQ ID NO 103
<211> LENGTH: 2820
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 103
atgcccaaga aaaagcgaaa ggtagaggac cccaaaaaga aacgcaaagt gggctccgga 60
agcgggaagc ccatcccaaa cccgctgttg ggcttggatt ccacgagtat ggaagagaag 120
gtcggaaatc tcaaacccaa catggagagc gtcaacgtga ctgtcagagt gcttgaggct 180
agtgaggctc gtcaaataca aactaagaac ggcgtgcgaa cgatctctga agcaatcgtg 240
ggagacgaga caggtcgggt caagcttaca ctttggggaa agcacgcagg gtccattaaa 300
gaggggcaag tggtcaagat cgaaaatgca tggaccacgg cctttaaggg tcaagtccaa 360
ctcaacgctg gctctaaaac aaagatcgcg gaagccagcg aggatgggtt tcccgagtct 420

```
tcccaaatac ctgagaatac ccccacagcc cctcaacaaa tgcgcggcgg cggaaggggt    480
tttaggggtg gcgggagacg gtacgggaga aggggcggaa ggagacagga gaatgaggaa    540
ggagaggaag agggtggagg aggaagtatg gtcggcggct ataaagtcag caatttgaca    600
gtggaagcgt tcgaaggtat cgggagtgtc aacccgatgc tgttttacca atacaaagtc    660
accggaaagg gaaagtacga taatgtgtat aagattatca aaagcgcacg gtacaagatg    720
cattctaaga accgattcaa gcccgtgttc atcaaggacg acaaactgta caccctcgag    780
aagctcccgg atatagagga cctggatttc gcaaacatta acttcgtgaa aagcgaggtt    840
ctcagcatag aggataatat gtcaatttat ggcgaggtgg tggaatacta tatcaatctc    900
aagctgaaaa aagtgaaggt gttgggaaaa taccccaagt acaggatcaa ttacagcaaa    960
gagattctca gtaatacgct gctgacacga gagctcaaag acgagtttaa gaaatcaaat   1020
aagggtttta acctgaaacg gaagtttaga atttcccccg tggtgaataa gatgggcaaa   1080
gtgatactct atttgtcctg cagtgctgat ttcagcacca acaagaacat ttacgaaatg   1140
ttgaaagagg gcttggaggt tgaggggctg gccgttaaga gcgagtggag caatatcagt   1200
ggcaacctgg tgatcgagag cgtactggaa accaagatat ccgagcccac tagcctgggc   1260
caatccctga tagactacta taagaataac aaccagggct atagggtgaa ggatttcacc   1320
gatgaggatc tgaatgccaa cattgtcaac gtgagaggaa ataagaagat ctatatgtat   1380
attccgcacg cgttgaagcc gataatcacc cgggagtacc tggccaagaa cgatccagag   1440
ttttctaagg agatcgagca gcttatcaag atgaatatga actaccgata tgaaaccctc   1500
aagtcatttg tgaatgacat cggggtcatt gaggagctga acaacctgag cttcaaaaac   1560
aaatactacg aagatgtgaa actgctgggt tactccagcg gcaaaataga cgaacccgtc   1620
ctgatggggg caaaagggat cataaagaac aaaatgcaga ttttttccaa tggattctac   1680
aaactccccg aaggcaaggt acgatttggc gttctgtacc caaaagaatt tgatggcgtg   1740
tcaaggaaag ctatccgcgc catttatgac ttcagtaagg agggcaaata ccacggcgaa   1800
agcaacaagt atatcgcgga acacctgata aacgtggagt tcaatccaaa ggagtgcata   1860
tttgagggat acgaactggg cgatatcacc gaatacaaga aggcggctct gaaacttaat   1920
aactacaaca atgtcgactt cgtaatcgca atagtcccga acatgtccga cgaagagata   1980
gagaacagct acaatccgtt caagaaaata tgggccgaac tgaatctgcc cagccagatg   2040
attagcgtca agacggccga aatctttgcc aatagcaggg ataacacggc gctttactat   2100
ctgcataaca tcgtcctcgg tatcctgggt aagataggag ggattccctg ggtggttaaa   2160
gacatgaagg gcgacgtgga ttgcttcgtt ggactcgatg tcggcaccag ggagaagggc   2220
atacattacc ccgcctgcag cgttgtgttt gacaagtacg gcaagcttat taactattac   2280
aagcctaaca tcccgcagaa cggagagaag attaacacag aaatacttca ggaaattttc   2340
gacaaggtgc tcataagcta tgaggaggag aatggagcct acccgaagaa tatcgtgatc   2400
cacagggacg gctttagccg agaggacctt gactggtatg agaactactt cggtaagaaa   2460
aacataaagt ttaacatcat cgaagtcaaa aagtcaactc cgttgaaaat cgccagtata   2520
aacgagggaa atatcacgaa tcctgaaaag ggttcctaca tcctgcgcgg caacaaagcc   2580
tacatggtga ccacagatat taaggaaaac ctgggaagcc caaagcccct gaagatagaa   2640
aagagctacg gcgacataga catgctcaca gctctcagcc aaatatacgc actcacgcaa   2700
atccatgtgg gggcgaccaa aagcctgcgc ctcccaatca ccaccggcta cgccgacaag   2760
```

atttgcaagg cgatcgagtt catcccccaa gggcgcgtgg acaaccgcct tttctttctg 2820

<210> SEQ ID NO 104
<211> LENGTH: 2363
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 104
atgcccaaga aaaagcgaaa ggtagaggac cccaaaaaga aacgcaaagt gggctccgaa 60
gcgggaagcc catcccaaac ccgctgttgg gcttggattc cacgggcagc ggaagctcta 120
tgaataatct gaccttcgag gccttcgagg gtatcggaca attgaacgag ttaaacttct 180
ataagtaccg cctcattggt aagggccaaa tcgacaatgt ccaccaggcc atctggtcag 240
tcaagtacaa acttcaagcg aataatttct tcaagccggt tttcgtcaag ggcgaaattc 300
tgtactcact tgacgagctg aaagtcatcc cggaattcga gaatgtcgag gttattcttg 360
acgggaacat tatcctgagc attagcgaga acaccgacat ttacaaggat gtgatcgtgt 420
tttatatcaa taacgcgttg aagaacatca aggacatcac caactaccgt aagtatatca 480
ctaagaacac ggatgaaatc atttgcaaga gtattttaac gacgaatctc aagtatcaat 540
atatgaagtc agagaaaggg ttcaagttac agcgcaagtt taagatctcc ccggtggtat 600
tccgtaatgg gaaggtcatc ttgtacctta attgcagtag cgacttcagc acagacaaat 660
ccatctacga aatgttaaat gatggactcg gtgttgtggg cctgcaagtg aagaataagt 720
ggactaatgc gaatggcaat atctttattg aaaaggtgct cgacaatacc atctccgatc 780
ccggcacgag tggaaagctg gggcagtccc tgatcgacta ctacatcaat gggaatcaaa 840
agtaccgtgt agagaaattt accgacgagg acaagaatgc aaaggttatc caggccaaaa 900
tcaagaataa aacatacaac tacatcccgc aagctctcac ccccgtaatt acgcgcgagt 960
atctgagtca taccgataag aagtttagca agcaaatcga gaatgtgatt aagatggata 1020
tgaactaccg ctaccagacg ttgaagtctt tcgttgagga cattggcgtg atcaaggagt 1080
taaacaatct gcactttaag aaccaatatt acaccaattt tgactttatg ggttcgaga 1140 gcggggtgct ggaagaacct gtcctgatgg gtgcgaacgg aaagatcaag gacaagaagc 1200
agattttcat caatgggttc tttaagaatc ccaaggagaa cgtaaaattc ggagtactct 1260
acccagaagg ctgtatggag aatgctcaga gcattgctcg ttccatcctc gacttcgcta 1320
cggccggtaa atacaataag caagagaaca agtatatttc gaagaattta atgaacatcg 1380
gattcaaacc ttctgagtgt atctttgagt cgtataagtt gggagacatc accgagtata 1440
aggcgacggc ccgtaagctc aaggagcatg agaaagttgg gttcgttatc gcagtgatcc 1500
ctgacatgaa tgagctggaa gtcgagaacc cttataaccc cttcaagaag gtctgggcga 1560
aactcaatat cccatcccag atgatcacat tgaagaccac cgaaaagttc aagaatatcg 1620
tcgacaagtc aggcttgtac tacttacaca atatcgccct taatattctc ggcaaaatcg 1680
gcggaatccc gtggattatt aaagacatgc ctggcaacat cgactgtttc atcggtttag 1740
acgtcggcac gcgcgagaag ggcatccact tcccggcatg ttctgtgttg ttcgacaagt 1800
acggaaagtt aatcaattat tacaagccga ctattccgca gagcggagag aagattgctg 1860
agacaatttt acaggagatc ttcgacaacg tgttaatcag ctacaaagag gaaaacgggg 1920
agtaccccaa gaatatcgtt atccatcgtg atggcttcag ccgtgagaac atcgattggt 1980
acaaagaata cttcgataag aagggtatca agttcaacat tattgaggtt aagaagaaca 2040
ttcccgtaaa gatcgcgaag gtggttggat ccaatatctg caacccgatc aagggctctt 2100
atgtgcttaa gaatgataag gcattcatcg taaccaccga tatcaaagac ggtgtggctt 2160
ctccaaatcc acttaaaatc gagaaaacct atggtgacgt tgagatgaag agtattctgg 2220
agcagatcta cagtctgagc caaattcatg ttggctcaac caagtccctg cgtcttccta 2280
tcacaacggg atatgccgat aagatctgta aggcaattga atacattccg caaggagtcg 2340
tagacaatcg tttgttcttt ctt 2363

<210> SEQ ID NO 105
<211> LENGTH: 2235
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 105
atgcccaaga aaaagcgaaa ggtagaggac cccaaaaaga aacgcaaagt gggctccgga 60
agcgggaagc ccatcccaaa cccgctgttg ggcttggatt ccacgggcag cggaagctct 120
atgaaggagt ttaacgtcat cacagagttc aagaacggta ttaattcgaa gagcatcgag 180
atctatattt acaagatgat ggttcgtgac tttgagaagc gtcacaatga aaattatgac 240
gtggtaaaag agcttattaa cctgaacaat aatagtacga ttgtctttta tgagcaatat 300
atcgcctcat tcaaggaaat cgagaagtgg ggtaacgagc aatacattaa tgttgagaaa 360
cgcgcaatta acctggaaag caacgagaag aagattcttg aacgccttct gttaaaggag 420
atcaagaaca acatcgataa caataagtac aaggtagtga aggattcgat ctacatcaac 480
aagcctgtgt ataacgaaaa gggtatcaaa atcgaccgct acttcaactt agacatcaac 540
gtagaatcaa acggagacat cattattggc ttcgatatta gccataattt cgagtatatt 600
aacacgttag agtacgaaat caagaacaac aatatcaaga ttggagaccg cgtaaaggat 660
tacttttaca accttactta tgaatatgtt ggcatcgcgc cgttcactat ttccgaagag 720
aatgaatata tgggatgtag catcgtggac tactatgaaa ataagaacca gagctacatc 780
gtgaacaagt tgccaaagga tatgaaggca atcttagtta agaacaataa gaacagcatt 840
ttcccgtaca tcccttcacg tcttaagaag gtttgtcgtt tcgagaatct gccccaaaac 900
gtactccgtg attttaacac gcgcgtcaag cagaaaacta atgagaagat gcaatttatg 960
gtggacgagg ttatcaacat tgtaaagaat agcgagcata tcgacgtaaa gaagaagaac 1020
atgatgtgtg acaatatcgg gtacaagatt gaggacctgc aacaacctga ccttttgttt 1080
ggaaacgccc gcgcgcagcg ttacccactg tatggattga agaactttgg cgtgtacgaa 1140
aacaagcgca ttgaaatcaa gtactttatc gacccgattc tcgccaagag caagatgaat 1200
ctggaaaaga tctccaagtt ctgtgatgag ctggagcagt ttagctccaa gttaggagta 1260
ggattaaatc gcgtaaaact gaacaatatt gttaacttca aggagattcg tatggacaat 1320
gaggacatct tctcctacga gattcgcaaa attgtgagca actataatga gacaacgatc 1380
gtgattctgt cggaagagaa ccttaataag tattacaaca tcattaagaa aaccttcagc 1440
ggtggcaacg aggttccgac gcaatgcatt ggtttcaaca cactttccta cacggagaag 1500
aacaaggact caattttctt aaatatttta cttggtgttt acgccaagtc aggaatccaa 1560
ccgtggatcc tcaatgagaa attgaattcc gactgtttca ttggtttaga tgtctcccgt 1620
gagaataagg taaacaaggc cggcgtcatt caagttgtcg gaaaagatgg ccgcgtactc 1680
aagaccaagg tcatcagttc gagccaaagc ggggagaaga tcaagctgga aacgttacgc 1740
gagatcgtgt tcgaggcgat taactcgtat gagaatacct accgctgtaa accaaaacac 1800
attacattcc accgtgacgg tattaatcgt gaggagctgg agaatcttaa gaatacgatg 1860
accaatcttg gtgttgagtt tgactacatc gagatcacca agggcattaa ccgccgcatt 1920
gccaccatca gtgagggcga ggagtggaag actatcatgg gccgctgtta ttataaggac 1980
aattctgcct acgtctgcac tactaagcct tatgagggaa tcggaatggc aaagcccatt 2040
cgcatccgcc gcgtgtttgg cacgcttgat atcgagaaaa ttgttgaaga cgcgtataaa 2100
cttactttta tgcatgtagg cgcgatcaat aaaattcgtc ttccaattac aacctattac 2160
gcagatctca gctccactta cggaaatcgc gacttaattc cgacgaatat tgataccaat 2220
tgcctctact tcatt 2235

<210> SEQ ID NO 106
<211> LENGTH: 2877
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 106
atgggcaaac caatacctaa cccactcctc ggactggact ctaccgggag tggctccatg 60
ccaaagaaga aaaggaaagt ggaagatcct aagaagaagc gaaaggtcgg tagcggttca 120
agtatggaag agaaggtcgg aaatctcaaa cccaacatgg agagcgtcaa cgtgactgtc 180
agagtgcttg aggctagtga ggctcgtcaa atacaaacta agaacggcgt gcgaacgatc 240
tctgaagcaa tcgtgggaga cgagacaggt cgggtcaagc ttacactttg gggaaagcac 300
gcagggtcca ttaaagaggg gcaagtggtc aagatcgaaa atgcatggac cacggccttt 360
aagggtcaag tccaactcaa cgctggctct aaaacaaaga tcgcggaagc cagcgaggat 420
gggtttcccg agtcttccca aatacctgag aataccccca cagcccctca acaaatgcgc 480
ggcggcggaa ggggttttag gggtggcggg agacggtacg ggagaagggg cggaaggaga 540
caggagaatg aggaaggaga ggaagagggt ggaggaggaa gtccagcagc caaacgggtc 600
aagcttgacg gcggcggcgg gtctatggtg ggcgggtaca aggtgtcaaa cctcactgtc 660
gaggcctttg aggggattgg ctcagtaaat cccatgctct tctatcagta taaggtgaca 720
ggcaaaggca aatatgacaa cgtctacaaa atcattaagt ccgccagata taaaatgcac 780
tccaagaacc ggtttaaacc tgtattcatt aaagatgaca agctgtacac cctcgagaag 840
ctcccggata tagaggacct ggatttcgca aacattaact tcgtgaaaag cgaggttctc 900
agcatagagg ataatatgtc aatttatggc gaggtggtgg aatactatat caatctcaag 960
ctgaaaaaag tgaaggtgtt gggaaaatac cccaagtaca ggatcaatta cagcaaagag 1020
attctcagta atacgctgct gacacgagag ctcaaagacg agtttaagaa atcaaataag 1080
ggttttaacc tgaaacggaa gtttagaatt tccccccgtgg tgaataagat gggcaaagtg 1140
atactctatt tgtcctgcag tgctgatttc agcaccaaca agaacattta cgaaatgttg 1200
aaagagggct tggaggttga ggggctggcc gttaagagcg agtggagcaa tatcagtggc 1260
aacctggtga tcgagagcgt actggaaacc aagatatccg agcccactag cctgggccaa 1320
tccctgatag actactataa gaataacaac cagggctata gggtgaagga tttcaccgat 1380

-continued

```
gaggatctga atgccaacat tgtcaacgtg agaggaaata agaagatcta tatgtatatt   1440

ccgcacgcgt tgaagccgat aatcacccgg gagtacctgg ccaagaacga tccagagttt   1500

tctaaggaga tcgagcagct tatcaagatg aatatgaact accgatatga aaccctcaag   1560

tcatttgtga atgacatcgg ggtcattgag gagctgaaca acctgagctt caaaaacaaa   1620

tactacgaag atgtgaaact gctgggttac tccagcggca aaatagacga acccgtcctg   1680

atgggggcaa aagggatcat aaagaacaaa atgcagattt tttccaatgg attctacaaa   1740

ctccccgaag gcaaggtacg atttggcgtt ctgtacccaa aagaatttga tggcgtgtca   1800

aggaaagcta tccgcgccat ttatgacttc agtaaggagg gcaaatacca cggcgaaagc   1860

aacaagtata tcgcggaaca cctgataaac gtggagttca atccaaagga gtgcatattt   1920

gagggatacg aactgggcga tatcaccgaa tacaagaagg cggctctgaa acttaataac   1980

tacaacaatg tcgacttcgt aatcgcaata gtcccgaaca tgtccgacga agagatagag   2040

aacagctaca atccgttcaa gaaaatatgg gccgaactga atctgcccag ccagatgatt   2100

agcgtcaaga cggccgaaat ctttgccaat agcagggata acacggcgct ttactatctg   2160

cataacatcg tcctcggtat cctgggtaag ataggaggga ttccctgggt ggttaaagac   2220

atgaagggcg acgtggattg cttcgttgga ctcgatgtcg gcaccaggga gaagggcata   2280

cattaccccg cctgcagcgt tgtgtttgac aagtacggca agcttattaa ctattacaag   2340

cctaacatcc cgcagaacgg agagaagatt aacacagaaa tacttcagga aattttcgac   2400

aaggtgctca taagctatga ggaggagaat ggagcctacc cgaagaatat cgtgatccac   2460

agggacggct ttagccgaga ggaccttgac tggtatgaga actacttcgg taagaaaaac   2520

ataaagttta acatcatcga agtcaaaaag tcaactccgt tgaaaatcgc cagtataaac   2580

gagggaaata tcacgaatcc tgaaaagggt tcctacatcc tgcgcggcaa caaagcctac   2640

atggtgacca cagatattaa ggaaaacctg ggaagcccaa agcccctgaa gatagaaaag   2700

agctacggcg acatagacat gctcacagct ctcagccaaa tatacgcact cacgcaaatc   2760

catgtggggg cgaccaaaag cctgcgcctc ccaatcacca ccggctacgc cgacaagatt   2820

tgcaaggcga tcgagttcat cccccaaggg cgcgtggaca accgcctttt ctttctg      2877
```

<210> SEQ ID NO 107
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 107

```
gctgccatcc agatcgttat c                                               21
```

<210> SEQ ID NO 108
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 108

```
ggagctgtag tagccgccgt c                                               21
```

<210> SEQ ID NO 109
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 109
tagccgccgt cgcgcaggct g 21

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 110
gataacgatc tggatggcag c 21

<210> SEQ ID NO 111
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 111
ggagctgtag tagccgccgt c 21

<210> SEQ ID NO 112
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 112
cagcctgcgc gacggcggct a 21

<210> SEQ ID NO 113
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 113
aattcgcgtt aaatttttgt t 21

<210> SEQ ID NO 114
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 114
aacaaaaatt taacgcgaat t 21

<210> SEQ ID NO 115
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 115

gccctgaaaa taaagattct c                                              21


<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116

gagaatcttt attttcaggg c                                              21


<210> SEQ ID NO 117
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117

gcccccgatt tagagcttga c                                              21


<210> SEQ ID NO 118
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118

gtcaagctct aaatcggggg c                                              21


<210> SEQ ID NO 119
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119

ccacacccgc cgcgcttaat g                                              21


<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120

cattaagcgc ggcgggtgtg g                                              21


<210> SEQ ID NO 121
<211> LENGTH: 21
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 121
ggggaaagcc ggcgaacgtg g 21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 122
ccacgttcgc cggctttccc c 21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 123
ggccccaagg ggttatgcta g 21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 124
ctagcataac cccttggggc c 21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 125
tattattttc tcccatgaag a 21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 126
tcttcatggg agaaaataat a 21

<210> SEQ ID NO 127
<211> LENGTH: 21
<212> TYPE: DNA
<213> ORGANISM: Artificial Sequence
<220> FEATURE:

<223> OTHER INFORMATION: Description of Artificial Sequence: Synthetic
oligonucleotide

<400> SEQUENCE: 127
agaacgtgga ctccaacgtc a 21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 128
tgacgttgga gtccacgttc t 21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 129
taaccaatag gccgaaatcg g 21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 130
ccgatttcgg cctattggtt a 21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 131
tatttagaaa aataaacaaa t 21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 132
atttgtttat ttttctaaat a 21

<210> SEQ ID NO 133
<211> LENGTH: 144
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 133
attagacata atttatagta gaaatataga aattctatct aactatattt aagttcaatt 60
gatatcttta aagattatag tcacagtaat aagaattgtt aactatactt tgatatcttt 120
gacttattag ttaagtctta gaaa 144

<210> SEQ ID NO 134
<211> LENGTH: 748
<212> TYPE: PRT
<213> ORGANISM: Clostridium butyricum

<400> SEQUENCE: 134

Met Asn Asn Leu Thr Phe Glu Ala Phe Glu Gly Ile Gly Gln Leu Asn
1 5 10 15

Glu Leu Asn Phe Tyr Lys Tyr Arg Leu Ile Gly Lys Gly Gln Ile Asp
20 25 30

Asn Val His Gln Ala Ile Trp Ser Val Lys Tyr Lys Leu Gln Ala Asn
35 40 45

Asn Phe Phe Lys Pro Val Phe Val Lys Gly Glu Ile Leu Tyr Ser Leu
50 55 60

Asp Glu Leu Lys Val Ile Pro Glu Phe Glu Asn Val Glu Val Ile Leu
65 70 75 80

Asp Gly Asn Ile Ile Leu Ser Ile Ser Glu Asn Thr Asp Ile Tyr Lys
85 90 95

Asp Val Ile Val Phe Tyr Ile Asn Asn Ala Leu Lys Asn Ile Lys Asp
100 105 110

Ile Thr Asn Tyr Arg Lys Tyr Ile Thr Lys Asn Thr Asp Glu Ile Ile
115 120 125

Cys Lys Ser Ile Leu Thr Thr Asn Leu Lys Tyr Gln Tyr Met Lys Ser
130 135 140

Glu Lys Gly Phe Lys Leu Gln Arg Lys Phe Lys Ile Ser Pro Val Val
145 150 155 160

Phe Arg Asn Gly Lys Val Ile Leu Tyr Leu Asn Cys Ser Ser Asp Phe
165 170 175

Ser Thr Asp Lys Ser Ile Tyr Glu Met Leu Asn Asp Gly Leu Gly Val
180 185 190

Val Gly Leu Gln Val Lys Asn Lys Trp Thr Asn Ala Asn Gly Asn Ile
195 200 205

Phe Ile Glu Lys Val Leu Asp Asn Thr Ile Ser Asp Pro Gly Thr Ser
210 215 220

Gly Lys Leu Gly Gln Ser Leu Ile Asp Tyr Tyr Ile Asn Gly Asn Gln
225 230 235 240

Lys Tyr Arg Val Glu Lys Phe Thr Asp Glu Asp Lys Asn Ala Lys Val
245 250 255

Ile Gln Ala Lys Ile Lys Asn Lys Thr Tyr Asn Tyr Ile Pro Gln Ala
260 265 270

Leu Thr Pro Val Ile Thr Arg Glu Tyr Leu Ser His Thr Asp Lys Lys
275 280 285

Phe Ser Lys Gln Ile Glu Asn Val Ile Lys Met Asp Met Asn Tyr Arg
290 295 300

Tyr Gln Thr Leu Lys Ser Phe Val Glu Asp Ile Gly Val Ile Lys Glu
305 310 315 320

Leu Asn Asn Leu His Phe Lys Asn Gln Tyr Tyr Thr Asn Phe Asp Phe

```
                325                 330                 335

Met Gly Phe Glu Ser Gly Val Leu Glu Glu Pro Val Leu Met Gly Ala
            340                 345                 350

Asn Gly Lys Ile Lys Asp Lys Lys Gln Ile Phe Ile Asn Gly Phe Phe
        355                 360                 365

Lys Asn Pro Lys Glu Asn Val Lys Phe Gly Val Leu Tyr Pro Glu Gly
    370                 375                 380

Cys Met Glu Asn Ala Gln Ser Ile Ala Arg Ser Ile Leu Asp Phe Ala
385                 390                 395                 400

Thr Ala Gly Lys Tyr Asn Lys Gln Glu Asn Lys Tyr Ile Ser Lys Asn
                405                 410                 415

Leu Met Asn Ile Gly Phe Lys Pro Ser Glu Cys Ile Phe Glu Ser Tyr
            420                 425                 430

Lys Leu Gly Asp Ile Thr Glu Tyr Lys Ala Thr Ala Arg Lys Leu Lys
        435                 440                 445

Glu His Glu Lys Val Gly Phe Val Ile Ala Val Ile Pro Asp Met Asn
    450                 455                 460

Glu Leu Glu Val Glu Asn Pro Tyr Asn Pro Phe Lys Lys Val Trp Ala
465                 470                 475                 480

Lys Leu Asn Ile Pro Ser Gln Met Ile Thr Leu Lys Thr Thr Glu Lys
                485                 490                 495

Phe Lys Asn Ile Val Asp Lys Ser Gly Leu Tyr Tyr Leu His Asn Ile
            500                 505                 510

Ala Leu Asn Ile Leu Gly Lys Ile Gly Gly Ile Pro Trp Ile Ile Lys
        515                 520                 525

Asp Met Pro Gly Asn Ile Asp Cys Phe Ile Gly Leu Asp Val Gly Thr
    530                 535                 540

Arg Glu Lys Gly Ile His Phe Pro Ala Cys Ser Val Leu Phe Asp Lys
545                 550                 555                 560

Tyr Gly Lys Leu Ile Asn Tyr Tyr Lys Pro Thr Ile Pro Gln Ser Gly
                565                 570                 575

Glu Lys Ile Ala Glu Thr Ile Leu Gln Glu Ile Phe Asp Asn Val Leu
            580                 585                 590

Ile Ser Tyr Lys Glu Glu Asn Gly Glu Tyr Pro Lys Asn Ile Val Ile
        595                 600                 605

His Arg Asp Gly Phe Ser Arg Glu Asn Ile Asp Trp Tyr Lys Glu Tyr
    610                 615                 620

Phe Asp Lys Lys Gly Ile Lys Phe Asn Ile Ile Glu Val Lys Lys Asn
625                 630                 635                 640

Ile Pro Val Lys Ile Ala Lys Val Val Gly Ser Asn Ile Cys Asn Pro
                645                 650                 655

Ile Lys Gly Ser Tyr Val Leu Lys Asn Asp Lys Ala Phe Ile Val Thr
            660                 665                 670

Thr Asp Ile Lys Asp Gly Val Ala Ser Pro Asn Pro Leu Lys Ile Glu
        675                 680                 685

Lys Thr Tyr Gly Asp Val Glu Met Lys Ser Ile Leu Glu Gln Ile Tyr
    690                 695                 700

Ser Leu Ser Gln Ile His Val Gly Ser Thr Lys Ser Leu Arg Leu Pro
705                 710                 715                 720

Ile Thr Thr Gly Tyr Ala Asp Lys Ile Cys Lys Ala Ile Glu Tyr Ile
                725                 730                 735

Pro Gln Gly Val Val Asp Asn Arg Leu Phe Phe Leu
            740                 745
```

<210> SEQ ID NO 135
<211> LENGTH: 705
<212> TYPE: PRT
<213> ORGANISM: Clostridium saragoforme

<400> SEQUENCE: 135

Met Lys Glu Phe Asn Val Ile Thr Glu Phe Lys Asn Gly Ile Asn Ser
1               5                   10                  15

Lys Ser Ile Glu Ile Tyr Ile Tyr Lys Met Met Val Arg Asp Phe Glu
            20                  25                  30

Lys Arg His Asn Glu Asn Tyr Asp Val Val Lys Glu Leu Ile Asn Leu
        35                  40                  45

Asn Asn Asn Ser Thr Ile Val Phe Tyr Glu Gln Tyr Ile Ala Ser Phe
    50                  55                  60

Lys Glu Ile Glu Lys Trp Gly Asn Glu Gln Tyr Ile Asn Val Glu Lys
65                  70                  75                  80

Arg Ala Ile Asn Leu Glu Ser Asn Glu Lys Lys Ile Leu Glu Arg Leu
                85                  90                  95

Leu Leu Lys Glu Ile Lys Asn Asn Ile Asp Asn Asn Lys Tyr Lys Val
            100                 105                 110

Val Lys Asp Ser Ile Tyr Ile Asn Lys Pro Val Tyr Asn Glu Lys Gly
        115                 120                 125

Ile Lys Ile Asp Arg Tyr Phe Asn Leu Asp Ile Asn Val Glu Ser Asn
    130                 135                 140

Gly Asp Ile Ile Ile Gly Phe Asp Ile Ser His Asn Phe Glu Tyr Ile
145                 150                 155                 160

Asn Thr Leu Glu Tyr Glu Ile Lys Asn Asn Asn Ile Lys Ile Gly Asp
                165                 170                 175

Arg Val Lys Asp Tyr Phe Tyr Asn Leu Thr Tyr Glu Tyr Val Gly Ile
            180                 185                 190

Ala Pro Phe Thr Ile Ser Glu Glu Asn Glu Tyr Met Gly Cys Ser Ile
        195                 200                 205

Val Asp Tyr Tyr Glu Asn Lys Asn Gln Ser Tyr Ile Val Asn Lys Leu
    210                 215                 220

Pro Lys Asp Met Lys Ala Ile Leu Val Lys Asn Asn Lys Asn Ser Ile
225                 230                 235                 240

Phe Pro Tyr Ile Pro Ser Arg Leu Lys Lys Val Cys Arg Phe Glu Asn
                245                 250                 255

Leu Pro Gln Asn Val Leu Arg Asp Phe Asn Thr Arg Val Lys Gln Lys
            260                 265                 270

Thr Asn Glu Lys Met Gln Phe Met Val Asp Glu Val Ile Asn Ile Val
        275                 280                 285

Lys Asn Ser Glu His Ile Asp Val Lys Lys Lys Asn Met Met Cys Asp
    290                 295                 300

Asn Ile Gly Tyr Lys Ile Glu Asp Leu Gln Gln Pro Asp Leu Leu Phe
305                 310                 315                 320

Gly Asn Ala Arg Ala Gln Arg Tyr Pro Leu Tyr Gly Leu Lys Asn Phe
                325                 330                 335

Gly Val Tyr Glu Asn Lys Arg Ile Glu Ile Lys Tyr Phe Ile Asp Pro
            340                 345                 350

Ile Leu Ala Lys Ser Lys Met Asn Leu Glu Lys Ile Ser Lys Phe Cys
        355                 360                 365

Asp Glu Leu Glu Gln Phe Ser Ser Lys Leu Gly Val Gly Leu Asn Arg 370 375 380

Val Lys Leu Asn Asn Ile Val Asn Phe Lys Glu Ile Arg Met Asp Asn
385 390 395 400

Glu Asp Ile Phe Ser Tyr Glu Ile Arg Lys Ile Val Ser Asn Tyr Asn
405 410 415

Glu Thr Thr Ile Val Ile Leu Ser Glu Glu Asn Leu Asn Lys Tyr Tyr
420 425 430

Asn Ile Ile Lys Lys Thr Phe Ser Gly Gly Asn Glu Val Pro Thr Gln
435 440 445

Cys Ile Gly Phe Asn Thr Leu Ser Tyr Thr Glu Lys Asn Lys Asp Ser
450 455 460

Ile Phe Leu Asn Ile Leu Leu Gly Val Tyr Ala Lys Ser Gly Ile Gln
465 470 475 480

Pro Trp Ile Leu Asn Glu Lys Leu Asn Ser Asp Cys Phe Ile Gly Leu
485 490 495

Asp Val Ser Arg Glu Asn Lys Val Asn Lys Ala Gly Val Ile Gln Val
500 505 510

Val Gly Lys Asp Gly Arg Val Leu Lys Thr Lys Val Ile Ser Ser Ser
515 520 525

Gln Ser Gly Glu Lys Ile Lys Leu Glu Thr Leu Arg Glu Ile Val Phe
530 535 540

Glu Ala Ile Asn Ser Tyr Glu Asn Thr Tyr Arg Cys Lys Pro Lys His
545 550 555 560

Ile Thr Phe His Arg Asp Gly Ile Asn Arg Glu Glu Leu Glu Asn Leu
565 570 575

Lys Asn Thr Met Thr Asn Leu Gly Val Glu Phe Asp Tyr Ile Glu Ile
580 585 590

Thr Lys Gly Ile Asn Arg Arg Ile Ala Thr Ile Ser Glu Gly Glu Glu
595 600 605

Trp Lys Thr Ile Met Gly Arg Cys Tyr Tyr Lys Asp Asn Ser Ala Tyr
610 615 620

Val Cys Thr Thr Lys Pro Tyr Glu Gly Ile Gly Met Ala Lys Pro Ile
625 630 635 640

Arg Ile Arg Arg Val Phe Gly Thr Leu Asp Ile Glu Lys Ile Val Glu
645 650 655

Asp Ala Tyr Lys Leu Thr Phe Met His Val Gly Ala Ile Asn Lys Ile
660 665 670

Arg Leu Pro Ile Thr Thr Tyr Tyr Ala Asp Leu Ser Ser Thr Tyr Gly
675 680 685

Asn Arg Asp Leu Ile Pro Thr Asn Ile Asp Thr Asn Cys Leu Tyr Phe
690 695 700

Ile
705

<210> SEQ ID NO 136
<211> LENGTH: 736
<212> TYPE: PRT
<213> ORGANISM: Clostridium sp.

<400> SEQUENCE: 136

Met Val Gly Leu Asp Arg Glu Phe Asn Val Ile Thr Glu Phe Lys Asn
1 5 10 15

Glu Leu Lys Pro Glu Asp Ile Lys Ile Phe Leu Tyr Ser Met Pro Ile
20 25 30

```
Lys Asp Ile Asn Glu Arg His Ser Glu Asn Tyr Ala Ile Val Gln Glu
        35                  40                  45

Leu Lys Lys Ile Asn Glu Asn Pro Asn Ile Val Phe Asn Glu Tyr Ile
    50                  55                  60

Ile Ala Ser Phe Asn Pro Ile Ile Asn Trp Gly Lys Tyr Lys Asp Ile
65                  70                  75                  80

Asp Val Lys Pro Asp Asn Arg Asn Ile Asn Leu Asp Asn His Thr Glu
                85                  90                  95

Arg Lys Ile Leu Glu Arg Leu Leu Leu Cys Asp Ile Lys Asn Asn Ile
            100                 105                 110

Asn Asn Asn Thr Thr Trp Glu Gln Gln Asn Lys Tyr Glu Ile Arg Gly
        115                 120                 125

Asn Ala Asn Pro Ala Val Tyr Leu Arg Lys Pro Ile Tyr Leu Asn Asp
    130                 135                 140

Asn Leu Ile Ile Arg Arg Lys Leu Asn Phe Asp Val Asn Ile Asp Lys
145                 150                 155                 160

Lys Asp Ile Ile Ile Gly Phe Phe Leu Asn His Glu Phe Glu Tyr Gln
                165                 170                 175

Lys Thr Leu Asp Glu Glu Ile Lys Cys Gly Asn Ile Gln Lys Gly Asp
            180                 185                 190

Lys Val Lys Asp Phe Tyr Asn Asn Ile Thr Tyr Glu Phe Leu Glu Met
        195                 200                 205

Ala Pro Phe Ser Ile Ser Gln Glu Asn Lys Tyr Met Arg Ser Ser Ile
    210                 215                 220

Ile Glu Tyr Tyr Leu Asn Lys Gly Gln Ser Tyr Ile Ile Ser Gly Leu
225                 230                 235                 240

Asp Lys Asn Thr Lys Ala Val Leu Val Lys Asn Lys Glu Gly Ser Ile
                245                 250                 255

Phe Pro Tyr Ile Pro Asn Arg Leu Lys Lys Ile Cys Val Phe Glu Asn
            260                 265                 270

Leu Gly Asn Arg Gln Ile Ile Glu Gly Asn Lys Tyr Ile Lys Met Asn
        275                 280                 285

Pro Ser Gln Asn Met Ser Glu Ser Ile Lys Leu Ala Glu Asp Ile Leu
    290                 295                 300

Lys Asn Ser Lys Tyr Val Lys Phe Asn Lys Ala Asn Met Ile Val Glu
305                 310                 315                 320

Lys Ile Gly Tyr Lys Lys Asp Ile Val Lys Arg Pro Ala Leu Lys Phe
                325                 330                 335

Gly Lys Asn Glu Ser Asn Phe Ser Ala Met Tyr Gly Leu Asn Lys Ser
            340                 345                 350

Gly Ser Tyr Glu Gln Lys Asn Ile Lys Ile Asp Tyr Phe Ile Asp Pro
        355                 360                 365

Lys Ile Leu Asn Asn Lys Arg Asp Tyr Gln Ile Val Tyr Ser Phe Leu
    370                 375                 380

Asn Asp Ile Ile Ser Lys Ser Lys Asp Leu Gly Val Glu Ile Asn Thr
385                 390                 395                 400

Asp Lys Ser Tyr Ile Asn Leu Thr Pro Ile Asn Ile Lys Asn Glu Asn
                405                 410                 415

Glu Phe Glu Leu Asn Val Met Glu Ile Ile Lys Asn Tyr Asn Asn Pro
            420                 425                 430

Val Leu Val Ile Leu Glu Lys Glu Asn Ile Asp Lys Tyr Tyr Glu Thr
        435                 440                 445

Leu Lys Lys Ile Phe Gly Gly Arg Asn Ser Ile Ala Thr Gln Phe Val
```

```
    450                 455                 460

Asp Leu Asp Thr Ile Lys Arg Cys Asp Pro Lys Ile Asp Asn Lys Arg
465                 470                 475                 480

Gly Lys Glu Ser Ile Phe Leu Asn Ile Leu Leu Gly Ile Tyr Cys Lys
                485                 490                 495

Ser Gly Ile Gln Pro Trp Val Leu Ala Asn Gly Leu Ser Ala Asp Cys
            500                 505                 510

Tyr Ile Gly Leu Asp Val Cys Arg Glu Asn Asn Met Ser Thr Val Gly
        515                 520                 525

Leu Ile Gln Val Ile Gly Lys Asp Gly Arg Val Leu Lys Ser Lys Thr
    530                 535                 540

Ile Ser Ser His Gln Ser Gly Glu Lys Ile Gln Ile Asn Ile Leu Lys
545                 550                 555                 560

Asp Ile Ile Phe Glu Ala Lys Gln Ala Tyr Lys Asn Thr Tyr Asn Lys
                565                 570                 575

Lys Leu Glu His Ile Val Phe His Arg Asp Gly Ile Asn Arg Glu Asp
            580                 585                 590

Ile Asp Leu Leu Lys Glu Ile Thr Asn Ser Leu Glu Ile Lys Phe Asp
        595                 600                 605

Tyr Val Glu Val Thr Lys Asn Ile Asn Arg Arg Met Ala Met Leu Glu
    610                 615                 620

Lys Ser Asp Glu Asn Tyr Asn His Arg Asp Lys Glu Asn Lys Lys Trp
625                 630                 635                 640

Ile Thr Glu Ile Gly Met Cys Leu Lys Lys Glu Asn Glu Ala Tyr Leu
                645                 650                 655

Ile Thr Thr Asn Pro Ser Glu Asn Met Gly Met Ala Arg Pro Leu Arg
            660                 665                 670

Ile Lys Lys Val Tyr Gly Asn Gln Asn Met Asp Asp Ile Val Lys Asp
        675                 680                 685

Ile Tyr Lys Leu Ser Phe Met His Ile Gly Ser Ile Met Lys Ser Arg
    690                 695                 700

Leu Pro Ile Thr Thr His Tyr Ala Asp Leu Ser Ser Ile Tyr Ser His
705                 710                 715                 720

Arg Glu Leu Met Pro Lys Ser Val Asp Asn Asn Ile Leu His Phe Ile
                725                 730                 735
```

<210> SEQ ID NO 137
<211> LENGTH: 2347
<212> TYPE: DNA
<213> ORGANISM: Clostridium butyricum

<400> SEQUENCE: 137

```
tgtacaagct tgccaccatg ggtccgaaga agaaacgcaa ggtcgaggac ccaaagaaga      60

agcgtaaggt tggatcgggt tctatgaata atctgacctt cgaggccttc gagggtatcg     120

gacaattgaa cgagttaaac ttctataagt accgcctcat tggtaagggc caaatcgaca     180

atgtccacca ggccatctgg tcagtcaagt acaaacttca agcgaataat ttcttcaagc     240

cggttttcgt caagggcgaa attctgtact cacttgacga gctgaaagtc atcccggaat     300

tcgagaatgt cgaggttatt cttgacggga acattatcct gagcattagc gagaacaccg     360

acatttacaa ggatgtgatc gtgttttata tcaataacgc gttgaagaac atcaaggaca     420

tcaccaacta ccgtaagtat atcactaaga acacggatga aatcatttgc aagagtattt     480

taacgacgaa tctcaagtat caatatatga agtcagagaa agggttcaag ttacagcgca     540
```

agtttaagat ctccccggtg gtattccgta atgggaaggt catcttgtac cttaattgca 600
gtagcgactt cagcacagac aaatccatct acgaaatgtt aaatgatgga ctcggtgttg 660
tgggcctgca agtgaagaat aagtggacta atgcgaatgg caatatcttt attgaaaagg 720
tgctcgacaa taccatctcc gatcccggca cgagtggaaa gctggggcag tccctgatcg 780
actactacat caatgggaat caaaagtacc gtgtagagaa atttaccgac gaggacaaga 840
atgcaaaggt tatccaggcc aaaatcaaga ataaaacata caactacatc ccgcaagctc 900
tcacccccgt aattacgcgc gagtatctga gtcataccga taagaagttt agcaagcaaa 960
tcgagaatgt gattaagatg gatatgaact accgctacca gacgttgaag tctttcgttg 1020
aggacattgg cgtgatcaag gagttaaaca atctgcactt taagaaccaa tattacacca 1080
attttgactt tatggggttc gagagcgggg tgctggaaga acctgtcctg atgggtgcga 1140
acggaaagat caaggacaag aagcagattt tcatcaatgg gttctttaag aatcccaagg 1200
agaacgtaaa attcggagta ctctacccag aaggctgtat ggagaatgct cagagcattg 1260
ctcgttccat cctcgacttc gctacggccg gtaaatacaa taagcaagag aacaagtata 1320
tttcgaagaa tttaatgaac atcggattca aaccttctga gtgtatcttt gagtcgtata 1380
agttgggaga catcaccgag tataaggcga cggcccgtaa gctcaaggag catgagaaag 1440
ttgggttcgt tatcgcagtg atccctgaca tgaatgagct ggaagtcgag aacccttata 1500
accccttcaa gaaggtctgg gcgaaactca atatcccatc ccagatgatc acattgaaga 1560
ccaccgaaaa gttcaagaat atcgtcgaca agtcaggctt gtactactta cacaatatcg 1620
cccttaatat tctcggcaaa atcggcggaa tcccgtggat tattaaagac atgcctggca 1680
acatcgactg tttcatcggt ttagacgtcg gcacgcgcga gaagggcatc cacttcccgg 1740
catgttctgt gttgttcgac aagtacggaa agttaatcaa ttattacaag ccgactattc 1800
cgcagagcgg agagaagatt gctgagacaa ttttacagga gatcttcgac aacgtgttaa 1860
tcagctacaa agaggaaaac ggggagtacc ccaagaatat cgttatccat cgtgatggct 1920
tcagccgtga gaacatcgat tggtacaaag aatacttcga taagaagggt atcaagttca 1980
acattattga ggttaagaag aacattcccg taaagatcgc gaaggtggtt ggatccaata 2040
tctgcaaccc gatcaagggc tcttatgtgc ttaagaatga taaggcattc atcgtaacca 2100
ccgatatcaa agacggtgtg gcttctccaa atccacttaa aatcgagaaa acctatggtg 2160
acgttgagat gaagagtatt ctggagcaga tctacagtct gagccaaatt catgttggct 2220
caaccaagtc cctgcgtctt cctatcacaa cgggatatgc cgataagatc tgtaaggcaa 2280
ttgaatacat tccgcaagga gtcgtagaca atcgtttgtt ctttctttaa cgtctcgagg 2340
cggccgc 2347

<210> SEQ ID NO 138
<211> LENGTH: 2218
<212> TYPE: DNA
<213> ORGANISM: Clostridium saragoforme

<400> SEQUENCE: 138
tgtacaagct tgccaccatg ggccctaaga agaaacgcaa ggtagaggat ccgaagaaga 60
agcgtaaggt aggttccggt tcgatgaagg agtttaacgt catcacagag ttcaagaacg 120
gtattaattc gaagagcatc gagatctata tttacaagat gatggttcgt gactttgaga 180
agcgtcacaa tgaaaattat gacgtggtaa aagagcttat taacctgaac aataatagta 240
cgattgtctt ttatgagcaa tatatcgcct cattcaagga aatcgagaag tggggtaacg 300

```
agcaatacat taatgttgag aaacgcgcaa ttaacctgga aagcaacgag aagaagattc    360
ttgaacgcct tctgttaaag gagatcaaga acaacatcga taacaataag tacaaggtag    420
tgaaggattc gatctacatc aacaagcctg tgtataacga aaagggtatc aaaatcgacc    480
gctacttcaa cttagacatc aacgtagaat caaacggaga catcattatt ggcttcgata    540
ttagccataa tttcgagtat attaacacgt tagagtacga aatcaagaac aacaatatca    600
agattggaga ccgcgtaaag gattactttt acaaccttac ttatgaatat gttggcatcg    660
cgccgttcac tatttccgaa gagaatgaat atatgggatg tagcatcgtg gactactatg    720
aaaataagaa ccagagctac atcgtgaaca agttgccaaa ggatatgaag gcaatcttag    780
ttaagaacaa taagaacagc attttcccgt acatcccttc acgtcttaag aaggtttgtc    840
gtttcgagaa tctgccccaa aacgtactcc gtgattttaa cacgcgcgtc aagcagaaaa    900
ctaatgagaa gatgcaattt atggtggacg aggttatcaa cattgtaaag aatagcgagc    960
atatcgacgt aaagaagaag aacatgatgt gtgacaatat cgggtacaag attgaggacc   1020
tgcaacaacc tgacctttg tttggaaacg cccgcgcgca gcgttaccca ctgtatggat   1080
tgaagaactt tggcgtgtac gaaaacaagc gcattgaaat caagtacttt atcgacccga   1140
ttctcgccaa gagcaagatg aatctggaaa agatctccaa gttctgtgat gagctggagc   1200
agtttagctc caagttagga gtaggattaa atcgcgtaaa actgaacaat attgttaact   1260
tcaaggagat tcgtatggac aatgaggaca tcttctccta cgagattcgc aaaattgtga   1320
gcaactataa tgagacaacg atcgtgattc tgtcggaaga gaaccttaat aagtattaca   1380
acatcattaa gaaaaccttc agcggtggca acgaggttcc gacgcaatgc attggtttca   1440
acacactttc ctacacggag aagaacaagg actcaatttt cttaaatatt ttacttggtg   1500
tttacgccaa gtcaggaatc caaccgtgga tcctcaatga gaaattgaat tccgactgtt   1560
tcattggttt agatgtctcc cgtgagaata aggtaaacaa ggccggcgtc attcaagttg   1620
tcggaaaaga tggccgcgta ctcaagacca aggtcatcag ttcgagccaa agcggggaga   1680
agatcaagct ggaaacgtta cgcgagatcg tgttcgaggc gattaactcg tatgagaata   1740
cctaccgctg taaaccaaaa cacattacat tccaccgtga cggtattaat cgtgaggagc   1800
tggagaatct taagaatacg atgaccaatc ttggtgttga gtttgactac atcgagatca   1860
ccaagggcat taaccgccgc attgccacca tcagtgaggg cgaggagtgg aagactatca   1920
tgggccgctg ttattataag gacaattctg cctacgtctg cactactaag ccttatgagg   1980
gaatcggaat ggcaaagccc attcgcatcc gccgcgtgtt tggcacgctt gatatcgaga   2040
aaattgttga agacgcgtat aaacttactt ttatgcatgt aggcgcgatc aataaaattc   2100
gtcttccaat tacaacctat tacgcagatc tcagctccac ttacggaaat cgcgacttaa   2160
ttccgacgaa tattgatacc aattgcctct acttcattta acgtctcgag gcggccgc    2218
```

<210> SEQ ID NO 139
<211> LENGTH: 2311
<212> TYPE: DNA
<213> ORGANISM: Clostridium sp.

<400> SEQUENCE: 139

```
tgtacaagct tgccaccatg ggaccgaaga agaagcgtaa ggtcgaggat cccaagaaga     60
agcgtaaggt gggatccggg tcgatggtgg gcctggaccg cgaattcaac gtgatcaccg    120
agttcaagaa tgagcttaag cccgaggaca tcaagatctt cttatactcg atgccgatca    180
```

```
aggatattaa tgagcgccat tcagagaatt atgcaattgt ccaagagctc aagaagatca    240
acgagaaccc taacattgta tttaacgagt acatcatcgc cagcttcaat cctattatta    300
attggggcaa gtacaaggac atcgatgtta agccggacaa tcgtaatatt aatctggata    360
accacactga gcgcaaaatc ctggagcgtt tattactctg tgacattaag aataacatta    420
acaataatac tacctgggag caacagaata aatacgagat tcgcggtaat gctaacccgg    480
cagtatatct tcgcaagccc atctatctga acgataactt gattatccgc cgtaagctga    540
attttgacgt taatattgac aagaaagaca tcattatcgg cttcttcctg aatcatgagt    600
ttgaatacca aaagacgtta gacgaggaaa tcaagtgtgg caacattcag aagggcgaca    660
aagtgaagga cttctataat aatattacat atgaattctt ggagatggcc ccatttagca    720
tctcacaaga aaataaatac atgcgcagta gcattatcga gtattatttg aacaagggcc    780
aaagctacat catttccggc ttggataaga acactaaggc cgtacttgtt aagaacaaag    840
agggcagtat cttcccctat atccccaatc gccttaagaa aatctgcgtc tttgagaatc    900
tcggcaaccg ccagatcatc gaagggaata agtacatcaa gatgaaccct agtcaaaata    960
tgagtgaaag catcaagttg gcggaagata tccttaagaa ttcgaagtat gtgaagttta   1020
acaaggcgaa catgatcgtg gagaaaatcg gttacaagaa ggacatcgtg aagcgccctg   1080
cgttaaagtt tggcaagaat gagagcaatt tcagcgccat gtacggcctt aacaagagcg   1140
gtagttacga gcagaagaat attaagatcg actatttcat tgacccgaag attcttaata   1200
acaagcgcga ttaccagatc gtatactcct tcctcaacga tattattagt aaatcgaagg   1260
acttgggagt cgagatcaac acggacaaga gctatatcaa tttaactcca atcaacatta   1320
agaatgaaaa tgagtttgag ctgaacgtca tggaaatcat taagaattac aataacccag   1380
tacttgtgat tcttgagaag gagaatatcg acaagtatta tgaaaccctt aagaagatct   1440
tcggcggccg taactcaatc gcaacccaat tcgtggatct ggacacgatc aagcgctgcg   1500
accctaagat cgataacaag cgtggaaagg aatcgatctt cttaaacatc ctcttgggca   1560
tctactgtaa gtcgggtatt caaccttggg ttttagcgaa tggtctgagc gctgactgtt   1620
acattggcct cgacgtttgt cgcgagaata atatgtccac tgtggggttg attcaagtca   1680
tcgggaagga cggtcgtgta ctcaaaagta agactattag cagccatcaa agtggggaaa   1740
agattcaaat taatattttg aaggatatca tcttcgaggc caagcaagcg tataagaata   1800
cgtataacaa gaagctggaa cacatcgttt tccaccgcga cggcatcaat cgtgaagaca   1860
ttgacctttt gaaggagatt acgaactccc tggagattaa gtttgactac gtcgaggtaa   1920
caaagaatat taaccgccgt atggcgatgt tagagaaaag cgatgagaac tataaccacc   1980
gtgacaagga gaataagaag tggattacgg aaattggtat gtgccttaag aaggaaaatg   2040
aggcctatct cattaccacc aatcctagcg agaatatggg tatggcccgt cctcttcgca   2100
ttaagaaggt gtacggtaac cagaacatgg acgacatcgt taaggacatc tacaagctgt   2160
ccttcatgca cattggtagc attatgaagt ctcgtcttcc aatcacaacc cattacgcgg   2220
atttatcttc tatctacagc caccgtgaat tgatgcctaa gtccgtcgat aataacatcc   2280
tgcactttat ttaacgtctc gaggcggccg c                                  2311
```

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 140

Gly Ser Gly Ser Ser
1 5

<210> SEQ ID NO 141
<211> LENGTH: 281
<212> TYPE: PRT
<213> ORGANISM: Clostridium perfringens

<400> SEQUENCE: 141

Phe Val Ile Ala Ile Val Pro Asn Met Ser Asp Glu Glu Ile Glu Asn
1 5 10 15

Ser Tyr Asn Pro Phe Lys Lys Ile Trp Ala Glu Leu Asn Leu Pro Ser
20 25 30

Gln Met Ile Ser Val Lys Thr Ala Glu Ile Phe Ala Asn Ser Arg Asp
35 40 45

Asn Thr Ala Leu Tyr Tyr Leu His Asn Ile Val Leu Gly Ile Leu Gly
50 55 60

Lys Ile Gly Gly Ile Pro Trp Val Val Lys Asp Met Lys Gly Asp Val
65 70 75 80

Asp Cys Phe Val Gly Leu Asp Val Gly Thr Arg Glu Lys Gly Ile His
85 90 95

Tyr Pro Ala Cys Ser Val Val Phe Asp Lys Tyr Gly Lys Leu Ile Asn
100 105 110

Tyr Tyr Lys Pro Asn Ile Pro Gln Asn Gly Glu Lys Ile Asn Thr Glu
115 120 125

Ile Leu Gln Glu Ile Phe Asp Lys Val Leu Ile Ser Tyr Glu Glu Glu
130 135 140

Asn Gly Ala Tyr Pro Lys Asn Ile Val Ile His Arg Asp Gly Phe Ser
145 150 155 160

Arg Glu Asp Leu Asp Trp Tyr Glu Asn Tyr Phe Gly Lys Lys Asn Ile
165 170 175

Lys Phe Asn Ile Ile Glu Val Lys Lys Ser Thr Pro Leu Lys Ile Ala
180 185 190

Ser Ile Asn Glu Gly Asn Ile Thr Asn Pro Glu Lys Gly Ser Tyr Ile
195 200 205

Leu Arg Gly Asn Lys Ala Tyr Met Val Thr Thr Asp Ile Lys Glu Asn
210 215 220

Leu Gly Ser Pro Lys Pro Leu Lys Ile Glu Lys Ser Tyr Gly Asp Ile
225 230 235 240

Asp Met Leu Thr Ala Leu Ser Gln Ile Tyr Ala Leu Thr Gln Ile His
245 250 255

Val Gly Ala Thr Lys Ser Leu Arg Leu Pro Ile Thr Thr Gly Tyr Ala
260 265 270

Asp Lys Ile Cys Lys Ala Ile Glu Phe
275 280

<210> SEQ ID NO 142
<211> LENGTH: 282
<212> TYPE: PRT
<213> ORGANISM: Clostridium butyricum

<400> SEQUENCE: 142

Phe Val Ile Ala Val Ile Pro Asp Met Asn Glu Leu Glu Val Glu Asn
1 5 10 15

```
Pro Tyr Asn Pro Phe Lys Lys Val Trp Ala Lys Leu Asn Ile Pro Ser
            20                  25                  30

Gln Met Ile Thr Leu Lys Thr Thr Glu Lys Phe Lys Asn Ile Val Asp
        35                  40                  45

Lys Ser Gly Leu Tyr Tyr Leu His Asn Ile Ala Leu Asn Ile Leu Gly
    50                  55                  60

Lys Ile Gly Gly Ile Pro Trp Ile Ile Lys Asp Met Pro Gly Asn Ile
65                  70                  75                  80

Asp Cys Phe Ile Gly Leu Asp Val Gly Thr Arg Glu Lys Gly Ile His
                85                  90                  95

Phe Pro Ala Cys Ser Val Leu Phe Asp Lys Tyr Gly Lys Leu Ile Asn
            100                 105                 110

Tyr Tyr Lys Pro Thr Ile Pro Gln Ser Gly Glu Lys Ile Ala Glu Thr
        115                 120                 125

Ile Leu Gln Glu Ile Phe Asp Asn Val Leu Ile Ser Tyr Lys Glu Glu
    130                 135                 140

Asn Gly Glu Tyr Pro Lys Asn Ile Val Ile His Arg Asp Gly Phe Ser
145                 150                 155                 160

Arg Glu Asn Ile Asp Trp Tyr Lys Glu Tyr Phe Asp Lys Lys Gly Ile
                165                 170                 175

Lys Phe Asn Ile Ile Glu Val Lys Lys Asn Ile Pro Val Lys Ile Ala
            180                 185                 190

Lys Val Val Gly Ser Asn Ile Cys Asn Pro Ile Lys Gly Ser Tyr Val
        195                 200                 205

Leu Lys Asn Asp Lys Ala Phe Ile Val Thr Thr Asp Ile Lys Asp Gly
    210                 215                 220

Val Ala Ser Pro Asn Pro Leu Lys Ile Glu Lys Thr Tyr Gly Asp Val
225                 230                 235                 240

Glu Met Lys Ser Ile Leu Glu Gln Ile Tyr Ser Leu Ser Gln Ile His
                245                 250                 255

Val Gly Ser Thr Lys Ser Leu Arg Leu Pro Ile Thr Thr Gly Tyr Ala
            260                 265                 270

Asp Lys Ile Cys Lys Ala Ile Glu Tyr Ile
        275                 280


<210> SEQ ID NO 143
<211> LENGTH: 276
<212> TYPE: PRT
<213> ORGANISM: Clostridium saragoforme

<400> SEQUENCE: 143

Thr Thr Ile Val Ile Leu Ser Glu Glu Asn Leu Asn Lys Tyr Tyr Asn
1               5                   10                  15

Ile Ile Lys Lys Thr Phe Ser Gly Gly Asn Glu Val Pro Thr Gln Cys
            20                  25                  30

Ile Gly Phe Asn Thr Leu Ser Tyr Thr Glu Lys Asn Lys Asp Ser Ile
        35                  40                  45

Phe Leu Asn Ile Leu Leu Gly Val Tyr Ala Lys Ser Gly Ile Gln Pro
    50                  55                  60

Trp Ile Leu Asn Glu Lys Leu Asn Ser Asp Cys Phe Ile Gly Leu Asp
65                  70                  75                  80

Val Ser Arg Glu Asn Lys Val Asn Lys Ala Gly Val Ile Gln Val Val
                85                  90                  95

Gly Lys Asp Gly Arg Val Leu Lys Thr Lys Val Ile Ser Ser Ser Gln
```

```
            100                 105                 110

Ser Gly Glu Lys Ile Lys Leu Glu Thr Leu Arg Glu Ile Val Phe Glu
        115                 120                 125

Ala Ile Asn Ser Tyr Glu Asn Thr Tyr Arg Cys Lys Pro Lys His Ile
    130                 135                 140

Thr Phe His Arg Asp Gly Ile Asn Arg Glu Glu Leu Glu Asn Leu Lys
145                 150                 155                 160

Asn Thr Met Thr Asn Leu Gly Val Glu Phe Asp Tyr Ile Glu Ile Thr
                165                 170                 175

Lys Gly Ile Asn Arg Arg Ile Ala Thr Ile Ser Glu Gly Glu Glu Trp
            180                 185                 190

Lys Thr Ile Met Gly Arg Cys Tyr Tyr Lys Asp Asn Ser Ala Tyr Val
        195                 200                 205

Cys Thr Thr Lys Pro Tyr Glu Gly Ile Gly Met Ala Lys Pro Ile Arg
    210                 215                 220

Ile Arg Arg Val Phe Gly Thr Leu Asp Ile Glu Lys Ile Val Glu Asp
225                 230                 235                 240

Ala Tyr Lys Leu Thr Phe Met His Val Gly Ala Ile Asn Lys Ile Arg
                245                 250                 255

Leu Pro Ile Thr Thr Tyr Tyr Ala Asp Leu Ser Ser Thr Tyr Gly Asn
            260                 265                 270

Arg Asp Leu Ile
        275


<210> SEQ ID NO 144
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 144

catggactaa ttatggacag                                                20


<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 145

tcatggacta attatggaca g                                              21


<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 146

ctgtccataa ttagtccatg a                                              21


<210> SEQ ID NO 147
<211> LENGTH: 21
<212> TYPE: DNA
<213> ORGANISM: Artificial Sequence
```

<220> FEATURE:
<223> OTHER INFORMATION: Description of Artificial Sequence: Synthetic
oligonucleotide

<400> SEQUENCE: 147
tatgaaactt tctattaaat t 21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
aatttaatag aaagtttcat a 21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
ttttttactt tttcttgtgt t 21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 150
aacacaagaa aaagtaaaaa a 21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
aattcgcgtt aaatttttgt t 21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
aacaaaaatt taacgcgaat t 21

<210> SEQ ID NO 153
<211> LENGTH: 6
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 153

Gly Ser Gly Ser Gly Ser
1               5

<210> SEQ ID NO 154
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154

Gly Ser Gly Ser
1

<210> SEQ ID NO 155
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Gly Gly Ser
1

<210> SEQ ID NO 156
<211> LENGTH: 748
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: E, V or not present
<220> FEATURE:
<221> NAME/KEY: MOD_RES
<222> LOCATION: (4)..(4)
<223> OTHER INFORMATION: F, N or S
<220> FEATURE:
<221> NAME/KEY: MOD_RES
<222> LOCATION: (8)..(8)
<223> OTHER INFORMATION: T, F or V
<220> FEATURE:
<221> NAME/KEY: MOD_RES
<222> LOCATION: (17)..(17)
<223> OTHER INFORMATION: L, V or not present
<220> FEATURE:
<221> NAME/KEY: MOD_RES
<222> LOCATION: (19)..(19)
<223> OTHER INFORMATION: S, E or P
<220> FEATURE:
<221> NAME/KEY: MOD_RES
<222> LOCATION: (20)..(20)
<223> OTHER INFORMATION: I, L or M
<220> FEATURE:
<221> NAME/KEY: MOD_RES
<222> LOCATION: (21)..(21)
<223> OTHER INFORMATION: E, N or L
<220> FEATURE:
<221> NAME/KEY: MOD_RES
<222> LOCATION: (24)..(24)
<223> OTHER INFORMATION: I, K or Q
<220> FEATURE:
<221> NAME/KEY: MOD_RES
<222> LOCATION: (27)..(27)

<223> OTHER INFORMATION: M, L or V
<220> FEATURE:
<221> NAME/KEY: MOD_RES
<222> LOCATION: (28)..(28)
<223> OTHER INFORMATION: M, I or T
<220> FEATURE:
<221> NAME/KEY: MOD_RES
<222> LOCATION: (32)..(32)
<223> OTHER INFORMATION: R, Q or K
<220> FEATURE:
<221> NAME/KEY: MOD_RES
<222> LOCATION: (33)..(33)
<223> OTHER INFORMATION: M, I or Y
<220> FEATURE:
<221> NAME/KEY: MOD_RES
<222> LOCATION: (38)..(38)
<223> OTHER INFORMATION: D, Q or K
<220> FEATURE:
<221> NAME/KEY: MOD_RES
<222> LOCATION: (39)..(39)
<223> OTHER INFORMATION: V, A or I
<220> FEATURE:
<221> NAME/KEY: MOD_RES
<222> LOCATION: (43)..(43)
<223> OTHER INFORMATION: V, A or not present
<220> FEATURE:
<221> NAME/KEY: MOD_RES
<222> LOCATION: (44)..(44)
<223> OTHER INFORMATION: K, R or not present
<220> FEATURE:
<221> NAME/KEY: MOD_RES
<222> LOCATION: (48)..(48)
<223> OTHER INFORMATION: I, Q or H
<220> FEATURE:
<221> NAME/KEY: MOD_RES
<222> LOCATION: (49)..(49)
<223> OTHER INFORMATION: N, A or S
<220> FEATURE:
<221> NAME/KEY: MOD_RES
<222> LOCATION: (50)..(50)
<223> OTHER INFORMATION: L, N or K
<220> FEATURE:
<221> NAME/KEY: MOD_RES
<222> LOCATION: (52)..(52)
<223> OTHER INFORMATION: N, F or R
<220> FEATURE:
<221> NAME/KEY: MOD_RES
<222> LOCATION: (58)..(58)
<223> OTHER INFORMATION: F, V or I
<220> FEATURE:
<221> NAME/KEY: MOD_RES
<222> LOCATION: (60)..(60)
<223> OTHER INFORMATION: E, G or D
<220> FEATURE:
<221> NAME/KEY: MOD_RES
<222> LOCATION: (61)..(61)
<223> OTHER INFORMATION: Q, E or D
<220> FEATURE:
<221> NAME/KEY: MOD_RES
<222> LOCATION: (62)..(62)
<223> OTHER INFORMATION: Y, I or K
<220> FEATURE:
<221> NAME/KEY: MOD_RES
<222> LOCATION: (67)..(67)
<223> OTHER INFORMATION: K, D or E
<220> FEATURE:
<221> NAME/KEY: MOD_RES
<222> LOCATION: (70)..(70)
<223> OTHER INFORMATION: E, K or P
<220> FEATURE:
<221> NAME/KEY: MOD_RES
<222> LOCATION: (71)..(71)
<223> OTHER INFORMATION: K, V or D
<220> FEATURE:
<221> NAME/KEY: MOD_RES
<222> LOCATION: (73)..(73)
<223> OTHER INFORMATION: G, P or E
<220> FEATURE:
<221> NAME/KEY: MOD_RES
<222> LOCATION: (74)..(74)
<223> OTHER INFORMATION: N, E or D
<220> FEATURE:
<221> NAME/KEY: MOD_RES
<222> LOCATION: (75)..(75)
<223> OTHER INFORMATION: E, F or L
<220> FEATURE:
<221> NAME/KEY: MOD_RES
<222> LOCATION: (76)..(76)
<223> OTHER INFORMATION: Q, E or D
<220> FEATURE:
<221> NAME/KEY: MOD_RES
<222> LOCATION: (77)..(77)
<223> OTHER INFORMATION: Y, N or F
<220> FEATURE:
<221> NAME/KEY: MOD_RES
<222> LOCATION: (78)..(78)
<223> OTHER INFORMATION: I, V or A
<220> FEATURE:
<221> NAME/KEY: MOD_RES
<222> LOCATION: (81)..(81)
<223> OTHER INFORMATION: I, N or not present
<220> FEATURE:
<221> NAME/KEY: MOD_RES
<222> LOCATION: (82)..(82)
<223> OTHER INFORMATION: L, F or not present
<220> FEATURE:
<221> NAME/KEY: MOD_RES
<222> LOCATION: (83)..(83)
<223> OTHER INFORMATION: D, V or not present
<220> FEATURE:
<221> NAME/KEY: MOD_RES
<222> LOCATION: (84)..(84)
<223> OTHER INFORMATION: E, G or K
<220> FEATURE:
<221> NAME/KEY: MOD_RES
<222> LOCATION: (85)..(85)
<223> OTHER INFORMATION: K, N or S
<220> FEATURE:
<221> NAME/KEY: MOD_RES
<222> LOCATION: (86)..(86)
<223> OTHER INFORMATION: R, I or E
<220> FEATURE:
<221> NAME/KEY: MOD_RES
<222> LOCATION: (87)..(87)
<223> OTHER INFORMATION: A, I or V
<220> FEATURE:
<221> NAME/KEY: MOD_RES
<222> LOCATION: (92)..(92)
<223> OTHER INFORMATION: S, E or D
<220> FEATURE:
<221> NAME/KEY: MOD_RES
<222> LOCATION: (94)..(94)
<223> OTHER INFORMATION: E, T or M
<220> FEATURE:
<221> NAME/KEY: MOD_RES
<222> LOCATION: (95)..(95)
<223> OTHER INFORMATION: K, D or S
<220> FEATURE:
<221> NAME/KEY: MOD_RES
<222> LOCATION: (98)..(98)
<223> OTHER INFORMATION: L, K or G
<220> FEATURE:
<221> NAME/KEY: MOD_RES
<222> LOCATION: (101)..(101)
<223> OTHER INFORMATION: I, V or not present
<220> FEATURE:
<221> NAME/KEY: MOD_RES
<222> LOCATION: (102)..(102)
<223> OTHER INFORMATION: V, E or not present
<220> FEATURE:
<221> NAME/KEY: MOD_RES
<222> LOCATION: (103)..(103)
<223> OTHER INFORMATION: F, Y or not present
<220> FEATURE:
<221> NAME/KEY: MOD_RES
<222> LOCATION: (108)..(108)
<223> OTHER INFORMATION: L, A or K
<220> FEATURE:

<221> NAME/KEY: MOD_RES
<222> LOCATION: (111)..(111)
<223> OTHER INFORMATION: E, N or K
<220> FEATURE:
<221> NAME/KEY: MOD_RES
<222> LOCATION: (114)..(114)
<223> OTHER INFORMATION: N, D or V
<220> FEATURE:
<221> NAME/KEY: MOD_RES
<222> LOCATION: (115)..(115)
<223> OTHER INFORMATION: N, I or L
<220> FEATURE:
<221> NAME/KEY: MOD_RES
<222> LOCATION: (116)..(116)
<223> OTHER INFORMATION: I, T or G
<220> FEATURE:
<221> NAME/KEY: MOD_RES
<222> LOCATION: (117)..(117)
<223> OTHER INFORMATION: D, N or K
<220> FEATURE:
<221> NAME/KEY: MOD_RES
<222> LOCATION: (119)..(119)
<223> OTHER INFORMATION: N, R or P
<220> FEATURE:
<221> NAME/KEY: MOD_RES
<222> LOCATION: (122)..(122)
<223> OTHER INFORMATION: K, I or R
<220> FEATURE:
<221> NAME/KEY: MOD_RES
<222> LOCATION: (123)..(123)
<223> OTHER INFORMATION: V, T or I
<220> FEATURE:
<221> NAME/KEY: MOD_RES
<222> LOCATION: (124)..(124)
<223> OTHER INFORMATION: K, N or not present
<220> FEATURE:
<221> NAME/KEY: MOD_RES
<222> LOCATION: (125)..(125)
<223> OTHER INFORMATION: N, Y or not present
<220> FEATURE:
<221> NAME/KEY: MOD_RES
<222> LOCATION: (126)..(126)
<223> OTHER INFORMATION: T, S or not present
<220> FEATURE:
<221> NAME/KEY: MOD_RES
<222> LOCATION: (127)..(127)
<223> OTHER INFORMATION: D, K or not present
<220> FEATURE:
<221> NAME/KEY: MOD_RES
<222> LOCATION: (130)..(130)
<223> OTHER INFORMATION: K, I or L
<220> FEATURE:
<221> NAME/KEY: MOD_RES
<222> LOCATION: (131)..(131)
<223> OTHER INFORMATION: D, C or S
<220> FEATURE:
<221> NAME/KEY: MOD_RES
<222> LOCATION: (132)..(132)
<223> OTHER INFORMATION: S, K or N
<220> FEATURE:
<221> NAME/KEY: MOD_RES
<222> LOCATION: (133)..(133)
<223> OTHER INFORMATION: I, S or T
<220> FEATURE:
<221> NAME/KEY: MOD_RES
<222> LOCATION: (134)..(134)
<223> OTHER INFORMATION: Y, I or L
<220> FEATURE:
<221> NAME/KEY: MOD_RES
<222> LOCATION: (137)..(137)
<223> OTHER INFORMATION: K, T or R
<220> FEATURE:
<221> NAME/KEY: MOD_RES
<222> LOCATION: (138)..(138)
<223> OTHER INFORMATION: P, N or E
<220> FEATURE:
<221> NAME/KEY: MOD_RES
<222> LOCATION: (141)..(141)
<223> OTHER INFORMATION: Y, D or not present
<220> FEATURE:
<221> NAME/KEY: MOD_RES
<222> LOCATION: (142)..(142)
<223> OTHER INFORMATION: Q, E or not present
<220> FEATURE:
<221> NAME/KEY: MOD_RES
<222> LOCATION: (143)..(143)
<223> OTHER INFORMATION: Y, F or not present
<220> FEATURE:
<221> NAME/KEY: MOD_RES
<222> LOCATION: (144)..(144)
<223> OTHER INFORMATION: M, K or not present
<220> FEATURE:
<221> NAME/KEY: MOD_RES
<222> LOCATION: (153)..(153)
<223> OTHER INFORMATION: D, Q or K
<220> FEATURE:
<221> NAME/KEY: MOD_RES
<222> LOCATION: (157)..(157)
<223> OTHER INFORMATION: N, K or R
<220> FEATURE:
<221> NAME/KEY: MOD_RES
<222> LOCATION: (163)..(163)
<223> OTHER INFORMATION: E, F or N
<220> FEATURE:
<221> NAME/KEY: MOD_RES
<222> LOCATION: (164)..(164)
<223> OTHER INFORMATION: S, R or K
<220> FEATURE:
<221> NAME/KEY: MOD_RES
<222> LOCATION: (173)..(173)
<223> OTHER INFORMATION: D, N or S
<220> FEATURE:
<221> NAME/KEY: MOD_RES
<222> LOCATION: (176)..(176)
<223> OTHER INFORMATION: H, S or A
<220> FEATURE:
<221> NAME/KEY: MOD_RES
<222> LOCATION: (181)..(181)
<223> OTHER INFORMATION: I, D or N
<220> FEATURE:
<221> NAME/KEY: MOD_RES
<222> LOCATION: (183)..(183)
<223> OTHER INFORMATION: T, S or N
<220> FEATURE:
<221> NAME/KEY: MOD_RES
<222> LOCATION: (190)..(190)
<223> OTHER INFORMATION: N, D or E
<220> FEATURE:
<221> NAME/KEY: MOD_RES
<222> LOCATION: (193)..(193)
<223> OTHER INFORMATION: K, G or E
<220> FEATURE:
<221> NAME/KEY: MOD_RES
<222> LOCATION: (195)..(195)
<223> OTHER INFORMATION: V, E or not present
<220> FEATURE:
<221> NAME/KEY: MOD_RES
<222> LOCATION: (198)..(198)
<223> OTHER INFORMATION: R, Q or A
<220> FEATURE:
<221> NAME/KEY: MOD_RES
<222> LOCATION: (201)..(201)
<223> OTHER INFORMATION: D, N or S
<220> FEATURE:
<221> NAME/KEY: MOD_RES
<222> LOCATION: (202)..(202)
<223> OTHER INFORMATION: Y, K or E
<220> FEATURE:
<221> NAME/KEY: MOD_RES
<222> LOCATION: (204)..(204)
<223> OTHER INFORMATION: Y, T or S
<220> FEATURE:
<221> NAME/KEY: MOD_RES
<222> LOCATION: (206)..(206)
<223> OTHER INFORMATION: L, A or I
<220> FEATURE:
<221> NAME/KEY: MOD_RES
<222> LOCATION: (207)..(207)

<223> OTHER INFORMATION: T, N or S
<220> FEATURE:
<221> NAME/KEY: MOD_RES
<222> LOCATION: (210)..(210)
<223> OTHER INFORMATION: Y, I or L
<220> FEATURE:
<221> NAME/KEY: MOD_RES
<222> LOCATION: (214)..(214)
<223> OTHER INFORMATION: G, K or S
<220> FEATURE:
<221> NAME/KEY: MOD_RES
<222> LOCATION: (217)..(217)
<223> OTHER INFORMATION: P, D or E
<220> FEATURE:
<221> NAME/KEY: MOD_RES
<222> LOCATION: (218)..(218)
<223> OTHER INFORMATION: F, N or T
<220> FEATURE:
<221> NAME/KEY: MOD_RES
<222> LOCATION: (224)..(224)
<223> OTHER INFORMATION: N, G or T
<220> FEATURE:
<221> NAME/KEY: MOD_RES
<222> LOCATION: (225)..(225)
<223> OTHER INFORMATION: E, T or S
<220> FEATURE:
<221> NAME/KEY: MOD_RES
<222> LOCATION: (226)..(226)
<223> OTHER INFORMATION: Y, K or not present
<220> FEATURE:
<221> NAME/KEY: MOD_RES
<222> LOCATION: (236)..(236)
<223> OTHER INFORMATION: E, I or K
<220> FEATURE:
<221> NAME/KEY: MOD_RES
<222> LOCATION: (238)..(238)
<223> OTHER INFORMATION: K, G or N
<220> FEATURE:
<221> NAME/KEY: MOD_RES
<222> LOCATION: (241)..(241)
<223> OTHER INFORMATION: S, K or G
<220> FEATURE:
<221> NAME/KEY: MOD_RES
<222> LOCATION: (245)..(245)
<223> OTHER INFORMATION: N, E or K
<220> FEATURE:
<221> NAME/KEY: MOD_RES
<222> LOCATION: (252)..(252)
<223> OTHER INFORMATION: M, K or L
<220> FEATURE:
<221> NAME/KEY: MOD_RES
<222> LOCATION: (255)..(255)
<223> OTHER INFORMATION: I, K or N
<220> FEATURE:
<221> NAME/KEY: MOD_RES
<222> LOCATION: (256)..(256)
<223> OTHER INFORMATION: L, V or I
<220> FEATURE:
<221> NAME/KEY: MOD_RES
<222> LOCATION: (258)..(258)
<223> OTHER INFORMATION: K, Q or N
<220> FEATURE:
<221> NAME/KEY: MOD_RES
<222> LOCATION: (259)..(259)
<223> OTHER INFORMATION: A, V or not present
<220> FEATURE:
<221> NAME/KEY: MOD_RES
<222> LOCATION: (260)..(260)
<223> OTHER INFORMATION: N, K or R
<220> FEATURE:
<221> NAME/KEY: MOD_RES
<222> LOCATION: (261)..(261)
<223> OTHER INFORMATION: N, I or G
<220> FEATURE:
<221> NAME/KEY: MOD_RES
<222> LOCATION: (267)..(267)
<223> OTHER INFORMATION: P, N or M
<220> FEATURE:
<221> NAME/KEY: MOD_RES
<222> LOCATION: (271)..(271)
<223> OTHER INFORMATION: S, Q or H
<220> FEATURE:
<221> NAME/KEY: MOD_RES
<222> LOCATION: (283)..(283)
<223> OTHER INFORMATION: P, S or A
<220> FEATURE:
<221> NAME/KEY: MOD_RES
<222> LOCATION: (284)..(284)
<223> OTHER INFORMATION: Q, H or K
<220> FEATURE:
<221> NAME/KEY: MOD_RES
<222> LOCATION: (287)..(287)
<223> OTHER INFORMATION: K, P or not present
<220> FEATURE:
<221> NAME/KEY: MOD_RES
<222> LOCATION: (288)..(288)
<223> OTHER INFORMATION: K, E or not present
<220> FEATURE:
<221> NAME/KEY: MOD_RES
<222> LOCATION: (292)..(292)
<223> OTHER INFORMATION: D, Q or E
<220> FEATURE:
<221> NAME/KEY: MOD_RES
<222> LOCATION: (295)..(295)
<223> OTHER INFORMATION: T, N or Q
<220> FEATURE:
<221> NAME/KEY: MOD_RES
<222> LOCATION: (296)..(296)
<223> OTHER INFORMATION: R, V or L
<220> FEATURE:
<221> NAME/KEY: MOD_RES
<222> LOCATION: (300)..(300)
<223> OTHER INFORMATION: K, D or N
<220> FEATURE:
<221> NAME/KEY: MOD_RES
<222> LOCATION: (325)..(325)
<223> OTHER INFORMATION: D, H or S
<220> FEATURE:
<221> NAME/KEY: MOD_RES
<222> LOCATION: (332)..(332)
<223> OTHER INFORMATION: M, T or E
<220> FEATURE:
<221> NAME/KEY: MOD_RES
<222> LOCATION: (333)..(333)
<223> OTHER INFORMATION: N, D or not present
<220> FEATURE:
<221> NAME/KEY: MOD_RES
<222> LOCATION: (334)..(334)
<223> OTHER INFORMATION: C, F or V
<220> FEATURE:
<221> NAME/KEY: MOD_RES
<222> LOCATION: (336)..(336)
<223> OTHER INFORMATION: N, F or L
<220> FEATURE:
<221> NAME/KEY: MOD_RES
<222> LOCATION: (337)..(337)
<223> OTHER INFORMATION: I, M or L
<220> FEATURE:
<221> NAME/KEY: MOD_RES
<222> LOCATION: (340)..(340)
<223> OTHER INFORMATION: K, E or S
<220> FEATURE:
<221> NAME/KEY: MOD_RES
<222> LOCATION: (343)..(343)
<223> OTHER INFORMATION: D, V or K
<220> FEATURE:
<221> NAME/KEY: MOD_RES
<222> LOCATION: (345)..(345)
<223> OTHER INFORMATION: Q, E or D
<220> FEATURE:
<221> NAME/KEY: MOD_RES
<222> LOCATION: (355)..(355)
<223> OTHER INFORMATION: R, K or I
<220> FEATURE:
<221> NAME/KEY: MOD_RES
<222> LOCATION: (358)..(358)
<223> OTHER INFORMATION: R, D or N
<220> FEATURE:

<221> NAME/KEY: MOD_RES
<222> LOCATION: (360)..(360)
<223> OTHER INFORMATION: P, K or M
<220> FEATURE:
<221> NAME/KEY: MOD_RES
<222> LOCATION: (364)..(364)
<223> OTHER INFORMATION: L, I or S
<220> FEATURE:
<221> NAME/KEY: MOD_RES
<222> LOCATION: (372)..(372)
<223> OTHER INFORMATION: R, K or E
<220> FEATURE:
<221> NAME/KEY: MOD_RES
<222> LOCATION: (373)..(373)
<223> OTHER INFORMATION: I, E or G
<220> FEATURE:
<221> NAME/KEY: MOD_RES
<222> LOCATION: (374)..(374)
<223> OTHER INFORMATION: E, N or K
<220> FEATURE:
<221> NAME/KEY: MOD_RES
<222> LOCATION: (383)..(383)
<223> OTHER INFORMATION: D, E or K
<220> FEATURE:
<221> NAME/KEY: MOD_RES
<222> LOCATION: (384)..(384)
<223> OTHER INFORMATION: P, G or E
<220> FEATURE:
<221> NAME/KEY: MOD_RES
<222> LOCATION: (385)..(385)
<223> OTHER INFORMATION: I, C or F
<220> FEATURE:
<221> NAME/KEY: MOD_RES
<222> LOCATION: (386)..(386)
<223> OTHER INFORMATION: L, M or D
<220> FEATURE:
<221> NAME/KEY: MOD_RES
<222> LOCATION: (387)..(387)
<223> OTHER INFORMATION: A, E or G
<220> FEATURE:
<221> NAME/KEY: MOD_RES
<222> LOCATION: (388)..(388)
<223> OTHER INFORMATION: K, N or V
<220> FEATURE:
<221> NAME/KEY: MOD_RES
<222> LOCATION: (390)..(390)
<223> OTHER INFORMATION: K, Q or R
<220> FEATURE:
<221> NAME/KEY: MOD_RES
<222> LOCATION: (391)..(391)
<223> OTHER INFORMATION: M, S or K
<220> FEATURE:
<221> NAME/KEY: MOD_RES
<222> LOCATION: (392)..(392)
<223> OTHER INFORMATION: N, I or A
<220> FEATURE:
<221> NAME/KEY: MOD_RES
<222> LOCATION: (393)..(393)
<223> OTHER INFORMATION: L, A or I
<220> FEATURE:
<221> NAME/KEY: MOD_RES
<222> LOCATION: (395)..(395)
<223> OTHER INFORMATION: K, S or A
<220> FEATURE:
<221> NAME/KEY: MOD_RES
<222> LOCATION: (397)..(397)
<223> OTHER INFORMATION: S, L or Y
<220> FEATURE:
<221> NAME/KEY: MOD_RES
<222> LOCATION: (400)..(400)
<223> OTHER INFORMATION: C, A or S
<220> FEATURE:
<221> NAME/KEY: MOD_RES
<222> LOCATION: (401)..(401)
<223> OTHER INFORMATION: D, T or K
<220> FEATURE:
<221> NAME/KEY: MOD_RES
<222> LOCATION: (406)..(406)
<223> OTHER INFORMATION: S, N or H

<220> FEATURE:
<221> NAME/KEY: MOD_RES
<222> LOCATION: (407)..(407)
<223> OTHER INFORMATION: S, K or G
<220> FEATURE:
<221> NAME/KEY: MOD_RES
<222> LOCATION: (408)..(408)
<223> OTHER INFORMATION: K, Q or E
<220> FEATURE:
<221> NAME/KEY: MOD_RES
<222> LOCATION: (409)..(409)
<223> OTHER INFORMATION: L, E or S
<220> FEATURE:
<221> NAME/KEY: MOD_RES
<222> LOCATION: (414)..(414)
<223> OTHER INFORMATION: N, S or A
<220> FEATURE:
<221> NAME/KEY: MOD_RES
<222> LOCATION: (415)..(415)
<223> OTHER INFORMATION: R, K or E
<220> FEATURE:
<221> NAME/KEY: MOD_RES
<222> LOCATION: (416)..(416)
<223> OTHER INFORMATION: V, N or H
<220> FEATURE:
<221> NAME/KEY: MOD_RES
<222> LOCATION: (418)..(418)
<223> OTHER INFORMATION: L, M or I
<220> FEATURE:
<221> NAME/KEY: MOD_RES
<222> LOCATION: (420)..(420)
<223> OTHER INFORMATION: N, I or V
<220> FEATURE:
<221> NAME/KEY: MOD_RES
<222> LOCATION: (421)..(421)
<223> OTHER INFORMATION: I, G or E
<220> FEATURE:
<221> NAME/KEY: MOD_RES
<222> LOCATION: (431)..(431)
<223> OTHER INFORMATION: N, S or G
<220> FEATURE:
<221> NAME/KEY: MOD_RES
<222> LOCATION: (433)..(433)
<223> OTHER INFORMATION: K, E or not present
<220> FEATURE:
<221> NAME/KEY: MOD_RES
<222> LOCATION: (442)..(442)
<223> OTHER INFORMATION: I, A or K
<220> FEATURE:
<221> NAME/KEY: MOD_RES
<222> LOCATION: (443)..(443)
<223> OTHER INFORMATION: R, T or A
<220> FEATURE:
<221> NAME/KEY: MOD_RES
<222> LOCATION: (445)..(445)
<223> OTHER INFORMATION: I, R or L
<220> FEATURE:
<221> NAME/KEY: MOD_RES
<222> LOCATION: (448)..(448)
<223> OTHER INFORMATION: S, K or N
<220> FEATURE:
<221> NAME/KEY: MOD_RES
<222> LOCATION: (452)..(452)
<223> OTHER INFORMATION: E, K or N
<220> FEATURE:
<221> NAME/KEY: MOD_RES
<222> LOCATION: (454)..(454)
<223> OTHER INFORMATION: T, G or D
<220> FEATURE:
<221> NAME/KEY: MOD_RES
<222> LOCATION: (459)..(459)
<223> OTHER INFORMATION: V, I or not present
<220> FEATURE:
<221> NAME/KEY: MOD_RES
<222> LOCATION: (460)..(460)
<223> OTHER INFORMATION: I, V or not present
<220> FEATURE:
<221> NAME/KEY: MOD_RES
<222> LOCATION: (462)..(462)

<223> OTHER INFORMATION: D, N or not present
<220> FEATURE:
<221> NAME/KEY: MOD_RES
<222> LOCATION: (468)..(468)
<223> OTHER INFORMATION: L, V or I
<220> FEATURE:
<221> NAME/KEY: MOD_RES
<222> LOCATION: (471)..(471)
<223> OTHER INFORMATION: Y, P or S
<220> FEATURE:
<221> NAME/KEY: MOD_RES
<222> LOCATION: (478)..(478)
<223> OTHER INFORMATION: T, V or I
<220> FEATURE:
<221> NAME/KEY: MOD_RES
<222> LOCATION: (481)..(481)
<223> OTHER INFORMATION: G, K or E
<220> FEATURE:
<221> NAME/KEY: MOD_RES
<222> LOCATION: (484)..(484)
<223> OTHER INFORMATION: V, I or L
<220> FEATURE:
<221> NAME/KEY: MOD_RES
<222> LOCATION: (490)..(490)
<223> OTHER INFORMATION: G, T or S
<220> FEATURE:
<221> NAME/KEY: MOD_RES
<222> LOCATION: (491)..(491)
<223> OTHER INFORMATION: F, L or V
<220> FEATURE:
<221> NAME/KEY: MOD_RES
<222> LOCATION: (494)..(494)
<223> OTHER INFORMATION: L, T or A
<220> FEATURE:
<221> NAME/KEY: MOD_RES
<222> LOCATION: (496)..(496)
<223> OTHER INFORMATION: Y, K or I
<220> FEATURE:
<221> NAME/KEY: MOD_RES
<222> LOCATION: (498)..(498)
<223> OTHER INFORMATION: E, K or A
<220> FEATURE:
<221> NAME/KEY: MOD_RES
<222> LOCATION: (500)..(500)
<223> OTHER INFORMATION: N, I or S
<220> FEATURE:
<221> NAME/KEY: MOD_RES
<222> LOCATION: (501)..(501)
<223> OTHER INFORMATION: K, V or R
<220> FEATURE:
<221> NAME/KEY: MOD_RES
<222> LOCATION: (503)..(503)
<223> OTHER INFORMATION: S, K or N
<220> FEATURE:
<221> NAME/KEY: MOD_RES
<222> LOCATION: (504)..(504)
<223> OTHER INFORMATION: I, S or T
<220> FEATURE:
<221> NAME/KEY: MOD_RES
<222> LOCATION: (505)..(505)
<223> OTHER INFORMATION: F, G or A
<220> FEATURE:
<221> NAME/KEY: MOD_RES
<222> LOCATION: (513)..(513)
<223> OTHER INFORMATION: L, A or V
<220> FEATURE:
<221> NAME/KEY: MOD_RES
<222> LOCATION: (527)..(527)
<223> OTHER INFORMATION: L, I or V
<220> FEATURE:
<221> NAME/KEY: MOD_RES
<222> LOCATION: (534)..(534)
<223> OTHER INFORMATION: S, I or V
<220> FEATURE:
<221> NAME/KEY: MOD_RES
<222> LOCATION: (551)..(551)
<223> OTHER INFORMATION: K, F or Y
<220> FEATURE:
<221> NAME/KEY: MOD_RES
<222> LOCATION: (571)..(571)
<223> OTHER INFORMATION: S, T or N
<220> FEATURE:
<221> NAME/KEY: MOD_RES
<222> LOCATION: (580)..(580)
<223> OTHER INFORMATION: K, A or N
<220> FEATURE:
<221> NAME/KEY: MOD_RES
<222> LOCATION: (581)..(581)
<223> OTHER INFORMATION: L, E or T
<220> FEATURE:
<221> NAME/KEY: MOD_RES
<222> LOCATION: (590)..(590)
<223> OTHER INFORMATION: E, N or K
<220> FEATURE:
<221> NAME/KEY: MOD_RES
<222> LOCATION: (601)..(601)
<223> OTHER INFORMATION: C, E or A
<220> FEATURE:
<221> NAME/KEY: MOD_RES
<222> LOCATION: (617)..(617)
<223> OTHER INFORMATION: E, N or D
<220> FEATURE:
<221> NAME/KEY: MOD_RES
<222> LOCATION: (626)..(626)
<223> OTHER INFORMATION: T, D or G
<220> FEATURE:
<221> NAME/KEY: MOD_RES
<222> LOCATION: (640)..(640)
<223> OTHER INFORMATION: G, N or S
<220> FEATURE:
<221> NAME/KEY: MOD_RES
<222> LOCATION: (643)..(643)
<223> OTHER INFORMATION: R, V or L
<220> FEATURE:
<221> NAME/KEY: MOD_RES
<222> LOCATION: (647)..(647)
<223> OTHER INFORMATION: T, K or S
<220> FEATURE:
<221> NAME/KEY: MOD_RES
<222> LOCATION: (649)..(649)
<223> OTHER INFORMATION: S, V or N
<220> FEATURE:
<221> NAME/KEY: MOD_RES
<222> LOCATION: (654)..(654)
<223> OTHER INFORMATION: W, C or T
<220> FEATURE:
<221> NAME/KEY: MOD_RES
<222> LOCATION: (662)..(662)
<223> OTHER INFORMATION: Y, V or I
<220> FEATURE:
<221> NAME/KEY: MOD_RES
<222> LOCATION: (665)..(665)
<223> OTHER INFORMATION: D, N or G
<220> FEATURE:
<221> NAME/KEY: MOD_RES
<222> LOCATION: (670)..(670)
<223> OTHER INFORMATION: V, I or M
<220> FEATURE:
<221> NAME/KEY: MOD_RES
<222> LOCATION: (679)..(679)
<223> OTHER INFORMATION: I, V or L
<220> FEATURE:
<221> NAME/KEY: MOD_RES
<222> LOCATION: (690)..(690)
<223> OTHER INFORMATION: V, T or S
<220> FEATURE:
<221> NAME/KEY: MOD_RES
<222> LOCATION: (694)..(694)
<223> OTHER INFORMATION: L, V or I
<220> FEATURE:
<221> NAME/KEY: MOD_RES
<222> LOCATION: (697)..(697)
<223> OTHER INFORMATION: E, K or L
<220> FEATURE:
<221> NAME/KEY: MOD_RES
<222> LOCATION: (698)..(698)
<223> OTHER INFORMATION: K, S or T
<220> FEATURE:

```
<221> NAME/KEY: MOD_RES
<222> LOCATION: (705)..(705)
<223> OTHER INFORMATION: K, S or A
<220> FEATURE:
<221> NAME/KEY: MOD_RES
<222> LOCATION: (735)..(735)
<223> OTHER INFORMATION: L, Y or F
<220> FEATURE:
<221> NAME/KEY: MOD_RES
<222> LOCATION: (740)..(740)
<223> OTHER INFORMATION: I, V or R

<400> SEQUENCE: 156

Met Lys Xaa Xaa Asn Leu Thr Xaa Glu Ala Phe Glu Gly Ile Gly Ser
1               5                   10                  15

Xaa Asn Xaa Xaa Xaa Phe Tyr Xaa Tyr Lys Xaa Xaa Gly Lys Gly Xaa
            20                  25                  30

Xaa Asp Asn Val Tyr Xaa Xaa Ile Lys Ser Xaa Xaa Tyr Lys Leu Xaa
        35                  40                  45

Xaa Xaa Asn Xaa Phe Lys Pro Val Phe Xaa Lys Xaa Xaa Xaa Leu Tyr
    50                  55                  60

Ser Leu Xaa Glu Leu Xaa Xaa Ile Xaa Xaa Xaa Xaa Xaa Xaa Asn Val
65                  70                  75                  80

Xaa Xaa Xaa Xaa Xaa Xaa Xaa Leu Ser Ile Glu Xaa Asn Xaa Xaa Ile
                85                  90                  95

Tyr Xaa Glu Val Xaa Xaa Xaa Tyr Ile Asn Leu Xaa Leu Lys Xaa Ile
            100                 105                 110

Lys Xaa Xaa Xaa Xaa Tyr Xaa Lys Tyr Xaa Xaa Xaa Xaa Xaa Xaa Glu
        115                 120                 125

Ile Xaa Xaa Xaa Xaa Xaa Leu Thr Xaa Xaa Leu Lys Xaa Xaa Xaa Xaa
    130                 135                 140

Lys Ser Glu Lys Gly Phe Lys Leu Xaa Arg Lys Phe Xaa Ile Ser Pro
145                 150                 155                 160

Val Val Xaa Xaa Asn Gly Lys Val Ile Leu Tyr Leu Xaa Cys Ser Xaa
                165                 170                 175

Asp Phe Ser Thr Xaa Lys Xaa Ile Tyr Glu Met Leu Asn Xaa Gly Leu
            180                 185                 190

Xaa Val Xaa Gly Leu Xaa Val Lys Xaa Xaa Trp Xaa Asn Xaa Xaa Gly
        195                 200                 205

Asn Xaa Val Ile Glu Xaa Val Leu Xaa Xaa Thr Ile Ser Glu Pro Xaa
    210                 215                 220

Xaa Xaa Leu Gly Gln Ser Leu Ile Asp Tyr Tyr Xaa Asn Xaa Asn Gln
225                 230                 235                 240

Xaa Tyr Arg Val Xaa Lys Phe Thr Asp Glu Asp Xaa Asn Ala Xaa Xaa
                245                 250                 255

Val Xaa Xaa Xaa Xaa Lys Asn Lys Ile Tyr Xaa Tyr Ile Pro Xaa Ala
            260                 265                 270

Leu Lys Pro Val Ile Thr Arg Glu Tyr Leu Xaa Xaa Asn Asp Xaa Xaa
        275                 280                 285

Phe Ser Lys Xaa Ile Glu Xaa Xaa Ile Lys Met Xaa Met Asn Tyr Arg
    290                 295                 300

Tyr Gln Thr Leu Lys Ser Phe Val Glu Asp Ile Gly Val Ile Lys Glu
305                 310                 315                 320

Leu Asn Asn Leu Xaa Phe Lys Asn Lys Tyr Tyr Xaa Xaa Xaa Asp Xaa
                325                 330                 335

Xaa Gly Tyr Xaa Ser Gly Xaa Leu Xaa Glu Pro Val Leu Met Gly Ala
            340                 345                 350
```

```
Asn Gly Xaa Ile Lys Xaa Lys Xaa Gln Ile Phe Xaa Asn Gly Phe Tyr
        355                 360                 365

Lys Asn Pro Xaa Xaa Xaa Val Lys Phe Gly Val Leu Tyr Pro Xaa Xaa
    370                 375                 380

Xaa Xaa Xaa Xaa Ser Xaa Xaa Xaa Xaa Arg Xaa Ile Xaa Asp Phe Xaa
385                 390                 395                 400

Xaa Glu Gly Lys Tyr Xaa Xaa Xaa Xaa Asn Lys Tyr Ile Xaa Xaa Xaa
                405                 410                 415

Leu Xaa Asn Xaa Xaa Phe Asn Pro Lys Glu Cys Ile Phe Glu Xaa Tyr
            420                 425                 430

Xaa Leu Gly Asp Ile Thr Glu Tyr Lys Xaa Xaa Ala Xaa Lys Leu Xaa
        435                 440                 445

Asn Tyr Asn Xaa Val Xaa Phe Val Ile Ala Xaa Xaa Pro Xaa Met Ser
    450                 455                 460

Glu Glu Glu Xaa Glu Asn Xaa Tyr Asn Pro Phe Lys Lys Xaa Trp Ala
465                 470                 475                 480

Xaa Leu Asn Xaa Pro Ser Gln Met Ile Xaa Xaa Lys Thr Xaa Glu Xaa
                485                 490                 495

Phe Xaa Asn Xaa Xaa Asp Xaa Xaa Xaa Leu Tyr Tyr Leu His Asn Ile
            500                 505                 510

Xaa Leu Gly Ile Leu Gly Lys Ile Gly Gly Ile Pro Trp Ile Xaa Lys
        515                 520                 525

Asp Met Lys Gly Asn Xaa Asp Cys Phe Ile Gly Leu Asp Val Gly Thr
    530                 535                 540

Arg Glu Lys Gly Ile His Xaa Pro Ala Cys Ser Val Val Phe Asp Lys
545                 550                 555                 560

Tyr Gly Lys Leu Ile Asn Tyr Tyr Lys Pro Xaa Ile Pro Gln Ser Gly
                565                 570                 575

Glu Lys Ile Xaa Xaa Glu Ile Leu Gln Glu Ile Phe Asp Xaa Val Leu
            580                 585                 590

Ile Ser Tyr Glu Glu Glu Asn Gly Xaa Tyr Pro Lys Asn Ile Val Ile
        595                 600                 605

His Arg Asp Gly Phe Ser Arg Glu Xaa Leu Asp Trp Tyr Lys Asn Tyr
    610                 615                 620

Phe Xaa Lys Lys Gly Ile Lys Phe Asn Ile Ile Glu Val Lys Lys Xaa
625                 630                 635                 640

Ile Pro Xaa Lys Ile Ala Xaa Ile Xaa Glu Gly Asn Ile Xaa Asn Pro
                645                 650                 655

Ile Lys Gly Ser Tyr Xaa Leu Lys Xaa Asn Lys Ala Tyr Xaa Val Thr
            660                 665                 670

Thr Asp Ile Lys Glu Gly Xaa Gly Ser Pro Lys Pro Leu Lys Ile Glu
        675                 680                 685

Lys Xaa Tyr Gly Asp Xaa Asp Met Xaa Xaa Ile Leu Glu Gln Ile Tyr
    690                 695                 700

Xaa Leu Thr Gln Ile His Val Gly Ala Thr Lys Ser Leu Arg Leu Pro
705                 710                 715                 720

Ile Thr Thr Gly Tyr Ala Asp Lys Ile Cys Lys Ala Ile Glu Xaa Ile
                725                 730                 735

Pro Gln Gly Xaa Val Asp Asn Arg Leu Phe Phe Leu
            740                 745
```

<210> SEQ ID NO 157
<211> LENGTH: 21

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 157
gctgccatcc agatcgttat c 21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 158
cgttatcgcc catggggtgc a 21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 159
gatcgttatc gcccatgggg t 21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 160
ggtgcgggtg aagctgccat c 21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 161
acttagactg aaggtgcggg t 21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 162
agtaatcgtc atcacttaga c 21

<210> SEQ ID NO 163
<211> LENGTH: 772
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 163

Met Pro Lys Lys Lys Arg Lys Val Glu Asp Pro Lys Lys Lys Arg Lys
1 5 10 15

Val Gly Ser Gly Ser Met Val Gly Gly Tyr Lys Val Ser Asn Leu Thr
20 25 30

Val Glu Ala Phe Glu Gly Ile Gly Ser Val Asn Pro Met Leu Phe Tyr
35 40 45

Gln Tyr Lys Val Thr Gly Lys Gly Lys Tyr Asp Asn Val Tyr Lys Ile
50 55 60

Ile Lys Ser Ala Arg Tyr Lys Met His Ser Lys Asn Arg Phe Lys Pro
65 70 75 80

Val Phe Ile Lys Asp Asp Lys Leu Tyr Thr Leu Glu Lys Leu Pro Asp
85 90 95

Ile Glu Asp Leu Asp Phe Ala Asn Ile Asn Phe Val Lys Ser Glu Val
100 105 110

Leu Ser Ile Glu Asp Asn Met Ser Ile Tyr Gly Glu Val Val Glu Tyr
115 120 125

Tyr Ile Asn Leu Lys Leu Lys Lys Val Lys Val Leu Gly Lys Tyr Pro
130 135 140

Lys Tyr Arg Ile Asn Tyr Ser Lys Glu Ile Leu Ser Asn Thr Leu Leu
145 150 155 160

Thr Arg Glu Leu Lys Asp Glu Phe Lys Lys Ser Asn Lys Gly Phe Asn
165 170 175

Leu Lys Arg Lys Phe Arg Ile Ser Pro Val Val Asn Lys Met Gly Lys
180 185 190

Val Ile Leu Tyr Leu Ser Cys Ser Ala Asp Phe Ser Thr Asn Lys Asn
195 200 205

Ile Tyr Glu Met Leu Lys Glu Gly Leu Glu Val Glu Gly Leu Ala Val
210 215 220

Lys Ser Glu Trp Ser Asn Ile Ser Gly Asn Leu Val Ile Glu Ser Val
225 230 235 240

Leu Glu Thr Lys Ile Ser Glu Pro Thr Ser Leu Gly Gln Ser Leu Ile
245 250 255

Asp Tyr Tyr Lys Asn Asn Asn Gln Gly Tyr Arg Val Lys Asp Phe Thr
260 265 270

Asp Glu Asp Leu Asn Ala Asn Ile Val Asn Val Arg Gly Asn Lys Lys
275 280 285

Ile Tyr Met Tyr Ile Pro His Ala Leu Lys Pro Ile Ile Thr Arg Glu
290 295 300

Tyr Leu Ala Lys Asn Asp Pro Glu Phe Ser Lys Glu Ile Glu Gln Leu
305 310 315 320

Ile Lys Met Asn Met Asn Tyr Arg Tyr Glu Thr Leu Lys Ser Phe Val
325 330 335

Asn Asp Ile Gly Val Ile Glu Glu Leu Asn Asn Leu Ser Phe Lys Asn
340 345 350

Lys Tyr Tyr Glu Asp Val Lys Leu Leu Gly Tyr Ser Ser Gly Lys Ile
355 360 365

Asp Glu Pro Val Leu Met Gly Ala Lys Gly Ile Ile Lys Asn Lys Met
370 375 380

```
Gln Ile Phe Ser Asn Gly Phe Tyr Lys Leu Pro Glu Gly Lys Val Arg
385                 390                 395                 400

Phe Gly Val Leu Tyr Pro Lys Glu Phe Asp Gly Val Ser Arg Lys Ala
                405                 410                 415

Ile Arg Ala Ile Tyr Asp Phe Ser Lys Glu Gly Lys Tyr His Gly Glu
            420                 425                 430

Ser Asn Lys Tyr Ile Ala Glu His Leu Ile Asn Val Glu Phe Asn Pro
        435                 440                 445

Lys Glu Cys Ile Phe Glu Gly Tyr Glu Leu Gly Asp Ile Thr Glu Tyr
    450                 455                 460

Lys Lys Ala Ala Leu Lys Leu Asn Asn Tyr Asn Asn Val Asp Phe Val
465                 470                 475                 480

Ile Ala Ile Val Pro Asn Met Ser Asp Glu Glu Ile Glu Asn Ser Tyr
                485                 490                 495

Asn Pro Phe Lys Lys Ile Trp Ala Glu Leu Asn Leu Pro Ser Gln Met
            500                 505                 510

Ile Ser Val Lys Thr Ala Glu Ile Phe Ala Asn Ser Arg Asp Asn Thr
        515                 520                 525

Ala Leu Tyr Tyr Leu His Asn Ile Val Leu Gly Ile Leu Gly Lys Ile
    530                 535                 540

Gly Gly Ile Pro Trp Val Val Lys Asp Met Lys Gly Asp Val Asp Cys
545                 550                 555                 560

Phe Val Gly Leu Asp Val Gly Thr Arg Glu Lys Gly Ile His Tyr Pro
                565                 570                 575

Ala Cys Ser Val Val Phe Asp Lys Tyr Gly Lys Leu Ile Asn Tyr Tyr
            580                 585                 590

Lys Pro Asn Ile Pro Gln Asn Gly Glu Lys Ile Asn Thr Glu Ile Leu
        595                 600                 605

Gln Glu Ile Phe Asp Lys Val Leu Ile Ser Tyr Glu Glu Glu Asn Gly
    610                 615                 620

Ala Tyr Pro Lys Asn Ile Val Ile His Arg Asp Gly Phe Ser Arg Glu
625                 630                 635                 640

Asp Leu Asp Trp Tyr Glu Asn Tyr Phe Gly Lys Lys Asn Ile Lys Phe
                645                 650                 655

Asn Ile Ile Glu Val Lys Lys Ser Thr Pro Leu Lys Ile Ala Ser Ile
            660                 665                 670

Asn Glu Gly Asn Ile Thr Asn Pro Glu Lys Gly Ser Tyr Ile Leu Arg
        675                 680                 685

Gly Asn Lys Ala Tyr Met Val Thr Thr Asp Ile Lys Glu Asn Leu Gly
    690                 695                 700

Ser Pro Lys Pro Leu Lys Ile Glu Lys Ser Tyr Gly Asp Ile Asp Met
705                 710                 715                 720

Leu Thr Ala Leu Ser Gln Ile Tyr Ala Leu Thr Gln Ile His Val Gly
                725                 730                 735

Ala Thr Lys Ser Leu Arg Leu Pro Ile Thr Thr Gly Tyr Ala Asp Lys
            740                 745                 750

Ile Cys Lys Ala Ile Glu Phe Ile Pro Gln Gly Arg Val Asp Asn Arg
        755                 760                 765

Leu Phe Phe Leu
    770
```

<210> SEQ ID NO 164
<211> LENGTH: 766
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 164

Met Pro Lys Lys Lys Arg Lys Val Glu Asp Pro Lys Lys Lys Arg Lys
1               5                   10                  15

Val Gly Ser Gly Ser Met Asn Asn Leu Thr Leu Glu Ala Phe Arg Gly
            20                  25                  30

Ile Gly Thr Ile Lys Pro Leu Leu Phe Tyr Arg Tyr Lys Leu Ile Gly
        35                  40                  45

Lys Gly Lys Ile Glu Asn Thr Tyr Lys Thr Ile Arg Asn Ala Gln Asn
    50                  55                  60

Arg Met Ser Phe Asn Asn Lys Phe Lys Ala Thr Phe Ser Lys Asp Glu
65                  70                  75                  80

Ile Ile Tyr Thr Leu Glu Lys Phe Glu Ile Ile Pro Thr Leu Asp Asp
                85                  90                  95

Val Thr Ile Ile Phe Asp Gly Glu Glu Val Leu Pro Ile Lys Asp Asn
            100                 105                 110

Asn Lys Ile Tyr Ser Glu Val Ile Glu Phe Tyr Ile Asn Asn Asn Leu
        115                 120                 125

Arg Asn Val Lys Phe Asn Tyr Lys Tyr Pro Lys Tyr Arg Ala Ala Asn
    130                 135                 140

Thr Arg Glu Ile Thr Gly Asn Val Ile Leu Asp Lys Asp Met Asn Glu
145                 150                 155                 160

Lys Tyr Lys Lys Ser Asn Lys Gly Phe Glu Leu Lys Arg Lys Phe Ile
                165                 170                 175

Ile Ser Pro Lys Val Asp Asp Glu Gly Lys Val Thr Leu Phe Leu Asp
            180                 185                 190

Leu Asn Ala Ser Phe Asp Tyr Asp Lys Asn Ile Tyr Gln Met Ile Lys
        195                 200                 205

Ala Gly Ile Asp Val Val Gly Glu Glu Val Ile Asn Ile Trp Ser Asn
    210                 215                 220

Lys Lys Gln Arg Gly Lys Ile Lys Glu Ile Ser Asp Ile Lys Ile Asn
225                 230                 235                 240

Glu Pro Cys Asn Phe Gly Gln Ser Leu Ile Asp Tyr Tyr Ile Ser Ser
                245                 250                 255

Asn Gln Ala Ser Arg Val Asn Gly Phe Thr Glu Glu Glu Lys Asn Thr
            260                 265                 270

Asn Val Ile Ile Val Glu Ser Gly Lys Ser Arg Leu Ser Tyr Ile Pro
        275                 280                 285

His Ala Leu Lys Pro Ile Ile Thr Arg Glu Tyr Ile Ala Lys Asn Asp
    290                 295                 300

Glu Val Phe Ser Lys Glu Ile Glu Gly Leu Ile Lys Ile Asn Met Asn
305                 310                 315                 320

Tyr Arg Tyr Glu Ile Leu Lys Arg Phe Val Ser Asp Ile Gly Thr Ile
                325                 330                 335

Lys Glu Leu Asn Asn Leu Arg Phe Glu Lys Ile Tyr Met Asp Asn Ile
            340                 345                 350

Glu Ser Leu Gly Tyr Glu Gln Gly Gln Leu Lys Asp Pro Val Leu Ile
        355                 360                 365

Gly Gly Lys Gly Ile Leu Lys Asp Lys Ile His Val Phe Lys Ser Gly
    370                 375                 380
```

```
Phe Tyr Lys Ser Pro Asn Asp Glu Ile Lys Phe Gly Val Ile Tyr Pro
385                 390                 395                 400

Arg Gly Tyr Ile Lys Asp Thr Gln Ser Val Ile Arg Ala Ile Tyr Asp
                405                 410                 415

Phe Cys Thr Glu Gly Lys Tyr Gln Gly Lys Asp Asn Ile Phe Ile Asn
            420                 425                 430

Asn Lys Leu Met Asn Ile Lys Phe Ser Asn Lys Glu Cys Val Phe Glu
        435                 440                 445

Glu Tyr Glu Leu Asn Asp Ile Thr Glu Tyr Lys Arg Ala Ala Asn Lys
    450                 455                 460

Leu Lys Lys Asn Glu Asn Ile Lys Phe Val Ile Ala Ile Ile Pro Thr
465                 470                 475                 480

Ile Asn Glu Ser Asp Ile Glu Asn Pro Tyr Asn Pro Phe Lys Arg Val
                485                 490                 495

Cys Ala Glu Ile Asn Leu Pro Ser Gln Met Ile Ser Leu Lys Thr Ala
            500                 505                 510

Lys Arg Phe Ser Thr Ser Arg Gly Gln Ser Glu Leu Tyr Phe Leu His
        515                 520                 525

Asn Ile Ser Leu Gly Ile Leu Gly Lys Ile Gly Gly Val Pro Trp Val
    530                 535                 540

Ile Lys Asp Met Pro Gly Glu Val Asp Cys Phe Val Gly Leu Asp Val
545                 550                 555                 560

Gly Thr Lys Glu Lys Gly Ile His Tyr Pro Ala Cys Ser Val Leu Phe
                565                 570                 575

Asp Lys Tyr Gly Lys Leu Ile Asn Tyr Tyr Lys Pro Thr Ile Pro Gln
            580                 585                 590

Ser Gly Glu Ile Ile Lys Thr Asp Val Leu Gln Glu Ile Phe Asp Lys
        595                 600                 605

Val Leu Leu Ser Tyr Glu Glu Glu Asn Gly Gln Tyr Pro Arg Asn Ile
    610                 615                 620

Val Ile His Arg Asp Gly Phe Ser Arg Glu Asp Leu Glu Trp Tyr Lys
625                 630                 635                 640

Asn Tyr Phe Leu Lys Lys Asn Ile Glu Phe Ser Ile Val Glu Val Arg
                645                 650                 655

Lys Asn Phe Ala Thr Arg Leu Val Asn Asn Phe Asn Asp Glu Val Ser
            660                 665                 670

Asn Pro Ser Lys Gly Ser Phe Ile Leu Arg Asp Asn Glu Ala Ile Val
        675                 680                 685

Val Thr Thr Asp Ile Asn Asp Asn Met Gly Ala Pro Lys Pro Ile Lys
    690                 695                 700

Val Glu Lys Thr Tyr Gly Asp Ile Asp Met Leu Thr Ile Ile Asn Gln
705                 710                 715                 720

Ile Tyr Ala Leu Thr Gln Ile His Val Gly Ser Ala Lys Ser Leu Arg
                725                 730                 735

Leu Pro Ile Thr Thr Gly Tyr Ala Asp Lys Ile Cys Lys Ala Ile Asp
            740                 745                 750

Tyr Ile Pro Ser Gly Gln Val Asp Asn Arg Leu Phe Phe Leu
        755                 760                 765
```

<210> SEQ ID NO 165
<211> LENGTH: 766
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 165

```
Met Pro Lys Lys Lys Arg Lys Val Glu Asp Pro Lys Lys Lys Arg Lys
1               5                   10                  15

Val Gly Ser Gly Ser Met Asn Asn Leu Met Leu Glu Ala Phe Lys Gly
            20                  25                  30

Ile Gly Thr Ile Lys Pro Leu Val Phe Tyr Arg Tyr Lys Leu Ile Gly
        35                  40                  45

Lys Gly Lys Ile Glu Asn Thr Tyr Lys Thr Ile Ser Asn Ala Lys Asn
    50                  55                  60

Lys Met Ser Phe Asn Asn Lys Phe Lys Ala Thr Phe Ser Lys Gly Glu
65                  70                  75                  80

Thr Ile Tyr Thr Leu Glu Lys Phe Glu Val Met Pro Asn Leu Asn Asp
                85                  90                  95

Val Thr Ile Glu Phe Asp Gly Glu Glu Val Leu Pro Ile Lys Asp Asn
            100                 105                 110

Asn Glu Ile Tyr Ser Glu Val Val Gln Phe Tyr Ile Asn Asn Asn Leu
        115                 120                 125

Arg Lys Ile Lys Leu Asp Asn Lys Tyr Gln Lys Tyr Arg Ala Thr Asn
    130                 135                 140

Thr Arg Glu Ile Thr Gly Asn Val Ile Leu Asp Lys Asp Phe Lys Glu
145                 150                 155                 160

Lys Tyr Lys Lys Ser Lys Ser Gly Phe Gln Leu Lys Arg Lys Phe Ile
                165                 170                 175

Ile Ser Pro Lys Val Asn Asp Glu Gly Lys Val Thr Leu Phe Leu Asp
            180                 185                 190

Leu Asn Ser Ser Phe Asp Tyr Asp Lys Asn Ile Tyr Gln Met Ile Lys
        195                 200                 205

Ala Gly Met Asp Val Val Gly Gln Glu Val Ile Asn Thr Trp Asn Asn
    210                 215                 220

Lys Lys Gln Lys Gly Lys Ile Lys Lys Ile Ser Glu Leu Thr Ile Ser
225                 230                 235                 240

Glu Pro Cys Asn Phe Gly Gln Ser Leu Ile Asp Tyr Tyr Val Ser Leu
                245                 250                 255

Asn Gln Ala Val Arg Val Lys Asn Phe Thr Glu Glu Glu Lys Asn Thr
            260                 265                 270

Asn Val Ile Val Val Gln Val Gly Lys Gly Glu Val Glu Tyr Ile Pro
        275                 280                 285

His Ala Leu Lys Pro Ile Ile Thr Arg Glu Tyr Ile Lys Lys Tyr Asp
    290                 295                 300

Glu Ala Phe Ser Lys Glu Val Glu Asn Leu Ile Lys Ile Asn Met Ser
305                 310                 315                 320

Tyr Arg Tyr Glu Ile Leu Lys Lys Phe Ile Asp Asp Ile Gly Ser Ile
                325                 330                 335

Thr Glu Leu Asn Asn Leu Lys Phe Glu Asn Thr Tyr Ile Asp Asn Ile
            340                 345                 350

Glu Ser Leu Gly Tyr Gln Gln Gly Lys Leu Asn Asp Pro Val Leu Ile
        355                 360                 365

Gly Gly Lys Gly Ile Leu Lys Asp Lys Ile His Val Phe Lys Ser Gly
    370                 375                 380

Phe Tyr Lys Ser Pro Ile Asp Glu Val Lys Phe Gly Val Ile Tyr Pro
385                 390                 395                 400
```

```
Lys Gly His Thr Asn Asp Ser Lys Ser Thr Ile Arg Ala Ile Tyr Asp
                405                 410                 415

Phe Cys Thr Asp Gly Lys Tyr Gln Gly Lys Asp Asn Ile Phe Ile Asn
            420                 425                 430

Asn Lys Leu Met Asn Ile Lys Phe Ser Asn Gln Asp Cys Val Phe Glu
        435                 440                 445

Glu Tyr Glu Leu Asn Asp Ile Thr Glu Tyr Lys Arg Ala Ala Asn Lys
    450                 455                 460

Leu Lys Asn Asn Glu Asn Ile Lys Phe Val Ile Ala Ile Ile Pro Ala
465                 470                 475                 480

Ile Asp Glu Ser Asp Ile Glu Asn Pro Tyr Asn Pro Phe Lys Arg Val
                485                 490                 495

Cys Ala Glu Leu Asn Leu Pro Ser Gln Met Val Ser Leu Lys Thr Ala
            500                 505                 510

Lys Arg Phe Gly Thr Ser Lys Gly Asn Asn Glu Leu Tyr Phe Leu His
        515                 520                 525

Asn Ile Ser Leu Gly Ile Leu Gly Lys Ile Gly Gly Val Pro Trp Val
    530                 535                 540

Ile Lys Asp Met Pro Gly Glu Val Asp Cys Phe Val Gly Leu Asp Val
545                 550                 555                 560

Gly Thr Lys Glu Lys Gly Ile His Tyr Pro Ala Cys Ser Val Leu Phe
                565                 570                 575

Asp Lys Tyr Gly Lys Leu Ile Asn Tyr Tyr Lys Pro Thr Ile Pro Gln
            580                 585                 590

Ser Gly Glu Ile Ile Lys Thr Asp Val Leu Gln Glu Ile Phe Asp Lys
        595                 600                 605

Val Leu Leu Ser Tyr Glu Glu Asn Gly Gln Tyr Pro Arg Asn Ile
    610                 615                 620

Val Ile His Arg Asp Gly Phe Ser Arg Glu Asp Leu Glu Trp Tyr Lys
625                 630                 635                 640

Asn Tyr Phe Ile Lys Lys Asn Ile Asn Phe Thr Ile Val Glu Ile Lys
                645                 650                 655

Lys Asn Phe Ala Thr Arg Val Ala Asn Asn Ile Asn Asn Glu Val Ser
            660                 665                 670

Asn Pro Phe Lys Gly Ser Phe Ile Leu Arg Glu Asn Glu Ala Ile Val
        675                 680                 685

Val Thr Thr Asp Ile Lys Asp Asn Ile Gly Ala Pro Lys Pro Ile Lys
    690                 695                 700

Val Glu Lys Thr Tyr Gly Asp Ile Asp Met Met Thr Ile Ile Asn Gln
705                 710                 715                 720

Ile Tyr Ala Leu Thr Gln Ile His Val Gly Ser Ala Lys Ser Met Arg
                725                 730                 735

Leu Pro Ile Thr Thr Gly Tyr Ala Asp Lys Ile Cys Lys Ser Ile Glu
            740                 745                 750

Tyr Ile Pro Ser Gly Arg Val Asp Asn Arg Leu Phe Phe Leu
        755                 760                 765
```

<210> SEQ ID NO 166
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (6)..(10)
<223> OTHER INFORMATION: a, c, t, g, unknown or other

<400> SEQUENCE: 166 ggatcnnnnn 10

<210> SEQ ID NO 167
<211> LENGTH: 202
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 167
atatcgatta gacataattt atagtagaaa tatagaaatt ctatctaact atatttaagt 60
tcaattgata tctttaaaga ttatagtcac agtaataaga attgttaact atactttgat 120
atctttgact tattagttaa gtcttagaaa gtacagagta attcatacaa aaggactcgc 180
ccctgccttg gggaatccca gg 202

<210> SEQ ID NO 168
<211> LENGTH: 84
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 168
gctgccatcc agatgatcct ccattttcaa tccgcctggc tgtcattgag gatcatctgg 60
atggcagccg gcccatgggg tgca 84

<210> SEQ ID NO 169
<211> LENGTH: 90
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 169
tgcaccccat gggcgataac gatctggatg gcagcttcac ccgcaccttc agtctaagtg 60
atgacgatta ctgaagctcc gtggtggaca 90

<210> SEQ ID NO 170
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 170
ccacctaaat tgtaagcgtt aatattttgt taaaattcgc gttaaatttt tgttaaatca 60
gctcatttt 69

MESOPHILIC ARGONAUTE SYSTEMS AND USES THEREOF

CROSS-REFERENCE TO RELATED APPLICATIONS

This application is a continuation of International Application No. PCT/US2020/021163, filed on Mar. 5, 2020, which claims priority to U.S. Provisional Patent Application No. 62/814,787 filed on Mar. 6, 2019, the disclosures of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Sep. 1, 2021, is named 2021-09-01 SEQUENCE LISTING 079445-1269242-002410US.txt and is 543,275 bytes in size.

BACKGROUND

With the rapid progress being made in genome sciences, effective genome engineering holds great promise both in understanding the molecular bases of human diseases and in treating human disorders with identifiable alterations in the genome. The past few years have witnessed a rapid rise of the RNA-guided CRISPR/Cas9 technology from obscurity. Significant efforts are being devoted to optimizing the current CRISPR/Cas9 system and to identifying more Cas9-like nucleases with better efficiency and specificity. Similarly, significant efforts are being employed to identify new systems that can be harnessed for genome editing with improved specificity and efficiency.

INCORPORATION BY REFERENCE

All publications, patents, and patent applications herein are incorporated by reference to the same extent as if each individual publication, patent, or patent application was specifically and individually indicated to be incorporated by reference. In the event of a conflict between a term herein and a term in an incorporated reference, the term herein controls.

SUMMARY

In one aspect, provided herein are systems comprising: a. an Argonaute (Ago) polypeptide, or a polynucleic acid encoding the same, wherein said Ago polypeptide is a Clostridia Ago polypeptide, or a functional fragment or functional variant thereof, and b. a non-naturally occurring guiding polynucleic acid comprising a sequence that is complementary to a target polynucleic acid sequence.

In some embodiments, the Ago polypeptide is a mesophilic Clostridia Ago polypeptide.

In some embodiments, the Ago polypeptide demonstrates nucleic acid-cleaving activity of the target polynucleic acid.

In some embodiments, the Ago polypeptide demonstrates nucleic acid-cleaving activity of the target polynucleic acid in a range of temperature of from about 19° C. to about 40° C., 19° C. to about 50° C., 19° C. to about 60° C., 19° C. to about 70° C., 19° C. to about 80° C., 20° C. to about 40° C., 20° C. to about 30° C., 20° C. to about 50° C., 20° C. to about 60° C., 20° C. to about 70° C., 20° C. to about 80° C., 25° C. to about 40° C., 25° C. to about 30° C., or 25° C. to about 50° C. In some embodiments, the Ago polypeptide demonstrates nucleic acid-cleaving activity of the target polynucleic acid at about 19° C., 20° C., 21° C., 22° C., 23° C., 24° C., 25° C., 26° C., 27° C., 28° C., 29° C. 30° C., 31° C., 32° C., 33° C., 34° C., 35° C., 36° C., 37° C., 38° C., 39° C., or 40° C. In some embodiments, the Ago polypeptide demonstrates nucleic acid-cleaving activity of the target polynucleic acid at about 37° C. In some embodiments, the Ago polypeptide demonstrates a maximal nucleic acid-cleaving activity of the target polynucleic acid in a range of temperature of from about 19° C. to about 45° C., 19° C. to about 40° C., 20° C. to about 45° C., 25° C. to about 45° C., 30° C. to about 45° C., or 30° C. to about 40° C., as compared to nucleic acid-cleaving activity at a different temperature.

In some embodiments, the nucleic acid-cleaving activity of the target polynucleic acid is directed by the guiding polynucleic acid.

In some embodiments, the Ago polypeptide demonstrates one, two, three, or four of: single stranded DNA (ssDNA) cleaving activity, double stranded DNA (dsDNA) cleaving activity, single stranded RNA (ssRNA) cleaving activity, or double stranded RNA (dsRNA) cleaving activity. In some embodiments, the Ago polypeptide demonstrates single stranded DNA (ssDNA) cleaving activity In some embodiments, the target polynucleic acid is a single stranded DNA (ssDNA) sequence, a double stranded DNA (dsDNA) sequence, a single stranded RNA (ssRNA) sequence, or a double stranded RNA (dsRNA) sequence. In some embodiments, the target polynucleic acid is a single stranded DNA (ssDNA) sequence.

In some embodiments, the target polynucleic acid is DNA.

In some embodiments, a region of the target DNA sequence that the Ago polypeptide cleaves is about at least 50%, 60%, 70%, 80%, or 90% deoxyadenosine and deoxythymidine.

In some embodiments, said target polynucleic acid comprises a gene sequence. In some embodiments, said Ago polypeptide produces a disruption in said gene sequence when introduced into a cell. In some embodiments, said disruption comprises a double strand break or a single strand break.

In some embodiments, said guiding polynucleic acid is capable of interacting with said Ago polypeptide and directing said Ago polypeptide to said target polynucleic acid. In some embodiments, the guiding polynucleic acid is a guide DNA or a guide RNA. In some embodiments, said guiding polynucleic acid is from about 1 nucleotide to about 30 nucleotides in length.

In some embodiments, said system comprises a complex, and wherein said complex comprises said Ago polypeptide and said guiding polynucleic acid.

In some embodiments, the Ago polypeptide comprises a PIWI-like domain. In some embodiments, the Ago polypeptide comprises a PIWI domain. In some embodiments, the Ago polypeptide comprises a PAZ domain. In some embodiments, the Ago polypeptide comprises a PAZ-like domain.

In some embodiments, the Ago polypeptide is an Ago polypeptide, or a functional fragment or a functional variant thereof, from: Candidatus Comantemales, Clostridiales, Halanaerobiales, Natranaerobiales, Thermoanaerobacterales, or Negativicutes.

In some embodiments, the Ago polypeptide is an Ago polypeptide, or a functional fragment or a functional variant thereof, from: Caldicoprobacteraceae, Christensenellaceae, Clostridiaceae, Defluviitaleaceae, Eubacteriaceae, Graciibacteraceae, Heliobacteriaceae, Lachnospiraceae, Oscillospiraceae, Peptococcaceae, Peptostreptococcaceae, Ruminococcaceae, Syntrophomonadaceae, Halanaerobiaceae, Halobacteroidaceae, Natranaerobiaceae, Thermoanaerobacteraceae, or Thermodesulfobiaceae.

In some embodiments, the Ago polypeptide is a Clostridiaceae Ago polypeptide, or a functional fragment or a functional variant thereof.

In some embodiments, the Ago polypeptide is a *Clostridium, Acetanaerobacterium, Acetivibrio, Acidaminobacter, Alkaliphilus, Anaerobacter, Anaerostipes, Anaerotruncus, Anoxynatronum, Bryantella, Butyricicoccus, Caldanaerocella, Caldisalinibacter, Caloramator, Caloranaerobacter, Caminicella*, Candidatus Arthromitus, *Cellulosibacter, Coprobacillus, Crassaminicella, Dorea, Ethanologenbacterium, Faecalibacterium, Garciella, Guggenheimella, Hespellia, Linmingia, Natronincola, Oxobacter, Parasporobacterium, Sarcina, Soehngenia, Sporobacter, Subdoligranulum, Tepidibacter, Tepidimicrobium, Thermobrachium, Thermohalobacter*, or *Tindallia* Ago polypeptide, or a functional fragment or a functional variant thereof.

In some embodiments, the Ago polypeptide is a *Clostridium* Ago polypeptide, or a functional fragment or a functional variant thereof.

In some embodiments, the Ago polypeptide is a *Clostridium absonum, Clostridium aceticum, Clostridium acetireducens, Clostridium acetobutylicum, Clostridium acidisoli, Clostridium aciditolerans, Clostridium acidurici, Clostridium aerotolerans, Clostridium aestuarii, Clostridium akagii, Clostridium aldenense, Clostridium aldrichii, Clostridium algidicarnis, Clostridium algidixylanolyticum, Clostridium algifaecis, Clostridium algoriphilum, Clostridium alkalicellulosi, Clostridium amazonense, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium budayi, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium cocleatum, Clostridium colicanis, Clostridium colinum, Clostridium collagenovorans, Clostridium combesii, Clostridium cylindrosporum, Clostridium difficile, Clostridium diolis, Clostridium disporicum, Clostridium drakei, Clostridium durum, Clostridium estertheticum, Clostridium estertheticum* sub sp. *Estertheticum, Clostridium estertheticum* sub sp. *Laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium gasigenes, Clostridium ghonii, Clostridium glycolicum, Clostridium glycyrrhizinilyticum, Clostridium grantii, Clostridium guangxiense, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogeniformans, Clostridium hydroxybenzoicum, Clostridium hylemonae, Clostridium indolis, Clostridium innocuum, Clostridium intestinale, Clostridium irregulare, Clostridium isatidis, Clostridium jeddahense, Clostridium jejuense, Clostridium josui, Clostridium kluyveri, Clostridium lactatifermentans, Clostridium lacusfryxellense, Clostridium laramiense, Clostridium lavalense, Clostridium lentocellum, Clostridium lentoputrescens, Clostridium leptum, Clostridium limosum, Clostridium liquoris, Clostridium litorale, Clostridium lituseburense, Clostridium ljungdahlii, Clostridium lortetii, Clostridium lundense, Clostridium luticellarii, Clostridium magnum, Clostridium malenominatum, Clostridium mangenotii, Clostridium maximum, Clostridium mayombei, Clostridium methoxybenzovorans, Clostridium methylpentosum, Clostridium moniliforme, Clostridium neonatale, Clostridium neopropionicum, Clostridium neuense, Clostridium nexile, Clostridium nitritogenes, Clostridium nitrophenolicum, Clostridium novyi, Clostridium oceanicum, Clostridium orbiscindens, Clostridium oroticum, Clostridium oryzae, Clostridium oxalicum, Clostridium pabulibutyricum, Clostridium papyrosolvens, Clostridium paradoxum, Clostridium paraperfringens, Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polyendosporum, Clostridium polysaccharolyticum, Clostridium populeti, Clostridium propionicum, Clostridium proteoclasticum, Clostridium proteolyticum, Clostridium psychrophilum, Clostridium punense, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium saudiense, Clostridium scatologenes, Clostridium schirmacherense, Clostridium scindens, Clostridium senegalense, Clostridium septicum, Clostridium sordellii, Clostridium sphenoides, Clostridium spiroforme, Clostridium sporogenes, Clostridium sporosphaeroides, Clostridium stercorarium, Clostridium stercorarium* sub sp. *leptospartum, Clostridium stercorarium* sub sp. *stercorarium, Clostridium stercorarium* sub sp. *thermolacticum, Clostridium sticklandii, Clostridium straminisolvens, Clostridium subterminale, Clostridium sufflavum, Clostridium sulfidigenes, Clostridium swellfunianum, Clostridium symbiosum, Clostridium tarantellae, Clostridium tagluense, Clostridium tepidiprofundi, Clostridium tepidum, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium ventriculi, Clostridium villosum, Clostridium vincentii, Clostridium viride,*

*Clostridium vulturis*, and *Clostridium xylanolyticum*, or *Clostridium xylanovorans* Ago polypeptide, or a functional fragment or a functional variant thereof.

In some embodiments, the Ago polypeptide is a *Clostridium perfringens*, *Clostridium butyricum*, *Clostridium saudiense*, or *Clostridium disporicum* Ago polypeptide, or a functional fragment or a functional variant thereof.

In some embodiments, said Ago polypeptide comprises an amino acid sequence having at least 80%, 85%, 90%, 95%, 96%, 97%, 98%, 99%, or 100% sequence identity with one of SEQ ID NOs: 1-3 or 134-136.

In some embodiments, said Ago polypeptide is encoded by a polynucleic acid sequence having at least 80%, 85%, 90%, 95%, 96%, 97%, 98%, 99% or 100% sequence identity with one of SEQ ID NOs: 11-14 or 137-139.

In some embodiments, said system comprises a nucleic acid unwinding polypeptide or a polynucleic acid encoding the same.

In some embodiments, said nucleic acid unwinding polypeptide is a helicase, a single strand DNA binding (SSB) protein, or a Clustered Regularly Interspaced Short Palindromic Repeats (CRISPR) associated (Cas) protein domain.

In some embodiments, said nucleic acid unwinding polypeptide is a single strand DNA binding protein (SSB) polypeptide. In some embodiments, said SSB polypeptide comprises an amino acid sequence having at least 80%, 85%, 90%, 95%, 96%, 97%, 98%, 99%, or 100% sequence identity with one of SEQ ID NOs: 22-35. In some embodiments, said SSB polypeptide is encoded by a nucleic acid sequence having at least 80%, 85%, 90%, 95%, 96%, 97%, 98%, 99%, or 100% sequence identity with one of SEQ ID NOs: 36-49. In some embodiments, said SSB polypeptide comprises an amino acid sequence having at least 80%, 85%, 90%, 95%, 96%, 97%, 98%, 99%, or 100% sequence identity with SEQ ID NO: 22. In some embodiments, said SSB polypeptide is encoded by a nucleic acid sequence having at least 80%, 85%, 90%, 95%, 96%, 97%, 98%, 99%, or 100% sequence identity with SEQ ID NO: 36.

In some embodiments, said nucleic acid unwinding polypeptide is a Clustered Regularly Interspaced Short Palindromic Repeats (CRISPR) associated (Cas) protein domain. In some embodiments, said Cas protein domain is a catalytically dead Cas polypeptide.

In some embodiments, said Ago polypeptide is fused either directly or indirectly to a nuclear localization signal (NLS). In some embodiments, said nucleic acid unwinding polypeptide is fused either directly or indirectly to a NLS.

In some embodiments, said Ago polypeptide and said nucleic acid unwinding polypeptide are fused either directly or indirectly. In some embodiments, said Argonaute polypeptide and said nucleic acid unwinding polypeptide are fused and a NLS is in between said Ago polypeptide and said nucleic acid unwinding polypeptide.

In some embodiments, said Ago polypeptide is encoded by a gene located in an adjacent operon to at least one of a gene involved in defense, stress response, gene editing, CRISPR, DNA replication, DNA recombination, DNA repair, and transcription.

In some embodiments, said system comprises one or more recombinant expression vectors. In some embodiments, said one or more recombinant expression vectors comprise an adeno-associated virus vector, a plasmid vector, a retroviral vector, a lentiviral vector, an adenovirus vectors, a poxvirus vectors, a herpesvirus vector, or a split-intron vector.

In some embodiments, said Ago polypeptide, or functional fragment or variant thereof, comprises a DEDX motif sequence. In some embodiments, said DEDX motif sequence comprises a mutation, wherein said mutation reduces catalytic activity of said Ago polypeptide as compared to a corresponding Ago polypeptide without said mutation in said DEDX motif sequence.

In one aspect, provided herein is ex vivo cell (or population of cells) comprising a system described herein. In some embodiments, the cell is a human cell. In some embodiments, the cell is an immune cell, a stem cell, or a germ cell.

In one aspect, provided herein is a recombinant expression vector encoding a system described herein.

In one aspect, provided herein is a pharmaceutical composition comprising a system described herein, and at least one of: an excipient, a diluent, or a carrier. In some embodiments, said pharmaceutical composition is in a form of intravenous, subcutaneous, or intramuscular administration formulation.

In one aspect, provided herein is a kit comprising: (a) a system described herein (b) instructions for use thereof, and optionally (c) a container.

In one aspect, provided herein are polypeptide constructs, wherein said constructs comprise a mesophilic Clostridia Ago (C-Ago) polypeptide sequence, or a functional fragment or a functional variant thereof, wherein said C-Ago polypeptide sequence cleaves a nucleic acid in a target polynucleic acid sequence at a mesophilic temperature, wherein said target polynucleic acid sequence is bound by a non-naturally occurring guide polynucleic acid sequence.

In some embodiments, said C-Ago polypeptide sequence or functional fragment or variant thereof comprises a DEDX motif sequence. In some embodiments, said DEDX motif sequence comprises a mutation, wherein said mutation reduces catalytic activity of said C-Ago polypeptide as compared to a corresponding C-Ago polypeptide without said mutation in said DEDX motif sequence.

In one aspect, provided herein is a nucleic acid molecule encoding a polypeptide construct described herein.

In one aspect, provided herein are recombinant fusion polypeptides, wherein said fusion polypeptides comprise: (a) an Argonaute (Ago) polypeptide, wherein said Ago polypeptide is a Clostridia Ago (C-Ago) polypeptide; and (b) a nucleic acid unwinding polypeptide.

In some embodiments, the nucleic acid unwinding polypeptide comprises a helicase, a single strand DNA binding protein (SSB) polypeptide, or a Cas protein domain.

In some embodiments, the nucleic acid unwinding polypeptide is a single strand DNA binding protein (SSB) polypeptide. In some embodiments, said SSB polypeptide comprises an amino acid sequence having at least 80%, 85%, 90%, 95%, 96%, 97%, 98%, 99%, or 100% sequence identity with one of SEQ ID NOs: 22-35. In some embodiments, said SSB polypeptide is encoded by a nucleic acid sequence having at least 80%, 85%, 90%, 95%, 96%, 97%, 98%, 99%, or 100% sequence identity with one of SEQ ID NOs: 36-49. In some embodiments, said SSB polypeptide comprises an amino acid sequence having at least 80%, 85%, 90%, 95%, 96%, 97%, 98%, 99%, or 100% sequence identity with SEQ ID NO: 22. In some embodiments, said SSB polypeptide is encoded by a nucleic acid sequence having at least 80%, 85%, 90%, 95%, 96%, 97%, 98%, 99%, or 100% sequence identity with SEQ ID NO: 36.

In some embodiments, said nucleic acid unwinding polypeptide is a Cas protein domain. In some embodiments, said Cas protein domain is a catalytically dead Cas polypeptide.

In some embodiments, said fusion polypeptide comprises at least one nuclear localization signal (NLS) polypeptide. In some embodiments, said fusion polypeptide comprises at least two, three, or four NLSs polypeptides. In some embodiments, said fusion polypeptide comprises a nuclear localization signal between said nucleic acid unwinding polypeptide and said C-Ago.

In some embodiments, said C-Ago polypeptide comprises a DEDX motif sequence. In some embodiments, said DEDX motif sequence comprises a mutation, wherein said mutation reduces catalytic activity of said C-Ago polypeptide as compared to a corresponding C-Ago polypeptide without said mutation in said DEDX motif sequence.

In one aspect, provided herein is a nucleic acid encoding a recombinant fusion polypeptide described herein.

In one aspect, provided herein are methods of modifying a target polynucleic acid, said methods comprising: introducing into a cell a system described herein; or a polypeptide construct described herein; or a recombinant fusion polypeptide described herein and a non-naturally occurring guiding polynucleic acid that is complementary to said target polynucleic acid; and modifying said target polynucleic acid.

In one aspect, provided herein are methods of treating a disease or disorder in a subject in need thereof, said method comprising administering to the subject: system described herein, a polypeptide construct described herein, a recombinant fusion polypeptide described herein, a cell described herein, a vector described herein, or a pharmaceutical composition described herein. In some embodiments, said disease is cancer, an autoimmune disease, a genetic disease, or an infection. In some embodiments, said disease is cancer.

In one aspect, provided herein are systems comprising: a mesophilic Argonaute (Ago) polypeptide, or a polynucleic acid encoding the same, or a functional fragment or variant thereof; and an exogenous non-naturally occurring guiding polynucleic acid comprising a sequence that is complementary to a target polynucleic acid sequence.

In some embodiments, said Ago polypeptide comprises an amino acid sequence having at least 80%, 85%, 90%, 95%, 96%, 97%, 98%, 99%, or 100% sequence identity with one of SEQ ID NOs: 4-10 or 134-136. In some embodiments, said Ago polypeptide is encoded by a polynucleic acid sequence having at least 80%, 85%, 90%, 95%, 96%, 97%, 98%, 99%, or 100% sequence identity with one of SEQ ID NOs: 15-21.

In some embodiments, said Ago polypeptide comprises a DEDX motif sequence. In some embodiments, said DEDX motif sequence comprises a mutation, wherein said mutation reduces catalytic activity of said Ago polypeptide as compared to a corresponding Ago polypeptide without said mutation in said DEDX motif sequence.

In some embodiments, the Ago polypeptide demonstrates nucleic acid-cleaving activity of the target polynucleic acid.

In some embodiments, the Ago polypeptide demonstrates nucleic acid-cleaving activity of the target polynucleic acid in a range of temperature of from about 19° C. to about 40° C., 19° C. to about 50° C., 19° C. to about 60° C., 19° C. to about 70° C., 19° C. to about 80° C., 20° C. to about 40° C., 20° C. to about 30° C., 20° C. to about 50° C., 20° C. to about 60° C., 20° C. to about 70° C., 20° C. to about 80° C., 25° C. to about 40° C., 25° C. to about 30° C., or 25° C. to about 50° C. In some embodiments, the Ago polypeptide demonstrates nucleic acid-cleaving activity of the target polynucleic acid at about 19° C., 20° C., 21° C., 22° C., 23° C., 24° C., 25° C., 26° C., 27° C., 28° C., 29° C. 30° C., 31° C., 32° C., 33° C., 34° C., 35° C., 36° C., 37° C., 38° C., 39° C., or 40° C. In some embodiments, the Ago polypeptide demonstrates nucleic acid-cleaving activity of the target polynucleic acid at about 37° C. In some embodiments, the Ago polypeptide demonstrates a maximal nucleic acid-cleaving activity of the target polynucleic acid in a range of temperature of from about 19° C. to about 45° C., 19° C. to about 40° C., 20° C. to about 45° C., 25° C. to about 45° C., 30° C. to about 45° C., or 30° C. to about 40° C., as compared to nucleic acid-cleaving activity at a different temperature.

In some embodiments, the nucleic acid-cleaving activity of the target polynucleic acid is directed by the guiding polynucleic acid. In some embodiments, the Ago polypeptide demonstrates one, two, three, or four of: single stranded DNA (ssDNA) cleaving activity, double stranded DNA (dsDNA) cleaving activity, single stranded RNA (ssRNA) cleaving activity, or double stranded RNA (dsRNA) cleaving activity. In some embodiments, the Ago polypeptide demonstrates single stranded DNA (ssDNA) cleaving activity. In some embodiments, the target polynucleic acid is a single stranded DNA (ssDNA) sequence, a double stranded DNA (dsDNA) sequence, a single stranded RNA (ssRNA) sequence, or a double stranded RNA (dsRNA) sequence. In some embodiments, the target polynucleic acid is a single stranded DNA (ssDNA) sequence.

In some embodiments, the target polynucleic acid is DNA. In some embodiments, a region of the target DNA sequence that the C-Ago polypeptide cleaves is about at least 50%, 60%, 70%, 80%, or 90% deoxyadenosine and deoxythymidine.

In some embodiments, said target polynucleic acid comprises a gene sequence. In some embodiments, said Ago polypeptide sequence produces a disruption in said gene sequence when introduced into a cell. In some embodiments, said disruption comprises a double strand break or a single strand break.

In some embodiments, said guiding polynucleic acid is capable of interacting with said Ago polypeptide and directing said Ago polypeptide to said target polynucleic acid.

In some embodiments, the guiding polynucleic acid is a guide DNA or a guide RNA.

In some embodiments, said guiding polynucleic acid is from about 1 nucleotide to about 30 nucleotides in length.

In some embodiments, said system comprises a complex, and wherein said complex comprises said Ago polypeptide and said guiding polynucleic acid.

In some embodiments, the Ago polypeptide comprises a PIWI-like domain. In some embodiments, the Ago polypeptide comprises a PIWI domain. In some embodiments, the Ago polypeptide comprises a PAZ domain. In some embodiments, the Ago polypeptide comprises a PAZ-like domain.

In some embodiments, said system comprises a nucleic acid unwinding polypeptide or a polynucleic acid encoding the same. In some embodiments, said nucleic acid unwinding polypeptide is a helicase, a single strand DNA binding (SSB) protein, or a Clustered Regularly Interspaced Short Palindromic Repeats (CRISPR) associated (Cas) protein domain.

In some embodiments, said nucleic acid unwinding polypeptide is a single strand DNA binding protein (SSB) polypeptide. In some embodiments, said SSB polypeptide comprises an amino acid sequence having at least 80%, 85%, 90%, 95%, 96%, 97%, 98%, 99%, or 100% sequence identity with one of SEQ ID NOs: 22-35. In some embodiments, said SSB polypeptide is encoded by a nucleic acid sequence having at least 80%, 85%, 90%, 95%, 96%, 97%, 98%, 99%, or 100% sequence identity with one of SEQ ID NOs: 36-49. In some embodiments, said SSB polypeptide comprises an amino acid sequence having at least 80%, 85%, 90%, 95%, 96%, 97%, 98%, 99%, or 100% sequence identity with SEQ ID NO: 22. In some embodiments, said SSB polypeptide is encoded by a nucleic acid sequence having at least 80%, 85%, 90%, 95%, 96%, 97%, 98%, 99%, or 100% sequence identity with SEQ ID NO: 36.

In some embodiments, said nucleic acid unwinding polypeptide is a Cas protein domain. In some embodiments, said Cas protein domain is a catalytically dead Cas polypeptide.

In some embodiments, said Ago polypeptide is fused either directly or indirectly to a NLS. In some embodiments, said nucleic acid unwinding polypeptide is fused either directly or indirectly to a NLS. In some embodiments, said Ago polypeptide and said nucleic acid unwinding polypeptide are fused either directly or indirectly. In some embodiments, said Ago polypeptide and said nucleic acid unwinding polypeptide are fused and a NLS is in between said Ago polypeptide and said nucleic acid unwinding polypeptide.

In some embodiments, said Ago polypeptide is encoded by a gene located in an adjacent operon to at least one of a gene involved in defense, stress response, gene editing, CRISPR, DNA replication, DNA recombination, DNA repair, and transcription.

In some embodiments, said system comprises one or more recombinant expression vectors. In some embodiments, said one or more recombinant expression vectors comprise an adeno-associated virus vector, a plasmid vector, a retroviral vector, a lentiviral vector, an adenovirus vectors, a poxvirus vectors, a herpesvirus vector, or a split-intron vector.

In one aspect, provided herein is an ex vivo cell (or population thereof) comprising a system described herein. In some embodiments, the cell is a human cell. In some embodiments, the cell is an immune cell, a stem cell, or a germ cell.

In one aspect, provided herein is a recombinant expression vector encoding a system described herein.

In one aspect, provided herein is a pharmaceutical composition comprising a system described herein, and at least one of: an excipient, a diluent, or a carrier.

In some embodiments, said pharmaceutical composition is in a form of intravenous, subcutaneous, or intramuscular administration formulation.

In one aspect, provided herein is a kit comprising: (a) a system described herein; and (b) instructions for use thereof, and optionally (c) a container.

In one aspect, provided herein are polypeptide constructs, wherein said constructs comprise a mesophilic Ago polypeptide sequence, or a functional fragment or a functional variant thereof, wherein said Ago polypeptide sequence cleaves a nucleic acid in a target polynucleic acid sequence at a mesophilic temperature, wherein said target polynucleic acid sequence is bound by a non-naturally occurring guide polynucleic acid sequence.

In some embodiments, said Ago polypeptide comprises an amino acid sequence having at least 80%, 85%, 90%, 95%, 96%, 97%, 98%, 99%, or 100% sequence identity with one of SEQ ID NOs: 4-10. In some embodiments, said Ago polypeptide is encoded by a polynucleic acid sequence having at least 80%, 85%, 90%, 95%, 96%, 97%, 98%, 99%, or 100% sequence identity with one of SEQ ID NOs: 15-21.

In some embodiments, said Ago polypeptide comprises a DEDX motif sequence. In some embodiments, said DEDX motif sequence comprises a mutation, wherein said mutation reduces catalytic activity of said Ago polypeptide as compared to a corresponding Ago polypeptide without said mutation in said DEDX motif sequence.

In one aspect, provided herein is a nucleic acid sequence encoding a polypeptide described herein.

In one aspect, provided herein are recombinant fusion polypeptides, said fusion polypeptides comprising: a mesophilic Argonaute (Ago) polypeptide; and a nucleic acid unwinding polypeptide.

In some embodiments, the nucleic acid unwinding polypeptide comprises a helicase, a single strand DNA binding protein (SSB), or a Clustered Regularly Interspaced Short Palindromic Repeats (CRISPR) associated (Cas) protein domain.

In some embodiments, said Ago polypeptide comprises an amino acid sequence having at least 80%, 85%, 90%, 95%, 96%, 97%, 98%, 99%, or 100% sequence identity with one of SEQ ID NOs: 4-10. In some embodiments, said Ago polypeptide is encoded by a polynucleic acid sequence having at least 80%, 85%, 90%, 95%, 96%, 97%, 98%, 99% or more sequence identity with one of SEQ ID NOs: 15-21.

In some embodiments, the nucleic acid unwinding polypeptide is a single strand DNA binding protein (SSB) polypeptide. In some embodiments, said SSB polypeptide comprises an amino acid sequence having at least 80%, 85%, 90%, 95%, 96%, 97%, 98%, 99%, or 100% sequence identity with one of SEQ ID NOs: 22-35. In some embodiments, said SSB polypeptide is encoded by a nucleic acid sequence having at least 80%, 85%, 90%, 95%, 96%, 97%, 98%, 99%, or 100% sequence identity with one of SEQ ID NOs: 36-49. In some embodiments, said SSB polypeptide comprises an amino acid sequence having at least 80%, 85%, 90%, 95%, 96%, 97%, 98%, 99%, or 100% sequence identity with SEQ ID NO: 22. In some embodiments, said SSB polypeptide is encoded by a nucleic acid sequence having at least 80%, 85%, 90%, 95%, 96%, 97%, 98%, 99%, or 100% sequence identity with SEQ ID NO: 36.

In some embodiments, said nucleic acid unwinding polypeptide is a Cas protein domain. In some embodiments, said Cas protein domain is a catalytically dead Cas polypeptide.

In some embodiments, said fusion polypeptide comprises at least one nuclear localization signal (NLS) polypeptide. In some embodiments, said fusion polypeptide comprises at least two, three, or four NLS polypeptides. In some embodiments, said fusion polypeptide comprises a NLS between said nucleic acid unwinding polypeptide and said Ago polypeptide.

In some embodiments, said Ago polypeptide comprises a DEDX motif sequence. In some embodiments, said DEDX motif sequence comprises a mutation, wherein said mutation reduces catalytic activity of said Ago polypeptide as compared to a corresponding Ago polypeptide without said mutation in said DEDX motif sequence.

In one aspect, provided herein is a nucleic acid encoding a recombinant fusion polypeptide described herein.

In one aspect, provided herein are methods of modifying a target polynucleic acid, said methods comprising: introducing into a cell a system described herein; or a polypeptide construct described herein; or a recombinant fusion polypeptide described herein, and a non-naturally occurring guiding polynucleic acid that is complementary to said target polynucleic acid; and modifying said target polynucleic acid.

In one aspect, provided herein are methods of treating a disease or disorder in a subject in need thereof, said method comprising administering to the subject: a system described herein, a polypeptide construct described herein, a recombinant fusion polypeptide described herein, a cell described herein, a vector described herein, or a pharmaceutical composition described herein. In some embodiments, said disease is cancer, an autoimmune disease, a genetic disease, or an infection. In some embodiments, said disease is cancer.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3 shows the taxonomy information of bacteria of the Ago 41/69/70 branch; this includes NCBI ID number, the organism, and the taxonomy. Each of the thirteen are domain: bacteria, Phylum: Firmicutes, Class: Clostridia, Order: Clostridiales, Family: Clostridiaceae, and Genus: *Clostridium.*

FIG. 4 shows the host and environmental information of bacteria in the Ago 41/69/70 branch.

FIG. 5 shows the representative taxonomy-specificity, including Kingdom, Phylum, Class, Order, Family, Genus, and Species) of the Ago41 branch.

FIG. 13 shows an image of an electrophoresis gel showing the single stranded DNA (ssDNA) cleavage by Ago69 at different temperatures with ssDNA guide. "gDNA$^P$" indicates the 5' most nucleotide of the gDNA is phosphorylated.

FIG. 18 shows a sequence comparison of the amino acid sequence of Ago41, Ago69, and Ago70. FIG. 18 discloses SEQ ID NOS 163-165, respectively, in order of appearance.

Figure 26A:
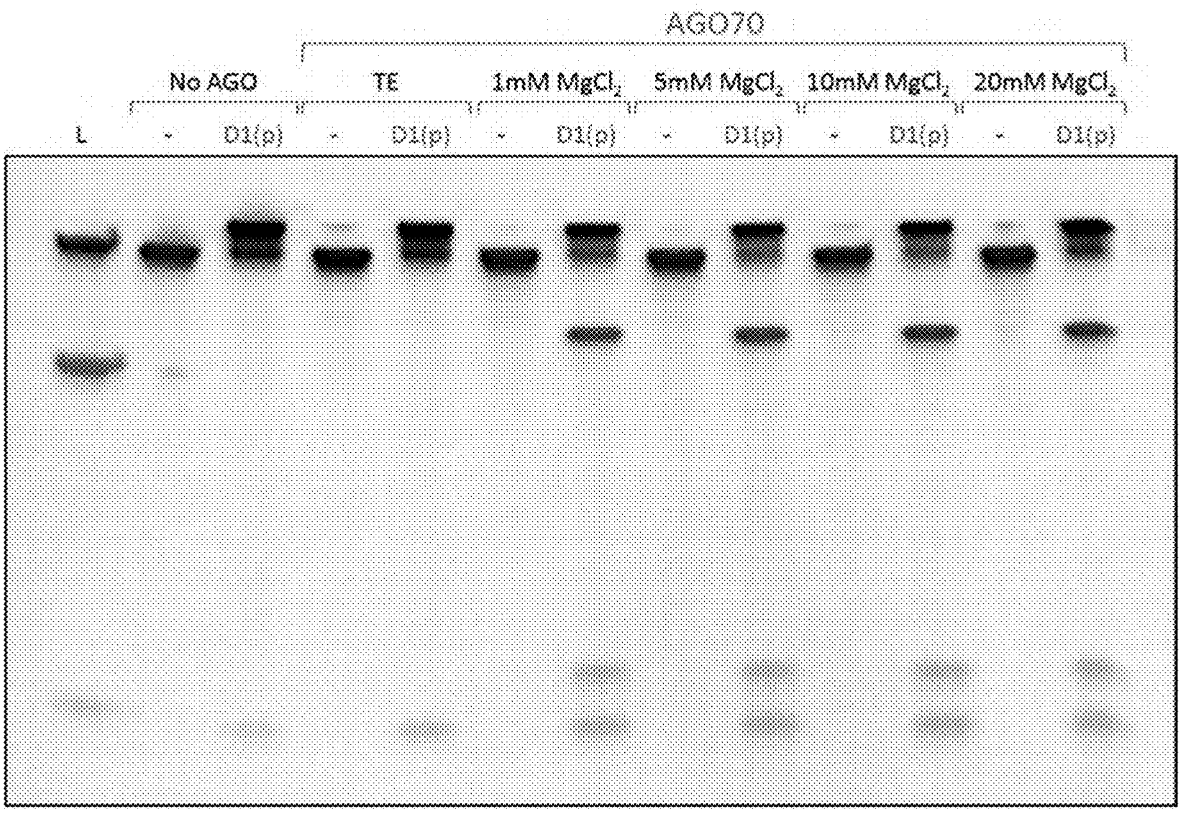
Figure 26B:
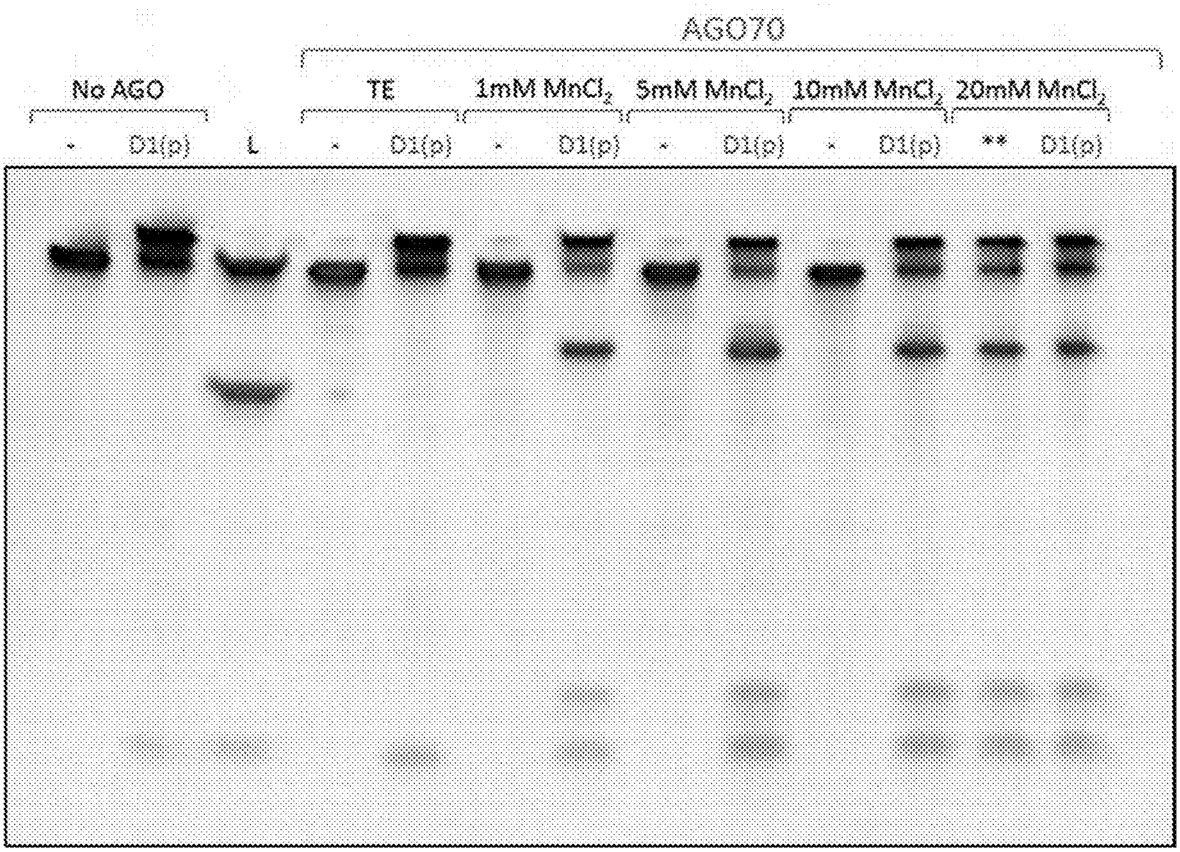

FIG. 26A shows an image of an electrophoresis gel showing the cleavage of single stranded DNA template (90 nucleotides) by Ago70 with guide DNA (gDNA) and a $Mg^{2+}$ titration of 1 mM $MgCl_2$, 5 mM $MgCl_2$, 10 mM $MgCl_2$, and 20 mM $MgCl_2$. "D1(p)" indicates the 5' most nucleotide of the gDNA is phosphorylated. FIG. 26B shows an image of an electrophoresis gel showing the cleavage of single stranded DNA template (90 nucleotides) by Ago70 with guide DNA (gDNA) and a $Mn^{2+}$ titration of 1 mM $MnCl_2$, 5 mM $MnCl_2$, 10 mM $MnCl_2$, and 20 mM $MnCl_2$. "D1(p)" indicates the 5' most nucleotide of the gDNA is phosphorylated.

Figure 27:
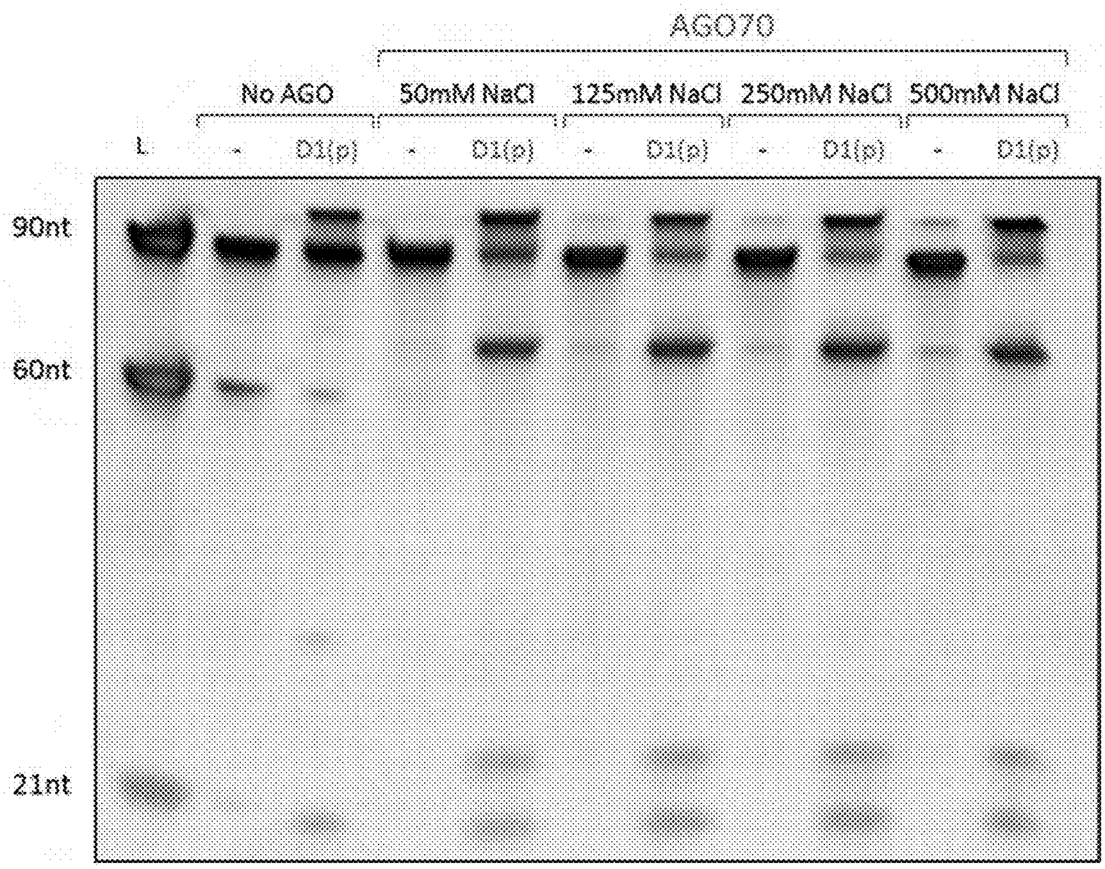

FIG. 27 shows an image of an electrophoresis gel showing the cleavage of single stranded DNA template (90 nucleotides) by Ago70 with guide DNA (gDNA) and a $NaCl_2$ titration of 50 mM $NaCl_2$, 125 mM $NaCl_2$, 250 mM $NaCl_2$, and 500 mM $NaCl_2$. "D1(p)" indicates the 5' most nucleotide of the gDNA is phosphorylated.

Figure 28:
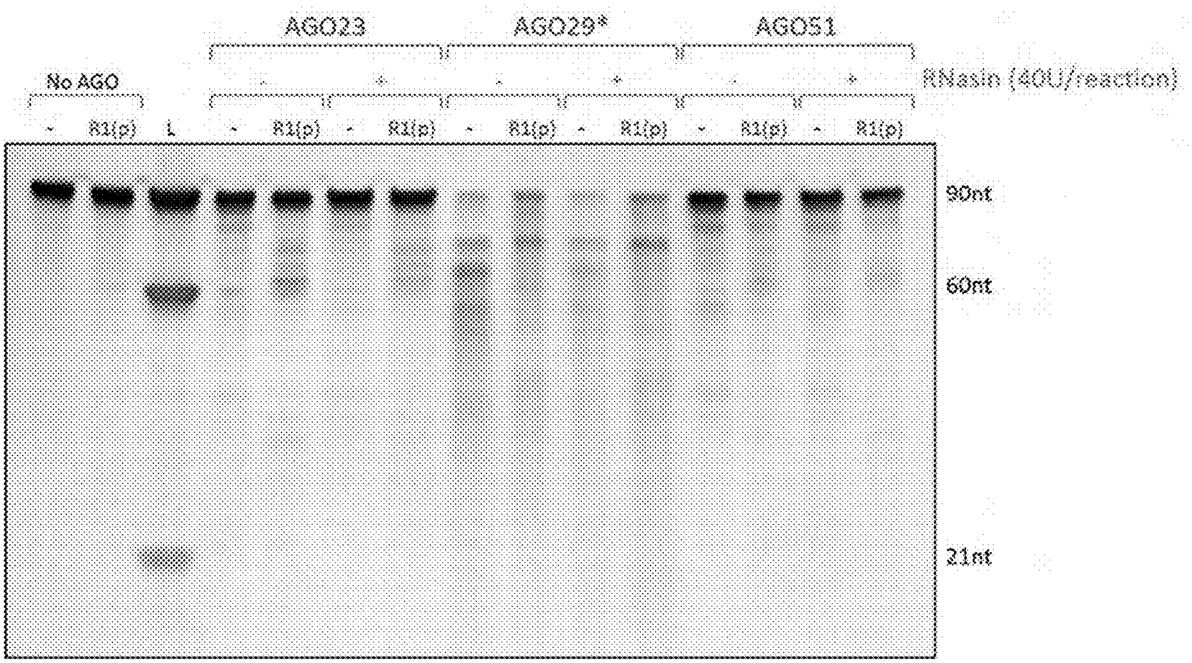

FIG. 28 shows an image of an electrophoresis gel showing the stability of guide RNA (gRNA) during Ago23, Ago29, and Ago51 cleavage. RNase inhibition was mediated by the addition of RNasin as indicated (40 U/reaction). For the Ago29 experiments, 125 ng of Ago29 was used per reaction. "R1(p)" indicates the 5' most nucleotide of the gRNA is phosphorylated.

Figure 29A:
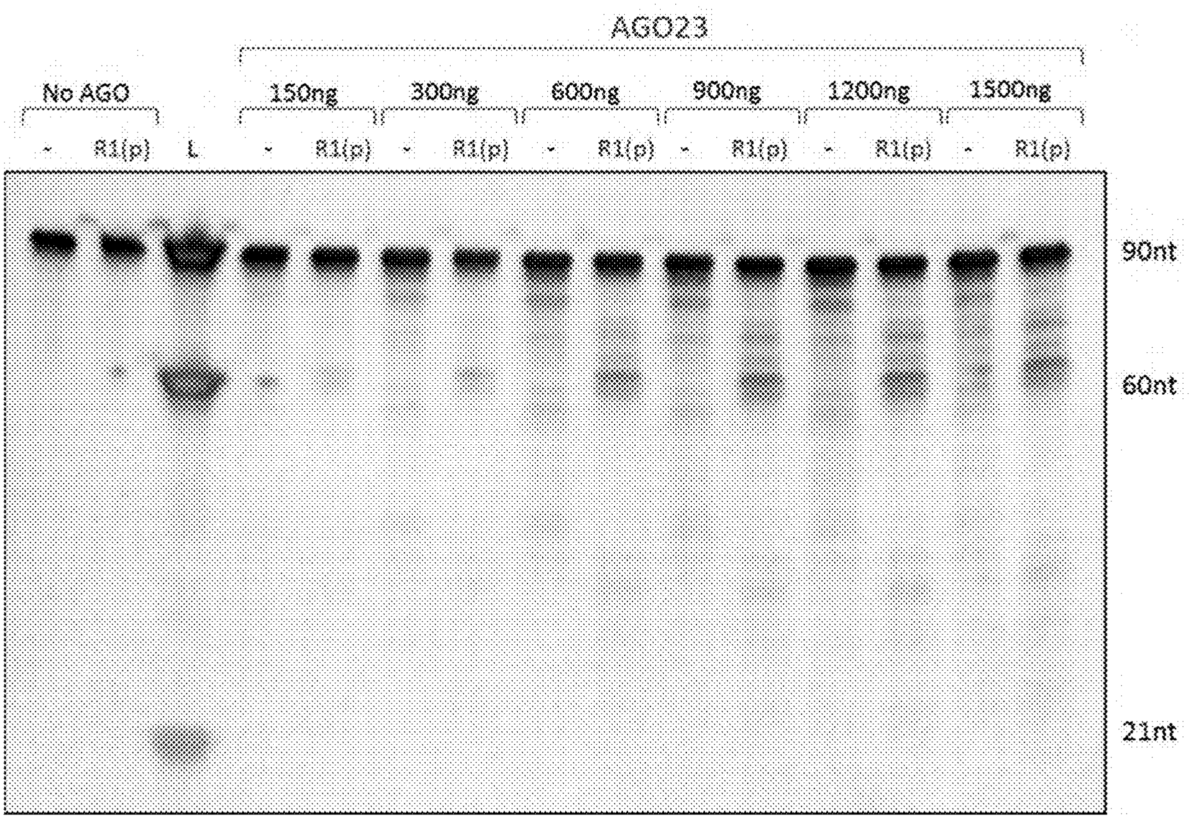
Figure 29B:
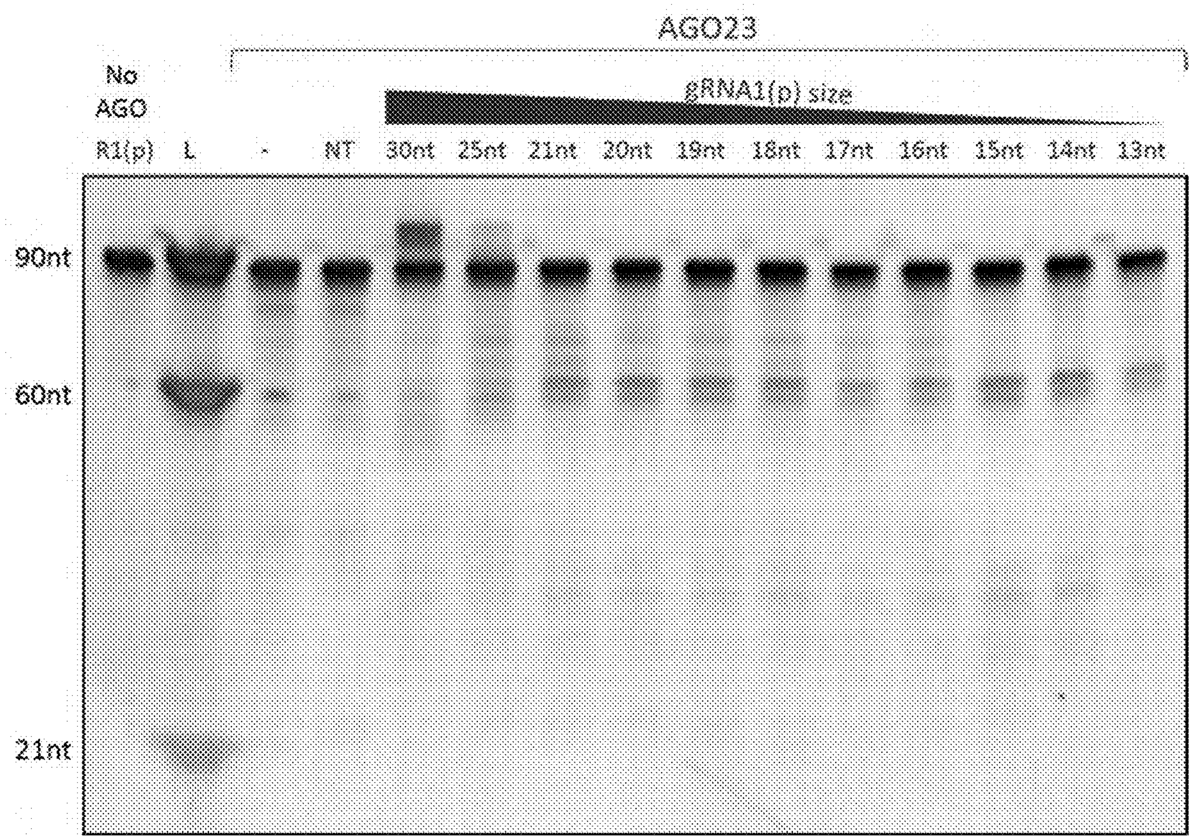

FIG. 29A shows an image of an electrophoresis gel showing the cleavage of single stranded DNA template (90 nucleotides) by Ago23 with guide RNA (gRNA) ranging in amount from 150 ng-1500 ng. "R1(p)" indicates the 5' most nucleotide of the gRNA is phosphorylated. FIG. 29B shows an image of an electrophoresis gel showing cleavage of single stranded DNA template (90 nucleotides) by Ago23 with guide RNA (gRNA) ranging in length from 13-30 nucleotides. "R1(p)" indicates the 5' most nucleotide of the gRNA is phosphorylated.

Figure 30A:
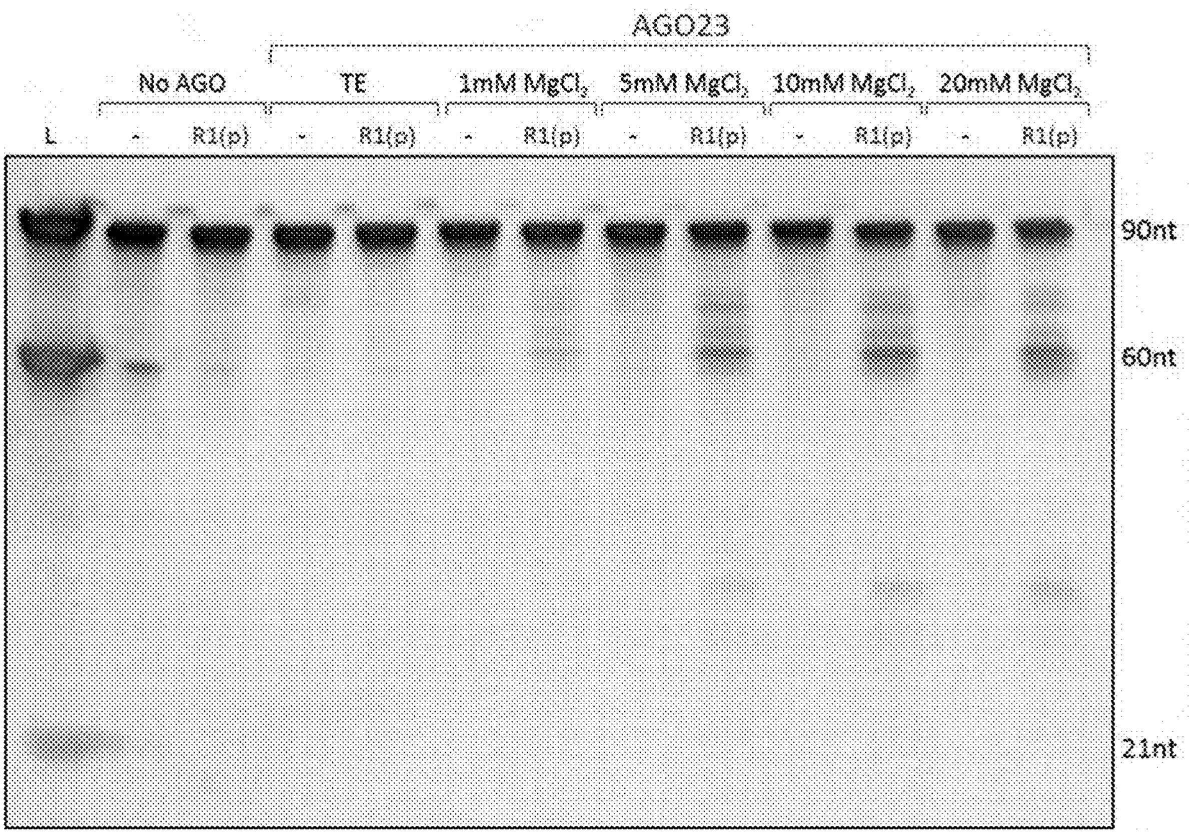
Figure 30B:
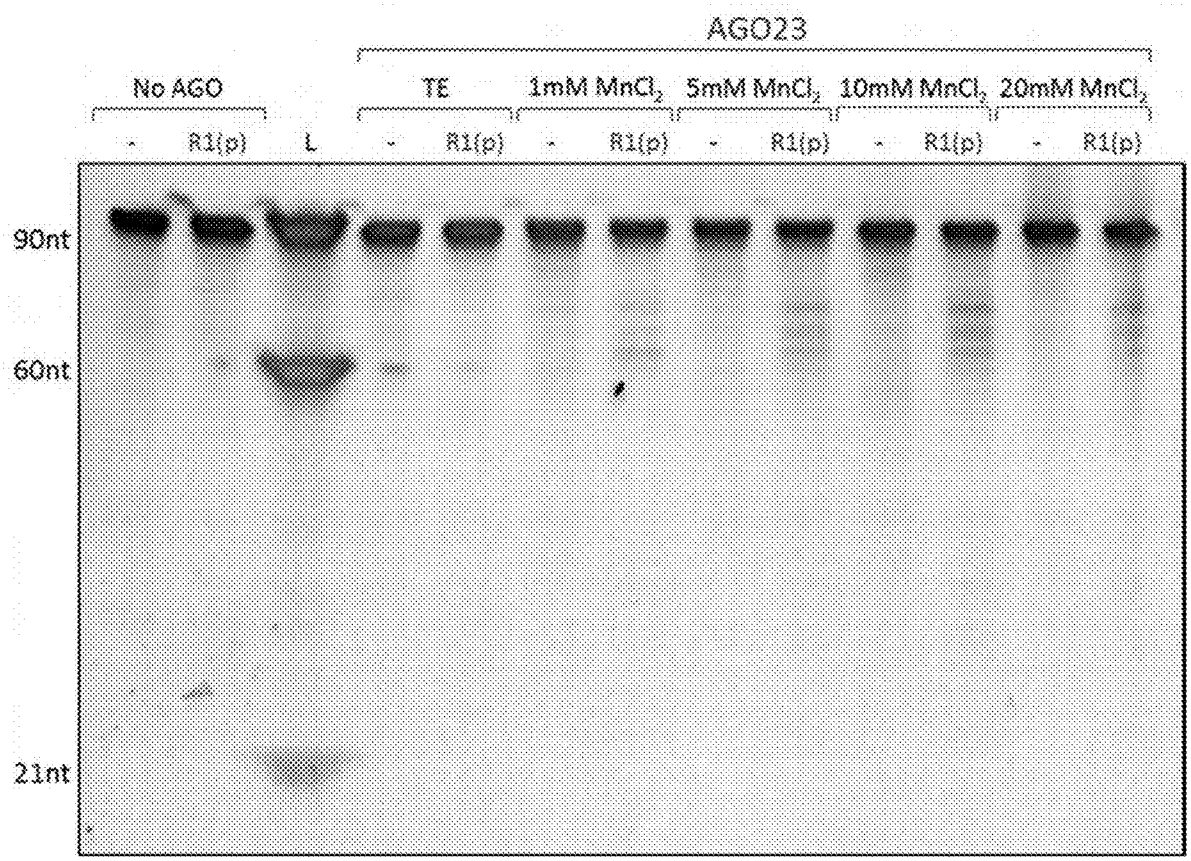

FIG. 30A shows an image of an electrophoresis gel showing the cleavage of single stranded DNA template (90 nucleotides) by Ago23 with guide RNA (gRNA) and a $Mg^{2+}$ titration of 1 mM $MgCl_2$, 5 mM $MgCl_2$, 10 mM $MgCl_2$, and 20 mM $MgCl_2$. "R1(p)" indicates the 5' most nucleotide of the gRNA is phosphorylated. FIG. 30B shows an image of an electrophoresis gel showing the cleavage of single stranded DNA template (90 nucleotides) by Ago23 with guide RNA (gRNA) and a $Mn^{2+}$ titration of 1 mM $MnCl_2$, 5 mM $MnCl_2$, 10 mM $MnCl_2$, and 20 mM $MnCl_2$. "R1(p)" indicates the 5' most nucleotide of the gRNA is phosphorylated.

Figure 31:
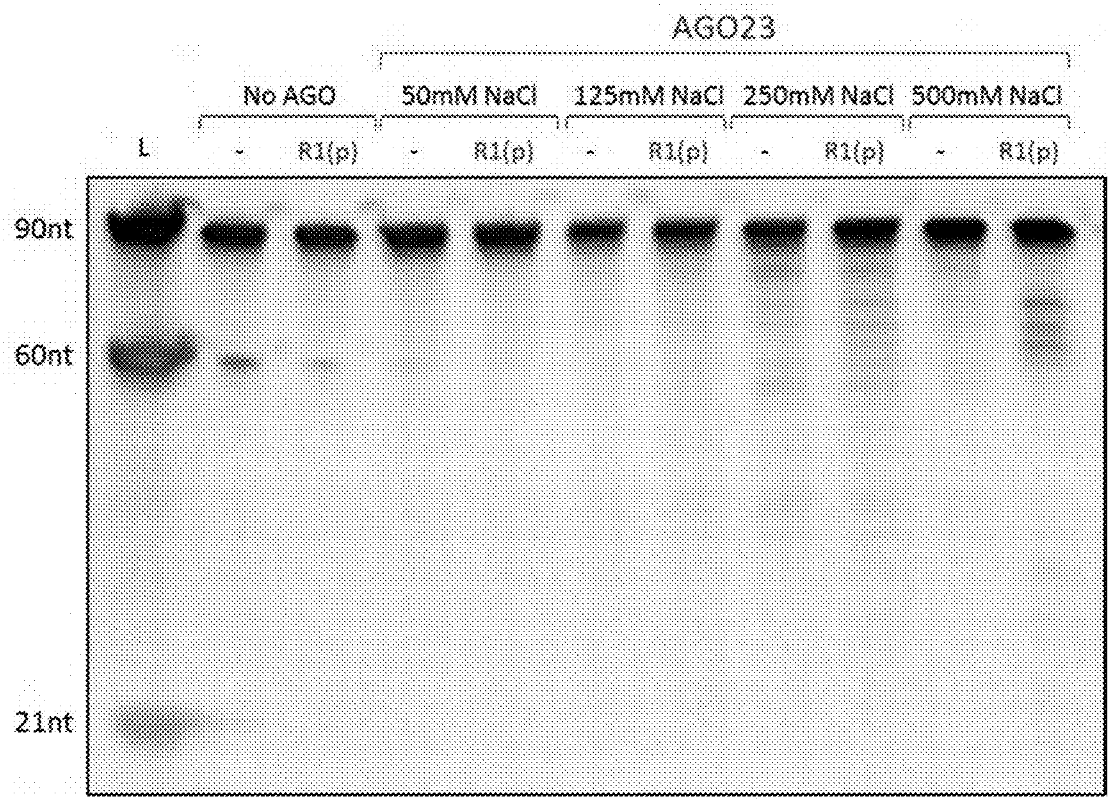

FIG. 31 shows an image of an electrophoresis gel showing the cleavage of single stranded DNA template (90 nucleotides) by Ago23 with guide RNA (gRNA) and a $NaCl_2$ titration of 50 mM $NaCl_2$, 125 mM $NaCl_2$, 250 mM $NaCl_2$, and 500 mM $NaCl_2$. "R1(p)" indicates the 5' most nucleotide of the gRNA is phosphorylated.

Figure 32A:
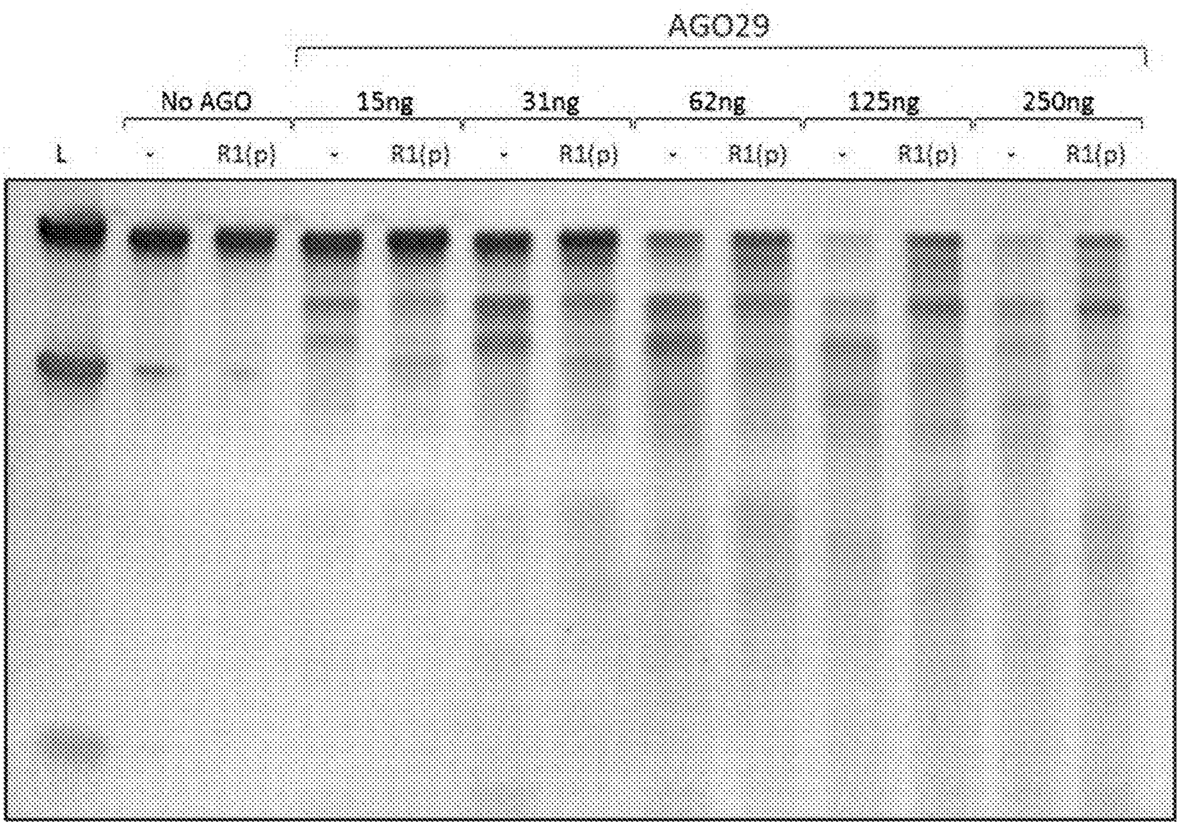
Figure 32B:
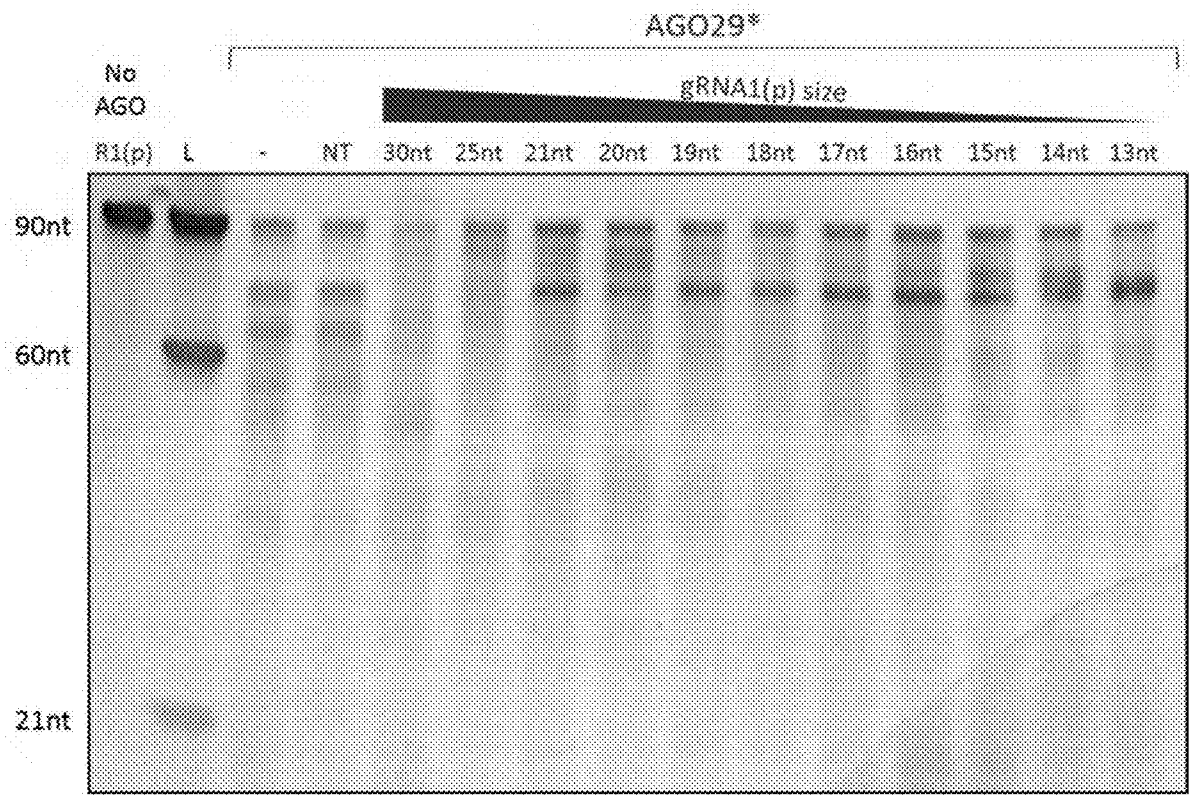

FIG. 32A shows an image of an electrophoresis gel showing the cleavage of single stranded DNA template (90 nucleotides) by Ago29 with guide RNA (gRNA) ranging in amount from 150 ng-1500 ng. "R1(p)" indicates the 5' most nucleotide of the gRNA is phosphorylated. FIG. 32B shows an image of an electrophoresis gel showing the cleavage of single stranded DNA template (90 nucleotides) by Ago29 with guide RNA (gRNA) ranging in length from 13-30 nucleotides. "R1(p)" indicates the 5' most nucleotide of the gRNA is phosphorylated.

Figure 33A:
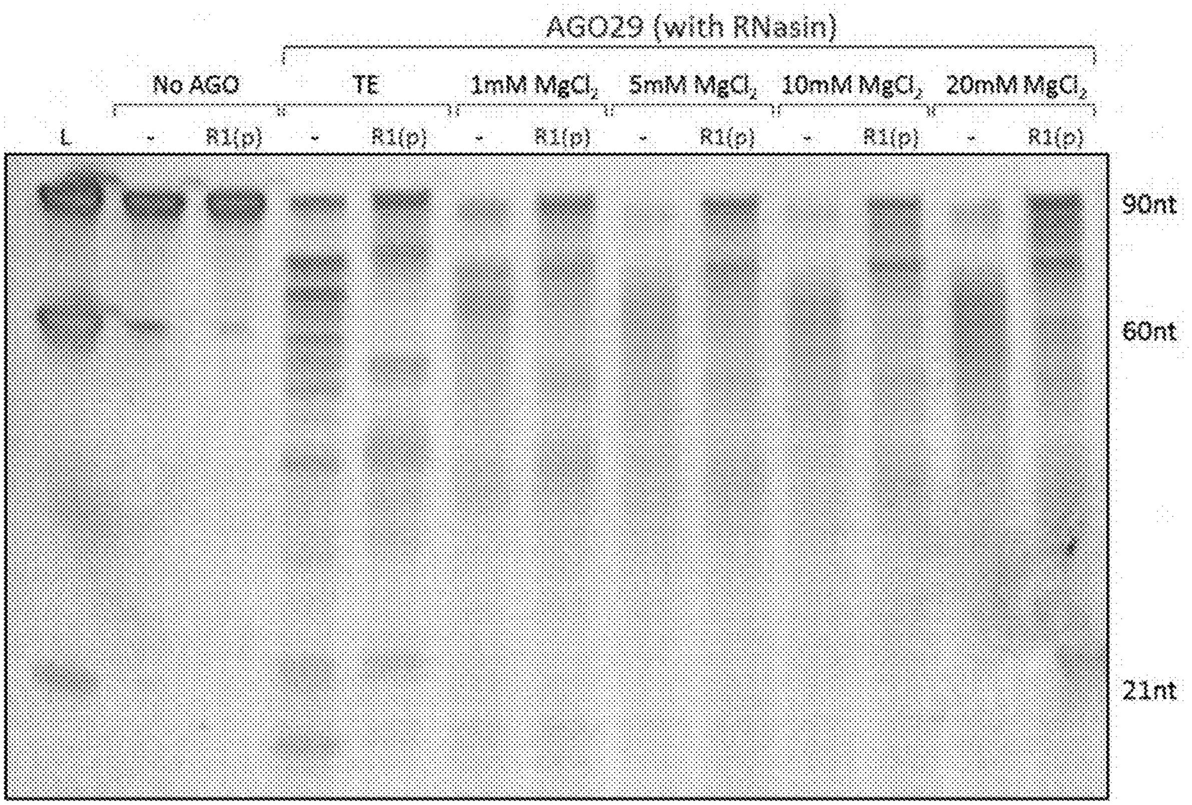
Figure 33B:
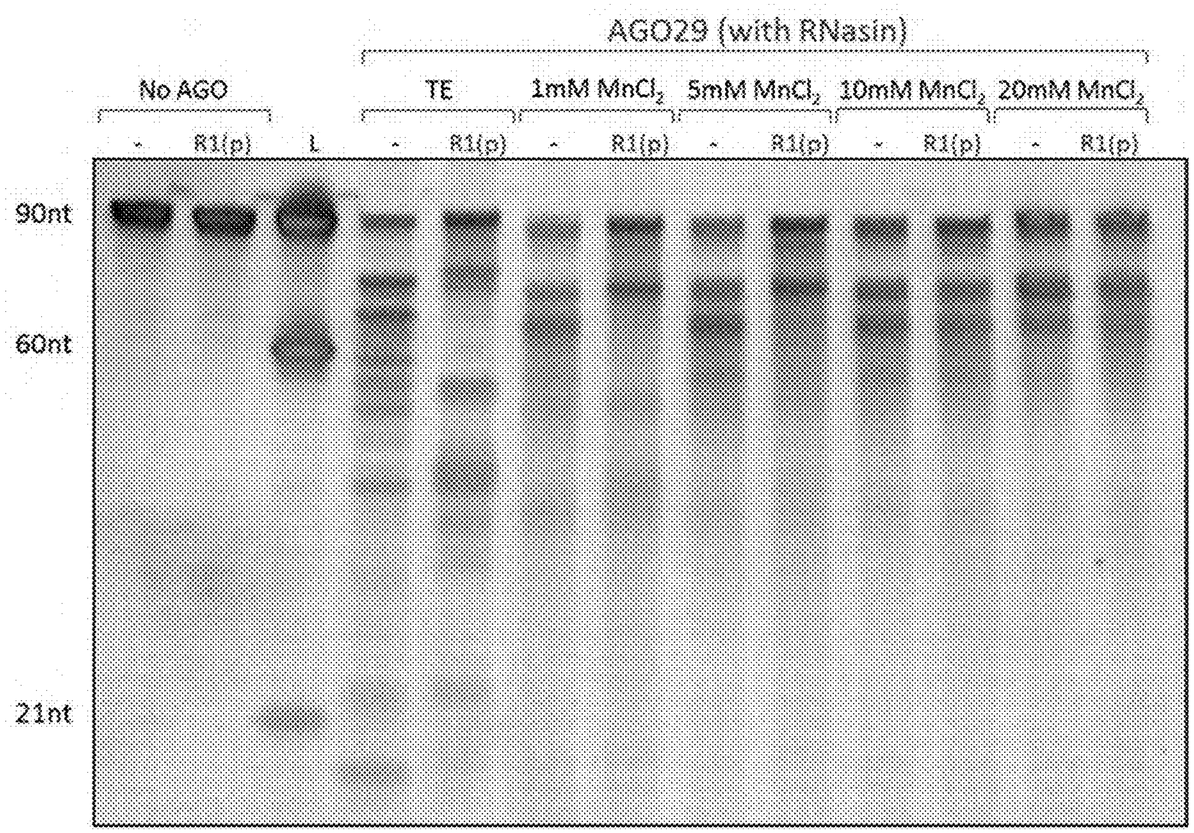

FIG. 33A shows an image of an electrophoresis gel showing the cleavage of single stranded DNA template (90 nucleotides) by Ago29 with guide RNA (gRNA) and a $Mg^{2+}$ titration of 1 mM $MgCl_2$, 5 mM $MgCl_2$, 10 mM $MgCl_2$, and 20 mM $MgCl_2$. "R1(p)" indicates the 5' most nucleotide of the gRNA is phosphorylated. FIG. 33B shows an image of an electrophoresis gel showing the cleavage of single stranded DNA template (90 nucleotides) by Ago29 with guide RNA (gRNA) and a $Mn^{2+}$ titration of 1 mM $MnCl_2$, 5 mM $MnCl_2$, 10 mM $MnCl_2$, and 20 mM $MnCl_2$. "R1(p)" indicates the 5' most nucleotide of the gRNA is phosphorylated.

Figure 34:
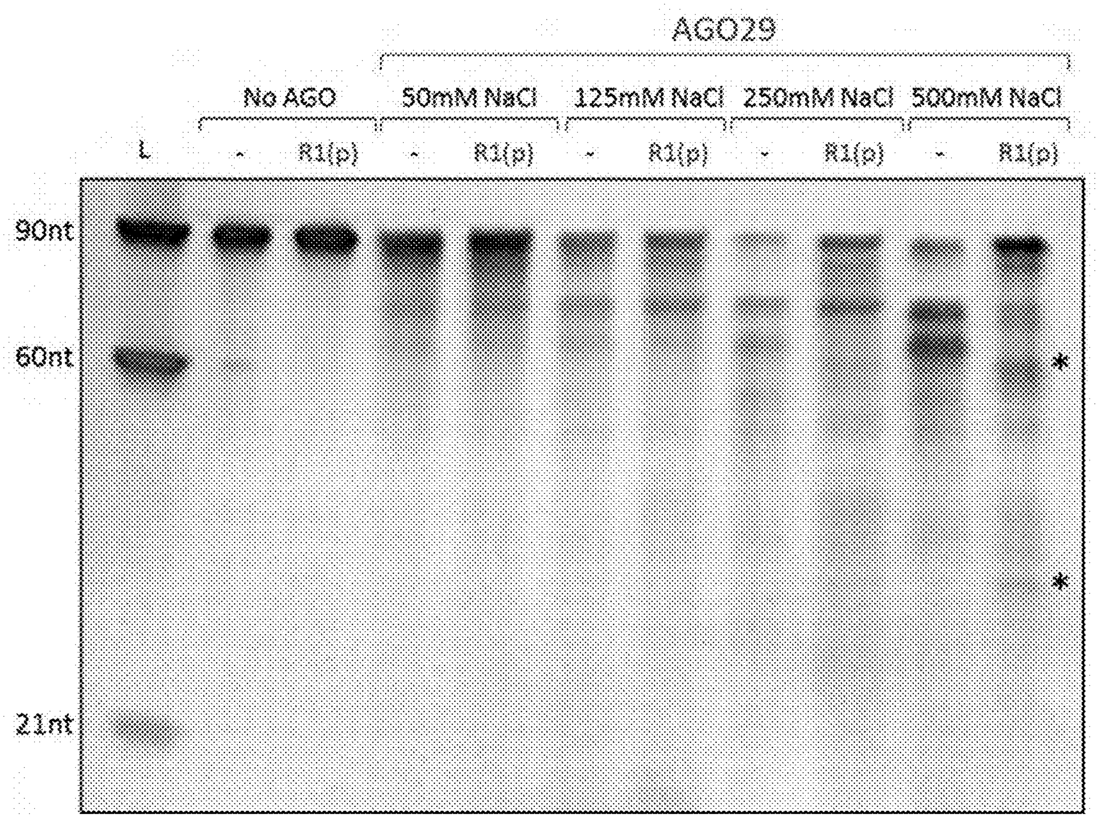

FIG. 34 shows an image of an electrophoresis gel showing the cleavage of single stranded DNA template (90 nucleotides) by Ago29 with guide RNA (gRNA) and a $NaCl_2$ titration of 50 mM $NaCl_2$, 125 mM $NaCl_2$, 250 mM $NaCl_2$, and 500 mM $NaCl_2$. "R1(p)" indicates the 5' most nucleotide of the gRNA is phosphorylated.

Figure 35A:
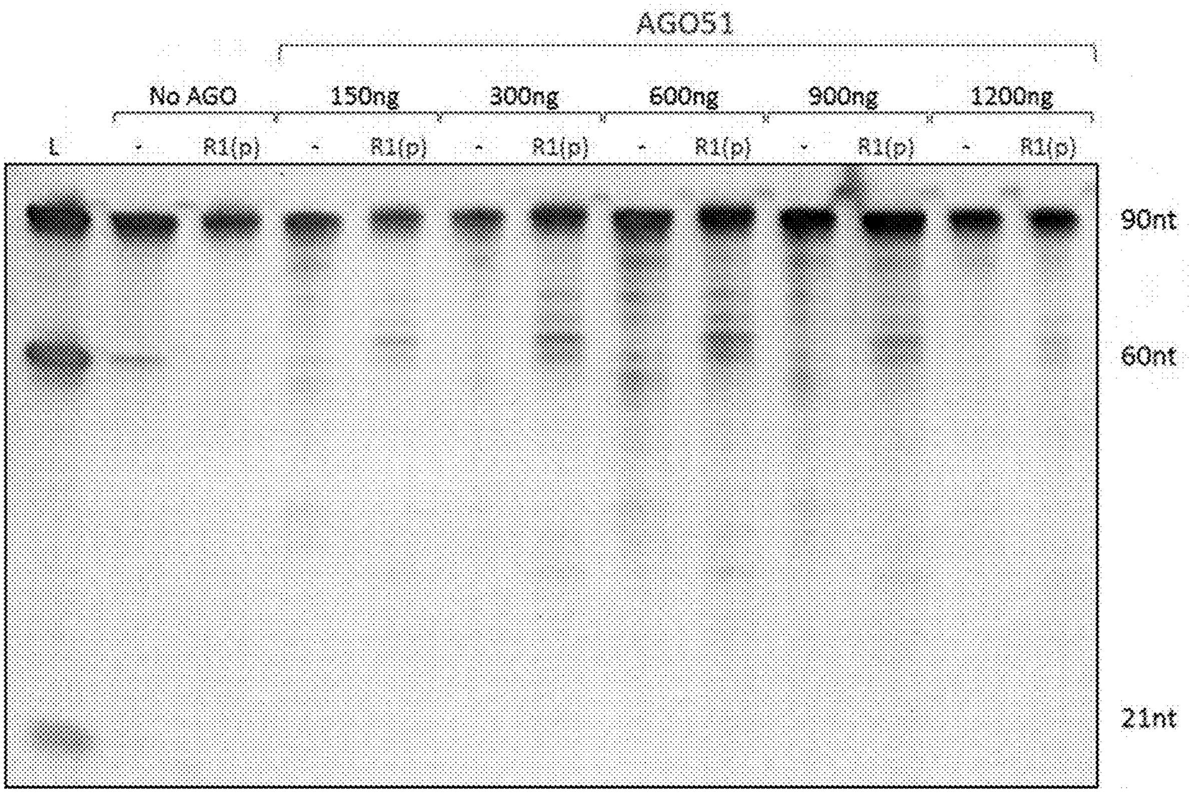
Figure 35B:
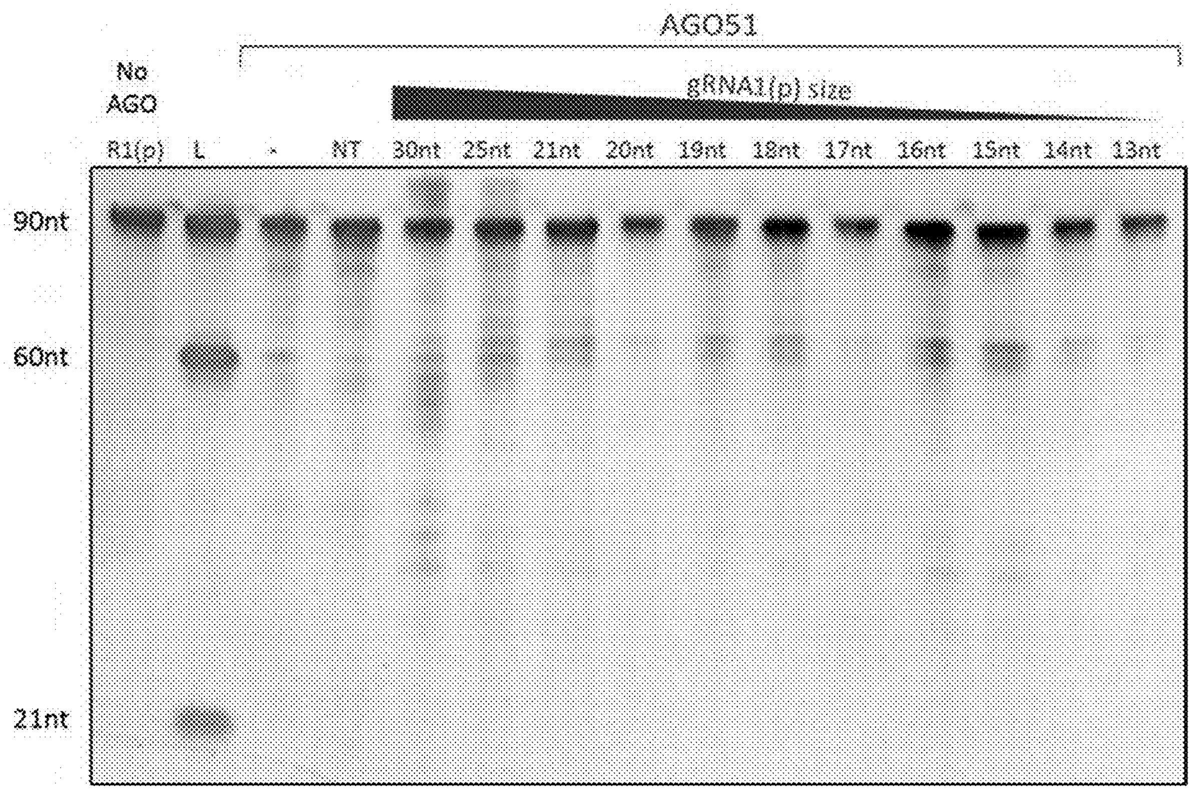

FIG. 35A shows an image of an electrophoresis gel showing the cleavage of single stranded DNA template (90 nucleotides) by Ago51 with guide RNA (gRNA) ranging in amount from 150 ng-1500 ng. "R1(p)" indicates the 5' most nucleotide of the gRNA is phosphorylated. FIG. 35B shows an image of an electrophoresis gel showing cleavage of single stranded DNA template (90 nucleotides) by Ago51 with guide RNA (gRNA) ranging in length from 13-30 nucleotides. "R1(p)" indicates the 5' most nucleotide of the gRNA is phosphorylated.

Figure 36A:
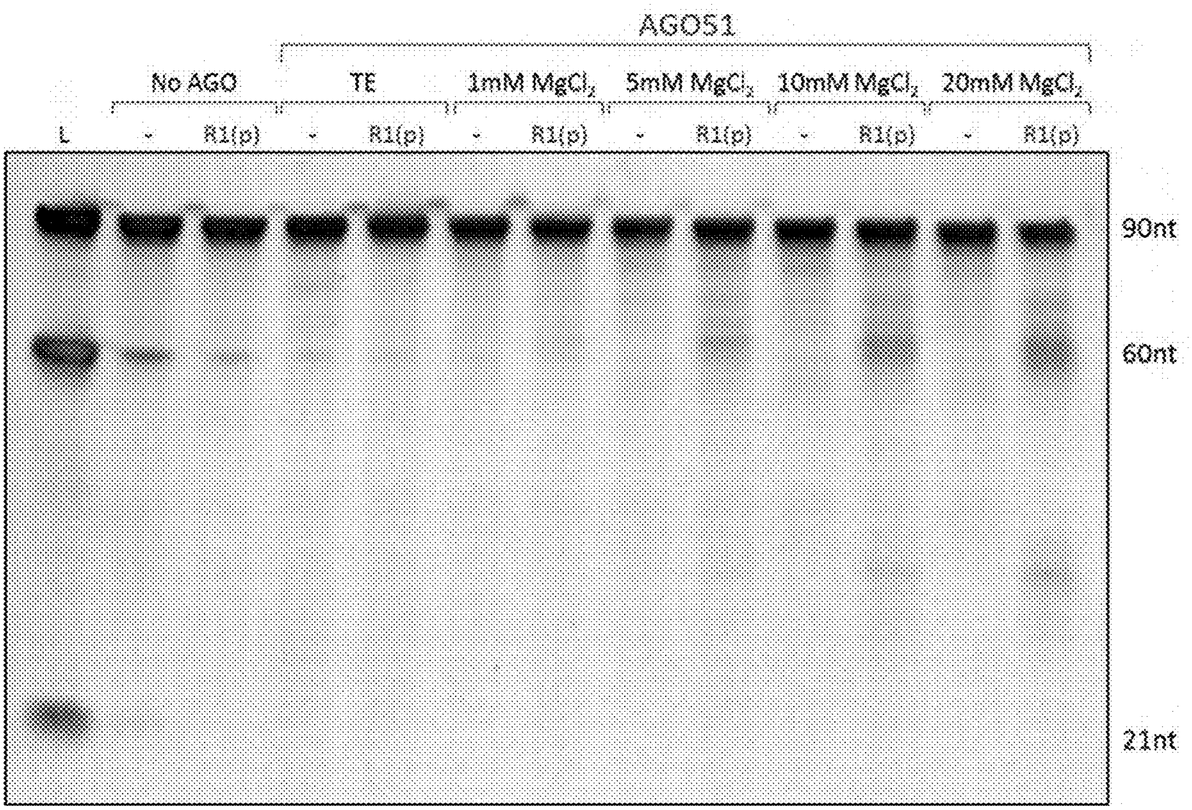
Figure 36B:
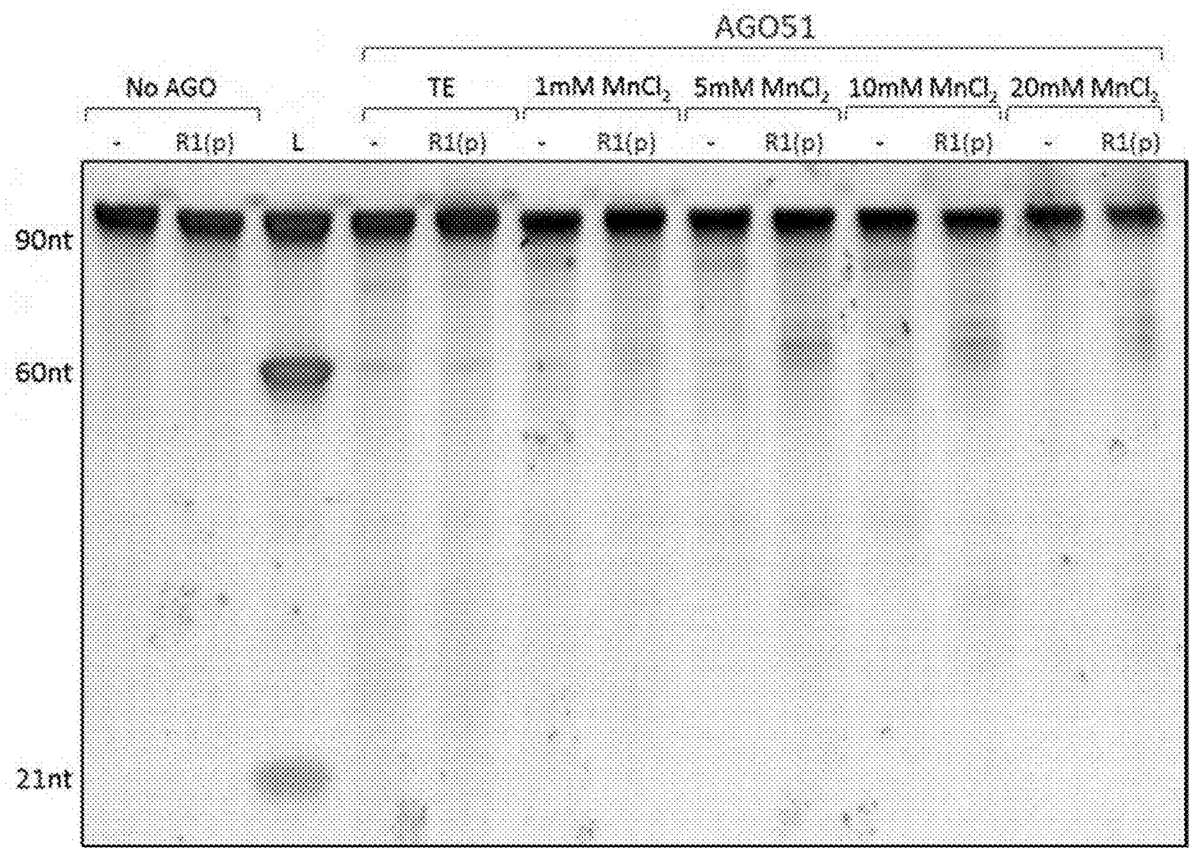

FIG. 36A shows an image of an electrophoresis gel showing the cleavage of single stranded DNA template (90 nucleotides) by Ago51 with guide RNA (gRNA) and a $Mg^{2+}$ titration of 1 mM $MgCl_2$, 5 mM $MgCl_2$, 10 mM $MgCl_2$, and 20 mM $MgCl_2$. "R1(p)" indicates the 5' most nucleotide of the gRNA is phosphorylated. FIG. 36B shows an image of an electrophoresis gel showing the cleavage of single stranded DNA template (90 nucleotides) by Ago51 with guide RNA (gRNA) and a $Mn^{2+}$ titration of 1 mM $MnCl_2$, 5 mM $MnCl_2$, 10 mM $MnCl_2$, and 20 mM $MnCl_2$. "R1(p)" indicates the 5' most nucleotide of the gRNA is phosphorylated.

Figure 37:
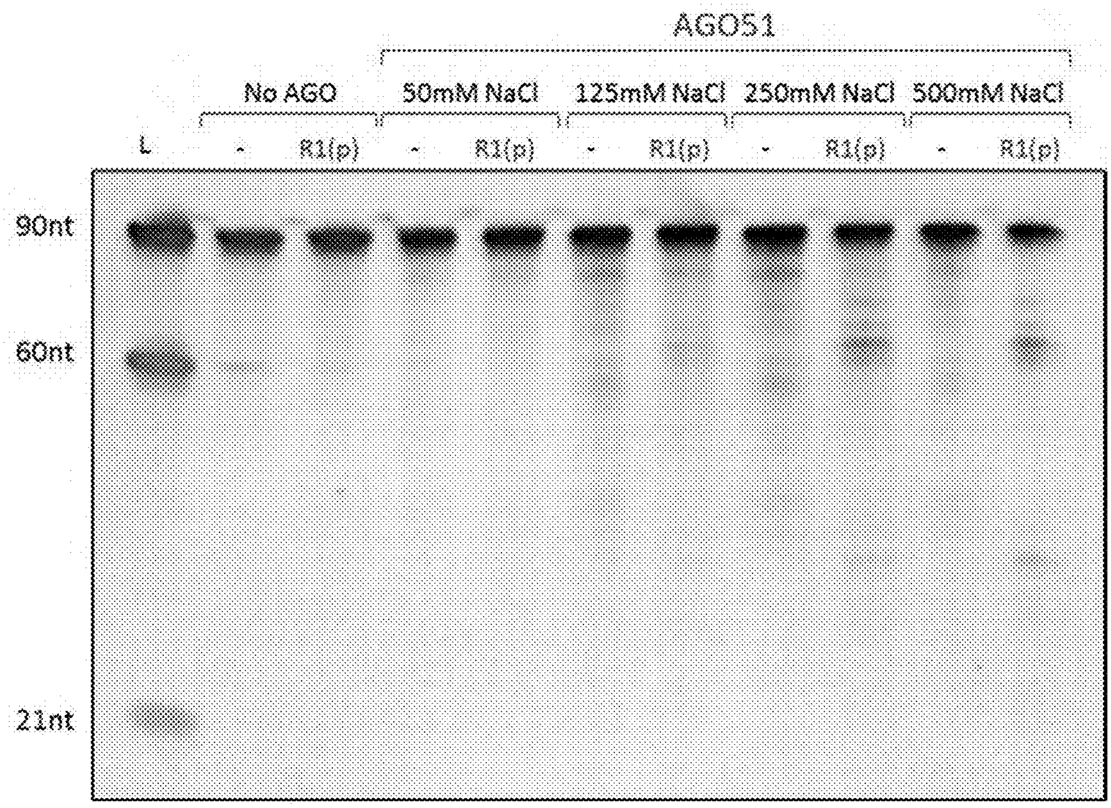

FIG. 37 shows an image of an electrophoresis gel showing the cleavage of single stranded DNA template (90 nucleotides) by Ago51 with guide RNA (gRNA) and a $NaCl_2$ titration of 50 mM $NaCl_2$, 125 mM $NaCl_2$, 250 mM $NaCl_2$, and 500 mM $NaCl_2$. "R1(p)" indicates the 5' most nucleotide of the gRNA is phosphorylated.

Figure 38:
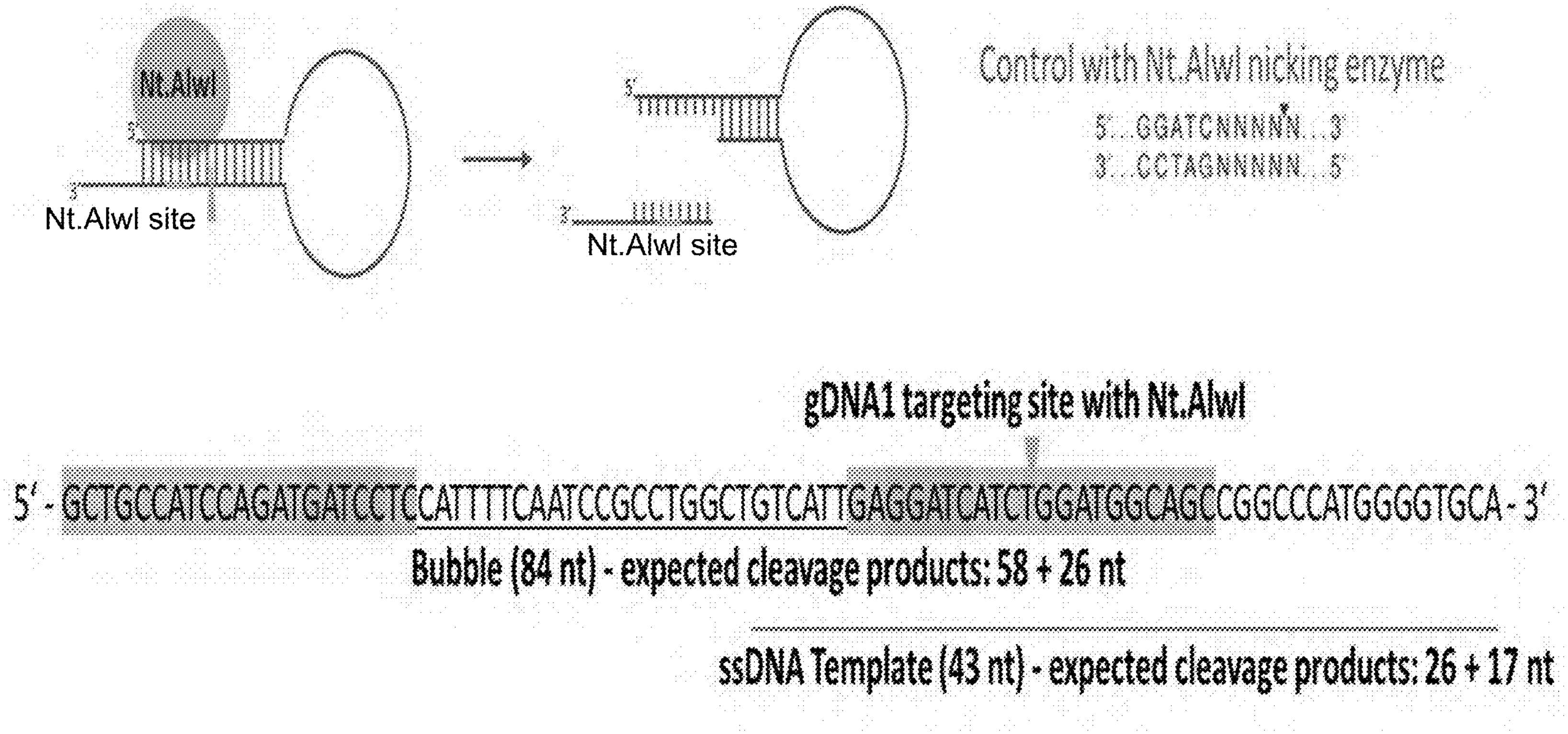

FIG. 38 shows a schematic of the double strand DNA "bubble" nicking assay. Bubble template: ssDNA oligo with complementary regions to assure that no ssDNA is present. 3'overhangs: RecQ Helicase unwinds substrates with 3'overhangs. Nt.AlwI site: positive control. ssDNA template: gDNA/cleavage control. FIG. 38 discloses SEQ ID NOS 166 and 168, respectively, in order of appearance.

Figure 39:
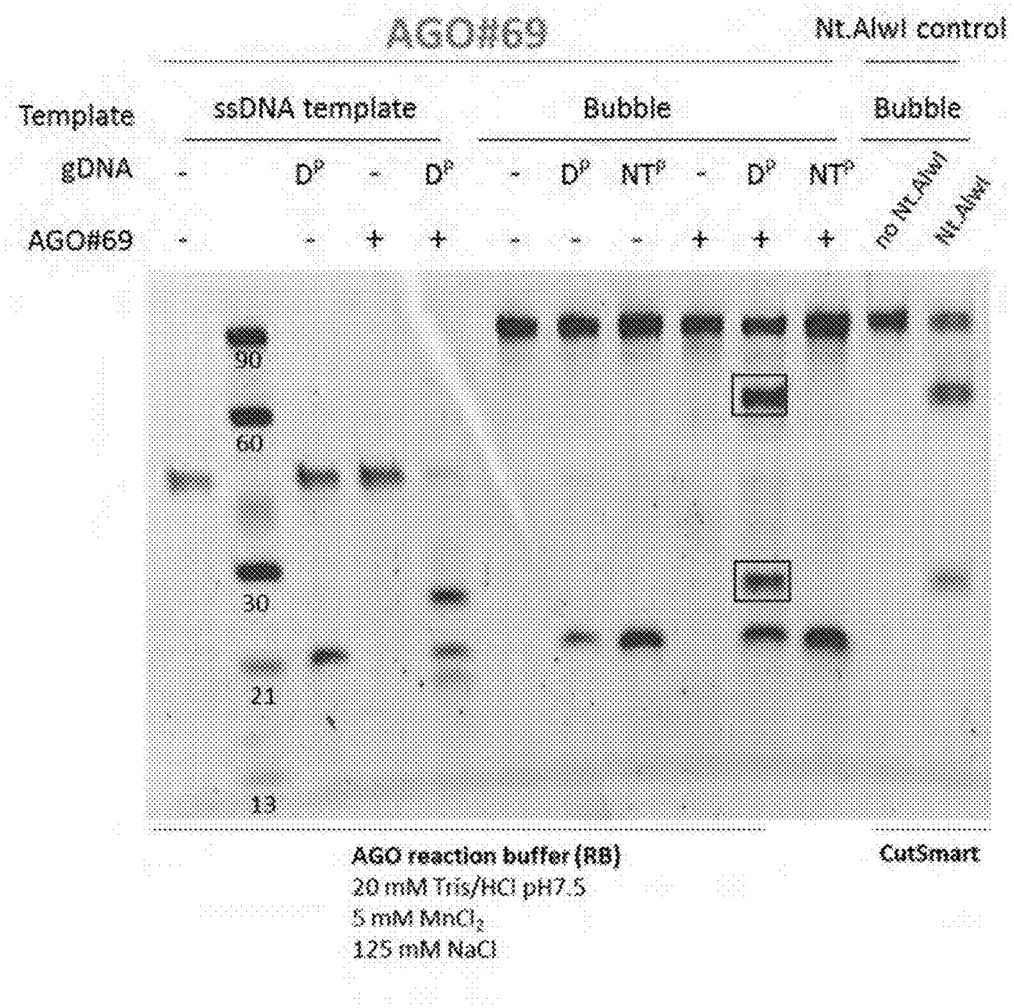

FIG. 39 shows an image of an electrophoresis gel showing single stranded DNA (ssDNA) guide dependent nicking of double stranded DNA (dsDNA) bubble template of Ago69. "D" indicates the 5' most nucleotide of the gDNA is phosphorylated. "$NT^p$" indicates the gDNA is a non-target guide DNA (negative control); and the 5' most nucleotide of the gDNA is phosphorylated.

FIG. 40 shows an image of an electrophoresis gel showing the effect of GC content of guide DNA (gDNA) on the cleavage activity of Ago69. "D" indicates the 5' most nucleotide of the gDNA is phosphorylated. FIG. 40 discloses SEQ ID NOS 157-162 and 169, respectively, in order of appearance.

FIG. 41 shows an image of an electrophoresis gel showing the effect of GC content of guide DNA (gDNA) on the cleavage activity of Ago02. "DP" indicates the 5' most nucleotide of the gDNA is phosphorylated. FIG. 41 discloses SEQ ID NOS 157-162 and 169, respectively, in order of appearance.

FIG. 42 shows an image of an electrophoresis gel showing the effect of GC content of guide DNA (gDNA) on the cleavage activity of Ago41. "DP" indicates the 5' most nucleotide of the gDNA is phosphorylated. FIG. 42 discloses SEQ ID NOS 157-162 and 169, respectively, in order of appearance.

FIG. 43 shows an image of an electrophoresis gel showing the effect of GC content of guide DNA (gDNA) on the cleavage activity of Ago70. "DP" indicates the 5' most nucleotide of the gDNA is phosphorylated. FIG. 43 discloses SEQ ID NOS 157-162 and 169, respectively, in order of appearance.

Figure 44:
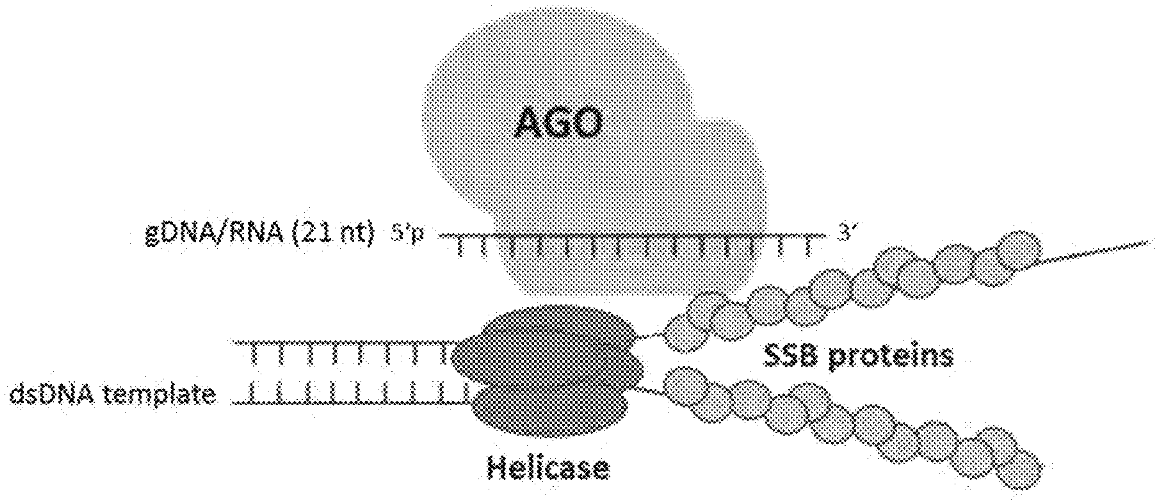

FIG. 44 shows the testing impact of SSB proteins on the processivity of DNA unwinding by RecQ helicase.

Figure 45:
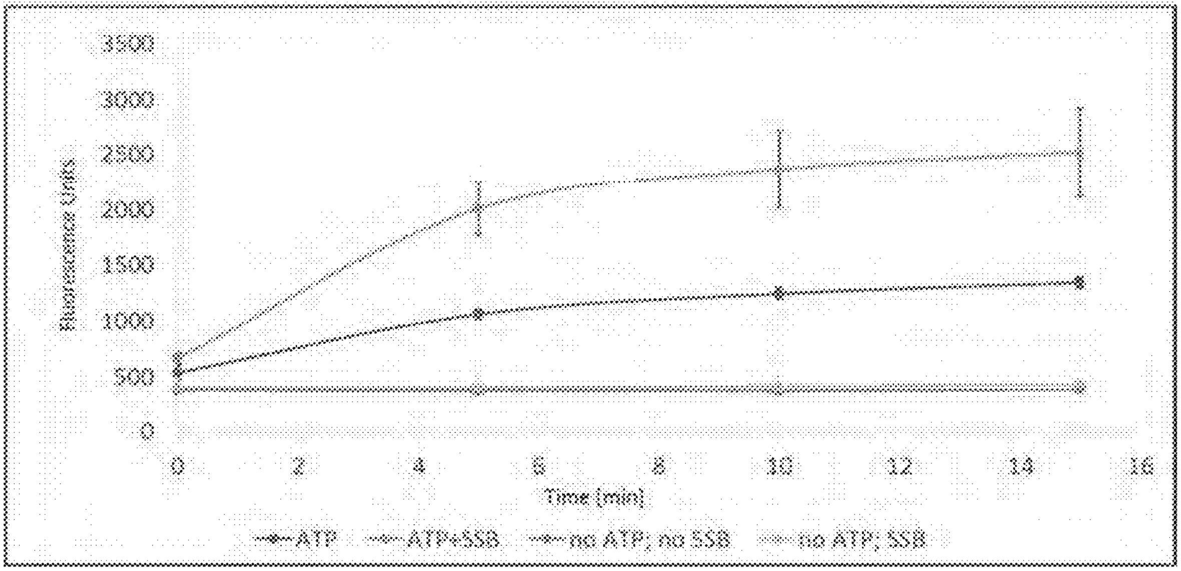

FIG. 45 shows a line a graph showing the effect of ET-SSB on RecQ mediated DNA unwinding using 3' overhang long substrate.

Figure 46:
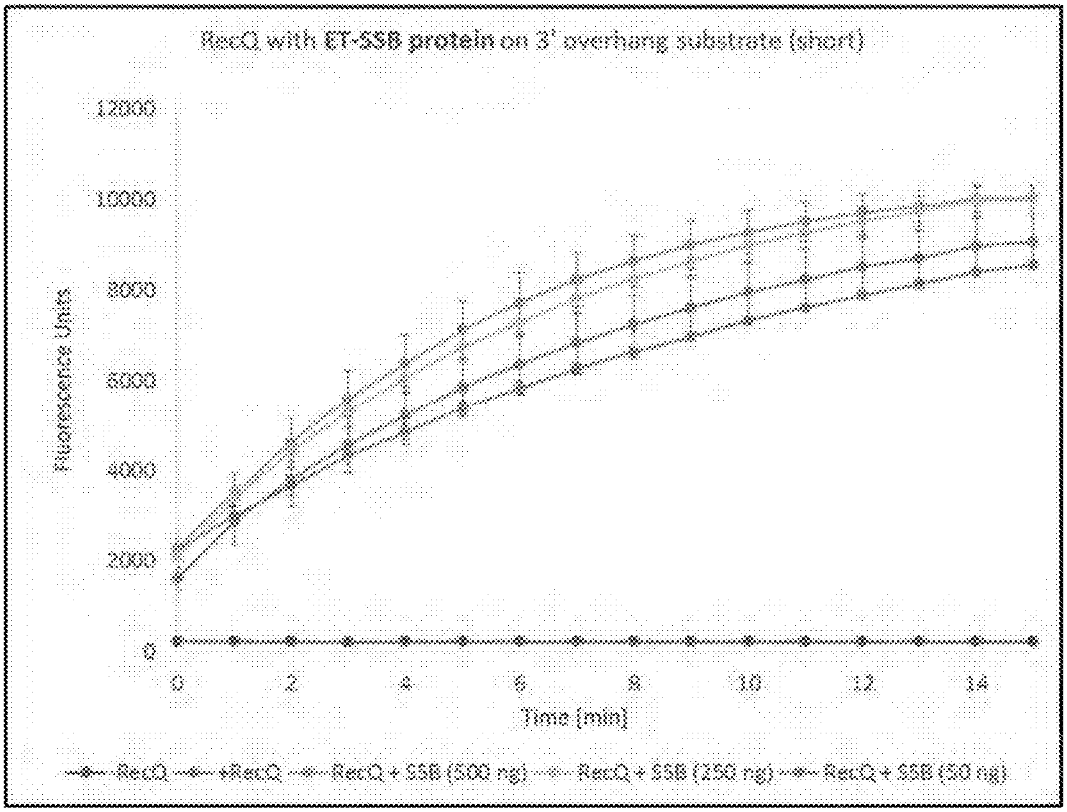

FIG. 46 shows a line a graph showing the effect of ET-SSB on RecQ mediated DNA unwinding using 3' overhang short substrate.

Figure 47:
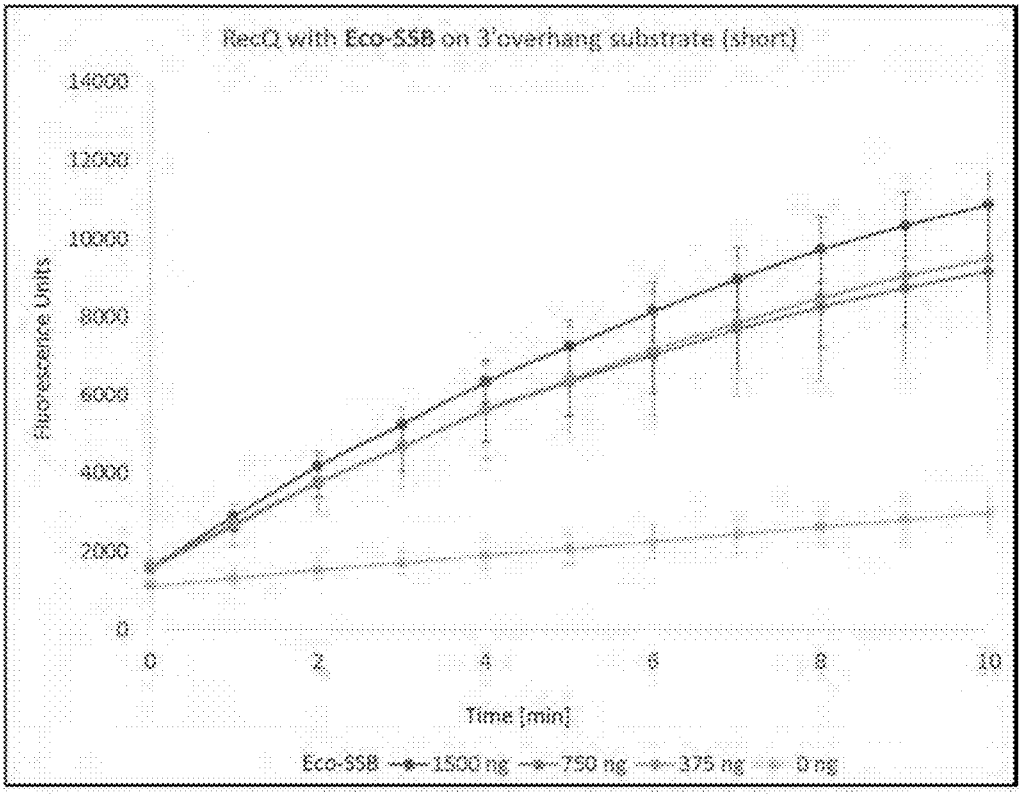

FIG. 47 shows a line a graph showing the effect of Eco-SSB on RecQ mediated DNA unwinding using 3' overhang short substrate.

Figure 48:
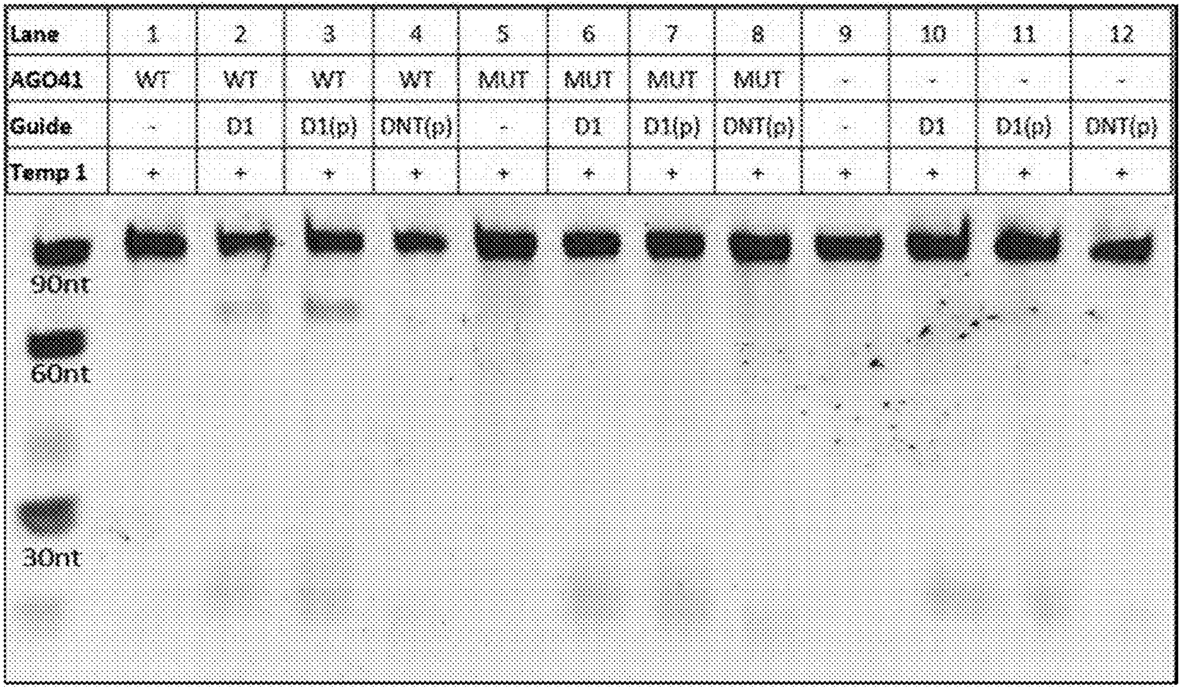

FIG. 48 shows an image of an electrophoresis gel showing the elimination of cleavage activity of Ago41 with guide DNA (gDNA) when the DEDX catalytic domain of Ago41 is mutated. Mutations D559A, E595A, and D629A result in an inhibition of Ago41 cleavage activity on gDNA. "D1(p)" indicates the 5' most nucleotide of the gDNA is phosphorylated. "DNT(p)" indicates the gDNA is a non-target guide DNA (negative control); and the 5' most nucleotide of the gDNA is phosphorylated.

FIG. 49 shows the amino acid sequence of Ago69 with the comparable mutations in Ago69 to those of the DEDX motif in Ago41 (see FIG. 48). FIG. 49 discloses SEQ ID NO: 163.

FIG. 50 shows the amino acid sequence of Ago69 with the conserved lysine residues highlighted that are putatively involved in DNA binding specificity are potential sites for mutagenesis. FIG. 50 discloses SEQ ID NO: 163.

Figure 51:
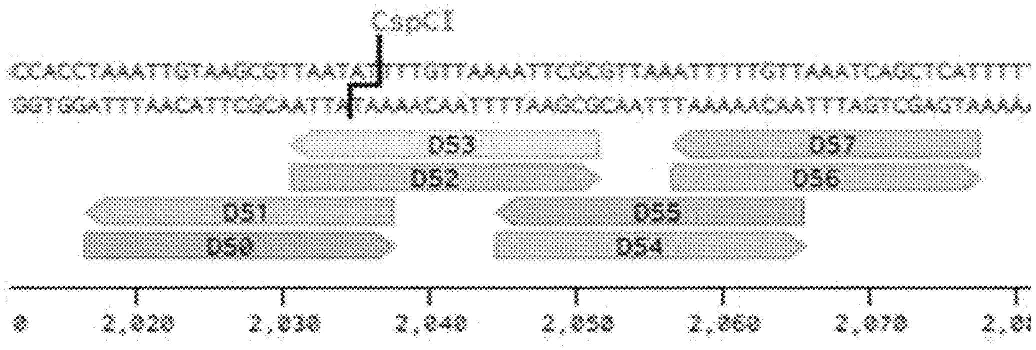

FIG. 51 shows a depiction of the location of the eight guide DNAs (gDNAs) used in the dsDNA cleavage assay described in Example 21. The depiction further includes the GC content and Tm for each gDNA. FIG. 51 discloses SEQ ID NO: 170.

Figure 52A:
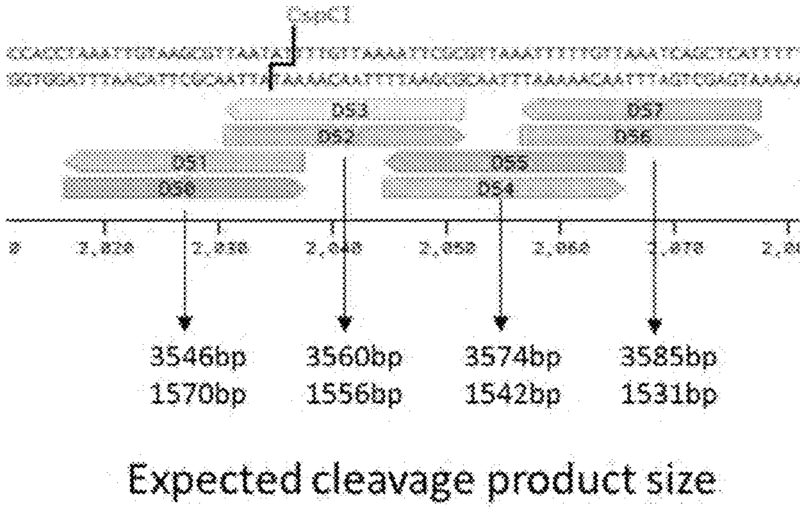
Figure 52B:
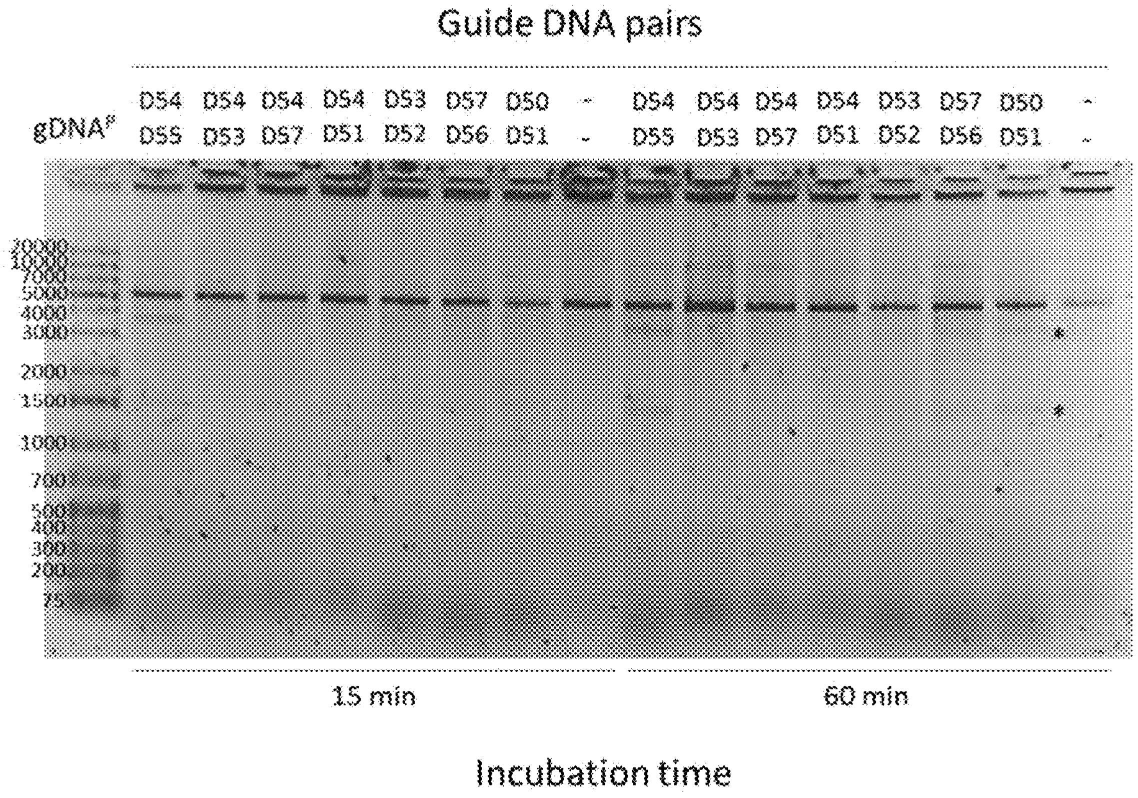

FIG. 52A shows a depiction of the location of the eight guide DNAs (gDNAs) and expected cleavage products used in the dsDNA cleavage assay described in Example 21. FIG. 52A discloses SEQ ID NO: 170. FIG. 52B shows an image of an electrophoresis gel showing double stranded DNA (dsDNA) cleavage by Ago69. "gDNA$^P$" indicates the 5' most nucleotide of the gDNA is phosphorylated.

Figure 53A:
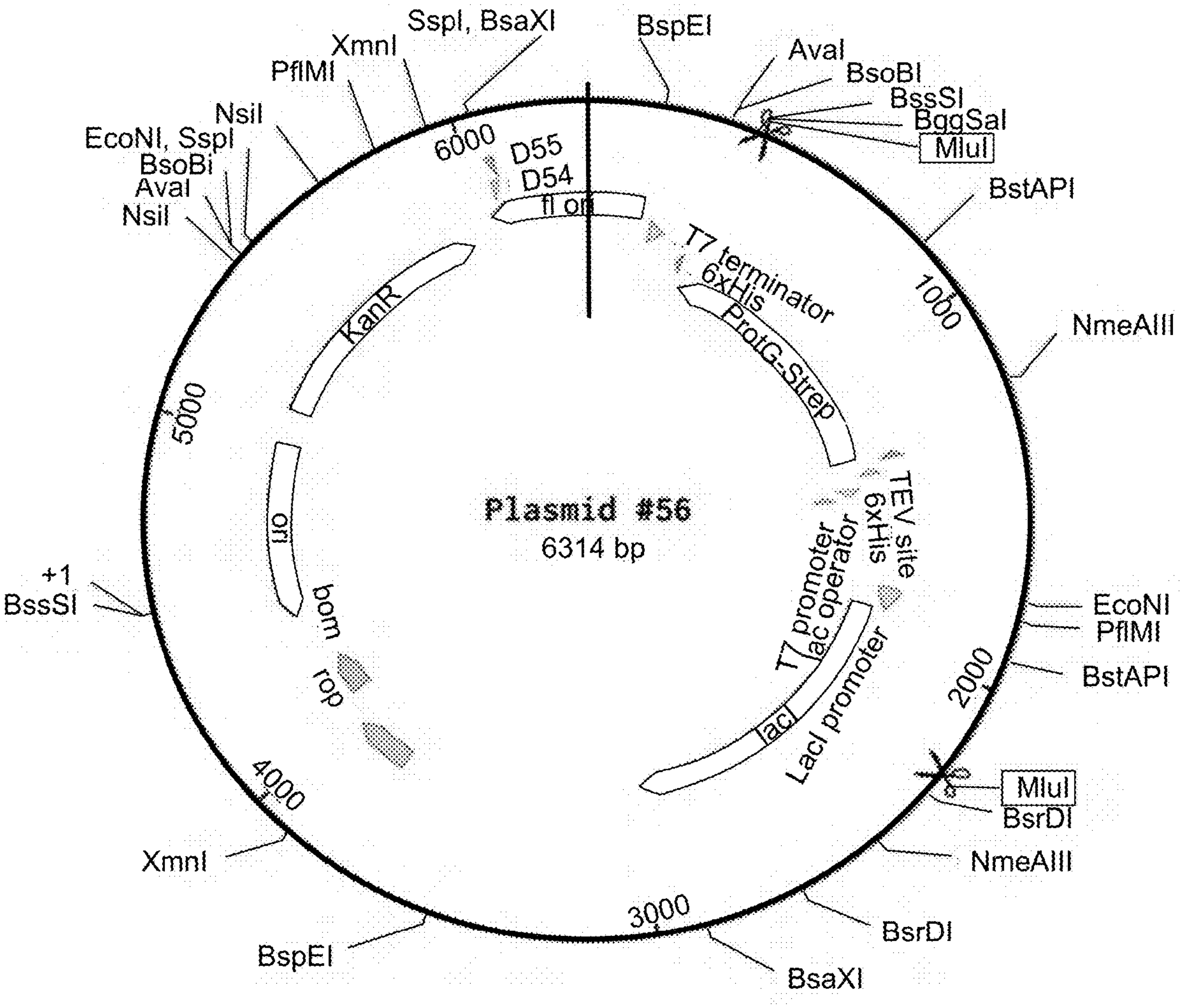
Figure 53B:
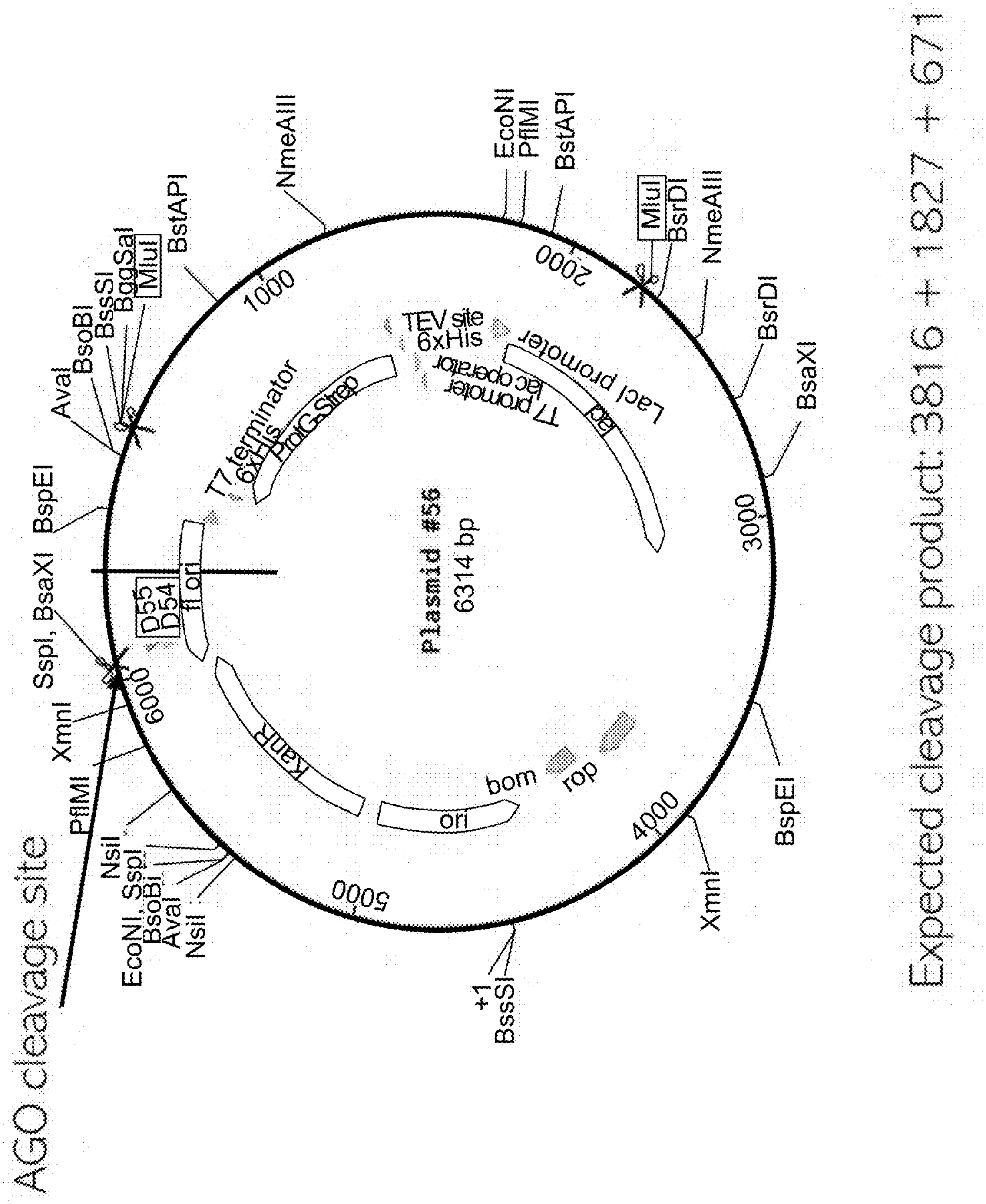

FIG. 53A shows a map of plasmid #56. The MluI digestion sites are marked with scissors. The expected cleavage products produced by cleavage of plasmid #56 with MluI are 4487 bp and 1827 bp fragments. FIG. 53B shows a map of plasmid #56. The MluI digestion sites are marked with scissors; as well as the Ago69 cleavage site. The expected cleavage products produced by cleavage of plasmid #56 with MluI and Ago69 are 3816 bp, 1827 bp, and 671 bp fragments.

Figure 54:
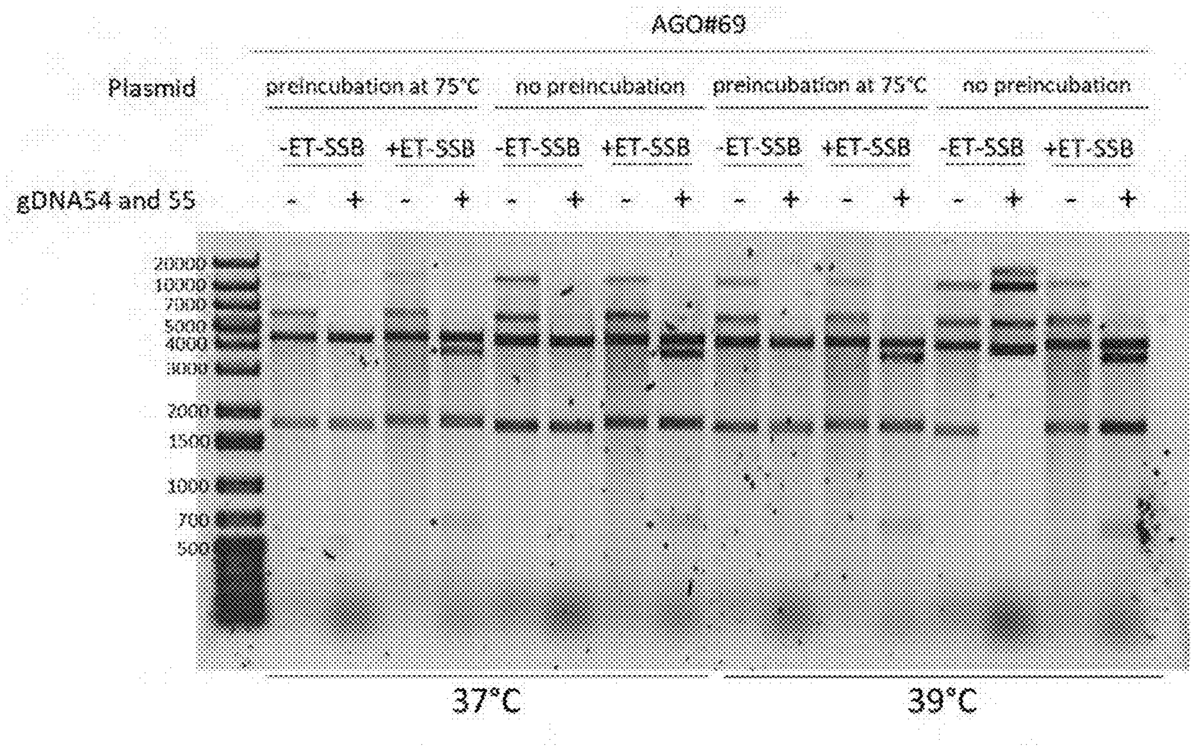

FIG. 54 shows an image of an electrophoresis gel showing cleavage of plasmid #56 by Ago69 with or without preincubation of plasmid at 75° C.; with and without ET-SSB; and with and without gDNAs 54 and 55. The cleavage was conducted at both 37° C. (left) and 39° C. (right). Stars mark the expected cleavage products.

Figure 55:
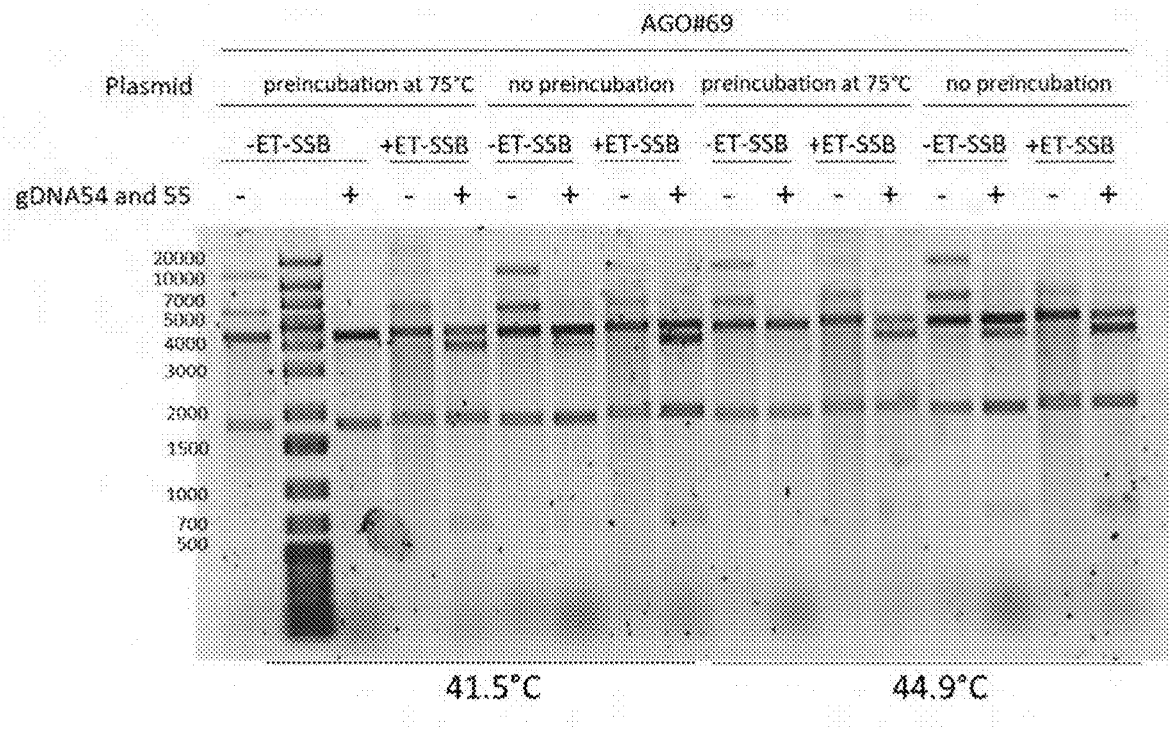

FIG. 55 shows an image of an electrophoresis gel showing cleavage of plasmid #56 by Ago69 with or without preincubation of plasmid at 75° C.; with and without ET-SSB; and with and without gDNAs 54 and 55. The cleavage was conducted at both 41.5° C. (left) and 44.9° C. (right).

Figure 56:
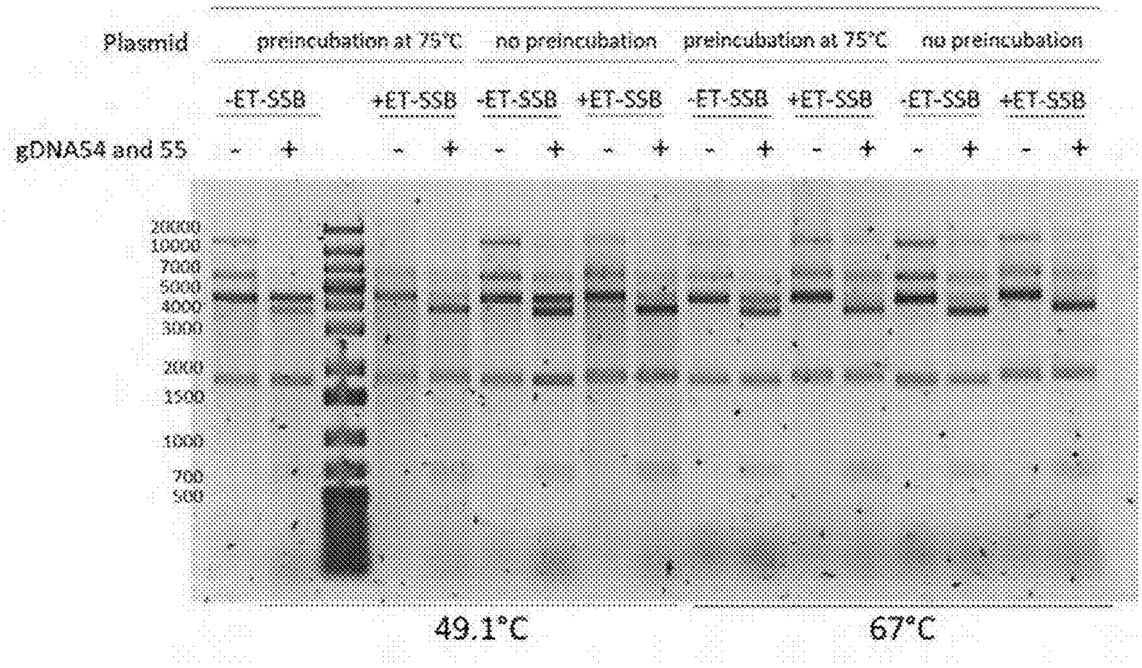

FIG. 56 shows an image of an electrophoresis gel showing cleavage of plasmid #56 by Ago69 with or without preincubation of plasmid at 75° C.; with and without ET-SSB; and with and without gDNAs 54 and 55. The cleavage was conducted at both 49.1° C. (left) and 67° C. (right).

Figure 57A:
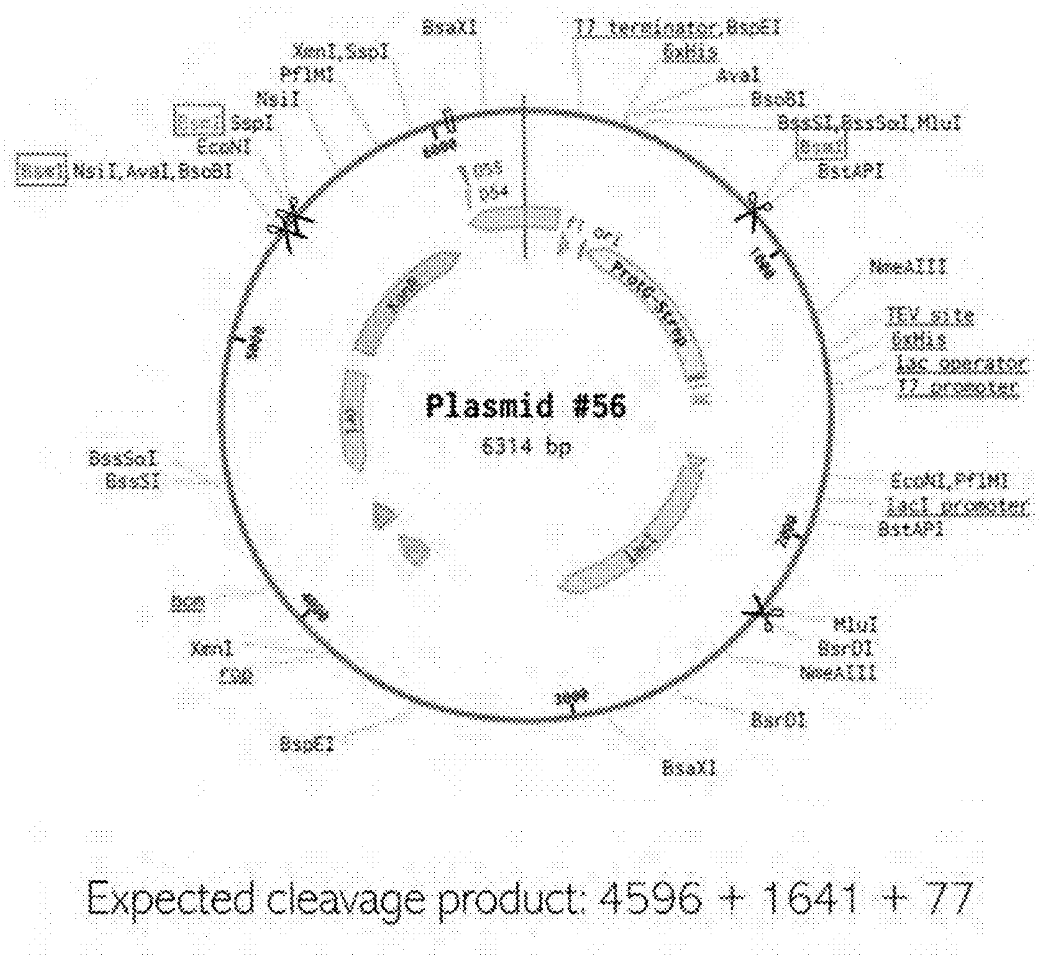
Figure 57B:
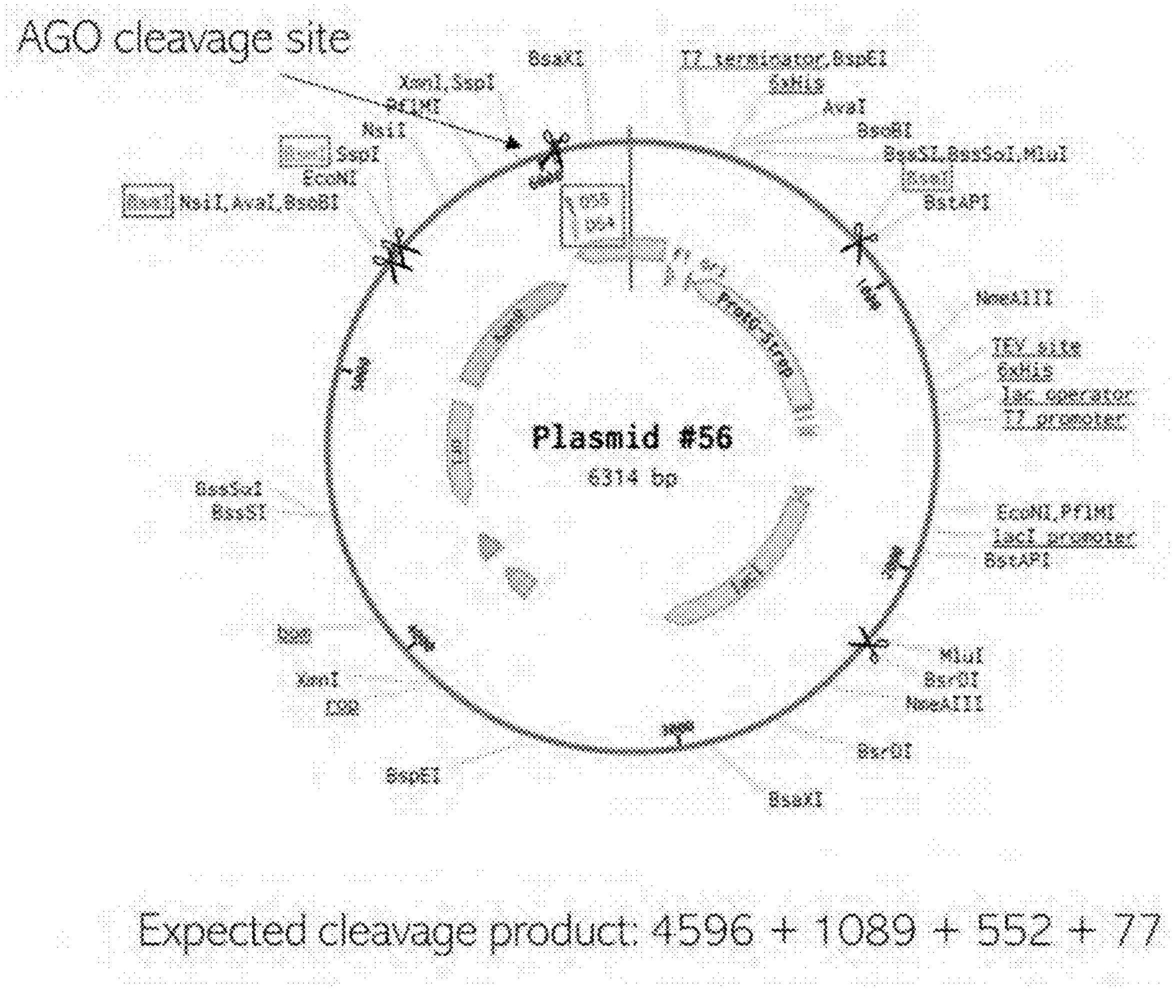

FIG. 57A shows a map of plasmid #56. The BsmI digestion sites are marked with scissors. The expected cleavage products produced by cleavage of plasmid #56 with BsmI are 4596 bp, 1641 bp, and 77 bp fragments. FIG. 57B shows a map of plasmid #56. The BsmI digestion sites are marked with scissors; as well as the Ago69 cleavage site. The expected cleavage products produced by cleavage of plasmid #56 with BsmI and Ago69 are 4596 bp, 1081 bp, 552 bp, and 77 bp fragments.

Figure 58:
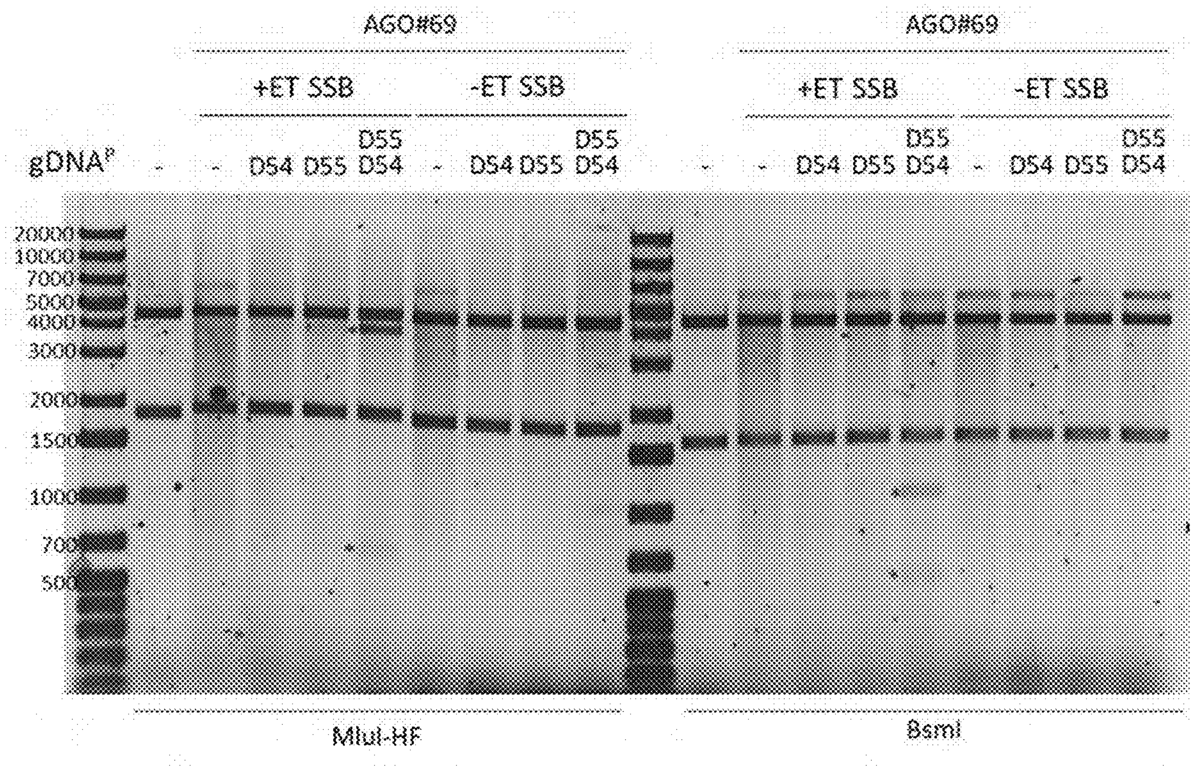

FIG. 58 shows an image of an electrophoresis gel showing cleavage of plasmid #56 by Ago69 and MluI (left) or BsmI (right); with and without ET-SSB; and with gDNA 54 alone, 55 alone, 55 and 54, or no gDNA. The cleavage was conducted at both 41.5° C. (left) and 44.9° C. (right). "gDNA$^P$" indicates the 5' most nucleotide of the gDNA is phosphorylated. Stars indicate the expected cleavage products.

Figure 59:
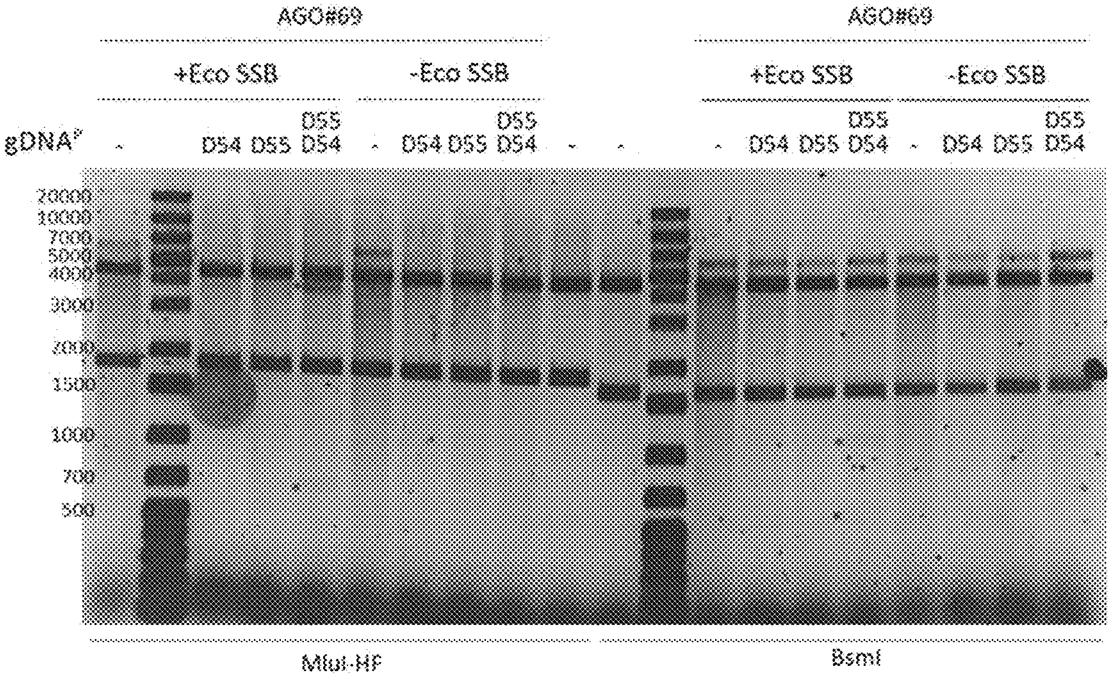

FIG. 59 shows an image of a high exposure electrophoresis gel showing cleavage of plasmid #56 by Ago69 and MluI (left) or BsmI (right); with and without ET-SSB; and with gDNA 54 alone, 55 alone, 55 and 54, or no gDNA. "gDNA$^P$" indicates the 5' most nucleotide of the gDNA is phosphorylated. Stars indicate the expected cleavage products.

Figure 60:
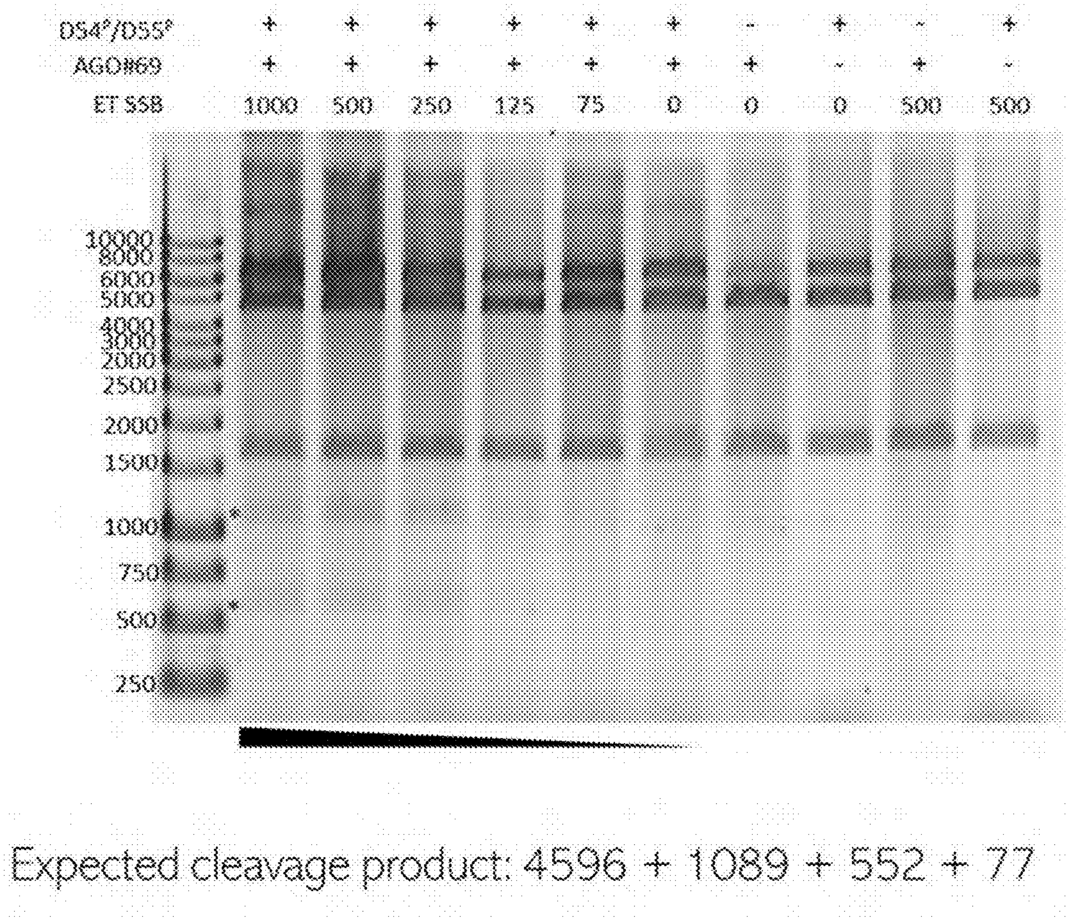

FIG. 60 shows an image of an electrophoresis gel showing cleavage of plasmid #56 by Ago69 and BsmI; with and without ET-SSB; and with or without gDNAs 54 and 55. "gDNA$^P$" indicates the 5' most nucleotide of the gDNA is phosphorylated. Stars indicate the expected cleavage products. "gDNA$^P$" indicates the 5' most nucleotide of the gDNA is phosphorylated. Stars indicate the expected cleavage products.

Figure 61:
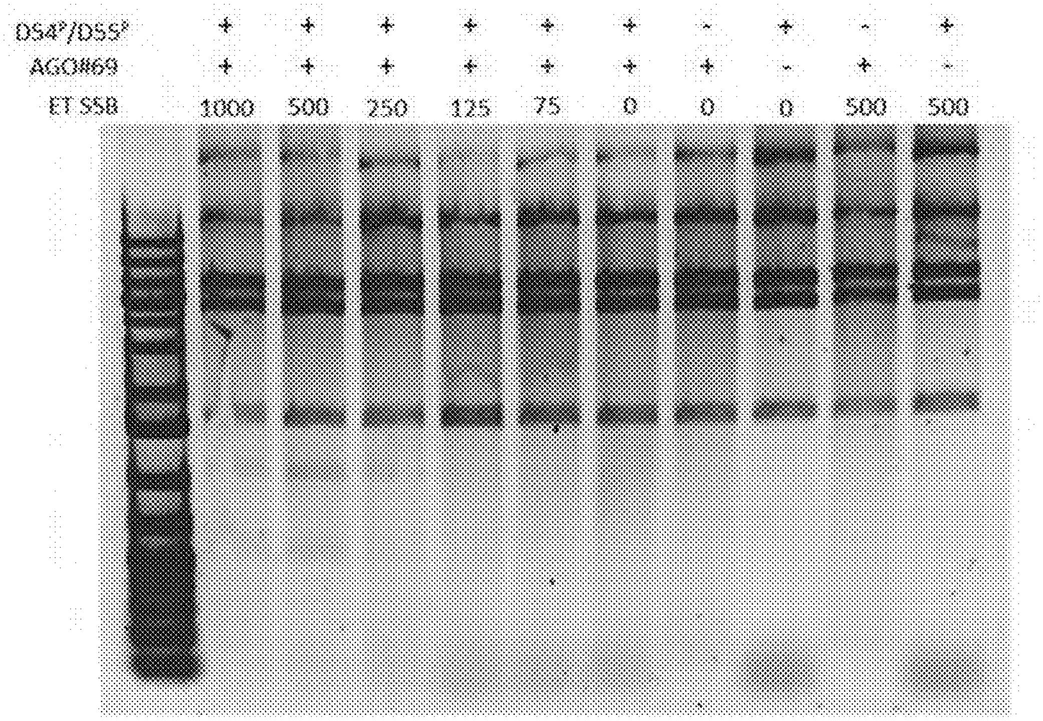

FIG. 61 shows an image of a high exposure electrophoresis gel showing cleavage of plasmid #56 by Ago69 and BsmI; with and without ET-SSB; and with or without gDNAs 54 and 55. "gDNA$^P$" indicates the 5' most nucleotide of the gDNA is phosphorylated. Stars indicate the expected cleavage products. "gDNA$^P$" indicates the 5' most nucleotide of the gDNA is phosphorylated. Stars indicate the expected cleavage products.

Figure 62:
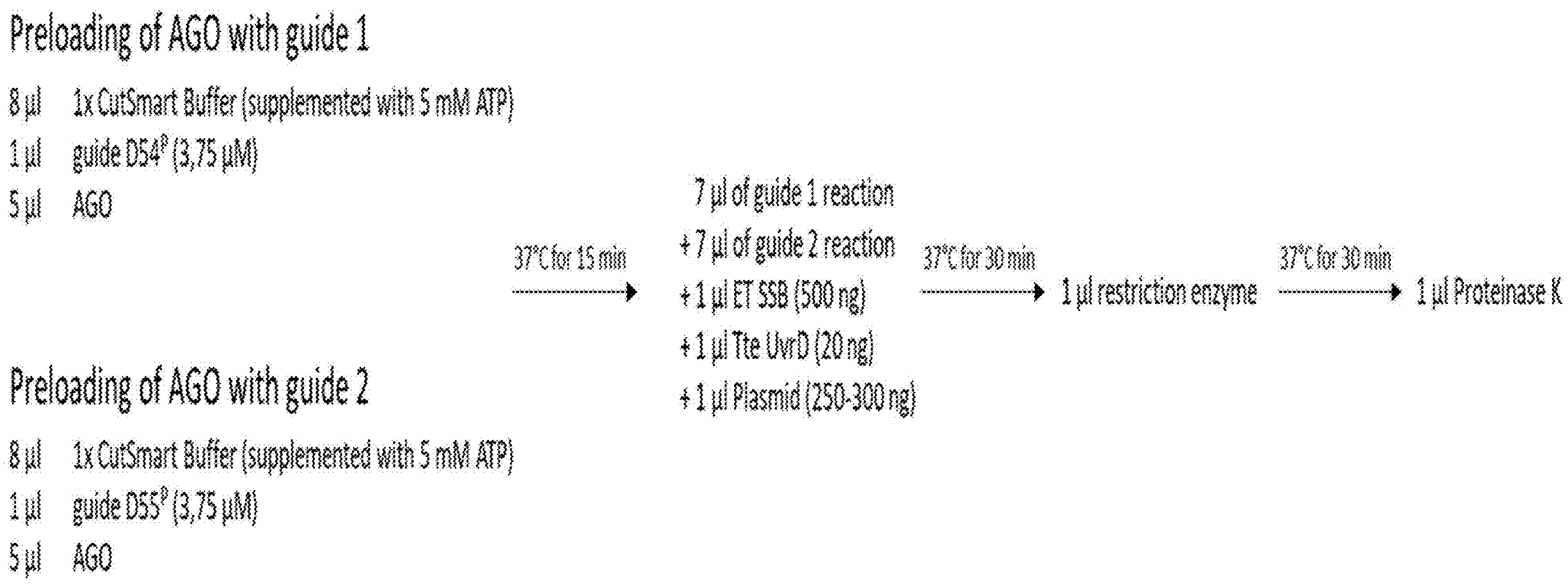

FIG. 62 shows a graphical depiction of a protocol of plasmid DNA cleavage assay.

Figure 63:
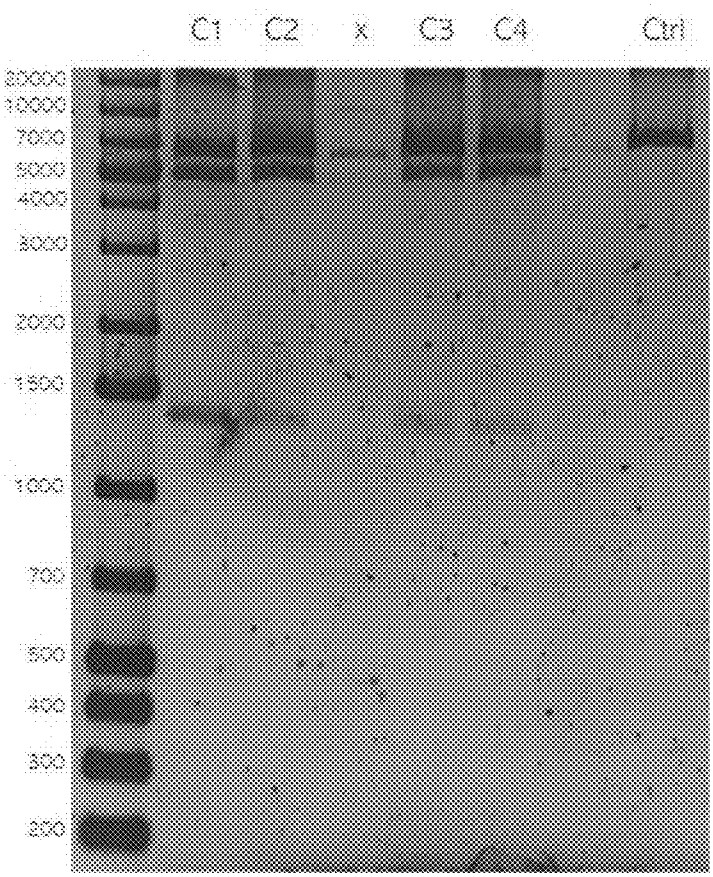

FIG. 63 shows an image of an electrophoresis gel showing cleavage of plasmid 56 by Ago69 and Bsal-HF. The expected cleavage products produced by cleavage of plasmid #56 with BsalI are 4973 bp and 1341 bp fragments. C1: preloading of AGO with D54$^P$/D55$^P$+SSB+UvrD+plasmid (standard condition. C2: preloading of AGO with D54P/D55P in presence of SSB+plasmid preincubated with Tte UvrD. C3: preloading of AGO with D54P/D55P in presence of SSB and UvrD+plasmid. C4: preloading of AGO with D54P/D55P+plasmid preincubated with SSB and UvrD. Ctrl: preloading of AGO with no gDNA+SSB+UvrD+plasmid. X: pipetting mistake. Stars indicate the expected cleavage products.

Figure 64A:
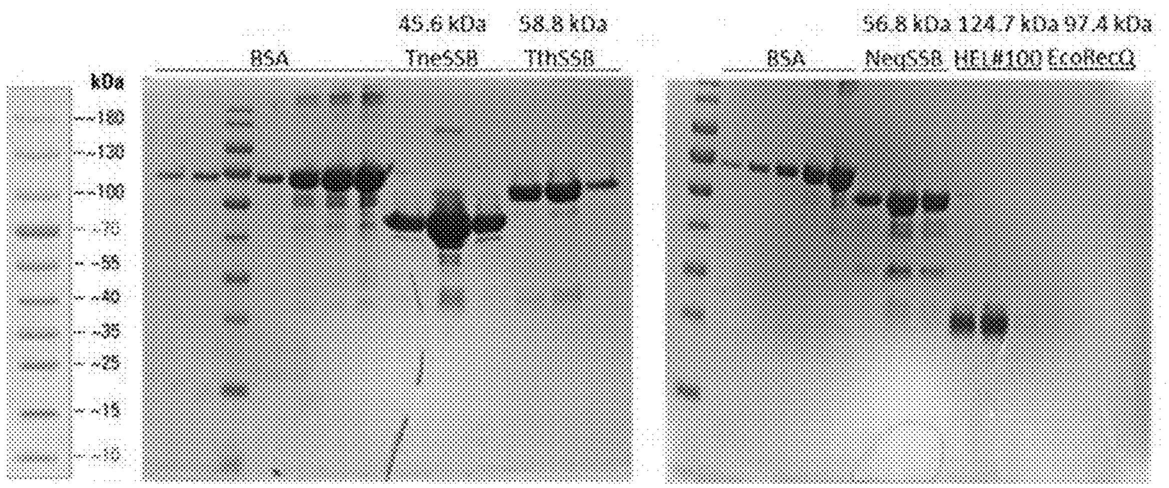
Figure 64B:
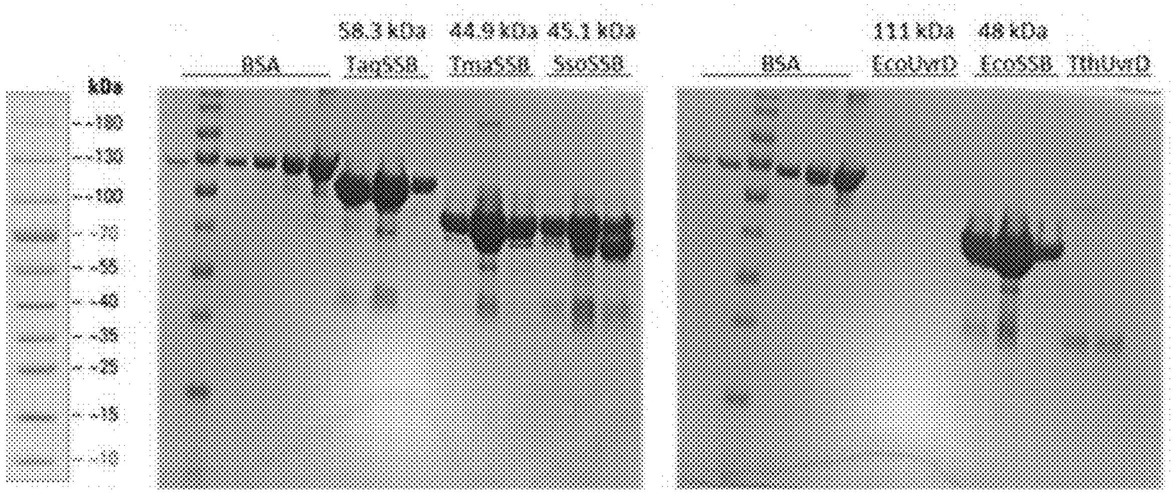

FIG. 64A shows an image of an electrophoresis gel showing the expression and purification of SSBs, including TneSSB, TthSSB, NeqSSB; and helicases including HEL #100, and EcoRecQ. FIG. 64B shows an image of an electrophoresis gel showing the expression and purification of SSBs, including TaqSSB, TmaSSB, SsoSSB, EcoSSB; and helicases including EcoUvrD and TthUvrD.

Figure 65:
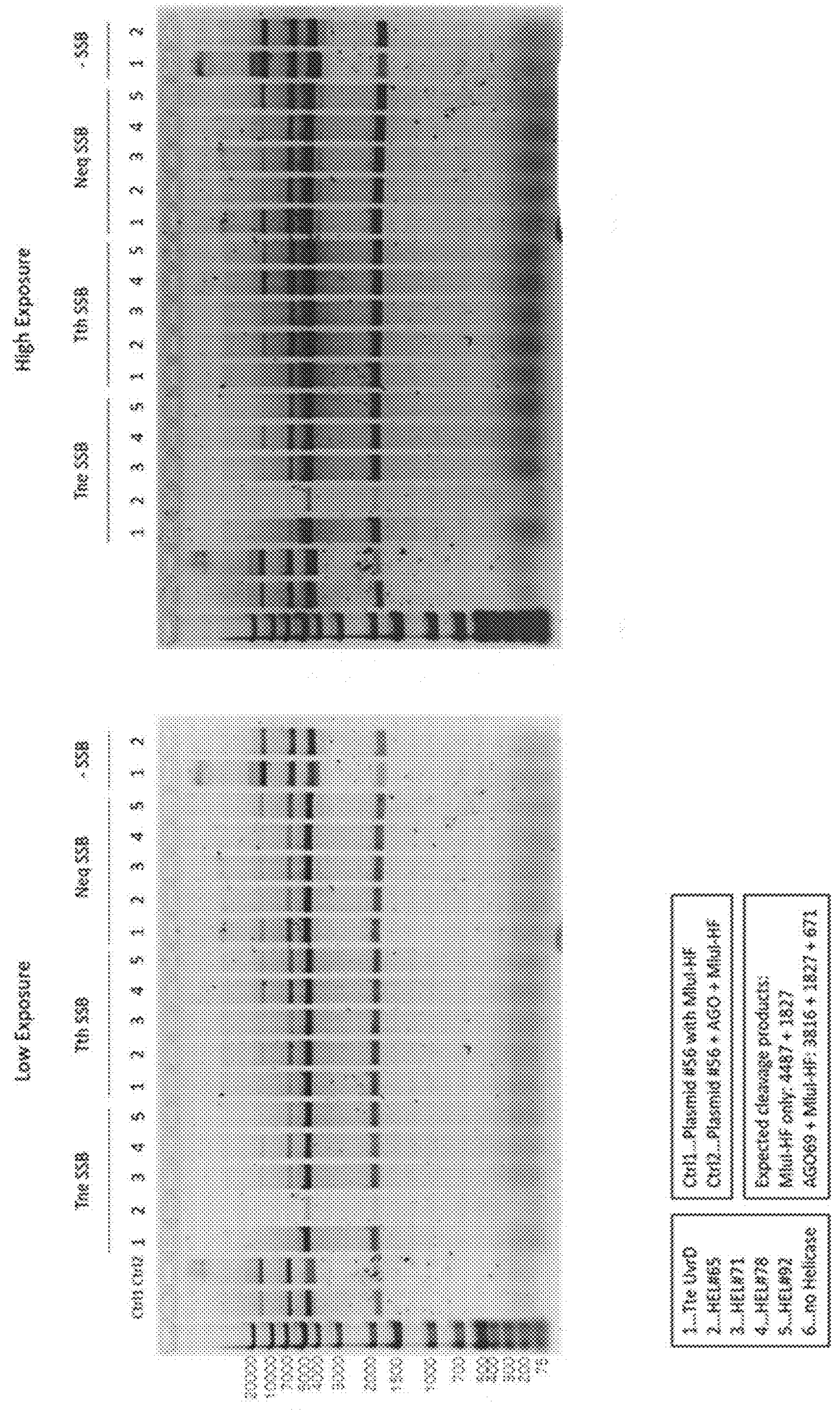

FIG. 65 shows an image of an electrophoresis gel showing cleavage of plasmid #56 by Ago69 with the indicated SSB and helicase. The left gel is a short exposure. The right gel is a high exposure. 1: Tte UvrD; 2: HEL #65; 3: HEL #71, 4: HEL #78, 5: HEL #92, 6: No helicase, Ctr11: Plasmid 56 with MuI-HF, Ctr12: Plasmid #56+Ago69+MuI-HIF. The expected cleavage products of MluI only: 4487 bp and 1827 bp fragments. The expected cleavage products of MuI+Ago69: 3816 bp, 1827 bp, and 671 bp fragments.

Figure 66:
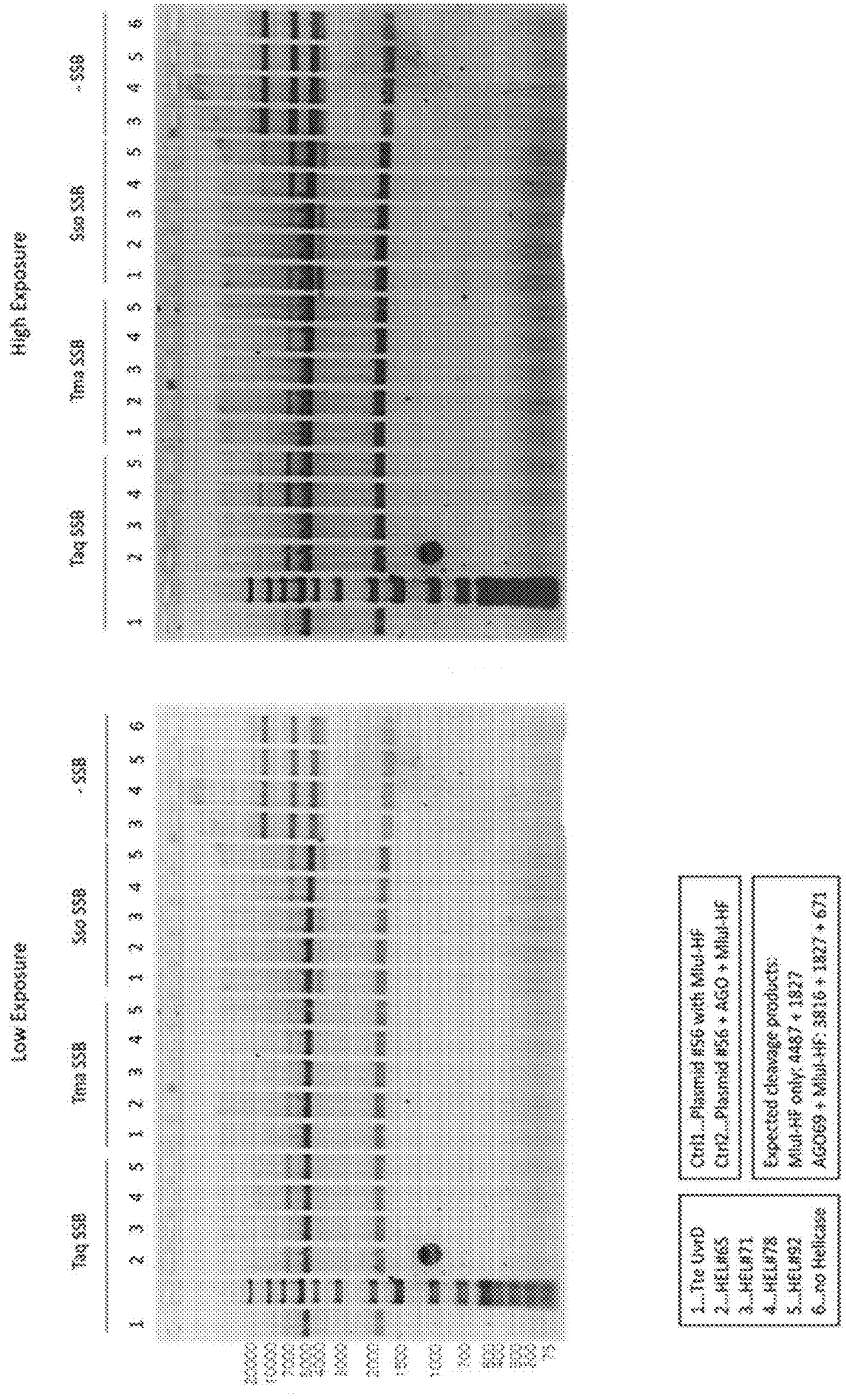

FIG. 66 shows an image of an electrophoresis gel showing cleavage of plasmid #56 by Ago69 with the indicated SSB and helicase. The left gel is a short exposure. The right gel is a high exposure. 1: Tte UvrD; 2: HEL #65; 3: HEL #71, 4: HEL #78, 5: HEL #92, 6: No helicase, Ctr11: Plasmid 56 with MuI-HF, Ctr12: Plasmid #56+Ago69+MuI-HIF. The expected cleavage products of MluI only: 4487 bp and 1827 bp fragments. The expected cleavage products of MuI+Ago69: 3816 bp, 1827 bp, and 671 bp fragments.

Figure 67:
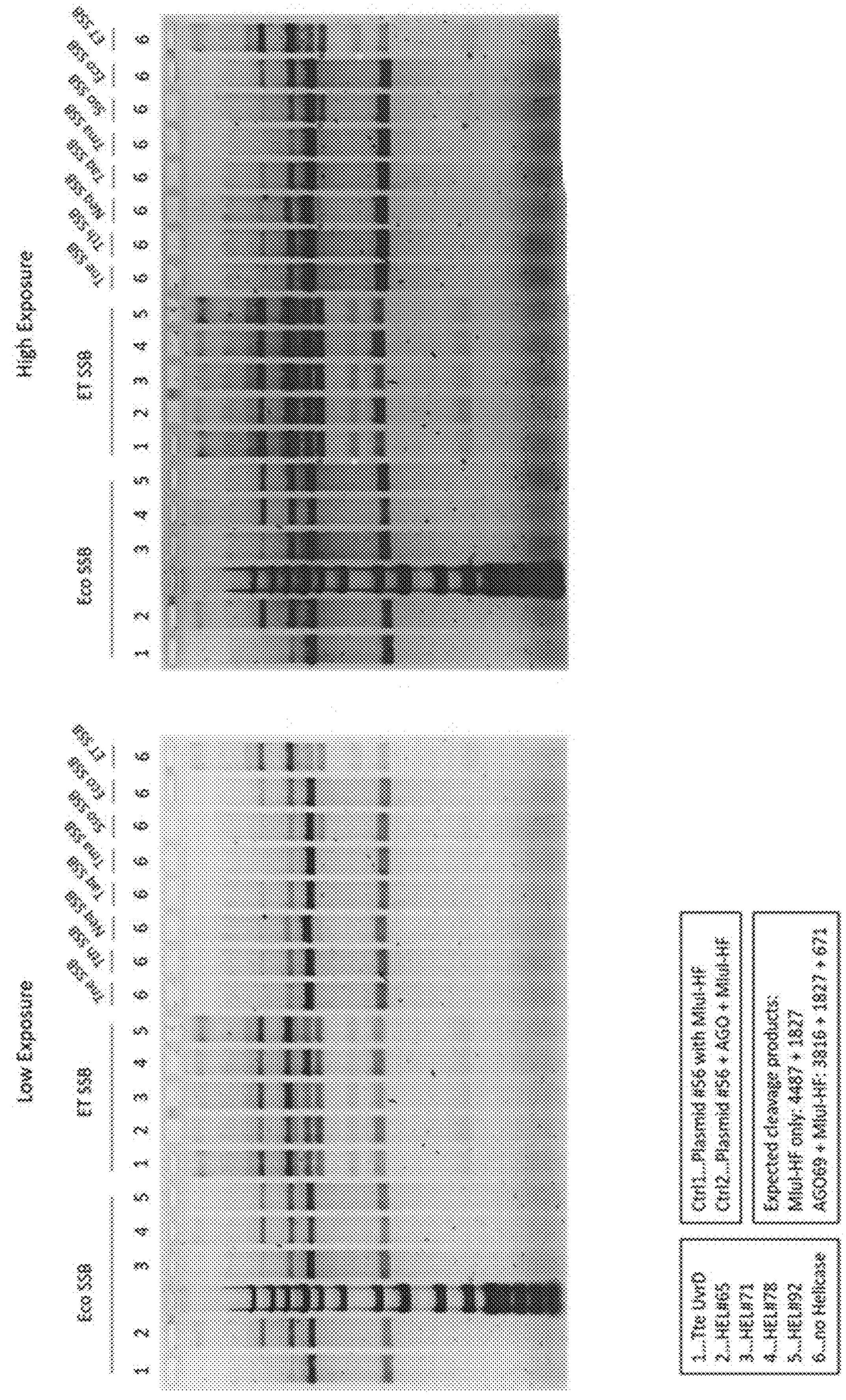

FIG. 67 shows an image of an electrophoresis gel showing cleavage of plasmid #56 by Ago69 with the indicated SSB and helicase. The left gel is a short exposure. The right gel is a high exposure. 1: Tte UvrD; 2: HEL #65; 3: HEL #71, 4: HEL #78, 5: HEL #92, 6: No helicase, Ctr11: Plasmid 56 with MuI-HF, Ctr12: Plasmid #56+Ago69+MuI-HIF. The expected cleavage products of MluI only: 4487 bp and 1827 bp fragments. The expected cleavage products of MuI+Ago69: 3816 bp, 1827 bp, and 671 bp fragments.

Figure 68:

FIG. 68 shows a graphical depiction of Ago69 containing fusion proteins. L: linker; SV40NLS: SV40 nuclear localization signal.

Figure 69A:
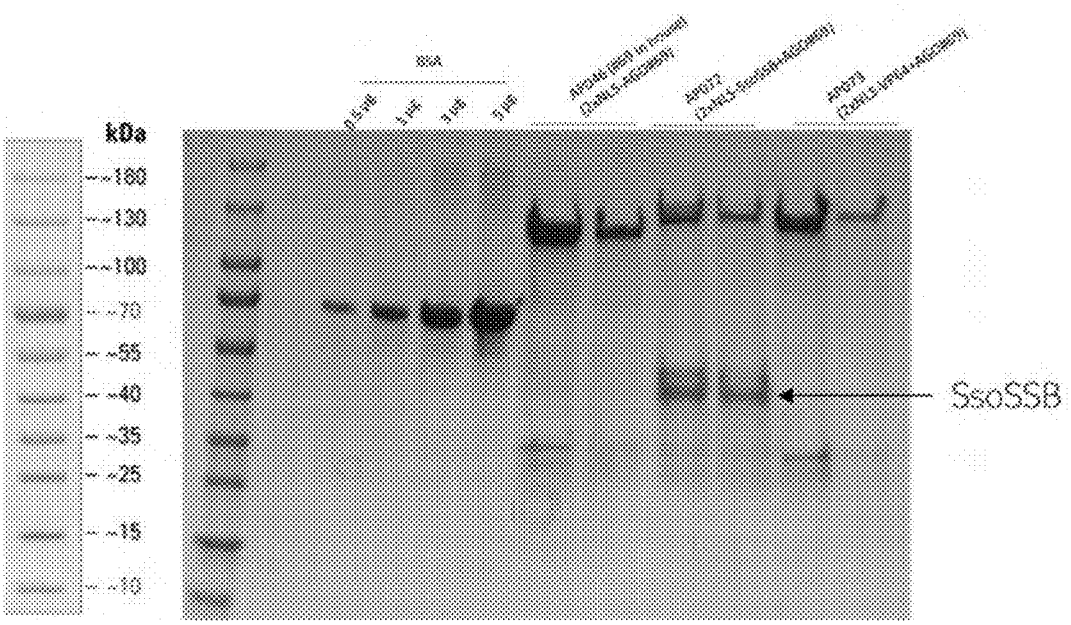
Figure 69B:
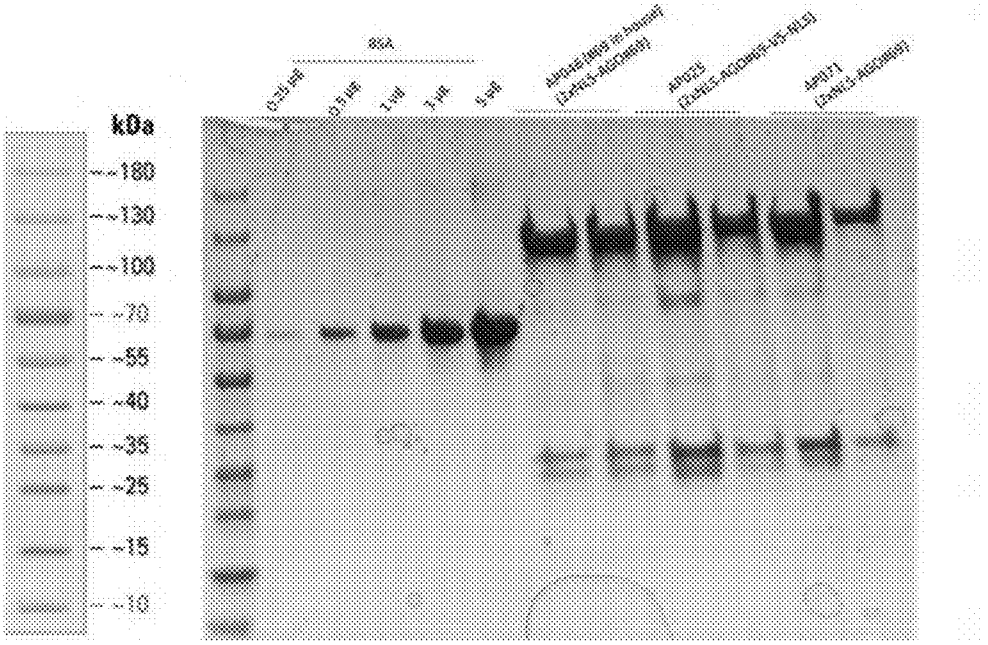

FIG. 69A shows an image of an electrophoresis gel showing expression and purification of the indicated fusion protein. FIG. 69B shows an image of an electrophoresis gel showing expression and purification of the indicated fusion protein.

Figure 70:
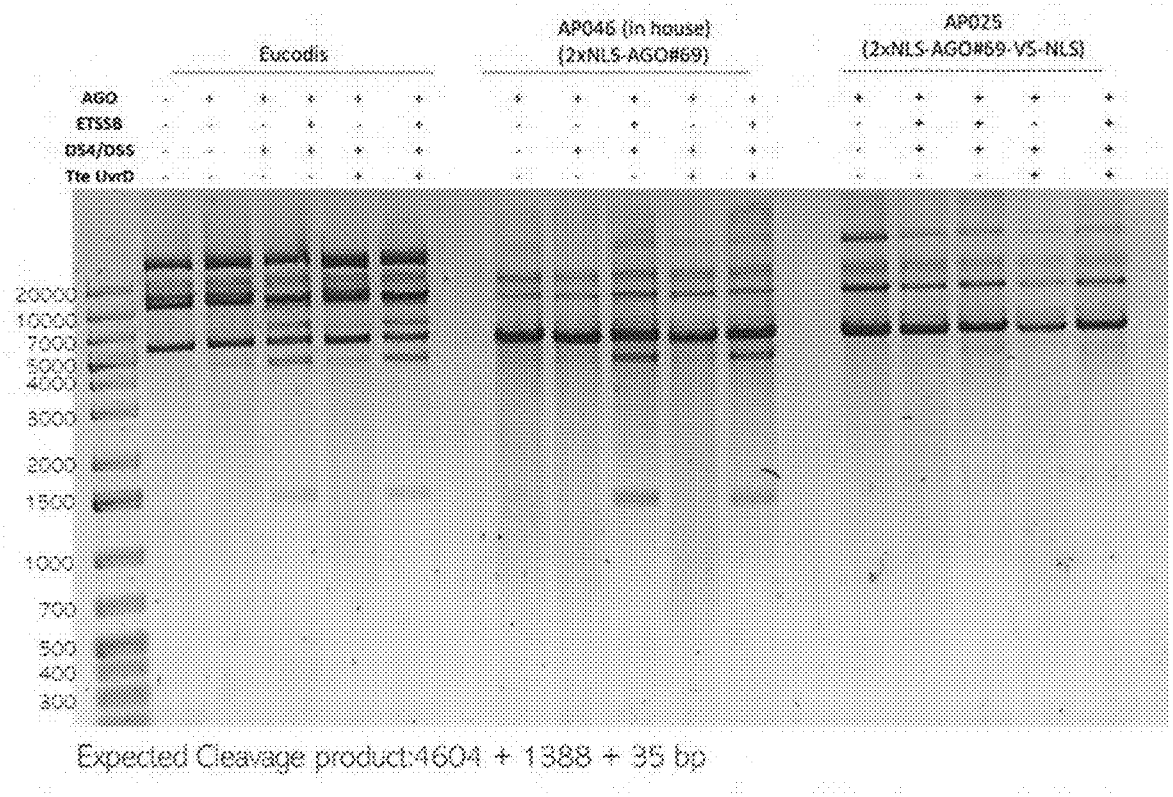

FIG. 70 shows an image of an electrophoresis gel showing cleavage of plasmid 56 by the indicated Ago69 containing fusion protein. ET-SSB, guides D54 and D55, and helicase Tte UvrD were included as indicated. The expected cleavage products were 4604, 1388, and 35 bp fragments.

Figure 71:
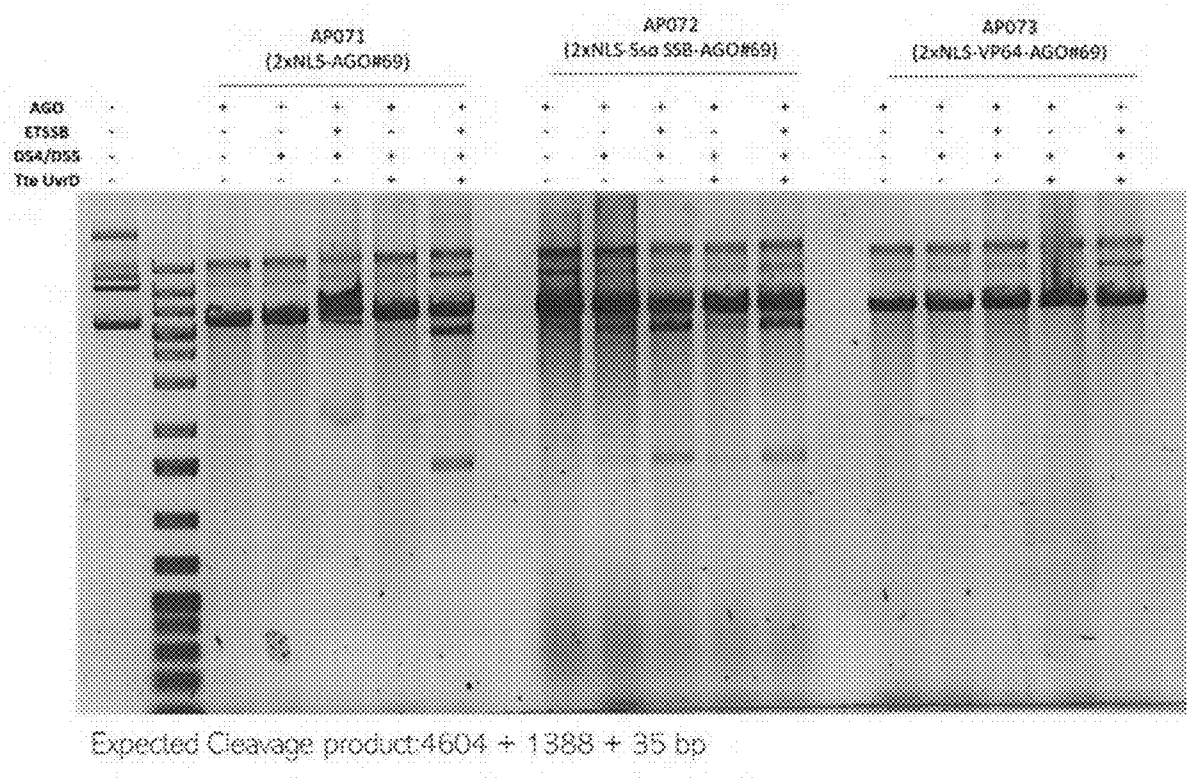

FIG. 71 shows an image of an electrophoresis gel showing cleavage of plasmid 56 by the indicated Ago69 containing fusion protein. ET-SSB, guides D54 and D55, and helicase Tte UvrD were included as indicated. The expected cleavage products were 4604, 1388, and 35 bp fragments.

Figure 72A:
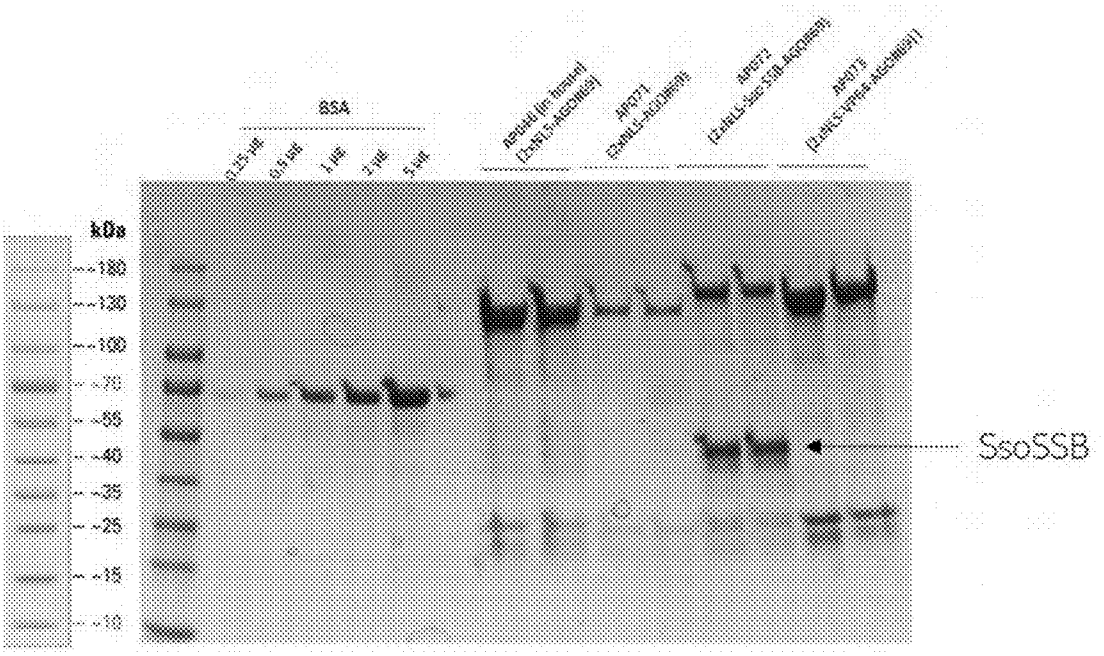
Figure 72B:
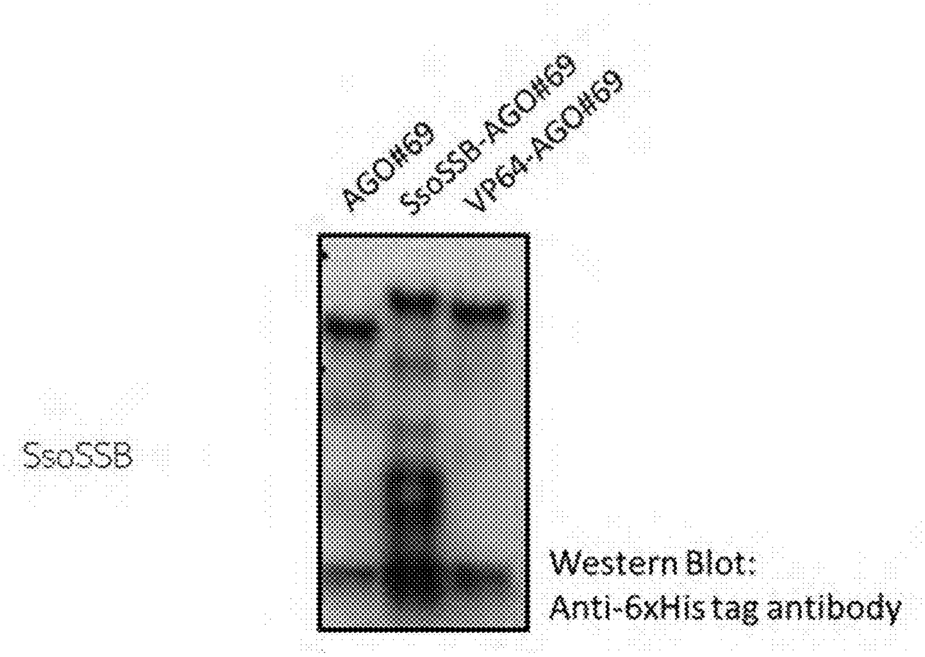

FIG. 72A shows an image of an electrophoresis gel showing expression and purification of the indicated fusion protein. FIG. 72B shows western blot of the indicated fusion protein using an anti-6×His tag antibody for detection of each fusion protein.

Figure 73:
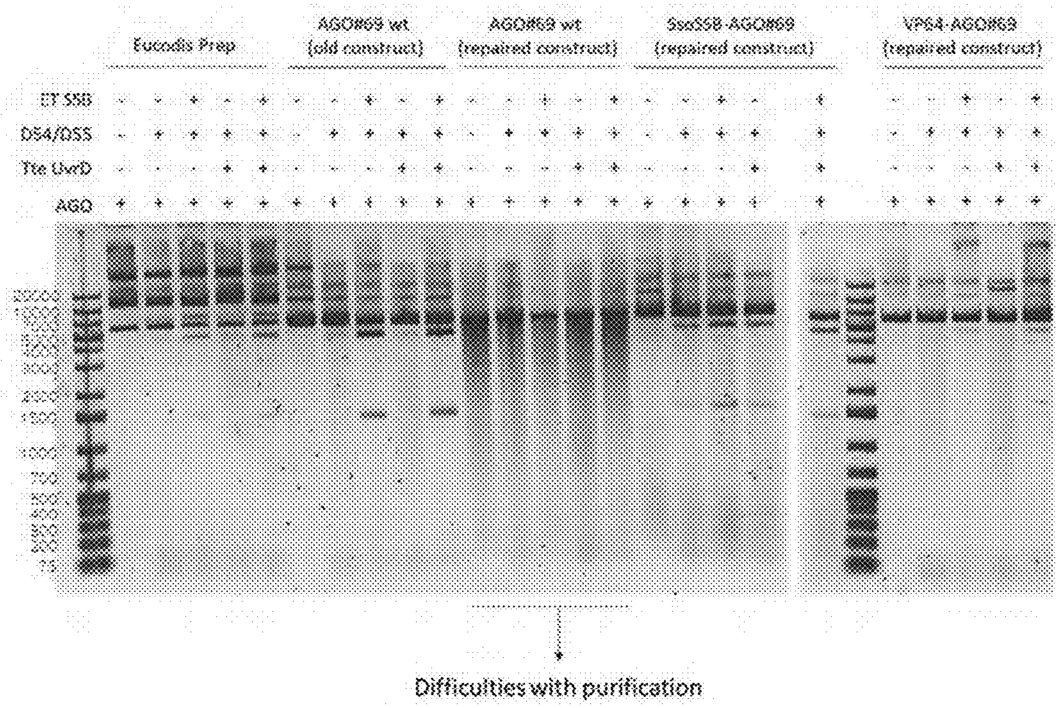

FIG. 73 shows an image of an electrophoresis gel showing cleavage of plasmid 56 by the indicated Ago69 containing fusion protein. ET-SSB, guides D54 and D55, and helicase Tte UvrD were included as indicated. The expected cleavage products were 4604, 1388, and 35 bp fragments.

Figure 74:
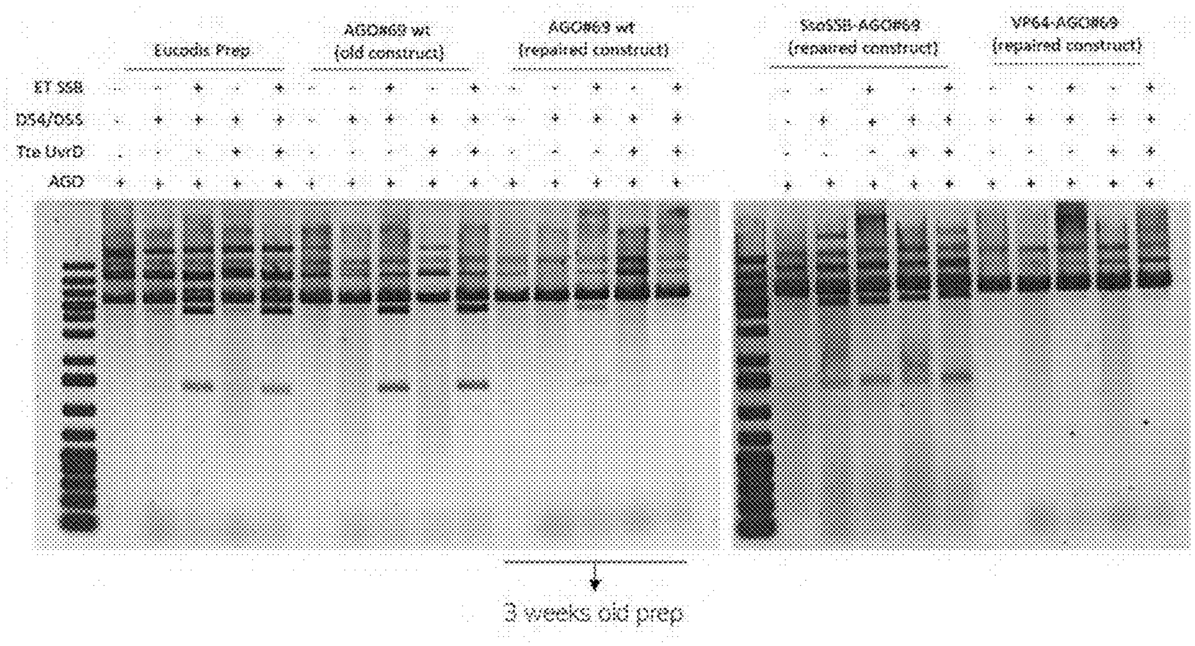

FIG. 74 shows an image of an electrophoresis gel showing cleavage of plasmid 56 by the indicated Ago69 containing fusion protein. ET-SSB, guides D54 and D55, and helicase Tte UvrD were included as indicated. The expected cleavage products were 4604, 1388, and 35 bp fragments.

Figure 75:
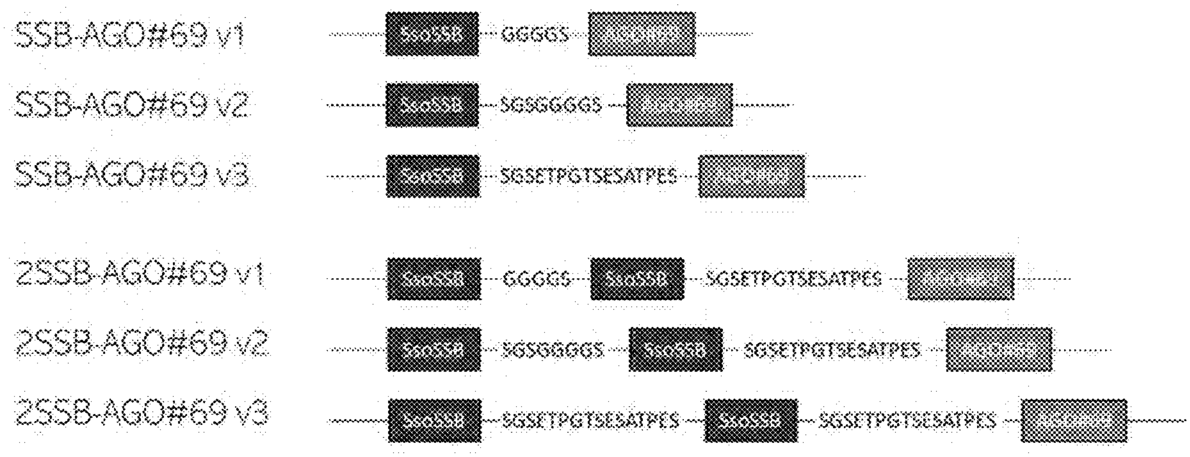

FIG. 75 shows a graphical depiction of Ago69 and SsoSSB containing fusion proteins. FIG. 75 discloses “GGGGS” as SEQ ID NO: 70, “SGSGGGGS” as SEQ ID NO: 71 and “SGSETPGTSESATPES” as SEQ ID NO: 72.

Figure 76A:
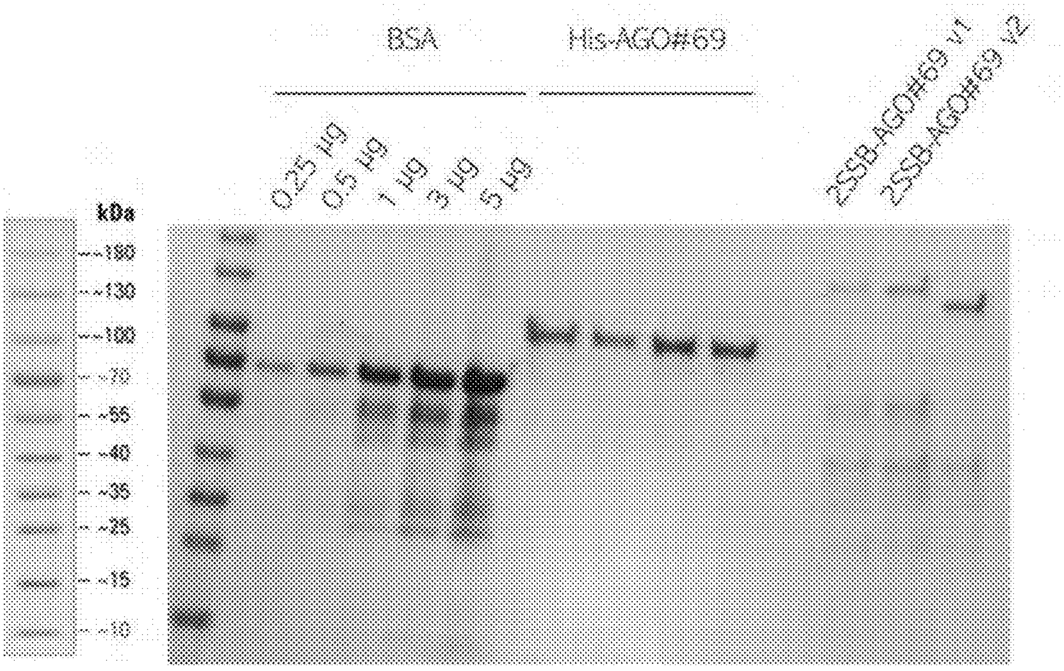
Figure 76B:
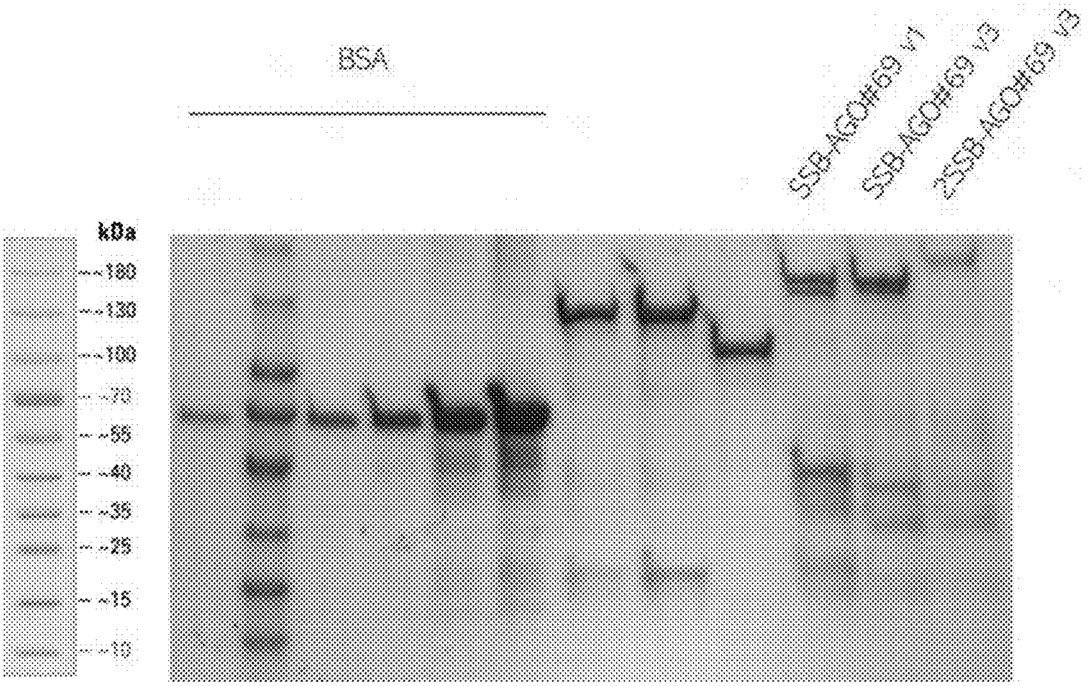

FIG. 76A shows an image of an electrophoresis gel showing expression and purification of the indicated fusion protein. FIG. 76B shows an image of an electrophoresis gel showing expression and purification of the indicated fusion protein.

Figure 77:
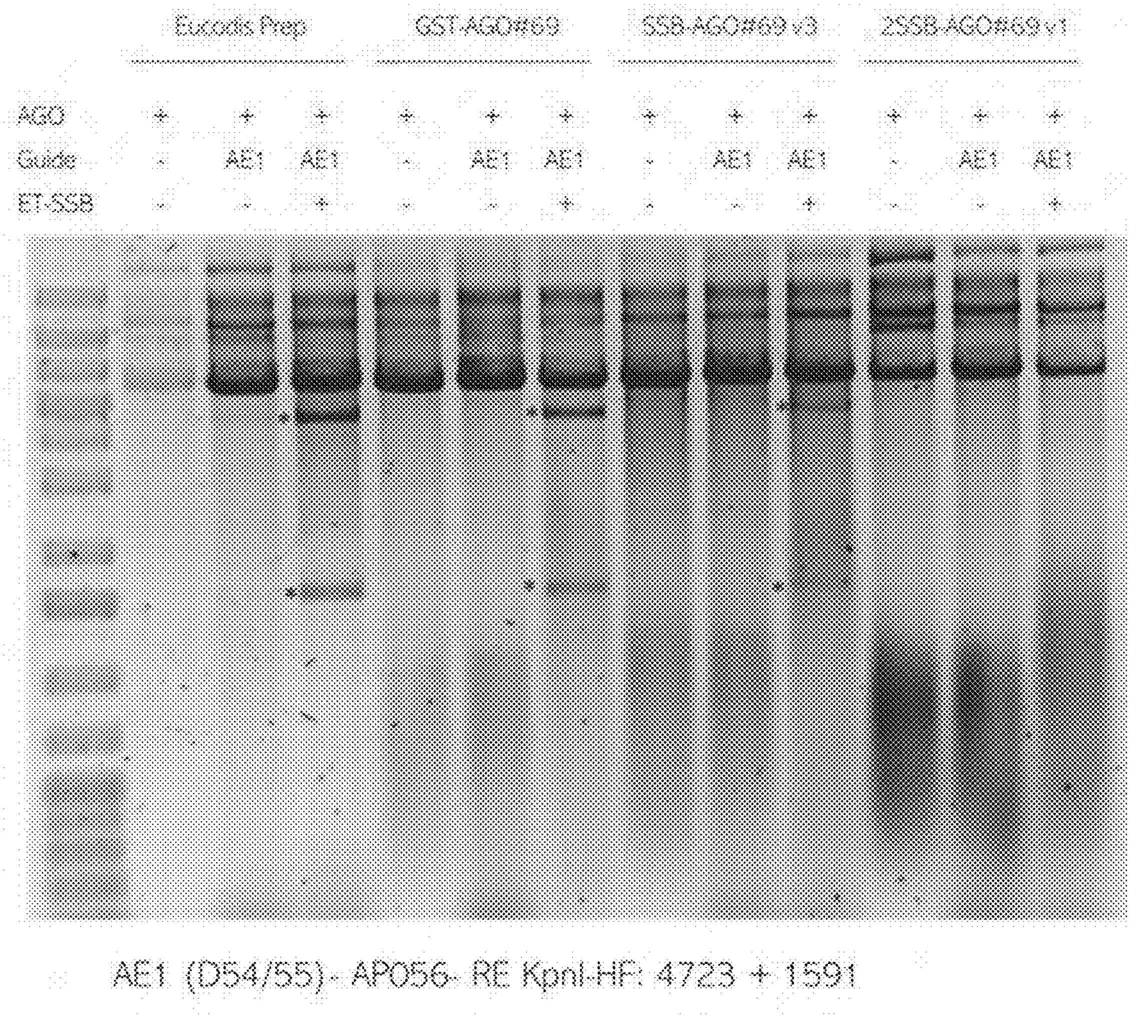

FIG. 77 shows an image of an electrophoresis gel showing cleavage of plasmid 56 by the indicated Ago69 containing fusion protein. ET-SSB and guide AE1 (gDNA 54 and 55) were included as indicated. The expected cleavage products were 4723 bp and 159 bp fragments. Cleavage reactions were carried out at 37° C.

Figure 78:
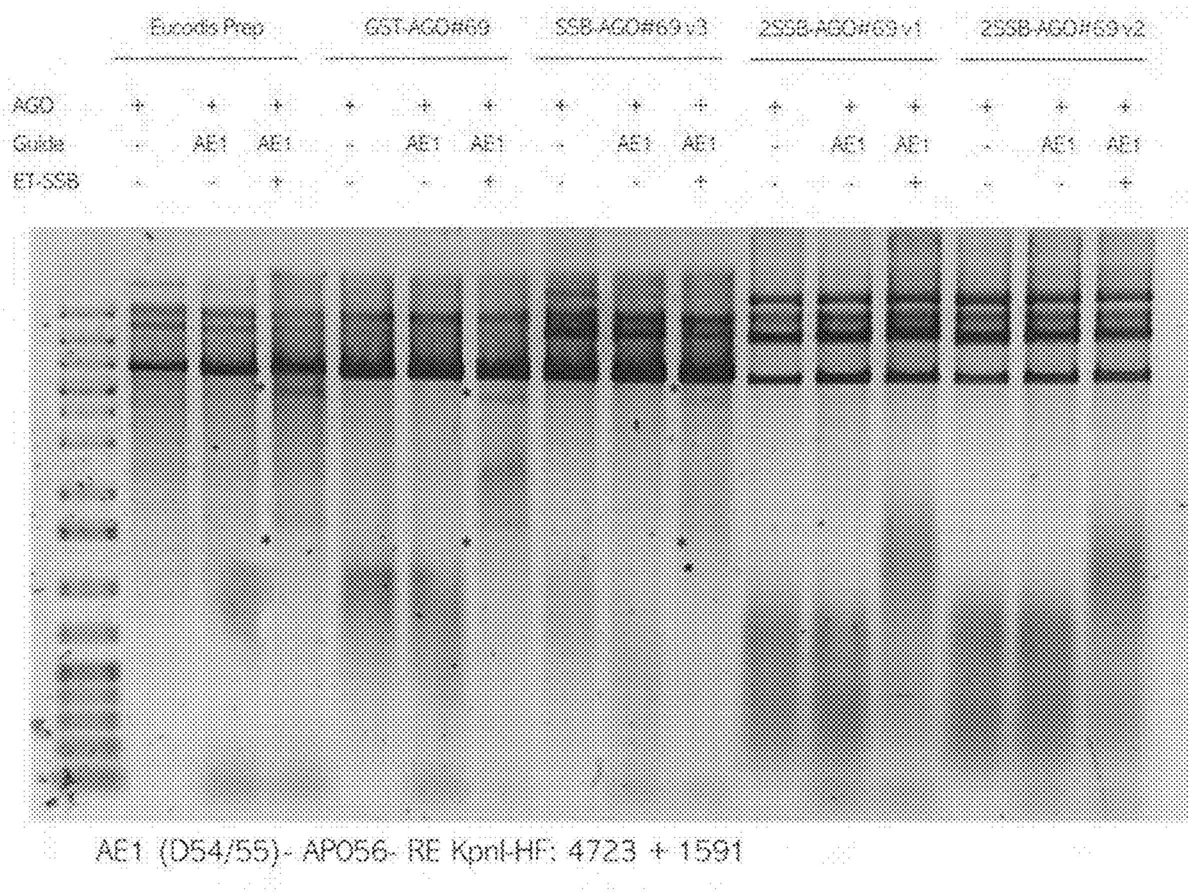

FIG. 78 shows an image of an electrophoresis gel showing cleavage of plasmid 56 by the indicated Ago69 containing fusion protein. ET-SSB and guide AE1 (gDNA 54 and 55) were included as indicated. The expected cleavage products were 4723 bp and 159 bp fragments. Cleavage reactions were carried out at 37° C.

Figure 79:
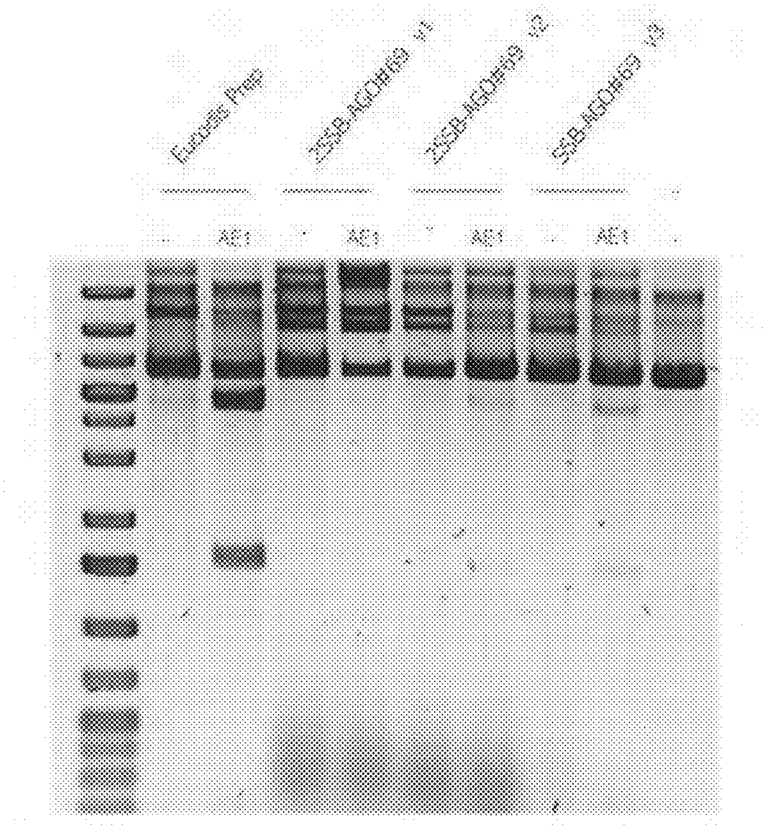

FIG. 79 shows an image of an electrophoresis gel showing cleavage of plasmid 56 by the indicated Ago69 containing fusion protein. ET-SSB and guide AE1 (gDNA 54 and 55) were included as indicated. The expected cleavage products were 4723 bp and 159 bp fragments. Cleavage reactions were carried out at 75° C.

Figure 80:
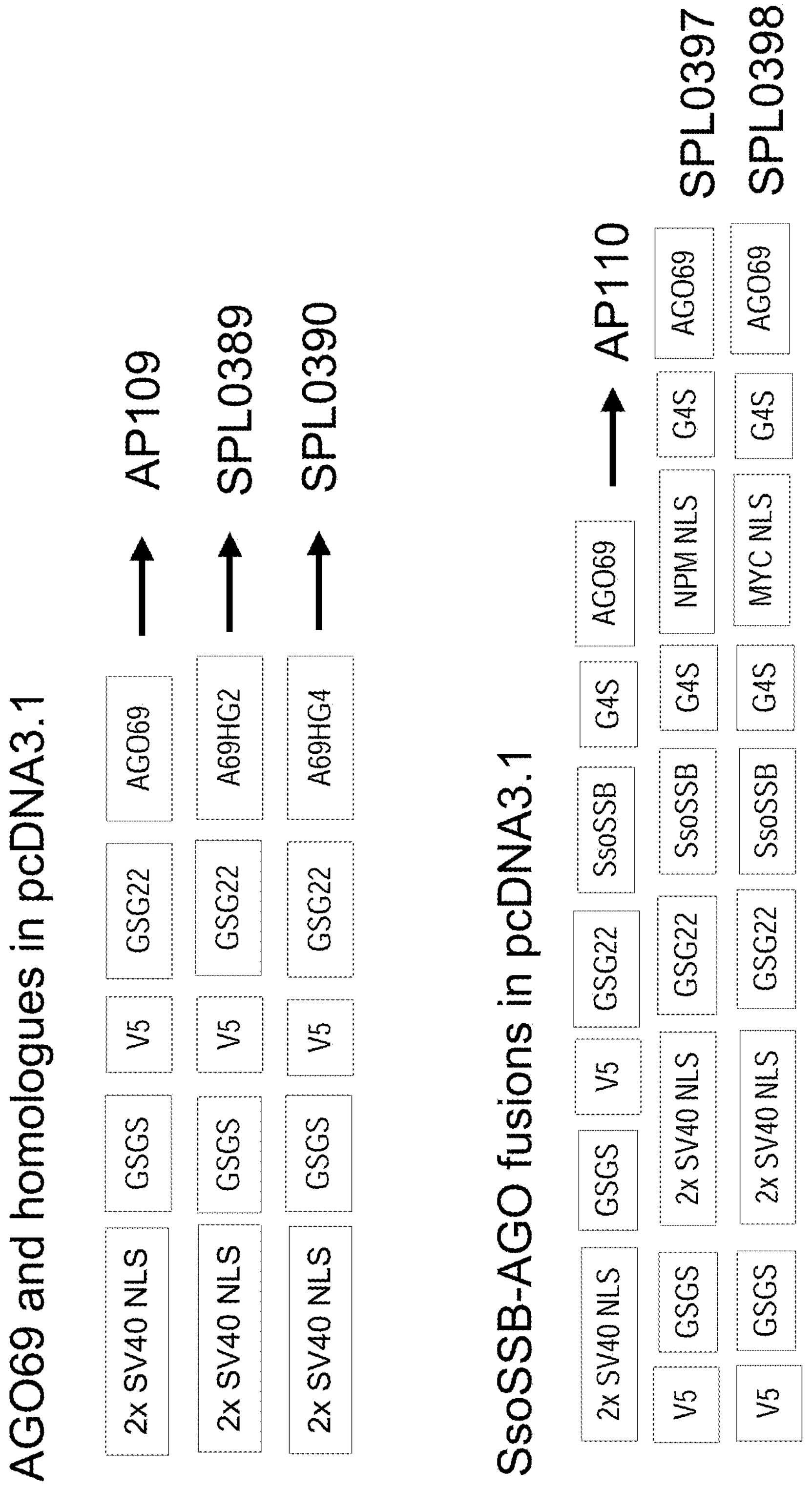

FIG. 80 shows a schematic of Ago69 fusion constructs containing two SV40 nuclear localization signals. FIG. 80 discloses “GSGS” as SEQ ID NO: 154, “GSGSS” as SEQ ID NO: 140 and “G4S” as SEQ ID NO: 70.

Figure 81:
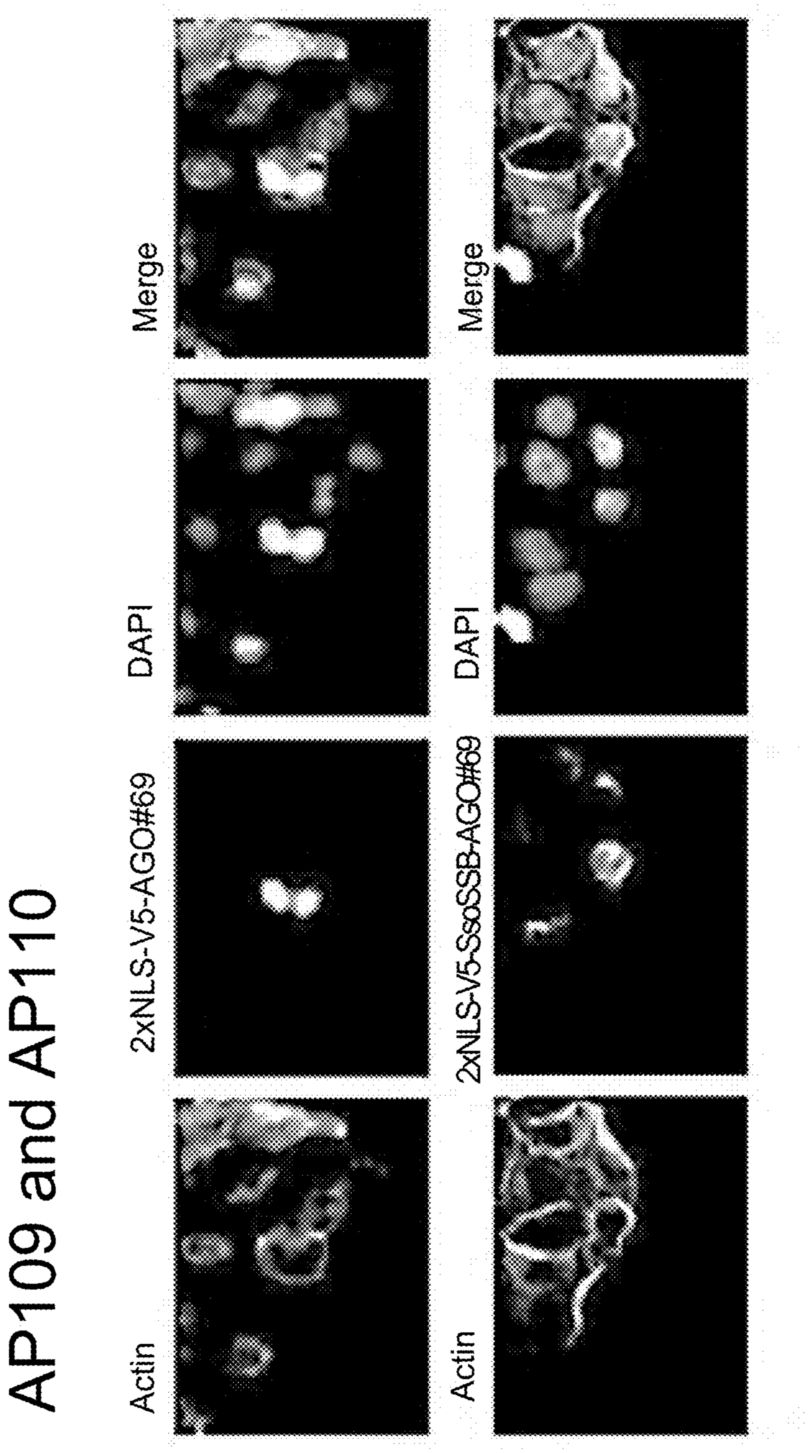

FIG. 81 shows a series of microscopy images showing nuclear localization of construct AP109.

Figure 82:
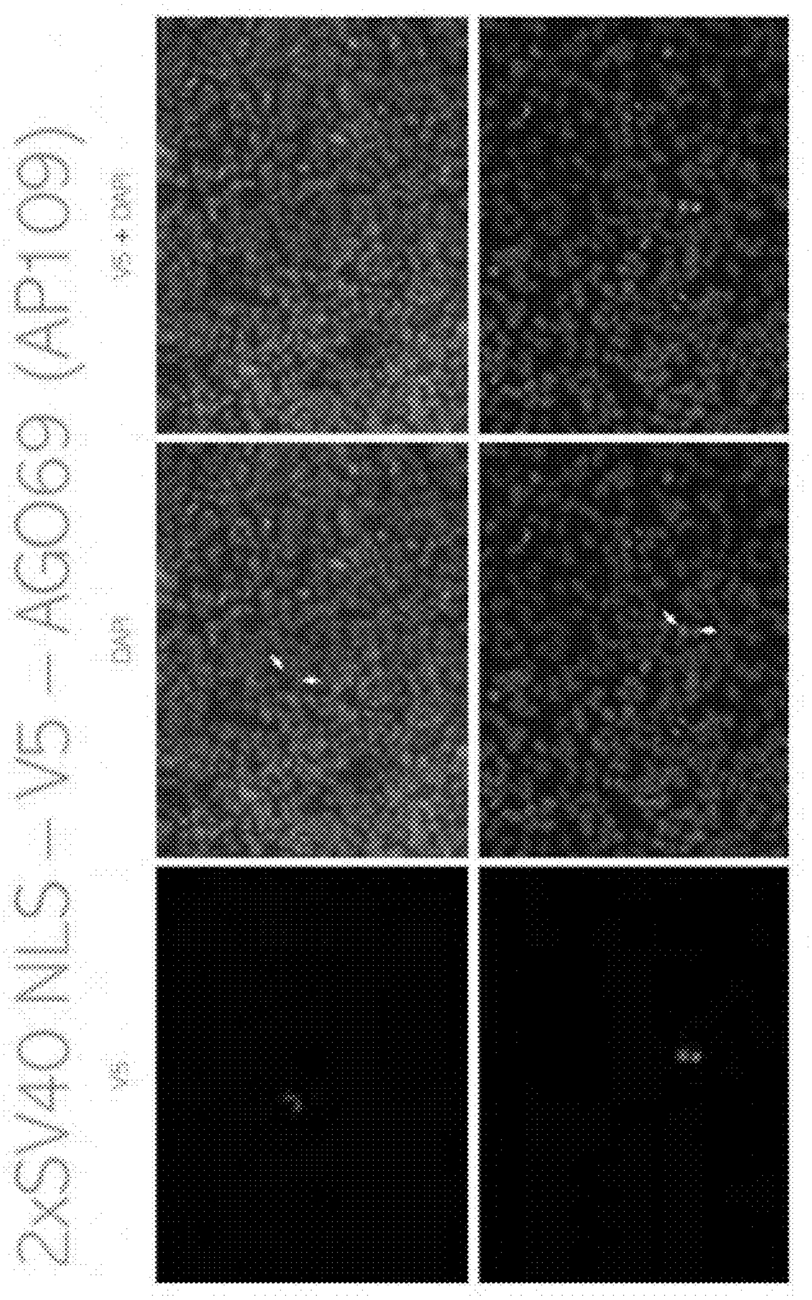

FIG. 82 shows a series of microscopy images showing nuclear localization of construct AP109.

Figure 83:
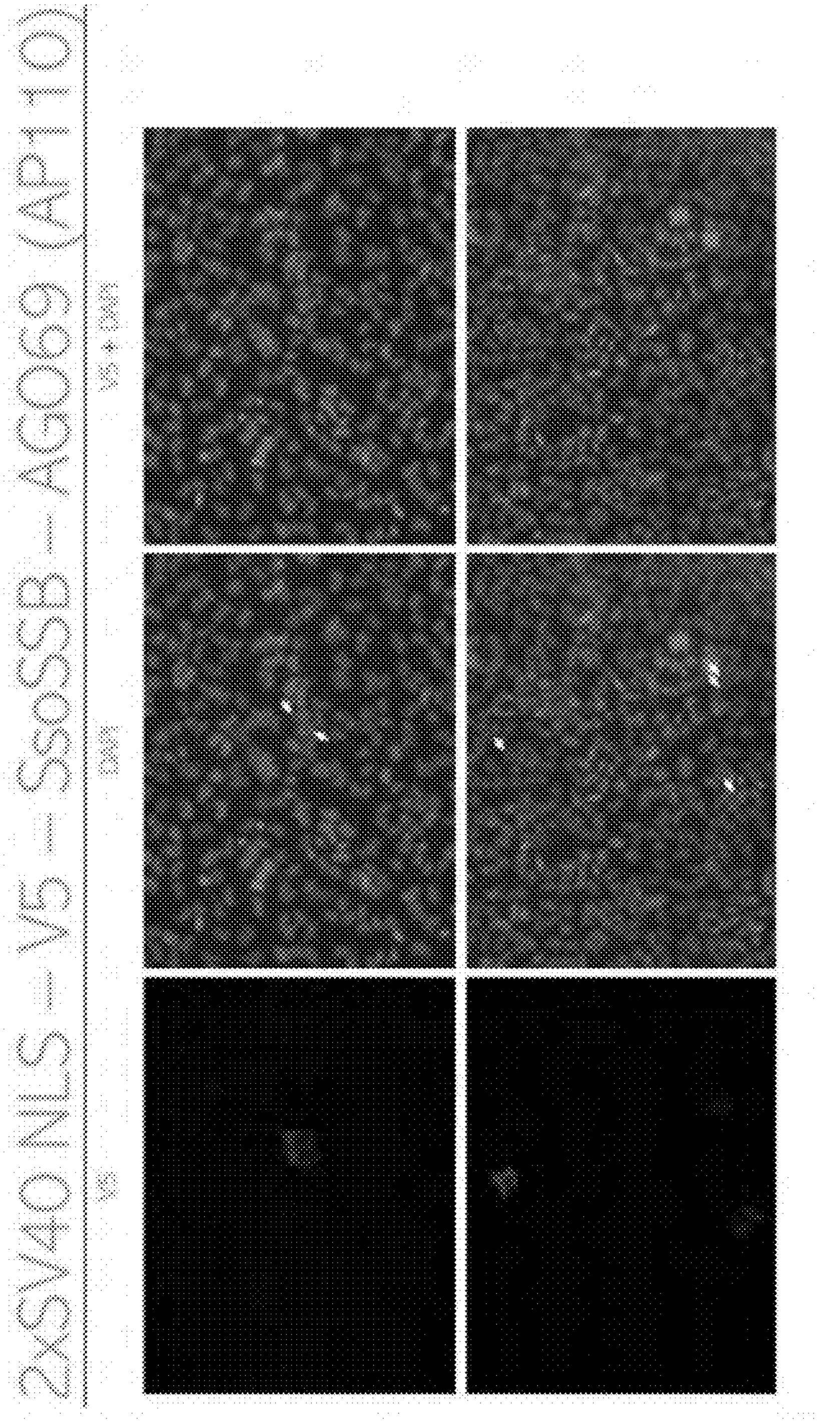

FIG. 83 shows a series of microscopy images showing cytosol localization of construct AP110.

Figure 84:
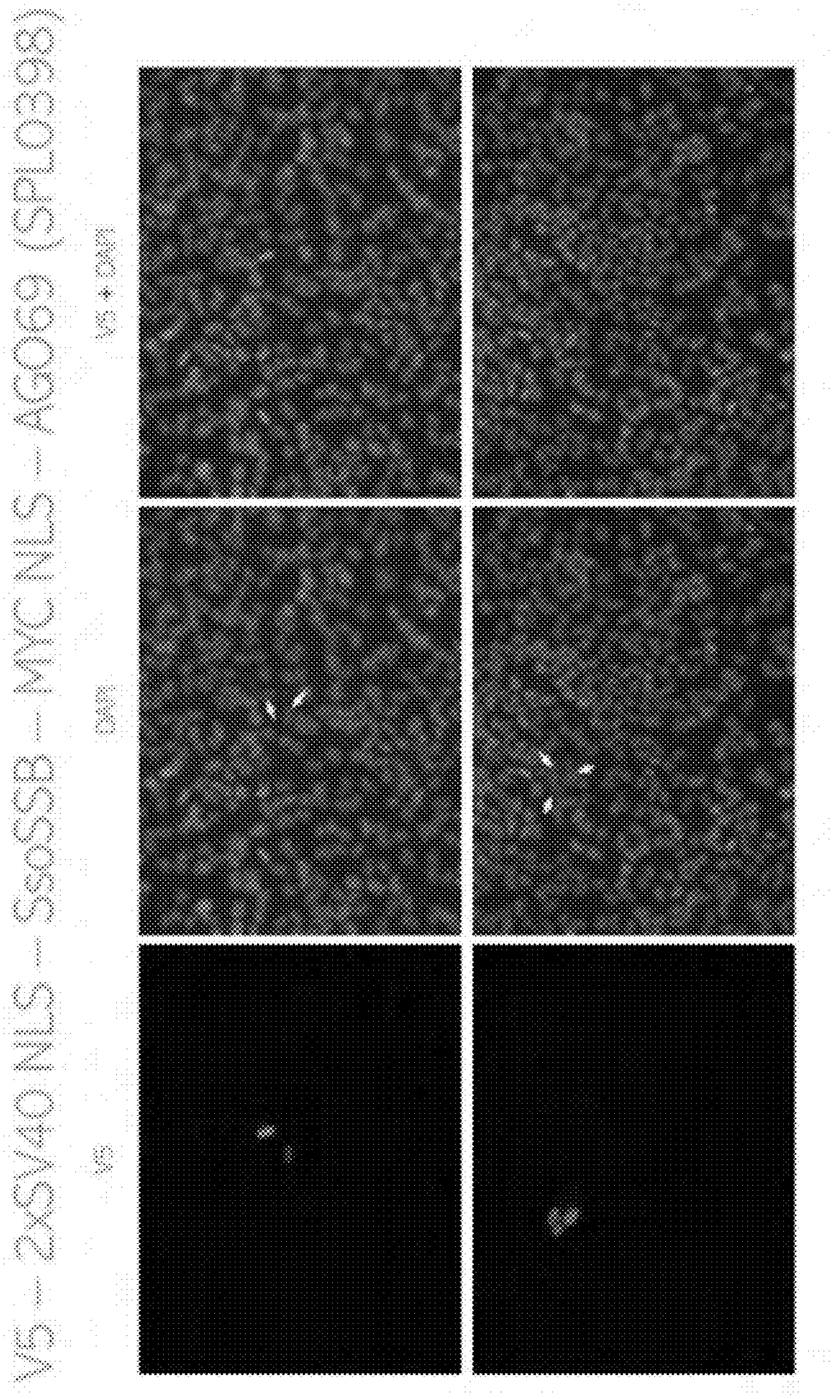

FIG. 84 shows a series of microscopy images showing nuclear localization of construct SPL0398.

Figure 85:
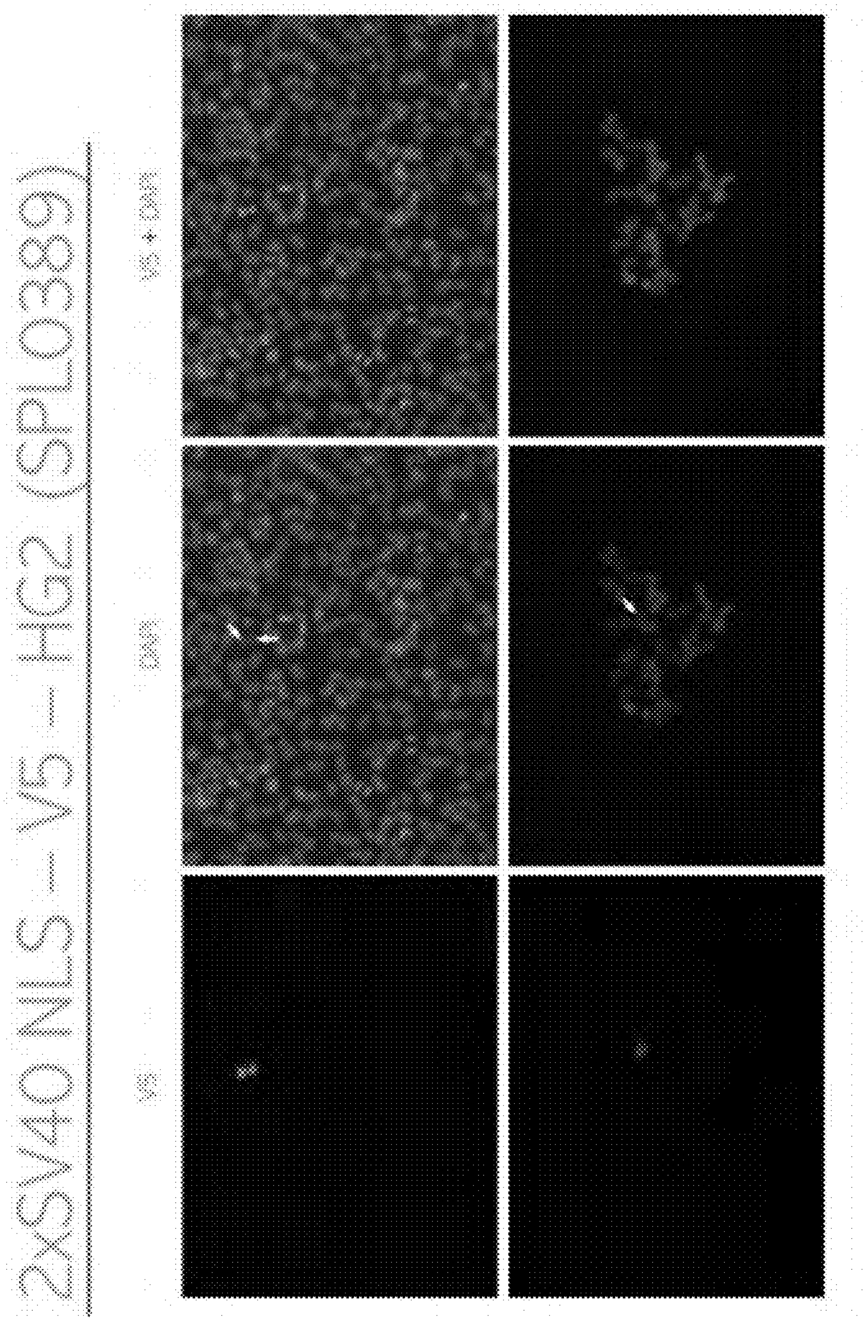

FIG. 85 shows a series of microscopy images showing nuclear localization of construct SPL0389.

Figure 86:
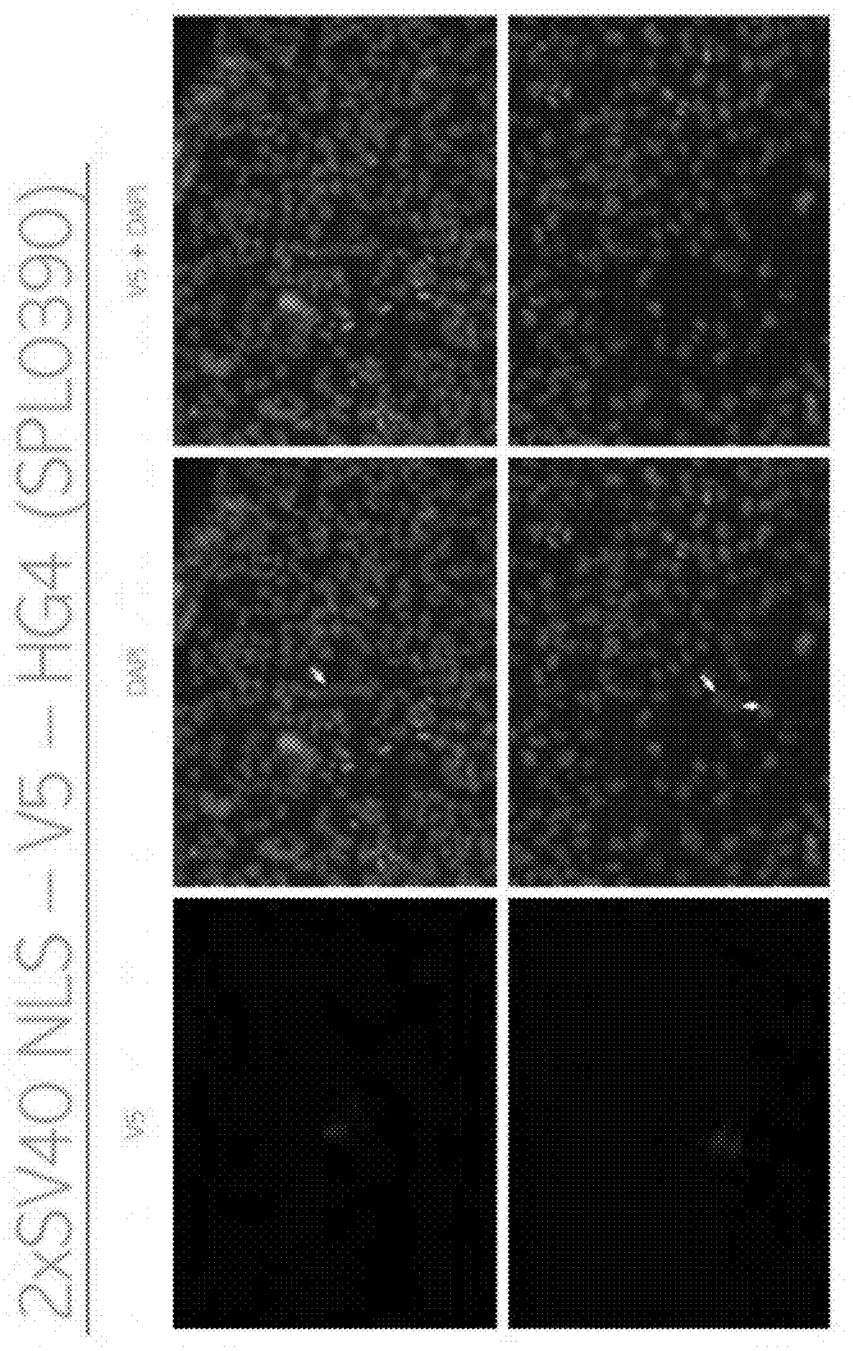

FIG. 86 shows a series of microscopy images showing nuclear localization of construct SPL0390.

Figure 87:
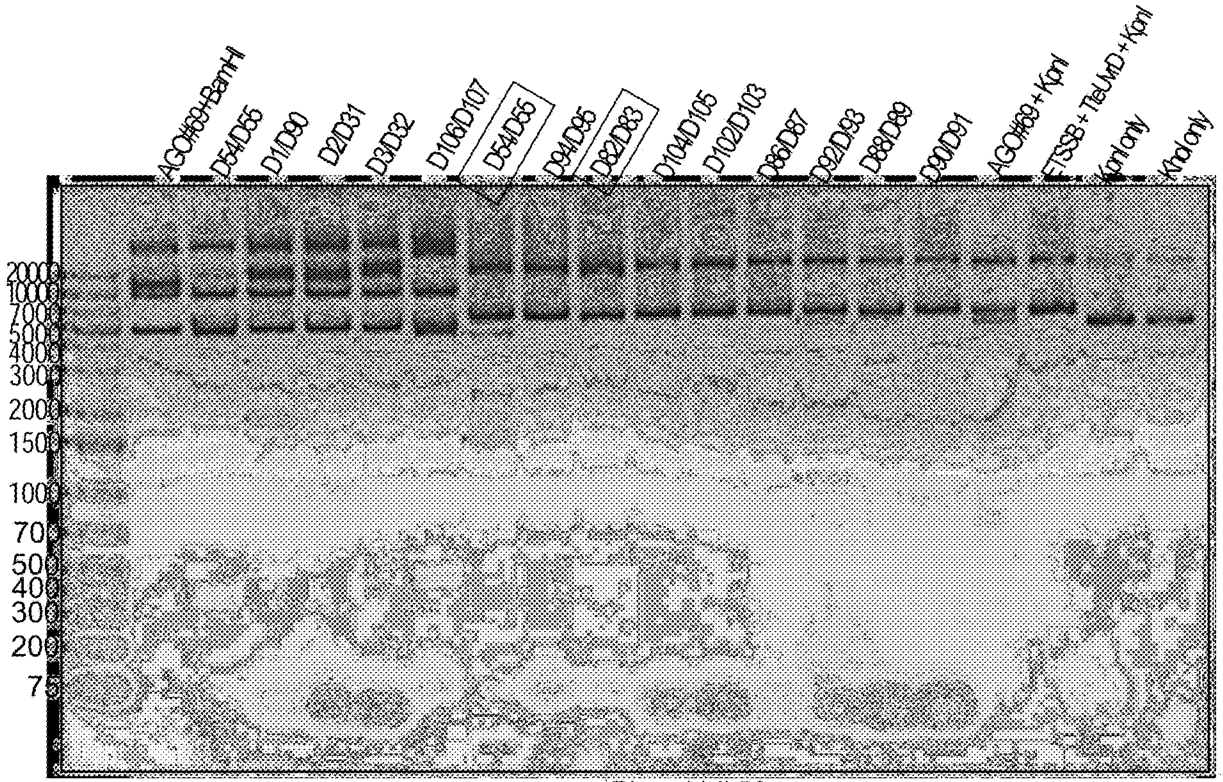

FIG. 87 shows the GC content of the guide DNAs and cleavage of plasmid 70 or plasmid 56 by Ago69 utilizing the indicated guide DNA.

Figure 88A:
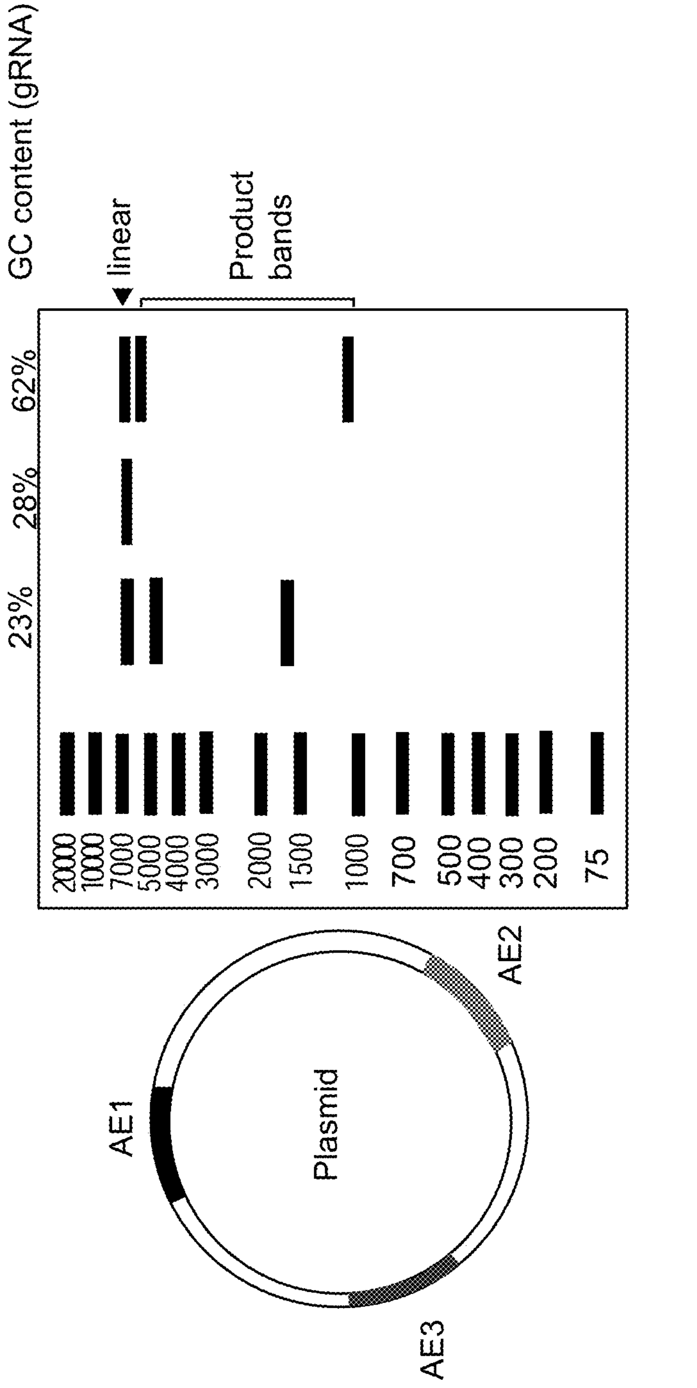
Figure 88B:
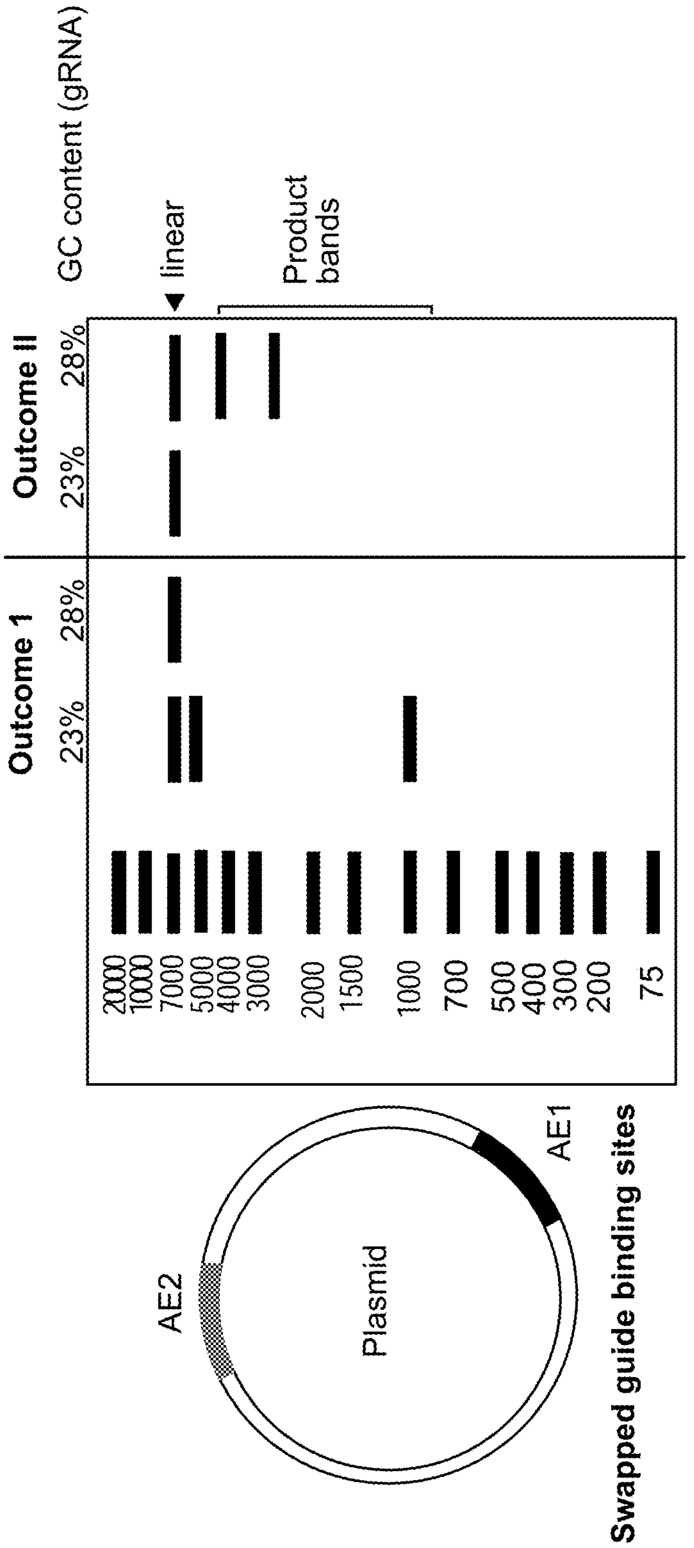

FIG. 88A shows standard plasmid construct wherein the indicated regions have the indicated GC content. FIG. 88B shows a guide swapping construct wherein the indicated regions have the indicated GC content.

Figure 89:
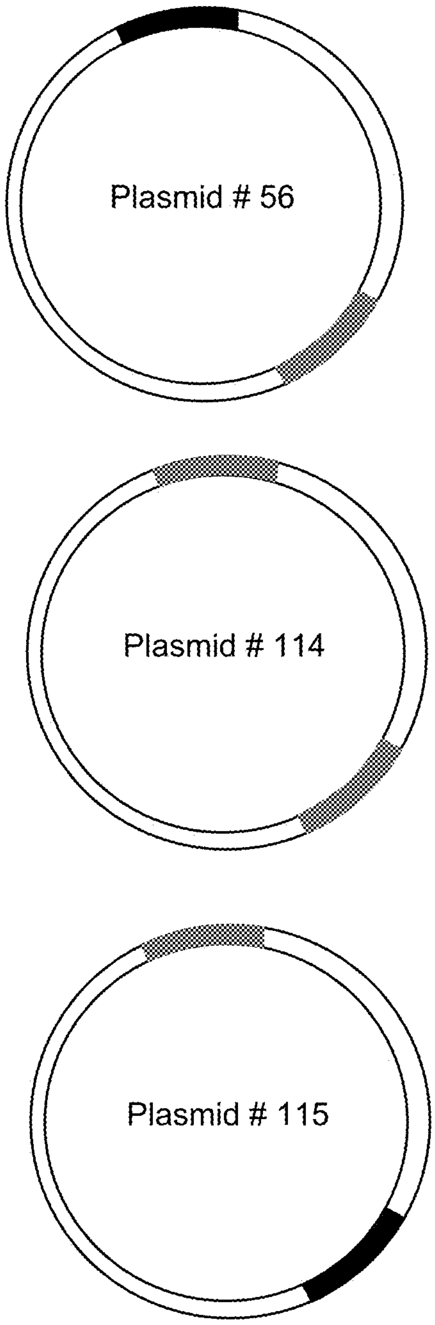

FIG. 89 shows a schematic of plasmid 56, plasmid 114, and plasmid 115.

Figure 90:
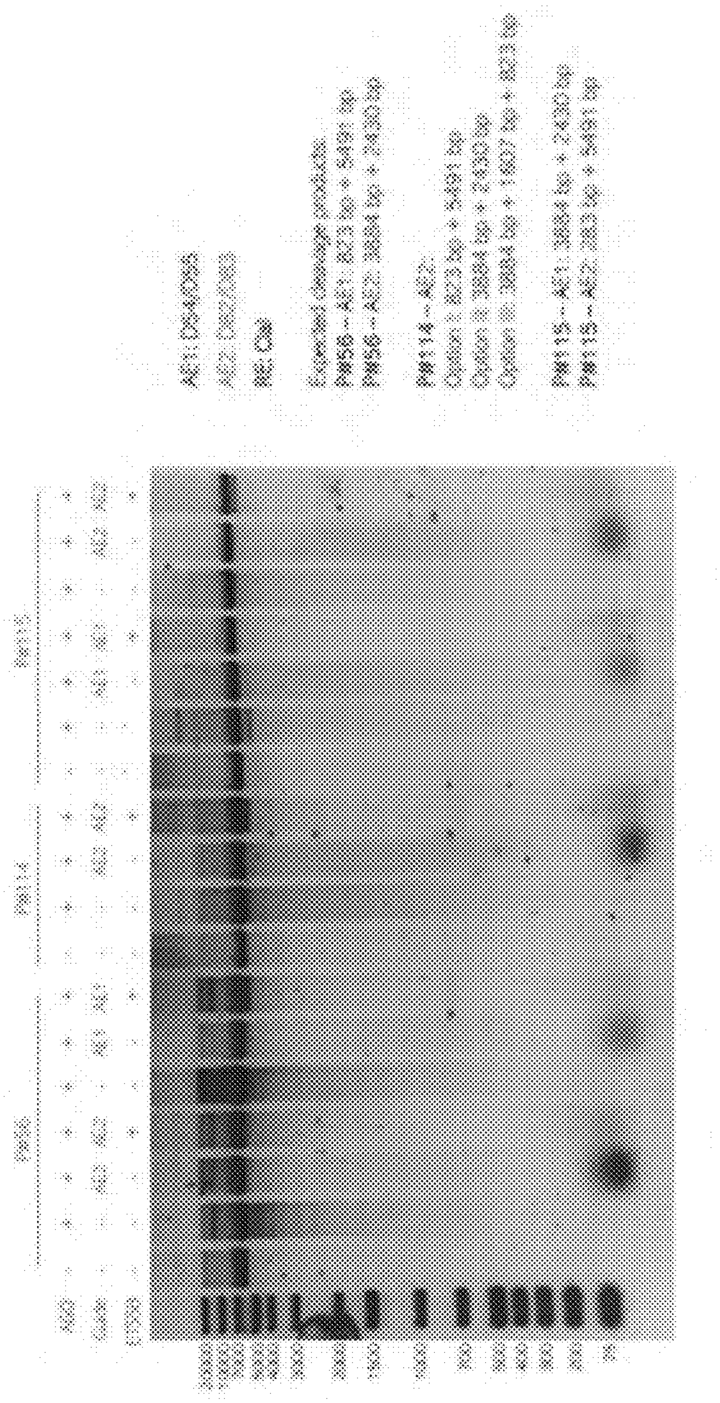

FIG. 90 shows cleavage of plasmid 56, plasmid 114, and plasmid 115 in the presence or absence of the indicated guide, ETSSB, and ClaI restriction enzyme.

Figure 91:
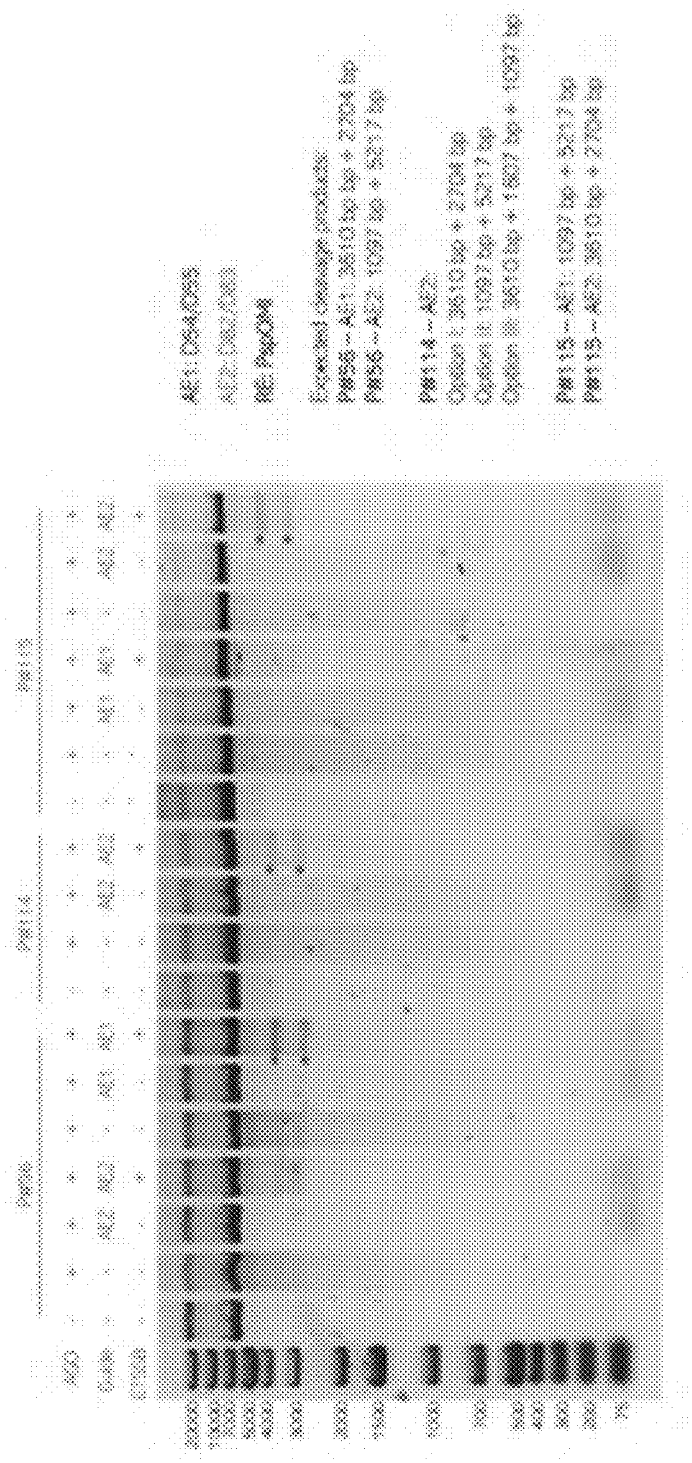

FIG. 91 shows cleavage of plasmid 56, plasmid 114, and plasmid 115 in the presence or absence of the indicated guide, ETSSB, and PspOMI restriction enzyme.

Figure 92:
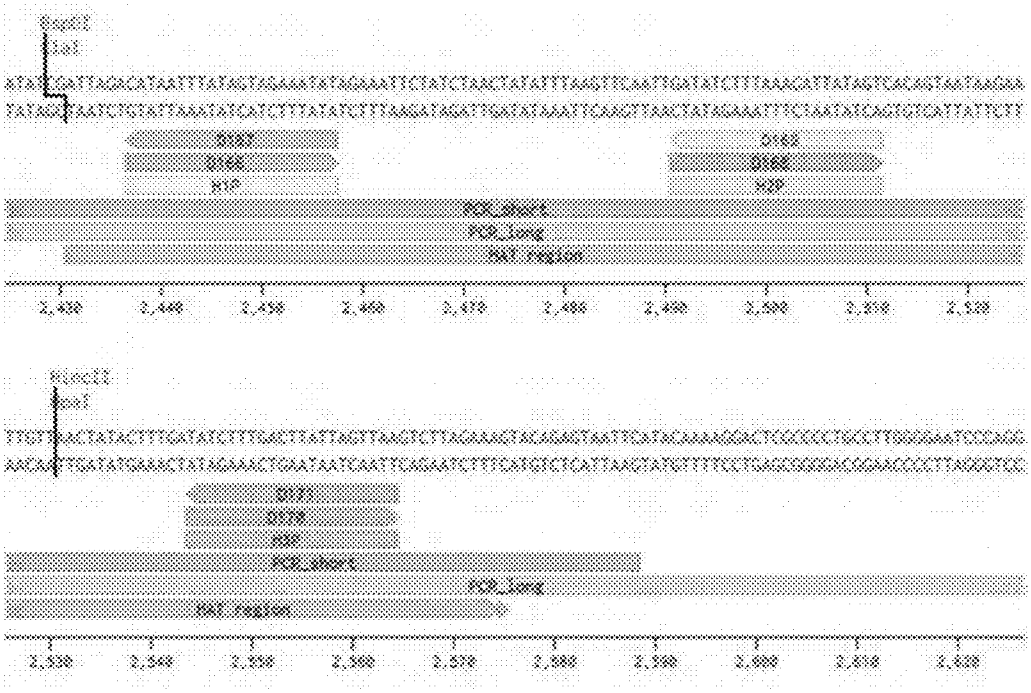

FIG. 92 is a schematic showing where the indicated DNA guides bind within the HAT region of a HAT plasmid generated according to Example 34. FIG. 92 discloses SEQ ID NO: 167.

Figure 93:
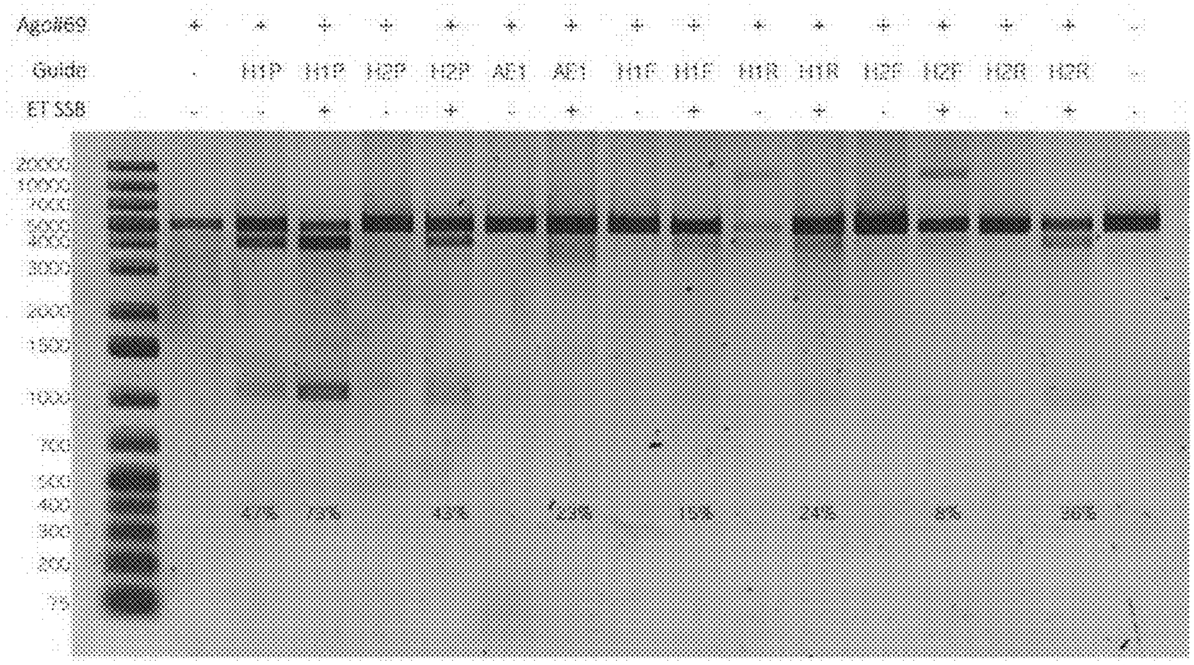

FIG. 93 shows an image of an electrophoresis gel showing cleavage of plasmid 70-HAT by Ago69 with or without ET SSB and with the indicated guide DNA.

Figure 94:
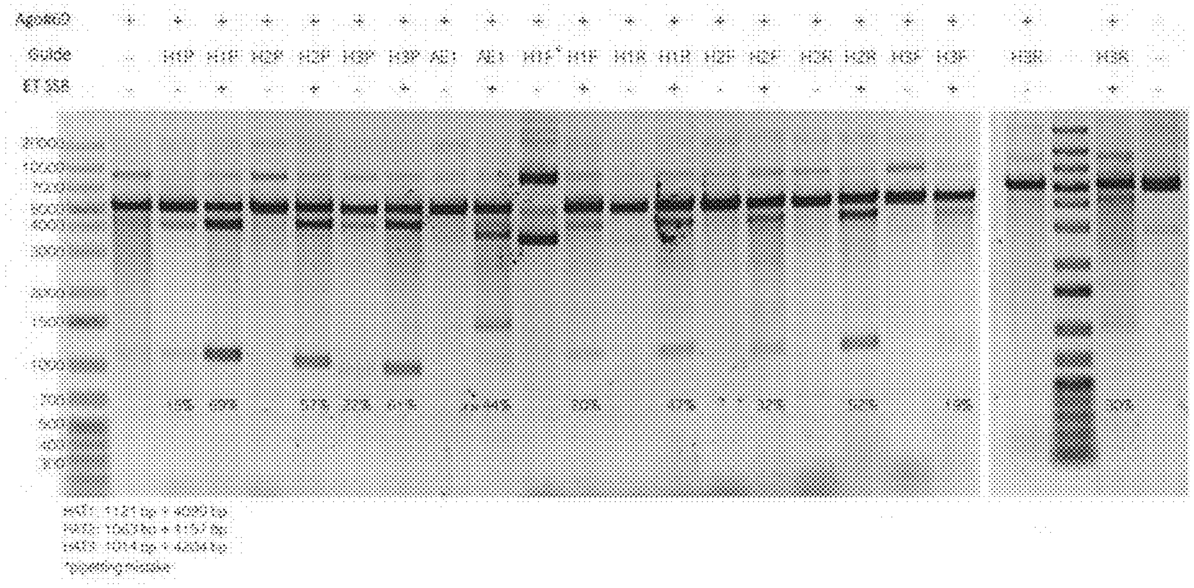

FIG. 94 shows an image of an electrophoresis gel showing cleavage of plasmid 70-HAT by Ago69 with or without ET SSB and with the indicated guide DNA.

Figure 95:
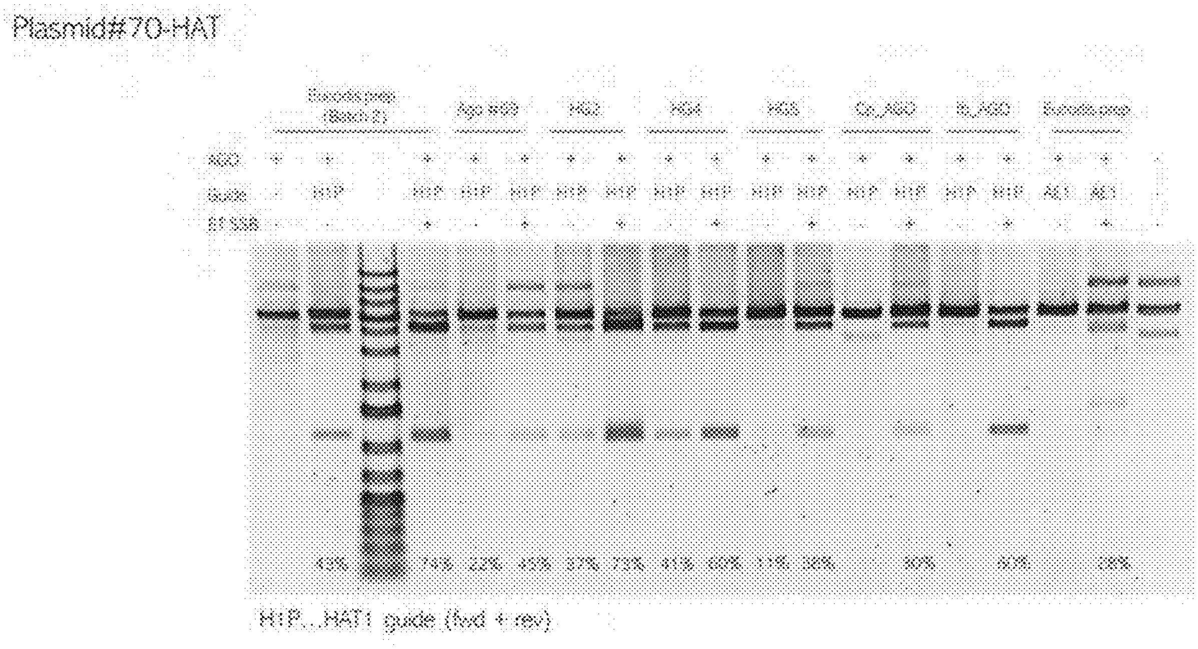

FIG. 95 shows an image of an electrophoresis gel showing cleavage of plasmid 70-HAT by Ago69 or the indicated Ago69 homologue (HG2, HG4, HG5) with or without ET SSB and with the indicated guide DNA.

Figures 96A, 96B:
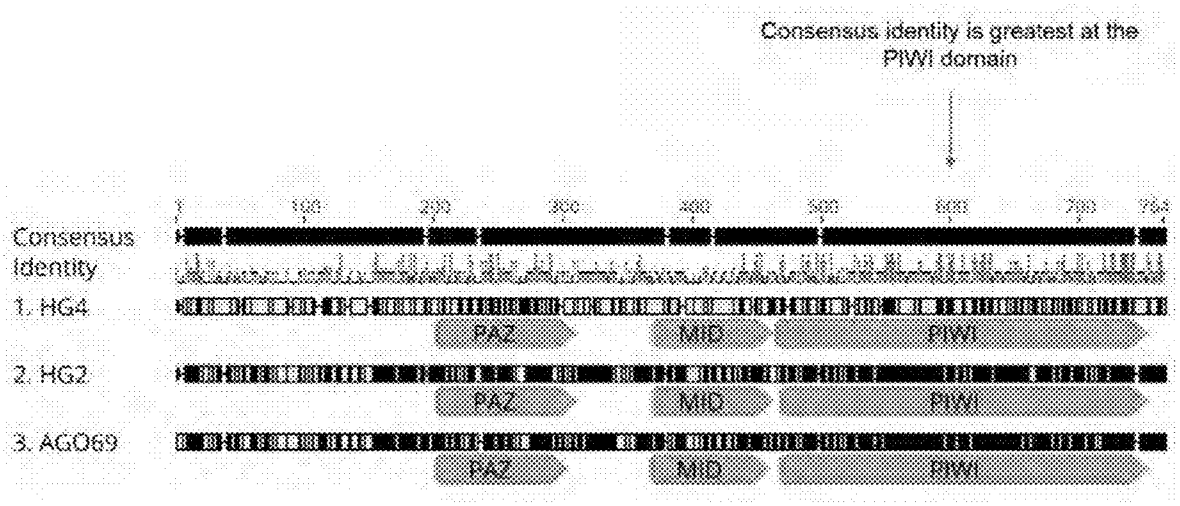

FIG. 96A is a schematic showing sequence identity between Ago69, HG2, and HG4, including the PAZ, MID, and PIWI. FIG. 96B is a table showing the percent Percent sequence identity between Ago69, HG2, and HG4.

FIG. 97 shows the Ago69 homologues identified, expressed, and purified.

Figure 98B:
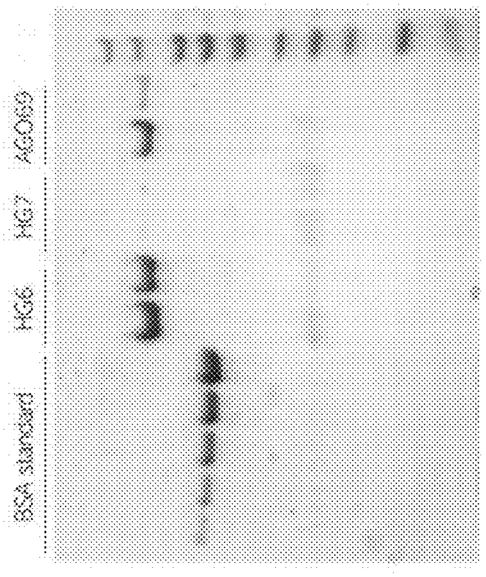
Figure 98A:
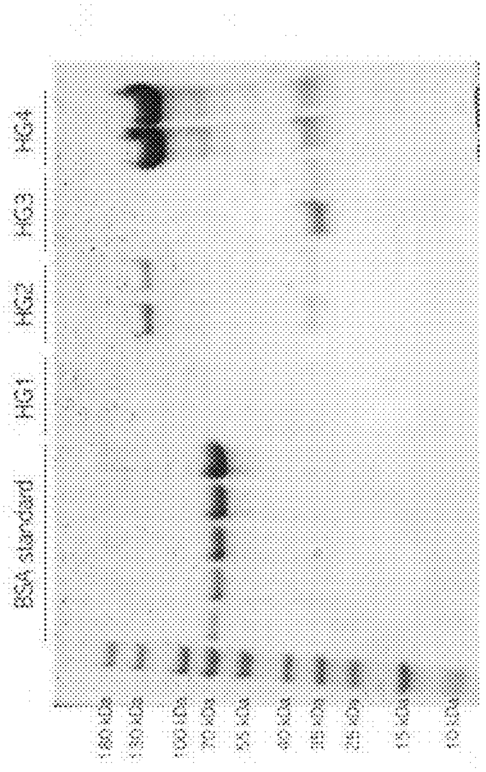

FIG. 98A shows an image of an electrophoresis gel showing purified Ago69 homologues HG1, HG2, HG3, and HG4. FIG. 98B shows an image of an electrophoresis gel showing purified Ago69 homologues HG6 and HG7.

Figure 99:
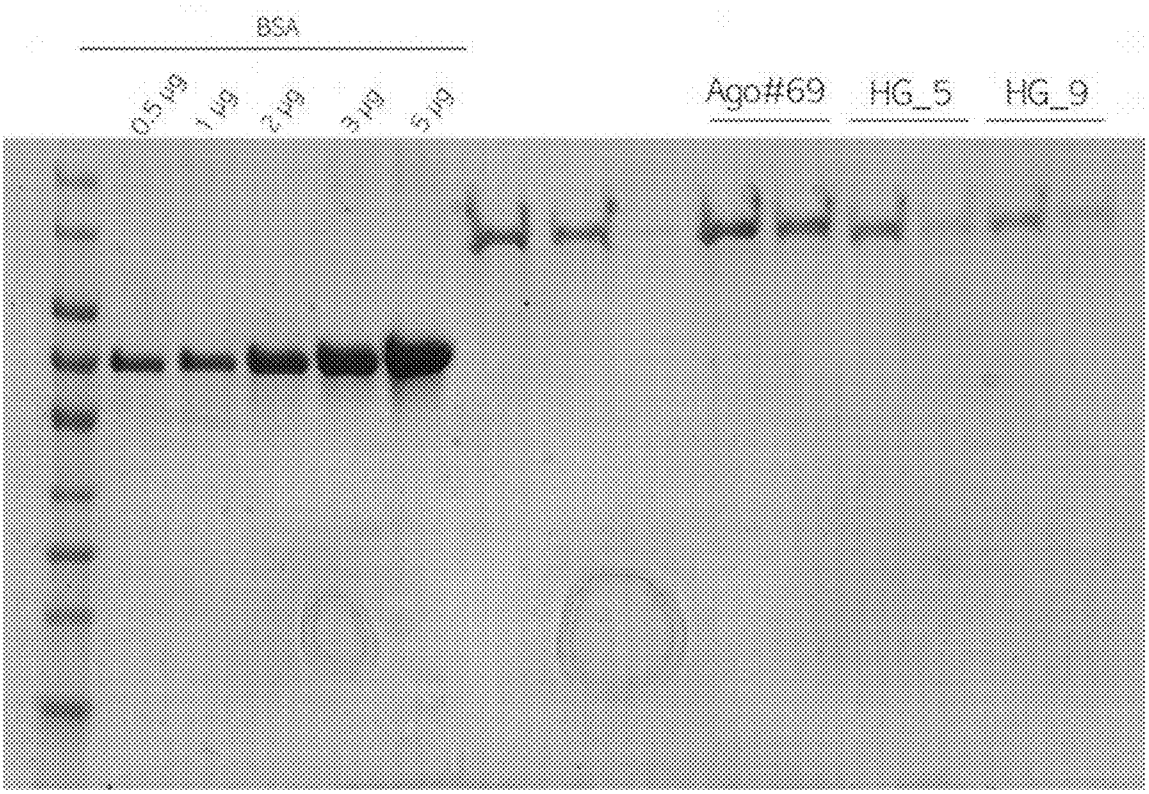

FIG. 99 shows an image of an electrophoresis gel showing purified Ago69 homologues HG5 and HG9.

Figure 100:
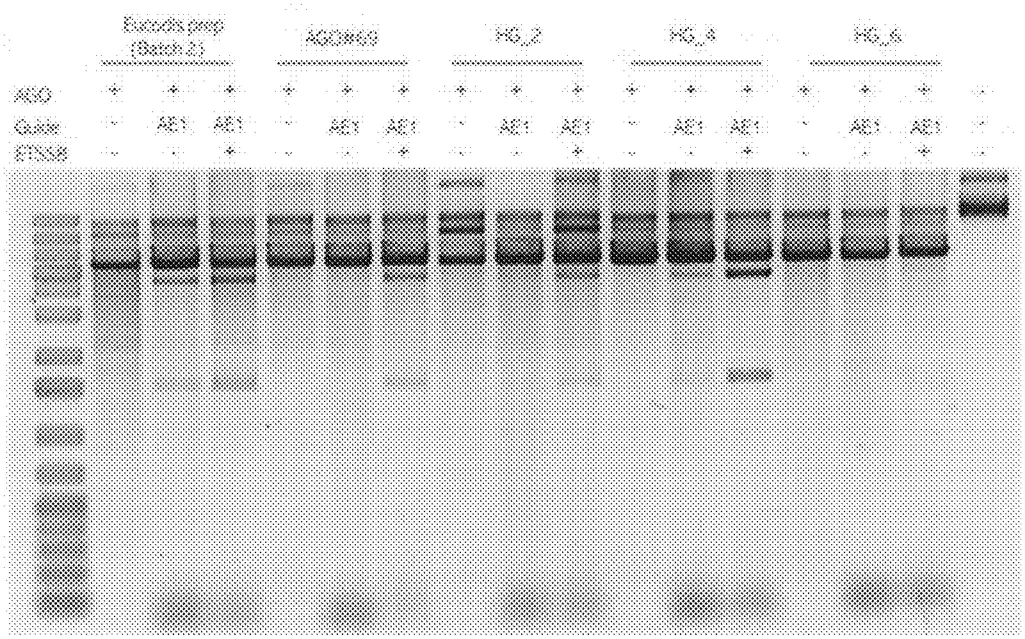

FIG. 100 shows an image of an electrophoresis gel showing plasmid DNA cleavage by Ago69 homologues HG2, HG4, and HG6.

Figure 101:
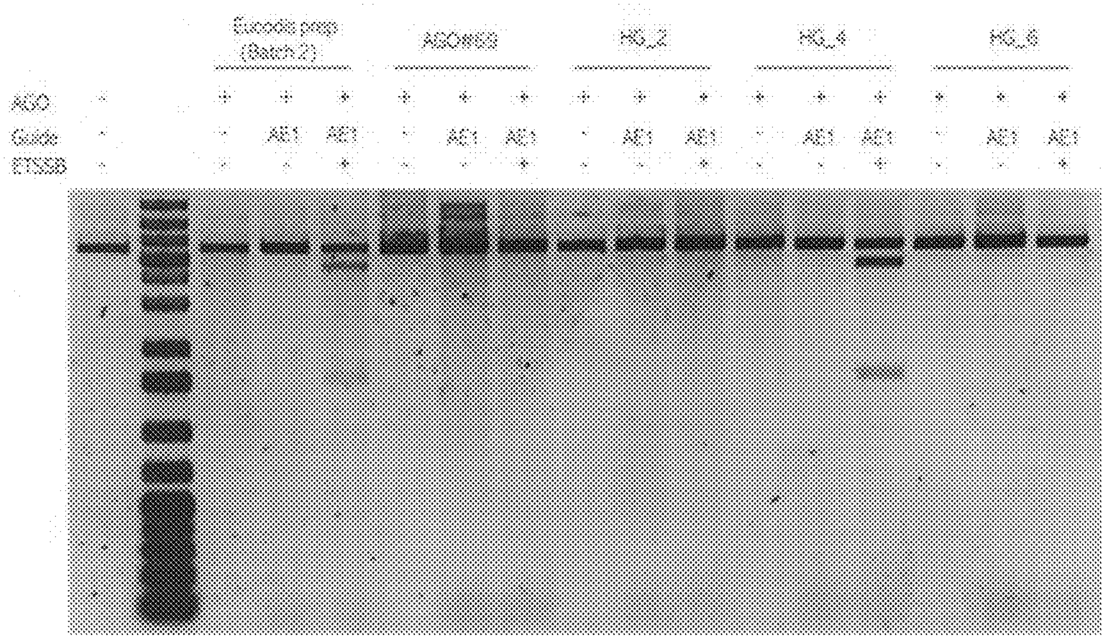

FIG. 101 shows an image of an electrophoresis gel showing plasmid DNA cleavage by Ago69 homologues HG2, HG4, and HG6.

Figure 102:

FIG. 102 shows a sequence alignment and indicates homology of Ago69, HG2, and HG4. FIG. 102 discloses SEQ ID NOS 1 and 134-135, respectively, in order of appearance.

Figure 103A:
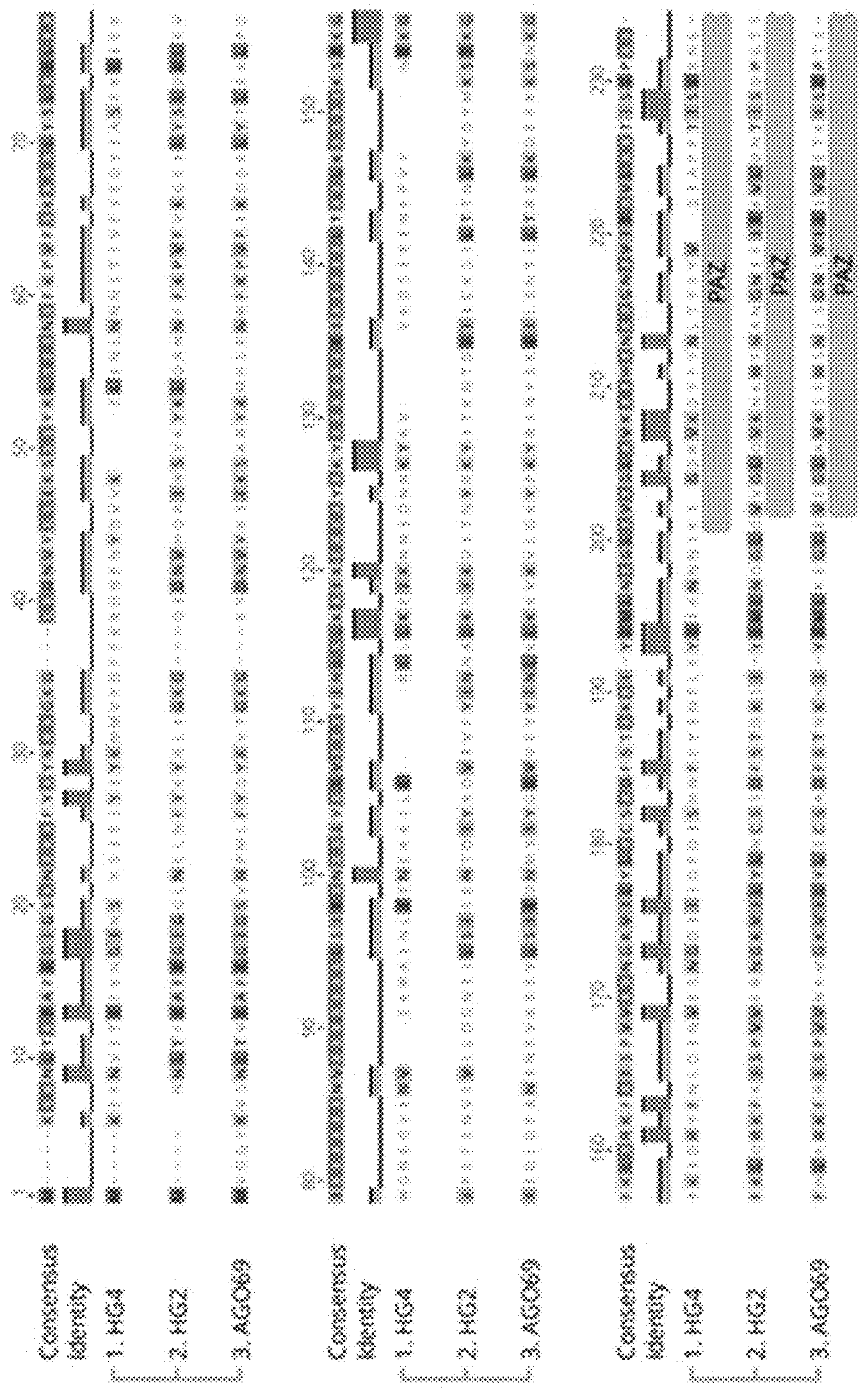

FIG. 103A shows a first (N terminal) part of a sequence alignment and homology of Ago69, HG2, and HG4 along with an indication of the PAZ, MID, and PIWI domains.

Figure 103B:
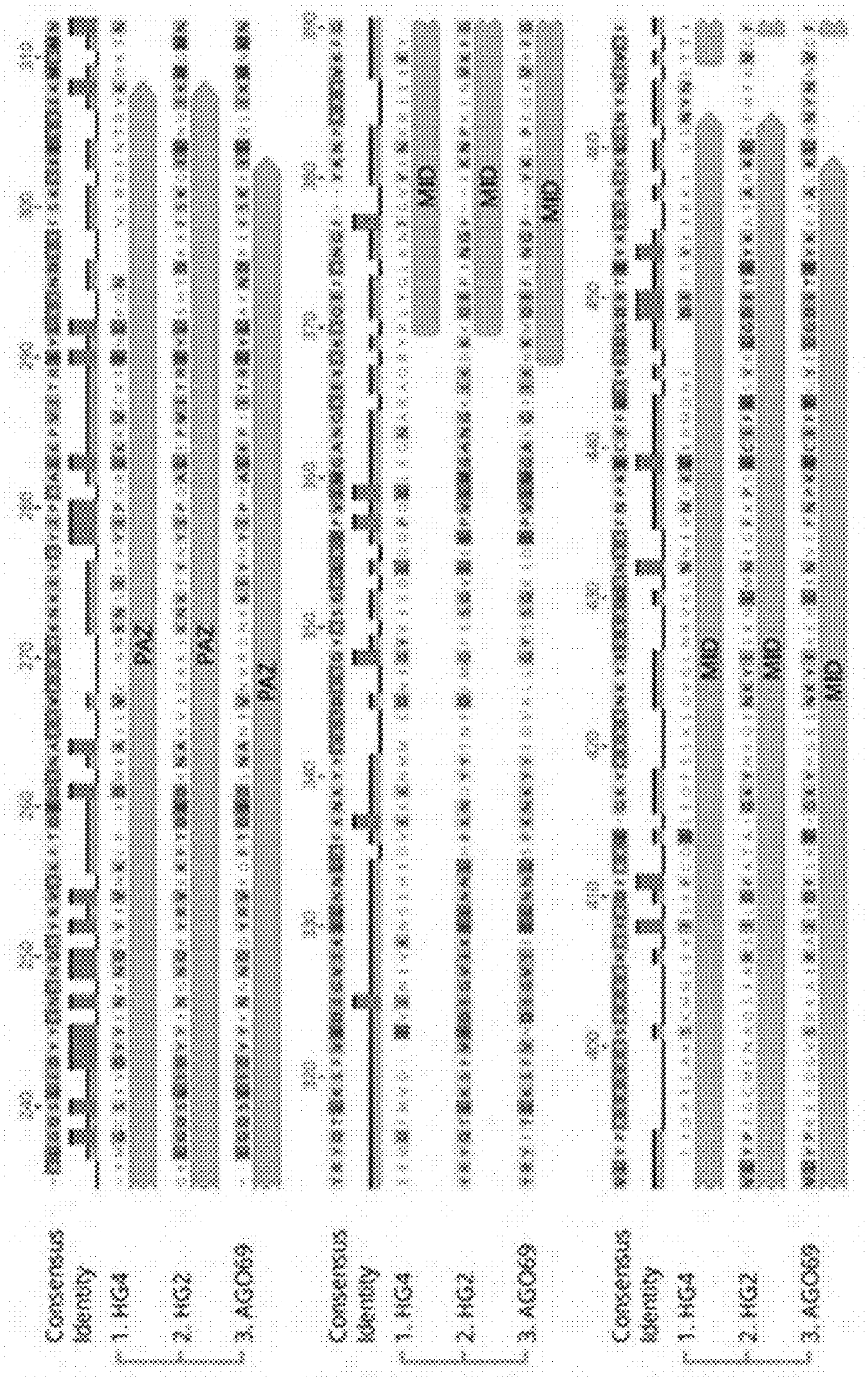
Figure 103C:
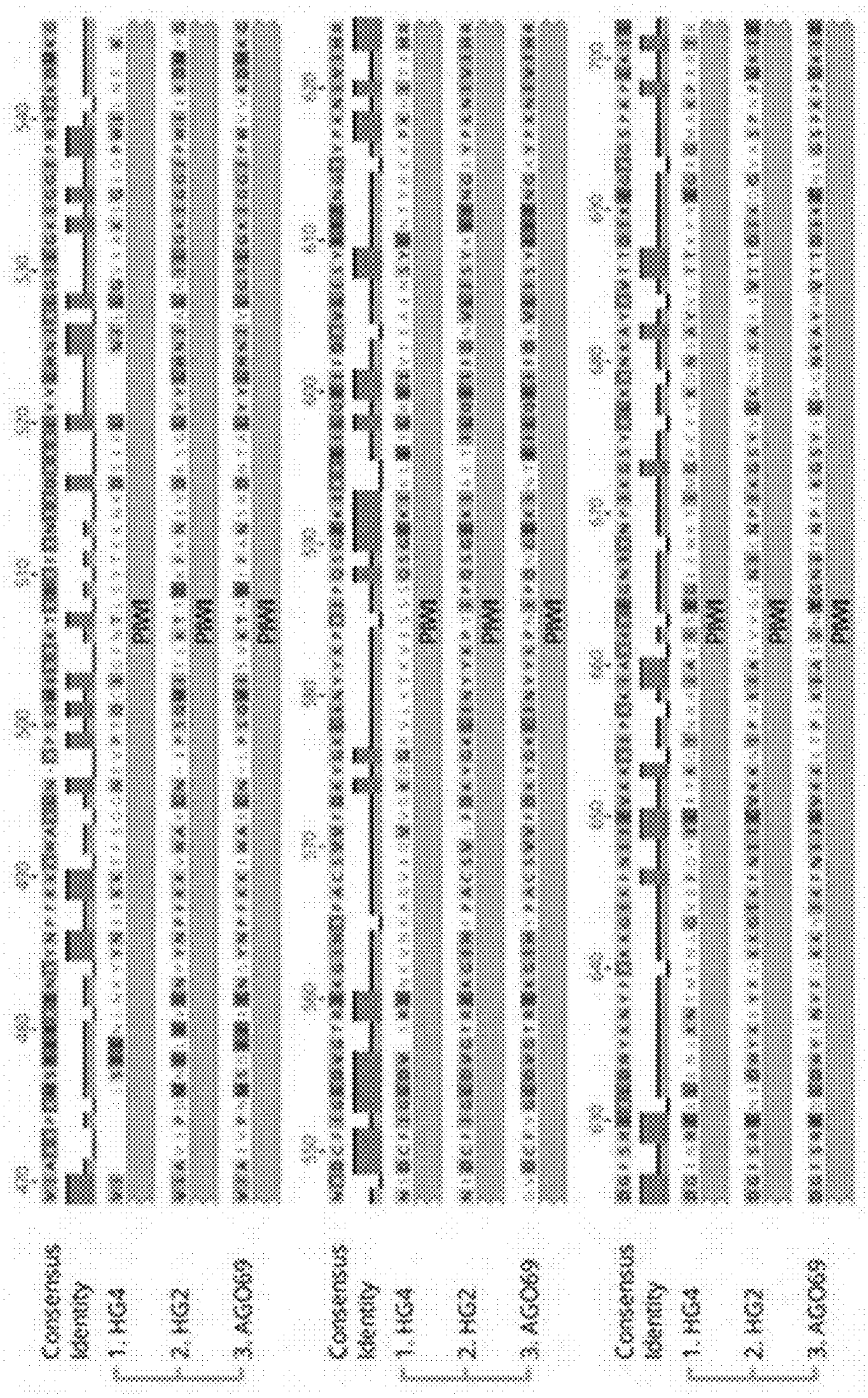
Figure 103D:
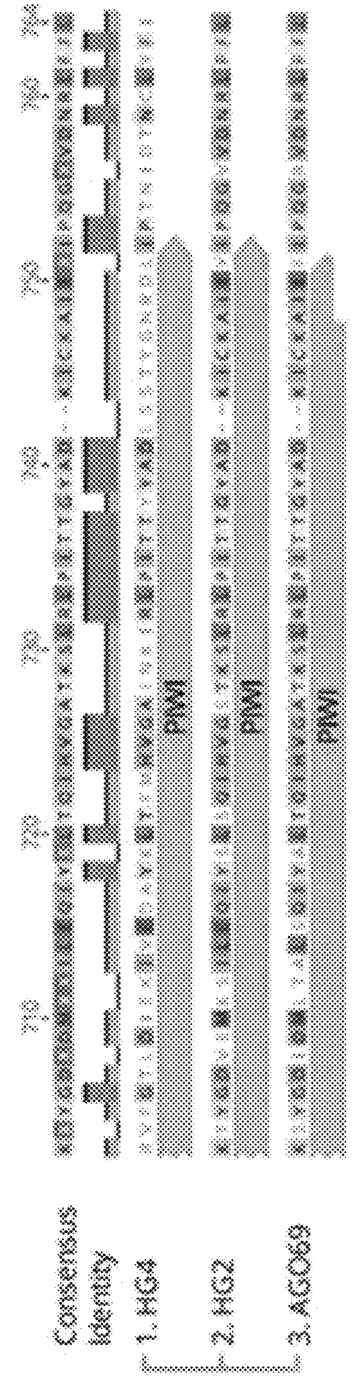

FIG. 103B shows a second part of a sequence alignment and homology of Ago69, HG2, and HG4 along with an indication of the PAZ, MID, and PIWI domains. FIG. 103C shows a third part of a sequence alignment and homology of Ago69, HG2, and HG4 along with an indication of the PAZ, MID, and PIWI domains. FIG. 103D shows a fourth (C terminal) part of a sequence alignment and homology of Ago69, HG2, and HG4 along with an indication of the PAZ, MID, and PIWI domains. FIGS. 103A-103D disclose SEQ ID NOS 156, 135, 134 and 1, respectively, in order of appearance.

Figure 104:
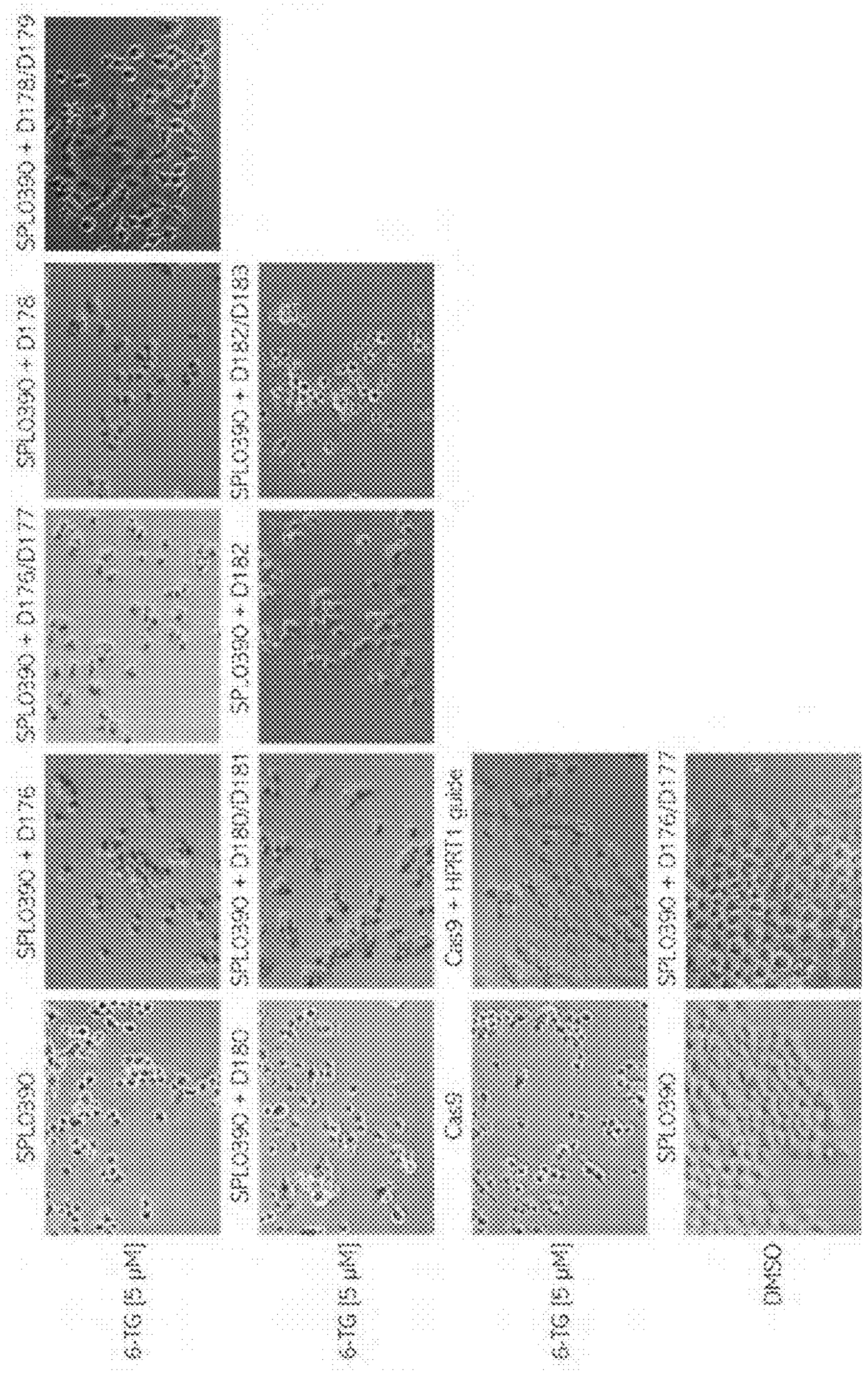

FIG. 104 shows microscopy image of cells transfected with the SPL0390 construct, indicated guide DNA, and treatment (6-TG or DSMO control).

Figure 105:
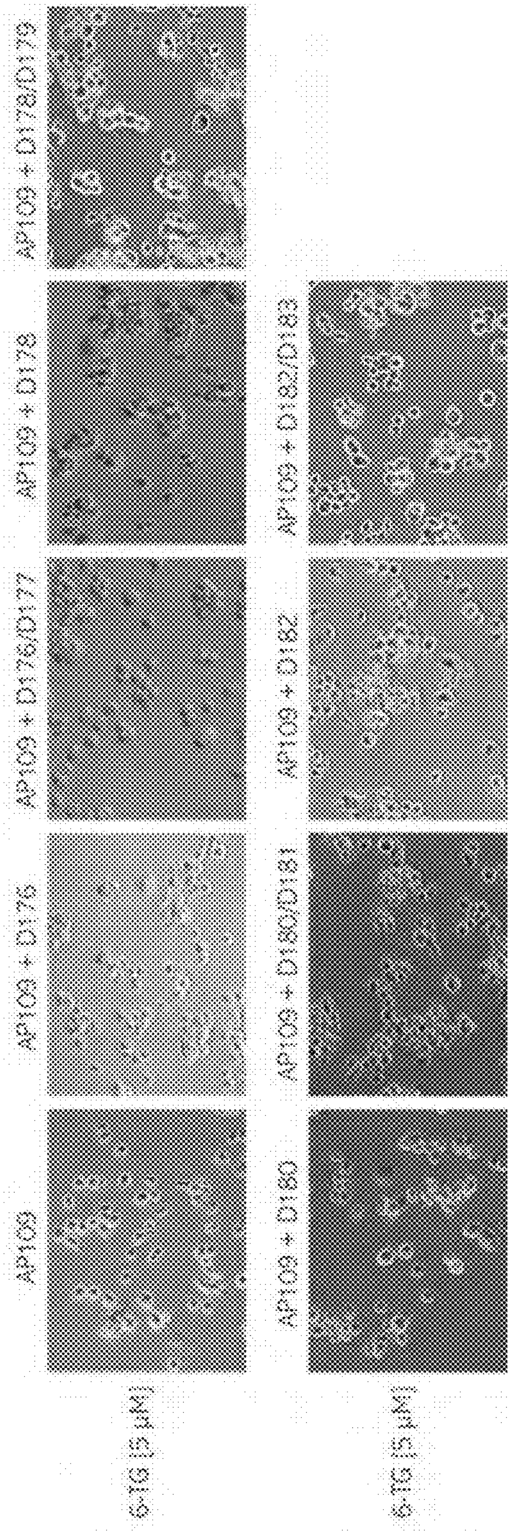

FIG. 105 shows microscopy image of cells transfected with the AP109 contract, indicated guide DNA, and 6-TG.

Figure 106:
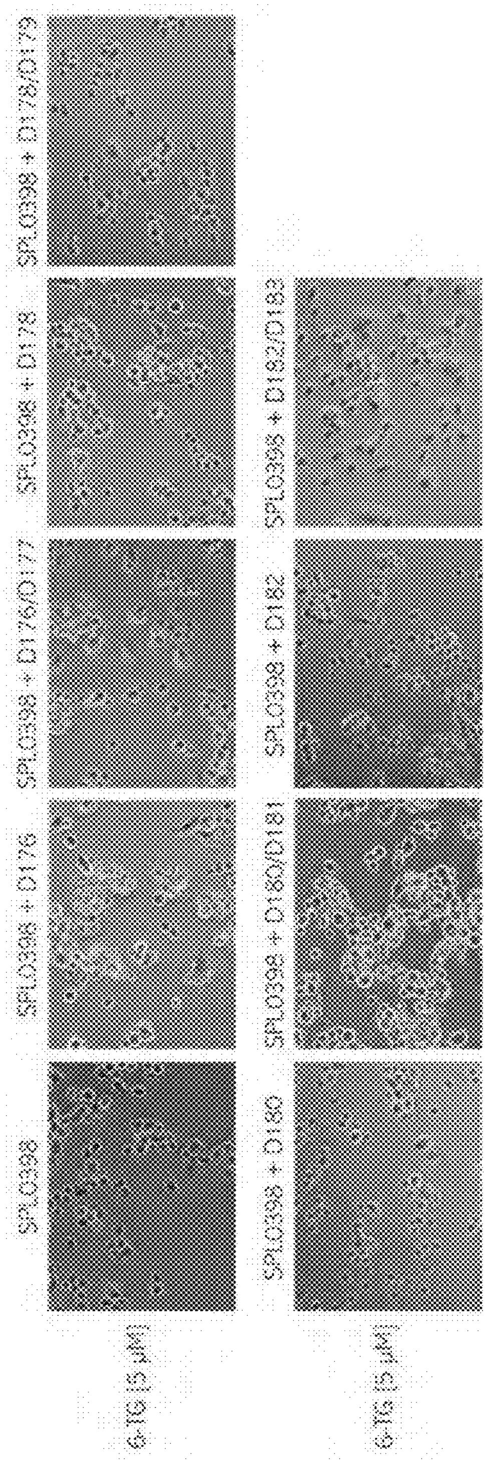

FIG. 106 shows microscopy image of cells transfected with the SPL0398 construct, indicated guide DNA, and 6-TG.

DETAILED DESCRIPTION

The following description and examples illustrate embodiments of the invention in detail. It is to be understood that this invention is not limited to the particular embodiments described herein and as such can vary. Those of skill in the art will recognize that there are numerous variations and modifications of this invention, which are encompassed within its scope.

Definitions

The term "activation" and its grammatical equivalents as used herein refers to a process whereby a cell transitions from a resting state to an active state. This process can comprise a response to an antigen, migration, and/or a phenotypic or genetic change to a functionally active state. For example, the term "activation" can refer to the stepwise process of T cell activation. For example, a T cell can require at least two signals to become fully activated. The first signal can occur after engagement of a TCR by the antigen-MHC complex, and the second signal can occur by engagement of co-stimulatory molecules. Anti-CD3 can mimic the first signal and anti-CD28 can mimic the second signal in vitro.

The term "adjacent" and its grammatical equivalents as used herein refers to right next to the object of reference. For example, the term adjacent in the context of a nucleotide sequence can mean without any nucleotides in between. For instance, polynucleotide A adjacent to polynucleotide B can mean AB without any nucleotides in between A and B.

The term "Argonaute," "Ago," and its grammatical equivalents as used herein refer to a naturally occurring or engineered domain or protein having at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to a wild type Argonaute polypeptide as measured by protein-protein BLAST algorithm. Some Ago domains or proteins, also referred to herein as "Argonaute nucleases" have endonuclease activity, e.g., the ability to cleave an internal phosphodiester bond in a target nucleic acid.

A "Clostridia argonaute" or "C-Ago" as used interchangeably herein refers to a naturally occurring or engineered domain or protein having at least 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% sequence identity to a wild type Argonaute polypeptide derived from a bacterium of the class Clostridia as measured by protein-protein BLAST algorithm.

The term "autologous" and its grammatical equivalents as used herein refers to as originating from the same being. For example, a sample (e.g., cells) can be removed, processed, and given back to the same subject (e.g., subject) at a later time. An autologous process is distinguished from an allogenic process where the donor and the recipient are different subjects.

The term "cancer" or "tumor," used interchangeably herein, and their grammatical equivalents as used herein refers to a hyperproliferation of cells whose unique trait-loss of normal controls-results in unregulated growth, lack of differentiation, local tissue invasion, and/or metastasis. With respect to the inventive methods, the cancer can be any cancer, including any of acute lymphocytic cancer, acute myeloid leukemia, alveolar rhabdomyosarcoma, bladder cancer, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and/or urinary bladder cancer.

The term "engineered" and its grammatical equivalents as used herein refers to one or more alterations of a nucleic acid, e.g., the nucleic acid within an organism's genome. The term "engineered" can refer to alterations, additions, and/or deletion of genes. An engineered cell can also refer to a cell with an added, deleted and/or altered gene.

The term "checkpoint gene" and its grammatical equivalents as used herein refers to any gene that is involved in an inhibitory process (e.g., feedback loop) that acts to regulate the amplitude of an immune response, for example, an immune inhibitory feedback loop that mitigates uncontrolled propagation of harmful responses. These responses can include contributing to a molecular shield that protects against collateral tissue damage that might occur during immune responses to infections and/or maintenance of peripheral self-tolerance. Non-limiting examples of checkpoint genes can include members of the extended CD28 family of receptors and their ligands as well as genes involved in co-inhibitory pathways (e.g., CTLA-4 and PD-1). The term checkpoint gene, in some embodiments, refers to an immune checkpoint gene.

A "CRISPR," "CRISPR system," or "CRISPR nuclease system" and their grammatical equivalents refer to a system that comprises an RNA molecule (e.g., guide RNA) that binds to DNA and a Cas protein (e.g., Cas9) with nuclease functionality (e.g., two nuclease domains). See, e.g., Sander, J. D., et al., "CRISPR-Cas systems for editing, regulating and targeting genomes," Nature Biotechnology, 32:347-355 (2014); see also e.g., Hsu, P. D., et al., "Development and applications of CRISPR-Cas9 for genome engineering," Cell 157(6):1262-1278 (2014). In some embodiments, a CRISPR system includes a Cas protein with nickase functionality (e.g., one catalytically dead nuclease domain and one catalytically active nuclease domain). A Cas can be partially catalytically dead.

The term "disrupting" and its grammatical equivalents as used herein refers to a process of altering a gene, e.g., by deletion, insertion, mutation, rearrangement, or any combination thereof. For example, a gene can be disrupted by knockout. Disrupting a gene can, for example, partially or completely suppress expression of the gene. Disrupting a gene can also cause activation of a different gene, for example, a downstream gene.

The term "function" and its grammatical equivalents as used herein refers to the capability of operating, having, or serving an intended purpose. Functional can comprise any percent from baseline to 100% of normal function. For example, functional can comprise or comprise about 5, 10, 15, 20, 25, 30, 35, 40, 45, 50, 55, 60, 65, 70, 75, 80, 85, 90, 95, and/or 100% of normal function. In some cases, the term functional can mean over or over about 100% of normal function, for example, 125, 150, 175, 200, 250, 300% and/or above normal function.

The term "gene editing," "genome editing," and their grammatical equivalents as used herein refers to genetic engineering in which one or more nucleotides are inserted, replaced, or removed from a genome. Gene editing can be performed using a nuclease (e.g., a natural-existing nuclease or an artificially engineered nuclease).

The term "mutation" and its grammatical equivalents as used herein include the substitution, deletion, and insertion of at least one nucleotide in a polynucleotide. For example, up to 1, 2, 3, 4, 5, 6, 7, 8, 9, 10, 11, 12, 13, 14, 15, 20, 25, 30, 40, 50, or more nucleotides/amino acids in a polynucleotide (cDNA, gene) or a polypeptide sequence can be substituted, deleted, and/or inserted. A mutation can affect the coding sequence of a gene or its regulatory sequence. A mutation can also affect the structure of the genomic sequence or the structure/stability of the encoded mRNA.

The term "non-human animal" and its grammatical equivalents as used herein includes all animal species other than humans, including non-human mammals, which can be a native animal or a genetically modified non-human animal.

The terms "nucleic acid," "polynucleotide," "polynucleic acid," and "oligonucleotide" and their grammatical equivalents are used interchangeably herein and refer to a deoxyribonucleotide or ribonucleotide polymer, in linear or circular conformation, and in either single- or double-stranded form. For the purposes of the present disclosure, these terms should not to be construed as limiting with respect to length, unless the context clearly indicates otherwise. The terms can also encompass analogues of natural nucleotides, as well as nucleotides that are modified in the base, sugar and/or phosphate moieties (e.g., phosphorothioate backbones). Modifications of the terms can also encompass demethylation, addition of CpG methylation, removal of bacterial methylation, and/or addition of mammalian methylation. In general, an analogue of a particular nucleotide can have the same base-pairing specificity, e.g., an analogue of A can base-pair with T.

The term "construct" refers to an artificial or synthetic construct. For example, a polypeptide construct can refer to an artificial or synthetic polypeptide, e.g., comprising one or more polypeptide sequences. Similarly, a nucleic acid construct can refer to an artificial or synthetic nucleic acid, e.g., comprising one or more nucleic acid sequences.

The term "percent (%) identity" can be readily determined for nucleic acid or amino acid sequences, over the full-length of a sequence, or a fragment thereof. Generally, when referring to "identity", "homology", or "similarity" between two different sequences (e.g., nucleotide or amino acid sequences), "identity", "homology" or "similarity" is determined in reference to "aligned" sequences. "Aligned" sequences or "alignments" refer to multiple nucleic acid sequences or protein (amino acids) sequences, often containing corrections for missing or additional bases or amino acids as compared to a reference sequence.

The term "phenotype" and its grammatical equivalents as used herein refer to a composite of an organism's observable characteristics or traits, such as its morphology, development, biochemical or physiological properties, phenology, behavior, and/or products of behavior. Depending on the context, the term "phenotype" can sometimes refer to a composite of a population's observable characteristics or traits.

"Polypeptide," "peptide," and their grammatical equivalents as used herein refer to a polymer of amino acid residues. A "mature protein" is a protein which is full-length and which, optionally, includes glycosylation or other modifications typical for the protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and O-linked), amidation, hydroxylation, alkylation including methylation and ethylation, ubiquitination, addition of pyrrolidone carboxylic acid, formation of disulfide bridges, sulfation, myristoylation, palmitoylation, isoprenylation, farnesylation, geranylation, glypiation, lipoylation and iodination. The term polypeptide includes a polypeptide that has been separated from components that naturally accompany it. Typically, the polypeptide is isolated when it is at least 60%, by weight, free from the proteins and naturally-occurring organic molecules with which it is naturally associated. In some embodiments, the preparation is at least 75%, at least 90%, or at least 99%, by weight, a polypeptide. An isolated polypeptide may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

The term "protospacer" and its grammatical equivalents as used herein refers to a PAM-adjacent nucleic acid sequence capable to hybridizing to a portion of a guide RNA, such as the spacer sequence or engineered targeting portion of the guide RNA. A protospacer can be a nucleotide sequence within gene, genome, or chromosome that is targeted by a guide RNA. In the native state, a protospacer is adjacent to a PAM (protospacer adjacent motif). The site of cleavage by an RNA-guided nuclease is within a protospacer sequence. For example, when a guide RNA targets a specific protospacer, the Cas protein will generate a double strand break within the protospacer sequence, thereby cleaving the protospacer. Following cleavage, disruption of the protospacer can result though non-homologous end joining (NHEJ) or homology-directed repair (HDR). Disruption of the protospacer can result in the deletion of the protospacer. Additionally or alternatively, disruption of the protospacer can result in an exogenous nucleic acid sequence being inserted into or replacing the protospacer.

The term "recipient" and their grammatical equivalents as used herein refers to a human or non-human animal. The recipient can also be in need thereof.

The term "recombination" and its grammatical equivalents as used herein refers to a process of exchange of genetic information between two polynucleic acids. For the purposes of this disclosure, "homologous recombination" or "HR" can refer to a specialized form of such genetic exchange that can take place, for example, during repair of double-strand breaks. This process can require nucleotide sequence homology, for example, using a donor molecule to template repair of a target molecule (e.g., a molecule that experienced the double-strand break), and is sometimes known as non-crossover gene conversion or short tract gene conversion. Such transfer can also involve mismatch correction of heteroduplex DNA that forms between the broken target and the donor, and/or synthesis-dependent strand annealing, in which the donor can be used to resynthesize genetic information that can become part of the target, and/or related processes. Such specialized HR can often result in an alteration of the sequence of the target molecule such that part or all of the sequence of the donor polynucleotide can be incorporated into the target polynucleotide. In some cases, the terms "recombination arms" and "homology arms" can be used interchangeably.

The term "transgene" and its grammatical equivalents as used herein refer to a gene or genetic material that is transferred into an organism. For example, a transgene can be a stretch or segment of DNA containing a gene that is introduced into an organism. When a transgene is transferred into an organism, the organism is then referred to as a transgenic organism. A transgene can retain its ability to produce RNA or polypeptides (e.g., proteins) in a transgenic organism. A transgene can be composed of different nucleic acids, for example RNA or DNA. A transgene can encode for an engineered T cell receptor, for example a TCR transgene. A transgene can be a TCR sequence. A transgene can be a receptor. A transgene can comprise recombination arms. A transgene can comprise engineered sites.

A "therapeutic effect" occurs if there is a change in the condition being treated. The change can be positive or negative. For example, a 'positive effect' can correspond to an increase in the number of activated T-cells in a subject. In another example, a 'negative effect' can correspond to a decrease in the amount or size of a tumor in a subject. There is a "change" in the condition being treated if there is at least 10% improvement, preferably at least 25%, more preferably at least 50%, even more preferably at least 75%, and most preferably 100%. The change can be based on improvements in the severity of the treated condition in an individual, or on a difference in the frequency of improved conditions in populations of individuals with and without treatment with the therapeutic compositions with which the compositions of the present invention are administered in combination. Similarly, a method of the present disclosure can comprise administering to a subject an amount of cells that is "therapeutically effective." The term "therapeutically effective" should be understood to have a definition corresponding to 'having a therapeutic effect.'

The term "sequence" and its grammatical equivalents as used herein refers to a nucleotide sequence, which can be DNA or RNA; can be linear, circular or branched; and can be either single-stranded or double stranded. A sequence can be mutated. A sequence can be of any length, for example, between 2 and 1,000,000 or more nucleotides in length (or any integer value there between or there above), e.g., between about 100 and about 10,000 nucleotides or between about 200 and about 500 nucleotides.

Overview

The present disclosure provides methods, systems, compositions, and kits for modifying a target polynucleic acid using a system comprising an Argonaute (Ago) polypeptide. The present disclosure also provides methods of treating a disease or disorder using the herein described systems, compositions, or kits. In some embodiments, the systems described herein comprise, for example, a nuclease and a helicase. These systems overcome technical challenges associated with argonaute proteins including, for example, a lack of activity at temperatures that are conducive for gene editing in human cells. The methods, systems, compositions and kits described herein allow for this physiologicallyrelevant gene editing by providing an argonaute system from a bacterium. In some embodiments, the argonaute is a mesophilic argonaute or a mesothermic argonaute. Without wishing to be bound by theory, such systems are able to induce single- or double-stranded polynucleic acid breaks at physiological temperatures. In some embodiments, the herein described systems comprise a fragment of a mesophilic Ago polypeptide gene or protein. In some embodiments, the system comprises one or more associated genes. In some embodiments, the one or more associated genes are found in proximity to the argonaute gene in its genome of origin. In some embodiments, a herein described Ago polypeptide and a protein encoded by an associated gene are provided as a fusion protein.

I. ARGONAUTE PROTEINS

Provided herein are a gene editing systems comprising Ago polypeptides, or functional fragments or functional variants thereof. Provided herein are also compositions, constructs, systems, and methods for disrupting a genomic sequence in a subject (e.g. mammal, non-mammal, or plant). Also provided herein are compositions, constructs, systems, and methods of treating or inhibiting a condition caused by a defect in a target sequence in a genomic locus of interest in a subject (e.g., mammal or human) or a non-human subject (e.g., mammal) in need thereof. In some embodiments, a method comprises modifying a subject or a non-human subject by manipulation of a target sequence and wherein a condition is susceptible to treatment or inhibition by manipulation of a target sequence.

Disclosed herein is a system comprising a Clostridia Argonaute (Ago) polypeptide, or a polynucleic acid encoding the same, and an exogenous guiding polynucleic acid. The Ago polypeptide is a prokaryotic Ago (p-Ago) polypeptide. In some embodiments the Ago polypeptide comprises an amino acid sequence having at least 85%, 90%, 91%, 92%, 93%, 94%, 95%, 96%, 97%, 98%, 99%, or 100% sequence identity with one of SEQ ID NOs: 1-10 or 134-136 as measured by protein-protein BLAST algorithm. In some cases, the system comprises an Ago polypeptide. In some cases, the system comprises a polynucleic acid encoding the Ago polypeptide. In some embodiments, the polynucleic acid encoding the Ago polypeptide comprises a nucleic acid sequence having at least 85%, 90%, 91%, 92%, 93%, 94%, 95%, 96%, 97%, 98%, 99%, or 100% sequence identity with one of SEQ ID NOs: 11-21 or 137-139 as measured by nucleotide-nucleotide BLAST algorithm.

In one aspect, disclosed herein is a system comprising (a) an Ago polypeptide, or a polynucleic acid encoding the same; and (b) an exogenous guiding polynucleic acid comprising a sequence that is complementary to a target polynucleic acid sequence. In one aspect, disclosed herein is a system comprising (a) an Ago polypeptide, or a polynucleic acid encoding the same, wherein said Ago polypeptide comprises an amino acid sequence having at least 85%, 90%, 91%, 92%, 93%, 94%, 95%, 96%, 97%, 98%, 99%, or 100% sequence identity with one of SEQ ID NOs: 1-10 or 134-136 as measured by protein-protein BLAST algorithm; and (b) an exogenous guiding polynucleic acid comprising a sequence that is complementary to a target polynucleic acid sequence. In another aspect, disclosed herein is a system comprising (a) an Ago polypeptide, or a polynucleic acid encoding the same, wherein said Ago polypeptide is a mesophilic Ago; and (b) an exogenous guiding polynucleic acid comprising a sequence that is complementary to a target polynucleic acid sequence.

Examples of an Ago include, but are not limited to, Ago polypeptides comprising an amino acid sequence having 75%, 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100% identity with one of SEQ ID NOs: 1-10 or 134-136. Percent sequence identity can be determined by BLAST (basic local alignment search tool) algorithm, specifically protein-protein BLAST (BLASTP). BLAST is provided by National Center for Biotechnology Information (NCBI) for aligning query sequences against those present in databases. The parameters of BLASTP can be set as Matrix BLOSUM62, Gap Costs Existence: 11, Extension: 1, and Compositional Adjustments Conditional Compositional Score Matrix Adjustment, with applying any filters or masks. In some embodiments, alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) Adv. Appl. Math. 2: 482-489.

In some cases, the Ago may be an argonaute polypeptide or a protein with sequence similarity to a known Argonaute. Examples of known Argonautes include, but are not limited to, Clostridia Agos. In some cases, the Ago may be an argonaute polypeptide or a protein with at least 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4% 99.5%, 99.6%, 99.7%, 99.8%, 99.9%, or 100% positive scoring matches relative to a known Argonaute.

In some cases, the Ago comprises one or more domains or motifs commonly found in argonaute polypeptide. In some cases, the Ago comprises a PAZ domain. In some cases, the Ago lacks a PAZ domain. In some cases, the Ago comprises a domain with sequence similarity to a PAZ domain. In some cases, the Ago comprises a Sir2 domain. In some cases, the Ago comprises a Sir2-like domain. In some cases, the Ago comprises an additional Sir2 or Sir2-like domain. In some cases, the Ago comprises a Sir2 and a Sir2-like domain. In some cases, the Ago lacks a Sir2 domain. In some cases, the Sir2 domain is an N-terminus Sir2 domain. In some cases, the Sir2-like domain is an N-terminus Sir2-like domain. In some cases, the Ago lacks a Sir2-like domain. In some cases, the Ago comprises a functional DEDX motif. In other cases, the Ago lacks a functional DEDX motif. A DEDX motif is a catalytic tetrad in the PIWI domain, wherein the “X” can vary. In some embodiments, a polypeptide as described herein comprises an RNAse H-like domain with a DEDX motif, or a functional variant thereof. In some cases, the Ago comprises a PIWI domain. In other cases, the Ago lacks a PIWI domain. In some cases, the Ago comprises a PIWI-like domain. In other cases, the Ago lacks a PIWI-like domain. In some cases, the PIWI domain or the PIWI-like domain is at a C-terminus of the Ago.

In some embodiments, the Ago described herein, or a fragment thereof, is a polypeptide or a protein with nucleic acid-cleaving activity. In some embodiments, the protein or polypeptide with nucleic acid-cleaving activity (e.g., a nuclease) is an enzyme (i.e., enzymatic protein or polypeptide) that cleaves a chain of nucleotides in a nucleic acid into smaller units. In some embodiments, the protein or polypeptide with nucleic acid-cleaving activity is from a eukaryote or a prokaryote. In some embodiments, the protein or polypeptide with nucleic acid-cleaving activity is from a eukaryote. In some embodiments, the protein or polypeptide with nucleic acid-cleaving activity is from a prokaryote. In some embodiments, the protein or polypeptide with nucleic acid-cleaving activity is from archaea. In some embodiments, the protein or polypeptide with nucleic acid-cleaving activity is from bacteria. In some embodiments, a nuclease is a protein that is located in proximity to the Ago gene in a microbiome genome.

In some embodiments, the enzymatic polypeptide is an RNA-dependent DNase editor, an RNA-dependent RNase editor, a DNA-dependent DNase editor, or a DNA-dependent RNase editor. Examples of an RNA-dependent DNase editor are Cas9 and Cpf1 to name a couple. An example of an RNA-dependent RNase editor is Cas13. An enzymatic protein can contain multiple domains. For example, in some embodiments, an enzymatic polypeptide contains domains that can bind to a duplex of DNA-RNA, DNA-DNA, or RNA-RNA. For example, RuvC can bind Cas9 and Cpf1; HNH can bind Cas9, RNase-H can bind ribonuclease, and PIWI can bind Ago.

In some cases, the nuclease activity is double stranded polynucleic acid cleaving activity. In some cases, nuclease activity is single stranded polynucleic acid cleaving activity. In some cases, the Ago polypeptide or Ago polypeptide fragment has nickase activity. In some embodiments, the Nickase activity is single stranded DNA or RNA cleaving activity. In some cases, the Ago polypeptide or Ago polypeptide fragment has RNase activity. In some cases, RNase activity is double stranded RNA cleaving activity. In some cases, RNase activity is RNA cleaving activity. In some cases, the Ago polypeptide or Ago polypeptide fragment or polypeptide has RNase-H activity. In some cases, RNase-H activity is RNA cleaving activity. In some cases, the Ago polypeptide or Ago polypeptide fragment has recombinase activity. In some embodiments, the Ago polypeptide or Ago polypeptide fragment also has DNA-flipping activity. In some cases, the Ago polypeptide or Ago polypeptide fragment has transposase activity.

In some cases, the Ago polypeptide or Ago polypeptide fragment demonstrates nucleic acid-cleaving activity in a range of temperatures of from about 19° C. to about 41° C. In some cases, the Ago polypeptide or Ago polypeptide fragment has nucleic acid-cleaving activity at temperatures of about 17° C., about 18° C., 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., or up to 40° C. In some embodiments, the Ago polypeptide or Ago polypeptide fragment has nucleic acid-cleaving activity at temperatures from about 17° C. to 40° C. In some cases, the Ago polypeptide or Ago polypeptide fragment has nucleic acid-cleaving activity at temperatures of about 37° C. In some cases, a mesophilic Ago can be active at temperatures of at least about 17° C. In some cases, when the Ago polypeptide is a mesophilic. In some cases, the Ago polypeptide is derived from a mesophilic Clostridia bacterium.

In some cases, the Ago polypeptide is expressed by a gene located adjacent to an operon of at least one of DNA replication, recombination or repair gene. In some cases, the Ago polypeptide is expressed by a gene located adjacent to an operon of at least one of a defense mechanism related gene, or a transcription related gene. In some cases, the Ago polypeptide is derived from a polypeptide encoded by a gene located in an adjacent operon to at least one of a P-element induced Wimpy testis (PIWI) gene, RuvC, Cas, Sir2, Mrr, TIR, PLD, REase, restriction endonuclease, DExD/H, superfamily II helicase, RRXRR, DUF460, DUF3010, DUF429, DUF1092, COG5558, OrfB_IS605, Peptidase_A17, Ribonuclease H-like domain, 3'-5' exonuclease domain, 3'-5' exoribonuclease Rv2179c-like domain, Bacteriophage Mu, transposase, DNA-directed DNA polymerase, family B, exonuclease domain, Exonuclease, RNase T/DNA polymerase III, yqgF gene, HEPN, RNase LS domain, LsoA catalytic domain, KEN domain, RNaseL, Irel, RNase domain, RloC, or PrrC. In some cases, the Ago polypeptide is derived from a polypeptide encoded by a gene located in an adjacent operon to at least one of a gene involved in defense, stress response, a Clustered Regularly Interspaced Short Palindromic Repeats (CRISPR), or DNA repair.

In some cases, the Ago polypeptide or Ago polypeptide fragment is chosen based on proximity to a secondary gene in a genome. For example, in some embodiments, the Ago polypeptide or Ago polypeptide fragment is chosen based on proximity to DNA repair associated genes. In some cases, the Ago polypeptide or Ago polypeptide fragment is chosen based on a predicted alignment (e.g., structural analysis) or phylogenetic analysis. For example, the Ago polypeptide or Ago polypeptide fragment may have homology or be conserved in relation to a gene sequence of a secondary gene. In some embodiments, conservation refers to a sequence or structure. In some embodiments, the structural conservation refers to the presence or absence of structural features. A structural feature can be a secondary structural feature such as an alpha helix or beta pleated sheet. An Ago polypeptide can be screened or chosen based on a secondary structure.

In some cases, the Ago polypeptide or portion thereof is a naturally-occurring Ago polypeptide (e.g., naturally occurs in a Clostridia bacterial cell). In other cases, the Ago polypeptide may not be a naturally-occurring polypeptide (e.g., the Ago polypeptide is a variant, chimeric, or fusion). In some cases, the Ago polypeptide has nuclease activity. In some cases, the Ago polypeptide may not have nuclease activity.

In some cases, the Ago is a type I prokaryotic Argonaute. In some cases, a type I prokaryotic Argonaute carries a DNA nucleic acid-targeting nucleic acid. In some cases, a DNA nucleic acid-targeting nucleic acid targets one strand of a double stranded DNA (dsDNA) to produce a nick or a break of the dsDNA. In some embodiments, a nick or break triggers host DNA repair. In some cases, a host DNA repair is nonhomologous end joining (NHEJ) or homologous directed recombination (HDR). In some cases, a dsDNA is selected from a genome, a chromosome, and a plasmid. In some embodiments, a type I prokaryotic Argonaute is a long type I prokaryotic Argonaute, which may possess an N-PAZ-MID-PIWI domain architecture. In some cases, a long type I prokaryotic Argonaute possesses a catalytically active PIWI domain. In some embodiments, the long type I prokaryotic Argonaute possesses a catalytic tetrad encoded by aspartate-glutamate-aspartate-aspartate/histidine (DEDX). In some embodiments, a DEDX motif is mutated at any of the positions, which can suppress catalytic activity. In some embodiments, the catalytic tetrad can bind one or more magnesium ions or manganese ions. In some cases, the type I prokaryotic Argonaute anchors the 5' phosphate end of a DNA guide. In some cases, a DNA guide has a deoxycytosine at its 5' end.

In some embodiments, the Ago is a type II Ago, for instance a type II prokaryotic Argonaute A type II prokaryotic Argonaute carries an RNA nucleic acid-targeting nucleic acid. In some embodiments, an RNA nucleic acid-targeting nucleic acid targets one strand of a double stranded DNA (dsDNA) to produce a nick or a break of the dsDNA which may trigger host DNA repair; the host DNA repair can be non-homologous end joining (NHEJ) or homologous directed recombination (HDR). In some cases, a dsDNA is selected from a genome, a chromosome and a plasmid. A type II prokaryotic Argonaute may be a long type II prokaryotic Argonaute or a short type II prokaryotic Argonaute. A long type II prokaryotic Argonaute may have an N-PAZ-MID-PIWI domain architecture. A short type II prokaryotic Argonaute may have a MID and PrWI domain, but may not have a PAZ domain. In some cases, a short type II Ago has an analog of a PAZ domain. In some cases a type II Ago may not have a catalytically active PIWI domain. A type II Ago may lack a catalytic tetrad encoded by aspartate-glutamate-aspartate-aspartate/histidine (DEDX). In some cases, a gene encoding a type II prokaryotic Argonaute clusters with one or more genes encoding a nuclease, a helicase or a combination thereof. A nuclease may be natural, designed or a domain thereof. In some cases, the nuclease is selected from a Sir2, RE1 and TIR. The type II Ago may anchor the 5' phosphate end of an RNA guide. In some cases, the RNA guide has a uracil at its 5' end. In some cases, the type II prokaryotic Argonaute is a *Rhodobacter sphaeroides* Argonaute. In some cases, it may be desirable to use an Argonaute nuclease that has lost its ability to cleave a nucleic acid, such as in applications where the Argonaute: guide molecule complex is used as a probe. In some cases, a dead Argonaute system may utilize secondary nucleases to perform a genomic disruption. In such cases, one or more of the amino acid residues in a catalytic domain are substituted or deleted, such that catalytic activity is abolished, or diminished. In other cases, using a cleavage temperature-inducible Argonaute may be desired to control the timing of cleavage, or if cleavage should be inhibited at non-inducible temperatures.

In some cases, the Ago has at least one active domain. For example, in some embodiments, the Ago's active domain is a PIWI domain. In some embodiments, in addition to a catalytic PIWI domain the Ago contains non-catalytic domains such as PAZ (PIWI-Argonaute-Zwille), MID (Middle) and N domain, along with two domain linkers, L1 and L2. A MID domain can be utilized for binding the 5'-end of a guiding polynucleic acid and can be present in an Ago protein. A PAZ domain can contain an OB-fold core. An OB-fold core can be involved in stabilizing a guiding polynucleic acid from a 3'end. An N domain may contribute to a dissociation of the second, passenger strand of a loaded double stranded genome and to a target cleavage. In some cases, an Argonaute family may contain PIWI and MID domains. In some cases, an Argonaute family may or may not contain PAZ and N domains.

In some cases, the Ago is or comprises a naturally-occurring polypeptide (e.g., naturally occurs in Clostridia bacterial cell), such as a nuclease. In other cases, the Ago is or comprises a non-naturally-occurring polypeptide. A non-naturally occurring polypeptide can be engineered. In some embodiments, an engineered Ago polypeptide is a chimeric nuclease, mutated, conjugated, or otherwise modified version thereof. In some cases, the Ago comprises a sequence encoded by any one of the sequences of Table 1 (SEQ ID NOs: 1-10), modified versions thereof, derivatives thereof, or truncations thereof. In some cases, the Ago polypeptide or portion thereof comprises a percent identity to any one of SEQ ID NOs: 1-10 from at least about 80%, 85%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, or 100%. In some embodiments, the Ago comprises an amino acid sequence 100% identical to SEQ ID NO: 1. In some embodiments, the Ago comprises an amino acid sequence 100% identical to SEQ ID NO: 1, except there is a non-lysine amino acid residue at one or more of (e.g., 1, 2, 3, 4, or 5) positions 479, 522, 563, 581, 642 of SEQ ID NO: 1. In some embodiments, the Ago has a mutation in one or more residue of the DEDX domain. In some embodiments, these one or more mutations reduce catalytic activity of the Ago as compared to a corresponding Ago without the one or more mutations.

TABLE 1

Mesophilic Ago Amino Acid Sequences

| SEQ ID NO | Ago/Genus Species | Amino Acid Sequence |
|---|---|---|
| 1 | 69 (Referred to herein as Ago69 or Argonaute 69) (*Clostridium perfringens* WAL-14572; Accession No. NZ_JH594533.1) Underlined: PIWI Domain | MVGGYKVSNLTVEAFEGIGSVNPMLFYQYKVTGKGKYDNVYKII<br>KSARYKMHSKNRFKPVFIKDDKLYTLEKLPDIEDLDFANINFVK<br>SEVLSIEDNMSIYGEVVEYYINLKLKKVKVLGKYPKYRINYSKE<br>ILSNTLLTRELKDEFKKSNKGFNLKRKFRISPVVNKMGKVILYL<br>SCSADFSTNKNIYEMLKEGLEVEGLAVKSEWSNISGNLVIESVL<br>ETKISEPTSLGQSLIDYYKNNNQGYRVKDFTDEDLNANIVNVRG<br>NKKIYMYIPHALKPIITREYLAKNDPEFSKEIEQLIKMNMNYRY<br>ETLKSFVNDIGVIEELNNLSFKNKYYEDVKLLGYSSGKIDEPVL<br>MGAKGIIKNKMQIFSNGFYKLPEGKVRFGVLYPKEFDGVSRKAI<br>RAIYDFSKEGKYHGESNKYIAEHLINVEFNPKECIFEGYELGDI<br>TEYKKAALKLNNYNNVDFVIAIVPNMSDEEIENSYNPFKKIWAE<br>LNLPSQMISVKTAEIFANSRDNTALYYLHNIVLGILGKIGGIPW<br>VVKDMKGDVDCFVGLDVGTREKGIHYPACSVVFDKYGKLINYYK<br>PNIPQNGEKINTEILQEIFDKVLISYEEENGAYPKNIVIHRDGF<br>SREDLDWYENYFGKKNIKFNIIEVKKSTPLKIASINEGNITNPE<br>KGSYILRGNKAYMVTTDIKENLGSPKPLKIEKSYGDIDMLTALS<br>QIYALTQIHVGATKSLRLPITTGYADKICKAIEFIPQGRVDNRL<br>FFL |
| 2 | 41 *Clostridium disporicum* | MNNLTLEAFRGIGTIKPLLFYRYKLIGKGKIENTYKTIRNAQNR<br>MSFNNKFKATFSKDEIIYTLEKFEIIPTLDDVTIIFDGEEVLPI<br>KDNNKIYSEVIEFYINNNLRNVKFNYKYPKYRAANTREITGNVI |

TABLE 1-continued

Mesophilic Ago Amino Acid Sequences

| SEQ ID NO | Ago/Genus Species | Amino Acid Sequence |
|---|---|---|
| | | LDKDMNEKYKKSNKGFELKRKFIISPKVDDEGKVTLFLDLNASF DYDKNIYQMIKAGIDVVGEEVINIWSNKKQRGKIKEISDIKINE PCNFGQSLIDYYISSNQASRVNGFTEEEKNTNVIIVESGKSRLS YIPHALKPIITREYIAKNDEVFSKEIEGLIKINMNYRYEILKRF VSDIGTIKELNNLRFEKIYMDNIESLGYEQGQLKDPVLIGGKGI LKDKIHVFKSGFYKSPNDEIKFGVIYPRGYIKDTQSVIRAIYDF CTEGKYQGKDNIFINNKLMNIKFSNKECVFEEYELNDITEYKRA ANKLKKNENIKFVIAIIPTINESDIENPYNPFKRVCAEINLPSQ MISLKTAKRFSTSRGQSELYFLHNISLGILGKIGGVPWVIKDMP GEVDCFVGLDVGTKEKGIHYPACSVLFDKYGKLINYYKPTIPQS GEIIKTDVLQEIFDKVLLSYEEENGQYPRNIVIHRDGFSREDLE WYKNYFLKKNIEFSIVEVRKNFATRLVNNFNDEVSNPSKGSFIL RDNEAIVVTTDINDNMGAPKPIKVEKTYGDIDMLTIINQIYALT QIHVGSAKSLRLPITTGYADKICKAIDYIPSGQVDNRLFFL |
| 3 | 70 *Clostridium saudiense* | MNNLMLEAFKGIGTIKPLVFYRYKLIGKGKIENTYKTISNAKNK MSFNNKFKATFSKGETIYTLEKFEVMPNLNDVTIEFDGEEVLPI KDNNEIYSEVVQFYINNNLRKIKLDNKYQKYRATNTREITGNVI LDKDFKEKYKKSKSGFQLKRKFIISPKVNDEGKVTLFLDLNSSF DYDKNIYQMIKAGMDVVGQEVINTWNNKKQKGKIKKISELTISE PCNFGQSLIDYYVSLNQAVRVKNFTEEEKNTNVIVVQVGKGEVE YIPHALKPIITREYIKKYDEAFSKEVENLIKINMSYRYEILKKF IDDIGSITELNNLKFENTYIDNIESLGYQQGKLNDPVLIGGKGI LKDKIHVFKSGFYKSPIDEVKFGVIYPKGHTNDSKSTIRAIYDF CTDGKYQGKDNIFINNKLMNIKFSNQDCVFEEYELNDITEYKRA ANKLKNNENIKFVIAIIPAIDESDIENPYNPFKRVCAELNLPSQ MVSLKTAKRFGTSKGNNELYFLHNISLGILGKIGGVPWVIKDMP GEVDCFVGLDVGTKEKGIHYPACSVLFDKYGKLINYYKPTIPQS GEIIKTDVLQEIFDKVLLSYEEENGQYPRNIVIHRDGFSREDLE WYKNYFIKKNINFTIVEIKKNFATRVANNINNEVSNPFKGSFIL RENEAIVVTTDIKDNIGAPKPIKVEKTYGDIDMMTIINQIYALT QIHVGSAKSMRLPITTGYADKICKSIEYIPSGRVDNRLFFL |
| 4 | 51 *Rhodopirellula maiorica* | MLQLNGFSIEIAGGSLTVLKSKIAPTDVKETRRSLEDDWFTMYH EGHLYSLAKNSNASGGLGETELLVLSDHLGLRFVKAMLDQAMRG VFEAYDPVRDRPFTFLARNVDLVALAAENLESKPSLLSKFEIRP KYELEAKVVEFRPGELELMLALNLTTRWICNASVDELIEKNIPV RGMHLIRRNREPGQRSLVGTFDRMEGDNALLQDAYDGQDKIAAS QVRIEGSKEVFATSLRRLLGNRYTSFMHSVDNEYGKLCGGLGFD GELRKMQGFLAKKSPIQLHGGVEVSVGQRVQLTNQPGYKTTVEL LQSKYCFDRSRTKLHPYAWDGLARFGPFDRGSFPTRSPRILLVT PDSASGKVSQALKKFRDGFGSSQSSMYDGFLDTFHLSNAPFFPL PVKLDGVQRSDVGKAYRKAIEDKLARDDDFDAAFNILLDEHANL PDSHNPYLVAKSILLSHGIPVQEARVSTLTANEYSLQHTFRNVA TALYAKMGGVPWTVDHGETVDDELVVGIGNAELSGSRFEKRQRH IGITTVFRGDGNYLLSNLSKECRYEDYPDVLRESTIAVLREVKQ RNNWLPGQTVRIVFHAFKPLKNVEIADIIASSVKEVGSEQTIEF AFLNVSLDHSFTLLDMAQRGITKKNQTKGIYVPRRGMTVQVGRY TRLVTSIGPHMVKRANLALPRPLLIHLHKQSTYRDLSYLSEQVL NFTTLSWRSTLPSEKPVTILYSSLIADLLGRLKSVDDWSPAVLN TKLRNSKWFL |
| 5 | 02 *Paenibacillus odorifer* | MNTPLTHYVLTEWESDINTNVLHIHLYTLPVRNVFEQHKENGNA CFDLRKLNRSLIIDFYDQYIVSWQPIENWGEYTFTQHEYRSINP TILAERAILERLLLRTIESVQPKKEIAAGSRKFTWLKAEKVVEN ISIHRVIQCDVTVDYAGKISVGFDLNHSYRTNESVYDLMKSNAI FKGDRVIDIYNNLHYEFVEISNSTINDSIPELNQSVVNYFTKER KQAWKVDKLEQSMPVVYLKAFNGSRIAYAPAMLQKELTFESLPT NVVRQTSEIFKQNANQKIKTLLDEIQKILARTDKIKFNKQKLLV QQAGYEILELSNPNLQFGKNVTQTQLKYGLDKGGVVASKPLSIN LLVYPELIDTKLDVINDFNDKLNALSHKWGVPLSILKKSGAYRN RPIDFTNPHQLAILLKELTKNLFQELTLVIIPEKISGMWYDLVK KEFGGNSSVPTQFITIETLQKANDYILGNLLLGLYSKSGIQPWI LNSPLSSDCFIGLDVSHEAGRHSTGIVQVVGKDGRVLSSKANTS NEAGEKIRHETMCQIVYSAIDQYQQHYNERPKHVTFHRDGFCRE DLLSLDEVMNSLDVQYDMVEIIKKTNRRMALTVGKQGWETKPGL CYLKDESAYLIATNPHPRVGTAQPIKIIKKKGSLPIEAIIQDIY HLSFMHIGSLLKCRLPITTYYADLSSTFFNRQWLPIDSGEALHF V |
| 6 | 29 *Hyphomonas* | MPHTSLLLNFLPVSLSGDTRIHVGYRPYNEDVLRELREEFGESH VFKRDYQEDTISEIPVIPGAEPLSDKSTGVDLAEARWLWKPLLN AALLRLFSGSREITSDYPVSVLGNPKNNFISHANLPDWVRILPL LEFESRTLFGGKSGPQFGLVCNARTRHQVLAGCDHLIERGISPI |

TABLE 1-continued

| SEQ ID NO | Ago/Genus Species | Amino Acid Sequence |
|---|---|---|
| | | GRYVQIDQPQRDSRLAPRGLTVGKVSSIDGDTLILEDHRKGYER VKASDARLTGNRADFDWCVNALLPGQGQATLSRAWDAMSALNQG PGRLQMINQTAEYLRTVNLEAVPGVAFEIGEWLSSTDAQFPVTE TIDRPTLVFHPSGRPNDTWNERGIKDNGPHDQRTFTPKQLNIAV ICQGRFEGQVDRFVGKLLDGIPDFQLRNGRKPYDDGFLSRFRLE RANVQTFQANSASREAYEAACEDALKHAADNGFGWDLAIVQIEE DFKALPGPQNPYYATKAMLLRNNVAVQNIRIETMSEPDKSLVYT MNQVSLACYAKLGGRPWLLGAQQSVAHELVIGLGSHTEQQSRFD QSVRYVGITTVFSSDGGYHLSERTGVVPFEDYAKELTDTLTRTI ERVRREDNWKNTDRVRLVFHAFKQIKDIEAEAIKQAVESLDLEN VVFAFVHVAEHHPYLIFDQNQEGLPHWEKNRSKRKGVLGPSRGV HIKLADSESLVVFAGASELKQAAHGMPRACLLKLHRNSTFRDMT YLARQAFDFTAHSWRVMTPEPFPITIKYSDLIAERLAGLKQIET WDDDAVRFRNIGKAPWFL |
| 7 | 23 *Calothrix* sp. PCC 7103 | MIMSLESNIFTFSNLGTLTTQYRLYEIRGLQKRHQEYYQNRQIL IHRLSYLLKNAVTIIERDEKLYLVVAADAPEPPNSYPIVRGVIY FKPTGQILTLDYSLRTPQNEEICQRFLHFMVQSALFQNANLWQP SAGKAFFEKKPSFEFGSILLFQGFSVRPIFTKDKIGLCVDIHHK FVSKEPLPSYLNFNEFQKYRGVSCIYHFGHQWYEIQLSELSELN ATEAMVPIENKFVTLINYITQQARKPIPEELANVSQDAAVVHYF NNQNQDRMAVTSLCYQVYDNSYPEIRKYHQHTILKPHIRRSAIH GIVQKYLAELRFGDITLKVSTIPELVPQEMFNLPDYCFGNDYKL SVKGSEGTAQISLDQVGKQRLELLSKAEAGIYVQEKFDRQYILL PQTVGDSFGSRFIDDLKKTVDKLYPAGGGYDPKIIYYPDRGLRT YIEQGRAILKTVEENELQPGYGIVMLHDSPDRLLRQHDKLAALV IRELKDYDLYVAVIHSKTGRECYELRYNNQGEPFYAVIHEKRGK LYGYMRGVALNKVLLTNERWPFVLSTPLNADVVIGIDVKHHTAG YIVVNKNGSRIWTLPTITSKQKERLPSIQIKASLIEIITKEAEQ TVDQLHNIVIHRDGRIHESEIEGAKQAMAELISRCTLPVNATLT ILEVAKSSPVSFRLFDVSNTNSKDPFVQNPQVGCYYIANSTDAY LCSTGRAFLKFGTVNPLHIRYVEGTLPLKLCLEDVYYLTALPWT KPDGCIRYPITVKINDRRLGEDASEYDEDALRFELFESLESEDD FDEMTDSDFNQEETMV |
| 8 | 04 *Deinococcus* sp. YIM 77859 | LKLNHFPLNPDLPLYITEYAHRNPRALLGFVRGQGFWAQQVGEQ VQVYHGRPQPTFRGVQVISHTRLDPDHPAFDQGVLSLIRQALVR AGYVLTYRERMAIHPRLERVVLRPPDRHPAELTVHAHLRWEWEL ERHSGQRWLVLRPGRRHLSALPWPAEAVQMWSAALPATCQKLHA LCLDRGQQMALLRQEDGWHFANPGAATQGRWHLSFSPQALHELG LAQAAHHAAAFRWDEVQRLVQLTDLWKPFVTSLEPLEVAAPIIA GKRLRFGRGLGRDVTEVHKRGILEPPPLPVRLAVVSPHLPDEHA NAQLRRELLAHLLPRHQVLRSAESRQGLHEHLRRQDQDDTLYTF WSGGEYRKLGLPPFDLARGLHTYDPASGQLQQPAALAPAPAQAT QAGRQLIALVVLPDDLTRSVRDTLFQQLQQLGLRCLFSVSRILL HRPRTEYMAWVNMAVKLARTAGAVPWDLADLPGVTEQTFFVGVD LGHDHTHQQSLPAFTLHDHRGRPLQSWTPPRRTNNERLSLAELK KGLHRLLARRSVDQVIVHRDGRFLAGEVDDFTLALHDLGIPQFS LLAIKKSNHSVAVQAEEGSVLSLDERRCLLVTNTQAALPRPTEL ELVHSDRLSLATLTEQVFWLTRVFMNNAQHAGSDPATIEWANGI ARTGQRVPLAGWRL |
| 9 | 37 *Chroococcidiopsis thermalis* | MNNVMQEFPVASFPTFLSEISLLDITPKNFICFRLTPEIERKTG NSFSWRFSQKFPDAVVIWHNKFFWVLAKPNRPMPSQEQWREKLL EICEELKKDIGDRTYAIQWVSQPQITPEILSQLAVRVLKINCRF SSPSVISVNQVEVKREIDFWAETIEIQTQIQPALTITVHSSFFY QRHLEEFYNNHPYRQNPEQLLIGLKVRDIERNSFATITDIVGTI ADHRQKLLEDATGAISKQALIEAPEEQPVVAVQFGKNQQPFYYA MAALRPCITAETARKFDVDYGKLLSATKIPYLERKELLALYKKE AGQSLATYGFQLKISINSRRHPELFFSPSVKLSETKLVFGKNQI GVQGQILSGLSKGGVYRRHEDFSDLSRPIRIAALKLCDYPANSF LQETRQRLKRYGFETLLPVENKKTLLVDDLSGVEARAKAEEAVD ELMVNHPDIVLTFLPTSDRHSDNTEGGSLYSWIYSRLLRRGIAS QVIYEDTLKSVEAKYLLNQVIPGILAKLGNLPFVLAEPLGIADY FIGLDISRSAKKRGSGTMNACASVRLYGRKGEFIRYRLEDALIE GEEIPQRILESFLPAAQLKGKVVLIYRDGRFCGDEVQHLKERAK AIGSEFILVECYKSGIPRLYNWEEEVIKAPTLGLALRLSAREVI LVTTELNSAKIGLPLPLRLRIHEAGHQVSLESLVEATLKLTLLH HGSLNEPRLPIPLFGSDRMAYRRLQGIYPGLLEGDRQFWL |
| 10 | 27 *Thermosynechococcus elongates* | MPTQFQEVEVILNRFFVKKLSRPDLTFHEYQCQFTQVPEQGSEQ KAISSVCYKLGVTAVRLGSCIITREPIDPERMRTKDWQLQLIGC RELSCQNYRERQALETFERKILEEKLKETFKKTIIEKDYELGLI WWISGEEGLEKTGHGWEVHRGRQIDLKIETDEKLYLEIDIHHRF |

TABLE 1-continued

| Mesophilic Ago Amino Acid Sequences | | |
|---|---|---|
| SEQ ID NO | Ago/Genus Species | Amino Acid Sequence |
| | | YTPFKLEWWLSEYPNIQIKYVRNTYKDKKKWILENFADKSPNEI QIEALGISLAEYHRQEGATQQEIDESRVVIVKKISDYKAKPVYH LSQRLSPILTMETLAQIAEQGREKKEIQGVFDYIRKNIGTRLQE SQKIAQVIFKNVYNLSSQPEIMKVNGFVMPRAKLLARNNKEVNQ TARIKSFGCAKIGETKFGCLNLFDNKPEYPEEVHKCLLAIARSS GVQIKIDSYFTGSDYPKDDLAQQRFWQQWAAQGIKTVLVVMPWS PHEEKTRLRIQALKAGIATQFMIPTPQDNPYKALNVALGLLCKA KWQPVYLKPLDDPQAADLIIGFDTSTNRRLYYGTSAFAILANGQ SLGWELPDIQRGETFSGQSIWQVVSKLVLKFQDNYDSYPKKILL MRDGLVQDGEFEQTIRELTHQGIDVDILSVRKSGSGRMGRELTS GNTAITYDDAEVGTVIFYSATDSFILQTTEVIKTKTGPLGSARP LRVVRHYGNTPLELLALQTYHLTQLHPASGFRSCRLPWVLHLAD RSSKEFQRIGQISLLQNVDREKLIAV |

TABLE 2

| Mesophilic Ago Nucleic Acid Sequences | | |
|---|---|---|
| SEQ ID NO | Ago/Genus Species | Nucleic Acid Sequence |
| 11 | 69 (Referred to herein as Ago69 or Argonaute 69) *Clostridium perfringens* WAL-14572 Accession No. NZ_JH594533.1 | ATGGTAGGAGGCTATAAAGTGTCAAATTTAACAGTTGAAGCATT TGAAGGAATTGGAAGTGTAAACCCTATGTTGTTTTATCAATATA AGGTAACTGGAAAAGGCAAATATGATAATGTGTATAAAATCATT AAGAGTGCAAGGTATAAAATGCATTCAAAAAATAGATTTAAGCC TGTATTTATAAAAGATGATAAGCTTTATACATTAGAAAAACTTC CAGATATAGAAGATTTAGATTTTGCAAATATAAACTTTGTTAAA AGCGAGGTTTTGAGTATAGAGGACAATATGAGTATATATGGGGA GGTTGTTGAGTATTATATAAATTTAAAGCTTAAGAAAGTTAAAG TTTTAGGTAAGTATCCTAAATATAGAATTAATTATTCTAAGGAG ATACTTAGCAATACTTTGTTAACAAGAGAGTTAAAGGATGAATT TAAGAAAAGTAATAAAGGATTTAATTTAAAGCGTAAATTTCGAA TTTCACCAGTAGTTAATAAAATGGGTAAAGTGATTTTATATTTA AGCTGTTCAGCTGATTTTTCAACTAATAAGAATATTTATGAAAT GCTTAAAGAAGGATTAGAAGTAGAAGGGTTAGCTGTAAAAAGTG AATGGTCAAATATAAGTGGAAACTTAGTTATAGAAAGTGTATTA GAAACAAAAATAAGTGAGCCAACAAGTTTAGGGCAATCTTTGAT AGATTACTATAAAAATAATAATCAAGGGTATAGAGTTAAAGATT TTACTGATGAGGATTTAAATGCAAACATAGTAAATGTAAGGGGC AATAAGAAAATATATATGTACATACCACATGCATTAAAACCTAT TATAACTAGGGAGTATTTAGCTAAAAATGATCCAGAATTTTCTA AAGAGATAGAACAATTAATAAAAATGAATATGAATTATAGATAT GAGACCTTAAAGTCATTTGTGAATGATATTGGAGTTATTGAAGA ACTTAATAACTTAAGTTTTAAAAATAAATATTATGAAGATGTTA AATTATTAGGTTATAGCAGTGGGAAAATAGATGAACCAGTACTT ATGGGAGCAAAAGGGATTATAAAAAATAAGATGCAAATCTTTTC TAATGGATTTTATAAGTTACCAGAGGGGAAAGTTAGGTTTGGAG TTTTATATCCTAAAGAGTTTGATGGAGTAAGTAGAAAAGCTATA AGAGCTATATATGATTTTTCTAAAGAGGGAAAATATCATGGCGA AAGTAATAAATACATAGCAGAGCATTTAATAAATGTAGAATTTA ATCCTAAAGAATGTATCTTTGAAGGATATGAACTAGGAGATATT ACTGAATATAAAAAGGCTGCATTAAAGTTAAATAATTATAATAA TGTAGATTTTGTAATAGCTATTGTACCTAATATGAGTGATGAAG AGATAGAAAATTCATATAATCCTTTTAAGAAGATATGGGCTGAA TTGAATTTACCATCTCAAATGATATCTGTAAAGACAGCAGAAAT CTTTGCAAATAGTAGAGATAATACAGCATTATATTATTTACATA ATATAGTCTTAGGCATTTTGGGAAAAATAGGAGGAATACCATGG GTTGTTAAGGATATGAAGGGGGATGTAGATTGTTTTGTTGGATT AGATGTTGGAACTAGGGAGAAGGGAATACACTATCCAGCGTGTT CAGTTGTTTTTGATAAATATGGGAAGCTTATAAATTACTATAAA CCTAATATACCTCAAAATGGTGAAAAGATTAATACTGAAATACT TCAAGAGATTTTTGATAAAGTATTAATTTCATATGAAGAGGAAA ATGGAGCTTATCCTAAAAATATTGTTATACATAGGGATGGCTTT TCAAGAGAAGATTTAGATTGGTATGAAAATTATTTTGGAAAAAA GAATATAAAGTTTAATATAATAGAAGTTAAAAAAAGTACACCAT TAAAAATTGCATCTATTAATGAGGGCAATATAACAAACCCAGAA AAGGGAAGTTATATATTAAGAGGAAATAAGGCATATATGGTTAC TACTGATATTAAAGAAAATTTAGGATCACCAAAACCATTAAAGA TAGAAAAATCTTATGGGGATATAGATATGTTAACTGCATTGAGT CAGATATATGCACTAACTCAAATACATGTTGGAGCAACAAAGAG |

TABLE 2-continued

| Mesophilic Ago Nucleic Acid Sequences | | |
|---|---|---|
| SEQ ID NO | Ago/Genus Species | Nucleic Acid Sequence |
| | | TTTAAGACTTCCAATAACTACAGGATATGCAGATAAGATTTGTA<br>AAGCAATAGAGTTTATTCCTCAAGGAAGAGTTGATAATAGATTG<br>TTCTTTTTATGA |
| 12 | 69<br>*Clostridium perfringens* WAL-14572<br>NZ_JH594533.1<br>Human codon optimized nucleic acid sequence | ATGGTCGGCGGCTATAAAGTCAGCAATTTGACAGTGGAAGCGTT<br>CGAAGGTATCGGGAGTGTCAACCCGATGCTGTTTTACCAATACA<br>AAGTCACCGGAAAGGGAAAGTACGATAATGTGTATAAGATTATC<br>AAAAGCGCACGGTACAAGATGCATTCTAAGAACCGATTCAAGCC<br>CGTGTTCATCAAGGACGACAAACTGTACACCCTCGAGAAGCTCC<br>CGGATATAGAAGACCTGGATTTCGCAAACATTAACTTCGTGAAA<br>AGCGAGGTTCTCAGCATAGAGGATAATATGTCAATTTATGGCGA<br>GGTGGTGGAATACTATATCAATCTCAAGCTGAAAAAAGTGAAGG<br>TGTTGGGAAAATACCCCAAGTACAGGATCAATTACAGCAAAGAG<br>ATTCTCAGTAATACGCTGCTGACACGAGAGCTCAAAGACGAGTT<br>TAAGAAATCAAATAAGGGTTTTAACCTGAAACGGAAGTTTAGAA<br>TTTCCCCCGTGGTGAATAAGATGGGCAAAGTGATACTCTATTTG<br>TCCTGCAGTGCTGATTTCAGCACCAACAAGAACATTTACGAAAT<br>GTTGAAAGAGGGCTTGGAGGTTGAGGGGCTGGCCGTTAAGAGCG<br>AGTGGAGCAATATCAGTGGCAACCTGGTGATCGAGAGCGTACTG<br>GAAACCAAGATATCCGAGCCCACTAGCCTGGGCCAATCCCTGAT<br>AGACTACTATAAGAATAACAACCAGGGCTATAGGGTGAAGGATT<br>TCACCGATGAGGATCTGAATGCCAACATTGTCAACGTGAGAGGA<br>AATAAGAAGATCTATATGTATATTCCGCACGCGTTGAAGCCGAT<br>AATCACCCGGGAGTACCTGGCCAAGAACGATCCAGAGTTTTCTA<br>AGGAGATCGAGCAGCTTATCAAGATGAATATGAACTACCGATAT<br>GAAACCCTCAAGTCATTTGTGAATGACATCGGGGTCATTGAAGA<br>GCTGAACAACCTGAGCTTCAAAAACAAATACTACGAAGATGTGA<br>AACTGCTGGGTTACTCCAGCGGCAAAATAGACGAACCCGTCCTG<br>ATGGGGGCAAAAGGGATCATAAAGAACAAAATGCAGATTTTTTC<br>CAATGGATTCTACAAACTCCCCGAAGGCAAGGTACGATTTGGCG<br>TTCTGTACCCAAAAGAATTTGATGGCGTGTCAAGGAAAGCTATC<br>CGCGCCATTTATGACTTCAGTAAGGAGGGCAAATACCACGGCGA<br>AAGCAACAAGTATATCGCGGAACACCTGATAAACGTGGAGTTCA<br>ATCCAAAGGAGTGCATATTTGAGGGATACGAACTGGGCGATATC<br>ACCGAATACAAGAAGGCGGCTCTGAAACTTAATAACTACAACAA<br>TGTCGACTTCGTAATCGCAATAGTCCCGAACATGTCCGACGAAG<br>AGATAGAGAACAGCTACAATCCGTTCAAGAAAATATGGGCCGAA<br>CTGAATCTGCCCAGCCAGATGATTAGCGTCAAGACGGCCGAAAT<br>CTTTGCCAATAGCAGGGATAACACGGCGCTTTACTACCTGCATA<br>ACATCGTCCTCGGTATCCTGGGTAAGATAGGAGGGATTCCCTGG<br>GTGGTTAAAGACATGAAGGGCGACGTGGATTGCTTCGTTGGACT<br>CGATGTCGGCACCAGGGAGAAGGGCATACATTACCCCGCCTGCA<br>GCGTTGTGTTTGACAAGTACGGCAAGCTTATTAACTATTACAAG<br>CCTAACATCCCGCAGAACGGAGAGAAGATTAACACAGAAATACT<br>TCAGGAAATTTTCGACAAGGTGCTCATAAGCTATGAGGAGGAGA<br>ATGGAGCCTACCCGAAGAATATCGTGATCCACAGGGACGGCTTT<br>AGCCGAGAGGACCTTGACTGGTATGAGAACTACTTCGGTAAGAA<br>AAACATAAAGTTTAACATCATCGAAGTCAAAAAGTCAACTCCGT<br>TGAAAATCGCCAGTATAAACGAGGGAAATATCACGAATCCTGAA<br>AAGGGTTCCTACATCCTGCGCGGCAACAAAGCCTACATGGTGAC<br>CACAGATATTAAGGAAAACCTGGGAAGCCCAAAGCCCCTGAAGA<br>TAGAAAAGAGCTACGGCGACATAGACATGCTCACAGCTCTCAGC<br>CAAATATACGCACTCACGCAAATCCATGTGGGGGCGACCAAAAG<br>CCTGCGCCTCCCAATCACCACCGGCTACGCCGACAAGATTTGCA<br>AGGCGATCGAGTTCATCCCCCAAGGGCGCGTGGACAACCGCCTT<br>TTCTTTCTG |
| 13 | 70<br>*Clostridium saudiense* | ATGAATAATTTAATGTTAGAAGCTTTTAAAGGAATAGGAACAAT<br>AAAACCATTGGTTTTTTATAGATACAAATTAATAGGAAAAGGTA<br>AAATAGAAAATACATATAAAACCATAAGCAATGCTAAAAATAAG<br>ATGAGTTTTAATAATAAATTTAAAGCAACATTTAGTAAAGGAGA<br>AACAATATATACATTAGAAAAGTTTGAAGTAATGCCAAATTTAA<br>ATGATGTAACAATTGAATTTGATGGTGAGGAAGTATTACCTATA<br>AAAGATAATAATGAAATTTATTCTGAAGTTGTTCAATTTTATAT<br>TAATAATAATTTACGTAAGATTAAGTTAGATAATAAATATCAAA<br>AGTATAGAGCTACAAATACAAGGGAAATAACAGGTAATGTTATA<br>TTAGATAAAGATTTTAAGGAAAAATATAAAAAGAGTAAAAGTGG<br>ATTTCAATTAAAAAGAAAATTTATAATTTCTCCTAAGGTAAATG<br>ATGAGGGAAAAGTAACTTTATTTTTAGATTTAAATTCTAGTTTT<br>GATTATGATAAAAATATTTACCAAATGATAAAGGCTGGAATGGA<br>TGTAGTAGGTCAAGAGGTAATTAATACATGGAACAATAAAAAAC<br>AAAAAGGGAAGATCAAGAAAATATCAGAATTAACAATAAGTGAG<br>CCATGTAACTTTGGACAATCCTTAATTGATTACTATGTTAGTTT<br>AAATCAAGCTGTCAGGGTTAAGAACTTCACAGAAGAAGAGAAGA |

TABLE 2-continued

Mesophilic Ago Nucleic Acid Sequences

| SEQ ID NO | Ago/Genus Species | Nucleic Acid Sequence |
|---|---|---|
| | | ATACAAATGTTATAGTAGTTCAAGTTGGAAAAGGTGAAGTAGAA |
| | | TATATTCCACATGCATTAAAACCAATTATAACTAGGGAGTATAT |
| | | TAAAAAATATGATGAAGCTTTTTCAAAAGAAGTAGAAAATCTAA |
| | | TCAAAATAAATATGAGTTATAGGTATGAAATACTTAAGAAATTT |
| | | ATTGATGATATAGGAAGTATAACTGAGTTAAATAATTTAAAGTT |
| | | TGAAAATACATATATAGATAATATTGAAAGTTTGGGGTACCAGC |
| | | AAGGTAAATTGAATGATCCAGTATTAATTGGGGGTAAAGGGATA |
| | | CTAAAAGATAAGATTCATGTATTTAAAAGTGGATTTTATAAATC |
| | | TCCAATTGATGAGGTGAAGTTTGGAGTTATTTATCCAAAAGGAC |
| | | ATACTAATGATAGCAAAAGTACAATTAGAGCTATATATGATTTT |
| | | TGTACTGATGGAAAATATCAGGGAAAAGATAATATATTTATAAA |
| | | TAATAAATTAATGAATATAAAATTTAGTAATCAAGATTGTGTTT |
| | | TTGAAGAGTATGAATTAAATGATATTACAGAGTATAAAAGGGCT |
| | | GCTAATAAGCTTAAAAATAATGAAAATATTAAATTTGTCATTGC |
| | | TATTATACCAGCAATAGATGAAAGTGATATTGAAAATCCATATA |
| | | ATCCTTTTAAGAGAGTTTGTGCAGAATTAAATTTACCATCACAA |
| | | ATGGTTTCTTTAAAAACTGCAAAAAGATTTGGGACAAGTAAAGG |
| | | TAATAATGAACTTTATTTTTTACATAATATTTCTTTAGGTATAT |
| | | TAGGTAAGATAGGAGGAGTTCCATGGGTAATTAAAGATATGCCT |
| | | GGAGAAGTAGATTGTTTTGTTGGATTAGATGTGGGAACAAAGGA |
| | | GAAAGGAATACATTATCCCGCTTGTTCAGTGCTTTTTGATAAGT |
| | | ATGGTAAGTTAATAAATTATTATAAGCCTACAATACCTCAAAGT |
| | | GGAGAAATAATTAAAACGGATGTTTTACAAGAGATATTTGATAA |
| | | GGTACTACTTTCTTATGAAGAGGAAAATGGGCAGTATCCAAGAA |
| | | ATATTGTTATTCATAGGGATGGTTTTTCTAGGGAAGATTTAGAG |
| | | TGGTATAAGAATTATTTTATTAAAAAGAATATTAATTTTACAAT |
| | | AGTAGAAATTAAAAAGAACTTTGCAACTAGGGTAGCAAATAATA |
| | | TTAATAATGAAGTTAGTAATCCTTTTAAGGGAAGTTTTATTTTA |
| | | AGGGAAAATGAAGCAATAGTAGTTACAACGGATATTAAGGATAA |
| | | TATTGGAGCACCTAAGCCAATTAAGGTGGAAAAGACATATGGAG |
| | | ATATTGATATGATGACTATAATAAATCAAATATATGCATTAACT |
| | | CAAATTCATGTTGGATCTGCAAAGAGTATGAGATTGCCAATAAC |
| | | AACAGGTTATGCAGATAAGATTTGTAAATCTATAGAGTATATAC |
| | | CTTCAGGGCGAGTTGATAATAGATTGTTCTTTTTATAG |
| 14 | 41 *Clostridium disporicum* | ATGAATAACTTGACACTAGAAGCATTTAGAGGGATAGGAACAAT |
| | | AAAGCCACTACTTTTTTATAGATATAAATTGATAGGAAAAGGTA |
| | | AAATAGAAAATACATATAAAACAATAAGAAATGCTCAAAATAGA |
| | | ATGAGTTTTAATAATAAATTTAAAGCAACATTTAGTAAAGATGA |
| | | AATAATATATACATTAGAAAAATTTGAAATAATACCAACTTTAG |
| | | ATGATGTAACAATCATTTTTGATGGAGAAGAGGTTTTACCTATA |
| | | AAAGATAATAATAAAATTTATTCTGAAGTAATTGAGTTTTATAT |
| | | TAATAATAATTTACGTAATGTCAAATTTAATTATAAATATCCAA |
| | | AGTATAGGGCAGCAAATACAAGAGAAATAACAGGGAATGTTATA |
| | | TTAGATAAAGATATGAATGAGAAATACAAAAAGAGTAATAAGGG |
| | | GTTTGAGTTAAAAAGAAAATTTATAATTTCTCCTAAGGTAGATG |
| | | ATGAGGGAAAAGTAACTTTATTTTTAGATTTAAATGCAAGTTTT |
| | | GATTATGATAAAAATATTTATCAAATGATAAAAGCTGGAATAGA |
| | | TGTAGTAGGAGAAGAGGTTATTAATATCTGGAGTAATAAAAAAC |
| | | AAAGAGGAAAAATTAAAGAGATATCAGATATAAAAATAAACGAA |
| | | CCGTGTAATTTTGGACAATCATTAATTGATTATTATATTAGTTC |
| | | TAATCAAGCTTCTAGAGTTAATGGATTTACTGAAGAAGAAAAAA |
| | | ATACAAATGTAATAATAGTTGAATCAGGAAAAAGTCGCTTAAGT |
| | | TATATTCCACATGCATTAAAACCAATTATAACGAGAGAATATAT |
| | | TGCGAAAAATGATGAAGTTTTTTCAAAAGAAATTGAAGGTTTAA |
| | | TTAAAATTAATATGAACTATAGATATATGAAATACTTAAGAGATTT |
| | | GTTAGTGATATAGGAACTATAAAAGAATTAAATAATTTGAGGTT |
| | | TGAAAAAATATATATGGATAATATCGAAAGTTTAGGGTATGAGC |
| | | AAGGTCAATTAAAGGATCCAGTATTGATTGGGGGTAAAGGAATA |
| | | CTAAAAGATAAAATTCATGTTTTTAAAAGTGGATTTTATAAATC |
| | | ACCAAACGATGAAATAAAGTTTGGAGTTATTTATCCTAGGGGAT |
| | | ATATTAAGGATACTCAAAGTGTGATCAGAGCTATATATGACTTT |
| | | TGTACTGAAGGAAAATATCAGGGAAAAGATAATATATTTATAAA |
| | | TAATAAATTAATGAATATAAAGTTTAGTAATAAAGAGTGTGTTT |
| | | TTGAAGAGTATGAATTAAATGATATTACTGAGTATAAAAGAGCT |
| | | GCAAATAAACTTAAAAAGAATGAAAATATTAAATTTGTTATTGC |
| | | TATTATACCAACAATAAATGAAAGTGATATTGAAAATCCATATA |
| | | ATCCTTTTAAGAGAGTTTGTGCTGAAATAAATTTACCATCACAA |
| | | ATGATTTCTTTGAAAACAGCAAAAAGATTTAGTACAAGCAGGGG |
| | | ACAGAGTGAACTTTATTTTTTACATAATATTTCCTTAGGTATAT |
| | | TAGGAAAGATAGGAGGAGTTCCATGGGTAATTAAAGATATGCCT |
| | | GGAGAAGTAGATTGTTTTGTTGGATTAGATGTGGGAACAAAGGA |
| | | GAAAGGAATACATTATCCAGCTTGTTCAGTACTTTTTGATAAGT |
| | | ATGGTAAGTTAATAAATTATTATAAACCTACAATACCTCAAAGT |

TABLE 2-continued

| SEQ ID NO | Ago/Genus Species | Nucleic Acid Sequence |
|---|---|---|
| Mesophilic Ago Nucleic Acid Sequences | | |
| | | GGAGAAATAATTAAAACGGATGTTTTACAAGAGATATTTGATAA<br>GGTATTACTTTCTTATGAAGAGGAAAATGGTCAGTATCCAAGAA<br>ATATTGTTATTCATAGGGATGGTTTTTCTAGGGAAGATTTAGAA<br>TGGTATAAGAACTATTTTCTTAAAAAGAACATTGAATTCTCTAT<br>TGTAGAAGTAAGAAAGAATTTCGCAACTAGGTTAGTGAATAATT<br>TTAATGATGAAGTTAGCAATCCTAGTAAAGGAAGTTTTATTTTA<br>AGAGATAATGAAGCAATAGTAGTTACAACTGATATTAATGATAA<br>TATGGGGGCACCTAAGCCAATTAAGGTGGAAAAGACATATGGAG<br>ATATTGATATGTTAACTATAATAAATCAAATATACGCATTAACT<br>CAAATTCATGTTGGTTCTGCTAAGAGTTTAAGGTTGCCTATAAC<br>AACTGGATATGCAGATAAGATTTGTAAGGCTATAGATTATATAC<br>CTTCTGGACAAGTTGATAATAGGTTATTCTTTTTATAG |
| 15 | 51<br>*Rhodopirellula maiorica* | ATGCTGCAACTGAACGGATTTTCAATCGAGATTGCCGGCGGGTC<br>GTTGACGGTACTGAAGTCGAAGATCGCACCGACGGACGTCAAGG<br>AAACGCGACGTTCGCTCGAGGACGATTGGTTTACGATGTATCAC<br>GAAGGGCACCTCTATTCCCTTGCAAAGAACTCGAACGCATCGGG<br>CGGGCTTGGTGAGACGGAACTCTTGGTGCTCTCCGACCACCTCG<br>GGCTGCGTTTTGTAAAAGCCATGCTCGATCAGGCGATGCGAGGC<br>GTCTTTGAAGCGTACGATCCTGTACGCGATCGCCCGTTTACCTT<br>TCTGGCTCGCAATGTCGATCTTGTCGCGTTAGCTGCCGAGAATT<br>TGGAATCAAAGCCCAGTTTGCTTTCTAAGTTTGAGATTCGACCT<br>AAGTATGAACTAGAAGCAAAAGTGGTTGAGTTCCGGCCGGGCGA<br>GCTGGAATTGATGCTCGCACTCAATCTGACCACTCGTTGGATCT<br>GCAACGCCAGCGTGGATGAATTGATCGAAAAGAACATTCCAGTC<br>CGGGGAATGCATCTGATTCGCAGGAATCGTGAGCCAGGACAACG<br>AAGCTTGGTCGGGACTTTCGACCGAATGGAAGGAGACAACGCTC<br>TACTCCAGGATGCGTACGACGGCCAGGACAAGATCGCTGCATCG<br>CAAGTCCGAATCGAGGGATCGAAGGAGGTCTTCGCGACAAGTCT<br>CCGGCGTCTGCTTGGCAATCGGTACACCAGCTTTATGCACTCAG<br>TGGACAATGAGTATGGGAAGTTGTGTGGCGGTCTTGGGTTTGAC<br>GGTGAGCTTCGCAAAATGCAAGGATTTCTTGCGAAGAAGAGCCC<br>GATTCAATTGCATGGCGGTGTGGAGGTGTCGGTCGGACAGCGAG<br>TTCAGCTAACCAATCAGCCGGGGTACAAAACGACTGTCGAACTG<br>CTGCAAAGCAAATACTGCTTCGACCGATCTCGAACGAAACTACA<br>TCCATACGCTTGGGACGGTTTAGCTAGATTCGGGCCGTTTGACC<br>GCGGAAGCTTTCCCACACGATCTCCGCGCATTTTGCTTGTCACA<br>CCCGATTCGGCATCCGGCAAGGTCAGCCAAGCTTTGAAGAAATT<br>TCGCGACGGTTTCGGGTCAAGCCAATCGAGCATGTACGACGGAT<br>TTCTCGATACTTTCCATCTTTCGAACGCACCCTTTTTCCCGCTC<br>CCTGTCAAATTGGATGGCGTCCAGCGATCGGATGTTGGCAAGGC<br>ATATCGAAAAGCAATCGAAGACAAGTTGGCCCGTGATGATGATT<br>TCGATGCTGCGTTTAACATTCTGCTGGATGAACACGCCAATCTC<br>CCCGACTCGCACAACCCGTATCTGGTTGCCAAATCAATCCTGCT<br>CTCGCATGGAATCCCCGTGCAAGAAGCCAGGGTGTCGACGCTTA<br>CTGCGAACGAGTATTCGCTACAGCACACATTCAGAAATGTTGCC<br>ACCGCACTGTACGCAAAAATGGGCGGAGTCCCTTGGACGGTCGA<br>TCACGGCGAAACGGTTGACGATGAACTGGTGGTGGGAATTGGGA<br>ACGCTGAACTGTCCGGCAGCCGCTTCGAGAAACGACAGCGTCAC<br>ATCGGAATCACCACGGTATTCCGTGGCGATGGCAACTATCTTCT<br>CTCAAATCTGTCCAAAGAGTGCAGATACGAAGACTACCCCGACG<br>TGCTTCGCGAATCGACGATCGCAGTCCTTCGCGAAGTCAAACAA<br>CGAAACAACTGGCTGCCCGGACAAACAGTGAGAATTGTTTTCCA<br>TGCGTTCAAACCGCTGAAGAATGTCGAGATCGCGGACATCATCG<br>CGTCAAGCGTCAAAGAAGTCGGCAGCGAACAGACGATTGAATTC<br>GCTTTCTTGAATGTCTCGCTGGACCATTCGTTCACGTTGCTGGA<br>TATGGCCCAGCGAGGAATAACGAAGAAGAACCAGACGAAAGGAA<br>TTTACGTTCCTCGCCGAGGAATGACCGTTCAGGTTGGACGGTAC<br>ACACGGCTCGTCACGTCAATCGGTCCTCACATGGTCAAGCGTGC<br>AAACCTTGCGTTGCCCAGGCCCCTGTTGATCCACCTGCACAAGC<br>AATCGACTTACCGCGACCTTTCCTACCTTTCTGAGCAGGTGCTG<br>AACTTCACGACGCTGTCGTGGCGATCAACGCTGCCGTCGGAGAA<br>GCCGGTCACGATTCTTTACTCATCACTTATCGCTGACTTGCTGG<br>GCCGTCTCAAGTCCGTGGACGATTGGTCGCCAGCGGTCCTCAAT<br>ACCAAACTTCGCAACAGCAAGTGGTTTCTGTGA |
| 16 | 02<br>*Paenibacillus odorifer* | ATGAATACACCACTAACACACTACGTACTTACAGAATGGGAATC<br>AGACACGAACACAAATGTTCTACATATTCATTTATATACGCTAC<br>CAGTGCGTAATGTATTTGAACAGCATAAAGAAAACGGAAATGCT<br>TGTTTTGACCTTAGAAAATTAAACAGATCGCTCATTATCGATTT<br>TTATGATCAATATATTGTAAGTTGGCAACCTATTGAAAATTGGG<br>GTGAATACACATTCACTCAGCATGAATATCGCTCAATTAATCCC<br>ACCATCTTAGCAGAAAGAGCTATCTTGGAACGATTACTTTTAAG<br>AACTATAGAAAGCGTTCAGCCAAAAAAAGAAATTGCTGCTGGAA |

TABLE 2-continued

Mesophilic Ago Nucleic Acid Sequences

| SEQ ID NO | Ago/Genus Species | Nucleic Acid Sequence |
|---|---|---|
| | | GTCGAAAATTCACGTGGTTAAAAGCTGAAAAAGTCGTAGAAAAT |
| | | ATTTCAATACACAGGGTTATACAATGTGATGTTACTGTAGATTA |
| | | TGCGGGCAAAATTTCCGTTGGCTTTGATTTAAATCATAGTTATC |
| | | GTACAAATGAATCGGTATATGATCTCATGAAATCAAATGCTATT |
| | | TTTAAAGGCGATCGAGTAATTGATATATATAACAATCTTCATTA |
| | | TGAGTTTGTGGAAATCTCCAATTCCACAATCAATGATTCAATTC |
| | | CAGAACTTAATCAATCTGTTGTTAATTATTTTACTAAAGAACGA |
| | | AAGCAAGCTTGGAAAGTTGATAAACTTGAACAGAGTATGCCTGT |
| | | TGTCTATCTAAAAGCGTTTAATGGATCTCGTATTGCTTATGCAC |
| | | CTGCTATGCTACAAAAAGAACTTACTTTTGAGTCGCTTCCTACT |
| | | AATGTAGTACGTCAAACATCAGAAATTTTTAAACAAAACGCAAA |
| | | TCAAAAAATTAAGACATTGCTGGATGAAATACAAAAAATATTAG |
| | | CACGCACTGATAAAATTAAATTTAATAAACAAAAGCTCCTAGTC |
| | | CAGCAAGCTGGGTATGAAATATTGGAGTTGTCAAATCCTAATCT |
| | | TCAATTCGGAAAAAATGTTACTCAAACACAGCTTAAATATGGAC |
| | | TTGATAAGGGCGGTGTTGTAGCCTCAAAACCTTTATCAATTAAT |
| | | TTGCTTGTATACCCAGAACTGATAGATACAAAACTCGATGTCAT |
| | | AAATGACTTTAATGATAAATTAAATGCGCTATCCCATAAATGGG |
| | | GTGTACCATTATCAATCTTAAAAAAATCAGGAGCATATCGGAAC |
| | | AGACCGATAGATTTCACAAATCCACACCAACTTGCCATCCTACT |
| | | GAAAGAACTTACAAAAAATTTATTTCAAGAGTTGACGCTCGTGA |
| | | TAATTCCGGAGAAAATTTCAGGAATGTGGTATGACTTGGTAAAG |
| | | AAGGAATTCGGAGGAAATTCCTCAGTACCAACTCAGTTCATAAC |
| | | TATAGAAACTCTTCAAAAAGCTAATGACTACATTCTAGGCAATC |
| | | TATTATTAGGACTCTATTCTAAATCTGGCATTCAACCGTGGATC |
| | | TTAAATTCTCCTCTGTCATCTGATTGTTTTATTGGGTTGGATGT |
| | | ATCTCATGAAGCTGGTAGACACTCTACAGGAATTGTACAGGTCG |
| | | TAGGAAAAGACGGCAGAGTATTGTCTAGCAAGGCAAACACCTCT |
| | | AATGAGGCCGGTGAAAAAATCCGTCATGAAACTATGTGTCAAAT |
| | | TGTATACTCAGCTATAGACCAATATCAGCAACATTACAATGAAA |
| | | GACCAAAGCATGTTACTTTTCATCGGGATGGTTTTTGTAGAGAA |
| | | GATTTACTTAGTCTAGACGAAGTAATGAATAGTTTGGATGTACA |
| | | ATATGACATGGTTGAAATCATCAAGAAAACGAATCGTCGCATGG |
| | | CTCTAACCGTTGGTAAGCAAGGTTGGGAGACCAAGCCAGGATTG |
| | | TGTTATCTAAAAGATGAGTCGGCATATCTTATCGCCACAAATCC |
| | | TCATCCACGTGTCGGCACAGCACAACCGATTAAAATTATCAAGA |
| | | AAAAGGGATCACTACCGATTGAAGCAATAATTCAAGATATTTAT |
| | | CATCTTTCGTTCATGCACATTGGTTCATTATTAAAATGTCGCCT |
| | | ACCTATTACTACGTATTATGCTGATTTAAGCTCTACATTCTTCA |
| | | ACCGGCAATGGCTCCCGATCGATTCTGGCGAAGCCCTACATTTT |
| | | GTATAA |
| 17 | 29 *Hyphomonas* | ATGCCGCACACATCTCTTCTCTTGAACTTTTTGCCCGTATCGCT |
| | | CTCCGGCGATACGCGAATTCACGTTGGCTATCGGCCCTACAACG |
| | | AAGACGTTTTGCGGGAACTACGAGAGGAGTTCGGTGAAAGCCAC |
| | | GTTTTCAAACGCGACTATCAAGAAGACACAATATCGGAGATTCC |
| | | AGTAATCCCCGGTGCCGAACCACTCTCCGACAAATCGACCGGAG |
| | | TAGACCTCGCCGAAGCACGGTGGCTTTGGAAGCCGCTTCTGAAC |
| | | GCGGCTCTCCTGCGGCTGTTTTCAGGGTCCAGAGAGATTACAAG |
| | | CGATTATCCTGTCAGCGTTTTGGGCAATCCGAAGAACAATTTCA |
| | | TTTCGCATGCTAACTTACCTGATTGGGTAAGGATCTTGCCGTTA |
| | | CTGGAATTTGAGTCTCGCACGTTGTTCGGTGGCAAGTCGGGTCC |
| | | GCAGTTCGGACTGGTGTGTAATGCGCGGACCCGTCACCAGGTAT |
| | | TGGCAGGTTGCGATCATCTCATTGAGCGGGGCATTTCTCCGATT |
| | | GGGCGTTATGTTCAAATCGATCAACCGCAACGAGACTCCCGATT |
| | | GGCGCCGCGCGGCCTTACAGTGGGAAAGGTATCATCGATCGACG |
| | | GTGACACACTCATTTTGGAAGACCATCGCAAAGGCTATGAACGG |
| | | GTCAAAGCATCTGATGCGAGGTTGACCGGCAATCGCGCTGATTT |
| | | CGACTGGTGCGTCAATGCGCTTTTGCCGGGACAAGGGCAGGCTA |
| | | CCCTGTCGAGGGCGTGGGACGCCATGAGCGCATTGAACCAGGGC |
| | | CCAGGTCGCCTGCAAATGATCAACCAAACAGCCGAGTATTTGAG |
| | | GACAGTCAATCTGGAAGCTGTTCCAGGCGTTGCTTTTGAAATCG |
| | | GCGAATGGCTGTCGAGCACGGACGCTCAGTTTCCGGTGACGGAA |
| | | ACGATCGATCGCCCCACGCTTGTATTTCACCCTTCGGGAAGGCC |
| | | GAACGATACGTGGAACGAACGCGGCATCAAAGACAATGGACCGC |
| | | ACGACCAACGCACGTTCACGCCAAAGCAACTCAACATCGCTGTC |
| | | ATTTGCCAAGGCCGGTTCGAAGGACAAGTCGATCGTTTCGTGGG |
| | | AAAACTTCTCGATGGCATCCCCGACTTTCAACTCCGAAATGGGC |
| | | GCAAGCCTTATGATGACGGCTTCCTTAGTCGATTTCGTCTGGAA |
| | | CGAGCCAATGTGCAGACATTTCAGGCAAACTCAGCCTCGCGCGA |
| | | AGCATACGAAGCAGCTTGCGAAGACGCACTGAAACATGCTGCTG |
| | | ACAATGGCTTTGGCTGGGACTTGGCGATTGTCCAGATTGAAGAA |
| | | GACTTCAAGGCGTTGCCTGGGCCTCAGAACCCTTACTACGCCAC |
| | | GAAGGCCATGCTGCTCCGCAACAATGTAGCGGTACAGAATATTC |

TABLE 2-continued

Mesophilic Ago Nucleic Acid Sequences

| SEQ ID NO | Ago/Genus Species | Nucleic Acid Sequence |
|---|---|---|
| | | GTATCGAGACGATGAGCGAGCCGGACAAAAGTCTCGTGTATACA<br>ATGAATCAGGTGAGTCTTGCCTGCTATGCGAAGCTGGGCGGTCG<br>TCCGTGGCTTTTAGGGGCGCAGCAATCGGTTGCCCATGAACTCG<br>TCATTGGCCTCGGGTCGCACACAGAACAACAATCTCGATTTGAT<br>CAGAGCGTTCGGTATGTCGGCATTACCACTGTGTTTTCGAGCGA<br>TGGCGGGTATCACCTCAGTGAACGCACCGGCGTCGTGCCATTTG<br>AGGATTACGCCAAGGAATTAACCGACACGCTCACGCGCACCATC<br>GAACGGGTCCGCCGGGAAGATAACTGGAAAAACACAGACCGGGT<br>GCGGCTGGTCTTCCATGCGTTCAAGCAAATCAAGGACATTGAGG<br>CTGAGGCCATCAAGCAGGCGGTCGAATCTCTCGACCTCGAAAAC<br>GTGGTTTTCGCTTTCGTTCATGTTGCTGAACATCATCCGTATTT<br>GATCTTCGACCAGAACCAAGAGGGATTGCCGCATTGGGAGAAAA<br>ATCGGTCTAAACGAAAAGGCGTATTGGGCCCATCCCGAGGCGTG<br>CACATCAAACTGGCTGATTCTGAGTCGCTGGTTGTGTTTGCGGG<br>CGCAAGTGAACTTAAGCAAGCGGCCCACGGGATGCCGAGGGCCT<br>GCCTTCTAAAACTGCATCGCAATTCGACCTTCCGCGATATGACT<br>TATCTCGCACGCCAGGCGTTCGACTTCACCGCCCATTCTTGGCG<br>AGTTATGACGCCGGAACCGTTTCCGATCACAATTAAGTATTCCG<br>ACCTAATCGCTGAACGTCTTGCCGGCCTGAAGCAGATCGAGACG<br>TGGGATGATGACGCCGTCCGGTTTCGCAACATCGGCAAGGCGCC<br>CTGGTTCCTGTGA |
| 18 | 23<br>*Calothrix* sp. PCC 7103 | ATGATTATGAGTTTAGAAAGTAATATTTTCACCTTTTCCAATCT<br>CGGAACGCTTACAACTCAATATCGTTTGTATGAAATACGAGGAC<br>TTCAAAAGCGTCATCAAGAATACTATCAAAATCGACAAATTTTG<br>ATACATCGGTTGAGCTATCTTCTGAAAAACGCTGTCACAATTAT<br>AGAACGTGATGAAAAACTGTATCTTGTTGTTGCAGCAGATGCAC<br>CAGAACCTCCTAATTCTTATCCAATTGTTCGAGGAGTAATTTAT<br>TTTAAGCCAACTGGGCAAATTTTGACTTTAGACTATTCGTTACG<br>TACACCACAGAATGAAGAAATTTGCCAGCGATTCTTACATTTTA<br>TGGTACAGTCTGCATTATTCCAAAATGCAAATTTATGGCAACCA<br>TCTGCAGGAAAAGCTTTCTTTGAGAAAAAACCGTCTTTTGAATT<br>TGGCTCTATTCTATTGTTTCAAGGTTTTTCTGTTCGCCCTATAT<br>TTACAAAAGATAAAATTGGATTATGTGTAGATATCCATCATAAA<br>TTTGTAAGCAAAGAACCTCTCCCAAGTTATTTAAATTTTAACGA<br>GTTCCAGAAATATCGCGGTGTTAGCTGTATTTATCACTTTGGTC<br>ATCAATGGTATGAGATTCAACTTAGTGAACTTTCTGAGTTAAAT<br>GCTACAGAAGCAATGGTTCCTATAGAAAACAAATTTGTTACATT<br>GATCAACTATATTACTCAACAAGCTCGTAAGCCAATTCCAGAGG<br>AGTTAGCAAACGTTTCTCAAGATGCAGCAGTAGTTCATTACTTT<br>AATAACCAAAACCAAGACCGTATGGCTGTCACCTCGTTATGTTA<br>TCAAGTTTATGATAATTCTTATCCTGAGATAAGAAAATACCATC<br>AACATACGATTCTTAAGCCACATATTCGGCGTTCGGCAATCCAC<br>GGTATTGTCCAAAAATATTTAGCTGAGTTGAGATTTGGAGATAT<br>TACGTTAAAAGTTTCAACTATACCTGAACTAGTACCACAGGAAA<br>TGTTTAACTTACCCGATTATTGTTTTGGTAATGATTATAAATTG<br>TCAGTCAAGGGTAGTGAAGGAACTGCTCAAATAAGTTTGGATCA<br>GGTTGGAAAACAACGACTAGAATTACTCAGCAAGGCAGAAGCAG<br>GTATATATGTACAAGAGAAATTTGATAGACAATATATTCTACTA<br>CCTCAAACAGTTGGAGATAGCTTTGGAAGTAGATTTATAGATGA<br>TCTCAAAAAAACTGTTGATAAACTTTACCCAGCAGGTGGGGGAT<br>ACGACCCTAAGATTATTTACTATCCGGACCGTGGTTTACGAACT<br>TATATTGAACAAGGCAGAGCGATACTCAAAACTGTTGAGGAAAA<br>CGAGCTTCAGCCTGGATACGGTATAGTGATGTTGCATGATTCAC<br>CAGATAGACTACTACGTCAGCATGATAAGCTTGCAGCTTTAGTA<br>ATTCGTGAATTGAAAGATTATGACTTATATGTTGCTGTAATTCA<br>TTCTAAAACAGGTAGAGAATGCTATGAACTTCGGTATAACAATC<br>AAGGAGAACCATTCTATGCAGTTATACATGAAAAACGTGGGAAG<br>CTTTACGGGTACATGCGCGGTGTTGCTTTAAATAAGGTGTTGTT<br>AACAAACGAACGTTGGCCTTTTGTCTTAAGTACACCTCTCAATG<br>CGGATGTTGTTATTGGCATTGATGTTAAGCATCATACGGCAGGA<br>TATATAGTTGTTAATAAAAATGGAAGTCGAATTTGGACTCTTCC<br>AACAATTACTTCTAAACAAAAAGAGCGCTTGCCTAGTATCCAAA<br>TAAAAGCTAGTTTAATAGAGATTATCACAAAGGAAGCAGAACAA<br>ACAGTAGACCAGCTTCATAATATAGTTATTCATCGTGATGGTCG<br>AATTCATGAATCAGAAATTGAAGGAGCAAAACAAGCAATGGCTG<br>AATTAATATCAAGATGTACTTTGCCAGTAAATGCTACGCTTACT<br>ATTCTAGAAGTTGCTAAATCTTCACCAGTATCATTTAGGCTATT<br>TGACGTTTCAAATACTAATAGTAAAGACCCATTTGTTCAAAATC<br>CTCAAGTAGGTTGCTATTATATAGCAAATTCTACGGATGCATAT<br>CTCTGCTCTACAGGTCGGGCATTTCTCAAATTTGGAACTGTTAA<br>TCCACTTCATATTAGATATGTGGAAGGTACACTTCCTTTAAAAT<br>TATGCTTAGAAGATGTTTATTATCTCACGGCATTACCTTGGACA<br>AAACCAGATGGCTGCATTCGTTATCCAATTACAGTAAAAATTAA |

TABLE 2-continued

Mesophilic Ago Nucleic Acid Sequences

| SEQ ID NO | Ago/Genus Species | Nucleic Acid Sequence |
|---|---|---|
| | | CGATAGGCGCCTAGGGGAAGACGCAAGCGAGTACGATGAAGACG |
| | | CACTTCGTTTTGAATTATTTGAAAGTTTAGAATCTGAAGATGAT |
| | | TTTGACGAAATGACGGATAGTGATTTCAACCAAGAGGAAACAAT |
| | | GGTATGA |
| 19 | 04 | TTGAAGCTCAACCATTTTCCCCTGAACCCTGATCTGCCGCTCTA |
| | *Deinococcus* sp. | CATCACGGAATATGCTCACCGCAACCCCCGCGCCCTGCTGGGCT |
| | YIM 77859 | TTGTGCGCGGGCAGGGCTTTTGGGCTCAGCAGGTGGGCGAACAG |
| | | GTTCAGGTGTATCACGGCCGACCTCAGCCCACGTTTCGCGGCGT |
| | | CCAAGTCATTTCGCACACGCGGCTTGACCCCGACCACCCGGCTT |
| | | TCGACCAAGGGGTGTTGTCGCTGATTCGGCAGGCGCTTGTGCGA |
| | | GCGGGATATGTGCTGACGTACCGGGAACGAATGGCCATCCATCC |
| | | AAGGCTAGAACGGGTGGTCCTGCGCCCGCCCGACCGCCACCCGG |
| | | CAGAACTCACTGTCCACGCCCATCTCCGTTGGGAATGGGAGCTG |
| | | GAACGGCATTCCGGACAACGCTGGCTGGTGCTGCGGCCGGGGCG |
| | | CCGTCATCTGTCTGCGCTGCCCTGGCCAGCCGAGGCGGTCCAGA |
| | | TGTGGAGCGCAGCCTTGCCCGCCACCTGCCAAAAGCTTCATGCT |
| | | CTGTGTCTCGACCGAGGCCAGCAGATGGCGCTTTTGCGCCAAGA |
| | | GGACGGCTGGCACTTTGCCAACCCCGGAGCGGCGACCCAGGGCC |
| | | GCTGGCATCTTAGCTTTTCTCCACAAGCGCTGCATGAGCTGGGC |
| | | CTGGCCCAGGCCGCCCACCACGCCGCCGCGTTCCGCTGGGACGA |
| | | GGTGCAGCGGCTCGTGCAGCTCACAGACCTCTGGAAACCCTTTG |
| | | TGACCTCACTGGAACCGCTGGAGGTGGCTGCGCCCATCATTGCG |
| | | GGGAAGAGGCTGCGCTTTGGGCGTGGCCTGGGGCGTGACGTGAC |
| | | CGAGGTTCACAAGCGGGGAATTCTGGAACCGCCGCCCCTTCCCG |
| | | TCCGACTGGCGGTGGTTTCACCCCACCTTCCCGATGAGCACGCC |
| | | AACGCCCAACTGCGGCGCGAGCTGCTGGCCCACCTGCTGCCACG |
| | | TCACCAGGTGCTGCGTTCTGCTGAATCGCGGCAGGGGCTCCACG |
| | | AACACCTGCGGCGTCAGGACCAGGACGACACCCTGTATACCTTT |
| | | TGGAGTGGCGGCGAGTACCGTAAACTGGGCCTCCCGCCTTTTGA |
| | | TCTGGCGCGGGGCCTTCACACCTACGATCCCGCCAGCGGTCAGC |
| | | TGCAGCAGCCCGCCGCACTGGCACCCGCACCCGCGCAGGCCACC |
| | | CAAGCTGGCCGCCAACTGATCGCGCTGGTGGTCCTGCCCGACGA |
| | | CCTCACCCGCAGCGTGCGCGACACCCTGTTTCAGCAGCTCCAGC |
| | | AGCTTGGTCTCCGGTGCCTTTTTTCCGTAAGCCGCACACTCCTC |
| | | CACCGGCCGCGCACCGAGTACATGGCCTGGGTCAATATGGCGGT |
| | | CAAGCTGGCGCGCACCGCCGGCGCGGTGCCCTGGGATCTGGCCG |
| | | ACCTCCCGGGCGTCACCGAGCAGACTTTCTTTGTGGGGGTGGAT |
| | | TTGGGGCACGATCACACCCACCAACAGAGCCTGCCCGCCTTTAC |
| | | CCTCCACGACCACCGGGGCCGACCCCTGCAGAGCTGGACTCCGC |
| | | CTCGCCGCACCAACAACGAACGGCTCAGCCTGGCGGAGCTGAAA |
| | | AAAGGGTTGCACCGCCTGTTGGCCCGCCGCTCAGTGGATCAGGT |
| | | GATCGTGCACCGCGACGGCCGCTTTTTGGCGGGTGAGGTGGATG |
| | | ATTTCACCCTTGCGCTGCACGACCTGGGCATTCCCCAGTTTTCG |
| | | CTGCTGGCCATCAAGAAAAGCAACCACAGTGTGGCCGTGCAGGC |
| | | AGAAGAGGGCAGCGTATTGTCTCTGGATGAGCGGCGCTGCCTGC |
| | | TGGTCACCAACACCCAGGCGGCCCTGCCCCGACCCACGGAGCTT |
| | | GAGCTTGTTCACAGTGACCGCCTCAGCCTAGCGACACTCACCGA |
| | | GCAGGTGTTTTGGCTCACCCGCGTGTTTATGAATAACGCCCAGC |
| | | ACGCCGGAAGTGACCCGGCCACCATCGAGTGGGCCAATGGAATC |
| | | GCGCGCACAGGGCAGCGCGTGCCCCTCGCCGGTTGGAGGCTCTG |
| | | A |
| 20 | 37 | ATGAATAATGTTATGCAAGAATTTCCAGTTGCTTCATTTCCAAC |
| | *Chroococcidiopsis* | TTTTTTAAGTGAAATTTCACTTCTAGATATTACTCCGAAAAATT |
| | *thermalis* | TCATTTGTTTTCGATTAACTCCAGAAATCGAACGCAAAACTGGT |
| | | AATAGCTTTAGTTGGCGATTCAGTCAAAAATTTCCTGATGCAGT |
| | | TGTTATTTGGCACAATAAATTTTTCTGGGTTTTAGCCAAACCCA |
| | | ATCGACCAATGCCAAGCCAAGAACAGTGGCGCGAGAAACTGCTA |
| | | GAAATTTGCGAAGAATTAAAAAAAGATATTGGCGATCGCACTTA |
| | | TGCAATACAATGGGTAAGCCAGCCACAGATTACACCTGAGATTC |
| | | TTTCACAGTTAGCAGTGAGAGTATTAAAAATAAATTGCCGTTTT |
| | | TCATCTCCATCTGTAATATCAGTAAATCAAGTAGAAGTCAAACG |
| | | AGAGATTGATTTTTGGGCAGAAACGATTGAAATTCAAACTCAGA |
| | | TTCAGCCAGCTTTGACAATTACCGTCCATAGTAGTTTCTTCTAT |
| | | CAAAGGCATCTAGAAGAATTTTACAATAATCATCCCTATCGGCA |
| | | GAATCCAGAGCAACTGTTAATTGGCTTAAAAGTACGAGATATCG |
| | | AACGTAATAGCTTTGCAACAATAACTGATATTGTAGGTACTATT |
| | | GCCGACCACAGACAAAAACTACTTGAGGATGCAACTGGCGCAAT |
| | | TAGTAAACAAGCATTGATAGAAGCACCGGAAGAACAGCCAGTCG |
| | | TTGCCGTACAGTTTGGTAAAAATCAACAACCTTTTTATTATGCA |
| | | ATGGCAGCTTTACGTCCTTGCATAACAGCGGAAACTGCTAGAAA |
| | | ATTCGATGTAGATTATGGAAAATTACTGTCTGCAACTAAAATTC |
| | | CTTATTTAGAGCGAAAAGAACTTTTAGCATTGTACAAAAAAGAA |

TABLE 2-continued

| Mesophilic Ago Nucleic Acid Sequences | | |
|---|---|---|
| SEQ ID NO | Ago/Genus Species | Nucleic Acid Sequence |
| | | GCTGGACAAAGTTTAGCTACTTATGGATTTCAACTGAAGATTAG<br>TATAAATAGCCGCAGACATCCTGAATTATTCTTCTCTCCGTCAG<br>TTAAATTATCAGAAACAAAACTGGTGTTTGGAAAAAATCAAATT<br>GGCGTTCAAGGTCAAATTTTATCTGGTTTATCTAAAGGTGGCGT<br>GTATCGCCGTCATGAAGATTTTAGCGATTTGTCAAGACCAATTC<br>GGATTGCTGCATTGAAACTTTGCGATTATCCAGCAAATTCTTTT<br>CTGCAAGAAACGCGACAGAGACTCAAACGCTATGGTTTTGAAAC<br>TCTTCTTCCTGTTGAAAATAAAAAGACATTATTGGTAGATGATT<br>TATCTGGAGTTGAAGCGAGAGCCAAAGCTGAAGAAGCTGTCGAT<br>GAATTGATGGTAAATCATCCCGATATAGTTTTGACATTTTTACC<br>AACTAGCGATCGCCACAGCGATAATACAGAAGGAGGCAGCTTAT<br>ATTCTTGGATTTACTCACGCTTGCTCAGACGTGGAATTGCCAGC<br>CAAGTTATTTACGAAGATACTTTGAAAAGCGTTGAAGCTAAATA<br>TTTATTAAATCAGGTGATTCCAGGTATTCTAGCCAAGCTAGGCA<br>ACTTGCCTTTTGTGTTAGCTGAACCATTAGGAATTGCCGACTAT<br>TTCATCGGCTTAGATATTTCCAGAAGCGCCAAGAAGAGAGGTTC<br>TGGAACTATGAATGCTTGCGCTAGCGTGCGTCTATACGGTCGCA<br>AAGGAGAATTTATTCGCTATCGATTAGAAGATGCTTTAATTGAA<br>GGGGAAGAAATTCCCCAAAGAATTTTAGAAAGCTTTCTTCCCGC<br>AGCTCAACTGAAAGGTAAAGTCGTACTAATTTACCGCGATGGAC<br>GCTTTTGTGGTGATGAAGTGCAGCATTTAAAAGAAAGAGCGAAA<br>GCAATTGGTTCGGAGTTTATTTTAGTCGAGTGCTATAAATCTGG<br>GATTCCTCGGCTCTACAACTGGGAAGAAGAAGTTATTAAAGCAC<br>CAACGCTAGGATTAGCACTGCGCTTATCGGCGCGGGAAGTTATT<br>TTAGTCACGACAGAACTAAATICGGCGAAAATCGGITTGCCTCT<br>GCCTCTACGCTTGAGAATTCATGAAGCAGGACATCAGGTATCGT<br>TAGAAAGTTTAGTAGAGGCGACTTTGAAACTTACCTTACTACAT<br>CATGGTTCGCTGAACGAGCCGCGCTTACCAATACCGCTTTTTGG<br>TTCTGACCGTATGGCTTATCGACGGTTGCAAGGCATTTATCCAG<br>GTTTGCTAGAAGGCGATCGCCAATTTTGGTTATAA |
| 21 | 27<br>*Thermosynechococcus elongates* | ATGCCCACCCAATTCCAAGAAGTTGAAGTTATACTCAATCGTTT<br>TTTTGTAAAAAAATTGAGTCGACCTGATCTTACATTTCATGAAT<br>ACCAATGCCAATTTACTCAAGTGCCAGAACAAGGTAGCGAGCAA<br>AAAGCTATTTCCAGTGTTTGCTACAAACTAGGAGTCACTGCTGT<br>TCGACTAGGGAGCTGCATTATTACAAGGGAGCCTATTGACCCTG<br>AGAGAATGCGAACTAAGGATTGGCAGTTACAGCTAATAGGATGT<br>AGAGAACTGAGCTGTCAAAATTATCGTGAAAGGCAGGCTCTGGA<br>AACCTTTGAAAGAAAAATTCTAGAGGAAAAGTTAAAAGAAACAT<br>TTAAGAAAACTATAATTGAAAAAGACTATGAATTAGGGTTGATT<br>TGGTGGATTTCTGGCGAAGAAGGGTTAGAAAAAACAGGTCATGG<br>CTGGGAAGTACATAGAGGCAGACAAATTGATCTCAAAATAGAAA<br>CAGATGAAAAATTATACTTAGAAATTGATATTCATCATCGATTT<br>TATACTCCATTCAAACTTGAGTGGTGGCTCAGTGAATATCCTAA<br>TATCCAAATCAAGTACGTGAGGAATACCTACAAAGATAAGAAAA<br>AGTGGATCCTTGAAAATTTTGCGGACAAAAGTCCAAATGAAATA<br>CAAATAGAAGCCCTAGGAATAAGCCTAGCAGAGTATCACCGTCA<br>AGAGGGAGCAACTCAACAAGAAATAGATGAGTCCCGAGTTGTAA<br>TTGTTAAGAAAATCAGCGACTACAAGGCTAAGCCAGTATATCAT<br>TTGTCTCAAAGACTATCACCAATTCTCACAATGGAAACGTTAGC<br>GCAAATTGCTGAACAAGGAAGAGAAAAAAAGGAAATTCAAGGTG<br>TTTTTGACTACATCAGGAAAAACATTGGTACACGTTTGCAAGAA<br>TCACAAAAAAATAGCTCAGGTCATTTTCAAAAACGTTTATAATCT<br>CAGTAGTCAGCCAGAGATAATGAAAGTTAATGGTTTTGTCATGC<br>CTCGTGCAAAACTATTAGCTCGAAACAATAAAGAAGTCAATCAA<br>ACAGCTAGAATTAAATCCTTTGGCTGTGCCAAGATTGGCGAAAC<br>AAAATTCGGCTGCCTAAATTTATTTGATAATAAACCCGAGTATC<br>CAGAGGAAGTACACAAATGTTTACTGGCAATAGCAAGAAGTAGT<br>GGGGTACAGATAAAAATAGACTCCTACTTTACAGGAAGTGACTA<br>TCCAAAAGATGATTTAGCTCAACAACGATTTTGGCAACAATGGG<br>CTGCTCAAGGAATTAAAACTGTTTTAGTAGTGATGCCTTGGTCC<br>CCCCATGAGGAGAAAACAAGGCTACGAATTCAGGCATTAAAGGC<br>GGGAATCGCTACTCAGTTCATGATACCCACACCCCAGGATAATC<br>CCTACAAAGCTCTCAATGTTGCCTTGGGACTGTTGTGTAAAGCT<br>AAGTGGCAGCCTGTCTATCTAAAACCATTAGATGATCCTCAGGC<br>TGCTGACTTAATTATCGGTTTTGACACCAGTACAAACCGAAGGC<br>TGTACTATGGTACGTCTGCTTTTGCAATTTTAGCCAATGGTCAA<br>AGCTTGGGTTGGGAGTTGCCAGATATACAACGGGGCGAAACTTT<br>CTCTGGTCAATCCATTTGGCAAGTTGTGTCTAAGCTAGTGCTGA<br>AATTCCAAGACAACTATGATTCTTACCCTAAGAAGATCCTACTG<br>ATGCGGGACGGGCTTGTTCAAGACGGGGAGTTTGAACAAACAAT<br>CAGAGAACTAACTCACCAGGGTATCGATGTCGATATCTTAAGTG<br>TCCGTAAGAGTGGCTCGGGGAGGATGGGACGTGAATTGACTTCA<br>GGCAATACCGCAATAACCTATGATGATGCTGAAGTGGGCACTGT |

TABLE 2-continued

| Mesophilic Ago Nucleic Acid Sequences | | |
|---|---|---|
| SEQ ID NO | Ago/Genus Species | Nucleic Acid Sequence |
| | | AATTTTTATTCTGCAACTGACTCATTTATATTACAAACCACTG AGGTCATCAAGACGAAAACTGGCCCCCTTGGTAGTGCTAGACCT CTGCGGGTTGTGCGTCACTACGGCAATACACCTTTAGAGCTACT GGCTTTGCAGACCTATCACTTGACTCAATTGCATCCTGCCAGCG GATTTCGCTCCTGCCGGCTGCCTTGGGTACTGCACTTGGCTGAT CGGAGTAGTAAGGAGTTTCAGCGGATAGGTCAGATCAGCCTTTT GCAGAATGTTGATCGAGAAAAGTTAATTGCTGTTTGA |

In some embodiments, the Ago is codon optimized for expression in particular cells, such as eukaryotic cells. In some embodiments, a polynucleotide encoding the Ago is codon optimized for expression in particular cells, such as eukaryotic cells. This type of optimization can entail the mutation of foreign-derived (e.g., recombinant) nucleic acids to mimic the codon preferences of the intended host organism or cell while encoding the same protein.

The Ago may bind and/or modify (e.g., cleave, methylate, demethylate, etc.) a target nucleic acid and/or a polypeptide associated with target nucleic acid. As described in further detail below, in some cases, a subject nuclease has enzymatic activity that modifies target nucleic acid. Enzymatic activity may refer to nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity. In other cases, a subject Ago may have enzymatic activity that modifies a polypeptide associated with a target nucleic acid.

In some embodiments, in addition to or as a substitute for nucleic acid-cleaving activity, the compositions, fusion polypeptides, methods, and systems described herein have a "pasting" function. Accordingly, In some embodiments, the compositions, fusion polypeptides, methods, and systems can be used to insert a nucleic acid into a target sequence in addition to or instead of cleaving the target nucleic acid. Such exemplary nucleic acid-insertion activities include, but are not limited to, integrase, flippase, transposase, and recombinase activity. Thus, exemplary polypeptides having such function (nucleic acid-insertion polypeptides) include integrases, recombinases, and flippases. These nucleic acid-insertion polypeptides can, for example, insert a nucleic acid sequence at a site that has been cleaved by a polypeptide of the present disclosure.

In some cases, the Ago system comprises a nuclear localization sequence (NLS). In some embodiments, the nuclear localization sequence is from SV40. In some embodiments, the NLS is from at least one of: SV40, nucleoplasmin, importin alpha, C-myc, EGL-13, TUS, BORG, hnRNPA1, Mata2, or PY-NLS. In some embodiments, the NLS is on a C-terminus or an N-terminus of a nuclease polypeptide or nucleic acid. In some cases, the Ago system may contain from about 1 to about 10 NLS sequences. In some embodiments, the Ago system contains 1, 2, 3, 4, 5, 6, 7, 8, 9, or up to 10 NLS sequences. The Ago system may contain a SV40 and Nucleoplasmin NLS sequence. In some cases, an NLS is from Simian Vacuolating Virus 40.

In some cases, the system comprises an Ago polypeptide or Ago polypeptide fragment, and, optionally, an Ago associated protein, that performs a genomic alternation with favorable thermodynamics. In some embodiments, the genomic alteration is exothermic. In some embodiments, the genomic alteration is endothermic. In some cases, a genomic alteration utilizing the disclosed system is energetically favorable over alternate gene editing systems. In some embodiments, the present disclosure provides an ex vivo system comprising an Ago polypeptide or fragment and a guide nucleic acid, wherein the guide nucleic acid binds to a predetermined gene or to a nucleic acid sequence adjacent to the predetermined gene, wherein the Ago polypeptide or fragment thereof is capable of introducing a double strand break in the predetermined gene, wherein the Ago polypeptide or fragment comprises a nucleic acid unwinding sequence that lowers the energetic requirement for introducing the double strand break in comparison to introducing a double strand break with a comparable Ago polypeptide or fragment without the nucleic acid unwinding sequence, and the ex vivo system introduces the double strand break at a range of temperatures from 19° C. to 40° C. Without wishing to be bound by theory, the nucleic acid unwinding sequence can overcome the energetic barrier that prevents Argonaute proteins without such sequences from inducing single- or double-stranded nucleic acid breaks because the nucleic acid unwinding polypeptide exposes a nucleic acid sequence such that the RHDC polypeptide can cleave in the exposed region. The Ago polypeptide or Ago polypeptide fragment system can be more thermodynamically favorable, as measured by a biochemical system, for example by providing a finite amount of ATP into the reaction and measuring an amount of gene editing before, during, and after the genomic alteration has occurred. In some cases, the disclosed editing system utilizing the Ago polypeptide or Ago polypeptide fragment can reduce an energetic requirement by about 1%, 2%, 3%, 4%, 5%, 6%, 7%, 8%, 9%, 10%, 15%, 20%, 25%, 40%, 50%, or up to about 60% as compared to a system that does not employ the Ago polypeptide or Ago polypeptide fragment. In some cases, the disclosed editing system utilizing the Ago polypeptide or Ago polypeptide fragment can reduce an immune response to the Ago polypeptide or Ago polypeptide fragment by about 1%, 2%, 3%, 4%, 5%, 6%, 7%, 8%, 9%, 10%, 15%, 20%, 25%, 40%, 50%, or up to about 60% as compared to a system that does not employ the disclosed Ago polypeptide or Ago polypeptide fragment. In some cases, the Ago polypeptide or Ago polypeptide fragment can be harvested from bacteria that are endogenously present in the human body to prevent eliciting an immune response.

In some cases, the Ago system comprises a nucleic acid unwinding polypeptide or a polynucleic acid encoding the same. For example, the system can comprise the Ago and the nucleic acid unwinding polypeptide individually or as a fused polypeptide.

(a) Clostridia Argonautes

In some cases, the Ago (or variant or functional fragment thereof) does not naturally occur in a bacterium (e.g., a bacterium of class Clostridia, or genus *Clostridium*); rather it is e altered or engineered based on a naturally-occurring polypeptide or protein of that bacterium (e.g., a bacterium of class Clostridia, or genus *Clostridium*).

In some cases, the Ago (or a functional fragment thereof) is derived from phylum Firmicutes.

In some embodiments, the Ago (or variant or functional fragment thereof) described herein, is derived from a bacterium of the class Clostridia. In some cases, the Ago does not naturally occur in a Clostridia bacterium; rather it is altered or engineered based on a naturally-occurring polypeptide or protein of that Clostridia bacterium.

In some embodiments, the Ago (or variant or functional fragment thereof) is derived from the class Clostridia.

In some embodiments, the Ago (or variant or functional fragment thereof) is derived from the order: Candidatus Comantemales, Clostridiales, Halanaerobiales, Natranaerobiales, or Thermoanaerobacterales, or Negativicutes.

In some embodiments, the Ago (or variant or functional fragment thereof) is derived from the family: Caldicoprobacteraceae, Christensenellaceae, Clostridiaceae, Defluviitaleaceae, Eubacteriaceae, Graciibacteraceae, Heiiobacteriaceae, Lachnospiraceae, Oscillospiraceae, Peptococcaceae, Peptostreptococcaceae, Ruminococcaceae, or Syntrophomonadaceae.

In some embodiments, the Ago (or variant or functional fragment thereof) is derived from the family: Halanaerobiaceae or Halobacteroidaceae.

In some embodiments, the Ago (or variant or functional fragment thereof) is derived from the family: Natranaerobiaceae.

In some embodiments, the Ago (or variant or functional fragment thereof) is derived from the Family: Thermoanaerobacteraceae or Thermodesulfobiaceae.

In some embodiments, the Ago (or variant or functional fragment thereof) is derived from the genus: *Clostridium, Acetanaerobacterium, Acetivibrio, Acidaminobacter, Alkaliphilus, Anaerobacter, Anaerostipes, Anaerotruncus, Anoxynatronum, Bryantella, Butyricicoccus, Caldanaerocella, Caldisalinibacter, Caloramator, Caloranaerobacter, Caminicella*, Candidatus Arthromitus, *Cellulosibacter, Coprobacillus, Crassaminicella, Dorea, Ethanologenbacterium, Faecalibacterium, Garciella, Guggenheimella, Hespellia, Linmingia, Natronincola, Oxobacter, Parasporobacterium, Sarcina, Soehngenia, Sporobacter, Subdoligranulum, Tepidibacter, Tepidimicrobium, Thermobrachium, Thermohalobacter*, or *Tindallia*.

In some cases, the Ago (or variant or functional fragment thereof) is derived from the genus *Clostridium*.

In some embodiments, the Ago (or variant or functional fragment thereof) is derived from a species of *Anaerococcus prevotii, Butyrivibrio proteoclasticus*, Clostridiales genomo sp., *Clostridium acidurici, Clostridium cellulolyticum, Clostridium difficile, Clostridium lentocellum, Clostridium leptum, Clostridium phytofermentans, Clostridium sticklandii, Clostridium symbiosum, Clostridium thermocellum, Ethanoligenens harbinense, Eubacterium rectale, Filifactor alocis, Finegoldia magna, Peptostreptococcus anaerobius, Roseburia hominis, Ruminococcus albus*, Candidatus Arthromitus, *Clostridium acetobutylicum, Clostridium botulinum, Clostridium perfringens*, or *Clostridium tetani*.

In some embodiments, the Ago (or variant or functional fragment thereof) is derived from a species of *Clostridium absonum, Clostridium aceticum, Clostridium acetireducens, Clostridium acetobutylicum, Clostridium acidisoli, Clostridium aciditolerans, Clostridium acidurici, Clostridium aerotolerans, Clostridium aestuarii, Clostridium akagii, Clostridium aldenense, Clostridium aldrichii, Clostridium algidicarnis, Clostridium algidixylanolyticum, Clostridium algifaecis, Clostridium algoriphilum, Clostridium alkalicellulosi, Clostridium amazonense, Clostridium aminophilum, Clostridium aminovalericum, Clostridium amygdalinum, Clostridium amylolyticum, Clostridium arbusti, Clostridium arcticum, Clostridium argentinense, Clostridium asparagiforme, Clostridium aurantibutyricum, Clostridium baratii, Clostridium barkeri, Clostridium bartlettii, Clostridium beijerinckii, Clostridium bifermentans, Clostridium bolteae, Clostridium bornimense, Clostridium botulinum, Clostridium bowmanii, Clostridium bryantii, Clostridium budayi, Clostridium butyricum, Clostridium cadaveris, Clostridium caenicola, Clostridium caminithermale, Clostridium carboxidivorans, Clostridium carnis, Clostridium cavendishii, Clostridium celatum, Clostridium celerecrescens, Clostridium cellobioparum, Clostridium cellulofermentans, Clostridium cellulolyticum, Clostridium cellulosi, Clostridium cellulovorans, Clostridium chartatabidum, Clostridium chauvoei, Clostridium chromiireducens, Clostridium citroniae, Clostridium clariflavum, Clostridium clostridioforme, Clostridium coccoides, Clostridium cochlearium, Clostridium cocleatum, Clostridium colicanis, Clostridium colinum, Clostridium collagenovorans, Clostridium combesii, Clostridium cylindrosporum, Clostridium difficile, Clostridium diolis, Clostridium disporicum, Clostridium drakei, Clostridium durum, Clostridium estertheticum, Clostridium estertheticum* sub sp. *Estertheticum, Clostridium estertheticum* sub sp. *Laramiense, Clostridium fallax, Clostridium felsineum, Clostridium fervidum, Clostridium fimetarium, Clostridium formicaceticum, Clostridium frigidicarnis, Clostridium frigoris, Clostridium ganghwense, Clostridium gasigenes, Clostridium ghonii, Clostridium glycolicum, Clostridium glycyrrhizinilyticum, Clostridium grantii, Clostridium guangxiense, Clostridium haemolyticum, Clostridium halophilum, Clostridium hastiforme, Clostridium hathewayi, Clostridium herbivorans, Clostridium hiranonis, Clostridium histolyticum, Clostridium homopropionicum, Clostridium huakuii, Clostridium hungatei, Clostridium hydrogeniformans, Clostridium hydroxybenzoicum, Clostridium hylemonae, Clostridium indolis, Clostridium innocuum, Clostridium intestinale, Clostridium irregulare, Clostridium isatidis, Clostridium jeddahense, Clostridium jejuense, Clostridium josui, Clostridium kluyveri, Clostridium lactatifermentans, Clostridium lacusfryxellense, Clostridium laramiense, Clostridium lavalense, Clostridium lentocellum, Clostridium lentoputrescens, Clostridium leptum, Clostridium limosum, Clostridium liquoris, Clostridium litorale, Clostridium lituseburense, Clostridium ljungdahlii, Clostridium lortetii, Clostridium lundense, Clostridium luticellarii, Clostridium magnum, Clostridium malenominatum, Clostridium mangenotii, Clostridium maximum, Clostridium mayombei, Clostridium methoxybenzovorans, Clostridium methylpentosum, Clostridium moniliforme, Clostridium neonatale, Clostridium neopropionicum, Clostridium neuense, Clostridium nexile, Clostridium nitritogenes, Clostridium nitrophenolicum, Clostridium novyi, Clostridium oceanicum, Clostridium orbiscindens, Clostridium oroticum, Clostridium oryzae, Clostridium*

*oxalicum, Clostridium pabulibutyricum, Clostridium papyrosolvens, Clostridium paradoxum, Clostridium paraperfringens, Clostridium paraputrificum, Clostridium pascui, Clostridium pasteurianum, Clostridium peptidivorans, Clostridium perenne, Clostridium perfringens, Clostridium pfennigii, Clostridium phytofermentans, Clostridium piliforme, Clostridium polyendosporum, Clostridium polysaccharolyticum, Clostridium populeti, Clostridium propionicum, Clostridium proteoclasticum, Clostridium proteolyticum, Clostridium psychrophilum, Clostridium punense, Clostridium puniceum, Clostridium purinilyticum, Clostridium putrefaciens, Clostridium putrificum, Clostridium quercicolum, Clostridium quinii, Clostridium ramosum, Clostridium rectum, Clostridium roseum, Clostridium saccharobutylicum, Clostridium saccharogumia, Clostridium saccharolyticum, Clostridium saccharoperbutylacetonicum, Clostridium sardiniense, Clostridium sartagoforme, Clostridium saudiense, Clostridium scatologenes, Clostridium schirmacherense, Clostridium scindens, Clostridium senegalense, Clostridium septicum, Clostridium sordellii, Clostridium sphenoides, Clostridium spiroforme, Clostridium sporogenes, Clostridium sporosphaeroides, Clostridium stercorarium, Clostridium stercorarium* sub sp. *leptospartum, Clostridium stercorarium* sub sp. *stercorarium, Clostridium stercorarium* sub sp. *thermolacticum, Clostridium sticklandii, Clostridium straminisolvens, Clostridium subterminale, Clostridium sufflavum, Clostridium sulfidigenes, Clostridium swellfunianum, Clostridium symbiosum, Clostridium tarantellae, Clostridium tagluense, Clostridium tepidiprofundi, Clostridium tepidum, Clostridium termitidis, Clostridium tertium, Clostridium tetani, Clostridium tetanomorphum, Clostridium thermaceticum, Clostridium thermautotrophicum, Clostridium thermoalcaliphilum, Clostridium thermobutyricum, Clostridium thermocellum, Clostridium thermocopriae, Clostridium thermohydrosulfuricum, Clostridium thermolacticum, Clostridium thermopalmarium, Clostridium thermopapyrolyticum, Clostridium thermosaccharolyticum, Clostridium thermosuccinogenes, Clostridium thermosulfurigenes, Clostridium thiosulfatireducens, Clostridium tyrobutyricum, Clostridium uliginosum, Clostridium ultunense, Clostridium ventriculi, Clostridium villosum, Clostridium vincentii, Clostridium viride, Clostridium vulturis*, and *Clostridium xylanolyticum*, and *Clostridium xylanovorans.*

In some embodiments, the Ago or variant or functional fragment thereof is derived from a species of *Clostridium perfringens, Clostridium butyricum*, or *Clostridium sardiniense.*

In some embodiments, the Ago or variant or functional fragment thereof is derived from a species of Clostridiales bacterium NK3B98, *Geobacillus* sp. FW23, [*Clostridium*] *citroniae* WAL-19142, *Clostridium disporicum, Burkholderia vietnamiensis, Bacteroides fragilis* str. 3397 T14, *Leptolyngbya* sp. 'hensonii', *Acidobacterium capsulatum* ATCC 51196, *Clostridium perfringens* WAL-14572, *Geobacillus kaustophilus* GBlys, *Clostridium saudiense, Methylomicrobium buryatense* 5G, *Enterobacter kobei*, or *Deinococcus* sp. RL.

In some embodiments, the Ago or variant or functional fragment thereof is derived from a species *C. absonum, C. aerotolerans, C. aminobutyricum, C. caliptrosporurn, C. celatum, C. colinum, C. corinoforum, C. durum, C. favososporum, C. felsineum, C. jilarnentosum, C. formicoaceticum, C. glycolicum, C. halophilum, C. hastiforme, C. hornopropionicurn, C. intestinalis, C. kainantoi, C. lentocellum, C. litorale, C. longisporum, C. magnum, C. neopropionicum, C. oxalicum, C. pfennigii, C. polysaccharolyticum, C. propionicum, C. quinii, C. rectum, C. tetani, C. thermoamylolyticum*, and *C. xylanolyticum.*

In some embodiments the clostridia Ago has an amino acid sequence at least 80%, 85%, 90%, 95%, 96%, 97%, 98%, 99% or 100% identical to an amino acid sequence of SEQ ID NOs: 1-3. In some embodiments the clostridia Ago has an amino acid sequence at least 80%, 85%, 90%, 95%, 96%, 97%, 98%, 99% or 100% identical to an amino acid sequence of SEQ ID NOs: 134-136. In some embodiments the clostridia Ago has an amino acid sequence encoded by a nucleic acid at least 80%, 85%, 90%, 95%, 96%, 97%, 98%, 99% or 100% identical to an amino acid sequence of SEQ ID NOs: 11-14. In some embodiments the clostridia Ago has an amino acid sequence encoded by a nucleic acid at least 80%, 85%, 90%, 95%, 96%, 97%, 98%, 99% or 100% identical to an amino acid sequence of SEQ ID NOs: 137-139

In some embodiments, the Ago comprises an amino acid sequence 100% identical to SEQ ID NO: 1. In some embodiments, the Ago comprises an amino acid sequence 100% identical to SEQ ID NO: 1, except there is a non-lysine amino acid residue at one or more of (e.g., 1, 2, 3, 4, or 5) positions 479, 522, 563, 581, 642 of SEQ ID NO: 1.

(b) Clostridia Argonaute 69 Homologues

In some embodiments, the Argonaute is a homologue of Ago69 (SEQ ID NO: 1). In some embodiments, the Ago69 homologue comprises an amino acid sequence of an Ago69 homologue described in Table 14. In some embodiments, the Ago69 homologue comprises an amino acid sequence with at least 80%, 85%, 90%, 91%, 92%, 93%, 94%, 95%, 96%, 97%, 98%, or 100% sequence identity to an Ago69 homologue described in Table 14. In some embodiments, the Ago69 homologue comprises a nucleic acid sequence of an Ago69 homologue described in Table 15. In some embodiments, the Ago69 homologue comprises a nucleic acid sequence with at least 80%, 85%, 90%, 91%, 92%, 93%, 94%, 95%, 96%, 97%, 98%, or 100% sequence identity to an Ago69 homologue described in Table 15. In some embodiments, the Ago69 homologue is HG2, HG4, or HG5.

In some embodiments, the Ago69 homologue comprises an amino acid sequence with at least 80%, 85%, 90%, 91%, 92%, 93%, 94%, 95%, 96%, 97%, 98%, or 100% sequence identity to an Ago69 homologue HG2. HG2 has 78.3% pairwise sequence identity with Ago69. In some embodiments, the Ago69 homologue comprises an amino acid sequence with at least 80%, 85%, 90%, 91%, 92%, 93%, 94%, 95%, 96%, 97%, 98%, or 100% sequence identity to SEQ ID NO: 134. In some embodiments, the Ago69 homologue comprises a nucleic acid sequence with at least 80%, 85%, 90%, 91%, 92%, 93%, 94%, 95%, 96%, 97%, 98%, or 100% sequence identity to SEQ ID NO: 137.

In some embodiments, the Ago69 homologue comprises an amino acid sequence with at least 80%, 85%, 90%, 91%, 92%, 93%, 94%, 95%, 96%, 97%, 98%, or 100% sequence identity to an Ago69 homologue HG4. HG4 has 39.9% pairwise sequence identity with Ago69. In some embodiments, the Ago69 homologue comprises an amino acid sequence with at least 80%, 85%, 90%, 91%, 92%, 93%, 94%, 95%, 96%, 97%, 98%, or 100% sequence identity to SEQ ID NO: 135. In some embodiments, the Ago69 homologue comprises a nucleic acid sequence with at least 80%, 85%, 90%, 91%, 92%, 93%, 94%, 95%, 96%, 97%, 98%, or 100% sequence identity to SEQ ID NO: 138.

In some embodiments, the Ago69 homologue comprises an amino acid sequence with at least 80%, 85%, 90%, 91%, 92%, 93%, 94%, 95%, 96%, 97%, 98%, or 100% sequence identity to an Ago69 homologue HG5. HG5 has 38.5% pairwise sequence identity with Ago69. In some embodiments, the Ago69 homologue comprises an amino acid sequence with at least 80%, 85%, 90%, 91%, 92%, 93%, 94%, 95%, 96%, 97%, 98%, or 100% sequence identity to SEQ ID NO: 136. In some embodiments, the Ago69 homologue comprises a nucleic acid sequence with at least 80%, 85%, 90%, 91%, 92%, 93%, 94%, 95%, 96%, 97%, 98%, or 100% sequence identity to SEQ ID NO: 139.

TABLE 14

Amino Acid Sequence of Exemplary A2o69 Homologues

| Ago69 Homologue | Amino Acid Sequence | SEQ ID NO |
|---|---|---|
| HG2<br>*Clostridium butyricum*<br>Underlined: PIWI Domain | MNNLTFEAFEGIGQLNELNFYKYRLIGKGQI<br>DNVHQAIWSVKYKLQANNFFKPVFVKGEILY<br>SLDELKVIPEFENVEVILDGNIILSISENTD<br>IYKDVIVFYINNALKNIKDITNYRKYITKNT<br>DEIICKSILTTNLKYQYMKSEKGFKLQRKFK<br>ISPVVFRNGKVILYLNCSSDFSTDKSIYEML<br>NDGLGVVGLQVKNKWTNANGNIFIEKVLDNT<br>ISDPGTSGKLGQSLIDYYINGNQKYRVEKFT<br>DEDKNAKVIQAKIKNKTYNYIPQALTPVITR<br>EYLSHTDKKFSKQIENVIKMDMNYRYQTLKS<br>FVEDIGVIKELNNLHFKNQYYTNFDFMGFES<br>GVLEEPVLMGANGKIKDKKQIFINGFFKNPK<br>ENVKFGVLYPEGCMENAQSIARSILDFATAG<br>KYNKQENKYISKNLMNIGFKPSECIFESYKL<br>GDITEYKATARKLKEHEKVGFVIAVIPDMNE<br>LEVENPYNPFKKVWAKLNIPSQMITLKTTEK<br>FKNIVDKSGLYYLHNIALNILGKIGGIPWII<br>KDMPGNIDCFIGLDVGTREKGIHFPACSVLF<br>DKYGKLINYYKPTIPQSGEKIAETILQEIFD<br>NVLISYKEENGEYPKNIVIHRDGFSRENIDW<br>YKEYFDKKGIKFNIIEVKKNIPVKIAKVVGS<br>NICNPIKGSYVLKNDKAFIVTTDIKDGVASP<br>NPLKIEKTYGDVEMKSILEQIYSLSQIHVGS<br>TKSLRLPITTGYADKICKAIEYIPQGVVDNR<br>LFFL | 134 |
| HG4<br>*Clostridium saragoforme*<br>Underlined: PIWI Domain | MKEFNVITEFKNGINSKSIEIYIYKMMVRDF<br>EKRHNENYDVVKELINLNNNSTIVFYEQYIA<br>SFKEIEKWGNEQYINVEKRAINLESNEKKIL<br>ERLLLKEIKNNIDNNKYKVVKDSIYINKPVY<br>NEKGIKIDRYFNLDINVESNGDIIIGFDISH<br>NFEYINTLEYEIKNNNIKIGDRVKDYFYNLT<br>YEYVGIAPFTISEENEYMGCSIVDYYENKNQ<br>SYIVNKLPKDMKAILVKNNKNSIFPYIPSRL<br>KKVCRFENLPQNVLRDFNTRVKQKTNEKMQF<br>MVDEVINIVKNSEHIDVKKKNMMCDNIGYKI<br>EDLQQPDLLFGNARAQRYPLYGLKNFGVYEN<br>KRIEIKYFIDPILAKSKMNLEKISKFCDELE<br>QFSSKLGVGLNRVKLNNIVNFKEIRMDNEDI<br>FSYEIRKIVSNYNETTIVILSEENLNKYYNI<br>IKKTFSGGNEVPTQCIGFNTLSYTEKNKDSI<br>FLNILLGVYAKSGIQPWILNEKLNSDCFIGL<br>DVSRENKVNKAGVIQVVGKDGRVLKTKVISS<br>SQSGEKIKLETLREIVFEAINSYENTYRCKP<br>KHITFHRDGINREELENLKNTMTNLGVEFDY<br>IEITKGINRRIATISEGEEWKTIMGRCYYKD<br>NSAYVCITKPYEGIGMAKPIRIRRVFGTLDI<br>EKIVEDAYKLTFMHVGAINKIRLPITTYYAD<br>LSSTYGNRDLIPTNIDTNCLYFI | 135 |
| HG5<br>*Clostridium* sp. 1-1-41A1FAA | MVGLDREFNVITEFKNELKPEDIKIFLYSMP<br>IKDINERHSENYAIVQELKKINENPNIVFNE<br>YIIASFNPIINWGKYKDIDVKPDNRNINLDN<br>HTERKILERLLLCDIKNNINNNTTWEQQNKY<br>EIRGNANPAVYLRKPIYLNDNLIIRRKLNFD<br>VNIDKKDIIIGFFLNHEFEYQKTLDEEIKCG<br>NIQKGDKVKDFYNNITYEFLEMAPFSISQEN<br>KYMRSSIIEYYLNKGQSYIISGLDKNTKAVL<br>VKNKEGSIFPYIPNRLKKICVFENLGNRQII<br>EGNKYIKMNPSQNMSESIKLAEDILKNSKYV<br>KFNKANMIVEKIGYKKDIVKRPALKFGKNES | 136 |

TABLE 14-continued

Amino Acid Sequence of Exemplary A2o69 Homologues

| Ago69 Homologue | Amino Acid Sequence | SEQ ID NO |
|---|---|---|
| | NFSAMYGLNKSGSYEQKNIKIDYFIDPKILN<br>NKRDYQIVYSFLNDIISKSKDLGVEINTDKS<br>YINLTPINIKNENEFELNVMEIIKNYNNPVL<br>VILEKENIDKYYETLKKIFGGRNSIATQFVD<br>LDTIKRCDPKIDNKRGKESIFLNILLGIYCK<br>SGIQPWVLANGLSADCYIGLDVCRENNMSTV<br>GLIQVIGKDGRVLKSKTISSHQSGEKIQINI<br>LKDIIFEAKQAYKNTYNKKLEHIVFHRDGIN<br>REDIDLLKEIINSLEIKFDYVEVTKNINRRM<br>AMLEKSDENYNHRDKENKKWITEIGMCLKKE<br>NEAYLITTNPSENMGMARPLRIKKVYGNQNM<br>DDIVKDIYKLSFMHIGSIMKSRLPITTHYAD<br>LSSIYSHRELMPKSVDNNILHFI | |

TABLE 15

Nucleic Acid Sequence of Exemplary Ago69 Homologues

| Ago69 Homo-logue | Amino Acid Sequence | SEQ ID NO |
|---|---|---|
| HG2 | TGTACAAGCTTGCCACCATGGGTCCGAAGAAGAAACG<br>CAAGGTCGAGGACCCAAAGAAGAAGCGTAAGGTTGGA<br>TCGGGTTCTATGAATAATCTGACCTTCGAGGCCTTCG<br>AGGGTATCGGACAATTGAACGAGTTAAACTTCTATAA<br>GTACCGCCTCATTGGTAAGGGCCAAATCGACAATGTC<br>CACCAGGCCATCTGGTCAGTCAAGTACAAACTTCAAG<br>CGAATAATTTCTTCAAGCCGGTTTTCGTCAAGGGCGA<br>AATTCTGTACTCACTTGACGAGCTGAAAGTCATCCCG<br>GAATTCGAGAATGTCGAGGTTATTCTTGACGGGAACA<br>TTATCCTGAGCATTAGCGAGAACACCGACATTTACAA<br>GGATGTGATCGTGTTTTATATCAATAACGCGTTGAAG<br>AACATCAAGGACATCACCAACTACCGTAAGTATATCA<br>CTAAGAACACGGATGAAATCATTTGCAAGAGTATTTT<br>AACGACGAATCTCAAGTATCAATATATGAAGTCAGAG<br>AAAGGGTTCAAGTTACAGCGCAAGTTTAAGATCTCCC<br>CGGTGGTATTCCGTAATGGGAAGGTCATCTTGTACCT<br>TAATTGCAGTAGCGACTTCAGCACAGACAAATCCATC<br>TACGAAATGTTAAATGATGGACTCGGTGTTGTGGGCC<br>TGCAAGTGAAGAATAAGTGGACTAATGCGAATGGCAA<br>TATCTTTATTGAAAAGGTGCTCGACAATACCATCTCC<br>GATCCCGGCACGAGTGGAAAGCTGGGGCAGTCCCTGA<br>TCGACTACTACATCAATGGGAATCAAAAGTACCGTGT<br>AGAGAAATTTACCGACGAGGACAAGAATGCAAAGGTT<br>ATCCAGGCCAAAATCAAGAATAAAACATACAACTACA<br>TCCCGCAAGCTCTCACCCCCGTAATTACGCGCGAGTA<br>TCTGAGTCATACCGATAAGAAGTTTAGCAAGCAAATC<br>GAGAATGTGATTAAGATGGATATGAACTACCGCTACC<br>AGACGTTGAAGTCTTTCGTTGAGGACATTGGCGTGAT<br>CAAGGAGTTAAACAATCTGCACTTTAAGAACCAATAT<br>TACACCAATTTTGACTTTATGGGGTTCGAGAGCGGGG<br>TGCTGGAAGAACCTGTCCTGATGGGTGCGAACGGAAA<br>GATCAAGGACAAGAAGCAGATTTTCATCAATGGGTTC<br>TTTAAGAATCCCAAGGAGAACGTAAAATTCGGAGTAC<br>TCTACCCAGAAGGCTGTATGGAGAATGCTCAGAGCAT<br>TGCTCGTTCCATCCTCGACTTCGCTACGGCCGGTAAA<br>TACAATAAGCAAGAGAACAAGTATATTTCGAAGAATT<br>TAATGAACATCGGATTCAAACCTTCTGAGTGTATCTT<br>TGAGTCGTATAAGTTGGGAGACATCACCGAGTATAAG<br>GCGACGGCCCGTAAGCTCAAGGAGCATGAGAAAGTTG<br>GGTTCGTTATCGCAGTGATCCCTGACATGAATGAGCT<br>GGAAGTCGAGAACCCTTATAACCCCTTCAAGAAGGTC<br>TGGGCGAAACTCAATATCCCATCCCAGATGATCACAT<br>TGAAGACCACCGAAAAGTTCAAGAATATCGTCGACAA<br>GTCAGGCTTGTACTACTTACACAATATCGCCCTTAAT<br>ATTCTCGGCAAAATCGGCGGAATCCCGTGGATTATTA<br>AAGACATGCCTGGCAACATCGACTGTTTCATCGGTTT<br>AGACGTCGGCACGCGCGAGAAGGGCATCCACTTCCCG | 137 |

TABLE 15-continued

Nucleic Acid Sequence of Exemplary Ago69 Homologues

| Ago69 Homologue | Amino Acid Sequence | SEQ ID NO |
|---|---|---|
| | GCATGTTCTGTGTTGTTCGACAAGTACGGAAAGTTAA<br>TCAATTATTACAAGCCGACTATTCCGCAGAGCGGAGA<br>GAAGATTGCTGAGACAATTTTACAGGAGATCTTCGAC<br>AACGTGTTAATCAGCTACAAAGAGGAAAACGGGGAGT<br>ACCCCAAGAATATCGTTATCCATCGTGATGGCTTCAG<br>CCGTGAGAACATCGATTGGTACAAAGAATACTTCGAT<br>AAGAAGGGTATCAAGTTCAACATTATTGAGGTTAAGA<br>AGAACATTCCCGTAAAGATCGCGAAGGTGGTTGGATC<br>CAATATCTGCAACCCGATCAAGGGCTCTTATGTGCTT<br>AAGAATGATAAGGCATTCATCGTAACCACCGATATCA<br>AAGACGGTGTGGCTTCTCCAAATCCACTTAAAATCGA<br>GAAAACCTATGGTGACGTTGAGATGAAGAGTATTCTG<br>GAGCAGATCTACAGTCTGAGCCAAATTCATGTTGGCT<br>CAACCAAGTCCCTGCGTCTTCCTATCACAACGGGATA<br>TGCCGATAAGATCTGTAAGGCAATTGAATACATTCCG<br>CAAGGAGTCGTAGACAATCGTTTGTTCTTTCTTTAAC<br>GTCTCGAGGCGGCCGC | |
| HG4 | TGTACAAGCTTGCCACCATGGGCCCTAAGAAGAAACG<br>CAAGGTAGAGGATCCGAAGAAGAAGCGTAAGGTAGGT<br>TCCGGTTCGATGAAGGAGTTTAACGTCATCACAGAGT<br>TCAAGAACGGTATTAATTCGAAGAGCATCGAGATCTA<br>TATTTACAAGATGATGGTTCGTGACTTTGAGAAGCGT<br>CACAATGAAAATTATGACGTGGTAAAAGAGCTTATTA<br>ACCTGAACAATAATAGTACGATTGTCTTTTATGAGCA<br>ATATATCGCCTCATTCAAGGAAATCGAGAAGTGGGGT<br>AACGAGCAATACATTAATGTTGAGAAACGCGCAATTA<br>ACCTGGAAAGCAACGAGAAGAAGATTCTTGAACGCCT<br>TCTGTTAAAGGAGATCAAGAACAACATCGATAACAAT<br>AAGTACAAGGTAGTGAAGGATTCGATCTACATCAACA<br>AGCCTGTGTATAACGAAAAGGGTATCAAAATCGACCG<br>CTACTTCAACTTAGACATCAACGTAGAATCAAACGGA<br>GACATCATTATTGGCTTCGATATTAGCCATAATTTCG<br>AGTATATTAACACGTTAGAGTACGAAATCAAGAACAA<br>CAATATCAAGATTGGAGACCGCGTAAAGGATTACTTT<br>TACAACCTTACTTATGAATATGTTGGCATCGCGCCGT<br>TCACTATTTCCGAAGAGAATGAATATATGGGATGTAG<br>CATCGTGGACTACTATGAAAATAAGAACCAGAGCTAC<br>ATCGTGAACAAGTTGCCAAAGGATATGAAGGCAATCT<br>TAGTTAAGAACAATAAGAACAGCATTTTCCCGTACAT<br>CCCTTCACGTCTTAAGAAGGTTTGTCGTTTCGAGAAT<br>CTGCCCCAAAACGTACTCCGTGATTTTAACACGCGCG<br>TCAAGCAGAAAACTAATGAGAAGATGCAATTTATGGT<br>GGACGAGGTTATCAACATTGTAAAGAATAGCGAGCAT<br>ATCGACGTAAAGAAGAAGAACATGATGTGTGACAATA<br>TCGGGTACAAGATTGAGGACCTGCAACAACCTGACCT<br>TTTGTTTGGAAACGCCCGCGCGCAGCGTTACCCACTG<br>TATGGATTGAAGAACTTTGGCGTGTACGAAAACAAGC<br>GCATTGAAATCAAGTACTTTATCGACCCGATTCTCGC<br>CAAGAGCAAGATGAATCTGGAAAAGATCTCCAAGTTC<br>TGTGATGAGCTGGAGCAGTTTAGCTCCAAGTTAGGAG<br>TAGGATTAAATCGCGTAAAACTGAACAATATTGTTAA<br>CTTCAAGGAGATTCGTATGGACAATGAGGACATCTTC<br>TCCTACGAGATTCGCAAAATTGTGAGCAACTATAATG<br>AGACAACGATCGTGATTCTGTCGGAAGAGAACCTTAA<br>TAAGTATTACAACATCATTAAGAAAACCTTCAGCGGT<br>GGCAACGAGGTTCCGACGCAATGCATTGGTTTCAACA<br>CACTTTCCTACACGGAGAAGAACAAGGACTCAATTTT<br>CTTAAATATTTTACTTGGTGTTTACGCCAAGTCAGGA<br>ATCCAACCGTGGATCCTCAATGAGAAATTGAATTCCG<br>ACTGTTTCATTGGTTTAGATGTCTCCCGTGAGAATAA<br>GGTAAACAAGGCCGGCGTCATTCAAGTTGTCGGAAAA<br>GATGGCCGCGTACTCAAGACCAAGGTCATCAGTTCGA<br>GCCAAAGCGGGGAGAAGATCAAGCTGGAAACGTTACG<br>CGAGATCGTGTTCGAGGCGATTAACTCGTATGAGAAT<br>ACCTACCGCTGTAAACCAAAACACATTACATTCCACC<br>GTGACGGTATTAATCGTGAGGAGCTGGAGAATCTTAA<br>GAATACGATGACCAATCTTGGTGTTGAGTTTGACTAC<br>ATCGAGATCACCAAGGGCATTAACCGCCGCATTGCCA<br>CCATCAGTGAGGGCGAGGAGTGGAAGACTATCATGGG<br>CCGCTGTTATTATAAGGACAATTCTGCCTACGTCTGC<br>ACTACTAAGCCTTATGAGGGAATCGGAATGGCAAAGC<br>CCATTCGCATCCGCCGCGTGTTTGGCACGCTTGATAT | 138 |

TABLE 15-continued

Nucleic Acid Sequence of Exemplary Ago69 Homologues

| Ago69 Homologue | Amino Acid Sequence | SEQ ID NO |
|---|---|---|
| | CGAGAAAATTGTTGAAGACGCGTATAAACTTACTTTT<br>ATGCATGTAGGCGCGATCAATAAAATTCGTCTTCCAA<br>TTACAACCTATTACGCAGATCTCAGCTCCACTTACGG<br>AAATCGCGACTTAATTCCGACGAATATTGATACCAAT<br>TGCCTCTACTTCATTTAACGTCTCGAGGCGGCCGC | |
| HG5 | TGTACAAGCTTGCCACCATGGGACCGAAGAAGAAGCG<br>TAAGGTCGAGGATCCCAAGAAGAAGCGTAAGGTGGGA<br>TCCGGGTCGATGGTGGGCCTGGACCGCGAATTCAACG<br>TGATCACCGAGTTCAAGAATGAGCTTAAGCCCGAGGA<br>CATCAAGATCTTCTTATACTCGATGCCGATCAAGGAT<br>ATTAATGAGCGCCATTCAGAGAATTATGCAATTGTCC<br>AAGAGCTCAAGAAGATCAACGAGAACCCTAACATTGT<br>ATTTAACGAGTACATCATCGCCAGCTTCAATCCTATT<br>ATTAATTGGGGCAAGTACAAGGACATCGATGTTAAGC<br>CGGACAATCGTAATATTAATCTGGATAACCACACTGA<br>GCGCAAAATCCTGGAGCGTTTATTACTCTGTGACATT<br>AAGAATAACATTAACAATAATACTACCTGGGAGCAAC<br>AGAATAAATACGAGATTCGCGGTAATGCTAACCCGGC<br>AGTATATCTTCGCAAGCCCATCTATCTGAACGATAAC<br>TTGATTATCCGCCGTAAGCTGAATTTTGACGTTAATA<br>TTGACAAGAAAGACATCATTATCGGCTTCTTCCTGAA<br>TCATGAGTTTGAATACCAAAAGACGTTAGACGAGGAA<br>ATCAAGTGTGGCAACATTCAGAAGGGCGACAAAGTGA<br>AGGACTTCTATAATAATATTACATATGAATTCTTGGA<br>GATGGCCCCATTTAGCATCTCACAAGAAAATAAATAC<br>ATGCGCAGTAGCATTATCGAGTATTATTTGAACAAGG<br>GCCAAAGCTACATCATTTCCGGCTTGGATAAGAACAC<br>TAAGGCCGTACTTGTTAAGAACAAAGAGGGCAGTATC<br>TTCCCCTATATCCCCAATCGCCTTAAGAAAATCTGCG<br>TCTTTGAGAATCTCGGCAACCGCCAGATCATCGAAGG<br>GAATAAGTACATCAAGATGAACCCTAGTCAAAATATG<br>AGTGAAAGCATCAAGTTGGCGGAAGATATCCTTAAGA<br>ATTCGAAGTATGTGAAGTTTAACAAGGCGAACATGAT<br>CGTGGAGAAAATCGGTTACAAGAAGGACATCGTGAAG<br>CGCCCTGCGTTAAAGTTTGGCAAGAATGAGAGCAATT<br>TCAGCGCCATGTACGGCCTTAACAAGAGCGGTAGTTA<br>CGAGCAGAAGAATATTAAGATCGACTATTTCATTGAC<br>CCGAAGATTCTTAATAACAAGCGCGATTACCAGATCG<br>TATACTCCTTCCTCAACGATATTATTAGTAAATCGAA<br>GGACTTGGGAGTCGAGATCAACACGGACAAGAGCTAT<br>ATCAATTTAACTCCAATCAACATTAAGAATGAAAATG<br>AGTTTGAGCTGAACGTCATGGAAATCATTAAGAATTA<br>CAATAACCCAGTACTTGTGATTCTTGAGAAGGAGAAT<br>ATCGACAAGTATTATGAAACCCTTAAGAAGATCTTCG<br>GCGGCCGTAACTCAATCGCAACCCAATTCGTGGATCT<br>GGACACGATCAAGCGCTGCGACCCTAAGATCGATAAC<br>AAGCGTGGAAAGGAATCGATCTTCTTAAACATCCTCT<br>TGGGCATCTACTGTAAGTCGGGTATTCAACCTTGGGT<br>TTTAGCGAATGGTCTGAGCGCTGACTGTTACATTGGC<br>CTCGACGTTTGTCGCGAGAATAATATGTCCACTGTGG<br>GGTTGATTCAAGTCATCGGGAAGGACGGTCGTGTACT<br>CAAAAGTAAGACTATTAGCAGCCATCAAAGTGGGGAA<br>AAGATTCAAATTAATATTTTGAAGGATATCATCTTCG<br>AGGCCAAGCAAGCGTATAAGAATACGTATAACAAGAA<br>GCTGGAACACATCGTTTTCCACCGCGACGGCATCAAT<br>CGTGAAGACATTGACCTTTTGAAGGAGATTACGAACT<br>CCCTGGAGATTAAGTTTGACTACGTCGAGGTAACAAA<br>GAATATTAACCGCCGTATGGCGATGTTAGAGAAAAGC<br>GATGAGAACTATAACCACCGTGACAAGGAGAATAAGA<br>AGTGGATTACGGAAATTGGTATGTGCCTTAAGAAGGA<br>AAATGAGGCCTATCTCATTACCACCAATCCTAGCGAG<br>AATATGGGTATGGCCCGTCCTCTTCGCATTAAGAAGG<br>TGTACGGTAACCAGAACATGGACGACATCGTTAAGGA<br>CATCTACAAGCTGTCCTTCATGCACATTGGTAGCATT<br>ATGAAGTCTCGTCTTCCAATCACAACCCATTACGCGG<br>ATTTATCTTCTATCTACAGCCACCGTGAATTGATGCC<br>TAAGTCCGTCGATAATAACATCCTGCACTTTATTTAA<br>CGTCTCGAGGCGGCCGC | 139 |

TABLE 27

Amino Acid Sequences of Ago69 and Ago69 Homologue PIWI Domains

| SEQ ID NO | Ago/ Genus Species | Amino Acid Sequence |
|---|---|---|
| 141 | 69 PIWI Domain | FVIAIVPNMSDEEIENSYNPFKKIWAELNLPSQMISVKTAEIFANSRDNTALYYLHNIVLGILGKIGGIPWVVKDMKGDVDCFVGLDVGTREKGIHYPACSVVFDKYGKLINYYKPNIPQNGEKINTEILQEIFDKVLISYEEENGAYPKNIVIHRDGFSREDLDWYENYFGKKNIKFNIIEVKKSTPLKIASINEGNITNPEKGSYILRGNKAYMVTTDIKENLGSPKPLKIEKSYGDIDMLTALSQIYALTQIHVGATKSLRLPITTGYADKICKAIEF |
| 142 | HG2 PIWI Domain | FVIAVIPDMNELEVENPYNPFKKVWAKLNIPSQMITLKTTEKFKNIVDKSGLYYLHNIALNILGKIGGIPWIIKDMPGNIDCFIGLDVGTREKGIHFPACSVLFDKYGKLINYYKPTIPQSGEKIAETILQEIFDNVLISYKEENGEYPKNIVIHRDGFSRENIDWYKEYFDKKGIKFNIIEVKKNIPVKIAKVVGSNICNPIKGSYVLKNDKAFIVTTDIKDGVASPNPLKIEKTYGDVEMKSILEQIYSLSQIHVGSTKSLRLPITTGYADKICKAIEYI |
| 143 | HG4 PIWI Domain | TTIVILSEENLNKYYNIIKKTFSGGNEVPTQCIGFNTLSYTEKNKDSIFLNILLGVYAKSGIQPWILNEKLNSDCFIGLDVSRENKVNKAGVIQVVGKDGRVLKTKVISSSQSGEKIKLETLREIVFEAINSYENTYRCKPKHITFHRDGINREELENLKNTMTNLGVEFDYIEITKGINRRIATISEGEEWKTIMGRCYYKDNSAYVCTTKPYEGIGMAKPIRIRRVFGTLDIEKIVEDAYKLTFMHVGAINKIRLPITTYYADLSSTYGNRDLI |

FIG. 102 shows a sequence alignment and homology of Ago69, HG2, and HG4. FIGS. 103A-103D show a sequence alignment and homology of Ago69, HG2, and HG4 along with an indication of the PAZ, MID, and PIWI domains. The percent sequence identity across Ago69, HG2, and HG4 is provided in Table 18.

TABLE 18

Percent Sequence Identity between Ago69, HG2, and HG4

| % Amino Acid Identity Between: | Ago69, HG2, HG4 | Ago69, HG2 | Ago69, HG4 |
|---|---|---|---|
| PIWI Domains | 27.7% | 72.8% | 34.1% |
| Whole Protein Sequence | 19.1% | 61.3% | 25.2% |

In some embodiments, the Ago polypeptide comprises a PIWI domain. In some embodiments, the Ago polypeptide comprises a PIWI domain that comprises a sequence that has at least 50%, 55%, 60%, 65%, or 70% sequence identity to one of SEQ ID NOS: 141-143. In some embodiments, the Ago polypeptide comprises a PIWI domain that comprises a sequence that has at least 50%, 55%, 60%, 65%, or 70% sequence identity to one of SEQ ID NO: 141. In some embodiments, the Ago polypeptide comprises a PIWI domain that comprises a sequence that has at least 50%, 55%, 60%, 65%, or 70% sequence identity to one of SEQ ID NO: 142. In some embodiments, the Ago polypeptide comprises a PIWI domain that comprises a sequence that has at least 50%, 55%, 60%, 65%, or 70% sequence identity to one of SEQ ID NO: 143.

(c) Additional Mesophilic Argonautes

In some cases, the Ago (or variant or functional fragment thereof) does not naturally occur in a bacterium or archael organism; rather it is altered or engineered based on a naturally-occurring polypeptide or protein of that bacterium or archaeal organism.

In some embodiments, the Ago (or variant or functional fragment thereof) is derived from a bacterium of Phylum planctomycetes, cyanobacteria, or firmicutes.

In some embodiments, the Ago (or variant or functional fragment thereof) is derived from a bacterium of Phylum planctomycetes. In some embodiments, the Ago (or variant or functional fragment thereof) is derived from a bacterium of class Planctomycetacia. In some embodiments, the Ago (or variant or functional fragment thereof) is derived from a bacterium of order Planctomycetales. In some embodiments, the Ago (or variant or functional fragment thereof) is derived from a bacterium of family Planctomycetaceae. In some embodiments, the Ago (or variant or functional fragment thereof) is derived from a bacterium of genus *Rhodopirellula*. In some embodiments, the Ago (or variant or functional fragment thereof) is derived from a bacterium of species *Rhodopirellula bahusiensis, Rhodopirellula baltica, Rhodopirellula caenicola, Rhodopirellula europaea, Rhodopirellula lusitana, Rhodopirellula europaea, Rhodopirellula rosea, Rhodopirellula rubra*, or *Rhodopirellula sallentina*.

In some embodiments, an Ago polypeptide as described herein is a mesophilic Ago or a mesothermic Ago. In some embodiments the mesophilic Ago has an amino acid sequence at least 0%, 85%, 90%, 95%, 96%, 97%, 98%, 99% or 100% identical to an amino acid sequence of SEQ ID NO: 4. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NO: 15.

In some embodiments, the Ago (or variant or functional fragment thereof) is derived from a bacterium of Phylum firmicutes. In some embodiments, the Ago (or variant or functional fragment thereof) is derived from a bacterium of class bacilli. In some embodiments, the Ago (or variant or functional fragment thereof) is derived from a bacterium of order bacillales. In some embodiments, the Ago (or variant or functional fragment thereof) is derived from a bacterium of family paenibacillaceae. In some embodiments, the Ago (or variant or functional fragment thereof) is derived from a bacterium of genus *Paenibacillus*. In some embodiments, the Ago (or variant or functional fragment thereof) is derived from a bacterium of species *P. agarexedens, P. agaridevorans, P. alginolyticus, P. alkaliterrae, P. alvei, P. amylolyticus, P. anaericanus, P. antarcticus, P. apiarius, P. assamensis, P. azoreducens, P. azotofixans, P. barcinonensis, P. borealis, P. brasilensis, P. brassicae, P. campinasensis, P. chinjuensis, P. chitinolyticus, P. chondroitinus, P. cineris, P. cookii, P. curdlanolyticus, P. daejeonensis, P. dendritiformis, P. durum, P. ehimensis, P. elgii, P. favisporus, P. glucanolyticus, P. glycanilyticus, P. gordonae, P. graminis, P. granivorans, P. hodogayensis, P. illinoisensis, P. jamilae, P. kobensis, P. koleovorans, P. koreensis, P. kribbensis, P. lactis, P. larvae, P. lautus, P. lentimorbus, P. macerans, P. macquariensis, P. massiliensis, P. mendelii, P. motobuensis, P. naphthalenovorans, P. nematophilus, P. odorifer, P. pabuli, P. peoriae, P. phoenicis, P. phyllosphaerae, P. polymyxa, P. popilliae, P. pulvifaciens, P. rhizosphaerae, P. sanguinis, P. stellfer, P. terrae, P. thiaminolyticus, P. timonensis, P. tylopili, P. turicensis, P. validus, P. vortex, P. vulneris, P. wynnii*, or *P. xylanilyticus*. In some embodiments, the Ago (or variant or functional fragment thereof) is derived from a bacterium of species *P. odorifer*.

In some embodiments the mesophilic Ago has an amino acid sequence at least 80%, 85%, 90%, 95%, 96%, 97%, 98%, 99% or 100% identical to an amino acid sequence of SEQ ID NO: 5. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NOs: 16.

In some embodiments, the Ago (or variant or functional fragment thereof) is derived from a bacterium of Phylum proteobacteria. In some embodiments, the Ago (or variant or functional fragment thereof) is derived from a bacterium of class alphaproteobacteria. In some embodiments, the Ago (or variant or functional fragment thereof) is derived from a bacterium of order rhodobacterales. In some embodiments, the Ago (or variant or functional fragment thereof) is derived from a bacterium of family hyphomonadaceae. In some embodiments, the Ago (or variant or functional fragment thereof) is derived from a bacterium of genus *Hyphomonas*. In some embodiments, the Ago (or variant or functional fragment thereof) is derived from a bacterium of species *Hyphomonas adhaerens, Hyphomonas hirschiana, Hyphomonas jannaschiana, Hyphomonas johnsonii, Hyphomonas neptunium, Hyphomonas oceanitis, Hyphomonas polymorpha, Hyphomonas rosenbergii, Hyphomonas* sp., *Hyphomonas* sp. AP-32, *Hyphomonas* sp. BAL52, *Hyphomonas* sp. DG895, *Hyphomonas* sp. kbc20, *Hyphomonas* sp. MED623, *Hyphomonas* sp. MK02, *Hyphomonas* sp. MK06, *Hyphomonas* sp. MK08, or *Hyphomonas taiwanensis.*

In some embodiments the mesophilic Ago has an amino acid sequence at least 80%, 85%, 90%, 95%, 96%, 97%, 98%, 99% or 100% identical to an amino acid sequence of SEQ ID NO: 6. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NOs: 17.

In some embodiments, the Ago (or variant or functional fragment thereof) is derived from a bacterium of Phylum cyanobacteria. In some embodiments, the Ago (or variant or functional fragment thereof) is derived from a bacterium of class cyanophyceae. In some embodiments, the Ago (or variant or functional fragment thereof) is derived from a bacterium of order nostocales. In some embodiments, the Ago (or variant or functional fragment thereof) is derived from a bacterium of family rivulariaceae. In some embodiments, the Ago (or variant or functional fragment thereof) is derived from a bacterium of genus *Calothrix*. In some embodiments, the Ago (or variant or functional fragment thereof) is derived from a bacterium of species *Calothrix* sp. PCC 7103, *Calothrix adscendens, Calothrix atricha, Calothrix braunii, Calothrix breviarticulata, Calothrix caespitora, Calothrix confervicola, Calothrix crustacea, Calothrix donnelli, Calothrix elenkinii, Calothrix epiphytica, Calothrix fusca, Calothrix juiana, Calothrix parasitica, Calothrix parietina, Calothrix pilosa, Calothrix pulvinata, Calothrix scopulorum, Calothrix scytonemicola, Calothrix simulans, Calothrix solitaria, Calothrix stagnalis, Calothrix stellaris, Calothrix thermalis*, or *Calothrix* 336/3. In some embodiments, the Ago (or variant or functional fragment thereof) is derived from a bacterium of species *Calothrix* sp. PCC 7103.

In some embodiments the mesophilic Ago has an amino acid sequence at least 80%, 85%, 90%, 95%, 96%, 97%, 98%, 99% or 100% identical to an amino acid sequence of SEQ ID NO: 7. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NOs: 18.

In some embodiments, the Ago (or variant or functional fragment thereof) is derived from a bacterium of genus *Thermosynechococcus*. In some embodiments, the Ago (or variant or functional fragment thereof) is derived from a bacterium of species *Thermosynechococcus elongatus.*

In some embodiments the mesophilic Ago has an amino acid sequence at least 80%, 85%, 90%, 95%, 96%, 97%, 98%, 99% or 100% identical to an amino acid sequence of SEQ ID NO: 10. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NOs: 21.

In some embodiments, the Ago (or variant or functional fragment thereof) is derived from a bacterium of order chroococcidiopsidales. In some embodiments, the Ago (or variant or functional fragment thereof) is derived from a bacterium of family chroococcidiopsidaceae. In some embodiments, the Ago (or variant or functional fragment thereof) is derived from a bacterium of genus *Chroococcidiopsis*. In some embodiments, the Ago (or variant or functional fragment thereof) is derived from a bacterium of species *Chroococcopsis gigantea* or *Chroococcidiopsis thermalis*. In some embodiments, the Ago (or variant or functional fragment thereof) is derived from a bacterium of species *Chroococcidiopsis thermalis.*

In some embodiments the mesophilic Ago has an amino acid sequence at least 80%, 85%, 90%, 95%, 96%, 97%, 98%, 99% or 100% identical to an amino acid sequence of SEQ ID NO: 9. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NOs: 20.

In some embodiments, the Ago (or variant or functional fragment thereof) is derived from a bacterium of Phylum *Deinococcus*-thermus. In some embodiments, the Ago (or variant or functional fragment thereof) is derived from a bacterium of class deinocci. In some embodiments, the Ago (or variant or functional fragment thereof) is derived from a bacterium of order deinococcocales. In some embodiments, the Ago (or variant or functional fragment thereof) is derived from a bacterium of family deinococcaceae. In some embodiments, the Ago (or variant or functional fragment thereof) is derived from a bacterium of genus *Deinococcus*. In some embodiments, the Ago (or variant or functional fragment thereof) is derived from a bacterium of species Deinobacter Oyaizu or *Deinococcus* sp. YIM 77859.

In some embodiments the mesophilic Ago has an amino acid sequence at least 80%, 85%, 90%, 95%, 96%, 97%, 98%, 99% or 100% identical to an amino acid sequence of SEQ ID NO: 8. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NOs: 19.

In some embodiments the mesophilic Ago has an amino acid sequence at least 80%, 85%, 90%, 95%, 96%, 97%, 98%, 99% or 100% identical to an amino acid sequence of one of SEQ ID NOs: 4-10. In some embodiments the mesophilic Ago has an amino acid sequence encoded by a nucleic acid at least 80%, 85%, 90%, 95%, 96%, 97%, 98%, 99% or 100% identical to a nucleic acid sequence of one of SEQ ID NOs: 15-21.

II. SSB POLYPEPTIDES

In some embodiments, described herein are fusion proteins that comprise an single strand DNA binding protein (SSB) polypeptide. In some embodiments, described herein are methods of engineering cells comprising introducing into a cell an Ago (e.g., described herein) and an SSB (e.g., as described herein). Such introduction can be made by separately introducing an Ago and SSB; or by introducing a fusion polypeptide (or nucleic acid encoding said polypeptide) that comprises both an Ago polypeptide and an SSB polypeptide (e.g., Ago-SSB fusions described herein).

In some embodiments, the SSB polypeptide component of an Ago-SSB fusion comprises an SSB polypeptide described herein (or a functional fragment or functional variant thereof). In some embodiments, the SSB polypeptide component of an Ago-SSB fusion comprises an SSB derived from a microorganism. In some embodiments, the microorganism is a bacterium. In some embodiments, the microorganism is a hyperthermophilic microorganism. In some embodiments, the SSB is from *Saccharolobus solfataricus*. In some embodiments, the SSB is active at a temperature between 32° C.-42° C. In some embodiments, the SSB is active at a temperature between 35° C.-40° C. In some embodiments, the SSB is active at about 37° C.

In some embodiments, the SSB comprises an amino acid sequence with at least 80%, 85%, 90%, 91%, 92%, 93%, 94%, 95%, 96%, 97%, 98%, 99%, or 100% identity to one of SEQ ID NOS: 22-35. In some embodiments, the SSB is encoded by a nucleic acid sequence with at least 80%, 85%, 90%, 91%, 92%, 93%, 94%, 95%, 96%, 97%, 98%, 99%, or 100% identity to one of SEQ ID NOS: 36-49. In some embodiments, the SSB comprises an amino acid sequence with at least 80%, 85%, 90%, 91%, 92%, 93%, 94%, 95%, 96%, 97%, 98%, 99%, or 100% identity to one of SEQ ID NOS: 22, 24, 26, 58, 30, 32, or 34. In some embodiments, the SSB is encoded by a nucleic acid sequence with at least 80%, 85%, 90%, 91%, 92%, 93%, 94%, 95%, 96%, 97%, 98%, 99%, or 100% identity to one of SEQ ID NOS: 36, 38, 40, 42, 44, 46, or 48. In some embodiments, the SSB polypeptide is one selected from Table 4 or Table 5.

In some embodiments, the SSB is ET-SSB (Sso-SSB), Neq SSB, TaqSSB, TmaSSB, or EcoSSB. In some embodiments, the SSB is an ET-SSB (also referred to herein as Sso-SSB). In some embodiments, the SSB comprises an amino acid sequence with at least 80%, 85%, 90%, 91%, 92%, 93%, 94%, 95%, 96%, 97%, 98%, 99%, or 100% identity to SEQ ID NO: 22. In some embodiments, the SSB is encoded by a nucleic acid sequence with at least 80%, 85%, 90%, 91%, 92%, 93%, 94%, 95%, 96%, 97%, 98%, 99%, or 100% identity to SEQ ID NOS: 36.

TABLE 4

Amino Acid Sequence of Exemplary SSB Proteins

| SSB | Amino Acid Sequence | SEQ ID NO |
|---|---|---|
| ET-SSB<br>(also referred to herein as Sso-SSB)<br>*Saccharolobus solfataricus* | MEEKVGNLKPNMESVNVTVRVLEASEARQIQTKNGVR<br>TISEAIVGDETGRVKLTLWGKHAGSIKEGQVVKIENA<br>WTTAFKGQVQLNAGSKTKIAEASEDGFPESSQIPENT<br>PTAPQQMRGGGRGFRGGGRRYGRRGGRRQENEEGEEE | 22 |
| ET-SSB<br>(also referred to herein as Sso-SSB)<br>*Saccharolobus solfataricus*<br>Construct Sequence<br>*Italicized: His tag*<br>Underlined: GST<br>**Bold: Sso-SSB** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGA**MEEKVGNL**<br>**KPNMESVNVTVRVLEASEARQIQTKNGVRTISEAIVG**<br>**DETGRVKLTLWGKHAGSIKEGQVVKIENAWTTAFKGQ**<br>**VQLNAGSKTKIAEASEDGFPESSQIPENTPTAPQQMR**<br>**GGGRGFRGGGRRYGRRGGRRQENEEGEEE** | 23 |
| Neq SSB<br>*Nanoarchaeum equitans* | MDEEELIQLIIEKTGKSREEIEKMVEEKIKAFNNLIS<br>RRGALLLVAKKLGVLYKNTPKEKKIGELESWEYVKVK<br>GKILKSFGLISYSKGKFQPIILGDETGTIKAIIWNTD<br>KELPENTVIEAIGKTKINKKTGNLELHIDSYKILESD<br>LEIKPQKQEFVGICIVKYPKKQTQKGTIVSKAILTSL<br>DRELPVVYFNDFDWEIGHIYKVYGKLKKNIKTGKIEF<br>FADKVEEATLKDLKAFKGEAD | 24 |
| Neq SSB<br>*Nanoarchaeum equitans*<br>*Italicized: His tag*<br>Underlined: GST<br>**Bold: NeqSSB** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGALA**MDEEEL**<br>**IQLIIEKTGKSREEIEKMVEEKIKAFNNLISRRGALL**<br>**LVAKKLGVLYKNTPKEKKIGELESWEYVKVKGKILKS**<br>**FGLISYSKGKFQPIILGDETGTIKAIIWNTDKELPEN**<br>**TVIEAIGKTKINKKTGNLELHIDSYKILESDLEIKPQ**<br>**KQEFVGICIVKYPKKQTQKGTIVSKAILTSLDRELPV**<br>**VYFNDFDWEIGHIYKVYGKLKKNIKTGKIEFFADKVE**<br>**EATLKDLKAFKGEAD** | 25 |

TABLE 4-continued

Amino Acid Sequence of Exemplary SSB Proteins

| SSB | Amino Acid Sequence | SEQ ID NO |
|---|---|---|
| TaqSSB<br>*Thermus aquaticus* | MARGLNQVFLIGTLTARPDMRYTPGGLAILDLNLAGQ<br>DAFTDESGQEREVPWYHRVRLLGRQAEMWGDLLEKGQ<br>LIFVEGRLEYRQWEKDGEKKSEVQVRAEFIDPLEGRG<br>RETLEDARGQPRLRRALNQVILMGNLTRDPDLRYTPQ<br>GTAVVRLGLAVNERRRGQEEERTHFLEVQAWRELAEW<br>ASELRKGDGLLVIGRLVNDSWTSSSGERRFQTRVEAL<br>RLERPTRGPAQAGGSRPPTVQTGGVDIDEGLEDFPPE<br>EDLPF | 26 |
| TaqSSB<br>*Thermus aquaticus*<br>*Italicized: His tag*<br>Underlined: GST<br>**Bold: TaqSSB** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGA**MARGLNQV**<br>**FLIGTLTARPDMRYTPGGLAILDLNLAGQDAFTDESG**<br>**QEREVPWYHRVRLLGRQAEMWGDLLEKGQLIFVEGRL**<br>**EYRQWEKDGEKKSEVQVRAEFIDPLEGRGRETLEDAR**<br>**GQPRLRRALNQVILMGNLTRDPDLRYTPQGTAVVRLG**<br>**LAVNERRRGQEEERTHFLEVQAWRELAEWASELRKGD**<br>**GLLVIGRLVNDSWTSSSGERRFQTRVEALRLERPTRG**<br>**PAQAGGSRPPTVQTGGVDIDEGLEDFPPEEDLPF** | 27 |
| TmaSSB<br>*Thermotoga maritima* | MGSFFNKIILIGRLVRDPEERYTLSGTPVTTFTIAVD<br>RVPRKNAPDDAQTTDFFRIVTFGRLAEFARTYLTKGR<br>LVLVEGEMRMRRWETPTGEKRVSPEVVANVVRFMDRK<br>PAETVSETEEELEIPEEDFSSDTFSEDEPPF | 28 |
| TmaSSB<br>*Thermotoga maritima*<br>Construct Sequence<br>*Italicized: His tag*<br>Underlined: GST<br>**Bold: TmaSSB** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGA**MGSFFNKI**<br>**ILIGRLVRDPEERYTLSGTPVTTFTIAVDRVPRKNAP**<br>**DDAQTTDFFRIVTFGRLAEFARTYLTKGRLVLVEGEM**<br>**RMRRWETPTGEKRVSPEVVANVVRFMDRKPAETVSET**<br>**EEELEIPEEDFSSDTFSEDEPPF** | 29 |
| EcoSSB<br>*Escherichia coli*<br>(strain K12)<br>Construct Sequence<br>*Italicized: His tag*<br>Underlined: GST<br>**Bold: EcoSSB** | MASRGVNKVILVGNLGQDPEVRYMPNGGAVANITLAT<br>SESWRDKATGEMKEQTEWHRVVLFGKLAEVASEYLRK<br>GSQVYIEGQLRTRKWTDQSGQDRYTTEVVVNVGGTMQ<br>MLGGRQGGGAPAGGNIGGGQPQGGWGQPQQPQGGNQF<br>SGGAQSRPQQSAPAAPSNEPPMDFDDDIPF | 30 |
| EcoSSB<br>*Escherichia coli*<br>(strain K12)<br>Construct Sequence<br>*Italicized: His tag*<br>Underlined: GST<br>**Bold: EcoSSB** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGALA**MASRGV**<br>**NKVILVGNLGQDPEVRYMPNGGAVANITLATSESWRD**<br>**KATGEMKEQTEWHRVVLFGKLAEVASEYLRKGSQVY**<br>**IEGQLRTRKWTDQSGQDRYTTEVVVNVGGTMQMLGGR**<br>**QGGGAPAGGNIGGGQPQGGWGQPQQPQGGNQFSGGAQ**<br>**SRPQQSAPAAPSNEPPMDFDDDIPF** | 31 |
| TthSSB<br>*Thermus Thermophilus* | MARGLNRVFLIGALATRPDMRYTPAGLAILDLTL<br>AGQDLLLSDNGGEREVSWYHRVRLLGRQAEMW<br>GDLLDQGQLVFVEGRLEYRQWEREGEKRSELQIR<br>ADFLDPLDDRGKERAEDSRGQPRLRAALNQVFLMGNL<br>TRDPELRYTPQGTAVARLGLAVNERRQGAEERTHFVE<br>VQAWRDLAEWAAELRKGDGLFVIGRLVNDSWTSSSGE<br>RRFQTRVEALRLERPTRGPAQAGGSRSREAQTGGVDI<br>DEGLEDFPPEEELPF | 32 |
| TthSSB<br>*Thermus Thermophilus*<br>Construct Sequence | MK*HHHHHH*NTSSNSMSPILGYWKIKGLVQPTRL<br>LLEYLEEKYEEHLYERDEGDKWRNKKFELGLEF<br>PNLPYYIDGDVKLTQSMAIIRYIADKHNMLGGCP | 33 |

TABLE 4-continued

Amino Acid Sequence of Exemplary SSB Proteins

| SSB | Amino Acid Sequence | SEQ ID NO |
|---|---|---|
| *Italicized: His tag*<br>Underlined: GST<br>**Bold: TthSSB** | KERAEISMLEGAVLDIRYGVSRIAYSKDFETLKV<br>DFLSKLPEMLKMFEDRLCHKTYLNGDHVTHPDF<br>MLYDALDVVLYMDPMCLDAFPKLVCFKKRIEAI<br>PQIDKYLKSSKYIAWPLQGWQATFGGGDHPPTSG<br>SGGGGGWMSENLYFQGA**MARGLNRVFLIGALA**<br>**TRPDMRYTPAGLAILDLTLAGQDLLLSDNGGE**<br>**REVSWYHRVRLLGRQAEMWGDLLDQGQLVF**<br>**VEGRLEYRQWEREGEKRSELQIRADFLDPLDD**<br>**RGKERAEDSRGQPRLRAALNQVFLMGNLTRDPELRYT**<br>**PQGTAVARLGLAVNERRQGAEERTHFVEVQAWRDLAE**<br>**WAAELRKGDGLFVIGRLVNDSWTSSSGERRFQTRVEA**<br>**LRLERPTRGPAQAGGSRSREAQTGGVDIDEGLEDFPP**<br>**EEELPF** | |
| TneSSB<br>*Thermotoga neapolitana* | MGSFFNRIILIGRLVRDPEERYTLSGTPVTTFTIAVD<br>RVPRKNAPDDAQTTDFFRVVTFGRLAEFARTYLTKGR<br>LILVEGEMRMRRWETQTGEKRVSPEVVANVVRFMDRK<br>PVEMPSEDIEEKLEIPEEDFTDDTFSEDEPPF | 34 |
| TneSSB<br>*Thermotoga neapolitana*<br>Construct Sequence<br>*Italicized: His tag*<br>Underlined: GST<br>**Bold: TneSSB** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGA**MGSFFNRI**<br>**ILIGRLVRDPEERYTLSGTPVTTFTIAVDRVPRKNAP**<br>**DDAQTTDFFRVVTFGRLAEFARTYLTKGRLILVEGEM**<br>**RMRRWETQTGEKRVSPEVVANVVRFMDRKPVEMPSED**<br>**IEEKLEIPEEDFTDDTFSEDEPPF** | 35 |

TABLE 5

Nucleic Acid Sequence of Exemplary SSBs

| SSB | Nucleic Acid Sequence | SEQ ID NO |
|---|---|---|
| ET-SSB<br>(also referred to herein as Sso-SSB)<br>*Saccharolobus solfataricus* | ATGGAAGAAAAAGTAGGCAACCTGAAGCCTAATATGG<br>AATCCGTAAATGTAACCGTTCGCGTTTTAGAAGCCTC<br>TGAAGCACGGCAGATCCAGACCAAAAATGGTGTTCGC<br>ACCATTTCAGAGGCGATTGTAGGGGATGAAACCGGGC<br>GCGTGAAACTGACTCTGTGGGGCAAACATGCGGGCAG<br>CATCAAAGAAGGCCAGGTCGTTAAAATTGAGAACGCC<br>TGGACAACCGCGTTCAAAGGCCAGGTACAGCTGAATG<br>CCGGTAGCAAGACCAAAATTGCCGAGGCATCTGAAGA<br>CGGTTTCCCTGAAAGCAGCCAGATCCCAGAAAATACT<br>CCTACGGCACCGCAGCAGATGCGTGGCGGTGGGCGGG<br>GCTTTCGTGGCGGAGGCCGCCGTTATGGCCGTCGCGG<br>TGGGCGCCGGCAAGAAAACGAAGAAGGCGAAGAAGAA<br>TAG | 36 |
| ET-SSB<br>(also referred to herein as Sso-SSB)<br>Construct Sequence<br>*Italicized: His tag*<br>Underlined: GST<br>**Bold: Sso-SSB** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT<br>GCGTTCCCAAAATTAGTTTGTTTTAAAAAACGTATTG<br>AAGCTATCCCACAAATTGATAAGTACTTGAAATCCAG<br>CAAGTATATAGCATGGCCTTTGCAGGGCTGGCAAGCC | 37 |

TABLE 5-continued

Nucleic Acid Sequence of Exemplary SSBs

| SSB | Nucleic Acid Sequence | SEQ ID NO |
|---|---|---|
| | ACGTTTGGTGGTGGCGACCATCCTCCAACTAGTGGAT<br>CTGGTGGTGGTGGCGGATGGATG**AGCGAGAATCTTTA**<br>**TTTTCAGGGCGCCATGGAAGAAAAAGTAGGCAACCTG**<br>**AAGCCTAATATGGAATCCGTAAATGTAACCGTTCGCG**<br>**TTTTAGAAGCCTCTGAAGCACGGCAGATCCAGACCAA**<br>**AAATGGTGTTCGCACCATTTCAGAGGCGATTGTAGGG**<br>**GATGAAACCGGGCGCGTGAAACTGACTCTGTGGGGCA**<br>**AACATGCGGGCAGCATCAAAGAAGGCCAGGTCGTTAA**<br>**AATTGAGAACGCCTGGACAACCGCGTTCAAAGGCCAG**<br>**GTACAGCTGAATGCCGGTAGCAAGACCAAAATTGCCG**<br>**AGGCATCTGAAGACGGTTTCCCTGAAAGCAGCCAGAT**<br>**CCCAGAAAATACTCCTACGGCACCGCAGCAGATGCGT**<br>**GGCGGTGGGCGGGGCTTTCGTGGCGGAGGCCGCCGTT**<br>**ATGGCCGTCGCGGTGGGCGCCGGCAAGAAAACGAAGA**<br>**AGGCGAAGAAGAATAG** | |
| Neq SSB<br>*Nanoarchaeum equitans* | ATGGATGAAGAAGAGCTTATTCAGCTTATTATTGAAA<br>AAACTGGGAAGTCGCGCGAGGAAATTGAGAAGATGGT<br>AGAAGAAAAAATCAAGGCTTTCAACAACCTGATCTCG<br>CGCCGTGGCGCTTTGCTGTTAGTGGCGAAGAAACTTG<br>GTGTACTTTATAAAAACACGCCAAAAGAAAAAAAGAT<br>CGGGGAACTGGAGTCCTGGGAATACGTTAAGGTGAAA<br>GGTAAAATCCTGAAGTCCTTCGGCCTGATTAGTTATT<br>CAAAGGGCAAGTTTCAACCGATCATTCTTGGGGACGA<br>AACTGGCACTATCAAAGCTATTATCTGGAATACTGAT<br>AAGGAGTTACCTGAGAATACGGTCATTGAAGCTATTG<br>GAAAGACTAAGATTAACAAAAAAACAGGGAATCTTGA<br>GTTACATATTGATAGTTACAAAATTTTAGAGTCCGAC<br>TTAGAGATTAAGCCTCAGAAACAGGAATTTGTCGGTA<br>TTTGCATCGTTAAATACCCCAAGAAGCAGACCCAAAA<br>GGGTACGATTGTAAGCAAAGCTATCCTGACATCATTA<br>GACCGTGAGTTACCCGTCGTTTACTTTAATGATTTTG<br>ACTGGGAGATCGGGCATATCTATAAGGTCTACGGGAA<br>ACTGAAAAAAAAATATCAAAACTGGCAAAATCGAGTTT<br>TTTGCAGACAAGGTAGAGGAAGCCACCCTGAAAGATC<br>TTAAGGCGTTCAAGGGGGAAGCAGACTAGTGA | 38 |
| Neq SSB<br>*Nanoarchaeum equitans*<br>Construct Sequence<br>*Italicized: His tag*<br>Underlined: GST<br>**Bold: NeqSSB** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT<br>GCGTTCCCAAAATTAGTTTGTTTTAAAAAACGTATTG<br>AAGCTATCCCACAAATTGATAAGTACTTGAAATCCAG<br>CAAGTATATAGCATGGCCTTTGCAGGGCTGGCAAGCC<br>ACGTTTGGTGGTGGCGACCATCCTCCAACTAGTGGAT<br>CTGGTGGTGGTGGCGGATGGATGAGCGAGAATCTTTA<br>TTTTCAGGGCGCGCTAGCA**ATGGATGAAGAAGAGCTT**<br>**ATTCAGCTTATTATTGAAAAAACTGGGAAGTCGCGCG**<br>**AGGAAATTGAGAAGATGGTAGAAGAAAAAATCAAGGC**<br>**TTTCAACAACCTGATCTCGCGCCGTGGCGCTTTGCTG**<br>**TTAGTGGCGAAGAAACTTGGTGTACTTTATAAAAACA**<br>**CGCCAAAAGAAAAAAAGATCGGGGAACTGGAGTCCTG**<br>**GGAATACGTTAAGGTGAAAGGTAAAATCCTGAAGTCC**<br>**TTCGGCCTGATTAGTTATTCAAAGGGCAAGTTTCAAC**<br>**CGATCATTCTTGGGGACGAAACTGGCACTATCAAAGC**<br>**TATTATCTGGAATACTGATAAGGAGTTACCTGAGAAT**<br>**ACGGTCATTGAAGCTATTGGAAAGACTAAGATTAACA**<br>**AAAAAACAGGGAATCTTGAGTTACATATTGATAGTTA**<br>**CAAAATTTTAGAGTCCGACTTAGAGATTAAGCCTCAG**<br>**AAACAGGAATTTGTCGGTATTTGCATCGTTAAATACC**<br>**CCAAGAAGCAGACCCAAAAGGGTACGATTGTAAGCAA**<br>**AGCTATCCTGACATCATTAGACCGTGAGTTACCCGTC**<br>**GTTTACTTTAATGATTTTGACTGGGAGATCGGGCATA** | 39 |

TABLE 5-continued

Nucleic Acid Sequence of Exemplary SSBs

| SSB | Nucleic Acid Sequence | SEQ ID NO |
|---|---|---|
| | **TCTATAAGGTCTACGGGAAACTGAAAAAAAATATCAA**<br>**AACTGGCAAAATCGAGTTTTTTGCAGACAAGGTAGAG**<br>**GAAGCCACCCTGAAAGATCTTAAGGCGTTCAAGGGGG**<br>**AAGCAGACTAGTGA** | |
| TaqSSB<br>*Thermus aquaticus* | ATGGCGCGCGGTCTGAACCAGGTATTTCTGATCGGCA<br>CCCTCACTGCCCGTCCAGATATGCGCTATACCCCGGG<br>CGGGCTGGCAATTCTGGATCTCAATCTTGCTGGGCAG<br>GATGCGTTTACCGATGAAAGTGGGCAAGAGCGTGAAG<br>TCCCGTGGTATCATCGTGTGCGTCTGCTCGGCCGTCA<br>AGCGGAAATGTGGGGTGACCTGCTGGAAAAAGGTCAG<br>CTGATCTTTGTGGAAGGTCGCCTGGAATACCGCCAAT<br>GGGAAAAAGACGGCGAAAAAAAGAGCGAAGTCCAAGT<br>CCGTGCTGAGTTTATTGATCCGCTGGAAGGTCGCGGC<br>CGTGAGACGCTCGAAGATGCTCGTGGTCAGCCCCGCT<br>TACGTCGTGCACTGAACCAGGTTATTCTCATGGGTAA<br>CCTCACCCGCGATCCCGATTTACGCTATACCCCCCAG<br>GGTACGGCGGTGGTACGCCTGGGCCTTGCTGTGAACG<br>AGCGGCGTCGTGGCCAAGAAGAAGAACGTACCCATTT<br>TCTGGAAGTGCAGGCGTGGCGCGAGCTGGCCGAATGG<br>GCTAGCGAATTACGCAAAGGCGACGGTCTTCTGGTCA<br>TCGGTCGCTTGGTCAACGATTCCTGGACAAGCTCCTC<br>GGGTGAACGTCGCTTCCAAACGCGTGTGGAGGCACTG<br>CGGTTAGAACGTCCGACCCGCGGCCCGGCACAGGCGG<br>GGGGATCCCGGCCGCCCACCGTGCAGACGGGGGGTGT<br>GGATATCGATGAGGGGCTGGAAGACTTTCCGCCTGAA<br>GAAGATCTGCCTTTCTAG | 40 |
| TaqSSB<br>*Thermus aquaticus*<br>*Italicized: His tag*<br>Underlined: GST<br>**Bold: TaqSSB** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT<br>GCGTTCCCAAAATTAGTTTGTTTTAAAAAACGTATTG<br>AAGCTATCCCACAAATTGATAAGTACTTGAAATCCAG<br>CAAGTATATAGCATGGCCTTTGCAGGGCTGGCAAGCC<br>ACGTTTGGTGGTGGCGACCATCCTCCAACTAGTGGAT<br>CTGGTGGTGGTGGCGGATGGATGAGCGAGAATCTTTA<br>TTTTCAGGGCGCC**ATGGCGCGCGGTCTGAACCAGGTA**<br>**TTTCTGATCGGCACCCTCACTGCCCGTCCAGATATGC**<br>**GCTATACCCCGGGCGGGCTGGCAATTCTGGATCTCAA**<br>**TCTTGCTGGGCAGGATGCGTTTACCGATGAAAGTGGG**<br>**CAAGAGCGTGAAGTCCCGTGGTATCATCGTGTGCGTC**<br>**TGCTCGGCCGTCAAGCGGAAATGTGGGGTGACCTGCT**<br>**GGAAAAAGGTCAGCTGATCTTTGTGGAAGGTCGCCTG**<br>**GAATACCGCCAATGGGAAAAAGACGGCGAAAAAAAGA**<br>**GCGAAGTCCAAGTCCGTGCTGAGTTTATTGATCCGCT**<br>**GGAAGGTCGCGGCCGTGAGACGCTCGAAGATGCTCGT**<br>**GGTCAGCCCCGCTTACGTCGTGCACTGAACCAGGTTA**<br>**TTCTCATGGGTAACCTCACCCGCGATCCCGATTTACG**<br>**CTATACCCCCCAGGGTACGGCGGTGGTACGCCTGGGC**<br>**CTTGCTGTGAACGAGCGGCGTCGTGGCCAAGAAGAAG**<br>**AACGTACCCATTTTCTGGAAGTGCAGGCGTGGCGCGA**<br>**GCTGGCCGAATGGGCTAGCGAATTACGCAAAGGCGAC**<br>**GGTCTTCTGGTCATCGGTCGCTTGGTCAACGATTCCT**<br>**GGACAAGCTCCTCGGGTGAACGTCGCTTCCAAACGCG**<br>**TGTGGAGGCACTGCGGTTAGAACGTCCGACCCGCGGC**<br>**CCGGCACAGGCGGGGGGATCCCGGCCGCCCACCGTGC**<br>**AGACGGGGGGTGTGGATATCGATGAGGGGCTGGAAGA**<br>**CTTTCCGCCTGAAGAAGATCTGCCTTTCTAG** | 41 |
| TmaSSB<br>*Thermotoga maritima* | ATGGGATCTTTCTTCAACAAAATTATCCTTATCGGCC<br>GTCTGGTCCGCGACCCGGAAGAACGTTATACACTGTC<br>TGGCACACCGGTCACCACCTTTACTATTGCCGTCGAT | 42 |

TABLE 5-continued

Nucleic Acid Sequence of Exemplary SSBs

| SSB | Nucleic Acid Sequence | SEQ ID NO |
|---|---|---|
| | CGTGTTCCGCGCAAAAACGCACCGGATGATGCCCAGA<br>CCACCGATTTTTTTCGCATTGTGACTTTCGGCCGCCT<br>GGCGGAGTTTGCCCGTACTTATTTAACGAAAGGTCGT<br>CTCGTGCTCGTAGAGGGCGAGATGCGCATGCGCCGTT<br>GGGAAACACCAACGGGCGAAAAACGTGTGAGCCCGGA<br>AGTGGTGGCCAATGTGGTTCGTTTTATGGACCGCAAA<br>CCTGCCGAAACCGTCAGCGAAACGGAAGAGGAACTCG<br>AAATCCCAGAGGAGGACTTCAGCTCAGACACCTTTTC<br>GGAAGATGAACCCCCGTTTTAG | |
| TmaSSB<br>*Thermotoga maritima*<br>Construct Sequence<br>*Italicized*: *His tag*<br>Underlined: GST<br>**Bold**: **TmaSSB** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT<br>GCGTTCCCAAAATTAGTTTGTTTTAAAAAACGTATTG<br>AAGCTATCCCACAAATTGATAAGTACTTGAAATCCAG<br>CAAGTATATAGCATGGCCTTTGCAGGGCTGGCAAGCC<br>ACGTTTGGTGGTGGCGACCATCCTCCAACTAGTGGAT<br>CTGGTGGTGGTGGCGGATGGATGAGCGAGAATCTTTA<br>TTTTCAGGGCGCC**ATGGGATCTTTCTTCAACAAAATT**<br>**ATCCTTATCGGCCGTCTGGTCCGCGACCCGGAAGAAC**<br>**GTTATACACTGTCTGGCACACCGGTCACCACCTTTAC**<br>**TATTGCCGTCGATCGTGTTCCGCGCAAAAACGCACCG**<br>**GATGATGCCCAGACCACCGATTTTTTTCGCATTGTGA**<br>**CTTTCGGCCGCCTGGCGGAGTTTGCCCGTACTTATTT**<br>**AACGAAAGGTCGTCTCGTGCTCGTAGAGGGCGAGATG**<br>**CGCATGCGCCGTTGGGAAACACCAACGGGCGAAAAAC**<br>**GTGTGAGCCCGGAAGTGGTGGCCAATGTGGTTCGTTT**<br>**TATGGACCGCAAACCTGCCGAAACCGTCAGCGAAACG**<br>**GAAGAGGAACTCGAAATCCCAGAGGAGGACTTCAGCT**<br>**CAGACACCTTTTCGGAAGATGAACCCCCGTTTTAG** | 43 |
| EcoSSB<br>*Escherichia coli*<br>(strain K12) | ATGGCATCACGTGGCGTCAACAAGGTCATTTTAGTCG<br>GAAACCTTGGGCAGGATCCTGAAGTCCGCTACATGCC<br>CAATGGAGGCGCTGTTGCGAATATCACATTGGCAACT<br>AGTGAAAGCTGGCGCGATAAGGCTACGGGAGAGATGA<br>AGGAGCAAACGGAGTGGCACCGTGTGGTATTGTTCGG<br>CAAATTAGCTGAAGTGGCTAGTGAATATTTGCGTAAA<br>GGTTCGCAAGTGTATATTGAGGGCCAGCTTCGTACCC<br>GTAAGTGGACCGACCAAAGTGGACAGGACCGCTACAC<br>TACGGAAGTAGTGGTCAATGTAGGCGGGACGATGCAA<br>ATGCTTGGTGGACGTCAAGGTGGTGGAGCTCCAGCAG<br>GAGGTAATATCGGTGGTGGACAGCCCCAAGGGGGTTG<br>GGGCCAACCGCAACAGCCACAGGGGGGTAACCAATTT<br>TCCGGTGGGGCTCAGAGCCGTCCACAGCAGTCGGCTC<br>CCGCAGCACCAAGCAATGAACCCCCGATGGACTTTGA<br>TGACGATATTCCTTTCTAGTGA | 44 |
| EcoSSB<br>*Escherichia coli*<br>(strain K12)<br>Construct Sequence<br>*Italicized*: *His tag*<br>Underlined: GST<br>**Bold**: **Eco-SSB** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT | 45 |

TABLE 5-continued

Nucleic Acid Sequence of Exemplary SSBs

| SSB | Nucleic Acid Sequence | SEQ ID NO |
|---|---|---|
| | GCGTTCCCAAAATTAGTTTGTTTTAAAAAACGTATTG | |
| | AAGCTATCCCACAAATTGATAAGTACTTGAAATCCAG | |
| | CAAGTATATAGCATGGCCTTTGCAGGGCTGGCAAGCC | |
| | ACGTTTGGTGGTGGCGACCATCCTCCAACTAGTGGAT | |
| | CTGGTGGTGGTGGCGGATGGATGAGCGAGAATCTTTA | |
| | TTTTCAGGGCGCGCTAGCA**ATGGCATCACGTGGCGTC** | |
| | **AACAAGGTCATTTTAGTCGGAAACCTTGGGCAGGATC** | |
| | **CTGAAGTCCGCTACATGCCCAATGGAGGCGCTGTTGC** | |
| | **GAATATCACATTGGCAACTAGTGAAAGCTGGCGCGAT** | |
| | **AAGGCTACGGGAGAGATGAAGGAGCAAACGGAGTGGC** | |
| | **ACCGTGTGGTATTGTTCGGCAAATTAGCTGAAGTGGC** | |
| | **TAGTGAATATTTGCGTAAAGGTTCGCAAGTGTATATT** | |
| | **GAGGGCCAGCTTCGTACCCGTAAGTGGACCGACCAAA** | |
| | **GTGGACAGGACCGCTACACTACGGAAGTAGTGGTCAA** | |
| | **TGTAGGCGGGACGATGCAAATGCTTGGTGGACGTCAA** | |
| | **GGTGGTGGAGCTCCAGCAGGAGGTAATATCGGTGGTG** | |
| | **GACAGCCCCAAGGGGGTTGGGGCCAACCGCAACAGCC** | |
| | **ACAGGGGGGTAACCAATTTTCCGGTGGGGCTCAGAGC** | |
| | **CGTCCACAGCAGTCGGCTCCCGCAGCACCAAGCAATG** | |
| | **AACCCCCGATGGACTTTGATGACGATATTCCTTTCTA** | |
| | **GTGA** | |
| TthSSB | ATGGCACGCGGCCTGAACCGCGTTTTTCTGATTGGTG | 46 |
| *Thermus Thermophilus* | CACTGGCCACCCGCCCGGATATGCGCTATACCCCGGC | |
| | AGGCCTTGCAATTTTAGACCTGACCCTTGCGGGCCAA | |
| | GATTTACTGCTTTCAGACAATGGCGGTGAACGTGAGG | |
| | TGAGTTGGTACCATCGTGTACGCCTGTTAGGACGTCA | |
| | GGCCGAGATGTGGGGCGATCTGCTTGACCAGGGCCAG | |
| | CTGGTGTTTGTGGAGGGCCGCCTTGAGTATCGTCAAT | |
| | GGGAACGTGAAGGTGAAAAACGCTCCGAACTGCAGAT | |
| | TCGCGCTGATTTCCTCGATCCGTTGGATGATCGCGGT | |
| | AAGGAACGCGCAGAAGATAGCCGGGGTCAGCCACGGC | |
| | TCCGTGCCGCGCTGAACCAGGTATTTTTAATGGGCAA | |
| | TCTGACCCGCGATCCCGAACTGCGCTACACTCCACAG | |
| | GGCACCGCAGTCGCTCGTTTAGGCCTGGCTGTGAACG | |
| | AACGCCGTCAGGGCGCGGAAGAACGTACCCACTTCGT | |
| | TGAAGTCCAGGCCTGGCGCGACTTAGCAGAGTGGGCC | |
| | GCAGAGCTGCGTAAGGGTGACGGCCTGTTCGTTATCG | |
| | GGCGTCTCGTTAACGACTCTTGGACTAGCTCGTCAGG | |
| | TGAGCGTCGCTTTCAAACCCGTGTCGAAGCCCTGCGG | |
| | CTGGAACGCCCAACGCGGGGTCCGGCACAGGCCGGCG | |
| | GGTCGCGCTCTCGCGAGGCACAGACAGGCGGGGTTGA | |
| | TATTGACGAAGGGTTAGAGGATTTCCCGCCAGAGGAG | |
| | GAGCTGCCTTTTTAG | |
| TthSSB | ATGAAA*CATCACCATCACCATCAC*AACACTAGTAGCA | 47 |
| *Thermus Thermophilus* | ATTCCATGTCCCCTATACTAGGTTATTGGAAAATTAA | |
| Construct Sequence | GGGCCTTGTGCAACCCACTCGACTTCTTTTGGAATAT | |
| *Italicized: His tag* | CTTGAAGAAAAATATGAAGAGCATTTGTATGAGCGCG | |
| Underlined: GST | ATGAAGGTGATAAATGGCGAAACAAAAAGTTTGAATT | |
| **Bold: TthSSB** | GGGTTTGGAGTTTCCCAATCTTCCTTATTATATTGAT | |
| | GGTGATGTTAAATTAACACAGTCTATGGCCATCATAC | |
| | GTTATATAGCTGACAAGCACAACATGTTGGGTGGTTG | |
| | TCCAAAAGAGCGTGCAGAGATTTCAATGCTTGAAGGA | |
| | GCGGTTTTGGATATTAGATACGGTGTTTCGAGAATTG | |
| | CATATAGTAAAGACTTTGAAACTCTCAAAGTTGATTT | |
| | TCTTAGCAAGCTACCTGAAATGCTGAAAATGTTCGAA | |
| | GATCGTTTATGTCATAAAACATATTTAAATGGTGATC | |
| | ATGTAACCCATCCTGACTTCATGTTGTATGACGCTCT | |
| | TGATGTTGTTTTATACATGGACCCAATGTGCCTGGAT | |
| | GCGTTCCCAAAATTAGTTTGTTTTAAAAAACGTATTG | |
| | AAGCTATCCCACAAATTGATAAGTACTTGAAATCCAG | |
| | CAAGTATATAGCATGGCCTTTGCAGGGCTGGCAAGCC | |
| | ACGTTTGGTGGTGGCGACCATCCTCCAACTAGTGGAT | |
| | CTGGTGGTGGTGGCGGATGGATGAGCGAGAATCTTTA | |
| | TTTTCAGGGCGCC**ATGGCACGCGGCCTGAACCGCGTT** | |
| | **TTTCTGATTGGTGCACTGGCCACCCGCCCGGATATGC** | |
| | **GCTATACCCCGGCAGGCCTTGCAATTTTAGACCTGAC** | |
| | **CCTTGCGGGCCAAGATTTACTGCTTTCAGACAATGGC** | |
| | **GGTGAACGTGAGGTGAGTTGGTACCATCGTGTACGCC** | |
| | **TGTTAGGACGTCAGGCCGAGATGTGGGGCGATCTGCT** | |
| | **TGACCAGGGCCAGCTGGTGTTTGTGGAGGGCCGCCTT** | |
| | **GAGTATCGTCAATCGTGGGAAGAAGGTGAAAAACGCT** | |
| | **CCGAACTGCAGATTCGCGCTGATTTCCTCGATCCGTT** | |

TABLE 5-continued

Nucleic Acid Sequence of Exemplary SSBs

| SSB | Nucleic Acid Sequence | SEQ ID NO |
|---|---|---|
| | **GGATGATCGCGGTAAGGAACGCGCAGAAGATAGCCGG<br>GGTCAGCCACGGCTCCGTGCCGCGCTGAACCAGGTAT<br>TTTTAATGGGCAATCTGACCCGCGATCCCGAACTGCG<br>CTACACTCCACAGGGCACCGCAGTCGCTCGTTTAGGC<br>CTGGCTGTGAACGAACGCCGTCAGGGCGCGGAAGAAC<br>GTACCCACTTCGTTGAAGTCCAGGCCTGGCGCGACTT<br>AGCAGAGTGGGCCGCAGAGCTGCGTAAGGGTGACGGC<br>CTGTTCGTTATCGGGCGTCTCGTTAACGACTCTTGGA<br>CTAGCTCGTCAGGTGAGCGTCGCTTTCAAACCCGTGT<br>CGAAGCCCTGCGGCTGGAACGCCCAACGCGGGGTCCG<br>GCACAGGCCGGCGGGTCGCGCTCTCGCGAGGCACAGA<br>CAGGCGGGGTTGATATTGACGAAGGGTTAGAGGATTT<br>CCCGCCAGAGGAGGAGCTGCCTTTTTAG** | |
| TneSSB<br>*Thermotoga neapolitana* | ATGGGATCCTTCTTTAACCGTATTATTTTAATTGGCC<br>GCCTGGTTCGGGATCCTGAAGAACGCTATACCCTGTC<br>AGGGACTCCGGTGACGACTTTTACTATCGCGGTCGAT<br>CGCGTTCCTCGTAAGAATGCCCCTGATGATGCCCAGA<br>CAACTGACTTTTTTCGTGTTGTAACCTTTGGTCGCTT<br>GGCGGAATTCGCACGGACGTATCTGACCAAAGGCCGC<br>CTTATCCTGGTCGAGGGTGAAATGCGCATGCGTCGCT<br>GGGAAACCCAGACTGGCGAAAAACGCGTGAGCCCGGA<br>AGTAGTTGCAAATGTCGTGCGTTTTATGGACCGCAAA<br>CCCGTGGAAATGCCGAGCGAAGACATTGAAGAAAAAC<br>TGGAAATTCCCGAAGAAGACTTTACGGACGATACGTT<br>TTCGGAGGATGAACCCCCGTTTTAG | 48 |
| TneSSB<br>*Thermotoga neapolitana*<br>Construct Sequence<br>*Italicized: His tag*<br>Underlined: GST<br>**Bold: TneSSB** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT<br>GCGTTCCCAAAATTAGTTTGTTTTAAAAAACGTATTG<br>AAGCTATCCCACAAATTGATAAGTACTTGAAATCCAG<br>CAAGTATATAGCATGGCCTTTGCAGGGCTGGCAAGCC<br>ACGTTTGGTGGTGGCGACCATCCTCCAACTAGTGGAT<br>CTGGTGGTGGTGGCGGATGGATGAGCGAGAATCTTTA<br>TTTTCAGGGCGCC**ATGGGATCCTTCTTTAACCGTATT**<br>**ATTTTAATTGGCCGCCTGGTTCGGGATCCTGAAGAAC**<br>**GCTATACCCTGTCAGGGACTCCGGTGACGACTTTTAC**<br>**TATCGCGGTCGATCGCGTTCCTCGTAAGAATGCCCCT**<br>**GATGATGCCCAGACAACTGACTTTTTTCGTGTTGTAA**<br>**CCTTTGGTCGCTTGGCGGAATTCGCACGGACGTATCT**<br>**GACCAAAGGCCGCCTTATCCTGGTCGAGGGTGAAATG**<br>**CGCATGCGTCGCTGGGAAACCCAGACTGGCGAAAAAC**<br>**GCGTGAGCCCGGAAGTAGTTGCAAATGTCGTGCGTTT**<br>**TATGGACCGCAAACCCGTGGAAATGCCGAGCGAAGAC**<br>**ATTGAAGAAAAACTGGAAATTCCCGAAGAAGACTTTA**<br>**CGGACGATACGTTTTCGGAGGATGAACCCCCGTTTTA**<br>**G** | 49 |

III. HELICASE POLYPEPTIDES

In some embodiments, described herein are fusion proteins that comprise a helicase polypeptide. In some embodiments, described herein are methods of engineering cells comprising introducing into a cell an Ago (e.g., described herein) and a helicase (e.g., as described herein). Such introduction can be made by separately introducing an Ago and helicase; or by introducing a fusion polypeptide (or nucleic acid encoding said polypeptide) that comprises both an Ago polypeptide and a helicase (e.g., Ago-helicase fusions described herein).

In some embodiments, the helicase polypeptide component of an Ago-helicase fusion comprises a helicase polypeptide described herein (or a functional fragment or functional variant thereof). In some embodiments, the helicase polypeptide component of an Ago-helicase fusion comprises a helicase derived from a microorganism. In some embodiments, the microorganism is a bacterium. In some embodiments, the microorganism is a hyperthermophilic microorganism. In some embodiments, the helicase is active at a temperature between 32° C.-42° C. In some embodiments, the helicase is active at a temperature between 35° C.-40° C. In some embodiments, the helicase is active at about 37° C.

In some embodiments, the helicase has an amino acid sequence with at least 80%, 85%, 90%, 91%, 92%, 93%, 94%, 95%, 96%, 97%, 98%, 99%, or 100% identity to one of SEQ ID NOS: 50-59. In some embodiments, the helicase is encoded by a nucleic acid sequence with at least 80%, 85%, 90%, 91%, 92%, 93%, 94%, 95%, 96%, 97%, 98%, 99%, or 100% identity to one of SEQ ID NOS: 60-69. In some embodiments, the helicase has an amino acid sequence with at least 80%, 85%, 90%, 91%, 92%, 93%, 94%, 95%, 96%, 97%, 98%, 99%, or 100% identity to one of SEQ ID NOS: 50, 52, 54, 56, or 58. In some embodiments, the helicase is encoded by a nucleic acid sequence with at least 80%, 85%, 90%, 91%, 92%, 93%, 94%, 95%, 96%, 97%, 98%, 99%, or 100% identity to one of SEQ ID NOS: 60, 62, 64, 66, or 68. In some embodiments, the helicase polypeptide is one selected from Table 6 or Table 7. In some embodiments, the helicase is Eco RecQ, Tth UvrD, Eco UvrD, HEL #100, HEL #75, or HEL #76. Table 6. Amino Acid Sequence of Exemplary Helicases Helicase Amino Acid Sequence SEQ ID NO

TABLE 6

Amino Acid Sequence of Exemplary Helicases

| Helicase | Amino Acid Sequence | SEQ ID NO |
|---|---|---|
| Eco RecQ<br>*Escherichia coli* | MAQAEVLNLESGAKQVLQETFGYQQFRPGQEEIIDTV<br>LSGRDCLVVMPTGGGKSLCYQIPALLLNGLTVVVSPL<br>ISLMKDQVDQLQANGVAAACLNSTQTREQQLEVMTGC<br>RTGQIRLLYIAPERLMLDNFLEHLAHWNPVLLAVDEA<br>HCISQWGHDFRPEYAALGQLRQRFPTLPFMALTATAD<br>DTTRQDIVRLLGLNDPLIQISSFDRPNIRYMLMEKFK<br>PLDQLMRYVQEQRGKSGIIYCNSRAKVEDTAARLQSK<br>GISAAAYHAGLENNVRADVQEKFQRDDLQIVVATVAF<br>GMGINKPNVRFVVHFDIPRNIESYYQETGRAGRDGLP<br>AEAMLFYDPADMAWLRRCLEEKPQGQLQDIERHKLNA<br>MGAFAEAQTCRRLVLLNYFGEGRQEPCGNCDICLDPP<br>KQYDGSTDAQIALSTIGRVNQRFGMGYVVEVIRGANN<br>QRIRDYGHDKLKVYGMGRDKSHEHWVSVIRQLIHLGL<br>VTQNIAQHSALQLTEAARPVLRGESSLQLAVPRIVAL<br>KPKAMQKSFGGNYDRKLFAKLRKLRKSIADESNVPPY<br>VVFNDATLIEMAEQMPITASEMLSVNGVGMRKLERFG<br>KPFMALIRAHVDGDDEE | 50 |
| Eco RecQ<br>*Escherichia coli*<br>Construct Sequence<br>*Italicized: His tag*<br>Underlined: GST<br>**Bold: EcoReq** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGALA**MAQAEV**<br>**LNLESGAKQVLQETFGYQQFRPGQEEIIDTVLSGRDC**<br>**LVVMPTGGGKSLCYQIPALLLNGLTVVVSPLISLMKD**<br>**QVDQLQANGVAAACLNSTQTREQQLEVMTGCRTGQIR**<br>**LLYIAPERLMLDNFLEHLAHWNPVLLAVDEAHCISQW**<br>**GHDFRPEYAALGQLRQRFPTLPFMALTATADDTTRQD**<br>**IVRLLGLNDPLIQISSFDRPNIRYMLMEKFKPLDQLM**<br>**RYVQEQRGKSGIIYCNSRAKVEDTAARLQSKGISAAA**<br>**YHAGLENNVRADVQEKFQRDDLQIVVATVAFGMGINK**<br>**PNVREVVHFDIPRNIESYYQETGRAGRDGLPAEAMLF**<br>**YDPADMAWLRRCLEEKPQGQLQDIERHKLNAMGAFAE**<br>**AQTCRRLVLLNYFGEGRQEPCGNCDICLDPPKQYDGS**<br>**TDAQIALSTIGRVNQRFGMGYVVEVIRGANNQRIRDY**<br>**GHDKLKVYGMGRDKSHEHWVSVIRQLIHLGLVTQNIA**<br>**QHSALQLTEAARPVLRGESSLQLAVPRIVALKPKAMQ**<br>**KSFGGNYDRKLFAKLRKLRKSIADESNVPPYVVFNDA**<br>**TLIEMAEQMPITASEMLSVNGVGMRKLERFGKPFMAL**<br>**IRAHVDGDDEE** | 51 |
| Tth UvrD<br>*Thermus Thermophilus* | MSDALLAPLNEAQRQAVLHFEGPALVVAGAGSGKTRT<br>VVHRVAYLVARRGVFPSEILAVTFTNKAAEEMRERLR<br>GLVPGAGEVWVSTFHAAALRILRVYGERVGLRPGFVV<br>YDEDDQTALLKEVLKELALSARPGPIKALLDRAKNRG<br>VGLKALLGELPEYYAGLSRGRLGDVLVRYQEALKAQG<br>ALDFGDILLYALEAFRGGRGGPQARAQRARFIHVDEY<br>QDTSPVQYRFTRLLAGEEANLMAVGDPDQGIYSFRAA<br>DIKNILDFTRDYPEARVYRLEENYRSTEAILRFANAV<br>IVKNALRLEKALRPVKRGGEPVRLYRAEDAREEARFV<br>AEEIARLGPPWDRYAVLYRTNAQSRLLEQALAGRGIP<br>ARVVGGVGFFERAEVKDLLAYARLALNPLDAVSLKRV<br>LNTPPRGIGPATWARVQLLAQEKGLPPWEALKEAART<br>FSRPEPLRHFVALVEELQDLVFGPAEAFFRHLLEATD<br>YPAYLREAYPEDAEDRLENVEELLRAAKEAEDLQDFL<br>DRVALTAKAEEPAEAEGRVALMTLHNAKGLEFPVVFL | 52 |

TABLE 6-continued

Amino Acid Sequence of Exemplary Helicases

| Helicase | Amino Acid Sequence | SEQ ID NO |
|---|---|---|
| | VGVEEGLLPHRNSVSTLEGLEEERRLFYVGITRAQER<br>LYLSHAEEREVYGRREPARPSRFLEEVEEGLYEVYDP<br>YRRPPSPPPHRPRPGAFRGGERVVHPRFGPGTVVAAQ<br>GDEVTVHFEGFGLKRLSLKYAELKPA | |
| Tth UvrD<br>*Thermus Thermophilus*<br>Construct Sequence<br>*Italicized: His tag*<br><u>Underlined: GST</u><br>**Bold: Tht UvrD** | MKHHHHHHNTSSNSM<u>SPILGYWKIKGLVQPTRLLLEY</u><br><u>LEEKYEEHLYERDEGDKWRNKKFELGLEFPNLPYYID</u><br><u>GDVKLTQSMAIIRYIADKHNMLGGCPKERAEISMLEG</u><br><u>AVLDIRYGVSRIAYSKDFETLKVDFLSKLPEMLKMFE</u><br><u>DRLCHKTYLNGDHVTHPDFMLYDALDVVLYMDPMCLD</u><br><u>AFPKLVCFKKRIEAIPQIDKYLKSSKYIAWPLQGWQA</u><br><u>TFGGGDHPP</u>TSGSGGGGGWMSENLYFQGALAMSDALL<br>**APLNEAQRQAVLHFEGPALVVAGAGSGKTRTVVHRVA**<br>**YLVARRGVFPSEILAVTFTNKAAEEMRERLRGLVPGA**<br>**GEVWVSTFHAAALRILRVYGERVGLRPGFVVYDEDDQ**<br>**TALLKEVLKELALSARPGPIKALLDRAKNRGVGLKAL**<br>**LGELPEYYAGLSRGRLGDVLVRYQEALKAQGALDFGD**<br>**ILLYALEAFRGGRGGPQARAQRARFIHVDEYQDTSPV**<br>**QYRFTRLLAGEEANLMAVGDPDQGIYSFRAADIKNIL**<br>**DFTRDYPEARVYRLEENYRSTEAILRFANAVIVKNAL**<br>**RLEKALRPVKRGGEPVRLYRAEDAREEARFVAEEIAR**<br>**LGPPWDRYAVLYRTNAQSRLLEQALAGRGIPARVVGG**<br>**VGFFERAEVKDLLAYARLALNPLDAVSLKRVLNTPPR**<br>**GIGPATWARVQLLAQEKGLPPWEALKEAARTFSRPEP**<br>**LRHFVALVEELQDLVFGPAEAFFRHLLEATDYPAYLR**<br>**EAYPEDAEDRLENVEELLRAAKEAEDLQDFLDRVALT**<br>**AKAEEPAEAEGRVALMTLHNAKGLEFPVVFLVGVEEG**<br>**LLPHRNSVSTLEGLEEERRLFYVGITRAQERLYLSHA**<br>**EEREVYGRREPARPSRFLEEVEEGLYEVYDPYRRPPS**<br>**PPPHRPRPGAFRGGERVVHPRFGPGTVVAAQGDEVTV**<br>**HFEGFGLKRLSLKYAELKPA** | 53 |
| Eco UvrD<br>*Escherichia coli* | MDVSYLLDSLNDKQREAVAAPRSNLLVLAGAGSGKTR<br>VLVHRIAWLMSVENCSPYSIMAVTFTNKAAAEMRHRI<br>GQLMGTSQGGMWVGTFHGLAHRLLRAHHMDANLPQDF<br>QILDSEDQLRLLKRLIKAMNLDEKQWPPRQAMWYINS<br>QKDEGLRPHHIQSYGNPVEQTWQKVYQAYQEACDRAG<br>LVDFAELLLRAHELWLNKPHILQHYRERFTNILVDEF<br>QDTNNIQYAWIRLLAGDTGKVMIVGDDDQSIYGWRGA<br>QVENIQRFLNDFPGAETIRLEQNYRSTSNILSAANAL<br>IENNNGRLGKKLWTDGADGEPISLYCAFNELDEARFV<br>VNRIKTWQDNGGALAECAILYRSNAQSRVLEEALLQA<br>SMPYRIYGGMRFFERQEIKDALSYLRLIANRNDDAAF<br>ERVVNTPTRGIGDRTLDVVRQTSRDRQLTLWQACREL<br>LQEKALAGRAASALQRFMELIDALAQETADMPLHVQT<br>DRVIKDSGLRTMYEQEKGEKGQTRIENLEELVTATRQ<br>FSYNEEDEDLMPLQAFLSHAALEAGEGQADTWQDAVQ<br>LMTLHSAKGLEFPQVFIVGMEEGMFPSQMSLDEGGRL<br>EEERRLAYVGVTRAMQKLTLTYAETRRLYGKEVYHRP<br>SRFIGELPEECVEEVRLRATVSRPVSHQRMGTPMVEN<br>DSGYKLGQRVRHAKFGEGTIVNMEGSGEHSRLQVAFQ<br>GQGIKWLVAAYARLESV | 54 |
| Eco UvrD<br>*Escherichia coli*<br>Construct Sequence<br>*Italicized: His tag*<br><u>Underlined: GST</u><br>**Bold: Eco UvrD** | MKHHHHHHNTSSNSM<u>SPILGYWKIKGLVQPTRLLLEY</u><br><u>LEEKYEEHLYERDEGDKWRNKKFELGLEFPNLPYYID</u><br><u>GDVKLTQSMAIIRYIADKHNMLGGCPKERAEISMLEG</u><br><u>AVLDIRYGVSRIAYSKDFETLKVDFLSKLPEMLKMFE</u><br><u>DRLCHKTYLNGDHVTHPDFMLYDALDVVLYMDPMCLD</u><br><u>AFPKLVCFKKRIEAIPQIDKYLKSSKYIAWPLQGWQA</u><br><u>TFGGGDHPP</u>TSGSGGGGGWMSENLYFQGALAMDVSYL<br>**LDSLNDKQREAVAAPRSNLLVLAGAGSGKTRVLVHRI**<br>**AWLMSVENCSPYSIMAVTFTNKAAAEMRHRIGQLMGT**<br>**SQGGMWVGTFHGLAHRLLRAHHMDANLPQDFQILDSE**<br>**DQLRLLKRLIKAMNLDEKQWPPRQAMWYINSQKDEGL**<br>**RPHHIQSYGNPVEQTWQKVYQAYQEACDRAGLVDFAE**<br>**LLLRAHELWLNKPHILQHYRERFTNILVDEFQDTNNI**<br>**QYAWIRLLAGDTGKVMIVGDDDQSIYGWRGAQVENIQ**<br>**RFLNDFPGAETIRLEQNYRSTSNILSAANALIENNNG**<br>**RLGKKLWTDGADGEPISLYCAFNELDEARFVVNRIKT**<br>**WQDNGGALAECAILYRSNAQSRVLEEALLQASMPYRI**<br>**YGGMRFFERQEIKDALSYLRLIANRNDDAAFERVVNT**<br>**PIRGIGDRTLDVVRQTSRDRQLTLWQACRELLQEKAL**<br>**AGRAASALQRFMELIDALAQETADMPLHVQTDRVIKD**<br>**SGLRTMYEQEKGEKGQTRIENLEELVTATRQFSYNEE**<br>**DEDLMPLQAFLSHAALEAGEGQADTWQDAVQLMTLHS** | 55 |

TABLE 6-continued

Amino Acid Sequence of Exemplary Helicases

| Helicase | Amino Acid Sequence | SEQ ID NO |
| --- | --- | --- |
| | **AKGLEFPQVFIVGMEEGMFPSQMSLDEGGRLEEERRL**<br>**AYVGVTRAMQKLTLTYAETRRLYGKEVYHRPSRFIGE**<br>**LPEECVEEVRLRATVSRPVSHQRMGTPMVENDSGYKL**<br>**GQRVRHAKFGEGTIVNMEGSGEHSRLQVAFQGQGIKW**<br>**LVAAYARLESV** | |
| HEL#100<br>*Clostridium*<br>*perfringens* | MVLNPKYSIGVYYDELVEEDIEKVYSYLSRGIVVHLF<br>LRGILKEELELNEYDLNTFKLPKDNNLLFVYEEETSL<br>SSENIIIFVDNNILNKEAYKNITENRECEFNKDQYEI<br>ITAPVDDNIIVISGAGIGKITTMINRLIYLRSVMSDF<br>TFDQAVLITFTNKASIEMKERLLEVLDKYFRVTNDIK<br>YLDYMEEAAKGSISTIHKFAKKILNKSGRHIGINKDI<br>NVRSFKYKRQEAVNNALNKIYKEESELFSLIKYYPIY<br>EVERVILKMWEILDNYSIDLLSNK<br>VRVDFNFEEDKFTELISKTLKYAQEILDYDKENELEI<br>SDLMKKLAYEDIFKGIDSTYKVIMIDEFQDSDNTQIE<br>FISELEKKTGARILVVGDEKQSIYRFRGAEYTAFDKL<br>KKLLSNSKREVKEYEMTRNYRTNYNILNEINRIFIEV<br>DKKLECFNYKEKDYIYSNKDKDNPKEITCFNVSDNLK<br>RKEFFDDLLENKKEDESIAVLFRSN<br>SDIKEFKEFCDRNNILCMVDSTGGFYRHEAVRDFYIM<br>IKSIIDERNSRTMYSFINTPYILEDIDKNIILNGNSK<br>DKNEFLYYILEKNNWNYFRESSNFKNPIILIDEIIEK<br>LKPVKNYYVKVLLEAKKNQHNYVNIAKMKALEYKLNL<br>EHLVFILKKEFSENITSIEQIEQFLKVKISTDNLVDV<br>RKPKDYENDYIQCSTVHKAKGLEYDYVVLDKLTNRFL<br>SNSRKVNLILKPDGDKLLIGYKIRLGEDEFKNKIYSD<br>NLKYEKKEIKGEEARLLYVAL<br>TRCKKGIYLNMSGELAATESLNTWKSLIGGTINYV | 56 |
| HEL#100<br>*Clostridium*<br>*perfringens*<br>Construct Sequence<br>*Italicized: His tag*<br>Underlined: GST<br>**Bold: Hel#100** | MK*HHHHHH*NTSSNSMSPILGYWKIKGLVQPTRLLLEY<br>LEEKYEEHLYERDEGDKWRNKKFELGLEFPNLPYYID<br>GDVKLTQSMAIIRYIADKHNMLGGCPKERAEISMLEG<br>AVLDIRYGVSRIAYSKDFETLKVDFLSKLPEMLKMFE<br>DRLCHKTYLNGDHVTHPDFMLYDALDVVLYMDPMCLD<br>AFPKLVCFKKRIEAIPQIDKYLKSSKYIAWPLQGWQA<br>TFGGGDHPPTSGSGGGGGWMSENLYFQGALA**MVLNPK**<br>**YSIGVYYDELVEEDIEKVYSYLSRGIVVHLFLRGILK**<br>**EELELNEYDLNTFKLPKDNNLLFVYEEETSLSSENII**<br>**IFVDNNILNKEAYKNITENRECEFNKDQYEIITAPVD**<br>**DNIIVTSGAGIGKITTMINRLIYLRSVMSDFTEDQAV**<br>**LITFTNKASIEMKERLLEVLDKYFRVINDIKYLDYME**<br>**EAAKGSISTIHKFAKKILNKSGRHIGINKDINVRSFK**<br>**YKRQEAVNNALNKIYKEESELFSLIKYYPIYEVERVI**<br>**LKMWEILDNYSIDLLSNKVRVDFNFEEDKFTELISKT**<br>**LKYAQEILDYDKENELEISDLMKKLAYEDIFKGIDST**<br>**YKVIMIDEFQDSDNTQIEFISELEKKTGARILVVGDE**<br>**KQSIYRFRGAEYTAFDKLKKLLSNSKREVKEYEMTRN**<br>**YRTNYNILNEINRIFIEVDKKLECFNYKEKDYIYSNK**<br>**DKDNPKEITCFNVSDNLKRKEFFDDLLENKKEDESIA**<br>**VLFRSNSDIKEFKEFCDRNNILCMVDSTGGFYRHEAV**<br>**RDFYIMIKSIIDERNSRTMYSFINTPYILEDIDKNII**<br>**LNGNSKDKNEFLYYILEKNNWNYFRESSNFKNPIILI**<br>**DEIIEKLKPVKNYYVKVLLEAKKNQHNYVNIAKMKAL**<br>**EYKLNLEHLVFILKKEFSENITSIEQIEQFLKVKIST**<br>**DNLVDVRKPKDYENDYIQCSTVHKAKGLEYDYVVLDK**<br>**LTNRFLSNSRKVNLILKPDGDKLLIGYKIRLGEDEFK**<br>**NKIYSDNLKYEKKEIKGEEARLLYVALTRCKKGIYLN**<br>**MSGELAATESLNTWKSLIGGTINYV** | 57 |
| HEL#75<br>*Clostridium*<br>*perfringens* | MLGLNNESKEFFKGISRIWRNYKDYTYLDGIKLSQAQ<br>IDIIEKEEDQLLIEGYAGTGKSLTLIYKFINVLVRED<br>GKRVLYVTFNDTLIEDTKKRLSYCNEYNENKERHHVE<br>ICTFHEIASNILKKKKIIDRGIEKLTAKKIEDYKGAA<br>LRRIAGILARYIEGGKYYSELPKEERLYKTHDENFIR<br>EEVAWIKAMGFIEKEKYFEKDRIGRSKSIRLTRSQRK<br>TIFKIFEKYCEEQENKFFKSLDLEDYALKLIQNIDNF<br>DDLKFDYIFVDEVQDLDPMQIKALCLLTNTSIVLSGD<br>ANQRIYKKSPVKYEELGLRIKEKGKRKILNKNYRSTG<br>EIVKLANSIKFFDESINKYNEKQFVKSGDRPIIRKVN<br>DKKGAVKFLIGEIKKIHEEDPYKTIAIIHREKNELIG<br>FQKSEFRKYLEGQLYMEKFSDIKSFESKFDLREKNQV<br>FYTNGYDVKGLEFDVVFIINFNTANYPLSKELKKIKD<br>ENDGKEMTLIKDDVLEFINREKRLLYVAMTRAKEKLY<br>LVADCKNSNISSFIYDFNTKYYEAQNFKKKEIEENYN | 58 |

TABLE 6-continued

| Amino Acid Sequence of Exemplary Helicases | | |
|---|---|---|
| Helicase | Amino Acid Sequence | SEQ ID NO |
| | RYKINMEREYGIIIEDDDSNNVKNNDTKQENKFNTES KEKGKDDIDKIKVFFINKGIEVVDNRDKSGCLWIVAG KEAIPLMKKFGVLGYNFIFIANGGRASKNRPAWYLKN S | |
| HEL#75 *Clostridium perfringens* Construct Sequence *Italicized: His tag* Underlined: GST **Bold/Underlined: 2xSV40 NLS** **Bold: Hel#75** | MK*HHHHHH*NTSSNSMSPILGYWKIKGLVQPTRLLLEY LEEKYEEHLYERDEGDKWRNKKFELGLEFPNLPYYID GDVKLTQSMAIIRYIADKHNMLGGCPKERAEISMLEG AVLDIRYGVSRIAYSKDFETLKVDFLSKLPEMLKMFE DRLCHKTYLNGDHVTHPDFMLYDALDVVLYMDPMCLD AFPKLVCFKKRIEAIPQIDKYLKSSKYIAWPLQGWQA TFGGGDHPPTSGSGGGGGWMSENLYFQGA**MPKKKRKV EDPKKKRKV**GSGS**LGLNNESKEFFKGISRIWRNYKDY TYLDGIKLSQAQIDIIEKEEDQLLIEGYAGTGKSLTL IYKFINVLVREDGKRVLYVTENDTLIEDTKKRLSYCN EYNENKERHHVEICTFHEIASNILKKKKIIDRGIEKL TAKKIEDYKGAALRRIAGILARYIEGGKYYSELPKEE RLYKTHDENFIREEVAWIKAMGFIEKEKYFEKDRIGR SKSIRLTRSQRKTIFKIFEKYCEEQENKFFKSLDLED YALKLIQNIDNEDDLKEDYIFVDEVQDLDPMQIKALC LLTNTSIVLSGDANQRIYKKSPVKYEELGLRIKEKGK RKILNKNYRSTGEIVKLANSIKFFDESINKYNEKQFV KSGDRPIIRKVNDKKGAVKFLIGEIKKIHEEDPYKTI AIIHREKNELIGFQKSEFRKYLEGQLYMEKESDIKSF ESKFDLREKNQVFYINGYDVKGLEFDVVFIINFNTAN YPLSKELKKIKDENDGKEMTLIKDDVLEFINREKRLL YVAMTRAKEKLYLVADCKNSNISSFIYDFNTKYYEAQ NFKKKEIEENYNRYKINMEREYGIIIEDDDSNNVKNN DTKQENKFNTESKEKGKDDIDKIKVFFINKGIEVVDN RDKSGCLWIVAGKEAIPLMKKFGVLGYNFIFIANGGR ASKNRPAWYLKNS** | 59 |

TABLE 7

| Nucleic Acid Sequence of Exemplary Helicases | | |
|---|---|---|
| Helicase | Nucleic Acid Sequence | SEQ ID NO |
| Eco RecQ *Escherichia coli* | ATGGCACAGGCAGAAGTTCTGAACCTGGAATCCGGTG CTAAACAAGTATTACAGGAGACCTTCGGTTATCAGCA GTTCCGTCCCGGACAAGAAGAAATTATTGATACCGTA CTGTCCGGTCGTGATTGTTTGGTAGTCATGCCAACTG GTGGAGGAAAGAGCCTGTGCTATCAAATCCCTGCCTT ATTATTGAATGGGTTAACGGTAGTCGTATCACCATTA ATTTCTTTGATGAAGGATCAAGTTGATCAGCTTCAGG CGAATGGTGTAGCAGCTGCATGCCTTAATAGTACCCA AACACGCGAGCAACAGTTAGAAGTGATGACAGGTTGT CGTACGGGCCAAATTCGCCTGTTGTACATCGCCCCCG AACGTCTGATGCTGGACAATTTTTTAGAGCACCTGGC TCACTGGAATCCAGTTTTGCTGGCGGTGGACGAGGCA CACTGTATCAGTCAGTGGGGGCACGACTTCCGCCCTG AGTATGCTGCCCTGGGTCAGTTGCGTCAGCGTTTTCC TACCCTGCCTTTTATGGCTCTGACGGCGACTGCTGAC GACACAACTCGTCAGGATATCGTACGCCTGTTAGGAT TGAATGACCCACTGATCCAGATCAGTTCGTTTGACCG CCCAAATATCCGCTATATGTTAATGGAAAAATTTAAA CCCTTGGATCAATTAATGCGCTACGTACAAGAGCAGC GTGGTAAGAGCGGCATTATTTACTGTAACAGTCGCGC GAAGGTTGAGGACACAGCGGCACGCCTGCAGAGCAAA GGCATTTCAGCGGCGGCATACCATGCAGGTTTGGAGA ACAATGTACGCGCAGACGTTCAGGAGAAGTTCCAGCG CGATGATTTGCAGATCGTTGTGGCCACTGTAGCGTTC GGTATGGGGATCAACAAACCTAATGTACGTTTCGTTG TCCACTTTGACATCCCACGCAATATTGAGAGCTACTA TCAAGAGACCGGACGCGCAGGGCGTGATGGTTTACCA GCCGAGGCCATGTTGTTCTACGATCCGGCTGATATGG CCTGGCTGCGTCGCTGTTTGGAGGAAAAACCTCAAGG TCAGTTGCAAGACATCGAACGCCACAAATTAAATGCT ATGGGTGCGTTTGCCGAAGCTCAAACATGCCGTCGCT TAGTTTTACTTAATTATTTGGTGAGGGGCGTCAGGA GCCGTGTGGTAATTGCGATATTTGCTTGGACCCTCCT | 60 |

TABLE 7-continued

Nucleic Acid Sequence of Exemplary Helicases

| Helicase | Nucleic Acid Sequence | SEQ ID NO |
|---|---|---|
| | AAACAATATGACGGGTCAACAGACGCCCAGATTGCGT<br>TATCGACTATTGGACGCGTCAATCAGCGTTTTGGTAT<br>GGGGTACGTGGTCGAAGTAATTCGTGGAGCAAATAAC<br>CAACGTATCCGTGATTATGGGCACGATAAACTGAAAG<br>TATACGGTATGGGTCGCGATAAGAGTCATGAGCACTG<br>GGTGTCAGTCATCCGCCAATTAATTCACCTTGGTCTG<br>GTTACACAAAACATCGCGCAACACTCTGCACTGCAGC<br>TTACTGAAGCCGCTCGTCCTGTATTGCGTGGTGAGAG<br>CAGTCTGCAGTTGGCCGTGCCCCGCATTGTGGCCTTG<br>AAACCAAAAGCCATGCAGAAAAGCTTTGGGGGAAATT<br>ATGATCGCAAATTGTTTGCCAAGCTTCGCAAACTGCG<br>CAAATCAATCGCGGATGAGTCAAACGTACCACCGTAT<br>GTTGTCTTCAATGACGCAACTTTAATCGAGATGGCGG<br>AGCAAATGCCAATCACAGCTTCAGAGATGCTGAGTGT<br>AAATGGCGTTGGCATGCGCAAGCTTGAGCGCTTCGGA<br>AAGCCGTTCATGGCATTAATTCGCGCCCACGTCGATG<br>GGGATGACGAGGAGTAGTGA | |
| Eco RecQ<br>*Escherichia coli*<br>Construct Sequence<br>*Italicized: His tag*<br>Underlined: GST<br>**Bold: EcoReq** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT<br>GCGTTCCCAAAATTAGTTTGTTTTAAAAAACGTATTG<br>AAGCTATCCCACAAATTGATAAGTACTTGAAATCCAG<br>CAAGTATATAGCATGGCCTTTGCAGGGCTGGCAAGCC<br>ACGTTTGGTGGTGGCGACCATCCTCCAACTAGTGGAT<br>CTGGTGGTGGTGGCGGATGGATGAGCGAGAATCTTTA<br>TTTTCAGGGCGCGCTAGCA**ATGGCACAGGCAGAAGTT**<br>**CTGAACCTGGAATCCGGTGCTAAACAAGTATTACAGG**<br>**AGACCTTCGGTTATCAGCAGTTCCGTCCCGGACAAGA**<br>**AGAAATTATTGATACCGTACTGTCCGGTCGTGATTGT**<br>**TTGGTAGTCATGCCAACTGGTGGAGGAAAGAGCCTGT**<br>**GCTATCAAATCCCTGCCTTATTATTGAATGGGTTAAC**<br>**GGTAGTCGTATCACCATTAATTTCTTTGATGAAGGAT**<br>**CAAGTTGATCAGCTTCAGGCGAATGGTGTAGCAGCTG**<br>**CATGCCTTAATAGTACCCAAACACGCGAGCAACAGTT**<br>**AGAAGTGATGACAGGTTGTCGTACGGGCCAAATTCGC**<br>**CTGTTGTACATCGCCCCCGAACGTCTGATGCTGGACA**<br>**ATTTTTTAGAGCACCTGGCTCACTGGAATCCAGTTTT**<br>**GCTGGCGGTGGACGAGGCACACTGTATCAGTCAGTGG**<br>**GGGCACGACTTCCGCCCTGAGTATGCTGCCCTGGGTC**<br>**AGTTGCGTCAGCGTTTTCCTACCCTGCCTTTTATGGC**<br>**TCTGACGGCGACTGCTGACGACACAACTCGTCAGGAT**<br>**ATCGTACGCCTGTTAGGATTGAATGACCCACTGATCC**<br>**AGATCAGTTCGTTTGACCGCCCAAATATCCGCTATAT**<br>**GTTAATGGAAAAATTTAAACCCTTGGATCAATTAATG**<br>**CGCTACGTACAAGAGCAGCGTGGTAAGAGCGGCATTA**<br>**TTTACTGTAACAGTCGCGCGAAGGTTGAGGACACAGC**<br>**GGCACGCCTGCAGAGCAAAGGCATTTCAGCGGCGGCA**<br>**TACCATGCAGGTTTGGAGAACAATGTACGCGCAGACG**<br>**TTCAGGAGAAGTTCCAGCGCGATGATTTGCAGATCGT**<br>**TGTGGCCACTGTAGCGTTCGGTATGGGGATCAACAAA**<br>**CCTAATGTACGTTTCGTTGTCCACTTTGACATCCCAC**<br>**GCAATATTGAGAGCTACTATCAAGAGACCGGACGCGC**<br>**AGGGCGTGATGGTTTACCAGCCGAGGCCATGTTGTTC**<br>**TACGATCCGGCTGATATGGCCTGGCTGCGTCGCTGTT**<br>**TGGAGGAAAAACCTCAAGGTCAGTTGCAAGACATCGA**<br>**ACGCCACAAATTAAATGCTATGGGTGCGTTTGCCGAA**<br>**GCTCAAACATGCCGTCGCTTAGTTTTACTTAATTATT**<br>**TTGGTGAGGGGCGTCAGGAGCCGTGTGGTAATTGCGA**<br>**TATTTGCTTGGACCCTCCTAAACAATATGACGGGTCA**<br>**ACAGACGCCCAGATTGCGTTATCGACTATTGGACGCG**<br>**TCAATCAGCGTTTTGGTATGGGGTACGTGGTCGAAGT**<br>**AATTCGTGGAGCAAATAACCAACGTATCCGTGATTAT** | 61 |

TABLE 7-continued

Nucleic Acid Sequence of Exemplary Helicases

| Helicase | Nucleic Acid Sequence | SEQ ID NO |
|---|---|---|
| | **GGGCACGATAAACTGAAAGTATACGGTATGGGTCGCG** | |
| | **ATAAGAGTCATGAGCACTGGGTGTCAGTCATCCGCCA** | |
| | **ATTAATTCACCTTGGTCTGGTTACACAAAACATCGCG** | |
| | **CAACACTCTGCACTGCAGCTTACTGAAGCCGCTCGTC** | |
| | **CTGTATTGCGTGGTGAGAGCAGTCTGCAGTTGGCCGT** | |
| | **GCCCCGCATTGTGGCCTTGAAACCAAAAGCCATGCAG** | |
| | **AAAAGCTTTGGGGGAAATTATGATCGCAAATTGTTTG** | |
| | **CCAAGCTTCGCAAACTGCGCAAATCAATCGCGGATGA** | |
| | **GTCAAACGTACCACCGTATGTTGTCTTCAATGACGCA** | |
| | **ACTTTAATCGAGATGGCGGAGCAAATGCCAATCACAG** | |
| | **CTTCAGAGATGCTGAGTGTAAATGGCGTTGGCATGCG** | |
| | **CAAGCTTGAGCGCTTCGGAAAGCCGTTCATGGCATTA** | |
| | **ATTCGCGCCCACGTCGATGGGGATGACGAGGAGTAGT** | |
| | **GA** | |
| Tth UvrD | ATGAAACATCACCATCACCATCACAACACTAGTAGCA | 62 |
| *Thermus Thermophilus* | ATTCCATGTCCCCTATACTAGGTTATTGGAAAATTAA | |
| | GGGCCTTGTGCAACCCACTCGACTTCTTTTGGAATAT | |
| | CTTGAAGAAAAATATGAAGAGCATTTGTATGAGCGCG | |
| | ATGAAGGTGATAAATGGCGAAACAAAAAGTTTGAATT | |
| | GGGTTTGGAGTTTCCCAATCTTCCTTATTATATTGAT | |
| | GGTGATGTTAAATTAACACAGTCTATGGCCATCATAC | |
| | GTTATATAGCTGACAAGCACAACATGTTGGGTGGTTG | |
| | TCCAAAAGAGCGTGCAGAGATTTCAATGCTTGAAGGA | |
| | GCGGTTTTGGATATTAGATACGGTGTTTCGAGAATTG | |
| | CATATAGTAAAGACTTTGAAACTCTCAAAGTTGATTT | |
| | TCTTAGCAAGCTACCTGAAATGCTGAAAATGTTCGAA | |
| | GATCGTTTATGTCATAAAACATATTTAAATGGTGATC | |
| | ATGTAACCCATCCTGACTTCATGTTGTATGACGCTCT | |
| | TGATGTTGTTTTATACATGGACCCAATGTGCCTGGAT | |
| | GCGTTCCCAAAATTAGTTTGTTTTAAAAAACGTATTG | |
| | AAGCTATCCCACAAATTGATAAGTACTTGAAATCCAG | |
| | CAAGTATATAGCATGGCCTTTGCAGGGCTGGCAAGCC | |
| | ACGTTTGGTGGTGGCGACCATCCTCCAACTAGTGGAT | |
| | CTGGTGGTGGTGGCGGATGGATGAGCGAGAATCTTTA | |
| | TTTTCAGGGCGCGCTAGCaATGTCTGACGCCTTGCTG | |
| | GCACCATTAAACGAGGCACAACGCCAAGCCGTCCTGC | |
| | ATTTTGAGGGTCCAGCATTAGTAGTGGCAGGGGCCGG | |
| | ATCGGGGAAGACGCGTACCGTGGTTCACCGCGTCGCA | |
| | TATCTGGTGGCCCGCCGTGGCGTGTTCCCATCCGAGA | |
| | TTCTGGCGGTGACATTCACAAATAAGGCAGCCGAGGA | |
| | GATGCGTGAACGCTTGCGTGGCTTAGTCCCTGGAGCC | |
| | GGAGAAGTCTGGGTTTCGACTTTCCATGCTGCAGCGC | |
| | TGCGTATCTTACGCGTATACGGAGAACGCGTGGGCCT | |
| | GCGTCCCGGGTTCGTCGTATACGATGAGGATGACCAG | |
| | ACAGCATTATTGAAGGAGGTGCTGAAAGAACTGGCTC | |
| | TTTCGGCACGTCCCGGGCCGATTAAGGCATTGTTAGA | |
| | CCGCGCCAAGAATCGTGGTGTTGGCCTGAAAGCCTTA | |
| | CTGGGGGAACTTCCCGAGTACTACGCTGGGTTATCGC | |
| | GCGGTCGTCTGGGAGACGTGCTGGTACGTTACCAGGA | |
| | AGCCCTGAAGGCTCAAGGGGCTTTAGATTTCGGCGAC | |
| | ATTTTGTTGTATGCTCTTGAAGCGTTCCGTGGAGGAC | |
| | GCGGTGGTCCGCAGGCCCGCGCGCAACGTGCACGTTT | |
| | CATCCATGTGGATGAGTACCAGGACACCTCGCCGGTT | |
| | CAGTATCGTTTTACCCGTCTTTTGGCCGGTGAAGAAG | |
| | CAAACCTTATGGCTGTAGGAGACCCCGATCAAGGGAT | |
| | TTACTCTTTCCGCGCAGCGGATATTAAGAACATTTTA | |
| | GACTTCACACGTGATTATCCTGAGGCACGTGTATATC | |
| | GTCTTGAAGAGAACTATCGTTCGACCGAAGCCATTCT | |
| | GCGTTTCGCCAACGCCGTAATCGTCAAAAACGCGCTT | |
| | CGCTTGGAGAAAGCCTTACGCCCCGTCAAACGTGGGG | |
| | GAGAGCCTGTCCGCTTATATCGCGCAGAGGACGCACG | |
| | CGAAGAAGCACGCTTTGTCGCAGAAGAGATTGCTCGT | |
| | TTGGGACCCCCGTGGGATCGCTATGCAGTCTTATACC | |
| | GCACTAATGCTCAAAGCCGCCTTCTGGAACAGGCGTT | |
| | AGCAGGTCGTGGGATCCCCGCACGCGTCGTTGGAGGT | |
| | GTGGGTTTTTTCGAGCGTGCAGAGGTGAAGGACTTGT | |
| | TGGCGTACGCTCGTTTGGCCTTGAATCCCTTGGATGC | |
| | CGTGTCCCTTAAGCGCGTCCTGAACACTCCCCCACGC | |
| | GGTATCGGACCAGCCACGTGGGCCCGCGTGCAGTTAC | |
| | TTGCCCAAGAGAAAGGATTACCCCCCTGGGAGGCTCT | |
| | TAAAGAAGCGGCACGCACCTTTTCTCGCCCAGAACCA | |
| | CTGCGCCATTTCGTAGCCCTTGTTGAAGAGTTGCAAG | |
| | ATTTAGTATTCGGGCCTGCCGAGGCTTTCTTTCGCCA | |
| | CTTGCTGGAGGCGACTGATTACCCCGCCTACCTGCGT | |

TABLE 7-continued

| Nucleic Acid Sequence of Exemplary Helicases | | |
|---|---|---|
| Helicase | Nucleic Acid Sequence | SEQ ID NO |
| | GAAGCGTACCCAGAAGATGCGGAAGACCGCTTGGAAA | |
| | ATGTAGAAGAACTGTTGCGCGCCGCGAAAGAAGCGGA | |
| | GGATCTTCAGGACTTCCTTGATCGTGTCGCACTGACT | |
| | GCCAAGGCCGAGGAGCCGGCCGAAGCAGAAGGACGCG | |
| | TTGCATTGATGACATTGCATAACGCAAAGGGGTTGGA | |
| | GTTTCCAGTCGTTTTCCTGGTTGGCGTAGAGGAAGGG | |
| | TTACTGCCCCACCGTAACTCGGTGTCGACGTTAGAAG | |
| | GACTTGAAGAGGAACGTCGTTTGTTCTATGTCGGTAT | |
| | CACCCGTGCTCAGGAACGTTTGTACCTGTCACATGCG | |
| | GAAGAGCGCGAGGTTTATGGCCGCCGCGAGCCCGCGC | |
| | GTCCGTCCCGCTTTCTTGAAGAGGTTGAAGAGGGTTT | |
| | ATACGAAGTATACGACCCATATCGTCGCCCACCGTCA | |
| | CCCCCTCCACATCGCCCTCGCCCGGGGGCATTTCGTG | |
| | GAGGTGAACGCGTCGTACATCCGCGCTTTGGACCTGG | |
| | CACAGTCGTGGCCGCGCAGGGTGACGAGGTTACGGTC | |
| | CATTTTGAGGGTTTTGGTCTGAAACGCCTTTCATTAA | |
| | AATATGCAGAGCTGAAACCAGCTTAGTGA | |
| Tth UvrD | ATGAAA*CATCACCATCACCATCAC*AACACTAGTAGCA | 63 |
| *Thermus Thermophilus* | ATTCCATGTCCCCTATACTAGGTTATTGGAAAATTAA | |
| Construct Sequence | GGGCCTTGTGCAACCCACTCGACTTCTTTTGGAATAT | |
| *Italicized: His tag* | CTTGAAGAAAAATATGAAGAGCATTTGTATGAGCGCG | |
| Underlined: GST | ATGAAGGTGATAAATGGCGAAACAAAAAGTTTGAATT | |
| **Bold: Tht UvrD** | GGGTTTGGAGTTTCCCAATCTTCCTTATTATATTGAT | |
| | GGTGATGTTAAATTAACACAGTCTATGGCCATCATAC | |
| | GTTATATAGCTGACAAGCACAACATGTTGGGTGGTTG | |
| | TCCAAAAGAGCGTGCAGAGATTTCAATGCTTGAAGGA | |
| | GCGGTTTTGGATATTAGATACGGTGTTTCGAGAATTG | |
| | CATATAGTAAAGACTTTGAAACTCTCAAAGTTGATTT | |
| | TCTTAGCAAGCTACCTGAAATGCTGAAAATGTTCGAA | |
| | GATCGTTTATGTCATAAAACATATTTAAATGGTGATC | |
| | ATGTAACCCATCCTGACTTCATGTTGTATGACGCTCT | |
| | TGATGTTGTTTTATACATGGACCCAATGTGCCTGGAT | |
| | GCGTTCCCAAAATTAGTTTGTTTTAAAAAACGTATTG | |
| | AAGCTATCCCACAAATTGATAAGTACTTGAAATCCAG | |
| | CAAGTATATAGCATGGCCTTTGCAGGGCTGGCAAGCC | |
| | ACGTTTGGTGGTGGCGACCATCCTCCAACTAGTGGAT | |
| | CTGGTGGTGGTGGCGGATGGATGAGCGAGAATCTTTA | |
| | TTTTCAGGGCGCGCTAGCA**ATGAAACATCACCATCAC** | |
| | **CATCACAACACTAGTAGCAATTCCATGTCCCCTATAC** | |
| | **TAGGTTATTGGAAAATTAAGGGCCTTGTGCAACCCAC** | |
| | **TCGACTTCTTTTGGAATATCTTGAAGAAAAATATGAA** | |
| | **GAGCATTTGTATGAGCGCGATGAAGGTGATAAATGGC** | |
| | **GAAACAAAAAGTTTGAATTGGGTTTGGAGTTTCCCAA** | |
| | **TCTTCCTTATTATATTGATGGTGATGTTAAATTAACA** | |
| | **CAGTCTATGGCCATCATACGTTATATAGCTGACAAGC** | |
| | **ACAACATGTTGGGTGGTTGTCCAAAAGAGCGTGCAGA** | |
| | **GATTTCAATGCTTGAAGGAGCGGTTTTGGATATTAGA** | |
| | **TACGGTGTTTCGAGAATTGCATATAGTAAAGACTTTG** | |
| | **AAACTCTCAAAGTTGATTTTCTTAGCAAGCTACCTGA** | |
| | **AATGCTGAAAATGTTCGAAGATCGTTTATGTCATAAA** | |
| | **ACATATTTAAATGGTGATCATGTAACCCATCCTGACT** | |
| | **TCATGTTGTATGACGCTCTTGATGTTGTTTTATACAT** | |
| | **GGACCCAATGTGCCTGGATGCGTTCCCAAAATTAGTT** | |
| | **TGTTTTAAAAAACGTATTGAAGCTATCCCACAAATTG** | |
| | **ATAAGTACTTGAAATCCAGCAAGTATATAGCATGGCC** | |
| | **TTTGCAGGGCTGGCAAGCCACGTTTGGTGGTGGCGAC** | |
| | **CATCCTCCAACTAGTGGATCTGGTGGTGGTGGCGGAT** | |
| | **GGATGAGCGAGAATCTTTATTTTCAGGGCGCGCTAGC** | |
| | **aATGTCTGACGCCTTGCTGGCACCATTAAACGAGGCA** | |
| | **CAACGCCAAGCCGTCCTGCATTTTGAGGGTCCAGCAT** | |
| | **TAGTAGTGGCAGGGGCCGGATCGGGGAAGACGCGTAC** | |
| | **CGTGGTTCACCGCGTCGCATATCTGGTGGCCCGCCGT** | |
| | **GGCGTGTTCCCATCCGAGATTCTGGCGGTGACATTCA** | |
| | **CAAATAAGGCAGCCGAGGAGATGCGTGAACGCTTGCG** | |
| | **TGGCTTAGTCCCTGGAGCCGGAGAAGTCTGGGTTTCG** | |
| | **ACTTTCCATGCTGCAGCGCTGCGTATCTTACGCGTAT** | |
| | **ACGGAGAACGCGTGGGCCTGCGTCCCGGGTTCGTCGT** | |
| | **ATACGATGAGGATGACCAGACAGCATTATTGAAGGAG** | |
| | **GTGCTGAAAGAACTGGCTCTTTCGGCACGTCCCGGGC** | |
| | **CGATTAAGGCATTGTTAGACCGCGCCAAGAATCGTGG** | |
| | **TGTTGGCCTGAAAGCCTTACTGGGGGAACTTCCCGAG** | |
| | **TACTACGCTGGGTTATCGCGCGGTCGTCTGGGAGACG** | |
| | **TGCTGGTACGTTACCAGGAAGCCCTGAAGGCTCAAGG** | |
| | **GGCTTTAGATTTCGGCGACATTTTGTTGTATGCTCTT** | |

TABLE 7-continued

Nucleic Acid Sequence of Exemplary Helicases

| Helicase | Nucleic Acid Sequence | SEQ ID NO |
|---|---|---|
| | **GAAGCGTTCCGTGGAGGACGCGGTGGTCCGCAGGCCC<br>GCGCGCAACGTGCACGTTTCATCCATGTGGATGAGTA<br>CCAGGACACCTCGCCGGTTCAGTATCGTTTTACCCGT<br>CTTTTGGCCGGTGAAGAAGCAAACCTTATGGCTGTAG<br>GAGACCCCGATCAAGGGATTTACTCTTTCCGCGCAGC<br>GGATATTAAGAACATTTTAGACTTCACACGTGATTAT<br>CCTGAGGCACGTGTATATCGTCTTGAAGAGAACTATC<br>GTTCGACCGAAGCCATTCTGCGTTTCGCCAACGCCGT<br>AATCGTCAAAAACGCGCTTCGCTTGGAGAAAGCCTTA<br>CGCCCCGTCAAACGTGGGGGAGAGCCTGTCCGCTTAT<br>ATCGCGCAGAGGACGCACGCGAAGAAGCACGCTTTGT<br>CGCAGAAGAGATTGCTCGTTTGGGACCCCCGTGGGAT<br>CGCTATGCAGTCTTATACCGCACTAATGCTCAAAGCC<br>GCCTTCTGGAACAGGCGTTAGCAGGTCGTGGGATCCC<br>CGCACGCGTCGTTGGAGGTGTGGGTTTTTCGAGCGT<br>GCAGAGGTGAAGGACTTGTTGGCGTACGCTCGTTTGG<br>CCTTGAATCCCTTGGATGCCGTGTCCCTTAAGCGCGT<br>CCTGAACACTCCCCCACGCGGTATCGGACCAGCCACG<br>TGGGCCCGCGTGCAGTTACTTGCCCAAGAGAAAGGAT<br>TACCCCCCTGGGAGGCTCTTAAAGAAGCGGCACGCAC<br>CTTTTCTCGCCCAGAACCACTGCGCCATTTCGTAGCC<br>CTTGTTGAAGAGTTGCAAGATTTAGTATTCGGGCCTG<br>CCGAGGCTTTCTTTCGCCACTTGCTGGAGGCGACTGA<br>TTACCCCGCCTACCTGCGTGAAGCGTACCCAGAAGAT<br>GCGGAAGACCGCTTGGAAAATGTAGAAGAACTGTTGC<br>GCGCCGCGAAAGAAGCGGAGGATCTTCAGGACTTCCT<br>TGATCGTGTCGCACTGACTGCCAAGGCCGAGGAGCCG<br>GCCGAAGCAGAAGGACGCGTTGCATTGATGACATTGC<br>ATAACGCAAAGGGGTTGGAGTTTCCAGTCGTTTTCCT<br>GGTTGGCGTAGAGGAAGGGTTACTGCCCCACCGTAAC<br>TCGGTGTCGACGTTAGAAGGACTTGAAGAGGAACGTC<br>GTTTGTTCTATGTCGGTATCACCCGTGCTCAGGAACG<br>TTTGTACCTGTCACATGCGGAAGAGCGCGAGGTTTAT<br>GGCCGCCGCGAGCCCGCGCGTCCGTCCCGCTTTCTTG<br>AAGAGGTTGAAGAGGGTTTATACGAAGTATACGACCC<br>ATATCGTCGCCCACCGTCACCCCCTCCACATCGCCCT<br>CGCCCGGGGGCATTTCGTGGAGGTGAACGCGTCGTAC<br>ATCCGCGCTTTGGACCTGGCACAGTCGTGGCCGCGCA<br>GGGTGACGAGGTTACGGTCCATTTTGAGGGTTTTGGT<br>CTGAAACGCCTTTCATTAAAATATGCAGAGCTGAAAC<br>CAGCTTAGTGA** | |
| Eco UvrD<br>*Escherichia coli* | ATGGACGTTTCCTACTTGCTGGACTCGTTGAACGATA<br>AGCAACGTGAGGCCGTTGCCGCGCCTCGTTCCAACTT<br>ATTGGTGCTTGCCGGCGCAGGTTCCGGCAAGACACGC<br>GTCTTAGTTCATCGCATCGCGTGGTTAATGAGCGTGG<br>AGAATTGCTCACCGTATAGCATCATGGCAGTTACGTT<br>TACTAACAAGGCGGCCGCAGAAATGCGTCACCGCATT<br>GGACAACTGATGGGAACAAGCCAGGGAGGTATGTGGG<br>TAGGGACTTTCCACGGCCTTGCGCACCGTCTTCTTCG<br>CGCACACCACATGGATGCCAATCTGCCGCAGGACTTT<br>CAGATCCTTGATTCGGAGGATCAGTTGCGCTTGCTGA<br>AGCGCTTAATCAAAGCGATGAATTTAGATGAGAAGCA<br>GTGGCCACCCCGTCAGGCAATGTGGTACATCAATTCG<br>CAAAAGGATGAGGGTTTGCGCCCTCACCATATCCAGT<br>CGTATGGCAATCCAGTCGAGCAAACATGGCAGAAAGT<br>TTACCAGGCATATCAGGAGGCCTGTGATCGCGCAGGA<br>TTAGTAGACTTCGCAGAGCTTCTTCTTCGCGCCCACG<br>AGTTATGGCTGAATAAACCTCACATTTTACAACATTA<br>CCGTGAGCGTTTTACGAATATTTTAGTGGATGAGTTC<br>CAGGATACTAACAACATTCAGTACGCTTGGATCCGCT<br>TACTTGCCGGAGATACGGGGAAAGTTATGATCGTTGG<br>TGATGACGACCAGTCGATCTACGGCTGGCGTGGGGCA<br>CAGGTAGAGAACATCCAACGCTTCTTAAACGACTTCC<br>CTGGTGCTGAGACGATCCGCCTTGAACAGAATTACCG<br>TTCTACAAGCAATATCCTGTCCGCAGCGAATGCCCTT<br>ATTGAGAACAACAACGGGCGCCTTGGCAAGAAGTTGT<br>GGACTGACGGAGCTGATGGCGAACCGATCTCTCTGTA<br>TTGCGCATTCAATGAACTGGACGAGGCACGCTTCGTT<br>GTCAATCGCATTAAGACTTGGCAGGATAACGGCGGTG<br>CCTTGGCTGAGTGCGCTATTCTGTACCGTTCAAACGC<br>CCAGAGCCGTGTGCTGGAGGAAGCGTTACTGCAGGCT<br>TCTATGCCGTATCGCATTTACGGTGGTATGCGCTTTT<br>TTGAACGTCAAGAGATTAAGGACGCGCTGTCTTATCT<br>GCGTCTGATCGCTAACCGCAATGACGACGCCGCATTT | 64 |

TABLE 7-continued

Nucleic Acid Sequence of Exemplary Helicases

| Helicase | Nucleic Acid Sequence | SEQ ID NO |
|---|---|---|
| | GAGCGTGTCGTCAATACCCCCACTCGCGGGATCGGGG<br>ATCGCACACTGGACGTAGTCCGCCAAACAAGCCGCGA<br>CCGTCAATTAACACTTTGGCAGGCGTGCCGTGAATTA<br>CTTCAGGAAAAGGCATTGGCTGGTCGTGCCGCGAGCG<br>CCCTTCAACGTTTTATGGAGCTTATCGACGCCCTGGC<br>ACAAGAGACTGCAGACATGCCATTGCACGTACAGACT<br>GACCGTGTGATTAAGGACAGCGGGCTGCGTACAATGT<br>ATGAGCAAGAGAAAGGAGAGAAAGGGCAGACACGCAT<br>TGAGAACTTAGAAGAATTGGTAACGGCGACTCGTCAA<br>TTCTCCTACAACGAAGAAGATGAGGATTTAATGCCTC<br>TTCAGGCGTTCTTAAGTCATGCTGCGTTGGAAGCAGG<br>AGAAGGACAAGCTGATACCTGGCAAGACGCAGTCCAG<br>CTTATGACTTTGCATTCAGCGAAGGGCTTGGAATTTC<br>CGCAAGTTTTTATCGTCGGCATGGAAGAAGGGATGTT<br>TCCCTCCCAGATGAGTCTTGACGAAGGGGGACGTTTG<br>GAAGAGGAACGTCGTTTGGCTTATGTCGGGGTGACAC<br>GCGCAATGCAAAAGCTTACTCTGACCTATGCAGAAAC<br>CCGTCGCTTGTACGGGAAAGAAGTCTATCATCGTCCC<br>AGCCGTTTCATTGGCGAGCTGCCCGAAGAATGTGTCG<br>AAGAGGTACGCCTTCGTGCCACCGTATCTCGCCCGGT<br>GTCTCACCAACGTATGGGGACGCCTATGGTAGAAAAT<br>GACTCCGGTTACAAGTTGGGTCAACGTGTCCGCCATG<br>CCAAGTTCGGCGAGGGGACCATTGTCAATATGGAAGG<br>AAGCGGCGAACACTCGCGCTTGCAAGTGGCTTTCCAA<br>GGACAGGGCATCAAATGGCTGGTTGCCGCCTATGCTC<br>GCTTGGAGAGTGTGTAGTGA | |
| Eco UvrD<br>*Escherichia coli*<br>Construct Sequence<br>*Italicized: His tag*<br>Underlined: GST<br>**Bold: Eco UvrD** | ATGAAA*CATCACCATCACCATCAC*AACACTAGTAGCA<br>ATTCCATGTCCCCTATACTAGGTTATTGGAAAATTAA<br>GGGCCTTGTGCAACCCACTCGACTTCTTTTGGAATAT<br>CTTGAAGAAAAATATGAAGAGCATTTGTATGAGCGCG<br>ATGAAGGTGATAAATGGCGAAACAAAAAGTTTGAATT<br>GGGTTTGGAGTTTCCCAATCTTCCTTATTATATTGAT<br>GGTGATGTTAAATTAACACAGTCTATGGCCATCATAC<br>GTTATATAGCTGACAAGCACAACATGTTGGGTGGTTG<br>TCCAAAAGAGCGTGCAGAGATTTCAATGCTTGAAGGA<br>GCGGTTTTGGATATTAGATACGGTGTTTCGAGAATTG<br>CATATAGTAAAGACTTTGAAACTCTCAAAGTTGATTT<br>TCTTAGCAAGCTACCTGAAATGCTGAAAATGTTCGAA<br>GATCGTTTATGTCATAAAACATATTTAAATGGTGATC<br>ATGTAACCCATCCTGACTTCATGTTGTATGACGCTCT<br>TGATGTTGTTTTATACATGGACCCAATGTGCCTGGAT<br>GCGTTCCCAAAATTAGTTTGTTTTAAAAAACGTATTG<br>AAGCTATCCCACAAATTGATAAGTACTTGAAATCCAG<br>CAAGTATATAGCATGGCCTTTGCAGGGCTGGCAAGCC<br>ACGTTTGGTGGTGGCGACCATCCTCCAACTAGTGGAT<br>CTGGTGGTGGTGGCGGATGGATGAGCGAGAATCTTTA<br>TTTTCAGGGCGCGCTAGCA**ATGGACGTTTCCTACTTG**<br>**CTGGACTCGTTGAACGATAAGCAACGTGAGGCCGTTG**<br>**CCGCGCCTCGTTCCAACTTATTGGTGCTTGCCGGCGC**<br>**AGGTTCCGGCAAGACACGCGTCTTAGTTCATCGCATC**<br>**GCGTGGTTAATGAGCGTGGAGAATTGCTCACCGTATA**<br>**GCATCATGGCAGTTACGTTTACTAACAAGGCGGCCGC**<br>**AGAAATGCGTCACCGCATTGGACAACTGATGGGAACA**<br>**AGCCAGGGAGGTATGTGGGTAGGGACTTTCCACGGCC**<br>**TTGCGCACCGTCTTCTTCGCGCACACCACATGGATGC**<br>**CAATCTGCCGCAGGACTTTCAGATCCTTGATTCGGAG**<br>**GATCAGTTGCGCTTGCTGAAGCGCTTAATCAAAGCGA**<br>**TGAATTTAGATGAGAAGCAGTGGCCACCCCGTCAGGC**<br>**AATGTGGTACATCAATTCGCAAAAGGATGAGGGTTTG**<br>**CGCCCTCACCATATCCAGTCGTATGGCAATCCAGTCG**<br>**AGCAAACATGGCAGAAAGTTTACCAGGCATATCAGGA**<br>**GGCCTGTGATCGCGCAGGATTAGTAGACTTCGCAGAG**<br>**CTTCTTCTTCGCGCCCACGAGTTATGGCTGAATAAAC**<br>**CTCACATTTTACAACATTACCGTGAGCGTTTTACGAA**<br>**TATTTTAGTGGATGAGTTCCAGGATACTAACAACATT**<br>**CAGTACGCTTGGATCCGCTTACTTGCCGGAGATACGG**<br>**GGAAAGTTATGATCGTTGGTGATGACGACCAGTCGAT**<br>**CTACGGCTGGCGTGGGGCACAGGTAGAGAACATCCAA**<br>**CGCTTCTTAAACGACTTCCCTGGTGCTGAGACGATCC**<br>**GCCTTGAACAGAATTACCGTTCTACAAGCAATATCCT**<br>**GTCCGCAGCGAATGCCCTTATTGAGAACAACAACGGG**<br>**CGCCTTGGCAAGAAGTTGTGGACTGACGGAGCTGATG**<br>**GCGAACCGATCTCTCTGTATTGCGCATTCAATGAACT**<br>**GGACGAGGCACGCTTCGTTGTCAATCGCATTAAGACT** | 65 |

TABLE 7-continued

Nucleic Acid Sequence of Exemplary Helicases

| Helicase | Nucleic Acid Sequence | SEQ ID NO |
|---|---|---|
| | **TGGCAGGATAACGGCGGTGCCTTGGCTGAGTGCGCTA<br>TTCTGTACCGTTCAAACGCCCAGAGCCGTGTGCTGGA<br>GGAAGCGTTACTGCAGGCTTCTATGCCGTATCGCATT<br>TACGGTGGTATGCGCTTTTTTGAACGTCAAGAGATTA<br>AGGACGCGCTGTCTTATCTGCGTCTGATCGCTAACCG<br>CAATGACGACGCCGCATTTGAGCGTGTCGTCAATACC<br>CCCACTCGCGGGATCGGGGATCGCACACTGGACGTAG<br>TCCGCCAAACAAGCCGCGACCGTCAATTAACACTTTG<br>GCAGGCGTGCCGTGAATTACTTCAGGAAAAGGCATTG<br>GCTGGTCGTGCCGCGAGCGCCCTTCAACGTTTTATGG<br>AGCTTATCGACGCCCTGGCACAAGAGACTGCAGACAT<br>GCCATTGCACGTACAGACTGACCGTGTGATTAAGGAC<br>AGCGGGCTGCGTACAATGTATGAGCAAGAGAAAGGAG<br>AGAAAGGGCAGACACGCATTGAGAACTTAGAAGAATT<br>GGTAACGGCGACTCGTCAATTCTCCTACAACGAAGAA<br>GATGAGGATTTAATGCCTCTTCAGGCGTTCTTAAGTC<br>ATGCTGCGTTGGAAGCAGGAGAAGGACAAGCTGATAC<br>CTGGCAAGACGCAGTCCAGCTTATGACTTTGCATTCA<br>GCGAAGGGCTTGGAATTTCCGCAAGTTTTTATCGTCG<br>GCATGGAAGAAGGGATGTTTCCCTCCCAGATGAGTCT<br>TGACGAAGGGGGACGTTTGGAAGAGGAACGTCGTTTG<br>GCTTATGTCGGGGTGACACGCGCAATGCAAAAGCTTA<br>CTCTGACCTATGCAGAAACCCGTCGCTTGTACGGGAA<br>AGAAGTCTATCATCGTCCCAGCCGTTTCATTGGCGAG<br>CTGCCCGAAGAATGTGTCGAAGAGGTACGCCTTCGTG<br>CCACCGTATCTCGCCCGGTGTCTCACCAACGTATGGG<br>GACGCCTATGGTAGAAAATGACTCCGGTTACAAGTTG<br>GGTCAACGTGTCCGCCATGCCAAGTTCGGCGAGGGGA<br>CCATTGTCAATATGGAAGGAAGCGGCGAACACTCGCG<br>CTTGCAAGTGGCTTTCCAAGGACAGGGCATCAAATGG<br>CTGGTTGCCGCCTATGCTCGCTTGGAGAGTGTGTAGT<br>GA** | |
| HEL#100<br>*Clostridium perfringens* | ATGGTGCTTAACCCTAAGTACTCAATCGGAGTGTATT<br>ACGATGAATTAGTCGAAGAGGATATTGAGAAAGTCTA<br>TTCGTACCTGAGCCGTGGAATCGTGGTACATTTATTT<br>TTGCGTGGCATTTTAAAGGAAGAGCTGGAATTGAATG<br>AGTATGATTTGAATACATTCAAGCTGCCGAAAGACAA<br>TAACTTACTGTTTGTGTACGAGGAAGAGACCAGTTTG<br>TCTTCCGAAAACATCATCATCTTTGTCGATAACAACA<br>TTCTGAACAAGGAGGCGTATAAGAACATCACCGAAAA<br>TCGCGAGTGCGAGTTCAACAAAGACCAATATGAGATT<br>ATTACGGCGCCTGTAGATGATAACATCATTGTGACAA<br>GCGGCGCAGGAACCGGAAAGACAACAACCATGATCAA<br>CCGCCTTATTTATTTACGCTCCGTGATGTCAGACTTT<br>ACGTTTGACCAAGCGGTGTTAATCACTTTCACTAACA<br>AAGCATCGATTGAAATGAAAGAACGCCTTTTGGAAGT<br>GCTGGATAAGTATTTCCGCGTCACAAACGACATTAAA<br>TACTTGGACTATATGGAGGAAGCCGCAAAGGGGTCCA<br>TCAGCACTATTCACAAATTTGCCAAGAAGATTCTTAA<br>CAAGTCCGGACGTCATATTGGGATCAACAAAGACATT<br>AACGTGCGCTCGTTCAAGTACAAGCGTCAGGAGGCCG<br>TCAACAACGCCCTGAATAAAATCTATAAGGAAGAGTC<br>TGAGCTGTTTTCCCTGATCAAATACTACCCAATCTAT<br>GAAGTCGAACGTGTTATCTTAAAAATGTGGAAATCT<br>TAGACAATTACTCGATTGATCTTTTATCAAACAAAGT<br>GCGTGTCGACTTCAATTTTGAGGAGGATAAGTTCACA<br>GAGCTTATTAGCAAAACTTTAAAGTACGCACAGGAGA<br>TTTTGGATTATGATAAAGAGAACGAGTTAGAGATCTC<br>AGACTTGATGAAGAAATTAGCTTACGAAGATATTTTT<br>AAGGGGATCGACAGTACGTACAAAGTGATTATGATCG<br>ACGAATTTCAGGATAGCGACAACACCCAAATTGAGTT<br>TATTTCTGAATTGGAAAAAAAAACAGGAGCCCGCATC<br>TTGGTTGTGGGAGACGAAAAGCAATCAATTTACCGCT<br>TCCGCGGGGCAGAATATACAGCATTCGACAAATTGAA<br>GAAGCTTTTATCAAATTCTAAGCGTGAAGTCAAGGAA<br>TATGAGATGACACGCAATTATCGCACAAACTACAACA<br>TCTTGAATGAGATTAATCGTATTTTTATTGAGGTCGA<br>TAAAAAGTTAGAGTGCTTTAATTATAAAGAGAAGGAC<br>TACATCTATAGCAATAAGGACAAAGATAATCCTAAAG<br>AAATCACGTGTTTCAACGTTTCTGACAATCTTAAACG<br>TAAAGAGTTCTTTGACGACCTTCTGGAGAACAAAAAG<br>GAAGACGAATCAATTGCTGTCTTATTTCGCTCTAATT<br>CTGACATTAAAGAGTTCAAAGAGTTCTGCGATCGCAA<br>TAATATTCTTTGTATGGTTGATTCGACAGGAGGTTTT | 66 |

TABLE 7-continued

| Nucleic Acid Sequence of Exemplary Helicases | | |
|---|---|---|
| Helicase | Nucleic Acid Sequence | SEQ ID NO |
| | TATCGCCACGAAGCTGTACGCGACTTCTATATTATGA<br>TTAAATCGATTATTGATGAGCGCAACAGTCGCACGAT<br>GTACTCTTTCATCAATACACCGTACATTTTAGAAGAC<br>ATCGACAAAAACATTATTTTGAACGGTAACTCCAAAG<br>ACAAAAATGAGTTCCTTTACTACATTTTAGAAAAAAA<br>TAACTGGAACTATTTCCGCGAGTCCAGTAACTTTAAG<br>AACCCCATTATCCTGATTGACGAGATTATCGAAAAGT<br>TAAAGCCGGTCAAAAACTATTACGTTAAGGTGCTTCT<br>GGAGGCAAAGAAAAACCAGCATAATTATGTTAACATT<br>GCGAAAATGAAGGCGCTGGAATACAAGCTTAATCTGG<br>AACACTTAGTATTTATTCTTAAGAAAGAGTTTAGTGA<br>GAATATTACTTCAATCGAACAGATTGAACAGTTTCTG<br>AAAGTGAAGATCAGCACTGATAATCTTGTAGACGTAC<br>GCAAGCCAAAGGATTACGAGAATGACTACATCCAATG<br>TTCAACAGTTCATAAGGCGAAAGGTTTGGAGTATGAT<br>TACGTTGTGCTGGACAAGTTGACGAATCGCTTTTTGT<br>CTAATTCGCGTAAAGTTAACTTGATCTTAAAGCCCGA<br>CGGAGACAAGTTGTTAATTGGATACAAAATCCGTTTG<br>GGAGAAGACGAGTTCAAGAACAAGATCTACAGCGACA<br>ATCTGAAATACGAGAAGAAAGAGATTAAGGGGGAGGA<br>GGCACGCTTGTTATATGTTGCGTTGACCCGTTGCAAA<br>AAGGGGATCTATCTGAATATGTCTGGCGAACTGGCGG<br>CGACCGAGTCGCTTAACACCTGGAAAAGCCTGATTGG<br>AGGCACTATTAATTATGTTTAATAG | |
| HEL#100<br>*Clostridium perfringens*<br>Construct Sequence<br>*Italicized: His tag*<br>Underlined: GST<br>**Bold: Hel#100** | ATGAAA*CATCACCATCACCATCAC*AACACTAGTA<br>GCAATTCCATGTCCCCTATACTAGGTTATTGGAAAAT<br>TAAGGGCCTTGTGCAACCCACTCGACTTCTTTTGGAA<br>TATCTTGAAGAAAAATATGAAGAGCATTTGTATGAGC<br>GCGATGAAGGTGATAAATGGCGAAACAAAAAGTTTGA<br>ATTGGGTTTGGAGTTTCCCAATCTTCCTTATTATATT<br>GATGGTGATGTTAAATTAACACAGTCTATGGCCATCA<br>TACGTTATATAGCTGACAAGCACAACATGTTGGGTGG<br>TTGTCCAAAAGAGCGTGCAGAGATTTCAATGCTTGAA<br>GGAGCGGTTTTGGATATTAGATACGGTGTTTCGAGAA<br>TTGCATATAGTAAAGACTTTGAAACTCTCAAAGTTGA<br>TTTTCTTAGCAAGCTACCTGAAATGCTGAAAATGTTC<br>GAAGATCGTTTATGTCATAAAACATATTTAAATGGTG<br>ATCATGTAACCCATCCTGACTTCATGTTGTATGACGC<br>TCTTGATGTTGTTTTATACATGGACCCAATGTGCCTG<br>GATGCGTTCCCAAAATTAGTTTGTTTTAAAAAACGTA<br>TTGAAGCTATCCCACAAATTGATAAGTACTTGAAATC<br>CAGCAAGTATATAGCATGGCCTTTGCAGGGCTGGCAA<br>GCCACGTTTGGTGGTGGCGACCATCCTCCAACTAGTG<br>GATCTGGTGGTGGTGGCGGATGGATGAGCGAGAATCT<br>TTATTTTCAGGGCGCGCTAGCA**ATGGTGCTTAACCCT**<br>**AAGTACTCAATCGGAGTGTATTACGATGAATTAGTCG**<br>**AAGAGGATATTGAGAAAGTCTATTCGTACCTGAGCCG**<br>**TGGAATCGTGGTACATTTATTTTTGCGTGGCATTTTA**<br>**AAGGAAGAGCTGGAATTGAATGAGTATGATTTGAATA**<br>**CATTCAAGCTGCCGAAAGACAATAACTTACTGTTTGT**<br>**GTACGAGGAAGAGACCAGTTTGTCTTCCGAAAACATC**<br>**ATCATCTTTGTCGATAACAACATTCTGAACAAGGAGG**<br>**CGTATAAGAACATCACCGAAAATCGCGAGTGCGAGTT**<br>**CAACAAAGACCAATATGAGATTATTACGGCGCCTGTA**<br>**GATGATAACATCATTGTGACAAGCGGCGCAGGAACCG**<br>**GAAAGACAACAACCATGATCAACCGCCTTATTTATTT**<br>**ACGCTCCGTGATGTCAGACTTTACGTTTGACCAAGCG**<br>**GTGTTAATCACTTTCACTAACAAAGCATCGATTGAAA**<br>**TGAAAGAACGCCTTTTGGAAGTGCTGGATAAGTATTT**<br>**CCGCGTCACAAACGACATTAAATACTTGGACTATATG**<br>**GAGGAAGCCG**<br>**CAAAGGGGTCCATCAGCACTATTCACAAATTTGCCAA**<br>**GAAGATTCTTAACAAGTCCGGACGTCATATTGGGATC**<br>**AACAAAGACATTAACGTGCGCTCGTTCAAGTACAAGC**<br>**GTCAGGAGGCCGTCAACAACGCCCTGAATAAAATCTA**<br>**TAAGGAAGAGTCTGAGCTGTTTTCCCTGATCAAATAC**<br>**TACCCAATCTATGAAGTCGAACGTGTTATCTTAAAAA**<br>**TGTGGGAAATCTTAGACAATTACTCGATTGATCTTTT**<br>**ATCAAACAAAGTGCGTGTCGACTTCAATTTTGAGGAG**<br>**GATAAGTTCACAGAGCTTATTAGCAAAACTTTAAAGT**<br>**ACGCACAGGAGATTTTGGATTATGATAAAGAGAACGA**<br>**GTTAGAGATCTCAGACTTGATGAAGAAATTAGCTTAC**<br>**GAAGATATTTTTAAGGGGATCGACAGTACGTACAAAG**<br>**TGATTATGATCGACGAATTTCAGGATAGCGACAACAC** | 67 |

TABLE 7-continued

Nucleic Acid Sequence of Exemplary Helicases

| Helicase | Nucleic Acid Sequence | SEQ ID NO |
|---|---|---|
| | **CCAAATTGAGTTTATTTCTGAATTGGAAAAAAAAACA<br>GGAGCCCGCATCTTGGTTGTGGGAGACGAAAAGCAAT<br>CAATTTACCGCTTCCGCGGGGCAGAATATACAGCATT<br>CGACAAATTGAAGAAGCTTTTATCAAATTCTAAGCGT<br>GAAGTCAAGGAATATGAGATGACACGCAATTATCGCA<br>CAAACTACAACATCTTGAATGAGATTAATCGTATTTT<br>TATTGAGGTCGATAAAAAGTTAGAGTGCTTTAATTAT<br>AAAGAGAAGGACTACATCTATAGCAATAAGGACAAAG<br>ATAATCCTAAAGAAATCACGTGTTTCAACGTTTCTGA<br>CAATCTTAAACGTAAAGAGTTCTTTGACGACCTTCTG<br>GAGAACAAAAAGGAAGACGAATCAATTGCTGTCTTAT<br>TTCGCTCTAATTCTGACATTAAAGAGTTCAAAGAGTT<br>CTGCGATCGCAATAATATTCTTTGTATGGTTGATTCG<br>ACAGGAGGTTTTTATCGCCACGAAGCTGTACGCGACT<br>TCTATATTATGATTAAATCGATTATTGATGAGCGCAA<br>CAGTCGCACGATGTACTCTTTCATCAATACACCGTAC<br>ATTTTAGAAGACATCGACAAAAACATTATTTTGAACG<br>GTAACTCCAAAGACAAAAATGAGTTCCTTTACTACAT<br>TTTAGAAAAAAATAACTGGAACTATTTCCGCGAGTCC<br>AGTAACTTTAAGAACCCCATTATCCTGATTGACGAGA<br>TTATCGAAAAGTTAAAGCCGGTCAAAAACTATTACGT<br>TAAGGTGCTTCTGGAGGCAAAGAAAAACCAGCATAAT<br>TATGTTAACATTGCGAAAATGAAGGCGCTGGAATACA<br>AGCTTAATCTGGAACACTTAGTATTTATTCTTAAGAA<br>AGAGTTTAGTGAGAATATTACTTCAATCGAACAGATT<br>GAACAGTTTCTGAAAGTGAAGATCAGCACTGATAATC<br>TTGTAGACGTACGCAAGCCAAAGGATTACGAGAATGA<br>CTACATCCAATGTTCAACAGTTCATAAGGCGAAAGGT<br>TTGGAGTATGATTACGTTGTGCTGGACAAGTTGACGA<br>ATCGCTTTTTGTCTAATTCGCGTAAAGTTAACTTGAT<br>CTTAAAGCCCGACGGAGACAAGTTGTTAATTGGATAC<br>AAAATCCGTTTGGGAGAAGACGAGTTCAAGAACAAGA<br>TCTACAGCGACAATCTGAAATACGAGAAGAAAGAGAT<br>TAAGGGGGAGGAGGCACGCTTGTTATATGTTGCGTTG<br>ACCCGTTGCAAAAAGGGGATCTATCTGAATATGTCTG<br>GCGAACTGGCGGCGACCGAGTCGCTTAACACCTGGAA<br>AAGCCTGATTGGAGGCACTATTAATTATGTTTAATAG** | |
| HEL#75<br>*Clostridium perfringens* | ATGCTGGGGCTGAATAATGAGTCCAAAGAGTTCTTTA<br>AGGGCATTAGCCGCATTTGGAGAAATTACAAGGACTA<br>CACCTACCTTGACGGGATTAAGCTGAGCCAGGCGCAG<br>ATCGATATCATCGAGAAGGAGGAGGACCAATTGCTTA<br>TAGAGGGCTACGCCGGCACCGGTAAGTCCCTGACCCT<br>TATATACAAGTTCATTAACGTGCTGGTTCGGGAAGAT<br>GGGAAGAGGGTGCTGTATGTGACTTTTAACGATACGC<br>TGATCGAGGATACGAAGAAACGCCTTAGTTATTGCAA<br>CGAGTACAACGAGAATAAAGAGAGGCACCACGTAGAG<br>ATTTGCACATTCCATGAGATCGCCAGTAATATCCTGA<br>AGAAAAAGAAGATCATAGACAGGGGTATTGAGAAACT<br>GACGGCTAAAAAGATAGAAGATTACAAAGGTGCCGCT<br>CTCCGCAGAATTGCGGGAATCCTGGCTAGGTACATCG<br>AGGGGGGAAAGTATTATAGCGAGTTGCCTAAAGAGGA<br>ACGCCTCTACAAGACACATGACGAGAACTTTATCAGG<br>GAGGAGGTGGCCTGGATCAAGGCCATGGGCTTTATAG<br>AAAAGGAGAAGTATTTCGAGAAAGATCGCATTGGGAG<br>GTCCAAGAGTATCAGGCTGACGCGCTCACAACGCAAA<br>ACTATATTCAAGATATTTGAAAAGTACTGCGAGGAGC<br>AAGAAAACAAATTCTTCAAAAGCCTCGACTTGGAGGA<br>TTACGCCCTGAAGCTCATCCAGAACATAGATAATTTC<br>GATGACCTTAAGTTCGACTACATTTTTGTGGACGAGG<br>TACAGGATCTCGATCCCATGCAAATTAAGGCGCTGTG<br>TCTGCTGACCAATACGAGCATCGTGCTGTCAGGCGAC<br>GCGAATCAGCGGATTTACAAGAAATCTCCCGTGAAGT<br>ACGAGGAGCTCGGCCTCAGAATCAAAGAGAAGGGGAA<br>ACGGAAAATTCTGAACAAGAACTATCGGTCCACGGGT<br>GAGATTGTCAAGCTCGCGAACTCAATCAAGTTCTTCG<br>ACGAGTCCATCAATAAGTATAATGAAAAGCAGTTCGT<br>AAAATCCGGTGATCGCCCGATCATCCGGAAGGTGAAC<br>GACAAAAAGGGTGCGGTGAAGTTCCTGATCGGCGAGA<br>TCAAGAAAATCCACGAAGAGGACCCCTACAAAACAAT<br>CGCCATCATCCACCGAGAGAAAAACGAGCTTATCGGC<br>TTCCAAAAGTCCGAGTTCCGAAAGTACCTGGAAGGCC<br>AGCTGTACATGGAAAAATTCAGTGACATCAAGTCCTT<br>TGAGTCAAAGTTTGATTTGAGGGAAAAGAACCAGGTG<br>TTCTACACCAACGGCTACGATGTAAAGGGGCTGGAAT | 68 |

TABLE 7-continued

Nucleic Acid Sequence of Exemplary Helicases

| Helicase | Nucleic Acid Sequence | SEQ ID NO |
|---|---|---|
| | TTGATGTGGTGTTCATCATAAACTTCAACACGGCCAA | |
| | CTACCCACTGAGTAAAGAGCTGAAGAAAATCAAGGAC | |
| | GAAAACGACGGCAAGGAAATGACGCTCATTAAAGACG | |
| | ATGTGCTCGAGTTTATCAATCGCGAGAAGAGGCTGCT | |
| | GTACGTAGCTATGACCAGGGCCAAAGAAAAGCTGTAT | |
| | CTCGTGGCCGACTGCAAAAACAGCAACATCAGCAGCT | |
| | TCATCTACGACTTTAACACCAAGTACTATGAGGCACA | |
| | AAATTTCAAGAAGAAAGAGATAGAGGAGAACTACAAC | |
| | CGGTACAAGATTAACATGGAGCGCGAATACGGCATCA | |
| | TCATTGAGGACGACGACTCCAACAACGTTAAGAACAA | |
| | TGACACGAAACAAGAGAACAAGTTTAATACCGAATCT | |
| | AAGGAAAAGGGCAAAGATGACATCGACAAGATAAAGG | |
| | TGTTTTTCATCAACAAGGGAATCGAGGTGGTGGACAA | |
| | CCGAGATAAGAGCGGGTGCTTGTGGATCGTCGCCGGG | |
| | AAGGAAGCGATCCCTCTTATGAAGAAGTTCGGTGTCC | |
| | TGGGCTATAACTTCATATTTATCGCAAACGGCGGTCG | |
| | GGCATCTAAGAACCGGCCAGCCTGGTACCTCAAGAAT | |
| | AGC | |
| HEL#75 | ATGAAA*CATCACCATCACCATCAC*AACACTAGTAGCA | 69 |
| *Clostridium* | ATTCCATGTCCCCTATACTAGGTTATTGGAAAATTAA | |
| *perfringens* | GGGCCTTGTGCAACCCACTCGACTTCTTTTGGAATAT | |
| Construct Sequence | CTTGAAGAAAAATATGAAGAGCATTTGTATGAGCGCG | |
| *Italicized: His tag* | ATGAAGGTGATAAATGGCGAAACAAAAAGTTTGAATT | |
| Underlined: GST | GGGTTTGGAGTTTCCCAATCTTCCTTATTATATTGAT | |
| **Bold/Underlined:** | GGTGATGTTAAATTAACACAGTCTATGGCCATCATAC | |
| **2xSV40 NLS** | GTTATATAGCTGACAAGCACAACATGTTGGGTGGTTG | |
| **Bold: Hel#75** | TCCAAAAGAGCGTGCAGAGATTTCAATGCTTGAAGGA | |
| | GCGGTTTTGGATATTAGATACGGTGTTTCGAGAATTG | |
| | CATATAGTAAAGACTTTGAAACTCTCAAAGTTGATTT | |
| | TCTTAGCAAGCTACCTGAAATGCTGAAAATGTTCGAA | |
| | GATCGTTTATGTCATAAAACATATTTAAATGGTGATC | |
| | ATGTAACCCATCCTGACTTCATGTTGTATGACGCTCT | |
| | TGATGTTGTTTTATACATGGACCCAATGTGCCTGGAT | |
| | GCGTTCCCAAAATTAGTTTGTTTTAAAAAACGTATTG | |
| | AAGCTATCCCACAAATTGATAAGTACTTGAAATCCAG | |
| | CAAGTATATAGCATGGCCTTTGCAGGGCTGGCAAGCC | |
| | ACGTTTGGTGGTGGCGACCATCCTCCAACTAGTGGAT | |
| | CTGGTGGTGGTGGCGGATGGATGAGCGAGAATCTTTA | |
| | TTTTCAGGGCGCC**ATGCCTAAGAAAAAGCGGAAAGTT** | |
| | **GAGGACCCCAAAAAGAAACGAAAAGTC**GGAAGCGGCT | |
| | CA**CTGGGGCTGAATAATGAGTCCAAAGAGTTCTTTAA** | |
| | **GGGCATTAGCCGCATTTGGAGAAATTACAAGGACTAC** | |
| | **ACCTACCTTGACGGGATTAAGCTGAGCCAGGCGCAGA** | |
| | **TCGATATCATCGAGAAGGAGGAGGACCAATTGCTTAT** | |
| | **AGAGGGCTACGCCGGCACCGGTAAGTCCCTGACCCTT** | |
| | **ATATACAAGTTCATTAACGTGCTGGTTCGGGAAGATG** | |
| | **GGAAGAGGGTGCTGTATGTGACTTTTAACGATACGCT** | |
| | **GATCGAGGATACGAAGAAACGCCTTAGTTATTGCAAC** | |
| | **GAGTACAACGAGAATAAAGAGAGGCACCACGTAGAGA** | |
| | **TTTGCACATTCCATGAGATCGCCAGTAATATCCTGAA** | |
| | **GAAAAAGAAGATCATAGACAGGGGTATTGAGAAACTG** | |
| | **ACGGCTAAAAAGATAGAAGATTACAAAGGTGCCGCTC** | |
| | **TCCGCAGAATTGCGGGAATCCTGGCTAGGTACATCGA** | |
| | **GGGGGGAAAGTATTATAGCGAGTTGCCTAAAGAGGAA** | |
| | **CGCCTCTACAAGACACATGACGAGAACTTTATCAGGG** | |
| | **AGGAGGTGGCCTGGATCAAGGCCATGGGCTTTATAGA** | |
| | **AAAGGAGAAGTATTTCGAGAAAGATCGCATTGGGAGG** | |
| | **TCCAAGAGTATCAGGCTGACGCGCTCACAACGCAAAA** | |
| | **CTATATTCAAGATATTTGAAAAGTACTGCGAGGAGCA** | |
| | **AGAAAACAAATTCTTCAAAAGCCTCGACTTGGAGGAT** | |
| | **TACGCCCTGAAGCTCATCCAGAACATAGATAATTTCG** | |
| | **ATGACCTTAAGTTCGACTACATTTTTGTGGACGAGGT** | |
| | **ACAGGATCTCGATCCCATGCAAATTAAGGCGCTGTGT** | |
| | **CTGCTGACCAATACGAGCATCGTGCTGTCAGGCGACG** | |
| | **CGAATCAGCGGATTTACAAGAAATCTCCCGTGAAGTA** | |
| | **CGAGGAGCTCGGCCTCAGAATCAAAGAGAAGGGGAAA** | |
| | **CGGAAAATTCTGAACAAGAACTATCGGTCCACGGGTG** | |
| | **AGATTGTCAAGCTCGCGAACTCAATCAAGTTCTTCGA** | |
| | **CGAGTCCATCAATAAGTATAATGAAAAGCAGTTCGTA** | |
| | **AAATCCGGTGATCGCCCGATCATCCGGAAGGTGAACG** | |
| | **ACAAAAAGGGTGCGGTGAAGTTCCTGATCGGCGAGAT** | |
| | **CAAGAAAATCCACGAAGAGGACCCCTACAAAACAATC** | |
| | **GCCATCATCCACCGAGAGAAAAACGAGCTTATCGGCT** | |
| | **TCCAAAAGTCCGAGTTCCGAAAGTACCTGGAAGGCCA** | |

TABLE 7-continued

| Nucleic Acid Sequence of Exemplary Helicases | | |
|---|---|---|
| Helicase | Nucleic Acid Sequence | SEQ ID NO |
| | **GCTGTACATGGAAAAATTCAGTGACATCAAGTCCTTT GAGTCAAAGTTTGATTTGAGGGAAAAGAACCAGGTGT TCTACACCAACGGCTACGATGTAAAGGGGCTGGAATT TGATGTGGTGTTCATCATAAACTTCAACACGGCCAAC TACCCACTGAGTAAAGAGCTGAAGAAAATCAAGGACG AAAACGACGGCAAGGAAATGACGCTCATTAAAGACGA TGTGCTCGAGTTTATCAATCGCGAGAAGAGGCTGCTG TACGTAGCTATGACCAGGGCCAAAGAAAAGCTGTATC TCGTGGCCGACTGCAAAAACAGCAACATCAGCAGCTT CATCTACGACTTTAACACCAAGTACTATGAGGCACAA AATTTCAAGAAGAAAGAGATAGAGGAGAACTACAACC GGTACAAGATTAACATGGAGCGCGAATACGGCATCAT CATTGAGGACGACGACTCCAACAACGTTAAGAACAAT GACACGAAACAAGAGAACAAGTTTAATACCGAATCTA AGGAAAAGGGCAAAGATGACATCGACAAGATAAAGGT GTTTTTCATCAACAAGGGAATCGAGGTGGTGGACAAC CGAGATAAGAGCGGGTGCTTGTGGATCGTCGCCGGGA AGGAAGCGATCCCTCTTATGAAGAAGTTCGGTGTCCT GGGCTATAACTTCATATTTATCGCAAACGGCGGTCGG GCATCTAAGAACCGGCCAGCCTGGTACCTCAAGAATA GC** | |

IV. LINKERS

In some embodiments, a linker is used herein to connect one component of a fusion polypeptide to another component of a fusion polypeptide. For example, a linker can be a polypeptide linker, such as a linker that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids long. In some embodiments, the linker is a cleavable or non-cleavable linker. As described herein, two polypeptide sequences that are "fused" need not be directly adjacent to each other. Fused polypeptide sequences can be fused by a linker, or by an additional functional polypeptide sequence that is fused to the polypeptide sequences.

In some embodiments, a linker comprises glycine and serine amino acid residues. linker can comprise non-charged or charged amino acids. A linker can comprise alpha-helical domains. In some embodiments, a linker comprises a chemical cross linker. In some cases, a linker can be of different lengths to adjust the function of fused domains and their physical proximity. In some cases, a linker comprises peptides with ligand-inducible conformational changes.

Exemplary linkers are provided in Table 8. In some embodiments, the linker comprises a sequence with at least 90%, 91%, 92%, 93%, 94%, 95%, 96%, 97%, 98%, 99%, or 100% identity to a linker in Table 8. In some embodiments, the linker comprises an amino acid sequence with at least 90%, 91%, 92%, 93%, 94%, 95%, 96%, 97%, 98%, 99%, or 100% identity to one of SEQ ID NOs: 70-72 or 140.

TABLE 8

| Amino Acid Sequence of Exemplary Linkers | | |
|---|---|---|
| Linker | Amino Acid Sequence | SEQ ID NO |
| A | GGGGS | 70 |
| B | SGSGGGGS | 71 |
| C | SGSETPGTSESATPES | 72 |
| D | GSGSS | 140 |

V. NUCLEAR LOCALIZATION SIGNALS (NLS)

In some embodiments, Ago fusion proteins described herein comprise at least 1, 2, 3, or 4 nuclear localization signal (NLS) polypeptides. In some embodiments, the Ago fusion protein comprises at least 1 NLS. In some embodiments, the Ago fusion protein comprises at least 2 NLS. In some embodiments, the Ago fusion protein comprises at least 3 NLS. In some embodiments, the Ago fusion protein comprises at least 4 NLS.

In some embodiments, the Ago fusion protein comprises at least 2 NLS, wherein each NLS is different. In some embodiments, the Ago fusion protein comprises at least 2 NLS, wherein each NSL is the same. In some embodiments, the Ago fusion protein comprises at least 3 NLS, wherein each NLS is different. In some embodiments, the Ago fusion protein comprises at least 3 NLS, wherein each NSL is the same. In some embodiments, the Ago fusion protein comprises at least 3 NLS, wherein two NLSs are the same and one is different. In some embodiments, at least one NLS is located between the Ago and another functional component (e.g., nucleic acid unwinding polypeptide) of the fusion polypeptide, optionally via one or more linkers.

In some embodiments, the NLS is derived from a microorganism. In some embodiments, the microorganism is a virus. In some embodiments, the NLS is an SV40 NLS.

Exemplary NLSs are provided in Table 9. In some embodiments, the NLS comprises a sequence with at least 90%, 91%, 92%, 93%, 94%, 95%, 96%, 97%, 98%, 99%, or 100% identity to a linker in Table 9. In some embodiments, the linker comprises an amino acid sequence with at least 90%, 91%, 92%, 93%, 94%, 95%, 96%, 97%, 98%, 99%, or 100% identity to one of SEQ ID NOs: 73-78.

Exemplary NLS polypeptides are provided in Table 9.

TABLE 9

Amino Acid Sequence of Exemplary NLSs

| NLS | Amino Acid Sequence | SEQ ID NO |
|---|---|---|
| SV40 Large T-antigen | PKKKRKV | 73 |
| 2XSV40 Large T-antigen | PKKKRKVEDPKKKRKV | 74 |
| Nucleoplasmin (NPM) | KRPAATKKAGQAKKKK | 75 |
| c-Myc | PAAKRVKLD | 76 |
| EGL-13 | MSRRRKANPTKLSENA KKLAKEVEN | 77 |
| TUS-protein | KLKIKRPVK | 78 |

VI. FUSION POLYPEPTIDES

Described herein are fusion polypeptide constructs that comprise an Ago (e.g., an Ago described herein). Also described herein are nucleic acids encoding fusion polypeptide constructs comprising an Ago (e.g., an Ago described herein). In some embodiments, the fusion polypeptide comprises an Ago polypeptide that comprises an amino acid sequence having at least 85%, 90%, 91%, 92%, 93%, 94%, 95%, 96%, 97%, 98%, 99%, or 100% sequence identity with one of SEQ IDs NO: 1-10 or 134-136. In some embodiments, the fusion polypeptide comprises a nucleic acid unwinding polypeptide. In some embodiments, the nucleic acid unwinding polypeptide is a helicase. In some embodiments, the nucleic acid unwinding polypeptide comprises a CRISPR associated (Cas) protein domain.

In some cases, the Ago polypeptide or Ago polypeptide fragment is fused to at least one additional element, for example a helicase. In some cases, the Ago polypeptide or Ago polypeptide fragment is fused to an ATPase. In some cases, the Ago polypeptide or Ago polypeptide fragment is fused to another Ago polypeptide or Ago polypeptide fragment. In some cases, the Ago polypeptide or Ago polypeptide fragment is fused with a guiding polynucleic acid or guiding protein. In some cases, the Ago polypeptide or Ago polypeptide fragment is a fusion construct of the Ago polypeptide or Ago polypeptide fragment and a nucleic acid unwinding polypeptide. In some cases, the Ago system comprises an Ago and a nucleic acid unwinding polypeptide fused together. In some cases, the Ago system comprises an Ago and a nucleic acid unwinding polypeptide, which are not fused together.

Fusion proteins can be synthesized using known technologies, for instance, recombination DNA technology where the coding sequences of various portions of the fusion proteins can be linked together at the nucleic acid level. Subsequently a fusion protein can be produced using a host cell. In some embodiments, a fusion protein comprises a cleavable or non-cleavable linker between the different sections or domains of the protein. For example, a linker can be a polypeptide linker, such as a linker that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids long. As described herein, two polypeptide sequences that are "fused" need not be directly adjacent to each other. Fused polypeptide sequences can be fused by a linker, or by an additional functional polypeptide sequence that is fused to the polypeptide sequences.

In some embodiments, a linker is a GSGSGS (SEQ ID NO: 153) linker. In some cases, there are from 1, 2, 3, 4, 5, 6, 7, 8, 9, or up to 10 linkers on a genome editing construct. For example, there can be from 1 to 10 GSGSGS (SEQ ID NO: 153) linkers. linker can comprise non-charged or charged amino acids. A linker can comprise alpha-helical domains. In some embodiments, a linker comprises a chemical cross linker. In some cases, a linker can be of different lengths to adjust the function of fused domains and their physical proximity. In some cases, a linker comprises peptides with ligand-inducible conformational changes.

In some cases, a nucleic acid unwinding agent may be utilized with the Ago. A nucleic acid unwinding agent may be a polynucleic acid, protein, drug, or system that unwinds a nucleic acid. A nucleic acid unwinding agent can be energy. A nucleic acid unwinding agent can provide energy or heat. Unwinding can refer to the unwinding of a double helix (e.g., of DNA) as well as to unwinding a double-stranded nucleic acid to convert it to a single-stranded nucleic acid or to unwinding DNA from histones. In some embodiments, an unwinding agent is a helicase. In some embodiments, helicases are enzymes that bind nucleic acid or nucleic acid protein complexes. In some embodiments, a helicase is a DNA helicase. In some embodiments, a helicase is an RNA helicase. In some embodiments, a helicase unwinds a polynucleic acid at any position. In some cases, a position that is unwound is found within an immune checkpoint gene. In some cases, a position of a nucleic acid that is unwound encodes a gene involved in disease. In some embodiments, an unwinding agent is an ATPase, helicase, synthetic associated helicase, or topoisomerase.

In some embodiments, a nucleic acid unwinding agent functions by breaking hydrogen bonds between nucleotide base pairs in double-stranded DNA or RNA. In some cases, unwinding a nucleic acid (e.g., by breaking a hydrogen bond) requires energy. To break hydrogen bonds, nucleic acid unwinding agents can use energy stored in ATP. In some embodiments, a nucleic acid unwinding agent includes an ATPase. For example, in some embodiments, a polypeptide with nucleic acid unwinding activity comprises or be fused to an ATPase. In some embodiments, an ATPase is added to a cellular system.

In some embodiments, a nucleic acid unwinding agent is a polypeptide. For example, a nucleic acid unwinding peptide is of prokaryotic origin, archaeal origin, or eukaryotic origin. In some embodiments, a nucleic acid unwinding polypeptide comprises a helicase domain, a topoisomerase domain, a Cas protein domain e.g., a Cas protein domain selected from the group consisting of: Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx1S, Csf1, Csf2, CsO, Csf4, Cpf1, c2c1, c2c3, Cas9HiFi, xCas9, CasX, CasY, CasRX or a catalytically dead nucleic acid unwinding domain such as a dCas domain (e.g., a dCas9 domain).

In some embodiments, a nucleic acid unwinding agent is a small molecule. For example, in some embodiments, a small molecule nucleic acid unwinding agent unwinds a nucleic acid through intercalation, groove binding or covalent binding to the nucleic acid, or a combination thereof. Exemplary small molecule nucleic acid unwinding agents include, but are not limited to, 9-aminoacridine, quinacrine, chloroquine, acriflavin, amsacrine, (Z)-3-(acridin-9-ylamino)-2-(5-chloro-1,3-benzoxazol-2-yl)prop-2-enal, small molecules that can stabilize quadruplex structures, quarfloxin, quindoline, quinoline-based triazine compounds, BRACO-19, acridines, pyridostatin, and derivatives thereof.

In some embodiments, the nucleic acid unwinding agent is a single strand DNA binding protein (SSB) polypeptide, e.g., as described herein. In some embodiments, In some embodiments, the SSB polypeptide comprises an SSB polypeptide described herein (or a functional fragment or functional variant thereof). In some embodiments, the SSB polypeptide comprises an SSB derived from a microorganism. In some embodiments, the microorganism is a bacterium. In some embodiments, the microorganism is a hyperthermophilic microorganism. In some embodiments, the SSB is from *Saccharolobus solfataricus*. In some embodiments, the SSB is active at a temperature between 32° C.-42° C. In some embodiments, the SSB is active at a temperature between 35° C.-40° C. In some embodiments, the SSB is active at about 37° C. In some embodiments, the SSB comprises an amino acid sequence with at least 80%, 85%, 90%, 91%, 92%, 93%, 94%, 95%, 96%, 97%, 98%, 99%, or 100% identity to one of SEQ ID NOS: 22-35. In some embodiments, the SSB comprises an amino acid sequence with at least 80%, 85%, 90%, 91%, 92%, 93%, 94%, 95%, 96%, 97%, 98%, 99%, or 100% identity to one of SEQ ID NOS: 22, 24, 26, 28, 30, 34, OR 34. In some embodiments, the SSB is encoded by a nucleic acid sequence with at least 80%, 85%, 90%, 91%, 92%, 93%, 94%, 95%, 96%, 97%, 98%, 99%, or 100% identity to one of SEQ ID NOS: 36-49. In some embodiments, the SSB is encoded by a nucleic acid sequence with at least 80%, 85%, 90%, 91%, 92%, 93%, 94%, 95%, 96%, 97%, 98%, 99%, or 100% identity to one of SEQ ID NOS: 36, 38, 40, 42, 44, 46, OR 48. In some embodiments, the SSB polypeptide is one selected from Table 4. In some embodiments, the SSB is ET-SSB (Sso-SSB), Neq SSB, TaqSSB, TmaSSB, or EcoSSB. In some embodiments, the SSB is an ET-SSB (also referred to herein as Sso-SSB). In some embodiments, the SSB comprises an amino acid sequence with at least 80%, 85%, 90%, 91%, 92%, 93%, 94%, 95%, 96%, 97%, 98%, 99%, or 100% identity to SEQ ID NO: 22. In some embodiments, the SSB is encoded by a nucleic acid sequence with at least 80%, 85%, 90%, 91%, 92%, 93%, 94%, 95%, 96%, 97%, 98%, 99%, or 100% identity to SEQ ID NOS: 36.

In some embodiments, the nucleic acid unwinding agent is a helicase. In some embodiments, the helicase comprises a helicase polypeptide described herein (or a functional fragment or functional variant thereof). In some embodiments, the helicase polypeptide comprises a helicase derived from a microorganism. In some embodiments, the microorganism is a bacterium. In some embodiments, the microorganism is a hyperthermophilic microorganism. In some embodiments, the helicase is active at a temperature between 32° C.-42° C. In some embodiments, the helicase is active at a temperature between 35° C.-40° C. In some embodiments, the helicase is active at about 37° C. In some embodiments, the helicase comprises an amino acid sequence with at least 80%, 85%, 90%, 91%, 92%, 93%, 94%, 95%, 96%, 97%, 98%, 99%, or 100% identity to one of SEQ ID NOS: 50-59. In some embodiments, the helicase comprises an amino acid sequence with at least 80%, 85%, 90%, 91%, 92%, 93%, 94%, 95%, 96%, 97%, 98%, 99%, or 100% identity to one of SEQ ID NOS: 50, 52, 54, 56, or 58. In some embodiments, the helicase is encoded by a nucleic acid sequence with at least 80%, 85%, 90%, 91%, 92%, 93%, 94%, 95%, 96%, 97%, 98%, 99%, or 100% identity to one of SEQ ID NOS: 60-69. In some embodiments, the helicase is encoded by a nucleic acid sequence with at least 80%, 85%, 90%, 91%, 92%, 93%, 94%, 95%, 96%, 97%, 98%, 99%, or 100% identity to one of SEQ ID NOS: 60, 62, 64, or 68. In some embodiments, the helicase polypeptide is one selected from Table 6 or Table 7. In some embodiments, the helicase is Eco RecQ, Tth UvrD, Eco UvrD, HEL #100, HEL #75, or HEL #76.

In some embodiments, a polynucleic acid is unwound in a physical manner. A physical manner can include addition of heat or shearing for example. In some cases, a polynucleic acid such as DNA or RNA can be exposed to heat for nucleic acid unwinding. A DNA or RNA may denature at temperatures from about 50° C. to about 150° C. DNA or RNA denatures from about 50° C. to 60° C., from about 60° C. to about 70° C., from about 70° C. to about 80° C., from about 80° C. to about 90° C., from about 90° C. to about 100° C., from about 100° C. to about 110° C., from about 110° C. to about 120° C., from about 120° C. to about 130° C., from about 130° C. to about 140° C., from about 140° C. to about 150° C.

In some cases, a polynucleic acid can be denatured via changes in pH. For example, sodium hydroxide (NaOH) can be used to denature a polynucleic acid by increasing a pH to about 25 to about 29. In some cases, a polynucleic acid can be denatured via the addition of a salt.

In some cases, the disclosed editing system utilizing an unwinding agent can reduce a thermodynamic energetic requirement by about 1%, 2%, 3%, 4%, 5%, 6%, 7%, 8%, 9%, 10%, 15%, 20%, 25%, 40%, 50%, or up to about 60% as compared to a system that does not employ the disclosed unwinding agent. In some cases, the disclosed editing system utilizing an unwinding agent can reduce an immune response to the unwinding agent by about 1%, 2%, 3%, 4%, 5%, 6%, 7%, 8%, 9%, 10%, 15%, 20%, 25%, 40%, 50%, or up to about 60% as compared to a system that does not employ the disclosed unwinding agent. In some cases, an unwinding agent can be harvested from bacteria that are endogenously present in the human body to prevent eliciting an immune response.

VII. AGO-SSB FUSION POLYPEPTIDES

In one aspect, described herein are fusion polypeptides that comprises an Ago (or functional fragment or variant thereof) and a single strand DNA binding protein (SSB) described herein (or a functional fragment or variant thereof) (also referred to herein as an Ago-SSB fusion polypeptide).

In some embodiments, the Ago-SSB fusion polypeptide comprises from N to C terminus Ago-SSB; SSB-Ago, Ago-linker-SSB; SSB-linker-Ago.

In some embodiments, the Ago-SSB fusion polypeptide comprises at least one nuclear localization signal polypeptide (NLS). In some embodiments, the Ago-SSB fusion polypeptide comprises at least two nuclear localization signal polypeptides. In some embodiments, the Ago-SSB fusion polypeptide comprises at least three nuclear localization signal polypeptides. In some embodiments, the Ago-SSB fusion polypeptide comprises at least four nuclear localization signal polypeptides. In some embodiments, the Ago-SSB fusion polypeptide comprises at least five nuclear localization signal polypeptides.

In some embodiments, wherein the Ago-SSB comprises two nuclear localization signal polypeptides, said nuclear localization signal polypeptides are the same. In some embodiments, wherein the Ago-SSB comprises two nuclear localization signal polypeptides, said nuclear localization signal polypeptides are different. In some embodiments, wherein the Ago-SSB comprises three nuclear localization signal polypeptides, said nuclear localization signal polypeptides are the same. In some embodiments, wherein the Ago-SSB comprises three nuclear localization signal polypeptides, said nuclear localization signal polypeptides are different. In some embodiments, wherein the Ago-SSB comprises four nuclear localization signal polypeptides, said nuclear localization signal polypeptides are the same. In some embodiments, wherein the Ago-SSB comprises four nuclear localization signal polypeptides, said nuclear localization signal polypeptides are different.

In some embodiments, the Ago-SSB fusion polypeptide comprises from N to C terminus NLS-Ago-SSB; NLS-SSB-Ago; NLS-linker-Ago-SSB; NLS-linker-SSB-Ago, NLS-Ago-linker-SSB; NLS-SSB-linker-Ago; NLS-linker-Ago-linker-SSB; or NL S-linker-SSB-linker-Ago.

In some embodiments, the Ago-SSB fusion polypeptide comprises from N to C terminus NLS1-NLS2-Ago-SSB, wherein NLS1 and NLS2 are the same. In some embodiments, the Ago-SSB fusion polypeptide comprises from N to C terminus NLS1-NLS2-Ago-SSB, wherein NLS1 and NLS2 are different. In some embodiments, the Ago-SSB fusion polypeptide comprises from N to C terminus NLS1-NLS2-linker-Ago-SSB, wherein NLS1 and NLS2 are the same. In some embodiments, the Ago-SSB fusion polypeptide comprises from N to C terminus NLS1-NLS2-linker-Ago-SSB, wherein NLS1 and NLS2 are different.

In some embodiments, the Ago-SSB fusion polypeptide comprises from N to C terminus NLS1-NLS2-SSB-Ago, wherein NLS1 and NLS2 are the same. In some embodiments, the Ago-SSB fusion polypeptide comprises from N to C terminus NLS1-NLS2-SSB-Ago, wherein NLS1 and NLS2 are different.

In some embodiments, the Ago-SSB fusion polypeptide comprises from N to C terminus NLS1-NLS2-linker-SSB-Ago, wherein NLS1 and NLS2 are the same. In some embodiments, the Ago-SSB fusion polypeptide comprises from N to C terminus NLS1-NLS2-linker-SSB-Ago, wherein NLS1 and NLS2 are different.

In some embodiments, the Ago-SSB fusion polypeptide comprises from N to C terminus NLS1-NLS2-Ago-linker-SSB, wherein NLS1 and NLS2 are the same. In some embodiments, the Ago-SSB fusion polypeptide comprises from N to C terminus NLS1-NLS2-Ago-linker-SSB, wherein NLS1 and NLS2 are different.

In some embodiments, the Ago-SSB fusion polypeptide comprises from N to C terminus NLS1-NLS2-linker-Ago-linker-SSB, wherein NLS1 and NLS2 are the same. In some embodiments, the Ago-SSB fusion polypeptide comprises from N to C terminus NLS1-NLS2-linker-Ago-linker-SSB, wherein NLS1 and NLS2 are different.

In some embodiments, the Ago-SSB fusion polypeptide comprises from N to C terminus NLS1-NLS2-SSB-linker-Ago, wherein NLS1 and NLS2 are the same. In some embodiments, the Ago-SSB fusion polypeptide comprises from N to C terminus NLS1-NLS2-SSB-linker-Ago, wherein NLS1 and NLS2 are different.

In some embodiments, the Ago-SSB fusion polypeptide comprises from N to C terminus NLS1-NLS2-linker-SSB-linker-Ago, wherein NLS1 and NLS2 are the same. In some embodiments, the Ago-SSB fusion polypeptide comprises from N to C terminus NLS1-NLS2-linker-SSB-linker-Ago, wherein NLS1 and NLS2 are different.

In some embodiments, the Ago-SSB fusion polypeptide comprises from N to C terminus NLS1-NLS2-NLS3-Ago-SSB, wherein NLS1 and NLS2 are the same and NLS3 is different from NSL1 and NLS2. In some embodiments, the Ago-SSB fusion polypeptide comprises from N to C terminus NLS1-NLS2-NLS3-Ago-SSB, wherein NLS1 and NLS3 are the same and NLS2 is different from NSL1 and NLS3. In some embodiments, the Ago-SSB fusion polypeptide comprises from N to C terminus NLS1-NLS2-NLS3-Ago-SSB, wherein NLS2 and NLS3 are the same and NLS1 is different from NSL2 and NLS3. In some embodiments, the Ago-SSB fusion polypeptide comprises from N to C terminus NLS1-NLS2-NLS3-Ago-SSB, wherein NLS1, NSL2, and NSL3 are the same. In some embodiments, the Ago-SSB fusion polypeptide comprises from N to C terminus NLS1-NLS2-NLS3-Ago-SSB, wherein NLS1, NSL2, and NSL3 are each different.

In some embodiments, the Ago-SSB fusion polypeptide comprises from N to C terminus NLS1-NLS2-NLS3-linker-Ago-SSB, wherein NLS1 and NLS2 are the same and NLS3 is different from NSL1 and NLS2. In some embodiments, the Ago-SSB fusion polypeptide comprises from N to C terminus NLS1-NLS2-NLS3-linker-Ago-SSB, wherein NLS1 and NLS3 are the same and NLS2 is different from NSL1 and NLS3. In some embodiments, the Ago-SSB fusion polypeptide comprises from N to C terminus NLS1-NLS2-NLS3-linker-Ago-SSB, wherein NLS2 and NLS3 are the same and NLS1 is different from NSL2 and NLS3. In some embodiments, the Ago-SSB fusion polypeptide comprises from N to C terminus NLS1-NLS2-NLS3-linker-Ago-SSB, wherein NLS1, NSL2, and NSL3 are the same. In some embodiments, the Ago-SSB fusion polypeptide comprises from N to C terminus NLS1-NLS2-NLS3-linker-Ago-SSB, wherein NLS1, NSL2, and NSL3 are each different.

In some embodiments, the Ago-SSB fusion polypeptide comprises from N to C terminus NLS1-NLS2-NLS3-SSB-Ago, wherein NLS1 and NLS2 are the same and NLS3 is different from NSL1 and NLS2. In some embodiments, the Ago-SSB fusion polypeptide comprises from N to C terminus NLS1-NLS2-NLS3-SSB-Ago, wherein NLS1 and NLS3 are the same and NLS2 is different from NSL1 and NLS3. In some embodiments, the Ago-SSB fusion polypeptide comprises from N to C terminus NLS1-NLS2-NLS3-SSB-Ago, wherein NLS2 and NLS3 are the same and NLS1 is different from NSL2 and NLS3. In some embodiments, the Ago-SSB fusion polypeptide comprises from N to C terminus NLS1-NLS2-NLS3-SSB-Ago, wherein NLS1, NSL2, and NSL3 are the same. In some embodiments, the Ago-SSB fusion polypeptide comprises from N to C terminus NLS1-NLS2-NLS3-SSB-Ago, wherein NLS1, NSL2, and NSL3 are each different.

In some embodiments, the Ago-SSB fusion polypeptide comprises from N to C terminus NLS1-NLS2-NLS3-linker-SSB-Ago, wherein NLS1 and NLS2 are the same and NLS3 is different from NSL1 and NLS2. In some embodiments, the Ago-SSB fusion polypeptide comprises from N to C terminus NLS1-NLS2-NLS3-linker-SSB-Ago, wherein NLS1 and NLS3 are the same and NLS2 is different from NSL1 and NLS3. In some embodiments, the Ago-SSB fusion polypeptide comprises from N to C terminus NLS1-NLS2-NLS3-linker-SSB-Ago, wherein NLS2 and NLS3 are the same and NLS1 is different from NSL2 and NLS3. In some embodiments, the Ago-SSB fusion polypeptide comprises from N to C terminus NLS1-NLS2-NLS3-linker-SSB-Ago, wherein NLS1, NSL2, and NSL3 are the same. In some embodiments, the Ago-SSB fusion polypeptide comprises from N to C terminus NLS1-NLS2-NLS3-linker-SSB-Ago, wherein NLS1, NSL2, and NSL3 are each different.

In some embodiments, the Ago-SSB fusion polypeptide comprises from N to C terminus NLS1-NLS2-NLS3-Ago-linker-SSB, wherein NLS1 and NLS2 are the same and NLS3 is different from NSL1 and NLS2. In some embodiments, the Ago-SSB fusion polypeptide comprises from N to C terminus NLS1-NLS2-NLS3-Ago-linker-SSB, wherein NLS1 and NLS3 are the same and NLS2 is different from NSL1 and NLS3. In some embodiments, the Ago-SSB fusion polypeptide comprises from N to C terminus NLS1-NLS2-NLS3-Ago-linker-SSB, wherein NLS2 and NLS3 are the same and NLS1 is different from NSL2 and NLS3. In some embodiments, the Ago-SSB fusion polypeptide comprises from N to C terminus NLS1-NLS2-NLS3-Ago-linker-SSB, wherein NLS1, NSL2, and NSL3 are the same. In some embodiments, the Ago-SSB fusion polypeptide comprises from N to C terminus NLS1-NLS2-NLS3-Ago-linker-SSB, wherein NLS1, NSL2, and NSL3 are each different.

In some embodiments, the Ago-SSB fusion polypeptide comprises from N to C terminus NLS1-NLS2-NLS3-linker-Ago-linker-SSB, wherein NLS1 and NLS2 are the same and NLS3 is different from NSL1 and NLS2. In some embodiments, the Ago-SSB fusion polypeptide comprises from N to C terminus NLS1-NLS2-NLS3-linker-Ago-linker-SSB, wherein NLS1 and NLS3 are the same and NLS2 is different from NSL1 and NLS3. In some embodiments, the Ago-SSB fusion polypeptide comprises from N to C terminus NLS1-NLS2-NLS3-linker-Ago-linker-SSB, wherein NLS2 and NLS3 are the same and NLS1 is different from NSL2 and NLS3. In some embodiments, the Ago-SSB fusion polypeptide comprises from N to C terminus NLS1-NLS2-NLS3-linker-Ago-linker-SSB, wherein NLS1, NSL2, and NSL3 are the same. In some embodiments, the Ago-SSB fusion polypeptide comprises from N to C terminus NLS1-NLS2-NLS3-linker-Ago-linker-SSB, wherein NLS1, NSL2, and NSL3 are each different.

In some embodiments, the Ago-SSB fusion polypeptide comprises from N to C terminus NLS1-NLS2-NLS3-SSB-linker-Ago, wherein NLS1 and NLS2 are the same and NLS3 is different from NSL1 and NLS2. In some embodiments, the Ago-SSB fusion polypeptide comprises from N to C terminus NLS1-NLS2-NLS3-SSB-linker-Ago, wherein NLS1 and NLS3 are the same and NLS2 is different from NSL1 and NLS3. In some embodiments, the Ago-SSB fusion polypeptide comprises from N to C terminus NLS1-NLS2-NLS3-SSB-linker-Ago, wherein NLS2 and NLS3 are the same and NLS1 is different from NSL2 and NLS3. In some embodiments, the Ago-SSB fusion polypeptide comprises from N to C terminus NLS1-NLS2-NLS3-SSB-linker-Ago, wherein NLS1, NSL2, and NSL3 are the same. In some embodiments, the Ago-SSB fusion polypeptide comprises from N to C terminus NLS1-NLS2-NLS3-SSB-linker-Ago, wherein NLS1, NSL2, and NSL3 are each different.

In some embodiments, the Ago-SSB fusion polypeptide comprises from N to C terminus NLS1-NLS2-NLS3-linker-SSB-linker-Ago, wherein NLS1 and NLS2 are the same and NLS3 is different from NSL1 and NLS2. In some embodiments, the Ago-SSB fusion polypeptide comprises from N to C terminus NLS1-NLS2-NLS3-linker-SSB-linker-Ago, wherein NLS1 and NLS3 are the same and NLS2 is different from NSL1 and NLS3. In some embodiments, the Ago-SSB fusion polypeptide comprises from N to C terminus NLS1-NLS2-NLS3-linker-SSB-linker-Ago, wherein NLS2 and NLS3 are the same and NLS1 is different from NSL2 and NLS3. In some embodiments, the Ago-SSB fusion polypeptide comprises from N to C terminus NLS1-NLS2-NLS3-linker-SSB-linker-Ago, wherein NLS1, NSL2, and NSL3 are the same. In some embodiments, the Ago-SSB fusion polypeptide comprises from N to C terminus NLS1-NLS2-NLS3-linker-SSB-linker-Ago, wherein NLS1, NSL2, and NSL3 are each different.

In some embodiments, the Ago-SSB fusion polypeptide comprises from N to C terminus NLS1-NLS2-NLS3-NLS4-Ago-SSB; wherein each of NSL1, NSL2, NSL3, and NSL4 can be the same or different, or any combination thereof. In some embodiments, the Ago-SSB fusion polypeptide comprises from N to C terminus NLS1-NLS2-NLS3-NLS4-SSB-Ago, wherein each of NSL1, NSL2, NSL3, and NSL4 can be the same or different, or any combination thereof. In some embodiments, the Ago-SSB fusion polypeptide comprises from N to C terminus NLS1-NLS2-NLS3-NLS4-Ago-linker-SSB, wherein each of NSL1, NSL2, NSL3, and NSL4 can be the same or different, or any combination thereof. In some embodiments, the Ago-SSB fusion polypeptide comprises from N to C terminus NLS1-NLS2-NLS3-NLS4-SSB-linker-Ago, wherein each of NSL1, NSL2, NSL3, and NSL4 can be the same or different, or any combination thereof.

In some embodiments, the Ago-SSB fusion polypeptide comprises from N to C terminus NLS1-NLS2-NLS3-NLS4-linker-Ago-SSB; wherein each of NSL1, NSL2, NSL3, and NSL4 can be the same or different, or any combination thereof. In some embodiments, the Ago-SSB fusion polypeptide comprises from N to C terminus NLS1-NLS2-NLS3-NLS4-linker-SSB-Ago, wherein each of NSL1, NSL2, NSL3, and NSL4 can be the same or different, or any combination thereof. In some embodiments, the Ago-SSB fusion polypeptide comprises from N to C terminus NLS1-NLS2-NLS3-NLS4-linker-Ago-linker-SSB, wherein each of NSL1, NSL2, NSL3, and NSL4 can be the same or different, or any combination thereof. In some embodiments, the Ago-SSB fusion polypeptide comprises from N to C terminus NLS1-NLS2-NLS3-NLS4-linker-SSB-linker-Ago, wherein each of NSL1, NSL2, NSL3, and NSL4 can be the same or different, or any combination thereof.

In some embodiments, the Ago-SSB fusion polypeptide comprises from N to C terminus NLS1-NLS2-NLS3-NLS4-NLS5-Ago-SSB, wherein each of NSL1, NSL2, NSL3, NSL4, and NSL5 can be the same or different, or any combination thereof. In some embodiments, the Ago-SSB fusion polypeptide comprises from N to C terminus NLS1-NLS2-NLS3-NLS4-NLS5-SSB-Ago, wherein each of NSL1, NSL2, NSL3, NSL4, and NSL5 can be the same or different, or any combination thereof. In some embodiments, the Ago-SSB fusion polypeptide comprises from N to C terminus NLS1-NLS2-NLS3-NLS4-NLS5-Ago-linker-SSB, wherein each of NSL1, NSL2, NSL3, NSL4, and NSL5 can be the same or different, or any combination thereof. In some embodiments, the Ago-SSB fusion polypeptide comprises from N to C terminus NLS1-NLS2-NLS3-NLS4-NLS5-SSB-linker-Ago, wherein each of NSL1, NSL2, NSL3, NSL4, and NSL5 can be the same or different, or any combination thereof.

In some embodiments, the Ago-SSB fusion polypeptide comprises from N to C terminus NLS1-NLS2-NLS3-NLS4-NLS5-linker-Ago-SSB, wherein each of NSL1, NSL2, NSL3, NSL4, and NSL5 can be the same or different, or any combination thereof. In some embodiments, the Ago-SSB fusion polypeptide comprises from N to C terminus NLS1-NLS2-NLS3-NLS4-NLS5-linker-SSB-Ago, wherein each of NSL1, NSL2, NSL3, NSL4, and NSL5 can be the same or different, or any combination thereof. In some embodiments, the Ago-SSB fusion polypeptide comprises from N to C terminus NLS1-NLS2-NLS3-NLS4-NLS5-linker-Ago-linker-SSB, wherein each of NSL1, NSL2, NSL3, NSL4, and NSL5 can be the same or different, or any combination thereof. In some embodiments, the Ago-SSB fusion polypeptide comprises from N to C terminus NLS1-NLS2-NLS3-NLS4-NLS5-linker-SSB-linker-Ago, wherein each of NSL1, NSL2, NSL3, NSL4, and NSL5 can be the same or different, or any combination thereof.

In some embodiments, the Ago-SSB fusion polypeptide comprises from N to C terminus NLS1-Ago-NLS2-SSB, wherein NLS1 and NLS2 are the same. In some embodiments, the Ago-SSB fusion polypeptide comprises from N to C terminus NLS1-Ago-NLS2-SSB, wherein NLS1 and NLS2 are different. In any of the embodiments described herein, any component may be linked to an adjacent component via a linker polypeptide. For example, NLS2 may be linker to Ago via a linker polypeptide. Multiple linkers may be used to connect different components of the polypeptide fusion. In embodiments, where fusion polypeptides contain multiple linkers, each linker may be the same or different, e.g., in a polypeptide fusion comprising three linkers two linkers may be the same and one different, all three may be the same, or all three may be different.

In some embodiments, the Ago-SSB fusion polypeptide comprises from N to C terminus NLS1-SSB-NLS2-Ago, wherein NLS1 and NLS2 are the same. In some embodiments, the Ago-SSB fusion polypeptide comprises from N to C terminus NLS1-SSB-NLS2-Ago, wherein NLS1 and NLS2 are different. In any of the embodiments described herein, any component may be linked to an adjacent component via a linker polypeptide. For example, NLS2 may be linker to Ago via a linker polypeptide. Multiple linkers may be used to connect different components of the polypeptide fusion. In embodiments, where fusion polypeptides contain multiple linkers, each linker may be the same or different, e.g., in a polypeptide fusion comprising three linkers two linkers may be the same and one different, all three may be the same, or all three may be different.

In some embodiments, the Ago-SSB fusion polypeptide comprises from N to C terminus NLS1-linker-Ago-NLS2-SSB, wherein NLS1 and NLS2 are the same. In some embodiments, the Ago-SSB fusion polypeptide comprises from N to C terminus NLS1-linker-Ago-NLS2-SSB, wherein NLS1 and NLS2 are different.

In some embodiments, the Ago-SSB fusion polypeptide comprises from N to C terminus NLS1-linker-SSB-NLS2-Ago, wherein NLS1 and NLS2 are the same. In some embodiments, the Ago-SSB fusion polypeptide comprises from N to C terminus NLS1-linker-SSB-NLS2-Ago, wherein NLS1 and NLS2 are different.

In some embodiments, the Ago-SSB fusion polypeptide comprises from N to C terminus NLS1-Ago-linker-NLS2-SSB, wherein NLS1 and NLS2 are the same. In some embodiments, the Ago-SSB fusion polypeptide comprises from N to C terminus NLS1-Ago-linker-NLS2-SSB, wherein NLS1 and NLS2 are different.

In some embodiments, the Ago-SSB fusion polypeptide comprises from N to C terminus NLS1-Ago-linker1-NLS2-linker2-SSB, wherein NLS1 and NLS2 are the same. In some embodiments, the Ago-SSB fusion polypeptide comprises from N to C terminus NLS1-Ago-linker-NLS2-linker-SSB, wherein NLS1 and NLS2 are different. In any of the embodiments, described above, linker1 and linker 2 can be the same or different.

In some embodiments, the Ago-SSB fusion polypeptide comprises from N to C terminus NLS1-linker1-Ago-linker2-NLS2-SSB, wherein NLS1 and NLS2 are the same. In some embodiments, the Ago-SSB fusion polypeptide comprises from N to C terminus NLS1-linker1-Ago-linker2-NLS2-SSB, wherein NLS1 and NLS2 are different. In any of the embodiments described above, linker1 and linker 2 can be the same or different.

In some embodiments, the Ago-SSB fusion polypeptide comprises from N to C terminus NLS1-linker1-Ago-linker2-NLS2-linker3-SSB, wherein NLS1 and NLS2 are the same. In some embodiments, the Ago-SSB fusion polypeptide comprises from N to C terminus NLS1-linker1-Ago-linker2-NLS2-linker3-SSB, wherein NLS1 and NLS2 are different. In any of the embodiments described above, any of linker1, linker2, and linker3 can be the same or different.

In some embodiments, the Ago-SSB fusion polypeptide comprises from N to C terminus NLS1-SSB-linker-NLS2-Ago, wherein NLS1 and NLS2 are the same. In some embodiments, the Ago-SSB fusion polypeptide comprises from N to C terminus NLS1-SSB-linker-NLS2-Ago, wherein NLS1 and NLS2 are different.

In some embodiments, the Ago-SSB fusion polypeptide comprises from N to C terminus NLS1-SSB-linker1-NLS2-linker2-Ago, wherein NLS1 and NLS2 are the same. In some embodiments, the Ago-SSB fusion polypeptide comprises from N to C terminus NLS1-SSB-linker1-NLS2-linker2-Ago, wherein NLS1 and NLS2 are different. In any of the embodiments described above, linker1 and linker 2 can be the same or different.

In some embodiments, the Ago-SSB fusion polypeptide comprises from N to C terminus NLS1-linker1-SSB-linker2-NLS2-Ago, wherein NLS1 and NLS2 are the same. In some embodiments, the Ago-SSB fusion polypeptide comprises from N to C terminus NLS1-linker1-SSB-linker2-NLS2-Ago, wherein NLS1 and NLS2 are different. In any of the embodiments described above, linker1 and linker 2 can be the same or different.

In some embodiments, the Ago-SSB fusion polypeptide comprises from N to C terminus NLS1-linker1-SSB-linker2-NLS2-linker3-Ago, wherein NLS1 and NLS2 are the same. In some embodiments, the Ago-SSB fusion polypeptide comprises from N to C terminus NLS1-linker1-SSB-linker2-NLS2-linker3-Ago, wherein NLS1 and NLS2 are different. In any of the embodiments described above, any of linker1, linker2, and linker 3 can be the same or different.

In some embodiments, the Ago-SSB fusion polypeptide comprises from N to C terminus NLS1-NLS2-Ago-NLS3-SSB, wherein NLS1 and NLS2 are the same and NLS3 is different from NSL1 and NLS2. In some embodiments, the Ago-SSB fusion polypeptide comprises from N to C terminus NLS1-NLS2-Ago-NLS3-SSB, wherein NLS1 and NLS3 are the same and NLS2 is different from NSL1 and NLS3. In some embodiments, the Ago-SSB fusion polypeptide comprises from N to C terminus NLS1-NLS2-Ago-NLS3-SSB, wherein NLS2 and NLS3 are the same and NLS1 is different from NSL2 and NLS3. In some embodiments, the Ago-SSB fusion polypeptide comprises from N to C terminus NLS1-NLS2-Ago-NLS3-SSB, wherein NLS1, NSL2, and NSL3 are the same. In some embodiments, the Ago-SSB fusion polypeptide comprises from N to C terminus NLS1-NLS2-Ago-NLS3-SSB, wherein NLS1, NSL2, and NSL3 are each different. In any of the embodiments described herein, any component may be linked to an adjacent component via a linker polypeptide. For example, NLS2 may be linker to Ago via a linker polypeptide. Multiple linkers may be used to connect different components of the polypeptide fusion. In embodiments, where fusion polypeptides contain multiple linkers, each linker may be the same or different, e.g., in a polypeptide fusion comprising three linkers two linkers may be the same and one different, all three may be the same, or all three may be different.

In some embodiments, the Ago-SSB fusion polypeptide comprises from N to C terminus NLS1-NLS2-linker-Ago-NLS3-SSB, wherein NLS1 and NLS2 are the same and NLS3 is different from NSL1 and NLS2. In some embodiments, the Ago-SSB fusion polypeptide comprises from N to C terminus NLS1-NLS2-linker-Ago-NLS3-SSB, wherein NLS1 and NLS3 are the same and NLS2 is different from NSL1 and NLS3. In some embodiments, the Ago-SSB fusion polypeptide comprises from N to C terminus NLS1-NLS2-linker-Ago-NLS3-SSB, wherein NLS2 and NLS3 are the same and NLS1 is different from NSL2 and NLS3. In some embodiments, the Ago-SSB fusion polypeptide comprises from N to C terminus NLS1-NLS2-linker-Ago-NLS3-SSB, wherein NLS1, NSL2, and NSL3 are the same. In some embodiments, the Ago-SSB fusion polypeptide comprises from N to C terminus NLS1-NLS2-linker-Ago-NLS3-SSB, wherein NLS1, NSL2, and NSL3 are each different.

In some embodiments, the Ago-SSB fusion polypeptide comprises from N to C terminus NLS1-NLS2-SSB-NLS3-Ago, wherein NLS1 and NLS2 are the same and NLS3 is different from NSL1 and NLS2. In some embodiments, the Ago-SSB fusion polypeptide comprises from N to C terminus NLS1-NLS2-SSB-NLS3-Ago, wherein NLS1 and NLS3 are the same and NLS2 is different from NSL1 and NLS3. In some embodiments, the Ago-SSB fusion polypeptide comprises from N to C terminus NLS1-NLS2-SSB-NLS3-Ago, wherein NLS2 and NLS3 are the same and NLS1 is different from NSL2 and NLS3. In some embodiments, the Ago-SSB fusion polypeptide comprises from N to C terminus NLS1-NLS2-SSB-NLS3-Ago, wherein NLS1, NSL2, and NSL3 are the same. In some embodiments, the Ago-SSB fusion polypeptide comprises from N to C terminus NLS1-NLS2-SSB-NLS3-Ago, wherein NLS1, NSL2, and NSL3 are each different. In any of the embodiments described herein, any component may be linked to an adjacent component via a linker polypeptide. For example, NLS2 may be linker to Ago via a linker polypeptide. Multiple linkers may be used to connect different components of the polypeptide fusion. In embodiments, where fusion polypeptides contain multiple linkers, each linker may be the same or different, e.g., in a polypeptide fusion comprising three linkers two linkers may be the same and one different, all three may be the same, or all three may be different.

In some embodiments, the Ago-SSB fusion polypeptide comprises from N to C terminus NLS1-NLS2-linker-SSB-NLS3-Ago, wherein NLS1 and NLS2 are the same and NLS3 is different from NSL1 and NLS2. In some embodiments, the Ago-SSB fusion polypeptide comprises from N to C terminus NLS1-NLS2-linker-SSB-NLS3-Ago, wherein NLS1 and NLS3 are the same and NLS2 is different from NSL1 and NLS3. In some embodiments, the Ago-SSB fusion polypeptide comprises from N to C terminus NLS1-NLS2-linker-SSB-NLS3-Ago, wherein NLS2 and NLS3 are the same and NLS1 is different from NSL2 and NLS3. In some embodiments, the Ago-SSB fusion polypeptide comprises from N to C terminus NLS1-NLS2-linker-SSB-NLS3-Ago, wherein NLS1, NSL2, and NSL3 are the same. In some embodiments, the Ago-SSB fusion polypeptide comprises from N to C terminus NLS1-NLS2-linker-SSB-NLS3-Ago, wherein NLS1, NSL2, and NSL3 are each different.

In some embodiments, the Ago-SSB fusion polypeptide comprises from N to C terminus NLS1-NLS2-Ago-linker-NLS3-SSB, wherein NLS1 and NLS2 are the same and NLS3 is different from NSL1 and NLS2. In some embodiments, the Ago-SSB fusion polypeptide comprises from N to C terminus NLS1-NLS2-Ago-linker-NLS3-SSB, wherein NLS1 and NLS3 are the same and NLS2 is different from NSL1 and NLS3. In some embodiments, the Ago-SSB fusion polypeptide comprises from N to C terminus NLS1-NLS2-Ago-linker-NLS3-SSB, wherein NLS2 and NLS3 are the same and NLS1 is different from NSL2 and NLS3. In some embodiments, the Ago-SSB fusion polypeptide comprises from N to C terminus NLS1-NLS2-Ago-linker-NLS3-SSB, wherein NLS1, NSL2, and NSL3 are the same. In some embodiments, the Ago-SSB fusion polypeptide comprises from N to C terminus NLS1-NLS2-Ago-linker-NLS3-SSB, wherein NLS1, NSL2, and NSL3 are each different.

In some embodiments, the Ago-SSB fusion polypeptide comprises from N to C terminus NLS1-NLS2-Ago-NLS3-linker-SSB, wherein NLS1 and NLS2 are the same and NLS3 is different from NSL1 and NLS2. In some embodiments, the Ago-SSB fusion polypeptide comprises from N to C terminus NLS1-NLS2-Ago-NLS3-linker-SSB, wherein NLS1 and NLS3 are the same and NLS2 is different from NSL1 and NLS3. In some embodiments, the Ago-SSB fusion polypeptide comprises from N to C terminus NLS1-NLS2-Ago-NLS3-linker-SSB, wherein NLS2 and NLS3 are the same and NLS1 is different from NSL2 and NLS3. In some embodiments, the Ago-SSB fusion polypeptide comprises from N to C terminus NLS1-NLS2-Ago-NLS3-linker-SSB, wherein NLS1, NSL2, and NSL3 are the same. In some embodiments, the Ago-SSB fusion polypeptide comprises from N to C terminus NLS1-NLS2-Ago-NLS3-linker-SSB, wherein NLS1, NSL2, and NSL3 are each different.

In some embodiments, the Ago-SSB fusion polypeptide comprises from N to C terminus NLS1-NLS2-Ago-linker1-NLS3-linker2-SSB, wherein NLS1 and NLS2 are the same and NLS3 is different from NSL1 and NLS2. In some embodiments, the Ago-SSB fusion polypeptide comprises from N to C terminus NLS1-NLS2-Ago-linker1-NLS3-linker2-SSB, wherein NLS1 and NLS3 are the same and NLS2 is different from NSL1 and NLS3. In some embodiments, the Ago-SSB fusion polypeptide comprises from N to C terminus NLS1-NLS2-Ago-linker1-NLS3-linker2-SSB, wherein NLS2 and NLS3 are the same and NLS1 is different from NSL2 and NLS3. In some embodiments, the Ago-SSB fusion polypeptide comprises from N to C terminus NLS1-NLS2-Ago-linker1-NLS3-linker2-SSB, wherein NLS1, NSL2, and NSL3 are the same. In some embodiments, the Ago-SSB fusion polypeptide comprises from N to C terminus NLS1-NLS2-Ago-linker1-NLS3-linker2-SSB, wherein NLS1, NSL2, and NSL3 are each different. In any of the embodiments described above, linker1 and linker 2 can be the same or different.

In some embodiments, the Ago-SSB fusion polypeptide comprises from N to C terminus NLS1-NLS2-linker1-Ago-linker2-NLS3-SSB, wherein NLS1 and NLS2 are the same and NLS3 is different from NSL1 and NLS2. In some embodiments, the Ago-SSB fusion polypeptide comprises from N to C terminus NLS1-NLS2-linker1-Ago-linker2-NLS3-SSB, wherein NLS1 and NLS3 are the same and NLS2 is different from NSL1 and NLS3. In some embodiments, the Ago-SSB fusion polypeptide comprises from N to C terminus NLS1-NLS2-linker1-Ago-linker2-NLS3-SSB, wherein NLS2 and NLS3 are the same and NLS1 is different from NSL2 and NLS3. In some embodiments, the Ago-SSB fusion polypeptide comprises from N to C terminus NLS1-NLS2-linker1-Ago-linker2-NLS3-SSB, wherein NLS1, NSL2, and NSL3 are the same. In some embodiments, the Ago-SSB fusion polypeptide comprises from N to C terminus NLS1-NLS2-linker1-Ago-linker2-NLS3-SSB, wherein NLS1, NSL2, and NSL3 are each different. In any of the embodiments described above, linker1 and linker 2 can be the same or different.

In some embodiments, the Ago-SSB fusion polypeptide comprises from N to C terminus NLS1-NLS2-linker1-Ago-NLS3-linker2-SSB, wherein NLS1 and NLS2 are the same and NLS3 is different from NSL1 and NLS2. In some embodiments, the Ago-SSB fusion polypeptide comprises from N to C terminus NLS1-NLS2-linker1-Ago-NLS3-linker2-SSB, wherein NLS1 and NLS3 are the same and NLS2 is different from NSL1 and NLS3. In some embodiments, the Ago-SSB fusion polypeptide comprises from N to C terminus NLS1-NLS2-linker1-Ago-NLS3-linker2-SSB, wherein NLS2 and NLS3 are the same and NLS1 is different from NSL2 and NLS3. In some embodiments, the Ago-SSB fusion polypeptide comprises from N to C terminus NLS1-NLS2-linker1-Ago-NLS3-linker2-SSB, wherein NLS1, NSL2, and NSL3 are the same. In some embodiments, the Ago-SSB fusion polypeptide comprises from N to C terminus NLS1-NLS2-linker1-Ago-NLS3-linker2-SSB, wherein NLS1, NSL2, and NSL3 are each different. In any of the embodiments described above, linker1 and linker 2 can be the same or different.

In some embodiments, the Ago-SSB fusion polypeptide comprises from N to C terminus NLS1-NLS2-linker1-Ago-linker2-NLS3-linker3-SSB, wherein NLS1 and NLS2 are the same and NLS3 is different from NSL1 and NLS2. In some embodiments, the Ago-SSB fusion polypeptide comprises from N to C terminus NLS1-NLS2-linker1-Ago-linker2-NLS3-linker3-SSB, wherein NLS1 and NLS3 are the same and NLS2 is different from NSL1 and NLS3. In some embodiments, the Ago-SSB fusion polypeptide comprises from N to C terminus NLS1-NLS2-linker1-Ago-linker2-NLS3-linker3-SSB, wherein NLS2 and NLS3 are the same and NLS1 is different from NSL2 and NLS3. In some embodiments, the Ago-SSB fusion polypeptide comprises from N to C terminus NLS1-NLS2-linker1-Ago-linker2-NLS3-linker3-SSB, wherein NLS1, NSL2, and NSL3 are the same. In some embodiments, the Ago-SSB fusion polypeptide comprises from N to C terminus NLS1-NLS2-linker1-Ago-linker2-NLS3-linker3-SSB, wherein NLS1, NSL2, and NSL3 are each different. In any of the embodiments described above, any of linker1, linker2, and linker 3 can be the same or different.

In some embodiments, the Ago-SSB fusion polypeptide comprises from N to C terminus NLS1-NLS2-SSB-linker-NLS3-Ago, wherein NLS1 and NLS2 are the same and NLS3 is different from NSL1 and NLS2. In some embodiments, the Ago-SSB fusion polypeptide comprises from N to C terminus NLS1-NLS2-SSB-linker-NLS3-Ago, wherein NLS1 and NLS3 are the same and NLS2 is different from NSL1 and NLS3. In some embodiments, the Ago-SSB fusion polypeptide comprises from N to C terminus NLS1-NLS2-SSB-linker-NLS3-Ago, wherein NLS2 and NLS3 are the same and NLS1 is different from NSL2 and NLS3. In some embodiments, the Ago-SSB fusion polypeptide comprises from N to C terminus NLS1-NLS2-SSB-linker-NLS3-Ago, wherein NLS1, NSL2, and NSL3 are the same. In some embodiments, the Ago-SSB fusion polypeptide comprises from N to C terminus NLS1-NLS2-SSB-linker-NLS3-Ago, wherein NLS1, NSL2, and NSL3 are each different.

In some embodiments, the Ago-SSB fusion polypeptide comprises from N to C terminus NLS1-NLS2-SSB-NLS3-linker-Ago, wherein NLS1 and NLS2 are the same and NLS3 is different from NSL1 and NLS2. In some embodiments, the Ago-SSB fusion polypeptide comprises from N to C terminus NLS1-NLS2-SSB-NLS3-linker-Ago, wherein NLS1 and NLS3 are the same and NLS2 is different from NSL1 and NLS3. In some embodiments, the Ago-SSB fusion polypeptide comprises from N to C terminus NLS1-NLS2-SSB-NLS3-linker-Ago, wherein NLS2 and NLS3 are the same and NLS1 is different from NSL2 and NLS3. In some embodiments, the Ago-SSB fusion polypeptide comprises from N to C terminus NLS1-NLS2-SSB-NLS3-linker-Ago, wherein NLS1, NSL2, and NSL3 are the same. In some embodiments, the Ago-SSB fusion polypeptide comprises from N to C terminus NLS1-NLS2-SSB-NLS3-linker-Ago, wherein NLS1, NSL2, and NSL3 are each different.

In some embodiments, the Ago-SSB fusion polypeptide comprises from N to C terminus NLS1-NLS2-SSB-linker1-NLS3-linker2-Ago, wherein NLS1 and NLS2 are the same and NLS3 is different from NSL1 and NLS2. In some embodiments, the Ago-SSB fusion polypeptide comprises from N to C terminus NLS1-NLS2-SSB-linker1-NLS3-linker2-Ago, wherein NLS1 and NLS3 are the same and NLS2 is different from NSL1 and NLS3. In some embodiments, the Ago-SSB fusion polypeptide comprises from N to C terminus NLS1-NLS2-SSB-linker1-NLS3-linker2-Ago, wherein NLS2 and NLS3 are the same and NLS1 is different from NSL2 and NLS3. In some embodiments, the Ago-SSB fusion polypeptide comprises from N to C terminus NLS1-NLS2-SSB-linker1-NLS3-linker2-Ago, wherein NLS1, NSL2, and NSL3 are the same. In some embodiments, the Ago-SSB fusion polypeptide comprises from N to C terminus NLS1-NLS2-SSB-linker1-NLS3-linker2-Ago, wherein NLS1, NSL2, and NSL3 are each different. In any of the embodiments described above, linker1 and linker 2 can be the same or different.

In some embodiments, the Ago-SSB fusion polypeptide comprises from N to C terminus NLS1-NLS2-linker1-SSB-linker2-NLS3-Ago, wherein NLS1 and NLS2 are the same and NLS3 is different from NSL1 and NLS2. In some embodiments, the Ago-SSB fusion polypeptide comprises from N to C terminus NLS1-NLS2-linker1-SSB-linker2-NLS3-Ago, wherein NLS1 and NLS3 are the same and NLS2 is different from NSL1 and NLS3. In some embodiments, the Ago-SSB fusion polypeptide comprises from N to C terminus NLS1-NLS2-linker1-SSB-linker2-NLS3-Ago, wherein NLS2 and NLS3 are the same and NLS1 is different from NSL2 and NLS3. In some embodiments, the Ago-SSB fusion polypeptide comprises from N to C terminus NLS1-NLS2-linker1-SSB-linker2-NLS3-Ago, wherein NLS1, NSL2, and NSL3 are the same. In some embodiments, the Ago-SSB fusion polypeptide comprises from N to C terminus NLS1-NLS2-linker1-SSB-linker2-NLS3-Ago, wherein NLS1, NSL2, and NSL3 are each different. In any of the embodiments described above, linker1 and linker 2 can be the same or different.

In some embodiments, the Ago-SSB fusion polypeptide comprises from N to C terminus NLS1-NLS2-linker1-SSB-NLS3-linker2-Ago, wherein NLS1 and NLS2 are the same and NLS3 is different from NSL1 and NLS2. In some embodiments, the Ago-SSB fusion polypeptide comprises from N to C terminus NLS1-NLS2-linker1-SSB-NLS3-linker2-Ago, wherein NLS1 and NLS3 are the same and NLS2 is different from NSL1 and NLS3. In some embodiments, the Ago-SSB fusion polypeptide comprises from N to C terminus NLS1-NLS2-linker1-SSB-NLS3-linker2-Ago, wherein NLS2 and NLS3 are the same and NLS1 is different from NSL2 and NLS3. In some embodiments, the Ago-SSB fusion polypeptide comprises from N to C terminus NLS1-NLS2-linker1-SSB-NLS3-linker2-Ago, wherein NLS1, NSL2, and NSL3 are the same. In some embodiments, the Ago-SSB fusion polypeptide comprises from N to C terminus NLS1-NLS2-linker1-SSB-NLS3-linker2-Ago, wherein NLS1, NSL2, and NSL3 are each different. In any of the embodiments described above, linker1 and linker 2 can be the same or different.

In some embodiments, the Ago-SSB fusion polypeptide comprises from N to C terminus NLS1-NLS2-linker1-SSB-linker2-NLS3-linker3-Ago, wherein NLS1 and NLS2 are the same and NLS3 is different from NSL1 and NLS2. In some embodiments, the Ago-SSB fusion polypeptide comprises from N to C terminus NLS1-NLS2-linker1-SSB-linker2-NLS3-linker3-Ago, wherein NLS1 and NLS3 are the same and NLS2 is different from NSL1 and NLS3. In some embodiments, the Ago-SSB fusion polypeptide comprises from N to C terminus NLS1-NLS2-linker1-SSB-linker2-NLS3-linker3-Ago, wherein NLS2 and NLS3 are the same and NLS1 is different from NSL2 and NLS3. In some embodiments, the Ago-SSB fusion polypeptide comprises from N to C terminus NLS1-NLS2-linker1-SSB-linker2-NLS3-linker3-Ago, wherein NLS1, NSL2, and NSL3 are the same. In some embodiments, the Ago-SSB fusion polypeptide comprises from N to C terminus NLS1-NLS2-linker1-SSB-linker2-NLS3-linker3-Ago, wherein NLS1, NSL2, and NSL3 are each different. In any of the embodiments described above, any of linker1, linker2, and linker 3 can be the same or different. In some embodiments, linker2 and linker3 are the same and linker 1 is different. In some embodiments, linker1 and linker2 are the same and linker3 is different. In some embodiments, linker1 and linker3 are the same and linker2 is different.

In some embodiments, the Ago-SSB fusion polypeptide comprises from N to C terminus NLS1-NLS2-linker1-SSB-linker2-NLS3-linker3-Ago, wherein NLS1 and NLS2 are the same and NLS3 is different from NSL1 and NLS2; and wherein linker2 and linker3 are the same and linker1 is different.

(a) SSB Polypeptides

In some embodiments, the SSB polypeptide component of an Ago-SSB fusion comprises an SSB polypeptide described herein (or a functional fragment or functional variant thereof). In some embodiments, the SSB polypeptide component of an Ago-SSB fusion comprises an SSB derived from a microorganism. In some embodiments, the microorganism is a bacterium. In some embodiments, the microorganism is a hyperthermophilic microorganism. In some embodiments, the SSB is from *Saccharolobus solfataricus*. In some embodiments, the SSB is active at a temperature between 32° C.-42° C. In some embodiments, the SSB is active at a temperature between 35° C.-40° C. In some embodiments, the SSB is active at about 37° C.

In some embodiments, the SSB comprises an amino acid sequence with at least 80%, 85%, 90%, 91%, 92%, 93%, 94%, 95%, 96%, 97%, 98%, 99%, or 100% identity to one of SEQ ID NOS: 22-35. In some embodiments, the SSB comprises an amino acid sequence with at least 80%, 85%, 90%, 91%, 92%, 93%, 94%, 95%, 96%, 97%, 98%, 99%, or 100% identity to one of SEQ ID NOS: 22, 24, 26, 28, 30, 32, or 34. In some embodiments, the SSB is encoded by a nucleic acid sequence with at least 80%, 85%, 90%, 91%, 92%, 93%, 94%, 95%, 96%, 97%, 98%, 99%, or 100% identity to one of SEQ ID NOS: 36-49. In some embodiments, the SSB is encoded by a nucleic acid sequence with at least 80%, 85%, 90%, 91%, 92%, 93%, 94%, 95%, 96%, 97%, 98%, 99%, or 100% identity to one of SEQ ID NOS: 36, 38, 40, 42, 44, or 48. In some embodiments, the SSB polypeptide is one selected from Table 4.

In some embodiments, the SSB is ET-SSB (Sso-SSB), Neq SSB, TaqSSB, TmaSSB, or EcoSSB. In some embodiments, the SSB is an ET-SSB (also referred to herein as Sso-SSB). In some embodiments, the SSB comprises an amino acid sequence with at least 80%, 85%, 90%, 91%, 92%, 93%, 94%, 95%, 96%, 97%, 98%, 99%, or 100% identity to SEQ ID NO: 22. In some embodiments, the SSB is encoded by a nucleic acid sequence with at least 80%, 85%, 90%, 91%, 92%, 93%, 94%, 95%, 96%, 97%, 98%, 99%, or 100% identity to SEQ ID NOS: 36.

(b) Nuclear Localization Signals (NLS)

In some embodiments, Ago-SSB fusion proteins described herein comprise at least 1, 2, 3, or 4 nuclear localization signal (NLS) polypeptides. In some embodiments, the Ago-SSB fusion protein comprises at least 1 NLS. In some embodiments, the Ago-SSB fusion protein comprises at least 2 NLS. In some embodiments, the Ago-SSB fusion protein comprises at least 3 NLS. In some embodiments, the Ago-SSB fusion protein comprises at least 4 NLS.

In some embodiments, the Ago-SSB fusion protein comprises at least 2 NLS, wherein each NLS is different. In some embodiments, the Ago-SSB fusion protein comprises at least 2 NLS, wherein each NSL is the same. In some embodiments, the Ago-SSB fusion protein comprises at least 3 NLS, wherein each NLS is different. In some embodiments, the Ago-SSB fusion protein comprises at least 3 NLS, wherein each NSL is the same. In some embodiments, the Ago-SSB fusion protein comprises at least 3 NLS, wherein two NLSs are the same and one is different. In some embodiments, at least one NLS is located between the Ago and SSB polypeptides of the fusion polypeptide, optionally via one or more linkers.

In some embodiments, the NLS is derived from a microorganism. In some embodiments, the microorganism is a virus. In some embodiments, the NLS is an SV40 NLS.

In some embodiments, the NLS comprises a sequence with at least 90%, 91%, 92%, 93%, 94%, 95%, 96%, 97%, 98%, 99%, or 100% identity to a linker in Table 9. In some embodiments, the NLS comprises an amino acid sequence with at least 90%, 91%, 92%, 93%, 94%, 95%, 96%, 97%, 98%, 99%, or 100% identity to one of SEQ ID NOs: 73-78.

(c) Linkers

In some embodiments, Ago-SSB fusion proteins described herein comprise at least 1, 2, 3, 4, 5, or 6 linkers. In some embodiments, the linker is a linker described herein. In some embodiments in which a fusion construct has more than 1 linker, each linker may be the same or different from the other linkers, e.g., a in a fusion polypeptide construct have linker1, linker2, and linker3—each of linker1, linker2, and linker3 can be the same (e.g., 100% sequence identity); each of linker1, linker2, and linker3 can be the same (e.g., less than 100% sequence identity); or two of linkers1-3 may be the same and the other different.

In some embodiments, a linker is used herein to connect one component of a fusion polypeptide to another component of a fusion polypeptide. For example, a linker can be a polypeptide linker, such as a linker that is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more amino acids long. In some embodiments, the linker is a cleavable or non-cleavable linker. As described herein, two polypeptide sequences that are "fused" need not be directly adjacent to each other. Fused polypeptide sequences can be fused by a linker, or by an additional functional polypeptide sequence that is fused to the polypeptide sequences.

In some embodiments, a linker comprises glycine and serine amino acid residues. linker can comprise non-charged or charged amino acids. A linker can comprise alpha-helical domains. In some embodiments, a linker comprises a chemical cross linker. In some cases, a linker can be of different lengths to adjust the function of fused domains and their physical proximity. In some cases, a linker comprises peptides with ligand-inducible conformational changes.

Exemplary linkers include those described herein, e.g., Table 8, SEQ ID NOs: 70-72 or 140.

In some embodiments, the linker comprises a sequence with at least 90%, 91%, 92%, 93%, 94%, 95%, 96%, 97%, 98%, 99%, or 100% identity to a linker in Table 8. In some embodiments, the linker comprises an amino acid sequence with at least 90%, 91%, 92%, 93%, 94%, 95%, 96%, 97%, 98%, 99%, or 100% identity to one of SEQ ID NOs: 70-72 or 140.

(d) Exemplary Ago-SSB Fusion Polypeptides

In some embodiments, the Ago-SSB fusion protein comprises an amino acid sequence with at least 80%, 85%, 90%, 91%, 92%, 93%, 94%, 95%, 96%, 97%, 98%, 99%, or 100% identity to one of SEQ ID NOS: 79-87. In some embodiments, the Ago-SSB fusion protein is encoded by a nucleic acid sequence with at least 80%, 85%, 90%, 91%, 92%, 93%, 94%, 95%, 96%, 97%, 98%, 99%, or 100% identity to one of SEQ ID NOS: 88-96. The amino acid sequence of exemplary Ago-SSB fusion polypeptides are provided in Table 10. The nucleic acid sequence of exemplary Ago-SSB fusion polypeptides are provided in Table 11.

TABLE 10

Amino Acid Sequence of Exemplary Ago-SSB Fusion Polypeptides

| Fusion Polypeptide | Amino Acid Sequence | SEQ ID NO |
|---|---|---|
| AP072<br>(also referred to herein is SSB-Ago69_v1)<br>(See FIG. 68)<br>N to C terminus:<br>*Italicized: His Tag*<br>Underlined: GST<br>*Italicized/ Underlined: 2XSV40NLS*<br>**Bold: SsoSSB**<br>**Underlined/Bold: G4S** (SEQ ID NO: 70)<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>PKKKRKVEDPKKKRKVGSGSRLEMEEKVGNLKPNMESVNVTV<br>RVLEASEARQIQTKNGVRTISEAIVGDETGRVKLTLWGKHAG<br>SIKEGQVVKIENAWTTAFKGQVQLNAGSKTKIAEASEDGFPE<br>SSQIPENTPTAPQQMRGGGRGFRGGGRRYGRRGGRRQENEEG<br>EEEGGGGSMVGGYKVSNLTVEAFEGIGSVNPMLFYQYKVTGK<br>GKYDNVYKIIKSARYKMHSKNRFKPVFIKDDKLYTLEKLPDI<br>EDLDFANINFVKSEVLSIEDNMSIYGEVVEYYINLKLKKVKV<br>LGKYPKYRINYSKEILSNTLLTRELKDEFKKSNKGFNLKRKF<br>RISPVVNKMGKVILYLSCSADFSTNKNIYEMLKEGLEVEGLA<br>VKSEWSNISGNLVIESVLETKISEPTSLGQSLIDYYKNNNQG<br>YRVKDFTDEDLNANIVNVRGNKKIYMYIPHALKPIITREYLA<br>KNDPEFSKEIEQLIKMNMNYRYETLKSFVNDIGVIEELNNLS<br>FKNKYYEDVKLLGYSSGKIDEPVLMGAKGIIKNKMQIFSNGF<br>YKLPEGKVRFGVLYPKEFDGVSRKAIRAIYDFSKEGKYHGES<br>NKYIAEHLINVEFNPKECIFEGYELGDITEYKKAALKLNNYN<br>NVDFVIAIVPNMSDEEIENSYNPFKKIWAELNLPSQMISVKT<br>AEIFANSRDNTALYYLHNIVLGILGKIGGIPWVVKDMKGDVD<br>CFVGLDVGTREKGIHYPACSVVFDKYGKLINYYKPNIPQNGE<br>KINTEILQEIFDKVLISYEEENGAYPKNIVIHRDGFSREDLD<br>WYENYFGKKNIKFNIIEVKKSTPLKIASINEGNITNPEKGSY<br>ILRGNKAYMVTTDIKENLGSPKPLKIEKSYGDIDMLTALSQI<br>YALTQIHVGATKSLRLPITTGYADKICKAIEFIPQGRVDNRL<br>FFL | 79 |
| AP073<br>(See FIG. 68)<br>N to C terminus:<br>*Italicized: His Tag*<br>Underlined: GST<br>*Italicized/ Underlined: 2XSV40NLS*<br>**Bold: VP64**<br>**Underlined/Bold: G4S** (SEQ ID NO: 70)<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>PKKKRKVEDPKKKRKVGSGSRLEMDALDDFDLDMLGSDALDD<br>FDLDMLGSDALDDFDLDMLGSDALDDFDLDMLGGGGSMVGGY<br>KVSNLTVEAFEGIGSVNPMLFYQYKVTGKGKYDNVYKIIKSA<br>RYKMHSKNRFKPVFIKDDKLYTLEKLPDIEDLDFANINFVKS<br>EVLSIEDNMSIYGEVVEYYINLKLKKVKVLGKYPKYRINYSK<br>EILSNTLLTRELKDEFKKSNKGFNLKRKFRISPVVNKMGKVI<br>LYLSCSADFSTNKNIYEMLKEGLEVEGLAVKSEWSNISGNLV<br>IESVLETKISEPTSLGQSLIDYYKNNNQGYRVKDFTDEDLNA<br>NIVNVRGNKKIYMYIPHALKPIITREYLAKNDPEFSKEIEQL<br>IKMNMNYRYETLKSFVNDIGVIEELNNLSFKNKYYEDVKLLG<br>YSSGKIDEPVLMGAKGIIKNKMQIFSNGFYKLPEGKVRFGVL<br>YPKEFDGVSRKAIRAIYDFSKEGKYHGESNKYIAEHLINVEF<br>NPKECIFEGYELGDITEYKKAALKLNNYNNVDFVIAIVPNMS<br>DEEIENSYNPFKKIWAELNLPSQMISVKTAEIFANSRDNTAL | 80 |

TABLE 10-continued

Amino Acid Sequence of Exemplary Ago-SSB Fusion Polypeptides

| Fusion Polypeptide | Amino Acid Sequence | SEQ ID NO |
|---|---|---|
| | YYLHNIVLGILGKIGGIPWVVKDMKGDVDCFVGLDVGTREKG<br>IHYPACSVVFDKYGKLINYYKPNIPQNGEKINTEILQEIFDK<br>VLISYEEENGAYPKNIVIHRDGFSREDLDWYENYFGKKNIKF<br>NIIEVKKSTPLKIASINEGNITNPEKGSYILRGNKAYMVTTD<br>IKENLGSPKPLKIEKSYGDIDMLTALSQIYALTQIHVGATKS<br>LRLPITTGYADKICKAIEFIPQGRVDNRLFFL | |
| AP046<br>(See FIG. 69B)<br>N to C terminus:<br>*Italicized: His Tag*<br>Underlined: GST<br>*Italicized/* Underlined: *2XSV40NLS*<br>**Underlined/Bold: GSGS linker** (SEQ ID NO: 154)<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAV<br>SSPQGYPSLMPKKKRKVEDPKKKRKVGSGSMVGGYKVSNLTV<br>EAFEGIGSVNPMLFYQYKVTGKGKYDNVYKIIKSARYKMHSK<br>NRFKPVFIKDDKLYTLEKLPDIEDLDFANINFVKSEVLSIED<br>NMSIYGEVVEYYINLKLKKVKVLGKYPKYRINYSKEILSNTL<br>LTRELKDEFKKSNKGFNLKRKFRISPVVNKMGKVILYLSCSA<br>DFSTNKNIYEMLKEGLEVEGLAVKSEWSNISGNLVIESVLET<br>KISEPTSLGQSLIDYYKNNNQGYRVKDFTDEDLNANIVNVRG<br>NKKIYMYIPHALKPIITREYLAKNDPEFSKEIEQLIKMNMNY<br>RYETLKSFVNDIGVIEELNNLSFKNKYYEDVKLLGYSSGKID<br>EPVLMGAKGIIKNKMQIFSNGFYKLPEGKVRFGVLYPKEFDG<br>VSRKAIRAIYDFSKEGKYHGESNKYIAEHLINVEFNPKECIF<br>EGYELGDITEYKKAALKLNNYNNVDFVIAIVPNMSDEEIENS<br>YNPFKKIWAELNLPSQMISVKTAEIFANSRDNTALYYLHNIV<br>LGILGKIGGIPWVVKDMKGDVDCFVGLDVGTREKGIHYPACS<br>VVFDKYGKLINYYKPNIPQNGEKINTEILQEIFDKVLISYEE<br>ENGAYPKNIVIHRDGFSREDLDWYENYFGKKNIKENIIEVKK<br>STPLKIASINEGNITNPEKGSYILRGNKAYMVTTDIKENLGS<br>PKPLKIEKSYGDIDMLTALSQIYALTQIHVGATKSLRLPITT<br>GYADKICKAIEFIPQGRVDNRLFFL | 81 |
| AP025<br>(See FIG. 69B)<br>N to C terminus:<br>*Italicized: His Tag*<br>Underlined: GST<br>***Bold/Italicized/ Underlined: 2XSV40NLS***<br>**Underlined and Bold: GSGS linker** (SEQ ID NO: 154)<br>***Italicized and Bold: Ago69***<br>*Italicized and underlined: GGGS linker* (SEQ ID NO: 155)<br>**Bold: V5 tag**<br>*Italicized: NPM NLS* | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>PKKKRKVEDPKKKRKVGSGSRLEMVGGYKVSNLTVEAFEGIG<br>SVNPMLFYQYKVTGKGKYDNVYKIIKSARYKMHSKNRFKPVF<br>IKDDKLYTLEKLPDIEDLDFANINFVKSEVLSIEDNMSIYGE<br>VVEYYINLKLKKVKVLGKYPKYRINYSKEILSNTLLTRELKD<br>EFKKSNKGFNLKRKFRISPVVNKMGKVILYLSCSADFSTNKN<br>IYEMLKEGLEVEGLAVKSEWSNISGNLVIESVLETKISEPTS<br>LGQSLIDYYKNNNQGYRVKDFTDEDLNANIVNVRGNKKIYMY<br>IPHALKPIITREYLAKNDPEFSKEIEQLIKMNMNYRYETLKS<br>FVNDIGVIEELNNLSFKNKYYEDVKLLGYSSGKIDEPVLMGA<br>KGIIKNKMQIFSNGFYKLPEGKVRFGVLYPKEFDGVSRKAIR<br>AIYDFSKEGKYHGESNKYIAEHLINVEFNPKECIFEGYELGD<br>ITEYKKAALKLNNYNNVDFVIAIVPNMSDEEIENSYNPFKKI<br>WAELNLPSQMISVKTAEIFANSRDNTALYYLHNIVLGILGKI<br>GGIPWVVKDMKGDVDCFVGLDVGTREKGIHYPACSVVFDKYG<br>KLINYYKPNIPQNGEKINTEILQEIFDKVLISYEEENGAYPK<br>NIVIHRDGFSREDLDWYENYFGKKNIKFNIIEVKKSTPLKIA<br>SINEGNITNPEKGSYILRGNKAYMVTTDIKENLGSPKPLKIE<br>KSYGDIDMLTALSQIYALTQIHVGATKSLRLPITTGYADKIC<br>KAIEFIPQGRVDNRLFFLTSGGGGSGKPIPNPLLGLDSTKRP<br>AATKKAGQAKKKK | 82 |
| AP071<br>(See FIG. 69B)<br>N to C terminus:<br>*Italicized: His Tag*<br>Underlined: GST<br>**Bold: 2XSV40NLS**<br>**Underlined/Bold: GSGS linker** (SEQ ID NO: 154)<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>PKKKRKVEDPKKKRKVGSGSRLEMVGGYKVSNLTVEAFEGIG<br>SVNPMLFYQYKVTGKGKYDNVYKIIKSARYKMHSKNRFKPVF<br>IKDDKLYTLEKLPDIEDLDFANINFVKSEVLSIEDNMSIYGE<br>VVEYYINLKLKKVKVLGKYPKYRINYSKEILSNTLLTRELKD<br>EFKKSNKGFNLKRKFRISPVVNKMGKVILYLSCSADFSTNKN<br>IYEMLKEGLEVEGLAVKSEWSNISGNLVIESVLETKISEPTS<br>LGQSLIDYYKNNNQGYRVKDFTDEDLNANIVNVRGNKKIYMY<br>IPHALKPIITREYLAKNDPEFSKEIEQLIKMNMNYRYETLKS | 83 |

TABLE 10-continued

Amino Acid Sequence of Exemplary Ago-SSB Fusion Polypeptides

| Fusion Polypeptide | Amino Acid Sequence | SEQ ID NO |
|---|---|---|
| | FVNDIGVIEELNNLSFKNKYYEDVKLLGYSSGKIDEPVLMGA<br>KGIIKNKMQIFSNGFYKLPEGKVRFGVLYPKEFDGVSRKAIR<br>AIYDFSKEGKYHGESNKYIAEHLINVEFNPKECIFEGYELGD<br>ITEYKKAALKLNNYNNVDFVIAIVPNMSDEEIENSYNPFKKI<br>WAELNLPSQMISVKTAEIFANSRDNTALYYLHNIVLGILGKI<br>GGIPWVVKDMKGDVDCFVGLDVGTREKGIHYPACSVVFDKYG<br>KLINYYKPNIPQNGEKINTEILQEIFDKVLISYEEENGAYPK<br>NIVIHRDGFSREDLDWYENYFGKKNIKFNIIEVKKSTPLKIA<br>SINEGNITNPEKGSYILRGNKAYMVTTDIKENLGSPKPLKIE<br>KSYGDIDMLTALSQIYALTQIHVGATKSLRLPITTGYADKIC<br>KAIEFIPQGRVDNRLFFL | |
| SSB-AGO#69v3<br>(See FIG. 75)<br>N to C terminus:<br>*Italicized: His Tag*<br>Underlined: GST<br>**Bold: SsoSSB**<br>*Italicized/ Underlined: XTEN*<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>EEKVGNLKPNMESVNVTVRVLEASEARQIQTKNGVRTISEAI<br>VGDETGRVKLTLWGKHAGSIKEGQVVKIENAWTTAFKGQVQL<br>NAGSKTKIAEASEDGFPESSQIPENTPTAPQQMRGGGRGFRG<br>GGRRYGRRGGRRQENEEGEEESGSETPGTSESATPESVGGYK<br>VSNLTVEAFEGIGSVNPMLFYQYKVTGKGKYDNVYKIIKSAR<br>YKMHSKNRFKPVFIKDDKLYTLEKLPDIEDLDFANINFVKSE<br>VLSIEDNMSIYGEVVEYYINLKLKKVKVLGKYPKYRINYSKE<br>ILSNTLLTRELKDEFKKSNKGFNLKRKFRISPVVNKMGKVIL<br>YLSCSADFSTNKNIYEMLKEGLEVEGLAVKSEWSNISGNLVI<br>ESVLETKISEPTSLGQSLIDYYKNNNQGYRVKDFTDEDLNAN<br>IVNVRGNKKIYMYIPHALKPIITREYLAKNDPEFSKEIEQLI<br>KMNMNYRYETLKSFVNDIGVIEELNNLSFKNKYYEDVKLLGY<br>SSGKIDEPVLMGAKGIIKNKMQIFSNGFYKLPEGKVRFGVLY<br>PKEFDGVSRKAIRAIYDFSKEGKYHGESNKYIAEHLINVEFN<br>PKECIFEGYELGDITEYKKAALKLNNYNNVDFVIAIVPNMSD<br>EEIENSYNPFKKIWAELNLPSQMISVKTAEIFANSRDNTALY<br>YLHNIVLGILGKIGGIPWVVKDMKGDVDCFVGLDVGTREKGI<br>HYPACSVVFDKYGKLINYYKPNIPQNGEKINTEILQEIFDKV<br>LISYEEENGAYPKNIVIHRDGFSREDLDWYENYFGKKNIKFN<br>IIEVKKSTPLKIASINEGNITNPEKGSYILRGNKAYMVTTDI<br>KENLGSPKPLKIEKSYGDIDMLTALSQIYALTQIHVGATKSL<br>RLPITTGYADKICKAIEFIPQGRVDNRLFFL | 84 |
| 2SSB-AGO#69v1<br>(See FIG. 75)<br>N to C terminus:<br>*Italicized: His Tag*<br>Underlined: GST<br>**Bold: SsoSSB**<br>**Underlined/Bold: G4S** (SEQ ID NO: 70)<br>*Italicized/ Underlined: XTEN*<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>EEKVGNLKPNMESVNVTVRVLEASEARQIQTKNGVRTISEAI<br>VGDETGRVKLTLWGKHAGSIKEGQVVKIENAWTTAFKGQVQL<br>NAGSKTKIAEASEDGFPESSQIPENTPTAPQQMRGGGRGFRG<br>GGRRYGRRGGRRQENEEGEEEGGGGSEEKVGNLKPNMESVNV<br>TVRVLEASEARQIQTKNGVRTISEAIVGDETGRVKLTLWGKH<br>AGSIKEGQVVKIENAWTTAFKGQVQLNAGSKTKIAEASEDGF<br>PESSQIPENTPTAPQQMRGGGRGFRGGGRRYGRRGGRRQENE<br>EGEEESGSETPGTSESATPESVGGYKVSNLTVEAFEGIGSVN<br>PMLFYQYKVTGKGKYDNVYKIIKSARYKMHSKNRFKPVFIKD<br>DKLYTLEKLPDIEDLDFANINFVKSEVLSIEDNMSIYGEVVE<br>YYINLKLKKVKVLGKYPKYRINYSKEILSNTLLTRELKDEFK<br>KSNKGFNLKRKFRISPVVNKMGKVILYLSCSADFSTNKNIYE<br>MLKEGLEVEGLAVKSEWSNISGNLVIESVLETKISEPTSLGQ<br>SLIDYYKNNNQGYRVKDFTDEDLNANIVNVRGNKKIYMYIPH<br>ALKPIITREYLAKNDPEFSKEIEQLIKMNMNYRYETLKSFVN<br>DIGVIEELNNLSFKNKYYEDVKLLGYSSGKIDEPVLMGAKGI<br>IKNKMQIFSNGFYKLPEGKVRFGVLYPKEFDGVSRKAIRAIY<br>DFSKEGKYHGESNKYIAEHLINVEFNPKECIFEGYELGDITE<br>YKKAALKLNNYNNVDFVIAIVPNMSDEEIENSYNPFKKIWAE<br>LNLPSQMISVKTAEIFANSRDNTALYYLHNIVLGILGKIGGI<br>PWVVKDMKGDVDCFVGLDVGTREKGIHYPACSVVFDKYGKLI<br>NYYKPNIPQNGEKINTEILQEIFDKVLISYEEENGAYPKNIV<br>IHRDGFSREDLDWYENYFGKKNIKFNIIEVKKSTPLKIASIN<br>EGNITNPEKGSYILRGNKAYMVTTDIKENLGSPKPLKIEKSY<br>GDIDMLTALSQIYALTQIHVGATKSLRLPITTGYADKICKAI<br>EFIPQGRVDNRLFFL | 85 |

TABLE 10-continued

Amino Acid Sequence of Exemplary Ago-SSB Fusion Polypeptides

| Fusion Polypeptide | Amino Acid Sequence | SEQ ID NO |
|---|---|---|
| 2SSB-<br>AGO#69v2<br>(See FIG. 75)<br>N to C terminus:<br>*Italicized: His Tag*<br>Underlined: GST<br>**Bold: SsoSSB**<br>**Underlined/Bold: SGSG4S**<br>(SEQ ID NO: 71)<br>*Italicized/ Underlined: XTEN*<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>EEKVGNLKPNMESVNVTVRVLEASEARQIQTKNGVRTISEAI<br>VGDETGRVKLTLWGKHAGSIKEGQVVKIENAWTTAFKGQVQL<br>NAGSKTKIAEASEDGFPESSQIPENTPTAPQQMRGGGRGFRG<br>GGRRYGRRGGRRQENEEGEEESGSGGGGSEEKVGNLKPNMES<br>VNVTVRVLEASEARQIQTKNGVRTISEAIVGDETGRVKLTLW<br>GKHAGSIKEGQVVKIENAWTTAFKGQVQLNAGSKTKIAEASE<br>DGFPESSQIPENTPTAPQQMRGGGRGFRGGGRRYGRRGGRRQ<br>ENEEGEEESGSETPGTSESATPESVGGYKVSNLTVEAFEGIG<br>SVNPMLFYQYKVTGKGKYDNVYKIIKSARYKMHSKNRFKPVF<br>IKDDKLYTLEKLPDIEDLDFANINFVKSEVLSIEDNMSIYGE<br>VVEYYINLKLKKVKVLGKYPKYRINYSKEILSNTLLTRELKD<br>EFKKSNKGFNLKRKFRISPVVNKMGKVILYLSCSADFSTNKN<br>IYEMLKEGLEVEGLAVKSEWSNISGNLVIESVLETKISEPTS<br>LGQSLIDYYKNNNQGYRVKDFTDEDLNANIVNVRGNKKIYMY<br>IPHALKPIITREYLAKNDPEFSKEIEQLIKMNMNYRYETLKS<br>FVNDIGVIEELNNLSFKNKYYEDVKLLGYSSGKIDEPVLMGA<br>KGIIKNKMQIFSNGFYKLPEGKVRFGVLYPKEFDGVSRKAIR<br>AIYDESKEGKYHGESNKYIAEHLINVEFNPKECIFEGYELGD<br>ITEYKKAALKLNNYNNVDFVIAIVPNMSDEEIENSYNPFKKI<br>WAELNLPSQMISVKTAEIFANSRDNTALYYLHNIVLGILGKI<br>GGIPWVVKDMKGDVDCFVGLDVGTREKGIHYPACSVVFDKYG<br>KLINYYKPNIPQNGEKINTEILQEIFDKVLISYEEENGAYPK<br>NIVIHRDGFSREDLDWYENYFGKKNIKFNIIEVKKSTPLKIA<br>SINEGNITNPEKGSYILRGNKAYMVTTDIKENLGSPKPLKIE<br>KSYGDIDMLTALSQIYALTQIHVGATKSLRLPITTGYADKIC<br>KAIEFIPQGRVDNRLFFL | 86 |
| 2SSB-<br>AGO#69v3<br>(See FIG. 75)<br>N to C terminus:<br>*Italicized: His Tag*<br>Underlined: GST<br>**Bold: SsoSSB**<br>*Italicized/ Underlined: XTEN*<br>***Italicized/Bold: Ago69*** | MKHHHHHHNTSSNSMSPILGYWKIKGLVQPTRLLLEYLEEKY<br>EEHLYERDEGDKWRNKKFELGLEFPNLPYYIDGDVKLTQSMA<br>IIRYIADKHNMLGGCPKERAEISMLEGAVLDIRYGVSRIAYS<br>KDFETLKVDFLSKLPEMLKMFEDRLCHKTYLNGDHVTHPDFM<br>LYDALDVVLYMDPMCLDAFPKLVCFKKRIEAIPQIDKYLKSS<br>KYIAWPLQGWQATFGGGDHPPTSGSGGGGGWMSENLYFQGAM<br>EEKVGNLKPNMESVNVTVRVLEASEARQIQTKNGVRTISEAI<br>VGDETGRVKLTLWGKHAGSIKEGQVVKIENAWTTAFKGQVQL<br>NAGSKTKIAEASEDGFPESSQIPENTPTAPQQMRGGGRGFRG<br>GGRRYGRRGGRRQENEEGEEESGSETPGTSESATPESMEEKV<br>GNLKPNMESVNVTVRVLEASEARQIQTKNGVRTISEAIVGDE<br>TGRVKLTLWGKHAGSIKEGQVVKIENAWTTAFKGQVQLNAGS<br>KTKIAEASEDGFPESSQIPENTPTAPQQMRGGGRGFRGGGRR<br>YGRRGGRRQENEEGEEESGSETPGTSESATPESVGGYKVSNL<br>TVEAFEGIGSVNPMLFYQYKVTGKGKYDNVYKIIKSARYKMH<br>SKNRFKPVFIKDDKLYTLEKLPDIEDLDFANINFVKSEVLSI<br>EDNMSIYGEVVEYYINLKLKKVKVLGKYPKYRINYSKEILSN<br>TLLTRELKDEFKKSNKGFNLKRKFRISPVVNKMGKVILYLSC<br>SADFSTNKNIYEMLKEGLEVEGLAVKSEWSNISGNLVIESVL<br>ETKISEPTSLGQSLIDYYKNNNQGYRVKDFTDEDLNANIVNV<br>RGNKKIYMYIPHALKPIITREYLAKNDPEFSKEIEQLIKMNM<br>NYRYETLKSFVNDIGVIEELNNLSFKNKYYEDVKLLGYSSGK<br>IDEPVLMGAKGIIKNKMQIFSNGFYKLPEGKVRFGVLYPKEF<br>DGVSRKAIRAIYDFSKEGKYHGESNKYIAEHLINVEFNPKEC<br>IFEGYELGDITEYKKAALKLNNYNNVDFVIAIVPNMSDEEIE<br>NSYNPFKKIWAELNLPSQMISVKTAEIFANSRDNTALYYLHN<br>IVLGILGKIGGIPWVVKDMKGDVDCFVGLDVGTREKGIHYPA<br>CSVVFDKYGKLINYYKPNIPQNGEKINTEILQEIFDKVLISY<br>EEENGAYPKNIVIHRDGFSREDLDWYENYFGKKNIKFNIIEV<br>KKSTPLKIASINEGNITNPEKGSYILRGNKAYMVTTDIKENL<br>GSPKPLKIEKSYGDIDMLTALSQIYALTQIHVGATKSLRLPI<br>TTGYADKICKAIEFIPQGRVDNRLFFL | 87 |

TABLE 11

Nucleic Acid Sequence of Exemplary Ago-SSB Fusion Polypeptides

| Fusion Polypeptide | Nucleic Acid Sequence | SEQ ID NO |
|---|---|---|
| AP072 | ATGAAA*CATCACCATCACCATCAC*AACACTAGTAG | 88 |
| (also referred to herein is | CAATTCCATGTCCCCTATACTAGGTTATTGGAAAA | |
| SSB-Ago69_v1) | TTAAGGGCCTTGTGCAACCCACTCGACTTCTTTTG | |
| (See FIG. 68) | GAATATCTTGAAGAAAAATATGAAGAGCATTTGTA | |
| N to C terminus: | TGAGCGCGATGAAGGTGATAAATGGCGAAACAAAA | |
| *Italicized: His Tag* | AGTTTGAATTGGGTTTGGAGTTTCCCAATCTTCCT | |
| Underlined: GST | TATTATATTGATGGTGATGTTAAATTAACACAGTC | |
| *Italicized/Underlined:* | TATGGCCATCATACGTTATATAGCTGACAAGCACA | |
| *2XSV40NLS* | ACATGTTGGGTGGTTGTCCAAAAGAGCGTGCAGAG | |
| **Bold: SsoSSB** | ATTTCAATGCTTGAAGGAGCGGTTTTGGATATTAG | |
| **Underlined/Bold: G4S** | ATACGGTGTTTCGAGAATTGCATATAGTAAAGACT | |
| (SEQ ID NO: 70) | TTGAAACTCTCAAAGTTGATTTTCTTAGCAAGCTA | |
| ***Italicized/Bold: Ago69*** | CCTGAAATGCTGAAAATGTTCGAAGATCGTTTATG | |
| | TCATAAAACATATTTAAATGGTGATCATGTAACCC | |
| | ATCCTGACTTCATGTTGTATGACGCTCTTGATGTT | |
| | GTTTTATACATGGACCCAATGTGCCTGGATGCGTT | |
| | CCCAAAATTAGTTTGTTTTAAAAAACGTATTGAAG | |
| | CTATCCCACAAATTGATAAGTACTTGAAATCCAGC | |
| | AAGTATATAGCATGGCCTTTGCAGGGCTGGCAAGC | |
| | CACGTTTGGTGGTGGCGACCATCCTCCAACTAGTG | |
| | GATCTGGTGGTGGTGGCGGATGGATGAGCGAGAAT | |
| | CTTTATTTTCAGGGCGCA*ATGCCCAAGAAAAAGCG* | |
| | *AAAGGTAGAGGACCCCAAAAAGAAACGCAAAGTG*G | |
| | GCTCCGGAAGCCGTCTCGAA**ATGGAAGAAAAAGTA** | |
| | **GGCAACCTGAAGCCTAATATGGAATCCGTAAATGT** | |
| | **AACCGTTCGCGTTTTAGAAGCCTCTGAAGCACGGC** | |
| | **AGATCCAGACCAAAAATGGTGTTCGCACCATTTCA** | |
| | **GAGGCGATTGTAGGGGATGAAACCGGGCGCGTGAA** | |
| | **ACTGACTCTGTGGGGCAAACATGCGGGCAGCATCA** | |
| | **AAGAAGGCCAGGTCGTTAAAATTGAGAACGCCTGG** | |
| | **ACAACCGCGTTCAAAGGCCAGGTACAGCTGAATGC** | |
| | **CGGTAGCAAGACCAAAATTGCCGAGGCATCTGAAG** | |
| | **ACGGTTTCCCTGAAAGCAGCCAGATCCCAGAAAAT** | |
| | **ACTCCTACGGCACCGCAGCAGATGCGTGGCGGTGG** | |
| | **GCGGGGCTTTCGTGGCGGAGGCCGCCGTTATGGCC** | |
| | **GTCGCGGTGGGCGCCGGCAAGAAAACGAAGAAGGC** | |
| | **GAAGAAGAAGGCGGTGGTGGCTCA*ATGGTCGGCGG*** | |
| | ***CTATAAAGTCAGCAATTTGACAGTGGAAGCGTTCG*** | |
| | ***AAGGTATCGGGAGTGTCAACCCGATGCTGTTTTAC*** | |
| | ***CAATACAAAGTCACCGGAAAGGGAAAGTACGATAA*** | |
| | ***TGTGTATAAGATTATCAAAAGCGCACGGTACAAGA*** | |
| | ***TGCATTCTAAGAACCGATTCAAGCCCGTGTTCATC*** | |
| | ***AAGGACGACAAACTGTACACCCTCGAGAAGCTCCC*** | |
| | ***GGATATAGAGGACCTGGATTTCGCAAACATTAACT*** | |
| | ***TCGTGAAAAGCGAGGTTCTCAGCATAGAGGATAAT*** | |
| | ***ATGTCAATTTATGGCGAGGTGGTGGAATACTATAT*** | |
| | ***CAATCTCAAGCTGAAAAAAGTGAAGGTGTTGGGAA*** | |
| | ***AATACCCCAAGTACAGGATCAATTACAGCAAAGAG*** | |
| | ***ATTCTCAGTAATACGCTGCTGACACGAGAGCTCAA*** | |
| | ***AGACGAGTTTAAGAAATCAAATAAGGGTTTTAACC*** | |
| | ***TGAAACGGAAGTTTAGAATTTCCCCCGTGGTGAAT*** | |
| | ***AAGATGGGCAAAGTGATACTCTATTTGTCCTGCAG*** | |
| | ***TGCTGATTTCAGCACCAACAAGAACATTTACGAAA*** | |
| | ***TGTTGAAAGAGGGCTTGGAGGTTGAGGGGCTGGCC*** | |
| | ***GTTAAGAGCGAGTGGAGCAATATCAGTGGCAACCT*** | |
| | ***GGTGATCGAGAGCGTACTGGAAACCAAGATATCCG*** | |
| | ***AGCCCACTAGCCTGGGCCAATCCCTGATAGACTAC*** | |
| | ***TATAAGAATAACAACCAGGGCTATAGGGTGAAGGA*** | |
| | ***TTTCACCGATGAGGATCTGAATGCCAACATTGTCA*** | |
| | ***ACGTGAGAGGAAATAAGAAGATCTATATGTATATT*** | |
| | ***CCGCACGCGTTGAAGCCGATAATCACCCGGGAGTA*** | |
| | ***CCTGGCCAAGAACGATCCAGAGTTTTCTAAGGAGA*** | |
| | ***TCGAGCAGCTTATCAAGATGAATATGAACTACCGA*** | |
| | ***TATGAAACCCTCAAGTCATTTGTGAATGACATCGG*** | |
| | ***GGTCATTGAGGAGCTGAACAACCTGAGCTTCAAAA*** | |
| | ***ACAAATACTACGAAGATGTGAAACTGCTGGGTTAC*** | |
| | ***TCCAGCGGCAAAATAGACGAACCCGTCCTGATGGG*** | |
| | ***GGCAAAAGGGATCATAAAGAACAAAATGCAGATTT*** | |
| | ***TTTCCAATGGATTCTACAAACTCCCCGAAGGCAAG*** | |
| | ***GTACGATTTGGCGTTCTGTACCCAAAAGAATTTGA*** | |
| | ***TGGCGTGTCAAGGAAAGCTATCCGCGCCATTTATG*** | |
| | ***ACTTCAGTAAGGAGGGCAAATACCACGGCGAAAGC*** | |
| | ***AACAAGTATATCGCGGAACACCTGATAAACGTGGA*** | |
| | ***GTTCAATCCAAAGGAGTGCATATTTGAGGGATACG*** | |
| | ***AACTGGGCGATATCACCGAATACAAGAAGGCGGCT*** | |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | CTGAAACTTAATAACTACAACAATGTCGACTTCGT | |
| | AATCGCAATAGTCCCGAACATGTCCGACGAAGAGA | |
| | TAGAGAACAGCTACAATCCGTTCAAGAAAATATGG | |
| | GCCGAACTGAATCTGCCCAGCCAGATGATTAGCGT | |
| | CAAGACGGCCGAAATCTTTGCCAATAGCAGGGATA | |
| | ACACGGCGCTTTACTATCTGCATAACATCGTCCTC | |
| | GGTATCCTGGGTAAGATAGGAGGGATTCCCTGGGT | |
| | GGTTAAAGACATGAAGGGCGACGTGGATTGCTTCG | |
| | TTGGACTCGATGTCGGCACCAGGGAGAAGGGCATA | |
| | CATTACCCCGCCTGCAGCGTTGTGTTTGACAAGTA | |
| | CGGCAAGCTTATTAACTATTACAAGCCTAACATCC | |
| | CGCAGAACGGAGAGAAGATTAACACAGAAATACTT | |
| | CAGGAAATTTTCGACAAGGTGCTCATAAGCTATGA | |
| | GGAGGAGAATGGAGCCTACCCGAAGAATATCGTGA | |
| | TCCACAGGGACGGCTTTAGCCGAGAGGACCTTGAC | |
| | TGGTATGAGAACTACTTCGGTAAGAAAAACATAAA | |
| | GTTTAACATCATCGAAGTCAAAAAGTCAACTCCGT | |
| | TGAAAATCGCCAGTATAAACGAGGGAAATATCACG | |
| | AATCCTGAAAAGGGTTCCTACATCCTGCGCGGCAA | |
| | CAAAGCCTACATGGTGACCACAGATATTAAGGAAA | |
| | ACCTGGGAAGCCCAAAGCCCCTGAAGATAGAAAAG | |
| | AGCTACGGCGACATAGACATGCTCACAGCTCTCAG | |
| | CCAAATATACGCACTCACGCAAATCCATGTGGGGG | |
| | CGACCAAAAGCCTGCGCCTCCCAATCACCACCGGC | |
| | TACGCCGACAAGATTTGCAAGGCGATCGAGTTCAT | |
| | CCCCCAAGGGCGCGTGGACAACCGCCTTTTCTTTC | |
| | TG | |
| AP073 | ATGAAACATCACCATCACCATCACAACACTAGTAG | 89 |
| (See FIG. 68) | CAATTCCATGTCCCCTATACTAGGTTATTGGAAAA | |
| N to C terminus: | TTAAGGGCCTTGTGCAACCCACTCGACTTCTTTTG | |
| *Italicized: His Tag* | GAATATCTTGAAGAAAAATATGAAGAGCATTTGTA | |
| Underlined: GST | TGAGCGCGATGAAGGTGATAAATGGCGAAACAAAA | |
| *Italicized/Underlined:* | AGTTTGAATTGGGTTTGGAGTTTCCCAATCTTCCT | |
| *2XSV40NLS* | TATTATATTGATGGTGATGTTAAATTAACACAGTC | |
| **Bold: VP64** | TATGGCCATCATACGTTATATAGCTGACAAGCACA | |
| **Underlined/Bold: G4S** | ACATGTTGGGTGGTTGTCCAAAAGAGCGTGCAGAG | |
| (SEQ ID NO: 70) | ATTTCAATGCTTGAAGGAGCGGTTTTGGATATTAG | |
| ***Italicized/Bold: Ago69*** | ATACGGTGTTTCGAGAATTGCATATAGTAAAGACT | |
| | TTGAAACTCTCAAAGTTGATTTTCTTAGCAAGCTA | |
| | CCTGAAATGCTGAAAATGTTCGAAGATCGTTTATG | |
| | TCATAAAACATATTTAAATGGTGATCATGTAACCC | |
| | ATCCTGACTTCATGTTGTATGACGCTCTTGATGTT | |
| | GTTTTATACATGGACCCAATGTGCCTGGATGCGTT | |
| | CCCAAAATTAGTTTGTTTTAAAAAACGTATTGAAG | |
| | CTATCCCACAAATTGATAAGTACTTGAAATCCAGC | |
| | AAGTATATAGCATGGCCTTTGCAGGGCTGGCAAGC | |
| | CACGTTTGGTGGTGGCGACCATCCTCCAACTAGTG | |
| | GATCTGGTGGTGGTGGCGGATGGATGAGCGAGAAT | |
| | CTTTATTTTCAGGGCGCAATGCCCAAGAAAAAGCG | |
| | AAAGGTAGAGGACCCCAAAAAGAAACGCAAAGTGG | |
| | GCTCCGGAAGCCGTCTCGAAATGGACGCATTGGAC | |
| | GATTTTGATCTGGATATGCTGGGAAGTGACGCCCT | |
| | CGATGATTTTGACCTTGACATGCTTGGTTCGGATG | |
| | CCCTTGATGACTTTGACCTCGACATGCTCGGCAGT | |
| | GACGCCCTTGATGATTTCGACCTGGACATGCTGGG | |
| | CGGTGGTGGCTCAATGGTCGGCGGCTATAAAGTCA | |
| | GCAATTTGACAGTGGAAGCGTTCGAAGGTATCGGG | |
| | AGTGTCAACCCGATGCTGTTTTACCAATACAAAGT | |
| | CACCGGAAAGGGAAAGTACGATAATGTGTATAAGA | |
| | TTATCAAAAGCGCACGGTACAAGATGCATTCTAAG | |
| | AACCGATTCAAGCCCGTGTTCATCAAGGACGACAA | |
| | ACTGTACACCCTCGAGAAGCTCCCGGATATAGAGG | |
| | ACCTGGATTTCGCAAACATTAACTTCGTGAAAAGC | |
| | GAGGTTCTCAGCATAGAGGATAATATGTCAATTTA | |
| | TGGCGAGGTGGTGGAATACTATATCAATCTCAAGC | |
| | TGAAAAAAGTGAAGGTGTTGGGAAAATACCCCAAG | |
| | TACAGGATCAATTACAGCAAAGAGATTCTCAGTAA | |
| | TACGCTGCTGACACGAGAGCTCAAAGACGAGTTTA | |
| | AGAAATCAAATAAGGGTTTTAACCTGAAACGGAAG | |
| | TTTAGAATTTCCCCCGTGGTGAATAAGATGGGCAA | |
| | AGTGATACTCTATTTGTCCTGCAGTGCTGATTTCA | |
| | GCACCAACAAGAACATTTACGAAATGTTGAAAGAG | |
| | GGCTTGGAGGTTGAGGGGCTGGCCGTTAAGAGCGA | |
| | GTGGAGCAATATCAGTGGCAACCTGGTGATCGAGA | |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | GCGTACTGGAAACCAAGATATCCGAGCCCACTAGC<br>CTGGGCCAATCCCTGATAGACTACTATAAGAATAA<br>CAACCAGGGCTATAGGGTGAAGGATTTCACCGATG<br>AGGATCTGAATGCCAACATTGTCAACGTGAGAGGA<br>AATAAGAAGATCTATATGTATATTCCGCACGCGTT<br>GAAGCCGATAATCACCCGGGAGTACCTGGCCAAGA<br>ACGATCCAGAGTTTTCTAAGGAGATCGAGCAGCTT<br>ATCAAGATGAATATGAACTACCGATATGAAACCCT<br>CAAGTCATTTGTGAATGACATCGGGGTCATTGAGG<br>AGCTGAACAACCTGAGCTTCAAAAACAAATACTAC<br>GAAGATGTGAAACTGCTGGGTTACTCCAGCGGCAA<br>AATAGACGAACCCGTCCTGATGGGGGCAAAAGGGA<br>TCATAAAGAACAAAATGCAGATTTTTCCAATGGA<br>TTCTACAAACTCCCCGAAGGCAAGGTACGATTTGG<br>CGTTCTGTACCCAAAAGAATTTGATGGCGTGTCAA<br>GGAAAGCTATCCGCGCCATTTATGACTTCAGTAAG<br>GAGGGCAAATACCACGGCGAAAGCAACAAGTATAT<br>CGCGGAACACCTGATAAACGTGGAGTTCAATCCAA<br>AGGAGTGCATATTTGAGGGATACGAACTGGGCGAT<br>ATCACCGAATACAAGAAGGCGGCTCTGAAACTTAA<br>TAACTACAACAATGTCGACTTCGTAATCGCAATAG<br>TCCCGAACATGTCCGACGAAGAGATAGAGAACAGC<br>TACAATCCGTTCAAGAAAATATGGGCCGAACTGAA<br>TCTGCCCAGCCAGATGATTAGCGTCAAGACGGCCG<br>AAATCTTTGCCAATAGCAGGGATAACACGGCGCTT<br>TACTATCTGCATAACATCGTCCTCGGTATCCTGGG<br>TAAGATAGGAGGGATTCCCTGGGTGGTTAAAGACA<br>TGAAGGGCGACGTGGATTGCTTCGTTGGACTCGAT<br>GTCGGCACCAGGGAGAAGGGCATACATTACCCCGC<br>CTGCAGCGTTGTGTTTGACAAGTACGGCAAGCTTA<br>TTAACTATTACAAGCCTAACATCCCGCAGAACGGA<br>GAGAAGATTAACACAGAAATACTTCAGGAAATTTT<br>CGACAAGGTGCTCATAAGCTATGAGGAGGAGAATG<br>GAGCCTACCCGAAGAATATCGTGATCCACAGGGAC<br>GGCTTTAGCCGAGAGGACCTTGACTGGTATGAGAA<br>CTACTTCGGTAAGAAAAACATAAAGTTTAACATCA<br>TCGAAGTCAAAAAGTCAACTCCGTTGAAAATCGCC<br>AGTATAAACGAGGGAAATATCACGAATCCTGAAAA<br>GGGTTCCTACATCCTGCGCGGCAACAAAGCCTACA<br>TGGTGACCACAGATATTAAGGAAAACCTGGGAAGC<br>CCAAAGCCCCTGAAGATAGAAAAGAGCTACGGCGA<br>CATAGACATGCTCACAGCTCTCAGCCAAATATACG<br>CACTCACGCAAATCCATGTGGGGGCGACCAAAAGC<br>CTGCGCCTCCCAATCACCACCGGCTACGCCGACAA<br>GATTTGCAAGGCGATCGAGTTCATCCCCCAAGGGC<br>GCGTGGACAACCGCCTTTTCTTTCTG | |
| AP046<br>(See FIG. 69B)<br>N to C terminus:<br>*Italicized: His Tag*<br>Underlined: GST<br>*Italicized/Underlined: 2XSV40NLS*<br>**Underlined/Bold: GSGS linker** (SEQ ID NO: 154)<br>***Italicized/Bold: Ago69*** | ATGAAACATCACCATCACCATCACAACACTAGTAG<br>CAATTCCATGTCCCCTATACTAGGTTATTGGAAAA<br>TTAAGGGCCTTGTGCAACCCACTCGACTTCTTTTG<br>GAATATCTTGAAGAAAAATATGAAGAGCATTTGTA<br>TGAGCGCGATGAAGGTGATAAATGGCGAAACAAAA<br>AGTTTGAATTGGGTTTGGAGTTTCCCAATCTTCCT<br>TATTATATTGATGGTGATGTTAAATTAACACAGTC<br>TATGGCCATCATACGTTATATAGCTGACAAGCACA<br>ACATGTTGGGTGGTTGTCCAAAAGAGCGTGCAGAG<br>ATTTCAATGCTTGAAGGAGCGGTTTTGGATATTAG<br>ATACGGTGTTTCGAGAATTGCATATAGTAAAGACT<br>TTGAAACTCTCAAAGTTGATTTTCTTAGCAAGCTA<br>CCTGAAATGCTGAAAATGTTCGAAGATCGTTTATG<br>TCATAAAACATATTTAAATGGTGATCATGTAACCC<br>ATCCTGACTTCATGTTGTATGACGCTCTTGATGTT<br>GTTTTATACATGGACCCAATGTGCCTGGATGCGTT<br>CCCAAAATTAGTTTGTTTTAAAAAACGTATTGAAG<br>CTATCCCACAAATTGATAAGTACTTGAAATCCAGC<br>AAGTATATAGCATGGCCTTTGCAGGGCTGGCAAGC<br>CACGTTTGGTGGTGGCGACCATCCTCCAACTAGTG<br>GATCTGGTGGTGGTGGCGGATGGATGAGCGAGAAT<br>CTTTATTTTCAGGGCGCGGTCTCATCTCCACAGGG<br>GTACCCGTCTCTAATGCCCAAGAAGAAGAGAAAGG<br>TCGAGGACCCGAAAAAGAAGCGAAAGGTAGGTAGT<br>GGTTCCATGGTCGGCGGCTATAAAGTCAGCAATTT<br>GACAGTGGAAGCGTTCGAAGGTATCGGGAGTGTCA<br>ACCCGATGCTGTTTTACCAATACAAAGTCACCGGA<br>AAGGGAAAGTACGATAATGTGTATAAGATTATCAA | 90 |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | ***AAGCGCACGGTACAAGATGCATTCTAAGAACCGAT<br>TCAAGCCCGTGTTCATCAAGGACGACAAACTGTAC<br>ACCCTCGAGAAGCTCCCGGATATAGAGGACCTGGA<br>TTTCGCAAACATTAACTTCGTGAAAAGCGAGGTTC<br>TCAGCATAGAGGATAATATGTCAATTTATGGCGAG<br>GTGGTGGAATACTATATCAATCTCAAGCTGAAAAA<br>AGTGAAGGTGTTGGGAAAATACCCCAAGTACAGGA<br>TCAATTACAGCAAAGAGATTCTCAGTAATACGCTG<br>CTGACACGAGAGCTCAAAGACGAGTTTAAGAAATC<br>AAATAAGGGTTTTAACCTGAAACGGAAGTTTAGAA<br>TTTCCCCCGTGGTGAATAAGATGGGCAAAGTGATA<br>CTCTATTTGTCCTGCAGTGCTGATTTCAGCACCAA<br>CAAGAACATTTACGAAATGTTGAAAGAGGGCTTGG<br>AGGTTGAGGGGCTGGCCGTTAAGAGCGAGTGGAGC<br>AATATCAGTGGCAACCTGGTGATCGAGAGCGTACT<br>GGAAACCAAGATATCCGAGCCCACTAGCCTGGGCC<br>AATCCCTGATAGACTACTATAAGAATAACAACCAG<br>GGCTATAGGGTGAAGGATTTCACCGATGAGGATCT<br>GAATGCCAACATTGTCAACGTGAGAGGAAATAAGA<br>AGATCTATATGTATATTCCGCACGCGTTGAAGCCG<br>ATAATCACCCGGGAGTACCTGGCCAAGAACGATCC<br>AGAGTTTTCTAAGGAGATCGAGCAGCTTATCAAGA<br>TGAATATGAACTACCGATATGAAACCCTCAAGTCA<br>TTTGTGAATGACATCGGGGTCATTGAGGAGCTGAA<br>CAACCTGAGCTTCAAAAACAAATACTACGAAGATG<br>TGAAACTGCTGGGTTACTCCAGCGGCAAAATAGAC<br>GAACCCGTCCTGATGGGGGCAAAAGGGATCATAAA<br>GAACAAAATGCAGATTTTTTCCAATGGATTCTACA<br>AACTCCCCGAAGGCAAGGTACGATTTGGCGTTCTG<br>TACCCAAAAGAATTTGATGGCGTGTCAAGGAAAGC<br>TATCCGCGCCATTTATGACTTCAGTAAGGAGGGCA<br>AATACCACGGCGAAAGCAACAAGTATATCGCGGAA<br>CACCTGATAAACGTGGAGTTCAATCCAAAGGAGTG<br>CATATTTGAGGGATACGAACTGGGCGATATCACCG<br>AATACAAGAAGGCGGCTCTGAAACTTAATAACTAC<br>AACAATGTCGACTTCGTAATCGCAATAGTCCCGAA<br>CATGTCCGACGAAGAGATAGAGAACAGCTACAATC<br>CGTTCAAGAAAATATGGGCCGAACTGAATCTGCCC<br>AGCCAGATGATTAGCGTCAAGACGGCCGAAATCTT<br>TGCCAATAGCAGGGATAACACGGCGCTTTACTATC<br>TGCATAACATCGTCCTCGGTATCCTGGGTAAGATA<br>GGAGGGATTCCCTGGGTGGTTAAAGACATGAAGGG<br>CGACGTGGATTGCTTCGTTGGACTCGATGTCGGCA<br>CCAGGGAGAAGGGCATACATTACCCCGCCTGCAGC<br>GTTGTGTTTGACAAGTACGGCAAGCTTATTAACTA<br>TTACAAGCCTAACATCCCGCAGAACGGAGAGAAGA<br>TTAACACAGAAATACTTCAGGAAATTTTCGACAAG<br>GTGCTCATAAGCTATGAGGAGGAGAATGGAGCCTA<br>CCCGAAGAATATCGTGATCCACAGGGACGGCTTTA<br>GCCGAGAGGACCTTGACTGGTATGAGAACTACTTC<br>GGTAAGAAAAACATAAAGTTTAACATCATCGAAGT<br>CAAAAAGTCAACTCCGTTGAAAATCGCCAGTATAA<br>ACGAGGGAAATATCACGAATCCTGAAAAGGGTTCC<br>TACATCCTGCGCGGCAACAAAGCCTACATGGTGAC<br>CACAGATATTAAGGAAAACCTGGGAAGCCCAAAGC<br>CCCTGAAGATAGAAAAGAGCTACGGCGACATAGAC<br>ATGCTCACAGCTCTCAGCCAAATATACGCACTCAC<br>GCAAATCCATGTGGGGGCGACCAAAAGCCTGCGCC<br>TCCCAATCACCACCGGCTACGCCGACAAGATTTGC<br>AAGGCGATCGAGTTCATCCCCCAAGGGCGCGTGGA<br>CAACCGCCTTTTCTTTCTGTAGTGA*** | |
| AP025<br>(See FIG. 69B)<br>N to C terminus:<br>*Italicized: His Tag*<br>Underlined: GST<br>***Bold/Italicized/Underlined: 2XSV40NLS***<br>**Underlined and Bold: GSGS linker** (SEQ ID NO: 154)<br>***Italicized and Bold: Ago69***<br>*Italicized and underlined: GGGS linker* (SEQ ID NO: | ATGAAACATCACCATCACCATCACAACACTAGTAG<br>CAATTCCATGTCCCCTATACTAGGTTATTGGAAAA<br>TTAAGGGCCTTGTGCAACCCACTCGACTTCTTTTG<br>GAATATCTTGAAGAAAAATATGAAGAGCATTTGTA<br>TGAGCGCGATGAAGGTGATAAATGGCGAAACAAAA<br>AGTTTGAATTGGGTTTGGAGTTTCCCAATCTTCCT<br>TATTATATTGATGGTGATGTTAAATTAACACAGTC<br>TATGGCCATCATACGTTATATAGCTGACAAGCACA<br>ACATGTTGGGTGGTTGTCCAAAAGAGCGTGCAGAG<br>ATTTCAATGCTTGAAGGAGCGGTTTTGGATATTAG<br>ATACGGTGTTTCGAGAATTGCATATAGTAAAGACT<br>TTGAAACTCTCAAAGTTGATTTTCTTAGCAAGCTA<br>CCTGAAATGCTGAAAATGTTCGAAGATCGTTTATG | 91 |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| 155) | TCATAAAACATATTTAAATGGTGATCATGTAACCC | |
| **Bold: V5 tag** | ATCCTGACTTCATGTTGTATGACGCTCTTGATGTT | |
| *Italicized: NPM NLS* | GTTTTATACATGGACCCAATGTGCCTGGATGCGTT | |
| | CCCAAAATTAGTTTGTTTTAAAAAACGTATTGAAG | |
| | CTATCCCACAAATTGATAAGTACTTGAAATCCAGC | |
| | AAGTATATAGCATGGCCTTTGCAGGGCTGGCAAGC | |
| | CACGTTTGGTGGTGGCGACCATCCTCCAACTAGTG | |
| | GATCTGGTGGTGGTGGCGGATGGATGAGCGAGAAT | |
| | CTTTATTTTCAGGGCGCA***ATGCCCAAGAAAAAGCG*** | |
| | ***AAAGGTAGAGGACCCCAAAAAGAAACGCAAAGTG***G | |
| | GCTCCGGAAGCCGTCTCGAA***ATGGTCGGCGGCTAT*** | |
| | ***AAAGTCAGCAATTTGACAGTGGAAGCGTTCGAAGG*** | |
| | ***TATCGGGAGTGTCAACCCGATGCTGTTTTACCAAT*** | |
| | ***ACAAAGTCACCGGAAAGGGAAAGTACGATAATGTG*** | |
| | ***TATAAGATTATCAAAAGCGCACGGTACAAGATGCA*** | |
| | ***TTCTAAGAACCGATTCAAGCCCGTGTTCATCAAGG*** | |
| | ***ACGACAAACTGTACACCCTCGAGAAGCTCCCGGAT*** | |
| | ***ATAGAGGACCTGGATTTCGCAAACATTAACTTCGT*** | |
| | ***GAAAAGCGAGGTTCTCAGCATAGAGGATAATATGT*** | |
| | ***CAATTTATGGCGAGGTGGTGGAATACTATATCAAT*** | |
| | ***CTCAAGCTGAAAAAAGTGAAGGTGTTGGGAAAATA*** | |
| | ***CCCCAAGTACAGGATCAATTACAGCAAAGAGATTC*** | |
| | ***TCAGTAATACGCTGCTGACACGAGAGCTCAAAGAC*** | |
| | ***GAGTTTAAGAAATCAAATAAGGGTTTTAACCTGAA*** | |
| | ***ACGGAAGTTTAGAATTTCCCCCGTGGTGAATAAGA*** | |
| | ***TGGGCAAAGTGATACTCTATTTGTCCTGCAGTGCT*** | |
| | ***GATTTCAGCACCAACAAGAACATTTACGAAATGTT*** | |
| | ***GAAAGAGGGCTTGGAGGTTGAGGGGCTGGCCGTTA*** | |
| | ***AGAGCGAGTGGAGCAATATCAGTGGCAACCTGGTG*** | |
| | ***ATCGAGAGCGTACTGGAAACCAAGATATCCGAGCC*** | |
| | ***CACTAGCCTGGGCCAATCCCTGATAGACTACTATA*** | |
| | ***AGAATAACAACCAGGGCTATAGGGTGAAGGATTTC*** | |
| | ***ACCGATGAGGATCTGAATGCCAACATTGTCAACGT*** | |
| | ***GAGAGGAAATAAGAAGATCTATATGTATATTCCGC*** | |
| | ***ACGCGTTGAAGCCGATAATCACCCGGGAGTACCTG*** | |
| | ***GCCAAGAACGATCCAGAGTTTTCTAAGGAGATCGA*** | |
| | ***GCAGCTTATCAAGATGAATATGAACTACCGATATG*** | |
| | ***AAACCCTCAAGTCATTTGTGAATGACATCGGGGTC*** | |
| | ***ATTGAGGAGCTGAACAACCTGAGCTTCAAAAACAA*** | |
| | ***ATACTACGAAGATGTGAAACTGCTGGGTTACTCCA*** | |
| | ***GCGGCAAAATAGACGAACCCGTCCTGATGGGGGCA*** | |
| | ***AAAGGGATCATAAAGAACAAAATGCAGATTTTTTC*** | |
| | ***CAATGGATTCTACAAACTCCCCGAAGGCAAGGTAC*** | |
| | ***GATTTGGCGTTCTGTACCCAAAAGAATTTGATGGC*** | |
| | ***GTGTCAAGGAAAGCTATCCGCGCCATTTATGACTT*** | |
| | ***CAGTAAGGAGGGCAAATACCACGGCGAAAGCAACA*** | |
| | ***AGTATATCGCGGAACACCTGATAAACGTGGAGTTC*** | |
| | ***AATCCAAAGGAGTGCATATTTGAGGGATACGAACT*** | |
| | ***GGGCGATATCACCGAATACAAGAAGGCGGCTCTGA*** | |
| | ***AACTTAATAACTACAACAATGTCGACTTCGTAATC*** | |
| | ***GCAATAGTCCCGAACATGTCCGACGAAGAGATAGA*** | |
| | ***GAACAGCTACAATCCGTTCAAGAAAATATGGGCCG*** | |
| | ***AACTGAATCTGCCCAGCCAGATGATTAGCGTCAAG*** | |
| | ***ACGGCCGAAATCTTTGCCAATAGCAGGGATAACAC*** | |
| | ***GGCGCTTTACTATCTGCATAACATCGTCCTCGGTA*** | |
| | ***TCCTGGGTAAGATAGGAGGGATTCCCTGGGTGGTT*** | |
| | ***AAAGACATGAAGGGCGACGTGGATTGCTTCGTTGG*** | |
| | ***ACTCGATGTCGGCACCAGGGAGAAGGGCATACATT*** | |
| | ***ACCCCGCCTGCAGCGTTGTGTTTGACAAGTACGGC*** | |
| | ***AAGCTTATTAACTATTACAAGCCTAACATCCCGCA*** | |
| | ***GAACGGAGAGAAGATTAACACAGAAATACTTCAGG*** | |
| | ***AAATTTTCGACAAGGTGCTCATAAGCTATGAGGAG*** | |
| | ***GAGAATGGAGCCTACCCGAAGAATATCGTGATCCA*** | |
| | ***CAGGGACGGCTTTAGCCGAGAGGACCTTGACTGGT*** | |
| | ***ATGAGAACTACTTCGGTAAGAAAAACATAAAGTTT*** | |
| | ***AACATCATCGAAGTCAAAAAGTCAACTCCGTTGAA*** | |
| | ***AATCGCCAGTATAAACGAGGGAAATATCACGAATC*** | |
| | ***CTGAAAAGGGTTCCTACATCCTGCGCGGCAACAAA*** | |
| | ***GCCTACATGGTGACCACAGATATTAAGGAAAACCT*** | |
| | ***GGGAAGCCCAAAGCCCCTGAAGATAGAAAAGAGCT*** | |
| | ***ACGGCGACATAGACATGCTCACAGCTCTCAGCCAA*** | |
| | ***ATATACGCACTCACGCAAATCCATGTGGGGGCGAC*** | |
| | ***CAAAAGCCTGCGCCTCCCAATCACCACCGGCTACG*** | |
| | ***CCGACAAGATTTGCAAGGCGATCGAGTTCATCCCC*** | |
| | ***CAAGGGCGCGTGGACAACCGCCTTTTCTTTCTG***AC | |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | TAGTGGGGGAGGTGGATCT*GGGAAGCCCATCCCAA*<br>*ACCCGCTGTTGGGCTTGGATTCCACGAAGCGACCC*<br>*GCAGCGACTAAGAAAGCCGGCCAGGCCAAAAAGAA*<br>*GAAA* | |
| AP071<br>(See FIG. 69B)<br>N to C terminus:<br>*Italicized: His Tag*<br>Underlined: GST<br>**Bold: 2XSV40NLS**<br>**Underlined/Bold: GSGS linker** (SEQ ID NO: 154)<br>***Italicized/Bold: Ago69*** | ATGAAA*CATCACCATCACCATCAC*AACACTAGTAG<br>CAATTCCATGTCCCCTATACTAGGTTATTGGAAAA<br>TTAAGGGCCTTGTGCAACCCACTCGACTTCTTTTG<br>GAATATCTTGAAGAAAAATATGAAGAGCATTTGTA<br>TGAGCGCGATGAAGGTGATAAATGGCGAAACAAAA<br>AGTTTGAATTGGGTTTGGAGTTTCCCAATCTTCCT<br>TATTATATTGATGGTGATGTTAAATTAACACAGTC<br>TATGGCCATCATACGTTATATAGCTGACAAGCACA<br>ACATGTTGGGTGGTTGTCCAAAAGAGCGTGCAGAG<br>ATTTCAATGCTTGAAGGAGCGGTTTTGGATATTAG<br>ATACGGTGTTTCGAGAATTGCATATAGTAAAGACT<br>TTGAAACTCTCAAAGTTGATTTTCTTAGCAAGCTA<br>CCTGAAATGCTGAAAATGTTCGAAGATCGTTTATG<br>TCATAAAACATATTTAAATGGTGATCATGTAACCC<br>ATCCTGACTTCATGTTGTATGACGCTCTTGATGTT<br>GTTTTATACATGGACCCAATGTGCCTGGATGCGTT<br>CCCAAAATTAGTTTGTTTTAAAAAACGTATTGAAG<br>CTATCCCACAAATTGATAAGTACTTGAAATCCAGC<br>AAGTATATAGCATGGCCTTTGCAGGGCTGGCAAGC<br>CACGTTTGGTGGTGGCGACCATCCTCCAACTAGTG<br>GATCTGGTGGTGGTGGCGGATGG**ATGAGCGAGAAT**<br>**CTTTATTTTCAGGGCGCAATGCCCAAGAAAAAGCG**<br>**AAAGGTAGAGGACCCCAAAAAGAAACGCAAAGTGG**<br>**GCTCCGGAAGC**CGTCTCGAA***ATGGTCGGCGGCTAT***<br>***AAAGTCAGCAATTTGACAGTGGAAGCGTTCGAAGG***<br>***TATCGGGAGTGTCAACCCGATGCTGTTTTACCAAT***<br>***ACAAAGTCACCGGAAAGGGAAAGTACGATAATGTG***<br>***TATAAGATTATCAAAAGCGCACGGTACAAGATGCA***<br>***TTCTAAGAACCGATTCAAGCCCGTGTTCATCAAGG***<br>***ACGACAAACTGTACACCCTCGAGAAGCTCCCGGAT***<br>***ATAGAGGACCTGGATTTCGCAAACATTAACTTCGT***<br>***GAAAAGCGAGGTTCTCAGCATAGAGGATAATATGT***<br>***CAATTTATGGCGAGGTGGTGGAATACTATATCAAT***<br>***CTCAAGCTGAAAAAAGTGAAGGTGTTGGGAAAATA***<br>***CCCCAAGTACAGGATCAATTACAGCAAAGAGATTC***<br>***TCAGTAATACGCTGCTGACACGAGAGCTCAAAGAC***<br>***GAGTTTAAGAAATCAAATAAGGGTTTTAACCTGAA***<br>***ACGGAAGTTTAGAATTTCCCCCGTGGTGAATAAGA***<br>***TGGGCAAAGTGATACTCTATTTGTCCTGCAGTGCT***<br>***GATTTCAGCACCAACAAGAACATTTACGAAATGTT***<br>***GAAAGAGGGCTTGGAGGTTGAGGGGCTGGCCGTTA***<br>***AGAGCGAGTGGAGCAATATCAGTGGCAACCTGGTG***<br>***ATCGAGAGCGTACTGGAAACCAAGATATCCGAGCC***<br>***CACTAGCCTGGGCCAATCCCTGATAGACTACTATA***<br>***AGAATAACAACCAGGGCTATAGGGTGAAGGATTTC***<br>***ACCGATGAGGATCTGAATGCCAACATTGTCAACGT***<br>***GAGAGGAAATAAGAAGATCTATATGTATATTCCGC***<br>***ACGCGTTGAAGCCGATAATCACCCGGGAGTACCTG***<br>***GCCAAGAACGATCCAGAGTTTTCTAAGGAGATCGA***<br>***GCAGCTTATCAAGATGAATATGAACTACCGATATG***<br>***AAACCCTCAAGTCATTTGTGAATGACATCGGGGTC***<br>***ATTGAGGAGCTGAACAACCTGAGCTTCAAAAACAA***<br>***ATACTACGAAGATGTGAAACTGCTGGGTTACTCCA***<br>***GCGGCAAAATAGACGAACCCGTCCTGATGGGGGCA***<br>***AAAGGGATCATAAAGAACAAAATGCAGATTTTTTC***<br>***CAATGGATTCTACAAACTCCCCGAAGGCAAGGTAC***<br>***GATTTGGCGTTCTGTACCCAAAAGAATTTGATGGC***<br>***GTGTCAAGGAAAGCTATCCGCGCCATTTATGACTT***<br>***CAGTAAGGAGGGCAAATACCACGGCGAAAGCAACA***<br>***AGTATATCGCGGAACACCTGATAAACGTGGAGTTC***<br>***AATCCAAAGGAGTGCATATTTGAGGGATACGAACT***<br>***GGGCGATATCACCGAATACAAGAAGGCGGCTCTGA***<br>***AACTTAATAACTACAACAATGTCGACTTCGTAATC***<br>***GCAATAGTCCCGAACATGTCCGACGAAGAGATAGA***<br>***GAACAGCTACAATCCGTTCAAGAAAATATGGGCCG***<br>***AACTGAATCTGCCCAGCCAGATGATTAGCGTCAAG***<br>***ACGGCCGAAATCTTTGCCAATAGCAGGGATAACAC***<br>***GGCGCTTTACTATCTGCATAACATCGTCCTCGGTA***<br>***TCCTGGGTAAGATAGGAGGGATTCCCTGGGTGGTT***<br>***AAAGACATGAAGGGCGACGTGGATTGCTTCGTTGG*** | 92 |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | ***ACTCGATGTCGGCACCAGGGAGAAGGGCATACATT***<br>***ACCCCGCCTGCAGCGTTGTGTTTGACAAGTACGGC***<br>***AAGCTTATTAACTATTACAAGCCTAACATCCCGCA***<br>***GAACGGAGAGAAGATTAACACAGAAATACTTCAGG***<br>***AAATTTTCGACAAGGTGCTCATAAGCTATGAGGAG***<br>***GAGAATGGAGCCTACCCGAAGAATATCGTGATCCA***<br>***CAGGGACGGCTTTAGCCGAGAGGACCTTGACTGGT***<br>***ATGAGAACTACTTCGGTAAGAAAAACATAAAGTTT***<br>***AACATCATCGAAGTCAAAAAGTCAACTCCGTTGAA***<br>***AATCGCCAGTATAAACGAGGGAAATATCACGAATC***<br>***CTGAAAAGGGTTCCTACATCCTGCGCGGCAACAAA***<br>***GCCTACATGGTGACCACAGATATTAAGGAAAACCT***<br>***GGGAAGCCCAAAGCCCCTGAAGATAGAAAAGAGCT***<br>***ACGGCGACATAGACATGCTCACAGCTCTCAGCCAA***<br>***ATATACGCACTCACGCAAATCCATGTGGGGGCGAC***<br>***CAAAAGCCTGCGCCTCCCAATCACCACCGGCTACG***<br>***CCGACAAGATTTGCAAGGCGATCGAGTTCATCCCC***<br>***CAAGGGCGCGTGGACAACCGCCTTTTCTTTCTGTA***<br>***G*** | |
| SSB-AGO#69v3<br>(See FIG. 75)<br>N to C terminus:<br>*Italicized: His Tag*<br>Underlined: GST<br>**Bold: SsoSSB**<br>*Italicized/Underlined: XTEN*<br>***Italicized/Bold: Ago69*** | ATGAAA*CATCACCATCACCATCAC*AACACTAGTAG<br>CAATTCCATGTCCCCTATACTAGGTTATTGGAAAA<br>TTAAGGGCCTTGTGCAACCCACTCGACTTCTTTTG<br>GAATATCTTGAAGAAAAATATGAAGAGCATTTGTA<br>TGAGCGCGATGAAGGTGATAAATGGCGAAACAAAA<br>AGTTTGAATTGGGTTTGGAGTTTCCCAATCTTCCT<br>TATTATATTGATGGTGATGTTAAATTAACACAGTC<br>TATGGCCATCATACGTTATATAGCTGACAAGCACA<br>ACATGTTGGGTGGTTGTCCAAAAGAGCGTGCAGAG<br>ATTTCAATGCTTGAAGGAGCGGTTTTGGATATTAG<br>ATACGGTGTTTCGAGAATTGCATATAGTAAAGACT<br>TTGAAACTCTCAAAGTTGATTTTCTTAGCAAGCTA<br>CCTGAAATGCTGAAAATGTTCGAAGATCGTTTATG<br>TCATAAAACATATTTAAATGGTGATCATGTAACCC<br>ATCCTGACTTCATGTTGTATGACGCTCTTGATGTT<br>GTTTTATACATGGACCCAATGTGCCTGGATGCGTT<br>CCCAAAATTAGTTTGTTTTAAAAAACGTATTGAAG<br>CTATCCCACAAATTGATAAGTACTTGAAATCCAGC<br>AAGTATATAGCATGGCCTTTGCAGGGCTGGCAAGC<br>CACGTTTGGTGGTGGCGACCATCCTCCAACTAGTG<br>GATCTGGTGGTGGTGGCGGATGG**ATGAGCGAGAAT**<br>**CTTTATTTTCAGGGCGCAATGGAGGAGAAGGTCGG**<br>**TAACCTTAAGCCCAATATGGAATCTGTCAACGTTA**<br>**CTGTTAGAGTCCTGGAAGCCAGCGAGGCGCGCCAA**<br>**ATACAGACGAAGAACGGGGTAAGGACCATAAGCGA**<br>**GGCAATCGTCGGCGACGAGACTGGCAGAGTTAAAT**<br>**TGACCCCTTTGGGGAAAACACGCTGGTTCTATAAAG**<br>**GAAGGTCAAGTCGTAAAGATCGAAAATGCTTGGAC**<br>**GACCGCATTCAAGGGCCAGGTTCAACTCAACGCCG**<br>**GATCTAAAACTAAGATAGCTGAGGCGTCAGAAGAC**<br>**GGCTTCCCAGAATCAAGCCAGATACCTGAGAACAC**<br>**TCCAACGGCTCCTCAACAAATGAGAGGAGGTGGAC**<br>**GAGGATTTCGCGGGGGGGGACGAAGATATGGCCGA**<br>**CGCGGAGGACGACGCCAGGAAAATGAAGAGGGTGA**<br>**AGAGGAA***AGCGGCTCTGAGACTCCCGGCACATCCG*<br>*AAAGCGCAACCCCTGAGTCT****GTCGGCGGCTATAAA***<br>***GTCAGCAATTTGACAGTGGAAGCGTTCGAAGGTAT***<br>***CGGGAGTGTCAACCCGATGCTGTTTTACCAATACA***<br>***AAGTCACCGGAAAGGGAAAGTACGATAATGTGTAT***<br>***AAGATTATCAAAAGCGCACGGTACAAGATGCATTC***<br>***TAAGAACCGATTCAAGCCCGTGTTCATCAAGGACG***<br>***ACAAACTGTACACCCTCGAGAAGCTCCCGGATATA***<br>***GAGGACCTGGATTTCGCAAACATTAACTTCGTGAA***<br>***AAGCGAGGTTCTCAGCATAGAGGATAATATGTCAA***<br>***TTTATGGCGAGGTGGTGGAATACTATATCAATCTC***<br>***AAGCTGAAAAAAGTGAAGGTGTTGGGAAAATACCC***<br>***CAAGTACAGGATCAATTACAGCAAAGAGATTCTCA***<br>***GTAATACGCTGCTGACACGAGAGCTCAAAGACGAG***<br>***TTTAAGAAATCAAATAAGGGTTTTAACCTGAAACG***<br>***GAAGTTTAGAATTTCCCCCGTGGTGAATAAGATGG***<br>***GCAAAGTGATACTCTATTTGTCCTGCAGTGCTGAT***<br>***TTCAGCACCAACAAGAACATTTACGAAATGTTGAA***<br>***AGAGGGCTTGGAGGTTGAGGGGCTGGCCGTTAAGA***<br>***GCGAGTGGAGCAATATCAGTGGCAACCTGGTGATC***<br>***GAGAGCGTACTGGAAACCAAGATATCCGAGCCCAC*** | 93 |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | ***TAGCCTGGGCCAATCCCTGATAGACTACTATAAGA<br>ATAACAACCAGGGCTATAGGGTGAAGGATTTCACC<br>GATGAGGATCTGAATGCCAACATTGTCAACGTGAG<br>AGGAAATAAGAAGATCTATATGTATATTCCGCACG<br>CGTTGAAGCCGATAATCACCCGGGAGTACCTGGCC<br>AAGAACGATCCAGAGTTTTCTAAGGAGATCGAGCA<br>GCTTATCAAGATGAATATGAACTACCGATATGAAA<br>CCCTCAAGTCATTTGTGAATGACATCGGGGTCATT<br>GAGGAGCTGAACAACCTGAGCTTCAAAAACAAATA<br>CTACGAAGATGTGAAACTGCTGGGTTACTCCAGCG<br>GCAAAATAGACGAACCCGTCCTGATGGGGGCAAAA<br>GGGATCATAAAGAACAAAATGCAGATTTTTTCCAA<br>TGGATTCTACAAACTCCCCGAAGGCAAGGTACGAT<br>TTGGCGTTCTGTACCCAAAAGAATTTGATGGCGTG<br>TCAAGGAAAGCTATCCGCGCCATTTATGACTTCAG<br>TAAGGAGGGCAAATACCACGGCGAAAGCAACAAGT<br>ATATCGCGGAACACCTGATAAACGTGGAGTTCAAT<br>CCAAAGGAGTGCATATTTGAGGGATACGAACTGGG<br>CGATATCACCGAATACAAGAAGGCGGCTCTGAAAC<br>TTAATAACTACAACAATGTCGACTTCGTAATCGCA<br>ATAGTCCCGAACATGTCCGACGAAGAGATAGAGAA<br>CAGCTACAATCCGTTCAAGAAAATATGGGCCGAAC<br>TGAATCTGCCCAGCCAGATGATTAGCGTCAAGACG<br>GCCGAAATCTTTGCCAATAGCAGGGATAACACGGC<br>GCTTTACTATCTGCATAACATCGTCCTCGGTATCC<br>TGGGTAAGATAGGAGGGATTCCCTGGGTGGTTAAA<br>GACATGAAGGGCGACGTGGATTGCTTCGTTGGACT<br>CGATGTCGGCACCAGGGAGAAGGGCATACATTACC<br>CCGCCTGCAGCGTTGTGTTTGACAAGTACGGCAAG<br>CTTATTAACTATTACAAGCCTAACATCCCGCAGAA<br>CGGAGAGAAGATTAACACAGAAATACTTCAGGAAA<br>TTTTCGACAAGGTGCTCATAAGCTATGAGGAGGAG<br>AATGGAGCCTACCCGAAGAATATCGTGATCCACAG<br>GGACGGCTTTAGCCGAGAGGACCTTGACTGGTATG<br>AGAACTACTTCGGTAAGAAAAACATAAAGTTTAAC<br>ATCATCGAAGTCAAAAAGTCAACTCCGTTGAAAAT<br>CGCCAGTATAAACGAGGGAAATATCACGAATCCTG<br>AAAAGGGTTCCTACATCCTGCGCGGCAACAAAGCC<br>TACATGGTGACCACAGATATTAAGGAAAACCTGGG<br>AAGCCCAAAGCCCCTGAAGATAGAAAAGAGCTACG<br>GCGACATAGACATGCTCACAGCTCTCAGCCAAATA<br>TACGCACTCACGCAAATCCATGTGGGGGCGACCAA<br>AAGCCTGCGCCTCCCAATCACCACCGGCTACGCCG<br>ACAAGATTTGCAAGGCGATCGAGTTCATCCCCCAA<br>GGGCGCGTGGACAACCGCCTTTTCTTTCTGTAGTG<br>A*** | |
| 2SSB-AGO#69v1<br>(See FIG. 75)<br>N to C terminus:<br>*Italicized: His Tag*<br>Underlined: GST<br>**Bold: SsoSSB**<br>**Underlined/Bold: G4S**<br>(SEQ ID NO: 70)<br>*Italicized/Underlined: XTEN*<br>***Italicized/Bold: Ago69*** | ATGAAA*CATCACCATCACCATCAC*AACACTAGTAG<br>CAATTCCATGTCCCCTATACTAGGTTATTGGAAAA<br>TTAAGGGCCTTGTGCAACCCACTCGACTTCTTTTG<br>GAATATCTTGAAGAAAAATATGAAGAGCATTTGTA<br>TGAGCGCGATGAAGGTGATAAATGGCGAAACAAAA<br>AGTTTGAATTGGGTTTGGAGTTTCCCAATCTTCCT<br>TATTATATTGATGGTGATGTTAAATTAACACAGTC<br>TATGGCCATCATACGTTATATAGCTGACAAGCACA<br>ACATGTTGGGTGGTTGTCCAAAAGAGCGTGCAGAG<br>ATTTCAATGCTTGAAGGAGCGGTTTTGGATATTAG<br>ATACGGTGTTTCGAGAATTGCATATAGTAAAGACT<br>TTGAAACTCTCAAAGTTGATTTTCTTAGCAAGCTA<br>CCTGAAATGCTGAAAATGTTCGAAGATCGTTTATG<br>TCATAAAACATATTTAAATGGTGATCATGTAACCC<br>ATCCTGACTTCATGTTGTATGACGCTCTTGATGTT<br>GTTTTATACATGGACCCAATGTGCCTGGATGCGTT<br>CCCAAAATTAGTTTGTTTTAAAAAACGTATTGAAG<br>CTATCCCACAAATTGATAAGTACTTGAAATCCAGC<br>AAGTATATAGCATGGCCTTTGCAGGGCTGGCAAGC<br>CACGTTTGGTGGTGGCGACCATCCTCCAACTAGTG<br>GATCTGGTGGTGGTGGCGGATGGATGAGCGAGAAT<br>CTTTATTTTCAGGGCGCA**ATGGAGGAGAAGGTCGG<br>TAACCTTAAGCCCAATATGGAATCTGTCAACGTTA<br>CTGTTAGAGTCCTGGAAGCCAGCGAGGCGCGCCAA<br>ATACAGACGAAGAACGGGGTAAGGACCATAAGCGA<br>GGCAATCGTCGGCGACGAGACTGGCAGAGTTAAAT<br>TGACCCTTTGGGGAAAACACGCTGGTTCTATAAAG<br>GAAGGTCAAGTCGTAAAGATCGAAAATGCTTGGAC** | 94 |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | GACCGCATTCAAGGGCCAGGTTCAACTCAACGCCG | |
| | GATCTAAAACTAAGATAGCTGAGGCGTCAGAAGAC | |
| | GGCTTCCCAGAATCAAGCCAGATACCTGAGAACAC | |
| | TCCAACGGCTCCTCAACAAATGAGAGGAGGTGGAC | |
| | GAGGATTTCGCGGGGGGGGACGAAGATATGGCCGA | |
| | CGCGGAGGACGACGCCAGGAAAATGAAGAGGGTGA | |
| | AGAGGAAGGCGGTGGTGGCTCAGAAGAAAAAGTGG | |
| | GTAACCTTAAACCCAACATGGAGAGCGTTAACGTC | |
| | ACGGTCAGAGTACTCGAGGCGAGCGAGGCGCGGCA | |
| | GATACAAACAAAAAATGGTGTGCGCACCATTTCCG | |
| | AAGCTATAGTCGGTGACGAAACGGGCCGCGTTAAA | |
| | TTGACGCTCTGGGGAAAACATGCAGGTTCTATTAA | |
| | AGAGGGTCAGGTCGTGAAAATAGAGAACGCCTGGA | |
| | CTACGGCGTTCAAGGGTCAGGTCCAACTGAATGCA | |
| | GGGTCTAAAACTAAAATTGCGGAGGCTAGTGAAGA | |
| | TGGTTTTCCCGAATCAAGCCAGATTCCAGAAAATA | |
| | CACCTACGGCACCGCAACAGATGCGAGGAGGCGGG | |
| | CGAGGATTTCGAGGTGGAGGTCGACGCTACGGTAG | |
| | GAGGGGTGGGCGGCGCCAAGAGAACGAAGAAGGAG | |
| | AGGAAGAA*AGCGGCTCTGAGACTCCCGGCACATCC* | |
| | *GAAAGCGCAACCCCTGAGTCTGTCGGCGGCTATAA* | |
| | *AGTCAGCAATTTGACAGTGGAAGCGTTCGAAGGTA* | |
| | *TCGGGAGTGTCAACCCGATGCTGTTTTACCAATAC* | |
| | *AAAGTCACCGGAAAGGGAAAGTACGATAATGTGTA* | |
| | *TAAGATTATCAAAAGCGCACGGTACAAGATGCATT* | |
| | *CTAAGAACCGATTCAAGCCCGTGTTCATCAAGGAC* | |
| | *GACAAACTGTACACCCTCGAGAAGCTCCCGGATAT* | |
| | *AGAGGACCTGGATTTCGCAAACATTAACTTCGTGA* | |
| | *AAAGCGAGGTTCTCAGCATAGAGGATAATATGTCA* | |
| | *ATTTATGGCGAGGTGGTGGAATACTATATCAATCT* | |
| | *CAAGCTGAAAAAAGTGAAGGTGTTGGGAAAATACC* | |
| | *CCAAGTACAGGATCAATTACAGCAAAGAGATTCTC* | |
| | *AGTAATACGCTGCTGACACGAGAGCTCAAAGACGA* | |
| | *GTTTAAGAAATCAAATAAGGGTTTTAACCTGAAAC* | |
| | *GGAAGTTTAGAATTTCCCCCGTGGTGAATAAGATG* | |
| | *GGCAAAGTGATACTCTATTTGTCCTGCAGTGCTGA* | |
| | *TTTCAGCACCAACAAGAACATTTACGAAATGTTGA* | |
| | *AAGAGGGCTTGGAGGTTGAGGGGCTGGCCGTTAAG* | |
| | *AGCGAGTGGAGCAATATCAGTGGCAACCTGGTGAT* | |
| | *CGAGAGCGTACTGGAAACCAAGATATCCGAGCCCA* | |
| | *CTAGCCTGGGCCAATCCCTGATAGACTACTATAAG* | |
| | *AATAACAACCAGGGCTATAGGGTGAAGGATTTCAC* | |
| | *CGATGAGGATCTGAATGCCAACATTGTCAACGTGA* | |
| | *GAGGAAATAAGAAGATCTATATGTATATTCCGCAC* | |
| | *GCGTTGAAGCCGATAATCACCCGGGAGTACCTGGC* | |
| | *CAAGAACGATCCAGAGTTTTCTAAGGAGATCGAGC* | |
| | *AGCTTATCAAGATGAATATGAACTACCGATATGAA* | |
| | *ACCCTCAAGTCATTTGTGAATGACATCGGGGTCAT* | |
| | *TGAGGAGCTGAACAACCTGAGCTTCAAAAACAAAT* | |
| | *ACTACGAAGATGTGAAACTGCTGGGTTACTCCAGC* | |
| | *GGCAAAATAGACGAACCCGTCCTGATGGGGGCAAA* | |
| | *AGGGATCATAAAGAACAAAATGCAGATTTTTTCCA* | |
| | *ATGGATTCTACAAACTCCCCGAAGGCAAGGTACGA* | |
| | *TTTGGCGTTCTGTACCCAAAAGAATTTGATGGCGT* | |
| | *GTCAAGGAAAGCTATCCGCGCCATTTATGACTTCA* | |
| | *GTAAGGAGGGCAAATACCACGGCGAAAGCAACAAG* | |
| | *TATATCGCGGAACACCTGATAAACGTGGAGTTCAA* | |
| | *TCCAAAGGAGTGCATATTTGAGGGATACGAACTGG* | |
| | *GCGATATCACCGAATACAAGAAGGCGGCTCTGAAA* | |
| | *CTTAATAACTACAACAATGTCGACTTCGTAATCGC* | |
| | *AATAGTCCCGAACATGTCCGACGAAGAGATAGAGA* | |
| | *ACAGCTACAATCCGTTCAAGAAAATATGGGCCGAA* | |
| | *CTGAATCTGCCCAGCCAGATGATTAGCGTCAAGAC* | |
| | *GGCCGAAATCTTTGCCAATAGCAGGGATAACACGG* | |
| | *CGCTTTACTATCTGCATAACATCGTCCTCGGTATC* | |
| | *CTGGGTAAGATAGGAGGGATTCCCTGGGTGGTTAA* | |
| | *AGACATGAAGGGCGACGTGGATTGCTTCGTTGGAC* | |
| | *TCGATGTCGGCACCAGGGAGAAGGGCATACATTAC* | |
| | *CCCGCCTGCAGCGTTGTGTTTGACAAGTACGGCAA* | |
| | *GCTTATTAACTATTACAAGCCTAACATCCCGCAGA* | |
| | *ACGGAGAGAAGATTAACACAGAAATACTTCAGGAA* | |
| | *ATTTTCGACAAGGTGCTCATAAGCTATGAGGAGGA* | |
| | *GAATGGAGCCTACCCGAAGAATATCGTGATCCACA* | |
| | *GGGACGGCTTTAGCCGAGAGGACCTTGACTGGTAT* | |
| | *GAGAACTACTTCGGTAAGAAAAACATAAAGTTTAA* | |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | CATCATCGAAGTCAAAAAGTCAACTCCGTTGAAAA<br>TCGCCAGTATAAACGAGGGAAATATCACGAATCCT<br>GAAAAGGGTTCCTACATCCTGCGCGGCAACAAAGC<br>CTACATGGTGACCACAGATATTAAGGAAAACCTGG<br>GAAGCCCAAAGCCCCTGAAGATAGAAAAGAGCTAC<br>GGCGACATAGACATGCTCACAGCTCTCAGCCAAAT<br>ATACGCACTCACGCAAATCCATGTGGGGGCGACCA<br>AAAGCCTGCGCCTCCCAATCACCACCGGCTACGCC<br>GACAAGATTTGCAAGGCGATCGAGTTCATCCCCCA<br>AGGGCGCGTGGACAACCGCCTTTTCTTTCTGTAGT<br>GA | |
| 2SSB-AGO#69v2<br>(See FIG. 75)<br>N to C terminus:<br>*Italicized: His Tag*<br>Underlined: GST<br>**Bold: SsoSSB**<br>**Underlined/Bold:**<br>**SGSG4S** (SEQ ID NO: 71)<br>*Italicized/Underlined:*<br>*XTEN*<br>***Italicized/Bold: Ago69*** | ATGAAACATCACCATCACCATCACAACACTAGTAG<br>CAATTCCATGTCCCCTATACTAGGTTATTGGAAAA<br>TTAAGGGCCTTGTGCAACCCACTCGACTTCTTTTG<br>GAATATCTTGAAGAAAAATATGAAGAGCATTTGTA<br>TGAGCGCGATGAAGGTGATAAATGGCGAAACAAAA<br>AGTTTGAATTGGGTTTGGAGTTTCCCAATCTTCCT<br>TATTATATTGATGGTGATGTTAAATTAACACAGTC<br>TATGGCCATCATACGTTATATAGCTGACAAGCACA<br>ACATGTTGGGTGGTTGTCCAAAAGAGCGTGCAGAG<br>ATTTCAATGCTTGAAGGAGCGGTTTTGGATATTAG<br>ATACGGTGTTTCGAGAATTGCATATAGTAAAGACT<br>TTGAAACTCTCAAAGTTGATTTTCTTAGCAAGCTA<br>CCTGAAATGCTGAAAATGTTCGAAGATCGTTTATG<br>TCATAAAACATATTTAAATGGTGATCATGTAACCC<br>ATCCTGACTTCATGTTGTATGACGCTCTTGATGTT<br>GTTTTATACATGGACCCAATGTGCCTGGATGCGTT<br>CCCAAAATTAGTTTGTTTTAAAAAACGTATTGAAG<br>CTATCCCACAAATTGATAAGTACTTGAAATCCAGC<br>AAGTATATAGCATGGCCTTTGCAGGGCTGGCAAGC<br>CACGTTTGGTGGTGGCGACCATCCTCCAACTAGTG<br>GATCTGGTGGTGGTGGCGGATGGATGAGCGAGAAT<br>CTTTATTTTCAGGGCGCAATGGAGGAGAAGGTCGG<br>TAACCTTAAGCCCAATATGGAATCTGTCAACGTTA<br>CTGTTAGAGTCCTGGAAGCCAGCGAGGCGCGCCAA<br>ATACAGACGAAGAACGGGGTAAGGACCATAAGCGA<br>GGCAATCGTCGGCGACGAGACTGGCAGAGTTAAAT<br>TGACCCTTTGGGGAAAACACGCTGGTTCTATAAAG<br>GAAGGTCAAGTCGTAAAGATCGAAAATGCTTGGAC<br>GACCGCATTCAAGGGCCAGGTTCAACTCAACGCCG<br>GATCTAAAACTAAGATAGCTGAGGCGTCAGAAGAC<br>GGCTTCCCAGAATCAAGCCAGATACCTGAGAACAC<br>TCCAACGGCTCCTCAACAAATGAGAGGAGGTGGAC<br>GAGGATTTCGCGGGGGGGGACGAAGATATGGCCGA<br>CGCGGAGGACGACGCCAGGAAAATGAAGAGGGTGA<br>AGAGGAATCTGGTTCCGGTGGCGGTGGTAGCGAAG<br>AAAAAGTGGGTAACCTTAAACCCAACATGGAGAGC<br>GTTAACGTCACGGTCAGAGTACTCGAGGCGAGCGA<br>GGCGCGGCAGATACAAACAAAAAATGGTGTGCGCA<br>CCATTTCCGAAGCTATAGTCGGTGACGAAACGGGC<br>CGCGTTAAATTGACGCTCTGGGGAAAACATGCAGG<br>TTCTATTAAAGAGGGTCAGGTCGTGAAAATAGAGA<br>ACGCCTGGACTACGGCGTTCAAGGGTCAGGTCCAA<br>CTGAATGCAGGGTCTAAAACTAAAATTGCGGAGGC<br>TAGTGAAGATGGTTTTCCCGAATCAAGCCAGATTC<br>CAGAAAATACACCTACGGCACCGCAACAGATGCGA<br>GGAGGCGGGCGAGGATTTCGAGGTGGAGGTCGACG<br>CTACGGTAGGAGGGGTGGGCGGCGCCAAGAGAACG<br>AAGAAGGAGAGGAAGAAAGCGGCTCTGAGACTCCC<br>GGCACATCCGAAAGCGCAACCCCTGAGTCTGTCGG<br>CGGCTATAAAGTCAGCAATTTGACAGTGGAAGCGT<br>TCGAAGGTATCGGGAGTGTCAACCCGATGCTGTTT<br>TACCAATACAAAGTCACCGGAAAGGGAAAGTACGA<br>TAATGTGTATAAGATTATCAAAAGCGCACGGTACA<br>AGATGCATTCTAAGAACCGATTCAAGCCCGTGTTC<br>ATCAAGGACGACAAACTGTACACCCTCGAGAAGCT<br>CCCGGATATAGAGGACCTGGATTTCGCAAACATTA<br>ACTTCGTGAAAAGCGAGGTTCTCAGCATAGAGGAT<br>AATATGTCAATTTATGGCGAGGTGGTGGAATACTA<br>TATCAATCTCAAGCTGAAAAAAGTGAAGGTGTTGG<br>GAAAATACCCCAAGTACAGGATCAATTACAGCAAA<br>GAGATTCTCAGTAATACGCTGCTGACACGAGAGCT<br>CAAAGACGAGTTTAAGAAATCAAATAAGGGTTTTA<br>ACCTGAAACGGAAGTTTAGAATTTCCCCCGTGGTG | 95 |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | AATAAGATGGGCAAAGTGATACTCTATTTGTCCTG<br>CAGTGCTGATTTCAGCACCAACAAGAACATTTACG<br>AAATGTTGAAAGAGGGCTTGGAGGTTGAGGGGCTG<br>GCCGTTAAGAGCGAGTGGAGCAATATCAGTGGCAA<br>CCTGGTGATCGAGAGCGTACTGGAAACCAAGATAT<br>CCGAGCCCACTAGCCTGGGCCAATCCCTGATAGAC<br>TACTATAAGAATAACAACCAGGGCTATAGGGTGAA<br>GGATTTCACCGATGAGGATCTGAATGCCAACATTG<br>TCAACGTGAGAGGAAATAAGAAGATCTATATGTAT<br>ATTCCGCACGCGTTGAAGCCGATAATCACCCGGGA<br>GTACCTGGCCAAGAACGATCCAGAGTTTTCTAAGG<br>AGATCGAGCAGCTTATCAAGATGAATATGAACTAC<br>CGATATGAAACCCTCAAGTCATTTGTGAATGACAT<br>CGGGGTCATTGAGGAGCTGAACAACCTGAGCTTCA<br>AAAACAAATACTACGAAGATGTGAAACTGCTGGGT<br>TACTCCAGCGGCAAAATAGACGAACCCGTCCTGAT<br>GGGGGCAAAAGGGATCATAAAGAACAAAATGCAGA<br>TTTTTTCCAATGGATTCTACAAACTCCCCGAAGGC<br>AAGGTACGATTTGGCGTTCTGTACCCAAAAGAATT<br>TGATGGCGTGTCAAGGAAAGCTATCCGCGCCATTT<br>ATGACTTCAGTAAGGAGGGCAAATACCACGGCGAA<br>AGCAACAAGTATATCGCGGAACACCTGATAAACGT<br>GGAGTTCAATCCAAAGGAGTGCATATTTGAGGGAT<br>ACGAACTGGGCGATATCACCGAATACAAGAAGGCG<br>GCTCTGAAACTTAATAACTACAACAATGTCGACTT<br>CGTAATCGCAATAGTCCCGAACATGTCCGACGAAG<br>AGATAGAGAACAGCTACAATCCGTTCAAGAAAATA<br>TGGGCCGAACTGAATCTGCCCAGCCAGATGATTAG<br>CGTCAAGACGGCCGAAATCTTTGCCAATAGCAGGG<br>ATAACACGGCGCTTTACTATCTGCATAACATCGTC<br>CTCGGTATCCTGGGTAAGATAGGAGGGATTCCCTG<br>GGTGGTTAAAGACATGAAGGGCGACGTGGATTGCT<br>TCGTTGGACTCGATGTCGGCACCAGGGAGAAGGGC<br>ATACATTACCCCGCCTGCAGCGTTGTGTTTGACAA<br>GTACGGCAAGCTTATTAACTATTACAAGCCTAACA<br>TCCCGCAGAACGGAGAGAAGATTAACACAGAAATA<br>CTTCAGGAAATTTTCGACAAGGTGCTCATAAGCTA<br>TGAGGAGGAGAATGGAGCCTACCCGAAGAATATCG<br>TGATCCACAGGGACGGCTTTAGCCGAGAGGACCTT<br>GACTGGTATGAGAACTACTTCGGTAAGAAAAACAT<br>AAAGTTTAACATCATCGAAGTCAAAAAGTCAACTC<br>CGTTGAAAATCGCCAGTATAAACGAGGGAAATATC<br>ACGAATCCTGAAAAGGGTTCCTACATCCTGCGCGG<br>CAACAAAGCCTACATGGTGACCACAGATATTAAGG<br>AAAACCTGGGAAGCCCAAAGCCCCTGAAGATAGAA<br>AAGAGCTACGGCGACATAGACATGCTCACAGCTCT<br>CAGCCAAATATACGCACTCACGCAAATCCATGTGG<br>GGGCGACCAAAAGCCTGCGCCTCCCAATCACCACC<br>GGCTACGCCGACAAGATTTGCAAGGCGATCGAGTT<br>CATCCCCCAAGGGCGCGTGGACAACCGCCTTTTCT<br>TTCTGTAGTGA | |
| 2SSB-AGO#69v3<br>(See FIG. 75)<br>N to C terminus:<br>*Italicized: His Tag*<br>Underlined: GST<br>**Bold: SsoSSB**<br>*Italicized/Underlined:*<br>*XTEN*<br>***Italicized/Bold: Ago69*** | ATGAAACATCACCATCACCATCACAACACTAGTAG<br>CAATTCCATGTCCCCTATACTAGGTTATTGGAAAA<br>TTAAGGGCCTTGTGCAACCCACTCGACTTCTTTTG<br>GAATATCTTGAAGAAAAATATGAAGAGCATTTGTA<br>TGAGCGCGATGAAGGTGATAAATGGCGAAACAAAA<br>AGTTTGAATTGGGTTTGGAGTTTCCCAATCTTCCT<br>TATTATATTGATGGTGATGTTAAATTAACACAGTC<br>TATGGCCATCATACGTTATATAGCTGACAAGCACA<br>ACATGTTGGGTGGTTGTCCAAAAGAGCGTGCAGAG<br>ATTTCAATGCTTGAAGGAGCGGTTTTGGATATTAG<br>ATACGGTGTTTCGAGAATTGCATATAGTAAAGACT<br>TTGAAACTCTCAAAGTTGATTTTCTTAGCAAGCTA<br>CCTGAAATGCTGAAAATGTTCGAAGATCGTTTATG<br>TCATAAAACATATTTAAATGGTGATCATGTAACCC<br>ATCCTGACTTCATGTTGTATGACGCTCTTGATGTT<br>GTTTTATACATGGACCCAATGTGCCTGGATGCGTT<br>CCCAAAATTAGTTTGTTTTAAAAAACGTATTGAAG<br>CTATCCCACAAATTGATAAGTACTTGAAATCCAGC<br>AAGTATATAGCATGGCCTTTGCAGGGCTGGCAAGC<br>CACGTTTGGTGGTGGCGACCATCCTCCAACTAGTG<br>GATCTGGTGGTGGTGGCGGATGGATGAGCGAGAAT<br>CTTTATTTTCAGGGCGCAATGGAGGAGAAGGTCGG<br>TAACCTTAAGCCCAATATGGAATCTGTCAACGTTA | 96 |

TABLE 11-continued

Nucleic Acid Sequence of Exemplary Ago-SSB Fusion Polypeptides

| Fusion Polypeptide | Nucleic Acid Sequence | SEQ ID NO |
|---|---|---|
| | CTGTTAGAGTCCTGGAAGCCAGCGAGGCGCGCCAA | |
| | ATACAGACGAAGAACGGGGTAAGGACCATAAGCGA | |
| | GGCAATCGTCGGCGACGAGACTGGCAGAGTTAAAT | |
| | TGACCCTTTGGGGAAAACACGCTGGTTCTATAAAG | |
| | GAAGGTCAAGTCGTAAAGATCGAAAATGCTTGGAC | |
| | GACCGCATTCAAGGGCCAGGTTCAACTCAACGCCG | |
| | GATCTAAAACTAAGATAGCTGAGGCGTCAGAAGAC | |
| | GGCTTCCCAGAATCAAGCCAGATACCTGAGAACAC | |
| | TCCAACGGCTCCTCAACAAATGAGAGGAGGTGGAC | |
| | GAGGATTTCGCGGGGGGGACGAAGATATGGCCGA | |
| | CGCGGAGGACGACGCCAGGAAAATGAAGAGGGTGA | |
| | AGAGGAAAGCGGCTCTGAGACTCCCGGCACATCCG | |
| | AAAGCGCGAAGAAAAAGTGGGTAACCTTAAACCCA | |
| | ACATGGAGAGCGTTAACGTCACGGTCAGAGTACTC | |
| | GAGGCGAGCGAGGCGCGGCAGATACAAACAAAAAA | |
| | TGGTGTGCGCACCATTTCCGAAGCTATAGTCGGTG | |
| | ACGAAACGGGCCGCGTTAAATTGACGCTCTGGGGA | |
| | AAACATGCAGGTTCTATTAAAGAGGGTCAGGTCGT | |
| | GAAAATAGAGAACGCCTGGACTACGGCGTTCAAGG | |
| | GTCAGGTCCAACTGAATGCAGGGTCTAAAACTAAA | |
| | ATTGCGGAGGCTAGTGAAGATGGTTTTCCCGAATC | |
| | AAGCCAGATTCCAGAAAATACACCTACGGCACCGC | |
| | AACAGATGCGAGGAGGCGGGCGAGGATTTCGAGGT | |
| | GGAGGTCGACGCTACGGTAGGAGGGGTGGGCGGCG | |
| | CCAAGAGAACGAAGAAGGAGAGGAAGAAAGCGGCT | |
| | CTGAGACTCCCGGCACATCCGAAAGCGCAACCCCT | |
| | GAGTCTGTCGGCGGCTATAAAGTCAGCAATTTGAC | |
| | AGTGGAAGCGTTCGAAGGTATCGGGAGTGTCAACC | |
| | CGATGCTGTTTTACCAATACAAAGTCACCGGAAAG | |
| | GGAAAGTACGATAATGTGTATAAGATTATCAAAAG | |
| | CGCACGGTACAAGATGCATTCTAAGAACCGATTCA | |
| | AGCCCGTGTTCATCAAGGACGACAAACTGTACACC | |
| | CTCGAGAAGCTCCCGGATATAGAGGACCTGGATTT | |
| | CGCAAACATTAACTTCGTGAAAAGCGAGGTTCTCA | |
| | GCATAGAGGATAATATGTCAATTTATGGCGAGGTG | |
| | GTGGAATACTATATCAATCTCAAGCTGAAAAAAGT | |
| | GAAGGTGTTGGGAAAATACCCCAAGTACAGGATCA | |
| | ATTACAGCAAAGAGATTCTCAGTAATACGCTGCTG | |
| | ACACGAGAGCTCAAAGACGAGTTTAAGAAATCAAA | |
| | TAAGGGTTTTAACCTGAAACGGAAGTTTAGAATTT | |
| | CCCCCGTGGTGAATAAGATGGGCAAAGTGATACTC | |
| | TATTTGTCCTGCAGTGCTGATTTCAGCACCAACAA | |
| | GAACATTTACGAAATGTTGAAAGAGGGCTTGGAGG | |
| | TTGAGGGGCTGGCCGTTAAGAGCGAGTGGAGCAAT | |
| | ATCAGTGGCAACCTGGTGATCGAGAGCGTACTGGA | |
| | AACCAAGATATCCGAGCCCACTAGCCTGGGCCAAT | |
| | CCCTGATAGACTACTATAAGAATAACAACCAGGGC | |
| | TATAGGGTGAAGGATTTCACCGATGAGGATCTGAA | |
| | TGCCAACATTGTCAACGTGAGAGGAAATAAGAAGA | |
| | TCTATATGTATATTCCGCACGCGTTGAAGCCGATA | |
| | ATCACCCGGGAGTACCTGGCCAAGAACGATCCAGA | |
| | GTTTTCTAAGGAGATCGAGCAGCTTATCAAGATGA | |
| | ATATGAACTACCGATATGAAACCCTCAAGTCATTT | |
| | GTGAATGACATCGGGGTCATTGAGGAGCTGAACAA | |
| | CCTGAGCTTCAAAAACAAATACTACGAAGATGTGA | |
| | AACTGCTGGGTTACTCCAGCGGCAAAATAGACGAA | |
| | CCCGTCCTGATGGGGGCAAAAGGGATCATAAAGAA | |
| | CAAAATGCAGATTTTTTCCAATGGATTCTACAAAC | |
| | TCCCCGAAGGCAAGGTACGATTTGGCGTTCTGTAC | |
| | CCAAAAGAATTTGATGGCGTGTCAAGGAAAGCTAT | |
| | CCGCGCCATTTATGACTTCAGTAAGGAGGGCAAAT | |
| | ACCACGGCGAAAGCAACAAGTATATCGCGGAACAC | |
| | CTGATAAACGTGGAGTTCAATCCAAAGGAGTGCAT | |
| | ATTTGAGGGATACGAACTGGGCGATATCACCGAAT | |
| | ACAAGAAGGCGGCTCTGAAACTTAATAACTACAAC | |
| | AATGTCGACTTCGTAATCGCAATAGTCCCGAACAT | |
| | GTCCGACGAAGAGATAGAGAACAGCTACAATCCGT | |
| | TCAAGAAAATATGGGCCGAACTGAATCTGCCCAGC | |
| | CAGATGATTAGCGTCAAGACGGCCGAAATCTTTGC | |
| | CAATAGCAGGGATAACACGGCGCTTTACTATCTGC | |
| | ATAACATCGTCCTCGGTATCCTGGGTAAGATAGGA | |
| | GGGATTCCCTGGGTGGTTAAAGACATGAAGGGCGA | |
| | CGTGGATTGCTTCGTTGGACTCGATGTCGGCACCA | |
| | GGGAGAAGGGCATACATTACCCCGCCTGCAGCGTT | |
| | GTGTTTGACAAGTACGGCAAGCTTATTAACTATTA | |

TABLE 11-continued

| Fusion Polypeptide | Nucleic Acid Sequence | SEQ ID NO |
|---|---|---|
| | Nucleic Acid Sequence of Exemplary Ago-SSB Fusion Polypeptides | |
| | CAAGCCTAACATCCCGCAGAACGGAGAGAAGATTA<br>ACACAGAAATACTTCAGGAAATTTTCGACAAGGTG<br>CTCATAAGCTATGAGGAGGAGAATGGAGCCTACCC<br>GAAGAATATCGTGATCCACAGGGACGGCTTTAGCC<br>GAGAGGACCTTGACTGGTATGAGAACTACTTCGGT<br>AAGAAAAACATAAAGTTTAACATCATCGAAGTCAA<br>AAAGTCAACTCCGTTGAAAATCGCCAGTATAAACG<br>AGGGAAATATCACGAATCCTGAAAAGGGTTCCTAC<br>ATCCTGCGCGGCAACAAAGCCTACATGGTGACCAC<br>AGATATTAAGGAAAACCTGGGAAGCCCAAAGCCCC<br>TGAAGATAGAAAAGAGCTACGGCGACATAGACATG<br>CTCACAGCTCTCAGCCAAATATACGCACTCACGCA<br>AATCCATGTGGGGGCGACCAAAAGCCTGCGCCTCC<br>CAATCACCACCGGCTACGCCGACAAGATTTGCAAG<br>GCGATCGAGTTCATCCCCCAAGGGCGCGTGGACAA<br>CCGCCTTTTCTTTCTGTAGTGA | |

In some embodiments, the Ago-SSB fusion protein comprises an amino acid sequence with at least 80%, 85%, 90%, 91%, 92%, 93%, 94%, 95%, 96%, 97%, 98%, 99% or 100% identity to one of SEQ ID NOS: 97-101. In some embodiments, the Ago-SSB fusion protein is encoded by a nucleic acid sequence with at least 80%, 85%, 90%, 91%, 92%, 93%, 94%, 95%, 96%, 97%, 98%, 99% or 100% identity to one of SEQ TD NOS: 102-106. The amino acid sequence of exemplary Ago-SSB fusion polypeptides are provided in Table 12. The nucleic acid sequence of exemplary Ago-SSB fusion polypeptides are provided in Table 13.

TABLE 12

Amino Acid Sequence of Exemplary Ago-SSB 2XSV40NLS Fusion Polypeptides

| Fusion Polypeptide | Amino Acid Sequence | SEQ ID NO |
|---|---|---|
| AP109<br>N to C terminus:<br>Italicized/Underlined: 2XSV40NLS<br>Underlined: GSGS linker (SEQ ID NO: 154)<br>Italicized: V5 Tag<br>**Bold: Ago69** | MPKKKRKVEDPKKKRKVGSGSGKPIPNPLLGLDSTGSGSSMV<br>GGYKVSNLTVEAFEGIGSVNPMLFYQYKVTGKGKYDNVYKII<br>KSARYKMHSKNRFKPVFIKDDKLYTLEKLPDIEDLDFANINF<br>VKSEVLSIEDNMSIYGEVVEYYINLKLKKVKVLGKYPKYRIN<br>YSKEILSNTLLTRELKDEFKKSNKGFNLKRKFRISPVVNKMG<br>KVILYLSCSADFSTNKNIYEMLKEGLEVEGLAVKSEWSNISG<br>NLVIESVLETKISEPTSLGQSLIDYYKNNNQGYRVKDFTDED<br>LNANIVNVRGNKKIYMYIPHALKPIITREYLAKNDPEFSKEI<br>EQLIKMNMNYRYETLKSFVNDIGVIEELNNLSFKNKYYEDVK<br>LLGYSSGKIDEPVLMGAKGIIKNKMQIFSNGFYKLPEGKVRF<br>GVLYPKEFDGVSRKAIRAIYDFSKEGKYHGESNKYIAEHLIN<br>VEFNPKECIFEGYELGDITEYKKAALKLNNYNNVDFVIAIVP<br>NMSDEEIENSYNPFKKIWAELNLPSQMISVKTAEIFANSRDN<br>TALYYLHNIVLGILGKIGGIPWVVKDMKGDVDCFVGLDVGTR<br>EKGIHYPACSVVFDKYGKLINYYKPNIPONGEKINTEILQEI<br>FDKVLISYEEENGAYPKNIVIHRDGFSREDLDWYENYFGKKN<br>IKFNIIEVKKSTPLKIASINEGNITNPEKGSYILRGNKAYMV<br>TTDIKENLGSPKPLKIEKSYGDIDMLTALSQIYALTQIHVGA<br>TKSLRLPITTGYADKICKAIEFIPQGRVDNRLFFL | 97 |
| AP110<br>N to C terminus:<br>Italicized/Underlined/Bold: 2XSV40NLS<br>Underlined: GSGS linker (SEQ ID NO: 154)<br>Italicized: V5 Tag<br>***Italicized and Bold: Sso SSB***<br>Italicized and underlined: GGGGS linker (SEQ ID NO: 70)<br>**Bold: Ago69** | MPKKKRKVEDPKKKRKVGSGSGKPIPNPLLGLDSTGSGSSME<br>EKVGNLKPNMESVNVTVRVLEASEARQIQTKNGVRTISEAIV<br>GDETGRVKLTLWGKHAGSIKEGQVVKIENAWTTAFKGQVQLN<br>AGSKTKIAEASEDGFPESSQIPENTPTAPQQMRGGGRGFRGG<br>GRRYGRRGGRRQENEEGEEEGGGGSMVGGYKVSNLTVEAFEG<br>IGSVNPMLFYQYKVTGKGKYDNVYKIIKSARYKMHSKNRFKP<br>VFIKDDKLYTLEKLPDIEDLDFANINFVKSEVLSIEDNMSIY<br>GEVVEYYINLKLKKVKVLGKYPKYRINYSKEILSNTLLTREL<br>KDEFKKSNKGFNLKRKFRISPVVNKMGKVILYLSCSADFSTN<br>KNIYEMLKEGLEVEGLAVKSEWSNISGNLVIESVLETKISEP<br>TSLGQSLIDYYKNNNQGYRVKDFTDEDLNANIVNVRGNKKIY<br>MYIPHALKPIITREYLAKNDPEFSKEIEQLIKMNMNYRYETL<br>KSFVNDIGVIEELNNLSFKNKYYEDVKLLGYSSGKIDEPVLM<br>GAKGIIKNKMQIFSNGFYKLPEGKVRFGVLYPKEFDGVSRKA<br>IRAIYDFSKEGKYHGESNKYIAEHLINVEFNPKECIFEGYEL<br>GDITEYKKAALKLNNYNNVDFVIAIVPNMSDEEIENSYNPFK<br>KIWAELNLPSQMISVKTAEIFANSRDNTALYYLHNIVLGILG<br>KIGGIPWVVKDMKGDVDCFVGLDVGTREKGIHYPACSVVFDK<br>YGKLINYYKPNIPONGEKINTEILQEIFDKVLISYEEENGAY<br>PKNIVIHRDGFSREDLDWYENYFGKKNIKFNIIEVKKSTPLK | 98 |

TABLE 12-continued

Amino Acid Sequence of Exemplary Ago-SSB 2XSV40NLS Fusion Polypeptides

| Fusion Polypeptide | Amino Acid Sequence | SEQ ID NO |
|---|---|---|
| | IASINEGNITNPEKGSYILRGNKAYMVTTDIKENLGSPKPLK<br>IEKSYGDIDMLTALSQIYALTQIHVGATKSLRLPITTGYADK<br>ICKAIEFIPQGRVDNRLFFL | |
| SPL0389<br>N to C terminus:<br>Italicized/<br>Underlined:<br>2XSV40NLS<br>Underlined:<br>GSGS linker<br>(SEQ ID NO:<br>154)<br>Italicized: V5<br>Tag<br>Bold:<br>Homologue 2<br>(HG2) | MPKKKRKVEDPKKKRKVGSGSGKPIPNPLLGLDSTGSGSSMN<br>NLTFEAFEGIGQLNELNFYKYRLIGKGQIDNVHQAIWSVKYK<br>LOANNFFKPVFVKGEILYSLDELKVIPEFENVEVILDGNIIL<br>SISENTDIYKDVIVFYINNALKNIKDITNYRKYITKNTDEII<br>CKSILTTNLKYQYMKSEKGFKLORKFKISPVVFRNGKVILYL<br>NCSSDFSTDKSIYEMLNDGLGVVGLQVKNKWTNANGNIFIEK<br>VLDNTISDPGTSGKLGQSLIDYYINGNQKYRVEKFTDEDKNA<br>KVIQAKIKNKTYNYIPQALTPVITREYLSHTDKKFSKQIENV<br>IKMDMNYRYQTLKSFVEDIGVIKELNNLHFKNQYYTNFDFMG<br>FESGVLEEPVLMGANGKIKDKKQIFINGFFKNPKENVKFGVL<br>YPEGCMENAQSIARSILDFATAGKYNKQENKYISKNLMNIGF<br>KPSECIFESYKLGDITEYKATARKLKEHEKVGFVIAVIPDMN<br>ELEVENPYNPFKKVWAKLNIPSQMITLKTTEKFKNIVDKSGL<br>YYLHNIALNILGKIGGIPWIIKDMPGNIDCFIGLDVGTREKG<br>IHFPACSVLFDKYGKLINYYKPTIPOSGEKIAETILQEIFDN<br>VLISYKEENGEYPKNIVIHRDGFSRENIDWYKEYFDKKGIKF<br>NIIEVKKNIPVKIAKVVGSNICNPIKGSYVLKNDKAFIVTTD<br>IKDGVASPNPLKIEKTYGDVEMKSILEQIYSLSQIHVGSTKS<br>LRLPITTGYADKICKAIEYIPQGVVDNRLFFL | 99 |
| SPL0390<br>N to C terminus:<br>Italicized/<br>Underlined:<br>2XSV40NLS<br>Underlined:<br>GSGS linker<br>(SEQ ID NO:<br>154)<br>Italicized: V5<br>Tag<br>Bold:<br>Homologue<br>(HG4) | MPKKKRKVEDPKKKRKVGSGSGKPIPNPLLGLDSTGSGSSMK<br>EFNVITEFKNGINSKSIEIYIYKMMVRDFEKRHNENYDVVKE<br>LINLNNNSTIVFYEQYIASFKEIEKWGNEQYINVEKRAINLE<br>SNEKKILERLLLKEIKNNIDNNKYKVVKDSIYINKPVYNEKG<br>IKIDRYFNLDINVESNGDIIIGFDISHNFEYINTLEYEIKNN<br>NIKIGDRVKDYFYNLTYEYVGIAPFTISEENEYMGCSIVDYY<br>ENKNQSYIVNKLPKDMKAILVKNNKNSIFPYIPSRLKKVCRF<br>ENLPQNVLRDFNTRVKQKTNEKMQFMVDEVINIVKNSEHIDV<br>KKKNMMCDNIGYKIEDLQQPDLLFGNARAQRYPLYGLKNFGV<br>YENKRIEIKYFIDPILAKSKMNLEKISKFCDELEQFSSKLGV<br>GLNRVKLNNIVNFKEIRMDNEDIFSYEIRKIVSNYNETTIVI<br>LSEENLNKYYNIIKKTFSGGNEVPTQCIGENTLSYTEKNKDS<br>IFLNILLGVYAKSGIQPWILNEKLNSDCFIGLDVSRENKVNK<br>AGVIQVVGKDGRVLKTKVISSSQSGEKIKLETLREIVFEAIN<br>SYENTYRCKPKHITFHRDGINREELENLKNTMTNLGVEFDYI<br>EITKGINRRIATISEGEEWKTIMGRCYYKDNSAYVCTTKPYE<br>GIGMAKPIRIRRVFGTLDIEKIVEDAYKLTFMHVGAINKIRL<br>PITTYYADLSSTYGNRDLIPTNIDTNCLYFI | 100 |
| SPL0398<br>N to C terminus:<br>Italicized/Bold/<br>Underlined:<br>2XSV40NLS<br>Underlined:<br>GSGS linker<br>(SEQ ID NO:<br>154)<br>Italicized: V5<br>Tag<br>Italicized and<br>Bold: Sso SSB<br>Italicized and<br>underlined:<br>GGGGS linker<br>(SEQ ID NO:<br>70)<br>Italicized/Bold/<br>Underlined: c-<br>Myc NLS<br>Bold: Ago69 | MGKPIPNPLLGLDSTGSGSMPKKKRKVEDPKKKRKVGSGSSM<br>EEKVGNLKPNMESVNVTVRVLEASEARQIQTKNGVRTISEAI<br>VGDETGRVKLTLWGKHAGSIKEGQVVKIENAWTTAFKGQVQL<br>NAGSKTKIAEASEDGFPESSQIPENTPTAPQQMRGGGRGFRG<br>GGRRYGRRGGRRQENEEGEEEGGGGSPAAKRVKLDGGGGSMV<br>GGYKVSNLTVEAFEGIGSVNPMLFYQYKVTGKGKYDNVYKII<br>KSARYKMHSKNRFKPVFIKDDKLYTLEKLPDIEDLDFANINF<br>VKSEVLSIEDNMSIYGEVVEYYINLKLKKVKVLGKYPKYRIN<br>YSKEILSNTLLTRELKDEFKKSNKGFNLKRKFRISPVVNKMG<br>KVILYLSCSADFSTNKNIYEMLKEGLEVEGLAVKSEWSNISG<br>NLVIESVLETKISEPTSLGQSLIDYYKNNNQGYRVKDFTDED<br>LNANIVNVRGNKKIYMYIPHALKPIITREYLAKNDPEFSKEI<br>EQLIKMNMNYRYETLKSFVNDIGVIEELNNLSFKNKYYEDVK<br>LLGYSSGKIDEPVLMGAKGIIKNKMQIFSNGFYKLPEGKVRF<br>GVLYPKEFDGVSRKAIRAIYDFSKEGKYHGESNKYIAEHLIN<br>VEFNPKECIFEGYELGDITEYKKAALKLNNYNNVDFVIAIVP<br>NMSDEEIENSYNPFKKIWAELNLPSQMISVKTAEIFANSRDN<br>TALYYLHNIVLGILGKIGGIPWVVKDMKGDVDCFVGLDVGTR<br>EKGIHYPACSVVFDKYGKLINYYKPNIPONGEKINTEILQEI<br>FDKVLISYEEENGAYPKNIVIHRDGFSREDLDWYENYFGKKN<br>IKFNIIEVKKSTPLKIASINEGNITNPEKGSYILRGNKAYMV<br>TTDIKENLGSPKPLKIEKSYGDIDMLTALSQIYALTQIHVGA<br>TKSLRLPITTGYADKICKAIEFIPQGRVDNRLFFL | 101 |

TABLE 13

| Fusion Polypeptide | Nucleic Acid Sequence | SEQ ID NO |
|---|---|---|
| AP109<br>N to C terminus:<br>Italicized/ Underlined: 2XSV40NLS<br>Underlined: GSGS linker (SEQ ID NO: 154)<br>Italicized: V5 Tag<br>**Bold: Ago69** | ATGCCCAAGAAAAAGCGAAAGGTAGAGGACCCCAAAAAGAAA<br>CGCAAAGTGGGCTCCGGAAGCGGGAAGCCCATCCCAAACCCG<br>CTGTTGGGCTTGGATTCCACGGGCAGCGGAAGCTCTATGGTC<br>GGCGGCTATAAAGTCAGCAATTTGACAGTGGAAGCGTTCGAA<br>GGTATCGGGAGTGTCAACCCGATGCTGTTTTACCAATACAAA<br>GTCACCGGAAAGGGAAAGTACGATAATGTGTATAAGATTATC<br>AAAAGCGCACGGTACAAGATGCATTCTAAGAACCGATTCAAG<br>CCCGTGTTCATCAAGGACGACAAACTGTACACCCTCGAGAAG<br>CTCCCGGATATAGAGGACCTGGATTTCGCAAACATTAACTTC<br>GTGAAAAGCGAGGTTCTCAGCATAGAGGATAATATGTCAATT<br>TATGGCGAGGTGGTGGAATACTATATCAATCTCAAGCTGAAA<br>AAAGTGAAGGTGTTGGGAAAATACCCCAAGTACAGGATCAAT<br>TACAGCAAAGAGATTCTCAGTAATACGCTGCTGACACGAGAG<br>CTCAAAGACGAGTTTAAGAAATCAAATAAGGGTTTTAACCTG<br>AAACGGAAGTTTAGAATTTCCCCCGTGGTGAATAAGATGGGC<br>AAAGTGATACTCTATTTGTCCTGCAGTGCTGATTTCAGCACC<br>AACAAGAACATTTACGAAATGTTGAAAGAGGGCTTGGAGGTT<br>GAGGGGCTGGCCGTTAAGAGCGAGTGGAGCAATATCAGTGGC<br>AACCTGGTGATCGAGAGCGTACTGGAAACCAAGATATCCGAG<br>CCCACTAGCCTGGGCCAATCCCTGATAGACTACTATAAGAAT<br>AACAACCAGGGCTATAGGGTGAAGGATTTCACCGATGAGGAT<br>CTGAATGCCAACATTGTCAACGTGAGAGGAAATAAGAAGATC<br>TATATGTATATTCCGCACGCGTTGAAGCCGATAATCACCCGG<br>GAGTACCTGGCCAAGAACGATCCAGAGTTTTCTAAGGAGATC<br>GAGCAGCTTATCAAGATGAATATGAACTACCGATATGAAACC<br>CTCAAGTCATTTGTGAATGACATCGGGGTCATTGAGGAGCTG<br>AACAACCTGAGCTTCAAAAACAAATACTACGAAGATGTGAAA<br>CTGCTGGGTTACTCCAGCGGCAAAATAGACGAACCCGTCCTG<br>ATGGGGGCAAAAGGGATCATAAAGAACAAAATGCAGATTTTT<br>TCCAATGGATTCTACAAACTCCCCGAAGGCAAGGTACGATTT<br>GGCGTTCTGTACCCAAAAGAATTTGATGGCGTGTCAAGGAAA<br>GCTATCCGCGCCATTTATGACTTCAGTAAGGAGGGCAAATAC<br>CACGGCGAAAGCAACAAGTATATCGCGGAACACCTGATAAAC<br>GTGGAGTTCAATCCAAAGGAGTGCATATTTGAGGGATACGAA<br>CTGGGCGATATCACCGAATACAAGAAGGCGGCTCTGAAACTT<br>AATAACTACAACAATGTCGACTTCGTAATCGCAATAGTCCCG<br>AACATGTCCGACGAAGAGATAGAGAACAGCTACAATCCGTTC<br>AAGAAAATATGGGCCGAACTGAATCTGCCCAGCCAGATGATT<br>AGCGTCAAGACGGCCGAAATCTTTGCCAATAGCAGGGATAAC<br>ACGGCGCTTTACTATCTGCATAACATCGTCCTCGGTATCCTG<br>GGTAAGATAGGAGGGATTCCCTGGGTGGTTAAAGACATGAAG<br>GGCGACGTGGATTGCTTCGTTGGACTCGATGTCGGCACCAGG<br>GAGAAGGGCATACATTACCCCGCCTGCAGCGTTGTGTTTGAC<br>AAGTACGGCAAGCTTATTAACTATTACAAGCCTAACATCCCG<br>CAGAACGGAGAGAAGATTAACACAGAAATACTTCAGGAAATT<br>TTCGACAAGGTGCTCATAAGCTATGAGGAGGAGAATGGAGCC<br>TACCCGAAGAATATCGTGATCCACAGGGACGGCTTTAGCCGA<br>GAGGACCTTGACTGGTATGAGAACTACTTCGGTAAGAAAAAC<br>ATAAAGTTTAACATCATCGAAGTCAAAAAGTCAACTCCGTTG<br>AAAATCGCCAGTATAAACGAGGGAAATATCACGAATCCTGAA<br>AAGGGTTCCTACATCCTGCGCGGCAACAAAGCCTACATGGTG<br>ACCACAGATATTAAGGAAAACCTGGGAAGCCCAAAGCCCCTG<br>AAGATAGAAAAGAGCTACGGCGACATAGACATGCTCACAGCT<br>CTCAGCCAAATATACGCACTCACGCAAATCCATGTGGGGGCG<br>ACCAAAAGCCTGCGCCTCCCAATCACCACCGGCTACGCCGAC<br>AAGATTTGCAAGGCGATCGAGTTCATCCCCCAAGGGCGCGTG<br>GACAACCGCCTTTTCTTTCTG | 102 |
| AP110<br>N to C terminus:<br>***Italicized/ Underlined/ Bold: 2XSV40NLS***<br>Underlined: GSGS linker (SEQ ID NO: 154)<br>Italicized: V5 Tag<br>***Italicized and Bold: Sso SSB***<br>Italicized and underlined: GGGGS linker | ATGCCCAAGAAAAAGCGAAAGGTAGAGGACCCCAAAAAGAAA<br>CGCAAAGTGGGCTCCGGAAGCGGGAAGCCCATCCCAAACCCG<br>CTGTTGGGCTTGGATTCCACGAGTATGGAAGAGAAGGTCGGA<br>AATCTCAAACCCAACATGGAGAGCGTCAACGTGACTGTCAGA<br>GTGCTTGAGGCTAGTGAGGCTCGTCAAATACAAACTAAGAAC<br>GGCGTGCGAACGATCTCTGAAGCAATCGTGGGAGACGAGACA<br>GGTCGGGTCAAGCTTACACTTTGGGGAAAGCACGCAGGGTCC<br>ATTAAAGAGGGGCAAGTGGTCAAGATCGAAAATGCATGGACC<br>ACGGCCTTTAAGGGTCAAGTCCAACTCAACGCTGGCTCTAAA<br>ACAAAGATCGCGGAAGCCAGCGAGGATGGGTTTCCCGAGTCT<br>TCCCAAATACCTGAGAATACCCCCACAGCCCCTCAACAAATG<br>CGCGGCGGCGGAAGGGGTTTTAGGGGTGGCGGGAGACGGTAC<br>GGGAGAAGGGGCGGAAGGAGACAGGAGAATGAGGAAGGAGAG<br>GAAGAGGGTGGAGGAGGAAGTATGGTCGGCGGCTATAAAGTC<br>AGCAATTTGACAGTGGAAGCGTTCGAAGGTATCGGGAGTGTC<br>AACCCGATGCTGTTTTACCAATACAAAGTCACCGGAAAGGGA<br>AAGTACGATAATGTGTATAAGATTATCAAAAGCGCACGGTAC | 103 |

TABLE 13-continued

Amino Acid Sequence of Exemplary Ago-SSB 2XSV40NLS Fusion Polypeptides

| Fusion Polypeptide | Nucleic Acid Sequence | SEQ ID NO |
|---|---|---|
| (SEQ ID NO: 70)<br>**Bold: Ago69** | **AAGATGCATTCTAAGAACCGATTCAAGCCCGTGTTCATCAAG<br>GACGACAAACTGTACACCCTCGAGAAGCTCCCGGATATAGAG<br>GACCTGGATTTCGCAAACATTAACTTCGTGAAAAGCGAGGTT<br>CTCAGCATAGAGGATAATATGTCAATTTATGGCGAGGTGGTG<br>GAATACTATATCAATCTCAAGCTGAAAAAAGTGAAGGTGTTG<br>GGAAAATACCCCAAGTACAGGATCAATTACAGCAAAGAGATT<br>CTCAGTAATACGCTGCTGACACGAGAGCTCAAAGACGAGTTT<br>AAGAAATCAAATAAGGGTTTTAACCTGAAACGGAAGTTTAGA<br>ATTTCCCCCGTGGTGAATAAGATGGGCAAAGTGATACTCTAT<br>TTGTCCTGCAGTGCTGATTTCAGCACCAACAAGAACATTTAC<br>GAAATGTTGAAAGAGGGCTTGGAGGTTGAGGGGCTGGCCGTT<br>AAGAGCGAGTGGAGCAATATCAGTGGCAACCTGGTGATCGAG<br>AGCGTACTGGAAACCAAGATATCCGAGCCCACTAGCCTGGGC<br>CAATCCCTGATAGACTACTATAAGAATAACAACCAGGGCTAT<br>AGGGTGAAGGATTTCACCGATGAGGATCTGAATGCCAACATT<br>GTCAACGTGAGAGGAAATAAGAAGATCTATATGTATATTCCG<br>CACGCGTTGAAGCCGATAATCACCCGGGAGTACCTGGCCAAG<br>AACGATCCAGAGTTTTCTAAGGAGATCGAGCAGCTTATCAAG<br>ATGAATATGAACTACCGATATGAAACCCTCAAGTCATTTGTG<br>AATGACATCGGGGTCATTGAGGAGCTGAACAACCTGAGCTTC<br>AAAAACAAATACTACGAAGATGTGAAACTGCTGGGTTACTCC<br>AGCGGCAAAATAGACGAACCCGTCCTGATGGGGGCAAAAGGG<br>ATCATAAAGAACAAAATGCAGATTTTTTCCAATGGATTCTAC<br>AAACTCCCCGAAGGCAAGGTACGATTTGGCGTTCTGTACCCA<br>AAAGAATTTGATGGCGTGTCAAGGAAAGCTATCCGCGCCATT<br>TATGACTTCAGTAAGGAGGGCAAATACCACGGCGAAAGCAAC<br>AAGTATATCGCGGAACACCTGATAAACGTGGAGTTCAATCCA<br>AAGGAGTGCATATTTGAGGGATACGAACTGGGCGATATCACC<br>GAATACAAGAAGGCGGCTCTGAAACTTAATAACTACAACAAT<br>GTCGACTTCGTAATCGCAATAGTCCCGAACATGTCCGACGAA<br>GAGATAGAGAACAGCTACAATCCGTTCAAGAAAATATGGGCC<br>GAACTGAATCTGCCCAGCCAGATGATTAGCGTCAAGACGGCC<br>GAAATCTTTGCCAATAGCAGGGATAACACGGCGCTTTACTAT<br>CTGCATAACATCGTCCTCGGTATCCTGGGTAAGATAGGAGGG<br>ATTCCCTGGGTGGTTAAAGACATGAAGGGCGACGTGGATTGC<br>TTCGTTGGACTCGATGTCGGCACCAGGGAGAAGGGCATACAT<br>TACCCCGCCTGCAGCGTTGTGTTTGACAAGTACGGCAAGCTT<br>ATTAACTATTACAAGCCTAACATCCCGCAGAACGGAGAGAAG<br>ATTAACACAGAAATACTTCAGGAAATTTTCGACAAGGTGCTC<br>ATAAGCTATGAGGAGGAGAATGGAGCCTACCCGAAGAATATC<br>GTGATCCACAGGGACGGCTTTAGCCGAGAGGACCTTGACTGG<br>TATGAGAACTACTTCGGTAAGAAAAACATAAAGTTTAACATC<br>ATCGAAGTCAAAAAGTCAACTCCGTTGAAAATCGCCAGTATA<br>AACGAGGGAAATATCACGAATCCTGAAAAGGGTTCCTACATC<br>CTGCGCGGCAACAAAGCCTACATGGTGACCACAGATATTAAG<br>GAAAACCTGGGAAGCCCAAAGCCCCTGAAGATAGAAAAGAGC<br>TACGGCGACATAGACATGCTCACAGCTCTCAGCCAAATATAC<br>GCACTCACGCAAATCCATGTGGGGGCGACCAAAAGCCTGCGC<br>CTCCCAATCACCACCGGCTACGCCGACAAGATTTGCAAGGCG<br>ATCGAGTTCATCCCCCAAGGGCGCGTGGACAACCGCCTTTTC<br>TTTCTG** | |
| SPL0389<br>N to C terminus:<br>*Italicized/ Underlined: 2XSV40NLS*<br>Underlined: GSGS linker<br>*(SEQ ID NO: 154)*<br>*Italicized: V5 Tag*<br>**2XSV40NLS**<br>**Underlined: GSGS linker** | *ATGCCCAAGAAAAAGCGAAAGGTAGAGGACCCCAAAAAGAAA<br>CGCAAAGTG*GGCTCCGAAGC*GGGAAGCCCATCCCAAACCCGC<br>TGTTGGGCTTGGATTCCACG*GGCAGCGGAAGCTCT**ATGAATA<br>ATCTGACCTTCGAGGCCTTCGAGGGTATCGGACAATTGAACG<br>AGTTAAACTTCTATAAGTACCGCCTCATTGGTAAGGGCCAAA<br>TCGACAATGTCCACCAGGCCATCTGGTCAGTCAAGTACAAAC<br>TTCAAGCGAATAATTTCTTCAAGCCGGTTTTCGTCAAGGGCG<br>AAATTCTGTACTCACTTGACGAGCTGAAAGTCATCCCGGAAT<br>TCGAGAATGTCGAGGTTATTCTTGACGGGAACATTATCCTGA<br>GCATTAGCGAGAACACCGACATTTACAAGGATGTGATCGTGT<br>TTTATATCAATAACGCGTTGAAGAACATCAAGGACATCACCA<br>ACTACCGTAAGTATATCACTAAGAACACGGATGAAATCATTT<br>GCAAGAGTATTTTAACGACGAATCTCAAGTATCAATATATGA<br>AGTCAGAGAAAGGGTTCAAGTTACAGCGCAAGTTTAAGATCT<br>CCCCGGTGGTATTCCGTAATGGGAAGGTCATCTTGTACCTTA<br>ATTGCAGTAGCGACTTCAGCACAGACAAATCCATCTACGAAA<br>TGTTAAATGATGGACTCGGTGTTGTGGGCCTGCAAGTGAAGA<br>ATAAGTGGACTAATGCGAATGGCAATATCTTTATTGAAAAGG<br>TGCTCGACAATACCATCTCCGATCCCGGCACGAGTGGAAAGC<br>TGGGGCAGTCCCTGATCGACTACTACATCAATGGGAATCAAA<br>AGTACCGTGTAGAGAAATTTACCGACGAGGACAAGAATGCAA<br>AGGTTATCCAGGCCAAAATCAAGAATAAAACATACAACTACA<br>TCCCGCAAGCTCTCACCCCCGTAATTACGCGCGAGTATCTGA** | 104 |

TABLE 13-continued

Amino Acid Sequence of Exemplary Ago-SSB 2XSV40NLS Fusion Polypeptides

| Fusion Polypeptide | Nucleic Acid Sequence | SEQ ID NO |
|---|---|---|
| | **GTCATACCGATAAGAAGTTTAGCAAGCAAATCGAGAATGTGA**<br>**TTAAGATGGATATGAACTACCGCTACCAGACGTTGAAGTCTT**<br>**TCGTTGAGGACATTGGCGTGATCAAGGAGTTAAACAATCTGC**<br>**ACTTTAAGAACCAATATTACACCAATTTTGACTTTATGGGGT**<br>**TCGAGAGCGGGGTGCTGGAAGAACCTGTCCTGATGGGTGCGA**<br>**ACGGAAAGATCAAGGACAAGAAGCAGATTTTCATCAATGGGT**<br>**TCTTTAAGAATCCCAAGGAGAACGTAAAATTCGGAGTACTCT**<br>**ACCCAGAAGGCTGTATGGAGAATGCTCAGAGCATTGCTCGTT**<br>**CCATCCTCGACTTCGCTACGGCCGGTAAATACAATAAGCAAG**<br>**AGAACAAGTATATTTCGAAGAATTTAATGAACATCGGATTCA**<br>**AACCTTCTGAGTGTATCTTTGAGTCGTATAAGTTGGGAGACA**<br>**TCACCGAGTATAAGGCGACGGCCCGTAAGCTCAAGGAGCATG**<br>**AGAAAGTTGGGTTCGTTATCGCAGTGATCCCTGACATGAATG**<br>**AGCTGGAAGTCGAGAACCCTTATAACCCCTTCAAGAAGGTCT**<br>**GGGCGAAACTCAATATCCCATCCCAGATGATCACATTGAAGA**<br>**CCACCGAAAAGTTCAAGAATATCGTCGACAAGTCAGGCTTGT**<br>**ACTACTTACACAATATCGCCCTTAATATTCTCGGCAAAATCG**<br>**GCGGAATCCCGTGGATTATTAAAGACATGCCTGGCAACATCG**<br>**ACTGTTTCATCGGTTTAGACGTCGGCACGCGCGAGAAGGGCA**<br>**TCCACTTCCCGGCATGTTCTGTGTTGTTCGACAAGTACGGAA**<br>**AGTTAATCAATTATTACAAGCCGACTATTCCGCAGAGCGGAG**<br>**AGAAGATTGCTGAGACAATTTTACAGGAGATCTTCGACAACG**<br>**TGTTAATCAGCTACAAAGAGGAAAACGGGGAGTACCCCAAGA**<br>**ATATCGTTATCCATCGTGATGGCTTCAGCCGTGAGAACATCG**<br>**ATTGGTACAAAGAATACTTCGATAAGAAGGGTATCAAGTTCA**<br>**ACATTATTGAGGTTAAGAAGAACATTCCCGTAAAGATCGCGA**<br>**AGGTGGTTGGATCCAATATCTGCAACCCGATCAAGGGCTCTT**<br>**ATGTGCTTAAGAATGATAAGGCATTCATCGTAACCACCGATA**<br>**TCAAAGACGGTGTGGCTTCTCCAAATCCACTTAAAATCGAGA**<br>**AAACCTATGGTGACGTTGAGATGAAGAGTATTCTGGAGCAGA**<br>**TCTACAGTCTGAGCCAAATTCATGTTGGCTCAACCAAGTCCC**<br>**TGCGTCTTCCTATCACAACGGGATATGCCGATAAGATCTGTA**<br>**AGGCAATTGAATACATTCCGCAAGGAGTCGTAGACAATCGTT**<br>**TGTTCTTTCTT** | |
| SPL0390<br>N to C terminus:<br>*Italicized/ Underlined: 2XSV40NLS*<br>Underlined: GSGS linker (SEQ ID NO: 154)<br>*Italicized: V5 Tag*<br>**Bold: Homologue 4 (HG4)** | *ATGCCCAAGAAAAAGCGAAAGGTAGAGGACCCCAAAAAGAAA*<br>*CGCAAAGT*GGGCTCCGGAAGC*GGGAAGCCCATCCCAAACCCG*<br>*CTGTTGGGCTTGGATTCCAC*GGGCAGCGGAAGCTCT**ATGAAG**<br>**GAGTTTAACGTCATCACAGAGTTCAAGAACGGTATTAATTCG**<br>**AAGAGCATCGAGATCTATATTTACAAGATGATGGTTCGTGAC**<br>**TTTGAGAAGCGTCACAATGAAAATTATGACGTGGTAAAAGAG**<br>**CTTATTAACCTGAACAATAATAGTACGATTGTCTTTTATGAG**<br>**CAATATATCGCCTCATTCAAGGAAATCGAGAAGTGGGGTAAC**<br>**GAGCAATACATTAATGTTGAGAAACGCGCAATTAACCTGGAA**<br>**AGCAACGAGAAGAAGATTCTTGAACGCCTTCTGTTAAAGGAG**<br>**ATCAAGAACAACATCGATAACAATAAGTACAAGGTAGTGAAG**<br>**GATTCGATCTACATCAACAAGCCTGTGTATAACGAAAAGGGT**<br>**ATCAAAATCGACCGCTACTTCAACTTAGACATCAACGTAGAA**<br>**TCAAACGGAGACATCATTATTGGCTTCGATATTAGCCATAAT**<br>**TTCGAGTATATTAACACGTTAGAGTACGAAATCAAGAACAAC**<br>**AATATCAAGATTGGAGACCGCGTAAAGGATTACTTTTACAAC**<br>**CTTACTTATGAATATGTTGGCATCGCGCCGTTCACTATTTCC**<br>**GAAGAGAATGAATATATGGGATGTAGCATCGTGGACTACTAT**<br>**GAAAATAAGAACCAGAGCTACATCGTGAACAAGTTGCCAAAG**<br>**GATATGAAGGCAATCTTAGTTAAGAACAATAAGAACAGCATT**<br>**TTCCCGTACATCCCTTCACGTCTTAAGAAGGTTTGTCGTTTC**<br>**GAGAATCTGCCCCAAAACGTACTCCGTGATTTTAACACGCGC**<br>**GTCAAGCAGAAAACTAATGAGAAGATGCAATTTATGGTGGAC**<br>**GAGGTTATCAACATTGTAAAGAATAGCGAGCATATCGACGTA**<br>**AAGAAGAAGAACATGATGTGTGACAATATCGGGTACAAGATT**<br>**GAGGACCTGCAACAACCTGACCTTTTGTTTGGAAACGCCCGC**<br>**GCGCAGCGTTACCCACTGTATGGATTGAAGAACTTTGGCGTG**<br>**TACGAAAACAAGCGCATTGAAATCAAGTACTTTATCGACCCG**<br>**ATTCTCGCCAAGAGCAAGATGAATCTGGAAAAGATCTCCAAG**<br>**TTCTGTGATGAGCTGGAGCAGTTTAGCTCCAAGTTAGGAGTA**<br>**GGATTAAATCGCGTAAAACTGAACAATATTGTTAACTTCAAG**<br>**GAGATTCGTATGGACAATGAGGACATCTTCTCCTACGAGATT**<br>**CGCAAAATTGTGAGCAACTATAATGAGACAACGATCGTGATT**<br>**CTGTCGGAAGAGAACCTTAATAAGTATTACAACATCATTAAG**<br>**AAAACCTTCAGCGGTGGCAACGAGGTTCCGACGCAATGCATT**<br>**GGTTTCAACACACTTTCCTACACGGAGAAGAACAAGGACTCA**<br>**ATTTTCTTAAATATTTTACTTGGTGTTTACGCCAAGTCAGGA**<br>**ATCCAACCGTGGATCCTCAATGAGAAATTGAATTCCGACTGT**<br>**TTCATTGGTTTAGATGTCTCCCGTGAGAATAAGGTAAACAAG**<br>**GCCGGCGTCATTCAAGTTGTCGGAAAAGATGGCCGCGTACTC** | 105 |

TABLE 13-continued

| Fusion Polypeptide | Nucleic Acid Sequence | SEQ ID NO |
|---|---|---|
| | AAGACCAAGGTCATCAGTTCGAGCCAAAGCGGGGAGAAGATC<br>AAGCTGGAAACGTTACGCGAGATCGTGTTCGAGGCGATTAAC<br>TCGTATGAGAATACCTACCGCTGTAAACCAAAACACATTACA<br>TTCCACCGTGACGGTATTAATCGTGAGGAGCTGGAGAATCTT<br>AAGAATACGATGACCAATCTTGGTGTTGAGTTTGACTACATC<br>GAGATCACCAAGGGCATTAACCGCCGCATTGCCACCATCAGT<br>GAGGGCGAGGAGTGGAAGACTATCATGGGCCGCTGTTATTAT<br>AAGGACAATTCTGCCTACGTCTGCACTACTAAGCCTTATGAG<br>GGAATCGGAATGGCAAAGCCCATTCGCATCCGCCGCGTGTTT<br>GGCACGCTTGATATCGAGAAAATTGTTGAAGACGCGTATAAA<br>CTTACTTTTATGCATGTAGGCGCGATCAATAAAATTCGTCTT<br>CCAATTACAACCTATTACGCAGATCTCAGCTCCACTTACGGA<br>AATCGCGACTTAATTCCGACGAATATTGATACCAATTGCCTC<br>TACTTCATT | |
| SPL0398<br>N to C terminus:<br>***Italicized/Bold/ Underlined: 2XSV40NLS***<br>Underlined: GSGS linker (SEQ ID NO: 154)<br>*Italicized: V5 Tag*<br>***Italicized and Bold: Sso SSB***<br>*Italicized and underlined: GGGGS linker* (SEQ ID NO: 70)<br>***Italicized/Bold/Underlined: c-Myc NLS***<br>**Bold: Ago69** | ATGGGCAAACCAATACCTAACCCACTCCTCGGACTGGACTCT<br>ACCGGGAGTGGCTCCATGCCAAAGAAGAAAAGGAAAGTGGAA<br>GATCCTAAGAAGAAGCGAAAGGTCGGTAGCGGTTCAAGTATG<br>GAAGAGAAGGTCGGAAATCTCAAACCCAACATGGAGAGCGTC<br>AACGTGACTGTCAGAGTGCTTGAGGCTAGTGAGGCTCGTCAA<br>ATACAAACTAAGAACGGCGTGCGAACGATCTCTGAAGCAATC<br>GTGGGAGACGAGACAGGTCGGGTCAAGCTTACACTTTGGGGA<br>AAGCACGCAGGGTCCATTAAAGAGGGGCAAGTGGTCAAGATC<br>GAAAATGCATGGACCACGGCCTTTAAGGGTCAAGTCCAACTC<br>AACGCTGGCTCTAAAACAAAGATCGCGGAAGCCAGCGAGGAT<br>GGGTTTCCCGAGTCTTCCCAAATACCTGAGAATACCCCCACA<br>GCCCCTCAACAAATGCGCGGCGGCGGAAGGGGTTTTAGGGGT<br>GGCGGGAGACGGTACGGGAGAAGGGGCGGAAGGAGACAGGAG<br>AATGAGGAAGGAGAGGAAGAGGGTGGAGGAGGAAGTCCAGCA<br>GCCAAACGGGTCAAGCTTGACGGCGGCGGCGGGTCTATGGTG<br>GGCGGGTACAAGGTGTCAAACCTCACTGTCGAGGCCTTTGAG<br>GGGATTGGCTCAGTAAATCCCATGCTCTTCTATCAGTATAAG<br>GTGACAGGCAAAGGCAAATATGACAACGTCTACAAAATCATT<br>AAGTCCGCCAGATATAAAATGCACTCCAAGAACCGGTTTAAA<br>CCTGTATTCATTAAAGATGACAAGCTGTACACCCTCGAGAAG<br>CTCCCGGATATAGAGGACCTGGATTTCGCAAACATTAACTTC<br>GTGAAAAGCGAGGTTCTCAGCATAGAGGATAATATGTCAATT<br>TATGGCGAGGTGGTGGAATACTATATCAATCTCAAGCTGAAA<br>AAAGTGAAGGTGTTGGGAAAATACCCCAAGTACAGGATCAAT<br>TACAGCAAAGAGATTCTCAGTAATACGCTGCTGACACGAGAG<br>CTCAAAGACGAGTTTAAGAAATCAAATAAGGGTTTTAACCTG<br>AAACGGAAGTTTAGAATTTCCCCCGTGGTGAATAAGATGGGC<br>AAAGTGATACTCTATTTGTCCTGCAGTGCTGATTTCAGCACC<br>AACAAGAACATTTACGAAATGTTGAAAGAGGGCTTGGAGGTT<br>GAGGGGCTGGCCGTTAAGAGCGAGTGGAGCAATATCAGTGGC<br>AACCTGGTGATCGAGAGCGTACTGGAAACCAAGATATCCGAG<br>CCCACTAGCCTGGGCCAATCCCTGATAGACTACTATAAGAAT<br>AACAACCAGGGCTATAGGGTGAAGGATTTCACCGATGAGGAT<br>CTGAATGCCAACATTGTCAACGTGAGAGGAAATAAGAAGATC<br>TATATGTATATTCCGCACGCGTTGAAGCCGATAATCACCCGG<br>GAGTACCTGGCCAAGAACGATCCAGAGTTTTCTAAGGAGATC<br>GAGCAGCTTATCAAGATGAATATGAACTACCGATATGAAACC<br>CTCAAGTCATTTGTGAATGACATCGGGGTCATTGAGGAGCTG<br>AACAACCTGAGCTTCAAAAACAAATACTACGAAGATGTGAAA<br>CTGCTGGGTTACTCCAGCGGCAAAATAGACGAACCCGTCCTG<br>ATGGGGGCAAAAGGGATCATAAAGAACAAAATGCAGATTTTT<br>TCCAATGGATTCTACAAACTCCCCGAAGGCAAGGTACGATTT<br>GGCGTTCTGTACCCAAAAGAATTTGATGGCGTGTCAAGGAAA<br>GCTATCCGCGCCATTTATGACTTCAGTAAGGAGGGCAAATAC<br>CACGGCGAAAGCAACAAGTATATCGCGGAACACCTGATAAAC<br>GTGGAGTTCAATCCAAAGGAGTGCATATTTGAGGGATACGAA<br>CTGGGCGATATCACCGAATACAAGAAGGCGGCTCTGAAACTT<br>AATAACTACAACAATGTCGACTTCGTAATCGCAATAGTCCCG<br>AACATGTCCGACGAAGAGATAGAGAACAGCTACAATCCGTTC<br>AAGAAAATATGGGCCGAACTGAATCTGCCCAGCCAGATGATT<br>AGCGTCAAGACGGCCGAAATCTTTGCCAATAGCAGGGATAAC<br>ACGGCGCTTTACTATCTGCATAACATCGTCCTCGGTATCCTG<br>GGTAAGATAGGAGGGATTCCCTGGGTGGTTAAAGACATGAAG<br>GGCGACGTGGATTGCTTCGTTGGACTCGATGTCGGCACCAGG<br>GAGAAGGGCATACATTACCCCGCCTGCAGCGTTGTGTTTGAC<br>AAGTACGGCAAGCTTATTAACTATTACAAGCCTAACATCCCG<br>CAGAACGGAGAGAAGATTAACACAGAAATACTTCAGGAAATT<br>TTCGACAAGGTGCTCATAAGCTATGAGGAGGAGAATGGAGCC<br>TACCCGAAGAATATCGTGATCCACAGGGACGGCTTTAGCCGA<br>GAGGACCTTGACTGGTATGAGAACTACTTCGGTAAGAAAAAC | 106 |

TABLE 13-continued

Amino Acid Sequence of Exemplary Ago-SSB 2XSV40NLS Fusion Polypeptides

| Fusion Polypeptide | Nucleic Acid Sequence | SEQ ID NO |
|---|---|---|
| | ATAAAGTTTAACATCATCGAAGTCAAAAAGTCAACTCCGTTG AAAATCGCCAGTATAAACGAGGGAAATATCACGAATCCTGAA AAGGGTTCCTACATCCTGCGCGGCAACAAAGCCTACATGGTG ACCACAGATATTAAGGAAAACCTGGGAAGCCCAAAGCCCCTG AAGATAGAAAAGAGCTACGGCGACATAGACATGCTCACAGCT CTCAGCCAAATATACGCACTCACGCAAATCCATGTGGGGGCG ACCAAAAGCCTGCGCCTCCCAATCACCACCGGCTACGCCGAC AAGATTTGCAAGGCGATCGAGTTCATCCCCCAAGGGCGCGTG GACAACCGCCTTTTCTTTCTG | |

VIII. REGULATORY DOMAIN POLYPEPTIDE (RDP)

In some cases, a regulatory domain polypeptide is part of a nucleic acid editing system. An RDP can regulate a level of an activity, such as editing, of a nucleic acid editing system. Non-limiting examples of RDPs include recombinases, epigenetic modulators, germ cell repair domains, or DNA repair proteins. In some cases, an RDP is mined by screening for co-localized DNA repair proteins in a region comprising an RNase-H like domain containing polypeptide. In some embodiments, the Agos described herein are an RNase-H like domain containing polypeptide.

Exemplary recombinases that can be used as RDPs include Cre, Hin, Tre, or FLP recombinases. In some cases, recombinases involved in homologous recombination are utilized. For example, in some embodiments, the RDP is RadA, Rad51, RecA, Dmc1, or UvsX.

In some embodiments, an epigenetic modulator is a protein that can modify an epigenome directly through DNA methylation, post-translational modification of chromatin, or by altering a structure of chromatin.

Exemplary germ cell repair domains include ATM, ATR, or DNA-PK to name a few. A germ cell repair domain can repair DNA damage though a variety of mechanisms such as nucleotide excision repair (NER), base excision repair (BER), mismatch repair (MMR), DNA double strand break repair (DSBR), and post replication repair (PRR).

An RDP can be a tunable component of a nucleic acid editing system. For example, an RDP can be swapped in the editing system to achieve a particular outcome. In some cases, an RDP can be selected based on a cell to be targeted, a level of editing efficiency that is sought, or in order to reduce off-target effects of a nucleic acid editing system. A dialing up or a tuning can enhance a parameter (efficiency, safety, speed, or accuracy) of a genomic break repair by about 5%, 10%, 15%, 20%, 30%, 40%, 50%, 60%, 70%, 80%, 90%, 95%, or up to about 100% as compared to a comparable gene editing system. A dialing down or a tuning can be performed by interchanging a domain such as an RDP to achieve a different effect during a genomic modification. For example, a different effect may be a skewing towards a particular genomic break repair, a recombination, an epigenetic modulation, or a high fidelity repair. In some cases, an RDP may be used to enhance a transgene insertion into a genomic break. In some cases, interchanging a module of a gene editing system can allow for HDR of a double strand break as opposed to NHEJ or MMEJ. Use of a gene editing system disclosed herein can allow for preferential HDR of a double strand break over that of comparable or alternate gene editing systems. In some cases, an HDR repair can preferentially occur in a population of cells from about 5%, 10%, 15%, 20%, 30%, 40%, 50%, 60%, 70%, 80%, 90%, 95%, or up to about 100% over that which occurs in a comparable gene editing system without said RDP.

In some cases, the disclosed editing system utilizing an RDP can reduce a thermodynamic energetic requirement by about 1%, 2%, 3%, 4%, 5%, 6%, 7%, 8%, 9%, 10%, 15%, 20%, 25%, 40%, 50%, or up to about 60% as compared to a system that does not employ the disclosed RDP. In some cases, the disclosed editing system utilizing an RDP can reduce an immune response to the RDP by about 1%, 2%, 3%, 4%, 5%, 6%, 7%, 8%, 9%, 10%, 15%, 20%, 25%, 40%, 50%, or up to about 60% as compared to a system that does not employ the disclosed RDP. In some cases, an RDP can be harvested from bacteria that are endogenously present in the human body to prevent eliciting an immune response.

IX. GUIDING POLYNUCLEIC ACID AND TARGET POLYNUCLEIC ACID

The guiding polynucleic acid can direct a gene editing system comprising the Ago polypeptide to a genomic location. The guiding polynucleic acid can direct a nucleic acid-cleaving activity of the described Ago polypeptides. The guiding polynucleic acid can also be capable of interacting with the Ago polypeptide. In some cases, the guiding polynucleic acid can be a DNA. In other cases, the guiding polynucleic acid can be RNA. The guiding polynucleic acid can be a combination of DNA and RNA. The guiding polynucleic acid can be single stranded, double stranded, or a combination thereof. The guiding polynucleic acid can be at least or at least about 5, 10, 15, 16, 17, 18, 19, 20, 21, 22, 23, 24, 25, 30 or more nucleotides long. The guiding polynucleotide can be at most or at most about 5, 10, 15, 16, 17, 18, 19, 20, 21, 22, 23, 24, 25, 30 or more nucleotides long. The guiding polynucleotide can be about 5, 10, 15, 16, 17, 18, 19, 20, 21, 22, 23, 24, 25, 30 or more nucleotides long. In some cases, the guiding polynucleic acid may be truncated. Truncated guiding polynucleic acids can be utilized to determine a minimum binding length.

The system described herein can comprise an exogenous guiding polynucleic acid. The system can comprise a non-naturally occurring guiding polynucleic acid. The system can also comprise a naturally occurring guiding polynucleic acid. In some cases, the system comprises one guiding polynucleic acid. In other cases, the system comprises two guiding polynucleic acids, each targeting an opposite strand of a double-stranded target polynucleic acid. In still other cases, the system comprises two or more guiding polynucleic acids targeting different sequences in the target polynucleic acid.

The guiding polynucleic acid can be a guide RNA (i.e., "gRNA") that can associate with and direct an Ago polypeptide, or the Ago containing complex, to a specific target sequence within a target nucleic acid by virtue of hybridization to a target site of the target nucleic acid. Similarly the guiding polynucleic acid can be a guide RNA (i.e., "gDNA") that can associate with and direct the Ago polypeptide or complex to a specific target sequence within a target nucleic acid by virtue of hybridization to a target site of the target nucleic acid. In some cases, the guiding polynucleic acid can hybridize with a mismatch between the guiding polynucleic acid and a target nucleic acid. The guiding polynucleic acid can comprise at least about 1, 2, 3, 4, 5, 6, 7, 8, 9, 10, 11, 12, 13, 14, 15, 16, 18, 19, 20, 25, 30, 35, or up to 40 mismatches when hybridized to a target nucleic acid. In some cases, the guiding polynucleic acid can tolerate mismatches in a recruiting domain, for example at g6, g7, and g8. In some cases, the guiding polynucleic acid can contain mismatches in a stabilization domain. A stabilization domain can be adjacent to a 3' end of the guiding molecule. For example, positions g6-g16, such as g6, g7, g8, g9, g10, g11, g12, g13, g14, g15, and g16 or any combination thereof, can be mismatched in 16 nucleotide long guide molecules. Mismatches in a recruiting domain can have mismatches preferably in positions g6, g7, and/or g8.

A method disclosed herein also can comprise introducing into a cell or embryo at least one guide RNA or polynucleic acid, e.g., DNA encoding at least one guide RNA. A guide RNA can interact with a RNA-guided endonuclease to direct the endonuclease to a specific target site, at which site the 5' end of the guide RNA base pairs with a specific protospacer sequence in a chromosomal sequence. Similarly, the method can comprise introducing into a cell or embryo at least one guide DNA or polynucleic acid, e.g., RNA that is complementary to the guide DNA. A guide DNA can interact with a DNA-guided endonuclease to direct the endonuclease to a specific target site. A guide DNA, or a DNA sequence that translates to a guide RNA, can be on the same polynucleic acid molecule that encodes for a chimeric polypeptide as described herein, or on a separate polynucleic acid molecule.

A guide RNA can comprise two RNAs, e.g., CRISPR RNA (crRNA) and transactivating crRNA (tracrRNA). A guide RNA can sometimes comprise a single-guide RNA (sgRNA) formed by fusion of a portion (e.g., a functional portion) of crRNA and tracrRNA. A guide RNA can also be a dual RNA comprising a crRNA and a tracrRNA. A guide RNA can comprise a crRNA and lack a tracrRNA. Furthermore, a crRNA can hybridize with a target DNA or protospacer sequence. A guide DNA can be double-stranded or single-stranded DNA.

As discussed above, a guide RNA can be an expression product. For example, a DNA that encodes a guide RNA can be a vector comprising a sequence coding for the guide RNA. A guide RNA can be transferred into a cell or organism by transfecting the cell or organism with an isolated guide RNA or plasmid DNA comprising a sequence coding for the guide RNA and a promoter. Similarly, a guide DNA can be transferred into a cell or organism by transfecting the cell or organism with an isolated guide DNA or RNA that is complementary to the guide DNA. A guide RNA or DNA can also be transferred into a cell or organism in other way, such as using virus-mediated gene delivery.

The guiding polynucleic acid can be isolated. For example, a guide RNA or DNA can be transfected in the form of an isolated RNA or DNA into a cell or organism. A guide RNA or DNA can be prepared by in vitro transcription using any in vitro transcription system. A guide RNA can be transferred to a cell in the form of isolated RNA rather than in the form of plasmid comprising encoding sequence for a guide RNA.

A guide RNA or DNA can comprise a DNA-targeting segment and a protein binding segment. A DNA-targeting segment (or DNA-targeting sequence, or spacer sequence) comprises a nucleotide sequence that can be complementary to a specific sequence within a target DNA (e.g., a protospacer). A protein-binding segment (or protein-binding sequence) can interact with a site-directed modifying polypeptide, e.g. an RNA-guided endonuclease such as a Cas protein. By "segment" it is meant a segment/section/region of a molecule, e.g., a contiguous stretch of nucleotides in RNA. A segment can also mean a region/section of a complex such that a segment can comprise regions of more than one molecule. For example, in some cases a protein-binding segment of a DNA-targeting RNA is one RNA molecule and the protein-binding segment therefore comprises a region of that RNA molecule. In other cases, the protein-binding segment of a DNA-targeting RNA comprises two separate molecules that are hybridized along a region of complementarity.

The guiding polynucleic acid can comprise two separate polynucleic acid molecules or a single polynucleic acid molecule. An exemplary single molecule guiding polynucleic acid (e.g., guide RNA) comprises both a DNA-targeting segment and a protein-binding segment.

In some cases, the Ago polypeptide or portion thereof can form a complex with the guiding polynucleic acid. In some cases, the system described herein comprises a complex comprising the Ago polypeptide and the guiding polynucleic acid. The guiding polynucleic acid can provide target specificity to a complex by comprising a nucleotide sequence that can be complementary to a sequence of a target nucleic acid. In some cases, a target nucleic acid can comprise at least a portion of a gene. In some cases, a target nucleic acid can be within an exon of a gene. In other cases, a target nucleic acid can be within an intron of a gene.

The guiding polynucleic acid can complex with the Ago polypeptide to provide the Ago polypeptide site-specific activity. In other words, the Ago polypeptide can be guided to a target site within a single stranded target nucleic acid sequence e.g. a single stranded region of a double stranded nucleic acid, a chromosomal sequence or an extrachromosomal sequence, e.g. an episomal sequence, a minicircle sequence, a mitochondrial sequence, a chloroplast sequence, an ssRNA, an ssDNA, etc. by virtue of its association with the guiding polynucleic acid.

In some cases, the guiding polynucleic acid can comprise one or more modifications (e.g., a base modification, a backbone modification), to provide the nucleic acid with a new or enhanced feature (e.g., improved stability). The guiding polynucleic acid can comprise a nucleic acid affinity tag. A nucleoside can be a base-sugar combination. A base portion of the nucleoside can be a heterocyclic base. The two most common classes of such heterocyclic bases can be purines and pyrimidines. Nucleotides can be nucleosides that further include a phosphate group covalently linked to a sugar portion of a nucleoside. For those nucleosides that include a pentofuranosyl sugar, a phosphate group can be linked to the 2', the 3', or the 5' hydroxyl moiety of a sugar. In forming guiding polynucleic acids, a phosphate group can covalently link adjacent nucleosides to one another to form a linear polymeric compound. In addition, linear compounds may have internal nucleotide base complementarity and may therefore fold in a manner as to produce a fully or partially double-stranded compound. Within guiding polynucleic acids, a phosphate groups can commonly be referred to as forming a internucleoside backbone of the guiding polynucleic acid. The linkage or backbone of the guiding polynucleic acid can be a 3' to 5' phosphodiester linkage. In some cases, the guiding polynucleic acid can comprise nucleoside analogs, which can be oxy- or deoxy-analogues of a naturally-occurring DNA and RNA nucleosides deoxycytidine, deoxyuridine, deoxyadenosine, deoxyguanosine and thymidine. The guiding polynucleic acid can also include a universal base, such as deoxyinosine, or 5-nitroindole. The guiding polynucleic acid can comprise a modified backbone and/or modified internucleoside linkages. Modified backbones can include those that can retain a phosphorus atom in the backbone and those that do not have a phosphorus atom in the backbone. Suitable modified guiding polynucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage. Suitable guiding polynucleic acids having inverted polarity can comprise a single 3' to 3' linkage at the 3'-most internucleotide linkage (i.e. a single inverted nucleoside residue in which the nucleobase is missing or has a hydroxyl group in place thereof).

In some cases, the guiding polynucleic acid (e.g., a guide RNA or DNA) can also comprise a tail region at a 5' or 3' end that can be essentially single-stranded. For example, a tail region is sometimes not complementarity to any chromosomal sequence in a cell of interest and can sometimes not be complementary to the rest of a guide polynucleic acid. Further, the length of a tail region can vary. A tail region can be more than or more than about 4 nucleotides in length. For example, the length of a tail region can range from or from about 5 to from or from about 60 nucleotides in length.

In some cases, the guiding polynucleic acid can bind to a region of a genome adjacent to a protospacer adjacent motif (PAM). A guide nucleic acid can comprise a nucleotide sequence (e.g., a spacer), for example, at or near a 5' end or 3' end, that can hybridize to a sequence in a target nucleic acid (e.g., a protospacer). A spacer of a guide nucleic acid can interact with a target nucleic acid in a sequence-specific manner via hybridization (i.e., base pairing). A spacer sequence can hybridize to a target nucleic acid that is located 5' or 3' of a protospacer adjacent motif (PAM). The length of a spacer sequence can be at least or at least about 5, 10, 15, 16, 17, 18, 19, 20, 21, 22, 23, 24, 25, 30 or more nucleotides. The length of a spacer sequence can be at most or at most about 5, 10, 15, 16, 17, 18, 19, 20, 21, 22, 23, 24, 25, 30 or more nucleotides. In some cases, the guiding polynucleic acid can bind to a region from about 1 to about 20 base pairs adjacent to a PAM. In other cases, the guiding polynucleic acid can bind from about 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, or up to 85 base pairs away from a PAM. Generally, the guiding polynucleic acid binding region can be designed to complement or substantially complement the target nucleic acid sequence or sequences. In some cases, a binding region of the guiding polynucleic acid can incorporate wobble or degenerate bases to bind multiple sequences. In some cases, the binding region can be altered to increase stability. For example, non-natural nucleotides can be incorporated to increase RNA resistance to degradation. In some cases, the binding region can be altered or designed to avoid or reduce secondary structure formation in the binding region. In some cases, the binding region can be designed to optimize G-C content. In some cases, G-C content is preferably between about 40% and about 60% (e.g., 40%, 45%, 50%, 55%, and 60%). In some cases, the binding region can contain modified nucleotides such as, without limitation, methylated or phosphorylated nucleotides.

In some cases, the guiding polynucleic acid can also comprise a double strand duplex region that can form a secondary structure. For example, a secondary structure formed by the guiding polynucleic acid can comprise a stem (or hairpin) and a loop. A length of a loop and a stem can vary. For example, a loop can range from about 3 to about 10 nucleotides in length, and a stem can range from about 6 to about 20 base pairs in length. A stem can comprise one or more bulges of 1 to about 10 nucleotides. The overall length of a second region can range from about 16 to about 60 nucleotides in length. For example, a loop can be or can be about 4 nucleotides in length and a stem can be or can be about 12 base pairs. In some cases, a 5' stem-loop region can be between about 15 and about 50 nucleotides in length (e.g., about 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides in length). In some cases, a 5' stem-loop region is between about 30-45 nucleotides in length (e.g., about 31, 32, 33, 34, 35, 36, 37, 38, 39, 40, 41, 42, 43, 44, or 45 nucleotides in length). In some cases, a 5' stem-loop region is at least about 31 nucleotides in length (e.g., at least about 31, 32, 33, 34, 35, 36, 37, 38, 39, 40, 41, 42, 43, 44, or 45 nucleotides in length). In some cases, a 5' stem-loop structure contains one or more loops or bulges, each loop or bulge of about 1, 2, 3, 4, 5, 6, 7, 8, 9, or 10 nucleotides. In some cases, a 5' stem-loop structure contains a stem of between about 10 and 30 complementary base pairs (e.g., 11, 12, 13, 14, 15, 16, 17, 18, 19, 20, 21, 22, 23, 24, 25, 26, 27, 28, 29, or 30 complementary base pairs). In some cases, a 5' stem-loop structure can contain protein-binding, or small molecule-binding structures. In some cases, a 5' stem-loop function (e.g., interacting or assembling with the guiding polynucleic acid-guided nuclease) can be conditionally activated by drugs, growth factors, small molecule ligands, or a protein that binds to the protein-binding structure of the 5' stem-loop. In some cases, a 5' stem-loop structure can contain non-natural nucleotides. For example, non-natural nucleotides can be incorporated to enhance protein-RNA interaction, protein DNA interaction, or to increase the thermal stability or resistance to degradation of the guiding polynucleic acid.

In some cases, the guiding polynucleic acid may have an intervening sequence between the 5' and 3' stem-loop structures that can be between about 10 and about 50 nucleotides in length (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or about 50 nucleotides in length). In some cases, the intervening sequence is designed to be linear, unstructured, substantially linear, or substantially unstructured. In some embodiments, the intervening sequence can contain non-natural nucleotides. For example, non-natural nucleotides can be incorporated to enhance protein-RNA interaction or to increase the activity of the gRNA: nuclease complex. Similarly, non-natural nucleotides can be incorporated to enhance protein-DNA interaction or to increase the activity of the gDNA: nuclease complex. As another example, natural nucleotides can be incorporated to enhance the thermal stability or resistance to degradation of the gRNA or gDNA. In some cases, a 3' stem-loop structure can contain about 3, 4, 5, 6, 7, or 8 nucleotide loop and an about 4, 5, 6, 7, 8, 9, 10, 11, 12, 13, 14, 15, 16, 17, 18, 19, 20, 21, 22, 23, 24, or 25 nucleotide or longer stem. In some cases, the 3' stem-loop can contain a protein-binding, small molecule-binding, hormone-binding, or metabolite-binding structure that can conditionally stabilize the secondary and/or tertiary structure of the gRNA or gDNA. In some embodiments, the 3' stem-loop can contain non-natural nucleotides. For example, non-natural nucleotides can be incorporated to enhance protein-guiding nucleic acid interaction or to increase the activity of the guiding polynucleic acid: nuclease complex. As another example, natural nucleotides can be incorporated to enhance the thermal stability or resistance to degradation of the gRNA or gDNA.

In some cases, the guiding polynucleic acid can include a termination structure at its 3' end. In some cases, the guiding polynucleic acid can include an additional 3' hairpin structure, e.g., before the termination structure, that can interact with proteins, small-molecules, hormones, or the like, for stabilization or additional functionality, such as conditional stabilization or conditional regulation of a guiding polynucleic acid: nuclease assembly or activity. In some cases, the guiding polynucleic acid can be optimized to enhance stability, assembly, and/or expression. In some case, the guiding polynucleic acid can be optimized to enhance the activity of the guiding polynucleic acid: nuclease complex as compared to control or comparable guiding polynucleic acid: nuclease structures (gRNA, CRISPR RNP, unmodified gRNA, or unmodified guiding polynucleic acids). In some cases, the guiding polynucleic acid can be optimized for expression by substituting, deleting, or adding one or more nucleotides. In some cases, a nucleotide sequence that provides inefficient transcription from an encoding template nucleic acid can be deleted or substituted. For example, in some cases, the guiding polynucleic acid can be transcribed from a nucleic acid operably linked to an RNA polymerase III promoter. In some cases, the guiding polynucleic acid can be modified for increased stability. Stability can be enhanced by optimizing the stability of the guiding polynucleic acid: nuclease interaction, optimizing assembly of the guiding polynucleic acid: nuclease complex, removing or altering RNA or DNA destabilizing sequence elements, or adding RNA or DNA stabilizing sequence elements. In some embodiments, the guiding polynucleic acid can contain a 5' stem-loop structure proximal to, or adjacent to, the binding region that interacts with the guiding polynucleic acid-guided nuclease. Optimization of the 5' stem-loop structure can provide enhanced stability or assembly of the guiding polynucleic acid: nuclease complex. In some cases, the 5' stem-loop structure is optimized by increasing the length of the stem portion of the stem-loop structure. For example, a 5' stem-loop optimization can be combined with mutations for increased transcription to provide an optimized guiding polynucleic acid. For example, an A-U flip and an elongated stem loop can be combined to provide an optimized guiding polynucleic acid.

A double stranded-guiding polynucleic acid duplex region can comprise a protein-binding segment that can form a complex with an RNA or DNA-binding protein, such as an Argonaute protein, polypeptide, or functional portion thereof.

In some cases, the guiding polynucleic acid can comprise a modification. A modification can be a chemical modification. A modification can be selected from 5'adenylate, 5' guanosine-triphosphate cap, 5'N7-Methylguanosine-triphosphate cap, 5'triphosphate cap, 3'phosphate, 3'thiophosphate, 5'phosphate, 5'thiophosphate, Cis-Syn thymidine dimer, trimers, C12 spacer, C3 spacer, C6 spacer, dSpacer, PC spacer, rSpacer, Spacer 18, Spacer 9,3'-3' modifications, 5'-5' modifications, abasic, acridine, azobenzene, biotin, biotin BB, biotin TEG, cholesteryl TEG, desthiobiotin TEG, DNP TEG, DNP-X, DOTA, dT-Biotin, dual biotin, PC biotin, psoralen C2, psoralen C6, TINA, 3'DABCYL, black hole quencher 1, black hole quencer 2, DABCYL SE, dT-DABCYL, IRDye QC-1, QSY-21, QSY-35, QSY-7, QSY-9, carboxyl linker, thiol linkers, 2'deoxyribonucleoside analog purine, 2'deoxyribonucleoside analog pyrimidine, ribonucleoside analog, 2'-O-methyl ribonucleoside analog, sugar modified analogs, wobble/universal bases, fluorescent dye label, 2'fluoro RNA, 2'O-methyl RNA, methylphosphonate, phosphodiester DNA, phosphodiester RNA, phosphothioate DNA, phosphorothioate RNA, UNA, pseudouridine-5'-triphosphate, 5-methylcytidine-5'-triphosphate, 2-O-methyl 3phosphorothioate or any combinations thereof. A modification can be a pseudouridine modification. In some cases, a modification cannot affect viability.

In some cases, a modification is a 2-O-methyl 3 phosphorothioate addition. A 2-O-methyl 3 phosphorothioate addition can be performed from 1 base to 150 bases. A 2-O-methyl 3 phosphorothioate addition can be performed from 1 base to 4 bases. A 2-O-methyl 3 phosphorothioate addition can be performed on 2 bases. A 2-O-methyl 3 phosphorothioate addition can be performed on 4 bases. A modification can also be a truncation. A truncation can be a 5 base truncation. Guiding polynucleic acids can be modified by methods known in the art. In some cases, the modifications can include, but are not limited to, the addition of one or more of the following sequence elements: a 5' cap (e.g., a 7-methylguanylate cap); a 3' polyadenylated tail; a riboswitch sequence; a stability control sequence; a hairpin; a subcellular localization sequence; a detection sequence or label; or a binding site for one or more proteins. Modifications can also include the introduction of non-natural nucleotides including, but not limited to, one or more of the following: fluorescent nucleotides and methylated nucleotides. In some embodiments, the guiding polynucleic acid can contain from 5' to 3': (i) a binding region of between about 10 and about 50 nucleotides; (ii) a 5' hairpin region containing fewer than four consecutive uracil nucleotides, or a length of at least 31 nucleotides (e.g., from about 31 to about 41 nucleotides); (iii) a 3' hairpin region; and (iv) a transcription termination sequence, wherein the small guide RNA is configured to form a complex with the guiding polynucleic acid-guided nuclease, the complex having increased stability or activity relative to an unmodified complex.

A guide RNA or guide DNA can target a nucleic acid sequence of or of about 20 nucleotides. A target nucleic acid can be less than or less than about 20 nucleotides. A target nucleic acid can be at least or at least about 5, 10, 15, 16, 17, 18, 19, 20, 21, 22, 23, 24, 25, 30 or more nucleotides. A target nucleic acid can be at most or at most about 5, 10, 15, 16, 17, 18, 19, 20, 21, 22, 23, 24, 25, 30 or more nucleotides. A target nucleic acid sequence can be or can be about 20 bases immediately 5' of the first nucleotide of the PAM. A guide RNA or guide DNA can target a nucleic acid sequence comprising a gene or portion thereof.

A guide RNA or guide DNA can target a genomic sequence comprising a gene. A gene that can be targeted can be involved in a disease. A disease can be a cancer, a cardiovascular condition, a reproductive condition, a neurological disease, an immunological disease, an organ condition, degeneration, an ocular condition, diabetes, a vascular condition, or a gastrointestinal condition. A gene that can be targeted can be involved in a signaling biochemical pathway.

In some cases, the target polynucleic acid comprises a sequence of the gene to be targeted. The target polynucleic acid can be a sequence of the gene that is associated with a disease or disorder.

A gene that can be disrupted can be a member of a family of genes. For example, a gene that can be disrupted can improve therapeutic potential of cancer immunotherapy. A gene that can be disrupted can ameliorate one or more symptoms or complications associated with human genetic diseases. In some cases, a method of treating a disease or disorder comprises disruption of the gene.

A gene that can be disrupted can be involved in attenuating TCR signaling, functional avidity, or immunity to cancer. In some cases, a gene to be disrupted is upregulated when a TCR is stimulated. A gene can be involved in inhibiting cellular expansion, functional avidity, or cytokine polyfunctionality. A gene can be involved in negatively regulating cellular cytokine production. For example, a gene can be involved in inhibiting production of effector cytokines, IFN-gamma and/or TNF for example. A gene can also be involved in inhibiting expression of supportive cytokines such as IL-2 after TCR stimulation.

A disease can be a neoplasia. Genes associated with neoplasia can be: PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc. A disease can be age-related macular degeneration. Genes associated with macular degeneration can be: Abcr; Ccl2; Cc2; cp (ceruloplasmin); Timp3; cathepsinD; Vldlr; Ccr2. A disease can be schizophrenia. Genes associated with schizophrenia can be: Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b. A disorder can be associated with a gene such as: 5-HTT (Slc6a4); COMT; DRD (Drdla); SLC6A3; DAOA; DTNBP1; Dao (Daol). A disease can be a trinucleotide repeat disorder. A trinucleotide repeat disorder can be associated with genes such as: HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP—global instability); VLDLR (Alzheimer's); Atxn7; Atxn10. A disease can be fragile X syndrome. Genes associated with fragile X syndrome can be: FMR2; FXR1; FXR2; mGLUR5. A disease can be secretase related with associated genes selected from: APH-1 (alpha and beta); Presenilin (Psen1); nicastrin, (Ncstn); PEN-2; Nos1; Parpl; Nat1; Nat2. A disease can be a prion related disorder with relevant genes being selected from: Prp. A disease can be ALS with relevant genes being: SOD1; ALS2; STEX; FUS; TARDBP; VEGF (VEGF-a; VEGF-b; VEGF-c). A disease can be drug addiction with relevant genes being; Prkce (alcohol); Drd2; Drd4; ABAT (alcohol); GRIA2; Grm5; Grin1; Htrlb; Grin2a; Drd3; Pdyn; Grial (alcohol). A disease can be autism with relevant genes being selected from: Mecp2; BZRAP1; MDGA2; Sema5A; Neurexin 1; Fragile X (FMR2 (AFF2); FXR1; FXR2; Mglur5). A disease can be Alzheimer's disease with relevant genes being selected from: E1; CHIP; UCH; UBB; Tau; LRP; PICALM; Clusterin; PSi; SORL1; CR1; Vldlr; Ubal; Uba3; CHIP28 (Aqpl, Aquaporin 1); Uchl1; Uchl3; APP. A disorder can be inflammation with relevant genes being selected from: IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1. A disease can be Parkinson's disease with relevant genes being selected from: x-Synuclein; DJ-1; LRRK2; Parkin; PINK1. A disease can be a blood and coagulation disorders: Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyte deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). Cell dysregulation and oncology diseases and disorders: B-cell non-Hodgkin lymphoma (BCL7A, BCL7); Leukemia (TAL1 TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AFIQ, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). A disease can be an inflammation and/or an immune related diseases and disorders: AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs) (JAK3, JAKL, DCLRE1C, ARTEMIS, SCIDA, RAG1, RAG2, ADA, PTPRC, CD45, LCA, TL7R, CD3D, T3D, TL2RG, SCIDX1, SCIDX, IMD4). A disease can be metabolic, liver, kidney and protein diseases and disorders: Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). A disease can be muscular/skeletal diseases and disorders: Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARDI). A disease can be neurological and neuronal diseases and disorders: ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drdla), SLC6A3, DAOA, DTNBP1, Dao (Daol)); Secretase Related Disorders (APH-1 (alpha and beta), Presenilin (Psen1), nicastrin, (Ncstn), PEN-2, Nos1, Parpl, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP—global instability), VLDLR (Alzheimer's), Atxn7, Atxn10). A disease can be an Ocular disease and/or disorder: Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQPO, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAEl, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, MiS1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPAl, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2).

In some cases a disease that can be treated with the disclosed editing system can be associated with a cellular condition. For example, genes associated with cellular performance may be disrupted with the disclosed editing system: PI3K/AKT Signaling: PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; TLK; TP53; RAF1; IKBKG; RELB; DYRKIA; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOXOl; SGK; HSP90AA1; RPS6KB1. For example, ERK/MAPK Signaling: PRKCE; ITGAM; ITGA5; HSPB1; IRAK1; PRKAA2; EIF2AK2; RAC1; RAPlA; TLN1; EIF4E; ELK1; GRK6; MAPK1; RAC2; PLK1; AKT2; PIK3CA; CDK8; CREB1; PRKC1; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRKIA; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK. Glucocorticoid Receptor Signaling: RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; TSC22D3; MAPK10; NRIP1; KRAS; MAPK13; RELA; STAT5A; MAPK9; NOS2A;

PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K2; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMP1; STAT1; IL6; HSP90AA1. Axonal Guidance Signaling: PRKCE; ITGAM; ROCK1; ITGA5; CXCR4; ADAM12; IGF1; RAC1; RAPlA; E1F4E; PRKCZ; NRP1; NTRK2; ARHGEF7; SMO; ROCK2; MAPK1; PGF; RAC2; PTPN11; GNAS; AKT2; PIK3CA; ERBB2; PRKC1; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA. Ephrin Receptor Signaling: PRKCE; ITGAM; ROCK1; ITGA5; CXCR4; IRAK1; PRKAA2; EIF2AK2; RAC1; RAPlA; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRKIA; ITGB1; MAP2K2; PAK4, AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK. Actin Cytoskeleton Signaling: ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3CB; MYH9; DIAPHI; PIK3C3; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRKIA; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK. Huntington's Disease Signaling: PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKC1; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3. Apoptosis Signaling: PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRKIA; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARPl. B Cell Receptor Signaling: RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1. Leukocyte Extravasation Signaling: ACTN4; CD44; PRKCE; ITGAM; ROCK1; CXCR4; CYBA; RAC1; RAPlA; PRKCZ; ROCK2; RAC2; PTPN11; MMP14; PIK3CA; PRKC1; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9. Integrin Signaling: ACTN4; ITGAM; ROCK1; ITGA5; RAC1; PTEN; RAPlA; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3. Acute Phase Response Signaling: IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6. PTEN Signaling: ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; TLK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXOl; CASP3; RPS6KB1. p53 Signaling: PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3. Aryl Hydrocarbon Receptor Signaling: HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1. Xenobiotic Metabolism Signaling: PRKCE; EP300; PRKCZ; RXRA; MAPK1; NQO1; NCOR2; PIK3CA; ARNT; PRKC1; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1. SAPK/JNK Signaling: PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRKIA; MAP2K2; PIK3R1; MAP2K1; PAK3; CDC42; JUN; TTK; CSNK1A1; CRKL; BRAF; SGK. PPAr/RXR Signaling: PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14;

STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; HSP90AA1; ADIPOQ. NF-KB Signaling: IRAK1; EIF2AK2; EP300; INS; MYD88; PRKCZ: TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4: PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1. Neuregulin Signaling: ERBB4; PRKCE; ITGAM; ITGA5: PTEN; PRKCZ; ELK1; MAPK1; PTPN11; AKT2; EGFR; ERBB2; PRKC1; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; HSP90AA1; RPS6KB1. Wnt & Beta catenin Signaling: CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2: ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2. Insulin Receptor Signaling: PTEN; INS; EIF4E; PTPN1; PRKCZ; MAPK1; TSC1; PTPN11; AKT2; CBL; PIK3CA; PRKC1; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOXOl; SGK; RPS6KB1. IL-6 Signaling: HSPB1; TRAF6; MAPKAPK2; ELK1; MAPK1; PTPN11; IKBKB; FOS; NFKB2: MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6. Hepatic Cholestasis: PRKCE; IRAK1; INS; MYD88; PRKCZ; TRAF6; PPARA; RXRA; IKBKB; PRKC1; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6. IGF-1 Signaling: IGF1; PRKCZ; ELK1; MAPK1; PTPN11; NEDD4; AKT2; PIK3CA; PRKC1; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXOl; SRF; CTGF; RPS6KB1. NRF2-mediated Oxidative Stress Response: PRKCE; EP300; SOD2; PRKCZ; MAPK1; SQSTMl; NQO1; PIK3CA; PRKC1; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; HSP90AA1. Hepatic Fibrosis/Hepatic Stellate Cell Activation: EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9. PPAR Signaling: EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1. Fc Epsilon RI Signaling: PRKCE; RAC1; PRKCZ; LYN; MAPK1; RAC2; PTPN11; AKT2; PIK3CA; SYK; PRKC1; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA. G-Protein Coupled Receptor Signaling: PRKCE; RAPlA; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA, Inositol Phosphate Metabolism: PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRKlA; MAP2K2; PIP5K1A; PIK3R1; MAP2K1; PAK3; ATM; TTK; CSNK1A1; BRAF; SGK. PDGF Signaling: EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2. VEGF Signaling: ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXOl; PRKCA. Natural Killer Cell Signaling: PRKCE; RAC1; PRKCZ; MAPK1; RAC2; PTPN11; KIR2DL3; AKT2; PIK3CA; SYK; PRKC1; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA. Cell Cycle: G1/S Checkpoint Regulation: HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6. T Cell Receptor Signaling: RAC1; ELK1; MAPK1; IKBKB; CBL; PIK3CA; FOS; NFKB2; PIK3CB; PIK3C3; MAPK8; MAPK3; KRAS; RELA, PIK3C2A; BTK; LCK; RAF1; IKBKG; RELB, FYN; MAP2K2; PIK3R1; CHUK; MAP2K1; NFKB1; ITK; BCL10; JUN; VAV3. Death Receptor Signaling: CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3. FGF Signaling: RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF. GM-CSF Signaling: LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1. Amyotrophic Lateral Sclerosis Signaling: BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3. JAK/Stat Signaling: PTPN1;

MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1. Nicotinate and Nicotinamide Metabolism: PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRKIA; MAP2K2; MAP2K1; PAK3; NT5E; TTK; CSNK1A1; BRAF; SGK. Chemokine Signaling: CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA. IL-2 Signaling: ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3. Synaptic Long Term Depression: PRKCE; IGF1; PRKCZ; PRDX6; LYN; MAPK1; GNAS; PRKC1; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA. Estrogen Receptor Signaling: TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2. Protein Ubiquitination Pathway: TRAF6; SMURF1; BIRC4; BRCA1; UCHL1; NEDD4; CBL; UBE2I; BTRC; HSPA5; USP7; USP10; FBXW7; USP9X; STUB1; USP22; B2M; BIRC2; PARK2; USP8; USP1; VHL; HSP90AA1; BIRC3. IL-10 Signaling: TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6. VDR/RXR Activation: PRKCE; EP300; PRKCZ; RXRA; GADD45A; HES1; NCOR2; SP1; PRKC1; CDKN1B; PRKD1; PRKCD; RUNX2; KLF4; YY1; NCOA3; CDKN1A; NCOA2; SPP1; LRP5; CEBPB; FOXOl; PRKCA. TGF-beta Signaling: EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5. Toll-like Receptor Signaling: IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN. p38 MAPK Signaling: HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1. Neurotrophin/TRK Signaling: NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4. FXR/RXR Activation: INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXOl. Synaptic Long Term Potentiation: PRKCE; RAPlA; EP300; PRKCZ; MAPK1; CREB1; PRKC1; GNAQ; CAMK2A; PRKD1; MAPK3; KRAS; PRKCD; PPP1CC; RAF1; CREBBP; MAP2K2; MAP2K1; ATF4; PRKCA. Calcium Signaling: RAPlA; EP300; HDAC4; MAPK1; HDAC5; CREB1; CAMK2A; MYH9; MAPK3; HDAC2; HDAC7A; HDAC11; HDAC9; HDAC3; CREBBP; CALR; CAMKK2; ATF4; HDAC6. EGF Signaling: ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1. Hypoxia Signaling in the Cardiovascular System: EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1. LPS/IL-1 Mediated Inhibition of RXR Function LXR/RXR Activation: IRAK1; MYD88; TRAF6; PPARA; RXRA; ABCA1, MAPK8; ALDH1A1; GSTP1; MAPK9; ABCB1; TRAF2; TLR4; TNF; MAP3K7; NR1H2; SREBF1; JUN; IL1R1 FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9. Amyloid Processing: PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP. IL-4 Signaling: AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1. Cell Cycle: G2/M DNA Damage Checkpoint Regulation: EP300; PCAF; BRCA1; GADD45A; PLK1; BTRC; CHEK1; ATR; CHEK2; YWHAZ; TP53; CDKN1A; PRKDC; ATM; SFN; CDKN2A. Nitric Oxide Signaling in the Cardiovascular System: KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1. Purine Metabolism: NME2; SMARCA4; MYH9; RRM2; ADAR; EIF2AK4; PKM2; ENTPD1; RAD51; RRM12B; TJP2; RAD51C; NT5E; POLD1; NME1. cAMP-mediated Signaling: RAPlA; MAPK1; GNAS; CREB1; CAMK2A; MAPK3; SRC; RAF1; MAP2K2; STAT3; MAP2K1; BRAF; ATF4. Mitochondrial Dysfunction Notch Signaling: SOD2; MAPK8; CASP8; MAPK10; MAPK9; CASP9; PARK7; PSEN1; PARK2; APP; CASP3 HES1; JAG1; NUMB; NOTCH4; ADAM17; NOTCH2; PSEN1; NOTCH3; NOTCHI; DLL4. Endoplasmic Reticulum Stress Pathway: HSPA5; MAPK8; XBP1; TRAF2; ATF6; CASP9; ATF4; EIF2AK3; CASP3. Pyrimidine Metabolism: NME2; AICDA; RRM2; EIF2AK4; ENTPD1; RRM2B; NT5E; POLD1; NME1. Parkinson's Signaling: UCHL1; MAPK8; MAPK13; MAPK14; CASP9; PARK7; PARK2; CASP3. Cardiac & Beta Adrenergic Signaling: GNAS; GNAQ; PPP2R1A; GNB2L1; PPP2CA; PPP1CC; PPP2R5C. Glycolysis/Gluconeogenesis: HK2; GCK; GPI; ALDH1A1; PKM2; LDHA; HK1. Interferon Signaling: IRF1; SOCS1; JAK1; JAK2; IFITM1; STAT1; IFIT3. Sonic Hedgehog Signaling: ARRB2; SMO; GLI2; DYRKIA; GLI1; GSK3B; DYRKIB. Glycerophospholipid Metabolism: PLD1; GRN; GPAM; YWHAZ; SPHK1; SPHK2. Phospholipid Degradation: PRDX6; PLD1; GRN; YWHAZ; SPHK1; SPHK2. Tryptophan Metabolism: SIAH2; PRMT5; NEDD4; ALDH1A1; CYP1B1; SIAH1. Lysine Degradation: SUV39H1; EHMT2; NSD1; SETD7; PPP2R5C. Nucleotide Excision Repair Pathway: ERCC5; ERCC4; XPA; XPC; ERCC1. Starch and Sucrose Metabolism: UCHL1; HK2; GCK; GPI; HK1. Aminosugars Metabolism: NQO1; HK2; GCK; HK1. Arachidonic Acid Metabolism: PRDX6; GRN; YWHAZ; CYP1BL. Circadian Rhythm Signaling: CSNK1E; CREB1; ATF4; NR1D1. Coagulation System: BDKRB1; F2R; SERPINE1; F3. Dopamine Receptor Signaling: PPP2R1A; PPP2CA; PPP1CC; PPP2R5C. Glutathione Metabolism: IDH2; GSTP1; ANPEP; IDH1. Glycerolipid Metabolism: ALDH1A1; GPAM; SPHK1; SPHK2. Linoleic Acid Metabolism: PRDX6; GRN; YWHAZ; CYP1B1. Methionine Metabolism: DNMT1; DNMT3B; AHCY; DNMT3A. Pyruvate Metabolism: GLO1; ALDH1A1; PKM2; LDHA. Arginine and Proline Metabolism: ALDH1A1; NOS3; NOS2A. Eicosanoid Signaling:

PRDX6; GRN; YWHAZ. Fructose and Mannose Metabolism: HK2; GCK; HK1. Galactose Metabolism: HK2; GCK; HK1. Stilbene, Coumarine and Lignin Biosynthesis: PRDX6; PRDX1; TYR. Antigen Presentation Pathway: CALR; B2M. Biosynthesis of Steroids: NQO1; DHCR7. Butanoate Metabolism: ALDH1A1; NLGN1. Citrate Cycle: IDH2; IDH1. Fatty Acid Metabolism: ALDH1A1; CYP1BL. Glycerophospholipid Metabolism: PRDX6; CHKA. Histidine Metabolism: PRMT5; ALDH1A1. Inositol Metabolism: ERO1L; APEX1. Metabolism of Xenobiotics by Cytochrome p450: GSTP1; CYP1BL. Methane Metabolism: PRDX6; PRDX1. Phenylalanine Metabolism: PRDX6; PRDX1. Propanoate Metabolism: ALDH1A1; LDHA. Selenoamino Acid Metabolism: PRMT5; AHCY. Sphingolipid Metabolism: SPHK1; SPHK2. Aminophosphonate Metabolism: PRMT5. Androgen and Estrogen Metabolism: PRMT5. Ascorbate and Aldarate Metabolism: ALDH1A1. Bile Acid Biosynthesis: ALDH1A1. Cysteine Metabolism: LDHA. Fatty Acid Biosynthesis: FASN. Glutamate Receptor Signaling: GNB2L1. NRF2-mediated Oxidative Stress Response: PRDX1. Pentose Phosphate Pathway: GPI. Pentose and Glucuronate Interconversions: UCHL1. Retinol Metabolism: ALDH1A1. Riboflavin Metabolism: TYR. Tyrosine Metabolism: PRMT5, TYR. Ubiquinone Biosynthesis: PRMT5. Valine, Leucine and Isoleucine Degradation: ALDH1A1. Glycine, Serine and Threonine Metabolism: CHKA. Lysine Degradation: ALDH1A1. Pain/Taste: TRPM5; TRPA1. Pain: TRPM7; TRPC5; TRPC6; TRPC1; Cnr1; cnr2; Grk2; Trpal; Pomc; Cgrp; Crf; Pka; Era; Nr2b; TRPM5; Prkaca; Prkacb; Prkarla; Prkar2a. Mitochondrial Function: AIF; CytC; SMAC (Diablo); Aifm-1; Aifm-2. Developmental Neurology: BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab1; unc-86 (Pou4fl or Brn3a); Numb; Reln.

In some cases, an editing system can be used to improve an immune cell performance. Examples of genes involved in cancer or tumor suppression may include ATM (ataxia telangiectasia mutated), ATR (ataxia telangiectasia and Rad3 related), EGFR (epidermal growth factor receptor), ERBB2 (v-erb-b2 erythroblastic leukemia viral oncogene homolog 2), ERBB3 (v-erb-b2 erythroblastic leukemia viral oncogene homolog 3), ERBB4 (v-erb-b2 erythroblastic leukemia viral oncogene homolog 4), Notch 1, Notch2, Notch 3, or Notch 4, for example. A gene and protein associated with a secretase disorder may also be disrupted or introduced and can include PSENEN (presenilin enhancer 2 homolog (*C. elegans*)), CTSB (cathepsin B), PSEN1 (presenilin 1), APP (amyloid beta (A4) precursor protein). APH1B (anterior pharynx defective 1 homolog B (*C. elegans*)), PSEN2 (presenilin 2 (Alzheimer disease 4)), or BACE1 (beta-site APP-cleaving enzyme 1). It is contemplated that genetic homologues (e.g., any mammalian version of the gene) of the genes within this applications are covered. For example, genes that can be targeted can further include CD27, CD40, CD122, OX40, GITR, CD137, CD28, ICOS, A2AR, B7-H3, B7-H4, BTLA, CTLA-4, IDO, KIR, LAG3, PD-1, TIM-3, VISTA, HPRT, CCR5, AAVS SITE (e.g. AAVS1, AAVS2, ETC.), PPP1R12C, TRAC, TCRB, or CISH. Therefore, it is contemplated that any one of the aforementioned gene that exhibits or exhibits about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity (at the nucleic acid or protein level) can be disrupted. It is also contemplated that any of the aforementioned genes that exhibits or exhibits about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or 100% identity (at the nucleic acid or protein level) can be disrupted. Some genetic homologues are known in the art, however, in some cases, homologues are unknown. However, homologous genes between mammals can be found by comparing nucleic acid (DNA or RNA) sequences or protein sequences using publicly available databases such as NCBI BLAST. Also disclosed herein can be non-human gene equivalents of any one of the aforementioned genes. A non-human equivalent of any of the aforementioned genes can be disrupted with the gene editing system disclosed herein.

In some cases, a genome that can be disrupted or modified can be from an organism or subject that can be a eukaryote (including mammals including human) or a non-human eukaryote or a non-human animal or a non-human mammal. In some cases, an organism or subject can be a non-human animal, and may be an arthropod, for example, an insect, or may be a nematode. In some cases, an organism or subject can be a plant. In some cases, an organism or subject can be a mammal or a non-human mammal. A non-human mammal may be for example a rodent (preferably a mouse or a rat), an ungulate, or a primate. In some methods of the invention the organism or subject is algae, including microalgae, or is a fungus. In some cases, a subject can be a human. A human subject can be an adult or a pediatric subject. A pediatric subject can be under the age of 18. An adult subject can be about 18 or over 18 years of age. In some cases, a subject can be a fetus or an embryo. In some cases, a genome that can be disrupted can be from a cell, tissue, or organ of an organism or subject. In some cases, a genome that can be disrupted may be from a stem cell. In some cases, a genome that can be disrupted may be from a germ cell.

A guide RNA can be introduced into a cell or embryo as an RNA molecule. For example, a RNA molecule can be transcribed in vitro and/or can be chemically synthesized. A guide RNA can then be introduced into a cell or embryo as an RNA molecule. A guide RNA can also be introduced into a cell or embryo in the form of a non-RNA nucleic acid molecule, e.g., DNA molecule. For example, a DNA encoding a guide RNA can be operably linked to promoter control sequence for expression of the guide RNA in a cell or embryo of interest. A RNA coding sequence can be operably linked to a promoter sequence that is recognized by RNA polymerase III (Pol III).

A nucleic acid encoding a guide RNA or guide DNA can be linear. A nucleic acid encoding a guide RNA or guide DNA can also be circular. A nucleic acid encoding the guiding polynucleic acid can also be part of a vector. Some examples of vectors can include plasmid vectors, phagemids, cosmids, artificial/mini-chromosomes, transposons, and viral vectors. For example, a DNA encoding a RNA-guided endonuclease is present in a plasmid vector. Other non-limiting examples of suitable plasmid vectors include pUC, pBR322, pET, pBluescript, and variants thereof. Further, a vector can comprise additional expression control sequences (e.g., enhancer sequences, Kozak sequences, polyadenylation sequences, transcriptional termination sequences, etc.), selectable marker sequences (e.g., antibiotic resistance genes), origins of replication, and the like.

Suitable methods for introduction of the guiding polynucleic acid, protein, or guiding polynucleic acid: nuclease complex are known in the art and include, for example, electroporation; calcium phosphate precipitation; or PEI, PEG, DEAE, nanoparticle, or liposome mediated transformation. Other suitable transfection methods include direct micro-injection. In some cases, the guiding polynucleic acid and nuclease are introduced separately and the guiding polynucleic acid: nuclease complexes are formed in a cell. In other cases, the guiding polynucleic acid: nuclease complex can be formed and then introduced into a cell. In some cases, multiple, differentially labeled, guiding polynucleic acid: nuclease complexes, each directed to a different genomic targets are formed and then introduced into a cell. When both a nucleic acid guided nuclease and a guide polynucleic acid are introduced into a cell, each can be part of a separate molecule (e.g., one vector containing fusion protein coding sequence and a second vector containing guide polynucleic acid coding sequence) or both can be part of a same molecule (e.g., one vector containing coding (and regulatory) sequence for both a fusion protein and the guiding polynucleic acid). In some cases, a nuclease can be pre-complexed with the guiding polynucleic acid. A complex can be a ribonucleoprotein (RNP) complex.

In some cases, a GUIDE-Seq analysis can be performed to determine the specificity of engineered guiding polynucleic acids. The general mechanism and protocol of GUIDE-Seq profiling of off-target cleavage by CRISPR system nucleases is discussed in Tsai, S. et al., "GUIDE-Seq enables genome-wide profiling of off-target cleavage by CRISPR system nucleases," Nature, 33: 187-197 (2015).

The guiding polynucleic acid can be introduced at any functional concentration. For example, the guiding polynucleic acid can be introduced to a cell at 10 micrograms. In other cases, the guiding polynucleic acid can be introduced from 0.5 micrograms to 100 micrograms. A gRNA can be introduced from 0.5, 5, 10, 15, 20, 25, 30, 35, 40, 45, 50, 55, 60, 65, 70, 75, 80, 85, 90, 95, or 100 micrograms.

A sequence of a guiding polynucleic acid need not be 100% complementary to that of its target polynucleic acid to be specifically hybridizable or hybridizable. Moreover, a guiding polynucleic acid may hybridize over one or more segments such that intervening or adjacent segments are not involved in the hybridization event (e.g., a loop structure or hairpin structure). For example, a polynucleotide can comprise 60% or more, 65% or more, 70% or more, 75% or more, 80% or more, 85% or more, 90% or more, 95% or more, 98% or more, 99% or more, 99.5%, or 100% sequence complementarity to a target region within the target nucleic acid sequence to which it will hybridize. For example, an antisense nucleic acid in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. Percent complementarity between particular stretches of nucleic acid sequences within nucleic acids can be determined using any convenient method. Exemplary methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

The guiding polynucleic acid can target a gene or portion thereof. In some cases, a cell that is modified can comprise one or more suppressed, disrupted, or knocked out genes and one or more transgenes, such as a receptor.

The target nucleic acid molecule can be DNA or RNA. The target nucleic acid can be double stranded or single stranded. The target nucleic acid can be double stranded DNA (dsDNA), single stranded DNA (ssDNA), double stranded RNA (dsRNA), or single stranded RNA (ssRNA). The Ago may be capable of cleaving 1, 2, 3, or 4 of dsDNA, ssDNA, dsRNA, or ssRNA.

Methods and compositions described herein can be used to target a gene from a mammal. A gene that can be targeted can be from any organ or tissue. A gene that can be targeted can be from skin, eyes, heart, liver, lung, kidney, reproductive tract, brain, to name a few. A gene that can be targeted can also be from a number of conditions and diseases In some cases, a disruption can result in a reduction of copy number of genomic transcript of a disrupted gene or portion thereof. For example, a target gene that can be disrupted can have reduced transcript quantities compared to the same target gene in an undisrupted cell. A disruption can result in disruption results in less than 145 copies/μL, 140 copies/μL, 135 copies/μL, 130 copies/μL, 125 copies/μL, 120 copies/μL, 115 copies/μL, 110 copies/μL, 105 copies/μL, 100 copies/μL, 95 copies/μL, 190 copies/μL, 185 copies/μL, 80 copies/μL, 75 copies/μL, 70 copies/μL, 65 copies/μL, 60 copies/μL, 55 copies/μL, 50 copies/μL, 45 copies/μL, 40 copies/μL, 35 copies/μL, 30 copies/μL, 25 copies/μL, 20 copies/μL, 15 copies/μL, 10 copies/μL, 5 copies/μL, 1 copies/μL, or 0.05 copies/μL. In some cases, a disruption can result in less than 100 copies/μL.

One or more genes in a cell can be knocked out or disrupted using any method. For example, knocking out one or more genes can comprise deleting one or more genes from a genome of a cell. Knocking out can also comprise removing all or a part of a gene sequence from a cell. It is also contemplated that knocking out can comprise replacing all or a part of a gene in a genome of a cell with one or more nucleotides. Knocking out one or more genes can also comprise inserting a sequence in one or more genes thereby disrupting expression of the one or more genes. For example, inserting a sequence can generate a stop codon in the middle of one or more genes. Inserting a sequence can also shift the open reading frame of one or more genes.

An animal or cell may comprise 1, 2, 3, 4, 5, 6, 7, 8, 9, 10, 11, 12, 13, 14, 15 or more disrupted genomic sequences encoding a protein associated with a disease and zero, 1, 2, 3, 4, 5, 6, 7, 8, 9, 10, 11, 12, 13, 14, 15 or more genomically integrated sequences encoding a protein associated with a disease.

X. DELIVERY AND CELLS

The Ago system, the fusion polypeptide, the polynucleotides encoding the same, and/or any transgene polynucleotides and compositions comprising the polypeptides and/or polynucleotides described herein can be delivered to one or more target cells by any suitable means. Accordingly, described herein are one or more cells that comprise the disclosed system and one or more cells that comprise the disclosed fusion polypeptide. The one or more cells can be ex vivo, in vivo, or in vitro cells. In some cases, the one or more cells are ex vivo cells. Similarly, the one or more cells can comprise an exogenous nucleic acid molecule that encodes the disclosed fusion polypeptide or the Ago. For example, described herein is a cell that comprises an exogenous nucleic acid molecule that encodes a disclosed Ago polypeptide. The Ago polypeptide can comprise an amino acid sequence having 70% or more sequence identity with one of SEQ ID NOs: 1-10 or 134-136.

The cells can include but are not limited to eukaryotic and prokaryotic cells and/or cell lines. The cells can be engineered cells. The one or more cells can comprise or can be a mammalian cell. The cells can be from an animal selected from a group consisting of mice, rats, rabbits, sheep, cattle, horses, dogs, cats, and humans. The one or more cells can comprise or can be a human primary cell.

The primary cell can be taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

The primary cell can be acquired from a variety of sources such as an organ, vasculature, buffy coat, whole blood, apheresis, plasma, bone marrow, tumor, cell-bank, cryopreservation bank, or a blood sample. The cell can be a stem cell. The cell can be a germ cell. The cells that can be edited with a genomic editing system comprising the Ago can be epithelial cells, fibroblast cells, neural cells, keratinocytes, hematopoietic cells, melanocytes, chondrocytes, lymphocytes (B, NK, and T), macrophages, monocytes, mononuclear cells, cardiac muscle cells, other muscle cells, granulosa cells, cumulus cells, epidermal cells, endothelial cells, pancreatic islet cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopamiergic cells, squamous epithelial cells, osteocytes, osteoblasts, osteoclasts, dopaminergic cells, embryonic stem cells, fibroblasts and fetal fibroblasts. Further, the one or more cells can be pancreatic islet cells and/or cell clusters or the like, including, but not limited to pancreatic a cells, pancreatic p cells, pancreatic 6 cells, pancreatic F cells (e.g., PP cells), or pancreatic F cells. In one instance, the one or more cells can be pancreatic a cells. In another instance, the one or more cells can be pancreatic R cells.

A human primary cell can be an immune cell. An immune cell can be a T cell, B cell, NK cell, and/or TTL. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, W138, V79, B14AF28-G3, BHK, HaK, NSO, SP2/0-Ag14, HeLa, HEK293 (e.g., HEK293-F, HEK293-H, HEK293-T), and perC6 cells as well as insect cells such as *Spodoptera frugiperda* (Sf), or fungal cells such as *Saccharomyces, Pichia* and *Schizosaccharomyces*. In some cases, a cell line can be a CHO-K1, MDCK or HEK293 cell line. In some cases, suitable primary cells include peripheral blood mononuclear cells (PBMC), peripheral blood lymphocytes (PBL), and other blood cell subsets such as, but not limited to, T cell, a natural killer cell, a monocyte, a natural killer T cell, a monocyte-precursor cell, a hematopoietic stem cell or a non-pluripotent stem cell. In some cases, the cell can be any immune cells including any T-cell such as tumor infiltrating cells (TILs), such as CD3+ T-cells, CD4+ T-cells, CD8+ T-cells, or any other type of T-cell. The T cell can also include memory T cells, memory stem T cells, or effector T cells. The T cells can also be selected from a bulk population, for example, selecting T cells from whole blood. The T cells can also be expanded from a bulk population. The T cells can also be skewed towards particular populations and phenotypes. For example, the T cells can be skewed to phenotypically comprise, CD45RO(−), CCR7(+), CD45RA(+), CD62L(+), CD27(+), CD28(+) and/or IL-7Rα(+). Suitable cells can be selected that comprise one of more markers selected from a list comprising: CD45RO(−), CCR7(+), CD45RA(+), CD62L(+), CD27(+), CD28(+) and/or IL-7Rα(+). Suitable cells also include stem cells such as, by way of example, embryonic stem cells, induced pluripotent stem cells, hematopoietic stem cells, neuronal stem cells and mesenchymal stem cells. Suitable cells can comprise any number of primary cells, such as human cells, non-human cells, and/or mouse cells. Suitable cells can be progenitor cells. Suitable cells can be derived from the subject to be treated (e.g., subject). Suitable cells can be derived from a human donor. Suitable cells can be stem memory $T_{SCM}$ cells comprised of CD45RO (−), CCR7(+), CD45RA (+), CD62L+ (L-selectin), CD27+, CD28+ and IL-7Rα+, stem memory cells can also express CD95, IL-2Rβ, CXCR3, and LFA-1, and show numerous functional attributes distinctive of stem memory cells. Suitable cells can be central memory $T_{CM}$ cells comprising L-selectin and CCR7, central memory cells can secrete, for example, IL-2, but not IFNγ or IL-4. Suitable cells can also be effector memory $T_{EM}$ cells comprising L-selectin or CCR7 and produce, for example, effector cytokines such as IFNγ and IL-4.

In some cases, modified cells can be a stem memory $T_{SCM}$ cell comprised of CD45RO (−), CCR7(+), CD45RA (+), CD62L+ (L-selectin), CD27+, CD28+ and IL-7Rα+, stem memory cells can also express CD95, IL-2Rβ, CXCR3, and LFA-1, and show numerous functional attributes distinctive of stem memory cells. Engineered cells, such as Argonaute polypeptide modified cells can also be central memory $T_{CM}$ cells comprising L-selectin and CCR7, where the central memory cells can secrete, for example, IL-2, but not IFNγ or IL-4. Engineered cells can also be effector memory $T_{EM}$ cells comprising L-selectin or CCR7 and produce, for example, effector cytokines such as IFNγ and IL-4. In some cases a population of cells can be introduced to a subject. For example, a population of cells can be a combination of T cells and NK cells. In other cases, a population can be a combination of naïve cells and effector cells.

A method of attaining suitable cells, such as human primary cells, can comprise selecting cells. In some cases, a cell can comprise a marker that can be selected for the cell. For example, such marker can comprise GFP, a resistance gene, a cell surface marker, an endogenous tag. Cells can be selected using any endogenous marker. Suitable cells can be selected using any technology. Such technology can comprise flow cytometry and/or magnetic columns. The selected cells can then be infused into a subject. The selected cells can also be expanded to large numbers. The selected cells can be expanded prior to infusion.

In some cases, a suitable cell can be a recombinant cell. A recombinant cell can be an immortalized cell line. A cell line can be: CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-1 16 cells; Hu-h7 cells; Huvec cells; Molt 4 cells. All these cell lines can be modified by the method described herein to provide cell line models to produce, express, quantify, detect, study a gene or a protein of interest; these models can also be used to screen biologically active molecules of interest in research and production and various fields such as chemical, biofuels, therapeutics and agronomy as non-limiting examples.

The system as described herein can be delivered using vectors, for example containing sequences encoding one or more of the proteins or polypeptides. Accordingly, the system can comprise one or more vectors such as recombinant expression vectors. In some cases, the system as described herein can be delivered absent a viral vector. In some cases, the system as described herein can be delivered absent a viral vector, for example, when the system is greater than one kilobase, without affecting cellular viability. Transgenes encoding polynucleotides can be similarly delivered. Any vector systems can be used including, but not limited to, plasmid vectors, retroviral vectors, lentiviral vectors, adenovirus vectors, poxvirus vectors, herpesvirus vectors, split-intron retroviral vectors, adeno-associated virus vectors, any combination thereof, etc. Furthermore, any of these vectors can comprise one or more Ago or fragments thereof, Ago associated genes, transcription factors, nucleases, and/or transgenes. Thus, when one or more Ago or Ago associated molecules and/or transgenes are introduced into the cell, they can be carried on the same vector or on different vectors.

Split-intron based vectors, such as split-intron retroviral vectors, can be used for delivery. The methods and compositions of split-intron vectors are described in, e.g., Ismail et al, Journal of Virology, March 2000, p. 2365-2371, and US20060281180, which are hereby incorporated by reference in their entirety. Further, intron vectors like the ones described in Ding et al., Molecular Plant, vol 11 (4), p 542, 2018, can be used for delivery. Ding et al., 2018, is hereby incorporated by reference in its entirety.

Conventional viral and non-viral based gene transfer methods can be used to introduce nucleic acids encoding engineered Ago, and Ago associated genes and/or transgenes in cells (e.g., mammalian cells) and target tissues. In some examples, nucleic acids encoding Ago, and Ago associated genes, can be administered for in vivo or ex vivo immunotherapy uses. Non-viral vector delivery systems can include DNA plasmids, naked nucleic acid, lipid nanoparticles, and nucleic acid complexed with a delivery vehicle such as a liposome or poloxamer. Viral vector delivery systems can include DNA and RNA viruses, which have either episomal or integrated genomes after delivery to the cell.

Methods of non-viral delivery of nucleic acids include electroporation, lipofection, nucleofection, gold nanoparticle delivery, microinjection, biolistics, virosomes, liposomes, immunoliposomes, polycationic lipid: nucleic acid conjugates, naked DNA, mRNA, artificial virions, and agent-enhanced uptake of DNA. Sonoporation using, e.g., the Sonitron 2000 system (Rich-Mar) can also be used for delivery of nucleic acids. Additional exemplary nucleic acid delivery systems include those provided by AMAXA® Biosystems (Cologne, Germany), Life Technologies (Frederick, Md.), MAXCYTE, Inc. (Rockville, Md.), BTX Molecular Delivery Systems (Holliston, Mass.) and Copernicus Therapeutics Inc. (see for example U.S. Pat. No. 6,008,336). Lipofection reagents are sold commercially (e.g., TRANSFECTAM® and LIPOFECTIN®). Delivery can be to cells (ex vivo administration) or target tissues (in vivo administration). Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis.

In some cases, the system, fusion polypeptide, and/or polynucleic acid is delivered using lipid nanoparticles. The methods and compositions of suitable lipid nanoparticles are described in, e.g., US20160375134, US20180147298, US20180200186, US20180263907, US20180092848, US20070087045, U.S. Pat. Nos. 9,758,795, 9,687,448, 9,415,109, 7,858,117, 7,780,983, 9,504,651, 6,586,410, 8,969,543, 9,061,063, and 9,365,610, which are hereby incorporated by reference in their entirety. The lipid nanoparticles can comprise a cationic lipid, or a pharmaceutically acceptable salt thereof. The lipid nanoparticles can comprise a steroid, a neutral lipid, a polyethyleneglycol-containing lipid (PEGylated lipid), a phospholipid, or any combination thereof. The amount of the cationic lipid component can be from about 10 mol % to about 90 mol % of the overall lipid content of the formulation. In some cases, the cationic lipid component is from about 50 mol % to about 85 mol % of the overall lipids in the lipid nanoparticle. The amount of the steroid can be from about 10 mol % to about 50 mol % of the overall lipid in the lipid particle formulation. In some cases, the steroid is present in the lipid particles in an amount of from about 20 mol % to about 45 mol % of the total lipid. In some cases, the steroid is cholesterol or a derivative thereof. The amount of the phospholipid can be from about 1 mol % to about 20 mol % of the overall lipids in the lipid particle formulation. In some cases, from about 2 mol % to about 15 mol % of the total lipids are phospholipids.

Vectors including viral and non-viral vectors containing nucleic acids encoding engineered Ago, and Ago associated genes can also be administered directly to an organism for transduction of cells in vivo. Alternatively, naked DNA or mRNA can be administered. Administration is by any of the routes normally used for introducing a molecule into ultimate contact with blood or tissue cells including, but not limited to, injection, infusion, topical application and electroporation. More than one route can be used to administer a particular composition. Pharmaceutically acceptable carriers are determined in part by the particular composition being administered, as well as by the particular method used to administer the composition.

Vectors can be delivered in vivo by administration to an individual subject, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual subject (e.g., lymphocytes, T cells, bone marrow aspirates, tissue biopsy), followed by reimplantation of the cells into a subject, usually after selection for cells which have incorporated the vector. Prior to or after selection, the cells can be expanded.

A cell can be transfected with a mutant or chimeric adeno-associated viral vector encoding one or more components of the editing system comprising the Ago, Ago fragment, the fusion polypeptide, the polynucleic acid, and/or the Ago associated genes. An AAV vector concentration can be from 0.5 nanograms to 50 micrograms. In some cases, the amount of nucleic acid (e.g., ssDNA, dsDNA, RNA) that can be introduced into the cell by electroporation can be varied to optimize transfection efficiency and/or cell viability. In some cases, less than about 100 picograms of nucleic acid can be added to each cell sample (e.g., one or more cells being electroporated). In some cases, at least about 100 picograms, at least about 200 picograms, at least about 300 picograms, at least about 400 picograms, at least about 500 picograms, at least about 600 picograms, at least about 700 picograms, at least about 800 picograms, at least about 900 picograms, at least about 1 microgram, at least about 1.5 micrograms, at least about 2 micrograms, at least about 2.5 micrograms, at least about 3 micrograms, at least about 3.5 micrograms, at least about 4 micrograms, at least about 4.5 micrograms, at least about 5 micrograms, at least about 5.5 micrograms, at least about 6 micrograms, at least about 6.5 micrograms, at least about 7 micrograms, at least about 7.5 micrograms, at least about 8 micrograms, at least about 8.5 micrograms, at least about 9 micrograms, at least about 9.5 micrograms, at least about 10 micrograms, at least about 11 micrograms, at least about 12 micrograms, at least about 13 micrograms, at least about 14 micrograms, at least about 15 micrograms, at least about 20 micrograms, at least about 25 micrograms, at least about 30 micrograms, at least about 35 micrograms, at least about 40 micrograms, at least about 45 micrograms, or at least about 50 micrograms, of nucleic acid can be added to each cell sample (e.g., one or more cells being electroporated). For example, 1 microgram of dsDNA can be added to each cell sample for electroporation. In some cases, the amount of nucleic acid (e.g., dsDNA) required for optimal transfection efficiency and/or cell viability can be specific to the cell type. In some cases, the amount of nucleic acid (e.g., dsDNA) used for each sample can directly correspond to the transfection efficiency and/or cell viability.

The transfection efficiency of cells with any of the nucleic acid delivery platforms described herein, for example, nucleofection or electroporation, can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9%.

Vectors, plasmids, and genomic editing systems described herein can be delivered by any suitable method, including transfection, electroporation, liposome delivery, membrane fusion techniques, high velocity DNA-coated pellets, viral infection and protoplast fusion. The methods used to construct any embodiment of this invention are known to those with skill in nucleic acid manipulation and include genetic engineering, recombinant engineering, and synthetic techniques. See, e.g., Sambrook et al, Molecular Cloning: A Laboratory Manual, Cold Spring Harbor Press, Cold Spring Harbor, NY. Electroporation using, for example, the Neon® Transfection System (ThermoFisher Scientific) or the AMAXA® Nucleofector (AMAXA® Biosystems) can also be used for delivery of nucleic acids into a cell. Electroporation parameters can be adjusted to optimize transfection efficiency and/or cell viability. Electroporation devices can have multiple electrical wave form pulse settings such as exponential decay, time constant and square wave. Every cell type has a unique optimal Field Strength (E) that is dependent on the pulse parameters applied (e.g., voltage, capacitance and resistance). Application of optimal field strength causes electropermeabilization through induction of transmembrane voltage, which allows nucleic acids to pass through the cell membrane. In some cases, the electroporation pulse voltage, the electroporation pulse width, number of pulses, cell density, and tip type can be adjusted to optimize transfection efficiency and/or cell viability.

In some cases, electroporation pulse voltage can be varied to optimize transfection efficiency and/or cell viability. In some cases, the electroporation voltage can be less than about 500 volts. In some cases, the electroporation voltage can be at least about 500 volts, at least about 600 volts, at least about 700 volts, at least about 800 volts, at least about 900 volts, at least about 1000 volts, at least about 1100 volts, at least about 1200 volts, at least about 1300 volts, at least about 1400 volts, at least about 1500 volts, at least about 1600 volts, at least about 1700 volts, at least about 1800 volts, at least about 1900 volts, at least about 2000 volts, at least about 2100 volts, at least about 2200 volts, at least about 2300 volts, at least about 2400 volts, at least about 2500 volts, at least about 2600 volts, at least about 2700 volts, at least about 2800 volts, at least about 2900 volts, or at least about 3000 volts. In some cases, the electroporation pulse voltage required for optimal transfection efficiency and/or cell viability can be specific to the cell type. For example, an electroporation voltage of 1900 volts can optimal (e.g., provide the highest viability and/or transfection efficiency) for macrophage cells. In another example, an electroporation voltage of about 1350 volts can optimal (e.g., provide the highest viability and/or transfection efficiency) for Jurkat cells or primary human cells such as T cells. In some cases, a range of electroporation voltages can be optimal for a given cell type. For example, an electroporation voltage between about 1000 volts and about 1300 volts can optimal (e.g., provide the highest viability and/or transfection efficiency) for human 578T cells.

In some cases, electroporation pulse width can be varied to optimize transfection efficiency and/or cell viability. In some cases, the electroporation pulse width can be less than about 5 milliseconds. In some cases, the electroporation width can be at least about 5 milliseconds, at least about 6 milliseconds, at least about 7 milliseconds, at least about 8 milliseconds, at least about 9 milliseconds, at least about 10 milliseconds, at least about 11 milliseconds, at least about 12 milliseconds, at least about 13 milliseconds, at least about 14 milliseconds, at least about 15 milliseconds, at least about 16 milliseconds, at least about 17 milliseconds, at least about 18 milliseconds, at least about 19 milliseconds, at least about 20 milliseconds, at least about 21 milliseconds, at least about 22 milliseconds, at least about 23 milliseconds, at least about 24 milliseconds, at least about 25 milliseconds, at least about 26 milliseconds, at least about 27 milliseconds, at least about 28 milliseconds, at least about 29 milliseconds, at least about 30 milliseconds, at least about 31 milliseconds, at least about 32 milliseconds, at least about 33 milliseconds, at least about 34 milliseconds, at least about 35 milliseconds, at least about 36 milliseconds, at least about 37 milliseconds, at least about 38 milliseconds, at least about 39 milliseconds, at least about 40 milliseconds, at least about 41 milliseconds, at least about 42 milliseconds, at least about 43 milliseconds, at least about 44 milliseconds, at least about 45 milliseconds, at least about 46 milliseconds, at least about 47 milliseconds, at least about 48 milliseconds, at least about 49 milliseconds, or at least about 50 milliseconds. In some cases, the electroporation pulse width required for optimal transfection efficiency and/or cell viability can be specific to the cell type. For example, an electroporation pulse width of 30 milliseconds can optimal (e.g., provide the highest viability and/or transfection efficiency) for macrophage cells. In another example, an electroporation width of about 10 milliseconds can optimal (e.g., provide the highest viability and/or transfection efficiency) for Jurkat cells. In some cases, a range of electroporation widths can be optimal for a given cell type. For example, an electroporation width between about 20 milliseconds and about 30 milliseconds can optimal (e.g., provide the highest viability and/or transfection efficiency) for human 578T cells.

In some cases, the number of electroporation pulses can be varied to optimize transfection efficiency and/or cell viability. In some cases, electroporation can comprise a single pulse. In some cases, electroporation can comprise more than one pulse. In some cases, electroporation can comprise 2 pulses, 3 pulses, 4 pulses, 5 pulses 6 pulses, 7 pulses, 8 pulses, 9 pulses, or 10 or more pulses. In some cases, the number of electroporation pulses required for optimal transfection efficiency and/or cell viability can be specific to the cell type. For example, electroporation with a single pulse can be optimal (e.g., provide the highest viability and/or transfection efficiency) for macrophage cells. In another example, electroporation with a 3 pulses can be optimal (e.g., provide the highest viability and/or transfection efficiency) for primary cells. In some cases, a range of electroporation widths can be optimal for a given cell type. For example, electroporation with between about 1 to about 3 pulses can be optimal (e.g., provide the highest viability and/or transfection efficiency) for human cells.

In some cases, the starting cell density for electroporation can be varied to optimize transfection efficiency and/or cell viability. In some cases, the starting cell density for electroporation can be less than about $1\times10^5$ cells. In some cases, the starting cell density for electroporation can be at least about $1\times10^5$ cells, at least about $2\times10^5$ cells, at least about $3\times10^5$ cells, at least about $4\times10^5$ cells, at least about $5\times10^5$ cells, at least about $6\times10^5$ cells, at least about $7\times10^5$ cells, at least about $8\times10^5$ cells, at least about $9\times10^5$ cells, at least about $1\times10^6$ cells, at least about $1.5\times10^6$ cells, at least about $2\times10^6$ cells, at least about $2.5\times10^6$ cells, at least about $3\times10^6$ cells, at least about $3.5\times10^6$ cells, at least about $4\times10^6$ cells, at least about $4.5\times10^6$ cells, at least about $5\times10^6$ cells, at least about $5.5\times10^6$ cells, at least about $6\times10^6$ cells, at least about $6.5\times10^6$ cells, at least about $7\times10^6$ cells, at least about $7.5\times10^6$ cells, at least about $8\times10^6$ cells, at least about $8.5\times10^6$ cells, at least about $9\times10^6$ cells, at least about $9.5\times10^6$ cells, at least about $1\times10^7$ cells, at least about $1.2\times10^7$ cells, at least about $1.4\times10^7$ cells, at least about $1.6\times10^7$ cells, at least about $1.8\times10^7$ cells, at least about $2\times10^7$ cells, at least about $2.2\times10^7$ cells, at least about $2.4\times10^7$ cells, at least about $2.6\times10^7$ cells, at least about $2.8\times10^7$ cells, at least about $3\times10^7$ cells, at least about $3.2\times10^7$ cells, at least about $3.4\times10^7$ cells, at least about $3.6\times10^7$ cells, at least about $3.8\times10^7$ cells, at least about $4\times10^7$ cells, at least about $4.2\times10^7$ cells, at least about $4.4\times10^7$ cells, at least about $4.6\times10^7$ cells, at least about $4.8\times10^7$ cells, or at least about $5\times10^7$ cells. In some cases, the starting cell density for electroporation required for optimal transfection efficiency and/or cell viability can be specific to the cell type. For example, a starting cell density for electroporation of $1.5\times10^6$ cells can optimal (e.g., provide the highest viability and/or transfection efficiency) for macrophage cells. In another example, a starting cell density for electroporation of $5\times10^6$ cells can optimal (e.g., provide the highest viability and/or transfection efficiency) for human cells. In some cases, a range of starting cell densities for electroporation can be optimal for a given cell type. For example, a starting cell density for electroporation between of $5.6\times10^6$ and $5\times10^7$ cells can optimal (e.g., provide the highest viability and/or transfection efficiency) for human cells such as T cells.

In some cases, the guiding polynucleic acid and the Ago can be introduced into cells as a complex. The complex can comprise a DNA and the Ago or it can comprise an RNA and the Ago. The complex can be a ribonuclear protein complex (RNP). Introduction of an RNP complex can be timed. In some cases, a cell can be synchronized with other cells at G1, S, and/or M phases of the cell cycle prior to introduction of a guiding polynucleic acid and the Ago. In some cases, an RNP complex can be delivered at a cell phase such that HDR, MMEJ, or NHEJ can be enhanced. In some cases an RNP complex can facilitate homology directed repair.

Non-homologous end joining (NHEJ) and Homology-directed repair (HDR) can be quantified using a variety of methods. In some cases, a percent of NHEJ, HDR, or a combination of both can be determined by co-delivering the gene editing molecules, for example a guiding polynucleic acid and an RNase H like domain containing polypeptide, with a donor DNA template that encodes a promoterless GFP into cells. After about 72 hrs, flow cytometry can be performed to quantify the total cell number ($N_{Total}$), GFP-positive cell number ($N_{GFP+}$), and GFP-negative cell number ($N_{GFP-}$). Among the GFP negative cells, next-generation sequencing can be performed to identify cells without mutations ($N_{GFP-}{}^{0}$), and with mutations ($N_{GFP-}{}^{1}$). HDR efficiency can be calculated as $N_{GFP+}/N_{Total}\times100\%$, and NHEJ efficiency will be calculated as $N_{GFP-}{}^{1}/N_{Total}\times100\%$.

In some cases, activity of a DNA editing system may be assayed using a cell expressing a reporter protein or containing a reporter gene. For example, a reporter protein may be engineered to contain an obstruction, such as a stop codon, a frameshift mutation, a spacer, a linker, or a transcriptional terminator; the DNA editing system may then be used to remove the obstruction and the resultant functional reporter protein may be detected. In some cases, the obstruction may be designed such that a specific sequence modification is required to restore functionality of the reporter protein. In other cases, the obstruction may be designed such that any insertion or deletion which results in a frame shift of one or two bases may be sufficient to restore functionality of the reporter protein. Examples of reporter proteins include colorimetric enzymes, metabolic enzymes, fluorescent proteins, enzymes and transporters associated with antibiotic resistance, and luminescent enzymes. Examples of such reporter proteins include β-galactosidase, Chloramphenicol acetyltransferase, Green fluorescent protein, Red fluorescent protein, luciferase, and *Renilla*. Different detection methods may be used for different reporter proteins. For example, the reporter protein may affect cell viability, cell growth, fluorescence, luminescence, or expression of a detectable product. In some cases, the reporter protein may be detected using a colorimetric assay. In some cases, the reporter protein may be a fluorescent protein, and DNA editing may be assayed by measuring the degree of fluorescence in treated cells, or the number of treated cells with at least a threshold level of fluorescence. In some cases, transcript levels of a reporter gene may be assessed. In other cases, a reporter gene may be assessed by sequencing. In some cases, an assay for measuring DNA editing may use a split fluorescence protein system, such as the self-complementing split $GFP_{1\text{-}10/11}$ systems, in which two fragments ($G_{1\text{-}10}$ and $G_{11}$) of the GFP protein which can associate by themselves to form a functional GFP signal are linked using a frame-shifting linker. Insertions or deletions within the frameshifting linker can restore the frame of the $G_{11}$ fragment allowing the two fragments to form a functional GFP signal. In some cases, the Ago polypeptides as described herein may result in at least about 1%, 1.1%, 1.2%, 1.3%, 1.4%, 1.5%, 1.6%, 1.7%, 1.8%, 1.9%, 2%, 2.5%, 3%, 4%, %, 6%, 7%, 8%, 9%, 10, 1%, 20%, 25%, 30%, 35%, 40%, 45%, 50%, 60%, 70%, 80%, 90%, 95%, 97%, 98%, or 99% of cells exhibiting restored activity of a reporter protein. In some cases, the Ago polypeptides as described herein may result in at least about 1% to 99%, 1% to 10%, 1% to 5%, 1% to 2%, 5% to 50%, 10% to 80%, 10% to 50%, 30% to 70%, or 50% to 80% of cells exhibiting restored activity of a reporter protein. In some cases, Ago polypeptides as described herein may result in at least about a 1.5 fold, 2 fold, 3 fold, 4 fold, 5 fold, 6 fold, 7 fold, 8 fold, 9 fold, 10 fold, 15 fold, 20 fold, 25 fold, 30 fold, 40 fold, 50 fold, 60 fold, 70 fold, 80 fold, 90 fold, or 100 fold increase in the percentage of cells with restored activity of a reporter as compared to baseline. In some cases, the Ago polypeptides as described herein may result in at least about a 1.2 fold to 10 fold, 1.5 fold to 10 fold, 2 fold to 10 fold, 2 fold to 5 fold, 2 fold to 20 fold, 3 fold to 5 fold, 4 fold to 10 fold, 5 fold to 20 fold, 10 fold to 100 fold, 10 fold to 50 fold or 1.2 fold to 100 fold increase in the percentage of cells with restored activity of a reporter as compared to baseline.

The percent occurrence of a genomic break repair utilizing HDR over NHEJ or MMEJ can be or can be about 20%, 25%, 30%, 35%0, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9% of cells that are contacted with a genomic editing system comprising the Ago or Ago fragment. The percent occurrence of a genomic break repair utilizing NHEJ over HDR or MMEJ can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9% of cells that are contacted with a genomic editing system comprising the Ago or Ago fragment. The percent occurrence of a genomic break repair utilizing MMEJ over HDR or NHEJ can be or can be about 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.5%, 99.9%, or more than 99.9% of cells that are contacted with a genomic editing system comprising the Ago or Ago fragment.

Integration of an exogenous polynucleic acid can be measured using any technique. For example, integration can be measured by flow cytometry, surveyor nuclease assay, tracking of indels by decomposition (TIDE), junction PCR, or any combination thereof. In other cases, transgene integration can be measured by PCR. A TIDE analysis can also be performed on engineered cells. Ex vivo cell transfection can also be used for diagnostics, research, or for gene therapy (e.g., via re-infusion of the transfected cells into the host organism). In some cases, cells are isolated from the subject organism, transfected with a nucleic acid (e.g., gene or cDNA), and re-infused back into the subject organism (e.g., subject).

The amount of the Ago or Ago fragment polypeptide-containing modified cells that can be necessary to be therapeutically effective in a subject can vary depending on the viability of the cells, and the efficiency with which the cells have been genetically modified (e.g., the efficiency with which a transgene has been integrated into one or more cells). In some cases, the product (e.g., multiplication) of the viability of cells post genetic modification and the efficiency of integration of a transgene can correspond to the therapeutic aliquot of cells available for administration to a subject. In some cases, an increase in the viability of cells post genetic modification can correspond to a decrease in the amount of cells that are necessary for administration to be therapeutically effective in a subject. In some cases, an increase in the efficiency with which a transgene has been integrated into one or more cells can correspond to a decrease in the amount of cells that are necessary for administration to be therapeutically effective in a subject. In some cases, determining an amount of cells that are necessary to be therapeutically effective can comprise determining a function corresponding to a change in the viability of cells over time. In some cases, determining an amount of cells that are necessary to be therapeutically effective can comprise determining a function corresponding to a change in the efficiency with which a transgene can be integrated into one or more cells with respect to time dependent variables (e.g., cell culture time, electroporation time, cell stimulation time).

As described herein, viral particles, such as AAV, can be used to deliver a viral vector comprising a gene of interest or a transgene, such as the polynucleic acid described herein, into a cell ex vivo or in vivo. In some embodiments, a mutated or chimeric adeno-associated viral vector as disclosed herein can be measured as pfu (plaque forming units). In some cases, the pfu of recombinant virus or mutated or chimeric adeno-associated viral vector of the compositions and methods of the disclosure can be about $10^8$ to about $5\times10^{10}$ pfu. In some cases, recombinant viruses of this disclosure are at least about $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, and $5\times10^{10}$ pfu. In some cases, recombinant viruses of this disclosure are at most about $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, and $5\times10^{10}$ pfu. In some aspects, a mutated or chimeric adeno-associated viral vector of the disclosure can be measured as vector genomes. In some cases, recombinant viruses of this disclosure are $1\times10^{10}$ to $3\times10^{12}$ vector genomes, or $1\times10^9$ to $3\times10^{13}$ vector genomes, or $1\times10^8$ to $3\times10^{14}$ vector genomes, or at least about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ vector genomes, or are $1\times10^8$ to $3\times10^{14}$ vector genomes, or are at most about $1\times10^1$, $1\times10^2$, $1\times10^3$, $1\times10^4$, $1\times10^5$, $1\times10^6$, $1\times10^7$, $1\times10^8$, $1\times10^9$, $1\times10^{10}$, $1\times10^{11}$, $1\times10^{12}$, $1\times10^{13}$, $1\times10^{14}$, $1\times10^{15}$, $1\times10^{16}$, $1\times10^{17}$, and $1\times10^{18}$ vector genomes.

In some cases, a mutated or chimeric adeno-associated viral vector of the disclosure can be measured using multiplicity of infection (MOI). In some cases, MOI can refer to the ratio, or multiple of vector or viral genomes to the cells to which the nucleic can be delivered. In some cases, the MOI can be $1\times10^6$ GC/mL. In some cases, the MOI can be $1\times10^5$ GC/mL to $1\times10^7$ GC/mL. In some cases, the MOI can be $1\times10^4$ GC/mL to $1\times10^8$ GC/mL. In some cases, recombinant viruses of the disclosure are at least about $1\times10^1$ GC/mL, $1\times10^2$ GC/mL, $1\times10^3$ GC/mL, $1\times10^4$ GC/mL, $1\times10^5$ GC/mL, $1\times10^6$ GC/mL, $1\times10^7$ GC/mL, $1\times10^8$ GC/mL, $1\times10^9$ GC/mL, $1\times10^{10}$ GC/mL, $1\times10^{11}$ GC/mL, $1\times10^{12}$ GC/mL, $1\times10^{13}$ GC/mL, $1\times10^{14}$ GC/mL, $1\times10^{15}$ GC/mL, $1\times10^{16}$ GC/mL, $1\times10^{17}$ GC/mL, and $1\times10^{18}$ GC/mL MOI. In some cases, a mutated or chimeric adeno-associated viruses of this disclosure are from about $1\times10^8$ GC/mL to about $3\times10^{14}$ GC/mL MOI, or are at most about $1\times10^1$ GC/mL, $1\times10^2$ GC/mL, $1\times10^3$ GC/mL, $1\times10^4$ GC/mL, 1×10$^5$ GC/mL, 1×10$^6$ GC/mL, 1×10$^7$ GC/mL, 1×10$^8$ GC/mL, 1×10$^9$ GC/mL, 1×10$^{10}$ GC/mL, 1×10$^{11}$ GC/mL, 1×10$^{12}$ GC/mL, 1×10$^{13}$ GC/mL, 1×10$^{14}$ GC/mL, 1×10$^{15}$ GC/mL, 1×10$^{16}$ GC/mL, 1×10$^{17}$ GC/mL, and 1×10$^{18}$ GC/mL MOI.

In some aspects, a non-viral vector or nucleic acid can be delivered without the use of a mutated or chimeric adeno-associated viral vector and can be measured according to the quantity of nucleic acid. Generally, any suitable amount of nucleic acid can be used with the compositions and methods of this disclosure. In some cases, nucleic acid can be at least about 1 pg, 10 pg, 100 pg, 1 pg, 10 pg, 100 pg, 200 pg, 300 pg, 400 pg, 500 pg, 600 pg, 700 pg, 800 pg, 900 pg, 1 μg, 10 μg, 100 μg, 200 μg, 300 μg, 400 μg, 500 μg, 600 μg, 700 μg, 800 μg, 900 μg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg, 1 g, 2 g, 3 g, 4 g, or 5 g. In some cases, nucleic acid can be at most about 1 pg, 10 pg, 100 pg, 1 pg, 10 pg, 100 pg, 200 pg, 300 pg, 400 pg, 500 pg, 600 pg, 700 pg, 800 pg, 900 pg, 1 μg, 10 μg, 100 μg, 200 μg, 300 μg, 400 μg, 500 μg, 600 μg, 700 μg, 800 μg, 900 μg, 1 ng, 10 ng, 100 ng, 200 ng, 300 ng, 400 ng, 500 ng, 600 ng, 700 ng, 800 ng, 900 ng, 1 mg, 10 mg, 100 mg, 200 mg, 300 mg, 400 mg, 500 mg, 600 mg, 700 mg, 800 mg, 900 mg, 1 g, 2 g, 3 g, 4 g, or 5 g.

Cells (e.g., engineered cells or engineered primary cells) before, after, and/or during transplantation can be functional. For example, transplanted cells can be functional for at least or at least about 1, 2, 3, 4, 5, 6, 7, 8, 9, 10, 11, 12, 13, 14, 15, 16, 17, 18, 19, 20, 21, 22, 23, 24, 25, 6, 27, 28, 29, 30, 40, 50, 60, 70, 80, 90, or 100 days after transplantation. Transplanted cells can be functional for at least or at least about 1, 2, 3, 4, 5, 6, 7, 8, 9, 10, 11, or 12 months after transplantation. Transplanted cells can be functional for at least or at least about 1, 2, 3, 4, 5, 6, 7, 8, 9, 10, 15, 20, 25, or 30 years after transplantation. In some cases, transplanted cells can be functional for up to the lifetime of a recipient.

Further, transplanted cells can function at 100% of its normal intended operation. Transplanted cells can also function 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of its normal intended operation.

Transplanted cells can also function over 100% of its normal intended operation. For example, transplanted cells can function 110, 120, 130, 140, 150, 160, 170, 180, 190, 200, 250, 300, 400, 500, 600, 700, 800, 900, 1000 or more % of its normal intended operation.

One or more cytokines can be introduced with cells of the invention. Cytokines can be utilized to boost cytotoxic T lymphocytes (including adoptively transferred tumor-specific cytotoxic T lymphocytes) to expand within a tumor microenvironment. In some cases, IL-2 can be used to facilitate expansion of the cells described herein. Cytokines such as IL-15 can also be employed. Other relevant cytokines in the field of immunotherapy can also be utilized, such as IL-2, IL-7, IL-12, IL-15, IL-21, or any combination thereof.

In some cases, IL-2 can be administered beginning within 24 hours of cell infusion and continuing for up to about 4 days (maximum 12 doses). In some cases, IL-2 can be administered for up to about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 days after an initial administration. Doses of IL-2 can be administered every eight hours. In some cases, IL-2 can be administered from about every 1, 2, 3, 4, 5, 6, 7, 8, 9, 10, 11, 12, 13, 14, 15, 16, 17, 18, 19, 20, 21, 22, 23, 24 hours after an initial administration. In some cases, IL-2 dosing can be stopped if toxicities are detected. In some cases, doses can be delayed or stopped if subjects reach Grade 3 or 4 toxicity due to aldesleukin except for the reversible Grade 3 toxicities common to Aldesleukin such as diarrhea, nausea, vomiting, hypotension, skin changes, anorexia, mucositis, dysphagia, or constitutional symptoms and laboratory changes. In some cases, if these toxicities can be easily reversed within 24 hours by supportive measures, then additional doses can be given. In addition, dosing can be held or stopped at the discretion of a treating physician.

XI. PHARMACEUTICAL COMPOSITIONS

The Ago systems, polypeptides, and polynucleic acid described throughout can be formulated into a pharmaceutical composition. The pharmaceutical composition can comprise the Ago polypeptide, the Ago system, the fusion polypeptide, the polynucleic acid encoding the same, or any combination thereof. The pharmaceutical composition can further comprise a pharmaceutically acceptable excipient, diluent, carrier, or a combination thereof. A pharmaceutically acceptable excipient, carrier, or diluent can refer to an excipient, carrier or diluent that can be administered to a subject, together with an agent, and which does not destroy the pharmacological activity thereof and is nontoxic when administered in doses sufficient to deliver a therapeutic amount of the agent.

The pharmaceutical composition can be in a unit dosage form. The pharmaceutical composition can be administered in both single and multiple dosages. In some cases, for example, in the compositions, formulations and methods of treatment, the unit dosage of the composition or formulation administered can be 5, 10, 15, 20, 25, 30, 35, 40, 45, 50, 55, 60, 65, 70, 75, 80, 85, 90, 95 or 100 mg. In some cases, the total amount of the composition or formulation administered can be 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 25, 30, 40, 50, 60, 70, 80, 90, or 100 g.

The pharmaceutical composition can be in the form of tablets, capsules, lozenges, troches, hand candies, powders, sprays, aqueous suspensions, injectable solutions, elixirs, syrups, and the like. In some cases, the pharmaceutical composition is in a form of parenteral administration formulation. For example, the pharmaceutical composition can be in a form of intravenous, subcutaneous, or intramuscular administration formulation.

The pharmaceutical composition can include solid diluents or fillers, sterile aqueous media and various non-toxic organic solvents, etc. In some cases, the carrier can be water, saline, ethanol, glycerol, lactose, sucrose, calcium phosphate, gelatin, dextran, agar, pectin, peanut oil, sesame oil, etc. For parenteral formulations, the carrier usually comprises sterile water or aqueous sodium chloride solution, though other ingredients including those which aid dispersion may be included. Injectable suspensions may also be prepared, in which case appropriate liquid carriers, suspending agents and the like may be employed. Formulations suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. If administered intravenously, carriers can include, for example, physiological saline or phosphate buffered saline (PBS). The formulations may be presented in unit-dose or multi-dose containers, for example, sealed ampules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the kind previously described. A thorough discussion of pharmaceutically acceptable excipients is available in Remington's pharmaceutical sciences (Mack Pub. Co., N.J. 1991) which is incorporated by reference herein.

The compositions can be co-administered with one or more T cells (e.g., engineered T cells) and/or one or more chemotherapeutic agents or chemotherapeutic compounds to a human or mammal. A chemotherapeutic agent can be a chemical compound useful in the treatment of cancer. The chemotherapeutic cancer agents that can be used in combination with the disclosed T cell include, but are not limited to, mitotic inhibitors (*vinca* alkaloids). These include vincristine, vinblastine, vindesine and Navelbine™ (vinorelbine, 5'-noranhydroblastine). In yet other cases, chemotherapeutic cancer agents include topoisomerase I inhibitors, such as camptothecin compounds. As used herein, "camptothecin compounds" include Camptosar™ (irinotecan HCL), Hycamtin™ (topotecan HCL) and other compounds derived from camptothecin and its analogues. Another category of chemotherapeutic cancer agents that can be used in the methods and compositions disclosed herein can be podophyllotoxin derivatives, such as etoposide, teniposide and mitopodozide. The present disclosure further encompasses other chemotherapeutic cancer agents known as alkylating agents, which alkylate the genetic material in tumor cells. These include without limitation cisplatin, cyclophosphamide, nitrogen mustard, trimethylene thiophosphoramide, carmustine, busulfan, chlorambucil, belustine, uracil mustard, chlomaphazin, and dacarbazine. The disclosure encompasses antimetabolites as chemotherapeutic agents. Examples of these types of agents include cytosine arabinoside, fluorouracil, methotrexate, mercaptopurine, azathioprime, and procarbazine. An additional category of chemotherapeutic cancer agents that can be used in the methods and compositions disclosed herein includes antibiotics. Examples include without limitation doxorubicin, bleomycin, dactinomycin, daunorubicin, mithramycin, mitomycin, mytomycin C, and daunomycin. There are numerous liposomal formulations commercially available for these compounds. The present disclosure further encompasses other chemotherapeutic cancer agents including without limitation anti-tumor antibodies, dacarbazine, azacytidine, amsacrine, melphalan, ifosfamide and mitoxantrone.

The pharmaceutical composition can comprise one or more herein described cells. Cells can be extracted from a human as described herein. Cells can be genetically altered ex vivo and used accordingly. These cells can be used for cell-based therapies. These cells can be used to treat disease in a recipient (e.g., a human). For example, these cells can be used to treat cancer.

In some cases, a subject may receive a percentage of described engineered cells in a total population of cells that can be introduced. A patient may be infused with as many cells that can be generated for them. In some cases, cells that are infused into a patient are not all engineered. For example, at least 90% of cells that can be introduced into a patient can be engineered. In other instances, at least 40% of cells that are introduced into a patient can be engineered. For example, a patient may receive any number of engineered cells, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100% of the total introduced population.

The disclosed cells herein can be administered in combination with other anti-tumor agents, including cytotoxic/antineoplastic agents and anti-angiogenic agents. Cytotoxic/antineoplastic agents can be defined as agents who attack and kill cancer cells. Anti-angiogenic agents can also be used. Suitable anti-angiogenic agents for use in the disclosed methods and compositions include anti-VEGF antibodies, including humanized and chimeric antibodies, anti-VEGF aptamers and antisense oligonucleotides. Other inhibitors of angiogenesis include angiostatin, endostatin, interferons, interleukin 1 (including α and β) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

XII. METHODS OF USE

Described herein are methods of treating a disease (e.g., cancer) or disorder. The methods can comprise administering to a subject in need thereof the Ago system, the Ago fusion polypeptide, the polynucleic acid, the cell, the pharmaceutical composition, or any combination thereof. In some cases, the method comprises parenteral injection such as intravenous, intramuscular, or subcutaneous injection.

Described herein is a method of treating a disease (e.g., cancer) in a recipient comprising transplanting to the recipient one or more Argonaute modified cells (including organs and/or tissues). Generally, modified cells described herein can be expanded by contact with a surface having attached thereto an agent that can stimulate a CD3 TCR complex associated signal and a ligand that can stimulate a co-stimulatory molecule on the surface of the T cells. In particular, cell populations can be stimulated in vitro such as by contact with an anti-CD3 antibody or antigen-binding fragment thereof, or an anti-CD2 antibody immobilized on a surface, or by contact with a protein kinase C activator (e.g., bryostatin) sometimes in conjunction with a calcium ionophore. For co-stimulation of an accessory molecule on the surface of modified cells, a ligand that binds the accessory molecule can be used. For example, a population of cells can be contacted with an anti-CD3 antibody and an anti-CD28 antibody, under conditions that can stimulate proliferation of the T cells. In some cases, 4-1BB can be used to stimulate cells. For example, cells can be stimulated with 4-1BB and IL-21 or another cytokine. In some cases $5\times10^{10}$ cells will be administered to a subject. In other cases, $5\times10^{11}$ cells will be administered to a subject.

In some embodiments, about $5\times10^{10}$ cells are administered to a subject. In some embodiments, about $5\times10^{10}$ cells represent the median amount of cells administered to a subject. In some embodiments, about $5\times10^{10}$ cells are necessary to affect a therapeutic response in a subject. In some embodiments, at least about at least about $1\times10^7$ cells, at least about $2\times10^7$ cells, at least about $3\times10^7$ cells, at least about $4\times10^7$ cells, at least about $5\times10^7$ cells, at least about $6\times10^7$ cells, at least about $6\times10^7$ cells, at least about $8\times10^7$ cells, at least about $9\times10^7$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least about $6\times10^{10}$ cells, at least about $8\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about $5\times10^{11}$ cells, at least about $6\times10^{11}$ cells, at least about $6\times10^{11}$ cells, at least about $8\times10^{11}$ cells, at least about $9\times10^{11}$ cells, or at least about $1\times10^{12}$ cells. For example, about $5\times10^{10}$ cells can be administered to a subject. In another example, starting with $3\times10^6$ cells, the cells can be expanded to about $5\times10^{10}$ cells and administered to a subject. In some cases, cells are expanded to sufficient numbers for therapy. For example, $5\times10^7$ cells can undergo rapid expansion to generate sufficient numbers for therapeutic use. In some cases, sufficient numbers for therapeutic use can be $5\times10^{10}$. Any number of cells can be infused for therapeutic use. For example, a subject can be infused with a number of cells between $1\times10^6$ to $5\times10^{12}$ inclusive. A subject can be infused with as many cells that can be generated for them. In some cases, cells that are infused into a subject are not all engineered. For example, at least 90% of cells that are infused into a subject can be engineered. In other instances, at least 40% of cells that are infused into a subject can be engineered.

In some embodiments, a method of the present disclosure comprises calculating and/or administering to a subject an amount of modified cells necessary to affect a therapeutic response in the subject. In some embodiments, calculating the amount of engineered cells necessary to affect a therapeutic response comprises the viability of the cells and/or the efficiency with which a transgene has been integrated into the genome of a cell. In some embodiments, in order to affect a therapeutic response in a subject, modified cells that can be administered to a subject can be viable. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells are viable cells. In some embodiments, in order to affect a therapeutic response in a subject, the Argonaute polypeptide modified cells administered to a subject can be cells that have had one or more transgenes successfully integrated into the genome of the cell. In some embodiments, in order to effect a therapeutic response in a subject, at least about 95%, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20%, at least about 15%, at least about 10% of the cells have had one or more transgenes successfully integrated into the genome of the cell.

The methods disclosed herein can be used for treating or preventing disease including, but not limited to, cancer, cardiovascular diseases, lung diseases, liver diseases, skin diseases, or neurological diseases by administering to a subject in need thereof. Ago modified cells.

In some embodiments, described herein are methods of treating cancer by administering to a subject in need thereof Ago modified cells. In some embodiments, the cancer is a solid tumor. In some embodiments, the cancer is a hematological malignancy. In some embodiments, the cancer is acute lymphocytic cancer, acute myeloid leukemia, alveolar rhabdomyosarcoma, bladder cancer, bone cancer, brain cancer, breast cancer, cancer of the anus, anal canal, rectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, Hodgkin lymphoma, hypopharynx cancer, kidney cancer, larynx cancer, leukemia, liquid tumors, liver cancer, lung cancer, lymphoma, malignant mesothelioma, mastocytoma, melanoma, multiple myeloma, nasopharynx cancer, non-Hodgkin lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, stomach cancer, testicular cancer, thyroid cancer, ureter cancer, and/or urinary bladder cancer.

Transplanting can be by any type of transplanting. Sites can include, but not limited to, liver subcapsular space, splenic subcapsular space, renal subcapsular space, omentum, gastric or intestinal submucosa, vascular segment of small intestine, venous sac, testis, brain, spleen, or cornea. For example, transplanting can be subcapsular transplanting. Transplanting can also be intramuscular transplanting. Transplanting can be intraportal transplanting.

Transplanting can be of one or more cells from a human. For example, the one or more cells can be from an organ, which can be a brain, heart, lungs, eye, stomach, pancreas, kidneys, liver, intestines, uterus, bladder, skin, hair, nails, ears, glands, nose, mouth, lips, spleen, gums, teeth, tongue, salivary glands, tonsils, pharynx, esophagus, large intestine, small intestine, rectum, anus, thyroid gland, thymus gland, bones, cartilage, tendons, ligaments, suprarenal capsule, skeletal muscles, smooth muscles, blood vessels, blood, spinal cord, trachea, ureters, urethra, hypothalamus, pituitary, pylorus, adrenal glands, ovaries, oviducts, uterus, vagina, mammary glands, testes, seminal vesicles, penis, lymph, lymph nodes or lymph vessels. The one or more cells can also be from a brain, heart, liver, skin, intestine, lung, kidney, eye, small bowel, or pancreas. The one or more cells can be from a pancreas, kidney, eye, liver, small bowel, lung, or heart. The one or more cells can be from a pancreas. The one or more cells can be pancreatic islet cells, for example, pancreatic R cells. The one or more cells can be any blood cells, such as peripheral blood mononuclear cell (PBMC), lymphocytes, monocytes or macrophages. The one or more cells can be any immune cells such as lymphocytes, B cells, or T cells.

The method disclosed herein can also comprise transplanting one or more cells (e.g., autologous cells or allogeneic cells), wherein the one or more cells can be any types of cells. For example, the one or more cells can be epithelial cells, fibroblast cells, neural cells, keratinocytes, hematopoietic cells, melanocytes, chondrocytes, lymphocytes (B and T), macrophages, monocytes, mononuclear cells, cardiac muscle cells, other muscle cells, granulosa cells, cumulus cells, epidermal cells, endothelial cells, pancreatic islet cells, blood cells, blood precursor cells, bone cells, bone precursor cells, neuronal stem cells, primordial stem cells, hepatocytes, keratinocytes, umbilical vein endothelial cells, aortic endothelial cells, microvascular endothelial cells, fibroblasts, liver stellate cells, aortic smooth muscle cells, cardiac myocytes, neurons, Kupffer cells, smooth muscle cells, Schwann cells, and epithelial cells, erythrocytes, platelets, neutrophils, lymphocytes, monocytes, eosinophils, basophils, adipocytes, chondrocytes, pancreatic islet cells, thyroid cells, parathyroid cells, parotid cells, tumor cells, glial cells, astrocytes, red blood cells, white blood cells, macrophages, epithelial cells, somatic cells, pituitary cells, adrenal cells, hair cells, bladder cells, kidney cells, retinal cells, rod cells, cone cells, heart cells, pacemaker cells, spleen cells, antigen presenting cells, memory cells, T cells, B cells, plasma cells, muscle cells, ovarian cells, uterine cells, prostate cells, vaginal epithelial cells, sperm cells, testicular cells, germ cells, egg cells, leydig cells, peritubular cells, sertoli cells, lutein cells, cervical cells, endometrial cells, mammary cells, follicle cells, mucous cells, ciliated cells, nonkeratinized epithelial cells, keratinized epithelial cells, lung cells, goblet cells, columnar epithelial cells, dopamiergic cells, squamous epithelial cells, osteocytes, osteoblasts, osteoclasts, dopaminergic cells, embryonic stem cells, fibroblasts and fetal fibroblasts. Further, the one or more cells can be pancreatic islet cells and/or cell clusters or the like, including, but not limited to pancreatic a cells, pancreatic R cells, pancreatic 6 cells, pancreatic F cells (e.g., PP cells), or pancreatic F cells. In one instance, the one or more cells can be pancreatic a cells. In another instance, the one or more cells can be pancreatic R cells.

A donor can be at any stage of development including, but not limited to, fetal, neonatal, young and adult. For example, donor T cells can be isolated from an adult human. Donor human T cells can be under the age of 10, 9, 8, 7, 6, 5, 4, 3, 2, or 1 year(s). For example, T cells can be isolated from a human under the age of 6 years. T cells can also be isolated from a human under the age of 3 years. A donor can be older than 10 years.

The instant disclosure also provides materials and methods comprising modified polynucleotides and methods of using such polynucleotides for ameliorating one or more symptoms or complications associated with human genetic diseases. For example, the method can comprise genome editing using the polynucleotides.

Disclosed herein is also a method of genomically editing a target polynucleic acid utilizing the system, the polypeptide, or the polynucleic acid described herein. The method of modifying a target polynucleic acid can comprise (a) contacting the target polynucleic acid with an Ago polypeptide and a guiding polynucleic acid and (b) modifying the target polynucleic acid. For example, the method can comprise introducing the Ago system or the fusion polypeptide into a cell that contains the target polynucleic acid. For another example, the method can comprise introducing into a cell the system that comprises an Ago and a nucleic acid unwinding polypeptide. The Ago and the polynucleic acid unwinding polypeptide can be introduced into the cell individually or as a fused polypeptide. The method can also comprise introducing into the cell the described polynucleic acid. As described herein, the Ago system, the fusion polypeptide, and/or the polynucleotides encoding the same can be delivered, i.e., introduced, into a cell by any suitable means such as vectors and lipid nanoparticles.

In some cases, the method also comprises contacting the target polynucleic acid with a protein expressed by a gene of the microbiome prokaryotic organism located in an adjacent operon to a gene encoding the Ago polypeptide. The gene located in an adjacent operon can be one that is involved in defense, stress response, a Clustered Regularly Interspaced Short Palindromic Repeats (CRISPR), DNA replication, DNA recombination, DNA repair, and transcription.

The instant disclosure describes a method of identifying an Ago polypeptide. The method of identifying an Ago polypeptide can comprise comparing the genome sequences with a nucleic acid sequence of a known Ago polypeptide. The known Ago polypeptide can be a *Clostridium* Argonaute. The method of identifying an Ago polypeptide can comprise identifying a sequence that has 20% or more sequence identity to the nucleic acid sequence of a known Ago polypeptide, as measured by Needleman-Wunsch algorithm. In some cases, the identified sequence encodes an Ago polypeptide having at least 900 amino acid residues.

XIII. KITS

Disclosed herein can be kits comprising the compositions, the Ago, the fusion polypeptides, the polynucleic acid, or any combination thereof. Disclosed herein can also be kits for the treatment or prevention of a cancer, pathogen infection, immune disorder or allogeneic transplant. The kit can comprise a disclosed Ago system. The kit can comprise a fusion polypeptide comprising the Ago. The kit can comprise a herein described polynucleic acid, such as one that encodes the Ago or the fusion polypeptide. The kit can comprise one or more of the cells. The kit can also comprise the pharmaceutical composition. The kit can further comprise instructions for using the component therein.

In one embodiment, the kit can include a therapeutic or prophylactic composition containing an effective amount of a composition of nuclease modified cells in unit dosage form. In some cases, the kit comprises one or more sterile containers, which can be boxes, ampules, bottles, vials, tubes, bags, pouches, blister-packs, or other suitable container forms known in the art. Such containers can be made of plastic, glass, laminated paper, metal foil, or other materials suitable for holding medicaments. In some cases, Ago modified cells can be provided together with instructions for administering the cells to a subject having or at risk of developing a cancer, pathogen infection, immune disorder or allogeneic transplant. Instructions can generally include information about the use of the composition for the treatment or prevention of cancer, pathogen infection, immune disorder or allogeneic transplant. In some cases, a kit can include from about $1\times10^4$ cells to about $1\times10^{12}$ cells. In some cases a kit can include at least about $1\times10^5$ cells, at least about $1\times10^6$ cells, at least about $1\times10^7$ cells, at least about $4\times10^7$ cells, at least about $5\times10^7$ cells, at least about $6\times10^7$ cells, at least about $6\times10^7$ cells, at least about $8\times10^7$ cells, at least about $9\times10^7$ cells, at least about $1\times10^8$ cells, at least about $2\times10^8$ cells, at least about $3\times10^8$ cells, at least about $4\times10^8$ cells, at least about $5\times10^8$ cells, at least about $6\times10^8$ cells, at least about $6\times10^8$ cells, at least about $8\times10^8$ cells, at least about $9\times10^8$ cells, at least about $1\times10^9$ cells, at least about $2\times10^9$ cells, at least about $3\times10^9$ cells, at least about $4\times10^9$ cells, at least about $5\times10^9$ cells, at least about $6\times10^9$ cells, at least about $6\times10^9$ cells, at least about $8\times10^9$ cells, at least about $9\times10^9$ cells, at least about $1\times10^{10}$ cells, at least about $2\times10^{10}$ cells, at least about $3\times10^{10}$ cells, at least about $4\times10^{10}$ cells, at least about $5\times10^{10}$ cells, at least about $6\times10^{10}$ cells, at least about $6\times10^{10}$ cells, at least about $8\times10^{10}$ cells, at least about $9\times10^{10}$ cells, at least about $1\times10^{11}$ cells, at least about $2\times10^{11}$ cells, at least about $3\times10^{11}$ cells, at least about $4\times10^{11}$ cells, at least about $5\times10^{11}$ cells, at least about $6\times10^{11}$ cells, at least about $6\times10^{11}$ cells, at least about $8\times10^{11}$ cells, at least about $9\times10^{11}$ cells, or at least about $1\times10^{12}$ cells. For example, about $5\times10^{10}$ cells can be included in a kit. In another example, a kit can include $3\times10^{6}$ cells; the cells can be expanded to about $5\times10^{10}$ cells and administered to a subject.

In some cases, a kit can include allogenic cells. In some cases, a kit can include cells that can comprise a genomic modification. In some cases, a kit can comprise "off-the-shelf" cells. In some cases, a kit can include cells that can be expanded for clinical use. In some cases, a kit can contain contents for a research purpose.

In some cases, the instructions include at least one of the following: description of the therapeutic agent; dosage schedule and administration for treatment or prevention of a neoplasia, pathogen infection, immune disorder or allogeneic transplant or symptoms thereof; precautions; warnings; indications; counter-indications; overdosage information; adverse reactions; animal pharmacology; clinical studies; and/or references. The instructions can be printed directly on the container (when present), or as a label applied to the container, or as a separate sheet, pamphlet, card, or folder supplied in or with the container. In some cases, instructions provide procedures for administering nuclease modified cells at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or up to 2 days, 3 days, 4 days, 5 days, 6 days, or 7 days after administering a chemotherapeutic agent. In some cases, instructions provide procedures for administering engineered cells at least 24 hours after administering a chemotherapeutic agent. Nuclease modified cells can be formulated for intravenous injection. Nuclease modified cells can be formulated for infusion. In some cases a kit can contain products at a pediatric dosage.

Further uses of the methods, compositions, or kits described herein can include one or more of the following: genome editing, transcriptional or epigenetic regulation, genome imaging, copy number analysis, analysis of living cells, detection of highly repetitive genome sequence or structure, detection of complex genome sequences or structures, detection of gene duplication or rearrangement, enhanced FISH labeling, unwinding of target nucleic acid, large scale diagnostics of diseases and genetic disorders related to genome deletion, duplication, and rearrangement, use of an RNA oligo chip with multiple unique gRNAs or gDNAs for high-throughput imaging and/or diagnostics, multicolor differential detection of target sequences, identification or diagnosis of diseases of unknown cause or origin, and 4-dimensional (e.g., time-lapse) or 5-dimensional (e.g., multicolor time-lapse) imaging of cells (e.g., live cells), tissues, or organisms.

EXAMPLES

Example 1. Identification of Clostridia Argonautes

Figure 1:
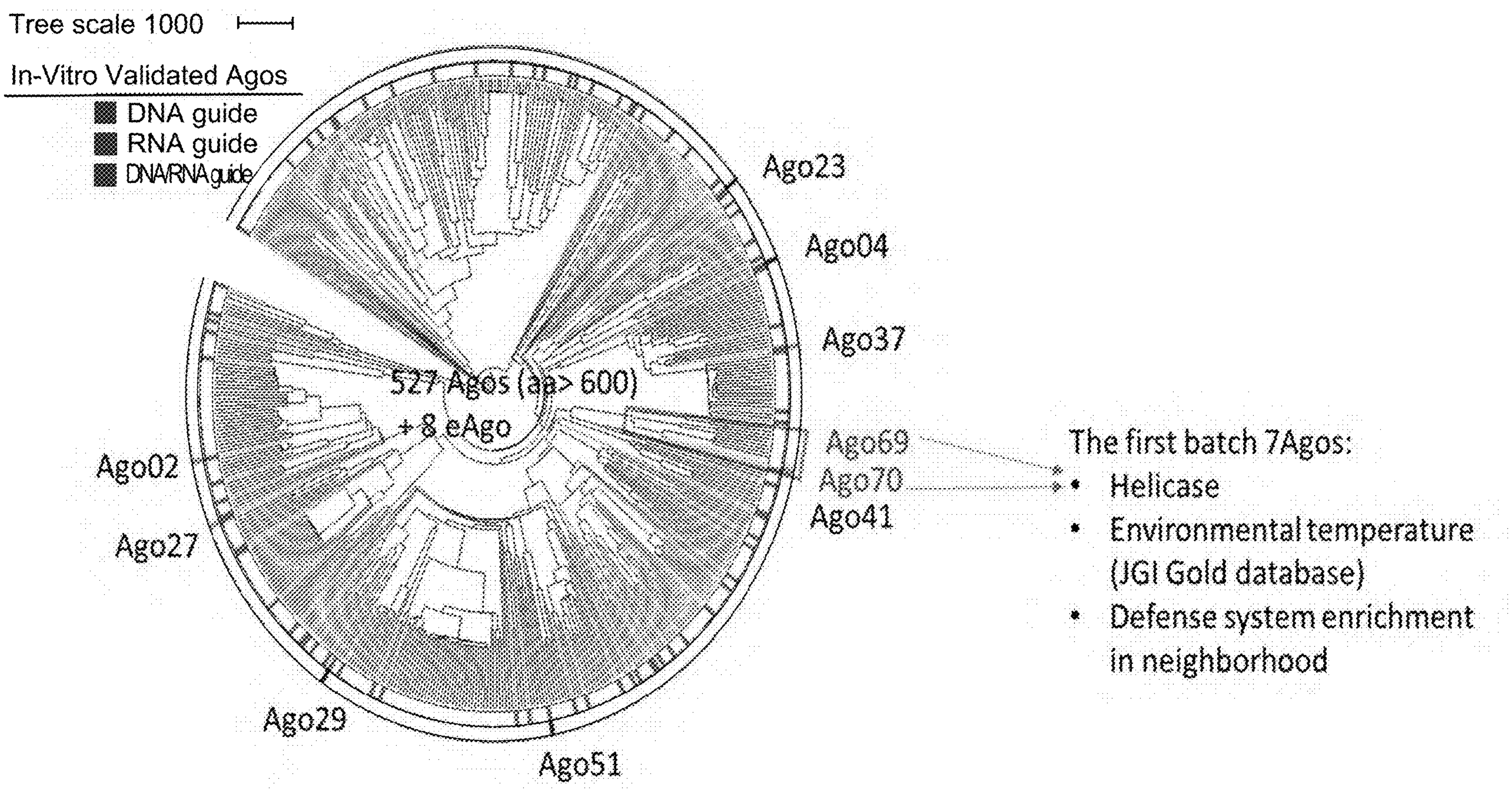
FIG. 1 shows the argonaute phylogenetic tree (1,091 Agos; NCBI marked with in-vitro validated Agos). Of the branch representatives 80 were selected and 8/8 (10%) were validated in vitro. A refined selection of 7 Agos was made, 2 of which (28.5%) were validated in vitro.
Figure 2:
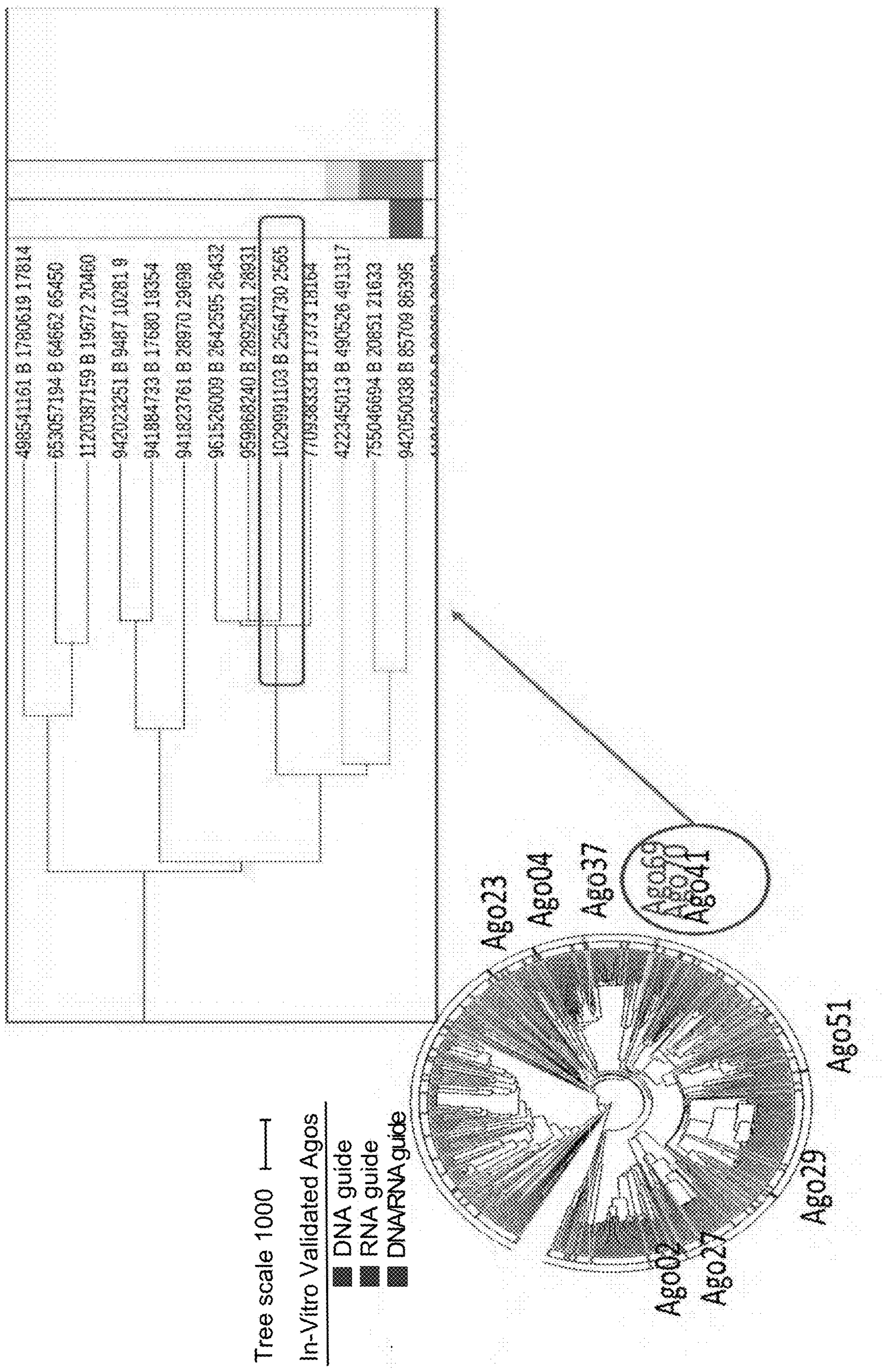
FIG. 2 shows the argonaute 41/69/70 branch of 13 Agos.
Figure 6:
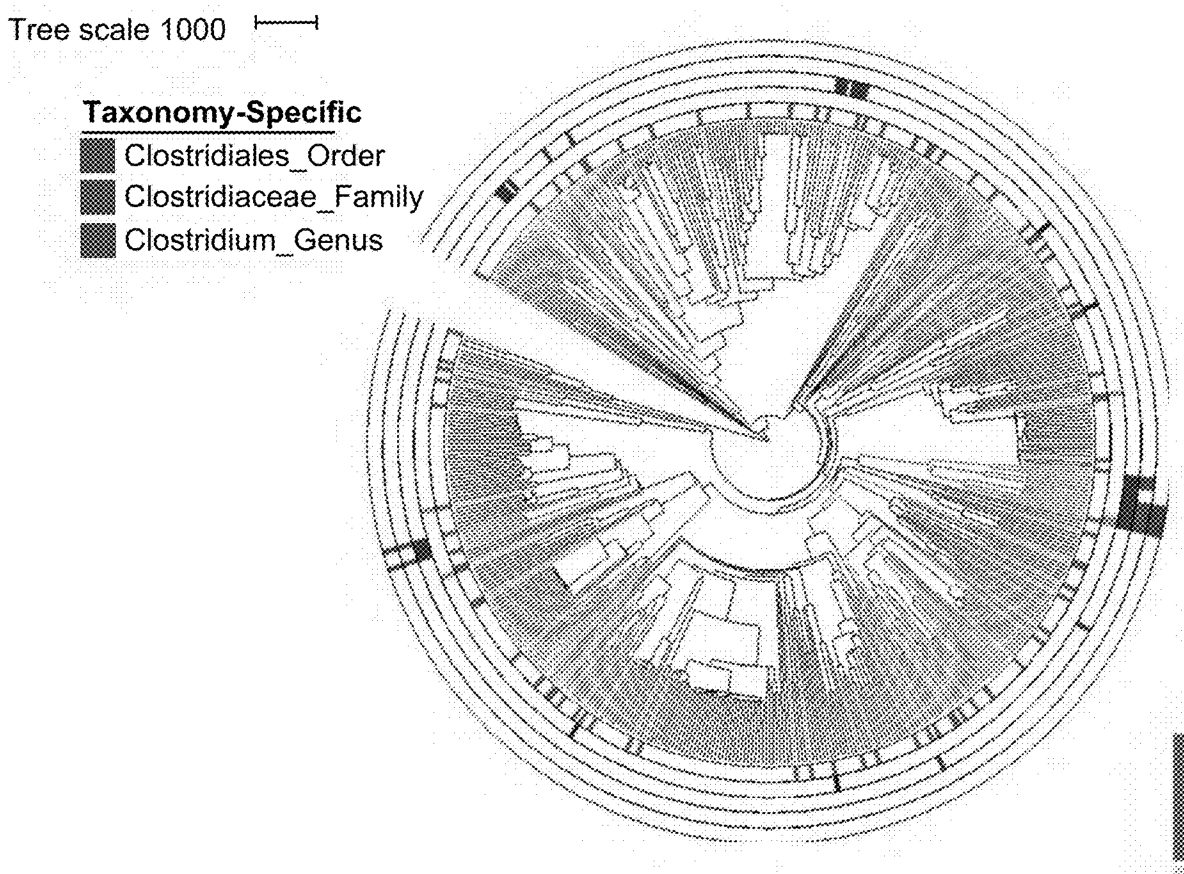
FIG. 6 shows the taxonomy-specificity of the Ago41 branch, showing Clostridiaceae family associated Agos are enriched in Ago41 branch.
Figure 7:
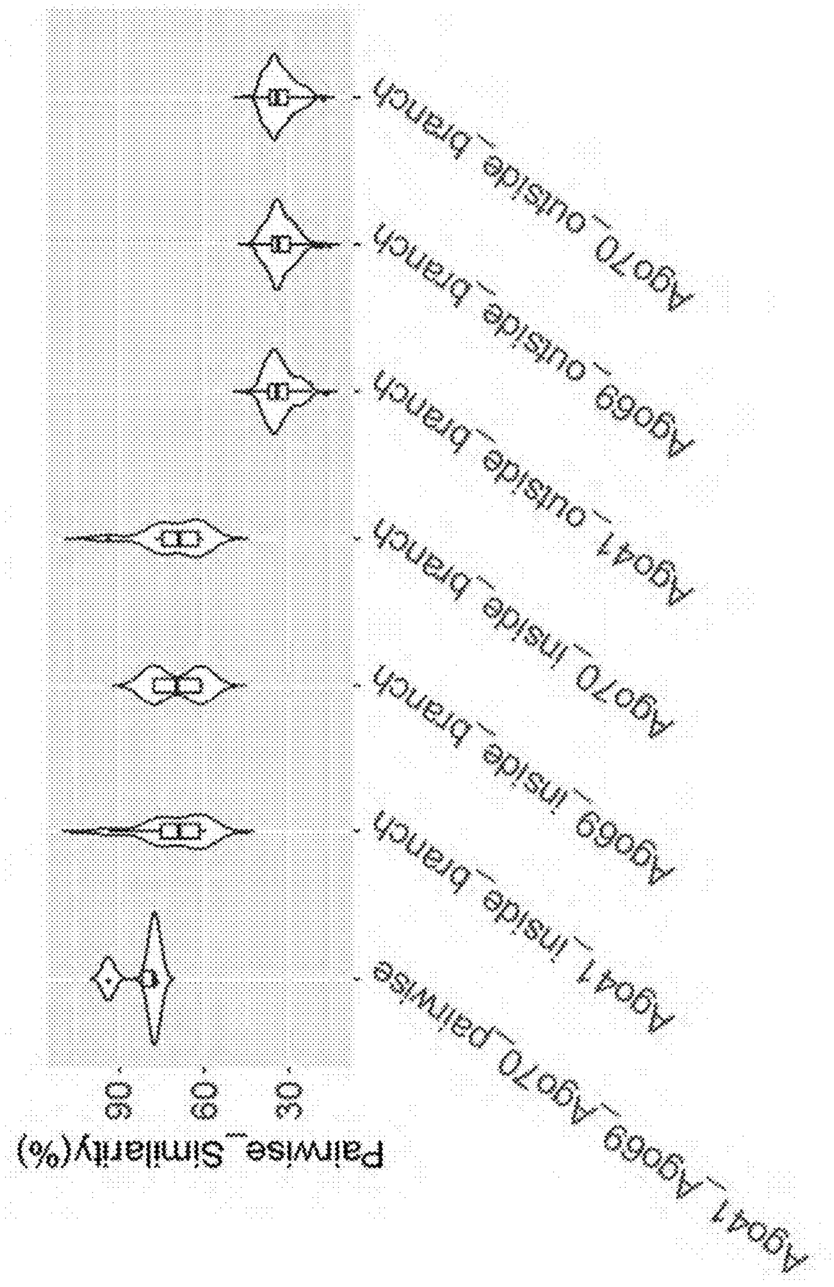
FIG. 7 shows the sequence-specificity for the Ago41 branch, based on a Needleman-Wunsch algorithm for global sequence pairwise comparison.

Argonautes of class Clostridia were identified as phylogenetic branch Ago41/69/70 (FIG. 2), including taxonomy (FIG. 3) and host and environmental information gathered from JGI database (FIG. 4). The exemplary taxonomy-specificity of the Ago41 branch is presented in FIG. 5 and FIG. 6. The sequence specificity for the Ago41/69/70 branch was determined and a pairwise sequence comparison using the Needleman-Wunsch algorithm for global sequence pairwise comparison was conducted (FIG. 7). The amino acid sequence and nucleic acid sequence of Clostridia Agos, Ago69, Ago41, and Ago70, were determined and are disclosed in Table 1 (amino acid sequences) and Table 2 (nucleic acid sequences).

Example 2. Cleavage of ssDNA by Clostridia Argonautes

Figure 8:
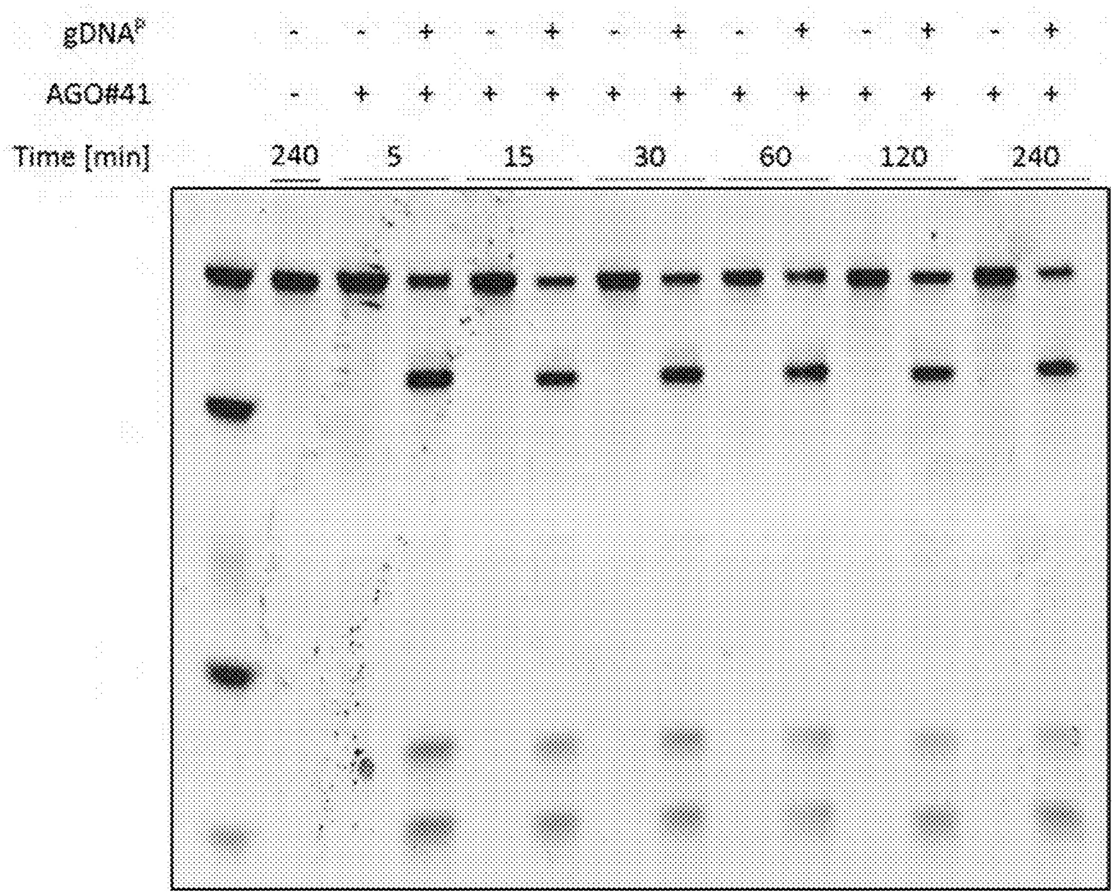
FIG. 8 shows an image of an electrophoresis gel showing a time course of the cleavage of single stranded DNA (ssDNA) by Ago41 with guide DNA (gDNA). Time course ranged from 5-240 minutes. "gDNA$^P$" indicates the 5' most nucleotide of the gDNA is phosphorylated.

The cleavage of single stranded DNA (ssDNA) by Ago41 with a guide DNA (gDNA) was tested. The reaction buffer contained 20 mM Tris/HCl at pH7.5, 125 mM NaCl, 5 mM $MnCl_2$, 1.6 mM b-MeOH, and 0.3% BSA. The template (T1) was a 90 nucleotide ssDNA with expected cleavage products of 66 nucleotides and 24 nucleotides. The Ago41:gDNA:Template were added at a ratio 1:1:1 (equaling 250 nM:250 nM:250 nM). The time course included two replicates of 5 minutes, 15 minutes, 30 minutes, 60 minutes, 120 minutes, and 240 minutes. The gDNA was preloaded with Ago41 by incubation of the gDNA and Ago41 protein at 37° C. for 15 min. As shown in FIG. 8, Ago41 is able to cleave ssDNA at each time point tested.

Figure 9:
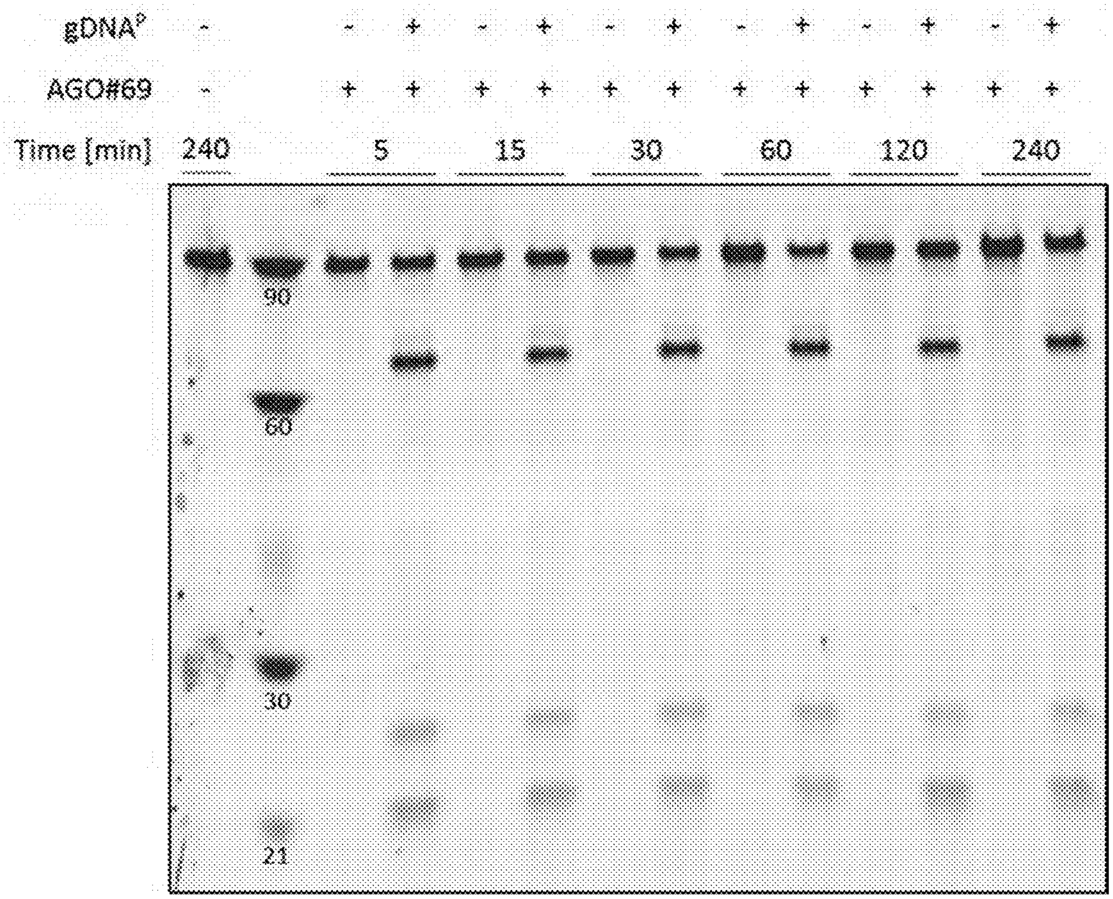
FIG. 9 shows an image of an electrophoresis gel showing a time course of the cleavage of single stranded DNA (ssDNA) by Ago69 with guide DNA (gDNA). Time course ranged from 5-240 minutes. "gDNA$^P$" indicates the 5' most nucleotide of the gDNA is phosphorylated.

The cleavage of single stranded DNA (ssDNA) by Ago69 with a guide DNA (gDNA) was also tested. The reaction buffer contained 20 mM Tris/HCl at pH7.5, 125 mM NaCl, 5 mM $MnCl_2$, 1.6 mM b-MeOH, and 0.3% BSA. The template (T1) was a 90 nucleotide ssDNA with expected cleavage products of 66 nucleotides and 24 nucleotides. The Ago41:gDNA:Template were added at a ratio 1:1:1 (equaling 250 nM:250 nM:250 nM). The time course included two replicates of 5 minutes, 15 minutes, 30 minutes, 60 minutes, 120 minutes, and 240 minutes. The gDNA was preloaded with Ago41 by incubation of Ago69 and gDNA at 37° C. for 15 min. As shown in FIG. 9, Ago69 is able to cleave ssDNA at each time point tested.

Figure 10:
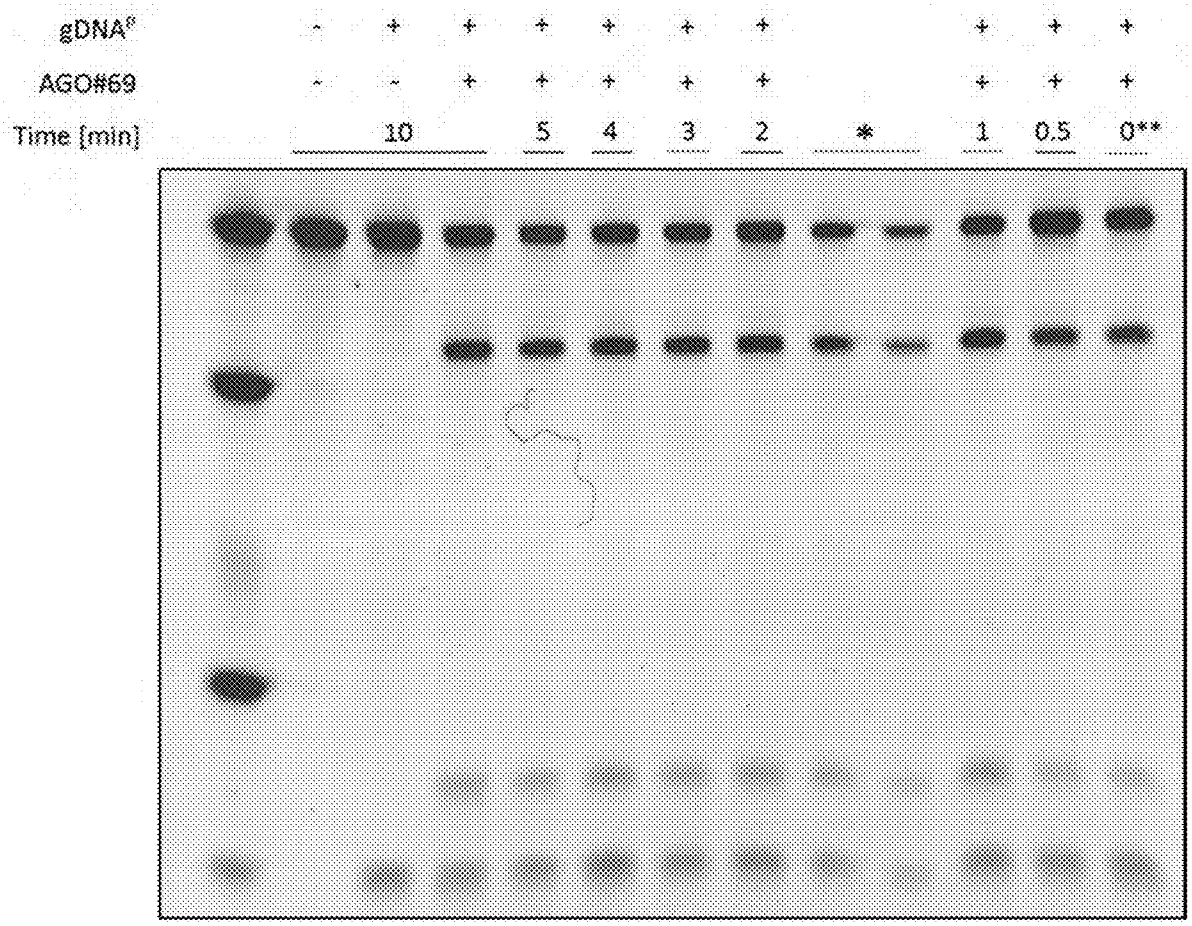
FIG. 10 shows an image of an electrophoresis gel showing a time course of cleavage of single stranded DNA (ssDNA) by Ago69 with guide DNA (gDNA). Time course ranged from 0-10 minutes. "gDNA$^P$" indicates the 5' most nucleotide of the gDNA is phosphorylated.

The cleavage of single stranded DNA (ssDNA) by Ago69 with a guide DNA (gDNA) was tested as above, but with varying cleavage times. The time course included two replicates of 0 minutes, 0.5 minutes, 1 minute, 60 minutes, 2 minutes, 3 minutes, 4 minutes, 5 minutes, and 10 minutes. The reaction buffer contained 20 mM Tris/HCl at pH7.5, 125 mM NaCl, 5 mM $MnCl_2$, 1.6 mM b-MeOH, 0.3% BSA. The template (T1) was a 90 nucleotide ssDNA with expected cleavage products of 66 nucleotides and 24 nucleotides. The Ago41:gDNA:Template were added at a ratio 1:1:1 (equaling 250 nM:250 nM:250 nM). The gDNA was preloaded with Ago69 by incubation of the gDNA and Ago69 protein at 37° C. for 15 min. As shown in FIG. 10, the Ago69 is able to cleave ssDNA at each time point tested. Cleavage at the 0 minute time point reflects that it take several seconds stop the reaction.

Example 3. The Effect of Mutating DEDX Domain in Clostridia Argonautes

The effect of mutating the DEDX domain of Ago41 on Ago41 mediated cleavage of ssDNA with guide DNA (gDNA) was evaluated. The cleavage assay was allowed to proceed for 1 hour with ssDNA template, gDNA, and either wild type (WT) Ago41 or mutant Ago41. The ssDNA template is 90 nucleotides in length with expected cleavage products of 64 and 24 nucleotides each. The mutated Ago41 (MUT) contained the following amino acid substitutions in the DEDX domain: D559A, E595A, and D629A. The template DNA was 90 nucleotides in length. The results show that inclusion of the MUT Ago41 inhibited Ago41 mediated cleavage of the template ssDNA (FIG. 48). This suggests that the catalytic activity of Ago41 (e.g., as shown in Example 2) is dependent on the known intact catalytic domain of the Ago.

The corresponding mutation sites used in Ago41 (DEDX domain) were mapped for Ago69 and presented in FIG. 49. These include D544A, E580A, and D730A. Potential additional mutations sites we also mapped on Ago69, including conserved lysine residues putatively involved in DNA binding specificity (FIG. 50).

Figure 11:
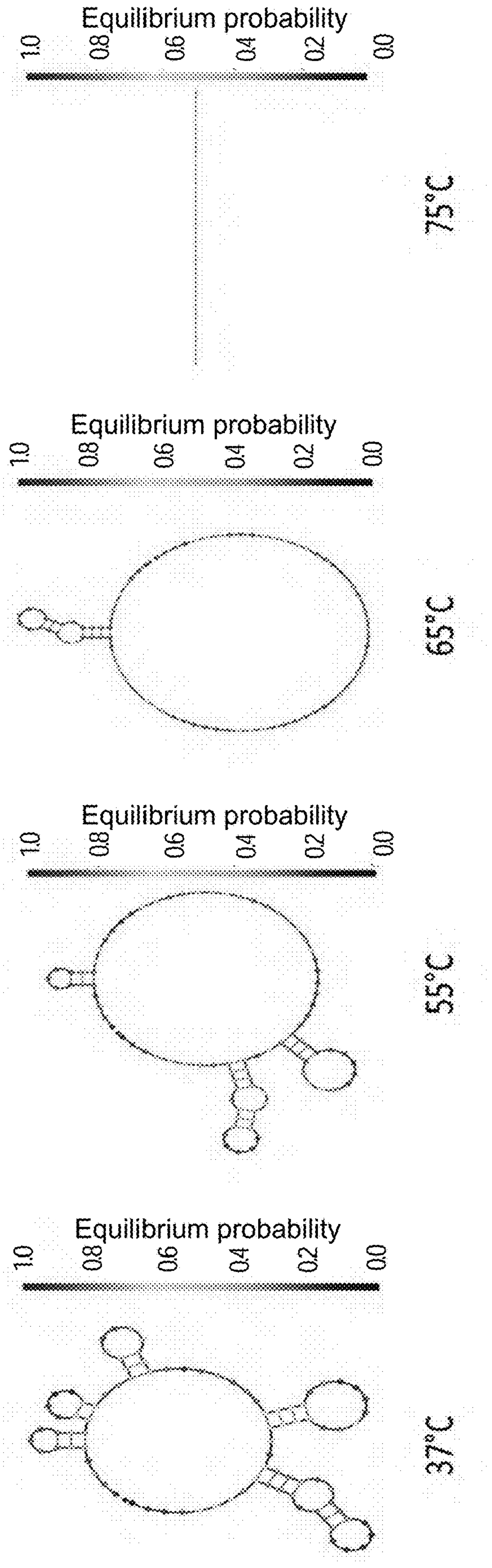
FIG. 11 is a graphic depiction showing the effect of temperature on single stranded DNA (ssDNA) template structure (NUPAK), with temperatures of 37° C., 55° C., 65° C., and 75° C.
Figure 12:
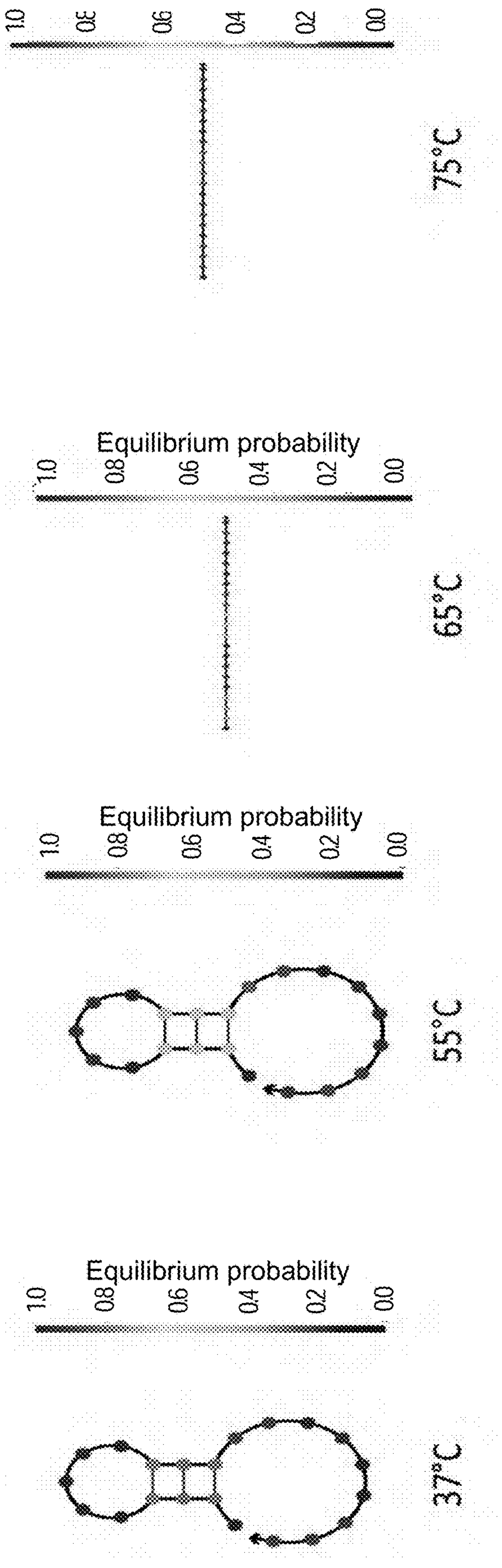
FIG. 12 is a graphic depiction showing the effect of temperature on single stranded DNA (ssDNA) guide structure (NUPAK), with temperatures of 37° C., 55° C., 65° C., and 75° C.

Example 4. The Effect of Temperature on Secondary Structure of ssDNA Template and gDNA The effect of temperature changes on the structure of single stranded DNA (ssDNA) template was analyzed by NUPAK. As shown in FIG. 11, increasing temperature to each of 37° C., 55° C., 65° C., and 75° C. changes (e.g., decreases the number of) secondary structures in the ssDNA template sequence, with no secondary structures present at 75° C. The effect of temperature changes on the structure of gDNA was also analyzed by NUPAK. As shown in FIG. 12, increasing the temperature to each of 37° C., 55° C., 65° C., and 75° C. changes (e.g., decreases the number of) secondary structures in the ssDNA template sequence, with no secondary structures present at 65° C. or 75° C.

Example 5. The Effect of Temperature on Clostridia Ago Cleavage

The effect of temperature on single strand DNA (ssDNA) cleavage by Ago69 with a ssDNA guide (gDNA) was analyzed. The gDNA was preloaded with Ago69 by incubation of the gDNA and Ago69 protein at 37° C. for 15 min. The target ssDNA was added to the reaction for 15 minutes at 25° C., 37° C., 42.1° C., 46.5° C., 55° C., 65° C., and 75° C., with a subsequent denaturation step utilizing TBE/Urea sample buffer. The nucleic acids were then resolved by gel electrophoresis. The reaction buffer used contained 20 mM Tris/HCl at pH7.5, 125 mM NaCl, 5 mM MnCl2, 1.6 mM b-MeOH, and 0.3% BSA. The template (T1) was a 90 nucleotide ssDNA with expected cleavage products of 66 nucleotides and 24 nucleotides. The Ago41:gDNA:Template were added at a ratio 1:1:1 (equaling 250 nM:250 nM:250 nM). The results are shown in FIG. 13, with Ago69 cleaving at each temperature, including at physiological temperature of 37° C.

Figure 14:
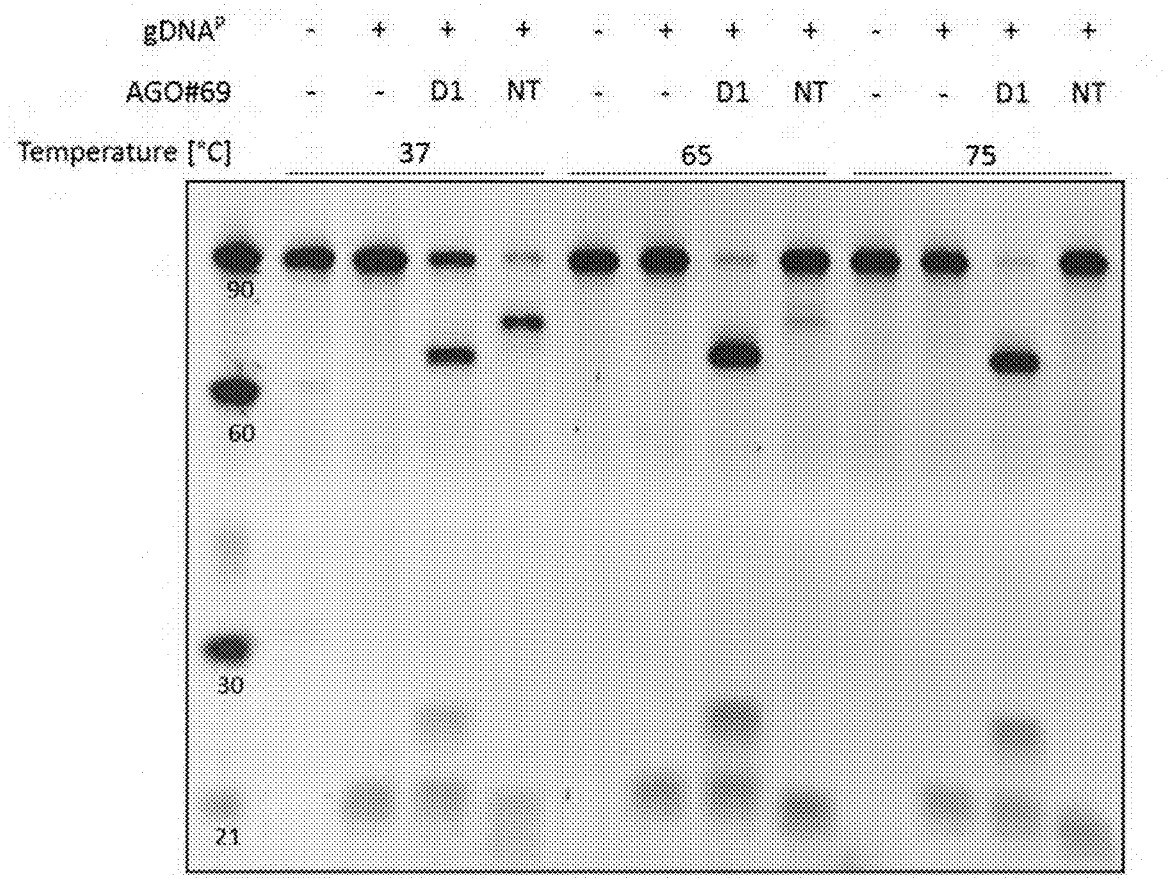
FIG. 14 shows an image of an electrophoresis gel showing single stranded DNA (ssDNA) cleavage by Ago69 at different temperatures with target (D) and non-target (NT) ssDNA guide. "gDNA$^P$" indicates the 5' most nucleotide of the gDNA is phosphorylated.

Cleavage of single strand DNA (ssDNA) by Ago69 at different temperatures with target (D) and non-target (NT) ssDNA guides was also analyzed. The target ssDNA was added to the reaction for 15 minutes at 37° C., 65° C., and 75° C., with a subsequent denaturation step utilizing TBE/Urea sample buffer. The nucleic acids were then resolved by gel electrophoresis. The reaction buffer used contained 20 mM Tris/HCl at pH7.5, 125 mM NaCl, 5 mM MnCl2, 1.6 mM b-MeOH, 0.3% BSA. The template (T1) was a 90 nucleotide ssDNA with expected cleavage products of 66 nucleotides and 24 nucleotides. The Ago41:gDNA:Template were added at a ratio 1:1:1 (equaling 250 nM:250 nM:250 nM). The results are shown in FIG. 14.

Figure 15A:
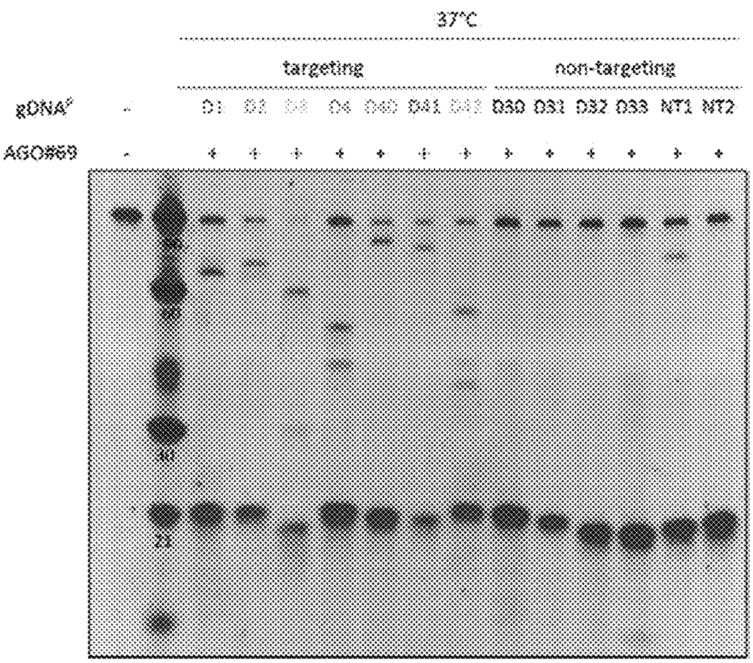
FIG. 15A shows an image of an electrophoresis gel showing single strand DNA (ssDNA) cleavage by Ago69 using different ssDNA guides. "gDNA$^P$" indicates the 5' most nucleotide of the gDNA is phosphorylated.
Figure 15B:
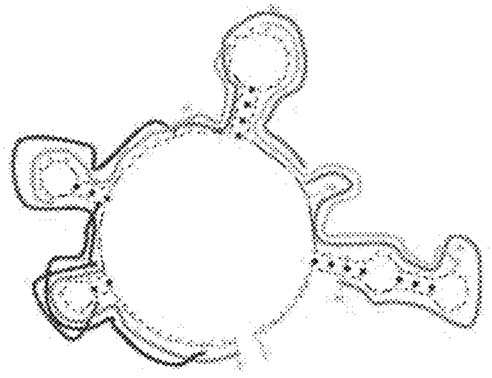
FIG. 15B shows the location of the ssDNA guides relative to ssDNA target sequence and secondary structure.

Example 6. The Effect of Unique ssDNA Guides on Clostridia Ago Cleavage of ssDNA The effect using different ssDNA guides on Ago69 cleavage of ssDNA was evaluated. The targeting guide DNAs as labeled D1, D2, D3, D4, D40, D41, D42, in FIG. 15A are shown in the corresponding map of the secondary structure of the nucleic acid in FIG. 15B. The non-targeting guide DNAs are labeled D30, D31, D32, D33, NT1, and NT2 in FIG. 15A. The results are presented in FIG. 15A.

Example 7. The Effect of Clostridia Ago Denaturation on Cleavage

Figure 16:
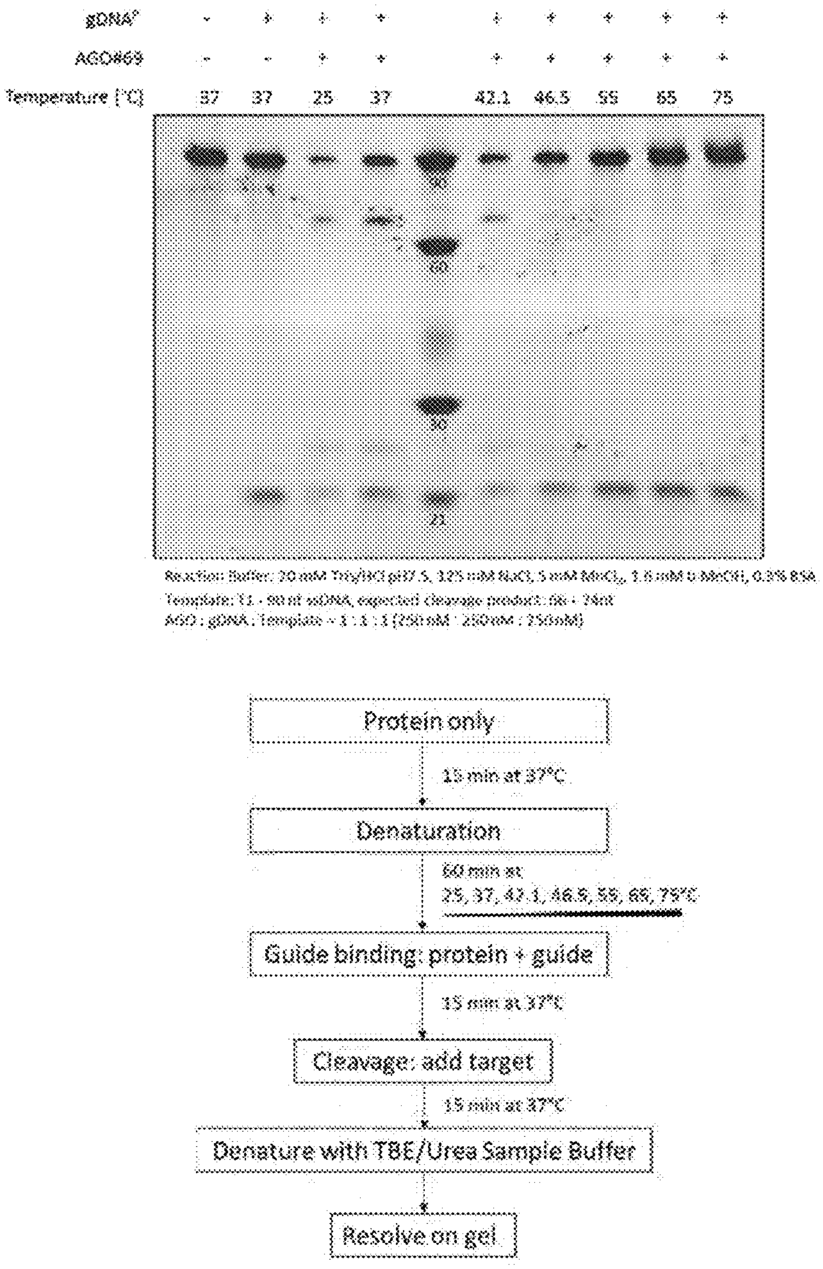
FIG. 16 shows an image of an electrophoresis gel showing single stranded DNA (ssDNA) cleavage by Ago69 after denaturation before ssDNA guide binding. "gDNA$^P$" indicates the 5' most nucleotide of the gDNA is phosphorylated.

The effect of denaturing Ago69 before gDNA binding on cleavage of ssDNA cleavage was evaluated. The Ago69 alone was incubated for 15 minutes at 37° C. The Ago69 protein was then denatured by incubation for 60 minutes at 25° C., 37° C., 42.1° C., 46.5° C., 55° C., 65° C., and 75° C. The gDNA was loaded with Ago69 by incubation at 37° C. for 15 min. Then the target ssDNA was added and incubated at 37° C. for 15 min to allow for cleavage, with a subsequent denaturation step utilizing TBE/Urea sample buffer. The nucleic acids were then resolved by gel electrophoresis. The reaction buffer used contained 20 mM Tris/HCl at pH7.5, 125 mM NaCl, 5 mM MnCl2, 1.6 mM b-MeOH, and 0.3% BSA. The template (T1) was a 90 nucleotide ssDNA with expected cleavage products of 66 nucleotides and 24 nucleotides. The Ago41:gDNA:Template were added at a ratio 1:1:1 (equaling 250 nM:250 nM:250 nM). The results are shown in FIG. 16.

Figure 17:
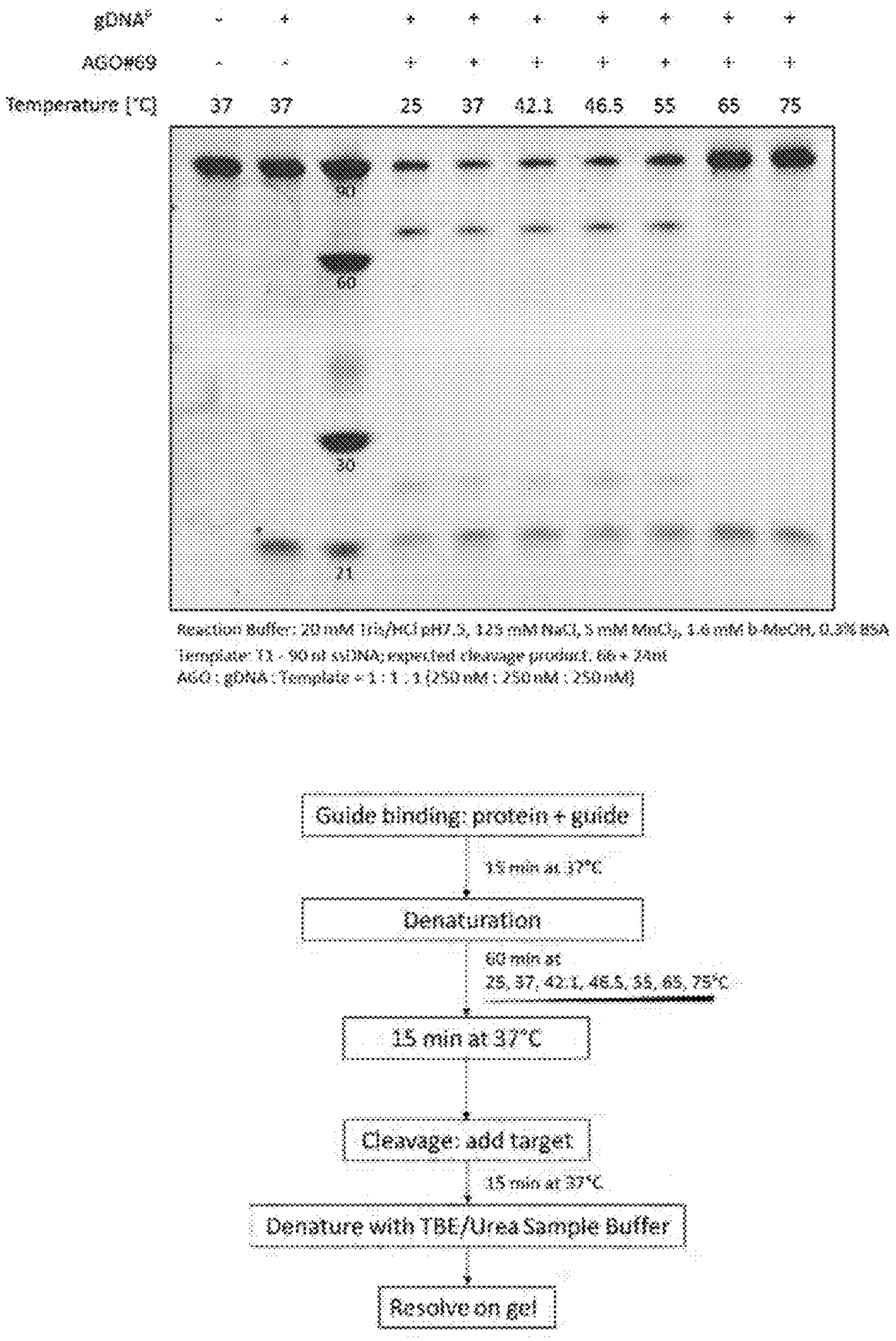
FIG. 17 shows an image of an electrophoresis gel showing single stranded DNA (ssDNA) cleavage by Ago69 after denaturation after ssDNA guide binding. "gDNA$^P$" indicates the 5' most nucleotide of the gDNA is phosphorylated.

The effect of denaturing Ago69 after gDNA binding on cleavage of ssDNA cleavage was evaluated. The gDNA was loaded with Ago69 by incubation at 37° C. for 15 min. The protein was then denatured by incubation for 60 minutes at 25° C., 37° C., 42.1° C., 46.5° C., 55° C., 65° C., and 75° C. Then the target ssDNA was added and incubated at 37° C. for 15 min to allow for cleavage, with a subsequent denaturation step utilizing TBE/Urea sample buffer. The nucleic acids were then resolved by gel electrophoresis. The reaction buffer used contained 20 mM Tris/HCl at pH7.5, 125 mM NaCl, 5 mM MnCl2, 1.6 mM b-MeOH, 0.3% BSA. The template (T1) was a 90 nucleotide ssDNA with expected cleavage products of 66 nucleotides and 24 nucleotides. The Ago41:gDNA:Template were added at a ratio 1:1:1 (equaling 250 nM:250 nM:250 nM). The results are shown in FIG. 17.

Example 8. Cleavage Activity of Ago41, 69, and 70

Figure 19:
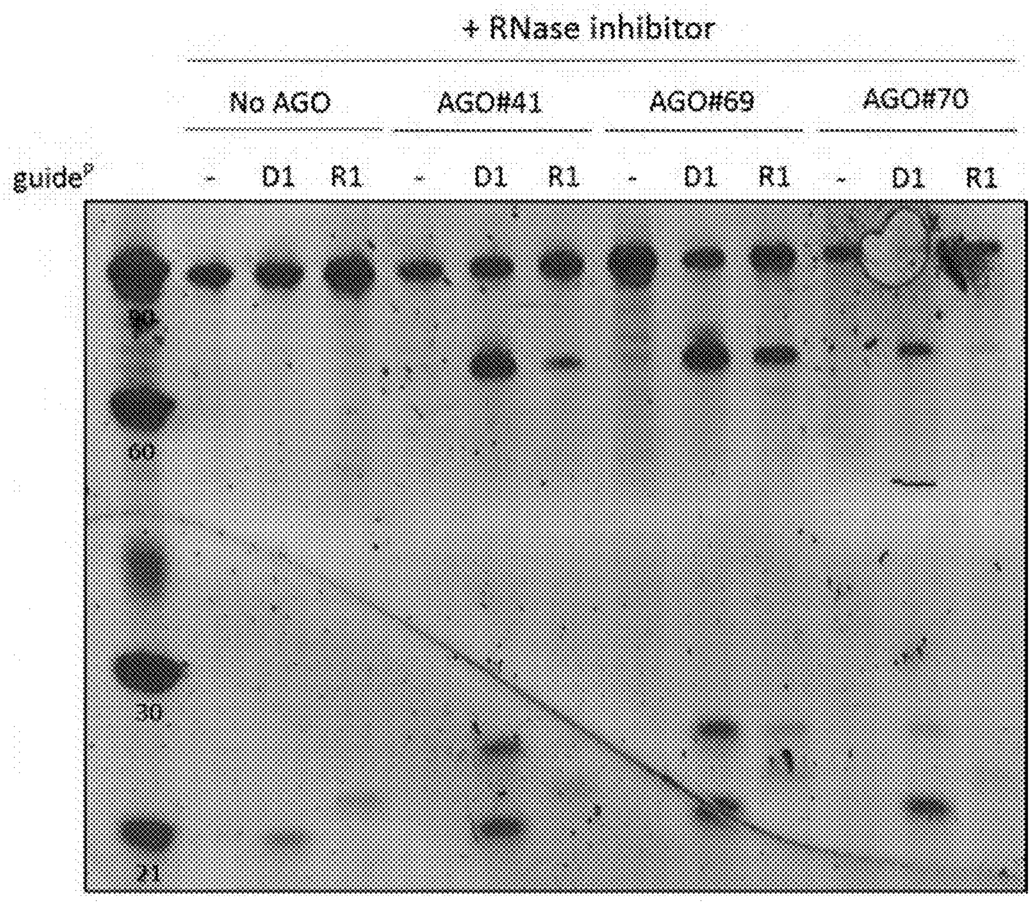
FIG. 19 shows an image of an electrophoresis gel showing single stranded DNA (ssDNA) cleavage by Ago41, Ago69, and Ago70 with ssDNA guide (D1) and ssRNA guide (R1). "gDNA$^P$" indicates the 5' most nucleotide of the gDNA is phosphorylated.

The ssDNA cleavage by Ago41, 69, and 70 with ssDNA guide (gDNA) (D1) or ssRNA guide (gRNA) (R1) was assessed according to methods described herein. The results are presented in FIG. 19, showing Ago41, 69, and 70 each catalyze ssDNA cleavage with gDNA (D1) or gRNA (R1).

Example 9. Cleavage of ssDNA by Clostridia Ago 69 with Guide RNA

Figure 20:
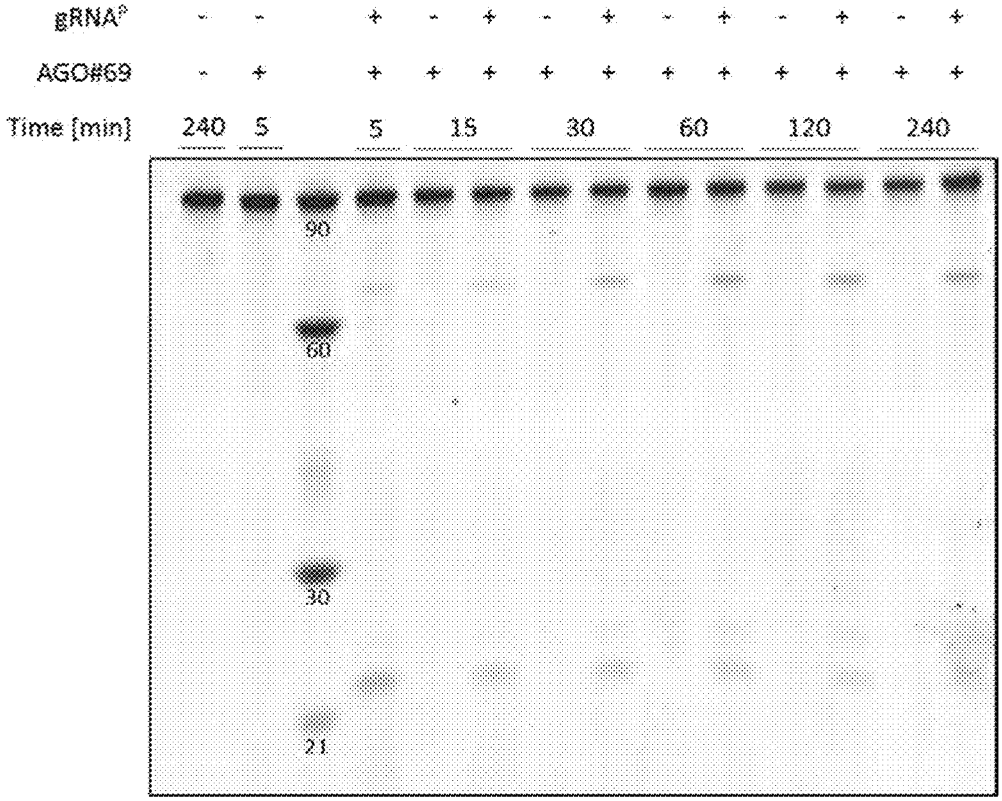
FIG. 20 shows an image of an electrophoresis gel showing single stranded DNA (ssDNA) cleavage by Ago69 with guide RNA (gRNA). "gDNA$^P$" indicates the 5' most nucleotide of the gDNA is phosphorylated.

The ability of Ago69 to cleave ssDNA with a guide RNA (gRNA) was evaluated. The reaction buffer used contained 20 mM Tris/HCl at pH7.5, 125 mM NaCl, 5 mM MnCl2, 1.6 mM b-MeOH, and 0.3% BSA. The template (T1) was a 90 nucleotide ssDNA with expected cleavage products of 66 nucleotides and 24 nucleotides. The guide RNA has phosphorothioate bonds on the 5' and 3' ends. The Ago41:gDNA: Template were added at a ratio 1:1:1 (equaling 250 nM: 250 nM:250 nM). The gDNA was loaded with Ago69 by incubation at 37° C. for 15 min. The cleavage reactions were allowed to proceed for 5 minus, 15 minutes, 30 minutes, 60 minutes, 120 minutes, or 240 minutes. The results are presented in FIG. 20, showing Ago69 mediated cleavage of the ssDNA at each time point measured.

Example 10. The Effect of Clostridia Ago Level and Guide DNA Length on Cleavage

Figure 25A:
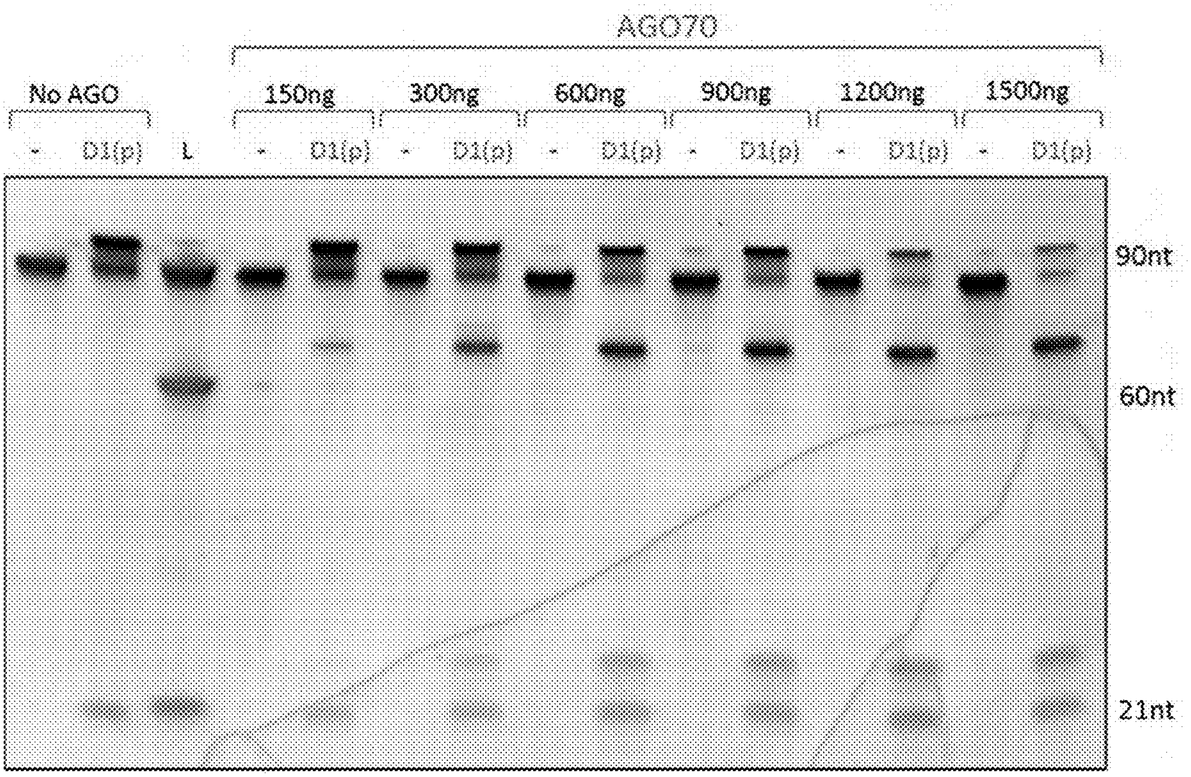
FIG. 25A shows an image of an electrophoresis gel showing the cleavage of single stranded DNA template (90 nucleotides) by Ago70 with guide DNA (gDNA) ranging in amount from 150 ng-1500 ng. "D1(p)" indicates the 5' most nucleotide of the gDNA is phosphorylated.

The effect of the level of Ago70 in a cleavage reaction was evaluated. The cleavage reactions were allowed to proceed for 1 hour. Template ssDNA of 90 nucleotides in length was used with a gDNA. The amount of Ago70 added to each cleavage reaction included 150 ng, 300 ng, 600 ng, 900 ng, 1200 ng, and 1500 ng. The results show a clear dose response with an increase in cleavage as the level of Ago70 increases, with saturation between 900 ng and 1200 ng of Ago70 (FIG. 25A).

Figure 25B:
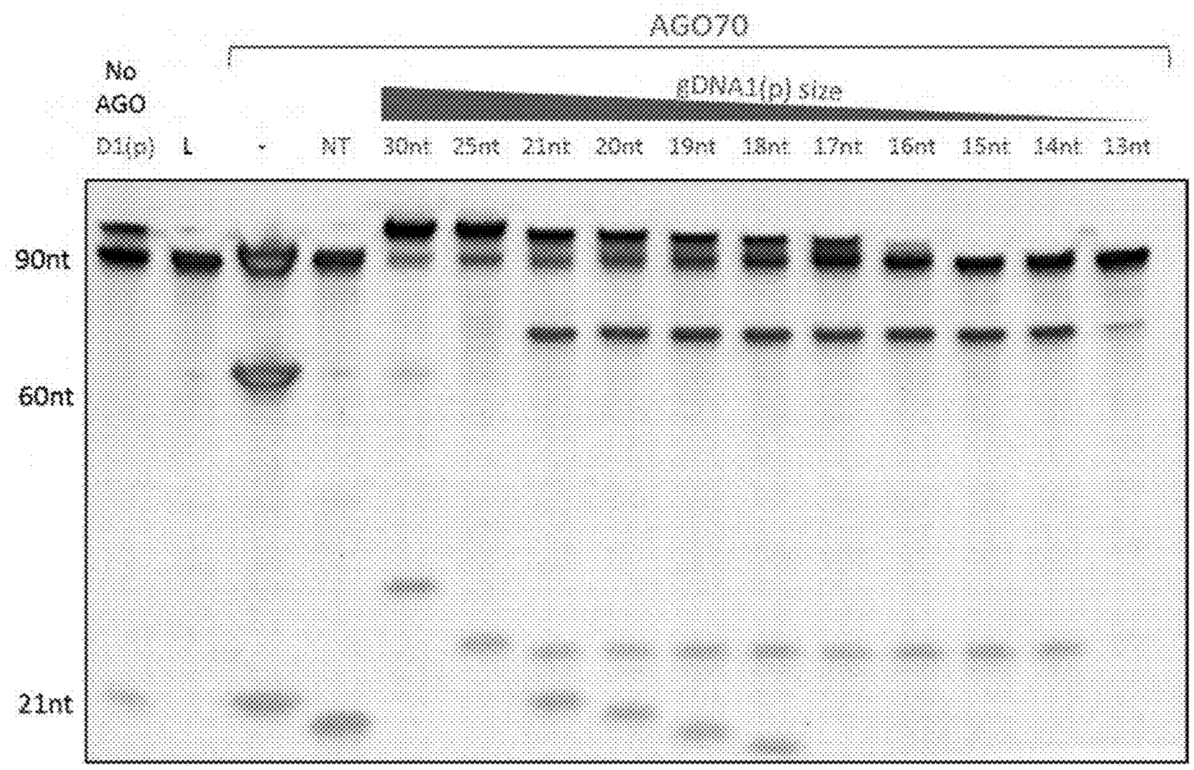
FIG. 25B shows an image of an electrophoresis gel showing cleavage of single stranded DNA template (90 nucleotides) by Ago70 with guide DNA (gDNA) ranging in length from 13-30 nucleotides. "D1(p)" indicates the 5' most nucleotide of the gDNA is phosphorylated.

The effect of the length of the guide DNA (gDNA) on Ago70 cleavage was also evaluated. The cleavage reactions were allowed to proceed for 1 hour. Template ssDNA of 90 nucleotides in length was used. The length of the gDNA used in each reaction included 30 nucleotides, 25 nucleotides, 21 nucleotides, 20 nucleotides, 19 nucleotides, 18 nucleotides, 17 nucleotides, 16 nucleotides, 15 nucleotides, 15 nucleotides, 14 nucleotides, and 13 nucleotides. The results show that Ago70 cleaves ssDNA with a gDNA of 14-21 nucleotides in length (FIG. 25B).

Example 11. Effect of Ionic Strength and Divalent Cation Concentration on Clostridia Ago Cleavage The effect of $Mg^{2+}$ and $Mn^{2+}$ concentration on Ago70 was evaluated. Cleavage was allowed to proceed for 1 hour with a template ssDNA of 90 nucleotides in all reactions and a gDNA. $MgCl_2$ concentrations were varied from 1 mM $MgCl_2$, 5 mM $MgCl_2$, 10 mM $MgCl_2$, 20 mM $MgCl_2$. In a separate experiment, $MnCl_2$ concentrations were varied from 1 mM $MnCl_2$, 5 mM $MnCl_2$, 10 mM $ngCl_2$, 20 mM $MnCl_2$. The results show no obvious sensitivity of Ago70 to the $Mg^{2+}$ (FIG. 26A) or $Mn^{2+}$ (FIG. 26B) at concentrations tested.

The effect of NaCl concentration was evaluated for Ago70 mediated cleavage of ssDNA with a DNA guide. The NaCl concentrations tested included 50 mM, 125 mM, 250 mM, and 500 mM. Template ssDNA 90 nucleotides in length was used in all reactions. Cleavage was allowed to proceed for 1 hour. The results show no obvious sensitive of Ag70 to the $NaCl_2$ concentrations tested (FIG. 27).

Figure 21A:
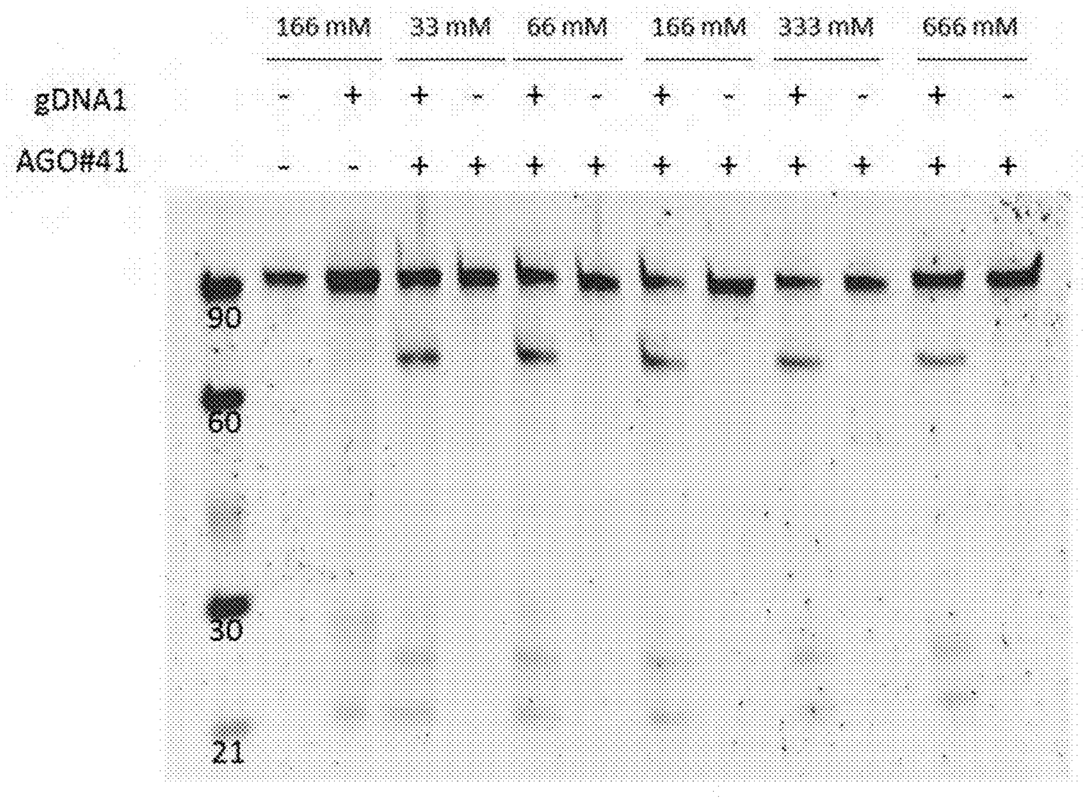
FIG. 21A shows an image of an electrophoresis gel showing optimization of NaCl concentration during cleavage by Ago 41 with guide DNA (gDNA).
Figure 21B:
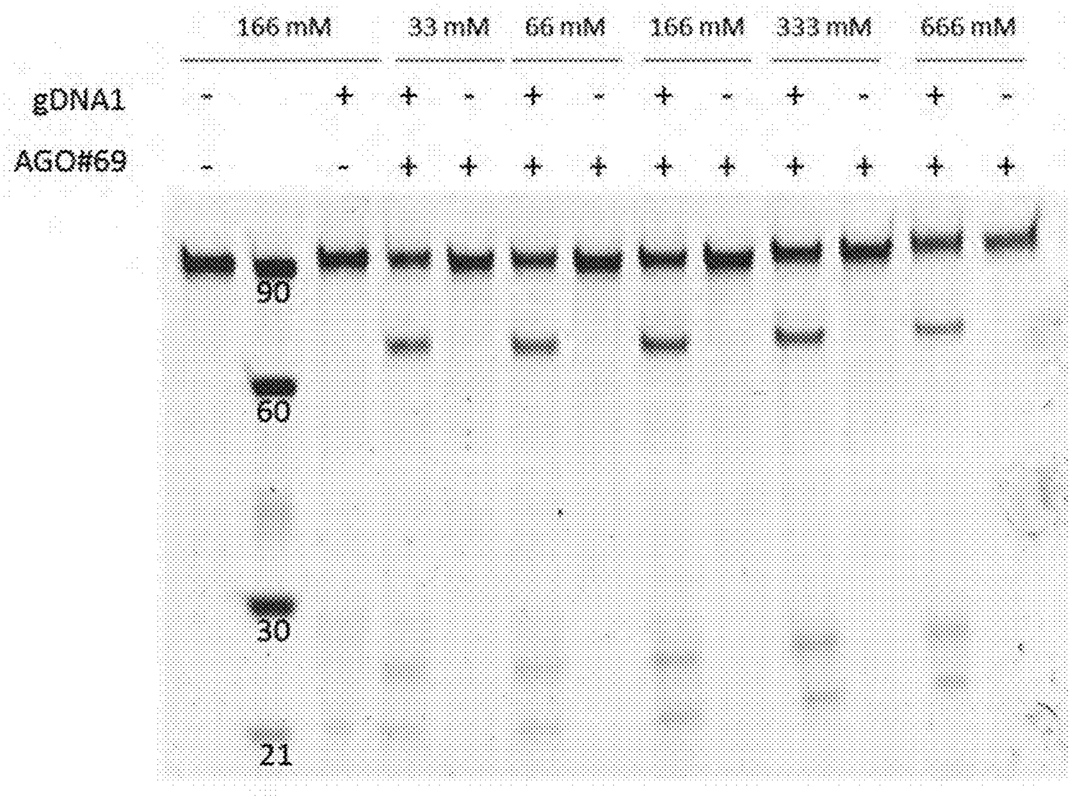
FIG. 21B shows an image of an electrophoresis gel showing optimization of NaCl concentration during cleavage by Ago69 with guide DNA (gDNA).

The effect of NaCl concentration on Ago 41 and Ago69 mediated cleavage of ssDNA with a gDNA was also evaluated. The NaCl concentrations tested included 666 mM, 333 mM, 166 mM, 66 mM, or 33 mM. The results are presented in FIG. 21.

Example 12. Analysis of Mesophilic Ago Using Guide DNA—Ago02

Figure 22A:
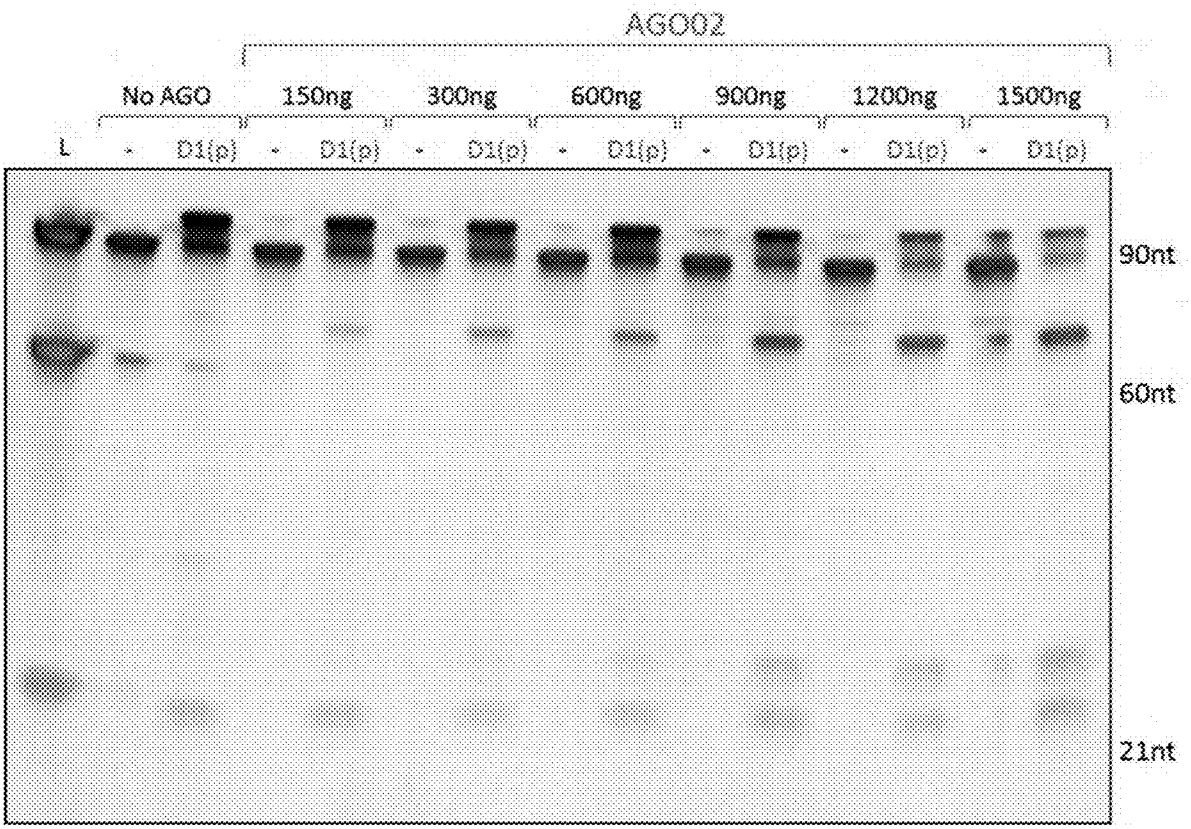
FIG. 22A shows an image of an electrophoresis gel showing the cleavage of single stranded DNA template (90 nucleotides) by Ago02 with guide DNA (gDNA) with different levels of Ago02. The level of Ago02 added to each reaction is 150 ng, 300 ng, 600 ng, 900 ng, 1200 ng, and 1500 ng. "D1(p)" indicates the 5' most nucleotide of the gDNA is phosphorylated.

The effect of the level of Ago02 on cleavage of ssDNA was evaluated. The cleavage reactions were allowed to proceed for 1 hour. Template ssDNA of 90 nucleotides in length was used. The amount of Ago02 added to each cleavage reaction included 150 ng, 300 ng, 600 ng, 900 ng, 1200 ng, and 1500 ng. The results show a clear dose response with an increase in cleavage as the level of Ago70 increases, with no saturation at the concentrations of Ago20 tested (FIG. 22A).

Figure 22B:
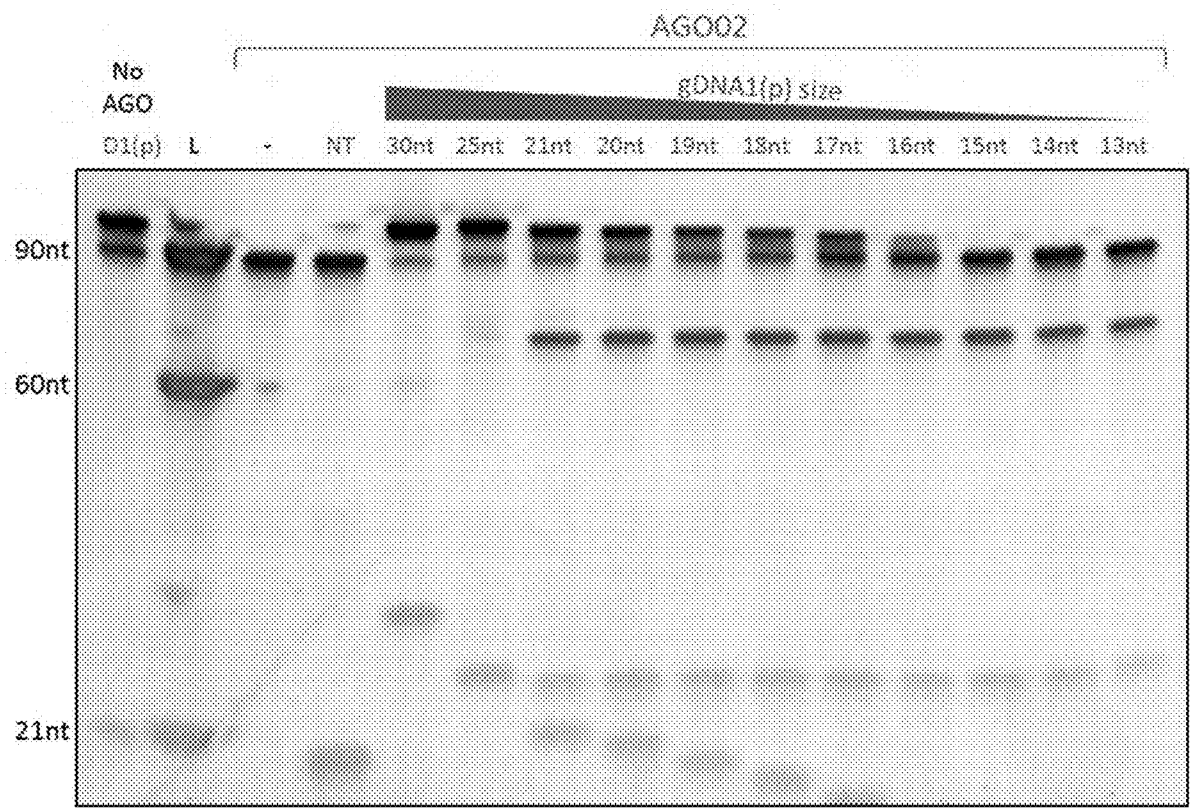
FIG. 22B shows an image of an electrophoresis gel showing cleavage of single stranded DNA template (90 nucleotides) by Ago02 with guide DNA (gDNA) ranging in length from 13-30 nucleotides. "D1(p)" indicates the 5' most nucleotide of the gDNA is phosphorylated.

The effect of the length of the guide DNA (gDNA) on Ago02 cleavage was also evaluated. The cleavage reactions were allowed to proceed for 1 hour. Template ssDNA of 90 nucleotides in length was used. The length of the gDNA used in each reaction included 30 nucleotides, 25 nucleotides, 21 nucleotides, 20 nucleotides, 19 nucleotides, 18 nucleotides, 17 nucleotides, 16 nucleotides, 15 nucleotides, 15 nucleotides, 14 nucleotides, and 13 nucleotides. The results show that Ago20 cleaves ssDNA with a gDNA of 13-21 nucleotides in length (FIG. 22B).

Figure 23A:
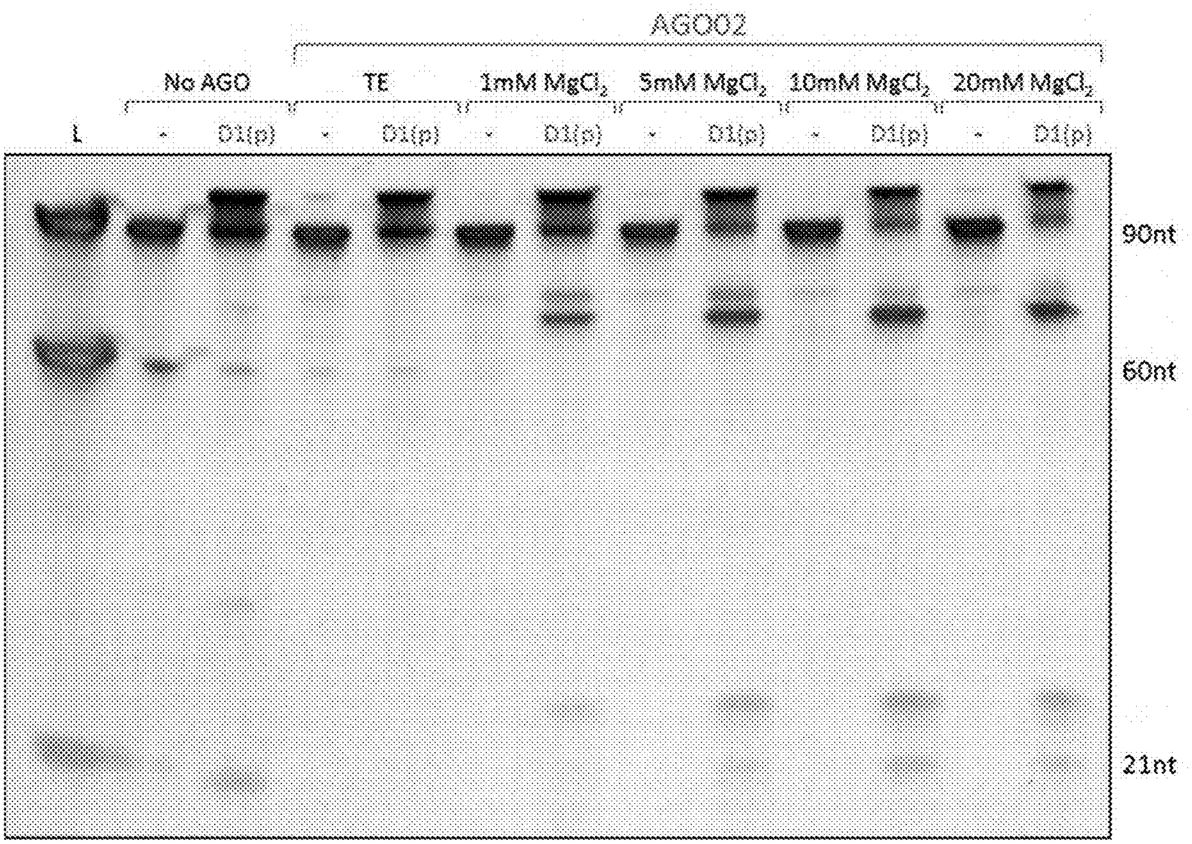
FIG. 23A shows an image of an electrophoresis gel showing the cleavage of single stranded DNA template (90 nucleotides) by Ago02 with guide DNA (gDNA) and a $Mg^{2+}$ titration of 1 mM $MgCl_2$, 5 mM $MgCl_2$, 10 mM $MgCl_2$, and 20 mM $MgCl_2$. "D1(p)" indicates the 5' most nucleotide of the gDNA is phosphorylated.
Figure 23B:
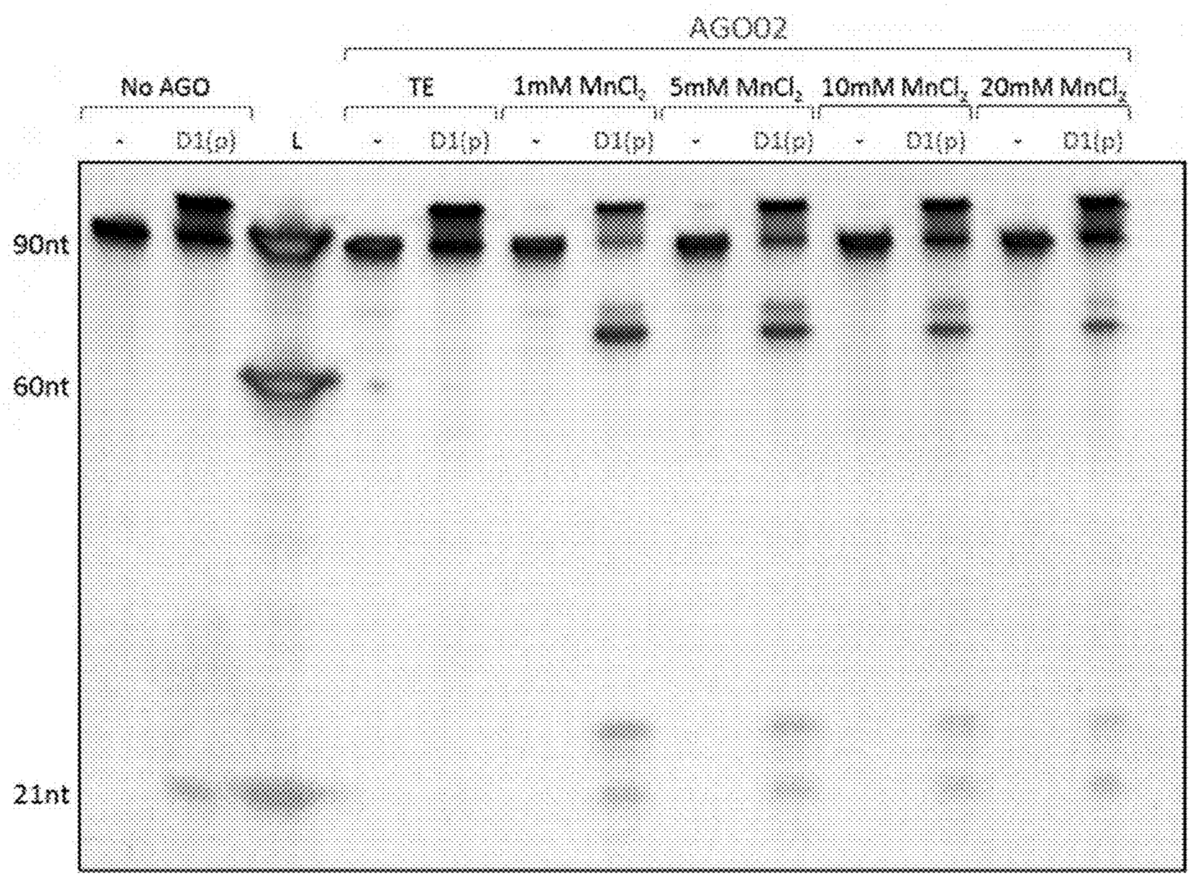
FIG. 23B shows an image of an electrophoresis gel showing the cleavage of single stranded DNA template (90 nucleotides) by Ago02 with guide DNA (gDNA) and a $Mn^{2+}$ titration of 1 mM $MnCl_2$, 5 mM $MnCl_2$, 10 mM $MnCl_2$, and 20 mM $MnCl_2$. "D1(p)" indicates the 5' most nucleotide of the gDNA is phosphorylated.

The effect of $Mg^{2+}$ and $Mn^{2+}$ concentration on Ago02 mediated cleavage was evaluated. Cleavage was allowed to proceed for 1 hour with a template ssDNA of 90 nucleotides in all reactions, and guide DNA. $MgCl_2$ concentrations were varied from 1 mM $MgCl_2$, 5 mM $MgCl_2$, 10 mM $MgCl_2$, 20 mM $MgCl_2$. In a separate experiment, $MnCl_2$ concentrations were varied from 1 mM $MnCl_2$, 5 mM $MnCl_2$, 10 mM $ngCl_2$, 20 mM $MnCl_2$. The results show no obvious sensitivity of Ago02 to the $Mg^{2+}$ (FIG. 23A). The results indicate that Ago02 may cleave less efficiently with the high $Mn^{2+}$ concentrations tested (FIG. 23B).

Figure 24:
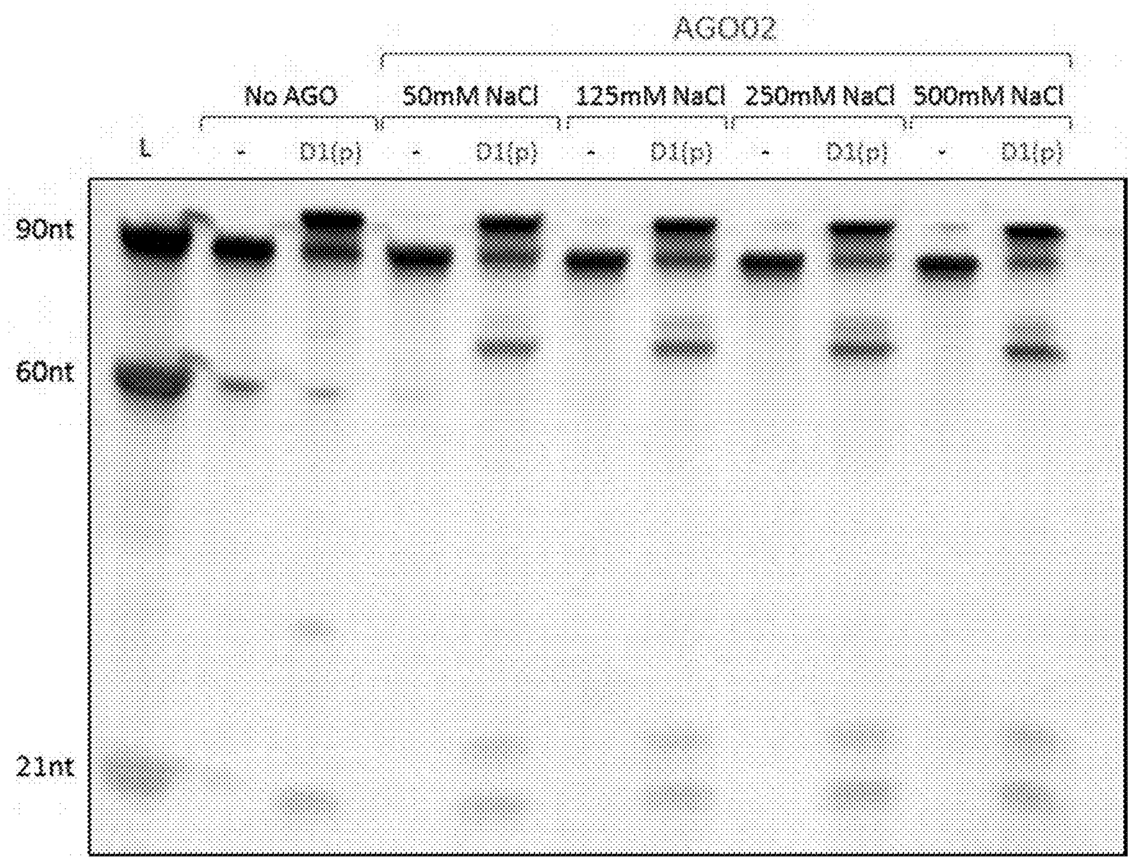
FIG. 24 shows an image of an electrophoresis gel showing the cleavage of single stranded DNA template (90 nucleotides) by Ago02 with guide DNA (gDNA) and a $NaCl_2$ titration of 50 mM $NaCl_2$, 125 mM $NaCl_2$, 250 mM $NaCl_2$, and 500 mM $NaCl_2$. "D1(p)" indicates the 5' most nucleotide of the gDNA is phosphorylated.

The effect of NaCl concentration was evaluated for Ago02 mediated cleavage of ssDNA with a DNA guide. The NaCl concentrations tested included 50 mM, 125 mM, 250 mM, and 500 mM. Template ssDNA 90 nucleotides in length was used in all reactions. Cleavage was allowed to proceed for 1 hour. The results show no obvious sensitivity of Ag02 to the $NaCl_2$ concentrations tested (FIG. 24).

Example 13. Effect of Guide RNA Stability on Mesophilic Ago Cleavage of ssDNA

The effect of the stability of the guide RNA (gRNA) was evaluated for Ago23, Ago29, and Ago51. RNase was inhibited with the addition of RNasin to the cleavage reactions (40 U/reaction). The cleavage reactions were allowed to proceed for 1 hour. Template ssDNA of 90 nucleotides in length was used in each reaction. For the Ago29 experiments, 125 ng of protein was used. The results show no obvious increase in cutting efficiency with RNasin (FIG. 28).

Example 14. Analysis of Mesophilic Ago Using Guide RNA—Ago23

The effect of the level of Ago23 on cleavage of ssDNA was evaluated. The cleavage reactions were allowed to proceed for 1 hour. Template ssDNA of 90 nucleotides in length was used with a guide RNA (gRNA) (R1p). The amount of Ago23 added to each cleavage reaction included 150 ng, 300 ng, 600 ng, 900 ng, 1200 ng, and 1500 ng. The results show a clear dose response with an increase in cleavage as the level of Ago23 increases (FIG. 29A).

The effect of the length of the guide RNA (gRNA) on Ago23 cleavage was also evaluated. The cleavage reactions were allowed to proceed for 1 hour. Template ssDNA of 90 nucleotides in length was used. The length of the gRNA used in each reaction included 30 nucleotides, 25 nucleotides, 21 nucleotides, 20 nucleotides, 19 nucleotides, 18 nucleotides, 17 nucleotides, 16 nucleotides, 15 nucleotides, 15 nucleotides, 14 nucleotides, and 13 nucleotides. The results show that Ago23 cleaves ssDNA with a gRNA of 13-21 nucleotides in length (FIG. 29B).

The effect of $Mg^{2+}$ and $Mn^{2+}$ concentration on Ago23 mediated cleavage was evaluated. Cleavage was allowed to proceed for 1 hour with a template ssDNA of 90 nucleotides and a gRNA (R1p) in all reactions. $MgCl_2$ concentrations were varied from 1 mM $MgCl_2$, 5 mM $MgCl_2$, 10 mM $MgCl_2$, 20 mM $MgCl_2$. In a separate experiment, $MnCl_2$ concentrations were varied from 1 mM $MnCl_2$, 5 mM $MnCl_2$, 10 mM $ngCl_2$, 20 mM $MnCl_2$. The results indicate that Ago23 may cleave less efficiently with the low $Mg^{2+}$ concentrations tested (FIG. 30A). The results also indicate that Ago23 may cleave less efficiently with the low $Mn^{2+}$ concentrations tested (FIG. 30B). The results further indicate that Ago23 may cleave with better efficiency with $Mg^{2+}$ versus $Mn^{2+}$ (FIG. 30A-30B).

The effect of NaCl concentration was evaluated for Ago23 mediated cleavage of ssDNA with a RNA guide (gRNA). The NaCl concentrations tested included 50 mM, 125 mM, 250 mM, and 500 mM. Template ssDNA 90 nucleotides in length was used in all reactions. Cleavage was allowed to proceed for 1 hour. The results show that Ago23 cleaves ssDNA only at $NaCl_2$ concentrations above 250 mM and has better cleavage efficiency at 500 mM (FIG. 31).

Example 15. Analysis of Mesophilic Ago—Ago29

The effect of the level of Ago29 on cleavage of ssDNA was evaluated. The cleavage reactions were allowed to proceed for 1 hour. Template ssDNA of 90 nucleotides in length and a guide RNA (R1p) was used. The amount of Ago29 added to each cleavage reaction included 150 ng, 300 ng, 600 ng, 900 ng, 1200 ng, and 1500 ng. The protein titration shows a strong non-specific DNA degradation, which is stronger without targeting gRNA (FIG. 32A).

The effect of the length of the guide RNA (gRNA) on Ago29 cleavage was also evaluated. The cleavage reactions were allowed to proceed for 1 hour. Template ssDNA of 90 nucleotides in length was used. Ago29 was added at a concentration of 125 ng/reaction. The length of the gRNA used in each reaction included 30 nucleotides, 25 nucleotides, 21 nucleotides, 20 nucleotides, 19 nucleotides, 18 nucleotides, 17 nucleotides, 16 nucleotides, 15 nucleotides, 15 nucleotides, 14 nucleotides, and 13 nucleotides. The results show that Ago29 cleaves ssDNA with a gDNA of 13-21 nucleotides in length (FIG. 32B). The results further show strong non-specific DNA degradation, which is stronger without targeting gRNA (FIG. 32B).

The effect of $Mg^{2+}$ and $Mn^{2+}$ concentration on Ago29 mediated cleavage was also evaluated. Cleavage was allowed to proceed for 1 hour with a template ssDNA of 90 nucleotides and a gRNA (R1p) in all reactions. $MgCl_2$ concentrations were varied from 1 mM $MgCl_2$, 5 mM $MgCl_2$, 10 mM $MgCl_2$, 20 mM $MgCl_2$. In a separate experiment, $MnCl_2$ concentrations were varied from 1 mM $MnCl_2$, 5 mM $MnCl_2$, 10 mM $ngCl_2$, 20 mM $MnCl_2$. The results indicate that the non-specific activity of Ago29 is weaker with the low $Mn^{2+}$ concentrations tested (FIG. 33B). The results further indicate that Ago29 may cleave with better efficiency with $Mn^{2+}$ versus $Mg^{2+}$ (FIG. 33A-33B).

The effect of NaCl concentration was evaluated for Ago29 mediated cleavage of ssDNA with a RNA guide. The NaCl concentrations tested included 50 mM, 125 mM, 250 mM, and 500 mM. Template ssDNA 90 nucleotides in length was used in all reactions. Cleavage was allowed to proceed for 1 hour. The results are presented in FIG. 34.

Example 16. Analysis of Mesophilic Ago—Ago51

The effect of the level of Ago51 on cleavage of ssDNA was evaluated. The cleavage reactions were allowed to proceed for 1 hour. Template ssDNA of 90 nucleotides in length and a guide RNA (R1p) was used. The amount of Ago51 added to each cleavage reaction included 150 ng, 300 ng, 600 ng, 900 ng, 1200 ng, and 1500 ng. The protein titration shows good cleavage activity from 300 ng Ago51 (FIG. 35A).

The effect of the length of the guide RNA (gRNA) on Ago51 cleavage was evaluated. The cleavage reactions were allowed to proceed for 1 hour. Template ssDNA of 90 nucleotides in length was used. The length of the gRNA used in each reaction included 30 nucleotides, 25 nucleotides, 21 nucleotides, 20 nucleotides, 19 nucleotides, 18 nucleotides, 17 nucleotides, 16 nucleotides, 15 nucleotides, 15 nucleotides, 14 nucleotides, and 13 nucleotides. The results show that Ago51 cleaves ssDNA with a gDNA of 13-25 nucleotides in length (FIG. 35B).

The effect of $Mg^{2+}$ and $Mn^{2+}$ concentration on Ago51 mediated cleavage was also evaluated. Cleavage was allowed to proceed for 1 hour with a template ssDNA of 90 nucleotides and a gRNA (R1p) in all reactions. $MgCl_2$ concentrations were varied from 1 mM $MgCl_2$, 5 mM $MgCl_2$, 10 mM $MgCl_2$, 20 mM $MgCl_2$. In a separate experiment, $MnCl_2$ concentrations were varied from 1 mM $MnCl_2$, 5 mM $MnCl_2$, 10 mM $ngCl_2$, 20 mM $MnCl_2$. The results indicate that Ago51 cleavage efficiency may be weaker with the lower $Mg^{2+}$ concentrations (FIG. 36A) tested and the lower $Mn^{2+}$ concentrations (FIG. 36B) tested. The results further indicate that Ago29 may cleave with better efficiency with $Mg^{2+}$ versus $Mn^{2+}$ (FIG. 36A-36B).

The effect of NaCl concentration was evaluated for Ago51 mediated cleavage of ssDNA with a RNA guide. The NaCl concentrations tested included 50 mM, 125 mM, 250 mM, and 500 mM. Template ssDNA 90 nucleotides in length was used in all reactions. Cleavage was allowed to proceed for 1 hour. The results show that Ago51 only cuts at NaCl concentrations greater than 125 mM, and has much better cleavage efficiency at over 250 mM NaCl (FIG. 37).

Example 17. The Effect of dsDNA Nicking on Clostridia Ago Cleavage

The effect of dsDNA nicking on Ago69 was evaluated. The experimental protocol utilized for the dsDNA "bubble" nicking assay is outlined in FIG. 38. The bubble template used was a ssDNA oligo with complementary regions to ensure that no ssDNA is present. The bubble template is 84 nucleotides in length with expected cleavage products of 58 nucleotides and 26 nucleotides. The ssDNA template was 43 nucleotides in length with expected cleavage products of 26 nucleotides and 17 nucleotides. The RecQ helicase unwinds substrates with 3' overhangs. The Nt.AlwI site is included as a positive control. The reaction includes, ssDNA template: gDNA/cleavage control. The reaction buffer includes 20 mM Tris/HCl pH7.5, 5 mM $MnCl_2$, 125 mM NaCl. The results show Ago69 ssDNA guide dependent nicking of dsDNA bubble template (FIG. 39).

Example 18. The Effect of GC Content on Clostridia Ago Cleavage

The effect of GC content of guide DNA (gDNA) on Ago69 mediated cleavage was evaluated. The sequences of each of the different guide DNAs (D1, D40, D41, D42, D43, and D44), the GC content, and the expected cleavage products are presented in Table 3.

TABLE 3 gDNA sequence, GC content, and cleavage products

| gDNA# | Sequence | SEQ ID NO: | GC content | Expected cleavage products |
|---|---|---|---|---|
| D1$^P$ | 5'-GCTGCCATCCAGATCGTTATC-3' | 157 | 52% | 66 + 24 |
| D40$^P$ | 5'-CGTTATCGCCCATGGGGTGCA-3' | 158 | 62% | 79 + 11 |
| D41$^P$ | 5'-GATCGTTATCGCCCATGGGGT-3' | 159 | 57% | 76 + 14 |
| D42$^P$ | 5'-GGTGCGGGTGAAGCTGCCATC-3' | 160 | 67% | 53 + 37 |
| D43$^P$ | 5'-ACTTAGACTGAAGGTGCGGGT-3' | 161 | 52% | 49 + 41 |
| D44$^P$ | 5'-AGTAATCGTCATCACTTAGAC-3' | 162 | 38% | 62 + 28 |

The positioning of each gDNA within the larger nucleic acid sequence is presented in FIG. 40. The results of the cleavage assay are presented in FIG. 40.

The effect of GC content of guide DNA (gDNA) on Ago41 mediated cleavage was also evaluated. The sequences of each of the different guide DNAs (D1, D40, D41, D42, D43, and D44), the GC content, and the expected cleavage products are presented in Table 3. The positioning of each gDNA within the larger nucleic acid sequence is presented in FIG. 42. The results of the cleavage assay are presented in FIG. 42.

The effect of GC content of guide DNA (gDNA) on Ago70 mediated cleavage was evaluated. The sequences of each of the different guide DNAs (D1, D40, D41, D42, D43, and D44), the GC content, and the expected cleavage products are presented in Table 3. The positioning of each gDNA within the larger nucleic acid sequence is presented in FIG. 43. The results of the cleavage assay are presented in FIG. 43.

Example 19. The Effect of GC Content on Mesophilic Ago Cleavage

The effect of GC content of guide DNA (gDNA) on Ago02 mediated cleavage was evaluated. The sequences of each of the different guide DNAs (D1, D40, D41, D42, D43, and D44), the GC content, and the expected cleavage products are presented in Table 3. The positioning of each gDNA within the larger nucleic acid sequence is presented in FIG. 41. The results of the cleavage assay are presented in FIG. 41.

Example 20. Double Stranded DNA Cleavage by Clostridia Ago

The ability of Ago69 to cleave double stranded DNA (dsDNA) was evaluated. The cleavage assay was performed in 1× CutSmart buffer (NEB). The guide DNA (gDNA) was preloaded with Ago69 by incubation of the gDNA with Ago69 at 37° C. for 15 minutes. Each of the 8 gDNAs tested were preloaded separately. The gDNAs including the location, CG content, and Tm are presented in FIG. 51. Double stranded target plasmid DNA was preincubated for 15 minutes at 37° C. Half reactions were combined before the plasmid template was added. Reactions were incubated for 15 or 60 minutes at 75° C. Linearization was completed with Xhol incubation for 30 minutes at 37° C. The DNA was resolved on a 1% agarose gel stained with SYBR gold. The expected cleavage products are approximately 1.5 kb and 3.5 kb (FIG. 52A). The results show that Ago69 can cleave dsDNA (FIG. 52B).

Example 21. The Impact of ET-SSB and Eco-SSB Proteins on DNA Unwinding

The impact of single strand DNA binding (SSB) proteins on the processivity of DNA unwinding by RecQ helicase was evaluated. The experimental design is outlined in FIG. 44. A helicase substrate was used which contained the guide DNA1 (gDNA1) sequence. The initial experiment was conducted with RecQ and ET-SSB on a 3' overhang long substrate. The results show the ET-SSB has a beneficial effect on DNA unwinding (FIG. 45). The experiment was repeated with shorter substrate, which produced a better noise/signal ratio (FIG. 46). The experiment confirmed that ET-SSB has a beneficial effect on DNA unwinding with the short substrate, with no strong dose dependency effect observed (FIG. 46). A third experiment was conducted with RecQ and Eco-SSB on a 3' overhang short substrate. The initial experiment with Eco-SSB showed saturation within 5 minutes, this for the Eco-SSB experiment 10× less RecQ was used. The results show the Eco-SSB has the same beneficial effect on DNA unwinding as ET-SSB, with no strong dose dependency effect (FIG. 47). As used herein the terms "ET-SSB" and "Sso-SSB" refer to the same SSB protein from *Saccharolobus solfataricus* of SEQ ID NO: 22, or a functional fragment or variant thereof.

Example 22. The Impact of ET-SSB and Eco-SSB Proteins on Ago Mediated DNA Cleavage A separate experiment was conducted to evaluate dsDNA cleavage with and without preincubation of plasmid DNA at 75° C. and with and without ET-SSB protein. The cleavage assay was performed in 1× CutSmart buffer (NEB). The guide DNA (gDNA) was preloaded with Ago69 by incubation of the gDNA with Ago69 at 37° C. for 15 minutes. Guides were preloaded separately. Plasmid DNA was incubated at 75° C. for 15 minutes/no preincubation. Half reactions were combined with ET-SSB protein (0.5 μg/reaction) (or control) and plasmid template; incubated for 30 minutes at either 37° C. or 39° C. (FIG. 54), 41.5° C. or 44.9° C. (FIG. 55), 49.1° C. or 67° C. (FIG. 56); and a MluI plasmid restriction digest was carried out for 30 minutes at 37° C. Proteinase K was added to stop the reaction. The DNA was run on a 1% agarose gel and stained with SYBR gold. The expected cleavage products of the MluI plasmid digest are 4487 and 1827 bp (FIG. 53A). The expected cleavage products of the MluI plasmid digest and Ago69 cleavage are 3816, 1827, and 671 bp (FIG. 53B). As shown in FIG. 54-FIG. 56, Ago69 cleavage was dependent on the inclusion of guide DNA (gDNA54 and gDNA 55) and was increased with inclusion of ET-SSB across the temperatures measured, including at 37° C.

A separate experiment, to confirm the effect of ET-SSB and Eco-SSB on Ago69 mediated dsDNA cleavage was conducted. The cleavage assay was performed in 1× CutSmart buffer (NEB). The guide DNA (gDNA) was preloaded with Ago69 by incubation of the gDNA with Ago69 at 37° C. for 15 minutes. Guides were preloaded separately. Half reactions were combined with ET-SSB protein (0.5 μg/reaction), Eco-SSB protein, or control, and plasmid template; incubated for 30 minutes at either 37° C., and a MluI-HF or Bsml plasmid restriction digest was carried out for 30 minutes at 37° C. Proteinase K was added to stop the reaction. The DNA was run on a 1% agarose gel and stained with SYBR gold. The expected cleavage products of the MluI-HF plasmid digest are 4487 and 1827 bp (FIG. 53A). The expected cleavage products of the MluI-HF plasmid digest and Ago69 cleavage are 3816, 1827, and 671 bp (FIG. 53B). The expected cleavage products of the Bsml plasmid digest are 4596, 1641, and 77 bp (FIG. 57A). The expected cleavage products of the Bsml plasmid digest and Ago69 cleavage are 4596, 1089, 552, and 77 bp (FIG. 57B). FIG. 58 shows the cleavage of the plasmid DNA from both the MluI-HF (left) and Bsml (right) digests (high exposure agarose gel) with ET-SSB at 37° C. FIG. 59 shows the cleavage of the plasmid DNA from both the MluI-HF (left) and Bsml (right) digests (high exposure agarose gel) with Eco-SSB at 37° C. FIG. 60 (low exposure gel) and FIG. 61 (high exposure gel) shows a dose response cleavage of plasmid DNA with ET SSB at the indicate ng/reaction (i.e. 1000 ng/reaction, 500 ng/reaction, 250 ng/reaction, 125 ng/reaction, 75 ng/reaction, or 0 ng/reaction) in a Bsml digestion. The expected cleavage products are the same as previously shown in FIG. 57A and FIG. 57B.

Example 23. The Impact of ET-SSB and TteUvrD Helicase on Ago Mediated DNA Cleavage As set out in FIG. 62, Ago69 was preloaded with guide DNA 54 (guide 54) (3.75 μM) in 1× CutSmart buffer (NEB) supplemented with 5 mM ATP and the preloading reaction allowed to proceed for 15 minutes at 37° C. to produce a guide 1 reaction. Similarly, Ago69 was preloaded with guide DNA 55 (guide 55) (3.75 μM) in 1× CutSmart buffer (NEB) supplemented with 5 mM ATP and the preloading reaction allowed to proceed for 15 minutes at 37° C. to produce a guide 2 reaction. A reaction mixture of 7 μl of guide 1 reaction, 7 μl of guide 2 reaction, 1 μl ET SSB (500 ng), 11 Tte UvrD helicase (20 ng), and 1 μl plasmid #56 DNA (250-300 ng) was incubated for 30 minutes at 37° C. 1 μl of restriction enzyme (Bsal-HF) was added and incubated for 30 minutes at 37° C. to mediate digestion. 1 μl of proteinase K was added to stop the digestion. The protocol as described is further set out in FIG. 62. The expected cleavage products with Bsal-HF digest alone are 6314 bp (linearized plasmid). The expected cleavage products with Ago mediated cleavage with D54 and D55 guides and Bsal-HF digest are 4937 and 1341 bp. The results of the cleavage analysis are shown in FIG. 63.

Example 24. Expression and Purification of Helicases and SSBs

All SSB proteins were expressed and purified as shown in FIG. 64A-64B, including TnsSSB, TthSSB, and NeqSSB. Repeat helicase expression and purification were also carried out as shown in FIG. 64A-64B, including Eco RecQ, Tth UvrD, Eco UvrD, HEL #100, HEL #75, HEL #76. The helicases and SSBs were then tested in combination with Ago69 as shown in Example 25.

Example 25. Effect of Helicases and SSBs on Ago69 Mediated Cleavage

Ago69 was preloaded with guides 54 and 55 at a ratio of Ago69:gDNA of 1:1. Guides 54 and 55 were preloaded separately for 15 min at 37° C. Half reactions were combined with 1000 ng of SSB (TneSSB, Tth SSB, Neq SSB, Taq SSB, Tma SSB, Sso SSB, Eco SSB, ET SSB, or control with no SSB protein) and 40 ng of helicase (tTE uVRd, hel #65, HEL #71, HEL #78, HEL #92, or no helicase control). Plasmid #56 DNA was added last (~250 ng/reaction) and incubated for 30 minutes at 37° C. Mlul-HF restriction enzyme was added for 30 minutes at 37° C. Proteinase K was added and incubated for 30 minutes at room temperature to the to stop the digestion. The expected cleavage products of Mlul-HF digest alone are 4487 and 1827 bp. The cleavage products of Ago69 cleavage and Mlul-HF digestion are 3816, 1827, and 671. The results are shown in FIG. 65, FIG. 66, and FIG. 67.

Example 26. First Round Expression and Purification of Ago69 Fusion Proteins

Three Ago69 fusion constructs were expressed and purified. Each of the constructs is shown graphically in FIG. 68. One construct comprises Ago69 fused to SV40 nuclear localization signal via a linker (Ago69 construct (APO71)); a second construct comprises Ago69 further fused to SsoSSB via a linker (SsoSSB-AGO #69 construct (AP072)); a third construct comprises Ago69 further fused to VP64 (transcriptional activator) (VP64-AGO #69 construct (AP073)). The purified constructs were detected via western blot as shown in FIG. 69A and FIG. 69B.

Example 27. Cleavage of Plasmid DNA Mediated by Ago69 Fusion Proteins

Plasmid DNA cleavage mediated by the Ago69 containing fusion proteins described in Example 26 was carried out as previously described. The expected cleavage products of Plasmid #56 using XbaI restriction enzyme and Ago mediated cleavage were 4604, 1388, and 35 bp. The results are shown in FIG. 70 and FIG. 71.

Example 28. Second Round Expression and Purification of Ago69 Fusion Proteins The three Ago fusion constructs described in Example 26 were expressed and purified again in a second round experiment. Each of the constructs is shown graphically in FIG. 68. One construct comprises Ago69 fused to SV40 nuclear localization signal via a linker (Ago69 construct (APO71)); a second construct comprises Ago69 further fused to SsoSSB via a linker (SsoSSB-AGO #69 construct (AP072)); a third construct comprises Ago69 further fused to VP64 (transcriptional activator) (VP64-AGO #69 construct (AP073)). The purified constructs were detected via western blot as shown in FIG. 72A and FIG. 72B.

Example 29. Cleavage of Plasmid DNA Mediated by Ago69 Fusion Proteins

Plasmid DNA cleavage mediated by the Ago69 containing fusion proteins described in Example 28 was carried out as previously described. The expected cleavage products of Plasmid #56 using XbaI restriction enzyme and Ago mediated cleavage were 4604, 1388, and 35 bp. The results of one cleavage experiment are presented in FIG. 73; and the results from a second cleavage experiment are presented in FIG. 74.

Example 30. Expression and Purification of SsoSSB-Ago69 Fusion Proteins

Six SsoSSB-Ago69 fusion constructs were expressed and purified. The constructs are shown in FIG. 75. The constructs included an N-terminal His tag. The purified fusion preparations are shown in FIG. 76A and FIG. 76B.

Example 31. Cleavage of Plasmid DNA Mediated by SsoSSB-Ago69 Fusion Proteins

Plasmid DNA cleavage mediated by the SsoSSB-Ago69 containing fusion proteins described in Example 30 was carried out per the protocol below. SsoSSB-Ago69 fusion constructs were separately preloaded with guide DNA 55 (guide 55) or guide DNA 54 (guide 54) in 1× CutSmart buffer (NEB) and the preloading reaction allowed to proceed for 15 minutes at 37° C. to produce a guide 2 reaction. Half reaction mixtures were combined with plasmid DNA template (plasmid 56) and incubated for 30 minutes at 37° C. (in some samples ET-SSB was also added to the reaction mixture where indicated). Restriction enzyme (Kpn1-HF) was added and incubated for 30 minutes at 37° C. to mediate digestion. Proteinase K was added to stop the digestion through incubation at 50° C. for 30 minutes. The expected cleavage products using Kpn1-HF restriction enzyme and Ago mediated cleavage were 4723 and 1591 bp. The results of one cleavage experiment are presented in FIG. 77; and the results from a second cleavage experiment are presented in FIG. 78.

The ability of the SsoSSB fusion constructs to mediate cleavage at 75° C. was also tested. SsoSSB-Ago69 fusion constructs were separately preloaded with guide DNA 55 (guide 55) or guide DNA 54 (guide 54) in 1× CutSmart buffer (NEB) and the preloading reaction allowed to proceed for 15 minutes at 37° C. to produce a guide 2 reaction. Half reaction mixtures were combined with plasmid DNA template (plasmid 56) and incubated for 30 minutes at 75° C. Restriction enzyme (Kpn1-HF) was added and incubated for 30 minutes at 37° C. to mediate digestion. Proteinase K was added to stop the digestion through incubation at 50° C. for 30 minutes. The expected cleavage products using Kpn1-HF restriction enzyme and Ago mediated cleavage were 4723 and 1591 bp. The results of the cleavage experiment are presented in FIG. 79.

Example 32. Localization of Ago69 Fusion Constructs to the Nucleus

Gene editing happens in the nucleus of a mammalian cell. Consequently, delivery of an Argonaute to the nucleus becomes a key prerequisite for its ability to function as a gene editing machine. We determined that Ago69 that it may only tolerate N-terminal fusions as its C-terminus is quite hydrophobic and folds back into the hydrophobic core of the molecule. Consequently, a construct was created in which two SV40-derived nuclear localization signals were fused to the N-terminus of Ago #69 as outlined in the schematic presented in FIG. 80 (SEQ ID NO: 97; AP109). To assess the subcellular localization, this construct was expressed in Hela cells and localization was assessed by immunofluorescence microscopy, staining for Ago #69 using the V5-specific antibody R960-25 (Invitrogen). The data shown in FIG. 81, FIG. 82, FIG. 85, and FIG. 86 suggest that Ago #69, Ago homologs 2 (SEQ ID NO: 99; SPL0389) and 4 (SEQ ID NO: 100; SPL0390) upon fusion with two SV40-derived NLSs localize in the nucleus.

Fusion constructs were created that include the SsoSSB in the fusion construct as outlined in FIG. 80 (SEQ ID NO: 98; AP110), essentially adding SsoSSB between the V5-tag and the N-terminus of Ago69. This construct was found to localize almost exclusively in the cytosol (FIG. 83). This suggested that the presence of SsoSSB at this position hampered the two SV40-derived NLSs to function.

To solve this issue, a new series of constructs were made in which we changed the identity and positioning of the nuclear localization signals. In some constructs, the SV40 NLS was exchanged for NPM NLS and the spacing was adjusted as outlined in FIG. 80. Flexible linkers (GSGS (SEQ ID NO: 154) or GSGSS (SEQ ID NO: 140)) were also added to ensure accessibility (see FIG. 80). The constructs were tested for their subcellular localization in Hela cells as described above. The V5-2xSV40 NLS-SsoSSB-MYC NLS-AGO69 (SEQ ID NO: 101; SPL0398) was found localized almost exclusively in the nucleus (FIG. 84). This is in stark contrast to the SsoSSB fusion tested above (AP110) which showed compromised nuclear localization.

In summary, these data suggest an effective configuration/construct design that allows the nuclear localization of Ago69 fusions with SsoSSB. This represents a key prerequisite for Ago69 functioning as gene editing tool.

Example 33. Importance of Sequence Context of Guide DNA Recognition Site

Argonautes are guided by short DNA or RNA sequences (so called guide DNAs or RNAs) to their target sequence which is complementary. As is the case with Cas9 endonuclease, Argonaute guide DNA sequences may differ in terms of their ability to induce target cleavage by the Argonaute. To test this experimentally, a set of guide DNA pairs were designed (see Table 16) targeting two plasmids (plasmid #56 and #70). Linearization of the plasmid by the Argonaute-induced DNA double-strand break was followed by the digestion with a cognate restriction enzyme, leading to a defined cleavage pattern.

TABLE 16

Guide DNA Sequences

| Guide ID | Guide sequence | SEQ ID NO |
|---|---|---|
| D1 | 5Phos/GCTGCCATCCAGATCGTTATC | 107 |
| D2 | 5Phos/GGAGCTGTAGTAGCCGCCGTC | 108 |
| D3 | 5Phos/TAGCCGCCGTCGCGCAGGCTG | 109 |
| D30 | 5Phos/GATAACGATCTGGATGGCAGC | 110 |
| D31 | 5Phos/GGAGCTGTAGTAGCCGCCGTC | 111 |
| D32 | 5Phos/CAGCCTGCGCGACGGCGGCTA | 112 |
| D54 | 5Phos/AATTCGCGTTAAATTTTTGTT | 113 |
| D55 | 5Phos/AACAAAAATTTAACGCGAATT | 114 |
| D82 | 5Phos/GCCCTGAAAATAAAGATTCTC | 115 |
| D83 | 5Phos/GAGAATCTTTATTTTCAGGGC | 116 |
| D86 | 5Phos/GCCCCCGATTTAGAGCTTGAC | 117 |
| D87 | 5Phos/GTCAAGCTCTAAATCGGGGGC | 118 |
| D88 | 5Phos/CCACACCCGCCGCGCTTAATG | 119 |
| D89 | 5Phos/CATTAAGCGCGGCGGGTGTGG | 120 |
| D90 | 5Phos/GGGGAAAGCCGGCGAACGTGG | 121 |
| D91 | 5Phos/CCACGTTCGCCGGCTTTCCCC | 122 |

TABLE 16 -continued

| Guide DNA Sequences | | |
|---|---|---|
| Guide ID | Guide sequence | SEQ ID NO |
| D92 | 5Phos/GGCCCCAAGGGGTTATGCTAG | 123 |
| D93 | 5Phos/CTAGCATAACCCCTTGGGGCC | 124 |
| D94 | 5Phos/TATTATTTTCTCCCATGAAGA | 125 |
| D95 | 5Phos/TCTTCATGGGAGAAAATAATA | 126 |
| D102 | 5Phos/AGAACGTGGACTCCAACGTCA | 127 |
| D103 | 5Phos/TGACGTTGGAGTCCACGTTCT | 128 |
| D104 | 5Phos/TAACCAATAGGCCGAAATCGG | 129 |
| D105 | 5Phos/CCGATTTCGGCCTATTGGTTA | 130 |
| D106 | 5Phos/TATTTAGAAAAATAAACAAAT | 131 |
| D107 | 5Phos/ATTTGTTTATTTTTCTAAATA | 132 |

When testing a set of ~10 guide DNA pairs on these two plasmids, the guide DNAs clearly differed in their ability to induce target cleavage (FIG. 87). It was initially hypothesized that the GC content of the guide DNA sequences was responsible for this difference, but upon closer inspection, we found guide DNA pairs which were effective despite a high GC content (e.g. guide pair 92/93 targeting a sequence with 62% GC content) (FIG. 87).

Consequently, it was hypothesized that it may not be guide DNA sequence itself, but rather the sequence context in which the guide DNA recognition lies. If that hypothesis were true, it should be possible to take an inactive guide DNA recognition site and "transplant" it into a region in which guide DNA cutting is permitted. Likewise, transplanting an active guide DNA recognition site into an inactive region should prevent cutting from occurring.

To test this hypothesis, a series of "guide swapping constructs" were created (FIG. 88A, FIG. 88B, FIG. 89). We started with plasmid #p56 which bears two guide RNA recognition sites: AE1 is recognized by the guide pair D54/55 and recognition leads to the effective cleavage of the target sequence. AE2 is recognized by the guide pair D82/83, but its recognition does not trigger effective cleavage. We then created two derivates of plasmid #56: In plasmid #114, the AE1 site was replaced by AE2 (FIG. 89). In plasmid #115 the position of AE1 and AE2 were swapped, i.e. AE1 now lies within the sequence context of AE2 and vice versa (FIG. 89).

When testing these plasmids, we made the following key observations: 1) In plasmid #56, the AE1 is effectively cleaved, whereas the AE2 remains uncleaved. This was the starting assumption of the experiment (FIG. 90 and FIG. 91); 2) in plasmid #114, the AE2 site which was previously inactive, is now accessible for cleavage (FIG. 90 and FIG. 91); and 3) in plasmid #115, the AE2 site which was previously inactive, can now induce the target site cleavage and the AE1 which was previously active is now inactive (FIG. 90 and FIG. 91).

These data suggest that, at least in these assays, the guide DNA recognition site is not the only determinant for enzymatic AGO activity. Instead, the sequence context has a significant impact on the ability of guide DNAs to trigger target cleavage. This implies that certain regions in the plasmid may be more accessible and that accessibility may be a limiting factor for the Argonaute to exert its action.

Example 34. Generation of HAT Plasmid

HAT plasmids were generated in order to test the cleavage efficiency of Agos on regions of DNA with low GC content. HAT versions of plasmid #70 and plasmid #56 were generated. To generate plasmid #70-HAT (high AT region) plasmid #70 was digested with BamH1 and BsrG1. HAT high AT region was subcloned by using NEBuilder HiFi DNA Assembly. HAT sequence is 144 bp with a 20.14% GC content. The HAT region comprises the following sequence:

```
                                          (SEQ ID NO: 133)
ATTAGACATAATTTATAGTAGAAATATAGAAATTCTATCTAACTATATTT

AAGTTCAATTGATATCTTTAAAGATTATAGTCACAGTAATAAGAATTGTT

AACTATACTTTGATATCTTTGACTTATTAGTTAAGTCTTAGAAA).
```

Example 35. Ago69 Cleavage of HAT Plasmid

The ability of Ago69 to cleavage HAT plasmid DNA was assessed. The HAT plasmid was generated as described in Example 34. The cleavage assay was performed in 1× CutSmart buffer (NEB). The guide DNAs (gDNAs) was separately preloaded with Ago69 by incubation of the gDNA with Ago69 at 37° C. for 15 minutes. The guides used in the analysis included HIP (D166 (H1F), D167 (H1R)); H2P (D168 (H2F), D169 (H2R)); H3P (D170 (H3F), D171 (H3R)); AE1, H1F, H1R, H2F, and H2R. (see FIG. 92). Half reactions were combined with ET-SSB protein (0.5 μg/reaction) (or control) and plasmid #70-HAT (see below) template DNA; incubated for 30 minutes at either 37° C.; and a SacI-HF plasmid restriction digest was carried out for 30 minutes at 37° C. Proteinase K was added to stop the reaction. The DNA was run on a 1% agarose gel and stained. The data shows that single guides show detectable cleavage only in presence of ET SSB (FIG. 93 and FIG. 94).

Example 36. Single Strand DNA Cleavage Mediated by Ago69 Homologues

Nine Ago69 homologue proteins were expressed and purified, denoted HG1, HG2, HG3, HG4, HG5, HG6, HG7, HG8 and HG9 (FIG. 97, FIG. 98A, FIG. 98B, FIG. 99). HG1, HG3, and HG7 appeared to be insoluble. The ability of Ago69 homologues to cleave single strand plasmid DNA was assessed. In one experiment the homologues tested included HG2 (SEQ ID NO: 134), HG4 (SEQ ID NO: 135), and HG5 (SEQ ID NO: 136). The cleavage assay was performed in 1× CutSmart buffer (NEB). The guide DNAs (gDNAs) was separately preloaded with Ago69 or Ago69 homologue by incubation of the gDNA with Ago69 or Ago69 homologue at 37° C. for 15 minutes. The guides used in the analysis included H1P (D166 (H1F), D167 (H1R)) and AE1 (see FIG. 92). Half reactions were combined with ET-SSB protein (0.5 μg/reaction) (or control) and plasmid #70-HAT (as described in Example 34) template DNA; incubated for 30 minutes at either 37° C.; and a SacI-HF plasmid restriction digest was carried out for 30 minutes at 37° C. Proteinase K was added to stop the reaction. The DNA was run on a 1% agarose gel and stained. The expected cleavage products of the SacI-HF plasmid digest are 1402 and 1118 bp. The data shows that Ago69 homologues HG2, HG4, and HG5 all show cleavage activity on single strand DNA, and the cleavage efficiency is increased with the inclusion of Sso-SSB (FIG. 95).

In another experiment the homologues tested included HG2 (SEQ ID NO: 134), HG4 (SEQ ID NO: 135), and HG6. The cleavage assay was performed in 1× CutSmart buffer (NEB). The guide DNAs (gDNAs) was separately preloaded with Ago69 or Ago69 homologue by incubation of the gDNA with Ago69 or Ago69 homologue at 37° C. for 15 minutes. The guides used in the analysis included AE1. The restriction digests were run without column purification (FIG. 100) and with column purification (FIG. 101) of the Ago69 homologue. As shown in FIG. 100 and FIG. 101, HG2 and HG4 showed the highest cleavage efficiency of the homologues tested, while HG6 did not appear to show cleavage activity.

Example 37. HPRT Assay

The HPRT1 gene encodes for an enzyme called hypoxanthine phosphoribosyltransferase 1 which is involved in purine metabolism. Addition of 6-thioguanine (6-TG) to cells harbouring the wild-type HPRT1 will lead to cell death, mediated by the product of 6-TG conversion by HPRT1. Cells harbouring inactive HPRT1 can no longer convert 6-TG to its toxic metabolite. Conversely, these cells will be resistant to 6-TG (A4882; Sigma Aldrich).

Hela cells were transfected with the following series of constructs using Turbofectin 8.0 (TF81001; BioCat GmbH) according to manufacturer's instructions: AP109, SPL0390, SPL0398. Importantly, cells were co-transfected with the set of DNA guides shown in Table 19.

TABLE 19

DNA Guides

| Guide ID | Guide Sequence | SEQ ID NO: |
|---|---|---|
| D176 | 5Phos/T*C*A*TGGACTAATTATGGA*C*A*G | 145 |
| D177 | 5Phos/C*T*G*TCCATAATTAGTCCA*T*G*A | 146 |
| D178 | 5Phos/T*A*T*GAAACTTTCTATTAA*A*T*T | 147 |
| D179 | 5Phos/A*A*T*TTAATAGAAAGTTTC*A*T*A | 148 |

TABLE 19 -continued

DNA Guides

| Guide ID | Guide Sequence | SEQ ID NO: |
|---|---|---|
| D180 | 5Phos/T*T*T*TTTACTTTTTCTTGT*G*T*T | 149 |
| D181 | 5Phos/A*A*C*ACAAGAAAAAGTAAA*A*A*A | 150 |
| D182 | 5Phos/A*A*T*TCGCGTTAAATTTTT*G*T*T | 151 |
| D183 | 5Phos/A*A*C*AAAAATTTAACGCGA*A*T*T | 152 |

*. . . Phosphorothioate bonds

Some of these guides (D176-D181) target the HPRT1 gene, whereas other guides (D182-183) were non-targeting controls which served as negative controls. Guides were either included as single guides or as pairs of guides. Importantly, when used as pairs, guides were designed to targeting opposing DNA strands.

Following transfection, the cells were allowed to rest for 2-3 days. Then, they were seeded in 96 well plates and treated with 5 μM 6-TG. Cells were analysed by microscopy at day 4 post drug treatment. Controls in the experiment included Hela cells that were not treated with 6-TG (alive) and Hela cells treated with 6-TG (rounded shape; compromised viability). In addition, HPRT1 was also targeted using Cas9 and the following sgRNA targeting the human HPRT1 gene: CATGGACTAATTATGGACAG (SEQ ID NO: 144). Inactivation of cells using Cas9 and the HPRT1-specific sgRNA lead to 6-TG resistance as expected. The results for the SPL0390 construct are presented in FIG. 104. The results for the AP109 construct are presented in FIG. 105. The results for the SPL0398 construct are presented in FIG. 106.

The only condition in the experiment conferring resistance to 6-TG is the condition in which Ago69 homolog 4 (HG4) (SPL0390 construct) was combined with the guide pair D178/179 (FIG. 104). Ago69 homolog 4 did not induce this survival phenotype when combined with the single guide (D178), suggesting that the pair of guides is necessary to establish the 6-TG resistance phenotype. Overall, these data suggest that Ago69 homolog 4 can edit the HPRT1 gene in human cells, leading to the establishment of 6-TG-resistant colonies that can be visualized in the microscope.

What is claimed is:

1. A system comprising:

a mesophilic Argonaute (Ago) polypeptide, or a polynucleic acid encoding the mesophilic Ago polypeptide, or a functional fragment or variant thereof, wherein the Ago polypeptide has an amino acid sequence set forth in any one of SEQ ID NOs 1-10; and an exogenous non-naturally occurring guiding polynucleic acid that binds a target polynucleic acid, wherein upon contacting the target polynucleic acid with the Ago polypeptide and the exogenous non-naturally occurring guiding polynucleic acid at a mesophilic temperature, the Ago polypeptide cleaves the target polynucleic acid.

2. The system of claim 1, wherein the Ago polypeptide demonstrates nucleic acid-cleaving activity of the target polynucleic acid at about 37° C.

3. The system of claim 1, wherein the guiding polynucleic acid is a guide DNA or a guide RNA.

4. The system of claim 1, wherein said system further comprises a nucleic acid unwinding polypeptide or a polynucleic acid encoding the nucleic acid unwinding polypeptide.

5. The system of claim 4, wherein said nucleic acid unwinding polypeptide is a helicase, a single strand DNA binding (SSB) protein, or a Clustered Regularly Interspaced Short Palindromic Repeats (CRISPR) associated (Cas) protein domain.

6. The system of claim 5, wherein said nucleic acid unwinding polypeptide is a single strand DNA binding protein (SSB) polypeptide.

7. The system of claim 5, wherein said nucleic acid unwinding polypeptide is a Cas protein domain.

8. The system of claim 7, wherein said Cas protein domain is a catalytically dead Cas polypeptide.

9. The system of claim 1, wherein said Ago polypeptide is fused either directly or indirectly to a nuclear localization signal (NLS).

* * * * *